United States Patent
Fischer et al.

(10) Patent No.: US 9,278,964 B2
(45) Date of Patent: *Mar. 8, 2016

(54) MOLECULES HAVING CERTAIN PESTICIDAL UTILITIES, AND INTERMEDIATES, COMPOSITIONS, AND PROCESSES RELATED THERETO

(71) Applicant: Dow AgroSciences LLC, Indianapolis, IN (US)

(72) Inventors: Lindsey G. Fischer, Indianapolis, IN (US); Erich W. Baum, Greenwood, IN (US); Gary D. Crouse, Noblesville, IN (US); Jeff Petkus, Indianapolis, IN (US); Andrew Ward, Carmel, IN (US); Thomas C. Sparks, Greenfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,389

(22) Filed: Mar. 18, 2015

(65) Prior Publication Data

US 2015/0225391 A1 Aug. 13, 2015

Related U.S. Application Data

(63) Continuation of application No. 14/208,430, filed on Mar. 13, 2014, now Pat. No. 9,029,560.

(60) Provisional application No. 61/784,020, filed on Mar. 14, 2013.

(51) Int. Cl.

| C07D 417/12 | (2006.01) |
|---|---|
| C07D 249/08 | (2006.01) |
| A01N 47/42 | (2006.01) |
| A01N 47/36 | (2006.01) |
| A01N 47/34 | (2006.01) |
| A01N 25/00 | (2006.01) |
| A01N 25/32 | (2006.01) |
| A01N 43/653 | (2006.01) |
| A01N 47/12 | (2006.01) |
| A01N 53/00 | (2006.01) |
| A01N 55/08 | (2006.01) |
| C07C 335/26 | (2006.01) |
| C07D 277/54 | (2006.01) |
| C07D 403/10 | (2006.01) |
| C07C 211/45 | (2006.01) |
| C07C 335/16 | (2006.01) |

(52) U.S. Cl.
CPC .............. *C07D 417/12* (2013.01); *A01N 25/00* (2013.01); *A01N 25/32* (2013.01); *A01N 43/653* (2013.01); *A01N 47/12* (2013.01); *A01N 47/34* (2013.01); *A01N 47/36* (2013.01); *A01N 47/42* (2013.01); *A01N 53/00* (2013.01); *A01N 55/08* (2013.01); *C07C 211/45* (2013.01); *C07C 335/26* (2013.01); *C07D 249/08* (2013.01); *C07D 277/54* (2013.01); *C07D 403/10* (2013.01); *C07C 335/16* (2013.01)

(58) Field of Classification Search
CPC ....... A01N 47/42; A01N 47/36; A01N 47/34; C07D 417/12; C07D 249/08
See application file for complete search history.

(56) References Cited

U.S. PATENT DOCUMENTS

| 9,029,560 B2 * | 5/2015 | Fischer et al. ................. 548/146 |
|---|---|---|
| 2012/0053216 A1 | 3/2012 | Creemer et al. |
| 2012/0122805 A1 | 5/2012 | Crouse et al. |
| 2013/0019348 A1 * | 1/2013 | Crouse et al. ................. 800/298 |

FOREIGN PATENT DOCUMENTS

WO   PCTUS2014025674    6/2014

* cited by examiner

*Primary Examiner* — Matthew Coughlin
(74) *Attorney, Agent, or Firm* — Yung H. Lee

(57) ABSTRACT

This disclosure relates to the field of molecules having pesticidal utility against pests in phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the following formula ("Formula One").

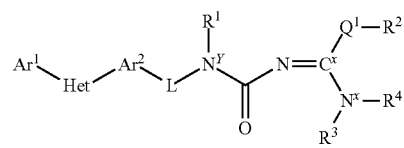

3 Claims, No Drawings

MOLECULES HAVING CERTAIN PESTICIDAL UTILITIES, AND INTERMEDIATES, COMPOSITIONS, AND PROCESSES RELATED THERETO

CROSS-REFERENCE TO RELATED APPLICATIONS

This Application is a continuation of, and claims the benefit of, U.S. patent application Ser. No. 14/208,430, which was filed on Mar. 13, 2014, and which claims the benefit of, and priority from, U.S. provisional application Ser. No. 61/784,020, which was filed on Mar. 14, 2013. The entire content of the U.S. patent application Ser. No. 14/208,430 is hereby incorporated by reference into this Application.

FIELD OF THE DISCLOSURE

This disclosure relates to the field of molecules having pesticidal utility against pests in Phyla Nematoda, Arthropoda, and Mollusca, processes to produce such molecules and intermediates used in such processes, compositions containing such molecules, and processes of using such molecules against such pests. These molecules may be used, for example, as nematicides, acaricides, insecticides, miticides, and molluscicides.

BACKGROUND OF THE DISCLOSURE

"Many of the most dangerous human diseases are transmitted by insect vectors" (Rivero, A. et al., Insect Control of Vector-Borne Diseases: When is Insect Resistance a Problem? Public Library of Science Pathogens, 6(8) (2010)). Historically, vector-borne diseases, such as, malaria, dengue, yellow fever, plague, and louse-borne typhus, among others, were responsible for more human disease and death from the 1600's through the early 1900's than all other causes combined (Gubler D., Resurgent Vector-Borne Diseases as a Global Health Problem, Emerging Infectious Diseases, Vol. 4, No. 3, July-September (1998)). Currently, vector-borne diseases are responsible for about 17% of the global parasitic and infectious diseases. It has been estimated that about 250 million people around the world have malaria and about 800,000 deaths occur each year—85% of those deaths are children under the age of five. A further 250,000 to 500,000 cases of dengue hemorrhagic fever occur each year (Matthews, G., Integrated Vector Management: controlling vectors of malaria and other insect vector borne diseases (2011)). Vector control plays a critical role in the prevention and control of infectious diseases. However, insecticide resistance, including resistance to multiple insecticides, has arisen in all insect species that are major vectors of human diseases (Rivero, A. et al.).

Each year insects, plant pathogens, and weeds destroy more than 40% of all potential food production. This loss occurs despite the application of pesticides and the use of a wide array of non-chemical controls, such as crop rotations and biological controls. If just some of this food could be saved, it could be used to feed the more than three billion people in the world who are malnourished (Pimental, D., Pest Control in World Agriculture, Agricultural Sciences—Vol. II (2009)).

Plant parasitic nematodes are among the most widespread pests, and are frequently one of the most insidious and costly. It has been estimated that losses attributable to nematodes are from about 9% in developed countries to about 15% in undeveloped countries. However, in the United States of America, a survey of 35 States on various crops indicated nematode-derived losses of up to 25% (Nicol, J. et al., Current Nematode Threats to World Agriculture, Genomic and Molecular Genetics of Plant—Nematode Interactions (Eds. Jones, J. et al.), Chapter 2, (2011)).

It is noted that gastropods (slugs and snails) are pests of less economic importance than insects or nematodes, but in certain areas, gastropods may reduce yields substantially, severely affecting the quality of harvested products, as well as transmitting human, animal, and plant diseases. While only a few dozen species of gastropods are serious regional pests, a handful of species are important pests on a world-wide scale. In particular, gastropods affect a wide variety of agricultural and horticultural crops, such as arable, pastoral, and fiber crops; vegetables; bush and tree fruits; herbs; and ornamentals (Speiser, B., Molluscicides, Encyclopedia of Pest Management (2002)).

Termites cause damage to all kinds of private and public structures, as well as to agricultural and forestry resources. In 2003, it was estimated that termites cause over US $20 billion in damage world-wide each year (Su, N.Y., Overview of the global distribution and control of the Formosan subterranean termite, *Sociobiology* 2003, 41, 177-192).

Therefore, for many reasons, including the above reasons, a need exists for new pesticides.

DEFINITIONS

The examples given in the definitions are generally non-exhaustive and must not be construed as limiting the molecules disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, tetrahydrofuranyl, and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

DETAILED DESCRIPTION OF THE DISCLOSURE

This document discloses molecules having the following formula ("Formula One")

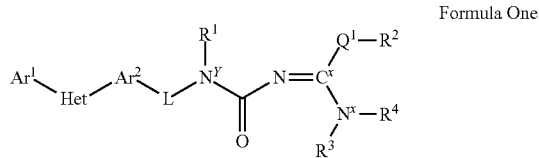

Formula One wherein:
(A) $Ar^1$ is selected from
 (1) phenyl, pyridazinyl, pyridyl, pyrimidinyl, or
 (2) substituted phenyl, substituted pyridazinyl, substituted pyridyl, or substituted pyrimidinyl,
  wherein said substituted phenyl, substituted pyridazinyl, substituted pyridyl, and substituted pyrimidinyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy
wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(B) Het is a 5- or 6-membered, saturated or unsaturated, heterocyclic ring, containing one or more heteroatoms independently selected from nitrogen, sulfur, or oxygen, and where $Ar^1$ and $Ar^2$ are not ortho to each other (but may be meta or para, such as, for a five-membered ring they are 1,3 and for a 6-membered ring they are either 1,3 or 1,4) and where said heterocyclic ring may also be substituted with one or more substituents independently selected from H, F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy
wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), phenyl, and phenoxy;

(C) $Ar^2$ is selected from
 (1) phenyl, pyridazinyl, pyridyl, pyrimidinyl, or
 (2) substituted phenyl, substituted pyridazinyl, substituted pyridyl, or substituted pyrimidinyl, wherein said substituted phenyl, substituted pyridazinyl, substituted pyridyl, and substituted pyrimidinyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(D) $R^1$ is selected from H, $C_1$-$C_6$ alkyl, $C_3$-$C_6$ cycloalkyl, $C_2$-$C_6$ alkenyl, $C_2$-$C_6$ alkynyl, $S(=O)_n(C_1$-$C_6$ alkyl), $C(=O)NR^xR^y$, $(C_1$-$C_6$ alkyl)$NR^xR^y$, $C(=O)O(C_1$-$C_6$ alkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$OC(=O)(C_1$-$C_6$ alkyl), $(C_1$-$C_6$ alkyl)$S(C_1$-$C_6$ alkyl), and $(C_1$-$C_6$ alkyl)$OC(=O)O(C_1$-$C_6$ alkyl), wherein each alkyl, cycloalkyl, cycloalkoxy, alkoxy, alkenyl, and alkynyl are optionally substituted with one or more substituents independently selected from F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(E) $R^2$ is selected from (J), H, $C_1$-$C_6$ alkyl, $C_3$-$C_6$ cycloalkyl, $C_2$-$C_6$ alkenyl, $C_2$-$C_6$ alkynyl, $C(=O)(C_1$-$C_6$ alkyl), $(C_1$-$C_6$ alkyl)$O(C_1$-$C_6$ alkyl), $(C_1$-$C_6$ alkyl)$S(C_1$-$C_6$ alkyl), $C_1$-$C_6$ alkylphenyl, $C_1$-$C_6$ alkyl-O-phenyl, $C(=O)$(Het-1), (Het-1), $(C_1$-$C_6$ alkyl)-(Het-1), $C_1$-$C_6$ alkyl-O—C$(=O)C_1$-$C_6$ alkyl, $C_1$-$C_6$ alkyl-O—C$(=O)(C_1$-$C_6$ alkyl), $C_1$-$C_6$ alkyl-O—C$(=O)OC_1$-$C_6$ alkyl, $C_1$-$C_6$ alkyl-O—C$(=O)NR^xR^y$, $C_1$-$C_6$ alkyl $C(=O)N(R^x)C_1$-$C_6$ alkyl-(Het-1), $C_1$-$C_6$ alkylC$(=O)$(Het-1), $C_1$-$C_6$ alkylC$(=O)N(R^x)C_1$-$C_6$ alkyl(N($R^y$)($R^y$))($C(=O)OH$), $C_1$-$C_6$ alkylC$(=O)N(R^x)C_1$-$C_6$ alkylN($R^x$)($R^y$), $C_1$-$C_6$ alkylC$(=O)N(R^x)C_1$-$C_6$ alkylN($R^x$)C$(=O)$—O—$C_1$-$C_6$ alkyl, $C_1$-$C_6$ alkylC$(=O)N(R^x)C_1$-$C_6$ alkyl(N($R^x$)C$(=O)$—O—$C_1$-$C_6$ alkyl)($C(=O)OH$), $C_1$-$C_6$ alkylC$(=O)$(Het-1)$C(=O)$—O—$C_1$-$C_6$ alkyl, $C_1$-$C_6$ alkyl-O—C$(=O)$—O—$C_1$-$C_6$ alkyl, $C_1$-$C_6$ alkyl-O—C$(=O)C_1$-$C_6$ alkyl, $C_1$-$C_6$ alkyl-O—C$(=O)C_3$-$C_6$ cycloalkyl, $C_1$-$C_6$ alkyl-O—C$(=O)$(Het-1), $C_1$-$C_6$ alkyl-O—C$(=O)C_1$-$C_6$ alkyl-N($R^x$)C$(=O)$—O—$C_1$-$C_6$ alkyl, $C_1$-$C_6$ alkyl-NR$^x$R$^y$, $(C_1$-$C_6$ alkyl)S-(Het-1) or $C_1$-$C_6$ alkyl-O-(Het-1), wherein each alkyl, cycloalkyl, alkenyl, alkynyl, phenyl, and (Het-1) are optionally substituted with one or more substituents independently selected from F, Cl, Br, I, CN, $NO_2$, $NR^xR^y$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, $Si(C_1$-$C_6$ alkyl)$_3$, $S(=O)_nNR^xR^y$, or (Het-1);

(F) $R^3$ is selected from phenyl, $C_1$-$C_6$ alkylphenyl, $C_1$-$C_6$ alkyl-O-phenyl, $C_2$-$C_6$ alkenyl-O-phenyl, (Het-1), $C_1$-$C_6$ alkyl(Het-1), or $C_1$-$C_6$ alkyl-O-(Het-1), wherein each alkyl, cycloalkyl, alkenyl, alkynyl, phenyl, and (Het-1) are optionally substituted with one or more substituents independently selected from F, Cl, Br, I, CN, $NO_2$, $NR^xR^y$, $C_1$-$C_6$ alkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $O(C_1$-$C_6$ alkyl), $S(C_1$-$C_6$ alkyl), $C(=O)(C_1$-$C_6$ alkyl)$C(=O)O(C_1$-$C_6$ alkyl), phenyl, phenoxy, and (Het-1);

(G) $R^4$ is selected from (J), H, or $C_1$-$C_6$ alkyl;

(H) $Q^1$ is selected from O or S, (I) $R^x$ and $R^y$ are independently selected from H, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), and phenyl, wherein each alkyl, cycloalkyl, cycloalkoxy, alkoxy, alkenyl, alkynyl, phenyl, phenoxy, and (Het-1), are optionally substituted with one or more substituents independently selected from F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, halophenyl, phenoxy, and (Het-1), or R$^x$ and R$^y$ together can optionally form a 5- to 7-membered saturated or unsaturated cyclic group which may contain one or more heteroatoms selected from nitrogen, sulfur, and oxygen, and where said cyclic group may be substituted with F, Cl, Br, I, CN, oxo, thioxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, substituted phenyl, phenoxy, and (Het-1);

(J) R$^2$ and R$^4$ may be a 1- to 4-membered saturated or unsaturated, hydrocarbyl link, which may contain one or more heteroatoms selected from nitrogen, sulfur, and oxygen, and together with C$^x$(Q$^1$)(N$^x$) forms a cyclic structure, wherein said hydrocarbyl link may optionally be substituted with one or more substituents independently selected from R$^5$, R$^6$, and R$^7$, wherein each R$^5$, R$^6$, and R$^7$ is selected from H, F, Cl, Br, I, CN, C$_1$-C$_6$ alkyl, oxo, thioxo, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, substituted phenyl, phenoxy, or (Het-1);

(K) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, NO$_2$, oxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy, wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), phenyl, and phenoxy;

(L) L is linker selected from
(1) a saturated or unsaturated, substituted or unsubstituted, linear (C$_1$-C$_4$)hydrocarbyl linker, or
(2) a saturated or unsaturated, substituted or unsubstituted, cyclic (C$_3$-C$_8$)hydrocarbyl group linker,
wherein each of said linkers connects Ar$^2$ to N$^Y$ and
wherein said substituted linear (C$_1$-C$_4$)hydrocarbyl linker and substituted cyclic (C$_3$-C$_8$)hydrocarbyl linker has one or more substituents independently selected from R$^8$, R$^9$, R$^{10}$, R$^{11}$, and R$^{12}$, wherein each R$^8$, R$^9$, R$^{10}$, R$^{11}$, and R$^{12}$, is selected from F, Cl, Br, I, CN, oxo, C$_1$-C$_6$ alkyl, C$_2$-C$_6$ alkenyl, C$_2$-C$_6$ haloalkenyl, C$_2$-C$_6$ alkynyl, C$_1$-C$_6$ haloalkyl, C$_3$-C$_6$ cycloalkyl, C$_3$-C$_6$ cycloalkenyl, C$_3$-C$_6$ halocycloalkyl, or phenyl; and (M) n is each individually 0, 1, or 2.

In another embodiment Ar$^1$ is a substituted phenyl. This embodiment may be used in combination with the other embodiments of Het, Ar$^2$, R$^1$, R$^2$, R$^3$, R$^4$, Q$^1$, R$^2$ and R$^4$ hydrocarbyl links, and/or L.

In another embodiment Ar$^1$ is a substituted phenyl that has one or more substituents selected from C$_1$-C$_6$ haloalkyl and C$_1$-C$_6$ haloalkoxy. This embodiment may be used in combination with the other embodiments of Het, Ar$^2$, R$^1$, R$^2$, R$^3$, R$^4$, Q$^1$, R$^2$ and R$^4$ hydrocarbyl links, and/or L.

In another embodiment Ar$^1$ is a substituted phenyl that has one or more substituents selected from CF$_3$, OCF$_3$, and OC$_2$F$_5$. This embodiment may be used in combination with the other embodiments of Het, Ar$^2$, R$^1$, R$^2$, R$^3$, R$^4$, Q$^1$, R$^2$ and R$^4$ hydrocarbyl links, and/or L.

In another embodiment Het is selected from benzofuranyl, benzoisothiazolyl, benzoisoxazolyl, benzoxazolyl, benzothienyl, benzothiazolyl, cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, triazolyl, piperazinyl, piperidinyl, morpholinyl, pyrrolidinyl, tetrahydrofuranyl, tetrahydropyranyl, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

In another embodiment Het is triazolyl. This embodiment may be used in combination with the other embodiments of Ar$^1$, Ar$^2$, R$^1$, R$^2$, R$^3$, R$^4$, Q$^1$, R$^2$ and R$^4$ hydrocarbyl links, and/or L.

In another embodiment Het is 1,2,4 triazolyl. This embodiment may be used in combination with the other embodiments of Ar$^1$, Ar$^2$, R$^1$, R$^2$, R$^3$, R$^4$, Q$^1$, R$^2$ and R$^4$ hydrocarbyl links, and/or L.

In another embodiment Het is oxadiazolyl. This embodiment may be used in combination with the other embodiments of Ar$^1$, Ar$^2$, R$^1$, R$^2$, R$^3$, R$^4$, Q$^1$, R$^2$ and R$^4$ hydrocarbyl links, and/or L.

In another embodiment Het is 1,3,4 oxadiazolyl. This embodiment may be used in combination with the other embodiments of Ar$^1$, Ar$^2$, R$^1$, R$^2$, R$^3$, R$^4$, Q$^1$, R$^2$ and R$^4$ hydrocarbyl links, and/or L.

In another embodiment Het is pyrazolyl. This embodiment may be used in combination with the other embodiments of Ar$^1$, Ar$^2$, R$^1$, R$^2$, R$^3$, R$^4$, Q$^1$, R$^2$ and R$^4$ hydrocarbyl links, and/or L.

In another embodiment $Ar^2$ is phenyl. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $Ar^2$ is a substituted phenyl. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $Ar^2$ is a substituted phenyl that has one or more substituents selected from $C_1$-$C_6$ alkyl. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $Ar^2$ is a substituted phenyl that has one or more substituents wherein said substituent is $CH_3$. This embodiment may be used in combination with the other embodiments of $Ar^1$, Het, $R^1$, $R^2$, $R^3$, $R^4$, $Q^1$, $R^2$ and $R^4$ hydrocarbyl links, and/or L.

In another embodiment $R^1$ is H. This embodiment may be used in combination with the other embodiments of $Ar^1$, Het, $Ar^2$, $R^2$, $R^3$, $R^4$, $Q^1$, $R^2$ and $R^4$ hydrocarbyl links, and/or L.

In another embodiment $R^2$ is (J), H, $C_1$-$C_6$ alkyl, $C_1$-$C_6$ alkyl-O—C(=O)$C_1$-$C_6$ alkyl, $C_1$-$C_6$ alkyl-O—C(=O)N($R^xR^y$), or ($C_1$-$C_6$ alkyl)S-(Het-1). This embodiment may be used in combination with the other embodiments of $Ar^1$, Het, $Ar^2$, $R^1$, $R^3$, $R^4$, $Q^1$, $R^2$ and $R^4$ hydrocarbyl links, and/or L.

In another embodiment $R^2$ is (J), H, $CH_3$, $C_1$-$C_6$ alkyl, $CH_2OC(=O)CH(CH_3)_2$, $CH_2OC(=O)N(H)(C(=O)OCH_2Ph)$, or $CH_2S(3,4,5$-trimethoxy-2-tetrahydropyran). This embodiment may be used in combination with the other embodiments of $Ar^1$, Het, $Ar^2$, $R^1$, $R^3$, $R^4$, $Q^1$, $R^2$ and $R^4$ hydrocarbyl links, and/or L.

In another embodiment $R^3$ is substituted phenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is substituted phenyl wherein said substituted phenyl has one or more substituents selected from F, Cl, $C_1$-$C_6$ alkyl, $C_3$-$C_6$ cycloalkyl, $C_1$-$C_6$ alkoxy, and phenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is substituted phenyl wherein said substituted phenyl has one or more substituents selected from F, $CH_3$, 2-$CH(CH_3)_2$, $CH(CH_3)(C_2H_5)$, $OCH_3$, and phenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is substituted phenyl wherein said substituted phenyl has more than one substituent and at least one pair of said substituents are not ortho to each other. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is $C_1$-$C_6$ alkylphenyl. This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^3$ is (Het-1). This embodiment may be used in combination with the other embodiments of $Ar^1$, Het, $Ar^2$, $R^1$, $R^2$, $R^4$, $Q^1$, $R^2$ and $R^4$ hydrocarbyl links, and/or L.

In another embodiment $R^4$ is H. This embodiment may be used in combination with the other embodiments of $Ar^1$, Het, $Ar^2$, $R^1$, $R^2$, $R^3$, $Q^1$, $R^2$ and $R^4$ hydrocarbyl links, and/or L.

In another embodiment $Q^1$ is O. This embodiment may be used in combination with the other embodiments of $Ar^1$, Het, $Ar^2$, $R^1$, $R^2$, $R^3$, $R^4$, $R^2$ and $R^4$ hydrocarbyl links, and/or L.

In another embodiment $R^2$ and $R^4$ is a hydrocarbyl link wherein said hydrocarbyl link is substituted with oxo or $C_1$-$C_6$ alkyl. This embodiment may be used in combination with the other embodiments of $Ar^1$, Het, $Ar^2$, $R^1$, $R^2$, $R^3$, $R^4$, $Q^1$, and/or L.

In another embodiment $R^2$ and $R^4$ is a hydrocarbyl link wherein said hydrocarbyl link is $CH_2C(=O)$, $C(C(OH)(CH_3)_2)C(=O)$, $C(cyclopropyl)C(=O)$, $C(CH_3)_2C(=O)$, $CFHC(=O)$, $CBrHC(=O)$, $CH(CH_3)C(=O)$, $CH_2CH_2$, $CH_2C(OH)(CH_3)$, $CH_2CH_2CH_2$, $CH_2CH_2C(=O)$, $CH_2CH(CH_3)CH_2$, $N(CH_3)C(=O)$, $N(CH_2CH_3)C(=O)$, $CH=C(CH_3)$, or $CH_2CH(CH_3)$. This embodiment may be used in combination with the other embodiments of $Ar^1$, Het, $Ar^2$, $R^1$, $R^2$, $R^3$, $R^4$, $Q^1$, and/or L.

In another embodiment L is $CH_2$, $CH_2CH_2$, $CH_2CH(CH_3)$, $CH_2C(CH_3)_2$, $CH_2CH(CH_2CH_3)$, $CH=CH$, $CH(CH_3)CH_2$, $C(CH_3)_2CH_2$, $CHBrCH_2$, $CH_2C(cyclopropyl)$, $CH(CH_2CH_3)CH_2$, $C(CH_3)=CH$, $CH_2CH_2CH_2$, $CH(CH_3)CH(CH_3)$, $CH_2CH_2CH_2CH_2$, $C≡CCH_2CH_2$, cyclopropyl, or cyclohexyl. This embodiment may be used in combination with the other embodiments of $Ar^1$, Het, $Ar^2$, $R^1$, $R^2$, $R^3$, $R^4$, $Q^1$, and/or $R^2$ and $R^4$ hydrocarbyl links.

Many of the molecules of Formula One may be depicted in two or more tautomeric forms such as when $R^1$, $R^2$, or $R^4$, is H (see for example, "Scheme TAU" below). For the sake of simplifying the schemes, all molecules have been depicted as existing as a single tautomer. Any and all alternative tautomers are included within the scope of this Formula One, and no inference should be made as to whether the molecule exists as the tautomeric form in which it is drawn.

"Scheme TAU"

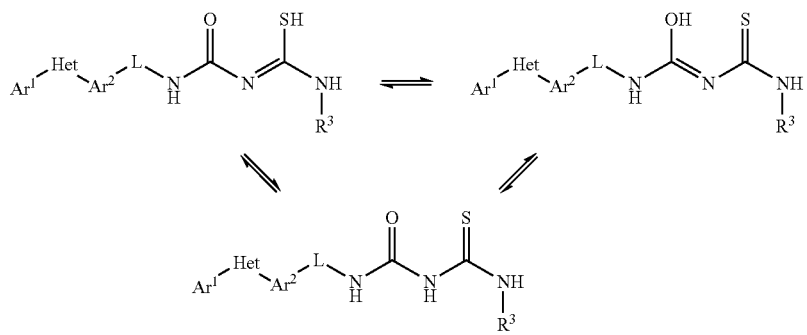

The molecules of Formula One will generally have a molecular mass of about 400 Daltons to about 1200 Daltons. However, it is generally preferred if the molecular mass is from about 300 Daltons to about 1000 Daltons, and it is even more generally preferred if the molecular mass is from about 400 Daltons to about 750 Daltons.

Preparation of Thiobiurets

Thiobiurets disclosed herein are prepared from the corresponding isocyanate, $Ar^1$-Het-$Ar^2$-L-NCO (1-2). Usually, these isocyanates are not isolated, but are instead generated in situ from a suitable precursor and used directly in the preparation of a thiobiuret. One such suitable precursor is an amine (1-1) which can be converted into an isocyanate by using one of several common reagents such as phosgene, diphosgene, triphosgene, or carbonyldiimidazole (Scheme 1, step a), in a mixed solvent system such as dichloromethane and water or diethyl ether and water, in the presence of a base such as sodium bicarbonate or triethylamine, at temperatures from about −10° C. to about 50° C.

Alternatively, the isocyanates may be generated via a Curtius rearrangement of an acyl azide, $Ar^1$-Het-$Ar^2$-L-C(O)$N_3$ (1-4), which is, in turn, prepared from the corresponding carboxylic acid precursor, $Ar^1$-Het-$Ar^2$-L-$CO_2$H (1-3). Formation of an acyl azide (Scheme 1, step b) occurs either by treatment of the acid with ethyl chloroformate and sodium azide in the presence of an amine base such as triethylamine, or with diphenylphosphoryl azide in the presence of an amine base such as triethylamine. The acyl azide is then made to undergo a Curtius rearrangement (which may need to be thermally induced), leading to the corresponding isocyanate (1-3). Depending on the nature of the particular acyl azide, this rearrangement may occur spontaneously at ambient temperature, or it may require heating from about 40° C. to about 100° C. in a suitable solvent, such as toluene, or acetonitrile, or an ethereal solvent such as dioxane or tetrahydrofuran. Azides of arylacetic acids are known, though frequently, due to their reactivity, they are not isolated as pure solids. Accordingly, the acyl azide intermediate is not always fully characterized, but may simply be heated directly without characterization, to generate the isocyanate.

An isocyanate, $Ar^1$-Het-$Ar^2$-L-NCO (1-2), can be treated directly with an N-aryl thiourea (2-1) in the presence of about 0.1 to about 2 equivalents of an inorganic base such as cesium carbonate or sodium hydride, resulting in the formation of a thiobiuret (2-2, Scheme 2). The reaction can be performed at temperatures from about 0° C. to about 100° C., preferably from about 20° C. to about 80° C., in an aprotic solvent or solvent mixture chosen from acetonitrile, acetone, toluene, tetrahydrofuran, 1,2-dichloroethane, dichloromethane, or mixtures thereof, but use of acetonitrile is preferred.

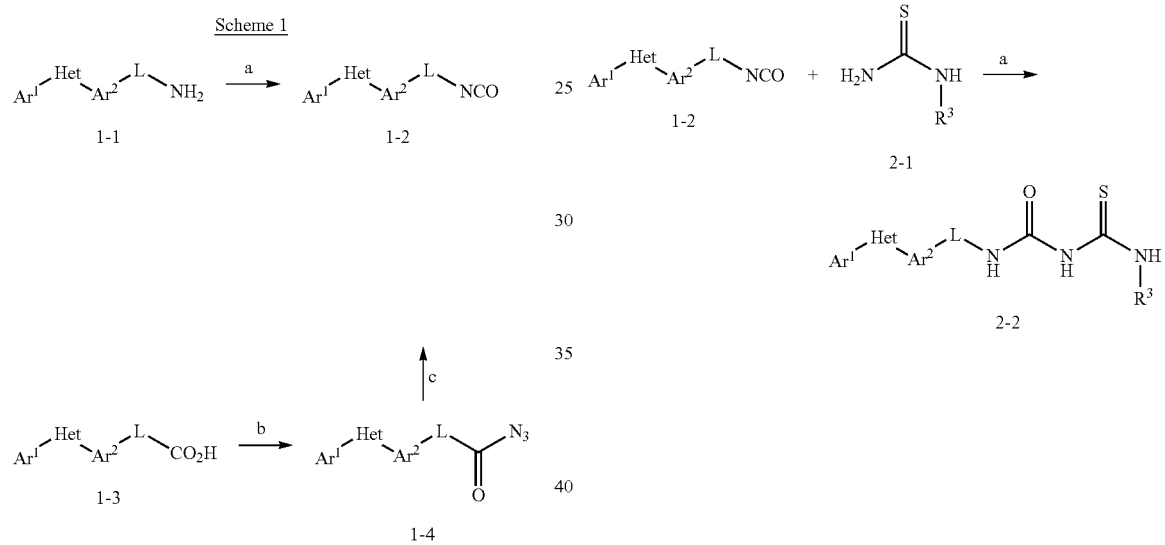

Scheme 1

Scheme 2

Thiobiurets (2-2) generated in situ can be converted directly without purification into a variety of cyclized analogs (Scheme 3), or they can be isolated from the reaction medium prior to cyclization. Cyclization can be achieved by treatment with an α-halo ester such as methyl bromoacetate to form 2-imino 1,3-thiazolin-4-ones (3-1, step a) unsubstituted or mono- or di-substituted with $R^5$; vicinal dihalides such as 1-bromo-2-chloroethane or 1,2-dichloroethane, to form 2-imino-1,3-thiazolines (3-2, step b) unsubstituted or mono-substituted with $R^5$ or $R^6$; α-halo ketones such as chloroacetone to form 2-imino-1,3-thiazoles (3-3, step c) unsubstituted with $R^5$ or $R^6$; or 1,3-dihalopropanes such as 1-bromo-3-chloropropane to form 2-imino-1,3-thiazinanes (3-4, step d) unsubstituted or mono-substituted with $R^5$ or $R^6$ or unsubstituted or mono- or di-substituted with $R^7$. With step a, use of sodium acetate in a protic solvent such as ethanol or methanol, at temperatures ranging from about 20° C. to about 70° C. is preferred. With step b, use of an inorganic base such as potassium carbonate in a solvent such as acetonitrile or (preferably) 2-butanone, at a temperature between about 0° C. and about 80° C., is preferred.

Scheme 3

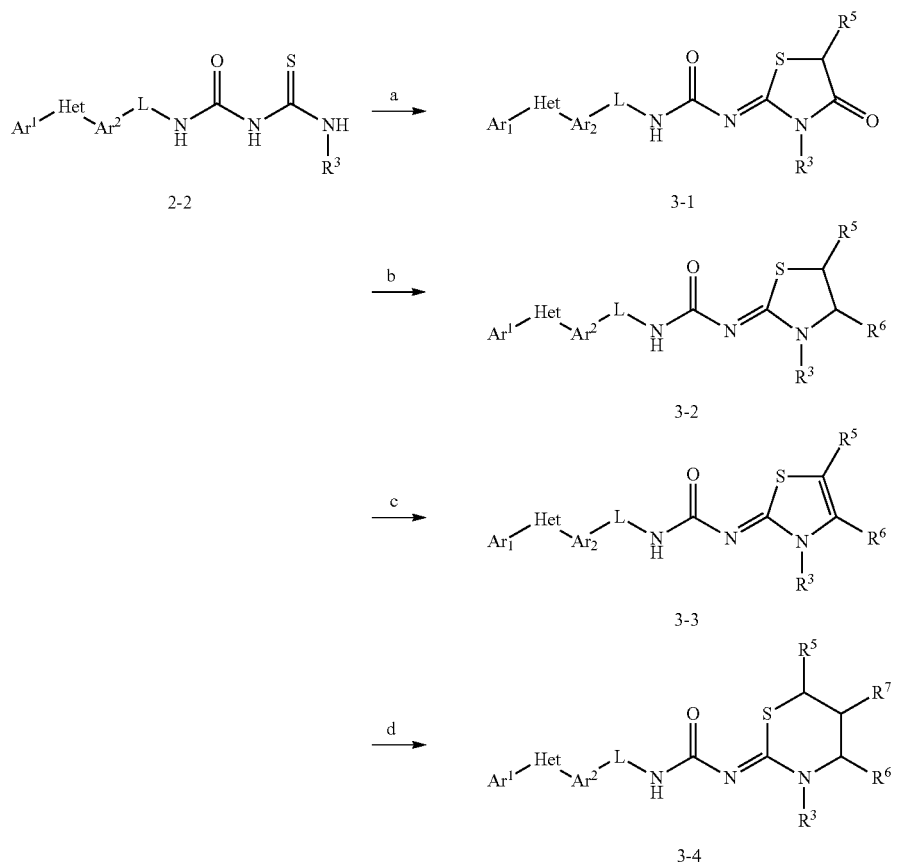

An alternative method for preparing analogs having the general structure 3-1' (Scheme 3) is described in Scheme 3a, Intermediate 2-iminolthiazolidin-4-one (3-1a, step a) is reacted directly with an isocyanate (1-2), in the presence of about 0.1 to about 2 equivalents of an inorganic base such as cesium carbonate or sodium hydride to form cyclized thiobiuret (3-1'). The reaction can be performed at temperatures from about 0° C. to about 100° C., preferably from about 20° C. to about 80° C., in an aprotic solvent or solvent mixture chosen from acetonitrile, acetone, toluene, tetrahydrofuran, 1,2-dichloroethane, dichloromethane, or mixtures thereof, but use of acetonitrile is preferred.

Alternatively, the 2-iminothiazolidin-2-one (3-1a) may be reacted with 4-nitrophenyl chloroformate (step b), forming a 4-nitrophenyl carbamate intermediate (3-2a). This reaction is conducted with equimolar quantities of the imine and the chloroformate, in a polar aprotic solvent such as tetrahydrofuran or dioxane, and in the presence of from about 0.1 to about 2 equivalents of an inorganic base such as cesium carbonate or potassium carbonate, preferably at room temperature. The intermediate (3-2a) may be isolated by filtration from inorganic salts and evaporation of solvent, or it can be used directly in step c. In step c, treatment of 3-2a with a primary alkyl amine $Ar_1$-Het-$Ar_2$-L-$NHR^1$, wherein $R^1$ is H or alkyl, may generate cyclized thiobiuret (3-1'). Step c may also be conducted in the presence of an inorganic base such as cesium carbonate or potassium carbonate, from about 0.1 to about 2 equivalents, preferably about 1 to about 1.2 equivalents; it is also most conveniently run at room temperature, although it may be run at temperatures from about 0° C. to about 100° C.

Scheme 3a

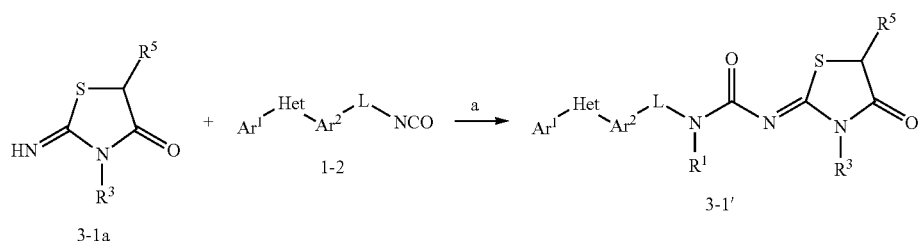

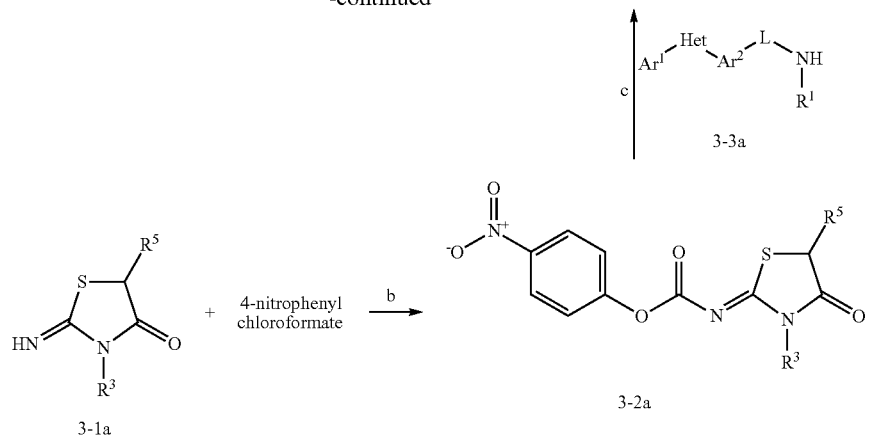

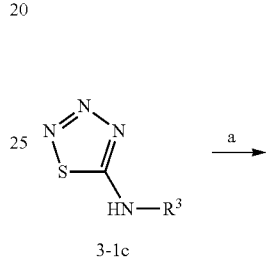

Thiobiurets (2-2) can also be converted into novel S-alkylated analogs as described in Scheme 3b. For example, reaction of a thiobiuret 2-2 with an alkyl iodide (step a), in a protic solvent such as ethanol, and in the presence of a base such as sodium acetate, at temperatures from about 0° C. to about 60° C., results in formation of an S—$R^2$ substituted product (3-1b). A variation of the reaction conditions described in Scheme 3, step c, employs careful control of reaction conditions to ensure that the temperature does not exceed 20° C. Under these conditions, 4-hydroxy-2-iminothiazolidines (3-2b, step b) may be isolated.

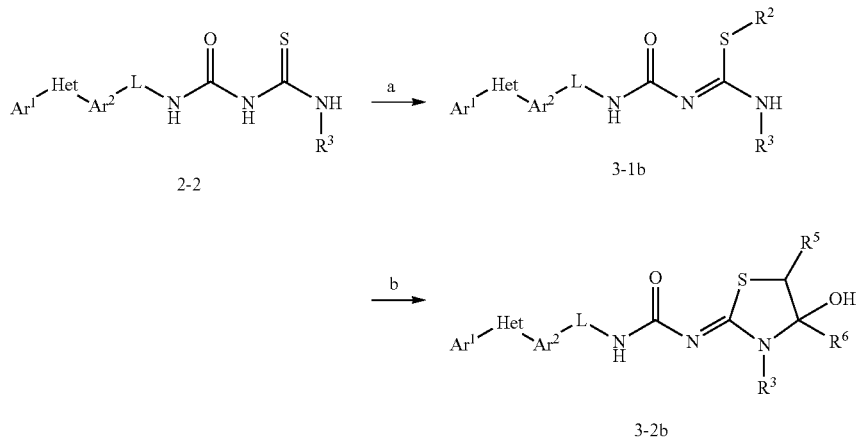

Analogs of Formula 1 wherein $R^2$ and $R^4$ are cyclized to form a 2-($R^5$)-4-($R^3$)-5-imino-1,2,4-thiadiazolidin-3-one (3-4c) may be constructed as described in Scheme 3c. Following the work described by Kaugers, et al (J. Org. Chem 1992, 57, 1671), an N-arylamino 1,2,3,4-thiatriazole (3-1c), prepared in one step from the corresponding $N^3$-aryl thiosemicarbazone by oxidation with sodium nitrite, is treated with an alkyl isocyanate to form 3-2c. Treatment of 3-2c with a base such as sodium methoxide in methanol at room temperature (step b) results in cleavage of the urea bond and formation of a 2-($R^5$)-4-($R^3$)-5-imino-1,2,4-thiadiazolidin-3-one (3-3c). This imine may then be treated with an isocyanate under conditions equivalent to those described in Scheme 3a, step a, to form 3-4c.

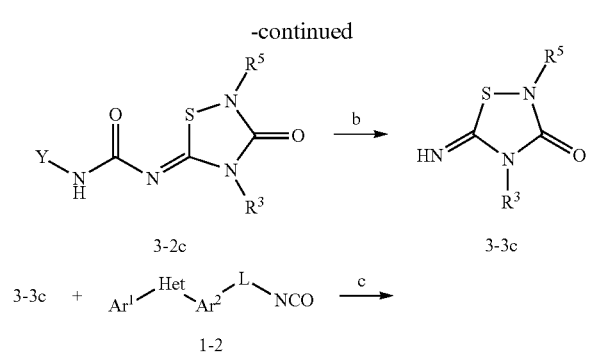

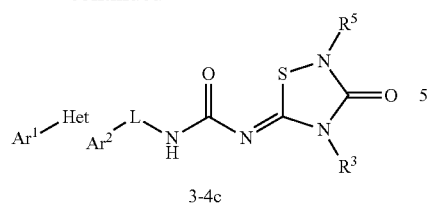

3-4c

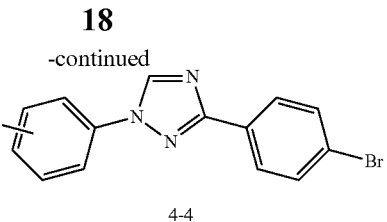

4-4

Preparation of Triaryl-Intermediates

Molecules of Formula One can be prepared by making a triaryl intermediate, $Ar^1$-Het-$Ar^2$, and then linking it to an appropriate intermediate to form a desired compound. A wide variety of triaryl intermediates can be used to prepare molecules of Formula One, provided that such triaryl intermediates contain a suitable functional group on $Ar^2$ to which the rest of the desired functional group can be attached. Suitable functional groups include an amino, isocyanate, carboxyl, or a halogen (preferably bromo or iodo). These triaryl intermediates can be prepared by methods previously described in the chemical literature, including Crouse, et al., WO2009102736 (the entire disclosure of which is hereby incorporated by reference).

The triaryl aldehydes used as precursors in preparation of the molecules of Formula One can be prepared according to procedures described in Crouse, et al., US 2012/0202688 A1. Some of the procedures described above require use of haloaryl intermediates, $Ar^1$-Het-Ph-Br, which are novel intermediates. These may be prepared as described in Scheme 4. 3-(4-bromophenyl)-1,2,4-triazole (4-2, step a) is prepared in two steps from 4-bromobenzamide (4-1) under conditions described previously (Crouse, et al., WO2009102736). This triazole can then be coupled to an aryl halide (R=$C_1$-$C_6$ haloalkoxy) such as 4-trifluoromethoxyphenyl bromobenzene, in the presence of cesium carbonate or potassium phosphate, in a polar aprotic solvent such as dimethylformamide. This reaction is catalyzed by a copper salt such as copper(I) iodide and a chelator such as 8-hydroxyquinoline, both present in about 0.05 to about 0.25 equivalents, at a temperature ranging between about 80° C. and about 140° C., to form the 1-aryl-3-(4-bromophenyl)triazole (4-4, step b).

Preparation of 1-Atom Linked Intermediates

Molecules of Formula One wherein L is a one-carbon linker, can be prepared from acid or amine intermediates described in Scheme 5 and Scheme 6, respectively. Acid precursors $Ar^1$-Het-$Ar^2$-L-$CO_2$H, unsubstituted or mono- or di-substituted with $R^8$; can be prepared as shown in the Scheme 5. Boronic esters (5-2, step a) can be prepared using Miyaura conditions from halophenyl esters (5-1). Coupling of the boronate esters with a bromo-heterocycle (5-3, step b) can be accomplished using a palladium catalyst and phosphine ligand, in the presence of a base, such as sodium bicarbonate, potassium phosphate, or cesium fluoride, in a suitable solvent system, such as dioxane/water, at temperatures from about 50° C. to about 120° C. to form triaryl ester intermediates (5-4, step c). Among palladium catalysts, tetrakis(triphenylphosphine) palladium(0) is preferred, although other well-known palladium catalysts may be used. Saponification of the ester may be achieved by using a strong base such as sodium hydroxide or lithium hydroxide in methanol or ethanol with or without tetrahydrofuran/water to furnish the desired carboxylic acid (5-5, step c).

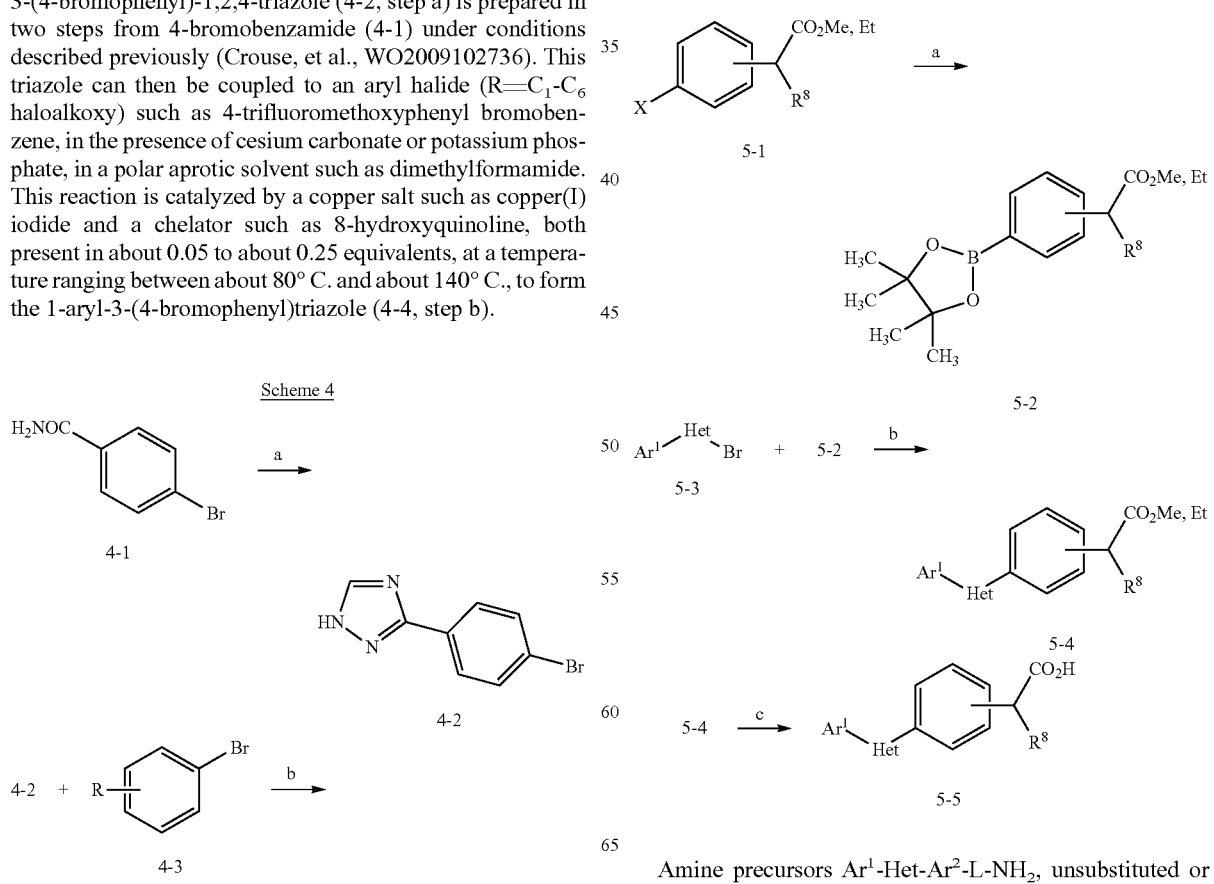

Amine precursors $Ar^1$-Het-$Ar^2$-L-$NH_2$, unsubstituted or mono- or di-substituted with $R^8$, can be prepared as shown in the Scheme 6. Halobenzyl amines (6-1) may be protected using benzyl chloroformate in the presence of a base such as triethylamine in an aprotic solvent such as dichloromethane at about −10° C. to about 10° C. to provide N-carboxybenzyl (Cbz) protected benzyl amines (6-2, step a). Alternatively, other N-protecting groups such as tert-butoxycarbonyl (BOC) or 9-fluorenylmethylcarbonyl (Fmoc) may be employed in step a using similar conditions described above for Cbz. The Cbz protected boronic ester 6-3 can be prepared using Miyaura conditions (step b). Coupling of the boronate esters with a bromo-heterocycle (5-3) can be accomplished using a palladium catalyst and phosphine ligand, in the presence of a base, such as sodium bicarbonate, potassium phosphate, or cesium fluoride, in a suitable solvent system, such as dioxane/water, at temperatures from about 50° C. to about 120° C. to form N-protected aminoalkylphenyl intermediates (6-4, step c). Deprotection of the Cbz group can be accomplished under acidic conditions with a strong acid such as hydrogen bromide, followed by free basing with a base such as sodium bicarbonate or sodium hydroxide, to furnish the free amine precursors $Ar^1$-Het-$Ar^2$-L-$NH_2$ (6-5, step d). Similar methods could be applied to compounds wherein L is greater than 1-carbon.

Scheme 6

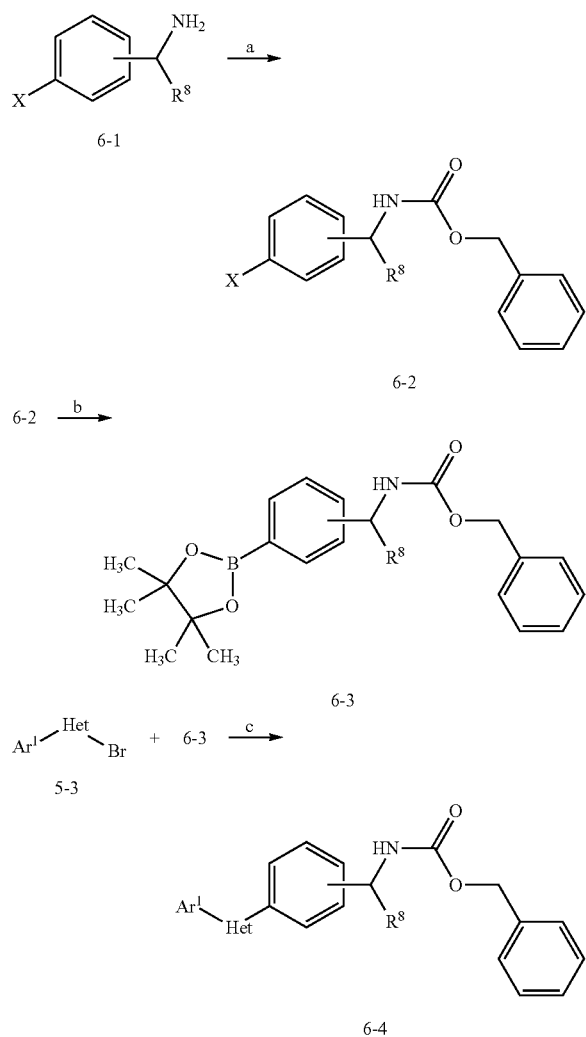

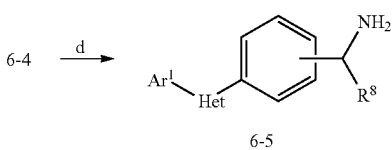

Preparation of Ethyl Linked Intermediates

Preparation of compounds wherein L is a two-atom group is described in Schemes 7 to Schemes 9. Condensation of the aldehyde (7-1, $R^9$=H) (described in US 2012/0202688 A1) with reagents such as ethyl diethylphosphonoacetate or a Wittig reagent such as ethyl 2-(triphenylphosphoranylidene) propanoate) or α-substituted acetates such as ethyl 2-fluoroacetate or ethyl 2-cyanoacetate in the presence of a suitable base such as sodium hydride or n-butyl lithium in aprotic solvents such as tetrahydrofuran or diethyl ether at temperatures from about −78° C. to about 20° C. can be used to prepare acrylic esters (7-2, step a) unsubstituted or monosubstituted with $R^9$ and $R^{10}$. Saponification of the resultant ester may be achieved by using a strong base such as sodium hydroxide in methanol or ethanol with or without tetrahydrofuran/water to furnish the vinyl carboxylic acid (7-3, step b). In some cases the partial condensation of aldehyde (7-1, $R^9$=H) may result in the isolation of the alcohol intermediate (7-4, step c) especially when $R^{10}$ is electron withdrawing. Substitution of this alcohol with nucleophilic reagents such as Deoxo-Fluor® (step d) followed by saponification as described above (step e) can generate highly substituted ethyl carboxylic acids (7-5) additionally substituted with $R^{11}$, wherein $R^{11}$ is defined as $R^8$ above. When the saturated linkage is preferred, the acrylate ester (7-2) can be converted to the corresponding cyclopropane (7-6, step f) unsubstituted or mono- or di-substituted with $R^{12}$; with sulfur ylides such as those formed in situ from trimethyl sulfonium iodide in the presence of an inorganic base such as sodium hydride in a polar aprotic solvent such as dimethyl sulfoxide or tetrahydrofuran. Likewise the acrylate ester (7-2) can be reduced to the parent alkane (7-8, step h) using hydrogen gas and a palladium catalyst. Both the cyclopropane and the alkane can be hydrolyzed under basic conditions described above to generate the free carboxylic acids 7-7 (step g) and 7-9 (step i), respectively.

In a similar manner, condensation of the ketone (7-1, $R^9$=Alkyl) (described in WO 2011017504 A1) with either ethyl diethylphosphonoacetate or a Wittig reagent such as ethyl 2-(triphenylphosphoranylidene)propanoate or α-substituted alkyl esters such as ethyl 2-fluoroacetate or ethyl 2-cyanoacetate under similar conditions described above may generate the α-alkyl acrylate esters 7-2 or alcohols 7-4. Subsequent treatment of 7-2 or 7-4 as described above for $R^9$=H may lead to either the corresponding unsaturated (7-3) or saturated (7-5, 7-7, 7-9) carboxylic acids.

Scheme 7

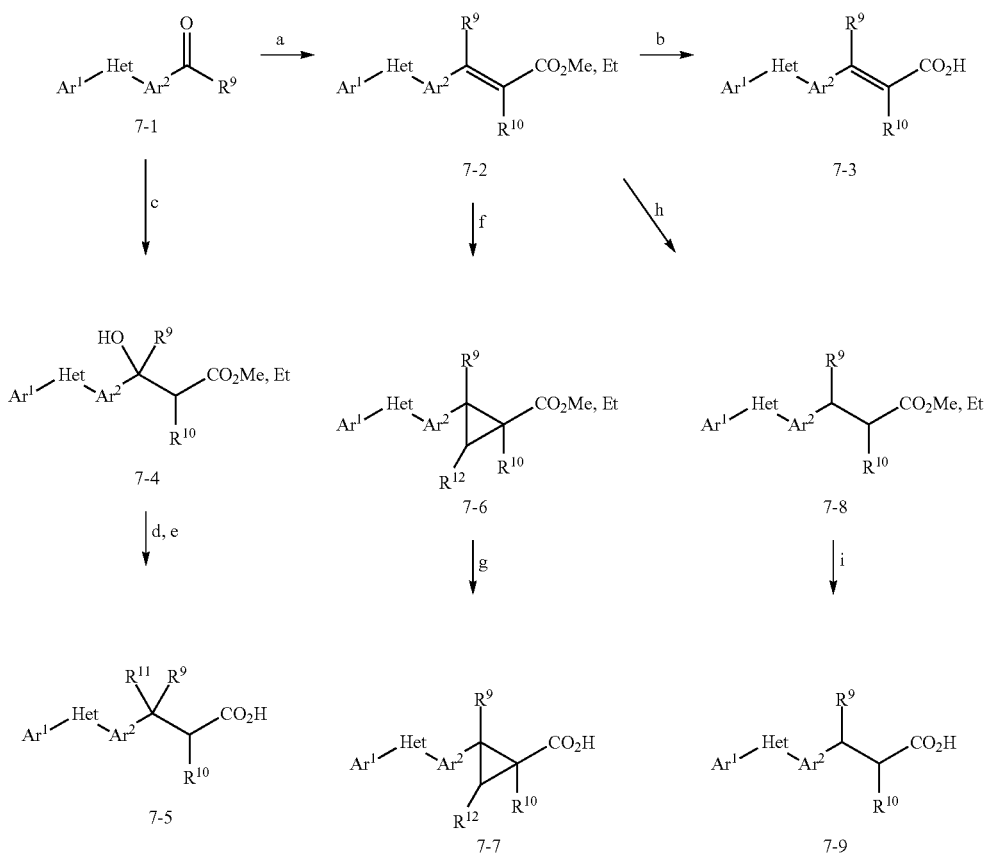

Alternatively, compounds wherein L is a 2-carbon linker may also be prepared as shown in Scheme 8. Using conditions first described by Molander et al. *Org. Lett.,* 2007, 9 (2), pp 203-206, coupling of a bromide $Ar^1$-Het-$Ar^2$—Br (8-1, step a), with potassium (2-((tert-butoxycarbonyl)amino)ethyl)trifluoroborate in the presence of a palladium catalyst such as palladium(II) acetate, and a base such as cesium carbonate, at temperatures from about 80° C. to about 120° C., results in the formation of the corresponding 2-(tert-butoxycarbonyl) amino)ethyl derivative 8-2. Further treatment of this material with from about 1 to about 5 equivalents of an acid such as trifluoroacetic acid or hydrogen chloride, in an aprotic solvent such as dichloromethane or dioxane at temperatures from about 0° C. to about 50° C., results in the cleavage of the tert-butoxycarbonyl group and formation of the trifluoroacetic acid salt of the amine $Ar^1$-Het-$Ar^2$-L-$NH_2$ (8-3, step b).

Scheme 8

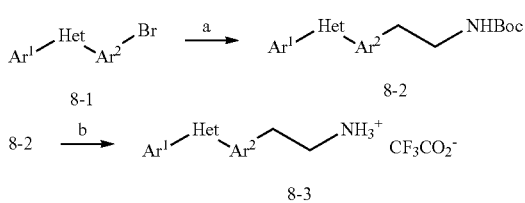

Aminoalkyl precursors $Ar^1$-Het-$Ar^2$-L-$NH_2$, wherein L is 2-carbon atoms, mono- or di-substituted with $R^9$, wherein $R^9$ is defined as above; and unsubstituted or mono-substituted with $R^{10}$, wherein $R^{10}$ is defined as above, can be prepared as shown in Scheme 9. Halophenyl carbinols 9-1, wherein X can be selected from Cl, Br, or I, unsubstituted at $R^9$ and $R^{10}$ are available commercially. Carbinols 9-1 that are mono- or di-substituted at $R^9$ can be prepared from the corresponding halophenyl acetate (9-I, step a) in similar fashion to that described by Shin et al. *Bioorg. Med. Chem. Lett.,* 2008, 18, pp 4424-4427 followed by reduction with a metal hydride such as lithium aluminum hydride in an ethereal solvent such as tetrahydrofuran or diethyl ether at temperatures at or below about 0° C. Both 9-I and 9-II may be further mono-substituted (step b or step c) with $R^{10}$ via reduction to the corresponding aldehyde with a metal hydride such as diisobutylaluminum hydride and further treatment with a Grignard reagent in a similar fashion to that described by Brimble et al. *Org. Lett.,* 2012, 14 (23), pp 5820-5823. Carbinols 9-1 can be treated with phthalimide under Mitsunobu conditions to generate N-phthalimido intermediates 9-2 (step d). The halide can be converted into a boronic ester under Miyaura conditions to form boronate esters (9-3, step e). Coupling of the boronate esters with a bromo-heterocycle can be accomplished using a palladium catalyst, such tetrakis(triphenylphosphine) palladium(0), in the presence of a base, such as sodium bicarbonate, in a suitable solvent system, such as dioxane/water, at temperatures from about 50° C. to about 120° C. to provide N-phthalimido intermediates 9-4 (step f). Deprotection using hydrazine and methanol or other suitable solvent can furnish the amine 9-5 (step g).

Scheme 9

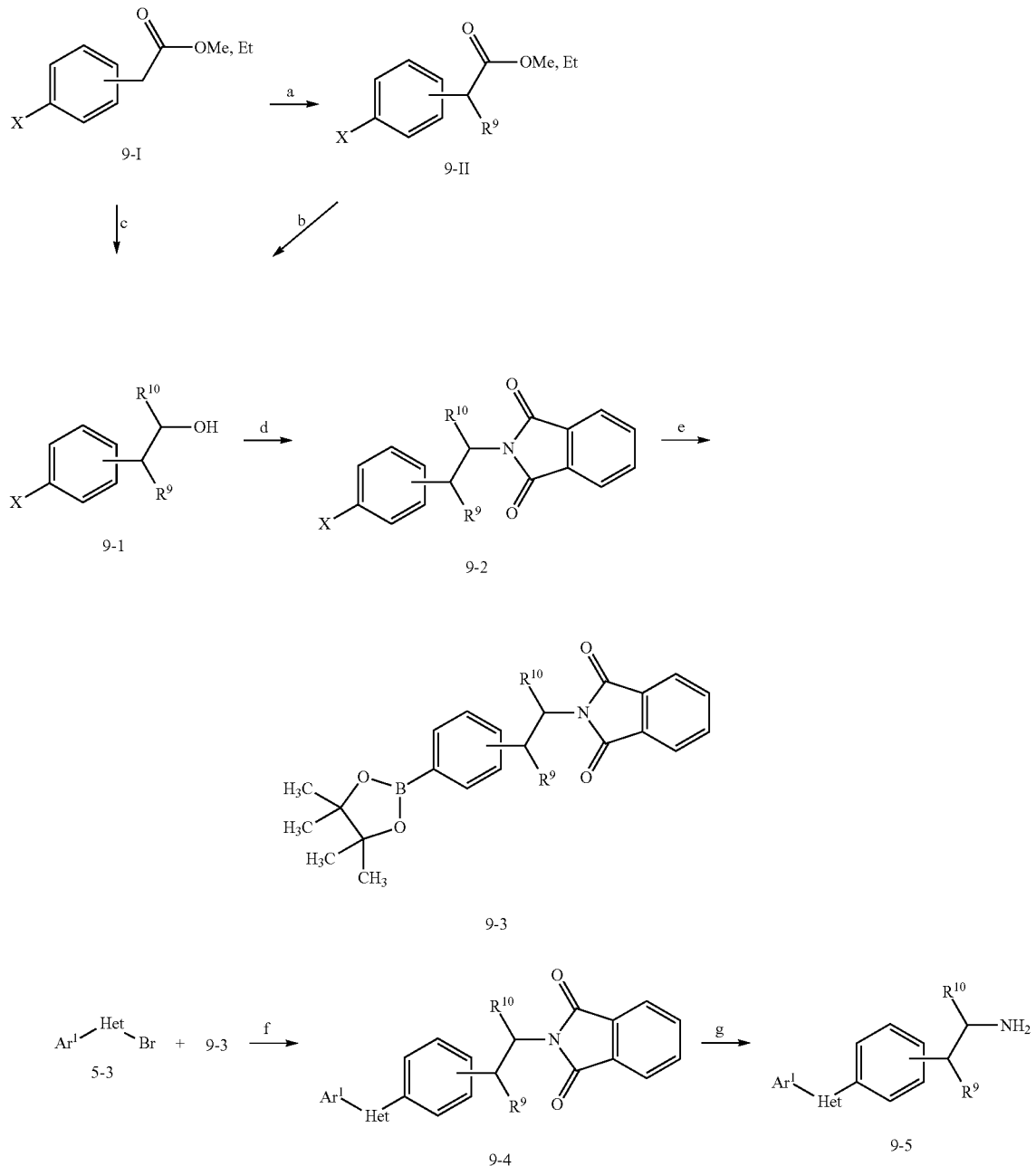

Alternatively, compounds wherein L is a 2-atom linker may also be prepared as shown in Scheme 9a. Olefination of aldehyde (7-1, $R^9$=H, step a) may be achieved with methylenetriphenylphosphorane which can be prepared from methyl triphenylphosphonium iodide in the presence of a base such as sodium hydride or 1,8-diazabicycloundec-7-ene in an aprotic solvent such as tetrahydrofuran or dichloromethane at temperatures of about −78° C. to about 40° C. Further treatment of this material (9-2a) with a hydroborating reagent such as 9-borabicyclo(3.3.1)nonane in an aprotic solvent such as tetrahydrofuran followed by oxidation with an oxidant such as hydrogen peroxide can generate ethyl alcohol 9-3a (step b). Carbinols 9-3a can be treated with phthalimide under Mitsunobu conditions to generate N-phthalimido intermediates 9-5a (step c), wherein $R^{10}$=H. Deprotection using hydrazine and methanol or other suitable solvent can furnish the amine 9-6a (step f). Additionally, 9-3a may be further mono-substituted (step d) with $R^{10}$, wherein $R^{10}$ is defined as above, via oxidation to the corresponding aldehyde under Swern conditions followed by addition of a Grignard reagent such as described above (Scheme 9). Carbinols 9-4a can be further treated with phthalimide under Mitsunobu conditions to generate N-phthalimido intermediates 9-5a (step e). Deprotection using hydrazine and methanol or other suitable solvent can furnish the amine 9-6a (step f).

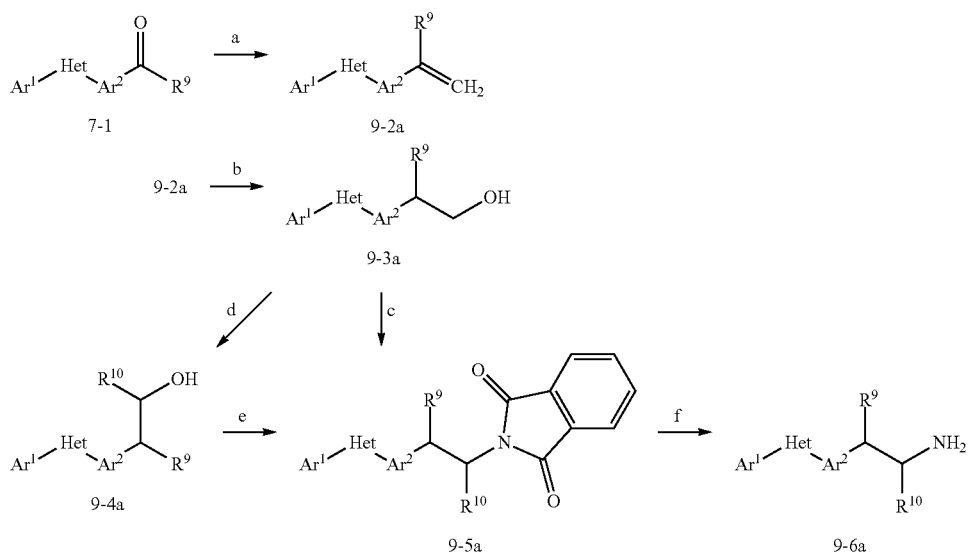

Scheme 9b outlines an alternative route for constructing analogs wherein the linker L is a two-atom linker. Copper-catalyzed arylation of 2,4-pantane-2,4-dione with 8-1 (*JACS*, 2010, 132, 8273.) may provide the substituted acetone intermediate 9-1 b (step a). Reductive amination (step b), using any of a variety of conditions familiar to those skilled in the art, may generate amine 9-2b, which may be converted into the target molecules using conditions described previously in Scheme 2. When a linker contains a chiral center, such as with intermediate 9-2b, these intermediates may be separated into their pure isomeric forms either by means of a chiral column, or by fractional crystallization of the salt prepared from a chiral acid such as (+) and (−) tartaric acid.

Construction of analogs wherein the ethyl linking group is part of a 6-membered ring is may also be accomplished starting from bromide 8-1. Coupling of 8-1 with 2-cyclohex-1-enyl-4,4,5,5-tetramethyl-1,3,2-dioxaborolane (Scheme 9b, step c) under standard Suzuki coupling conditions can lead to alkene 9-3b. Epoxidation with standard reagents, such as meta-chloroperoxybenzoic acid (step d), followed by acid-catalyzed rearrangement using indium trichloride (*J. Org. Chem.* 1998, 63(23), 8212.) may generates ketone 9-5b. Reductive amination and conversion into the target molecules can be accomplished using conditions described above.

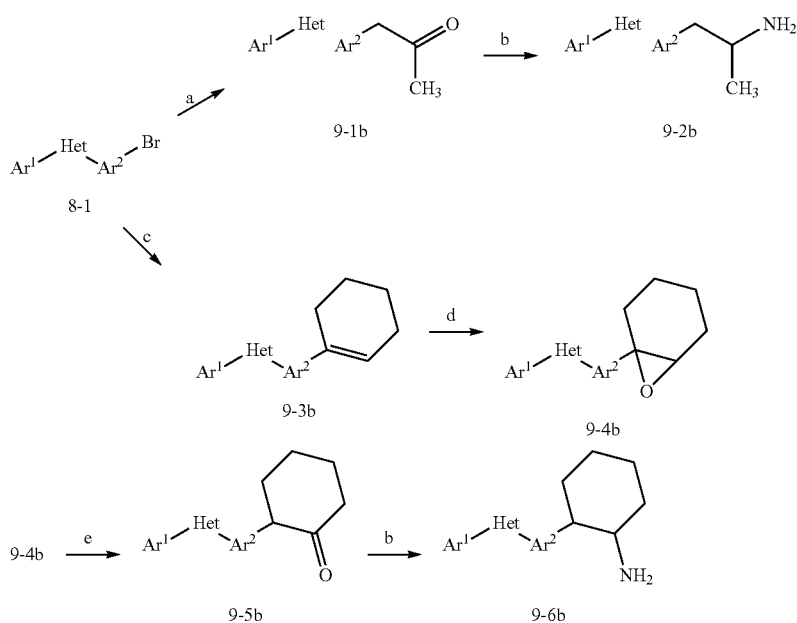

Preparation of Propyl Linked Intermediates

Preparation of compounds wherein L is a three-atom group is described in Schemes 10 and 11. Aminoalkyl precursors $Ar^1$-Het-$Ar^2$-L-$NH_2$, wherein L is 3-carbon atoms, mono- or di-substituted with $R^9$, wherein $R^9$ is defined as above; and unsubstituted or mono-substituted with $R^{10}$, wherein $R^{10}$ is defined as above; can be prepared as shown in Scheme 10. Halophenyl carbinol 10-1, wherein X is Br and $R^9$ and $R^{10}$ are H, is available commercially. Carbinols 10-1 that are mono- or di-substituted at $R^9$ can be prepared from the corresponding halophenyl acetate (10-1, step a) in similar fashion to that described by Shin et al. *Bioorg. Med. Chem. Lett.*, 2008, 18, pp 4424-4427, followed by reduction with a metal hydride such as lithium aluminum hydride in an ethereal solvent such as tetrahydrofuran at temperatures at or below about 0° C. Both 10-I and 10-II may be further mono-substituted (step b or step c) with $R^{10}$ via reduction to the corresponding aldehyde with a metal hydride such as diisobutylaluminum hydride and further treatment with a Grignard reagent such as methylmagnesium bromide in a similar fashion to that described by Brimble et al. *Org. Lett.*, 2012, 14 (23), pp 5820-5823; Carbinols 10-1 can be treated with phthalimide under Mitsunobu conditions to generate N-phthalimido intermediates 10-2 (step d).

The halide can be converted into boronic ester under Miyaura conditions to form boronate esters (10-3, step e). Coupling of the boronate esters with a bromo-heterocycle can be accomplished using a palladium catalyst, such tetrakis(triphenylphosphine) palladium(0), in the presence of a base, such as sodium bicarbonate, in a suitable solvent system, such as dioxane/water, at temperatures from about 50° C. to about 120° C. to provide N-phthalimido intermediates 10-4 (step f). Deprotection using hydrazine and methanol or other suitable solvent can furnish the amine 10-5 (step g).

Alternatively, compounds wherein L is a 3-atom linker may also be prepared as shown in Scheme 11. Bromide $Ar^1$-Het-$Ar^2$—Br (8-1) can be coupled with an appropriate alkynyl alcohol (11-1, step a) unsubstituted or mono-substituted with $R^{10}$, wherein $R^{10}$ is defined as above; in the presence of a palladium catalyst such as bistriphenylphosphine dichloropalladium(II), copper(I) iodide, and a base such as triethylamine, at temperatures from about 50° C. to about 120° C., to generate the corresponding alkynyl alcohol derivatives 11-2. The resultant carbinols 11-2 can be treated with phthalimide under Mitsunobu conditions to generate N-phthalimido intermediates 11-3 (step b) which can be converted to amine (11-7, step e) using hydrazine and methanol or other suitable solvent. Carbinols 11-2 can be reduced using a transition metal

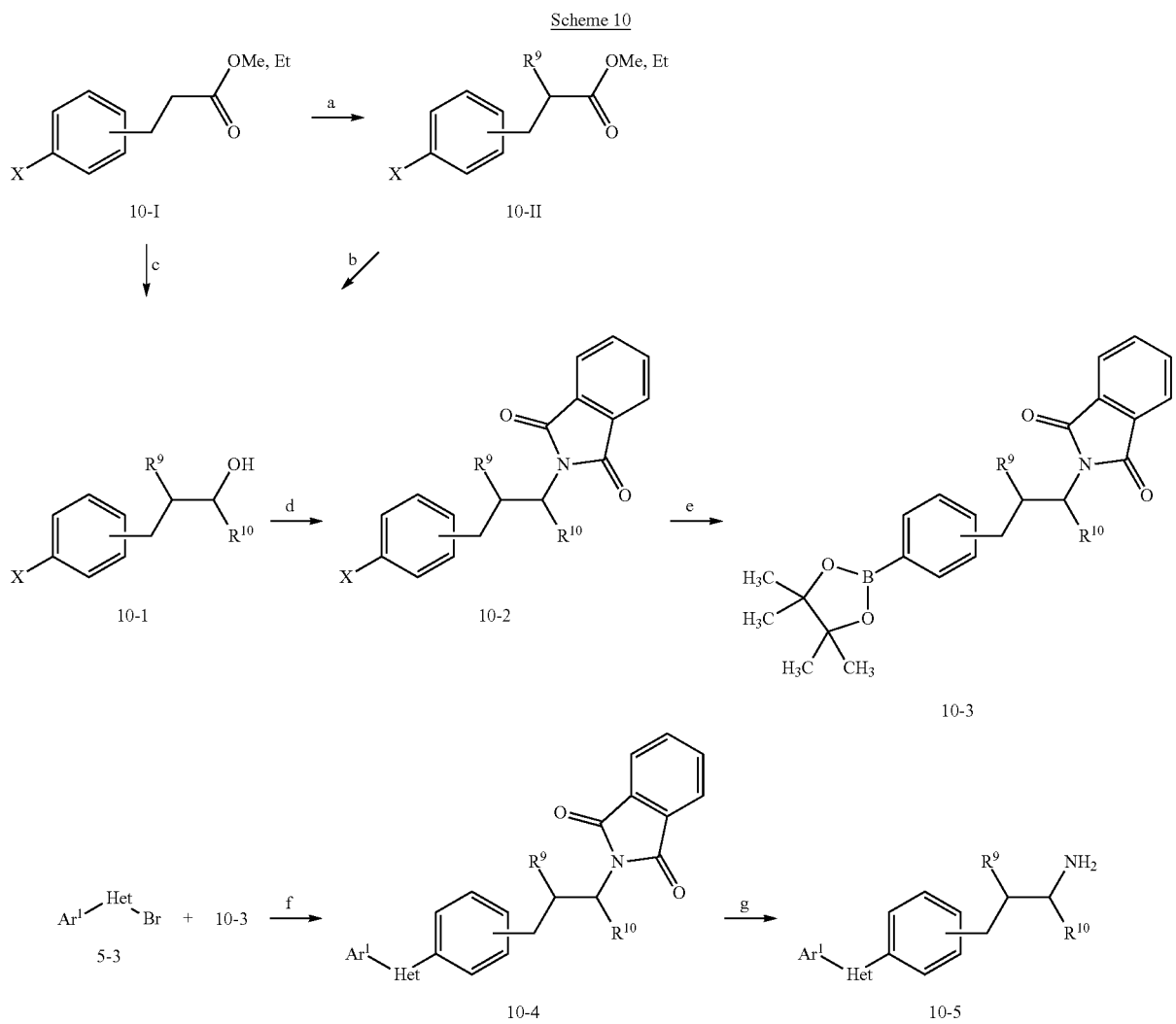

catalyst, such as palladium under an atmosphere of hydrogen to provide alkenyl or fully saturated alkyl carbinols 11-4 unsubstituted at $R^{10}$. Additionally, carbinols 11-2 can be treated with a metal hydride such as lithium aluminum hydride to provide the (E)-alkenyl carbinol 11-4. Likewise, carbinol 11-2 may be protected with a protecting group such as tert-butyl diphenyl silane, and treated with a hydrometallation reagent such as Schwartz' reagent followed by an electrophile quench, with, for example, elemental iodine or NBS. Alternatively, the carbinol 11-2 may be treated with a transmetallation reagent such as pinacol diboron for further use in transition metal-catalyzed coupling reactions, such as Suzuki or Negishi, to prepare carbinols 11-4 mono- or di-substituted with $R^9$, wherein $R^9$ is defined as above (step c). Following deprotection, the resultant carbinols 11-4 can be treated with phthalimide under Mitsunobu conditions to generate N-phthalimido intermediates 11-5 (step d) which can be converted to an amine (11-6, step e) using hydrazine and methanol or other suitable solvent.

defined as above; mono- or di-substituted with $R^9$, wherein $R^9$ is defined as above; in the presence of a palladium catalyst such as bistriphenylphosphine dichloropalladium, copper(I) iodide, and a base such as triethylamine, at temperatures from about 50° C. to about 120° C., to generate the corresponding alkynyl alcohol derivatives 12-2. The resultant carbinols 12-2 can be treated with phthalimide under Mitsunobu conditions (step b) to generate N-phthalimido intermediates 12-3 which can be converted to an amine (12-7, step e) using hydrazine and methanol or other suitable solvents. Carbinols 12-2 can be reduced using a transition metal catalyst, such as palladium under an atmosphere of hydrogen to provide alkenyl or fully saturated alkyl carbinols 12-4 (step c) unsubstituted at $R^{13}$. Additionally, carbinols 12-2 can be treated with a metal hydride such as lithium aluminum hydride to provide the (E)-alkenyl carbinols 12-4 (step c). Likewise, carbinol 12-2 may be protected with a protecting group such as tert-butyl diphenyl silane, and treated with a hydrometallation reagent such as Schwartz' reagent followed by an electrophile

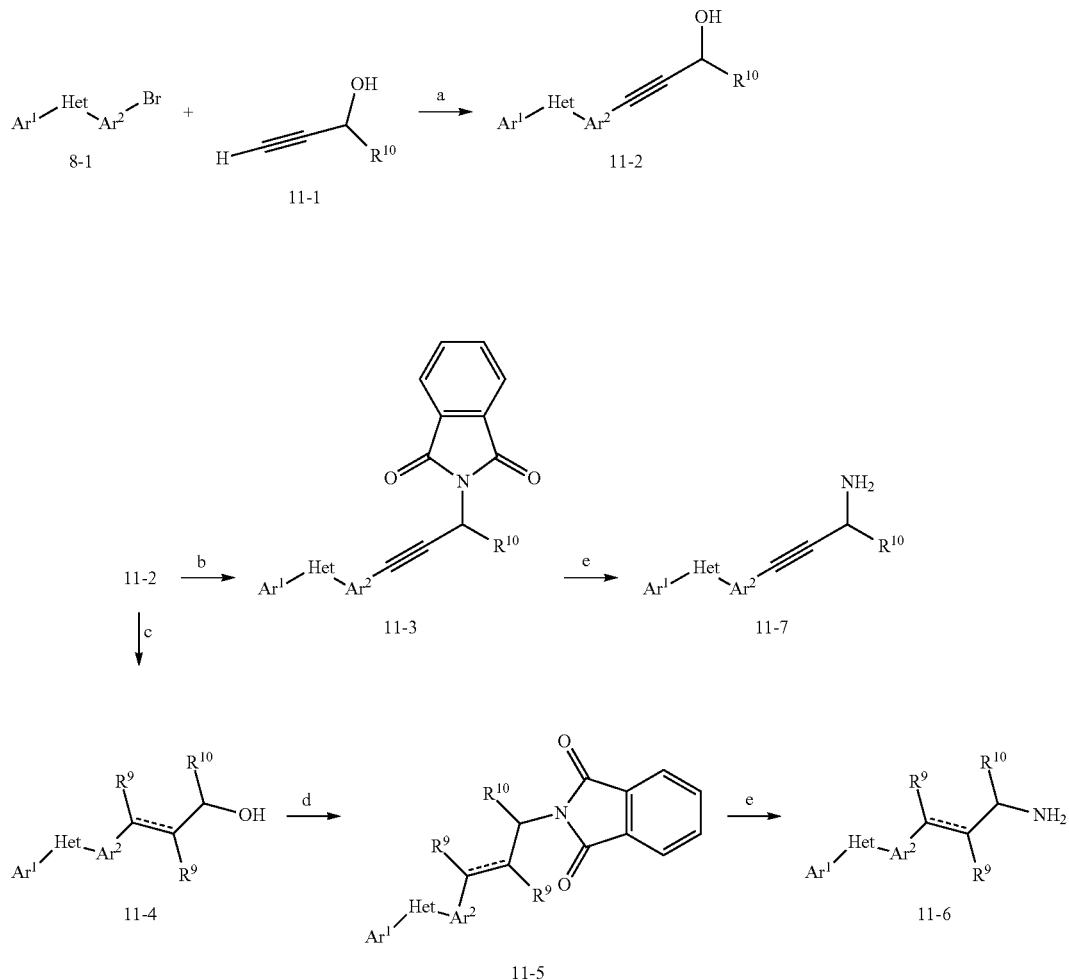

Preparation of Butyl Linked Intermediates

Compounds wherein L is a 4-atom linker may be prepared as shown in Scheme 12. Bromide $Ar^1$-Het-$Ar^2$—Br (8-1) can be coupled with an appropriate alkynyl alcohol (12-1, step a) unsubstituted or mono-substituted with $R^{10}$, wherein $R^{10}$ is quench, with, for example, elemental iodine or NBS. Alternatively the carbinol 12-2 may be treated with a transmetallation reagent such as pinacol diboron for further use in transition metal-catalyzed coupling reactions, such as Suzuki or Negishi, to prepare carbinols 12-4 mono- or di-substituted with $R^{13}$, wherein $R^{13}$ is defined as $R^8$ above (step c).

Scheme 12

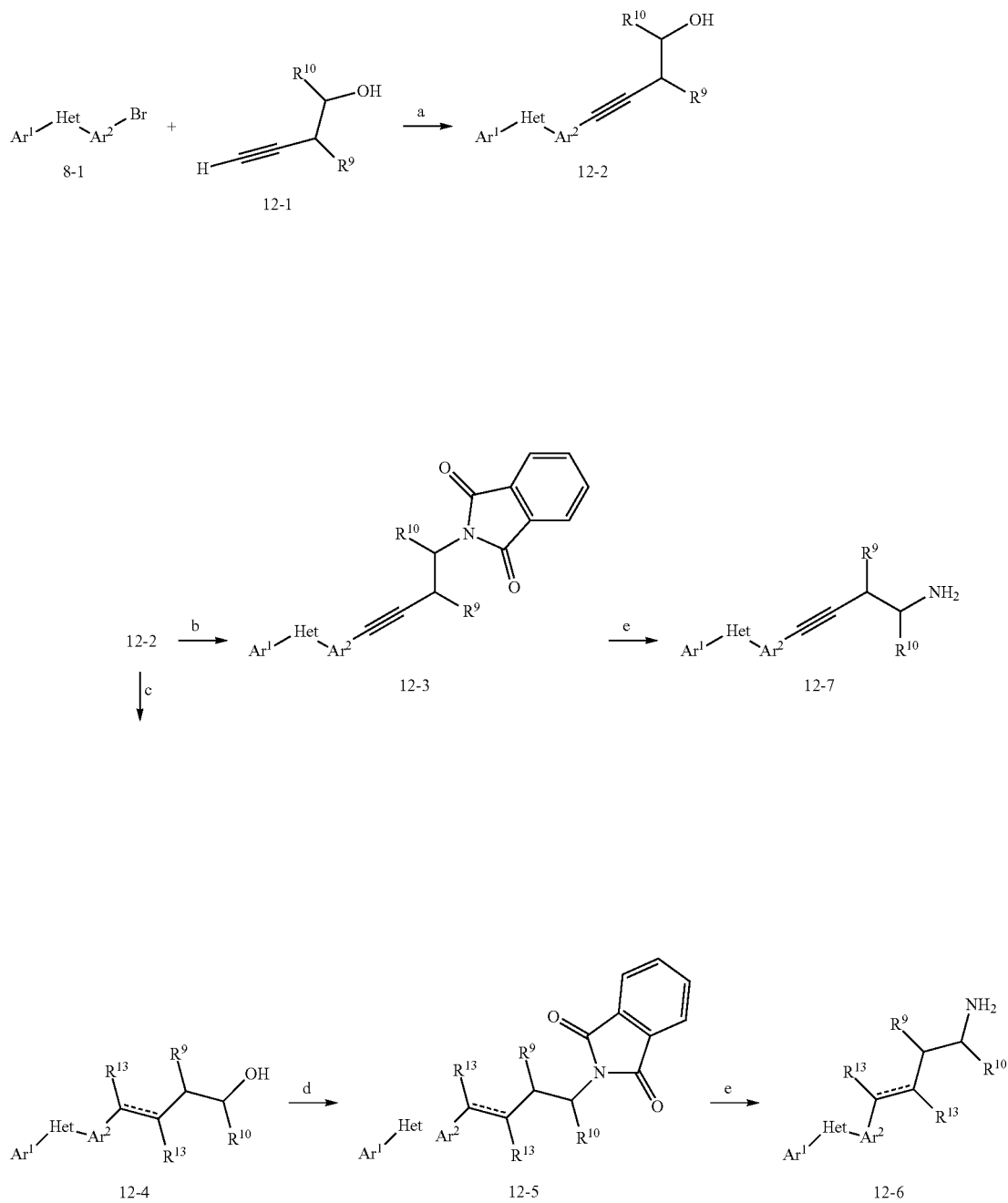

Following deprotection, the resultant carbinols 12-4 can be treated with phthalimide under Mitsunobu conditions (step d) to generate N-phthalimido intermediates 12-5 which can be converted to an amine (12-6, step e) using hydrazine and methanol or other suitable solvent.

Preparation of Substituted Thiobiurets

2-Imino 1,3-thiazolin-4-ones (3-1) may be further functionalized using a variety of conditions. When treated with Selectfluor® and 9-fluorenone in anhydrous acetonitrile (*JACS*. 2013, 135, 17494.), molecules having the formula 3-1 may be converted into the mono-fluoro analogs (13-1).

Scheme 13

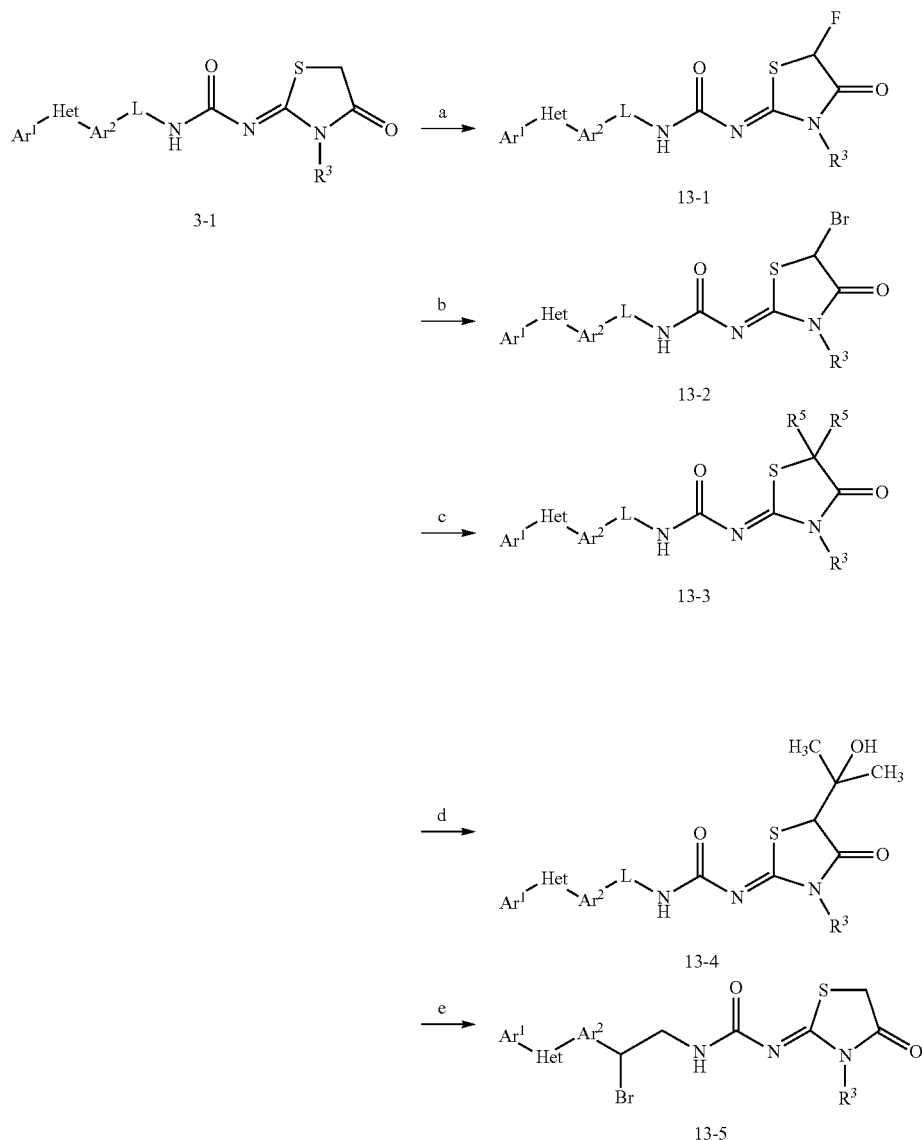

Treatment with molecular bromine in a non-protic solvent such as dichloromethane at from about 0° C. to about 30° C. (step b) may result in mono-bromination on the thiazolinone ring (13-2). Alkylation (step c), using at least 2 equivalents of an alkylating agent $R^5$—I and a strong base such as sodium hydride or lithium diisopropylamide in a polar aprotic solvent such as dimethylformamide or tetrahydrofuran may lead to a di-alkylated product (13-3). Treatment with a ketone or an aldehyde and an inorganic base such as potassium carbonate or cesium carbonate may result in the formation of a carbinol (13-4). For analogs of compounds of the formula 3-1 wherein L is a —$CH_2CH_2$— group, free-radical bromination using N-bromosuccinimide and a free radical initiator such as azo-bis(isobutyronitrile) in carbon tetrachloride at about 30° C. to about 77° C. may lead to the mono-brominated product (13-5) wherein the bromine is incorporated into the ethyl linker.

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw or ACD Name Pro. If such programs are unable to name a molecule, the molecule is named using conventional naming rules. $^1$H NMR spectral data are in ppm (δ) and were recorded at 300, 400 or 600 MHz, and $^{13}$C NMR spectral data are in ppm (δ) and were recorded at 75, 100 or 150 MHz, unless otherwise stated.

Example 1

Preparation of 3-bromo-1-(4-(trifluoromethoxy)phenyl)-1H-1,2,4-triazole (C1)

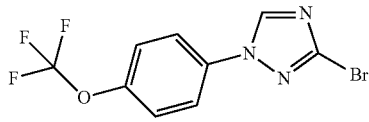 [SMILES: FC(F)(F)Oc1ccc(-n2cnc(Br)n2)cc1]

To a 100 mL round bottomed flask, equipped with a stir bar, was added copper(I) iodide (0.397 g, 2.08 mmol), 3-bromo-1H-1,2,4-triazole (4.62 g, 31.2 mmol), and cesium carbonate (6.79 g, 20.83 mmol), as solids. These solids were diluted with anhydrous dimethyl sulfoxide (34.7 mL). Then 1-iodo-4-(trifluoromethoxy)benzene (1.65 mL, 10.4 mmol) was added as a liquid. The flask was placed under nitrogen atmosphere, and the suspension was heated to an internal temperature of 100° C. for 20 hours. The reaction mixture was allowed to cool to room temperature and filtered through a pad of Celite®, washing with excess ethyl acetate (200 mL). The filtrate was poured into a brine solution (200 mL), and the layers were partitioned. The aqueous phase was extracted with additional ethyl acetate (2×100 mL). The combined organic layers were dried over anhydrous magnesium sulfate, filtered, and concentrated. The resulting residue was purified via flash column chromatography using 10-50% ethyl acetate/hexanes as eluent to afford the title compound as a white solid (1.80 g, 54%): $^1$H NMR (400 MHz, DMSO-d$_6$) δ 9.35 (s, 1H), 7.97 (d, J=8.9 Hz, 2H), 7.60 (d, J=8.4 Hz, 2H); $^{19}$F NMR (376 MHz, DMSO-d$_6$) δ −57.06; ESIMS m/z 308, 310 ([M+H]$^+$).

The following compounds were prepared in accordance to the procedure in Example 1.

Preparation of 3-bromo-1-(4-(pentafluoroethoxy)phenyl)-1H-1,2,4-triazole (C1a)

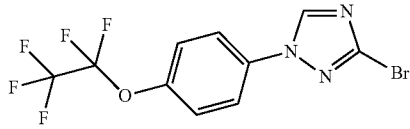

The title compound was prepared as described in Example 1 using 1-iodo-4-pentafluoroethoxybenzene and isolated as a white solid (1.60 g, 31%): mp 72-74° C.; $^1$H NMR (400 MHz, CDCl$_3$) δ 8.44 (s, 1H), 7.75-7.68 (m, 2H), 7.42-7.36 (m, 2H); $^{19}$F NMR (376 MHz, CDCl$_3$) δ −85.94, −87.92; ESIMS m/z 357, 359 ([M+H]$^+$).

Preparation of 3-bromo-1-(4-(trifluoromethyl)phenyl)-1H-1,2,4-triazole (C1b)

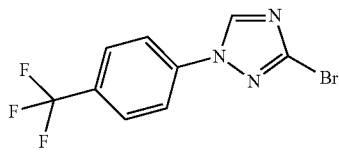 [SMILES: FC(F)(F)c1ccc(-n2cnc(Br)n2)cc1]

The title compound was prepared as described in Example 1 using 1-iodo-4-trifluoromethylbenzene and isolated as a white solid (2.32 g, 31%): mp 104-105° C., $^1$H NMR (400 MHz, CDCl$_3$) δ 8.52 (s, 1H), 7.81 (s, 4H); $^{19}$F NMR (376 MHz, CDCl$_3$) δ −62.64; ESIMS m/z 292, 294 ([M+H]$^+$).

Example 2

Preparation of methyl 2-(4-(4,4,5,5-tetramethyl-1,3,2-dioxaborolan-2-yl)phenyl)acetate (C2)

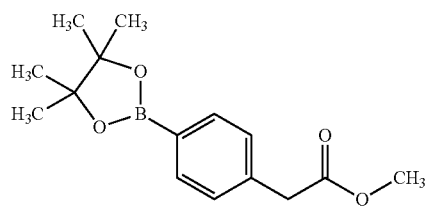

To a 200 mL round bottomed flask, equipped with a stir bar, was added [1,1'-bis(diphenylphosphino)ferrocene]dichloropalladium(II) (0.799 g, 1.09 mmol), 4,4,4',4',5,5,5',5'-octamethyl-2,2'-bi(1,3,2-dioxaborolane) (6.65 g, 26.2 mmol), and potassium acetate (4.28 g, 43.7 mmol) as solids. These solids were diluted with dioxane (100 mL). The flask was sealed and pumped and purged with nitrogen atmosphere. Then methyl 2-(4-bromophenyl)acetate (5.00 g, 21.8 mmol) was added. The reaction mixture was then warmed to an internal temperature of 70° C. for 6 hours. The reaction mixture was allowed to cool to room temperature, and was poured into a brine solution and the layers were partitioned. The aqueous phase was extracted with ethyl acetate (3×125 mL). The combined organic layers were dried over anhydrous magnesium sulfate, filtered, and concentrated. The resulting residue was purified via flash column chromatography using 0-30% ethyl acetate/hexanes as eluent to afford the title compound as a clear liquid (4.93 g, 70%): $^1$H NMR (400 MHz, DMSO-d$_6$) δ 7.68-7.58 (m, 2H), 7.35-7.23 (m, 2H), 3.71 (5, 2H), 3.61 (5, 3H), 1.29 (s, 12H); $^{13}$C NMR (101 MHz, DMSO-d$_6$) δ 171.29, 137.72, 134.45, 128.86, 83.56, 82.79, 51.68, 40.23, 24.62; EIMS m/z 276 ([M]$^+$).

Example 3

Preparation of methyl 2-(4-(1-(4-(trifluoromethoxy)phenyl)-1H-1,2,4-triazol-3-yl)phenyl)acetate (C3)

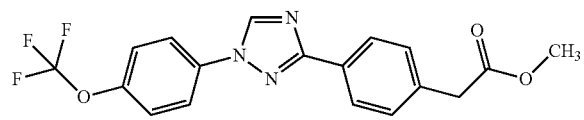 [SMILES: COC(=O)Cc1ccc(-c2ncn(-c3ccc(OC(F)(F)F)cc3)n2)cc1]

To a 200 mL round bottomed flask equipped with a magnetic stir bar was added 3-bromo-1-(4-(trifluoromethoxy)phenyl)-1H-1,2,4-triazole (C1) (3.45 g, 11.2 mmol), and methyl 2-(4-(4,4,5,5-tetramethyl-1,3,2-dioxaborolan-2-yl)phenyl)acetate (C2) (3.71 g, 13.4 mmol). These reagents were diluted with dioxane (45.0 mL) and water (11.3 mL) and the resulting solution was sparged with nitrogen gas for 10 minutes. Tri-tert-butylphosphonium tetrafluoroborate (0.325 g, 1.12 mmol), palladium(II) acetate (0.126 g, 0.560 mmol) and cesium fluoride (3.40 g, 22.4 mmol) were added as solids. The flask was sealed and placed under nitrogen atmosphere. The reaction mixture was heated to an internal temperature of 60° C. The reaction mixture was allowed to cool to room temperature, and was poured into a brine solution and the layers were partitioned. The aqueous phase was extracted with ethyl acetate (3×100 mL). The combined organic layers were dried over anhydrous magnesium sulfate, filtered, and concentrated. The resulting residue was purified via flash column chromatography using 0-10% ethyl acetate/hexanes as eluent to afford the title compound as an off-white solid (3.45 g, 82%): $^1$H NMR (400 MHz, DMSO-$d_6$) δ 9.41 (s, 1H), 8.11-8.04 (m, 4H), 7.63 (ddt, J=7.9, 2.1, 1.1 Hz, 2H), 7.48-7.36 (m, 2H), 3.77 (s, 2H), 3.64 (s, 3H); $^{19}$F NMR (376 MHz, DMSO-$d_6$) δ −57.02; ESIMS m/z 378 ([M+H]$^+$).

The following compounds were prepared in accordance to the procedure in Example 3.

Preparation of methyl 2-(4-(1-(4-(perfluoroethoxy)phenyl)-1H-1,2,4-triazol-3-yl)phenyl)acetate (C4)

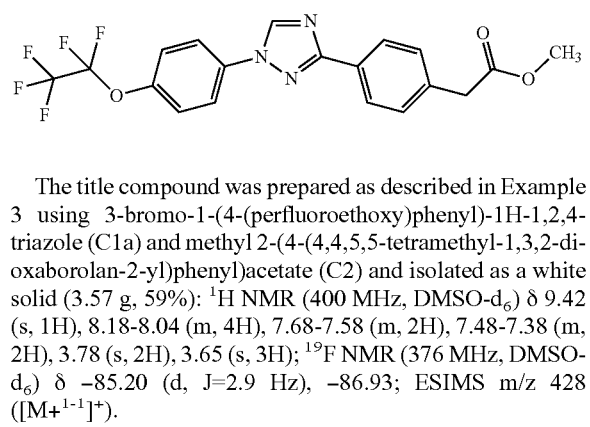

The title compound was prepared as described in Example 3 using 3-bromo-1-(4-(perfluoroethoxy)phenyl)-1H-1,2,4-triazole (C1a) and methyl 2-(4-(4,4,5,5-tetramethyl-1,3,2-dioxaborolan-2-yl)phenyl)acetate (C2) and isolated as a white solid (3.57 g, 59%): $^1$H NMR (400 MHz, DMSO-$d_6$) δ 9.42 (s, 1H), 8.18-8.04 (m, 4H), 7.68-7.58 (m, 2H), 7.48-7.38 (m, 2H), 3.78 (s, 2H), 3.65 (s, 3H); $^{19}$F NMR (376 MHz, DMSO-$d_6$) δ −85.20 (d, J=2.9 Hz), −86.93; ESIMS m/z 428 ([M+1-1]$^+$).

Preparation of methyl 2-(4-(1-(4-(trifluoromethyl)phenyl)-1H-1,2,4-triazol-3-yl)phenyl)acetate (C5)

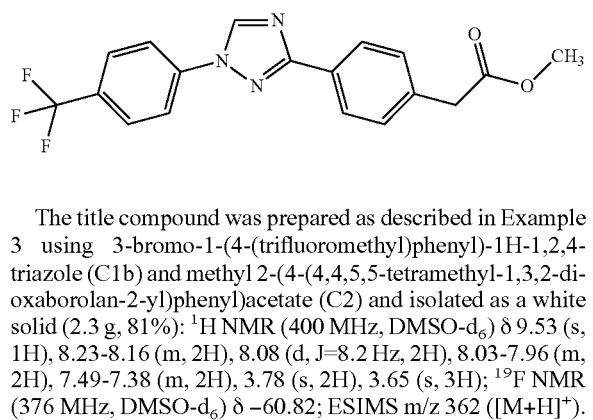

The title compound was prepared as described in Example 3 using 3-bromo-1-(4-(trifluoromethyl)phenyl)-1H-1,2,4-triazole (C1b) and methyl 2-(4-(4,4,5,5-tetramethyl-1,3,2-dioxaborolan-2-yl)phenyl)acetate (C2) and isolated as a white solid (2.3 g, 81%): $^1$H NMR (400 MHz, DMSO-$d_6$) δ 9.53 (s, 1H), 8.23-8.16 (m, 2H), 8.08 (d, J=8.2 Hz, 2H), 8.03-7.96 (m, 2H), 7.49-7.38 (m, 2H), 3.78 (s, 2H), 3.65 (s, 3H); $^{19}$F NMR (376 MHz, DMSO-$d_6$) δ −60.82; ESIMS m/z 362 ([M+H]$^+$).

Example 4

Preparation of 2-(4-(1-(4-(trifluoromethoxy)phenyl)-1H-1,2,4-triazol-3-yl)phenyl)acetic acid (C6)

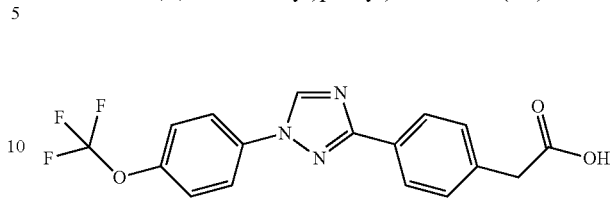

To a 100 mL round bottomed flask, equipped with a magnetic stir bar, was added methyl 2-(4-(1-(4-(trifluoromethoxy)phenyl)-1H-1,2,4-triazol-3-yl)phenyl)acetate (C3) (3.45 g, 9.14 mmol) and lithium hydroxide.hydrate (1.15 g, 27.4 mmol) as solids. These solids were diluted with tetrahydrofuran (24 mL), methanol (24 mL), and water (12 mL). The reaction was stirred at room temperature for 2 hours. The reaction mixture was then concentrated to dryness. The resulting solid was then diluted with water, and the resulting suspension was adjusted to pH 2.9. The subsequent precipitate was extracted with ethyl acetate (5×100 mL). The combined organic extracts were dried over anhydrous magnesium sulfate, filtered, and concentrated to afford the title compound as a white solid (3.27 g, 96%): $^1$H NMR (400 MHz, DMSO-$d_6$) δ 12.41 (s, 1H), 9.40 (s, 1H), 8.15-8.03 (m, 4H), 7.63 (dq, J=7.9, 1.0 Hz, 2H), 7.49-7.36 (m, 2H), 3.66 (s, 2H); $^{19}$F NMR (376 MHz, DMSO-$d_6$) δ −56.98; ESIMS m/z 364 ([M+H]$^+$).

The following compounds were prepared in accordance to the procedure in Example 4.

Preparation of 2-(4-(1-(4-(perfluoroethoxy)phenyl)-1H-1,2,4-triazol-3-yl)phenyl)acetic acid (C7)

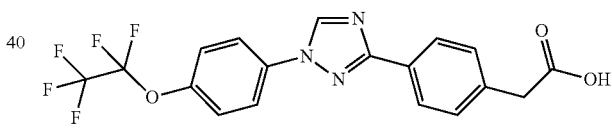

The title compound was prepared as described in Example 4 using methyl 2-(4-(1-(4-(perfluoroethoxy)phenyl)-1H-1,2,4-triazol-3-yl)phenyl)acetate (C4) and isolated as a white solid (3.4 g, 94%): $^1$H NMR (400 MHz, DMSO-$d_6$) δ 12.41 (s, 1H), 9.41 (s, 1H), 8.15-8.02 (m, 4H), 7.67-7.58 (m, 2H), 7.47-7.37 (m, 2H), 3.66 (s, 2H); $^{19}$F NMR (376 MHz, DMSO-$d_6$) δ −85.20, −86.92; ESIMS m/z 414 ([M+H]$^+$).

Preparation of 2-(4-(1-(4-(trifluoromethyl)phenyl)-1H-1,2,4-triazol-3-yl)phenyl)acetic acid (C8)

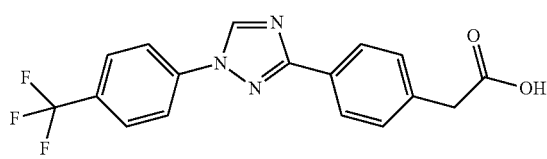 [SMILES: O=C(O)Cc1ccc(-c2ncn(-c3ccc(C(F)(F)F)cc3)n2)cc1]

The title compound was prepared as described in Example 4 with methyl 2-(4-(1-(4-(trifluoromethyl)phenyl)-1H-1,2,4-triazol-3-yl)phenyl)acetate (C5) and isolated as a white solid (0.378 g, 98%): ¹H NMR (400 MHz, DMSO-d₆) δ 12.42 (s, 1H), 9.53 (s, 1H), 8.25-8.16 (m, 2H), 8.11-8.04 (m, 2H), 7.99 (d, J=8.6 Hz, 2H), 7.47-7.39 (m, 2H), 3.66 (s, 2H); ¹⁹F NMR (376 MHz, DMSO-d₆) δ −60.79; ESIMS m/z 348 ([M+H]⁺).

Example 5

Preparation of (2-(4-(1-(4-(trifluoromethoxy)phenyl)-1H-1,2,4-triazol-3-yl)phenyl)acetyl azide/2-(4-(1-(4-(trifluoromethoxy)phenyl)-1H-1,2,4-triazol-3-yl)phenyl)methyl isocyanate (C9)

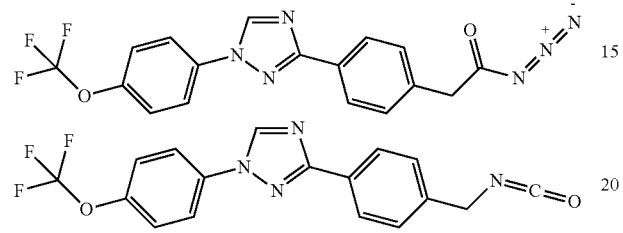

In a 100 mL round bottomed flask, equipped with a magnetic stir bar, 2-(4-(1-(4-(trifluoromethoxy)phenyl)-1H-1,2,4-triazol-3-yl)phenyl)acetic acid (C6) (2.00 g, 5.51 mmol) was diluted with toluene (37 mL). Then triethylamine (0.767 mL, 5.51 mmol) and diphenyl phosphorazidate (1.19 mL, 5.51 mmol) were added. The reaction was allowed to stir for 2.5 hours at room temperature. The reaction was then poured in to water and extracted with ethyl acetate (3×50 mL). The combined organic layers were dried over anhydrous magnesium sulfate, filtered, and concentrated. The resulting residue was purified via flash column chromatography using 0-10% ethyl acetate/hexanes as eluent to afford the title compound as an off-white solid (0.800 g, 37%): ¹H NMR (400 MHz, DMSO-d₆) δ 9.41 (d, J=5.9 Hz, 1H), 8.21-7.99 (m, 4H), 7.69-7.57 (m, 2H), 7.57-7.38 (m, 2H), 4.70 (s, 2H); ¹⁹F NMR (376 MHz, DMSO-d₆) δ −56.99 (d, J=4.1 Hz); ESIMS m/z 361 ([M+H]⁺) (methyl carbamate).

The following compounds were prepared in accordance to the procedure in Example 5. Physical properties indicate that the isolated products are often a mixture of the acyl azide and rearranged isocyanate.

Preparation of 2-(4-(1-(4-(perfluoroethoxy)phenyl)-1H-1,2,4-triazol-3-yl)phenyl)acetyl azide/2-(4-(1-(4-(perfluoroethoxy)phenyl)-1H-1,2,4-triazol-3-yl)phenyl)methyl isocyanate (C10)

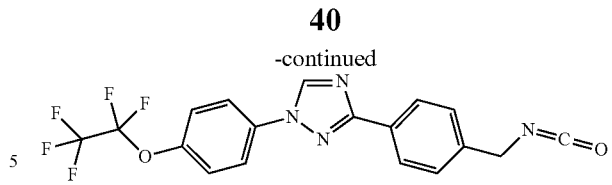

The title compound was prepared as described in Example 5 using 2-(4-(1-(4-(perfluoroethoxy)phenyl)-1H-1,2,4-triazol-3-yl)phenyl)acetic acid (C7) and isolated as a white solid (1.45 g, 46%): ¹H NMR (400 MHz, DMSO-d₆) δ 9.46-9.32 (m, 1H), 8.19-7.97 (m, 4H), 7.68-7.36 (m, 4H), 4.70 (s, 1H), 4.34 (d, J=6.1 Hz, 1H); ¹⁹F NMR (376 MHz, DMSO-d₆) δ −85.23 (d, J=9.8 Hz), −86.95 (d, J=8.0 Hz); ESIMS m/z 442 ([M+H]⁺) (methyl carbamate).

Preparation of 2-(4-(1-(4-(trifluoromethyl)phenyl)-1H-1,2,4-triazol-3-yl)phenyl)acetyl azide/2-(4-(1-(4-(trifluromethoxy)phenyl)-1H-1,2,4-triazol-3-yl)phenyl)methyl isocyanate (C11)

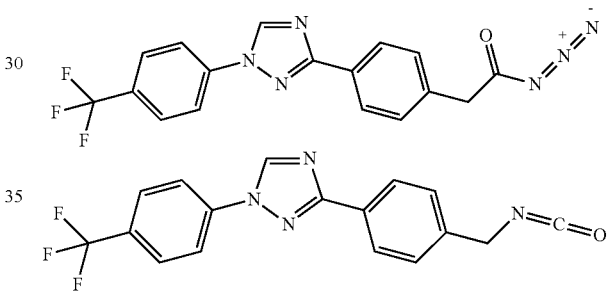

The title compound was prepared as described in Example 5 with 2-(4-(1-(4-(trifluoromethyl)phenyl)-1H-1,2,4-triazol-3-yl)phenyl)acetic acid (C8) and isolated as a white solid (0.082 g, 25%): ¹H NMR (400 MHz, DMSO-d₆) δ 9.55 (s, 1H), 8.27-8.06 (m, 4H), 7.99 (d, J=8.5 Hz, 2H), 7.56-7.49 (m, 1H), 7.44 (dd, J=8.4, 6.9 Hz, 1H), 4.71 (s, 1H), 3.87 (s, 1H); ¹⁹F NMR (376 MHz, DMSO-d₆) δ −60.80 (d, J=2.9 Hz); ESIMS m/z 345 ([M+H]⁺).

Example 6

Preparation of N-[2-(propan-2-yl)phenyl]-N'-(4-{1-[4-(trifluoromethoxy)phenyl]-1H-1,2,4-triazol-3-yl}benzyl)dicarbonimidothioic diamide (F14)

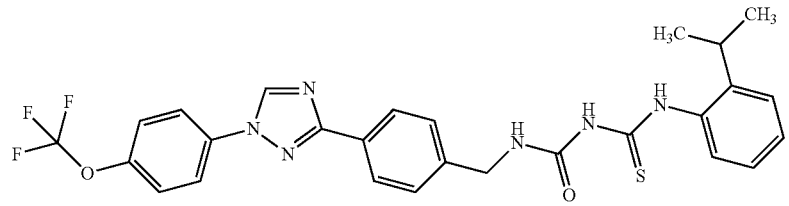 [SMILES: CC(C)c1ccccc1NC(=S)NC(=O)NCc1ccc(-c2ncn(-c3ccc(OC(F)(F)F)cc3)n2)cc1]

In a 20 mL vial, equipped with a magnetic stir bar, (2-(4-(1-(4-(trifluoromethoxy)phenyl)-1H-1,2,4-triazol-3-yl)phenyl)acetyl azide/2-(4-(1-(4-(trifluoromethoxy)phenyl)-1H-1,2,4-triazol-3-yl)phenyl)methyl isocyanate (C9) (0.200 g, 0.515 mmol) was suspended in acetonitrile (3.3 mL). The vial was capped and the suspension was heated at 80° C., for 3 hours. The suspension was cooled to room temperature and 1-(2-isopropylphenyl)thiourea (0.110 g, 0.567 mmol) and cesium carbonate (0.201 g, 0.618 mmol) were charged as solids. This suspension was stirred at room temperature for 18 hours. The reaction mixture was filtered through a glass-fritted funnel. The filtrate was concentrated and the resulting residue was purified via reverse-phase flash column chromatography ($C_{18}$ column) using 5-100% acetonitrile/water as eluent to afford the title compound as a light yellow solid (0.104 g, 36%).

The following compounds were prepared in accordance to the procedure in Example 6.

Preparation of N-(4-{1-[4-(pentafluoroethoxy)phenyl]-1H-1,2,4-triazol-3-yl}benzyl)-N'-[2-(propan-2-yl)phenyl]dicarbonimidothioic diamide (F15)

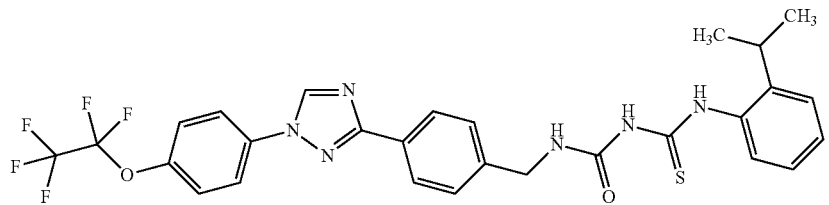 [SMILES: CC(C)c1ccccc1NC(=S)NC(=O)NCc1ccc(-c2ncn(-c3ccc(OC(F)(F)C(F)(F)F)cc3)n2)cc1]

The title compound was prepared as described in Example 6 using 2-(4-(1-(4-(perfluoroethoxy)phenyl)-1H-1,2,4-triazol-3-yl)phenyl)acetyl azide/2-(4-(1-(4-(perfluoroethoxy)phenyl)-1H-1,2,4-triazol-3-yl)phenyl)methyl isocyanate (C10) and 1-(2-isopropylphenyl)thiourea and isolated as a yellow solid (0.102 g, 36%).

Preparation of N-[5-methyl-2-(propan-2-yl)phenyl]-N'-(4-{1-[4-(pentafluoroethoxy)phenyl]-1H-1,2,4-triazol-3-yl}benzyl)dicarbonimidothioic diamide (F16)

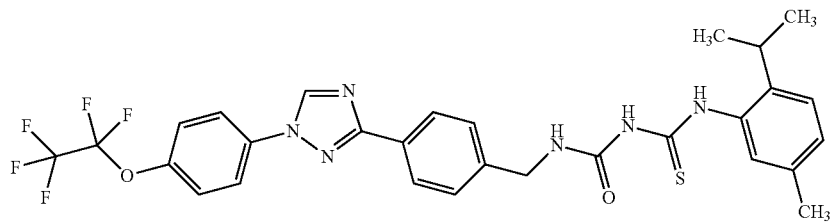 [SMILES: Cc1ccc(C(C)C)c(NC(=S)NC(=O)NCc2ccc(-c3ncn(-c4ccc(OC(F)(F)C(F)(F)F)cc4)n3)cc2)c1]

The title compound was prepared as describe in Example 6 using 2-(4-(1-(4-(perfluoroethoxy)phenyl)-1H-1,2,4-triazol-3-yl)phenyl)acetyl azide/2-(4-(1-(4-(perfluoroethoxy)phenyl)-1H-1,2,4-triazol-3-yl)phenyl)methyl isocyanate (C10) and 1-(2-isopropyl-5-methylphenyl)thiourea and isolated as a yellow solid (0.130 g, 44%).

Preparation of N-[5-methyl-2-(propan-2-yl)phenyl]-N'-(4-{1-[4-(trifluoromethoxy)phenyl]-1H-1,2,4-triazol-3-yl}benzyl)dicarbonimidothioic diamide (F35)

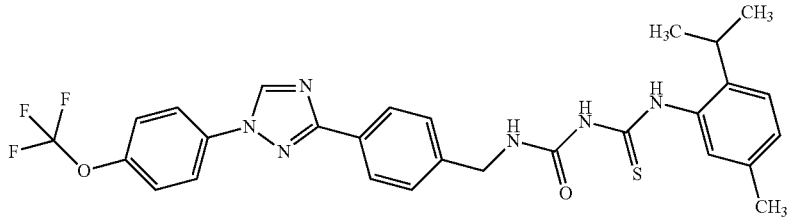 [SMILES: Cc1ccc(C(C)C)c(NC(=S)NC(=O)NCc2ccc(-c3ncn(-c4ccc(OC(F)(F)F)cc4)n3)cc2)c1]

The title compound was prepared as described in Example 6 using (2-(4-(1-(4-(trifluoromethoxy)phenyl)-1H-1,2,4-triazol-3-yl)phenyl)acetyl azide/2-(4-(1-(4-(trifluoromethoxy)phenyl)-1H-1,2,4-triazol-3-yl)phenyl)methyl isocyanate (C9) and 1-(2-isopropyl-5-methylphenyl)thiourea and isolated as a yellow solid (0.043 g, 15%).

Example 7

Preparation of (Z)-1-(3-(2-isopropylphenyl)-4-oxothiazolidin-2-ylidene)-3-(4-(1-(4-(trifluoromethoxy)phenyl)-1H-1,2,4-triazol-3-yl)benzyl)urea (F17)

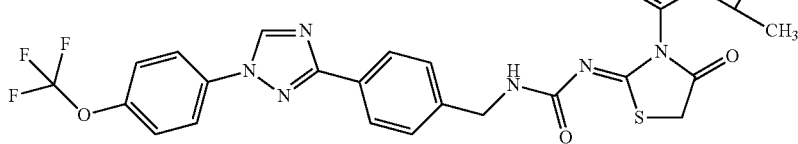

In a 50 mL round bottomed flask, equipped with a magnetic stir bar, N-[2-(propan-2-yl)phenyl]-N'-(4-{1-[4-(trifluoromethoxy)phenyl]-1H-1,2,4-triazol-3-yl}benzyl)dicarbonimidothioic diamide (F14) (0.067 g, 0.12 mmol) and sodium acetate (0.012 g, 0.15 mmol) was diluted with acetonitrile (1.2 mL), then methyl 2-bromoacetate (0.013 mL, 0.13 mmol) was added. The flask was fitted with a reflux condenser and the reaction mixture was heated at 70° C. After 4 hours, an additional aliquot of methyl 2-bromoacetate (0.013 mL, 0.13 mmol) was added, and the reaction was allowed to heat for an additional 18 hours. An additional aliquot of methyl 2-bromoacetate (0.013 mL, 0.13 mmol) and sodium acetate (0.012 g, 0.15 mmol) was added, and the reaction was allowed to heat for an additional 4 hours. The reaction mixture was cooled and diluted with water and extracted with ethyl acetate (50 mL). The organic layer was dried over anhydrous magnesium sulfate, filtered, and concentrated. The resulting residue was purified via reverse-phase flash column ($C_{18}$ column) chromatography using 5-100% acetonitrile/water as eluent to afford the title compound as a white solid (0.036 g, 49%).

The following compounds were prepared in accordance to the procedure in Example 7.

Preparation of (Z)-1-(3-(2-isopropylphenyl)-4-oxothiazolidin-2-ylidene)-3-(4-(1-(4-(perfluoroethoxy)phenyl)-1H-1,2,4-triazol-3-yl)benzyl)urea (F18)

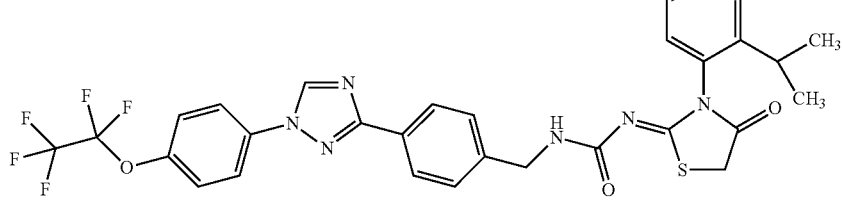

The title compound was prepared as described in Example 7 using N-(4-{1-[4-(pentafluoroethoxy)phenyl]-1H-1,2,4-triazol-3-yl}benzyl)-N'-[2-(propan-2-yl)phenyl]dicarbonimidothioic diamide (F15) and isolated as an off-white solid (0.043 g, 47%).

Preparation of (Z)-1-(3-(2-isopropyl-5-methylphenyl)-4-oxothiazolidin-2-ylidene)-3-(4-(1-(4-(perfluoroethoxy)phenyl)-1H-1,2,4-triazol-3-yl)benzyl)urea (F19)

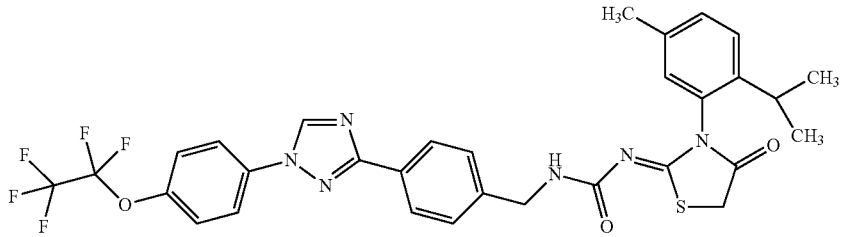 [SMILES: Cc1ccc(C(C)C)c(N2C(=O)CS/C2=N\C(=O)NCc2ccc(-c3ncn(-c4ccc(OC(F)(F)C(F)(F)F)cc4)n3)cc2)c1]

The title compound was prepared as described in Example 7 using N-[5-methyl-2-(propan-2-yl)phenyl]-N'-(4-{1-[4-(pentafluoroethoxy)phenyl]-1H-1,2,4-triazol-3-yl}benzyl) dicarbonimidothioic diamide (F16) and isolated as a white solid (0.056 g, 46%).

Example 8

Preparation of benzyl 4-bromobenzylcarbamate (C12)

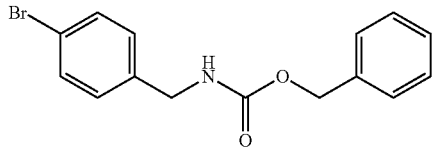 [SMILES: O=C(NCc1ccc(Br)cc1)OCc1ccccc1]

In a 500 mL round bottomed flask, equipped with a magnetic stir bar, (4-bromophenyl)methanaminium chloride (10.0 g, 44.9 mmol) and sodium hydroxide (4.00 g, 100 mmol) were dissolved in tetrahydrofuran (80 mL) and water (80 mL). The solution was cooled in an ice water bath, and benzyl chloroformate (7.06 mL, 49.4 mmol) was added dropwise. The reaction was allowed to stir for 1 hour. The reaction was poured into a brine solution and extracted with ethyl acetate (2×200 mL). The combined organic layers were dried over anhydrous magnesium sulfate, filtered, and concentrated to afford the title compound as a white solid (14.8 g, 102%): $^1$H NMR (400 MHz, DMSO-$d_6$) δ 7.92 (t, J=6.0 Hz, 1H), 7.64-7.53 (m, 2H), 7.47-7.33 (m, 5H), 7.32-7.20 (m, 2H), 5.10 (s, 2H), 4.23 (d, J=6.2 Hz, 2H); $^{13}$C NMR (101 MHz, DMSO-$d_6$) δ 156.33, 139.20, 137.05, 131.10, 129.22, 128.33, 127.72, 119.77, 65.42, 43.19; ESIMS m/z 320, 322 ([M+H]$^+$).

The following compounds were prepared in accordance to the procedure in Example 8.

Preparation of benzyl (1-(4-bromophenyl)-2-methylpropan-2-yl)carbamate (CB1)

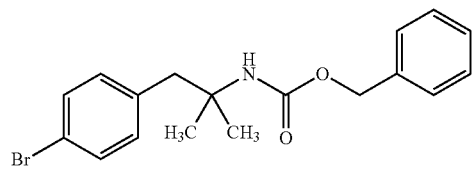 [SMILES: CC(C)(Cc1ccc(Br)cc1)NC(=O)OCc1ccccc1]

The title compound was prepared as described in Example 8 using 1-(4-bromophenyl)-2-methylpropan-2-amine and isolated as a off-white solid (6.67 g, 81%): mp 82-86° C.; $^1$H NMR (400 MHz, CDCl$_3$) δ 7.43-7.27 (m, 7H), 6.90 (d, J=8.3 Hz, 2H), 5.09 (s, 2H), 4.47 (s, 1H), 2.94 (s, 2H), 1.27 (s, 6H); $^{13}$C NMR (101 MHz, CDCl$_3$) δ 150.02, 136.77, 132.13, 131.02, 130.49, 128.54, 128.23, 128.15, 120.32, 69.73, 66.09, 53.02, 27.41; ESIMS m/z 363 ([M+H]$^+$).

Preparation of benzyl (2-(4-bromophenyl)-2-methylpropyl)carbamate (CB2)

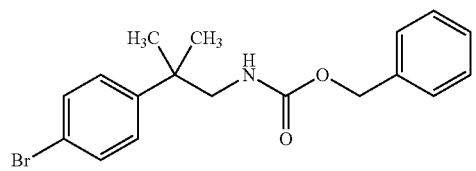 [SMILES: CC(C)(CNC(=O)OCc1ccccc1)c1ccc(Br)cc1]

The title compound was prepared as described in Example 8 using 2-(4-bromophenyl)-2-methylpropan-1-amine and isolated as a tan oil (7.83 g, 95%): $^1$H NMR (400 MHz, CDCl$_3$) δ 7.47-7.40 (m, 2H), 7.40-7.27 (m, 5H), 7.20 (d, J=8.6 Hz, 2H), 5.05 (s, 2H), 4.48 (t, J=6.1 Hz, 1H), 3.38 (d, J=6.3 Hz, 2H), 1.30 (s, 6H); $^{13}$C NMR (101 MHz, CDCl$_3$) δ 156.51, 145.44, 136.42, 131.54, 128.53, 128.17, 128.13, 127.87, 120.27, 66.77, 52.39, 38.86, 26.36; ESIMS m/z 363 ([M+H]$^+$).

Preparation of benzyl (1-(4-bromobenzyl)cyclopropyl)carbamate (CB3)

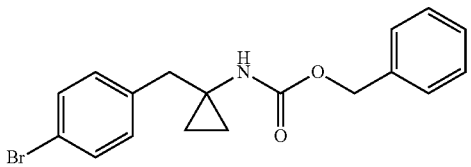 [SMILES: O=C(NC1(Cc2ccc(Br)cc2)CC1)OCc1ccccc1]

The title compound was prepared as described in Example 8 using 1-(4-bromobenzyl)cyclopropanamine (Ukrorgsyntez Ltd) and isolated as a pale yellow solid (3.33 g, 81%): mp 84-86° C., $^1$H NMR (400 MHz, CDCl$_3$) δ 7.51-7.28 (m, 7H), 5.08 (s, 2H), 2.82 (s, 2H), 0.85-0.69 (m, 4H) (NH not observed); $^{13}$C NMR (101 MHz, CDCl$_3$) δ 155.85, 136.52, 131.43, 131.07, 128.73, 128.57, 128.51, 128.14, 120.39, 66.47, 40.93, 34.36, 13.54; ESIMS m/z 362 ([M+2]$^+$).

Example 9

Preparation of benzyl 4-(4,4,5,5-tetramethyl-1,3,2-dioxaborolan-2-yl)benzylcarbamate (C13)

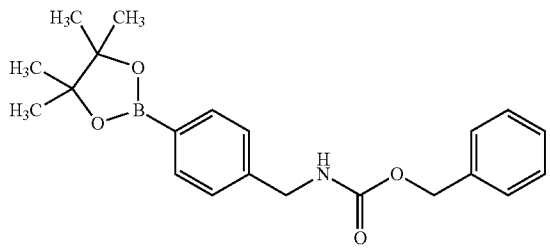 [SMILES: CC1(C)OB(c2ccc(CNC(=O)OCc3ccccc3)cc2)OC1(C)C]

In a 500 mL round bottomed flask, equipped with a magnetic stir bar, benzyl 4-bromobenzylcarbamate (C12) (14.3 g, 44.7 mmol), 4,4,4',4',5,5,5',5'-octamethyl-2,2'-bi(1,3,2-dioxaborolane) (12.5 g, 49.1 mmol), and potassium acetate (8.77 g, 89.0 mmol) were diluted with dioxane (170 mL). The suspension was sparged with nitrogen gas for 10 minutes. The [1,1'-bis(diphenylphosphino)ferrocene]dichloropalladium (II) (1.63 g, 2.23 mmol) was added as a solid. The flask was placed under nitrogen atmosphere and the reaction mixture was warmed to an internal temperature of 70° C. for 18 hours. The reaction mixture was cooled to room temperature, poured into a brine solution and extracted with ethyl acetate (3×250 mL). The combined organic layers were dried over anhydrous magnesium sulfate, filtered, and concentrated. The resulting residue was purified via flash column chromatography using 0-10% ethyl acetate/B, where B=1:1 dichloromethane:hexanes, as eluent to afford the title compound as an orange solid (11.8 g, 69%): $^1$H NMR (400 MHz, DMSO-d$_6$) δ 7.87 (t, J=6.2 Hz, 1H), 7.71-7.60 (m, 2H), 7.43-7.24 (m, 7H), 5.06 (s, 2H), 4.24 (d, J=6.2 Hz, 2H), 1.29 (s, 12H); $^{13}$C NMR (101 MHz, DMSO-d$_6$) δ 156.35, 143.18, 137.12, 134.45, 128.31, 127.69, 126.38, 83.51, 66.32, 65.37, 64.89, 43.83, 24.62; ESIMS m/z 368 ([M+H]$^+$).

The following compounds were prepared in accordance to the procedure in Example 9.

Preparation of methyl 3-(3-(4,4,5,5-tetramethyl-1,3,2-dioxaborolan-2-yl)phenyl)propanoate (C13a)

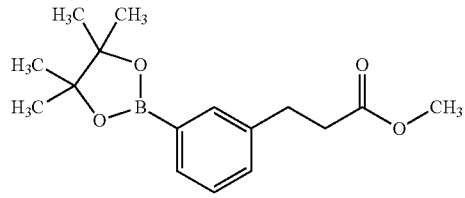

The title compound was prepared as described in Example 9 using methyl 3-(3-bromophenyl)propanoate and isolated as a tan solid (9.18 g, 75%): $^1$H NMR (400 MHz, DMSO-d$_6$) δ 7.56-7.47 (m, 2H), 7.35 (dt, J=7.7, 1.7 Hz, 1H), 7.33-7.23 (m, 1H), 3.57 (s, 3H), 2.86 (t, J=7.6 Hz, 2H), 2.62 (t, J=7.6 Hz, 2H), 1.29 (s, 12H); $^{13}$C NMR (101 MHz, DMSO-d$_6$) δ 172.57, 139.91, 134.28, 132.18, 131.32, 127.86, 83.54, 51.20, 34.88, 30.10, 24.63; EIMS m/z 290.

Preparation of 2-(4-(3-(4,4,5,5-tetramethyl-1,3,2-dioxaborolan-2-yl)phenyl)butyl)isoindoline-1,3-dione (C13b)

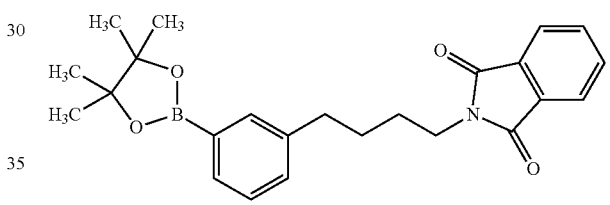

The title compound was prepared as described in Example 9 using 2-(4-(3-bromophenyl)butyl)isoindoline-1,3-dione (C57a) and isolated as a tan solid (5.50 g, 62%): $^1$H NMR (400 MHz, DMSO-d$_6$) δ 7.90-7.78 (m, 4H), 7.54-7.42 (m, 2H), 7.33-7.23 (m, 2H), 3.59 (t, J=6.5 Hz, 2H), 2.60 (t, J=7.2 Hz, 2H), 1.70-1.48 (m, 4H), 1.28 (s, 12H); $^{13}$C NMR (101 MHz, DMSO-d$_6$) δ 167.90, 141.32, 134.33, 131.83, 131.56, 131.40, 127.76, 122.93, 83.50, 37.17, 34.52, 28.49, 27.67, 24.64; ESIMS m/z 406 ([M+H]$^+$).

Preparation of 2-methyl-4-(4,4,5,5-tetramethyl-1,3,2-dioxaborolan-2-yl)benzaldehyde (CB4)

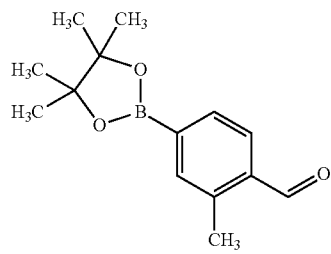 [SMILES: Cc1cc(B2OC(C)(C)C(C)(C)O2)ccc1C=O]

The title compound was prepared as described in Example 9 using 4-bromo-2-methylbenzaldehyde and isolated as a clear and colorless oil (0.623 g, 50%): $^1$H NMR (400 MHz, CDCl$_3$) δ 10.31 (s, 1H), 7.78 (d, J=0.8 Hz, 2H), 7.70 (s, 1H), 2.67 (s, 3H), 1.36 (s, 12H); $^{13}$C NMR (101 MHz, CDCl$_3$) δ 193.08, 139.40, 138.02, 135.89, 132.45, 130.86, 84.28, 24.87, 19.37; IR (thin film) cm$^{-1}$ 2978, 2927, 2728, 1700, 1355, 1194.

Preparation of 2-fluoro-4-(4,4,5,5-tetramethyl-1,3,2-dioxaborolan-2-yl)benzaldehyde (CB5)

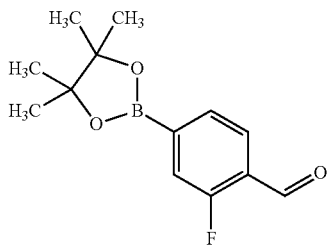

The title compound was prepared as described in Example 9 using 4-bromo-2-fluorobenzaldehyde and isolated as a white solid (4.1 g, 67%): $^1$H NMR (400 MHz, CDCl$_3$) δ 10.40 (d, J=0.8 Hz, 1H), 7.84 (dd, J=7.6, 6.7 Hz, 1H), 7.67 (dt, J=7.6, 0.8 Hz, 1H), 7.58 (dd, J=10.7, 0.9 Hz, 1H), 1.36 (s, 12H); $^{19}$F NMR (376 MHz, CDCl$_3$) δ −123.56.

Preparation of methyl 2-(3-(4,4,5,5-tetramethyl-1,3,2-dioxaborolan-2-yl)phenyl)acetate (CB6)

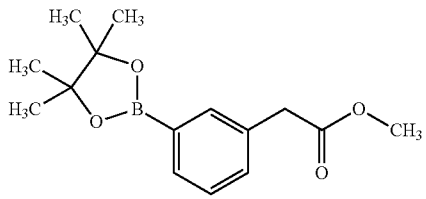

The title compound was prepared as described in Example 9 using methyl 2-(3-bromophenyl)acetate and isolated as a white solid (14.68 g, 97%, 80% pure): $^1$H NMR (400 MHz, DMSO-d$_6$) δ 7.58 (dt, J=8.4, 1.7 Hz, 2H), 7.44-7.28 (m, 2H), 3.71 (s, 2H), 3.62 (s, 3H), 1.30 (s, 12H); ESIMS m/z 276 ([M]$^+$).

Preparation of benzyl (2-methyl-1-(4-(4,4,5,5-tetramethyl-1,3,2-dioxaborolan-2-yl)phenyl)propan-2-yl)carbamate (CB7)

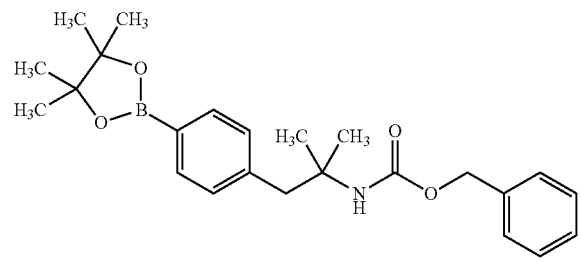 [SMILES: CC(C)(Cc1ccc(B2OC(C)(C)C(C)(C)O2)cc1)NC(=O)OCc1ccccc1]

The title compound was prepared as described in Example 9 using benzyl (1-(4-bromophenyl)-2-methylpropan-2-yl) carbamate (CB1) and isolated as a clear oil (6.12 g, 80%): $^1$H NMR (400 MHz, CDCl$_3$) δ 7.69 (d, J=7.9 Hz, 2H), 7.38 (d, J=5.6 Hz, 5H), 7.10 (d, J=7.9 Hz, 2H), 5.09 (s, 2H), 4.51 (s, 1H), 3.00 (s, 2H), 1.34 (s, 12H), 1.29 (s, 6H); $^{13}$C NMR (101 MHz, CDCl$_3$) δ 152.73, 141.11, 136.77, 134.45, 129.95, 128.52, 128.10, 128.06, 83.71, 66.09, 54.47, 53.21, 27.43, 24.88; ESIMS m/z 410 ([M+H]$^+$).

Preparation of benzyl (2-methyl-2-(4-(4,4,5,5-tetramethyl-1,3,2-dioxaborolan-2-yl)phenyl)propyl) carbamate (CB8)

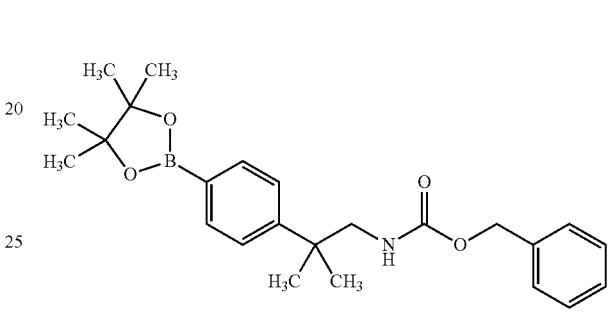

The title compound was prepared as described in Example 9 using benzyl (2-(4-bromophenyl)-2-methylpropyl)carbamate (CB2) and isolated as a pale yellow oil (8.47 g, 95%): $^1$H NMR (400 MHz, CDCl$_3$) δ 7.81-7.73 (m, 2H), 7.32 (dtd, J=14.5, 7.4, 6.8, 2.7 Hz, 7H), 5.04 (s, 2H), 4.50-4.37 (m, 1H), 3.41 (d, J=6.3 Hz, 2H), 1.34 (s, 12H), 1.33 (s, 6H); $^{13}$C NMR (101 MHz, CDCl$_3$) δ 156.56, 149.64, 136.52, 135.07, 131.54, 128.48, 128.06, 127.87, 125.34, 83.77, 66.66, 52.46, 39.15, 26.36, 24.86; ESIMS m/z 410 ([M+H]$^+$).

Preparation of benzyl (1-(4-(4,4,5,5-tetramethyl-1,3,2-dioxaborolan-2-yl)benzyl)cyclopropyl)carbamate (CB9)

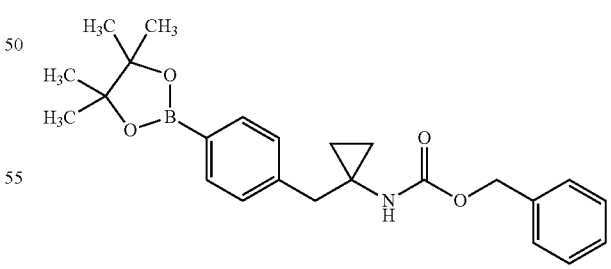

The title compound was prepared as described in Example 9 using benzyl (1-(4-bromobenzyl)cyclopropyl)carbamate (CB3) and purified using ethyl acetate/hexanes as eluent; isolated as a white solid (2.53 g, 67%): mp 102-104° C.; $^1$H NMR (400 MHz, CDCl$_3$) δ 7.79-7.63 (m, 2H), 7.51-7.28 (m, 5H), 7.16 (d, J=7.5 Hz, 2H), 5.08 (s, 2H), 4.90 (s, 1H), 2.89 (s, 2H), 1.34 (s, 12H), 0.80 (s, 4H); ESIMS m/z 408 ([M+H]$^+$).

Example 10

Preparation of benzyl 4-(1-(4-(trifluoromethoxy)phenyl)-1H-1,2,4-triazol-3-yl)benzylcarbamate (C14)

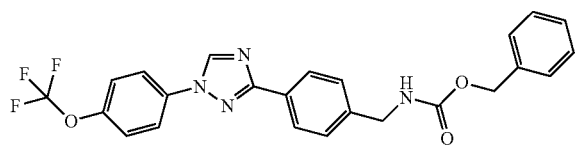 [SMILES: O=C(NCc1ccc(-c2ncn(-c3ccc(OC(F)(F)F)cc3)n2)cc1)OCc1ccccc1]

In a 50 mL round bottomed flask, equipped with a magnetic stir bar, 3-bromo-1-(4-(trifluoromethoxy)phenyl)-1H-1,2,4-triazole (C1) (1.0 g, 3.3 mmol), benzyl 4-(4,4,5,5-tetramethyl-1,3,2-dioxaborolan-2-yl)benzylcarbamate (C13) (1.3 g, 3.6 mmol), bistriphenylphosphine dichloropalladium(II) (0.120 g, 0.171 mmol), and potassium phosphate (1.38 g, 6.49 mmol) were charged as solids. The flask was sealed and placed under nitrogen atmosphere. Dioxane (17.3 mL) and water (4.3 mL) were added. The reaction was warmed to an internal temperature of 65° C. for 18 hours. The reaction mixture was cooled to room temperature, poured into a brine solution and extracted with ethyl acetate (3×75 mL). The combined organic layers were dried over anhydrous magnesium sulfate, filtered, and concentrated. The resulting residue was purified via flash column chromatography using 0-50% ethyl acetate/hexanes as eluent to afford the title compound as a white solid (0.850 g, 56%): $^1$H NMR (400 MHz, DMSO-$d_6$) δ 9.40 (s, 1H), 8.17-8.00 (m, 4H), 7.91 (t, J=6.2 Hz, 1H), 7.72-7.59 (m, 2H), 7.46-7.12 (m, 7H), 5.07 (s, 2H), 4.29 (d, J=6.1 Hz, 2H); $^{19}$F NMR (376 MHz, DMSO-$d_6$) δ −56.96; ESIMS m/z 469 ([M+H]$^+$).

The following compounds were prepared in accordance to the procedure in Example 10.

Preparation of benzyl 4-(1-(4-(trifluoromethyl)phenyl)-1H-1,2,4-triazol-3-yl)benzylcarbamate (C15)

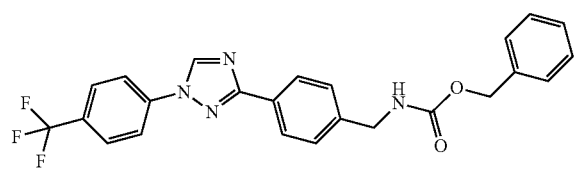 [SMILES: O=C(NCc1ccc(-c2ncn(-c3ccc(C(F)(F)F)cc3)n2)cc1)OCc1ccccc1]

The title compound was prepared as described in Example 10 using 3-bromo-1-(4-(trifluoromethyl)phenyl)-1H-1,2,4-triazole (C1b), benzyl 4-(4,4,5,5-tetramethyl-1,3,2-dioxaborolan-2-yl)benzylcarbamate (C13), tri-tert-butylphosphonium tetrafluoroborate, palladium(II) acetate, and cesium fluoride and isolated as a white solid (0.846 g, 36%): $^1$H NMR (400 MHz, DMSO-$d_6$) δ 9.53 (s, 1H), 8.28-8.14 (m, 2H), 8.16-8.04 (m, 2H), 8.04-7.95 (m, 2H), 7.92 (t, J=6.2 Hz, 1H), 7.49-7.13 (m, 7H), 5.07 (s, 2H), 4.29 (d, J=6.2 Hz, 2H); $^{19}$F NMR (376 MHz, DMSO-$d_6$) δ −60.79; ESIMS m/z 453 ([M+H]$^+$).

Preparation of methyl 3-(3-(1-(4-(trifluoromethoxy)phenyl)-1H-1,2,4-triazol-3-yl)phenyl)propanoate (CA1)

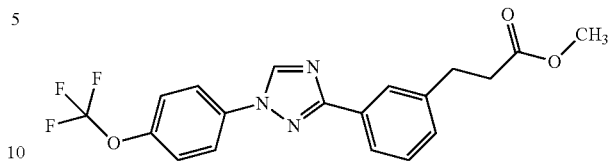

The title compound was prepared as described in Example 10 using 3-bromo-1-(4-(trifluoromethoxy)phenyl)-1H-1,2,4-triazole (C1), methyl 3-(3-(4,4,5,5-tetramethyl-1,3,2-dioxaborolan-2-yl)phenyl)propanoate (C13a), and [1,1'-bis(di-tert-butylphosphino)ferrocene]dichloropalladium(II) at 80° C. and isolated as a dark orange solid (9.86 g, 91%): $^1$H NMR (400 MHz, DMSO-$d_6$) δ 9.40 (s, 1H), 8.12-8.03 (m, 2H), 8.01-7.91 (m, 2H), 7.66-7.58 (m, 2H), 7.49-7.40 (m, 1H), 7.34 (dt, J=7.8, 1.6 Hz, 1H), 3.59 (s, 3H), 2.95 (t, J=7.5 Hz, 2H), 2.70 (t, J=7.6 Hz, 2H); $^{19}$F NMR (376 MHz, DMSO-$d_6$) δ −57.01; ESIMS m/z 392 ([M+H]$^+$).

Preparation of 2-(4-(3-(1-(4-(trifluoromethoxy)phenyl)-1H-1,2,4-triazol-3-yl)phenyl)butyl)isoindoline-1,3-dione (CA2)

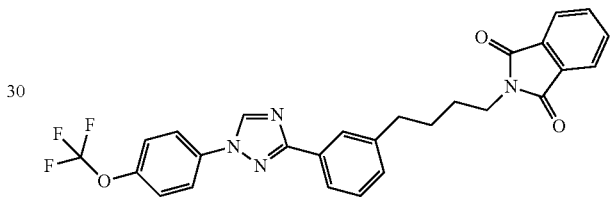

The title compound was prepared as described in Example 10 using 3-bromo-1-(4-(trifluoromethoxy)phenyl)-1H-1,2,4-triazole (C1), 2-(4-(3-(4,4,5,5-tetramethyl-1,3,2-dioxaborolan-2-yl)phenyl)butyl)isoindoline-1,3-dione (C13b), and [1,1'-bis(di-tert-butylphosphino)ferrocene]dichloropalladium(II) at 75° C. and isolated as a dark orange solid (5.48 g, 82%): $^1$H NMR (400 MHz, DMSO-$d_6$) δ 9.39 (s, 1H), 8.13-8.04 (m, 2H), 7.96-7.89 (m, 2H), 7.88-7.77 (m, 4H), 7.67-7.57 (m, 2H), 7.45-7.38 (m, 1H), 7.31 (dt, J=7.7, 1.5 Hz, 1H), 3.69-3.53 (m, 2H), 2.70 (t, J=6.8 Hz, 2H), 1.64 (dq, J=6.6, 3.1 Hz, 4H); $^{19}$F NMR (376 MHz, DMSO-$d_6$) δ −56.97; ESIMS m/z 507 ([M+H]$^+$).

Preparation of 3-(2',3',4',5'-tetrahydro-[1,1'-biphenyl]-4-yl)-1-(4-(trifluoromethoxy)phenyl)-1H-1,2,4-triazole (CB10)

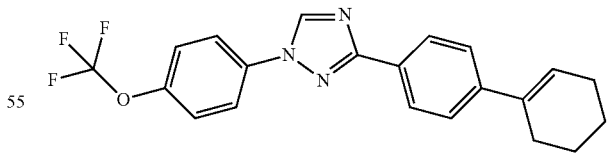

The title compound was prepared as described in Example 10 using 3-(4-bromophenyl)-1-(4-(trifluoromethoxy)phenyl)-1H-1,2,4-triazole (C52) with tetrakis(triphenylphosphine)palladium(0) as catalyst, sodium carbonate as base and heating to 100° C. for 3 hours; isolated as an orange solid (2.18 g, 57%, 79% pure): $^1$H NMR (400 MHz, CDCl$_3$) δ 8.56 (s, 1H), 8.15-8.06 (m, 2H), 7.80 (dd, J=9.0, 2.3 Hz, 2H), 7.50 (d, J=8.4 Hz, 2H), 7.39 (ddd, J=8.0, 2.5, 1.3 Hz, 2H), 6.28-6.21 (m, 1H), 2.46 (ddt, J=6.3, 4.1, 2.0 Hz, 2H), 2.24 (dtd, J=6.3, 3.8, 1.8 Hz, 2H), 1.85-1.75 (m, 2H), 1.71-1.63 (m, 2H); $^{19}$F NMR (376 MHz, DMSO-$d_6$) δ −58.03; ESIMS m/z 386 ([M+H]$^+$).

Preparation of methyl 2-(3-(1-(4-(trifluoromethoxy)phenyl)-1H-1,2,4-triazol-3-yl)phenyl)acetate (CB11)

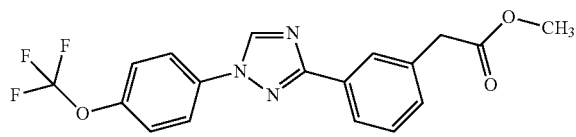

The title compound was prepared as described in Example 10 using methyl 2-(3-(4,4,5,5-tetramethyl-1,3,2-dioxaborolan-2-yl)phenyl)acetate (CB6) using [1,1'-bis(di-tert-butylphosphino)ferrocene]dichloropalladium(II) as catalyst, sodium carbonate as base and heating to 75° C. for 30 hours; isolated as a pink solid (4.96 g, 72%): $^1$H NMR (400 MHz, DMSO-$d_6$) δ 9.41 (s, 1H), 8.12-8.05 (m, 2H), 8.05-7.98 (m, 2H), 7.61 (ddt, J=7.9, 2.0, 1.0 Hz, 2H), 7.47 (td, J=7.6, 0.6 Hz, 1H), 7.38 (ddd, J=7.6, 2.0, 1.2 Hz, 1H), 3.81 (s, 2H), 3.64 (s, 3H); $^{19}$F NMR (376 MHz, DMSO-$d_6$) δ −57.06; ESIMS m/z 378 ([M+H]$^+$).

Example 10a

Preparation of tert-butyl 4-(1-(4-(trifluoromethoxy)phenyl)-1H-1,2,4-triazol-3-yl)benzylcarbamate (C15a)

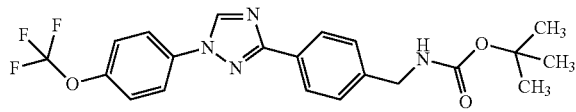 [SMILES: CC(C)(C)OC(=O)NCc1ccc(-c2ncn(-c3ccc(OC(F)(F)F)cc3)n2)cc1]

In a 20 mL vial (2-(4-(1-(4-(trifluoromethoxy)phenyl)-1H-1,2,4-triazol-3-yl)phenyl)acetyl azide/2-(4-(1-(4-(trifluoromethoxy)phenyl)-1H-1,2,4-triazol-3-yl)phenyl)methyl isocyanate (C9) (0.205 g, 0.528 mmol) was diluted with tert-butanol (10.0 mL, 105 mmol). The solution was heated to 80° C. overnight. The reaction was cooled and poured into a brine solution and extracted with ethyl acetate (4×). The combined organics were dried over magnesium sulfate, filtered, and concentrated. The resulting residue was purified by flash column chromatography using 0-40% ethyl acetate/B, where B=1:1 dichloromethane/hexanes, as eluent provided the title compound as a white solid (0.0890 g, 39%): $^1$H NMR (400 MHz, DMSO-$d_6$) δ 9.40 (s, 1H), 8.15-8.01 (m, 4H), 7.63 (dp, J=7.9, 1.0 Hz, 2H), 7.47 (t, J=6.1 Hz, 1H), 7.42-7.35 (m, 2H), 4.20 (d, J=6.2 Hz, 2H), 1.41 (s, 9H); $^{19}$F NMR (376 MHz, DMSO-$d_6$) δ −56.96; ESIMS m/z 435 ([M+H]$^+$).

Example 11

Preparation of (4-(1-(4-(trifluoromethoxy)phenyl)-1H-1,2,4-triazol-3-yl)phenyl)methanamine (C16)

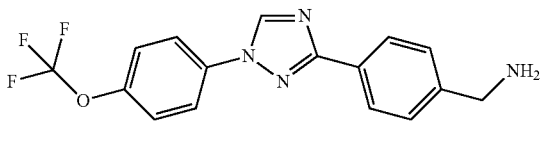 [SMILES: NCc1ccc(-c2ncn(-c3ccc(OC(F)(F)F)cc3)n2)cc1]

In a 200 mL round bottomed flask equipped with a magnetic stir bar, benzyl 4-(1-(4-(trifluoromethoxy)phenyl)-1H-1,2,4-triazol-3-yl)benzylcarbamate (C14) (0.850 g, 1.82 mmol) was diluted with a solution of hydrogen bromide in acetic acid (33 wt %, 15.0 mL, 1.82 mmol). The suspension was allowed to stir for 1 hour. Diethyl ether (150 mL) was added, and the reaction mixture was stirred for an additional 30 minutes. The resulting precipitate was collected via filtration and treated with aqueous sodium hydroxide. The resulting suspension was extracted with ethyl acetate (3×75 mL). The combined organic layers were dried over anhydrous magnesium sulfate, filtered, and concentrated to afford the title compound as a white solid (0.448 g, 74%): $^1$H NMR (400 MHz, DMSO-$d_6$) δ 9.39 (s, 1H), 8.07 (dd, J=10.6, 8.6 Hz, 4H), 7.69-7.56 (m, 2H), 7.48 (d, J=8.2 Hz, 2H), 3.79 (s, 2H); $^{19}$F NMR (376 MHz, DMSO-$d_6$) δ −56.98; ESMIS m/z 318 ([M+H]$^+$) (—NH$_2$).

The following compounds were prepared in accordance to the procedure in Example 11.

Preparation of (4-(1-(4-(trifluoromethyl)phenyl)-1H-1,2,4-triazol-3-yl)phenyl)methanamine (CA3)

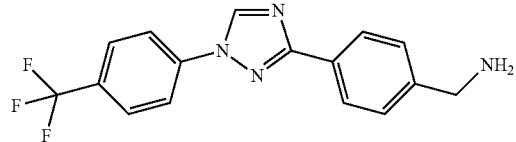 [SMILES: NCc1ccc(-c2ncn(-c3ccc(C(F)(F)F)cc3)n2)cc1]

The title compound was prepared as described in Example 11 from benzyl 4-(1-(4-(trifluoromethyl)phenyl)-1H-1,2,4-triazol-3-yl)benzylcarbamate (C15) and isolated as a tan solid (4.67 g, 79%): $^1$H NMR (400 MHz, DMSO-$d_6$) δ 9.52 (s, 1H), 8.21 (d, J=8.3 Hz, 2H), 8.09 (d, J=7.9 Hz, 2H), 8.00 (d, J=8.4 Hz, 2H), 7.51 (d, J=7.9 Hz, 2H), 3.82 (s, 2H).

Example 12

Preparation of N-[5-methyl-2-(propan-2-yl)phenyl]-N'-(4-{1-[4-(trifluoromethoxy)phenyl]-1H-1,2,4-triazol-3-yl}benzyl)dicarbonimidothioic diamide (F35)

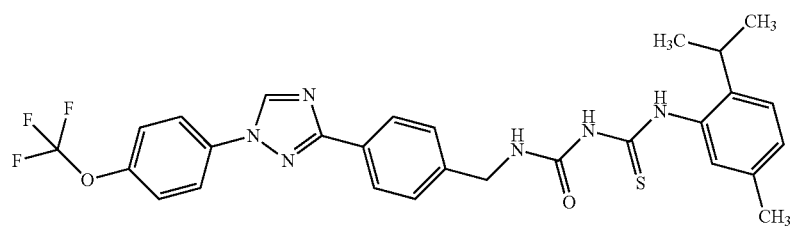 [SMILES: Cc1ccc(C(C)C)c(NC(=S)NC(=O)NCc2ccc(-c3ncn(-c4ccc(OC(F)(F)F)cc4)n3)cc2)c1]

In a 200 mL round bottomed flask equipped with a magnetic stir bar, (4-(1-(4-(trifluoromethoxy)phenyl)-1H-1,2,4-triazol-3-yl)phenyl)methanamine (C16) (0.448 g, 1.34 mmol) was diluted with tetrahydrofuran (9.0 mL). To the suspension was added triphosgene (0.398 g, 1.34 mmol) and triethylamine (0.374 mL, 2.68 mmol). The resulting suspension was stirred for 1 hour at room temperature. UPLC analysis of a methanol-quenched aliquot shows a mixture of the methyl carbamate and the isocyanate. To the reaction mixture 1-(2-isopropyl-5-methylphenyl)thiourea (0.279 g, 1.34 mmol) and cesium carbonate (0.480 g, 1.47 mmol) were added. The reaction mixture was allowed to stir at room temperature for 18 hours. An additional portion of 1-(2-isopropyl-5-methylphenyl)thiourea (0.279 g, 1.34 mmol) and cesium carbonate (0.480 g, 1.47 mmol) were added and the reaction mixture was warmed to an internal temperature of 60° C. for 1 hour. The reaction mixture was poured into water and extracted with ethyl acetate (3×75 mL). The combined organic layers were dried over anhydrous magnesium sulfate, filtered, and concentrated. The resulting residue was purified by reverse-phase flash column ($C_{18}$ column) chromatography using 5-100% acetonitrile/water as eluent followed by flash column chromatography using 0-100% ethyl acetate/hexanes as eluent to give the title compound as a white solid (0.007 g, 0.9%).

Example 13

Preparation of (E)-ethyl 3-(4-(1-(4-(trifluoromethoxy)phenyl)-1H-1,2,4-triazol-3-yl)phenyl)acrylate (C17)

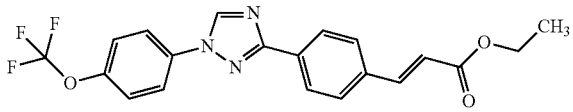 [SMILES: CCOC(=O)/C=C/c1ccc(-c2ncn(-c3ccc(OC(F)(F)F)cc3)n2)cc1]

To an oven-dried 2 L three-necked round bottomed flask equipped with a stirring bar was added sodium hydride (60% oil immersion, 7.20 g, 180 mmol) as a solid that was pre-weighed into a 25-mL vial. This was diluted with anhydrous tetrahydrofuran (1 L) under nitrogen, and the solution was stirred in an ice bath. Ethyl 2-(diethoxyphosphoryl)acetate (30.0 mL, 151 mmol) was added dropwise in portions over 20 minutes, and the reaction was stirred at 0° C. for an additional 2 hours. 4-(1-(4-(Trifluoromethoxy)phenyl)-1H-1,2,4-triazol-3-yl)benzaldehyde (50.0 g, 150 mmol) was added in solid portions over 20 minutes, and the reaction turned orange. After stirring for 30 minutes, the ice bath was removed and the reaction was warmed to room temperature over 1 hour. The reaction was quenched with slow addition of saturated aqueous ammonium chloride (500 mL) and allowed to stand at room temperature overnight. The biphasic reaction mixture was diluted with water and extracted with 1:1 ethyl acetate/hexanes (3×). The combined organic layers were dried over anhydrous sodium sulfate, filtered, and concentrated to afford the title compound as an orange solid (61.4 g, 100%): mp 135-137° C.; $^1$H NMR (400 MHz, CDCl$_3$) δ 8.59 (s, 1H), 8.22 (d, J=8.4 Hz, 2H), 7.85-7.77 (m, 2H), 7.73 (d, J=16.0 Hz, 1H), 7.64 (d, J=8.3 Hz, 2H), 7.40 (d, J=8.3 Hz, 2H), 6.51 (d, J=16.0 Hz, 1H), 4.29 (q, J=7.1 Hz, 2H), 1.35 (t, J=7.1 Hz, 3H); $^{19}$F NMR (376 MHz, CDCl$_3$) δ −58.02; ESIMS m/z 404 ([M+H]$^+$).

The following compounds were prepared in accordance to the procedure in Example 13.

Preparation of (E)-ethyl 3-(4-(1-(4-(perfluoroethoxy)phenyl)-1H-1,2,4-triazol-3-yl)phenyl)acrylate (C18)

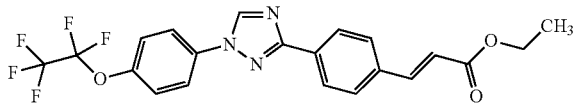 [SMILES: CCOC(=O)/C=C/c1ccc(-c2ncn(-c3ccc(OC(F)(F)C(F)(F)F)cc3)n2)cc1]

The title compound was prepared as described in Example 13 from 4-(1-(4-(perfluoroethoxy)phenyl)-1H-1,2,4-triazol-3-yl)benzaldehyde and isolated as a white solid (2.08 g, 100%): mp 149-153° C.; $^1$H NMR (400 MHz, CDCl$_3$) δ 8.59 (s, 1H), 8.32-8.16 (m, 2H), 7.89-7.77 (m, 2H), 7.73 (d, J=16.0 Hz, 1H), 7.68-7.58 (m, 2H), 7.47-7.35 (m, 2H), 6.51 (d, J=16.0 Hz, 1H), 4.29 (q, J=7.1 Hz, 2H), 1.35 (t, J=7.1 Hz, 3H); $^{19}$F NMR (376 MHz, CDCl$_3$) δ −85.89, −87.85, −87.86; ESIMS m/z 454 ([M+H]$^+$).

Preparation of (E)-ethyl 2-methyl-3-(4-(1-(4-(trifluoromethoxy)phenyl)-1H-1,2,4-triazol-3-yl)phenyl)but-2-enoate (CA4)


The title compound was prepared as described in Example 13 from 1-(4-(1-(4-(trifluoromethoxy)phenyl)-1H-1,2,4-triazol-3-yl)phenyl)ethanone (C25) and ethyl 2-(diethoxyphosphoryl)propanoate and isolated as a pale yellow solid (0.480 g, 27%): mp 68-70° C.; $^1$H NMR (400 MHz, CDCl$_3$) δ 8.58 (s, 1H), 8.22-8.13 (m, 2H), 7.86-7.77 (m, 2H), 7.40 (dt, J=8.0, 1.0 Hz, 2H), 7.31-7.25 (m, 2H), 4.28 (q, J=7.1 Hz, 2H), 2.29 (q, J=1.5 Hz, 3H), 1.80 (q, J=1.5 Hz, 3H), 1.36 (t, J=7.1 Hz, 3H); $^{19}$F NMR (376 MHz, CDCl$_3$) δ −58.03; $^{13}$C NMR (101 MHz, CDCl$_3$) δ 169.91, 163.24, 148.37, 144.86, 144.66, 141.54, 135.56, 129.10, 127.77, 126.57, 125.32, 122.42, 121.18, 60.45, 22.94, 17.45, 14.32; ESIMS m/z 432 ([M+H]$^+$).

Preparation of (E)-ethyl 3-(4-(1-(4-(trifluoromethyl)phenyl)-1H-1,2,4-triazol-3-yl)phenyl)acrylate (CA5)

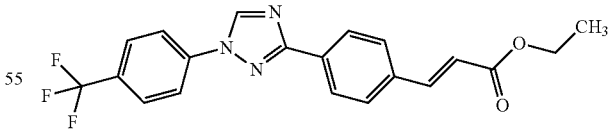

The title compound was prepared as described in Example 13 from 4-(1-(4-(trifluoromethyl)phenyl)-1H-1,2,4-triazol-3-yl)benzaldehyde and isolated as a pale yellow solid (4.02 g, 100%): mp 135-140° C.; $^1$H NMR (400 MHz, CDCl$_3$) δ 8.67 (s, 1H), 8.23 (d, J=8.3 Hz, 2H), 7.95-7.88 (m, 2H), 7.81 (dt, J=8.3, 0.7 Hz, 2H), 7.73 (d, J=16.0 Hz, 1H), 7.69-7.56 (m, 2H), 6.51 (d, J=16.0 Hz, 1H), 4.29 (q, J=7.1 Hz, 2H), 1.41-1.31 (m, 3H); $^{19}$F NMR (376 MHz, CDCl$_3$) δ −62.50; ESIMS m/z 388 ([M+H]$^+$).

Preparation of (E)-ethyl 3-(2-methyl-4-(1-(4-(trifluoromethoxy)phenyl)-1H-1,2,4-triazol-3-yl)phenyl)acrylate (CB12)

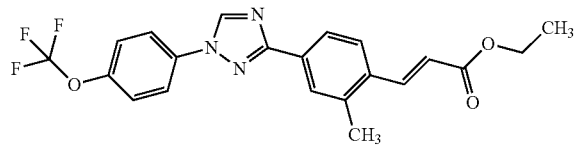

The title compound was prepared as described in Example 13 from 2-methyl-4-(1-(4-(trifluoromethoxy)phenyl)-1H-1,2,4-triazol-3-yl)benzaldehyde (CB35) and isolated as a white solid (1.16 g, 98%): mp 157-160° C.; $^1$H NMR (400 MHz, CDCl$_3$) δ 8.58 (s, 1H), 8.10-7.96 (m, 3H), 7.84-7.76 (m, 2H), 7.68 (d, J=8.1 Hz, 1H), 7.40 (dt, J=8.1, 1.0 Hz, 2H), 6.44 (d, J=15.9 Hz, 1H), 4.29 (q, J=7.1 Hz, 2H), 2.53 (s, 3H), 1.36 (t, J=7.1 Hz, 3H); $^{19}$F NMR (376 MHz, CDCl$_3$) δ −58.02; ESIMS m/z 418 ([M+H]$^+$).

Preparation of (E)-ethyl 3-(2-fluoro-4-(1-(4-(trifluoromethoxy)phenyl)-1H-1,2,4-triazol-3-yl)phenyl)acrylate (CB13)

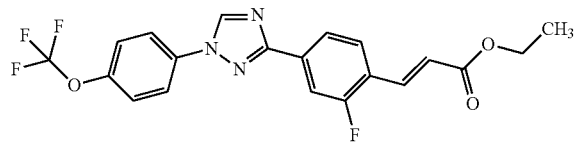 [SMILES: CCOC(=O)/C=C/c1ccc(-c2ncn(-c3ccc(OC(F)(F)F)cc3)n2)cc1F]

The title compound was prepared as described in Example 13 from 2-fluoro-4-(1-(4-(trifluoromethoxy)phenyl)-1H-1,2,4-triazol-3-yl)benzaldehyde (CB36) and isolated as a light orange solid (1.1 g, 92%): $^1$H NMR (400 MHz, CDCl$_3$) δ 8.58 (s, 1H), 8.03-7.91 (m, 2H), 7.80 (d, J=9.0 Hz, 2H), 7.65 (t, J=7.8 Hz, 1H), 7.40 (dt, J=8.1, 1.0 Hz, 2H), 6.63 (s, 1H), 6.59 (s, 1H), 4.29 (q, J=7.1 Hz, 2H), 1.35 (t, J=7.1 Hz, 3H); ESIMS m/z 422 ([M+H]$^+$).

Preparation of (E/Z)-ethyl 2-(4-(1-(4-(trifluoromethoxy)phenyl)-1H-1,2,4-triazol-3-yl)benzylidene)butanoate (CB14)

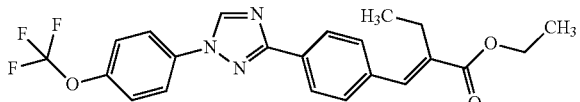

The title compound was prepared as described in Example 13 from 4-(1-(4-(trifluoromethoxy)phenyl)-1H-1,2,4-triazol-3-yl)benzaldehyde and ethyl 2-(diethoxyphosphoryl)butanoate; isolated as a yellow solid (4.36 g, 102%) as mixture of E and Z isomers: $^1$H NMR (400 MHz, CDCl$_3$) δ 8.66-8.53 (m, 1H), 8.29-8.10 (m, 2H), 7.86-7.66 (m, 3H), 7.58-7.48 (m, 2H), 7.44-7.31 (m, 2H), 4.23 (dq, J=53.7, 7.1 Hz, 2H), 2.70-2.42 (m, 2H), 1.42-1.09 (m, 6H); $^{19}$F NMR (376 MHz, CDCl$_3$) δ −58.02; ESIMS m/z 432 ([M+H]$^+$).

Example 14

Preparation of ethyl 2-(4-(1-(4-(trifluoromethoxy)phenyl)-1H-1,2,4-triazol-3-yl)phenyl)cyclopropanecarboxylate (C19)

To an oven-dried round bottomed flask was added sodium hydride (60% oil immersion, 0.380 g, 9.50 mmol) and anhydrous dimethyl sulfoxide (30 mL). Gas evolution occurred, and the solution was stirred at room temperature for 15 minutes. Trimethylsulfoxonium iodide (2.10 g, 9.54 mmol) was added, the flask neck was rinsed with anhydrous dimethyl sulfoxide (5 mL), and the reaction was stirred for 15 minutes. To the reaction was added (E)-ethyl 3-(4-(1-(4-(trifluoromethoxy)phenyl)-1H-1,2,4-triazol-3-yl)phenyl)acrylate (C17) (3.22 g, 7.98 mmol) as a solid. The reaction was stirred at room temperature for 30 minutes, and then quenched with water and extracted with 1:1 ethyl acetate/hexanes (2×). The combined organic layers were washed with water (3×), dried over anhydrous sodium sulfate, filtered, and concentrated to afford the title compound as a yellow oil (1.50 g, 41%): $^1$H NMR (400 MHz, CDCl$_3$) δ 8.55 (s, 1H), 8.10 (d, J=8.4 Hz, 2H), 7.80 (d, J=9.1 Hz, 2H), 7.39 (dd, J=6.6, 5.9 Hz, 2H), 7.20 (d, J=8.3 Hz, 2H), 4.19 (dt, J=14.0, 7.0 Hz, 2H), 2.64-2.52 (m, 2H), 1.97 (ddd, J=8.5, 5.3, 4.2 Hz, 1H), 1.71-1.61 (m, 1H), 1.42-1.32 (m, 1H), 1.29 (t, J=7.1 Hz, 3H); $^{19}$F NMR (376 MHz, CDCl$_3$) δ −58.03; ESIMS m/z 418 ([M+H]$^+$).

Example 15

Preparation of 2-(4-(1-(4-(trifluoromethoxy)phenyl)-1H-1,2,4-triazol-3-yl)phenyl)cyclopropanecarboxylic acid (C20)

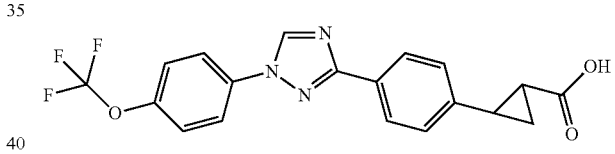

To ethyl 2-(4-(1-(4-(trifluoromethoxy)phenyl)-1H-1,2,4-triazol-3-yl)phenyl)-cyclopropane-carboxylate (C19) (1.50 g, 3.59 mmol) in methanol (24 mL) was added sodium hydroxide (2 N, 7.20 mL, 14.4 mmol) and stirred at room temperature for 4 hours. The reaction was acidified with hydrogen chloride (2 N) and the methanol was evaporated off under vacuum. The aqueous solution was extracted with ethyl acetate (2×), dried over anhydrous sodium sulfate, filtered, and concentrated to afford the title compound as a yellow oil (1.62 g, 98%): $^1$H NMR (400 MHz, CDCl$_3$) δ 8.58 (s, 1H), 8.13-8.08 (m, 2H), 7.83-7.77 (m, 3H), 7.40 (t, J=5.9 Hz, 4H), 7.22 (d, J=8.3 Hz, 2H), 2.65 (ddd, J=6.7, 5.3, 2.8 Hz, 2H), 2.03-1.95 (m, 1H), 1.76-1.66 (m, 2H), 1.47 (ddd, J=8.4, 6.6, 4.7 Hz, 2H); $^{19}$F NMR (376 MHz, CDCl$_3$) δ −58.03; ESIMS m/z 390 ([M+H]$^+$).

Example 16

Preparation 2-(4-(1-(4-(trifluoromethoxy)phenyl)-1H-1,2,4-triazol-3-yl)phenyl)cyclopropanecarbonyl azide (C21)

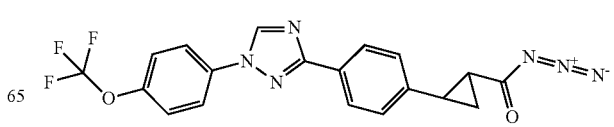

To 2-(4-(1-(4-(trifluoromethoxy)phenyl)-1H-1,2,4-triazol-3-yl)phenyl)-cyclopropanecarboxylic acid (C20) (2.49 g, 6.40 mmol) in toluene (30 mL) was added triethylamine (2.20 mL, 16.0 mmol), followed by diphenyl phosphorazidate (1.70 mL, 8.00 mmol). The yellow solution was stirred overnight at room temperature. The reaction was quenched with water and saturated aqueous sodium bicarbonate, extracted with 1:1 ethyl acetate/hexanes (2×), dried over anhydrous sodium sulfate, and filtered. The crude compound was adsorbed onto silica gel and purified by flash column chromatography using 0-100% ethyl acetate/hexanes as eluent to afford the title compound as a yellow oil (1.94 g, 73%): $^1$H NMR (400 MHz, CDCl$_3$) δ 8.56 (s, 1H), 8.16-8.03 (m, 2H), 7.83-7.72 (m, 2H), 7.44-7.34 (m, 2H), 7.20 (d, J=8.2 Hz, 2H), 2.70 (ddd, J=9.3, 6.8, 4.1 Hz, 1H), 1.98 (ddd, J=8.4, 5.3, 4.1 Hz, 1H), 1.78 (dt, J=9.4, 5.0 Hz, 1H), 1.53 (ddd, J=8.3, 6.8, 4.7 Hz, 1H); $^{19}$F NMR (376 MHz, CDCl$_3$) δ −58.03.

Example 17

Preparation of N-[2-(propan-2-yl)phenyl]-N'-,2-(4-{1-[4-(trifluoro methoxy)phenyl]-1H-1,2,4-triazol-3-yl}phenyl)cyclopropyl]dicarbonimidothioic diamide
(F22)

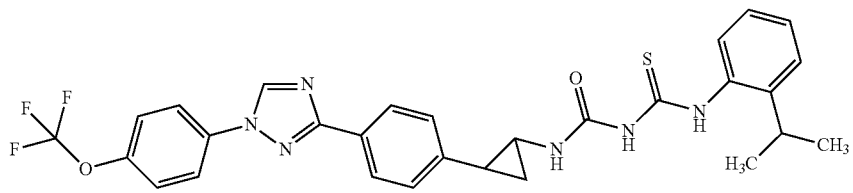 [SMILES: CC(C)c1ccccc1NC(=S)NC(=O)NC1CC1c1ccc(-c2ncn(-c3ccc(OC(F)(F)F)cc3)n2)cc1]

A solution of (2-(4-(1-(4-(trifluoromethoxy)phenyl)-1H-1,2,4-triazol-3-yl)phenyl)cyclopropanecarbonyl azide (C21) (0.250 g, 0.600 mmol) in 1,2-dichloroethane (3 mL) was heated at 80° C. for 3 hours. The reaction was cooled and 2-(isopropylphenyl)thiourea (0.129 g, 0.660 mmol) and cesium carbonate (0.443 g, 1.36 mmol) were added. The reaction mixture was stirred at room temperature overnight, and then diluted with ethyl acetate and washed with water. The organic layer was dried over anhydrous sodium sulfate, filtered, and concentrated. The crude compound was loaded onto a Celite® cartridge with dichloromethane and purified by flash column chromatography using 0-40% ethyl acetate/B, where B=1:1 dichloromethane/hexanes, as eluent to afford the title compound as a white solid (0.108 g, 31%).

The following compounds were prepared in accordance to the procedure in Example 17.

Preparation of N-(2-propylphenyl)-N'-[(2-(4-{1-[4-(trifluoromethoxy)phenyl]-1H-1,2,4-triazol-3-yl}phenyl)cyclopropyl]dicarbonimidothioic diamide
(F23)

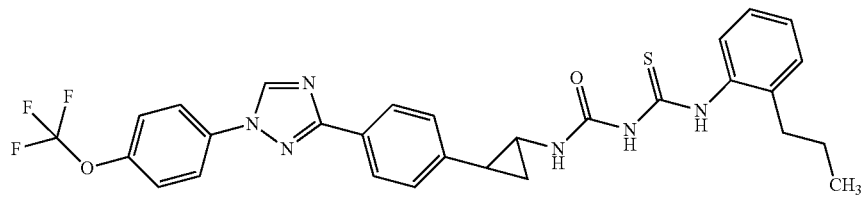 [SMILES: CCCc1ccccc1NC(=S)NC(=O)NC1CC1c1ccc(-c2ncn(-c3ccc(OC(F)(F)F)cc3)n2)cc1]

The title compound was prepared as described in Example 17 using (2-(4-(1-(4-(trifluoromethoxy)phenyl)-1H-1,2,4-triazol-3-yl)phenyl)cyclopropanecarbonyl azide (C21) and 1-(2-propylphenyl)thiourea and isolated as an off-white solid (0.059 g, 18%).

Preparation of N-(2-ethyl-6-methylphenyl)-N'-[2-(4-{1-[4-(trifluoromethoxy)phenyl]-1H-1,2,4-triazol-3-yl}phenyl)cyclopropyl]dicarbonimidothioic diamide (F24)

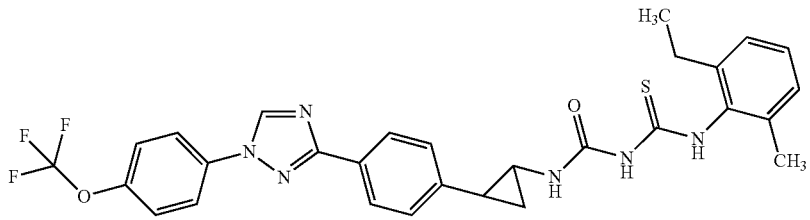 [SMILES: CCc1cccc(C)c1NC(=S)NC(=O)NC1CC1c1ccc(-c2ncn(-c3ccc(OC(F)(F)F)cc3)n2)cc1]

The title compound was prepared as described in Example 17 using (2-(4-(1-(4-(trifluoromethoxy)phenyl)-1H-1,2,4-triazol-3-yl)phenyl)cyclopropanecarbonyl azide (C21) and 1-(2-ethyl-6-methylphenyl)thiourea (CA39) and isolated as a white solid (0.105 g, 33%).

Preparation of N-(2,6-dimethylphenyl)-N'-[(2-(4-{1-[4-(trifluoromethoxy)phenyl]-1H-1,2,4-triazol-3-yl}phenyl)cyclopropyl]dicarbonimidothioic diamide (F25)

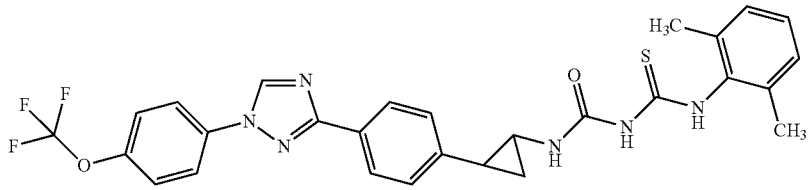 [SMILES: Cc1cccc(C)c1NC(=S)NC(=O)NC1CC1c1ccc(-c2ncn(-c3ccc(OC(F)(F)F)cc3)n2)cc1]

The title compound was prepared as described in Example 17 using (2-(4-(1-(4-(trifluoromethoxy)phenyl)-1H-1,2,4-triazol-3-yl)phenyl)cyclopropanecarbonyl azide (C21) and 1-(2,6-dimethylphenyl)thiourea and isolated as a white solid (0.105 g, 29%).

Preparation of N-(4-methoxy-2-methylphenyl)-N'-[(2-(4-{1-[4-(trifluoromethoxy)phenyl]-1H-1,2,4-triazol-3-yl}phenyl)cyclopropyl]dicarbonimidothioic diamide (F26)

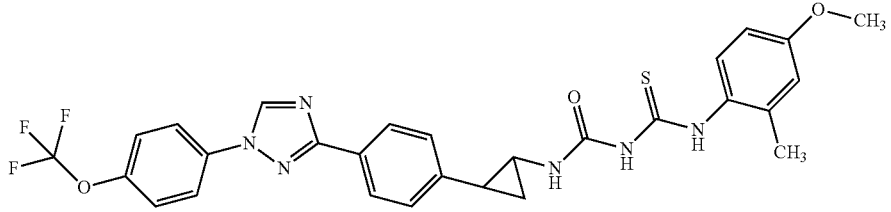 [SMILES: COc1ccc(NC(=S)NC(=O)NC2CC2c2ccc(-c3ncn(-c4ccc(OC(F)(F)F)cc4)n3)cc2)c(C)c1]

The title compound was prepared as described in Example 17 using (2-(4-(1-(4-(trifluoromethoxy)phenyl)-1H-1,2,4-triazol-3-yl)phenyl)cyclopropanecarbonyl azide (C21) and 1-(4-methoxy-2-methylphenyl)thiourea and isolated as a white oily solid (0.009 g, 3%).

Preparation of N-(2-ethyl-5-methylphenyl)-N'-[2-(4-{1-[4-(trifluoromethoxy)phenyl]-1H-1,2,4-triazol-3-yl}phenyl)cyclopropyl]dicarbonimidothioic diamide (F27)

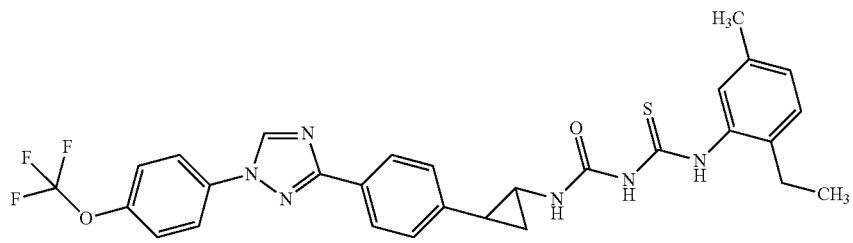 [SMILES: CCc1ccc(C)cc1NC(=S)NC(=O)NC1CC1c1ccc(-c2ncn(-c3ccc(OC(F)(F)F)cc3)n2)cc1]

The title compound was prepared as described in Example 17 using (2-(4-(1-(4-(trifluoromethoxy)phenyl)-1H-1,2,4-triazol-3-yl)phenyl)cyclopropanecarbonyl azide (C21) and 1-(2-ethyl-5-methylphenyl)thiourea (CA41) and isolated as an off-white solid (0.069 g, 22%).

Example 18

Preparation of (Z)-1-(3-(2-isopropylphenyl)-4-oxothiazolidin-2-ylidene)-3-(2-(4-(1-(4-(trifluoromethoxy)phenyl)-1H-1,2,4-triazol-3-yl)phenyl)cyclopropyl)urea (F29)

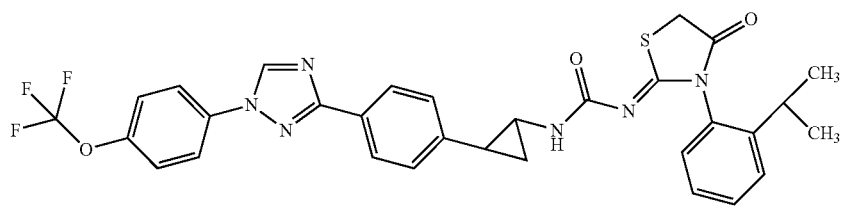 [SMILES: CC(C)c1ccccc1N1C(=O)CS/C1=N\C(=O)NC1CC1c1ccc(-c2ncn(-c3ccc(OC(F)(F)F)cc3)n2)cc1]

A solution of N-[2-(propan-2-yl)phenyl]-N'-,2-(4-{1-[4-(trifluoromethoxy)phenyl]-1H-1,2,4-triazol-3-yl}phenyl)cyclopropyl]dicarbonimidothioic diamide (F22) (0.082 g, 0.14 mmol), methyl 2-bromoacetate (0.020 mL, 0.21 mmol), and sodium acetate (0.027 g, 0.33 mmol) in ethanol (1.8 mL) was heated at 65° C. overnight. The reaction was cooled, loaded onto a Celite® cartridge, and purified by flash column chromatography using 0-40% ethyl acetate/B, where B=1:1 dichloromethane/hexanes, as eluent to afford the title compound as an off-white solid (0.061 g, 68%).

The following compounds were prepared in accordance to the procedure in Example 18.

Preparation of (Z)-1-(4-oxo-3-(2-propylphenyl)thia- zolidin-2-ylidene)-3-(2-(4-(1-(4-(trifluoromethoxy) phenyl)-1H-1,2,4-triazol-3-yl)phenyl)cyclopropyl) urea (F30)

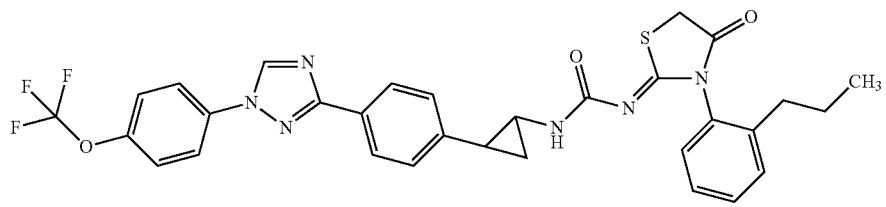 [SMILES: CCCc1ccccc1N1C(=O)CS/C1=N\C(=O)NC1CC1c1ccc(-c2ncn(-c3ccc(OC(F)(F)F)cc3)n2)cc1]

The title compound was prepared as described in Example 18 from N-(2-propylphenyl)-N'-[2-(4-{1-[4-(trifluoromethoxy)phenyl]-1H-1,2,4-triazol-3-yl}phenyl)cyclopropyl]dicarbonimidothioic diamide (F23) and isolated as an off-white oily solid (0.026 g, 68%).

Preparation of (Z)-1-(3-(2-ethyl-6-methylphenyl)-4- oxothiazolidin-2-ylidene)-3-(2-(4-(1-(4-(trifluoromethoxy)phenyl)-1H-1,2,4-triazol-3-yl)phenyl) cyclopropyl)urea (F31)

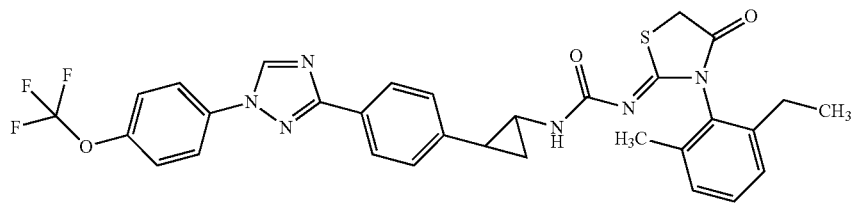 [SMILES: CCc1cccc(C)c1N1C(=O)CS/C1=N\C(=O)NC1CC1c1ccc(-c2ncn(-c3ccc(OC(F)(F)F)cc3)n2)cc1]

The title compound was prepared as described in Example 18 from N-(2-ethyl-6-methylphenyl)-N'-[2-(4-{1-[4-(trifluoromethoxy)phenyl]-1H-1,2,4-triazol-3-yl}phenyl)cyclopropyl]dicarbonimidothioic diamide (F24) and isolated as an oil (0.006 g, 8%).

Preparation of (Z)-1-(3-(2,6-dimethylphenyl)-4- oxothiazolidin-2-ylidene)-3-(2-(4-(1-(4-(trifluoromethoxy)phenyl)-1H-1,2,4-triazol-3-yl)phenyl) cyclopropyl)urea (F32)

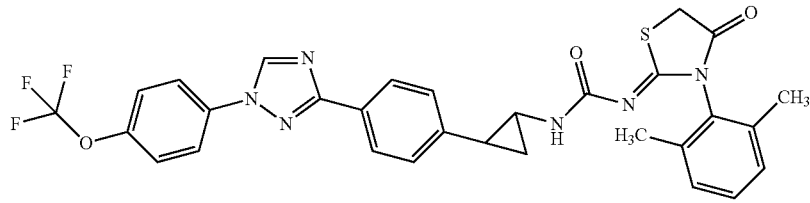 [SMILES: Cc1cccc(C)c1N1C(=O)CS/C1=N\C(=O)NC1CC1c1ccc(-c2ncn(-c3ccc(OC(F)(F)F)cc3)n2)cc1]

The title compound was prepared as described in Example 18 from N-(2,6-dimethylphenyl)-N'-[2-(4-{1-[4-(trifluoromethoxy)phenyl]-1H-1,2,4-triazol-3-yl}phenyl)cyclopropyl]dicarbonimidothioic diamide (F25) and isolated as an oil (0.006 g, 7%).

Preparation of (Z)-1-(3-(2-ethyl-5-methylphenyl)-4-oxothiazolidin-2-ylidene)-3-(2-(4-(1-(4-(trifluoromethoxy)phenyl)-1H-1,2,4-triazol-3-yl)phenyl)cyclopropyl)urea (F33)

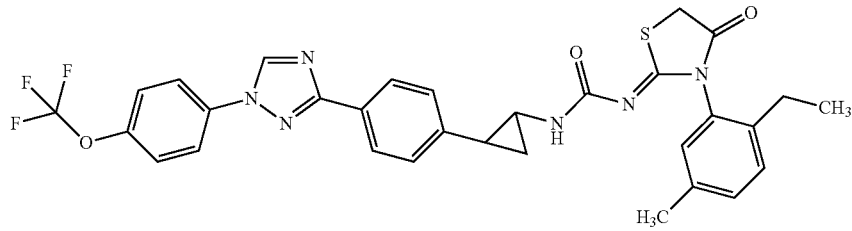 [SMILES: CCc1ccc(C)cc1N1C(=O)CS/C1=N\C(=O)NC1CC1c1ccc(-c2ncn(-c3ccc(OC(F)(F)F)cc3)n2)cc1]

The title compound was prepared as described in Example 18 from N-(2-ethyl-5-methylphenyl)-N'-[2-(4-{1-[4-(trifluoromethoxy)phenyl]-1H-1,2,4-triazol-3-yl}phenyl)cyclopropyl]dicarbonimidothioic diamide (F27) and isolated as a yellow solid (0.035 g, 71%).

Example 19

Preparation of N-[5-methyl-2-(propan-2-yl)phenyl]-N'-[2-(4-{1-[4-(trifluoromethoxy)phenyl]-1H-1,2,4-triazol-3-yl}phenyl)cyclopropyl]dicarbonimidothioic diamide (F28) and (Z)-1-(3-(2-isopropyl-5-methylphenyl)thiazolidin-2-ylidene)-3-(2-(4-(1-(4-(trifluoromethoxy)-phenyl)-1H-1,2,4-triazol-3-yl)phenyl)cyclopropyl)urea (F34)

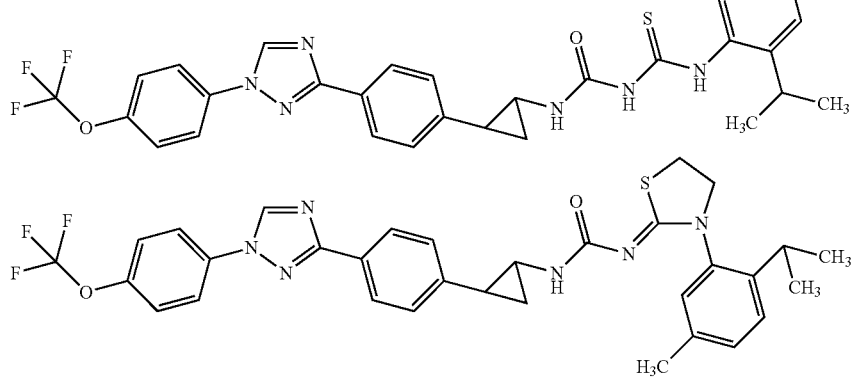

A solution of (2-(4-(1-(4-(trifluoromethoxy)phenyl)-1H-1,2,4-triazol-3-yl)phenyl)cyclopropanecarbonyl azide (C21) (0.210 g, 0.510 mmol) in 1,2-dichloroethane (2.5 mL) was heated at 80° C. for 3 hours. The reaction was cooled to room temperature and 1-(2-isopropyl-5-methylphenyl)thiourea (0.127 g, 0.610 mmol) and cesium carbonate (0.345 g, 1.06 mmol) were added. The reaction mixture was stirred at room temperature overnight. The reaction was diluted with ethyl acetate and washed with water. The aqueous layer was extracted with ethyl acetate (2×), the organic layers were dried over anhydrous sodium sulfate, filtered, and concentrated. The crude material was loaded onto a Celite® cartridge with dichloromethane and purified by flash column chromatography using 0-100% ethyl acetate/B, where B=1:1 dichloromethane/hexanes, as eluent to afford the title compound (F28) as a white solid (0.025 g, 8%) and the title compound (F34) as a yellow oil (0.028 g, 8%).

Example 20

Preparation of (E)-3-(4-(1-(4-(trifluoromethoxy)phenyl)-1H-1,2,4-triazol-3-yl)phenyl)acrylic acid (C22)

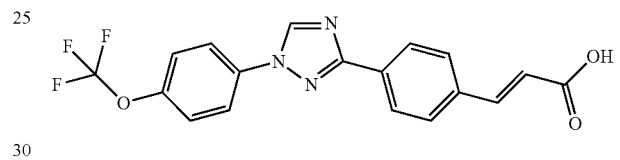

To (E)-ethyl 3-(4-(1-(4-(trifluoromethoxy)phenyl)-1H-1,2,4-triazol-3-yl)phenyl)acrylate (C17) (1.95 g, 4.83 mmol) in methanol (25 mL) was added sodium hydroxide (2 N, 10 mL, 20.0 mmol) and the solution was stirred at room temperature overnight. The methanol was evaporated off under reduced pressure, the reagents were diluted with acetonitrile, and additional sodium hydroxide (2 N, 20 mL, 40.0 mmol) was added. The reaction was stirred at room temperature for 5 hours and then acidified with hydrogen chloride (2 N). The white precipitate was vacuum-filtered to afford the title compound as a white solid (1.72 g, 94%): mp 239-241° C.; $^1$H NMR (400 MHz, DMSO-$d_6$) δ 12.48 (s, 1H), 9.44 (s, 1H), 8.14 (d, J=8.4 Hz, 2H), 8.12-8.05 (m, 2H), 7.85 (d, J=8.4 Hz, 2H), 7.69-7.59 (m, 3H), 6.61 (d, J=16.0 Hz, 1H); $^{19}$F NMR (376 MHz, DMSO-$d_6$) δ −56.96; ESIMS m/z 376 ([M+H]$^+$).

Example 21

Preparation of (E)-3-(4-(1-(4-(trifluoromethoxy)phenyl)-1H-1,2,4-triazol-3-yl)phenyl)acryloyl azide (C23)

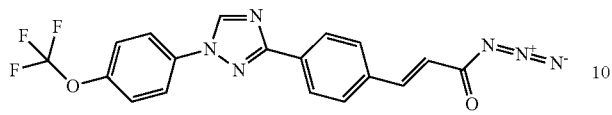

To (E)-3-(4-(1-(4-(trifluoromethoxy)phenyl)-1H-1,2,4-triazol-3-yl)phenyl)acrylic acid (C22) (1.72 g, 4.59 mmol) in isopropanol (15.3 mL) was diphenyl phosphorazidate (1.3 mL, 6.03 mmol) and triethylamine (0.96 mL, 6.89 mmol) and stirred at room temperature for 6 hours. The white precipitate for filtered, rinsed with isopropanol, and dried to afford the title compound as a white solid (1.46 g, 78%): mp 106° C. (dec); $^1$H NMR (400 MHz, CDCl$_3$) δ 8.59 (s, 1H), 8.24 (d, J=8.4 Hz, 2H), 7.86-7.73 (m, 3H), 7.66 (d, J=8.3 Hz, 2H), 7.40 (d, J=8.3 Hz, 2H), 6.52 (t, J=14.6 Hz, 1H); $^{19}$F NMR (376 MHz, CDCl$_3$) δ −58.02; ESIMS m/z 401 ([M+H]$^+$).

Example 22

Preparation of N-[2-(propan-2-yl)phenyl]-N'-[(E)-2-(4-{1-[4-(trifluoro methoxy)phenyl]-1H-1,2,4-triazol-3-yl}phenyl)ethenyl]dicarbonimidothioic diamide (F11)

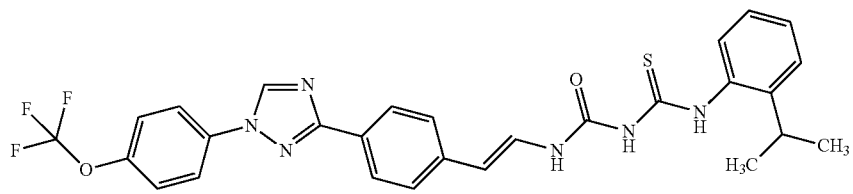 [SMILES: CC(C)c1ccccc1NC(=S)NC(=O)N/C=C/c1ccc(-c2ncn(-c3ccc(OC(F)(F)F)cc3)n2)cc1]

(E)-3-(4-(1-(4-(Trifluoromethoxy)phenyl)-1H-1,2,4-triazol-3-yl)phenyl)acryloyl azide (C23) (0.175 g, 0.440 mmol) in anhydrous acetonitrile (2.2 mL) was heated at 80° C. for 2 hours. The reaction was cooled and 1-(2-isopropylphenyl)thiourea (0.110 g, 0.570 mmol) and cesium carbonate (0.214 g, 0.660 mmol) were added. The reaction mixture was stirred at room temperature overnight, and then diluted with ethyl acetate and washed with water. The organic layer was dried over anhydrous sodium sulfate, filtered, and concentrated. The crude material was loaded onto a Celite® cartridge and purified by flash column chromatography using 0-40% ethyl acetate/B, where B=1:1 dichloromethane/hexanes, as eluent to afford the title compound as a yellow solid (0.0800 g, 32%).

Example 23

Preparation of (Z)-1-(3-(2-isopropylphenyl)-4-oxothiazolidin-2-ylidene)-3-((E)-4-(1-(4-(trifluoromethoxy)phenyl)-1H-1,2,4-triazol-3-yl)styryl)urea (F12)

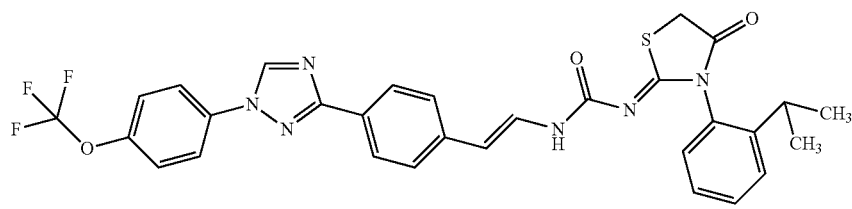 [SMILES: CC(C)c1ccccc1N1C(=O)CS/C1=N\C(=O)N/C=C/c1ccc(-c2ncn(-c3ccc(OC(F)(F)F)cc3)n2)cc1]

To N-[2-(propan-2-yl)phenyl]-N'-[(E)-2-(4-{1-[4-(trifluoromethoxy)phenyl]-1H-1,2,4-triazol-3-yl}phenyl)ethenyl] dicarbonimidothioic diamide (F11) (0.056 g, 0.099 mmol) and sodium acetate (0.020 g, 0.24 mmol) in ethanol (0.86 mL) was added methyl 2-bromoacetate (0.012 mL, 0.12 mmol), and the solution was heated at 65° C. for 2 hours. The reaction mixture was loaded directly onto a Celite® cartridge and purified by flash column chromatography using 0-50% ethyl acetate/B, where B=1:1 dichloromethane/hexanes, as eluent to afford the title compound as an orange solid (0.052 g, 84%).

Example 24

Preparation of 1-(4-(1-(4-(trifluoromethoxy)phenyl)-1H-1,2,4-triazol-3-yl)phenyl)ethanol (C24)

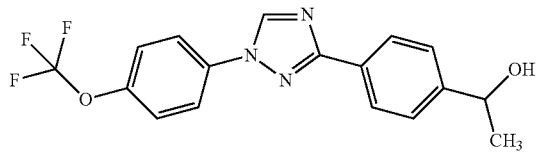 [SMILES: CC(O)c1ccc(-c2ncn(-c3ccc(OC(F)(F)F)cc3)n2)cc1]

To 4-(1-(4-(trifluoromethoxy)phenyl)-1H-1,2,4-triazol-3-yl)benzaldehyde (8.49 g, 25.5 mmol) in anhydrous tetrahydrofuran (102 mL) in dry ice/acetone bath was added methylmagnesium bromide (1 M in butyl ether, 25.5 mL, 25.5 mmol). The solution was then warmed to room temperature and stirred overnight. The reaction was acidified with hydrogen chloride (2 N, 10 mL) until pH 2, diluted with water, and extracted with ethyl acetate (2×). The organic layers were dried over anhydrous sodium sulfate, filtered, and concentrated to afford the title compound as an orange liquid (8.80 g, 94%): $^1$H NMR (400 MHz, CDCl$_3$) δ 8.55 (s, 1H), 8.27-8.11 (m, 2H), 7.90-7.68 (m, 2H), 7.49 (d, J=8.1 Hz, 2H), 7.39 (d, J=8.3 Hz, 2H), 4.98 (q, J=6.5 Hz, 1H), 1.54 (d, J=6.5 Hz, 3H); $^{19}$F NMR (376 MHz, CDCl$_3$) δ −58.03; ESIMS m/z 350 ([M+H]$^+$).

The following compounds were prepared in accordance to the procedure in Example 24.

Preparation of 1-(4-(1-(4-(trifluoromethoxy)phenyl)-1H-1,2,4-triazol-3-yl)phenyl)propan-1-ol (CA6)

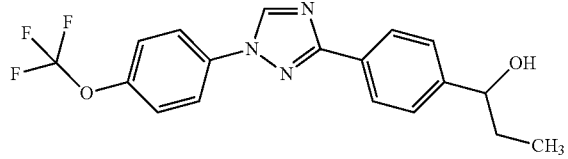

The title compound was prepared as described in Example 24 from 4-(1-(4-(trifluoromethoxy)phenyl)-1H-1,2,4-triazol-3-yl)benzaldehyde and ethylmagnesium bromide and isolated as a yellow oil (5.00 g, 100%): $^1$H NMR (400 MHz, CDCl$_3$) δ 8.56 (s, 1H), 8.20-8.12 (m, 2H), 7.85-7.76 (m, 2H), 7.50-7.44 (m, 2H), 7.39 (dq, J=8.0, 1.0 Hz, 2H), 4.68 (t, J=6.5 Hz, 1H), 1.93-1.75 (m, 2H), 1.59 (s, 1H), 0.95 (t, J=7.4 Hz, 3H); $^{19}$F NMR (376 MHz, CDCl$_3$) δ −58.03; ESIMS m/z 364 ([M+H]$^+$).

Example 25

Preparation of 1-(4-(1-(4-(trifluoromethoxy)phenyl)-1H-1,2,4-triazol-3-yl)phenyl)ethanone (C25)

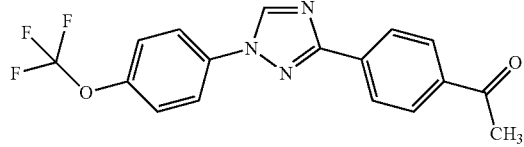 [SMILES: CC(=O)c1ccc(-c2ncn(-c3ccc(OC(F)(F)F)cc3)n2)cc1]

To 1-(4-(1-(4-(trifluoromethoxy)phenyl)-1H-1,2,4-triazol-3-yl)phenyl)ethanol (C24) (8.80 g, 25.2 mmol) in dichloromethane (168 mL) and dimethyl sulfoxide (84 mL) was added triethylamine (17 mL) and stirred in an ice bath. Pyridine.sulfur trioxide (16.0 g, 101 mmol) was added in two portions. The reaction was warmed to room temperature over 3 hours, diluted with dichloromethane, and washed with water. The aqueous layer was extracted one additional time with dichloromethane. The combined dichloromethane layers were washed with water, dried over anhydrous sodium sulfate, filtered, and adsorbed onto silica gel. Purification by flash column chromatography using 0-100% ethyl acetate/hexanes as eluent provided the title compound as a white solid (6.71 g, 73%): mp 140-141.5° C.; $^1$H NMR (400 MHz, CDCl$_3$) δ 8.61 (s, 1H), 8.33-8.27 (m, 2H), 8.11-8.05 (m, 2H), 7.85-7.78 (m, 2H), 7.41 (dd, J=9.0, 0.8 Hz, 2H), 2.66 (s, 3H); $^{19}$F NMR (376 MHz, CDCl$_3$) δ −58.01; ESIMS m/z 348 ([M+H]$^+$).

The following compounds were prepared in accordance to the procedure in Example 25.

Preparation of 1-(4-(1-(4-(trifluoromethoxy)phenyl)-1H-1,2,4-triazol-3-yl)phenyl)propan-1-one (CA7)

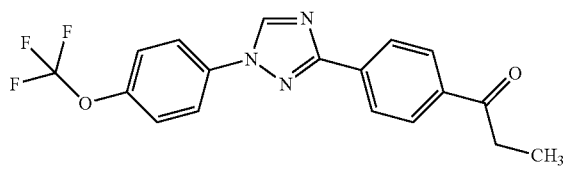 [SMILES: CCC(=O)c1ccc(-c2ncn(-c3ccc(OC(F)(F)F)cc3)n2)cc1]

The title compound was prepared from 1-(4-(1-(4-(trifluoromethoxy)phenyl)-1H-1,2,4-triazol-3-yl)phenyl)propan-1-ol (CA6) and isolated as a white solid (4.1 g, 63%, 75% pure): $^1$H NMR (400 MHz, CDCl$_3$) δ 8.60 (s, 1H), 8.32-8.25 (m, 2H), 8.11-8.05 (m, 2H), 7.82 (dd, J=8.9, 1.9 Hz, 2H), 7.41 (dt, J=8.1, 1.0 Hz, 2H), 3.06 (q, J=7.2 Hz, 2H), 1.26 (t, J=7.2 Hz, 3H); $^{19}$F NMR (376 MHz, CDCl$_3$) δ −58.02; ESIMS m/z 362 ([M+H]$^+$).

Example 26

Preparation of (E)-ethyl 3-(4-(1-(4-(trifluoromethoxy)phenyl)-1H-1,2,4-triazol-3-yl)phenyl)but-2-enoate (C26) and (Z)-ethyl 3-(4-(1-(4-(trifluoromethoxy)phenyl)-1H-1,2,4-triazol-3-yl)phenyl)but-2-enoate (C27)

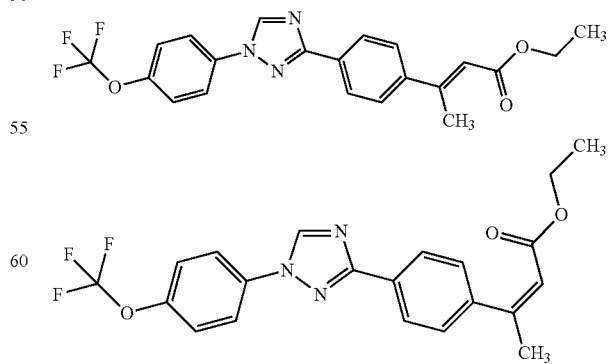

To an oven-dried round bottomed flask was added sodium hydride (60% oil suspension, 0.880 g, 1.53 mmol) and anhydrous tetrahydrofuran (36 mL) and the solution was stirred under nitrogen in an ice bath. Ethyl 2-(diethoxyphosphoryl) acetate (3.4 mL, 17.3 mmol) was added dropwise and stirred for 30 minutes in an ice bath. 1-(4-(1-(4-(Trifluoromethoxy) phenyl)-1H-1,2,4-triazol-3-yl)phenyl)ethanone (C25) (5.00 g, 14.4 mmol) was added in solid portions to the solution, in which the solution turned yellow. The reaction was warmed to room temperature overnight, quenched with saturated aqueous ammonium chloride, and extracted with diethyl ether (2×). The organic layers were dried over anhydrous sodium sulfate, filtered, and concentrated. The crude material was loaded onto a Celite® cartridge with dichloromethane, and the cartridge was dried in vacuum oven. Purification by reverse-phase flash column chromatography using 0-100% acetonitrile/water as eluent afforded title compound (C26) as a white solid (4.06 g, 67%): mp 109-110.5° C.; $^1$H NMR (400 MHz, CDCl$_3$) δ 8.58 (s, 1H), 8.28-8.16 (m, 2H), 7.88-7.77 (m, 2H), 7.66-7.55 (m, 2H), 7.45-7.34 (m, 2H), 6.22 (d, J=1.3 Hz, 1H), 4.24 (q, J=7.1 Hz, 2H), 2.62 (d, J=1.3 Hz, 3H), 1.33 (t, J=7.1 Hz, 3H); $^{19}$F NMR (376 MHz, CDCl$_3$) δ −58.02; ESIMS m/z 418 ([M+H]$^+$), and title compound (C27) as a white solid (1.08 g, 18%): mp 83-86° C.; $^1$H NMR (400 MHz, CDCl$_3$) δ 8.57 (s, 1H), 8.22-8.15 (m, 2H), 7.86-7.76 (m, 2H), 7.39 (dd, J=9.0, 0.8 Hz, 2H), 7.36-7.31 (m, 2H), 5.95 (d, J=1.4 Hz, 1H), 4.02 (q, J=7.1 Hz, 2H), 2.22 (d, J=1.4 Hz, 3H), 1.09 (t, J=7.1 Hz, 3H); $^{19}$F NMR (376 MHz, CDCl$_3$) δ −58.03; ESIMS m/z 418 ([M+H]$^+$).

Example 27

Preparation of (E)-3-(4-(1-(4-(trifluoromethoxy) phenyl)-1H-1,2,4-triazol-3-yl)phenyl)but-2-enoic acid (C28)

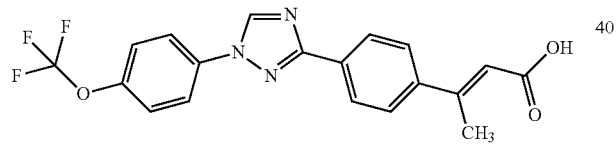

To (E)-ethyl 3-(4-(1-(4-(trifluoromethoxy)phenyl)-1H-1,2,4-triazol-3-yl)phenyl)but-2-enoate (C26) (1.30 g, 3.10 mmol) in methanol (10 mL) was added sodium hydroxide (2 N, 12.3 mL, 24.6 mmol) and stirred at room temperature overnight. Additional sodium hydroxide (2 N) was added and the reaction was heated to 50° C. for 3 days. The reaction was acidified with hydrogen chloride (2 N) and the white precipitate was collected by vacuum filtration to afford the title compound as a white solid (1.16 g, 95%): mp 234-238° C.; $^1$H NMR (400 MHz, DMSO-d$_6$) δ 12.32 (s, 1H), 9.43 (s, 1H), 8.14 (d, J=8.6 Hz, 2H), 8.09 (d, J=9.1 Hz, 2H), 7.73 (d, J=8.6 Hz, 2H), 7.68-7.53 (m, 2H), 6.22 (d, J=1.3 Hz, 1H), 2.54 (d, J=1.3 Hz, 3H); $^{19}$F NMR (376 MHz, DMSO-d$_6$) δ −56.96; ESIMS m/z 390 ([M+H]$^+$).

Example 28

Preparation of (E)-3-(4-(1-(4-(trifluoromethoxy) phenyl)-1H-1,2,4-triazol-3-yl)phenyl)but-2-enoyl azide (C29)

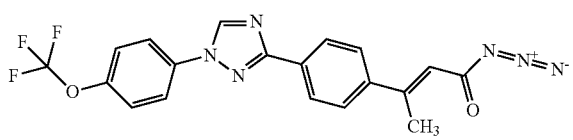

To (E)-3-(4-(1-(4-(trifluoromethoxy)phenyl)-1H-1,2,4-triazol-3-yl)phenyl)but-2-enoic acid (C28) (1.14 g, 2.93 mmol) in isopropanol (9.8 mL) was added triethylamine (0.53 mL, 3.81 mmol) and diphenyl phosphorazidate (0.68 mL, 3.23 mmol). The reaction was stirred at room temperature overnight. The white precipitate was vacuum-filtered and dried in a vacuum oven to afford the title compound as a white solid (0.978 g, 80%): $^1$H NMR (400 MHz, CDCl$_3$) δ 8.59 (s, 1H), 8.25-8.19 (m, 2H), 7.85-7.78 (m, 2H), 7.65-7.58 (m, 2H), 7.44-7.37 (m, 2H), 6.16 (d, J=1.3 Hz, 1H), 2.68 (d, J=1.2 Hz, 3H); $^{19}$F NMR (376 MHz, CDCl$_3$) δ −58.02; ESIMS m/z 387 ([M+H]$^+$) (isocyanate).

Example 29

Preparation of (Z)-1-(3-(2-isopropylphenyl)-4-oxothiazolidin-2-ylidene)-3-((E)-2-(4-(1-(4-(trifluoromethoxy)phenyl)-1H-1,2,4-triazol-3-yl)phenyl) prop-1-en-1-yl)urea (F13)

(E)-3-(4-(1-(4-(Trifluoromethoxy)phenyl)-1H-1,2,4-triazol-3-yl)phenyl)but-2-enoyl azide (C29) (0.28 g, 0.68 mmol) in acetonitrile (3.4 mL) was heated at 80° C. for 3 hours. The reaction was cooled and 1-(2-isopropylphenyl)thiourea (0.14 g, 0.74 mmol) and cesium carbonate (0.28 g, 0.86 mmol) were added. The reaction was stirred at room temperature overnight, diluted with ethyl acetate and washed with water. The organic layers were dried over anhydrous sodium sulfate, filtered, and concentrated to provide an orange foam. To the crude material (0.39 g) was added sodium acetate (0.082 g, 1.0 mmol), ethanol (3.4 mL), and methyl 2-bromoacetate (0.10 mL, 1.0 mmol). The reaction mixture was heated at 65° C. for 3 hours. The reaction was cooled, diluted with ethyl acetate, and washed with water. The organic layers were dried over anhydrous sodium sulfate, filtered, and concentrated. The crude compound was loaded onto a Celite® cartridge with dichloromethane and purified by flash column chromatography using 0-100% ethyl acetate/B, where B=1:1 dichloromethane/hexanes, as eluent to afford the title compound as an orange sticky gum (0.16 g, 37%).

The following compounds were prepared in accordance to the procedure in Example 29.

Preparation of (Z)-1-(3-(5-chloro-2-isopropylphenyl)-4-oxothiazolidin-2-ylidene)-3-(2-methyl-4-(1-(4-(trifluoromethoxy)phenyl)-1H-1,2,4-triazol-3-yl)phenethyl)urea (FB7)

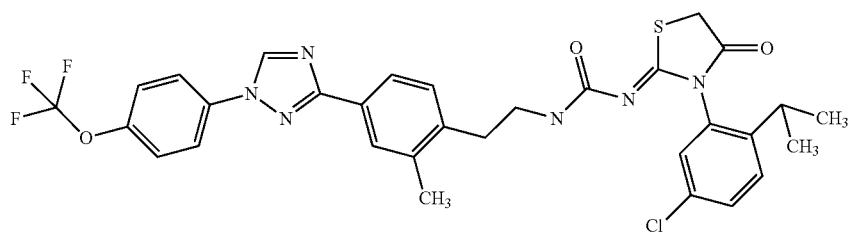 [SMILES: Cc1cc(-c2ncn(-c3ccc(OC(F)(F)F)cc3)n2)ccc1CCNC(=O)/N=C1\SCC(=O)N1c1cc(Cl)ccc1C(C)C]

The title compound was prepared as described in Example 29, using 3-(2-methyl-4-(1-(4-(trifluoromethoxy)phenyl)-1H-1,2,4-triazol-3-yl)phenyl)propanoyl azide (CB20) and 1-(5-chloro-2-isopropylphenyl)thiourea (CB32) and heating to a temperature of 60° C. after methyl 2-bromoacetate was added; purified via reverse phase chromatography and isolated as a pink solid (0.033 g, 17%).

Preparation of (Z)-1-(2-fluoro-4-(1-(4-(trifluoromethoxy)phenyl)-1H-1,2,4-triazol-3-yl)phenethyl)-3-(3-(2-isopropyl-5-methoxyphenyl)-4-oxothiazolidin-2-ylidene)urea (FB9)

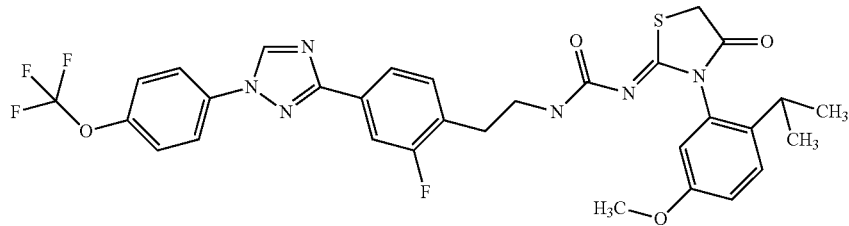 [SMILES: COc1ccc(C(C)C)c(N2C(=O)CS/C2=N\C(=O)NCCc2ccc(-c3ncn(-c4ccc(OC(F)(F)F)cc4)n3)cc2F)c1]

The title compound was prepared as described in Example 29, using 3-(2-fluoro-4-(1-(4-(trifluoromethoxy)phenyl)-1H-1,2,4-triazol-3-yl)phenyl)propanoyl azide (CB21) and 1-(5-chloro-2-isopropylphenyl)thiourea (CB32) and heating to a temperature of 60° C. when methyl 2-bromoacetate added; purified via reverse phase chromatography and isolated as a pink solid (0.023 g, 11%).

Example 30

Preparation of ethyl 3-(4-(1-(4-(trifluoromethoxy)phenyl)-1H-1,2,4-triazol-3-yl)phenyl)propanoate (C30)

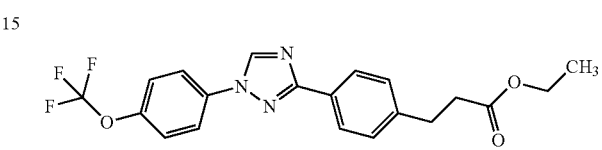

A mixture of (E)-ethyl 3-(4-(1-(4-(trifluoromethoxy)phenyl)-1H-1,2,4-triazol-3-yl)phenyl)acrylate (C17) (1.08 g, 2.68 mmol) and palladium on carbon (10%, 0.285 g, 0.270 mmol) in ethyl acetate (10.7 mL) was stirred at room temperature. The reaction flask was evacuated under vacuum, backfilled with nitrogen, evacuated under vacuum again, and then backfilled with hydrogen by balloon (~1 atm). The reaction was stirred at room temperature overnight and then filtered through a pad of Celite® and concentrated to afford the title compound as a gray oil that solidified to a wax upon standing at room temperature (0.999 g, 87%): $^1$H NMR (400 MHz, CDCl$_3$) δ 8.56 (s, 1H), 8.14-8.07 (m, 2H), 7.80 (d, J=9.1 Hz, 2H), 7.42-7.36 (m, 2H), 7.32 (d, J=8.4 Hz, 2H), 4.14 (q, J=7.1 Hz, 2H), 3.02 (t, J=7.8 Hz, 2H), 2.67 (t, J=7.8 Hz, 2H), 1.24 (t, J=7.1 Hz, 3H); $^{19}$F NMR (376 MHz, CDCl$_3$) δ −58.03; ESIMS m/z 406 ([M+H]$^+$).

The following compounds were prepared in accordance to the procedure in Example 30.

Preparation of ethyl 3-(4-(1-(4-(perfluoroethoxy)phenyl)-1H-1,2,4-triazol-3-yl)phenyl)propanoate (C31)

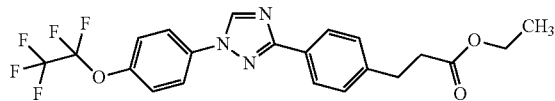 [SMILES: CCOC(=O)CCc1ccc(-c2ncn(-c3ccc(OC(F)(F)C(F)(F)F)cc3)n2)cc1]

The title compound was prepared from (E)-ethyl 3-(4-(1-(4-(perfluoroethoxy)phenyl)-1H-1,2,4-triazol-3-yl)phenyl)acrylate (C18) and isolated as an off-white fluffy solid (2.00 g, 97%): mp 109-110.5° C.; $^1$H NMR (400 MHz, CDCl$_3$) δ 8.56 (d, J=1.3 Hz, 1H), 8.14-8.08 (m, 2H), 7.84-7.77 (m, 2H), 7.42-7.36 (m, 2H), 7.35-7.29 (m, 2H), 4.14 (q, J=7.2 Hz, 2H), 3.02 (t, J=7.8 Hz, 2H), 2.67 (dd, J=8.3, 7.2 Hz, 2H), 1.24 (t, J=7.1 Hz, 3H); $^{19}$F NMR (376 MHz, CDCl$_3$) δ −85.90, −87.85; ESIMS m/z 456 ([M+H]$^+$).

Preparation of ethyl 2-methyl-3-(4-(1-(4-(trifluoromethoxy)phenyl)-1H-1,2,4-triazol-3-yl)phenyl)butanoate (CA8)

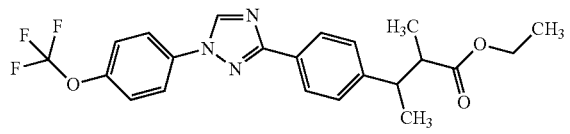 [SMILES: CCOC(=O)C(C)C(C)c1ccc(-c2ncn(-c3ccc(OC(F)(F)F)cc3)n2)cc1]

The title compound was prepared from (E)-ethyl 2-methyl-3-(4-(1-(4-(trifluoromethoxy)phenyl)-1H-1,2,4-triazol-3-yl)phenyl)but-2-enoate (CA4) and isolated as a yellow oil (0.495 g, 100%): $^1$H NMR (400 MHz, CDCl$_3$) δ 8.55 (s, 1H), 8.12-8.05 (m, 2H), 7.83-7.73 (m, 2H), 7.38 (dq, J=8.0, 1.1 Hz, 2H), 7.34-7.29 (m, 2H), 3.94 (q, J=7.1 Hz, 2H), 3.11 (dq, J=8.8, 7.1 Hz, 1H), 2.69 (dd, J=8.6, 6.9 Hz, 1H), 1.31 (d, J=7.1 Hz, 3H), 1.21 (d, J=6.9 Hz, 3H), 1.04 (t, J=7.1 Hz, 3H); $^{19}$F NMR (376 MHz, CDCl$_3$) δ −58.03; ESIMS m/z 434 ([M+H]$^+$).

Preparation of ethyl 3-(4-(1-(4-(trifluoromethyl)phenyl)-1H-1,2,4-triazol-3-yl)phenyl)propanoate (CA9)

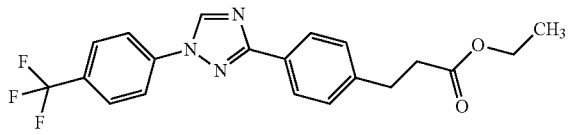 [SMILES: CCOC(=O)CCc1ccc(-c2ncn(-c3ccc(C(F)(F)F)cc3)n2)cc1]

The title compound was prepared from (E)-ethyl 3-(4-(1-(4-(trifluoromethyl)phenyl)-1H-1,2,4-triazol-3-yl)phenyl)acrylate (CA5) and isolated as a white solid (3.88 g, 96%): mp 81-84° C.; $^1$H NMR (400 MHz, CDCl$_3$) δ 8.64 (s, 1H), 8.12 (d, J=8.2 Hz, 2H), 7.91 (dt, J=8.2, 0.8 Hz, 2H), 7.83-7.74 (m, 2H), 7.33 (dd, J=8.0, 0.7 Hz, 2H), 4.14 (q, J=7.1 Hz, 2H), 3.02 (t, J=7.8 Hz, 2H), 2.67 (dd, J=8.3, 7.2 Hz, 2H), 1.35 (td, J=7.1, 0.6 Hz, 3H); $^{19}$F NMR (376 MHz, CDCl$_3$) δ −62.50; ESIMS m/z 390 ([M+H]$^+$).

Preparation of ethyl 3-(2-methyl-4-(1-(4-(trifluoromethoxy)phenyl)-1H-1,2,4-triazol-3-yl)phenyl)propanoate (CB15)

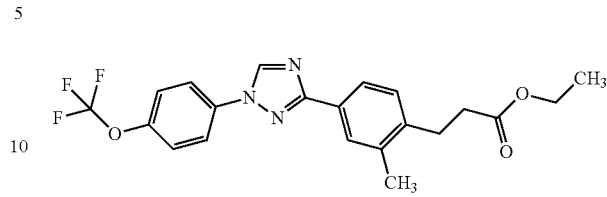

The title compound was prepared from (E)-ethyl 3-(2-methyl-4-(1-(4-(trifluoromethoxy)phenyl)-1H-1,2,4-triazol-3-yl)phenyl)acrylate (CB12) and isolated as a gray solid (1.14 g, 98%): mp 109-111° C.; $^1$H NMR (400 MHz, CDCl$_3$) δ 8.55 (s, 1H), 7.99 (d, J=1.8 Hz, 1H), 7.95 (ddd, J=7.8, 2.0, 0.7 Hz, 1H), 7.83-7.77 (m, 2H), 7.38 (dq, J=7.9, 1.0 Hz, 2H), 7.26 (s, 1H), 4.15 (q, J=7.1 Hz, 2H), 3.00 (dd, J=8.9, 7.0 Hz, 2H), 2.69-2.55 (m, 2H), 2.41 (s, 3H), 1.26 (t, J=7.1 Hz, 3H); $^{19}$F NMR (376 MHz, CDCl$_3$) δ −58.03; ESIMS m/z 420 ([M+H]$^+$).

Preparation of ethyl 3-(2-fluoro-4-(1-(4-(trifluoromethoxy)phenyl)-1H-1,2,4-triazol-3-yl)phenyl)propanoate (CB16)

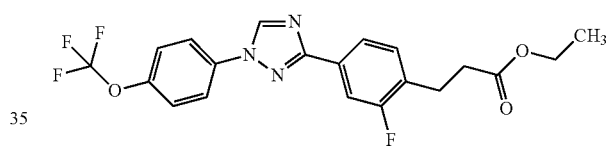

The title compound was prepared from (E)-ethyl 3-(2-fluoro-4-(1-(4-(trifluoromethoxy)phenyl)-1H-1,2,4-triazol-3-yl)phenyl)acrylate (CB13) using palladium hydroxide on carbon and ethanol as solvent; isolated as a tan solid (0.871 g, 67%, 85% pure): $^1$H NMR (400 MHz, CDCl$_3$) δ 8.56 (s, 1H), 7.92-7.82 (m, 2H), 7.79 (d, J=9.0 Hz, 2H), 7.43-7.36 (m, 2H), 7.32 (t, J=7.8 Hz, 1H), 4.14 (q, J=7.1 Hz, 2H), 3.03 (t, J=7.7 Hz, 2H), 2.67 (dd, J=8.2, 7.2 Hz, 2H), 1.24 (t, J=7.1 Hz, 3H); $^{19}$F NMR (376 MHz, CDCl$_3$) δ (376 MHz, CDCl$_3$) δ −58.03, −117.98; ESIMS m/z 423 ([M]$^+$).

Preparation of 2-(4-(1-(4-(trifluoromethoxy)phenyl)-1H-1,2,4-triazol-3-yl)benzyl)butanoic acid (CB17)

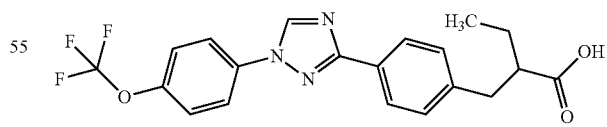

The title compound was prepared from (E/Z)-ethyl 2-(4-(1-(4-(trifluoromethoxy)phenyl)-1H-1,2,4-triazol-3-yl)benzylidene)butanoate (CB14) and isolated as a brown solid (1.15 g, 28%): mp 149-150° C.; $^1$H NMR (400 MHz, CDCl$_3$) δ 8.58 (s, 1H), 8.13-8.02 (m, 2H), 7.82-7.74 (m, 2H), 7.38 (dq, J=8.9, 0.9 Hz, 2H), 7.35-7.28 (m, 2H), 3.04 (dd, J=13.7, 8.3 Hz, 1H), 2.85 (dd, J=13.8, 6.6 Hz, 1H), 2.75-2.61 (m, 1H), 1.77-1.60 (m, 2H), 1.00 (t, J=7.4 Hz, 3H) (OH not observed);

$^{19}$F NMR (376 MHz, CDCl$_3$) δ (376 MHz, CDCl$_3$) δ −58.03, −117.98; ESIMS m/z 406 ([M+H]$^+$).

Example 31

Preparation of 3-(4-(1-(4-(trifluoromethoxy)phenyl)-1H-1,2,4-triazol-3-yl)phenyl)propanoic acid (C32)

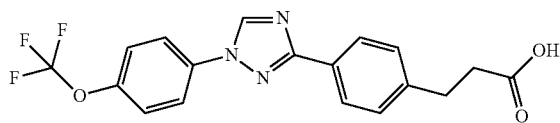 [SMILES: O=C(O)CCc1ccc(-c2ncn(-c3ccc(OC(F)(F)F)cc3)n2)cc1]

To ethyl 3-(4-(1-(4-(trifluoromethoxy)phenyl)-1H-1,2,4-triazol-3-yl)phenyl) propanoate (C30) (0.975 g, 2.41 mmol) in methanol (60 mL) was added sodium hydroxide (2 N, 12.0 mL, 24.1 mmol) and the solution was stirred at room temperature overnight. The methanol was concentrated under vacuum, and the residue was acidified with hydrogen chloride (2 N). The white precipitate was vacuum filtered and dried to afford the title compound as a white solid (0.945 g, 99%): mp 145° C. (dec); $^1$H NMR (400 MHz, DMSO-d$_6$) δ 9.39 (s, 1H), 8.04 (dd, J=21.4, 8.7 Hz, 4H), 7.62 (d, J=8.3 Hz, 2H), 7.38 (d, J=8.4 Hz, 2H), 2.89 (t, J=7.6 Hz, 2H), 2.59 (t, J=7.6 Hz, 2H); $^{19}$F NMR (376 MHz, DMSO-d$_6$) δ −56.98; ESIMS m/z 378 ([M+H]$^+$).

The following compounds were prepared in accordance to the procedure in Example 31.

Preparation of 3-(4-(1-(4-(perfluoroethoxy)phenyl)-1H-1,2,4-triazol-3-yl)phenyl) propanoic acid (C33)

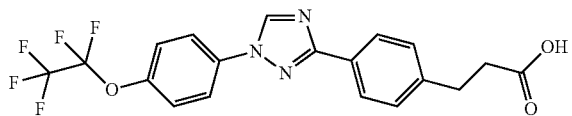 [SMILES: O=C(O)CCc1ccc(-c2ncn(-c3ccc(OC(F)(F)C(F)(F)F)cc3)n2)cc1]

The title compound was prepared from ethyl 3-(4-(1-(4-(perfluoroethoxy)phenyl)-1H-1,2,4-triazol-3-yl)phenyl)propanoate (C31) and isolated as a white solid (2.25 g, 100%): mp 142-144° C.; $^1$H NMR (400 MHz, DMSO-d$_6$) δ 9.40 (s, 1H), 8.05 (dd, J=24.5, 8.6 Hz, 4H), 7.62 (d, J=8.9 Hz, 2H), 7.38 (d, J=8.3 Hz, 2H), 2.89 (t, J=7.6 Hz, 2H), 2.59 (t, J=7.6 Hz, 2H); $^{19}$F NMR (376 MHz, DMSO-d$_6$) δ −74.86, −85.19, −86.92; ESIMS m/z 428 ([M+H]$^+$).

Preparation of 2-methyl-3-(4-(1-(4-(trifluoromethoxy)phenyl)-1H-1,2,4-triazol-3-yl)phenyl)butanoic acid (CA10)

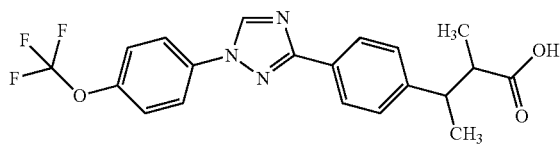 [SMILES: CC(C(=O)O)C(C)c1ccc(-c2ncn(-c3ccc(OC(F)(F)F)cc3)n2)cc1]

The title compound was prepared from ethyl 2-methyl-3-(4-(1-(4-(trifluoromethoxy)phenyl)-1H-1,2,4-triazol-3-yl)phenyl)butanoate (CA8) and isolated as a yellow oil (0.370 g, 33%): $^1$H NMR (400 MHz, CDCl$_3$) δ 8.57 (d, J=4.0 Hz, 1H), 8.15-8.03 (m, 2H), 7.83-7.73 (m, 2H), 7.40-7.27 (m, 4H), 3.18 (p, J=7.2 Hz, 1H), 2.76 (dq, J=8.3, 7.0 Hz, 1H), 1.35-1.29 (m, 3H), 1.23 (d, J=6.9 Hz, 3H); $^{19}$F NMR (376 MHz, CDCl$_3$) δ −58.03; ESIMS m/z 406 ([M+H]$^+$).

Preparation of 3-(4-(1-(4-(trifluoromethyl)phenyl)-1H-1,2,4-triazol-3-yl)phenyl)propanoic acid (CA11)

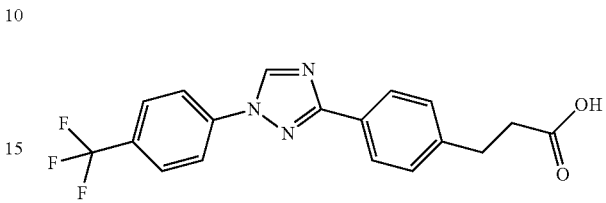

The title compound was prepared from ethyl 3-(4-(1-(4-(trifluoromethyl)phenyl)-1H-1,2,4-triazol-3-yl)phenyl)propanoate (CA9) and isolated as a white solid (2.85 g, 79%): mp 155-157° C.; $^1$H NMR (400 MHz, DMSO-d$_6$) δ 12.17 (s, 1H), 9.52 (s, 1H), 8.26-8.12 (m, 2H), 8.12-7.86 (m, 3H), 7.39 (d, J=8.2 Hz, 2H), 2.89 (t, J=7.6 Hz, 2H), 2.59 (t, J=7.6 Hz, 2H); $^{19}$F NMR (376 MHz, DMSO-d$_6$) δ −60.79; ESIMS m/z 362 ([M+H]$^+$).

Preparation of 3-(2-methyl-4-(1-(4-(trifluoromethoxy)phenyl)-1H-1,2,4-triazol-3-yl)phenyl) propanoic acid (CB18)

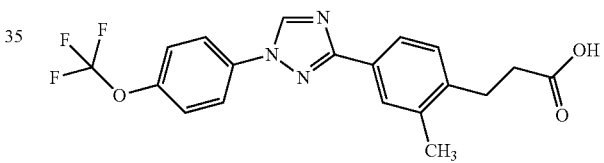

The title compound was prepared from ethyl 3-(2-methyl-4-(1-(4-(trifluoromethoxy)phenyl)-1H-1,2,4-triazol-3-yl)phenyl)propanoate (CB15) and isolated as a white solid (1.039 g, 96%): $^1$H NMR (400 MHz, CD$_3$OD) δ 9.13 (s, 1H), 8.06-7.99 (m, 2H), 7.94 (d, J=1.8 Hz, 1H), 7.89 (dd, J=7.8, 1.9 Hz, 1H), 7.54-7.46 (m, 2H), 7.30 (d, J=7.9 Hz, 1H), 2.99 (t, J=7.9 Hz, 2H), 2.61 (dd, J=8.5, 7.2 Hz, 2H), 2.42 (s, 3H); $^{19}$F NMR (376 MHz, CD$_3$OD) δ −59.68; ESIMS m/z 391 ([M]$^+$).

Preparation of 3-(2-fluoro-4-(1-(4-(trifluoromethoxy)phenyl)-1H-1,2,4-triazol-3-yl)phenyl) propanoic acid (CB19)

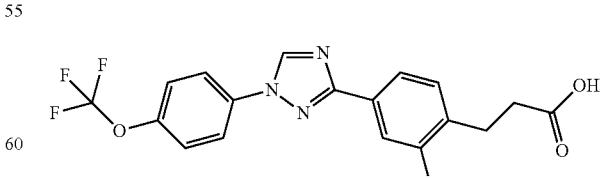

The crude title compound was prepared from ethyl 3-(2-fluoro-4-(1-(4-(trifluoromethoxy)phenyl)-1H-1,2,4-triazol-3-yl)phenyl)propanoate (CB16) and isolated as a white solid and used without further purification: $^1$H NMR (400 MHz, CDCl₃) δ 9.14 (s, 1H), 8.01 (d, J=9.0 Hz, 2H), 7.93-7.83 (m, 1H), 7.80 (dd, J=11.4, 1.6 Hz, 1H), 7.49 (d, J=8.6 Hz, 2H), 7.41 (t, J=7.8 Hz, 1H), 3.00 (t, J=7.7 Hz, 2H), 2.64 (t, J=7.6 Hz, 2H); ¹⁹F NMR (376 MHz, CDCl₃) δ −55.72, −116.16; ESIMS m/z 395 ([M]⁺).

Example 32

Preparation of 3-(4-(1-(4-(trifluoromethoxy)phenyl)-1H-1,2,4-triazol-3-yl)phenyl)propanoyl azide (34) and 3-(4-(2-isocyanatoethyl)phenyl)-1-(4-(trifluoromethoxy)phenyl)-1H-1,2,4-triazole (C34a)

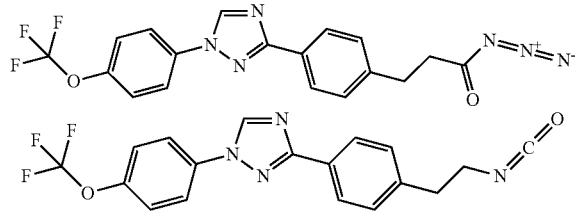

To 3-(4-(1-(4-(trifluoromethoxy)phenyl)-1H-1,2,4-triazol-3-yl)phenyl)propanoic acid (C32) (0.70 g, 1.9 mmol) in anhydrous toluene (12 mL) was added triethylamine (0.26 mL, 1.9 mmol) and diphenyl phosphorazidate (0.40 mL, 1.9 mmol). The reaction mixture was stirred at room temperature for 2 hours, loaded directly onto a Celite® cartridge, and purified by flash column chromatography using 0-100% ethyl acetate/hexanes as eluent affording the title compound as a white solid (0.37 g, 50%). ¹H NMR is consistent with a mixture of the acyl azide (34) and the rearranged isocyanate (34a): ¹H NMR (400 MHz, CDCl₃) δ 8.56 (two singlets, total=1H), 8.20-8.07 (m, 2H), 7.80 (m, 2H), 7.44-7.27 (m, 4H), 3.59 (t, J=6.9 Hz, 1H), 3.00 (t, J=7.2 Hz, 2H), 2.72 (d, J=7.2 Hz, 1H); ¹⁹F NMR (376 MHz, CDCl₃) δ −58.03; ESIMS m/z 403 ([M+H]⁺) (acyl azide).

The following compounds were prepared in accordance to the procedure in Example 32.

Preparation of 3-(4-(1-(4-(perfluoroethoxy)phenyl)-1H-1,2,4-triazol-3-yl)phenyl) propanoyl azide (C35)

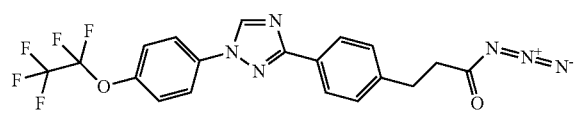 [SMILES: [N-]=[N+]=NC(=O)CCc1ccc(-c2ncn(-c3ccc(OC(F)(F)C(F)(F)F)cc3)n2)cc1]

The title compound was prepared from 3-(4-(1-(4-(perfluoroethoxy)phenyl)-1H-1,2,4-triazol-3-yl)phenyl)propanoic acid (C33) and was isolated as a white solid (0.416 g, 57%): mp 68° C. (dec.): ¹H NMR is consistent with a mixture of the acyl azide and the rearranged isocyanate: ¹H NMR (400 MHz, CDCl₃) δ 8.64-8.53 (m, 1H), 8.23-8.06 (m, 2H), 7.85-7.75 (m, 2H), 7.39 (m, 2H), 7.36-7.28 (m, 2H), 3.59 (t, J=6.8 Hz, 1H), 3.00 (t, J=7.3 Hz, 2H), 2.70 (d, J=7.2 Hz, 1H); ¹⁹F NMR (376 MHz, CDCl₃) δ −85.90, −87.85; ESIMS m/z 453 ([M+H]⁺).

Preparation of 2-methyl-3-(4-(1-(4-(trifluoromethoxy)phenyl)-1H-1,2,4-triazol-3-yl)phenyl)butanoyl azide/3-(4-(3-isocyanatobutan-2-yl)phenyl)-1-(4-(trifluoromethoxy)phenyl)-1H-1,2,4-triazole (C35a)

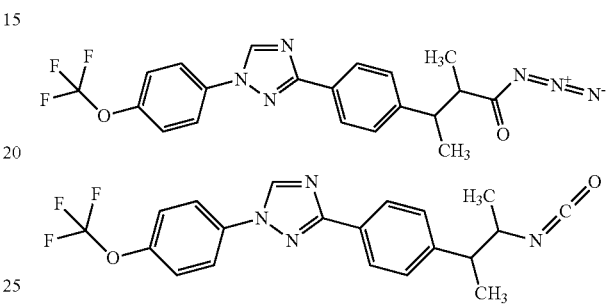

The title compounds were prepared from 2-methyl-3-(4-(1-(4-(trifluoromethoxy)phenyl)-1H-1,2,4-triazol-3-yl)phenyl)butanoic acid (CA10) and isolated as a clear oil (3:1 azide:isocyanate, 0.246 g, 67%): ¹H NMR (400 MHz, CDCl₃) δ 8.56 (s, 1H), 8.20-8.10 (m, 2H), 7.83-7.73 (m, 2H), 7.42-7.28 (m, 4H), 3.77 (m, 1H), 2.86 (m, 1H), 1.39 (two d, J=7.0 Hz, 3H), 1.25 (two d, J=6.5 Hz, 3H); ¹⁹F NMR (376 MHz, CDCl₃) δ −58.03; ESIMS m/z 431 ([M+H]⁺).

Preparation of 3-(4-(1-(4-(trifluoromethyl)phenyl)-1H-1,2,4-triazol-3-yl)phenyl) propanoyl azide/3-(4-(2-isocyanatoethyl)phenyl)-1-(4-(trifluoromethyl)phenyl)-1H-1,2,4-triazole (C35b)

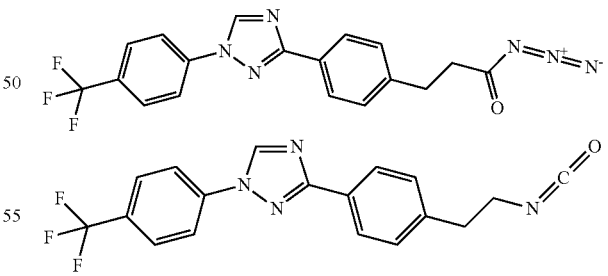

The title compounds were prepared from 3-(4-(1-(4-(trifluoromethyl)phenyl)-1H-1,2,4-triazol-3-yl)phenyl)propanoic acid (CA11) and isolated as a clear oil (mixture azide:isocyanate, 0.595 g, 57%): ¹H NMR (400 MHz, CDCl₃) δ 8.65 (d, J=2.8 Hz, 1H), 8.21-8.10 (m, 2H), 7.91 (m, 2H), 7.80 (m, 2H), 7.38-7.29 (m, 2H), 3.59 (t, J=6.9 Hz, 1H), 3.00 (t, J=7.2 Hz, 2H), 2.72 (d, J=7.2 Hz, 1H); ¹⁹F NMR (376 MHz, CDCl₃) δ −62.49.

Preparation of 3-(2-methyl-4-(1-(4-(trifluoromethoxy)phenyl)-1H-1,2,4-triazol-3-yl)phenyl) propanoyl azide (CB20)

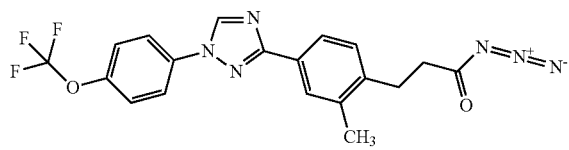

The title compound was prepared from 3-(2-methyl-4-(1-(4-(trifluoromethoxy)phenyl)-1H-1,2,4-triazol-3-yl)phenyl) propanoic acid (CB18) using acetonitrile as co-solvent and was isolated as a white solid (0.636 g, 57%): $^1$H NMR (400 MHz, CDCl$_3$) δ 8.55 (s, 1H), 8.00 (d, J=1.8 Hz, 1H), 7.98-7.94 (m, 1H), 7.84-7.75 (m, 2H), 7.39 (ddt, J=7.9, 2.0, 1.0 Hz, 2H), 7.24 (d, J=7.9 Hz, 1H), 3.06-2.90 (m, 2H), 2.75-2.59 (m, 2H), 2.41 (s, 3H); $^{19}$F NMR (376 MHz, CDCl$_3$) δ −58.04; ESIMS m/z 389 ([M+H]−N$_2^+$).

Preparation of 3-(2-fluoro-4-(1-(4-(trifluoromethoxy)phenyl)-1H-1,2,4-triazol-3-yl)phenyl) propanoyl azide (CB21)

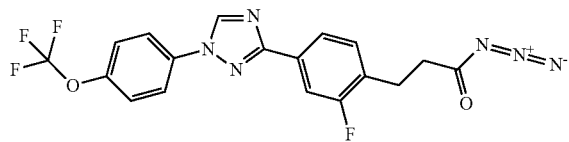 [SMILES: [N-]=[N+]=NC(=O)CCc1ccc(-c2ncn(-c3ccc(OC(F)(F)F)cc3)n2)cc1F]

The title compound was prepared from 3-(2-fluoro-4-(1-(4-(trifluoromethoxy)phenyl)-1H-1,2,4-triazol-3-yl)phenyl) propanoic acid (CB19) using acetonitrile as co-solvent and was isolated as a white solid (0.084 g, 29%): $^1$H NMR (400 MHz, CDCl$_3$) δ 8.56 (s, 1H), 7.94-7.83 (m, 2H), 7.83-7.75 (m, 2H), 7.39 (ddd, J=7.7, 1.9, 0.9 Hz, 2H), 7.35-7.29 (m, 1H), 3.10-2.96 (m, 2H), 2.81-2.66 (m, 2H); $^{19}$F NMR (376 MHz, CDCl$_3$) δ −58.03, −117.86.

Preparation of 2-(4-(1-(4-(trifluoromethoxy)phenyl)-1H-1,2,4-triazol-3-yl)benzyl)butanoyl azide (CB22)

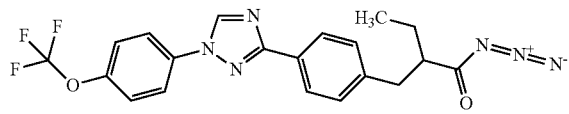 [SMILES: CCC(Cc1ccc(-c2ncn(-c3ccc(OC(F)(F)F)cc3)n2)cc1)C(=O)N=[N+]=[N-]]

The title compound was prepared from 2-(4-(1-(4-(trifluoromethoxy)phenyl)-1H-1,2,4-triazol-3-yl)benzyl)butanoic acid (CB17) and was isolated as a clear oil (0.512 g, 56%): $^1$H NMR (400 MHz, CDCl$_3$) δ 8.56 (s, 1H), 8.20-8.10 (m, 2H), 7.84-7.74 (m, 2H), 7.39 (dt, J=8.0, 1.0 Hz, 2H), 7.36-7.29 (m, 2H), 3.68 (tdd, J=8.3, 5.3, 4.4 Hz, 1H), 2.98-2.77 (m, 2H), 1.76-1.64 (m, 1H), 1.61-1.51 (m, 1H), 1.05 (t, J=7.4 Hz, 3H); $^{19}$F NMR (376 MHz, CDCl$_3$) δ −58.03, −117.86; ESIMS m/z 431 ([M+H]$^+$).

Example 32a

Preparation of 3-(4-(2-isocyanatoethyl)phenyl)-1-(4-(trifluoro methoxy)phenyl)-1H-1,2,4-triazole (C34a)

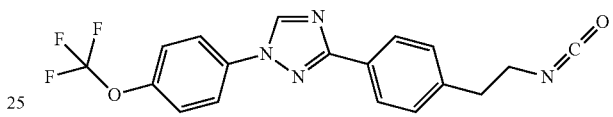

A 1 L three-neck round bottomed flask was equipped with mechanic stirrer, thermocouple, and condenser. Tetrahydrofuran (120 mL) was added. After it was cooled to −3° C., ethyl carbonochloridate (3.16 mL, 33.2 mmol) and triethylamine (4.64 mL, 33.2 mmol) were added. 3-(4-(1-(4-(Trifluoromethoxy)phenyl)-1H-1,2,4-triazol-3-yl)phenyl)propanoic acid (C32) (11.4 g, 30.2 mmol) was added in portions, keeping the reaction temperature below 0° C. The reaction mixture turned into white suspension quickly. LC-MS showed no starting material left after 1 hr. A solution of sodium azide (2.16 g, 33.2 mmol) in water (44 mL) was added slowly, keeping the reaction temperature below −2° C. The reaction mixture was stirred at −2° C. for 2 hours. Cold water (200 mL) was added to the reaction mixture very slowly while stirring at 0° C. It was stirred at 0° C. for 30 minutes after the addition. The white solid that formed was filtered while it was cold. The solid was dried in vacuum under a stream of nitrogen at room temperature for 48 hours to afford the isocyanate as a tan solid (10.5 g, 86%): $^1$H NMR (400 MHz, CDCl$_3$) δ 8.56 (s, 1H), 8.20-8.11 (m, 2H), 7.85-7.76 (m, 2H), 7.47-7.30 (m, 4H), 3.59 (t, J=6.9 Hz, 2H), 2.97 (t, J=6.9 Hz, 2H); $^{19}$F NMR (376 MHz, CDCl$_3$) δ −58.02; ESIMS m/z 375.2 ([M+H]$^+$).

Example 33

Preparation of N-[2-isopropylphenyl]-N'-[2-(4-{1-[4-(trifluoromethoxy)phenyl]-1H-1,2,4-triazol-3-yl}phenyl)ethyl]dicarbonimidothioic diamide (F2)

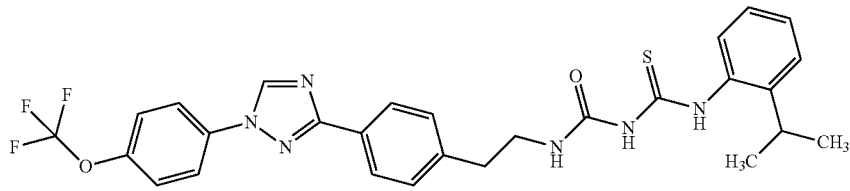 [SMILES: CC(C)c1ccccc1NC(=S)NC(=O)NCCc1ccc(-c2ncn(-c3ccc(OC(F)(F)F)cc3)n2)cc1]

3-(4-(1-(4-(Trifluoromethoxy)phenyl)-1H-1,2,4-triazol-3-yl)phenyl)propanoyl azide (C34) (0.19 g, 0.46 mmol) in acetonitrile (2.3 mL) was heated at 80° C. for 2 hours. The reaction mixture was cooled and 1-(2-isopropylphenyl)thiourea (0.11 g, 0.55 mmol) and cesium carbonate (0.20 g, 0.60 mmol) were added. The reaction was stirred at room temperature for 4 hours, and then quenched with water and extracted with ethyl acetate (2×). The organic layers were dried over anhydrous sodium sulfate, filtered, concentrated, and loaded onto a Celite® cartridge with dichloromethane. Purification by flash column chromatography using 0-100% ethyl acetate/B, where B=1:1 dichloromethane/hexanes, as eluent afforded the title compound as a white powder (0.097 g, 36%).

The following compounds were prepared in accordance to the procedure in Example 33.

Preparation of N-[5-methyl-2-isopropylphenyl]-N'-[2-(4-{1-[4-(trifluoromethoxy)-phenyl]-1H-1,2,4-triazol-3-yl}phenyl)ethyl]dicarbonimidothioic diamide (F3)

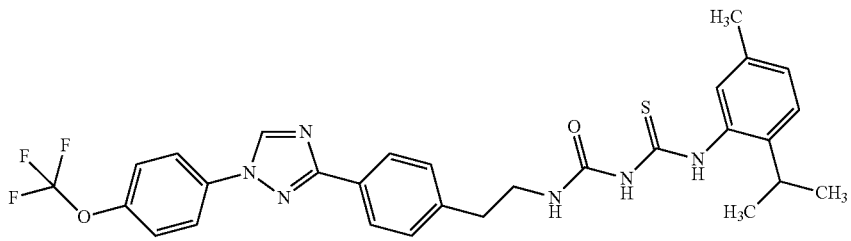 [SMILES: Cc1ccc(C(C)C)c(NC(=S)NC(=O)NCCc2ccc(-c3ncn(-c4ccc(OC(F)(F)F)cc4)n3)cc2)c1]

The title compound was prepared from 3-(4-(1-(4-(trifluoromethoxy)phenyl)-1H-1,2,4-triazol-3-yl)phenyl)propanoyl azide (C34) and 1-(2-isopropyl-5-methylphenyl)thiourea and isolated as a white solid (0.158 g, 43%).

Preparation of 1-[(2-isopropyl-5-methyl-phenyl)carbamothioyl]-3-[2-[2-methyl-4-[1-[4-(trifluoromethoxy)phenyl]-1H-1,2,4-triazol-3-yl]phenyl]ethyl]urea (FB1)

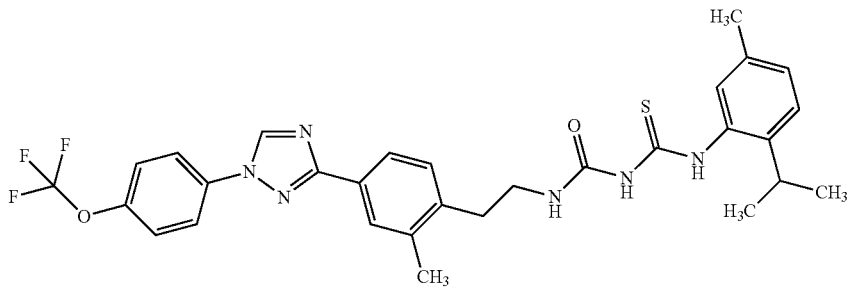 [SMILES: Cc1ccc(C(C)C)c(NC(=S)NC(=O)NCCc2ccc(-c3ncn(-c4ccc(OC(F)(F)F)cc4)n3)cc2C)c1]

The title compound was prepared from 3-(2-methyl-4-(1-(4-(trifluoromethoxy)phenyl)-1H-1,2,4-triazol-3-yl)phenyl)propanoyl azide (CB20) and 1-(2-isopropyl-5-methylphenyl)thiourea and isolated, without purification, as a white solid (0.180 g, 79%, 88% pure).

Preparation of 1-[(2-isopropyl-5-methoxy-phenyl)carbamothioyl]-3-[2-[2-methyl-4-[1-[4-(trifluoromethoxy)phenyl]-1H-1,2,4-triazol-3-yl]phenyl]ethyl]urea (FB2)

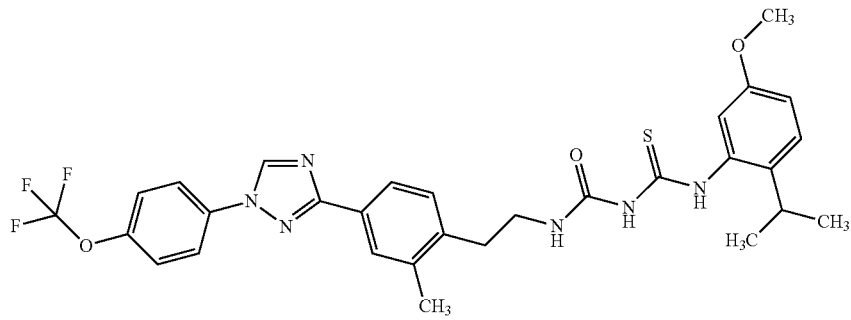 [SMILES: COc1ccc(C(C)C)c(NC(=S)NC(=O)NCCc2ccc(-c3ncn(-c4ccc(OC(F)(F)F)cc4)n3)cc2C)c1]

The title compound was prepared from 3-(2-methyl-4-(1-(4-(trifluoromethoxy)phenyl)-1H-1,2,4-triazol-3-yl)phenyl)propanoyl azide (CB20) and 1-(2-isopropyl-5-methoxyphenyl)thiourea (CA40) and isolated, without purification, as a yellow solid (0.165 g, 75%).

Preparation of 1-[(2-ethylphenyl)carbamothioyl]-3-[2-[2-methyl-4-[1-[4-(trifluoromethoxy)phenyl]-1H-1,2,4-triazol-3-yl]phenyl]ethyl]urea (FB5)

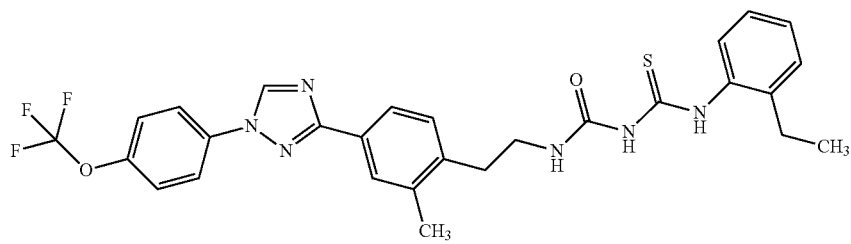 [SMILES: CCc1ccccc1NC(=S)NC(=O)NCCc1ccc(-c2ncn(-c3ccc(OC(F)(F)F)cc3)n2)cc1C]

The title compound was prepared from 3-(2-methyl-4-(1-(4-(trifluoromethoxy)phenyl)-1H-1,2,4-triazol-3-yl)phenyl)propanoyl azide (CB20) and 1-(2-ethylphenyl)thiourea and isolated, without purification, as a yellow solid (0.144 g, 83%).

Example 34

Preparation of (Z)-1-(3-(2-isopropylphenyl)-4-oxothiazolidin-2-ylidene)-3-(4-(1-(4-(trifluoromethoxy)phenyl)-1H-1,2,4-triazol-3-yl)phenethyl)urea (F1), Method A

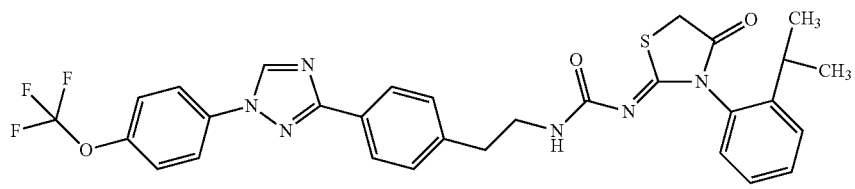 [SMILES: CC(C)c1ccccc1N1C(=O)CS/C1=N\C(=O)NCCc1ccc(-c2ncn(-c3ccc(OC(F)(F)F)cc3)n2)cc1]

To N-[2-isopropylphenyl]-N'-[2-(4-{1-[4-(trifluoromethoxy)phenyl]-1H-1,2,4-triazol-3-yl}phenyl)ethyl]dicarbonimidothioic diamide (F2) (0.030 g, 0.053 mmol) and sodium acetate (0.016 g, 0.20 mmol) in ethanol (0.5 mL) was added methyl 2-bromoacetate (0.01 mL, 0.10 mmol) and the solution was heated at 65° C. for 1.5 hours. The reaction was cooled and loaded directly onto a Celite® cartridge. Purification by flash column chromatography using 0-100% ethyl acetate/B, where B=1:1 dichloromethane/hexanes as eluent afforded the title compound as a clear oil (0.016 g, 49%).

Example 35

Preparation of (Z)-1-(3-(2-isopropylphenyl)-4-oxothiazolidin-2-ylidene)-3-(4-(1-(4-(trifluoromethoxy)phenyl)-1H-1,2,4-triazol-3-yl)phenethyl)urea (F1), Method B

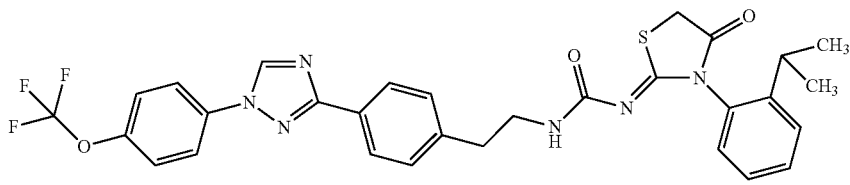 [SMILES: CC(C)c1ccccc1N1C(=O)CS/C1=N\C(=O)NCCc1ccc(-c2ncn(-c3ccc(OC(F)(F)F)cc3)n2)cc1]

3-(4-(1-(4-(Trifluoromethoxy)phenyl)-1H-1,2,4-triazol-3-yl)phenyl)propanoyl azide (C34) (0.24 g, 0.59 mmol) in acetonitrile (2.9 mL) was heated at 80° C. for 2 hours. The reaction was cooled and cesium carbonate (0.29 g, 0.88 mmol) and 1-(2-isopropylphenyl)thiourea (0.14 g, 0.70 mmol) were added. The reaction was stirred at room temperature overnight. LC/MS showed formation of the thiobiuret was complete. The reaction mixture was diluted with ethanol (2.9 mL) and sodium acetate (0.19 g, 2.4 mmol) and methyl 2-bromoacetate (0.12 mL, 1.2 mmol) were added. The solution was heated at 65° C. for 2 hours. The reaction was diluted with ethyl acetate and washed with water. The organic layer was dried over anhydrous sodium sulfate, filtered, concentrated, and loaded onto a Celite® cartridge with dichloromethane. Purification by flash column chromatography using 0-100% ethyl acetate/B, where B=1:1 dichloromethane/hexanes, as eluent afforded the title compound as a tan oil (0.22 g, 62%).

The following compounds were prepared in accordance to the procedure in Examples 34 or 35.

Preparation of (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5)

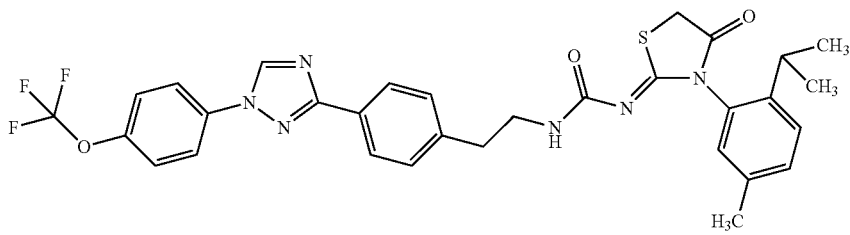 [SMILES: Cc1ccc(C(C)C)c(N2C(=O)CS/C2=N\C(=O)NCCc2ccc(-c3ncn(-c4ccc(OC(F)(F)F)cc4)n3)cc2)c1]

The title compound was prepared as described in Example 34 using N-[5-methyl-2-isopropylphenyl]-N'-[2-(4-{1-[4-(trifluoromethoxy)-phenyl]-1H-1,2,4-triazol-3-yl}phenyl)ethyl]dicarbonimidothioic diamide (F3) and 1-(2-isopropyl-5-methylphenyl)thiourea and isolated as a pale pink solid (0.114 g, 29%).

Preparation of (Z)-1-(3-(2-isopropyl-5-methoxyphenyl)-4-oxothiazolidin-2-ylidene)-3-(4-(1-(4-(trifluoromethoxy)phenyl)-1H-1,2,4-triazol-3-yl)phenethyl)urea (F6)

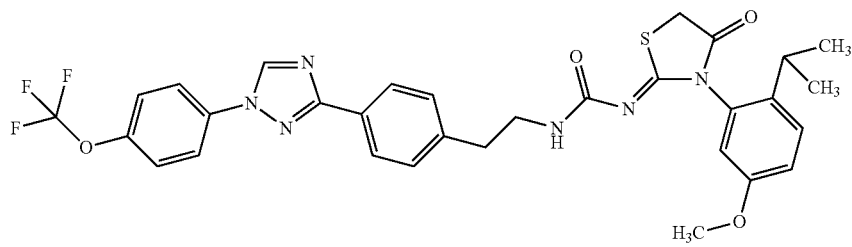 [SMILES: COc1ccc(C(C)C)c(N2C(=O)CS/C2=N\C(=O)NCCc2ccc(-c3ncn(-c4ccc(OC(F)(F)F)cc4)n3)cc2)c1]

The title compound was prepared as described in Example 35 using 3-(4-(1-(4-(trifluoromethoxy)phenyl)-1H-1,2,4-triazol-3-yl)phenyl)propanoyl azide (C34) and 1-(2-isopropyl-5-methoxyphenyl)thiourea (CA40) and isolated as an orange solid (0.075 g, 35%).

Preparation of (Z)-1-(3-(2-isopropyl-5-methylphenyl)-4-oxothiazolidin-2-ylidene)-3-(4-(1-(4-(perfluoroethoxy)phenyl)-1H-1,2,4-triazol-3-yl)phenethyl)urea (F9)

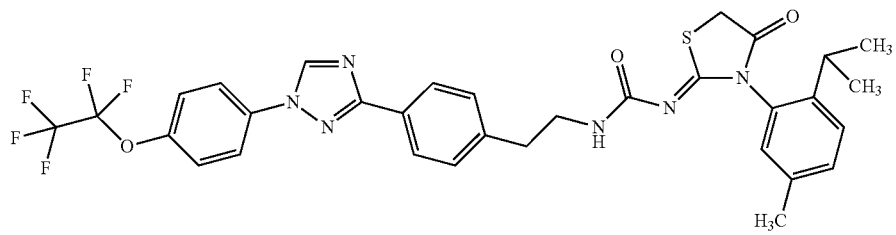 [SMILES: Cc1ccc(C(C)C)c(N2C(=O)CS/C2=N\C(=O)NCCc2ccc(-c3ncn(-c4ccc(OC(F)(F)C(F)(F)F)cc4)n3)cc2)c1]

The title compound was prepared as described in Example 35 using 1-(2-isopropyl-5-methylphenyl)thiourea and 3-(4-(1-(4-(perfluoroethoxy)phenyl)-1H-1,2,4-triazol-3-yl)phenyl)-propanoyl azide (C35) and isolated as a brown gum (0.146 g, 43%).

Preparation of (Z)-1-(3-(2-isopropyl-5-methylphenyl)-4-oxothiazolidin-2-ylidene)-3-(3-(4-(1-(4-(trifluoromethoxy)phenyl)-1H-1,2,4-triazol-3-yl)phenyl)butan-2-yl)urea (P66, P353)

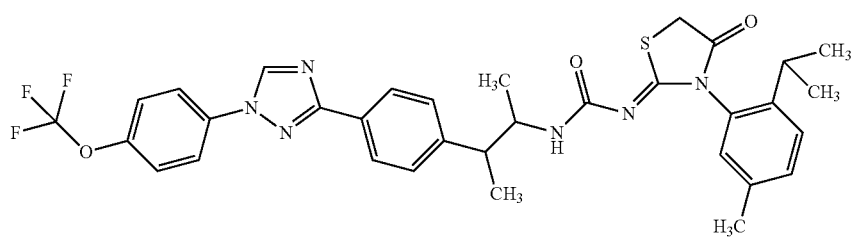 [SMILES: Cc1ccc(C(C)C)c(N2C(=O)CS/C2=N\C(=O)NC(C)C(C)c2ccc(-c3ncn(-c4ccc(OC(F)(F)F)cc4)n3)cc2)c1]

The title compound was prepared as described in Example 35 using 1-(2-isopropyl-5-methylphenyl)thiourea and 2-methyl-3-(4-(1-(4-(trifluoromethoxy)phenyl)-1H-1,2,4-triazol-3-yl)phenyl)butanoyl azide/3-(4-(3-isocyanatobutan-2-yl)phenyl)-1-(4-(trifluoromethoxy)phenyl)-1H-1,2,4-triazole (C35a) and isolated as an off-white powder (0.146 g, 39%).

Preparation of (Z)-1-(3-(2-isopropyl-5-methylphenyl)-4-oxothiazolidin-2-ylidene)-3-(4-(1-(4-(trifluoromethyl)phenyl)-1H-1,2,4-triazol-3-yl)phenethyl) urea (P52)

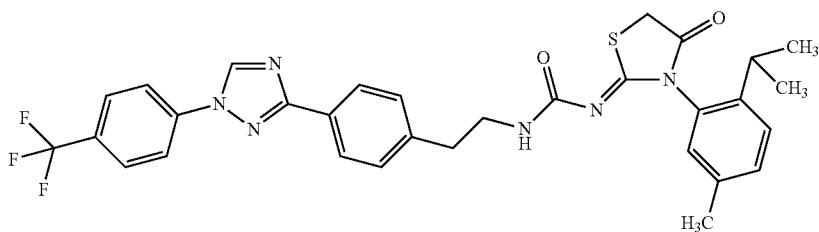 [SMILES: Cc1ccc(C(C)C)c(N2C(=O)CS/C2=N\C(=O)NCCc2ccc(-c3ncn(-c4ccc(C(F)(F)F)cc4)n3)cc2)c1]

The title compound was prepared as described in Example 35 using 3-(4-(1-(4-(trifluoromethyl)phenyl)-1H-1,2,4-triazol-3-yl)phenyl)propanoyl azide/3-(4-(2-isocyanatoethyl)phenyl)-1-(4-(trifluoromethyl)phenyl)-1H-1,2,4-triazole (C35b) and 1-(2-isopropyl-5-methylphenyl)thiourea and isolated as a tan glassy foam (0.132 g, 46%).

Preparation of (Z)-1-(3-(2-isopropyl-5-methoxyphenyl)-4-oxothiazolidin-2-ylidene)-3-(4-(1-(4-(trifluoromethyl)phenyl)-1H-1,2,4-triazol-3-yl)phenethyl) urea (P53)

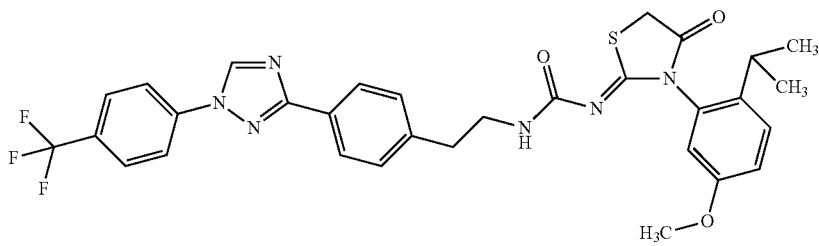 [SMILES: COc1ccc(C(C)C)c(N2C(=O)CS/C2=N\C(=O)NCCc2ccc(-c3ncn(-c4ccc(C(F)(F)F)cc4)n3)cc2)c1]

The title compound was prepared as described in Example 35 using 3-(4-(1-(4-(trifluoromethyl)phenyl)-1H-1,2,4-triazol-3-yl)phenyl)propanoyl azide/3-(4-(2-isocyanatoethyl)phenyl)-1-(4-(trifluoromethyl)phenyl)-1H-1,2,4-triazole (C35b) and 1-(2-isopropyl-5-methoxyphenyl)thiourea (CA40) and isolated as a brown foam (0.040 g, 30%).

Preparation of (Z)-1-(2-fluoro-4-(1-(4-(trifluoromethoxy)phenyl)-1H-1,2,4-triazol-3-yl)phenethyl)-3-(3-(2-isopropyl-5-methylphenyl)-4-oxothiazolidin-2-ylidene)urea (FB8)

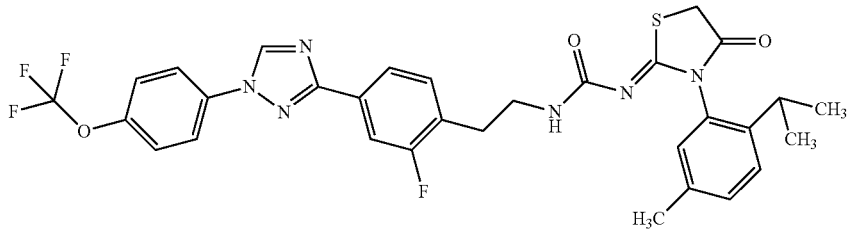 [SMILES: Cc1ccc(C(C)C)c(N2C(=O)CS/C2=N\C(=O)NCCc2ccc(-c3ncn(-c4ccc(OC(F)(F)F)cc4)n3)cc2F)c1]

The title compound was prepared as described in Example 35 using 3-(2-fluoro-4-(1-(4-(trifluoromethoxy)phenyl)-1H-1,2,4-triazol-3-yl)phenyl)propanoyl azide (CB21) and 1-(2-isopropyl-5-methylphenyl)thiourea at a temperature of 60° C. and followed by reverse phase chromatography; isolated as an orange oil (0.028 g, 13%).

Preparation of (Z)-1-(3-(5-chloro-2-isopropylphenyl)-4-oxothiazolidin-2-ylidene)-3-(4-(1-(4-(trifluoromethyl)phenyl)-1H-1,2,4-triazol-3-yl)phenethyl)urea (FB50)

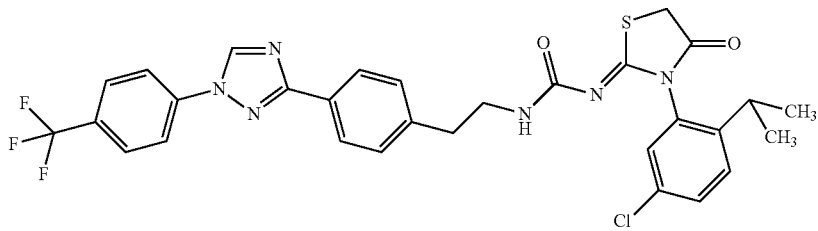 [SMILES: CC(C)c1ccc(Cl)cc1N1C(=O)CS/C1=N\C(=O)NCCc1ccc(-c2ncn(-c3ccc(C(F)(F)F)cc3)n2)cc1]

The title compound was prepared as described in Example 35 using 3-(4-(1-(4-(trifluoromethyl)phenyl)-1H-1,2,4-triazol-3-yl)phenyl)propanoyl azide/3-(4-(2-isocyanatoethyl)phenyl)-1-(4-(trifluoromethyl)phenyl)-1H-1,2,4-triazole (C35b) and 1-(5-chloro-2-isopropylphenyl)thiourea (CB32) at a temperature of 60° C., isolated as a clear oil (0.019 g, 12%).

Example 35a

Preparation of (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5)

To a 250 mL round bottomed flask was added acetonitrile (100 mL). 3-(4-(2-Isocyanatoethyl)phenyl)-1-(4-(trifluoromethoxy)phenyl)-1H-1,2,4-triazole (34a) (11.0 g, 29.4 mmol) was added in one portion. 1-(2-Isopropyl-5-methylphenyl)thiourea (6.73 g, 32.3 mmol) and cesium carbonate (9.57 g, 29.4 mmol) were added to the above solution. The reaction mixture was stirred at room temperature under nitrogen overnight. Ethanol (100 mL) was added to the mixture. Methyl 2-bromoacetate (8.99 g, 58.8 mmol) and sodium acetate (9.64 g, 118 mmol) were then added. The reaction mixture was stirred at 60° C. for 2 hours, forming an orange suspension. The reaction mixture was cooled and filtered through a filter paper, and the solids were washed with ethyl acetate (2×100 mL). The orange filtrate was concentrated. The solid residue was purified by flash column chromatography using 10-20% dichloromethane/B, where B=1:1 ethyl acetate/acetone, as eluent to afford the title compound as a slightly orange foam (8.60 g, 45%).

The following compounds were prepared in accordance to the procedure in Example 35a.

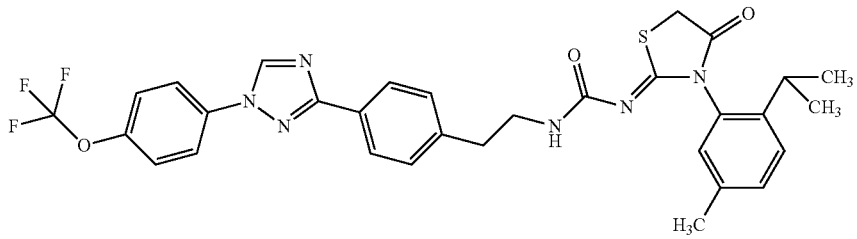 [SMILES: Cc1ccc(C(C)C)c(N2C(=O)CS/C2=N\C(=O)NCCc2ccc(-c3ncn(-c4ccc(OC(F)(F)F)cc4)n3)cc2)c1]

Preparation of (Z)-1-(3-(2-isopropyl-4-methylphenyl)-4-oxothiazolidin-2-ylidene)-3-(4-(1-(4-(trifluoromethoxy)phenyl)-1H-1,2,4-triazol-3-yl)phenethyl) urea (P26)

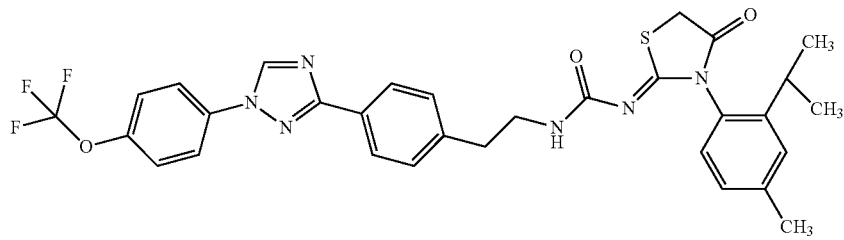 [SMILES: Cc1ccc(N2C(=O)CS/C2=N\C(=O)NCCc2ccc(-c3ncn(-c4ccc(OC(F)(F)F)cc4)n3)cc2)c(C(C)C)c1]

The title compound was prepared from 1-(2-isopropyl-4-methylphenyl)thiourea and 3-(4-(2-isocyanatoethyl)phenyl)-1-(4-(trifluoromethoxy)phenyl)-1H-1,2,4-triazole (C34a) and isolated as a brown oil (0.121 g, 47%).

Preparation of (Z)-1-(3-(2-isopropyl-3-methylphenyl)-4-oxothiazolidin-2-ylidene)-3-(4-(1-(4-(trifluoromethoxy)phenyl)-1H-1,2,4-triazol-3-yl)phenethyl) urea (P27)

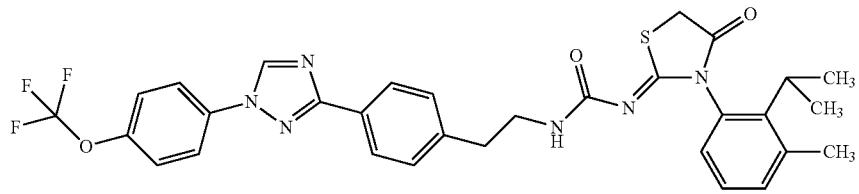 [SMILES: Cc1cccc(N2C(=O)CS/C2=N\C(=O)NCCc2ccc(-c3ncn(-c4ccc(OC(F)(F)F)cc4)n3)cc2)c1C(C)C]

The title compound was prepared from 1-(2-isopropyl-3-methylphenyl)thiourea and 3-(4-(2-Isocyanatoethyl)phenyl)-1-(4-(trifluoromethoxy)phenyl)-1H-1,2,4-triazole (C34a) and isolated as a yellow oil (0.075 g, 31%).

Preparation of (Z)-1-(3-(5-methyl-2-propylphenyl)-4-oxothiazolidin-2-ylidene)-3-(4-(1-(4-(trifluoromethoxy)phenyl)-1H-1,2,4-triazol-3-yl)phenethyl) urea (P29)

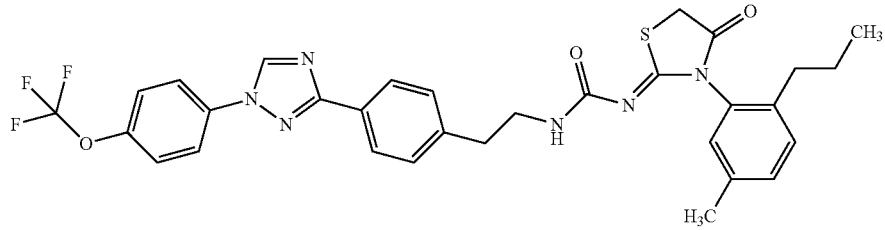 [SMILES: CCCc1ccc(C)cc1N1C(=O)CS/C1=N\C(=O)NCCc1ccc(-c2ncn(-c3ccc(OC(F)(F)F)cc3)n2)cc1]

The title compound was prepared from 1-(5-methyl-2-propylphenyl)thiourea (CA38) and 3-(4-(2-isocyanatoethyl) phenyl)-1-(4-(trifluoromethoxy)phenyl)-1H-1,2,4-triazole (C34a) and isolated as a pale pink solid (0.113 g, 43%).

Preparation of (Z)-1-(3-(2-(tert-butyl)phenyl)-4-oxothiazolidin-2-ylidene)-3-(4-(1-(4-(trifluoromethoxy)phenyl)-1H-1,2,4-triazol-3-yl)phenethyl)urea (P30)

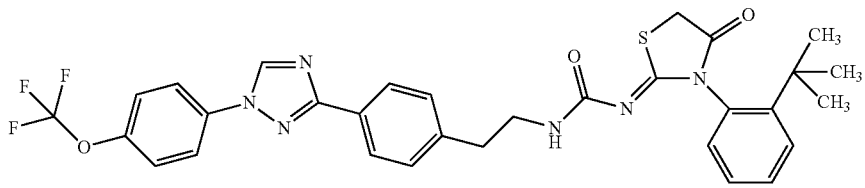 [SMILES: CC(C)(C)c1ccccc1N1C(=O)CS/C1=N\C(=O)NCCc1ccc(-c2ncn(-c3ccc(OC(F)(F)F)cc3)n2)cc1]

The title compound was prepared from 1-(2-(tert-butyl)phenyl)thiourea and 3-(4-(2-isocyanatoethyl)phenyl)-1-(4-(trifluoromethoxy)phenyl)-1H-1,2,4-triazole (C34a) and isolated as a pink solid (0.076 g, 31%).

Preparation of (Z)-1-(3-(2-ethyl-4-methylphenyl)-4-oxothiazolidin-2-ylidene)-3-(4-(1-(4-(trifluoromethoxy)phenyl)-1H-1,2,4-triazol-3-yl)phenethyl)urea (P31)

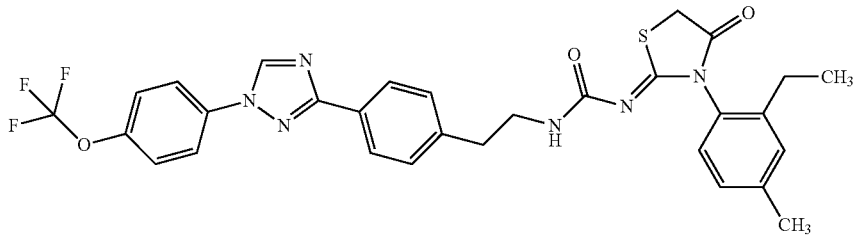 [SMILES: CCc1cc(C)ccc1N1C(=O)CS/C1=N\C(=O)NCCc1ccc(-c2ncn(-c3ccc(OC(F)(F)F)cc3)n2)cc1]

The title compound was prepared from 1-(2-ethyl-4-methylphenyl)thiourea (CA42) and 3-(4-(2-isocyanatoethyl)phenyl)-1-(4-(trifluoromethoxy)phenyl)-1H-1,2,4-triazole (C34a) and isolated as a pink solid (0.114 g, 47%).

Preparation of (Z)-1-(3-(4-methoxy-2-methylphenyl)-4-oxothiazolidin-2-ylidene)-3-(4-(1-(4-(trifluoromethoxy)phenyl)-1H-1,2,4-triazol-3-yl)phenethyl)urea (P44)

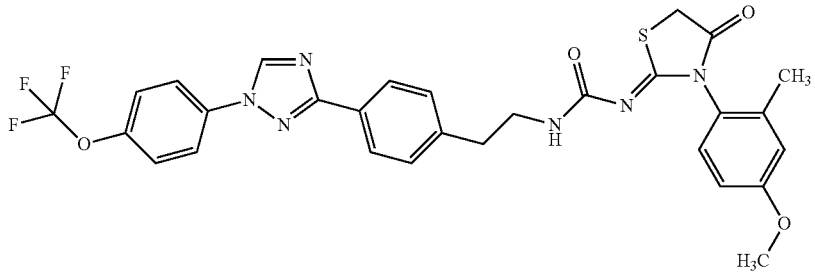 [SMILES: COc1ccc(N2C(=O)CS/C2=N\C(=O)NCCc2ccc(-c3ncn(-c4ccc(OC(F)(F)F)cc4)n3)cc2)c(C)c1]

The title compound was prepared as described in Example 35a using 1-(4-methoxy-2-methylphenyl)thiourea and 3-(4-(2-isocyanatoethyl)phenyl)-1-(4-(trifluoromethoxy)phenyl)-1H-1,2,4-triazole (C34a) and isolated as a yellow solid (0.120 g, 49%).

Preparation of (Z)-1-(3-(2-ethyl-5-methylphenyl)-4-oxothiazolidin-2-ylidene)-3-(4-(1-(4-(trifluoromethoxy)phenyl)-1H-1,2,4-triazol-3-yl)phenethyl)urea (P49)

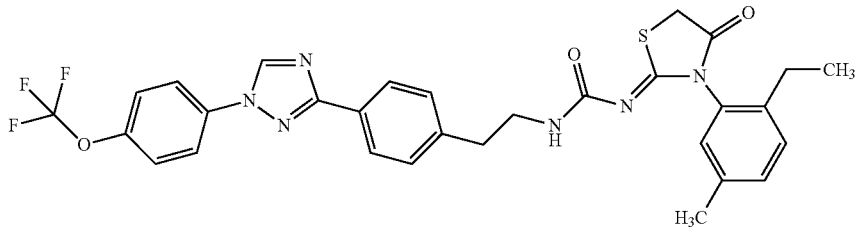 [SMILES: CCc1ccc(C)cc1N1C(=O)CS/C1=N\C(=O)NCCc1ccc(-c2ncn(-c3ccc(OC(F)(F)F)cc3)n2)cc1]

The title compound was prepared from 1-(2-ethyl-5-methylphenyl)thiourea (CA41) and 3-(4-(2-isocyanatoethyl)phenyl)-1-(4-(trifluoromethoxy)phenyl)-1H-1,2,4-triazole (C34a) and isolated as a pink solid (0.099 g, 43%).

Preparation of (Z)-1-(3-(2-ethyl-6-methylphenyl)-4-oxothiazolidin-2-ylidene)-3-(4-(1-(4-(trifluoromethoxy)phenyl)-1H-1,2,4-triazol-3-yl)phenethyl)urea (P50)

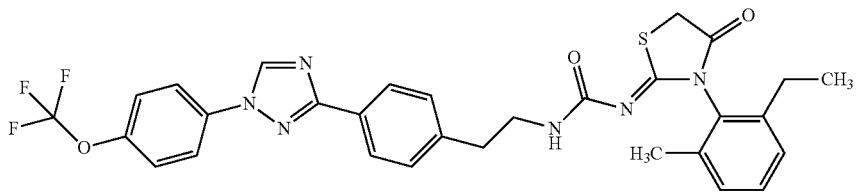 [SMILES: CCc1cccc(C)c1N1C(=O)CS/C1=N\C(=O)NCCc1ccc(-c2ncn(-c3ccc(OC(F)(F)F)cc3)n2)cc1]

The title compound was prepared from 1-(2-ethyl-6-methylphenyl)thiourea (CA39) and 3-(4-(2-isocyanatoethyl)phenyl)-1-(4-(trifluoromethoxy)phenyl)-1H-1,2,4-triazole (C34a) and isolated as an off-white solid (0.076 g, 33%).

Preparation of (Z)-1-(3-(4-methoxy-2,6-dimethylphenyl)-4-oxothiazolidin-2-ylidene)-3-(4-(1-(4-(trifluoromethoxy)phenyl)-1H-1,2,4-triazol-3-yl)phenethyl)urea (P47)

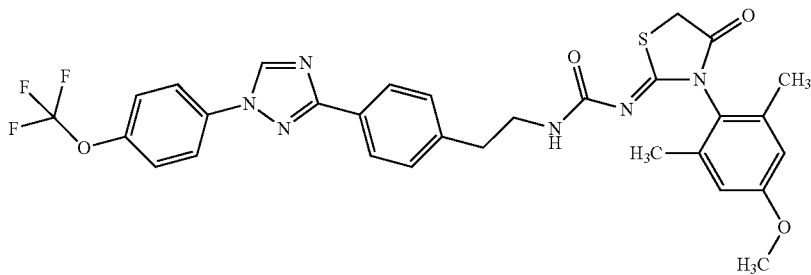 [SMILES: COc1cc(C)c(N2C(=O)CS/C2=N\C(=O)NCCc2ccc(-c3ncn(-c4ccc(OC(F)(F)F)cc4)n3)cc2)c(C)c1]

The title compound was prepared from 1-(4-methoxy-2,6-dimethylphenyl)thiourea and 3-(4-(2-isocyanatoethyl)phenyl)-1-(4-(trifluoromethoxy)phenyl)-1H-1,2,4-triazole (C34a) and isolated as a yellow oil (0.055 g, 23%).

Preparation of (Z)-1-(3-(3-isopropylphenyl)-4-
oxothiazolidin-2-ylidene)-3-(4-(1-(4-(trifluo-
romethoxy)phenyl)-1H-1,2,4-triazol-3-yl)phenethyl)
urea (P51)

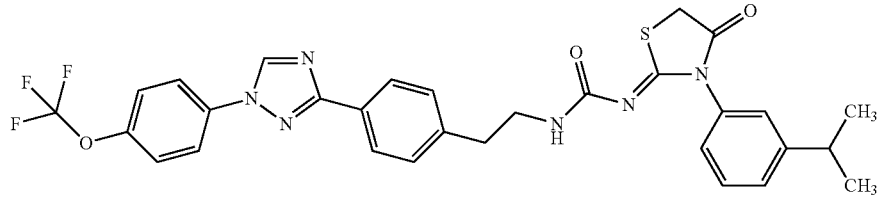

The title compound was prepared from 1-(3-isopropylphenyl)thiourea and 3-(4-(2-isocyanatoethyl)phenyl)-1-(4-(trifluoromethoxy)phenyl)-1H-1,2,4-triazole (C34a) and isolated as a dark brown oil (0.094 g, 37%).

Preparation of (Z)-1-(3-(4-fluoro-2-isopropylphenyl)-4-oxothiazolidin-2-ylidene)-3-(4-(1-(4-(trifluoromethoxy)phenyl)-1H-1,2,4-triazol-3-yl)phenethyl)
urea (P28)

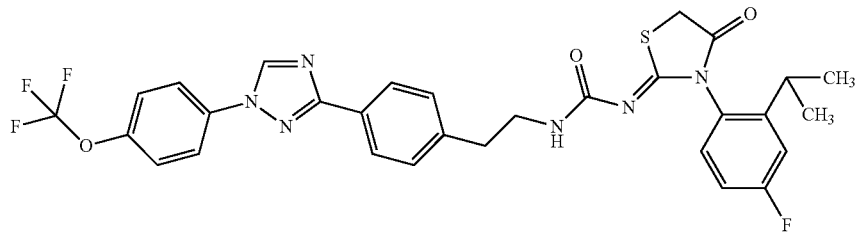 [SMILES: CC(C)c1cc(F)ccc1N1C(=O)CS/C1=N\C(=O)NCCc1ccc(-c2ncn(-c3ccc(OC(F)(F)F)cc3)n2)cc1]

The title compound was prepared from 1-(4-fluoro-2-isopropylphenyl)thiourea and 3-(4-(2-isocyanatoethyl)phenyl)-1-(4-(trifluoromethoxy)phenyl)-1H-1,2,4-triazole (C34a) and isolated as a brown foam (0.151 g, 37%).

Preparation of (Z)-1-(3-(2-isopropyl-5-methylphenyl)-5-methyl-4-oxothiazolidin-2-ylidene)-3-(4-(1-(4-(trifluoromethoxy)phenyl)-1H-1,2,4-triazol-3-yl)
phenethyl)urea (P57)

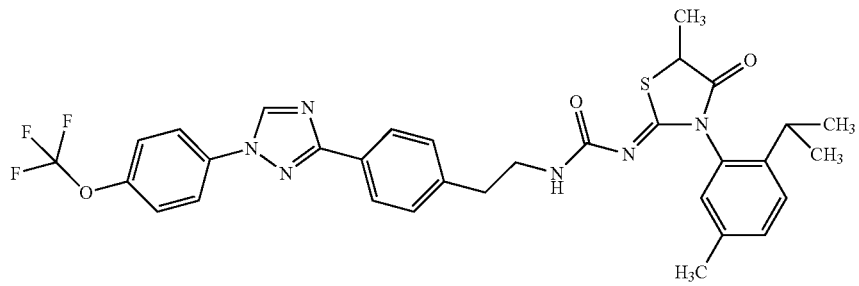 [SMILES: Cc1ccc(C(C)C)c(N2C(=O)C(C)S/C2=N\C(=O)NCCc2ccc(-c3ncn(-c4ccc(OC(F)(F)F)cc4)n3)cc2)c1]

The title compound was prepared from 1-(2-isopropyl-5-methylphenyl)thiourea, 3-(4-(2-isocyanatoethyl)phenyl)-1-(4-(trifluoromethoxy)phenyl)-1H-1,2,4-triazole (C34a), and methyl 2-brompropanoate and isolated as a clear sticky oil (0.192 g, 49%).

Preparation of (Z)-1-(3-(5-chloro-2-isopropylphenyl)-4-oxothiazolidin-2-ylidene)-3-(4-(1-(4-(trifluoromethoxy)phenyl)-1H-1,2,4-triazol-3-yl)phenethyl) urea (FB40)

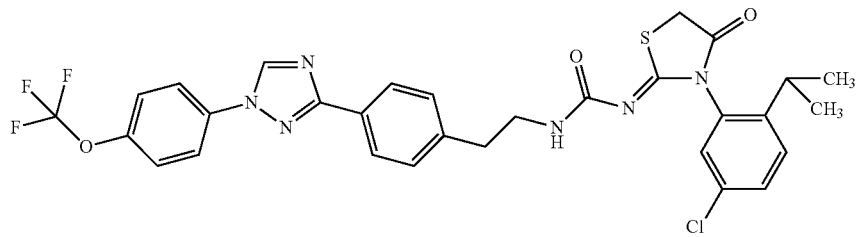 [SMILES: CC(C)c1ccc(Cl)cc1N1C(=O)CS/C1=N\C(=O)NCCc1ccc(-c2ncn(-c3ccc(OC(F)(F)F)cc3)n2)cc1]

The title compound was prepared from 1-(5-chloro-2-isopropylphenyl)thiourea (CB32) and 3-(4-(2-isocyanatoethyl)phenyl)-1-(4-(trifluoromethoxy)phenyl)-1H-1,2,4-triazole (C34a) and isolated as a brown glassy foam (0.173 g, 48%).

Example 36

Preparation of (E)-ethyl 2-methyl-3-(4-(1-(4-(trifluoromethoxy)phenyl)-1H-1,2,4-triazol-3-yl)phenyl) acrylate (C36)

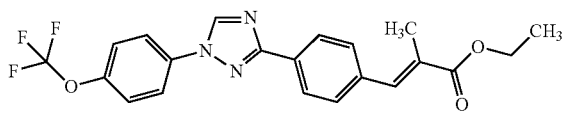

4-(1-(4-(Trifluoromethoxy)phenyl)-1H-1,2,4-triazol-3-yl)benzaldehyde (7.56 g, 22.7 mmol) and ethyl 2-(triphenylphosphoranylidene)propanoate (9.87 g, 27.2 mmol) in anhydrous toluene (30 mL) was heated at 110° C. for 16 hours. Additional ethyl 2-(triphenylphosphoranylidene)propanoate (2.40 g, 6.06 mmol) was then added, and the reaction was heated at 110° C. for 4 hours. The reaction was cooled, concentrated under vacuum, and loaded onto silica gel. Purification by flash column chromatography using 0-100% ethyl acetate/hexanes as eluent followed by reverse-phase flash column chromatography using 0-100% acetonitrile/water as eluent afforded the title compound as a white solid (5.92 g, 62%): mp 126-127.5° C.; $^1$H NMR (400 MHz, CDCl$_3$) δ 8.58 (s, 1H), 8.27-8.17 (m, 2H), 7.84-7.78 (m, 2H), 7.73 (s, 1H), 7.52 (d, J=8.2 Hz, 2H), 7.40 (d, J=8.3 Hz, 2H), 4.29 (q, J=7.1 Hz, 2H), 2.17 (d, J=1.5 Hz, 3H), 1.37 (t, J=7.1 Hz, 3H); $^{19}$F NMR (376 MHz, CDCl$_3$) δ −58.02; ESIMS m/z 418 ([M+H]$^+$).

Example 37

Preparation of ethyl 2-methyl-3-(4-(1-(4-(trifluoromethoxy)phenyl)-1H-1,2,4-triazol-3-yl)phenyl) propanoate (C37)

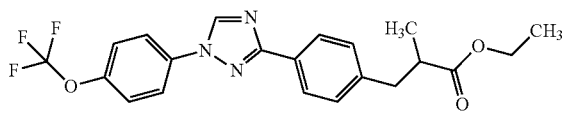 [SMILES: CCOC(=O)C(C)Cc1ccc(-c2ncn(-c3ccc(OC(F)(F)F)cc3)n2)cc1]

A flask containing (E)-ethyl 2-methyl-3-(4-(1-(4-(trifluoromethoxy)phenyl)-1H-1,2,4-triazol-3-yl)phenyl)acrylate (C36) (0.96 g, 2.3 mmol) and palladium on carbon (10 wt %, 0.24 g, 0.23 mmol) in ethyl acetate (10 mL) was evacuated under vacuum, filled with nitrogen, evacuated under vacuum, and then placed under hydrogen by balloon (~1 atm). After stirring at room temperature for 20 hours, the reaction was filtered through a pad of Celite® and concentrated to afford the title compound as a white solid (1.0 g, 100%): mp 73-75° C.; $^1$H NMR (400 MHz, CDCl$_3$) δ 8.56 (s, 1H), 8.14-8.07 (m, 2H), 7.86-7.76 (m, 2H), 7.39 (d, J=8.3 Hz, 2H), 7.29 (d, J=8.3 Hz, 2H), 4.10 (q, J=7.1 Hz, 2H), 3.22-2.99 (m, 1H), 2.75 (dq, J=13.3, 7.5 Hz, 2H), 1.24-1.15 (m, 6H); $^{19}$F NMR (376 MHz, CDCl$_3$) δ −58.03; ESIMS m/z 420 ([M+H]$^+$).

Example 38

Preparation of 2-methyl-3-(4-(1-(4-(trifluoromethoxy)phenyl)-1H-1,2,4-triazol-3-yl)phenyl) propanoic acid (C38)

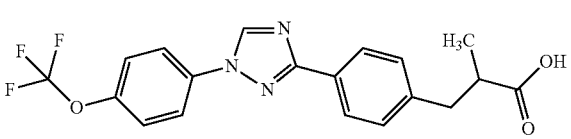 [SMILES: CC(Cc1ccc(-c2ncn(-c3ccc(OC(F)(F)F)cc3)n2)cc1)C(=O)O]

To ethyl 2-methyl-3-(4-(1-(4-(trifluoromethoxy)phenyl)-1H-1,2,4-triazol-3-yl)phenyl)propanoate (C37) (0.986 g, 2.35 mmol) in methanol (7.8 mL) was added sodium hydroxide (2 N, 5.9 mL, 11.8 mmol) and the solution was stirred at room temperature for 4 hours. The reaction was acidified with hydrogen chloride (2 N), and the white precipitate was vacuum-filtered to afford the title compound as a white solid (0.865 g, 93%): mp 142-144° C.; $^1$H NMR (400 MHz, DMSO-$d_6$) δ 12.19 (s, 1H), 9.39 (s, 1H), 8.14-7.95 (m, 4H), 7.71-7.55 (m, 2H), 7.42-7.27 (m, 2H), 3.04-2.89 (m, 1H), 2.75-2.62 (m, 2H), 1.07 (d, J=6.2 Hz, 3H). $^{19}$F NMR (376 MHz, acetone-$D_6$) δ −58.03; ESIMS m/z 392 ([M+H]$^+$).

Example 39

Preparation of 3-(4-(2-isocyanatopropyl)phenyl)-1-(4-(trifluoromethoxy)phenyl)-1H-1,2,4-triazole (C39)

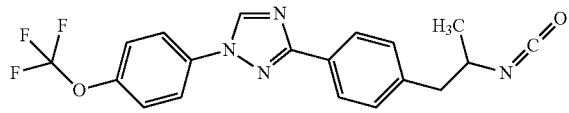 [SMILES: CC(Cc1ccc(-c2ncn(-c3ccc(OC(F)(F)F)cc3)n2)cc1)N=C=O]

To 2-methyl-3-(4-(1-(4-(trifluoromethoxy)phenyl)-1H-1,2,4-triazol-3-yl)phenyl)-propanoic acid (0.84 g, 2.2 mmol) in toluene (21.6 mL) was added triethylamine (0.33 mL, 2.4 mmol) and diphenyl phosphorazidate (0.47 mL, 2.2 mmol) and the solution was stirred at room temperature for 2 hours. The reaction was diluted with ethyl acetate and water and the layers separated. The organic layer was dried over anhydrous sodium sulfate, filtered, and concentrated. The crude material was loaded onto a Celite® cartridge and purified by flash column chromatography using 0-100% ethyl acetate/B, where B=1:1 dichloromethane/hexanes, as eluent to afford the title compound as a white solid (0.53 g, 58%): $^1$H NMR (400 MHz, CDCl$_3$) δ 8.56 (s, 1H), 8.21-8.11 (m, 2H), 7.88-7.77 (m, 2H), 7.39 (d, J=8.3 Hz, 2H), 7.32 (d, J=8.4 Hz, 2H), 3.94-3.80 (m, 1H), 2.87 (d, J=6.8 Hz, 2H), 1.35 (d, J=6.5 Hz, 3H); $^{19}$F NMR (376 MHz, CDCl$_3$) δ −58.03; ESIMS m/z 389 ([M+H]$^+$).

Example 40

Preparation of N-[2-(propan-2-yl)phenyl]-N'-[1-(4-{1-[4-(trifluoromethoxy)phenyl]-1H-1,2,4-triazol-3-yl}phenyl)propan-2-yl]dicarbonimidothioic diamide (F4)

3-(4-(2-Isocyanatopropyl)phenyl)-1-(4-(trifluoromethoxy)phenyl)-1H-1,2,4-triazole (C39) (0.17 g, 0.41 mmol) in acetonitrile (2.1 mL) was heated at 80° C. for 2 hours to ensure complete conversion to the isocyanate. The reaction was cooled and 1-(2-isopropylphenyl)thiourea (0.83 g, 0.43 mmol) and cesium carbonate (0.17 g, 0.53 mmol) were added and stirred at room temperature overnight. The reaction was diluted with ethyl acetate and washed with water. The aqueous layer was extracted with ethyl acetate, and the combined organic layers were dried over anhydrous sodium sulfate, filtered, and concentrated to afford the title compound as a white solid (0.25 g, 95%).

Example 41

Preparation of (Z)-1-(3-(2-isopropylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (F7)

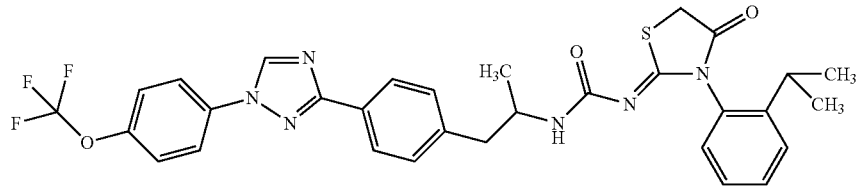

To N-[2-(propan-2-yl)phenyl]-N'-(4-{1-[4-(trifluoromethoxy)phenyl]-1H-1,2,4-triazol-3-yl}phenyl)propan-2-yl]dicarbonimidothioic diamide (F4) (0.20 g, 0.34 mmol) and sodium acetate (0.056 g, 0.68 mmol) in ethanol (2.3 mL) was added methyl 2-bromoacetate (0.05 mL, 0.51 mmol), and the reaction was heated at 65° C. for 2 hours. The reaction was cooled and diluted with water and extracted with ethyl acetate (2×). The organic layers were dried over anhydrous sodium sulfate, filtered, and concentrated. The crude material was loaded onto a silica gel cartridge with dichloromethane and purified by flash column chromatography using 0-100% ethyl acetate/B, where B=1:1 dichloromethane/hexanes, as eluent to afford the title compound as a white solid (0.070 g, 33%).

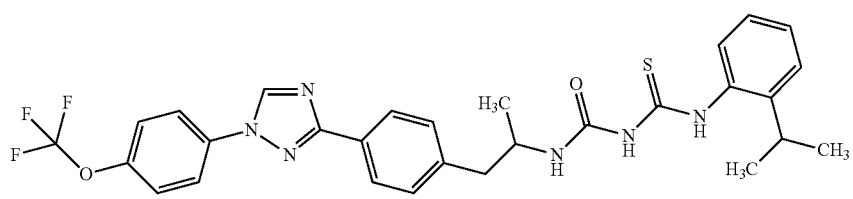 [SMILES: CC(Cc1ccc(-c2ncn(-c3ccc(OC(F)(F)F)cc3)n2)cc1)NC(=O)NC(=S)Nc1ccccc1C(C)C]

Example 42

Preparation of (Z)-1-(3-(2-isopropyl-5-methylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (F8)

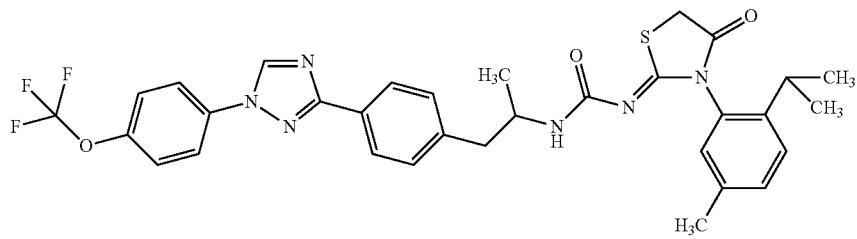 [SMILES: Cc1ccc(C(C)C)c(N2C(=O)CS/C2=N\C(=O)NC(C)Cc2ccc(-c3ncn(-c4ccc(OC(F)(F)F)cc4)n3)cc2)c1]

3-(4-(2-Isocyanatopropyl)phenyl)-1-(4-(trifluoromethoxy)phenyl)-1H-1,2,4-triazole (C39) (0.17 g, 0.41 mmol) in acetonitrile (2 mL) was heated at 80° C. for 2 hours to ensure complete conversion to the isocyanate. The reaction was cooled and 1-(2-isopropyl-5-methylphenyl)thiourea (0.095 g, 0.46 mmol) and cesium carbonate (0.20 g, 0.60 mmol) were added. The reaction was stirred at room temperature for 3 days. The reaction was diluted with ethanol (2.5 mL) and sodium acetate (0.064 g, 0.78 mmol) and methyl 2-bromoacetate (0.05 mL, 0.53 mmol) were added. The reaction was heated at 65° C. for 2.5 hours. The reaction mixture was diluted with ethyl acetate and washed with water. The aqueous layer was extracted an additional time with ethyl acetate. The combined organic layers were dried over anhydrous sodium sulfate, filtered, and concentrated. The crude material was loaded onto a Celite® cartridge and purified by flash column chromatography using 0-100% ethyl acetate/B, where B=1:1 dichloromethane/hexanes, as eluent to afford the title compound as an off-white solid (0.054 g, 20%).

The following compounds were prepared in accordance to the procedure in Example 42.

Preparation of (Z)-1-(3-(4-fluoro-2-isopropylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (P33)

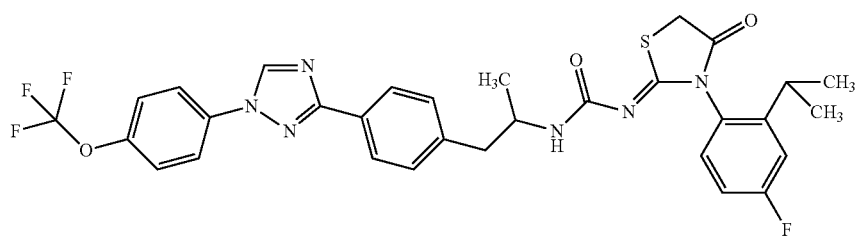 [SMILES: CC(Cc1ccc(-c2ncn(-c3ccc(OC(F)(F)F)cc3)n2)cc1)NC(=O)/N=C1\SCC(=O)N1c1ccc(F)cc1C(C)C]

The title compound was prepared from 2-methyl-3-(4-(1-(4-(trifluoromethoxy)phenyl)-1H-1,2,4-triazol-3-yl)phenyl) propanoyl azide (C39) and 1-(4-fluoro-2-isopropylphenyl) thiourea and isolated as a brown solid (0.183 g, 60%).

Preparation of (Z)-1-(3-(2-ethyl-6-methylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (P42)

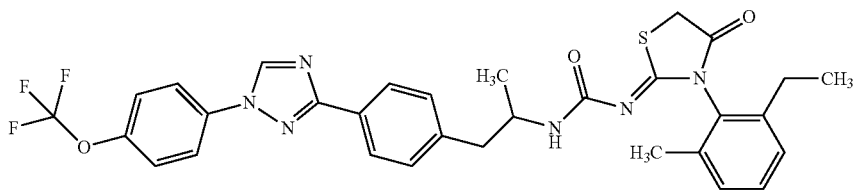 [SMILES: CCc1cccc(C)c1N1C(=O)CS/C1=N\C(=O)NC(C)Cc1ccc(-c2ncn(-c3ccc(OC(F)(F)F)cc3)n2)cc1]

The title compound was prepared from 2-methyl-3-(4-(1-(4-(trifluoromethoxy)phenyl)-1H-1,2,4-triazol-3-yl)phenyl) propanoyl azide (C39) and 1-(2-ethyl-6-methylphenyl)thiourea (CA39) and isolated as an off-white solid (0.117 g, 39%).

Preparation of (Z)-1-(3-(4-methoxy-2-methylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (P45)

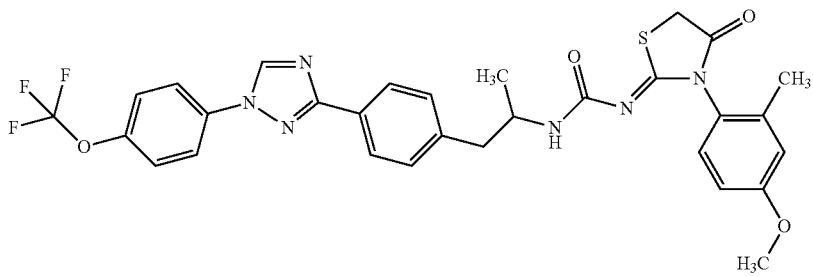 [SMILES: COc1ccc(N2C(=O)CS/C2=N\C(=O)NC(C)Cc2ccc(-c3ncn(-c4ccc(OC(F)(F)F)cc4)n3)cc2)c(C)c1]

The title compound was prepared from 2-methyl-3-(4-(1-(4-(trifluoromethoxy)phenyl)-1H-1,2,4-triazol-3-yl)phenyl) propanoyl azide (C39) and 1-(4-methoxy-2-methylphenyl) thiourea and isolated as a brown solid (0.224 g, 65%).

Preparation of (Z)-1-(3-(5-chloro-2-isopropylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (FB42)

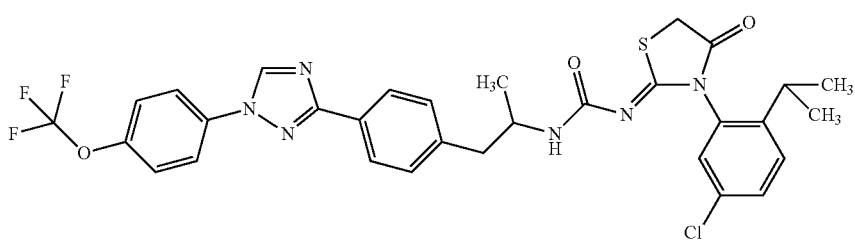 [SMILES: CC(Cc1ccc(-c2ncn(-c3ccc(OC(F)(F)F)cc3)n2)cc1)NC(=O)/N=C1\SCC(=O)N1c1cc(Cl)ccc1C(C)C]

The title compound was prepared from 2-methyl-3-(4-(1-(4-(trifluoromethoxy)phenyl)-1H-1,2,4-triazol-3-yl)phenyl)propanoyl azide (C39) and 1-(5-chloro-2-isopropylphenyl)thiourea (CB32) and isolated as a brown oil (0.110 g, 46%).

Preparation of (Z)-1-(3-(2-isopropyl-5-methylphenyl)-4-oxothiazolidin-2-ylidene)-3-(1-(4-(1-(4-(trifluoromethoxy)phenyl)-1H-1,2,4-triazol-3-yl)phenyl)butan-2-yl)urea (FB43) 12412827

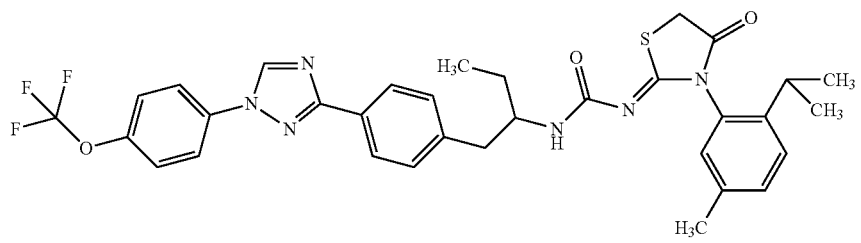 [SMILES: CCC(Cc1ccc(-c2ncn(-c3ccc(OC(F)(F)F)cc3)n2)cc1)NC(=O)/N=C1\SCC(=O)N1c1cc(C)ccc1C(C)C]

The title compound was prepared from 2-(4-(1-(4-(trifluoromethoxy)phenyl)-1H-1,2,4-triazol-3-yl)benzyl)butanoyl azide (CB22) and 1-(2-isopropyl-5-methylphenyl)thiourea and isolated as a peach glassy foam (0.122 g, 53%).

Preparation of (Z)-1-(3-(5-chloro-2-isopropylphenyl)-4-oxothiazolidin-2-ylidene)-3-(1-(4-(1-(4-(trifluoromethoxy)phenyl)-1H-1,2,4-triazol-3-yl)phenyl)butan-2-yl)urea (FB44)

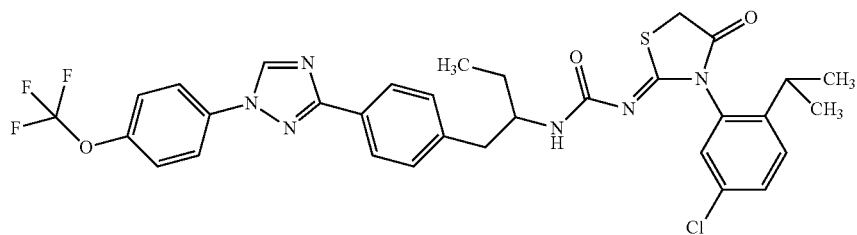 [SMILES: CCC(Cc1ccc(-c2ncn(-c3ccc(OC(F)(F)F)cc3)n2)cc1)NC(=O)/N=C1\SCC(=O)N1c1cc(Cl)ccc1C(C)C]

The title compound was prepared from 2-(4-(1-(4-(trifluoromethoxy)phenyl)-1H-1,2,4-triazol-3-yl)benzyl)butanoyl azide (CB22) and 1-(5-chloro-2-isopropylphenyl)thiourea (CB32) and isolated as a tan glassy foam (0.132 g, 60%).

Preparation of (Z)-1-(3-(2-isopropyl-5-methoxyphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (FB47)

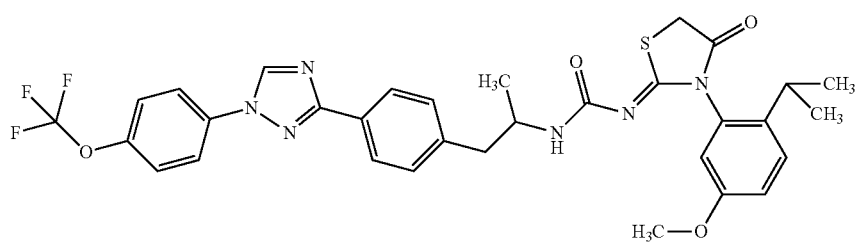 [SMILES: COc1ccc(C(C)C)c(N2C(=O)CS/C2=N\C(=O)NC(C)Cc2ccc(-c3ncn(-c4ccc(OC(F)(F)F)cc4)n3)cc2)c1]

The title compound was prepared from 2-methyl-3-(4-(1-(4-(trifluoromethoxy)phenyl)-1H-1,2,4-triazol-3-yl)phenyl)propanoyl azide (C39) and 1-(2-isopropyl-5-methoxyphenyl)thiourea (CA40) and isolated as a brown oil (0.146 g, 42%).

Preparation of (Z)-1-(3-(2-isopropyl-4-methylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (FB48)

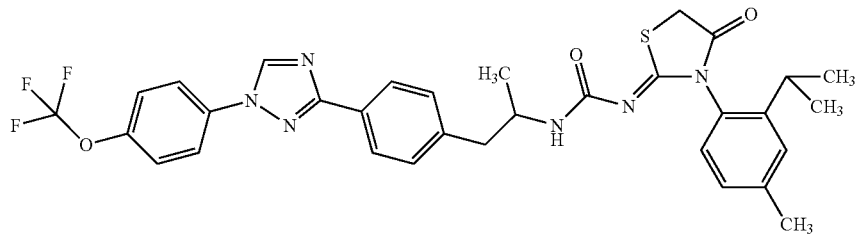 [SMILES: Cc1ccc(N2C(=O)CS/C2=N\C(=O)NC(C)Cc2ccc(-c3ncn(-c4ccc(OC(F)(F)F)cc4)n3)cc2)c(C(C)C)c1]

The title compound was prepared from 2-methyl-3-(4-(1-(4-(trifluoromethoxy)phenyl)-1H-1,2,4-triazol-3-yl)phenyl)propanoyl azide (C39) and 1-(2-isopropyl-4-methylphenyl)thiourea and isolated as a brown oil (0.130 g, 47%).

Example 43

Preparation of ethyl 3-(4-(1-(4-(trifluoromethoxy)phenyl)-1H-1,2,4-triazol-3-yl)phenyl)butanoate (C40)

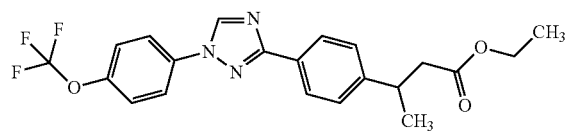 [SMILES: CCOC(=O)CC(C)c1ccc(-c2ncn(-c3ccc(OC(F)(F)F)cc3)n2)cc1]

A flask containing (E)-ethyl 3-(4-(1-(4-(trifluoromethoxy)phenyl)-1H-1,2,4-triazol-3-yl)phenyl)but-2-enoate (C26) (1.80 g, 4.31 mmol) and palladium on carbon (10 wt %, 0.46 g, 0.43 mmol) in ethyl acetate (14.5 mL) was evacuated and backfilled with nitrogen, and then evacuated and placed under hydrogen by balloon (~1 atm). The reaction was stirred at room temperature overnight, and then filtered through Celite® and concentrated to afford the title compound as a tan liquid (1.79 g, 98%): $^1$H NMR (400 MHz, CDCl$_3$) δ 8.55 (s, 1H), 8.17-8.07 (m, 2H), 7.87-7.75 (m, 2H), 7.38 (d, J=9.1 Hz, 2H), 7.36-7.31 (m, 2H), 4.08 (qd, J=7.1, 0.8 Hz, 2H), 3.35 (dd, J=14.6, 7.2 Hz, 1H), 2.62 (qd, J=15.1, 7.6 Hz, 2H), 1.34 (d, J=7.0 Hz, 3H), 1.19 (t, J=7.1 Hz, 3H); $^{19}$F NMR (376 MHz, CDCl$_3$) δ −58.03; ESIMS m/z 420 ([M+H]$^+$).

Example 44

Preparation of 3-(4-(1-(4-(trifluoromethoxy)phenyl)-1H-1,2,4-triazol-3-yl)phenyl)butanoic acid (C41)

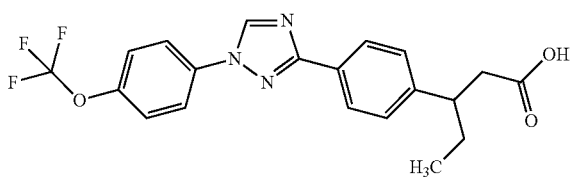

To ethyl 3-(4-(1-(4-(trifluoromethoxy)phenyl)-1H-1,2,4-triazol-3-yl)phenyl) butanoate (C40) (1.78 g, 4.24 mmol) in methanol (14 mL) was added sodium hydroxide (2 N, 12.7 mL, 25.4 mmol) and stirred at room temperature for 4 hours. The reaction acidified with hydrogen chloride (2 N), and the methanol was concentrated off under vacuum. The aqueous solution was extracted with ethyl acetate (3×). The organic layers were dried over anhydrous sodium sulfate, filtered, and concentrated to afford the title compound as a clear gum (0.470 g, 28%): $^1$H NMR (400 MHz, DMSO-d$_6$) δ 9.38 (s, 1H), 8.11-8.05 (m, 2H), 8.02 (d, J=8.3 Hz, 2H), 7.62 (d, J=8.3 Hz, 2H), 7.41 (d, J=8.3 Hz, 2H), 3.21 (dd, J=14.4, 7.1 Hz, 1H), 2.56 (d, J=7.4 Hz, 2H), 1.26 (d, J=7.0 Hz, 3H); $^{19}$F NMR (376 MHz, DMSO-d$_6$) δ −56.97; ESIMS m/z 392 ([M+H]$^+$).

The following compounds were prepared in accordance to the procedure in Example 44.

Preparation of 3-(4-(1-(4-(trifluoromethoxy)phenyl)-1H-1,2,4-triazol-3-yl)phenyl)pentanoic acid (CA12)

The title compound was prepared from ethyl 3-(4-(1-(4-(trifluoromethoxy)phenyl)-1H-1,2,4-triazol-3-yl)phenyl)pentanoate (CA48) and isolated as a white solid (0.927 g, 36%): $^1$H NMR (400 MHz, DMSO-d$_6$) δ 12.05 (s, 1H), 9.39 (s, 1H), 8.17-7.94 (m, 4H), 7.73-7.51 (m, 2H), 7.46-7.25 (m, 2H), 2.96 (ddd, J=14.7, 8.7, 6.0 Hz, 1H), 2.64 (dd, J=15.5, 6.6 Hz, 1H), 2.55-2.49 (m, 1H), 1.79-1.49 (m, 2H), 0.74 (t, J=7.3 Hz, 3H); $^{19}$F NMR (376 MHz, DMSO-d$_6$) δ −56.99; ESIMS m/z 406 ([M+H]$^+$).

Example 45

Preparation of 3-(4-(1-(4-(trifluoromethoxy)phenyl)-1H-1,2,4-triazol-3-yl)phenyl)butanoyl azide (C42)

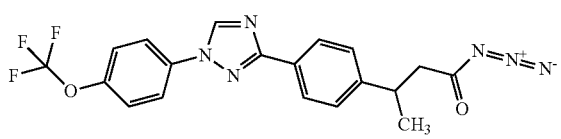

To 3-(4-(1-(4-(trifluoromethoxy)phenyl)-1H-1,2,4-triazol-3-yl)phenyl)butanoic acid (C41) (1.77 g, 4.52 mmol) in toluene (18 mL) was added triethylamine (0.82 mL, 5.88 mol)

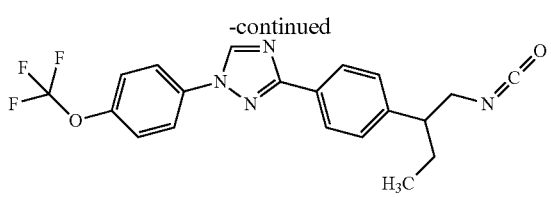

The title compound was prepared from 3-(4-(1-(4-(trifluoromethoxy)phenyl)-1H-1,2,4-triazol-3-yl)phenyl)pentanoic acid (CA12) to furnish a mixture of azide and isocyanate, 0.723 g, 72%): $^1$H NMR (400 MHz, CDCl$_3$) δ 8.56 (two s, 1H), 8.20-8.15 (m, 2H), 7.85-7.74 (m, 2H), 7.39 (dt, J=9.0, 1.0 Hz, 2H), 7.34-7.29 (m, 2H), 3.62-3.38 (m, 2H), 2.77-2.59 (m, 1H), 1.93-1.59 (m, 2H), 0.94-0.83 (m, 3H).

Example 46

Preparation of (Z)-1-(3-(2-isopropyl-5-methylphenyl)-4-oxothiazolidin-2-ylidene)-3-(2-(4-(1-(4-(trifluoromethoxy)phenyl)-1H-1,2,4-triazol-3-yl)phenyl)propyl)urea (F10)

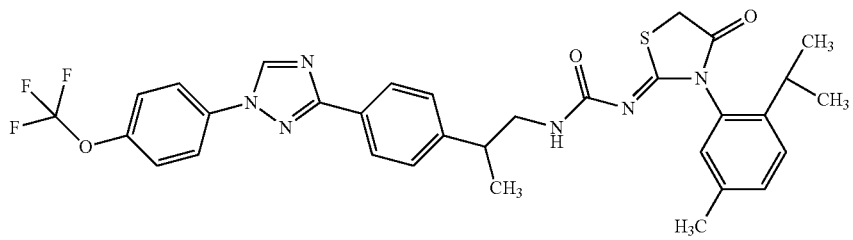 [SMILES: Cc1ccc(C(C)C)c(N2C(=O)CS/C2=N\C(=O)NCC(C)c2ccc(-c3ncn(-c4ccc(OC(F)(F)F)cc4)n3)cc2)c1]

and diphenyl phosphorazidate (1.05 mL, 4.98 mmol) and the solution was stirred at room temperature for 3 hours. The reaction was diluted with ethyl acetate and washed with water. The aqueous layer was extracted with ethyl acetate. The organic layers were dried over anhydrous sodium sulfate, filtered, and concentrated. The crude material was loaded onto a Celite® cartridge and purified by flash column chromatography using 0-100% ethyl acetate/B, where B=1:1 dichloromethane/hexanes, as eluent to afford the title compound as a clear oil (0.223 g, 12% yield): $^1$H NMR is consistent with a mixture of carbonyl azide and isocyanate. $^1$H NMR (400 MHz, CDCl$_3$) δ 8.56 (s, 1H), 8.28-8.03 (m, 2H), 7.88-7.66 (m, 2H), 7.48-7.30 (m, 4H), 3.60-3.40 (m, 2H), 3.08 (q, J=6.9 Hz, 1H), 2.81-2.49 (m, 1H), 1.37 (dd, J=10.4, 7.0 Hz, 3H); $^{19}$F NMR (376 MHz, CDCl$_3$) δ −58.03; ESIMS m/z 417 ([M+H]$^+$)

The following compounds were prepared in accordance to the procedure in Example 45.

Preparation of 3-(4-(1-(4-(trifluoromethoxy)phenyl)-1H-1,2,4-triazol-3-yl)phenyl)pentanoyl azide/3-(4-(1-isocyanatobutan-2-yl)phenyl)-1-(4-(trifluoromethoxy)phenyl)-1H-1,2,4-triazole (C42a)

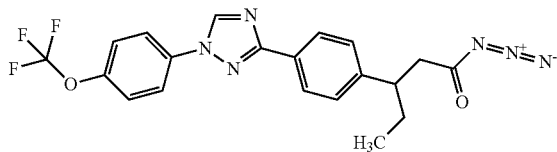

3-(4-(1-(4-(Trifluoromethoxy)phenyl)-1H-1,2,4-triazol-3-yl)phenyl)butanoyl azide (C42) (0.22 g, 0.52 mmol) in acetonitrile (2.6 mL) was heated at 80° C. for 2 hours. The reaction was cooled and 1-(2-isopropyl-5-methylphenyl)thiourea (0.12 g, 0.57 mmol) and cesium carbonate (0.20 g, 0.61 mmol) were added. The reaction was stirred at room temperature for 18 hours. Sodium acetate (0.093 g, 1.1 mmol), methyl 2-bromoacetate (0.07 mL, 0.78 mmol) and ethanol (2.6 mL) were added, and the reaction mixture was heated at 65° C. for 3 hours. The reaction was cooled, diluted with ethyl acetate, and washed with water. The aqueous layer was extracted once more with ethyl acetate. The combined organic layers were dried over anhydrous sodium sulfate, filtered, and concentrated. The crude material was loaded onto a Celite® cartridge and purified by flash column chromatography using 0-100% ethyl acetate/B, where B=1:1 dichloromethane/hexanes, as eluent to afford the title compound as an orange solid (0.12 g, 35%).

The following compounds were prepared in accordance to the procedure in Example 46.

Preparation of (Z)-1-(3-(2-isopropyl-5-methylphenyl)-4-oxothiazolidin-2-ylidene)-3-(2-(4-(1-(4-(trifluoromethoxy)phenyl)-1H-1,2,4-triazol-3-yl)phenyl)butyl)urea (P364)

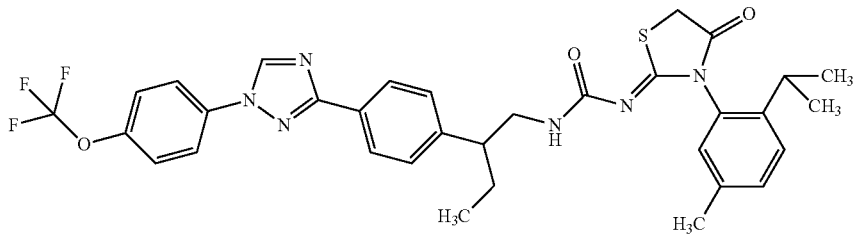 [SMILES: CCC(CNC(=O)/N=C1\SCC(=O)N1c1cc(C)ccc1C(C)C)c1ccc(-c2ncn(-c3ccc(OC(F)(F)F)cc3)n2)cc1]

The title compound was prepared from 3-(4-(1-(4-(trifluoromethoxy)phenyl)-1H-1,2,4-triazol-3-yl)phenyl)pentanoyl azide/3-(4-(1-isocyanatobutan-2-yl)phenyl)-1-(4-(trifluoromethoxy)phenyl)-1H-1,2,4-triazole (C42a) and 1-(2-isopropyl-5-methylphenyl)thiourea and isolated as a pink solid (0.110 g, 43%).

Preparation of (Z)-1-(3-(2-isopropyl-5-methoxyphenyl)-4-oxothiazolidin-2-ylidene)-3-(2-(4-(1-(4-(trifluoromethoxy)phenyl)-1H-1,2,4-triazol-3-yl)phenyl)butyl)urea (P683)

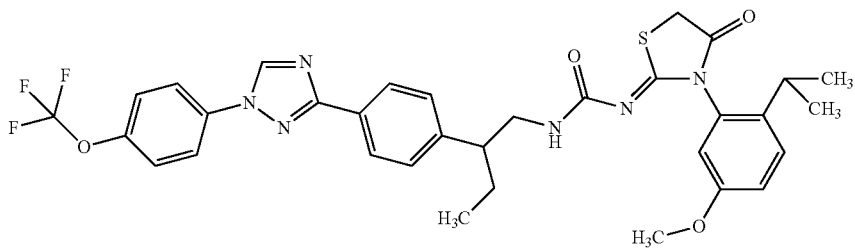 [SMILES: CCC(CNC(=O)/N=C1\SCC(=O)N1c1cc(OC)ccc1C(C)C)c1ccc(-c2ncn(-c3ccc(OC(F)(F)F)cc3)n2)cc1]

The title compound was prepared from 3-(4-(1-(4-(trifluoromethoxy)phenyl)-1H-1,2,4-triazol-3-yl)phenyl)pentanoyl azide/3-(4-(1-isocyanatobutan-2-yl)phenyl)-1-(4-(trifluoromethoxy)phenyl)-1H-1,2,4-triazole (C42a) and 1-(2-isopropyl-5-methoxyphenyl)thiourea (CA40) and isolated as a brown foam (0.091 g, 47%).

Preparation of (Z)-1-(3-(2-isopropylphenyl)-4-oxothiazolidin-2-ylidene)-3-(2-(4-(1-(4-(trifluoromethoxy)phenyl)-1H-1,2,4-triazol-3-yl)phenyl)butyl)urea (P209)

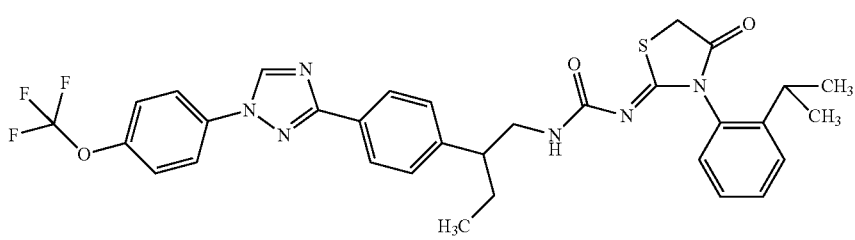 [SMILES: CCC(CNC(=O)/N=C1\SCC(=O)N1c1ccccc1C(C)C)c1ccc(-c2ncn(-c3ccc(OC(F)(F)F)cc3)n2)cc1]

The title compound was prepared from 3-(4-(1-(4-(trifluoromethoxy)phenyl)-1H-1,2,4-triazol-3-yl)phenyl)pentanoyl azide/3-(4-(1-isocyanatobutan-2-yl)phenyl)-1-(4-(trifluoromethoxy)phenyl)-1H-1,2,4-triazole (C42a) and 1-(2-isopropylphenyl)thiourea and isolated as a brown foam (0.041 g, 30%).

Preparation of (Z)-1-(3-(4-fluoro-2-isopropylphenyl)-4-oxothiazolidin-2-ylidene)-3-(2-(4-(1-(4-(trifluoromethoxy)phenyl)-1H-1,2,4-triazol-3-yl)phenyl)butyl)urea (P1163)

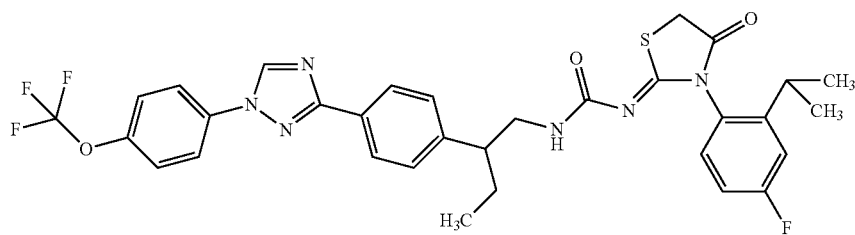 [SMILES: CCC(CNC(=O)/N=C1\SCC(=O)N1c1ccc(F)cc1C(C)C)c1ccc(-c2ncn(-c3ccc(OC(F)(F)F)cc3)n2)cc1]

The title compound was prepared from 3-(4-(1-(4-(trifluoromethoxy)phenyl)-1H-1,2,4-triazol-3-yl)phenyl)pentanoyl azide/3-(4-(1-isocyanatobutan-2-yl)phenyl)-1-(4-(trifluoromethoxy)phenyl)-1H-1,2,4-triazole (C42a) and 1-(4-fluoro-2-isopropylphenyl)thiourea and isolated as a brown foam (0.072 g, 30%).

Preparation of (Z)-1-(3-(2-isopropyl-5-methoxyphenyl)-4-oxothiazolidin-2-ylidene)-3-(2-(4-(1-(4-(trifluoromethoxy)phenyl)-1H-1,2,4-triazol-3-yl)phenyl)propyl)urea (P679)

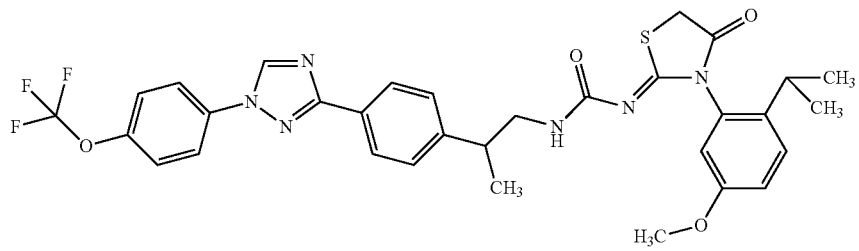 [SMILES: COc1ccc(C(C)C)c(N2C(=O)CS/C2=N\C(=O)NCC(C)c2ccc(-c3ncn(-c4ccc(OC(F)(F)F)cc4)n3)cc2)c1]

The title compound was prepared as described in Example 46 using 3-(4-(1-(4-(trifluoromethoxy)phenyl)-1H-1,2,4-triazol-3-yl)phenyl)butanoyl azide (C42) and 1-(2-isopropyl-5-methoxyphenyl)thiourea (CA40) and isolated as a brown solid (0.118 g, 54%).

Preparation of (Z)-1-(3-(2-isopropylphenyl)-4-oxothiazolidin-2-ylidene)-3-(2-(4-(1-(4-(trifluoromethoxy)phenyl)-1H-1,2,4-triazol-3-yl)phenyl)propyl)urea (P205)

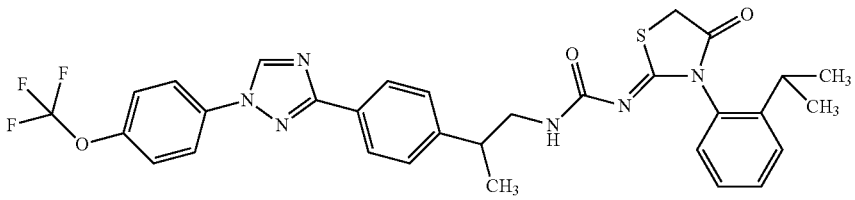 [SMILES: CC(C)c1ccccc1N1C(=O)CS/C1=N\C(=O)NCC(C)c1ccc(-c2ncn(-c3ccc(OC(F)(F)F)cc3)n2)cc1]

The title compound was prepared from 3-(4-(1-(4-(trifluoromethoxy)phenyl)-1H-1,2,4-triazol-3-yl)phenyl)butanoyl azide (C42) and 1-(2-isopropylphenyl)thiourea and isolated as a brown solid (0.105 g, 43%).

Preparation of (Z)-1-(3-(5-chloro-2-isopropylphenyl)-4-oxothiazolidin-2-ylidene)-3-(2-(4-(1-(4-(trifluoromethoxy)phenyl)-1H-1,2,4-triazol-3-yl)phenyl)propyl)urea (FB49)

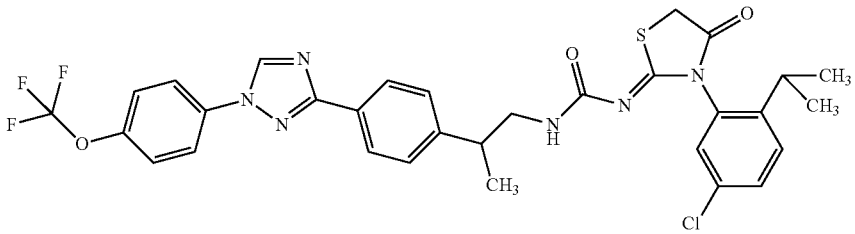 [SMILES: CC(C)c1ccc(Cl)cc1N1C(=O)CS/C1=N\C(=O)NCC(C)c1ccc(-c2ncn(-c3ccc(OC(F)(F)F)cc3)n2)cc1]

The title compound was prepared from 3-(4-(1-(4-(trifluoromethoxy)phenyl)-1H-1,2,4-triazol-3-yl)phenyl)butanoyl azide (C42) and 1-(5-chloro-2-isopropylphenyl)thiourea (CB32) and isolated as a brown oil (0.055 g, 22%).

Example 47

Preparation of 1-(4-(trifluoromethoxy)phenyl)-3-(4-vinylphenyl)-1H-1,2,4-triazole (C43)

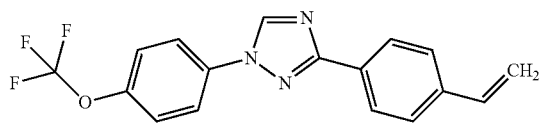 [SMILES: C=Cc1ccc(-c2ncn(-c3ccc(OC(F)(F)F)cc3)n2)cc1]

Methyltriphenylphosphonium bromide (32.2 g, 90.0 mmol) and 1,8-diazabicycloundec-7-ene (14.9 mL, 99.0 mmol) were dissolved in tetrahydrofuran (260 mL) and refluxed for 30 minutes. 4-(1-(4-(Trifluoromethoxy)phenyl)-1H-1,2,4-triazol-3-yl)benzaldehyde (15.0 g, 45.0 mmol) was added, and the reaction was heated at 65° C. for 5 hours. The solution was cooled and stirred at room temperature overnight. The reaction mixture was poured into water and extracted with hexanes. The organic layers were dried over anhydrous sodium sulfate, filtered, and concentrated. The crude compound was purified by flash column chromatography using 0-70% ethyl acetate/hexanes as eluent to afford the title compound as a white solid (10.4 g, 67%): $^1$H NMR (400 MHz, CDCl$_3$) δ 8.57 (s, 1H), 8.16 (d, J=8.3 Hz, 2H), 7.80 (d, J=9.0 Hz, 2H), 7.58-7.47 (m, 2H), 7.39 (d, J=9.1 Hz, 2H), 6.77 (dd, J=17.6, 10.9 Hz, 1H), 5.84 (dd, J=17.6, 0.8 Hz, 1H), 5.32 (dd, J=10.9, 0.8 Hz, 1H); $^{19}$F NMR (376 MHz, CDCl$_3$) δ −58.02; ESIMS m/z 332 ([M+H]$^+$).

Example 48

Preparation of 2-(4-(1-(4-(trifluoromethoxy)phenyl)-1H-1,2,4-triazol-3-yl)phenyl)ethanol (C44)

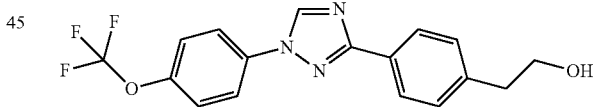

To 1-(4-(trifluoromethoxy)phenyl)-3-(4-vinylphenyl)-1H-1,2,4-triazole (C43) (2.0 g, 6.0 mmol) in tetrahydrofuran (50 mL) was added 9-borabicyclo(3.3.1)nonane (24 mL, 12.1 mmol), and the reaction was stirred at room temperature for 4.5 hours. Sodium hydroxide (3 N, 4.0 mL, 12.0 mmol) was added, followed by hydrogen peroxide (30% wt, 1.5 mL, 15.1 mmol). The light green solution was stirred at room temperature overnight. The reaction mixture was diluted with water and extracted with ethyl acetate. The organic layers were dried over anhydrous sodium sulfate, filtered, and concentrated to give a light green oil. The crude compound was purified by flash column chromatography using 0-50% ethyl acetate/hexanes as eluent to afford the title compound as a white solid (1.5 g, 69%): mp 85-98° C.; $^1$H NMR (400 MHz, DMSO-d$_6$) δ 9.37 (s, 1H), 8.06 (d, J=9.0 Hz, 2H), 8.01 (d, J=8.1 Hz, 2H), 7.61 (dd, J=9.2, 1.0 Hz, 2H), 7.41-7.30 (m, 2H), 4.69 (t, J=5.2 Hz, 1H), 3.65 (td, J=7.0, 5.1 Hz, 2H), 2.79

(t, J=6.9 Hz, 2H); $^{13}$C NMR (101 MHz, DMSO-d$_6$) δ 162.18, 147.08, 143.70, 141.45, 135.72, 129.39, 128.23, 127.93, 125.96, 122.57, 121.10, 61.90, 61.90; $^{19}$F NMR (376 MHz, DMSO-d$_6$) δ −56.98; ESIMS m/z 349 ([M+H]$^+$).

Example 49

Preparation of ethyl 2,3-difluoro-3-(4-(1-(4-(trifluoromethoxy)phenyl)-1H-1,2,4-triazol-3-yl)phenyl) propanoate (C45)

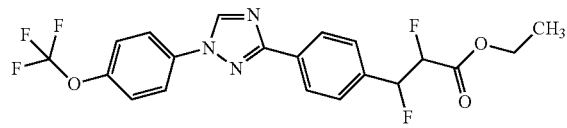 [SMILES: CCOC(=O)C(F)C(F)c1ccc(-c2ncn(-c3ccc(OC(F)(F)F)cc3)n2)cc1]

Step 1.

Sodium hydride (60% oil immersion, 0.48 g, 12 mmol) was added to a dry, oven-dried round bottomed flask and placed under nitrogen. Diethyl ether (9 mL) was added, followed by absolute ethanol (0.05 mL), and the reaction was cooled in an ice bath. Ethyl 2-fluoroacetate (0.87 mL, 9.0 mmol) was added dropwise. The reaction was stirred for 15 minutes in ice bath (gas evolution ceased). 4-(1-(4-(Trifluoromethoxy)phenyl)-1H-1,2,4-triazol-3-yl)benzaldehyde (2.2 g, 6.5 mmol) was added in solid portions. The solution slowly turned color to a golden yellow. The ice bath was removed after 1 hour and warmed to room temperature, stirring for an additional 2 hours until the reaction was quenched with saturated aqueous ammonium chloride, diluted with diethyl ether, and stirred at room temperature for 3 days. The biphasic solution was diluted with brine and extracted with ethyl acetate (2×). The organic layers were dried organic over anhydrous sodium sulfate, filtered, and concentrated to give an orange liquid. The crude material was purified by reverse-phase flash column chromatography using 0-100% acetonitrile/water as eluent to afford the intermediate ethyl 2-fluoro-3-hydroxy-3-(4-(1-(4-(trifluoromethoxy)phenyl)-1H-1,2,4-triazol-3-yl) phenyl)propanoate as a crude compound (0.11 g).

Step 2.

To the crude ethyl 2-fluoro-3-hydroxy-3-(4-(1-(4-(trifluoromethoxy)phenyl)-1H-1,2,4-triazol-3-yl)phenyl)propanoate (0.11 g, 0.26 mmol) in dichloromethane (1.7 mL) at 0° C. was added Deoxo-Fluor® (0.05 mL, 0.28 mmol) and stirred for 30 minutes. The reaction mixture was loaded onto a Celite® cartridge and purified by flash column chromatography using 0-60% ethyl acetate/hexanes as eluent to afford the title compound as a yellow oil (0.054 g, 47%): $^1$H NMR (400 MHz, CDCl$_3$) δ 8.58 (d, J=1.9 Hz, 1H), 8.32-8.14 (m, 2H), 7.87-7.73 (m, 2H), 7.50 (d, J=8.1 Hz, 2H), 7.39 (d, J=8.6 Hz, 2H), 6.11-5.76 (m, 1H), 5.52-4.90 (m, 1H), 4.27 (dqd, J=23.6, 7.1, 2.1 Hz, 2H), 1.27 (dt, J=19.4, 7.1 Hz, 3H); $^{19}$F NMR (376 MHz, CDCl$_3$) δ −58.04, −187.64, −187.68, −192.41, −192.44, −202.56, −202.60, −204.97, −205.00; ESIMS m/z 442 ([M+H]$^+$).

Example 50

Preparation of (Z)-ethyl 2-cyano-3-(4-(1-(4-(trifluoromethoxy)phenyl)-1H-1,2,4-triazol-3-yl)phenyl) acrylate (C46)

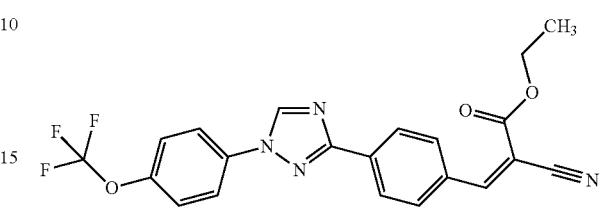

To 4-(1-(4-(trifluoromethoxy)phenyl)-1H-1,2,4-triazol-3-yl)benzaldehyde (3.0 g, 9.0 mmol) in ethanol (11.5 mL) was added ethyl 2-cyanoacetate (0.95 mL, 8.9 mmol) and pyrrolidine (0.97 mL, 12 mmol). A yellow precipitate formed immediately and additional ethanol (10 mL) was added. The reaction was stirred at room temperature for 18 hours and then concentrated onto Celite®. Purification by flash column chromatography using 0-100% ethyl acetate/B, where B=1:1 dichloromethane/hexanes as eluent afforded the title compound as a white solid (2.1 g, 50%): $^1$H NMR (400 MHz, CDCl$_3$) δ 8.61 (s, 1H), 8.36-8.31 (m, 2H), 8.29 (s, 1H), 8.12 (d, J=8.4 Hz, 2H), 7.85-7.79 (m, 2H), 7.41 (d, J=8.3 Hz, 2H), 4.41 (q, J=7.1 Hz, 2H), 1.42 (t, J=7.1 Hz, 3H); $^{13}$C NMR (101 MHz, CDCl$_3$) δ 162.46, 162.24, 154.18, 141.89, 135.36, 134.76, 132.41, 131.53, 127.22, 122.47, 121.33, 115.51, 103.28, 62.82, 14.19; ESIMS m/z 429 ([M+H]$^+$).

Example 51

Preparation of (Z)-2-cyano-3-(4-(1-(4-(trifluoromethoxy)phenyl)-1H-1,2,4-triazol-3-yl)phenyl) acrylic acid (C47)

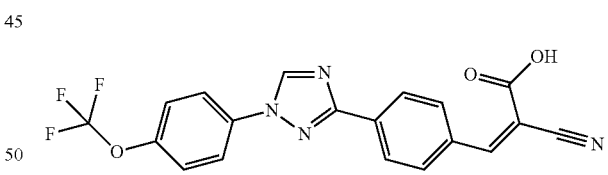

To (Z)-ethyl 2-cyano-3-(4-(1-(4-(trifluoromethoxy)phenyl)-1H-1,2,4-triazol-3-yl)phenyl)acrylate (C46) (2.5 g, 5.8 mmol) in tetrahydrofuran/methanol/water (3:2:1, 42 mL) was added lithium hydroxide (2.5 mL, 7.5 mmol) and stirred at room temperature for 18 hours. The reaction mixture was concentrated under vacuum, cooled in an ice bath, and acidified with hydrogen chloride (2 N). The precipitate was filtered and washed with cold water to afford the title compound as a brown solid (2.2 g, 82%): $^1$H NMR (400 MHz, DMSO-d$_6$) δ 9.49 (s, 1H), 8.39 (s, 1H), 8.28 (d, J=8.5 Hz, 2H), 8.18 (d, J=8.5 Hz, 2H), 8.13-8.08 (m, 2H), 7.64 (d, J=8.4 Hz, 2H); ESIMS m/z 401 ([M+H]$^+$).

The following compounds were prepared in accordance to the procedure in Example 51.

Preparation of 3-(3-(1-(4-(trifluoromethoxy)phenyl)-1H-1,2,4-triazol-3-yl)phenyl)propanoic acid (CA13)

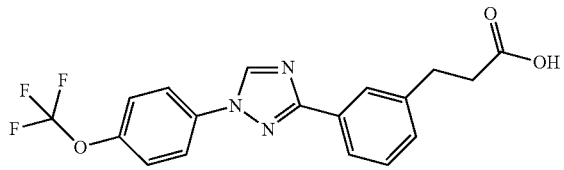 [SMILES: O=C(O)CCc1cccc(-c2ncn(-c3ccc(OC(F)(F)F)cc3)n2)c1]

The title compound was prepared from methyl 3-(3-(1-(4-(trifluoromethoxy)phenyl)-1H-1,2,4-triazol-3-yl)phenyl)propanoate (CA1) and isolated as a tan solid (9.09 g, 94%): $^1$H NMR (400 MHz, DMSO-$d_6$) δ 9.41 (s, 1H), 8.13-8.04 (m, 2H), 7.98 (t, J=1.7 Hz, 1H), 7.94 (dt, J=7.7, 1.4 Hz, 1H), 7.62 (d, J=8.8 Hz, 2H), 7.43 (t, J=7.6 Hz, 1H), 7.35 (dt, J=7.7, 1.4 Hz, 1H), 2.93 (t, J=7.5 Hz, 2H), 2.61 (t, J=7.5 Hz, 2H); $^{19}$F NMR (376 MHz, DMSO-$d_6$) δ −56.99; ESIMS m/z 378 ([M+H]$^+$), 376 ([M−H]$^−$).

Preparation of 2-(3-(1-(4-(trifluoromethoxy)phenyl)-1H-1,2,4-triazol-3-yl)phenyl)acetic acid (CB23)

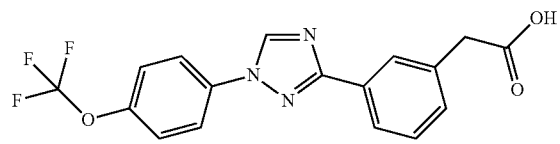

The title compound was prepared from methyl 2-(3-(1-(4-(trifluoromethoxy)phenyl)-1H-1,2,4-triazol-3-yl)phenyl)acetate (CB11) and isolated as a light brown solid (4.28 g, 88%): $^1$H NMR (400 MHz, DMSO-$d_6$) δ 12.40 (s, 1H), 9.42 (s, 1H), 8.13-8.06 (m, 2H), 8.06-7.96 (m, 2H), 7.63 (dq, J=8.0, 1.0 Hz, 2H), 7.47 (td, J=7.6, 0.6 Hz, 1H), 7.38 (dt, J=7.7, 1.5 Hz, 1H), 3.70 (s, 2H); $^{19}$F NMR (376 MHz, DMSO-$d_6$) δ −56.97; ESIMS m/z 364 ([M+H]$^+$), 362 ([M−H]$^−$).

Example 52

Preparation of tert-butyl 4-bromophenethylcarbamate (C48)

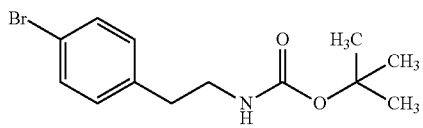 [SMILES: CC(C)(C)OC(=O)NCCc1ccc(Br)cc1]

To a stirring solution of 4-dimethylaminopyridine (0.19 g, 1.5 mmol) and di-tert-butyl dicarbonate (2.6 g, 12 mmol) in dichloromethane (40 mL) was added 4-bromophenethylamine (1.6 mL, 10 mmol) and stirring was continued at room temperature for 48 hours. The reaction mixture directly adsorbed onto silica gel and purified by flash column chromatography using 0-40% ethyl acetate/hexanes as eluent to afford the title compound as a white solid (0.68 g, 22%): mp 58-59° C.; $^1$H NMR (400 MHz, CDCl$_3$) δ 7.42 (d, J=8.3 Hz, 2H), 7.07 (d, J=8.3 Hz, 2H), 4.51 (s, 1H), 3.43-3.27 (m, 2H), 2.75 (t, J=7.0 Hz, 2H), 1.43 (s, 9H); $^{13}$C NMR (101 MHz, CDCl$_3$) δ 155.79, 137.97, 131.62, 130.55, 120.25, 77.21, 41.58, 35.65, 28.39; EIMS m/z 301 ([M]$^+$).

Example 53

Preparation of tert-butyl 4-(4,4,5,5-tetramethyl-1,3,2-dioxaborolan-2-yl)phenethylcarbamate (C49)

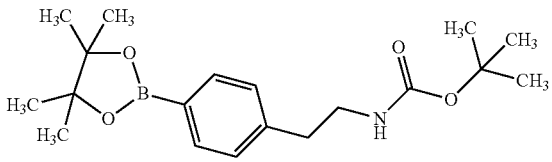 [SMILES: CC(C)(C)OC(=O)NCCc1ccc(B2OC(C)(C)C(C)(C)O2)cc1]

A mixture of tert-butyl 4-bromophenethylcarbamate (C48) (0.68 g, 2.3 mmol), bis(pinacolato)diborane (0.89 g, 3.5 mmol), potassium acetate (0.69 g, 7.0 mmol), [1,1'-bis(diphenylphosphino)ferrocene]dichloropalladium(II) (0.10 g, 0.14 mmol), and 1,1'-bis(diphenylphosphino)ferrocene (0.075 g, 0.14 mmol) in anhydrous dioxane (7 mL) was heated at 80° C. for 18 hours. The reaction was cooled, diluted with ethyl acetate, and washed with water. The aqueous layer was extracted with ethyl acetate. The combined organic layers were dried over anhydrous sodium sulfate, filtered and concentrated. The crude compound was adsorbed onto silica gel and purified by flash column chromatography using 0-60% ethyl acetate/hexanes as eluent to afford the title compound as a clear oil (0.86 g, 104%): $^1$H NMR (400 MHz, CDCl$_3$) δ 7.75 (d, J=7.9 Hz, 2H), 7.23-7.17 (m, 2H), 4.51 (s, 1H), 3.46-3.28 (m, 2H), 2.81 (t, J=7.1 Hz, 2H), 1.43 (s, 9H), 1.34 (s, 12H); ESIMS m/z 348 ([M+H]$^+$).

Example 54

Preparation of tert-butyl 4-(1-(4-(trifluoromethoxy)phenyl)-1H-1,2,4-triazol-3-yl)phenethyl)carbamate (C50)

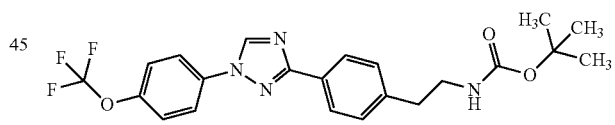

A mixture of 3-bromo-1-(4-(trifluoromethoxy)phenyl)-1H-1,2,4-triazole (C1) (0.55 g, 1.8 mmol), tert-butyl 4-(4,4,5,5-tetramethyl-1,3,2-dioxaborolan-2-yl)phenethyl carbamate (C49) (0.63 g, 1.8 mmol), tetrakis(triphenylphosphine)palladium(0) (0.21 g, 0.18 mmol), and sodium bicarbonate (0.33 g, 3.9 mmol) in dioxane/water (16 mL, 3:1) in a 20 mL vial was capped and heated at 140° C. for 30 minutes in a Biotage Initiator® microwave reactor with external IR-sensor temperature monitoring from the side of the vessel. The reaction was diluted with ethyl acetate and washed with water. The aqueous layers were extracted with ethyl acetate (2×), and the combined organic layers were dried over anhydrous sodium sulfate, filtered, and concentrated. The crude material was loaded onto a Celite® cartridge and purified by flash column chromatography using 0-100% ethyl acetate/B, where B=1:1 dichloromethane/hexanes, as eluent to provide the title compound as a white solid (0.48 g, 60%): mp 149-151° C.; $^1$H NMR (400 MHz, CDCl$_3$) δ 8.56 (s, 1H), 8.13 (d, J=8.1 Hz, 2H), 7.84-7.76 (m, 2H), 7.42-7.35 (m, 2H), 7.31 (d, J=7.9 Hz, 2H), 4.55 (s, 1H), 3.51-3.34 (m, 2H), 2.87 (t, J=7.0 Hz, 2H), 1.44 (s, 9H); $^{19}$F NMR (376 MHz, CDCl$_3$) δ −58.03; ESIMS m/z 449 ([M+H]$^+$).

Example 55

Preparation of 3-(4-bromophenyl)-1H-1,2,4-triazole (C51)

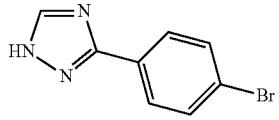

4-Bromo benzamide (28.0 g, 0.140 mol) was suspended in 1,1-dimethoxy-N,N-dimethylmethanamine (50 mL, 420 mmol) and the solution was stirred and heated to 90° C. for 2 hours. The solution was then cooled to ambient temperature and diethyl ether (150 mL) was added. The solution was cooled to 0° C. overnight and filtered to give (E)-4-bromo-N-((dimethylamino)methylene)benzamide as a colorless solid (25.6 g). This material was then dissolved in acetic acid (50 mL) and hydrazine (3.50 g, 110 mmol) was added slowly (exotherm) to the stirred solution, which solidified. The mixture was heated to 90° C. and a stir bar was added. The solid slowly dissolved over 8 hours and was then cooled to ambient temperature and the solution was diluted with water (35 mL). The resulting white solid was filtered and dried in vacuo to furnish the title compound as a colorless solid (19.8 g, 88%): $^1$H NMR (400 MHz, DMSO-d$_6$) δ 13.91 (s, 1H), 8.51 (s, 1H), 8.01-7.93 (m, 2H), 7.73-7.67 (m, 2H; ESIMS m/z 224, 226 ([M+H]$^+$).

Example 56

Preparation of 3-(4-bromophenyl)-1-(4-(trifluoromethoxy)phenyl)-1H-1,2,4-triazole (C52)

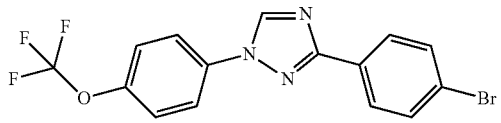 [SMILES: FC(F)(F)Oc1ccc(-n2cnc(-c3ccc(Br)cc3)n2)cc1]

To a solution of 1-iodo-4-(trifluoromethoxy)benzene (15.0 g, 52.0 mmol) in dimethylformamide (90 mL) and water (10 mL) was added 3-(4-bromophenyl)-1H-1,2,4-triazole (C51) (11.0 g, 49.0 mmol), cesium carbonate (34.0 g, 104 mmol), copper(I) iodide (2.80 g, 14.7 mmol), and 8-hydroxyquinoline (2.20 g, 15.0 mmol), and the solution was heated at 140° C. for 8 hours. The cooled solution was decanted from a layer of solid, diluted with a ammonium hydroxide (1 N, 100 mL) solution, and extracted with of diethyl ether (2×100 mL). The combined organic layer was dried and concentrated, and the brown solid was eluted through a short silica gel column using 20% ethyl acetate/hexanes as eluent to give the title compound as a light tan solid (9.50 g, 50%): mp 111-113° C., $^1$H NMR (400 MHz, CDCl$_3$) δ 8.56 (s, 1H), 8.07 (d, J=8.6 Hz, 2H), 7.79 (d, J=8.8 Hz, 2H), 7.62 (d, J=8.6 Hz, 2H), 7.39 (d, J=8.8 Hz, 2H); ESIMS m/z 384 ([M+H]$^+$).

Preparation of 3-(4-bromophenyl)-1-(4-(trifluoromethyl)phenyl)-1H-1,2,4-triazole (C53)

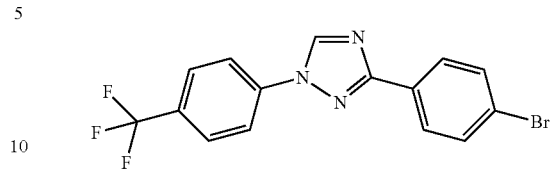

The title compound was prepared as described in Example 56 using 1-iodo-4-(trifluoromethyl)benzene to furnish the title compound as a white solid (3.21 g, 64%): $^1$H NMR (400 MHz, CDCl$_3$) δ 8.67 (s, 1H), 8.06 (d, J=8.6 Hz, 2H), 7.89 (d, J=8.5 Hz, 2H), 7.78 (d, J=8.5 Hz, 2H), 7.59 (d, J=8.6 Hz, 2H); ESIMS m/z 368, 370 ([M+H]$^+$).

Example 57

Preparation of tert-butyl 4-(1-(4-(trifluoromethoxy)phenyl)-1H-1,2,4-triazol-3-yl)phenethyl)carbamate (C50)

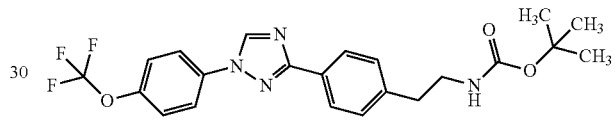

To a solution of 3-(4-bromophenyl)-1-(4-(trifluoromethoxy)phenyl)-1H-1,2,4-triazole (C52) (0.13 g, 0.32 mmol) in toluene (4 mL) and water (1 mL) was added potassium (2-((tert-butoxycarbonyl)amino)ethyl)trifluoroborate (0.082 g, 0.33 mmol), palladium(II) acetate (0.027 g, 0.027 mmol), cesium carbonate (0.33 g, 1.0 mmol), and dicyclohexyl(2',6'-diisopropoxy-[1,1'-biphenyl]-2-yl)phosphine (0.016 g, 0.034 mmol), and the solution was stirred under nitrogen and heated to 95° C. for 8 hours. The solution was then cooled and diluted with diethyl ether (5 mL) and adsorbed onto a silica gel pre-column. Flash column chromatography using 0-50% ethyl acetate/hexanes as eluent furnished the title compound as a light tan solid (0.095 g, 63%): mp 149-153° C., $^1$H NMR (400 MHz, CDCl$_3$) δ 8.56 (s, 1H), 8.18-8.10 (m, 2H), 7.84-7.77 (m, 2H), 7.43-7.35 (m, 2H), 7.31 (d, J=8.2 Hz, 2H), 4.58 (d, J=8.1 Hz, 1H), 3.49-3.34 (m, 1H), 2.87 (t, J=7.0 Hz, 1H), 1.44 (s, 9H); ESIMS m/z 449 ([M+H]$^+$).

Example 58

Preparation of 2-(4-(1-(4-(trifluoromethoxy)phenyl)-1H-1,2,4-triazol-3-yl)phenyl)ethanamine (C55)

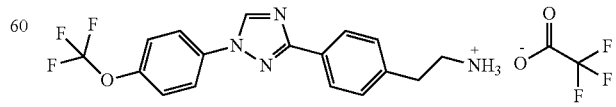

To a stirred and cooled (0° C.) solution of tert-butyl 4-(1-(4-(trifluoromethoxy)phenyl)-1H-1,2,4-triazol-3-yl)phenethylcarbamate (C50) (0.35 g, 0.77 mmol) in dichloromethane (2.6 mL) was added trifluoroacetic acid (0.060 mL, 0.78 mmol), and the solution was allowed to warm slowly to ambient temperature. After 18 hours, an additional amount of trifluoroacetic acid (0.060 mL, 0.78 mmol) was added. After 24 hours a third aliquot of trifluoroacetic acid (0.060 mL, 0.78 mmol) was added. After an additional 24 hours, the solution was concentrated to give the title compound as a tan solid (0.325 g, 88%): $^1$H NMR (400 MHz, DMSO-$d_6$) δ 9.41 (s, 1H), 8.08 (dd, J=8.8, 2.6 Hz, 4H), 7.87 (s, 2H), 7.63 (d, J=8.3 Hz, 2H), 7.43 (d, J=8.3 Hz, 2H), 3.17-3.06 (m, 2H), 2.99-2.89 (m, 2H); ESIMS m/z 349 ([M+H]+).

The following compounds were prepared in accordance to the procedure in Example 58.

Preparation of N-methyl-2-(4-(1-(4-(trifluoromethoxy)phenyl)-1H-1,2,4-triazol-3-yl)phenyl)ethanamine (CB24)

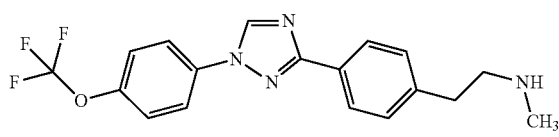 [SMILES: CNCCc1ccc(-c2ncn(-c3ccc(OC(F)(F)F)cc3)n2)cc1]

The title compound was prepared from tert-butyl methyl (4-(1-(4-(trifluoromethoxy)phenyl)-1H-1,2,4-triazol-3-yl)phenethyl)carbamate (CB63), neutralized with aqueous sodium bicarbonate, and isolated as a yellow waxy solid with excess trifluoroacetic acid (5.73 g, 111%): $^1$H NMR (400 MHz, CDCl$_3$) δ 8.53 (s, 1H), 8.12 (d, J=8.2 Hz, 2H), 7.77 (d, J=9.0 Hz, 2H), 7.37 (dd, J=9.0, 1.0 Hz, 2H), 7.31 (d, J=8.2 Hz, 2H), 3.23-3.12 (m, 2H), 3.05 (dd, J=9.4, 6.3 Hz, 2H), 2.67 (s, 3H), 1.29-1.22 (m, 1H); $^{19}$F NMR (376 MHz, CDCl$_3$) δ −58.04, −75.71; ESIMS m/z 363 ([M+H]+).

Preparation of N-ethyl-2-(4-(1-(4-(trifluoromethoxy)phenyl)-1H-1,2,4-triazol-3-yl)phenyl)ethanamine (CB25)

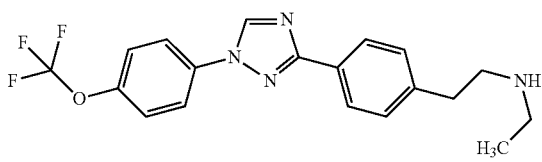 [SMILES: CCNCCc1ccc(-c2ncn(-c3ccc(OC(F)(F)F)cc3)n2)cc1]

The title compound was prepared from tert-butyl ethyl(4-(1-(4-(trifluoromethoxy)phenyl)-1H-1,2,4-triazol-3-yl)phenethyl)carbamate (CB64), neutralized with aqueous sodium bicarbonate, and isolated as an orange solid (0.167 g, 98%, 80% pure): $^1$H NMR (400 MHz, CDCl$_3$) δ 8.54 (s, 1H), 8.17-8.06 (m, 2H), 7.87-7.63 (m, 2H), 7.37 (dt, J=8.0, 1.0 Hz, 2H), 7.34-7.28 (m, 2H), 3.21 (s, 2H), 3.14-2.97 (m, 4H), 1.84 (s, 1H), 0.87 (ddd, J=12.0, 8.9, 6.6 Hz, 3H); $^{19}$F NMR (376 MHz, CDCl$_3$) δ −58.04; ESIMS m/z 377 ([M+H]+).

Preparation of N-(4-(1-(4-(trifluoromethoxy)phenyl)-1H-1,2,4-triazol-3-yl)phenethyl)prop-2-en-1-amine (CB26)

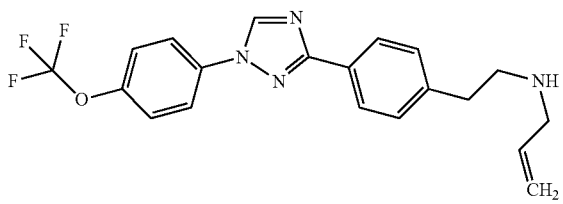 [SMILES: C=CCNCCc1ccc(-c2ncn(-c3ccc(OC(F)(F)F)cc3)n2)cc1]

The title compound was prepared from tert-butyl allyl(4-(1-(4-(trifluoromethoxy)phenyl)-1H-1,2,4-triazol-3-yl)phenethyl)carbamate (CB65), neutralized with aqueous sodium bicarbonate, and isolated as a yellow solid (0.124 g, 90%): mp 110-120° C.; $^1$H NMR (400 MHz, CDCl$_3$) δ 8.54 (s, 1H), 8.14-8.07 (m, 2H), 7.81-7.73 (m, 2H), 7.42-7.34 (m, 2H), 7.34-7.28 (m, 2H), 5.92 (ddt, J=16.9, 10.2, 6.6 Hz, 1H), 5.43-5.22 (m, 2H), 3.49 (dt, J=6.6, 1.2 Hz, 2H), 3.19-2.92 (m, 5H); $^{19}$F NMR (376 MHz, CDCl$_3$) δ −58.04; ESIMS m/z 389 ([M+H]+).

Preparation of N-(cyclopropylmethyl)-2-(4-(1-(4-(trifluoromethoxy)phenyl)-1H-1,2,4-triazol-3-yl)phenyl)ethanamine (CB27)

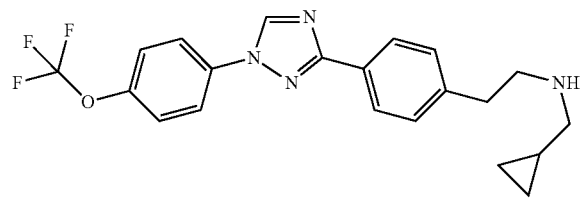 [SMILES: FC(F)(F)Oc1ccc(-n2cnc(-c3ccc(CCNCC4CC4)cc3)n2)cc1]

The title compound was prepared from tert-butyl (cyclopropylmethyl)(4-(1-(4-(trifluoromethoxy)phenyl)-1H-1,2,4-triazol-3-yl)phenethyl)carbamate (CB66), neutralized with aqueous sodium bicarbonate, and isolated as a white solid (0.125 g, 100%): mp 162-166° C.; $^1$H NMR (400 MHz, CDCl$_3$) δ 8.54 (s, 1H), 8.15-8.09 (m, 2H), 7.81-7.75 (m, 2H), 7.38 (dq, J=8.9, 0.9 Hz, 2H), 7.34-7.29 (m, 2H), 3.22 (dd, J=10.2, 6.0 Hz, 2H), 3.09 (dd, J=10.0, 6.1 Hz, 2H), 2.84 (d, J=7.3 Hz, 2H), 1.11 (ddd, J=12.7, 8.1, 4.8 Hz, 1H), 0.86 (dd, J=12.8, 5.8 Hz, 1H), 0.69-0.58 (m, 2H), 0.37-0.29 (m, 2H); $^{19}$F NMR (376 MHz, CDCl$_3$) δ −58.03; ESIMS m/z 403 ([M+H]+).

Example 58a

Preparation of 2-(4-(1-(4-(trifluoromethoxy)phenyl)-1H-1,2,4-triazol-3-yl)phenyl)ethanamine (CA51)

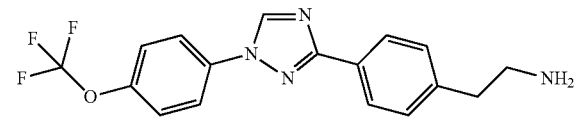 [SMILES: NCCc1ccc(-c2ncn(-c3ccc(OC(F)(F)F)cc3)n2)cc1]

To a stirred and cooled (0° C.) solution of tert-butyl 4-(1-(4-(trifluoromethoxy)phenyl)-1H-1,2,4-triazol-3-yl)phenethylcarbamate (C50) (0.10 g, 0.22 mmol) in dichloromethane (1.6 mL) was added trifluoroacetic acid (0.19 mL, 0.25 mmol), and the solution was allowed to warm slowly to ambient temperature and stirred overnight. The reaction mixture was concentrated, taken up in hexanes, and concentrated until a solid was obtained. The solid was dissolved in dichloromethane and washed with saturated sodium bicarbonate. The aqueous layer was extracted with dichloromethane (2×). The combined organic layers were washed with saturated sodium bicarbonate. The organic layers were dried over magnesium sulfate, filtered, and concentrated to give the title compound as a white solid (0.075 g, 97%): $^1$H NMR (400 MHz, CDCl$_3$) δ 8.56 (s, 1H), 8.18-8.07 (m, 2H), 7.83-7.74 (m, 2H), 7.41-7.29 (m, 4H), 3.02 (t, J=6.8 Hz, 2H), 2.81 (t, J=6.8 Hz, 2H), 1.45-1.29 (m, 2H); $^{19}$F NMR (376 MHz, CDCl$_3$) δ −58.04.

Example 59

Preparation of 2-(3-(4-bromophenyl)propyl)isoindoline-1,3-dione (C56)

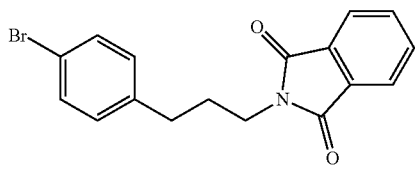 [SMILES: O=C1c2ccccc2C(=O)N1CCCc1ccc(Br)cc1]

To 3-(4-bromophenyl)propan-1-ol (4.70 g, 21.9 mmol), isoindoline-1,3-dione (3.54 g, 24.0 mmol) and triphenylphosphine (6.88 g, 26.2 mmol) in a 500 mL round bottomed flask equipped with a stir bar, nitrogen, and addition funnel, and cooled in an ice water bath was added diisopropyl azodicarboxylate (5.10 mL, 26.2 mmol). The reaction was allowed to warm to room temperature over the weekend. The reaction mixture was adsorbed onto Celite®. Purification by flash column chromatography using 5-20% ethyl acetate/hexanes as eluent provided a solid which was dried overnight at 50° C. in vacuo to afford the title compound as a white solid (6.51 g, 87%): mp 88-90° C., $^1$H NMR (400 MHz, CDCl$_3$) δ 7.86-7.79 (m, 2H), 7.71 (dd, J=5.5, 3.0 Hz, 2H), 7.38-7.32 (m, 2H), 7.11-7.04 (m, 2H), 3.73 (t, J=7.1 Hz, 2H), 2.68-2.59 (m, 2H), 2.07-1.96 (m, 2H); ESIMS m/z 346 [(M+2)$^+$].

The following compounds were prepared in accordance to the procedure in Example 59.

Preparation of 2-(3-bromophenethyl)isoindoline-1,3-dione (C57)

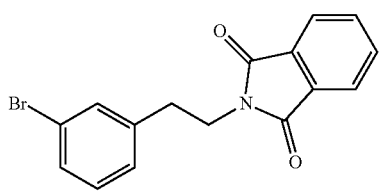 [SMILES: O=C1c2ccccc2C(=O)N1CCc1cccc(Br)c1]

The title compound was prepared from 2-(3-bromophenyl)ethanol to afford the title compound as a white solid (3.92 g, 81%): mp 100-104° C.; $^1$H NMR (400 MHz, CDCl$_3$) δ 7.88-7.81 (m, 2H), 7.76-7.69 (m, 2H), 7.43-7.39 (m, 1H), 7.35 (dt, J=7.4, 1.8 Hz, 1H), 7.22-7.13 (m, 2H), 3.94-3.87 (m, 2H), 2.99-2.92 (m, 2H); ESIMS m/z 332 ([M+2]$^+$).

Preparation of 2-(4-(3-bromophenyl)butyl)isoindoline-1,3-dione (C57a)

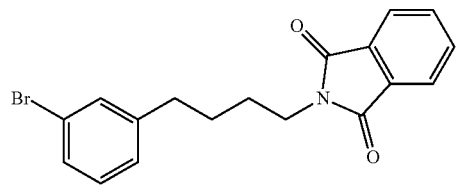 [SMILES: O=C1c2ccccc2C(=O)N1CCCCc1cccc(Br)c1]

The title compound was prepared from 4-(3-bromophenyl)butan-1-ol (C86) to afford the title compound as a white solid (7.68 g, 62%): $^1$H NMR (400 MHz, DMSO-d$_6$) δ 7.91-7.78 (m, 4H), 7.40 (t, J=1.9 Hz, 1H), 7.35 (dt, J=7.2, 2.0 Hz, 1H), 7.28-7.15 (m, 2H), 3.59 (t, J=6.5 Hz, 2H), 2.59 (t, J=7.1 Hz, 2H), 1.72-1.45 (m, 4H); $^{13}$C NMR (101 MHz, DMSO-d$_6$) δ 167.92, 144.86, 134.30, 131.57, 131.00, 130.34, 128.57, 127.41, 122.94, 121.55, 37.10, 34.08, 28.08, 27.50; EIMS m/z 357, 359.

Preparation of 2-(3-(3-(1-(4-(trifluoromethoxy)phenyl)-1H-1,2,4-triazol-3-yl)phenyl)propyl)isoindoline-1,3-dione (CA14)

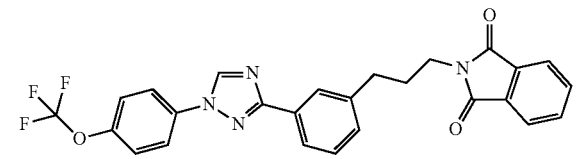 [SMILES: O=C1c2ccccc2C(=O)N1CCCc1cccc(-c2ncn(-c3ccc(OC(F)(F)F)cc3)n2)c1]

The title compound was prepared from 3-(3-(1-(4-(trifluoromethoxy)phenyl)-1H-1,2,4-triazol-3-yl)phenyl)propan-1-ol (CA45) and isolated as a light yellow solid (4.49 g, 81%): $^1$H NMR (400 MHz, DMSO-d$_6$) δ 9.39 (s, 1H), 8.18-8.02 (m, 2H), 7.96 (t, J=1.7 Hz, 1H), 7.89 (dt, J=7.7, 1.5 Hz, 1H), 7.87-7.76 (m, 4H), 7.62 (d, J=8.5 Hz, 2H), 7.40 (t, J=7.6 Hz, 1H), 7.34 (dt, J=7.7, 1.5 Hz, 1H), 3.65 (t, J=7.0 Hz, 2H), 2.73 (t, J=7.7 Hz, 2H), 1.97 (p, J=7.5 Hz, 2H); $^{19}$F NMR (376 MHz, DMSO-d$_6$) δ −56.98; ESIMS m/z 493 ([M+H]$^+$).

Preparation of 2-(4-(4-(1-(4-(trifluoromethyl)phenyl)-1H-1,2,4-triazol-3-yl)phenyl)butyl)isoindoline-1,3-dione (CA15)

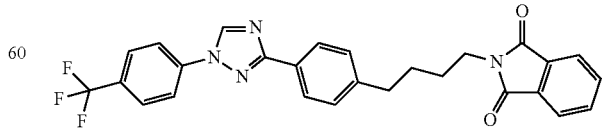

The title compound was prepared from 4-(4-(1-(4-(trifluoromethyl)phenyl)-1H-1,2,4-triazol-3-yl)phenyl)butan-1-ol (CA24), further purified by trituration with diethyl ether/ hexanes and isolated as a white solid (0.372 g, 76%): ¹H NMR (400 MHz, CDCl₃) δ 8.64 (s, 1H), 8.15-8.06 (m, 2H), 7.94-7.87 (m, 2H), 7.87-7.81 (m, 2H), 7.81-7.77 (m, 2H), 7.71 (dd, J=5.5, 3.0 Hz, 2H), 7.29 (d, J=8.2 Hz, 2H), 3.73 (t, J=6.7 Hz, 2H), 2.73 (t, J=7.1 Hz, 2H), 1.82-1.65 (m, 4H); ¹⁹F NMR (376 MHz, CDCl₃) δ −62.48; ESIMS m/z 491 ([M+H]⁺).

Preparation of 2-(4-(4-(1-(4-(trifluoromethoxy)phenyl)-1H-1,2,4-triazol-3-yl)phenyl)butyl)isoindoline-1,3-dione (CA16)

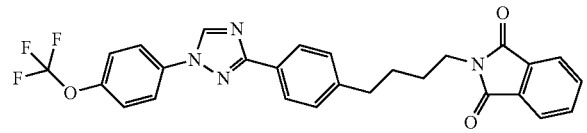 [SMILES: O=C1c2ccccc2C(=O)N1CCCCc1ccc(-c2ncn(-c3ccc(OC(F)(F)F)cc3)n2)cc1]

The title compound was prepared from 4-(4-(1-(4-(trifluoromethoxy)phenyl)-1H-1,2,4-triazol-3-yl)phenyl)butan-1-ol (CA25) and isolated as a white solid (2.39 g, 59%): ¹H NMR (400 MHz, CDCl₃) δ 8.55 (s, 1H), 8.12-8.06 (m, 2H), 7.84 (dd, J=5.4, 3.0 Hz, 2H), 7.83-7.77 (m, 2H), 7.75-7.66 (m, 2H), 7.38 (dd, J=9.2, 1.0 Hz, 2H), 7.29 (d, J=8.2 Hz, 2H), 3.73 (t, J=6.7 Hz, 2H), 2.72 (t, J=7.1 Hz, 2H), 1.85-1.61 (m, 4H); ¹⁹F NMR (376 MHz, CDCl₃) δ −58.03; ESIMS m/z 507 ([M+H]⁺).

Preparation of 2-(4-(4-(1-(4-(trifluoromethoxy)phenyl)-1H-1,2,4-triazol-3-yl)phenyl)but-3-yn-1-yl)isoindoline-1,3-dione (CA17)

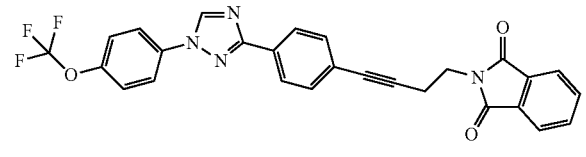 [SMILES: O=C1c2ccccc2C(=O)N1CCC#Cc1ccc(-c2ncn(-c3ccc(OC(F)(F)F)cc3)n2)cc1]

The title compound was prepared from 4-(4-(1-(4-(trifluoromethoxy)phenyl)-1H-1,2,4-triazol-3-yl)phenyl)but-3-yn-1-ol (CA23) and isolated as a white solid (0.393 g, 74%): ¹H NMR (400 MHz, CDCl₃) δ 8.56 (s, 1H), 8.09 (d, J=8.3 Hz, 2H), 7.88 (dd, J=5.5, 3.1 Hz, 2H), 7.79 (d, J=8.9 Hz, 2H), 7.73 (dd, J=5.5, 3.0 Hz, 2H), 7.43 (d, J=8.3 Hz, 2H), 7.39 (d, J=8.6 Hz, 2H), 4.00 (t, J=7.0 Hz, 2H), 2.86 (t, J=7.0 Hz, 2H); ¹⁹F NMR (376 MHz, CDCl₃) δ −58.02; ESIMS m/z 503 ([M+H]⁺).

Example 60

Preparation of 2-(3-(4-(4,4,5,5-tetramethyl-1,3,2-dioxaborolan-2-yl)phenyl)propyl)isoindoline-1,3-dione (C58)

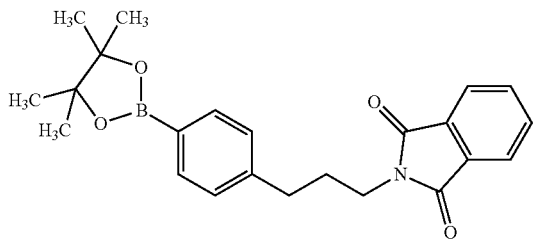 [SMILES: CC1(C)OB(c2ccc(CCCN3C(=O)c4ccccc4C3=O)cc2)OC1(C)C]

To 2-(3-(4-bromophenyl)propyl)isoindoline-1,3-dione (C56) (6.46 g, 18.8 mmol), 4,4,4',4',5,5,5',5'-octamethyl-2,2'-bi(1,3,2-dioxaborolane) (7.15 g, 28.2 mmol), [1,1'-bis(diphenylphosphino)ferrocene]dichloropalladium(II) (0.831 g, 1.13 mmol), and 1,1'-bis(diphenylphosphino)ferrocene (0.624 g, 1.13 mmol) in a 200 mL round bottomed flask equipped with a stir bar and nitrogen was added potassium(II) acetate (5.53 g, 56.3 mmol) followed by dioxane (56.9 mL). The reaction mixture was evacuated and purged with nitrogen. The reaction was heated to 80° C. overnight. The reaction was cooled. The reaction was diluted with ethyl acetate and washed with water. The aqueous layer was extracted with ethyl acetate. The combined organic layers were washed with brine, dried over sodium sulfate, filtered, and concentrated. Purification by flash column chromatography using 5-20% ethyl acetate/hexanes as eluent provided the title compound as a yellow oil (7.41 g, 101%): ¹H NMR (400 MHz, CDCl₃) δ 7.82 (dd, J=5.4, 3.0 Hz, 2H), 7.72-7.67 (m, 4H), 7.23-7.17 (m, 2H), 3.74 (t, J=7.2 Hz, 2H), 2.75-2.65 (m, 2H), 2.08-1.97 (m, 2H), 1.33 (s, 12H); ¹³C NMR (101 MHz, CDCl₃) δ 168.38, 144.40, 134.93, 133.84, 132.09, 127.73, 123.17, 83.62, 60.40, 37.81, 33.42, 29.71, 24.85; ESIMS m/z 392 ([M+H]⁺).

Example 61

Preparation of 2-(3-(4-(1-(4-(trifluoromethoxy)phenyl)-1H-1,2,4-triazol-3-yl)phenyl)propyl)isoindoline-1,3-dione (C59)

To 3-bromo-1-(4-(trifluoromethoxy)phenyl)-1H-1,2,4-triazole (C1) (0.50 g, 1.6 mmol), 2-(3-(4-(4,4,5,5-tetramethyl-1,3,2-dioxaborolan-2-yl)phenyl)propyl)isoindoline-1,3-dione (C58) (0.64 g, 1.6 mmol), sodium bicarbonate (0.27 g, 3.3 mmol), and tetrakis(triphenylphosphine)palladium(0) (0.19 g, 0.16 mmol) in a 10-20 mL microwave vial equipped with a stir bar was added dioxane (12 mL) and water (4.1 mL). The reaction was capped and heated at 140° C. for 30 minutes in a Biotage Initiator® microwave reactor with external IR-sensor temperature monitoring from the side of the vessel. The mixture was diluted with ethyl acetate and washed with water. The aqueous layer was extracted with ethyl acetate. The combined organic layers were washed with brine, dried over sodium sulfate, filtered, and concentrated. Purification by flash column chromatography using 0-30% ethyl acetate/B, where B=1:1 dichloromethane/hexanes, as eluent provided a solid which was dried under house vacuum overnight. The title compound was obtained as a white solid (0.42 g, 53%): mp 145-148° C., ¹H NMR (400 MHz, CDCl₃) δ 8.54 (d, J=0.8 Hz, 1H), 8.08 (d, J=8.1 Hz, 2H), 7.84 (ddd, J=5.5, 3.0, 0.8 Hz, 2H), 7.82-7.77 (m, 2H), 7.69 (ddd, J=5.5, 3.0, 0.8 Hz, 2H), 7.38 (dt, J=9.0, 1.0 Hz, 2H), 7.31 (d, J=8.0 Hz, 2H), 3.78 (t, J=7.2 Hz, 2H), 2.79-2.71 (m, 2H), 2.08 (p, J=7.5 Hz, 2H); ¹⁹F NMR (376 MHz, CDCl₃) δ −58.03; ESIMS m/z 493 ([M+H]⁺).

Example 62

Preparation of 3-(4-(1-(4-(trifluoromethoxy)phenyl)-1H-1,2,4-triazol-3-yl)phenyl)propan-1-amine (C60)

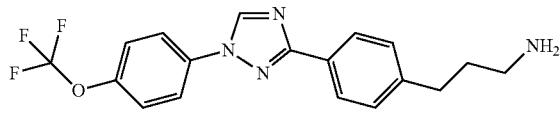 [SMILES: NCCCc1ccc(-c2ncn(-c3ccc(OC(F)(F)F)cc3)n2)cc1]

To 2-(3-(4-(1-(4-(trifluoromethoxy)phenyl)-1H-1,2,4-triazol-3-yl)phenyl)propyl)isoindoline-1,3-dione (C59) (0.373 g, 0.758 mmol) in a 25 mL vial equipped with a stir bar, Vigreux column, and nitrogen was added methanol (7.58 mL) followed by hydrazine monohydrate (0.110 mL, 2.27 mmol). The reaction was heated to 50° C. until determined to be complete by LCMS. The reaction mixture was cooled to room temperature and diluted with dichloromethane. The layers were separated and the aqueous layer was extracted with dichloromethane (2×). The organic layers were washed with sodium hydroxide (1 N, 4×), poured through a phase separator and concentrated. The resultant solid was dried in vacuo over 72 hours at 50° C. to provide the title compound as an off-white solid (0.262 g, 95%): $^1$H NMR (400 MHz, DMSO-$d_6$) δ 9.38 (s, 1H), 8.10-8.04 (m, 2H), 8.04-7.98 (m, 2H), 7.66-7.59 (m, 2H), 7.35 (d, J=8.1 Hz, 2H), 2.69-2.63 (m, 2H), 2.56 (t, J=6.9 Hz, 2H), 1.74-1.59 (m, 2H), (NH$_2$ not observed); $^{19}$F NMR (376 MHz, DMSO-$d_6$) δ −56.96; ESIMS m/z 363 ([M+H]$^+$).

The following compounds were prepared in accordance to the procedure in Example 62.

Preparation of 3-(3-(1-(4-(trifluoromethoxy)phenyl)-1H-1,2,4-triazol-3-yl)phenyl)propan-1-amine (CA18)

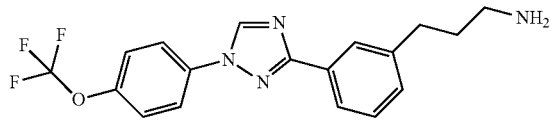 [SMILES: NCCCc1cccc(-c2ncn(-c3ccc(OC(F)(F)F)cc3)n2)c1]

The title compound was prepared as described in Example 62 using 2-(3-(3-(1-(4-(trifluoromethoxy)phenyl)-1H-1,2,4-triazol-3-yl)phenyl)propyl)isoindoline-1,3-dione (CA14) and isolated as a clear oil (3.49 g, 100%): $^1$H NMR (400 MHz, DMSO-$d_6$) δ 9.40 (s, 1H), 8.12-8.04 (m, 2H), 8.00-7.88 (m, 2H), 7.61 (d, J=8.6 Hz, 2H), 7.42 (t, J=7.6 Hz, 1H), 7.31 (dt, J=7.7, 1.5 Hz, 1H), 2.71 (q, J=9.0, 7.9 Hz, 2H), 2.57 (t, J=6.8 Hz, 2H), 1.74-1.62 (m, 2H); $^{19}$F NMR (376 MHz, DMSO-$d_6$) δ −57.01; ESIMS m/z 364 ([M+H]$^+$).

Preparation of 4-(4-(1-(4-(trifluoromethyl)phenyl)-1H-1,2,4-triazol-3-yl)phenyl)butan-1-amine (CA19)

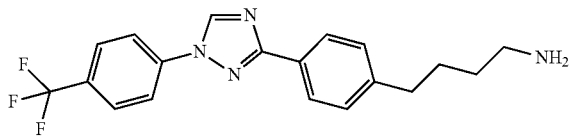 [SMILES: NCCCCc1ccc(-c2ncn(-c3ccc(C(F)(F)F)cc3)n2)cc1]

The title compound was prepared as described in Example 62 using 2-(4-(4-(1-(4-(trifluoromethyl)phenyl)-1H-1,2,4-triazol-3-yl)phenyl)butyl)isoindoline-1,3-dione (CA15), further purified with an SCX column and isolated as a yellow solid (0.215 g, 79%): $^1$H NMR (400 MHz, CDCl$_3$) δ 8.64 (s, 1H), 8.11 (d, J=8.2 Hz, 2H), 7.91 (d, J=8.4 Hz, 2H), 7.79 (d, J=8.5 Hz, 2H), 7.30 (d, J=8.1 Hz, 2H), 2.70 (t, J=7.6 Hz, 2H), 1.82-1.65 (m, 6H), 1.54 (d, J=8.1 Hz, 2H); $^{19}$F NMR (376 MHz, CDCl$_3$) δ −62.48; ESIMS m/z 361 ([M+H]$^+$).

Preparation of 4-(4-(1-(4-(trifluoromethoxy)phenyl)-1H-1,2,4-triazol-3-yl)phenyl)butan-1-amine (CA20)

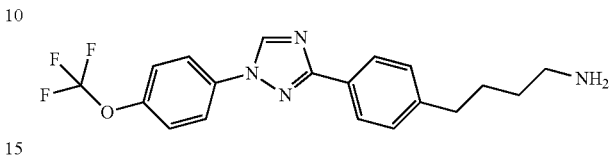

The title compound was prepared as described in Example 62 using 2-(4-(4-(1-(4-(trifluoromethoxy)phenyl)-1H-1,2,4-triazol-3-yl)phenyl)butyl)isoindoline-1,3-dione (CA16) and isolated as a white solid (1.76 g, 99%): $^1$H NMR (400 MHz, CDCl$_3$) δ 8.55 (s, 1H), 8.10 (d, J=8.2 Hz, 2H), 7.84-7.77 (m, 2H), 7.38 (dt, J=8.1, 1.0 Hz, 2H), 7.33-7.27 (m, 2H), 2.78-2.65 (m, 4H), 1.76-1.64 (m, 2H), 1.58-1.45 (m, 2H), 1.08 (bs, 2H); $^{19}$F NMR (376 MHz, CDCl$_3$) δ −58.03; ESIMS m/z 377 ([M+H]$^+$).

Preparation of 4-(3-(1-(4-(trifluoromethoxy)phenyl)-1H-1,2,4-triazol-3-yl)phenyl)butan-1-amine (CA21)

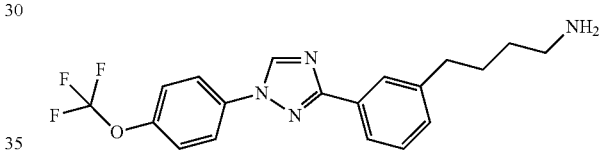

The title compound was prepared as described in Example 62 using 2-(4-(3-(1-(4-(trifluoromethoxy)phenyl)-1H-1,2,4-triazol-3-yl)phenyl)butyl)isoindoline-1,3-dione (CA2) and isolated as a light brown residue (1.94 g, 47%): $^1$H NMR (400 MHz, DMSO-$d_6$) δ 9.40 (s, 1H), 8.13-8.05 (m, 2H), 7.98-7.89 (m, 2H), 7.67-7.56 (m, 2H), 7.43 (t, J=7.6 Hz, 1H), 7.31 (dt, J=7.8, 1.5 Hz, 1H), 2.67 (t, J=7.7 Hz, 2H), 2.57 (t, J=6.9 Hz, 2H), 1.64 (tt, J=9.2, 6.8 Hz, 2H), 1.40 (p, J=7.1 Hz, 2H); $^{19}$F NMR (376 MHz, DMSO-$d_6$) δ −56.98; ESIMS m/z 378 ([M+H]$^+$).

Preparation of 4-(4-(1-(4-(trifluoromethoxy)phenyl)-1H-1,2,4-triazol-3-yl)phenyl)but-3-yn-1-amine (CA22)

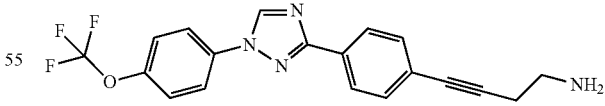

The title compound was prepared as described in Example 62 using 2-(4-(4-(1-(4-(trifluoromethoxy)phenyl)-1H-1,2,4-triazol-3-yl)phenyl)but-3-yn-1-yl)isoindoline-1,3-dione (CA17), further purified using an SCX column and isolated as a yellow solid (0.304 g, 104%): $^1$H NMR (400 MHz, CDCl$_3$) δ 8.56 (s, 1H), 8.16-8.09 (m, 2H), 7.84-7.76 (m, 2H), 7.56-7.48 (m, 2H), 7.44-7.34 (m, 2H), 2.95 (t, J=6.3 Hz, 2H), 2.59 (t, J=6.3 Hz, 2H), (NH$_2$ not observed); $^{19}$F NMR (376 MHz, CDCl$_3$) δ −58.02; ESIMS m/z 373 ([M+H]$^+$).

Example 63

Preparation of 1-[(2-isopropyl-5-methyl-phenyl)carbamothioyl]-3-[3-[4-[1-[4-(trifluoromethoxy)phenyl]-1H-1,2,4-triazol-3-yl]phenyl]propyl]urea (F21)

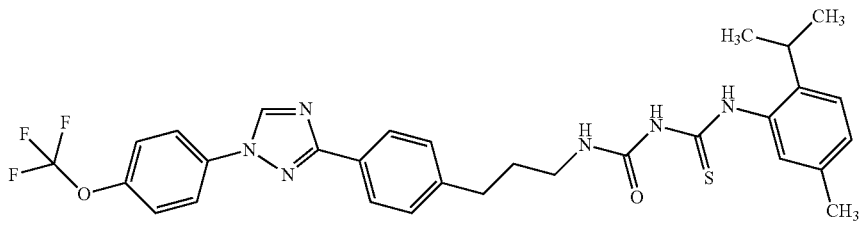 [SMILES: Cc1ccc(C(C)C)c(NC(=S)NC(=O)NCCCc2ccc(-c3ncn(-c4ccc(OC(F)(F)F)cc4)n3)cc2)c1]

To 3-(4-(1-(4-(trifluoromethoxy)phenyl)-1H-1,2,4-triazol-3-yl)phenyl)propan-1-amine (C60) (0.231 g, 0.639 mmol) in a 25 mL vial equipped with a stir bar and nitrogen was added dichloromethane (4.3 mL), water (2.1 mL), and sodium bicarbonate (0.161 g, 1.92 mmol). Triphosgene (0.0760 g, 0.255 mmol) was added in one portion and the reaction was stirred vigorously until the conversion of the starting material was observed by LCMS. The reaction mixture was diluted with dichloromethane, poured through a phase separator and concentrated. The resultant solid was suspended in acetonitrile (6.0 mL) in a 100 mL round bottomed flask equipped with a stir bar and nitrogen. To this was added cesium carbonate (0.229 g, 0.702 mmol) and 1-(2-isopropyl-5-methylphenyl)thiourea (0.133 g, 0.639 mmol). The reaction was stirred overnight at room temperature. The mixture was diluted with ethyl acetate and washed with water. The aqueous layer was extracted with ethyl acetate. The combined organic layers were dried over sodium sulfate, filtered and concentrated. Purification by flash column chromatography using 0-30% ethyl acetate/B, where B=1:1 dichloromethane/hexanes, as eluent provided mixed fractions. The fractions were combined and re-purified by flash column chromatography using 0-30% ethyl acetate/B, where B=1:1 dichloromethane/hexanes, as eluent and the resultant solid was dried in vacuo at 50° C. overnight to afford the title compound as a white solid (0.145 g, 38%).

The following compounds were prepared in accordance to the procedure in Example 63.

Preparation of 1-(o-tolylcarbamothioyl)-3-[3-[4-[1-[4-(trifluoromethoxy)phenyl]-1H-1,2,4-triazol-3-yl]phenyl]propyl]urea (PC92)

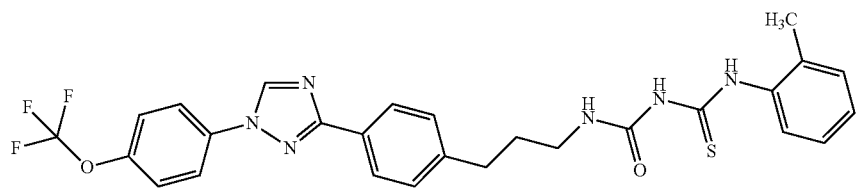 [SMILES: Cc1ccccc1NC(=S)NC(=O)NCCCc1ccc(-c2ncn(-c3ccc(OC(F)(F)F)cc3)n2)cc1]

The title compound was prepared as described in Example 63 using 3-(4-(1-(4-(trifluoromethoxy)phenyl)-1H-1,2,4-triazol-3-yl)phenyl)propan-1-amine (C60) and 1-(o-tolyl)thiourea. Sodium acetate was used in place of sodium bicarbonate. The title compound was isolated as a white solid (0.061 g, 21%): $^1$H NMR (400 MHz, DMSO-$d_6$) δ 12.02 (s, 1H), 10.06 (s, 1H), 9.39 (s, 1H), 8.14-7.99 (m, 3H), 7.63 (dt, J=7.3, 1.3 Hz, 3H), 7.45-7.35 (m, 2H), 7.33-7.14 (m, 4H), 7.09 (t, J=5.6 Hz, 1H), 3.17 (q, J=6.6 Hz, 2H), 2.70 (t, J=7.6 Hz, 2H), 2.21 (s, 3H), 1.92-1.74 (m, 2H); $^{19}$F NMR (376 MHz, DMSO-$d_6$) δ −56.97; ESIMS m/z 555 ([M+H]$^+$), 553 ([M−H]$^-$).

Preparation of 1-[(4-methoxy-2-methyl-phenyl)carbamothioyl]-3-[3-[4-[1-[4-(trifluoromethoxy)phenyl]-1H-1,2,4-triazol-3-yl]phenyl]propyl]urea (PC105)

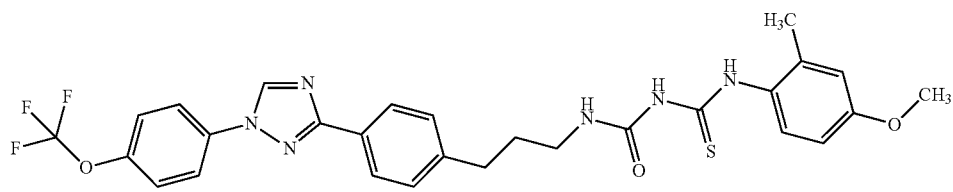 [SMILES: COc1ccc(NC(=S)NC(=O)NCCCc2ccc(-c3ncn(-c4ccc(OC(F)(F)F)cc4)n3)cc2)c(C)c1]

The title compound was prepared as described in Example 63 using 3-(4-(1-(4-(trifluoromethoxy)phenyl)-1H-1,2,4-triazol-3-yl)phenyl)propan-1-amine (C60) and 1-(4-methoxy-2-methylphenyl)thiourea. Sodium acetate was used in place of sodium bicarbonate. The title compound was isolated as a white solid (0.119 g, 38%): $^1$H NMR (400 MHz, DMSO-$d_6$) δ 11.79 (s, 1H), 10.00 (s, 1H), 9.39 (s, 1H), 8.16-7.98 (m, 4H), 7.70-7.57 (m, 2H), 7.38 (dd, J=8.4, 1.9 Hz, 3H), 7.08 (t, J=5.7 Hz, 1H), 6.84 (d, J=2.9 Hz, 1H), 6.77 (dd, J=8.7, 3.0 Hz, 1H), 3.75 (s, 3H), 3.16 (q, J=6.5 Hz, 2H), 2.70 (dd, J=8.5, 6.7 Hz, 2H), 2.17 (s, 3H), 1.81 (p, J=7.2 Hz, 2H); $^{19}$F NMR (376 MHz, DMSO-$d_6$) δ −56.96; ESIMS m/z 585 ([M+H]$^+$), 583 ([M−H]$^-$).

Preparation of 1-[(2-ethylphenyl)carbamothioyl]-3-[3-[4-[1-[4-(trifluoromethoxy)phenyl]-1H-1,2,4-triazol-3-yl]phenyl]propyl]urea (PC93)

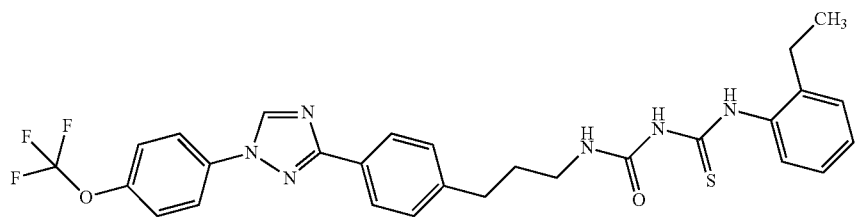 [SMILES: CCc1ccccc1NC(=S)NC(=O)NCCCc1ccc(-c2ncn(-c3ccc(OC(F)(F)F)cc3)n2)cc1]

The title compound was prepared as described in Example 63 using 3-(4-(1-(4-(trifluoromethoxy)phenyl)-1H-1,2,4-triazol-3-yl)phenyl)propan-1-amine (C60) and 1-(2-ethylphenyl)thiourea. Sodium acetate was used in place of sodium bicarbonate. The title compound was isolated as a white solid (0.112 g, 37%): $^1$H NMR (400 MHz, DMSO-$d_6$) δ 12.04 (s, 1H), 10.07 (s, 1H), 9.39 (s, 1H), 8.16-7.98 (m, 4H), 7.66-7.59 (m, 2H), 7.59-7.52 (m, 1H), 7.43-7.35 (m, 2H), 7.31-7.19 (m, 3H), 7.10 (t, J=5.6 Hz, 1H), 3.17 (q, J=6.5 Hz, 2H), 2.70 (t, J=7.6 Hz, 2H), 2.55 (q, J=7.6 Hz, 2H), 1.91-1.71 (m, 2H), 1.17-1.11 (m, 3H); $^{19}$F NMR (376 MHz, DMSO-$d_6$) δ −56.97; ESIMS m/z 569 ([M+H]$^+$), 567 ([M−H]$^-$).

Preparation of 1-[(2-ethyl-6-methyl-phenyl)carbamothioyl]-3-[3-[4-[1-[4-(trifluoromethoxy)phenyl]-1H-1,2,4-triazol-3-yl]phenyl]propyl]urea (PC101)

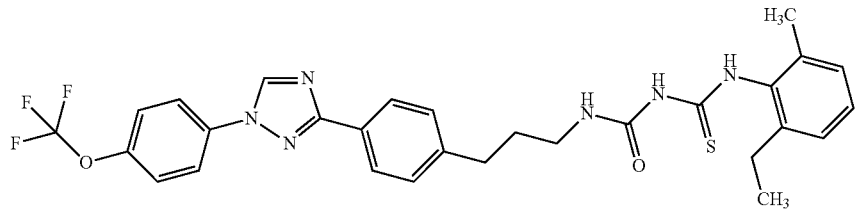

The title compound was prepared as described in Example 63 using 3-(4-(1-(4-(trifluoromethoxy)phenyl)-1H-1,2,4-triazol-3-yl)phenyl)propan-1-amine (C60) and 1-(2-ethyl-6-methylphenyl)thiourea (CA39). Sodium acetate was used in place of sodium bicarbonate. The title compound was isolated as a white solid (0.146 g, 47%): $^1$H NMR (400 MHz, DMSO-$d_6$) δ 11.59 (s, 1H), 10.07 (s, 1H), 9.39 (s, 1H), 8.14-8.00 (m, 4H), 7.68-7.59 (m, 2H), 7.45-7.33 (m, 2H), 7.23-7.02 (m, 4H), 3.17 (q, J=6.6 Hz, 2H), 2.70 (t, J=7.6 Hz, 2H), 2.51 (p, J=1.9 Hz, 2H), 2.18 (s, 3H), 1.90-1.73 (m, 2H), 1.12 (t, J=7.5 Hz, 3H); $^{19}$F NMR (376 MHz, DMSO-$d_6$) δ −56.97; ESIMS m/z 583 ([M+H]$^+$), 581 ([M−H]$^-$).

Preparation of 1-[(2-isopropylphenyl)carbamothioyl]-3-[3-[4-[1-[4-(trifluoromethoxy)phenyl]-1H-1,2,4-triazol-3-yl]phenyl]propyl]urea (PC94)

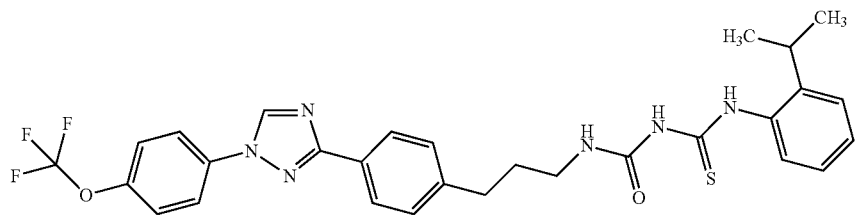 [SMILES: CC(C)c1ccccc1NC(=S)NC(=O)NCCCc1ccc(-c2ncn(-c3ccc(OC(F)(F)F)cc3)n2)cc1]

The title compound was prepared as described in Example 63 using 3-(4-(1-(4-(trifluoromethoxy)phenyl)-1H-1,2,4-triazol-3-yl)phenyl)propan-1-amine (C60) and 1-(2-isopropylphenyl)thiourea. Sodium acetate was used in place of sodium bicarbonate. The title compound was isolated as a white solid (0.161 g, 31%): $^1$H NMR (400 MHz, DMSO-$d_6$) δ 11.97 (s, 1H), 10.08 (s, 1H), 9.39 (s, 1H), 8.13-7.99 (m, 4H), 7.68-7.58 (m, 2H), 7.49-7.31 (m, 4H), 7.24 (dtd, J=24.9, 7.4, 1.6 Hz, 2H), 7.09 (t, J=5.4 Hz, 1H), 3.17 (q, J=6.5 Hz, 2H), 3.01 (p, J=6.8 Hz, 1H), 2.70 (t, J=7.7 Hz, 2H), 1.82 (p, J=7.3 Hz, 2H), 1.17 (d, J=6.9 Hz, 6H); $^{19}$F NMR (376 MHz, DMSO-$d_6$) δ −56.96; ESIMS m/z 583 ([M+H]$^+$), 581 ([M−H]$^-$).

Preparation of 1-[(2-isopropyl-4-methyl-phenyl)
carbamothioyl]-3-[3-[4-[1-[4-(trifluoromethoxy)
phenyl]-1H-1,2,4-triazol-3-yl]phenyl]propyl]urea
(PC102)

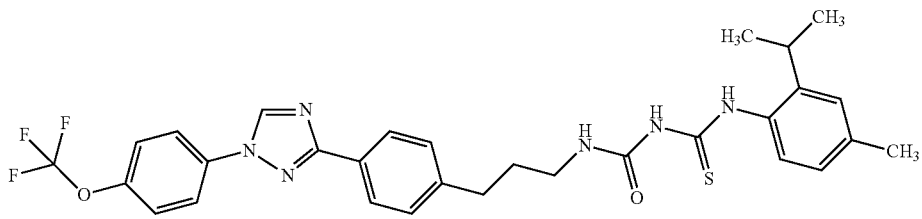 [SMILES: Cc1ccc(NC(=S)NC(=O)NCCCc2ccc(-c3ncn(-c4ccc(OC(F)(F)F)cc4)n3)cc2)c(C(C)C)c1]

The title compound was prepared as described in Example 63 using 3-(4-(1-(4-(trifluoromethoxy)phenyl)-1H-1,2,4-triazol-3-yl)phenyl)propan-1-amine (C60) and 1-(2-isopropyl-4-methylphenyl)thiourea. Sodium acetate was used in place of sodium bicarbonate. The title compound was isolated as a white solid (0.101 g, 32%): $^1$H NMR (400 MHz, DMSO-$d_6$) δ 11.87 (s, 1H), 10.04 (s, 1H), 9.39 (s, 1H), 8.14-7.99 (m, 4H), 7.71-7.55 (m, 2H), 7.46-7.33 (m, 2H), 7.26 (d, J=8.0 Hz, 1H), 7.14 (d, J=2.0 Hz, 1H), 7.08 (t, J=5.6 Hz, 1H), 7.04-6.95 (m, 1H), 3.17 (d, J=5.2 Hz, 2H), 2.96 (p, J=6.8 Hz, 1H), 2.70 (dd, J=8.6, 6.6 Hz, 2H), 2.31 (s, 3H), 1.81 (p, J=7.3 Hz, 2H), 1.16 (d, J=6.9 Hz, 6H); $^{19}$F NMR (376 MHz, DMSO-$d_6$) δ −56.96; ESIMS m/z 597 ([M+H]$^+$), 595 ([M−H]$^−$).

Preparation of 1-[(4-fluoro-2-isopropyl-phenyl)carbamothioyl]-3-[3-[4-[1-[4-(trifluoromethoxy)phenyl]-1H-1,2,4-triazol-3-yl]phenyl]propyl]urea
(PC103)

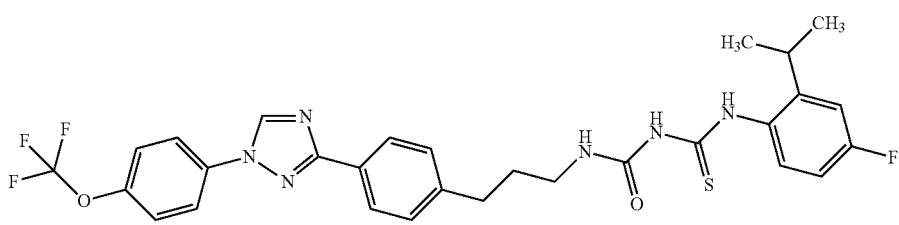 [SMILES: CC(C)c1cc(F)ccc1NC(=S)NC(=O)NCCCc1ccc(-c2ncn(-c3ccc(OC(F)(F)F)cc3)n2)cc1]

The title compound was prepared as described in Example 63 using 3-(4-(1-(4-(trifluoromethoxy)phenyl)-1H-1,2,4-triazol-3-yl)phenyl)propan-1-amine (C60) and 1-(4-fluoro-2-isopropylphenyl)thiourea. Sodium acetate was used in place of sodium bicarbonate. The title compound was isolated as a white solid (0.116 g, 36%): $^1$H NMR (400 MHz, DMSO-$d_6$) δ 11.85 (s, 1H), 10.11 (s, 1H), 9.39 (s, 1H), 8.15-7.97 (m, 4H), 7.63 (dd, J=8.7, 1.5 Hz, 2H), 7.39 (dd, J=8.5, 5.7 Hz, 3H), 7.16 (dd, J=10.4, 3.0 Hz, 1H), 7.12-6.97 (m, 2H), 3.26-3.11 (m, 2H), 3.05-2.89 (m, 1H), 2.70 (dd, J=8.6, 6.7 Hz, 2H), 1.92-1.71 (m, 2H), 1.16 (d, J=6.8 Hz, 6H); $^{19}$F NMR (376 MHz, DMSO-$d_6$) δ −56.97, −114.39; ESIMS m/z 601 ([M+H]$^+$), 599 ([M−H]$^−$).

Preparation of 1-[(5-methyl-2-propyl-phenyl)carbamothioyl]-3-[3-[4-[1-[4-(trifluoromethoxy)phenyl]-1H-1,2,4-triazol-3-yl]phenyl]propyl]urea (PC99)

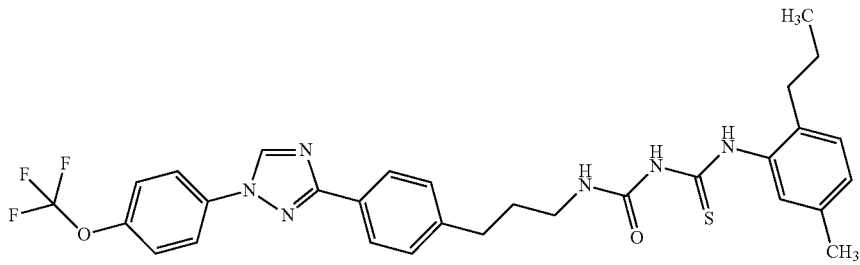 [SMILES: CCCc1ccc(C)cc1NC(=S)NC(=O)NCCCc1ccc(-c2ncn(-c3ccc(OC(F)(F)F)cc3)n2)cc1]

The title compound was prepared as described in Example 63 using 3-(4-(1-(4-(trifluoromethoxy)phenyl)-1H-1,2,4-triazol-3-yl)phenyl)propan-1-amine (C60) and 1-(5-methyl-2-propylphenyl)thiourea (CA38). Sodium acetate was used in place of sodium bicarbonate. The title compound was isolated as a white solid (0.111 g, 35%): $^1$H NMR (400 MHz, DMSO-$d_6$) δ 12.01 (s, 1H), 10.04 (s, 1H), 9.39 (s, 1H), 8.14-7.98 (m, 4H), 7.62 (d, J=8.6 Hz, 2H), 7.45-7.33 (m, 3H), 7.14 (d, J=7.8 Hz, 1H), 7.09 (t, J=5.7 Hz, 1H), 7.05-6.98 (m, 1H), 3.17 (q, J=6.5 Hz, 2H), 2.70 (t, J=7.6 Hz, 2H), 2.49-2.41 (m, 2H), 2.27 (s, 3H), 1.81 (dt, J=13.7, 6.7 Hz, 2H), 1.50 (q, J=7.4 Hz, 2H), 0.86 (t, J=7.3 Hz, 3H); $^{19}$F NMR (376 MHz, DMSO-$d_6$) δ −56.97; ESIMS m/z 597 ([M+H]$^+$), 595 ([M−H]$^-$).

Preparation of 1-(o-tolylcarbamothioyl)-3-[3-[3-[1-[4-(trifluoromethoxy)phenyl]-1H-1,2,4-triazol-3-yl]phenyl]propyl]urea (PC118)

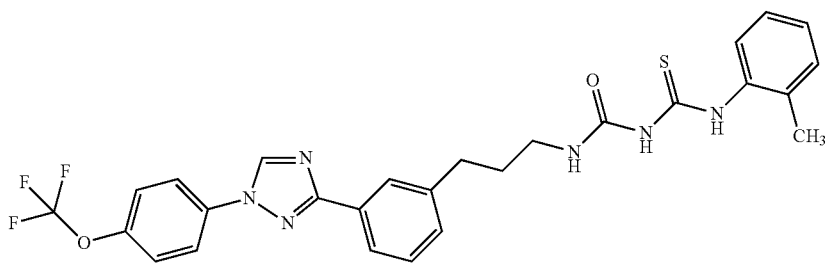 [SMILES: Cc1ccccc1NC(=S)NC(=O)NCCCc1cccc(-c2ncn(-c3ccc(OC(F)(F)F)cc3)n2)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(o-tolyl)thiourea. Sodium acetate was used in place of sodium bicarbonate. The title compound was isolated as a white solid (0.075 g, 24%): $^1$H NMR (400 MHz, DMSO-$d_6$) δ 12.03 (s, 1H), 10.05 (s, 1H), 9.40 (s, 1H), 8.12-8.04 (m, 2H), 8.01-7.92 (m, 2H), 7.68-7.57 (m, 3H), 7.46 (t, J=7.6 Hz, 1H), 7.36 (dt, J=7.7, 1.4 Hz, 1H), 7.29-7.24 (m, 1H), 7.24-7.13 (m, 2H), 7.10 (t, J=5.7 Hz, 1H), 3.18 (q, J=6.5 Hz, 2H), 2.73 (t, J=7.6 Hz, 2H), 2.20 (s, 3H), 1.93-1.74 (m, 2H); $^{19}$F NMR (376 MHz, DMSO-$d_6$) δ −56.96; ESIMS m/z 555 ([M+H]$^+$), 553 ([M−H]$^+$).

Preparation of 1-[(4-methoxy-2-methyl-phenyl)carbamothioyl]-3-[3-[3-[1-[4-(trifluoromethoxy)phenyl]-1H-1,2,4-triazol-3-yl]phenyl]propyl]urea (PC131)

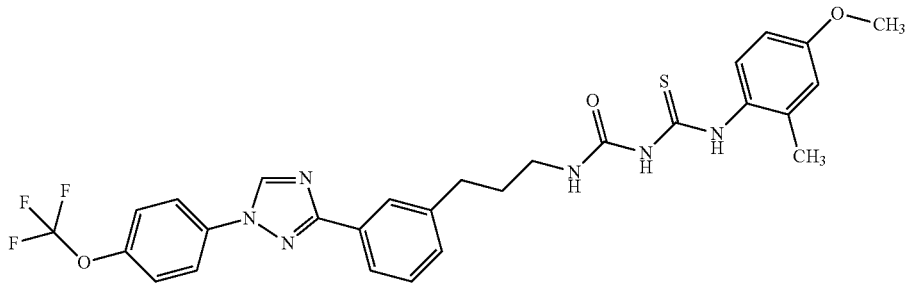 [SMILES: COc1ccc(NC(=S)NC(=O)NCCCc2cccc(-c3ncn(-c4ccc(OC(F)(F)F)cc4)n3)c2)c(C)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(4-methoxy-2-methylphenyl)thiourea. Sodium acetate was used in place of sodium bicarbonate. The title compound was isolated as a white solid (0.103 g, 31%): $^1$H NMR (400 MHz, DMSO-$d_6$) δ 11.80 (s, 1H), 10.00 (s, 1H), 9.40 (s, 1H), 8.13-8.04 (m, 2H), 8.02-7.92 (m, 2H), 7.67-7.57 (m, 2H), 7.46 (t, J=7.6 Hz, 1H), 7.42-7.30 (m, 2H), 7.08 (t, J=5.6 Hz, 1H), 6.83 (d, J=2.9 Hz, 1H), 6.76 (dd, J=8.7, 2.9 Hz, 1H), 3.74 (s, 3H), 3.17 (q, J=6.5 Hz, 2H), 2.73 (t, J=7.6 Hz, 2H), 2.16 (s, 3H), 1.93-1.72 (m, 2H); $^{19}$F NMR (376 MHz, DMSO-$d_6$) δ −56.97; ESIMS m/z 585 ([M+H]$^+$), 583 ([M−H]$^−$).

Preparation of 1-[(2-ethylphenyl)carbamothioyl]-3-[3-[3-[1-[4-(trifluoromethoxy)phenyl]-1H-1,2,4-triazol-3-yl]phenyl]propyl]urea (PC119)

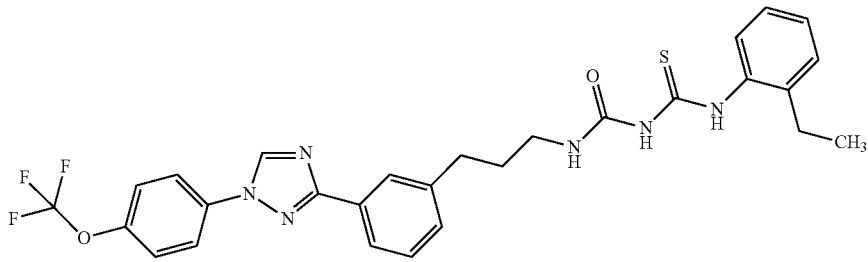 [SMILES: CCc1ccccc1NC(=S)NC(=O)NCCCc1cccc(-c2ncn(-c3ccc(OC(F)(F)F)cc3)n2)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(2-ethylphenyl)thiourea. Sodium acetate was used in place of sodium bicarbonate. The title compound was isolated as a white solid (0.175 g, 55%): $^1$H NMR (400 MHz, DMSO-$d_6$) δ 12.04 (s, 1H), 10.07 (s, 1H), 9.40 (s, 1H), 8.13-8.04 (m, 2H), 8.02-7.93 (m, 2H), 7.65-7.59 (m, 2H), 7.55 (dt, J=6.5, 3.7 Hz, 1H), 7.46 (t, J=7.6 Hz, 1H), 7.36 (dt, J=7.7, 1.4 Hz, 1H), 7.31-7.24 (m, 1H), 7.21 (dd, J=5.8, 3.5 Hz, 2H), 7.15-7.06 (m, 1H), 3.18 (q, J=6.5 Hz, 2H), 2.73 (t, J=7.6 Hz, 2H), 2.55 (t, J=7.5 Hz, 2H), 1.90-1.74 (m, 2H), 1.12 (t, J=7.5 Hz, 3H); $^{19}$F NMR (376 MHz, DMSO-$d_6$) δ −56.98; ESIMS m/z 569 ([M+H]$^+$), 567 ([M−H]$^−$).

Preparation of 1-[(2-ethyl-6-methyl-phenyl)carbam-othioyl]-3-[3-[3-[1-[4-(trifluoromethoxy)phenyl]-1H-1,2,4-triazol-3-yl]phenyl]propyl]urea (PC127)

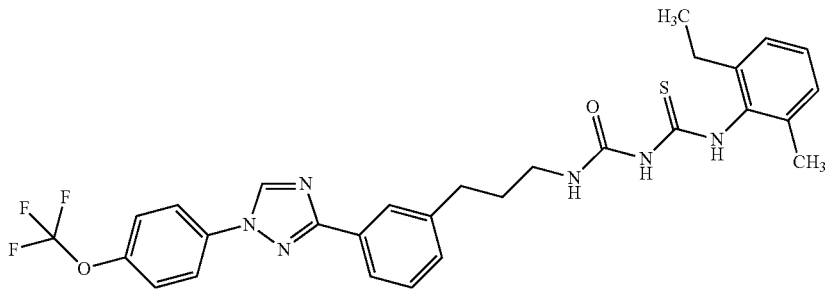 [SMILES: CCc1cccc(C)c1NC(=S)NC(=O)NCCCc1cccc(-c2ncn(-c3ccc(OC(F)(F)F)cc3)n2)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(2-ethyl-6-methylphenyl)thiourea (CA39). Sodium acetate was used in place of sodium bicarbonate. The title compound was isolated as a white solid (0.154 g, 47%): $^1$H NMR (400 MHz, DMSO-$d_6$) δ 11.59 (s, 1H), 10.07 (s, 1H), 9.41 (s, 1H), 8.13-8.05 (m, 2H), 8.03-7.92 (m, 2H), 7.62 (dt, J=7.8, 1.1 Hz, 2H), 7.46 (t, J=7.6 Hz, 1H), 7.36 (dt, J=7.7, 1.5 Hz, 1H), 7.21-7.14 (m, 1H), 7.14-7.04 (m, 3H), 3.18 (q, J=6.6 Hz, 2H), 2.83-2.67 (m, 2H), 2.48 (d, J=2.6 Hz, 2H), 2.17 (s, 3H), 1.92-1.76 (m, 2H), 1.11 (t, J=7.6 Hz, 3H); $^{19}$F NMR (376 MHz, DMSO-$d_6$) δ −56.97; ESIMS m/z 583 ([M+H]$^+$), 581 ([M−H]$^-$).

Preparation of 1-[(2-isopropylphenyl)carbam-othioyl]-3-[3-[3-[1-[4-(trifluoromethoxy)phenyl]-1H-1,2,4-triazol-3-yl]phenyl]propyl]urea (PC120)

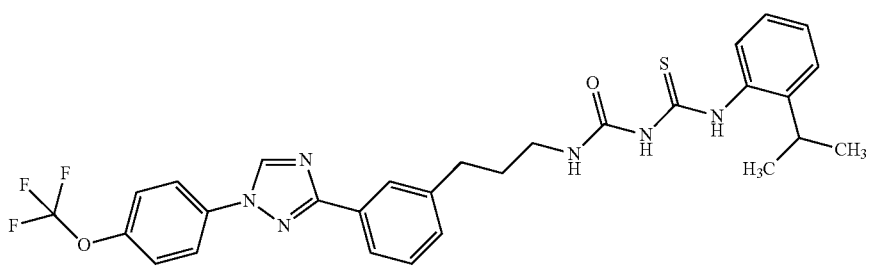 [SMILES: CC(C)c1ccccc1NC(=S)NC(=O)NCCCc1cccc(-c2ncn(-c3ccc(OC(F)(F)F)cc3)n2)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(2-isopropylphenyl)thiourea. Sodium acetate was used in place of sodium bicarbonate. The title compound was isolated as a white solid (0.131 g, 40%): $^1$H NMR (400 MHz, DMSO-$d_6$) δ 11.97 (s, 1H), 10.07 (s, 1H), 9.41 (s, 1H), 8.13-8.04 (m, 2H), 8.01-7.93 (m, 2H), 7.62 (ddd, J=7.9, 2.0, 1.0 Hz, 2H), 7.46 (t, J=7.6 Hz, 1H), 7.41 (dd, J=7.8, 1.5 Hz, 1H), 7.39-7.32 (m, 2H), 7.27 (td, J=7.5, 1.5 Hz, 1H), 7.20 (td, J=7.5, 1.7 Hz, 1H), 7.11 (t, J=5.6 Hz, 1H), 3.18 (q, J=6.5 Hz, 2H), 3.00 (hept, J=6.8 Hz, 1H), 2.73 (t, J=7.7 Hz, 2H), 1.93-1.75 (m, 2H), 1.16 (d, J=6.9 Hz, 6H); $^{19}$F NMR (376 MHz, DMSO-$d_6$) δ −56.96; ESIMS m/z 583 ([M+H]$^+$), 581 ([M−H]$^-$).

Preparation of 1-[(2-isopropyl-4-methyl-phenyl)carbamothioyl]-3-[3-[3-[1-[4-(trifluoromethoxy)phenyl]-1H-1,2,4-triazol-3-yl]phenyl]propyl]urea (PC128)

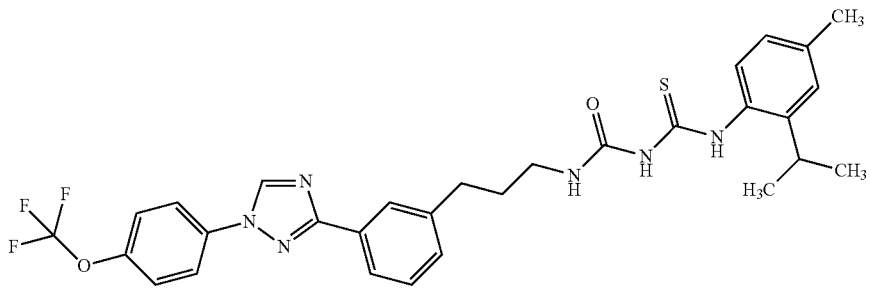 [SMILES: Cc1ccc(NC(=S)NC(=O)NCCCc2cccc(-c3ncn(-c4ccc(OC(F)(F)F)cc4)n3)c2)c(C(C)C)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(2-isopropyl-4-methylphenyl)thiourea. Sodium acetate was used in place of sodium bicarbonate. The title compound was isolated as a white solid (0.123 g, 37%): $^1$H NMR (400 MHz, DMSO-$d_6$) δ 11.87 (s, 1H), 10.04 (s, 1H), 9.41 (s, 1H), 8.12-8.04 (m, 2H), 8.02-7.91 (m, 2H), 7.61 (ddd, J=7.9, 2.0, 1.0 Hz, 2H), 7.46 (t, J=7.6 Hz, 1H), 7.36 (dt, J=7.7, 1.4 Hz, 1H), 7.26 (d, J=8.0 Hz, 1H), 7.13 (d, J=1.9 Hz, 1H), 7.09 (t, J=5.6 Hz, 1H), 7.04-6.97 (m, 1H), 3.17 (q, J=6.5 Hz, 2H), 2.95 (hept, J=7.0 Hz, 1H), 2.82-2.64 (m, 2H), 2.30 (s, 3H), 1.91-1.77 (m, 2H), 1.14 (d, J=6.8 Hz, 6H); $^{19}$F NMR (376 MHz, DMSO-$d_6$) δ −56.97; ESIMS m/z 597 ([M+H]$^+$), 595 ([M−H]$^−$).

Preparation of 1-[(4-fluoro-2-isopropyl-phenyl)carbamothioyl]-3-[3-[3-[1-[4-(trifluoromethoxy)phenyl]-1H-1,2,4-triazol-3-yl]phenyl]propyl]urea (PC129)

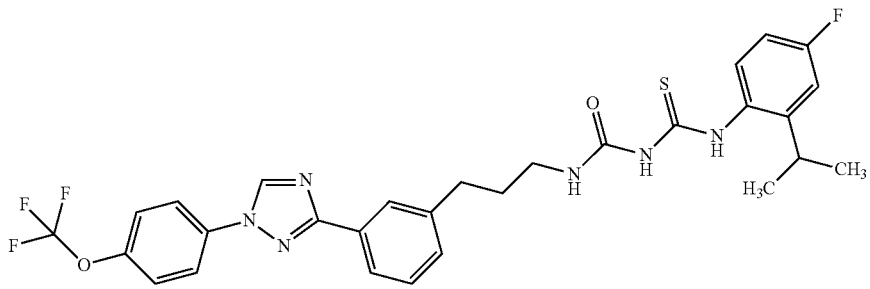

The title compound was prepared as described in Example 63 using 3-(3-(1-(4-(trifluoromethoxy)phenyl)-1H-1,2,4-triazol-3-yl)phenyl)propan-1-amine (CA18) and 1-(4-fluoro-2-isopropylphenyl)thiourea. Sodium acetate was used in place of sodium bicarbonate. The title compound was isolated as a white solid (0.140 g, 41%): $^1$H NMR (400 MHz, DMSO-$d_6$) δ 11.85 (s, 1H), 10.11 (s, 1H), 9.41 (s, 1H), 8.13-8.04 (m, 2H), 8.02-7.92 (m, 2H), 7.61 (dq, J=7.8, 1.0 Hz, 2H), 7.46 (t, J=7.6 Hz, 1H), 7.43-7.31 (m, 2H), 7.15 (dd, J=10.4, 3.0 Hz, 1H), 7.10 (t, J=5.6 Hz, 1H), 7.03 (td, J=8.5, 3.0 Hz, 1H), 3.26-3.10 (m, 2H), 2.97 (pd, J=6.9, 1.6 Hz, 1H), 2.73 (dd, J=8.5, 6.7 Hz, 2H), 1.90-1.76 (m, 2H), 1.15 (d, J=6.8 Hz, 6H); $^{19}$F NMR (376 MHz, DMSO-$d_6$) δ −56.97, −114.41; ESIMS m/z 601 ([M+H]$^+$), 599 ([M−H]$^−$).

Preparation of 1-[(2-isopropyl-5-methyl-phenyl)carbamothioyl]-3-[3-[3-[1-[4-(trifluoromethoxy)phenyl]-1H-1,2,4-triazol-3-yl]phenyl]propyl]urea (PC124)

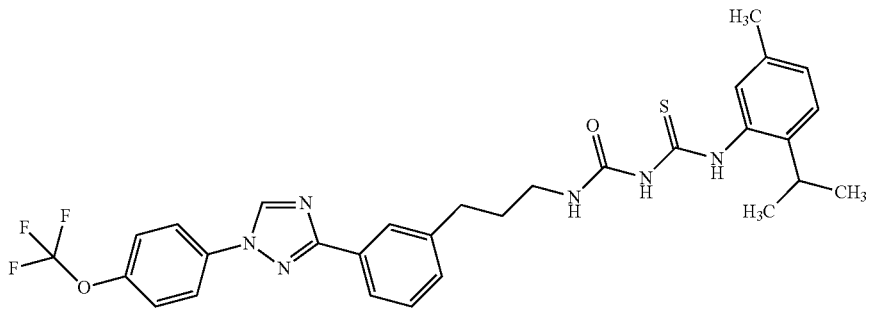 [SMILES: Cc1ccc(C(C)C)c(NC(=S)NC(=O)NCCCc2cccc(-c3ncn(-c4ccc(OC(F)(F)F)cc4)n3)c2)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(2-isopropyl-5-methylphenyl)thiourea. Sodium acetate was used in place of sodium bicarbonate. The title compound was isolated as a white solid (0.118 g, 35%): $^1$H NMR (400 MHz, DMSO-$d_6$) δ 11.91 (s, 1H), 10.05 (s, 1H), 9.40 (s, 1H), 8.13-8.04 (m, 2H), 8.03-7.93 (m, 2H), 7.61 (d, J=8.6 Hz, 2H), 7.46 (t, J=7.6 Hz, 1H), 7.36 (dt, J=7.8, 1.4 Hz, 1H), 7.21 (dd, J=4.9, 3.0 Hz, 2H), 7.15-7.03 (m, 2H), 3.18 (q, J=6.5 Hz, 2H), 2.95 (hept, J=6.7 Hz, 1H), 2.73 (t, J=7.7 Hz, 2H), 2.25 (s, 3H), 1.90-1.76 (m, 2H), 1.13 (d, J=6.8 Hz, 6H); $^{19}$F NMR (376 MHz, DMSO-$d_6$) δ −56.98; ESIMS m/z 597 ([M+H]$^+$), 595 ([M−H]$^-$).

Preparation of 1-[(5-methyl-2-propyl-phenyl)carbamothioyl]-3-[3-[3-[1-[4-(trifluoromethoxy)phenyl]-1H-1,2,4-triazol-3-yl]phenyl]propyl]urea (PC125)

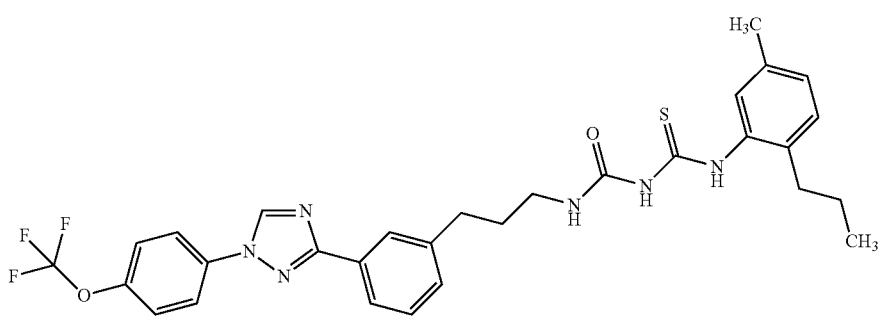 [SMILES: CCCc1ccc(C)cc1NC(=S)NC(=O)NCCCc1cccc(-c2ncn(-c3ccc(OC(F)(F)F)cc3)n2)c1]

The title compound was prepared as described in Example 63 using 3-(3-(1-(4-(trifluoromethoxy)phenyl)-1H-1,2,4-triazol-3-yl)phenyl)propan-1-amine (CA18) and 1-(5-methyl-2-propylphenyl)thiourea (CA38). Sodium acetate was used in place of sodium bicarbonate. The title compound was isolated as a white solid (0.134 g, 40%): $^1$H NMR (400 MHz, DMSO-$d_6$) δ 12.01 (s, 1H), 10.04 (s, 1H), 9.40 (s, 1H), 8.14-8.04 (m, 2H), 8.03-7.92 (m, 2H), 7.68-7.57 (m, 2H), 7.45 (t, J=7.6 Hz, 1H), 7.42-7.32 (m, 2H), 7.11 (t, J=7.1 Hz, 2H), 7.01 (ddd, J=7.9, 1.7, 0.8 Hz, 1H), 3.18 (q, J=6.5 Hz, 2H), 2.73 (dd, J=8.7, 6.6 Hz, 2H), 2.45 (dd, J=8.6, 6.6 Hz, 2H), 2.26 (s, 3H), 1.91-1.75 (m, 2H), 1.55-1.41 (m, 2H), 0.84 (t, J=7.3 Hz, 3H); $^{19}$F NMR (376 MHz, DMSO-$d_6$) δ −56.98; ESIMS m/z 597 ([M+H]$^+$), 595 ([M−H]$^-$).

Preparation of 1-[(2-isopropyl-5-methyl-phenyl)carbamothioyl]-3-[4-[4-[1-[4-(trifluoromethyl)phenyl]-1H-1,2,4-triazol-3-yl]phenyl]butyl]urea (PC159)

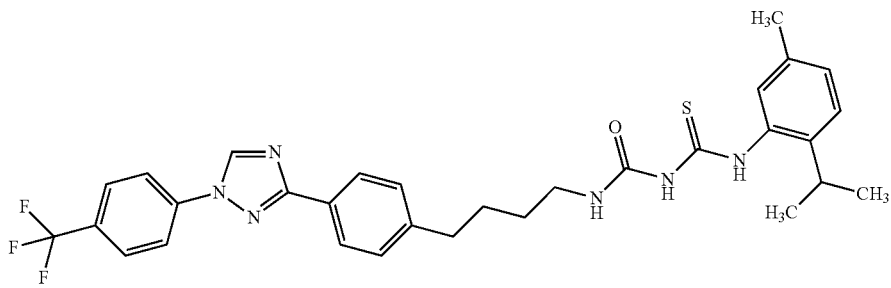 [SMILES: Cc1ccc(C(C)C)c(NC(=S)NC(=O)NCCCCc2ccc(-c3ncn(-c4ccc(C(F)(F)F)cc4)n3)cc2)c1]

The title compound was prepared as described in Example 63 using 4-(4-(1-(4-(trifluoromethyl)phenyl)-1H-1,2,4-triazol-3-yl)phenyl)butan-1-amine (CA19) and 1-(2-isopropyl-5-methylphenyl)thiourea and isolated as a white solid (0.101 g, 37%): $^1$H NMR (400 MHz, CDCl$_3$) δ 11.86 (bs, 1H), 9.77 (bs, 1H), 8.65 (s, 1H), 8.19-8.03 (m, 2H), 7.91 (d, J=8.4 Hz, 2H), 7.85-7.72 (m, 2H), 7.40-7.20 (m, 5H), 5.68 (bs, 1H), 3.29 (d, J=17.5 Hz, 2H), 3.13-2.94 (m, 1H), 2.69 (t, J=7.5 Hz, 2H), 2.32 (s, 3H), 1.69 (s, 2H), 1.56 (s, 2H), 1.21 (d, J=6.9 Hz, 6H); $^{19}$F NMR (376 MHz, CDCl$_3$) δ −62.48; ESIMS m/z 595 ([M+H]$^+$).

Preparation of 1-[(2-isopropyl-5-methyl-phenyl)carbamothioyl]-3-[4-[4-[1-[4-(trifluoromethoxy)phenyl]-1H-1,2,4-triazol-3-yl]phenyl]butyl]urea (PC150)

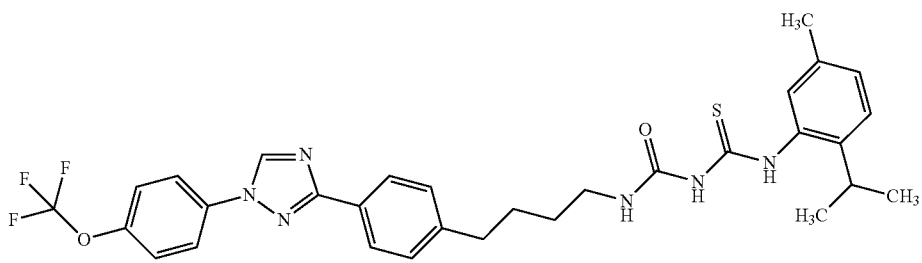 [SMILES: Cc1ccc(C(C)C)c(NC(=S)NC(=O)NCCCCc2ccc(-c3ncn(-c4ccc(OC(F)(F)F)cc4)n3)cc2)c1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2-isopropyl-5-methylphenyl)thiourea and isolated as a white solid (0.153 g, 38%): $^1$H NMR (400 MHz, DMSO-d$_6$) δ 11.91 (s, 1H), 10.01 (s, 1H), 9.38 (s, 1H), 8.11-8.00 (m, 4H), 7.67-7.59 (m, 2H), 7.37 (d, J=8.2 Hz, 2H), 7.22 (d, J=8.1 Hz, 2H), 7.12-7.05 (m, 1H), 7.05-6.98 (m, 1H), 3.17 (q, J=6.5 Hz, 2H), 2.94 (hept, J=6.7 Hz, 1H), 2.75-2.64 (m, 2H), 2.25 (s, 3H), 1.73-1.59 (m, 2H), 1.58-1.43 (m, 2H), 1.13 (d, J=6.9 Hz, 6H); $^{19}$F NMR (376 MHz, DMSO-d$_6$) δ −56.96; ESIMS m/z 611 ([M+H]$^+$).

Preparation of 1-[(2-isopropyl-5-methyl-phenyl)carbamothioyl]-3-[4-[4-[1-[4-(trifluoromethoxy)phenyl]-1H-1,2,4-triazol-3-yl]phenyl]but-3-ynyl]urea (PC160)

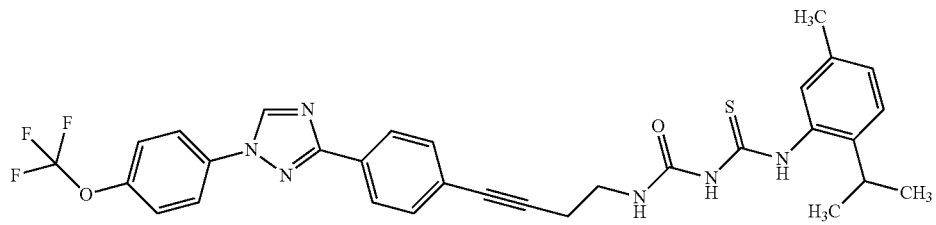 [SMILES: Cc1ccc(C(C)C)c(NC(=S)NC(=O)NCCC#Cc2ccc(-c3ncn(-c4ccc(OC(F)(F)F)cc4)n3)cc2)c1]

The title compound was prepared as described in Example 63 using 4-(4-(1-(4-(trifluoromethoxy)phenyl)-1H-1,2,4-triazol-3-yl)phenyl)but-3-yn-1-amine (CA22) and 1-(2-isopropyl-5-methylphenyl)thiourea and isolated as a white solid (0.183 g, 39%): $^1$H NMR (400 MHz, DMSO-$d_6$) δ 11.90 (s, 1H), 10.27 (s, 1H), 9.43 (s, 1H), 8.09 (m, 4H), 7.66-7.60 (m, 2H), 7.60-7.55 (m, 2H), 7.25-7.18 (m, 3H), 7.09 (d, J=7.7 Hz, 1H), 3.40 (q, J=6.4 Hz, 2H), 2.96 (hept, J=6.7 Hz, 1H), 2.68 (t, J=6.6 Hz, 2H), 2.26 (s, 3H), 1.14 (d, J=6.8 Hz, 6H); $^{19}$F NMR (376 MHz, DMSO-$d_6$) δ −56.96; ESIMS m/z 607 ([M+H]$^+$).

Preparation of 1-[(2-isopropylphenyl)carbamothioyl]-3-[4-[4-[1-[4-(trifluoromethoxy)phenyl]-1H-1,2,4-triazol-3-yl]phenyl]butyl]urea (PC146)

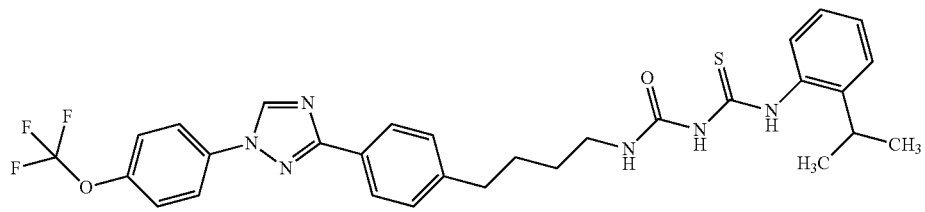 [SMILES: CC(C)c1ccccc1NC(=S)NC(=O)NCCCCc1ccc(-c2ncn(-c3ccc(OC(F)(F)F)cc3)n2)cc1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2-isopropylphenyl)thiourea and isolated as a white solid (0.091 g, 38%): $^1$H NMR (300 MHz, DMSO-$d_6$) δ 11.95 (s, 1H), 10.02 (s, 1H), 9.37 (s, 1H), 8.10-7.97 (m, 4H), 7.61 (d, J=8.6 Hz, 2H), 7.44-7.29 (m, 4H), 7.29-7.14 (m, 2H), 7.01 (s, 1H), 3.23-3.11 (m, 2H), 3.04-2.90 (m, 1H), 2.67 (t, J=7.4 Hz, 2H), 1.71-1.56 (m, 2H), 1.56-1.42 (m, 2H), 1.14 (d, J=6.9 Hz, 6H); $^{19}$F NMR (376 MHz, DMSO-$d_6$) δ −56.97; ESIMS m/z 597 ([M+H]$^+$).

Preparation of 1-[(2-ethylphenyl)carbamothioyl]-3-[4-[4-[1-[4-(trifluoromethoxy)phenyl]-1H-1,2,4-triazol-3-yl]phenyl]butyl]urea (PC145)

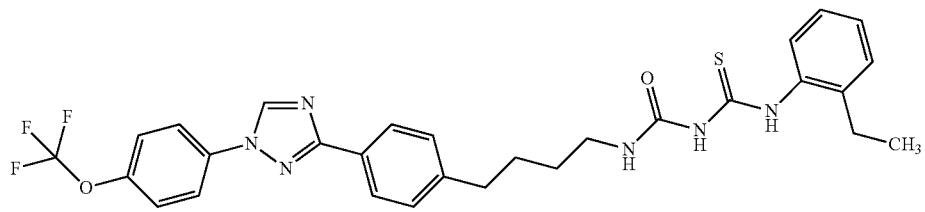 [SMILES: CCc1ccccc1NC(=S)NC(=O)NCCCCc1ccc(-c2ncn(-c3ccc(OC(F)(F)F)cc3)n2)cc1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2-ethylphenyl)thiourea and isolated as a white solid (0.111 g, 48%): $^1$H NMR (300 MHz, DMSO-$d_6$) δ 12.01 (s, 1H), 10.01 (s, 1H), 9.37 (s, 1H), 8.09-7.98 (m, 4H), 7.61 (d, J=8.6 Hz, 2H), 7.53 (dd, J=5.6, 3.7 Hz, 1H), 7.35 (d, J=8.1 Hz, 2H), 7.30-7.23 (m, 1H), 7.19 (dd, J=5.8, 3.5 Hz, 2H), 7.01 (s, 1H), 3.22-3.11 (m, 2H), 2.73-2.63 (m, 2H), 2.52 (d, J=7.6 Hz, 2H), 1.63 (m, 2H), 1.49 (m, 2H), 1.15-1.04 (m, 3H); $^{19}$F NMR (376 MHz, DMSO-$d_6$) δ −56.97; ESIMS m/z 583 ([M+H]$^+$).

Preparation of 1-[(5-methyl-2-propyl-phenyl)carbamothioyl]-3-[4-[4-[1-[4-(trifluoromethoxy)phenyl]-1H-1,2,4-triazol-3-yl]phenyl]butyl]urea (PC151)

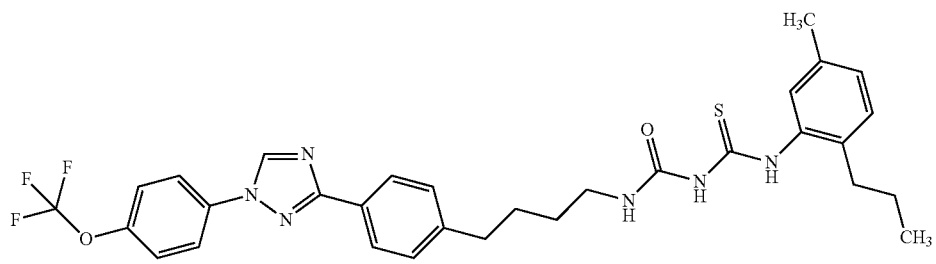 [SMILES: CCCc1ccc(C)cc1NC(=S)NC(=O)NCCCCc1ccc(-c2ncn(-c3ccc(OC(F)(F)F)cc3)n2)cc1]

The title compound was prepared as described in Example 63 using 4-(4-(1-(4-(trifluoromethoxy)phenyl)-1H-1,2,4-triazol-3-yl)phenyl)butan-1-amine (CA20) and 1-(5-methyl-2-propylphenyl)thiourea (CA38) and isolated as a white solid (0.110 g, 45%): $^1$H NMR (300 MHz, DMSO-$d_6$) δ 11.98 (s, 1H), 9.97 (s, 1H), 9.36 (s, 1H), 8.03 (m, 4H), 7.60 (d, J=8.7 Hz, 2H), 7.35 (m, 3H), 7.11 (d, J=7.8 Hz, 1H), 7.05-6.92 (m, 2H), 3.16 (q, J=6.3 Hz, 2H), 2.66 (t, J=7.5 Hz, 2H), 2.42 (t, J=7.6 Hz, 2H), 2.24 (s, 3H), 1.72-1.56 (m, 2H), 1.56-1.38 (m, 4H), 0.82 (t, J=7.3 Hz, 3H); $^{19}$F NMR (376 MHz, DMSO-$d_6$) δ −56.97; ESIMS m/z 611 ([M+H]$^+$).

Preparation of 1-[(2-isopropyl-4-methyl-phenyl)carbamothioyl]-3-[4-[4-[1-[4-(trifluoromethoxy)phenyl]-1H-1,2,4-triazol-3-yl]phenyl]butyl]urea (PC154)

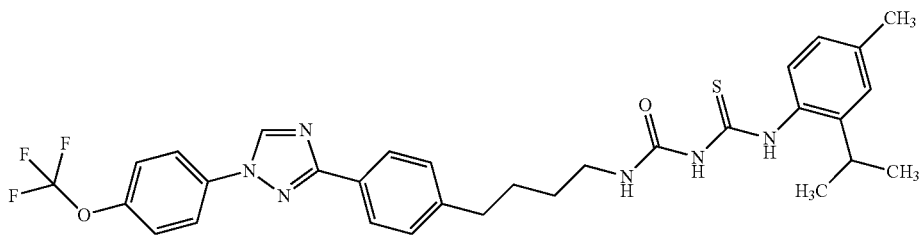 [SMILES: Cc1ccc(NC(=S)NC(=O)NCCCCc2ccc(-c3ncn(-c4ccc(OC(F)(F)F)cc4)n3)cc2)c(C(C)C)c1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2-isopropyl-4-methylphenyl)thiourea and isolated as a white solid (0.100 g, 41%): $^1$H NMR (300 MHz, DMSO-$d_6$) δ 11.84 (s, 1H), 9.97 (s, 1H), 9.36 (s, 1H), 8.11-7.96 (m, 4H), 7.60 (d, J=8.5 Hz, 2H), 7.35 (d, J=8.0 Hz, 2H), 7.23 (d, J=8.0 Hz, 1H), 7.11 (s, 1H), 6.98 (d, J=8.0 Hz, 2H), 3.15 (q, J=6.3 Hz, 2H), 3.00-2.83 (m, 1H), 2.66 (t, J=7.6 Hz, 2H), 2.28 (s, 3H), 1.72-1.55 (m, 2H), 1.55-1.42 (m, 2H), 1.12 (d, J=6.8 Hz, 6H); $^{19}$F NMR (376 MHz, DMSO-$d_6$) δ −56.97; ESIMS m/z 611 ([M+H]$^+$).

Preparation of 1-[(2-ethyl-6-methyl-phenyl)carbamothioyl]-3-[4-[4-[1-[4-(trifluoromethoxy)phenyl]-1H-1,2,4-triazol-3-yl]phenyl]butyl]urea (PC153)

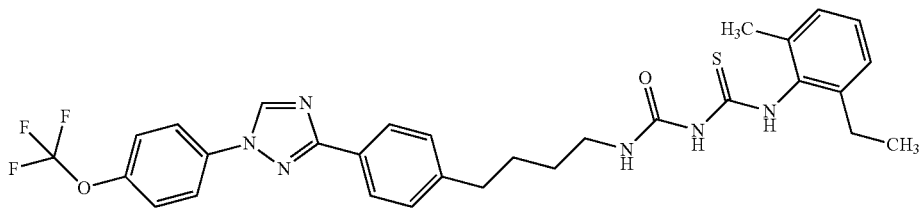 [SMILES: CCc1cccc(C)c1NC(=S)NC(=O)NCCCCc1ccc(-c2ncn(-c3ccc(OC(F)(F)F)cc3)n2)cc1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2-ethyl-6-methylphenyl)thiourea (CA39) and isolated as a white solid (0.141 g, 59%): $^1$H NMR (400 MHz, DMSO-$d_6$) δ 11.59 (s, 1H), 10.00 (s, 1H), 9.37 (s, 1H), 8.12-7.98 (m, 4H), 7.66-7.54 (m, 2H), 7.37 (d, J=8.2 Hz, 2H), 7.24-7.13 (m, 1H), 7.11 (d, J=2.9 Hz, 2H), 7.00 (d, J=5.7 Hz, 1H), 3.18 (q, J=6.5 Hz, 2H), 2.75-2.61 (m, 2H), 2.49-2.44 (m, 2H), 2.16 (s, 3H), 1.65 (q, J=7.7 Hz, 2H), 1.52 (q, J=7.3 Hz, 2H), 1.11 (t, J=7.6 Hz, 3H); $^{19}$F NMR (376 MHz, DMSO-$d_6$) δ −56.97; ESIMS m/z 597 ([M+H]$^+$).

Preparation of 1-(o-tolylcarbamothioyl)-3-[4-[4-[1-[4-(trifluoromethoxy)phenyl]-1H-1,2,4-triazol-3-yl]phenyl]butyl]urea (PC144)

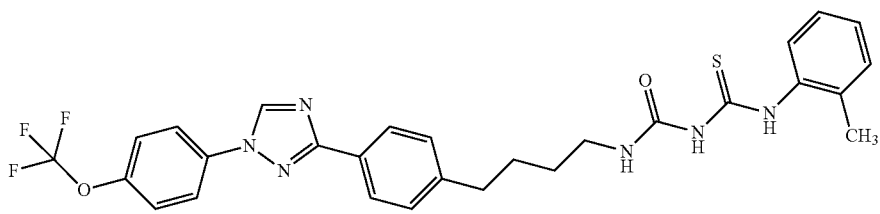 [SMILES: Cc1ccccc1NC(=S)NC(=O)NCCCCc1ccc(-c2ncn(-c3ccc(OC(F)(F)F)cc3)n2)cc1]

The title compound was prepared as described in Example 63 using 4-(4-(1-(4-(trifluoromethoxy)phenyl)-1H-1,2,4-triazol-3-yl)phenyl)butan-1-amine (CA20) and 1-(o-tolyl)thiourea and isolated as a white solid (0.097 g, 43%): $^1$H NMR (400 MHz, DMSO-$d_6$) δ 12.01 (s, 1H), 9.98 (s, 1H), 9.37 (s, 1H), 8.14-7.90 (m, 4H), 7.66-7.54 (m, 3H), 7.37 (d, J=8.1 Hz, 2H), 7.31-7.23 (m, 1H), 7.23-7.14 (m, 2H), 7.02 (s, 1H), 3.23-3.12 (m, 2H), 2.68 (t, J=7.5 Hz, 2H), 2.20 (s, 3H), 1.70-1.59 (m, 2H), 1.57-1.44 (m, 2H); $^{19}$F NMR (376 MHz, DMSO-$d_6$) δ −56.97; ESIMS m/z 569 ([M+H]$^+$).

Preparation of 1-[(2,6-dimethylphenyl)carbamothioyl]-3-[4-[4-[1-[4-(trifluoro methoxy)phenyl]-1H-1,2,4-triazol-3-yl]phenyl]butyl]urea (PC152)

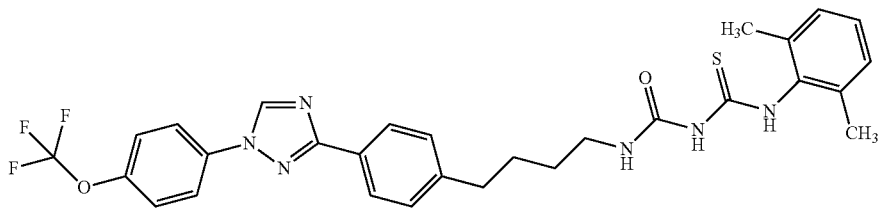 [SMILES: Cc1cccc(C)c1NC(=S)NC(=O)NCCCCc1ccc(-c2ncn(-c3ccc(OC(F)(F)F)cc3)n2)cc1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2,6-dimethylphenyl)thiourea and isolated as a white solid (0.122 g, 53%): $^1$H NMR (400 MHz, DMSO-$d_6$) δ 11.53 (s, 1H), 9.98 (s, 1H), 9.37 (s, 1H), 8.11-8.00 (m, 4H), 7.66-7.58 (m, 2H), 7.37 (d, J=8.1 Hz, 2H), 7.09 (q, J=5.2 Hz, 3H), 6.99 (t, J=5.7 Hz, 1H), 3.18 (q, J=6.5 Hz, 2H), 2.69 (t, J=7.6 Hz, 2H), 2.15 (s, 6H), 1.66 (p, J=7.5 Hz, 2H), 1.51 (p, J=6.9 Hz, 2H); $^{19}$F NMR (376 MHz, DMSO-$d_6$) δ −56.97; ESIMS m/z 583 ([M+H]$^+$).

Preparation of 1-[(2-isopropyl-5-methoxy-phenyl)carbamothioyl]-3-[4-[4-[1-[4-(trifluoromethoxy)phenyl]-1H-1,2,4-triazol-3-yl]phenyl]butyl]urea (PC156)

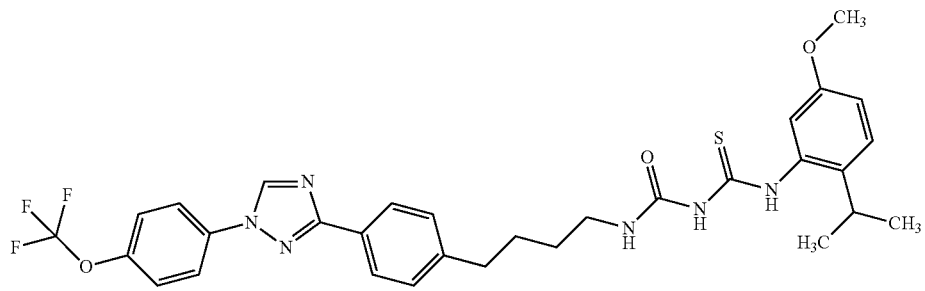 [SMILES: COc1ccc(C(C)C)c(NC(=S)NC(=O)NCCCCc2ccc(-c3ncn(-c4ccc(OC(F)(F)F)cc4)n3)cc2)c1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2-isopropyl-5-methoxyphenyl)thiourea (CA40) and isolated as a white solid (0.114 g, 46%): $^1$H NMR (400 MHz, DMSO-$d_6$) δ 12.01 (s, 1H), 10.01 (s, 1H), 9.36 (s, 1H), 8.13-7.97 (m, 4H), 7.68-7.56 (m, 2H), 7.37 (d, J=8.1 Hz, 2H), 7.23 (d, J=8.7 Hz, 1H), 7.11 (d, J=2.7 Hz, 1H), 7.01 (d, J=5.9 Hz, 1H), 6.84 (dd, J=8.6, 2.8 Hz, 1H), 3.71 (s, 3H), 3.18 (q, J=6.5 Hz, 2H), 2.92 (hept, J=6.9 Hz, 1H), 2.68 (t, J=7.6 Hz, 2H), 1.65 (p, J=7.6 Hz, 2H), 1.51 (q, J=7.2 Hz, 2H), 1.13 (d, J=6.8 Hz, 6H); $^{19}$F NMR (376 MHz, DMSO-$d_6$) δ −56.97; ESIMS m/z 627 ([M+H]$^+$).

Preparation of 1-[(4-fluoro-2-isopropyl-phenyl)carbamothioyl]-3-[4-[4-[1-[4-(trifluoromethoxy)phenyl]-1H-1,2,4-triazol-3-yl]phenyl]butyl]urea (PC155)

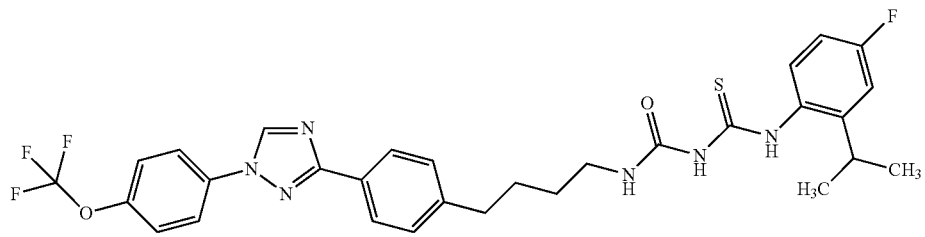 [SMILES: CC(C)c1cc(F)ccc1NC(=S)NC(=O)NCCCCc1ccc(-c2ncn(-c3ccc(OC(F)(F)F)cc3)n2)cc1]

The title compound was prepared as described in Example 63 using 4-(4-(1-(4-(trifluoromethoxy)phenyl)-1H-1,2,4-triazol-3-yl)phenyl)butan-1-amine (CA20) and 1-(4-fluoro-2-isopropylphenyl)thiourea and isolated as a white solid (0.089 g, 36%): $^1$H NMR (400 MHz, DMSO-$d_6$) δ 11.85 (s, 1H), 10.04 (s, 1H), 9.37 (s, 1H), 8.11-7.99 (m, 4H), 7.61 (d, J=8.8 Hz, 2H), 7.44-7.31 (m, 3H), 7.14 (dd, J=10.4, 2.9 Hz, 1H), 7.09-6.96 (m, 2H), 3.18 (q, J=6.5 Hz, 2H), 3.03-2.90 (m, 1H), 2.68 (t, J=7.5 Hz, 2H), 1.70-1.58 (m, 2H), 1.56-1.44 (m, 2H), 1.15 (d, J=6.8 Hz, 6H); $^{19}$F NMR (376 MHz, DMSO-$d_6$) δ −56.97, −114.40; ESIMS m/z 615 ([M+H]$^+$).

Preparation of 1-(o-tolylcarbamothioyl)-3-[4-[3-[1-[4-(trifluoromethoxy)phenyl]-1H-1,2,4-triazol-3-yl]phenyl]butyl]urea (PC170)

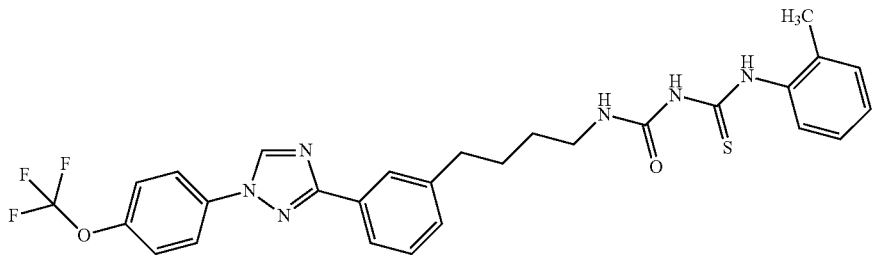 [SMILES: Cc1ccccc1NC(=S)NC(=O)NCCCCc1cccc(-c2ncn(-c3ccc(OC(F)(F)F)cc3)n2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(o-tolyl)thiourea and isolated as a white solid (0.102 g, 35%): $^1$H NMR (400 MHz, DMSO-d$_6$) δ 12.03 (s, 1H), 10.01 (s, 1H), 9.39 (s, 1H), 8.11-8.05 (m, 2H), 7.98 (t, J=1.7 Hz, 1H), 7.94 (dt, J=7.7, 1.4 Hz, 1H), 7.67-7.57 (m, 3H), 7.44 (t, J=7.6 Hz, 1H), 7.34 (dt, J=7.7, 1.5 Hz, 1H), 7.28-7.23 (m, 1H), 7.23-7.13 (m, 2H), 7.03 (t, J=5.7 Hz, 1H), 3.19 (q, J=6.5 Hz, 2H), 2.72 (t, J=7.6 Hz, 2H), 2.19 (s, 3H), 1.74-1.60 (m, 2H), 1.52 (p, J=6.9 Hz, 2H); $^{19}$F NMR (376 MHz, DMSO-d$_6$) δ −56.96; ESIMS m/z 569 ([M+H]$^+$).

Preparation of 1-[(2-ethylphenyl)carbamothioyl]-3-[4-[3-[1-[4-(trifluoromethoxy)phenyl]-1H-1,2,4-triazol-3-yl]phenyl]butyl]urea (PC171)

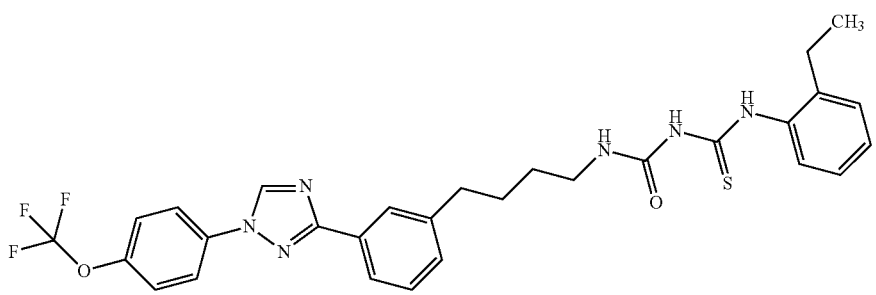 [SMILES: CCc1ccccc1NC(=S)NC(=O)NCCCCc1cccc(-c2ncn(-c3ccc(OC(F)(F)F)cc3)n2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(2-ethylphenyl)thiourea and isolated as a white solid (0.113 g, 38%): $^1$H NMR (400 MHz, DMSO-d$_6$) δ 12.05 (s, 1H), 10.04 (s, 1H), 9.41 (s, 1H), 8.13-8.06 (m, 2H), 8.00 (d, J=1.7 Hz, 1H), 7.96 (dt, J=7.7, 1.4 Hz, 1H), 7.69-7.60 (m, 2H), 7.56 (dd, J=5.6, 3.6 Hz, 1H), 7.46 (t, J=7.6 Hz, 1H), 7.36 (dt, J=7.7, 1.5 Hz, 1H), 7.31-7.26 (m, 1H), 7.26-7.19 (m, 2H), 7.05 (t, J=5.6 Hz, 1H), 3.21 (q, J=6.5 Hz, 2H), 2.74 (t, J=7.6 Hz, 2H), 2.59-2.53 (m, 2H), 1.69 (tt, J=9.0, 6.6 Hz, 2H), 1.54 (p, J=6.9 Hz, 2H), 1.12 (t, J=7.5 Hz, 3H); $^{19}$F NMR (376 MHz, DMSO-d$_6$) δ −56.96; ESIMS m/z 583 ([M+H]$^+$).

Preparation of 1-[(2-ethyl-6-methyl-phenyl)carbamothioyl]-3-[4-[3-[1-[4-(trifluoromethoxy)phenyl]-1H-1,2,4-triazol-3-yl]phenyl]butyl]urea (PC179)

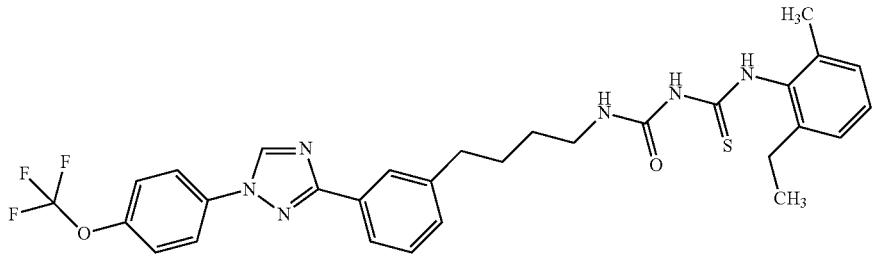 [SMILES: CCc1cccc(C)c1NC(=S)NC(=O)NCCCCc1cccc(-c2ncn(-c3ccc(OC(F)(F)F)cc3)n2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(2-ethyl-6-methylphenyl)thiourea (CA39) and isolated as a white solid (0.143 g, 47%): $^1$H NMR (400 MHz, DMSO-$d_6$) δ 11.62 (s, 1H), 10.04 (s, 1H), 9.40 (s, 1H), 8.12-8.06 (m, 2H), 8.00 (t, J=1.6 Hz, 1H), 7.96 (dt, J=7.7, 1.4 Hz, 1H), 7.64 (ddt, J=7.8, 1.9, 0.9 Hz, 2H), 7.46 (t, J=7.6 Hz, 1H), 7.36 (dt, J=7.7, 1.4 Hz, 1H), 7.22-7.15 (m, 1H), 7.10 (dq, J=6.3, 1.8 Hz, 2H), 7.02 (t, J=5.7 Hz, 1H), 3.21 (q, J=6.5 Hz, 2H), 2.74 (t, J=7.6 Hz, 2H), 2.48 (td, J=7.5, 1.9 Hz, 2H), 2.17 (s, 3H), 1.69 (p, J=7.6 Hz, 2H), 1.62-1.48 (m, 2H), 1.11 (t, J=7.6 Hz, 3H); $^{19}$F NMR (376 MHz, DMSO-$d_6$) δ −56.96; ESIMS m/z 597 ([M+H]$^+$).

Preparation of 1-[(2-isopropylphenyl)carbamothioyl]-3-[4-[3-[1-[4-(trifluoromethoxy)phenyl]-1H-1,2,4-triazol-3-yl]phenyl]butyl]urea (PC172)

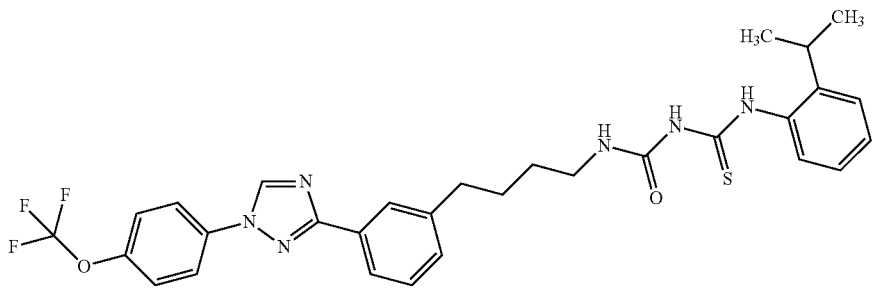 [SMILES: CC(C)c1ccccc1NC(=S)NC(=O)NCCCCc1cccc(-c2ncn(-c3ccc(OC(F)(F)F)cc3)n2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(2-isopropylphenyl)thiourea and isolated as a white solid (0.072 g, 24%): $^1$H NMR (400 MHz, DMSO-$d_6$) δ 11.99 (s, 1H), 10.05 (s, 1H), 9.41 (s, 1H), 8.13-8.07 (m, 2H), 8.00 (t, J=1.7 Hz, 1H), 7.96 (dt, J=7.8, 1.4 Hz, 1H), 7.64 (dq, J=7.7, 1.0 Hz, 2H), 7.46 (t, J=7.6 Hz, 1H), 7.42 (dd, J=7.9, 1.5 Hz, 1H), 7.36 (ddd, J=7.8, 3.3, 1.6 Hz, 2H), 7.28 (td, J=7.5, 1.5 Hz, 1H), 7.21 (td, J=7.5, 1.7 Hz, 1H), 7.05 (t, J=5.7 Hz, 1H), 3.21 (q, J=6.4 Hz, 2H), 3.00 (p, J=6.9 Hz, 1H), 2.74 (t, J=7.6 Hz, 2H), 1.69 (p, J=7.8 Hz, 2H), 1.54 (p, J=7.0 Hz, 2H), 1.16 (d, J=6.8 Hz, 6H); $^{19}$F NMR (376 MHz, DMSO-$d_6$) δ −56.96; ESIMS m/z 597 ([M+H]$^+$).

Preparation of 1-[(2-isopropyl-4-methyl-phenyl)carbamothioyl]-3-[4-[3-[1-[4-(trifluoromethoxy)phenyl]-1H-1,2,4-triazol-3-yl]phenyl]butyl]urea
(PC180)

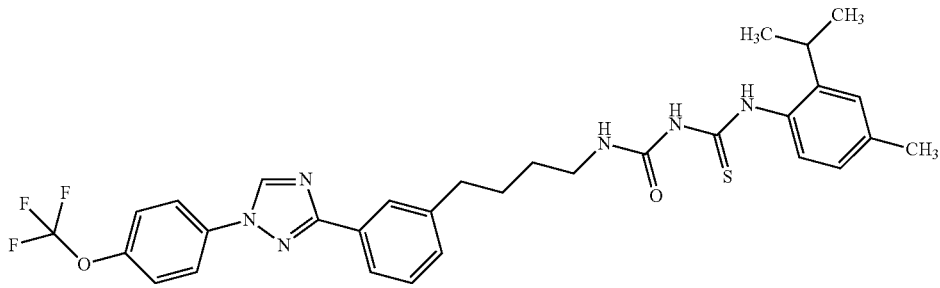 [SMILES: Cc1ccc(NC(=S)NC(=O)NCCCCc2cccc(-c3ncn(-c4ccc(OC(F)(F)F)cc4)n3)c2)c(C(C)C)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(2-isopropyl-4-methylphenyl)thiourea and isolated as a white solid (0.139 g, 45%): $^1$H NMR (400 MHz, DMSO-$d_6$) δ 11.89 (s, 1H), 10.01 (s, 1H), 9.40 (s, 1H), 8.13-8.07 (m, 2H), 8.00 (d, J=1.7 Hz, 1H), 7.96 (dt, J=7.7, 1.4 Hz, 1H), 7.64 (dq, J=7.8, 1.0 Hz, 2H), 7.46 (t, J=7.6 Hz, 1H), 7.36 (dt, J=7.7, 1.4 Hz, 1H), 7.26 (d, J=8.0 Hz, 1H), 7.15 (dd, J=2.0, 0.9 Hz, 1H), 7.07-6.97 (m, 2H), 3.20 (q, J=6.5 Hz, 2H), 2.95 (p, J=6.9 Hz, 1H), 2.74 (t, J=7.6 Hz, 2H), 2.32 (s, 3H), 1.68 (p, J=7.3 Hz, 2H), 1.61-1.47 (m, 2H), 1.15 (d, J=6.8 Hz, 6H); $^{19}$F NMR (376 MHz, DMSO-$d_6$) δ −56.96; ESIMS m/z 611 ([M+H]$^+$).

Preparation of 1-[(4-fluoro-2-isopropyl-phenyl)carbamothioyl]-3-[4-[3-[1-[4-(trifluoromethoxy)phenyl]-1H-1,2,4-triazol-3-yl]phenyl]butyl]urea
(PC181)

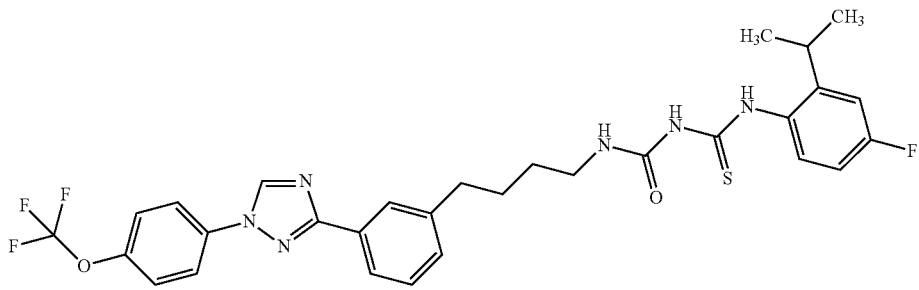 [SMILES: CC(C)c1cc(F)ccc1NC(=S)NC(=O)NCCCCc1cccc(-c2ncn(-c3ccc(OC(F)(F)F)cc3)n2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(4-fluoro-2-isopropylphenyl)thiourea and isolated as a white solid (0.114 g, 36%): $^1$H NMR (400 MHz, DMSO-$d_6$) δ 11.87 (s, 1H), 10.09 (s, 1H), 9.41 (s, 1H), 8.13-8.07 (m, 2H), 8.00 (t, J=1.6 Hz, 1H), 7.96 (dt, J=7.7, 1.4 Hz, 1H), 7.69-7.61 (m, 2H), 7.46 (t, J=7.6 Hz, 1H), 7.43-7.33 (m, 2H), 7.16 (dd, J=10.4, 3.0 Hz, 1H), 7.05 (td, J=8.3, 2.9 Hz, 2H), 3.20 (q, J=6.5 Hz, 2H), 3.05-2.90 (m, 1H), 2.74 (t, J=7.6 Hz, 2H), 1.76-1.62 (m, 2H), 1.61-1.48 (m, 2H), 1.15 (d, J=6.8 Hz, 6H); $^{19}$F NMR (376 MHz, DMSO-$d_6$) δ −56.96, −114.42; ESIMS m/z 615 ([M+H]$^+$).

Preparation of 1-[(2-isopropyl-5-methyl-phenyl)carbamothioyl]-3-[4-[3-[1-[4-(trifluoromethoxy)phenyl]-1H-1,2,4-triazol-3-yl]phenyl]butyl]urea
(PC176)

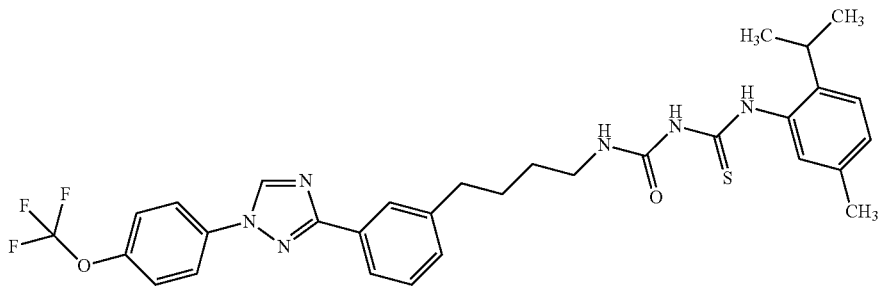 [SMILES: Cc1ccc(C(C)C)c(NC(=S)NC(=O)NCCCCc2cccc(-c3ncn(-c4ccc(OC(F)(F)F)cc4)n3)c2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(2-isopropyl-5-methylphenyl)thiourea and isolated as a white solid (0.119 g, 38%): $^1$H NMR (400 MHz, DMSO-$d_6$) δ 11.93 (s, 1H), 10.03 (s, 1H), 9.41 (s, 1H), 8.13-8.07 (m, 2H), 8.00 (t, J=1.7 Hz, 1H), 7.96 (dt, J=7.6, 1.4 Hz, 1H), 7.68-7.61 (m, 2H), 7.46 (t, J=7.6 Hz, 1H), 7.36 (dt, J=7.6, 1.5 Hz, 1H), 7.23 (d, J=8.0 Hz, 2H), 7.13-7.07 (m, 1H), 7.04 (t, J=5.5 Hz, 1H), 3.20 (q, J=6.5 Hz, 2H), 2.95 (p, J=6.9 Hz, 1H), 2.74 (t, J=7.6 Hz, 2H), 2.27 (s, 3H), 1.78-1.62 (m, 2H), 1.61-1.46 (m, 2H), 1.14 (d, J=6.8 Hz, 6H); $^{19}$F NMR (376 MHz, DMSO-$d_6$) δ −56.97; ESIMS m/z 611 ([M+H]$^+$).

Preparation of 1-[(2-isopropyl-5-methoxy-phenyl)carbamothioyl]-3-[4-[3-[1-[4-(trifluoromethoxy)phenyl]-1H-1,2,4-triazol-3-yl]phenyl]butyl]urea
(PC182)

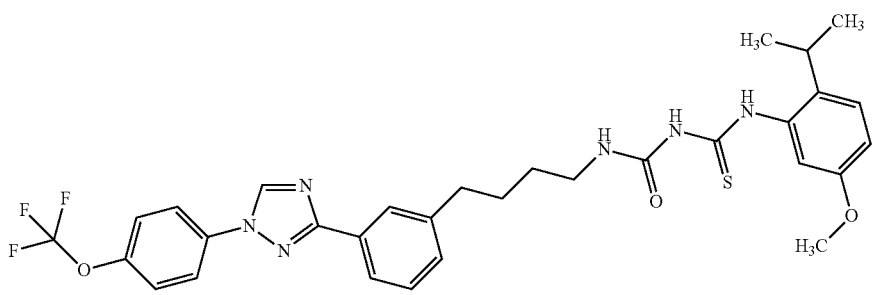 [SMILES: COc1ccc(C(C)C)c(NC(=S)NC(=O)NCCCCc2cccc(-c3ncn(-c4ccc(OC(F)(F)F)cc4)n3)c2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(2-isopropyl-5-methoxyphenyl)thiourea (CA40) and isolated as a white solid (0.141 g, 44%): $^1$H NMR (400 MHz, DMSO-$d_6$) δ 12.02 (s, 1H), 10.03 (s, 1H), 9.39 (s, 1H), 8.12-8.04 (m, 2H), 7.98 (t, J=1.6 Hz, 1H), 7.94 (dt, J=7.7, 1.4 Hz, 1H), 7.62 (ddd, J=7.7, 1.9, 1.0 Hz, 2H), 7.45 (t, J=7.6 Hz, 1H), 7.34 (dt, J=7.7, 1.5 Hz, 1H), 7.23 (d, J=8.7 Hz, 1H), 7.10 (d, J=2.7 Hz, 1H), 7.03 (t, J=5.6 Hz, 1H), 6.84 (dd, J=8.7, 2.8 Hz, 1H), 3.71 (s, 3H), 3.18 (q, J=6.4 Hz, 2H), 2.91 (p, J=6.8 Hz, 1H), 2.72 (t, J=7.6 Hz, 2H), 1.67 (p, J=7.7 Hz, 2H), 1.52 (p, J=6.9 Hz, 2H), 1.12 (d, J=6.8 Hz, 6H); $^{19}$F NMR (376 MHz, DMSO-$d_6$) δ −56.96; ESIMS m/z 627 ([M+H]$^+$).

Preparation of 1-[(2,4-dimethylphenyl)carbamothioyl]-3-[4-[4-[1-[4-(trifluoromethoxy)phenyl]-1H-1,2,4-triazol-3-yl]phenyl]butyl]urea (FB16)

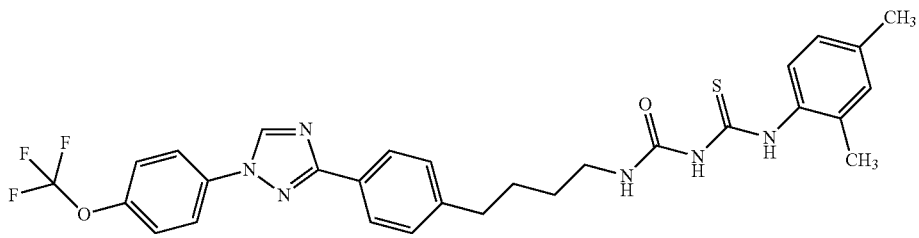 [SMILES: Cc1ccc(NC(=S)NC(=O)NCCCCc2ccc(-c3ncn(-c4ccc(OC(F)(F)F)cc4)n3)cc2)c(C)c1]

The title compound was prepared as described in Example 63 using 4-(4-(1-(4-(trifluoromethoxy)phenyl)-1H-1,2,4-triazol-3-yl)phenyl)butan-1-amine (CA20) and 1-(2,4-dimethylphenyl)thiourea and isolated as a white solid (0.106 g, 46%).

Preparation of 1-[(4-methoxy-2-methyl-phenyl)carbamothioyl]-3-[4-[3-[1-[4-(trifluoromethoxy)phenyl]-1H-1,2,4-triazol-3-yl]phenyl]butyl]urea (FB36)

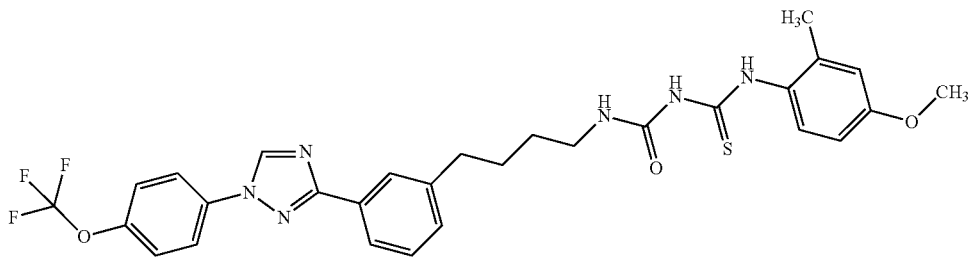 [SMILES: COc1ccc(NC(=S)NC(=O)NCCCCc2cccc(-c3ncn(-c4ccc(OC(F)(F)F)cc4)n3)c2)c(C)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(4-methoxy-2-methylphenyl)thiourea and isolated as a white solid (0.082 g, 27%).

Preparation of 1-[(5-chloro-2-isopropyl-phenyl)carbamothioyl]-3-[4-[3-[1-[4-(trifluoromethoxy)phenyl]-1H-1,2,4-triazol-3-yl]phenyl]butyl]urea (FB37)

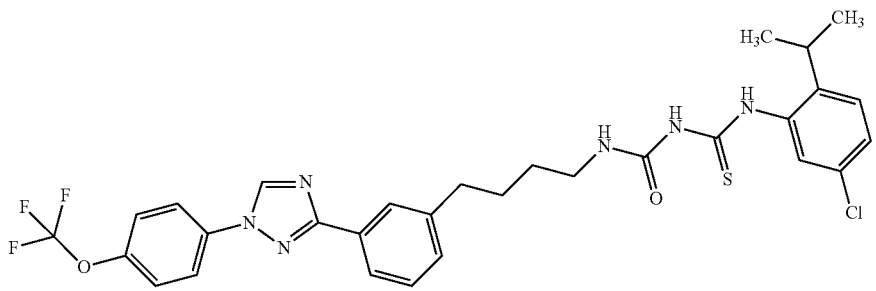 [SMILES: CC(C)c1ccc(Cl)cc1NC(=S)NC(=O)NCCCCc1cccc(-c2ncn(-c3ccc(OC(F)(F)F)cc3)n2)c1]

The title compound was prepared as described in Example 63 using 4-(3-(1-(4-(trifluoromethoxy)phenyl)-1H-1,2,4-triazol-3-yl)phenyl)butan-1-amine (CA21) and 1-(5-chloro-2-isopropylphenyl)thiourea (CB32) and isolated as a white solid (0.098 g, 31%).

Example 64

Preparation of (Z)-1-(3-(2-isopropyl-5-methylphenyl)-4-oxothiazolidin-2-ylidene)-3-(3-(4-(1-(4-(trifluoromethoxy)phenyl)-1H-1,2,4-triazol-3-yl)phenyl)propyl)urea (F20)

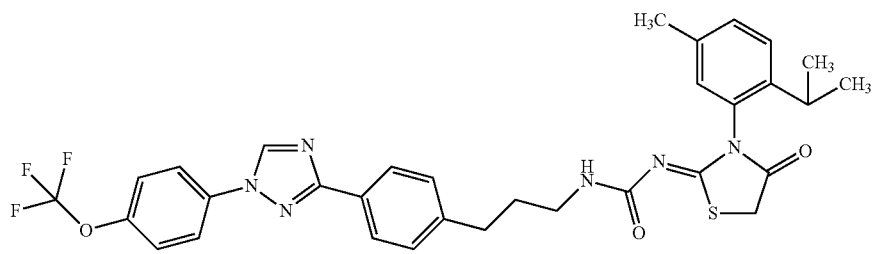 [SMILES: Cc1ccc(C(C)C)c(N2C(=O)CS/C2=N\C(=O)NCCCc2ccc(-c3ncn(-c4ccc(OC(F)(F)F)cc4)n3)cc2)c1]

To 1-[(2-isopropyl-5-methyl-phenyl)carbamothioyl]-3-[3-[4-[1-[4-(trifluoromethoxy)phenyl]-1,2,4-triazol-3-yl]phenyl]propyl]urea (F21) (0.110 g, 0.184 mmol) in a 25 mL vial equipped with a stir bar and Vigreux column was added sodium acetate (0.0600 g, 0.735 mmol), ethanol (2 mL) and methyl bromoacetate (0.0250 mL, 0.276 mmol). The reaction was heated to 70° C. overnight. The reaction was cooled and diluted with dichloromethane. The layers were separated and the aqueous layer was extracted with dichloromethane. The organic layers were poured through a phase separator and concentrated. Purification by flash column chromatography using 0-30% ethyl acetate/B, where B=1:1 dichloromethane/hexanes, as eluent provided a solid which was dried overnight at 50° C. in vacuo to afford the title compound as a white solid (0.0791 g, 68%).

The following compounds were prepared in accordance to the procedure in Example 64.

Preparation of (Z)-1-(4-oxo-3-(o-tolyl)thiazolidin-2-ylidene)-3-(3-(4-(1-(4-(trifluoromethoxy)phenyl)-1H-1,2,4-triazol-3-yl)phenyl)propyl)urea (P92)

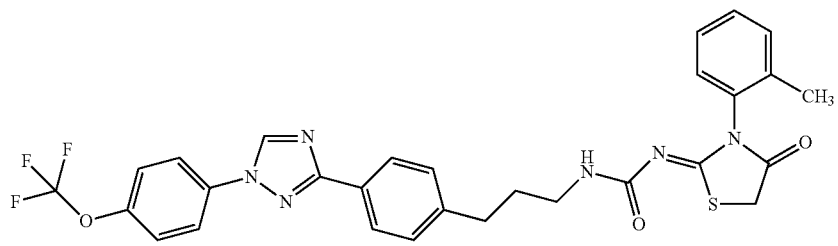 [SMILES: Cc1ccccc1N1C(=O)CS/C1=N\C(=O)NCCCc1ccc(-c2ncn(-c3ccc(OC(F)(F)F)cc3)n2)cc1]

The title compound was prepared as described in Example 64 using 1-(o-tolylcarbamothioyl)-3-[3-[3-[1-[4-(trifluoromethoxy)phenyl]-1,2,4-triazol-3-yl]phenyl]propyl]urea (PC92) and isolated as a light yellow solid (0.036 g, 72%).

Preparation of (Z)-1-(3-(4-methoxy-2-methylphenyl)-4-oxothiazolidin-2-ylidene)-3-(3-(4-(1-(4-(trifluoromethoxy)phenyl)-1H-1,2,4-triazol-3-yl)phenyl)propyl)urea (P105)

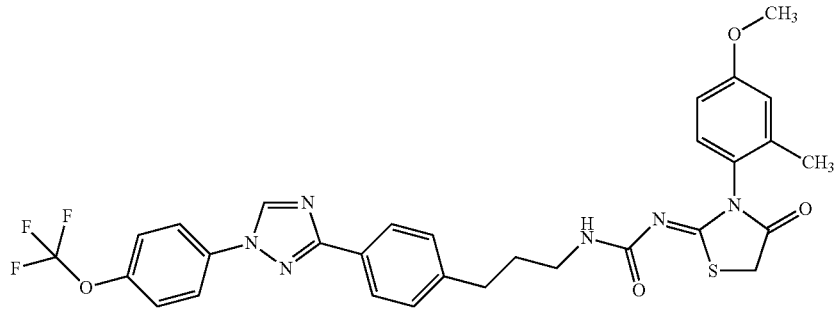 [SMILES: COc1ccc(N2C(=O)CS/C2=N\C(=O)NCCCc2ccc(-c3ncn(-c4ccc(OC(F)(F)F)cc4)n3)cc2)c(C)c1]

The title compound was prepared as described in Example 64 using 1-[(4-methoxy-2-methyl-phenyl)carbamothioyl]-3-[3-[4-[1-[4-(trifluoromethoxy)phenyl]-1,2,4-triazol-3-yl]phenyl]propyl]urea (PC105) and isolated as a light yellow solid (0.085 g, 75%).

Preparation of (Z)-1-(3-(2-ethylphenyl)-4-oxothiazolidin-2-ylidene)-3-(3-(4-(1-(4-(trifluoromethoxy)phenyl)-1H-1,2,4-triazol-3-yl)phenyl)propyl)urea (P93, P510)

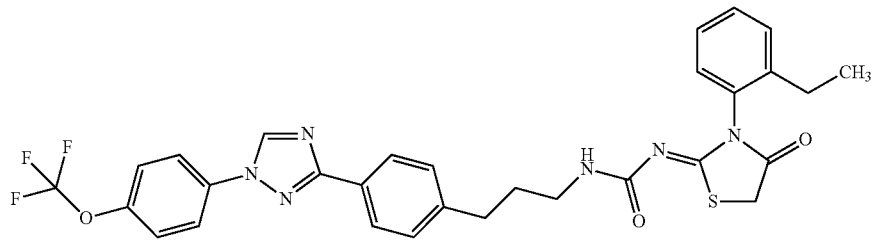 [SMILES: CCc1ccccc1N1C(=O)CS/C1=N\C(=O)NCCCc1ccc(-c2ncn(-c3ccc(OC(F)(F)F)cc3)n2)cc1]

The title compound was prepared as described in Example 64 using 1-[(2-ethylphenyl)carbamothioyl]-3-[3-[4-[1-[4-(trifluoromethoxy)phenyl]-1,2,4-triazol-3-yl]phenyl]propyl]urea (PC93) and isolated as a light yellow solid (0.057 g, 54%).

Preparation of (Z)-1-(3-(2-ethyl-6-methylphenyl)-4-oxothiazolidin-2-ylidene)-3-(3-(4-(1-(4-(trifluoromethoxy)phenyl)-1H-1,2,4-triazol-3-yl)phenyl)propyl)urea (P101)

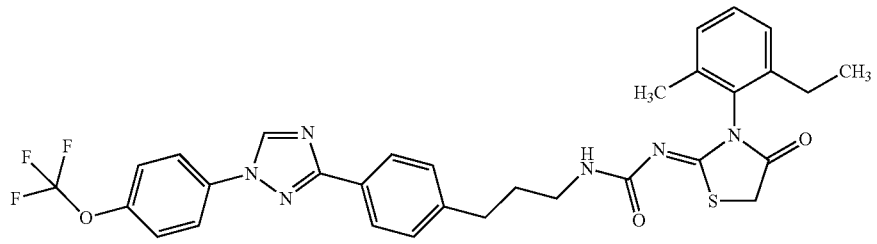 [SMILES: CCc1cccc(C)c1N1C(=O)CS/C1=N\C(=O)NCCCc1ccc(-c2ncn(-c3ccc(OC(F)(F)F)cc3)n2)cc1]

The title compound was prepared as described in Example 64 using 1-[(2-ethyl-6-methyl-phenyl)carbamothioyl]-3-[3-[4-[1-[4-(trifluoromethoxy)phenyl]-1,2,4-triazol-3-yl]phenyl]propyl]urea (PC101) and isolated as a light yellow solid (0.059 g, 41%).

Preparation of (Z)-1-(3-(2-isopropylphenyl)-4-oxothiazolidin-2-ylidene)-3-(3-(4-(1-(4-(trifluoromethoxy)phenyl)-1H-1,2,4-triazol-3-yl)phenyl)propyl)urea (P94, P197)

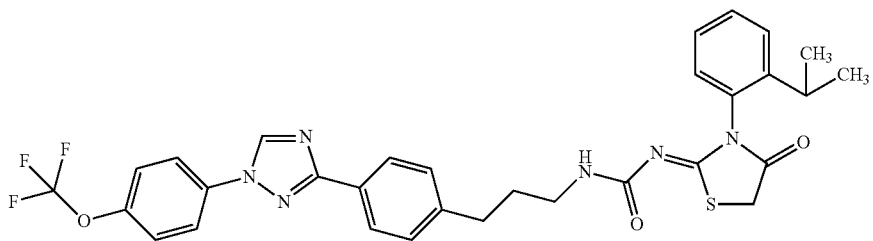 [SMILES: CC(C)c1ccccc1N1C(=O)CS/C1=N\C(=O)NCCCc1ccc(-c2ncn(-c3ccc(OC(F)(F)F)cc3)n2)cc1]

The title compound was prepared as described in Example 64 using 1-[(2-isopropylphenyl)carbamothioyl]-3-[3-[4-[1-[4-(trifluoromethoxy)phenyl]-1,2,4-triazol-3-yl]phenyl]propyl]urea (PC94) and isolated as a light yellow solid (0.071 g, 80%).

Preparation of (Z)-1-(3-(2-isopropyl-4-methylphenyl)-4-oxothiazolidin-2-ylidene)-3-(3-(4-(1-(4-(trifluoromethoxy)phenyl)-1H-1,2,4-triazol-3-yl)phenyl)propyl)urea (P102)

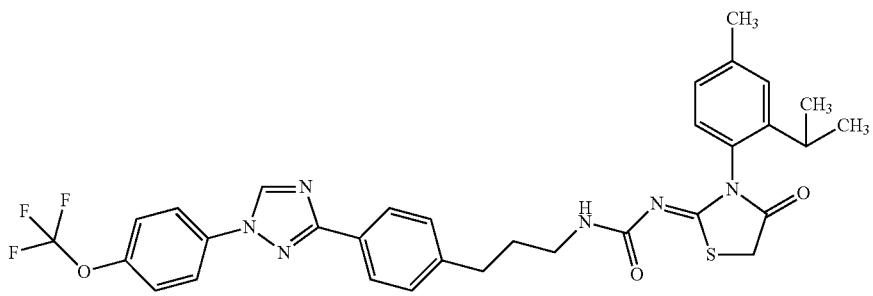

The title compound was prepared as described in Example 64 using 1-[(2-isopropyl-4-methyl-phenyl)carbamothioyl]-3-[3-[4-[1-[4-(trifluoromethoxy)phenyl]-1,2,4-triazol-3-yl]phenyl]propyl]urea (PC102) and isolated as a light yellow solid (0.070 g, 75%).

Preparation of (Z)-1-(3-(4-fluoro-2-isopropylphenyl)-4-oxothiazolidin-2-ylidene)-3-(3-(4-(1-(4-(trifluoromethoxy)phenyl)-1H-1,2,4-triazol-3-yl)phenyl)propyl)urea (P103, P1150)

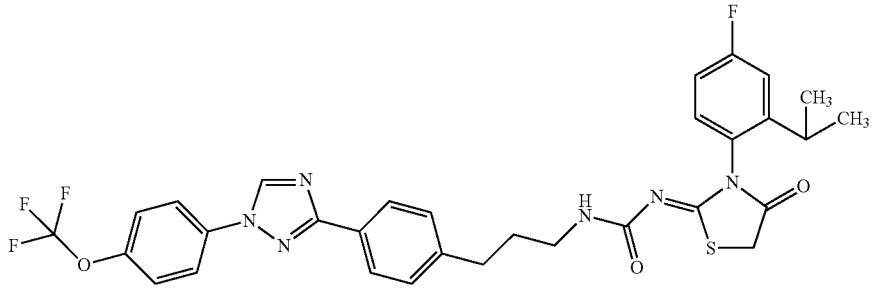 [SMILES: CC(C)c1cc(F)ccc1N1C(=O)CS/C1=N\C(=O)NCCCc1ccc(-c2ncn(-c3ccc(OC(F)(F)F)cc3)n2)cc1]

The title compound was prepared as described in Example 64 using 1-[(4-fluoro-2-isopropyl-phenyl)carbamothioyl]-3-[3-[4-[1-[4-(trifluoromethoxy)phenyl]-1,2,4-triazol-3-yl]phenyl]propyl]urea (PC103) and isolated as a light yellow solid (0.084 g, 77%).

Preparation of (Z)-1-(3-(5-methyl-2-propylphenyl)-4-oxothiazolidin-2-ylidene)-3-(3-(4-(1-(4-(trifluoromethoxy)phenyl)-1H-1,2,4-triazol-3-yl)phenyl)propyl)urea (P99, P830)

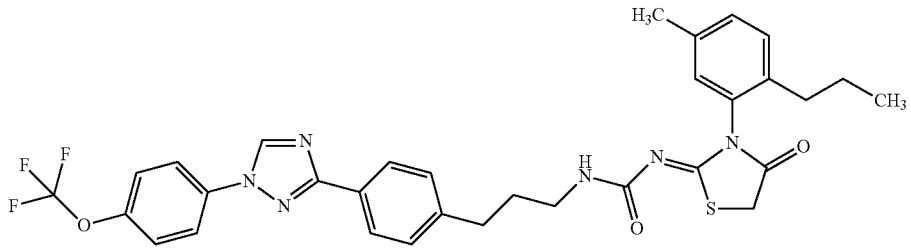 [SMILES: CCCc1ccc(C)cc1N1C(=O)CS/C1=N\C(=O)NCCCc1ccc(-c2ncn(-c3ccc(OC(F)(F)F)cc3)n2)cc1]

The title compound was prepared as described in Example 64 using 1-[(5-methyl-2-propyl-phenyl)carbamothioyl]-3-[3-[4-[1-[4-(trifluoromethoxy)phenyl]-1,2,4-triazol-3-yl]phenyl]propyl]urea (PC99) and isolated as a light yellow solid (0.075 g, 72%).

Preparation of (Z)-1-(4-oxo-3-(o-tolyl)thiazolidin-2-ylidene)-3-(3-(3-(1-(4-(trifluoromethoxy)phenyl)-1H-1,2,4-triazol-3-yl)phenyl)propyl)urea (P118)

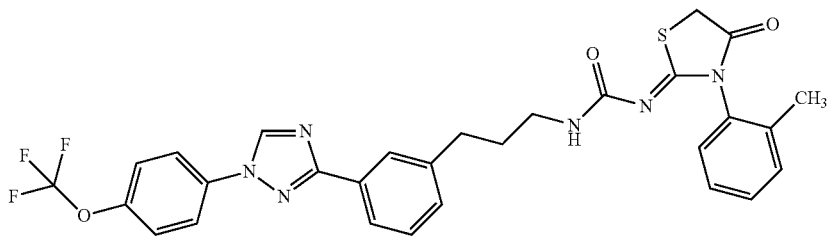 [SMILES: Cc1ccccc1N1C(=O)CS/C1=N\C(=O)NCCCc1cccc(-c2ncn(-c3ccc(OC(F)(F)F)cc3)n2)c1]

The title compound was prepared as described in Example 64 using 1-(o-tolylcarbamothioyl)-3-[3-[3-[1-[4-(trifluoromethoxy)phenyl]-1,2,4-triazol-3-yl]phenyl]propyl]urea (PC118) and isolated as an off-white solid (0.051 g, 80%).

Preparation of (Z)-1-(3-(4-methoxy-2-methylphenyl)-4-oxothiazolidin-2-ylidene)-3-(3-(3-(1-(4-(trifluoromethoxy)phenyl)-1H-1,2,4-triazol-3-yl)phenyl)propyl)urea (P131)

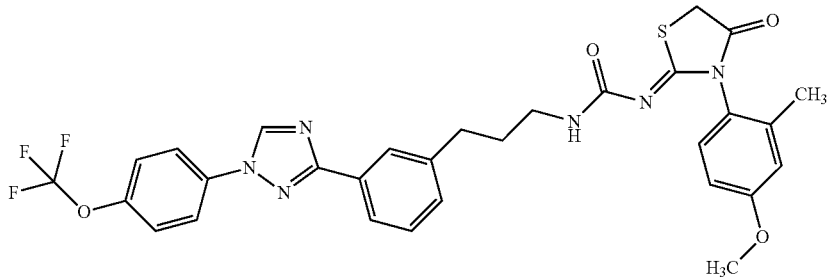 [SMILES: COc1ccc(N2C(=O)CS/C2=N\C(=O)NCCCc2cccc(-c3ncn(-c4ccc(OC(F)(F)F)cc4)n3)c2)c(C)c1]

The title compound was prepared as described in Example 64 using 1-[(4-methoxy-2-methyl-phenyl)carbamothioyl]-3-[3-[3-[1-[4-(trifluoromethoxy)phenyl]-1,2,4-triazol-3-yl]phenyl]propyl]urea (PC131) and isolated as an off-white solid (0.074 g, 89%).

Preparation of (Z)-1-(3-(2-ethylphenyl)-4-oxothiazolidin-2-ylidene)-3-(3-(3-(1-(4-(trifluoromethoxy)phenyl)-1H-1,2,4-triazol-3-yl)phenyl)propyl)urea (P119)

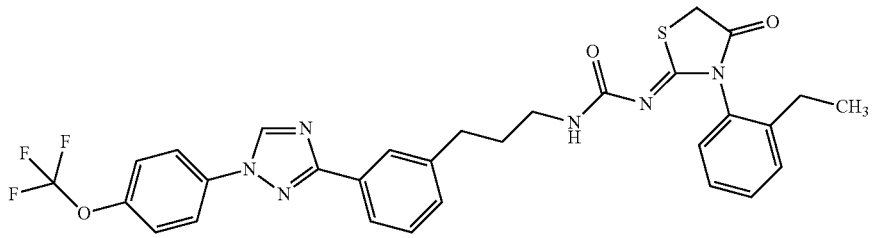 [SMILES: CCc1ccccc1N1C(=O)CS/C1=N\C(=O)NCCCc1cccc(-c2ncn(-c3ccc(OC(F)(F)F)cc3)n2)c1]

The title compound was prepared as described in Example 64 using 1-[(2-ethylphenyl)carbamothioyl]-3-[3-[3-[1-[4-(trifluoromethoxy)phenyl]-1,2,4-triazol-3-yl]phenyl]propyl]urea (PC119) and isolated as an off-white solid (0.071 g, 83%).

Preparation of (Z)-1-(3-(2-ethyl-6-methylphenyl)-4-oxothiazolidin-2-ylidene)-3-(3-(3-(1-(4-(trifluoromethoxy)phenyl)-1H-1,2,4-triazol-3-yl)phenyl)propyl)urea (P127)

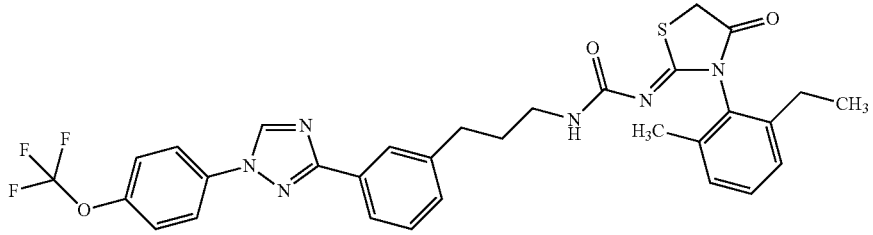 [SMILES: CCc1cccc(C)c1N1C(=O)CS/C1=N\C(=O)NCCCc1cccc(-c2ncn(-c3ccc(OC(F)(F)F)cc3)n2)c1]

The title compound was prepared as described in Example 64 using 1-[(2-ethyl-6-methyl-phenyl)carbamothioyl]-3-[3-[3-[1-[4-(trifluoromethoxy)phenyl]-1,2,4-triazol-3-yl]phenyl]propyl]urea (PC127) and isolated as an off-white solid (0.061 g, 43%).

Preparation of (Z)-1-(3-(2-isopropylphenyl)-4-oxothiazolidin-2-ylidene)-3-(3-(3-(1-(4-(trifluoromethoxy)phenyl)-1H-1,2,4-triazol-3-yl)phenyl)propyl)urea (P120)

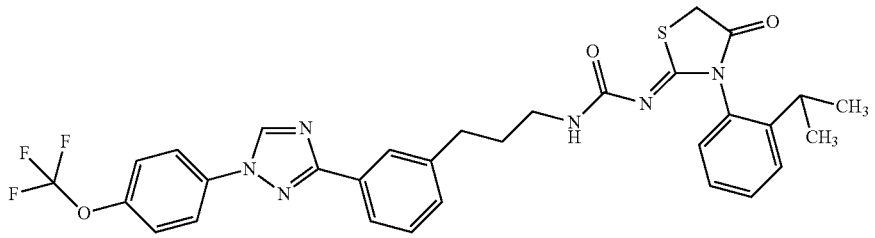 [SMILES: CC(C)c1ccccc1N1C(=O)CS/C1=N\C(=O)NCCCc1cccc(-c2ncn(-c3ccc(OC(F)(F)F)cc3)n2)c1]

The title compound was prepared as described in Example 64 using 1-[(2-isopropylphenyl)carbamothioyl]-3-[3-[3-[1-[4-(trifluoromethoxy)phenyl]-1,2,4-triazol-3-yl]phenyl]propyl]urea (PC120) and isolated as an off-white solid (0.091 g, 80%).

Preparation of (Z)-1-(3-(2-isopropyl-4-methylphenyl)-4-oxothiazolidin-2-ylidene)-3-(3-(3-(1-(4-(trifluoromethoxy)phenyl)-1H-1,2,4-triazol-3-yl)phenyl)propyl)urea (P128)

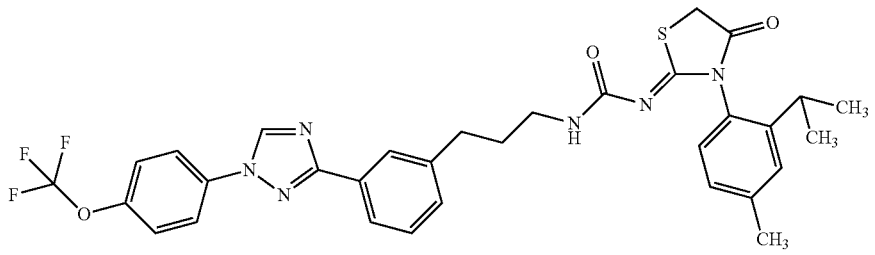 [SMILES: Cc1ccc(N2C(=O)CS/C2=N\C(=O)NCCCc2cccc(-c3ncn(-c4ccc(OC(F)(F)F)cc4)n3)c2)c(C(C)C)c1]

The title compound was prepared as described in Example 64 using 1-[(2-isopropyl-4-methyl-phenyl)carbamothioyl]-3-[3-[3-[1-[4-(trifluoromethoxy)phenyl]-1,2,4-triazol-3-yl]phenyl]propyl]urea (PC128) and isolated as an off-white solid (0.091 g, 84%).

Preparation of (Z)-1-(3-(4-fluoro-2-isopropylphenyl)-4-oxothiazolidin-2-ylidene)-3-(3-(3-(1-(4-(trifluoromethoxy)phenyl)-1H-1,2,4-triazol-3-yl)phenyl)propyl)urea (P129)

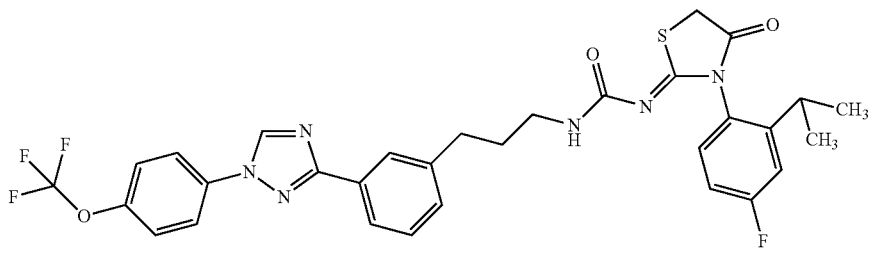 [SMILES: CC(C)c1cc(F)ccc1N1C(=O)CS/C1=N\C(=O)NCCCc1cccc(-c2ncn(-c3ccc(OC(F)(F)F)cc3)n2)c1]

The title compound was prepared as described in Example 64 using 1-[(4-fluoro-2-isopropyl-phenyl)carbamothioyl]-3-[3-[3-[1-[4-(trifluoromethoxy)phenyl]-1,2,4-triazol-3-yl]phenyl]propyl]urea (PC129) and isolated as an off-white solid (0.095 g, 81%).

Preparation of (Z)-1-(3-(2-isopropyl-5-methylphenyl)-4-oxothiazolidin-2-ylidene)-3-(3-(3-(1-(4-(trifluoromethoxy)phenyl)-1H-1,2,4-triazol-3-yl)phenyl)propyl)urea (P124)

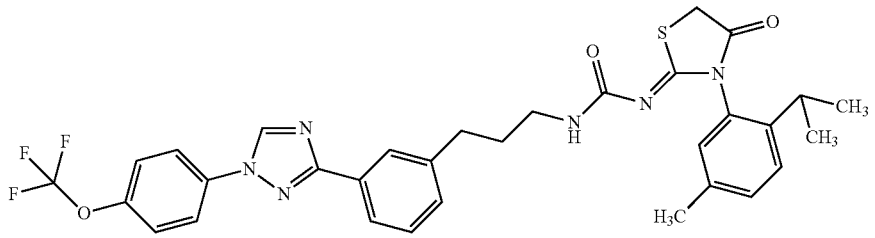 [SMILES: Cc1ccc(C(C)C)c(N2C(=O)CS/C2=N\C(=O)NCCCc2cccc(-c3ncn(-c4ccc(OC(F)(F)F)cc4)n3)c2)c1]

The title compound was prepared as described in Example 64 using 1-[(2-isopropyl-5-methyl-phenyl)carbamothioyl]-3-[3-[3-[1-[4-(trifluoromethoxy)phenyl]-1,2,4-triazol-3-yl]phenyl]propyl]urea (PC124) and isolated as an off-white solid (0.077 g, 80%).

Preparation of (Z)-1-(3-(5-methyl-2-propylphenyl)-4-oxothiazolidin-2-ylidene)-3-(3-(3-(1-(4-(trifluoromethoxy)phenyl)-1H-1,2,4-triazol-3-yl)phenyl)propyl)urea (P125)

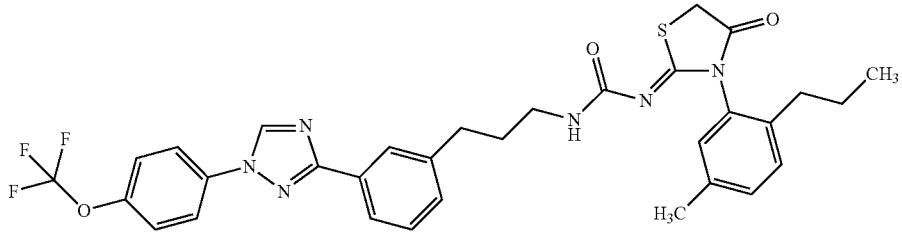 [SMILES: CCCc1ccc(C)cc1N1C(=O)CS/C1=N\C(=O)NCCCc1cccc(-c2ncn(-c3ccc(OC(F)(F)F)cc3)n2)c1]

The title compound was prepared as described in Example 64 using 1-[(5-methyl-2-propyl-phenyl)carbamothioyl]-3-[3-[4-[1-[4-(trifluoromethoxy)phenyl]-1,2,4-triazol-3-yl]phenyl]propyl]urea (PC125) and isolated as an off-white solid (0.097 g, 86%).

Preparation of (Z)-1-(3-(2-isopropyl-5-methylphenyl)-4-oxothiazolidin-2-ylidene)-3-(4-(4-(1-(4-(trifluoromethyl)phenyl)-1H-1,2,4-triazol-3-yl)phenyl)butyl)urea (P159)

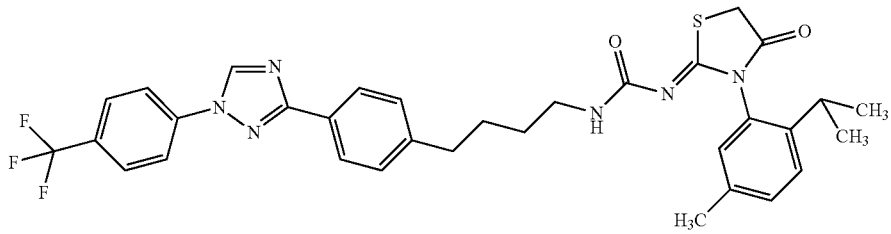 [SMILES: Cc1ccc(C(C)C)c(N2C(=O)CS/C2=N\C(=O)NCCCCc2ccc(-c3ncn(-c4ccc(C(F)(F)F)cc4)n3)cc2)c1]

The title compound was prepared as described in Example 64 using 1-[(2-isopropyl-5-methyl-phenyl)carbamothioyl]-3-[4-[4-[1-[4-(trifluoromethyl)phenyl]-1,2,4-triazol-3-yl]phenyl]butyl]urea (PC159) and isolated as a white solid (0.063 g, 70%).

Preparation of (Z)-1-(3-(2-isopropyl-5-methylphenyl)-4-oxothiazolidin-2-ylidene)-3-(4-(4-(1-(4-(trifluoromethoxy)phenyl)-1H-1,2,4-triazol-3-yl)phenyl)but-3-yn-1-yl)urea (P160)

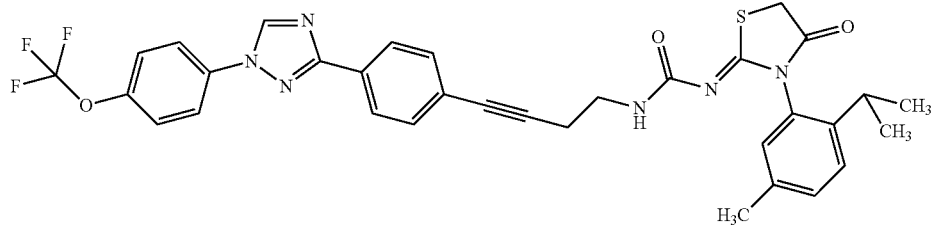 [SMILES: Cc1ccc(C(C)C)c(N2C(=O)CS/C2=N\C(=O)NCCC#Cc2ccc(-c3ncn(-c4ccc(OC(F)(F)F)cc4)n3)cc2)c1]

The title compound was prepared as described in Example 64 using 1-[(2-isopropyl-5-methyl-phenyl)carbamothioyl]-3-[4-[4-[1-[4-(trifluoromethoxy)phenyl]-1,2,4-triazol-3-yl]phenyl]but-3-ynyl]urea (PC160) and isolated as a yellow solid (0.122 g, 74%).

Preparation of (Z)-1-(3-(2-isopropyl-5-methylphenyl)-4-oxothiazolidin-2-ylidene)-3-(4-(4-(1-(4-(trifluoromethoxy)phenyl)-1H-1,2,4-triazol-3-yl)phenyl)butyl)urea (P150, P363)

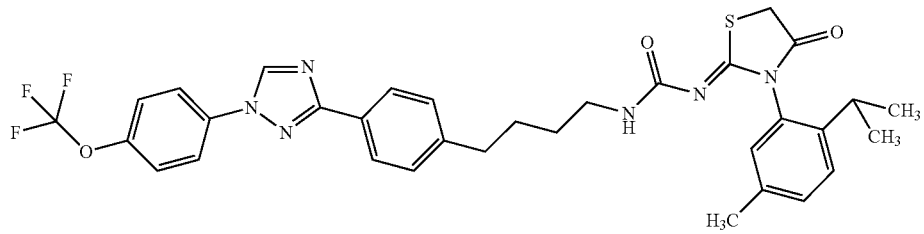 [SMILES: Cc1ccc(C(C)C)c(N2C(=O)CS/C2=N\C(=O)NCCCCc2ccc(-c3ncn(-c4ccc(OC(F)(F)F)cc4)n3)cc2)c1]

The title compound was prepared as described in Example 64 using 1-[(2-isopropyl-5-methyl-phenyl)carbamothioyl]-3-[4-[4-[1-[4-(trifluoromethoxy)phenyl]-1,2,4-triazol-3-yl]phenyl]butyl]urea (PC150) and isolated as a white solid (0.068 g, 78%).

Preparation of (Z)-1-(3-(2-isopropylphenyl)-4-oxothiazolidin-2-ylidene)-3-(4-(4-(1-(4-(trifluoromethoxy)phenyl)-1H-1,2,4-triazol-3-yl)phenyl)butyl)urea (P146, P208)

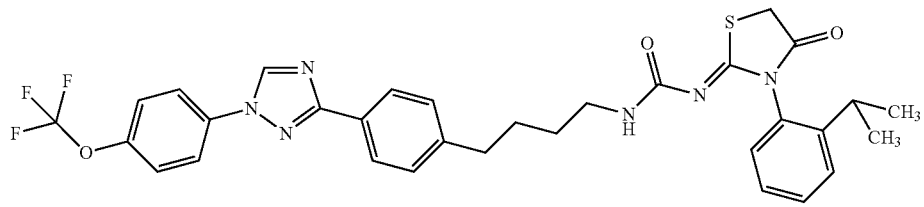 [SMILES: CC(C)c1ccccc1N1C(=O)CS/C1=N\C(=O)NCCCCc1ccc(-c2ncn(-c3ccc(OC(F)(F)F)cc3)n2)cc1]

The title compound was prepared as described in Example 64 using 1-[(2-isopropylphenyl)carbamothioyl]-3-[4-[4-[1-[4-(trifluoromethoxy)phenyl]-1,2,4-triazol-3-yl]phenyl]butyl]urea (PC146) isolated as a white solid (0.063 g, 80%).

Preparation of (Z)-1-(3-(2-ethylphenyl)-4-oxothiazo-
lidin-2-ylidene)-3-(4-(4-(1-(4-(trifluoromethoxy)
phenyl)-1H-1,2,4-triazol-3-yl)phenyl)butyl)urea
(P145, P522)

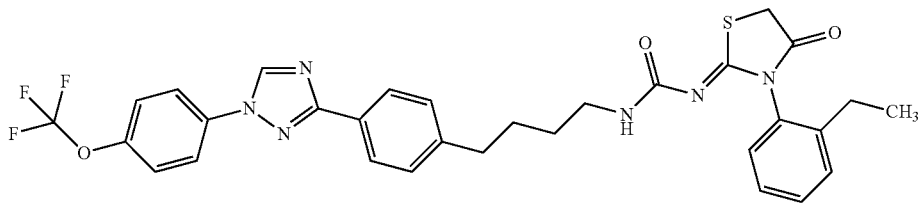 [SMILES: CCc1ccccc1N1C(=O)CS/C1=N\C(=O)NCCCCc1ccc(-c2ncn(-c3ccc(OC(F)(F)F)cc3)n2)cc1]

The title compound was prepared as described in Example 64 using 1-[(2-ethylphenyl)carbamothioyl]-3-[4-[4-[1-[4-(trifluoromethoxy)phenyl]-1,2,4-triazol-3-yl]phenyl]butyl]urea (PC145) and isolated as a white solid (0.084 g, 83%).

Preparation of (Z)-1-(3-(5-methyl-2-propylphenyl)-
4-oxothiazolidin-2-ylidene)-3-(4-(4-(1-(4-(trifluo-
romethoxy)phenyl)-1H-1,2,4-triazol-3-yl)phenyl)
butyl)urea (P151, P842)

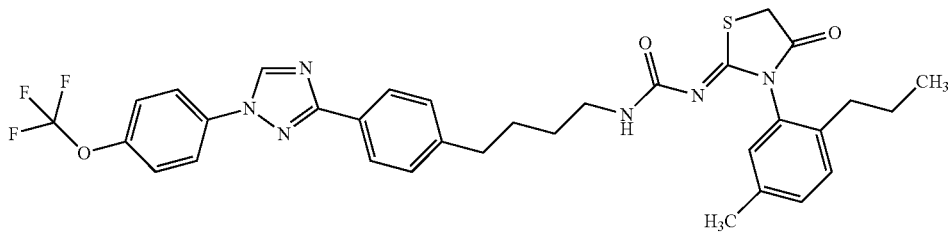 [SMILES: CCCc1ccc(C)cc1N1C(=O)CS/C1=N\C(=O)NCCCCc1ccc(-c2ncn(-c3ccc(OC(F)(F)F)cc3)n2)cc1]

The title compound was prepared as described in Example 64 using 1-[(5-methyl-2-propyl-phenyl)carbamothioyl]-3-[4-[4-[1-[4-(trifluoromethoxy)phenyl]-1,2,4-triazol-3-yl]phenyl]butyl]urea (PC151) and isolated as a white solid (0.081 g, 81%).

Preparation of (Z)-1-(3-(2-isopropyl-4-methylphe-
nyl)-4-oxothiazolidin-2-ylidene)-3-(4-(4-(1-(4-(trif-
luoromethoxy)phenyl)-1H-1,2,4-triazol-3-yl)phenyl)
butyl)urea (P154)

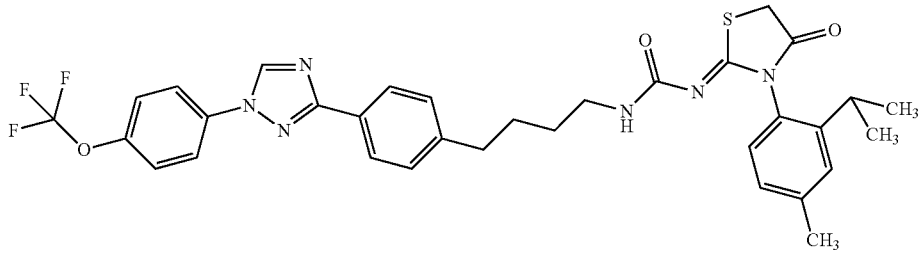 [SMILES: Cc1ccc(N2C(=O)CS/C2=N\C(=O)NCCCCc2ccc(-c3ncn(-c4ccc(OC(F)(F)F)cc4)n3)cc2)c(C(C)C)c1]

The title compound was prepared as described in Example 64 using 1-[(2-isopropyl-4-methyl-phenyl)carbamothioyl]-3-[4-[4-[1-[4-(trifluoromethoxy)phenyl]-1,2,4-triazol-3-yl]phenyl]butyl]urea (PC154) and isolated as a white solid (0.070 g, 82%).

Preparation of (Z)-1-(3-(2-ethyl-6-methylphenyl)-4-oxothiazolidin-2-ylidene)-3-(4-(4-(1-(4-(trifluoromethoxy)phenyl)-1H-1,2,4-triazol-3-yl)phenyl)butyl)urea (P153)

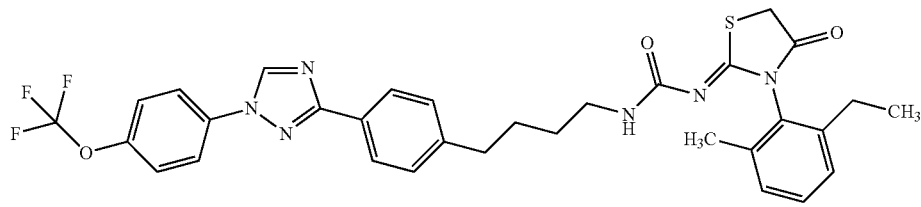 [SMILES: CCc1cccc(C)c1N1C(=O)CS/C1=N\C(=O)NCCCCc1ccc(-c2ncn(-c3ccc(OC(F)(F)F)cc3)n2)cc1]

The title compound was prepared as described in Example 64 using 1-[(2-ethyl-6-methyl-phenyl)carbamothioyl]-3-[4-[4-[1-[4-(trifluoromethoxy)phenyl]-1,2,4-triazol-3-yl]phenyl]butyl]urea (PC153) and isolated as a white foam (0.059 g, 52%).

Preparation of (Z)-1-(4-oxo-3-(o-tolyl)thiazolidin-2-ylidene)-3-(4-(4-(1-(4-(trifluoromethoxy)phenyl)-1H-1,2,4-triazol-3-yl)phenyl)butyl)urea (P144)

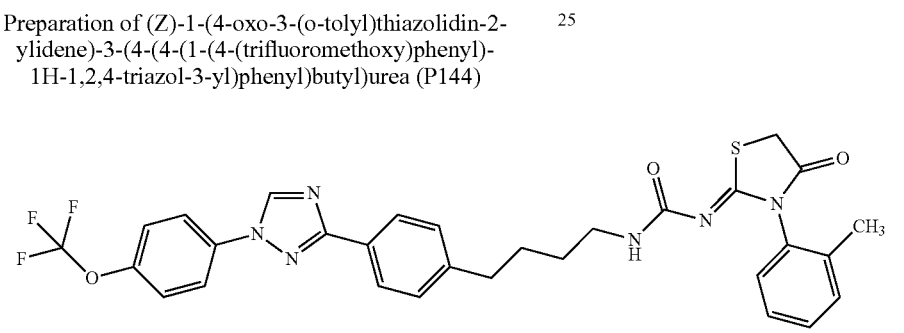

The title compound was prepared as described in Example 64 using 1-(o-tolylcarbamothioyl)-3-[4-[4-[1-[4-(trifluoromethoxy)phenyl]-1,2,4-triazol-3-yl]phenyl]butyl]urea (PC144) and isolated as a white foam (0.070 g, 76%).

Preparation of (Z)-1-(3-(2,6-dimethylphenyl)-4-oxothiazolidin-2-ylidene)-3-(4-(4-(1-(4-(trifluoromethoxy)phenyl)-1H-1,2,4-triazol-3-yl)phenyl)butyl)urea (P152, P1481)

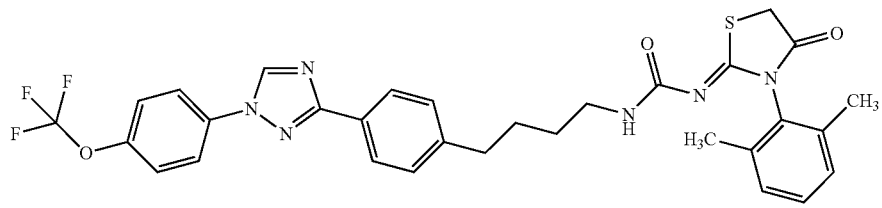 [SMILES: Cc1cccc(C)c1N1C(=O)CS/C1=N\C(=O)NCCCCc1ccc(-c2ncn(-c3ccc(OC(F)(F)F)cc3)n2)cc1]

The title compound was prepared as described in Example 64 using 1-[(2,6-dimethylphenyl)carbamothioyl]-3-[4-[4-[1-[4-(trifluoromethoxy)phenyl]-1,2,4-triazol-3-yl]phenyl]butyl]urea (PC152) and isolated as a white solid (0.078 g, 72%).

Preparation of (Z)-1-(3-(2-isopropyl-5-methoxyphenyl)-4-oxothiazolidin-2-ylidene)-3-(4-(4-(1-(4-(trifluoromethoxy)phenyl)-1H-1,2,4-triazol-3-yl)phenyl)butyl)urea (P156, P682)

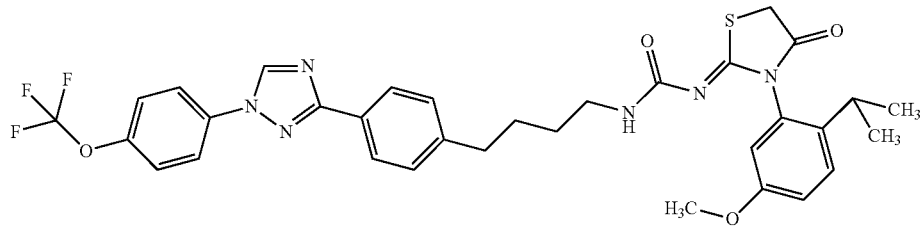 [SMILES: COc1ccc(C(C)C)c(N2C(=O)CS/C2=N\C(=O)NCCCCc2ccc(-c3ncn(-c4ccc(OC(F)(F)F)cc4)n3)cc2)c1]

The title compound was prepared as described in Example 64 using 1-[(2-isopropyl-5-methoxy-phenyl)carbamothioyl]-3-[4-[4-[1-[4-(trifluoromethoxy)phenyl]-1,2,4-triazol-3-yl]phenyl]butyl]urea (PC156) and isolated as a white solid (0.089 g, 82%).

Preparation of (Z)-1-(3-(4-fluoro-2-isopropylphenyl)-4-oxothiazolidin-2-ylidene)-3-(4-(4-(1-(4-(trifluoromethoxy)phenyl)-1H-1,2,4-triazol-3-yl)phenyl)butyl)urea (P155, P1162)

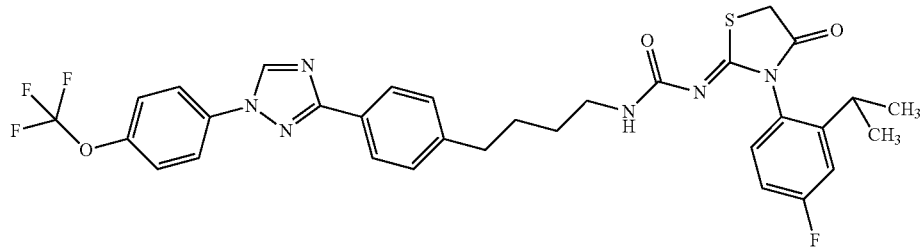 [SMILES: CC(C)c1cc(F)ccc1N1C(=O)CS/C1=N\C(=O)NCCCCc1ccc(-c2ncn(-c3ccc(OC(F)(F)F)cc3)n2)cc1]

The title compound was prepared as described in Example 64 using 1-[(4-fluoro-2-isopropyl-phenyl)carbamothioyl]-3-[4-[4-[1-[4-(trifluoromethoxy)phenyl]-1,2,4-triazol-3-yl]phenyl]butyl]urea (PC155) and isolated as a white foam (0.075 g, 88%).

Preparation of (Z)-1-(4-oxo-3-(o-tolyl)thiazolidin-2-ylidene)-3-(4-(3-(1-(4-(trifluoromethoxy)phenyl)-1H-1,2,4-triazol-3-yl)phenyl)butyl)urea (P170)

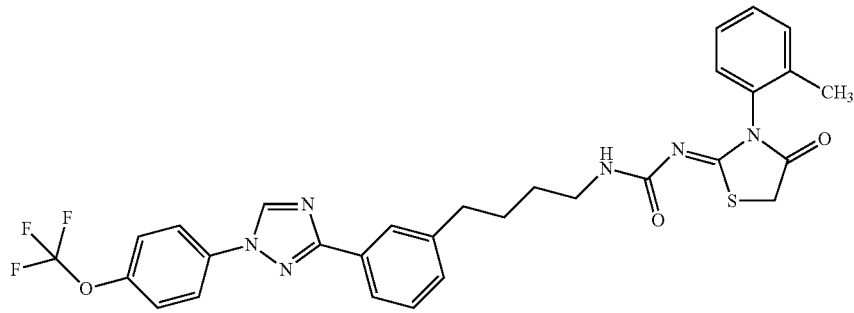 [SMILES: Cc1ccccc1N1C(=O)CS/C1=N\C(=O)NCCCCc1cccc(-c2ncn(-c3ccc(OC(F)(F)F)cc3)n2)c1]

The title compound was prepared as described in Example 64 using 1-(o-tolylcarbamothioyl)-3-[4-[3-[1-[4-(trifluoromethoxy)phenyl])-1H-1,2,4-triazol-3-yl]phenyl]butyl]urea (PC170) and isolated as a white solid (0.061 g, 72%).

Preparation of (Z)-1-(3-(2-ethylphenyl)-4-oxothiazo-
lidin-2-ylidene)-3-(4-(3-(1-(4-(trifluoromethoxy)
phenyl)-1H-1,2,4-triazol-3-yl)phenyl)butyl)urea
(P171)

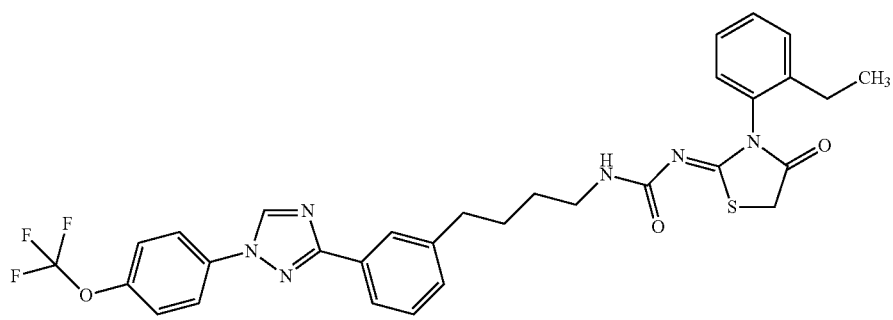 [SMILES: CCc1ccccc1N1C(=O)CS/C1=N\C(=O)NCCCCc1cccc(-c2ncn(-c3ccc(OC(F)(F)F)cc3)n2)c1]

The title compound was prepared as described in Example 64 using 1-[(2-ethylphenyl)carbamothioyl]-3-[4-[3-[1-[4-(trifluoromethoxy)phenyl]-1H-1,2,4-triazol-3-yl]phenyl]butyl]urea (PC171) and isolated as a white solid (0.078 g, 77%).

Preparation of (Z)-1-(3-(2-ethyl-6-methylphenyl)-4-
oxothiazolidin-2-ylidene)-3-(4-(3-(1-(4-(trifluo-
romethoxy)phenyl)-1H-1,2,4-triazol-3-yl)phenyl)
butyl)urea (P179)

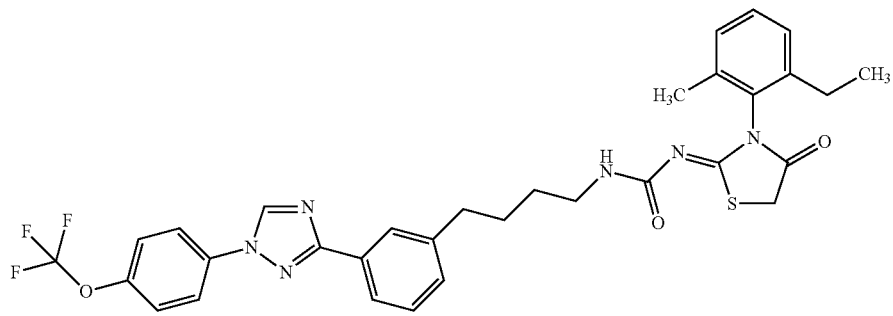 [SMILES: CCc1cccc(C)c1N1C(=O)CS/C1=N\C(=O)NCCCCc1cccc(-c2ncn(-c3ccc(OC(F)(F)F)cc3)n2)c1]

The title compound was prepared as described in Example 64 using 1-[(2-ethyl-6-methyl-phenyl)carbamothioyl]-3-[4-[3-[1-[4-(trifluoromethoxy)phenyl]-1H-1,2,4-triazol-3-yl]phenyl]butyl]urea (PC179) and isolated as a white solid (0.048 g, 37%).

Preparation of (Z)-1-(3-(2-isopropylphenyl)-4-oxothiazolidin-2-ylidene)-3-(4-(3-(1-(4-(trifluoromethoxy)phenyl)-1H-1,2,4-triazol-3-yl)phenyl)butyl)urea (P172)

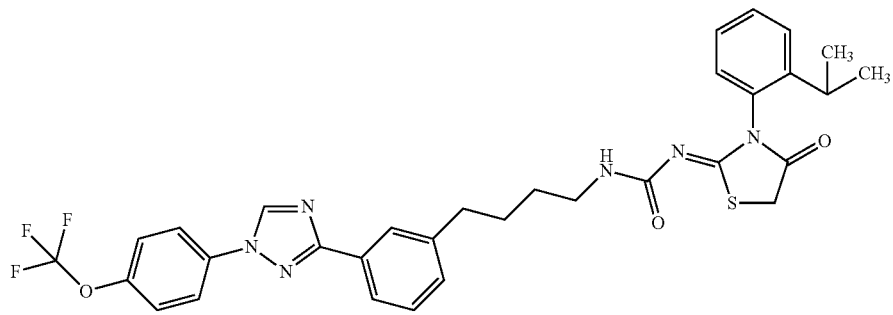 [SMILES: CC(C)c1ccccc1N1C(=O)CS/C1=N\C(=O)NCCCCc1cccc(-c2ncn(-c3ccc(OC(F)(F)F)cc3)n2)c1]

The title compound was prepared as described in Example 64 using 1-[(2-isopropylphenyl)carbamothioyl]-3-[4-[3-[1-[4-(trifluoromethoxy)phenyl]-1H-1,2,4-triazol-3-yl]phenyl]butyl]urea (PC172) and isolated as a white solid (0.048 g, 80%).

Preparation of (Z)-1-(3-(2-isopropyl-4-methylphenyl)-4-oxothiazolidin-2-ylidene)-3-(4-(3-(1-(4-(trifluoromethoxy)phenyl)-1H-1,2,4-triazol-3-yl)phenyl)butyl)urea (P180)

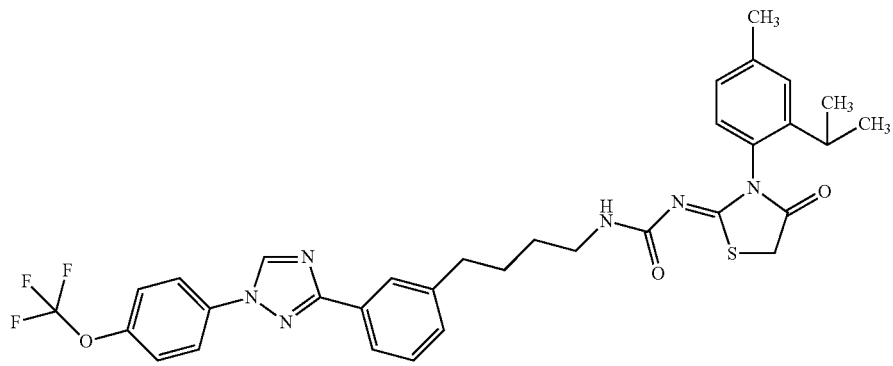 [SMILES: Cc1ccc(N2C(=O)CS/C2=N\C(=O)NCCCCc2cccc(-c3ncn(-c4ccc(OC(F)(F)F)cc4)n3)c2)c(C(C)C)c1]

The title compound was prepared as described in Example 64 using 1-[(2-isopropyl-4-methyl-phenyl)carbamothioyl]-3-[4-[3-[1-[4-(trifluoromethoxy)phenyl]-1H-1,2,4-triazol-3-yl]phenyl]butyl]urea (PC180) and isolated as a white solid (0.086 g, 66%).

Preparation of (Z)-1-(3-(4-fluoro-2-isopropylphenyl)-4-oxothiazolidin-2-ylidene)-3-(4-(3-(1-(4-(trifluoromethoxy)phenyl)-1H-1,2,4-triazol-3-yl)phenyl)butyl)urea (P181)

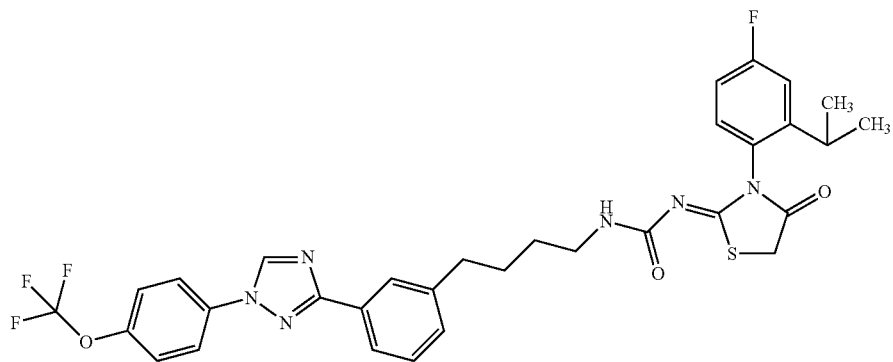 [SMILES: CC(C)c1cc(F)ccc1N1C(=O)CS/C1=N\C(=O)NCCCCc1cccc(-c2ncn(-c3ccc(OC(F)(F)F)cc3)n2)c1]

The title compound was prepared as described in Example 64 using 1-[(4-fluoro-2-isopropyl-phenyl)carbamothioyl]-3-[4-[3-[1-[4-(trifluoromethoxy)phenyl]-1H-1,2,4-triazol-3-yl]phenyl]butyl]urea (PC181) and isolated as a white solid (0.058 g, 57%).

Preparation of (Z)-1-(3-(2-isopropyl-5-methylphenyl)-4-oxothiazolidin-2-ylidene)-3-(4-(3-(1-(4-(trifluoromethoxy)phenyl)-1H-1,2,4-triazol-3-yl)phenyl)butyl)urea (P176)

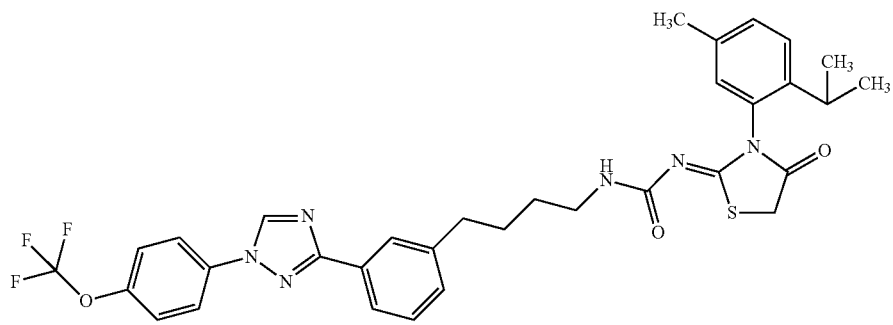 [SMILES: Cc1ccc(C(C)C)c(N2C(=O)CS/C2=N\C(=O)NCCCCc2cccc(-c3ncn(-c4ccc(OC(F)(F)F)cc4)n3)c2)c1]

The title compound was prepared as described in Example 64 using 1-[(2-isopropyl-5-methyl-phenyl)carbamothioyl]-3-[4-[3-[1-[4-(trifluoromethoxy)phenyl]-1H-1,2,4-triazol-3-yl]phenyl]butyl]urea (PC176) and isolated as a white solid (0.076 g, 74%).

Preparation of (Z)-1-(3-(2-isopropyl-5-methoxyphenyl)-4-oxothiazolidin-2-ylidene)-3-(4-(3-(1-(4-(trifluoromethoxy)phenyl)-1H-1,2,4-triazol-3-yl)phenyl)butyl)urea (P182)

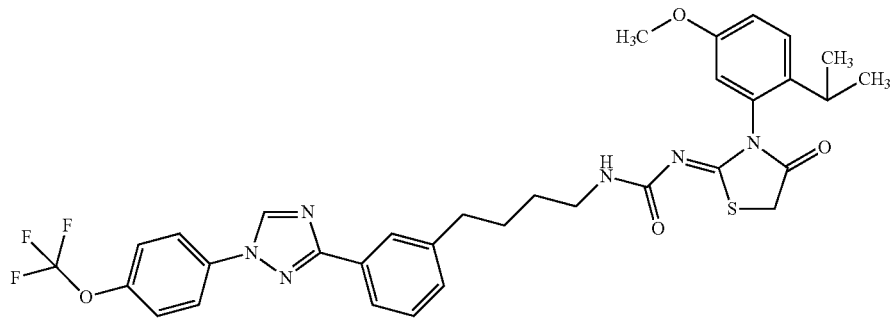 [SMILES: COc1ccc(C(C)C)c(N2C(=O)CS/C2=N\C(=O)NCCCCc2cccc(-c3ncn(-c4ccc(OC(F)(F)F)cc4)n3)c2)c1]

The title compound was prepared as described in Example 64 using 1-[(2-isopropyl-5-methoxy-phenyl)carbamothioyl]-3-[4-[3-[1-[4-(trifluoromethoxy)phenyl]-1H-1,2,4-triazol-3-yl]phenyl]butyl]urea (PC182) and isolated as a white solid (0.064 g, 58%).

Preparation of (Z)-1-(4-oxo-3-(o-tolyl)thiazolidin-2-ylidene)-3-(3-(1-(4-(trifluoromethoxy)phenyl)-1H-1,2,4-triazol-3-yl)phenethyl)urea (P74)

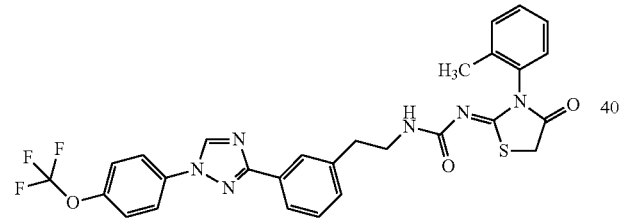

The title compound was prepared as described in Example 64 using 1-(o-tolylcarbamothioyl)-3-[2-[3-[1-[4-(trifluoromethoxy)phenyl]-1H-1,2,4-triazol-3-yl]phenyl]ethyl]urea (PC74) and isolated as a white solid (0.076 g, 77%).

Preparation of (Z)-1-(3-(4-methoxy-2-methylphenyl)-4-oxothiazolidin-2-ylidene)-3-(3-(1-(4-(trifluoromethoxy)phenyl)-1H-1,2,4-triazol-3-yl)phenethyl)urea (P87)

The title compound was prepared as described in Example 64 using 1-[(4-methoxy-2-methyl-phenyl)carbamothioyl]-3-[2-[3-[1-[4-(trifluoromethoxy)phenyl]-1H-1,2,4-triazol-3-yl]phenyl]ethyl]urea (PC87) and isolated as a white solid (0.079 g, 84%).

Preparation of (Z)-1-(3-(2-ethylphenyl)-4-oxothiazolidin-2-ylidene)-3-(3-(1-(4-(trifluoromethoxy)phenyl)-1H-1,2,4-triazol-3-yl)phenethyl)urea (P75)

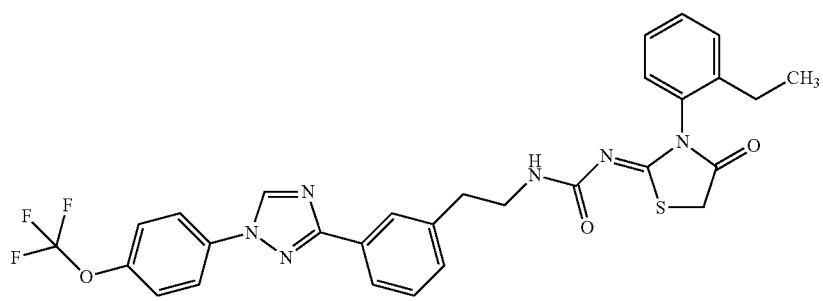 [SMILES: CCc1ccccc1N1C(=O)CS/C1=N\C(=O)NCCc1cccc(-c2ncn(-c3ccc(OC(F)(F)F)cc3)n2)c1]

The title compound was prepared as described in Example 64 using 1-[(2-ethylphenyl)carbamothioyl]-3-[2-[3-[1-[4-(trifluoromethoxy)phenyl]-1H-1,2,4-triazol-3-yl]phenyl]ethyl]urea (PC75) and isolated as a white solid (0.071 g, 73%).

Preparation of (Z)-1-(3-(2-ethyl-6-methylphenyl)-4-oxothiazolidin-2-ylidene)-3-(3-(1-(4-(trifluoromethoxy)phenyl)-1H-1,2,4-triazol-3-yl)phenethyl)urea (P83)

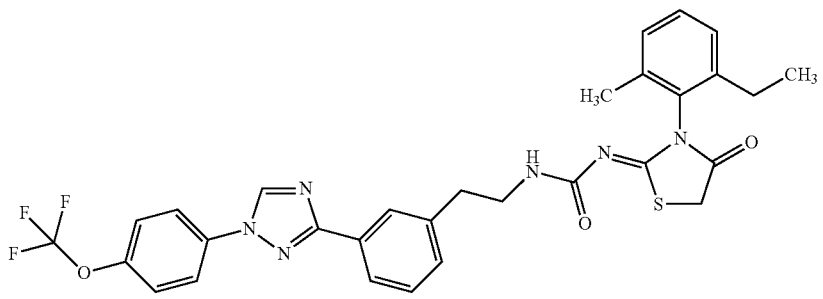 [SMILES: CCc1cccc(C)c1N1C(=O)CS/C1=N\C(=O)NCCc1cccc(-c2ncn(-c3ccc(OC(F)(F)F)cc3)n2)c1]

The title compound was prepared as described in Example 64 using 1-[(2-ethyl-6-methyl-phenyl)carbamothioyl]-3-[2-[3-[1-[4-(trifluoromethoxy)phenyl]-1H-1,2,4-triazol-3-yl]phenyl]ethyl]urea (PC83) and isolated as a white solid (0.042 g, 34%).

Preparation of (Z)-1-(3-(2-isopropylphenyl)-4-oxothiazolidin-2-ylidene)-3-(3-(1-(4-(trifluoromethoxy)phenyl)-1H-1,2,4-triazol-3-yl)phenethyl)urea (P76)

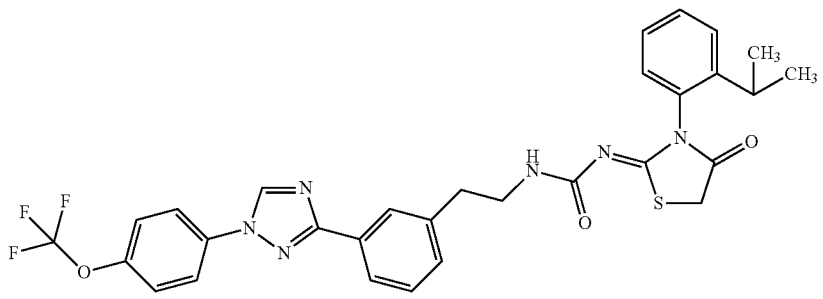 [SMILES: CC(C)c1ccccc1N1C(=O)CS/C1=N\C(=O)NCCc1cccc(-c2ncn(-c3ccc(OC(F)(F)F)cc3)n2)c1]

The title compound was prepared as described in Example 64 using 1-[(2-isopropylphenyl)carbamothioyl]-3-[2-[3-[1-[4-(trifluoromethoxy)phenyl]-1H-1,2,4-triazol-3-yl]phenyl]ethyl]urea (PC76) and isolated as a white solid (0.026 g, 72%).

Preparation of (Z)-1-(3-(2-isopropyl-4-methylphenyl)-4-oxothiazolidin-2-ylidene)-3-(3-(1-(4-(trifluoromethoxy)phenyl)-1H-1,2,4-triazol-3-yl)phenethyl)urea (P84)

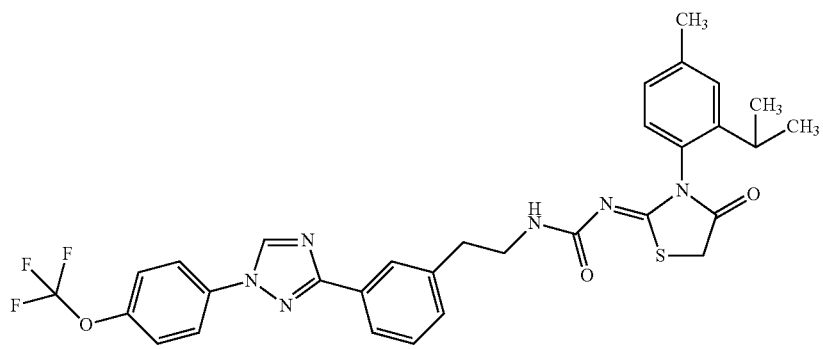 [SMILES: Cc1ccc(N2C(=O)CS/C2=N\C(=O)NCCc2cccc(-c3ncn(-c4ccc(OC(F)(F)F)cc4)n3)c2)c(C(C)C)c1]

The title compound was prepared as described in Example 64 using 1-[(2-isopropyl-4-methyl-phenyl)carbamothioyl]-3-[2-[3-[1-[4-(trifluoromethoxy)phenyl]-1H-1,2,4-triazol-3-yl]phenyl]ethyl]urea (PC84) and isolated as a white solid (0.056 g, 77%).

Preparation of (Z)-1-(3-(4-fluoro-2-isopropylphenyl)-4-oxothiazolidin-2-ylidene)-3-(3-(1-(4-(trifluoromethoxy)phenyl)-1H-1,2,4-triazol-3-yl)phenethyl)urea (P85)

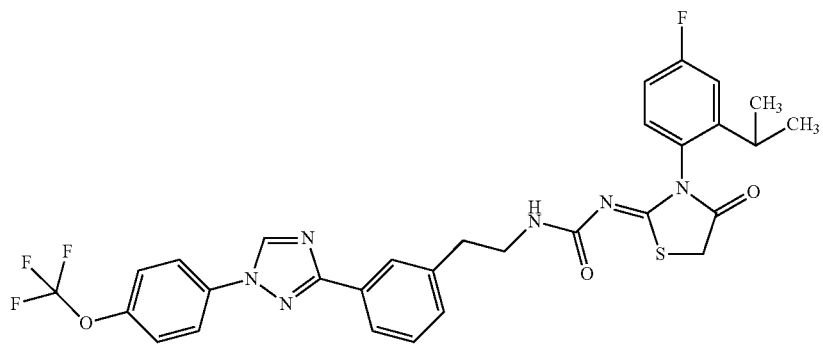

The title compound was prepared as described in Example 64 using 1-[(4-fluoro-2-isopropyl-phenyl)carbamothioyl]-3-[2-[3-[1-[4-(trifluoromethoxy)phenyl]-1H-1,2,4-triazol-3-yl]phenyl]ethyl]urea (PC85) and isolated as a white solid (0.063 g, 77%).

Preparation of (Z)-1-(3-(2-isopropyl-5-methylphenyl)-4-oxothiazolidin-2-ylidene)-3-(3-(1-(4-(trifluoromethoxy)phenyl)-1H-1,2,4-triazol-3-yl)phenethyl)urea (P81)

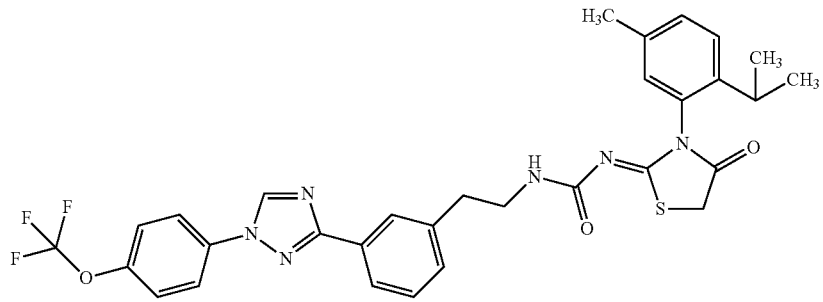 [SMILES: Cc1ccc(C(C)C)c(N2C(=O)CS/C2=N\C(=O)NCCc2cccc(-c3ncn(-c4ccc(OC(F)(F)F)cc4)n3)c2)c1]

The title compound was prepared as described in Example 64 using 1-[(2-isopropyl-5-methyl-phenyl)carbamothioyl]-3-[2-[3-[1-[4-(trifluoromethoxy)phenyl]-1H-1,2,4-triazol-3-yl]phenyl]ethyl]urea (PC81) and isolated as a yellow solid (0.014 g, 68%).

Preparation of (Z)-1-(3-(5-methyl-2-propylphenyl)-4-oxothiazolidin-2-ylidene)-3-(3-(1-(4-(trifluoromethoxy)phenyl)-1H-1,2,4-triazol-3-yl)phenethyl)urea (P80)

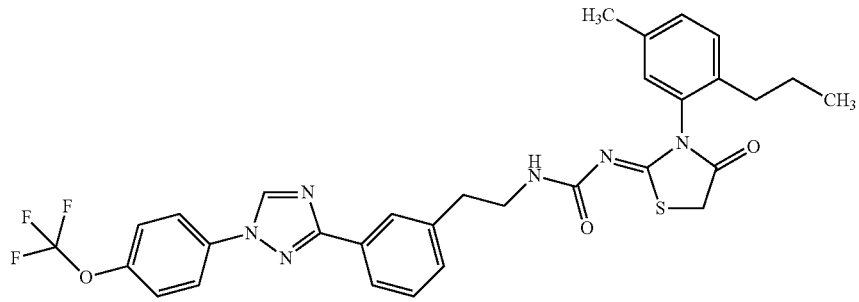 [SMILES: CCCc1ccc(C)cc1N1C(=O)CS/C1=N\C(=O)NCCc1cccc(-c2ncn(-c3ccc(OC(F)(F)F)cc3)n2)c1]

The title compound was prepared as described in Example 64 using 1-[(5-methyl-2-propyl-phenyl)carbamothioyl]-3-[2-[3-[1-[4-(trifluoromethoxy)phenyl]-1H-1,2,4-triazol-3-yl]phenyl]ethyl]urea (PC80) and isolated as a white solid (0.076 g, 74%).

Preparation of (Z)-1-(3-(2-isopropyl-5-methylphenyl)-4-oxothiazolidin-2-ylidene)-3-(2-methyl-4-(1-(4-(trifluoromethoxy)phenyl)-1H-1,2,4-triazol-3-yl)phenethyl)urea (FB3)

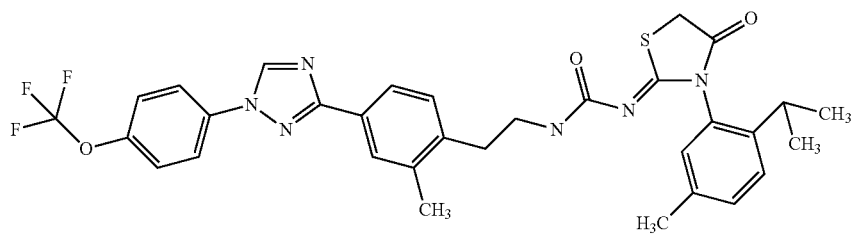 [SMILES: Cc1ccc(C(C)C)c(N2C(=O)CS/C2=N\C(=O)NCCc2ccc(-c3ncn(-c4ccc(OC(F)(F)F)cc4)n3)cc2C)c1]

The title compound was prepared as described in Example 64 using 1-[(2-isopropyl-5-methyl-phenyl)carbamothioyl]-3-[2-[2-methyl-4-[1-[4-(trifluoromethoxy)phenyl]-1H-1,2,4-triazol-3-yl]phenyl]ethyl]urea (F131) at a temperature of 60° C. and followed by reverse phase chromatography; isolated as a yellow wax (0.016 g, 10%).

Preparation of (Z)-1-(3-(2-isopropyl-5-methoxyphenyl)-4-oxothiazolidin-2-ylidene)-3-(2-methyl-4-(1-(4-(trifluoromethoxy)phenyl)-1H-1,2,4-triazol-3-yl)phenethyl)urea (FB4)

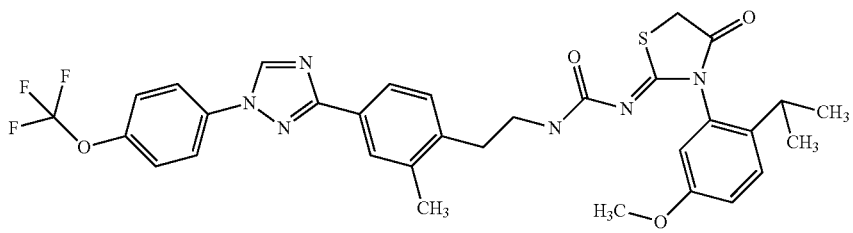 [SMILES: COc1ccc(C(C)C)c(N2C(=O)CS/C2=N\C(=O)NCCc2ccc(-c3ncn(-c4ccc(OC(F)(F)F)cc4)n3)cc2C)c1]

The title compound was prepared as described in Example 64 using 1-[(2-isopropyl-5-methoxy-phenyl)carbamothioyl]-3-[2-[2-methyl-4-[1-[4-(trifluoromethoxy)phenyl]-1H-1,2,4-triazol-3-yl]phenyl]ethyl]urea (FB2) at a temperature of 60° C. and followed by reverse phase chromatography isolated as a light yellow solid (0.034 g, 19%).

Preparation of (Z)-1-(3-(2-ethylphenyl)-4-oxothiazolidin-2-ylidene)-3-(2-methyl-4-(1-(4-(trifluoromethoxy)phenyl)-1H-1,2,4-triazol-3-yl)phenethyl)urea (FB6)

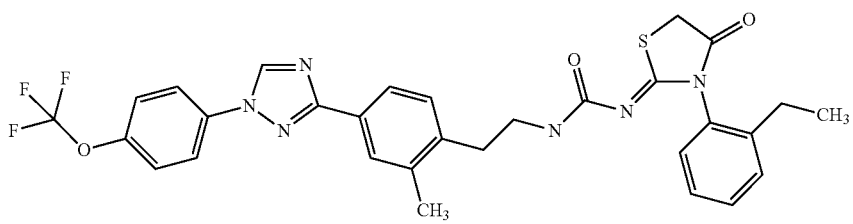 [SMILES: CCc1ccccc1N1C(=O)CS/C1=N\C(=O)NCCc1ccc(-c2ncn(-c3ccc(OC(F)(F)F)cc3)n2)cc1C]

The title compound was prepared as described in Example 64 using 1-[(2-ethylphenyl)carbamothioyl]-3-[2-[2-methyl-4-[1-[4-(trifluoromethoxy)phenyl]-1H-1,2,4-triazol-3-yl]phenyl]ethyl]urea (FB5) at a temperature of 60° C. and followed by reverse phase chromatography; isolated as a pink solid (0.010 g, 7%).

Preparation of (Z)-1-(3-(2,4-dimethylphenyl)-4-oxothiazolidin-2-ylidene)-3-(4-(4-(1-(4-(trifluoromethoxy)phenyl)-1H-1,2,4-triazol-3-yl)phenyl)butyl)urea (FB17)

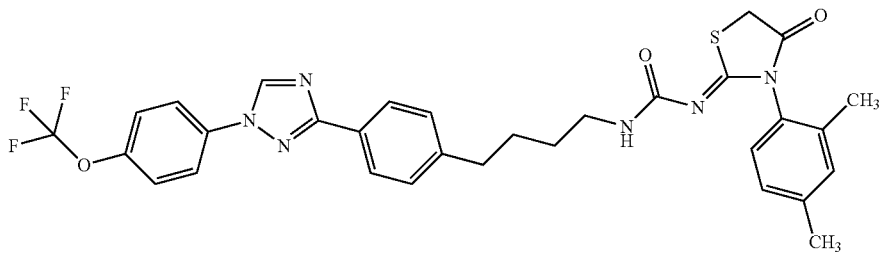 [SMILES: Cc1ccc(N2C(=O)CS/C2=N\C(=O)NCCCCc2ccc(-c3ncn(-c4ccc(OC(F)(F)F)cc4)n3)cc2)c(C)c1]

The title compound was prepared as described in Example 64 using 1-[(2,4-dimethylphenyl)carbamothioyl]-3-[4-[4-[1-[4-(trifluoromethoxy)phenyl]-1H-1,2,4-triazol-3-yl]phenyl]butyl]urea (FB16) and isolated as a white foam (0.078 g, 83%).

Preparation of (Z)-1-(4-oxo-3-(o-tolyl)thiazolidin-2-ylidene)-3-(3-(1-(4-(trifluoromethoxy)phenyl)-1H-1,2,4-triazol-3-yl)benzyl)urea (FB27)

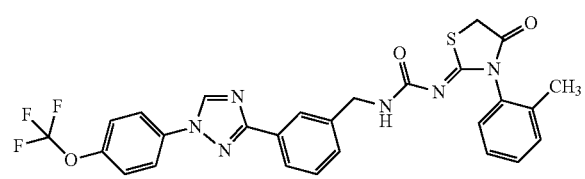 [SMILES: Cc1ccccc1N1C(=O)CS/C1=N\C(=O)NCc1cccc(-c2ncn(-c3ccc(OC(F)(F)F)cc3)n2)c1]

The title compound was prepared as described in Example 64 using 1-(o-tolylcarbamothioyl)-3-[[3-[1-[4-(trifluoromethoxy)phenyl]-1H-1,2,4-triazol-3-yl]phenyl]methyl]urea (FB18) and isolated as an off-white solid (0.090 g, 68%).

Preparation of (Z)-1-(3-(4-methoxy-2-methylphenyl)-4-oxothiazolidin-2-ylidene)-3-(3-(1-(4-(trifluoromethoxy)phenyl)-1H-1,2,4-triazol-3-yl)benzyl)urea (FB28)

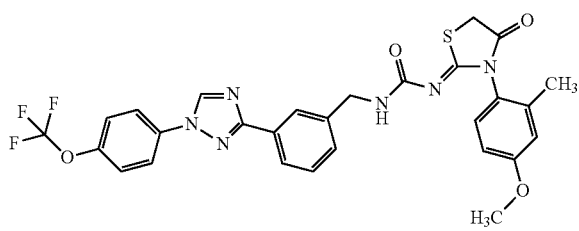 [SMILES: COc1ccc(N2C(=O)CS/C2=N\C(=O)NCc2cccc(-c3ncn(-c4ccc(OC(F)(F)F)cc4)n3)c2)c(C)c1]

The title compound was prepared as described in Example 64 using 1-[(4-methoxy-2-methyl-phenyl)carbamothioyl]-3-[[3-[1-[4-(trifluoromethoxy)phenyl]-1H-1,2,4-triazol-3-yl]phenyl]methyl]urea (FB19) and isolated as a light orange solid (0.042 g, 88%).

Preparation of (Z)-1-(3-(2-ethylphenyl)-4-oxothiazolidin-2-ylidene)-3-(3-(1-(4-(trifluoromethoxy)phenyl)-1H-1,2,4-triazol-3-yl)benzyl)urea (FB29)

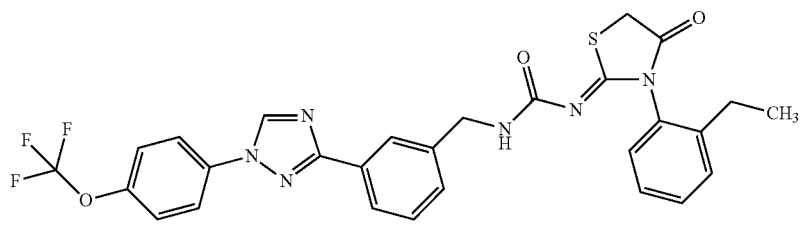 [SMILES: CCc1ccccc1N1C(=O)CS/C1=N\C(=O)NCc1cccc(-c2ncn(-c3ccc(OC(F)(F)F)cc3)n2)c1]

The title compound was prepared as described in Example 64 using 1-[(2-ethylphenyl)carbamothioyl]-3-[[3-[1-[4-(trifluoromethoxy)phenyl]-1H-1,2,4-triazol-3-yl]phenyl]methyl]urea (FB20) and isolated as a white solid (0.078 g, 57%).

Preparation of (Z)-1-(3-(2-ethyl-6-methylphenyl)-4-oxothiazolidin-2-ylidene)-3-(3-(1-(4-(trifluoromethoxy)phenyl)-1H-1,2,4-triazol-3-yl)benzyl)urea (FB30)

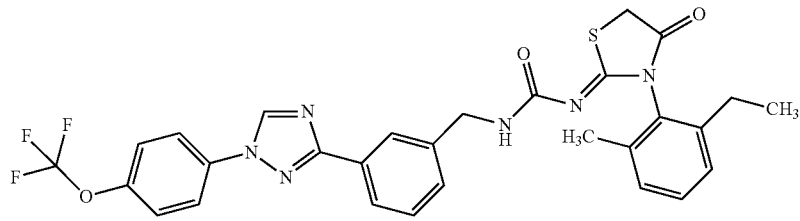 [SMILES: CCc1cccc(C)c1N1C(=O)CS/C1=N\C(=O)NCc1cccc(-c2ncn(-c3ccc(OC(F)(F)F)cc3)n2)c1]

The title compound was prepared as described in Example 64 using 1-[(2-ethyl-6-methyl-phenyl)carbamothioyl]-3-[[3-[1-[4-(trifluoromethoxy)phenyl]-1H-1,2,4-triazol-3-yl]phenyl]methyl]urea (FA21) and isolated as a white solid (0.035 g, 17%).

Preparation of (Z)-1-(3-(2-isopropylphenyl)-4-oxothiazolidin-2-ylidene)-3-(3-(1-(4-(trifluoromethoxy)phenyl)-1H-1,2,4-triazol-3-yl)benzyl)urea (FB31)

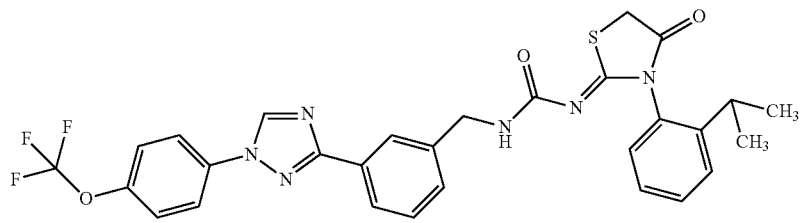 [SMILES: CC(C)c1ccccc1N1C(=O)CS/C1=N\C(=O)NCc1cccc(-c2ncn(-c3ccc(OC(F)(F)F)cc3)n2)c1]

The title compound was prepared as described in Example 64 using 1-[(2-isopropylphenyl)carbamothioyl]-3-[[3-[1-[4-(trifluoromethoxy)phenyl]-1H-1,2,4-triazol-3-yl]phenyl]methyl]urea (FA22) and isolated as a light yellow solid (0.115 g, 57%).

Preparation of (Z)-1-(3-(2-isopropyl-4-methylphenyl)-4-oxothiazolidin-2-ylidene)-3-(3-(1-(4-(trifluoromethoxy)phenyl)-1H-1,2,4-triazol-3-yl)benzyl)urea (FB32)

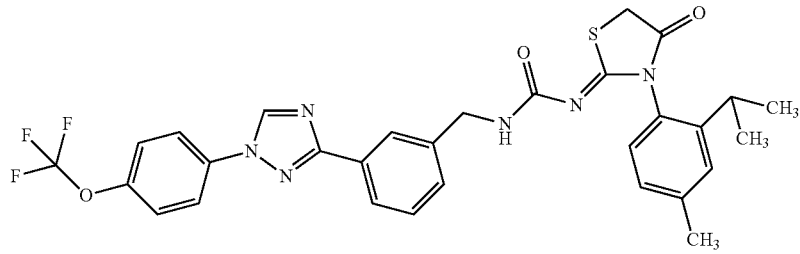 [SMILES: Cc1ccc(N2C(=O)CS/C2=N\C(=O)NCc2cccc(-c3ncn(-c4ccc(OC(F)(F)F)cc4)n3)c2)c(C(C)C)c1]

The title compound was prepared as described in Example 64 using 1-[(2-isopropyl-4-methyl-phenyl)carbamothioyl]-3-[[3-[1-[4-(trifluoromethoxy)phenyl]-1H-1,2,4-triazol-3-yl]phenyl]methyl]urea (FB23) and isolated as a light orange solid (0.144 g, 70%).

Preparation of (Z)-1-(3-(4-fluoro-2-isopropylphenyl)-4-oxothiazolidin-2-ylidene)-3-(3-(1-(4-(trifluoromethoxy)phenyl)-1H-1,2,4-triazol-3-yl)benzyl) urea (FB33)

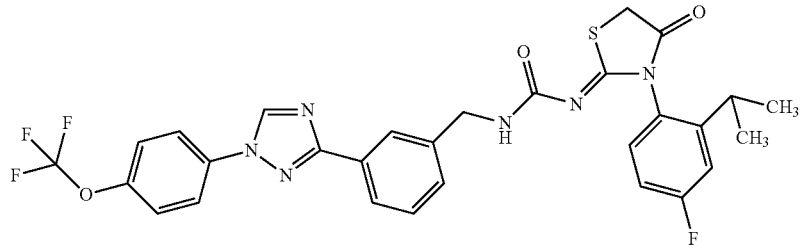 [SMILES: CC(C)c1cc(F)ccc1N1C(=O)CS/C1=N\C(=O)NCc1cccc(-c2ncn(-c3ccc(OC(F)(F)F)cc3)n2)c1]

The title compound was prepared as described in Example 64 using 1-[(4-fluoro-2-isopropyl-phenyl)carbamothioyl]-3-[[3-[1-[4-(trifluoromethoxy)phenyl]-1H-1,2,4-triazol-3-yl]phenyl]methyl]urea (FB24) and isolated as an off-white solid (0.097 g, 44%).

Preparation of (Z)-1-(3-(2-isopropyl-5-methylphenyl)-4-oxothiazolidin-2-ylidene)-3-(3-(1-(4-(trifluoromethoxy)phenyl)-1H-1,2,4-triazol-3-yl)benzyl) urea (FB34)

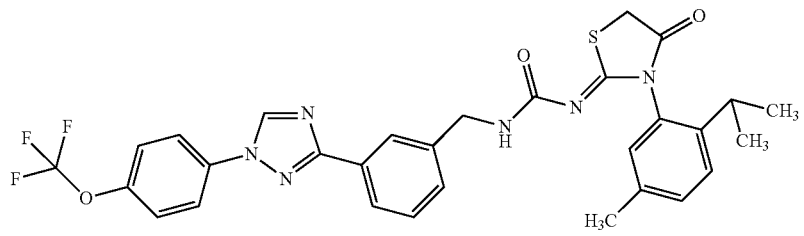 [SMILES: Cc1ccc(C(C)C)c(N2C(=O)CS/C2=N\C(=O)NCc2cccc(-c3ncn(-c4ccc(OC(F)(F)F)cc4)n3)c2)c1]

The title compound was prepared as described in Example 64 using 1-[(2-isopropyl-5-methyl-phenyl)carbamothioyl]-3-[[3-[1-[4-(trifluoromethoxy)phenyl]-1H-1,2,4-triazol-3-yl]phenyl]methyl]urea (FB25) and isolated as an off-white solid (0.091 g, 56%).

Preparation of (Z)-1-(3-(5-chloro-2-isopropylphenyl)-4-oxothiazolidin-2-ylidene)-3-(3-(1-(4-(trifluoromethoxy)phenyl)-1H-1,2,4-triazol-3-yl)benzyl) urea (FB35)


The title compound was prepared as described in Example 64 using 1-[(5-chloro-2-isopropyl-phenyl)carbamothioyl]-3-[[3-[1-[4-(trifluoromethoxy)phenyl]-1H-1,2,4-triazol-3-yl]phenyl]methyl]urea (FB26) and isolated as a light yellow solid (0.095 g, 62%).

Preparation of (Z)-1-(3-(4-methoxy-2-methylphenyl)-4-oxothiazolidin-2-ylidene)-3-(4-(3-(1-(4-(trifluoromethoxy)phenyl)-1H-1,2,4-triazol-3-yl)phenyl)butyl)urea (FB38)

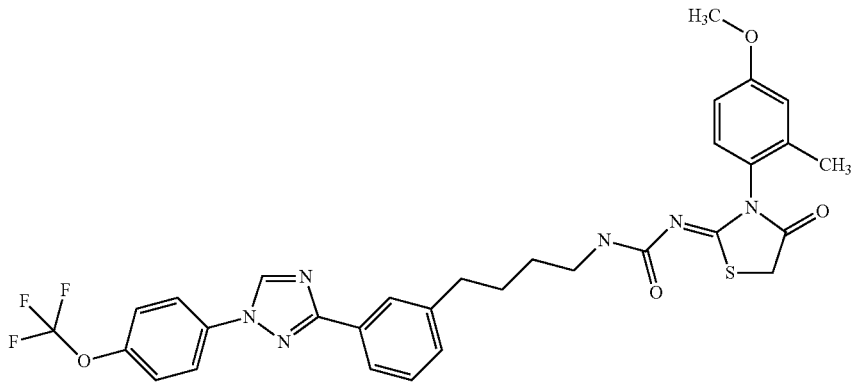 [SMILES: COc1ccc(N2C(=O)CS/C2=N\C(=O)NCCCCc2cccc(-c3ncn(-c4ccc(OC(F)(F)F)cc4)n3)c2)c(C)c1]

The title compound was prepared as described in Example 64 using 1-[(4-methoxy-2-methyl-phenyl)carbamothioyl]-3-[4-[3-[1-[4-(trifluoromethoxy)phenyl]-1H-1,2,4-triazol-3-yl]phenyl]butyl]urea (FB36) and isolated as a white solid (0.048 g, 67%).

Preparation of (Z)-1-(3-(5-chloro-2-isopropylphenyl)-4-oxothiazolidin-2-ylidene)-3-(4-(3-(1-(4-(trifluoromethoxy)phenyl)-1H-1,2,4-triazol-3-yl)phenyl)butyl)urea (FB39)

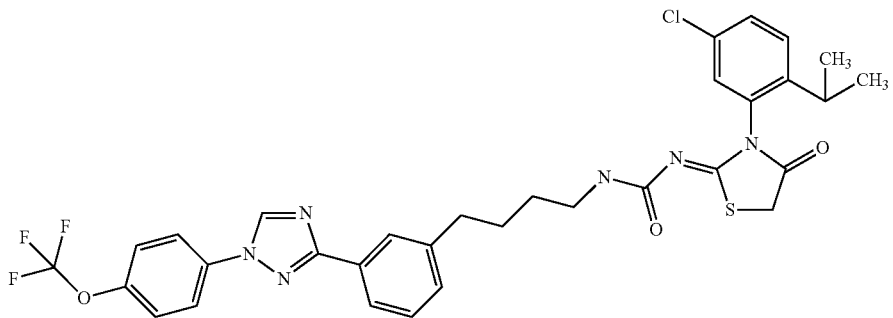 [SMILES: CC(C)c1ccc(Cl)cc1N1C(=O)CS/C1=N\C(=O)NCCCCc1cccc(-c2ncn(-c3ccc(OC(F)(F)F)cc3)n2)c1]

The title compound was prepared as described in Example 64 using 1-[(5-chloro-2-isopropyl-phenyl)carbamothioyl]-3-[4-[3-[1-[4-(trifluoromethoxy)phenyl]-1H-1,2,4-triazol-3-yl]phenyl]butyl]urea (FB37) and isolated as a white solid (0.060 g, 58%).

Example 65

Preparation of 4-(4-(1-(4-(trifluoromethyl)phenyl)-1H-1,2,4-triazol-3-yl)phenyl)but-3-yn-1-ol (C61)

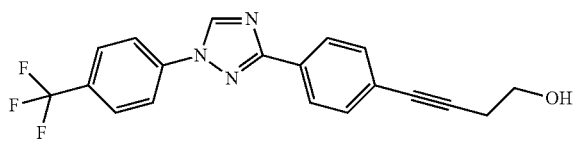

To 3-(4-bromophenyl)-1-(4-(trifluoromethyl)phenyl)-1H-1,2,4-triazole (C53) (0.50 g, 1.4 mmol) in a 25 mL vial equipped with a stir bar and cap with septa was added bis(triphenylphosphine)palladium(II) chloride (0.019 g, 0.027 mmol), copper(I) iodide (0.0026 g, 0.014 mmol) and triethylamine (8.5 mL) followed by but-3-yn-1-ol (0.12 mL, 1.6 mmol). The reaction was heated to 60° C. overnight. The reaction was stopped and cooled to room temperature. The reaction mixture was treated with 50% ethyl acetate/water. The aqueous layer was extracted with ethyl acetate. The combined organic layers were washed with water. The organic layer was dried over sodium sulfate, filtered, and concentrated. Purification by flash column chromatography using 0-50% ethyl acetate/B, where B=1:1 dichloromethane/hexanes, as eluent provided a solid which was dried overnight at 50° C. in vacuo to afford the title compound as a tan solid. It was calculated based on $^1$H NMR to be mixed with the starting butynol (8%), (0.38 g, 71%): $^1$H NMR (400 MHz, CDCl$_3$) δ 8.66 (s, 1H), 8.20-8.11 (m, 2H), 7.94-7.88 (m, 2H), 7.83-7.76 (m, 2H), 7.56-7.50 (m, 2H), 3.85 (q, J=6.3 Hz, 2H), 2.74 (t, J=6.2 Hz, 2H), 1.83 (t, J=6.3 Hz, 1H); $^{19}$F NMR (376 MHz, CDCl$_3$) δ −62.51; ESIMS m/z 358 ([M+H]$^+$).

The following compounds were prepared in accordance to the procedure in Example 65.

Preparation of 4-(4-(1-(4-(trifluoromethoxy)phenyl)-1H-1,2,4-triazol-3-yl)phenyl)but-3-yn-1-ol (CA23)

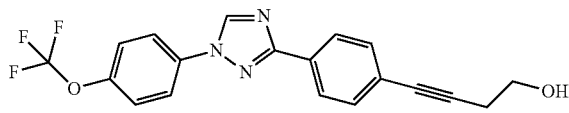 [SMILES: OCCC#Cc1ccc(-c2ncn(-c3ccc(OC(F)(F)F)cc3)n2)cc1]

The title compound was prepared as described in Example 65 using 3-(4-bromophenyl)-1-(4-(trifluoromethoxy)phenyl)-1H-1,2,4-triazole (C52), further purified by trituration with diethyl ether/hexanes and isolated as a white solid (5.46 g, 66%): $^1$H NMR (400 MHz, CDCl$_3$) δ 8.57 (s, 1H), 8.19-8.08 (m, 2H), 7.84-7.76 (m, 2H), 7.57-7.49 (m, 2H), 7.39 (dq, J=8.8, 0.9 Hz, 2H), 3.85 (q, J=6.3 Hz, 2H), 2.73 (t, J=6.3 Hz, 2H), 1.83 (t, J=6.3 Hz, 1H); $^{19}$F NMR (376 MHz, CDCl$_3$) δ −58.02; ESIMS m/z 374 ([M+H]$^+$).

Example 66

Preparation of 4-(4-(1-(4-(trifluoromethyl)phenyl)-1H-1,2,4-triazol-3-yl)phenyl)butan-1-ol (CA24)

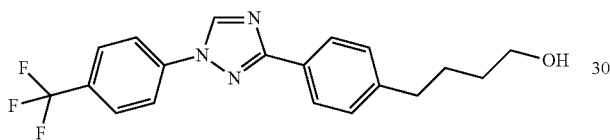

To 4-(4-(1-(4-(trifluoromethyl)phenyl)-1H-1,2,4-triazol-3-yl)phenyl)but-3-yn-1-ol (C61) (0.376 g, 0.967 mmol) in a 100 mL round bottomed flask equipped with a stir bar and septa was added ethyl acetate (9.67 mL) followed by palladium on carbon (0.103 g, 0.0970 mmol). The reaction mixture was evacuated with vacuum and purged with hydrogen (balloon) (2×) and stirred at room temperature overnight. The reaction mixture was filtered through Celite®, washed with ethyl acetate and concentrated to provide the title compound as a white solid (0.363 g, 104%): $^1$H NMR (400 MHz, CDCl$_3$) δ 8.65 (s, 1H), 8.15-8.08 (m, 2H), 7.94-7.88 (m, 2H), 7.80 (dd, J=8.2, 1.1 Hz, 2H), 7.34-7.28 (m, 2H), 3.74-3.66 (m, 2H), 3.66-3.60 (m, 1H), 2.72 (t, J=7.6 Hz, 2H), 1.81-1.71 (m, 2H), 1.69-1.60 (m, 2H); $^{19}$F NMR (376 MHz, CDCl$_3$) δ −62.48; ESIMS m/z 362 ([M+H]$^+$).

The following compounds were prepared in accordance to the procedure in Example 66.

Preparation of 4-(4-(1-(4-(trifluoromethoxy)phenyl)-1H-1,2,4-triazol-3-yl)phenyl)butan-1-ol (CA25)

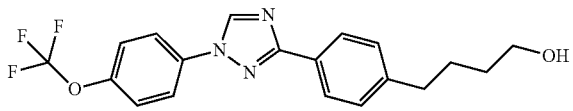 [SMILES: OCCCCc1ccc(-c2ncn(-c3ccc(OC(F)(F)F)cc3)n2)cc1]

The title compound was prepared as described in Example 66 using 4-(4-(1-(4-(trifluoromethoxy)phenyl)-1H-1,2,4-triazol-3-yl)phenyl)but-3-yn-1-ol (CA23) and isolated as a white solid (3.03 g, 100%): $^1$H NMR (400 MHz, CDCl$_3$) δ 8.55 (s, 1H), 8.10 (d, J=8.2 Hz, 2H), 7.86-7.76 (m, 2H), 7.39 (dq, J=9.0, 0.9 Hz, 2H), 7.33-7.27 (m, 2H), 3.73-3.59 (m, 3H), 2.72 (t, J=7.6 Hz, 2H), 1.82-1.70 (m, 2H), 1.70-1.59 (m, 2H); $^{19}$F NMR (376 MHz, CDCl$_3$) δ −58.03; ESIMS m/z 378 ([M+H]$^+$).

Preparation of 5-methyl-2-propylaniline (CA26)

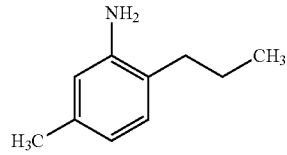

The title compound was prepared as described in Example 66 using 1-allyl-4-methyl-2-nitrobenzene (CA30) and isolated as a yellow liquid (1.39 g, 93%): $^1$H NMR (400 MHz, CDCl$_3$) δ 6.92 (d, J=7.6 Hz, 1H), 6.55 (d, J=7.6 Hz, 1H), 6.51 (s, 1H), 3.55 (s, 2H), 2.47-2.37 (m, 2H), 2.24 (s, 3H), 1.69-1.53 (m, 2H), 0.99 (t, J=7.3 Hz, 3H); $^{13}$C NMR (101 MHz, CDCl$_3$) δ 143.91, 136.52, 129.46, 123.83, 119.49, 116.29, 33.05, 22.10, 21.05, 14.19; EIMS m/z 149 ([M]$^+$).

Preparation of 2-isopropyl-5-methoxyaniline (CA27)

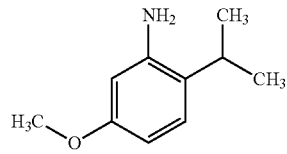

The title compound was prepared as described in Example 66 using 4-methoxy-2-nitro-1-(prop-1-en-2-yl)benzene (CA43) and isolated as a yellow liquid (2.23 g, 95%): $^1$H NMR (400 MHz, CDCl$_3$) δ 7.03 (d, J=8.4 Hz, 1H), 6.35 (dd, J=8.5, 2.6 Hz, 1H), 6.25 (d, J=2.6 Hz, 1H), 3.75 (s, 3H), 3.65 (s, 2H), 2.83 (p, J=6.8 Hz, 1H), 1.24 (d, J=6.8 Hz, 6H); EIMS m/z 165 ([M]$^+$).

Preparation of 2-ethyl-5-methylaniline (CA28)

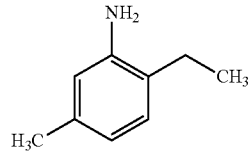

The title compound was prepared as described in Example 66 using 4-methyl-2-nitro-1-vinylbenzene (CA31) and isolated as a yellow liquid (0.926 g, 88%): $^1$H NMR (400 MHz, CDCl$_3$) δ 6.95 (d, J=7.6 Hz, 1H), 6.57 (d, J=7.6 Hz, 1H), 6.52 (s, 1H), 3.56 (s, 2H), 2.48 (q, J=7.5 Hz, 2H), 2.25 (s, 3H), 1.23 (t, J=7.6 Hz, 3H); $^{13}$C NMR (101 MHz, CDCl$_3$) δ 143.80, 136.48, 128.32, 125.22, 119.59, 116.15, 23.67, 21.03, 13.24; EIMS m/z 135 ([M]$^+$).

227

Preparation of 2-ethyl-4-methylaniline (CA29)

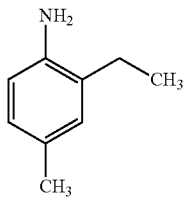

The title compound was prepared as described in Example 66 using 5-methyl-2-nitro-1-vinylbenzene (CA32) and isolated as a brown liquid (1.07 g, 88%): $^1$H NMR (400 MHz, CDCl$_3$) δ 6.88 (s, 1H), 6.86-6.82 (m, 1H), 6.60 (d, J=7.9 Hz, 1H), 3.55 (s, 2H), 2.50 (q, J=7.5 Hz, 2H), 2.24 (s, 3H), 1.24 (t, J=7.5 Hz, 3H); $^{13}$C NMR (101 MHz, CDCl$_3$) δ 141.35, 129.09, 128.25, 128.01, 127.19, 115.56, 24.05, 20.55, 13.17; EIMS m/z 135 ([M]$^+$).

Preparation of 5-chloro-2-isopropylaniline (CB27)

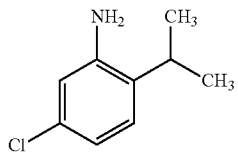

The title compound was prepared as described in Example 66 using 4-chloro-2-nitro-1-(prop-1-en-2-yl)benzene (CB33) and isolated as a brown liquid (1.82 g, 84%): $^1$H NMR (400 MHz, CDCl$_3$) δ 7.38-7.31 (m, 1H), 7.22-7.16 (m, 1H), 7.07 (d, J=8.1 Hz, 1H), 6.83-6.77 (m, 2H), 2.90 (p, J=6.8 Hz, 1H), 1.25 (d, J=6.8 Hz, 6H); $^{13}$C NMR (101 MHz, CDCl$_3$) δ 126.91, 126.83, 126.51, 121.34, 120.07, 116.37, 27.44, 22.34; EIMS m/z 169 ([M]$^+$).

Preparation of 2-methyl-1-(4-(1-(4-(trifluoromethoxy)phenyl)-1H-1,2,4-triazol-3-yl)phenyl)propan-2-amine (CB28)

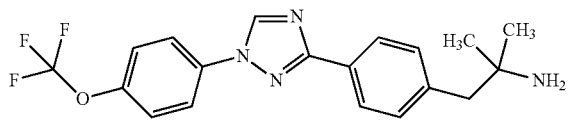

The title compound was prepared as described in Example 66 using benzyl (2-methyl-1-(4-(1-(4-(trifluoromethoxy)phenyl)-1H-1,2,4-triazol-3-yl)phenyl)propan-2-yl)carbamate (CB67) and methanol as solvent; isolated as a yellow gum (0.775 g, 92%): $^1$H NMR (400 MHz, CDCl$_3$) δ 8.57 (s, 1H), 8.13 (d, J=8.2 Hz, 2H), 7.81 (d, J=9.0 Hz, 2H), 7.39 (dd, J=9.1, 1.0 Hz, 2H), 7.31 (d, J=8.2 Hz, 2H), 2.74 (s, 2H), 2.05 (s, 2H), 1.16 (s, 6H); $^{19}$F NMR (376 MHz, CDCl$_3$) δ −58.03; ESIMS m/z 377 ([M+H]$^+$).

228

Preparation of 2-methyl-2-(4-(1-(4-(trifluoromethoxy)phenyl)-1H-1,2,4-triazol-3-yl)phenyl)propan-1-amine (CB29)

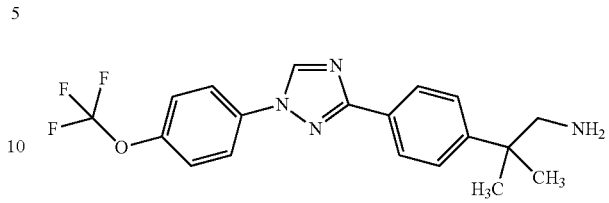

The title compound was prepared as described in Example 66 using benzyl (2-methyl-2-(4-(1-(4-(trifluoromethoxy)phenyl)-1H-1,2,4-triazol-3-yl)phenyl)propyl)carbamate (CB68) and methanol as solvent; isolated as a clear oil (0.427 g, 80%): $^1$H NMR (400 MHz, CDCl$_3$) δ 8.57 (s, 1H), 8.15 (d, J=8.4 Hz, 2H), 7.84-7.77 (m, 2H), 7.49-7.42 (m, 2H), 7.39 (dt, J=7.9, 1.0 Hz, 2H), 2.85 (s, 2H), 1.78 (s, 2H), 1.36 (s, 6H); $^{19}$F NMR (376 MHz, CDCl$_3$) δ −58.03; ESIMS m/z 377 ([M+H]$^+$).

Preparation of 1-(4-(1-(4-(trifluoromethoxy)phenyl)-1H-1,2,4-triazol-3-yl)benzyl)cyclopropanamine (CB30)

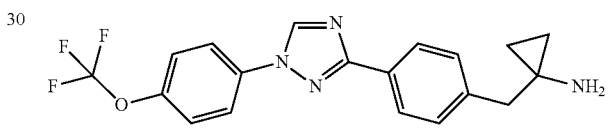

The title compound was prepared as described in Example 66 using benzyl (1-(4-(1-(4-(trifluoromethoxy)phenyl)-1H-1,2,4-triazol-3-yl)benzyl)cyclopropyl)carbamate (CB69) and isolated as a tan oil (0.392 g, 95%): $^1$H NMR (400 MHz, CDCl$_3$) δ 8.60-8.49 (m, 1H), 8.19-8.06 (m, 2H), 7.84-7.72 (m, 2H), 7.44-7.29 (m, 4H), 3.49 (s, 2H), 2.17 (s, 3H), 0.73-0.59 (m, 4H); $^{19}$F NMR (376 MHz, CDCl$_3$) δ −58.03; ESIMS m/z 375 ([M+H]$^+$).

Example 67

Preparation of 1-allyl-4-methyl-2-nitrobenzene (CA30)

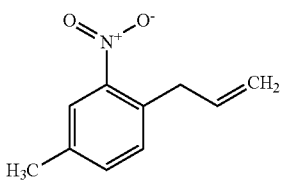

To 1-chloro-4-methyl-2-nitrobenzene (2.00 g, 11.7 mmol), allyltributylstannane (5.79 g, 17.5 mmol) and bis(triphenylphosphine)palladium(II) dichloride (0.818 g, 1.17 mmol) in two 25-mL reaction vials was added 1,2-dichloroethane (20 mL). The vials were capped and heated at 120° C. for 45 minutes in a Biotage Initiator® microwave reactor with an external IR-sensor temperature monitoring from the side of the vessel. The reaction mixture was loaded onto a Celite® cartridge. The crude material was purified by flash column chromatography using 0-50% ethyl acetate/hexanes as eluent followed by reverse-phase flash column chromatography using 0-100% acetonitrile/water as eluent. The combined acetonitrile/water fractions were concentrated, extracted with ethyl acetate, dried over sodium sulfate, filtered, concentrated, and dried in a vacuum oven to provide the title compound as a yellow liquid (1.76 g, 84%): $^1$H NMR (400 MHz, CDCl$_3$) δ 7.73 (d, J=0.9 Hz, 1H), 7.34 (dd, J=7.8, 1.2 Hz, 1H), 7.24 (d, J=7.8 Hz, 1H), 5.96 (ddt, J=16.6, 10.1, 6.4 Hz, 1H), 5.08 (ddq, J=18.5, 17.0, 1.5 Hz, 2H), 3.64 (d, J=6.4 Hz, 2H), 2.40 (s, 3H); $^{13}$C NMR (101 MHz, CDCl$_3$) δ 149.09, 137.62, 135.35, 133.81, 131.81, 131.72, 124.94, 116.81, 36.62, 20.72; EIMS m/z 176 ([M]$^+$).

The following compounds were prepared in accordance to the procedure in Example 67.

Preparation of 4-methyl-2-nitro-1-vinylbenzene (CA31)

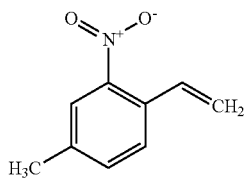

The title compound was prepared as described in Example 67 using 1-chloro-4-methyl-2-nitrobenzene and tributyl(vinyl)stannane, further purified by flash column chromatography and reverse phase chromatography and isolated as a yellow liquid (1.26 g, 65%): $^1$H NMR (400 MHz, CDCl$_3$) δ 7.73 (d, J=0.8 Hz, 1H), 7.52 (d, J=8.0 Hz, 1H), 7.46-7.35 (m, 1H), 7.13 (dd, J=17.3, 11.0 Hz, 1H), 5.71 (dd, J=17.3, 0.9 Hz, 1H), 5.43 (dd, J=11.0, 0.9 Hz, 1H), 2.42 (s, 3H); $^{13}$C NMR (101 MHz, CDCl$_3$) δ 147.71, 138.91, 133.92, 132.31, 130.52, 128.22, 124.63, 118.10, 20.88; EIMS m/z 163 ([M]$^+$).

Preparation of 5-methyl-2-nitro-1-vinylbenzene (CA32)

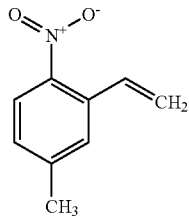

The title compound was prepared as described in Example 67 using 1-chloro-4-methyl-2-nitrobenzene and tributyl(vinyl)stannane, further purified by flash column chromatography and reverse phase chromatography and isolated as a yellow liquid (1.46 g, 75%): $^1$H NMR (400 MHz, CDCl$_3$) δ 7.88 (d, J=8.3 Hz, 1H), 7.40 (d, J=1.2 Hz, 1H), 7.21 (ddd, J=11.0, 9.9, 8.2 Hz, 2H), 5.71 (dd, J=17.3, 1.0 Hz, 1H), 5.46 (dd, J=11.0, 1.0 Hz, 1H), 2.44 (s, 3H); $^{13}$C NMR (101 MHz, CDCl$_3$) δ 145.56, 144.31, 133.64, 133.05, 129.08, 128.98, 124.68, 118.52, 21.49; EIMS m/z 163 ([M]$^+$).

Example 68

Preparation of N-((5-methyl-2-propylphenyl)carbamothioyl)benzamide (CA33)

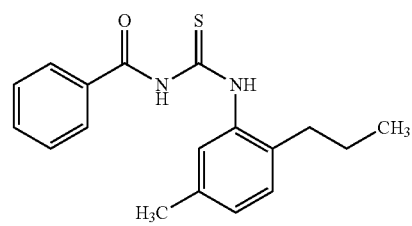 [SMILES: CCCc1ccc(C)cc1NC(=S)NC(=O)c1ccccc1]

To 5-methyl-2-propylaniline (CA26) (1.38 g, 9.22 mmol) and benzoyl isothiocyanate (1.24 mL, 9.22 mmol) was added acetone (13 mL). The reaction was heated at 60° C. for 4 h. The reaction was cooled and concentrated. The resulting oil was dried in a vacuum oven overnight providing the title compound as a brown oil (3.26 g, 100%): $^1$H NMR (400 MHz, CDCl$_3$) δ 12.20 (s, 1H), 9.15 (s, 1H), 7.92 (dt, J=8.5, 1.7 Hz, 2H), 7.71-7.60 (m, 1H), 7.55 (m, 3H), 7.18 (d, J=7.8 Hz, 1H), 7.09 (dd, J=7.8, 1.1 Hz, 1H), 2.66-2.55 (m, 2H), 2.36 (s, 3H), 1.72-1.57 (m, 2H), 0.97 (t, J=7.3 Hz, 3H); $^{13}$C NMR (101 MHz, CDCl$_3$) δ 179.64, 166.90, 136.22, 135.72, 134.57, 133.74, 131.68, 129.79, 129.22, 128.64, 127.55, 127.24, 33.28, 23.58, 21.01, 13.98; ESIMS m/z 313 ([M+H]$^+$).

The following compounds were prepared in accordance to the procedure in Example 68.

Preparation of N-((2-ethyl-6-methylphenyl)carbamothioyl)benzamide (CA34)

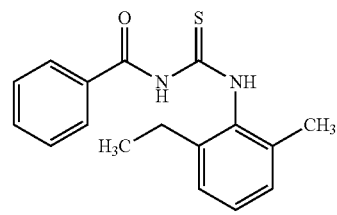 [SMILES: CCc1cccc(C)c1NC(=S)NC(=O)c1ccccc1]

The title compound was prepared as described in Example 68 using 2-ethyl-6-methylaniline and isolated as a yellow liquid (6.41 g, 100%): $^1$H NMR (400 MHz, CDCl$_3$) δ 11.88 (s, 1H), 9.21 (s, 1H), 8.02-7.85 (m, 2H), 7.73-7.63 (m, 1H), 7.62-7.50 (m, 2H), 7.29-7.23 (m, 1H), 7.20-7.14 (m, 2H), 2.75-2.57 (m, 2H), 2.33 (s, 3H), 1.25 (t, J=7.6 Hz, 3H); ESIMS m/z 299 ([M+H]$^+$).

Preparation of N-((2-isopropyl-5-methoxyphenyl)carbamothioyl)benzamide (CA35)

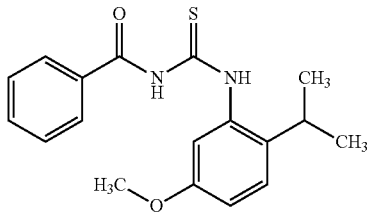 [SMILES: COc1ccc(C(C)C)c(NC(=S)NC(=O)c2ccccc2)c1]

The title compound was prepared as described in Example 68 using 2-isopropyl-5-methoxyaniline (CA27) and isolated as a yellow liquid (4.63 g, 100%): $^1$H NMR (400 MHz, CDCl$_3$) δ 12.23 (s, 1H), 9.13 (s, 1H), 7.98-7.82 (m, 2H), 7.74-7.61 (m, 1H), 7.61-7.51 (m, 2H), 7.32-7.26 (m, 2H), 6.89 (dd, J=8.7, 2.7 Hz, 1H), 3.81 (s, 3H), 3.10 (p, J=6.9 Hz, 1H), 1.26 (d, J=6.8 Hz, 6H); ESIMS m/z 329 ([M+H]$^+$).

Preparation of N-((2-ethyl-5-methylphenyl)carbamothioyl)benzamide (CA36)

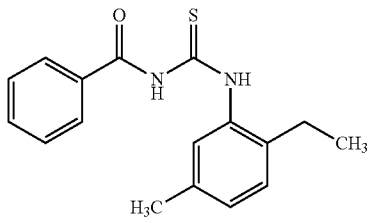 [SMILES: CCc1ccc(C)cc1NC(=S)NC(=O)c1ccccc1]

The title compound was prepared as described in Example 68 using 2-ethyl-5-methylaniline (CA28) and isolated as an orange solid (2.10 g, 97%): mp 105-107° C.; $^1$H NMR (400 MHz, CDCl$_3$) δ 12.18 (s, 1H), 9.14 (s, 1H), 7.92 (dt, J=8.6, 1.7 Hz, 2H), 7.73-7.60 (m, 1H), 7.59-7.53 (m, 2H), 7.50 (s, 1H), 7.21 (d, J=7.8 Hz, 1H), 7.11 (dd, J=7.8, 1.1 Hz, 1H), 2.71-2.59 (m, 2H), 2.37 (s, 3H), 1.24 (t, J=7.6 Hz, 3H); $^{13}$C NMR (101 MHz, CDCl$_3$) δ 179.72, 166.94, 136.22, 136.13, 135.53, 133.75, 131.65, 129.23, 128.88, 128.86, 127.53, 127.23, 24.26, 20.98, 14.56; ESIMS m/z 299 ([M+H]$^+$).

Preparation of N-((2-ethyl-4-methylphenyl)carbamothioyl)benzamide (CA37)

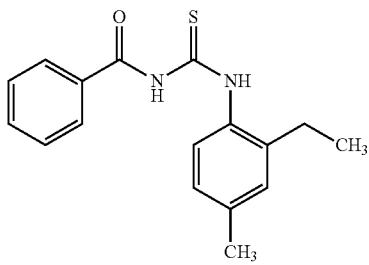 [SMILES: CCc1cc(C)ccc1NC(=S)NC(=O)c1ccccc1]

The title compound was prepared as described in Example 68 using 2-ethyl-4-methylaniline (CA29) and isolated as an orange solid (2.46 g, 100%): mp 103° C. (dec.); $^1$H NMR (400 MHz, CDCl$_3$) δ 12.16 (s, 1H), 9.18 (s, 1H), 7.95-7.86 (m, 2H), 7.68-7.60 (m, 1H), 7.60-7.51 (m, 4H), 7.15-7.05 (m, 2H), 2.66 (q, J=7.6 Hz, 2H), 2.37 (s, 3H), 1.25 (t, J=7.6 Hz, 3H); $^{13}$C NMR (101 MHz, CDCl$_3$) δ 179.89, 166.97, 138.94, 137.88, 133.75, 133.20, 131.67, 129.77, 129.23, 127.55, 127.15, 126.71, 24.63, 21.27, 14.52; ESIMS m/z 299 ([M+H]$^+$).

Preparation of N-((5-chloro-2-isopropylphenyl)carbamothioyl)benzamide (CB31)

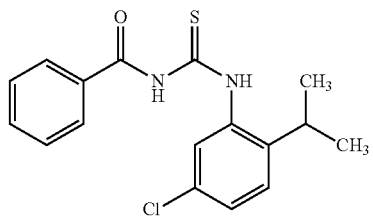 [SMILES: CC(C)c1ccc(Cl)cc1NC(=S)NC(=O)c1ccccc1]

The title compound was prepared as described in Example 68 using 5-chloro-2-isopropylaniline (CB27) followed by purification by flash column chromatography and isolated as a light yellow solid (16.3 g, 98%): $^1$H NMR (400 MHz, DMSO-d$_6$) δ 12.32 (s, 1H), 11.76 (s, 1H), 8.07-7.95 (m, 2H), 7.72-7.63 (m, 1H), 7.60-7.50 (m, 3H), 7.42 (d, J=8.5 Hz, 1H), 7.37 (dd, J=8.5, 2.2 Hz, 1H), 3.08 (hept, J=6.9 Hz, 1H), 1.19 (d, J=6.8 Hz, 6H); $^{13}$C NMR (101 MHz, DMSO) δ 181.12, 168.37, 142.95, 137.03, 133.18, 131.93, 129.67, 128.75, 128.40, 127.61, 127.55, 127.52, 27.63, 22.84; ESIMS m/z 333 ([M+H]$^+$).

Example 69

Preparation of 1-(5-methyl-2-propylphenyl)thiourea (CA38)

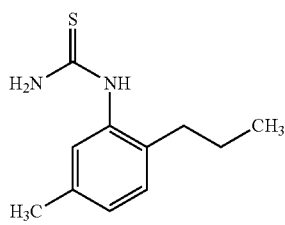

To N-((5-methyl-2-propylphenyl)carbamothioyl)benzamide (C72) (3.21 g, 10.3 mmol) in methanol (80 mL) was added sodium hydroxide (2 N, 10.3 mL, 20.5 mmol) and heated at 50° C. for 2 hours and then stirred at room temperature over the weekend. The reaction was concentrated, diluted with water, extracted with dichloromethane, filtered through a phase separator, concentrated, and dried in a vacuum oven to provide the title compound as a tan solid (1.80 g, 83%): mp 143-145° C.; $^1$H NMR (400 MHz, CDCl$_3$) δ 7.84 (s, 1H), 7.20 (d, J=7.8 Hz, 1H), 7.12 (dd, J=7.8, 1.2 Hz, 1H), 7.04 (s, 1H), 5.99 (d, J=254.5 Hz, 2H), 2.57 (d, J=7.5 Hz, 2H), 2.33 (s, 3H), 1.59 (dq, J=14.8, 7.4 Hz, 2H), 0.95 (t, J=7.3 Hz, 3H); $^{13}$C NMR (101 MHz, CDCl₃) δ 181.96, 137.53, 136.74, 134.00, 130.69, 129.72, 127.85, 32.90, 23.66, 20.80, 13.93; ESIMS m/z 209 ([M+H]$^+$).

The following compounds were prepared in accordance to the procedure in Example 69.

Preparation of 1-(2-ethyl-6-methylphenyl)thiourea (CA39)

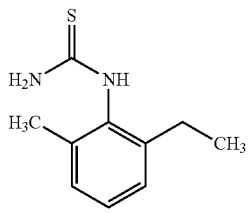

The title compound was prepared as described in Example 69 using N-((2-ethyl-6-methylphenyl)carbamothioyl)benzamide (CA34), further purified by trituration with water and isolated as a white solid (3.46 g, 83%): ¹H NMR (400 MHz, CDCl₃) δ 7.63 (s, 1H), 7.25 (d, J=7.9 Hz, 1H), 7.22-7.11 (m, 2H), 6.13 (bs, 1H), 5.33 (bs, 1H), 2.77-2.55 (m, 2H), 2.31 (s, 3H), 1.21 (t, J=7.6 Hz, 3H); ESIMS m/z 195 ([M+H]$^+$).

Preparation of 1-(2-isopropyl-5-methoxyphenyl)thiourea (CA40)

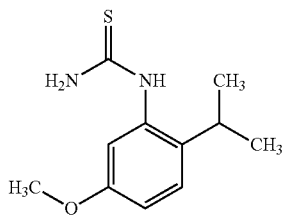

The title compound was prepared as described in Example 69 using N-((2-isopropyl-5-methoxyphenyl)carbamothioyl)benzamide (CA35) and isolated as an orange solid (2.65 g, 83%): mp 134-139° C.; ¹H NMR (400 MHz, CDCl₃) δ 7.60 (s, 1H), 7.30 (d, J=8.7 Hz, 1H), 6.93 (dd, J=8.7, 2.7 Hz, 1H), 6.75 (d, J=2.7 Hz, 1H), 5.88 (s, 2H), 3.79 (s, 3H), 3.10 (p, J=6.9 Hz, 1H), 1.19 (d, J=6.9 Hz, 6H); ESIMS m/z 225 ([M+H]$^+$).

Preparation of 1-(2-ethyl-5-methylphenyl)thiourea (CA41)

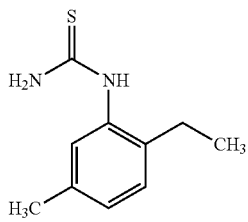

The title compound was prepared as described in Example 69 using N-((2-ethyl-5-methylphenyl)carbamothioyl)benzamide (CA36) and isolated as a pale orange solid (1.26 g, 94%): mp 143-147° C.; ¹H NMR (400 MHz, CDCl₃) δ 7.48 (s, 1H), 7.23 (d, J=7.8 Hz, 1H), 7.14 (d, J=8.0 Hz, 1H), 7.04 (s, 1H), 5.86 (s, 2H), 2.61 (q, J=7.5 Hz, 2H), 2.33 (s, 3H), 1.19 (t, J=7.6 Hz, 3H); ¹³C NMR (101 MHz, CDCl₃) δ 182.13, 138.27, 137.53, 133.74, 129.95, 129.93, 127.84, 24.00, 20.79, 14.77; ESIMS m/z 195 ([M+H]$^+$).

Preparation of 1-(2-ethyl-4-methylphenyl)thiourea (CA42)

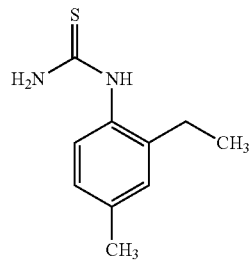

The title compound was prepared as described in Example 69 using N-((2-ethyl-4-methylphenyl)carbamothioyl)benzamide (CA37) and isolated as a tan solid (1.40 g, 86%): mp 153-155° C.; ¹H NMR (400 MHz, CDCl₃) δ 7.60 (s, 1H), 7.14 (d, J=0.5 Hz, 1H), 7.08 (dt, J=8.1, 4.8 Hz, 2H), 5.85 (d, J=184.3 Hz, 2H), 2.62 (q, J=7.6 Hz, 2H), 2.35 (s, 3H), 1.20 (t, J=7.6 Hz, 3H); ¹³C NMR (101 MHz, CDCl₃) δ 182.32, 141.33, 139.33, 131.29, 130.75, 128.15, 127.36, 24.36, 21.18, 14.74; ESIMS m/z 195 ([M+H]$^+$).

Preparation of 1-(5-chloro-2-isopropylphenyl)thiourea (CB32)

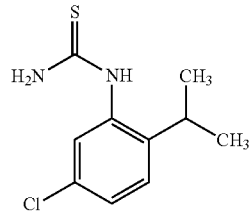

The title compound was prepared as described in Example 69 using N-((5-chloro-2-isopropylphenyl)carbamothioyl)benzamide (CB31) and isolated as a brown sticky gum (1.38 g, 93%): ¹H NMR (400 MHz, CDCl₃) δ 7.96 (s, 1H), 7.34 (d, J=1.4 Hz, 2H), 7.24 (t, J=1.3 Hz, 1H), 5.97 (s, 2H), 3.27-3.10 (m, 1H), 1.21 (d, J=6.8 Hz, 6H); ESIMS m/z 229 ([M+H]$^+$).

Example 70

Preparation of 4-methoxy-2-nitro-1-(prop-1-en-2-yl)benzene (CA43)

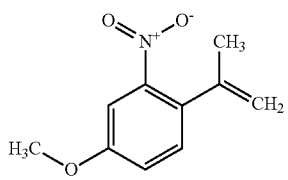

To 1-chloro-4-methoxy-2-nitrobenzene (5.03 g, 26.8 mmol), 4,4,5,5-tetramethyl-2-(prop-1-en-2-yl)-1,3,2-dioxaborolane (5.41 g, 32.2 mmol), bis(triphenylphosphine)palladium(II) chloride (1.50 g, 2.15 mmol), and sodium carbonate (3.41 g, 32.2 mmol) was added dioxane/water (4:1, 100 mL:25 mL). The reaction was heated at 80° C. for 5 hours. The reaction was cooled to room temperature overnight. The reaction mixture was diluted with water, extracted with ethyl acetate (3×), dried over sodium sulfate, filtered, and concentrated. Purification by flash column chromatography using 0-5% ethyl acetate/hexanes as eluent followed by drying in vacuum oven provided the title compound as an orange oil (2.74 g, 53%): $^1$H NMR (400 MHz, CDCl$_3$) δ 7.37 (d, J=2.7 Hz, 1H), 7.23 (d, J=8.6 Hz, 1H), 7.08 (dd, J=8.5, 2.6 Hz, 1H), 5.24-4.75 (m, 2H), 3.86 (s, 3H), 2.19-1.88 (m, 3H); $^{13}$C NMR (101 MHz, CDCl$_3$) δ 158.79, 148.61, 142.53, 131.41, 131.32, 119.24, 115.20, 108.64, 55.84, 23.38; EIMS m/z 193 ([M]$^+$).

The following compounds were prepared in accordance to the procedure in Example 70.

Preparation of 4-chloro-2-nitro-1-(prop-1-en-2-yl)benzene (CB33)

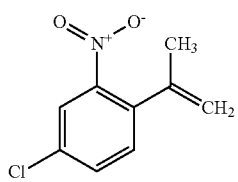

The title compound was prepared as described in Example 70 using 1-bromo-4-chloro-2-nitrobenzene heated overnight and isolated as a light orange liquid (10.73 g, 84%): $^1$H NMR (400 MHz, DMSO-d$_6$) δ 8.04 (d, J=2.2 Hz, 1H), 7.76 (dd, J=8.3, 2.2 Hz, 1H), 7.52 (d, J=8.3 Hz, 1H), 5.24 (p, J=1.5 Hz, 1H), 4.95 (p, J=1.0 Hz, 1H), 2.07 (dd, J=1.5, 0.9 Hz, 3H); $^{13}$C NMR (101 MHz, DMSO) δ 148.37, 140.83, 136.10, 132.62, 132.45, 131.63, 123.50, 115.98, 22.60; EIMS m/z 197 ([M]$^+$).

Example 71

Preparation of 1-[(2-ethylphenyl)carbamothioyl]-3-[[4-[1-[4-(trifluoromethoxy)phenyl]-1H-1,2,4-triazol-3-yl]phenyl]methyl]urea (PC2)

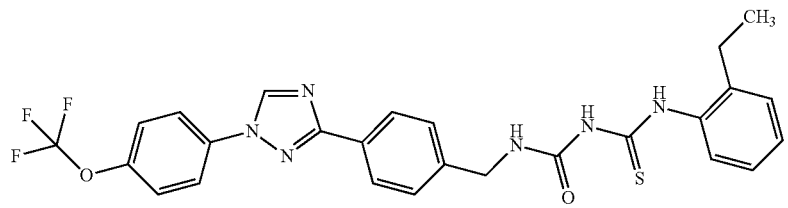 [SMILES: CCc1ccccc1NC(=S)NC(=O)NCc1ccc(-c2ncn(-c3ccc(OC(F)(F)F)cc3)n2)cc1]

A fine suspension of (4-(1-(4-(trifluoromethoxy)phenyl)-1H-1,2,4-triazol-3-yl)phenyl)methanamine (C16) (0.300 g, 0.897 mmol) in dichloromethane (4.0 mL) was added, in a slow dropwise fashion, to a biphasic solution of bis(trichloromethyl) carbonate (0.107 g, 0.359 mmol) and sodium acetate (0.221 g, 2.69 mmol) in dichloromethane (4.0 mL) and water (2.0 mL). The reaction was allowed to stir for 30 minutes. The reaction was passed through a phase separator, washing with additional dichloromethane and the organic layer was concentrated. The resulting residue was diluted with acetonitrile (4.0 mL), and 1-(2-ethylphenyl)thiourea (0.178 g, 0.987 mmol) and cesium carbonate (0.351 g, 1.08 mmol) were added as solids. The reaction was allowed to stir at room temperature overnight. The reaction mixture was diluted with dichloromethane and water and passed through a phase separator. The organic layer was concentrated on to Celite® and purified by reverse phase flash column chromatography (C$_{18}$) using 20-100% acetonitrile/water as eluent providing the title compound as a white solid (0.100 g, 16%) contaminated with ~20% of the dimer urea: $^1$H NMR (400 MHz, DMSO-d$_6$) δ 11.99 (s, 1H), 10.24 (s, 1H), 9.41 (s, 1H), 9.40 (d, J=1.0 Hz, 1H), 8.18-8.03 (m, 6H), 7.63 (dddd, J=9.2, 4.3, 2.0, 1.0 Hz, 3H), 7.54 (ddd, J=12.1, 7.0, 4.8 Hz, 2H), 7.50-7.38 (m, 3H), 7.35-7.26 (m, 1H), 7.26-7.20 (m, 2H), 4.44 (d, J=5.8 Hz, 2H), 2.56 (q, J=7.6 Hz, 2H), 1.14 (t, J=7.6 Hz, 3H); $^{19}$F NMR (376 MHz, DMSO-d$_6$) δ -56.96; ESIMS m/z 541 ([M+H]$^+$), 539 ([M-H]$^-$)

The following compounds were prepared in accordance to the procedure in Example 71.

Preparation of 1-[(4-fluoro-2-isopropyl-phenyl)car-
bamothioyl]-3-[[4-[1-[4-(trifluoromethoxy)phenyl]-
1H-1,2,4-triazol-3-yl]phenyl]methyl]urea (PC3)

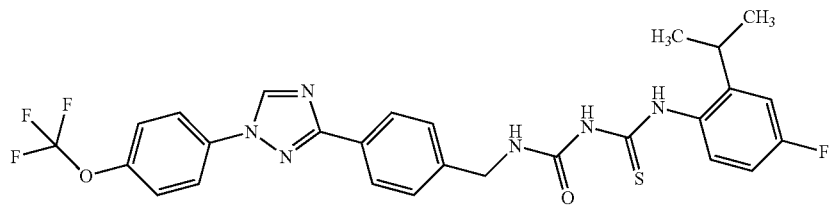 [SMILES: CC(C)c1cc(F)ccc1NC(=S)NC(=O)NCc1ccc(-c2ncn(-c3ccc(OC(F)(F)F)cc3)n2)cc1]

The title compound was prepared as described in Example 71 using (4-(1-(4-(trifluoromethoxy)phenyl)-1H-1,2,4-triazol-3-yl)phenyl)methanamine (C16) and 1-(4-fluoro-2-isopropylphenyl)thiourea and isolated as a white solid (0.157 g, 30%): $^1$H NMR (400 MHz, DMSO-$d_6$) δ 11.81 (s, 1H), 10.26 (s, 1H), 9.41 (s, 1H), 8.15-8.03 (m, 4H), 7.63 (ddt, J=7.8, 1.9, 0.9 Hz, 2H), 7.58-7.44 (m, 3H), 7.39 (dd, J=8.8, 5.6 Hz, 1H), 7.17 (dd, J=10.3, 3.0 Hz, 1H), 7.05 (td, J=8.5, 3.0 Hz, 1H), 4.44 (d, J=5.8 Hz, 2H), 3.05-2.93 (m, 1H), 1.16 (d, J=6.8 Hz, 6H); $^{19}$F NMR (376 MHz, DMSO-$d_6$) δ −56.96, −114.33; ESIMS m/z 573 ([M+H]$^+$), 571 ([M−H]$^-$).

Preparation of 1-[(2-isopropyl-4-methyl-phenyl)
carbamothioyl]-3-[[4-[1-[4-(trifluoromethoxy)phe-
nyl]-1H-1,2,4-triazol-3-yl]phenyl]methyl]urea (PC5)

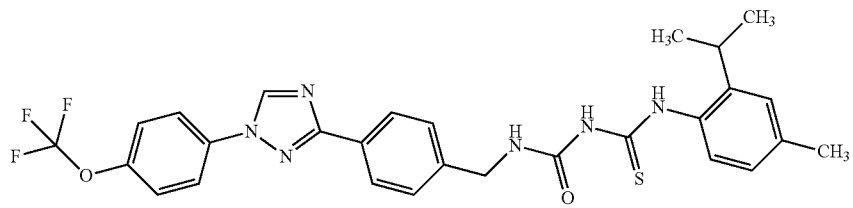 [SMILES: Cc1ccc(NC(=S)NC(=O)NCc2ccc(-c3ncn(-c4ccc(OC(F)(F)F)cc4)n3)cc2)c(C(C)C)c1]

The title compound was prepared as described in Example 71 using (4-(1-(4-(trifluoromethoxy)phenyl)-1H-1,2,4-triazol-3-yl)phenyl)methanamine (C16) and 1-(2-isopropyl-4-methylphenyl)thiourea and isolated as a white solid (0.110 g, 21%): $^1$H NMR (400 MHz, DMSO-$d_6$) δ 11.83 (s, 1H), 10.21 (s, 1H), 9.41 (s, 1H), 8.17-8.05 (m, 4H), 7.63 (dq, J=8.9, 0.9 Hz, 2H), 7.56-7.44 (m, 3H), 7.26 (d, J=8.0 Hz, 1H), 7.15 (d, J=2.0 Hz, 1H), 7.06-6.98 (m, 1H), 4.44 (d, J=5.8 Hz, 2H), 2.97 (hept, J=6.7 Hz, 1H), 2.31 (s, 3H), 1.16 (d, J=6.8 Hz, 6H); $^{19}$F NMR (376 MHz, DMSO-$d_6$) δ −56.96; ESIMS m/z 569 ([M+H]$^+$), 567 ([M−H]$^-$).

Preparation of 1-[(2-ethyl-5-methyl-phenyl)carbamothioyl]-3-[[4-[1-[4-(trifluoromethoxy)phenyl]-1H-1,2,4-triazol-3-yl]phenyl]methyl]urea (PC7)

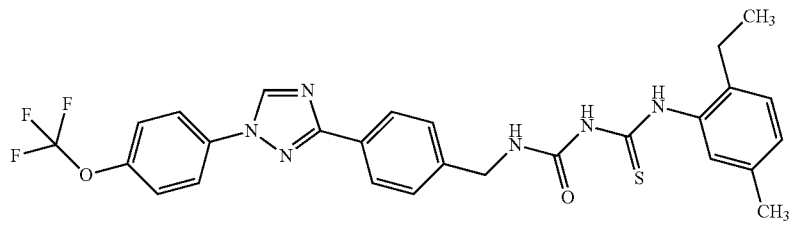 [SMILES: CCc1ccc(C)cc1NC(=S)NC(=O)NCc1ccc(-c2ncn(-c3ccc(OC(F)(F)F)cc3)n2)cc1]

The title compound was prepared as described in Example 71 using (4-(1-(4-(trifluoromethoxy)phenyl)-1H-1,2,4-triazol-3-yl)phenyl)methanamine (C16) and 1-(2-ethyl-5-methylphenyl)thiourea (CA41) and isolated as an off white solid (0.092 g, 18%): $^1$H NMR (400 MHz, DMSO-$d_6$) δ 11.94 (s, 1H), 10.22 (s, 1H), 9.41 (d, J=0.8 Hz, 1H), 8.18-8.04 (m, 4H), 7.63 (d, J=8.7 Hz, 2H), 7.57-7.44 (m, 3H), 7.39-7.31 (m, 1H), 7.17 (d, J=7.7 Hz, 1H), 7.04 (dd, J=8.0, 1.7 Hz, 1H), 4.44 (d, J=5.8 Hz, 2H), 2.51 (dt, J=3.6, 1.9 Hz, 2H), 2.27 (s, 3H), 1.14-1.08 (m, 3H); $^{19}$F NMR (376 MHz, DMSO-$d_6$) δ −56.96; ESIMS m/z 555 ([M+H]$^+$), 553 ([M−H]$^−$).

Preparation of 1-[(5-methyl-2-propyl-phenyl)carbamothioyl]-3-[[4-[1-[4-(trifluoromethoxy)phenyl]-1H-1,2,4-triazol-3-yl]phenyl]methyl]urea (PC8)

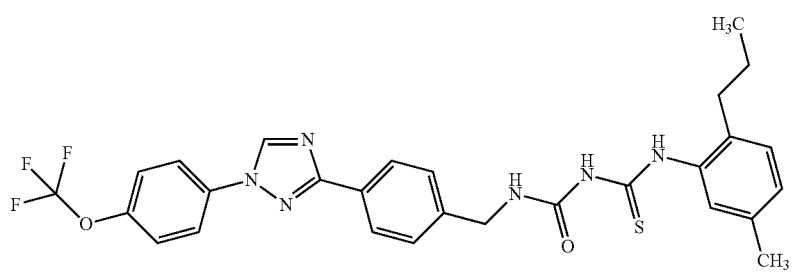 [SMILES: CCCc1ccc(C)cc1NC(=S)NC(=O)NCc1ccc(-c2ncn(-c3ccc(OC(F)(F)F)cc3)n2)cc1]

The title compound was prepared as described in Example 71 using (4-(1-(4-(trifluoromethoxy)phenyl)-1H-1,2,4-triazol-3-yl)phenyl)methanamine (C16) and 1-(5-methyl-2-propylphenyl)thiourea (CA38) and isolated as an off white solid (0.079 g, 15%): $^1$H NMR (400 MHz, DMSO-$d_6$) δ 11.98 (s, 1H), 10.22 (s, 1H), 9.41 (s, 1H), 8.14-8.06 (m, 4H), 7.69-7.61 (m, 2H), 7.56-7.44 (m, 3H), 7.39 (s, 1H), 7.14 (d, J=7.7 Hz, 1H), 7.08-6.99 (m, 1H), 4.44 (d, J=5.8 Hz, 2H), 2.49-2.43 (m, 2H), 2.27 (s, 3H), 1.50 (h, J=7.3 Hz, 2H), 0.86 (t, J=7.3 Hz, 3H); $^{19}$F NMR (376 MHz, DMSO-$d_6$) δ −56.96; ESIMS m/z 569 ([M+H]$^+$), 567 ([M−H]$^−$).

Preparation of 1-[(4-methoxy-2-methyl-phenyl)carbamothioyl]-3-[[4-[1-[4-(trifluoromethoxy)phenyl]-1H-1,2,4-triazol-3-yl]phenyl]methyl]urea (PC6)

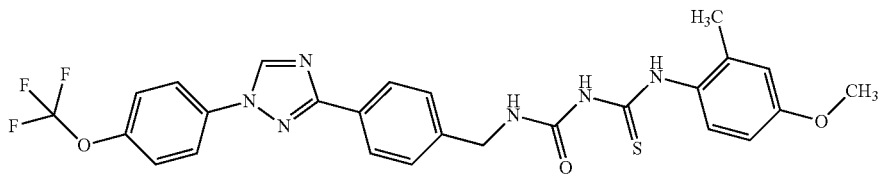 [SMILES: COc1ccc(NC(=S)NC(=O)NCc2ccc(-c3ncn(-c4ccc(OC(F)(F)F)cc4)n3)cc2)c(C)c1]

The title compound was prepared as described in Example 71 using (4-(1-(4-(trifluoromethoxy)phenyl)-1H-1,2,4-triazol-3-yl)phenyl)methanamine (C16) and 1-(4-methoxy-2-methylphenyl)thiourea and isolated as a white solid (0.076 g, 15%): $^1$H NMR (400 MHz, DMSO-$d_6$) δ 11.76 (s, 1H), 10.18 (s, 1H), 9.41 (s, 1H), 8.11-8.04 (m, 5H), 7.69-7.58 (m, 3H), 7.58-7.35 (m, 5H), 6.90-6.82 (m, 1H), 6.77 (dd, J=8.7, 2.9 Hz, 1H), 4.43 (d, J=5.8 Hz, 2H), 3.75 (s, 3H), 2.18 (s, 3H); $^{19}$F NMR (376 MHz, DMSO-$d_6$) δ −56.96; ESMIS m/z 557 ([M+H]$^+$), 555 ([M−H]$^-$).

Preparation of 1-(o-tolylcarbamothioyl)-3-[[4-[1-[4-(trifluoromethoxy)phenyl]-1H-1,2,4-triazol-3-yl]phenyl]methyl]urea (PC1)

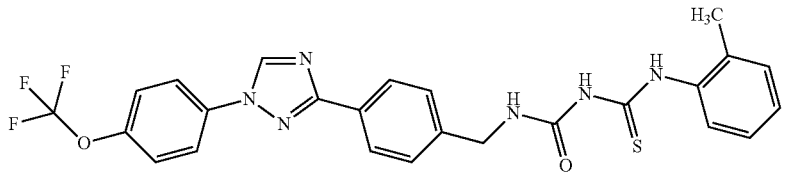 [SMILES: Cc1ccccc1NC(=S)NC(=O)NCc1ccc(-c2ncn(-c3ccc(OC(F)(F)F)cc3)n2)cc1]

The title compound was prepared as described in Example 71 using (4-(1-(4-(trifluoromethoxy)phenyl)-1H-1,2,4-triazol-3-yl)phenyl)methanamine (C16) and 1-(o-tolyl)thiourea and isolated as a white solid (0.116 g, 24%): $^1$H NMR (400 MHz, DMSO-$d_6$) δ 12.00 (s, 1H), 10.22 (s, 1H), 9.41 (s, 1H), 8.18-8.06 (m, 4H), 7.64 (dp, J=7.8, 0.9 Hz, 3H), 7.55 (t, J=5.9 Hz, 1H), 7.52-7.46 (m, 2H), 7.32-7.28 (m, 1H), 7.27-7.17 (m, 2H), 4.46 (d, J=5.8 Hz, 2H), 2.25 (s, 3H); $^{19}$F NMR (376 MHz, DMSO-$d_6$) δ −56.96; ESIMS m/z 527 ([M+H]$^+$), 525 ([M−H]$^-$).

Preparation of 1-[(2-isopropylphenyl)carbamothioyl]-3-[[4-[1-[4-(trifluoromethyl)phenyl]-1H-1,2,4-triazol-3-yl]phenyl]methyl]urea (PC14)

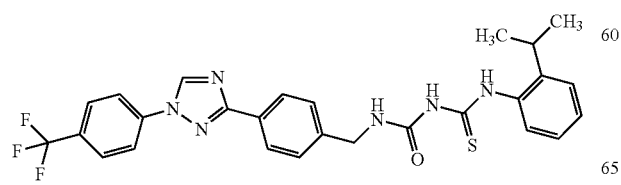

The title compound was prepared as described in Example 71 using (4-(1-(4-(trifluoromethyl)phenyl)-1H-1,2,4-triazol-3-yl)phenyl)methanamine (CA3) and 1-(2-isopropylphenyl)thiourea and isolated as a white solid (0.088 g, 17%): $^1$H NMR (400 MHz, DMSO-$d_6$) δ 11.94 (s, 1H), 10.24 (s, 1H), 9.55 (s, 1H), 8.22 (d, J=8.5 Hz, 2H), 8.19-8.13 (m, 2H), 8.01 (d, J=8.4 Hz, 2H), 7.56 (t, J=5.9 Hz, 1H), 7.53-7.48 (m, 2H), 7.45 (dd, J=7.8, 1.5 Hz, 1H), 7.38 (dd, J=7.7, 1.6 Hz, 1H), 7.30 (td, J=7.5, 1.5 Hz, 1H), 7.24 (td, J=7.6, 1.7 Hz, 1H), 4.47 (d, J=5.8 Hz, 2H), 3.05 (hept, J=7.0 Hz, 1H), 1.20 (d, J=6.8 Hz, 6H); $^{19}$F NMR (376 MHz, DMSO-$d_6$) δ −60.79; ESIMS m/z 539 ([M+H]$^+$), 537 ([M−H]$^-$).

Preparation of 1-[(2-isopropyl-4-methyl-phenyl)carbamothioyl]-3-[[4-[1-[4-(trifluoromethyl)phenyl]-1,2,4-triazol-3-yl]phenyl]methyl]urea (PC15)

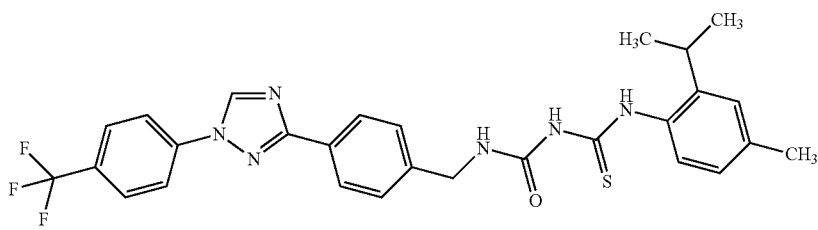

The title compound was prepared as described in Example 71 using (4-(1-(4-(trifluoromethyl)phenyl)-1H-1,2,4-triazol-3-yl)phenyl)methanamine (CA3) and 1-(2-isopropyl-4-methylphenyl)thiourea and isolated as a white solid (0.073 g, 14%): $^1$H NMR (400 MHz, DMSO-$d_6$) δ 11.84 (s, 1H), 10.21 (s, 1H), 9.55 (s, 1H), 8.22 (d, J=8.4 Hz, 2H), 8.19-8.12 (m, 2H), 8.01 (d, J=8.5 Hz, 2H), 7.54 (t, J=6.0 Hz, 1H), 7.52-7.47 (m, 2H), 7.29 (d, J=8.0 Hz, 1H), 7.17 (d, J=2.0 Hz, 1H), 7.07-7.01 (m, 1H), 4.47 (d, J=5.8 Hz, 2H), 3.00 (hept, J=6.9 Hz, 1H), 2.33 (s, 3H), 1.19 (d, J=6.8 Hz, 6H); $^{19}$F NMR (376 MHz, DMSO-$d_6$) δ −60.79; ESIMS m/z 553 ([M+H]$^+$), 551 ([M−H]$^-$).

Preparation of 1-[(4-methoxy-2-methyl-phenyl)carbamothioyl]-3-[[4-[1-[4-(trifluoromethyl)phenyl]-1H-1,2,4-triazol-3-yl]phenyl]methyl]urea (PC16)

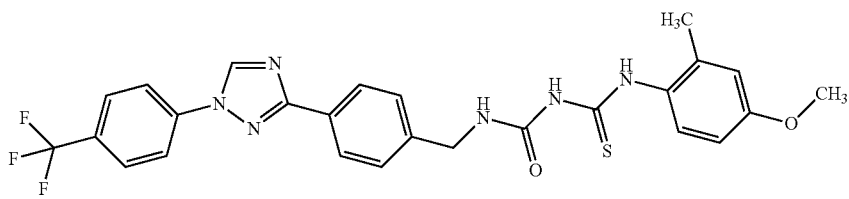 [SMILES: COc1ccc(NC(=S)NC(=O)NCc2ccc(-c3ncn(-c4ccc(C(F)(F)F)cc4)n3)cc2)c(C)c1]

The title compound was prepared as described in Example 71 using (4-(1-(4-(trifluoromethyl)phenyl)-1H-1,2,4-triazol-3-yl)phenyl)methanamine (CA3) and 1-(4-methoxy-2-methylphenyl)thiourea and isolated as a white solid (0.033 g, 6%): $^1$H NMR (400 MHz, DMSO-$d_6$) δ 10.17 (s, 1H), 9.53 (s, 1H), 9.18 (s, 1H), 8.22 (d, J=8.4 Hz, 2H), 8.15-8.06 (m, 2H), 8.01 (d, J=8.5 Hz, 2H), 7.37 (d, J=8.3 Hz, 2H), 7.12 (d, J=8.6 Hz, 1H), 7.07 (t, J=6.0 Hz, 1H), 6.92 (d, J=2.9 Hz, 1H), 6.88 (dd, J=8.6, 2.9 Hz, 1H), 4.29 (dd, J=5.9, 2.9 Hz, 2H), 3.82 (s, 3H), 2.11 (s, 3H); $^{19}$F NMR (376 MHz, DMSO-$d_6$) δ −60.79; ESIMS m/z 541 ([M+H]$^+$), 539 ([M−H]$^-$).

Example 72

Preparation of (Z)-1-(3-(4-fluoro-2-isopropylphenyl)-4-oxothiazolidin-2-ylidene)-3-(4-(1-(4-(trifluoromethoxy)phenyl)-1H-1,2,4-triazol-3-yl)benzyl)urea (P3, P1172)

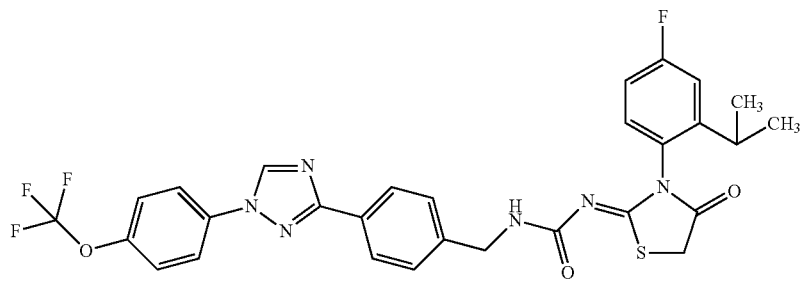 [SMILES: CC(C)c1cc(F)ccc1N1C(=O)CS/C1=N\C(=O)NCc1ccc(-c2ncn(-c3ccc(OC(F)(F)F)cc3)n2)cc1]

To a 20 mL vial was added 1-[(4-fluoro-2-isopropyl-phenyl)carbamothioyl]-3-[[4-[1-[4-(trifluoromethoxy)phenyl]-1H-1,2,4-triazol-3-yl]phenyl]methyl]urea (PC3) (0.092 g, 0.16 mmol), sodium acetate (0.040 g, 0.48 mmol), methyl 2-bromoacetate (0.084 mL, 0.80 mmol) and acetonitrile (2.0 mL). The vial was sealed and the reaction was heated overnight at 65° C. The reaction mixture was diluted with brine solution and dichloromethane and passed through a phase separator. The organic layer was concentrated and the resulting residue was purified by flash column chromatography using 10-80% ethyl acetate/hexanes as eluent providing the title compound as a white solid (0.058 g, 58%).

The following compounds were prepared in accordance to the procedure in Example 72.

Preparation of (Z)-1-(3-(2-ethyl-5-methylphenyl)-4-oxothiazolidin-2-ylidene)-3-(4-(1-(4-(trifluoromethoxy)phenyl)-1H-1,2,4-triazol-3-yl)benzyl)urea (P7)

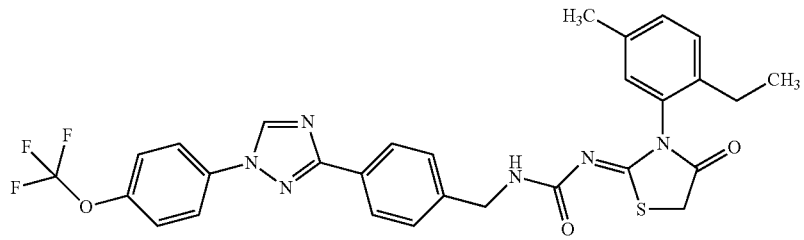

The title compound was prepared as described in Example 72 using 1-[(2-ethyl-5-methyl-phenyl)carbamothioyl]-3-[[4-[1-[4-(trifluoromethoxy)phenyl]-1H-1,2,4-triazol-3-yl]phenyl]methyl]urea (PC7) and isolated as an off-white solid (0.034 g, 44%).

Preparation of (Z)-1-(3-(5-methyl-2-propylphenyl)-
4-oxothiazolidin-2-ylidene)-3-(4-(1-(4-(trifluo-
romethoxy)phenyl)-1H-1,2,4-triazol-3-yl)benzyl)
urea (P8, P852)

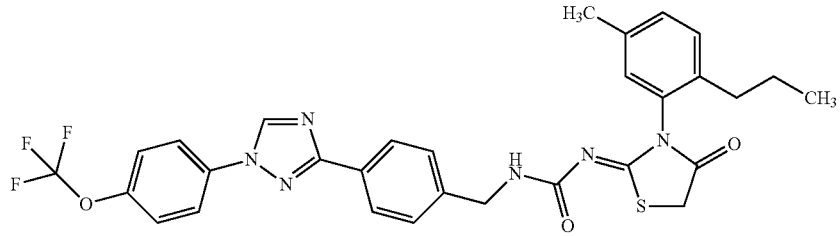 [SMILES: CCCc1ccc(C)cc1N1C(=O)CS/C1=N\C(=O)NCc1ccc(-c2ncn(-c3ccc(OC(F)(F)F)cc3)n2)cc1]

The title compound was prepared as described in Example 72 using 1-[(5-methyl-2-propyl-phenyl)carbamothioyl]-3-[[4-[1-[4-(trifluoromethoxy)phenyl]-1H-1,2,4-triazol-3-yl]phenyl]methyl]urea (PC8) and isolated as an off-white solid (0.018 g, 25%).

Preparation of (Z)-1-(3-(4-methoxy-2-methylphe-
nyl)-4-oxothiazolidin-2-ylidene)-3-(4-(1-(4-(trifluo-
romethoxy)phenyl)-1H-1,2,4-triazol-3-yl)benzyl)
urea (P6)

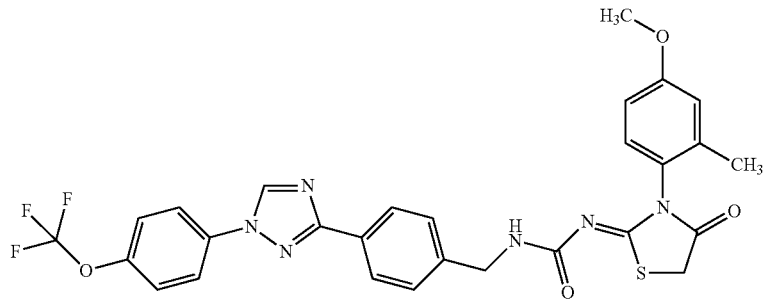 [SMILES: COc1ccc(N2C(=O)CS/C2=N\C(=O)NCc2ccc(-c3ncn(-c4ccc(OC(F)(F)F)cc4)n3)cc2)c(C)c1]

The title compound was prepared as described in Example 72 using 1-[(4-methoxy-2-methyl-phenyl)carbamothioyl]-3-[[4-[1-[4-(trifluoromethoxy)phenyl]-1H-1,2,4-triazol-3-yl]phenyl]methyl]urea (PC6) and isolated as an off-white solid (0.041 g, 46%).

Preparation of (Z)-1-(3-(2-isopropyl-4-methylphe-
nyl)-4-oxothiazolidin-2-ylidene)-3-(4-(1-(4-(trifluo-
romethoxy)phenyl)-1H-1,2,4-triazol-3-yl)benzyl)
urea (P5)

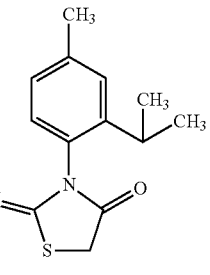

The title compound was prepared as described in Example 72 using 1-[(2-isopropyl-4-methyl-phenyl)carbamothioyl]-

3-[[4-[1-[4-(trifluoromethoxy)phenyl]-1H-1,2,4-triazol-3-yl]phenyl]methyl]urea (PC5) and isolated as an off-white solid (0.012 g, 25%).

Preparation of (Z)-1-(3-(2-ethylphenyl)-4-oxothiazolidin-2-ylidene)-3-(4-(1-(4-(trifluoromethoxy)phenyl)-1H-1,2,4-triazol-3-yl)benzyl)urea (P2, P532)

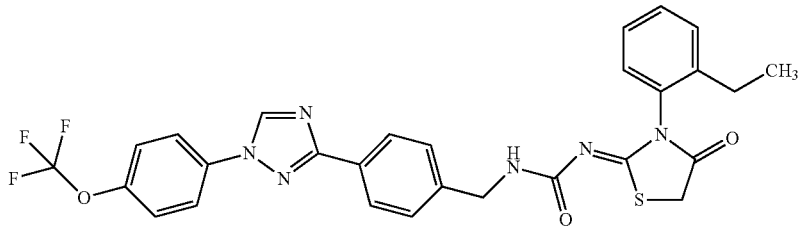 [SMILES: CCc1ccccc1N1C(=O)CS/C1=N\C(=O)NCc1ccc(-c2ncn(-c3ccc(OC(F)(F)F)cc3)n2)cc1]

The title compound was prepared as described in Example 72 using 1-[(2-ethylphenyl)carbamothioyl]-3-[[4-[1-[4-(trifluoromethoxy)phenyl]-1H-1,2,4-triazol-3-yl]phenyl]methyl]urea (PC2) and isolated as a white solid (0.031 g, 28%).

Preparation of (Z)-1-(4-oxo-3-(o-tolyl)thiazolidin-2-ylidene)-3-(4-(1-(4-(trifluoromethoxy)phenyl)-1H-1,2,4-triazol-3-yl)benzyl)urea (P1)

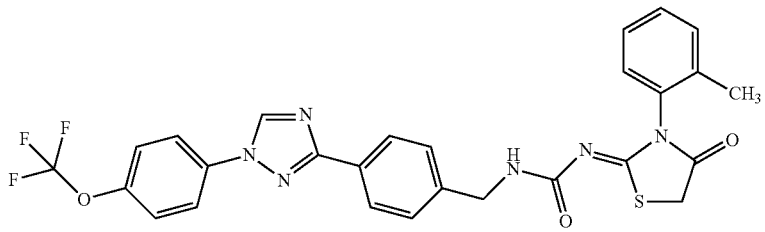 [SMILES: Cc1ccccc1N1C(=O)CS/C1=N\C(=O)NCc1ccc(-c2ncn(-c3ccc(OC(F)(F)F)cc3)n2)cc1]

The title compound was prepared as described in Example 72 using 1-(o-tolylcarbamothioyl)-3-[[4-[1-[4-(trifluoromethoxy)phenyl]-1H-1,2,4-triazol-3-yl]phenyl]methyl]urea (PC1) and ethanol as solvent and isolated as a white solid (0.086 g, 79%).

Preparation of (Z)-1-(3-(2-isopropylphenyl)-4-oxothiazolidin-2-ylidene)-3-(4-(1-(4-(trifluoromethyl)phenyl)-1H-1,2,4-triazol-3-yl)benzyl)urea (P14)

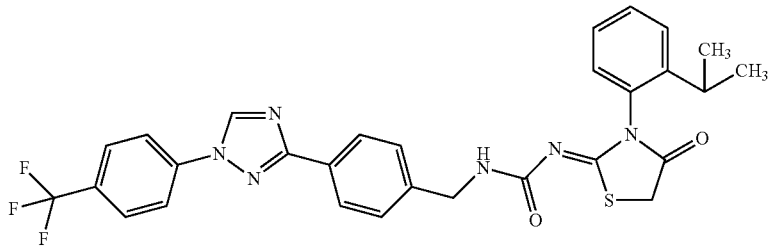 [SMILES: CC(C)c1ccccc1N1C(=O)CS/C1=N\C(=O)NCc1ccc(-c2ncn(-c3ccc(C(F)(F)F)cc3)n2)cc1]

The title compound was prepared as described in Example 72 using 1-[(2-isopropylphenyl)carbamothioyl]-3-[[4-[1-[4-

(trifluoromethyl)phenyl]-1H-1,2,4-triazol-3-yl]phenyl]methyl]urea (PC14) and ethanol as solvent and isolated as a white solid (0.055 g, 69%).

Preparation of (Z)-1-(3-(2-isopropyl-4-methylphenyl)-4-oxothiazolidin-2-ylidene)-3-(4-(1-(4-(trifluoromethyl)phenyl)-1H-1,2,4-triazol-3-yl)benzyl)urea (P15)

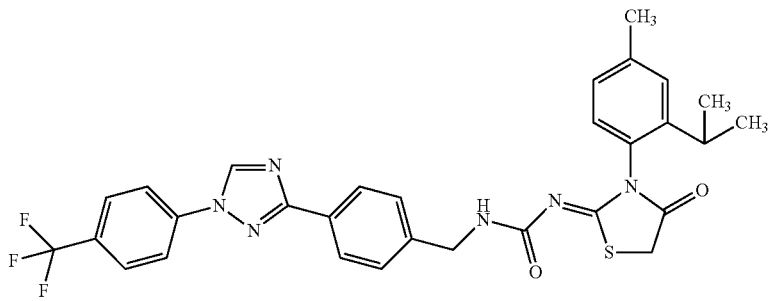 [SMILES: Cc1ccc(N2C(=O)CS/C2=N\C(=O)NCc2ccc(-c3ncn(-c4ccc(C(F)(F)F)cc4)n3)cc2)c(C(C)C)c1]

The title compound was prepared as described in Example 72 using 1-[(2-isopropyl-4-methyl-phenyl)carbamothioyl]-3-[[4-[1-[4-(trifluoromethyl)phenyl]-1H-1,2,4-triazol-3-yl]phenyl]methyl]urea (PC15) and ethanol as solvent and isolated as a white solid (0.049 g, 80%).

Example 73

Preparation of (Z)-1-(3-(2-isopropyl-4-methylphenyl)-4-methylthiazol-2(3H)-ylidene)-3-(4-(1-(4-(trifluoromethoxy)phenyl)-1H-1,2,4-triazol-3-yl)benzyl)urea (P20)

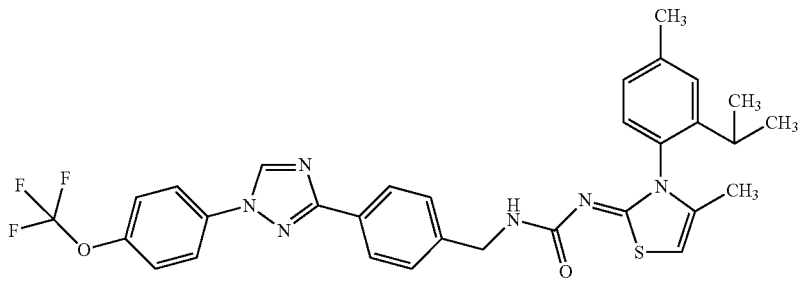 [SMILES: Cc1ccc(-n2c(C)cs/c2=N\C(=O)NCc2ccc(-c3ncn(-c4ccc(OC(F)(F)F)cc4)n3)cc2)c(C(C)C)c1]

To a 20 mL vial was added 1-[(2-isopropyl-4-methyl-phenyl)carbamothioyl]-3-[[4-[1-[4-(trifluoromethoxy)phenyl]-1H-1,2,4-triazol-3-yl]phenyl]methyl]urea (PC5) (0.044 g, 0.077 mmol), sodium acetate (0.019 g, 0.23 mmol), 1-chloropropan-2-one (0.0092 mL, 0.12 mmol) and acetonitrile (1.5 mL). The vial was sealed and heated overnight at 65° C. The reaction mixture was diluted with brine solution and dichloromethane and passed through a phase separator. The organic layer was concentrated and the resulting residue was purified by flash column chromatography using 10-80% ethyl acetate/hexanes as eluent providing the title compound as an off-white solid (0.010 g, 21%): $^1$H NMR (400 MHz, DMSO-$d_6$) δ 9.38 (s, 1H), 8.14-8.01 (m, 4H), 7.70 (s, 1H), 7.62 (dq, J=7.7, 1.0 Hz, 2H), 7.45-7.35 (m, 2H), 7.34-7.27 (m, 1H), 7.15 (t, J=1.3 Hz, 2H), 6.66 (q, J=0.9 Hz, 1H), 4.47-4.28 (m, 2H), 2.73-2.62 (m, 1H), 2.39 (s, 3H), 2.10 (d, J=1.1 Hz, 3H), 1.10 (d, J=6.8 Hz, 3H), 1.00 (d, J=6.8 Hz, 3H); $^{19}$F NMR (376 MHz, DMSO-$d_6$) δ −56.96; ESIMS m/z 607 ([M+H]$^+$).

Example 74

Preparation of 3-(3-(2-isocyanatoethyl)phenyl)-1-(4-(trifluoromethoxy)phenyl)-1H-1,2,4-triazole (CA44)

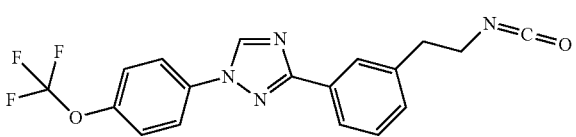 [SMILES: O=C=NCCc1cccc(-c2ncn(-c3ccc(OC(F)(F)F)cc3)n2)c1]

To a suspension of 3-(3-(1-(4-(trifluoromethoxy)phenyl)-1H-1,2,4-triazol-3-yl)phenyl)propanoic acid (CA13) (3.0 g, 8.0 mmol) and triethylamine (1.1 mL, 8.0 mmol) in toluene (80 mL) in a 200 mL round bottomed flask was added diphenyl phosphorazidate (1.7 mL, 8.0 mmol). The reaction mixture was stirred at room temperature for 2 hours. The reaction mixture was concentrated on to Celite®. Purification by flash column chromatography using 0-50% ethyl acetate/hexanes as eluent provided a pale yellow oil (1.8 g) which was stored overnight. The oil, which was determined by $^1$H NMR to be a mixture of acyl azide and isocyanate solidified over time and was stored an additional night under vacuum. The resultant solid was dissolved in 1,2-dichloroethane (50 mL) 1,2-dichloroethane and heated at 60° C. for 3 hours. The solvent was concentrated to give the title compound (1.8 g, 59%): $^1$H NMR (400 MHz, DMSO-$d_6$) δ 9.41 (s, 1H), 8.13-8.06 (m, 2H), 8.06-7.98 (m, 2H), 7.63 (dq, J=7.9, 1.0 Hz, 2H), 7.49 (td, J=7.6, 0.6 Hz, 1H), 7.41 (dt, J=7.7, 1.3 Hz, 1H), 3.66 (t, J=6.6 Hz, 2H), 2.99 (t, J=6.7 Hz, 2H); $^{19}$F NMR (376 MHz, DMSO-$d_6$) δ −56.97.

The following compounds were prepared in accordance to the procedure in Example 74.

Preparation of 3-(3-(isocyanatomethyl)phenyl)-1-(4-(trifluoromethoxy)phenyl)-1H-1,2,4-triazole (CB34)

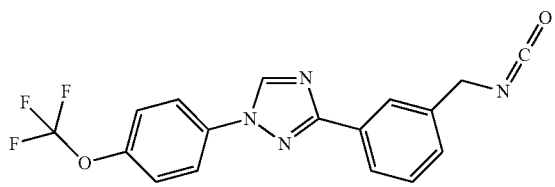 [SMILES: O=C=NCc1cccc(-c2ncn(-c3ccc(OC(F)(F)F)cc3)n2)c1]

The title compound was prepared as described in Example 74 using 2-(3-(1-(4-(trifluoromethoxy)phenyl)-1H-1,2,4-triazol-3-yl)phenyl)acetic acid (CB23) and isolated as a white solid (2.41 g, 48%, 85% pure): $^1$H NMR (400 MHz, DMSO-$d_6$) δ 9.43 (s, 1H), 8.17-8.03 (m, 4H), 7.65-7.44 (m, 4H), 4.73 (s, 2H); $^{19}$F NMR (376 MHz, DMSO-$d_6$) δ −57.00; ESIMS m/z 361 ([M+H]$^+$).

Example 75

Preparation of 1-(o-tolylcarbamothioyl)-3-[2-[3-[1-[4-(trifluoromethoxy)phenyl]-1H-1,2,4-triazol-3-yl]phenyl]ethyl]urea (PC74)

To a 20 mL vial, 1-(o-tolyl)thiourea (0.096 g, 0.58 mmol) and cesium carbonate (0.22 g, 0.68 mmol) were charged as solids. Then 3-(3-(2-isocyanatoethyl)phenyl)-1-(4-(trifluoromethoxy)phenyl)-1H-1,2,4-triazole (CA44) (0.20 g, 0.52 mmol) in acetonitrile (4.0 mL) was added. The reaction was allowed to stir at room temperature overnight. The reaction mixture was diluted with dichloromethane and filtered through a phase separator. The filtrate was purified by flash column chromatography using 0-50% ethyl acetate/hexanes as eluent followed by flash column chromatography using 10-50% ethyl acetate/B, where B=1:1 dichloromethane/hexanes, as eluent to provide the title compound as a white solid (0.11 g, 37%): $^1$H NMR (400 MHz, DMSO-$d_6$) δ 12.01 (s, 1H), 10.12 (s, 1H), 9.42 (s, 1H), 8.13-8.05 (m, 2H), 8.04-7.96 (m, 2H), 7.66-7.54 (m, 3H), 7.54-7.46 (m, 1H), 7.39 (dt, J=7.7, 1.5 Hz, 1H), 7.29-7.24 (m, 1H), 7.24-7.14 (m, 2H), 7.03 (t, J=5.6 Hz, 1H), 3.46 (q, J=6.6 Hz, 2H), 2.96-2.84 (m, 2H), 2.20 (s, 3H); $^{19}$F NMR (376 MHz, DMSO-$d_6$) δ −56.96; ESIMS m/z 541 ([M+H]$^+$), 539 ([M−H]$^−$).

The following compounds were prepared in accordance to the procedure in Example 75.

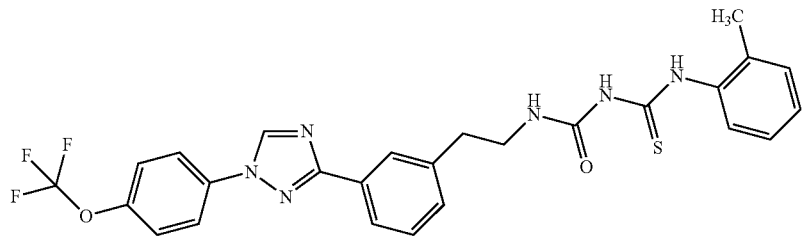 [SMILES: Cc1ccccc1NC(=S)NC(=O)NCCc1cccc(-c2ncn(-c3ccc(OC(F)(F)F)cc3)n2)c1]

Preparation of 1-[(4-methoxy-2-methyl-phenyl)carbamothioyl]-3-[2-[3-[1-[4-(trifluoromethoxy)phenyl]-1H-1,2,4-triazol-3-yl]phenyl]ethyl]urea (PC87)

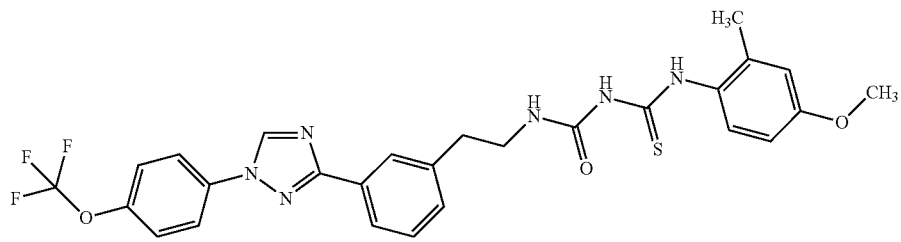 [SMILES: COc1ccc(NC(=S)NC(=O)NCCc2cccc(-c3ncn(-c4ccc(OC(F)(F)F)cc4)n3)c2)c(C)c1]

The title compound was prepared as described in Example 75 using 3-(3-(2-isocyanatoethyl)phenyl)-1-(4-(trifluoromethoxy)phenyl)-1H-1,2,4-triazole (CA44) and 1-(4-methoxy-2-methylphenyl)thiourea isolated as a white solid (0.105 g, 34%): $^1$H NMR (400 MHz, DMSO-$d_6$) δ 11.78 (s, 1H), 10.07 (s, 1H), 9.42 (s, 1H), 8.13-8.05 (m, 2H), 8.04-7.96 (m, 2H), 7.66-7.57 (m, 2H), 7.53-7.45 (m, 1H), 7.42-7.32 (m, 2H), 7.01 (t, J=5.7 Hz, 1H), 6.85-6.81 (m, 1H), 6.76 (dd, J=8.7, 2.9 Hz, 1H), 3.74 (s, 3H), 3.45 (q, J=6.6 Hz, 2H), 2.89 (t, J=6.9 Hz, 2H), 2.15 (s, 3H); $^{19}$F NMR (376 MHz, DMSO-$d_6$) δ −56.97; ESIMS m/z 517 ([M+H]$^+$), 569 [(M−H)$^+$].

Preparation of 1-[(2-ethylphenyl)carbamothioyl]-3-[2-[3-[1-[4-(trifluoromethoxy)phenyl]-1H-1,2,4-triazol-3-yl]phenyl]ethyl]urea (PC75)

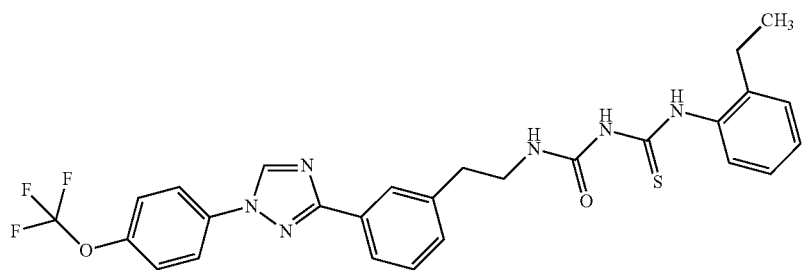 [SMILES: CCc1ccccc1NC(=S)NC(=O)NCCc1cccc(-c2ncn(-c3ccc(OC(F)(F)F)cc3)n2)c1]

The title compound was prepared as described in Example 75 using 3-(3-(2-isocyanatoethyl)phenyl)-1-(4-(trifluoromethoxy)phenyl)-1H-1,2,4-triazole (CA44) and 1-(2-ethylphenyl)thiourea isolated as a white solid (0.104 g, 35%): $^1$H NMR (400 MHz, DMSO-$d_6$) δ 12.01 (s, 1H), 10.13 (s, 1H), 9.42 (s, 1H), 8.15-8.05 (m, 2H), 8.05-7.96 (m, 2H), 7.67-7.57 (m, 2H), 7.56-7.45 (m, 2H), 7.39 (dt, J=7.7, 1.4 Hz, 1H), 7.33-7.25 (m, 1H), 7.25-7.17 (m, 2H), 7.09-6.96 (m, 1H), 3.47 (q, J=6.5 Hz, 2H), 2.89 (t, J=6.9 Hz, 2H), 2.58-2.51 (m, 2H), 1.11 (t, J=7.5 Hz, 3H); $^{19}$F NMR (376 MHz, DMSO-$d_6$) δ −56.97; ESIMS m/z 555 ([M+H]$^+$), 553 ([M−H]$^-$).

Preparation of 1-[(2-ethyl-6-methyl-phenyl)carbamothioyl]-3-[2-[3-[1-[4-(trifluoromethoxy)phenyl]-1H-1,2,4-triazol-3-yl]phenyl]ethyl]urea (PC83)

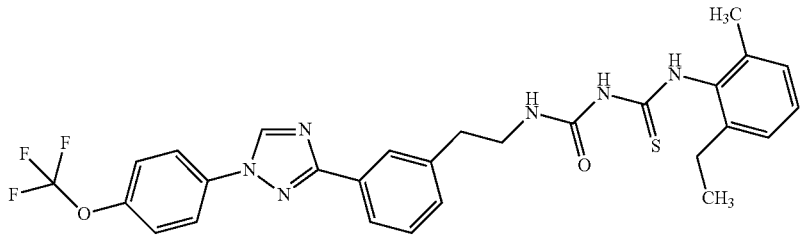 [SMILES: CCc1cccc(C)c1NC(=S)NC(=O)NCCc1cccc(-c2ncn(-c3ccc(OC(F)(F)F)cc3)n2)c1]

The title compound was prepared as described in Example 75 using 3-(3-(2-isocyanatoethyl)phenyl)-1-(4-(trifluoromethoxy)phenyl)-1H-1,2,4-triazole (CA44) and 1-(2-ethyl-6-methylphenyl)thiourea (CA39) isolated as a white solid (0.137 g, 45%): $^1$H NMR (400 MHz, DMSO-$d_6$) δ 11.58 (s, 1H), 10.13 (s, 1H), 9.42 (s, 1H), 8.16-8.05 (m, 2H), 8.05-7.96 (m, 2H), 7.62 (ddd, J=7.9, 2.0, 1.0 Hz, 2H), 7.49 (t, J=7.6 Hz, 1H), 7.39 (dt, J=7.7, 1.4 Hz, 1H), 7.21-7.12 (m, 1H), 7.13-7.05 (m, 2H), 7.00 (t, J=5.7 Hz, 1H), 3.47 (q, J=6.7 Hz, 2H), 2.90 (t, J=6.9 Hz, 2H), 2.47 (dd, J=7.6, 2.9 Hz, 2H), 2.14 (s, 3H), 1.14-1.08 (m, 3H); $^{19}$F NMR (376 MHz, DMSO-$d_6$) δ −56.97; ESIMS m/z 569 ([M+H]$^+$), 567 ([M−H]$^-$).

Preparation of 1-[(2-isopropylphenyl)carbamothioyl]-3-[2-[3-[1-[4-(trifluoromethoxy)phenyl]-1H-1,2,4-triazol-3-yl]phenyl]ethyl]urea (PC76)

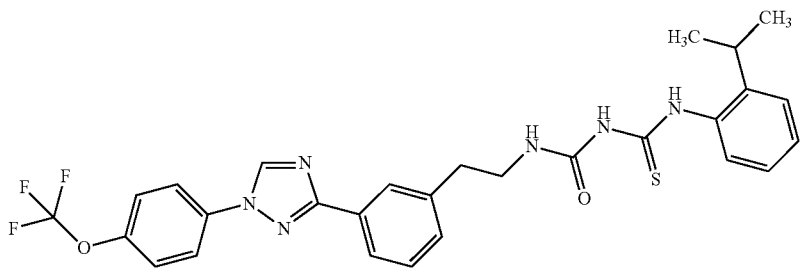 [SMILES: CC(C)c1ccccc1NC(=S)NC(=O)NCCc1cccc(-c2ncn(-c3ccc(OC(F)(F)F)cc3)n2)c1]

The title compound was prepared as described in Example 75 using 3-(3-(2-isocyanatoethyl)phenyl)-1-(4-(trifluoromethoxy)phenyl)-1H-1,2,4-triazole (CA44) and 1-(2-isopropylphenyl)thiourea isolated as a white solid (0.033 g, 11%): $^1$H NMR (400 MHz, DMSO-$d_6$) δ 11.95 (s, 1H), 10.14 (s, 1H), 9.42 (s, 1H), 8.14-8.05 (m, 2H), 8.05-7.94 (m, 2H), 7.68-7.57 (m, 2H), 7.49 (t, J=7.6 Hz, 1H), 7.39 (dq, J=7.8, 1.5 Hz, 2H), 7.34 (dd, J=7.8, 1.6 Hz, 1H), 7.26 (td, J=7.5, 1.5 Hz, 1H), 7.20 (td, J=7.5, 1.6 Hz, 1H), 7.03 (t, J=5.7 Hz, 1H), 3.47 (q, J=6.6 Hz, 2H), 2.98 (p, J=6.9 Hz, 1H), 2.89 (t, J=6.9 Hz, 2H), 1.15 (d, J=6.8 Hz, 6H); $^{19}$F NMR (376 MHz, DMSO-$d_6$) δ −56.96; ESIMS m/z 569 ([M+H]$^+$), 567 ([M−H]$^-$).

Preparation of 1-[(2-isopropyl-4-methyl-phenyl)carbamothioyl]-3-[2-[3-[1-[4-(trifluoromethoxy)phenyl]-1H-1,2,4-triazol-3-yl]phenyl]ethyl]urea (PC84)

The title compound was prepared as described in Example 75 using 3-(3-(2-isocyanatoethyl)phenyl)-1-(4-(trifluoromethoxy)phenyl)-1H-1,2,4-triazole (CA44) and 1-(2-isopropyl-4-methylphenyl)thiourea isolated as a white solid (0.077 g, 25%): $^1$H NMR (400 MHz, DMSO-$d_6$) δ 11.85 (s, 1H), 10.10 (s, 1H), 9.42 (s, 1H), 8.15-8.05 (m, 2H), 8.04-7.96 (m, 2H), 7.61 (ddd, J=7.9, 2.0, 1.0 Hz, 2H), 7.49 (t, J=7.6 Hz, 1H), 7.39 (dt, J=7.7, 1.4 Hz, 1H), 7.23 (d, J=8.0 Hz, 1H), 7.16-7.11 (m, 1H), 7.05-6.96 (m, 2H), 3.46 (q, J=6.7 Hz, 2H), 2.91 (dt, J=17.9, 6.9 Hz, 3H), 2.30 (s, 3H), 1.14 (d, J=6.8 Hz, 6H); $^{19}$F NMR (376 MHz, DMSO-$d_6$) δ −56.97; ESIMS m/z 583 ([M+H]$^+$), 581 ([M−H]$^-$).

Preparation of 1-[(4-fluoro-2-isopropyl-phenyl)carbamothioyl]-3-[2-[3-[1-[4-(trifluoromethoxy)phenyl]-1H-1,2,4-triazol-3-yl]phenyl]ethyl]urea (PC85)

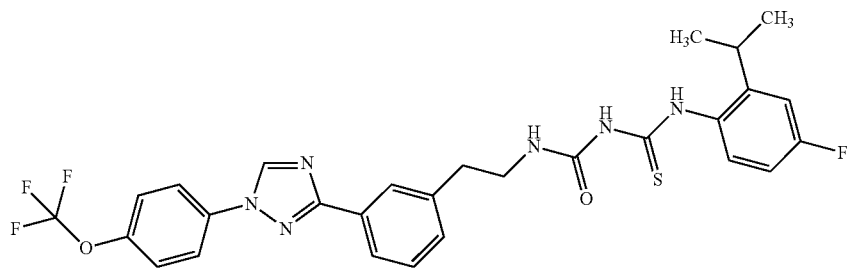 [SMILES: CC(C)c1cc(F)ccc1NC(=S)NC(=O)NCCc1cccc(-c2ncn(-c3ccc(OC(F)(F)F)cc3)n2)c1]

The title compound was prepared as described in Example 75 using 3-(3-(2-isocyanatoethyl)phenyl)-1-(4-(trifluoromethoxy)phenyl)-1H-1,2,4-triazole (CA44) and 1-(4-fluoro-2-isopropylphenyl)thiourea isolated as a white solid (0.085 g, 27%): $^1$H NMR (400 MHz, DMSO-$d_6$) δ 11.83 (s, 1H), 10.17 (s, 1H), 9.42 (s, 1H), 8.14-8.05 (m, 2H), 8.05-7.95 (m, 2H), 7.68-7.58 (m, 2H), 7.49 (t, J=7.6 Hz, 1H), 7.43-7.31 (m, 2H), 7.15 (dd, J=10.3, 3.0 Hz, 1H), 7.03 (td, J=8.3, 2.9 Hz, 2H), 3.47 (q, J=6.6 Hz, 2H), 3.01-2.82 (m, 3H), 1.14 (d, J=6.8 Hz, 6H); $^{19}$F NMR (376 MHz, DMSO-$d_6$) δ −56.97, −114.40; ESIMS m/z 587 ([M+H]$^+$), 585 ([M−H]$^-$).

Preparation of 1-[(2-isopropyl-5-methyl-phenyl)carbamothioyl]-3-[2-[3-[1-[4-(trifluoromethoxy)phenyl]-1H-1,2,4-triazol-3-yl]phenyl]ethyl]urea (PC81)

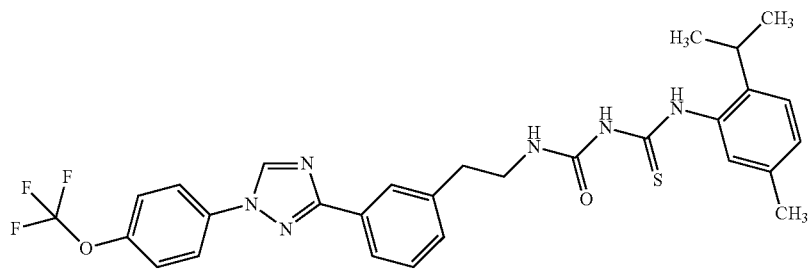 [SMILES: Cc1ccc(C(C)C)c(NC(=S)NC(=O)NCCc2cccc(-c3ncn(-c4ccc(OC(F)(F)F)cc4)n3)c2)c1]

The title compound was prepared as described in Example 75 using 3-(3-(2-isocyanatoethyl)phenyl)-1-(4-(trifluoromethoxy)phenyl)-1H-1,2,4-triazole (CA44) and 1-(2-isopropyl-5-methylphenyl)thiourea isolated as an off-white solid (0.019 g, 6%): $^1$H NMR (400 MHz, DMSO-$d_6$) δ 11.89 (s, 1H), 10.12 (s, 1H), 9.42 (s, 1H), 8.14-8.05 (m, 2H), 8.05-7.96 (m, 2H), 7.62 (ddd, J=7.8, 1.9, 0.9 Hz, 2H), 7.49 (t, J=7.6

Hz, 1H), 7.39 (dt, J=7.7, 1.5 Hz, 1H), 7.24-7.17 (m, 2H), 7.12-7.05 (m, 1H), 7.02 (t, J=5.8 Hz, 1H), 3.52-3.42 (m, 2H), 2.91 (dt, J=14.1, 6.9 Hz, 3H), 2.25 (s, 3H), 1.13 (d, J=6.8 Hz, 6H); $^{19}$F NMR (376 MHz, DMSO-$d_6$) δ −56.96; ESIMS m/z 583 ([M+H]$^+$), 581 ([M−H]$^−$).

Preparation of 1-[(5-methyl-2-propyl-phenyl)carbamothioyl]-3-[2-[3-[1-[4-(trifluoromethoxy)phenyl]-1H-1,2,4-triazol-3-yl]phenyl]ethyl]urea (PC80)

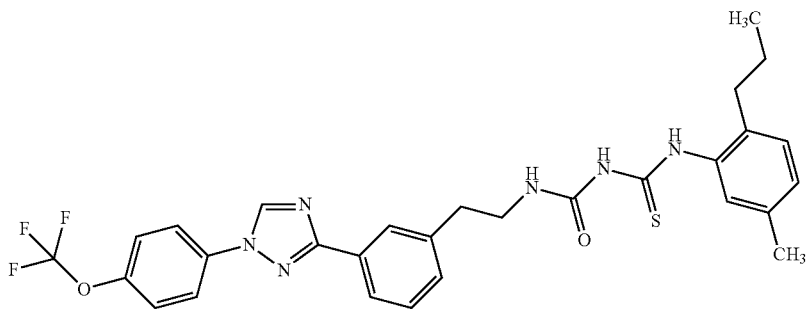 [SMILES: CCCc1ccc(C)cc1NC(=S)NC(=O)NCCc1cccc(-c2ncn(-c3ccc(OC(F)(F)F)cc3)n2)c1]

The title compound was prepared as described in Example 75 using 3-(3-(2-isocyanatoethyl)phenyl)-1-(4-(trifluoromethoxy)phenyl)-1H-1,2,4-triazole (CA44) and 1-(5-methyl-2-propylphenyl)thiourea (CA38) isolated as a white solid (0.107 g, 34%): $^1$H NMR (400 MHz, DMSO-$d_6$) δ 11.99 (s, 1H), 10.09 (s, 1H), 9.42 (s, 1H), 8.14-8.05 (m, 2H), 8.05-7.95 (m, 2H), 7.61 (dd, J=8.6, 1.3 Hz, 2H), 7.49 (t, J=7.6 Hz, 1H), 7.44-7.34 (m, 2H), 7.13 (d, J=7.8 Hz, 1H), 7.07-6.97 (m, 2H), 3.46 (q, J=6.5 Hz, 2H), 2.89 (t, J=6.9 Hz, 2H), 2.48-2.39 (m, 2H), 2.26 (s, 3H), 1.54-1.42 (m, 2H), 0.84 (t, J=7.3 Hz, 3H); $^{19}$F NMR (376 MHz, DMSO-$d_6$) δ −56.96; ESIMS m/z 583 ([M+H]$^+$), 581 ([M−H]$^−$).

Preparation of 1-(o-tolylcarbamothioyl)-3-[[3-[1-[4-(trifluoromethoxy)phenyl]-1H-1,2,4-triazol-3-yl]phenyl]methyl]urea (FB18)

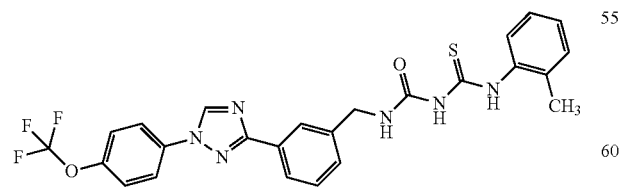

The title compound was prepared as described in Example 75 using 3-(3-(isocyanatomethyl)phenyl)-1-(4-(trifluoromethoxy)phenyl)-1H-1,2,4-triazole (CB34) and 1-(o-tolyl)thiourea and isolated as an off-white solid (0.148 g, 37%).

Preparation of 1-[(4-methoxy-2-methyl-phenyl)carbamothioyl]-3-[[3-[1-[4-(trifluoromethoxy)phenyl]-1H-1,2,4-triazol-3-yl]phenyl]methyl]urea (FB19)

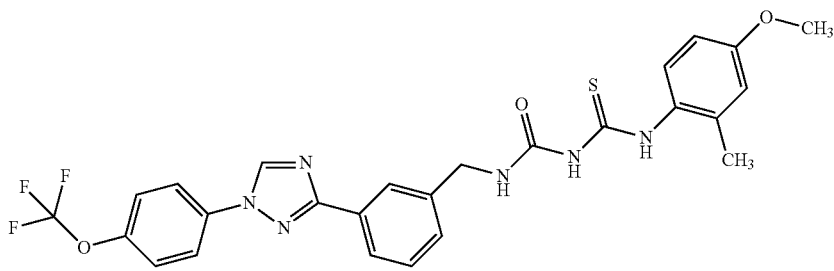 [SMILES: COc1ccc(NC(=S)NC(=O)NCc2cccc(-c3ncn(-c4ccc(OC(F)(F)F)cc4)n3)c2)c(C)c1]

The title compound was prepared as described in Example 75 using 3-(3-(isocyanatomethyl)phenyl)-1-(4-(trifluoromethoxy)phenyl)-1H-1,2,4-triazole (CB34) and 1-(4-methoxy-2-methylphenyl)thiourea and isolated as an off-white solid (0.212 g, 50%).

Preparation of 1-[(2-ethylphenyl)carbamothioyl]-3-[[3-[1-[4-(trifluoromethoxy)phenyl]-1H-1,2,4-triazol-3-yl]phenyl]methyl]urea (FB20)

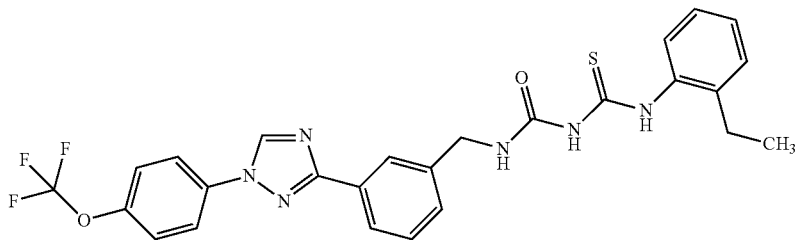 [SMILES: CCc1ccccc1NC(=S)NC(=O)NCc1cccc(-c2ncn(-c3ccc(OC(F)(F)F)cc3)n2)c1]

The title compound was prepared as described in Example 75 using 3-(3-(isocyanatomethyl)phenyl)-1-(4-(trifluoromethoxy)phenyl)-1H-1,2,4-triazole (CB34) and 1-(2-ethylphenyl)thiourea and isolated as an off-white solid (0.152 g, 37%).

Preparation of 1-[(2-ethyl-6-methyl-phenyl)carbamothioyl]-3-[[3-[1-[4-(trifluoromethoxy)phenyl]-1H-1,2,4-triazol-3-yl]phenyl]methyl]urea (FB21)

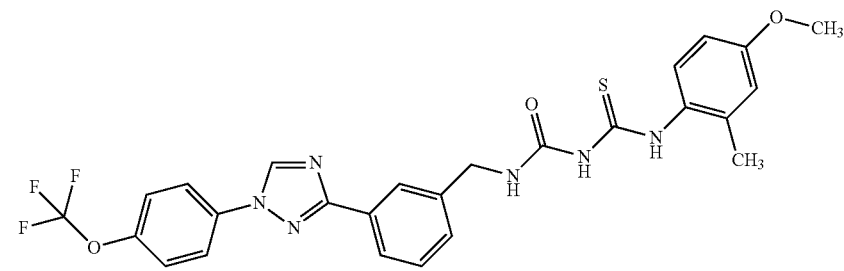

The title compound was prepared as described in Example 75 using 3-(3-(isocyanatomethyl)phenyl)-1-(4-(trifluoromethoxy)phenyl)-1H-1,2,4-triazole (CB34) and 1-(2-ethyl-6-methylphenyl)thiourea (CA39) and isolated as an off-white solid (0.212 g, 50%).

Preparation of 1-[(2-isopropylphenyl)carbamothioyl]-3-[[3-[1-[4-(trifluoromethoxy)phenyl]-1H-1,2,4-triazol-3-yl]phenyl]methyl]urea (FB22)

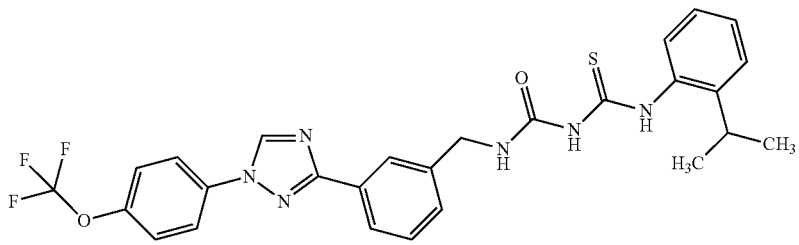 [SMILES: CC(C)c1ccccc1NC(=S)NC(=O)NCc1cccc(-c2ncn(-c3ccc(OC(F)(F)F)cc3)n2)c1]

The title compound was prepared as described in Example 75 using 3-(3-(isocyanatomethyl)phenyl)-1-(4-(trifluoromethoxy)phenyl)-1H-1,2,4-triazole (CB34) and 1-(2-isopropylphenyl)thiourea and isolated as an off-white solid (0.213 g, 47%).

Preparation of 1-[(2-isopropyl-4-methyl-phenyl)carbamothioyl]-3-[[3-[1-[4-(trifluoromethoxy)phenyl]-1H-1,2,4-triazol-3-yl]phenyl]methyl]urea (FB23)

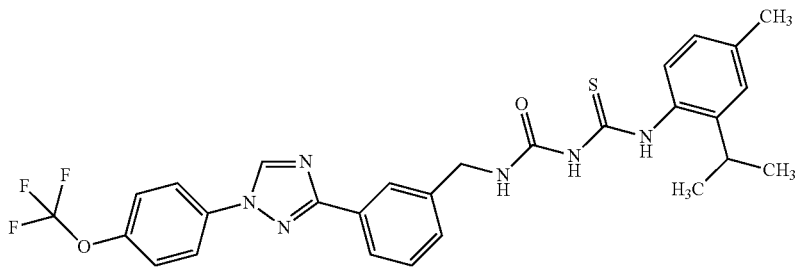 [SMILES: Cc1ccc(NC(=S)NC(=O)NCc2cccc(-c3ncn(-c4ccc(OC(F)(F)F)cc4)n3)c2)c(C(C)C)c1]

The title compound was prepared as described in Example 75 using 3-(3-(isocyanatomethyl)phenyl)-1-(4-(trifluoromethoxy)phenyl)-1H-1,2,4-triazole (CB34) and 1-(2-isopropyl-4-methylphenyl)thiourea and isolated as an off-white solid (0.216 g, 50%).

Preparation of 1-[(4-fluoro-2-isopropyl-phenyl)carbamothioyl]-3-[[3-[1-[4-(trifluoromethoxy)phenyl]-1H-1,2,4-triazol-3-yl]phenyl]methyl]urea (FB24)

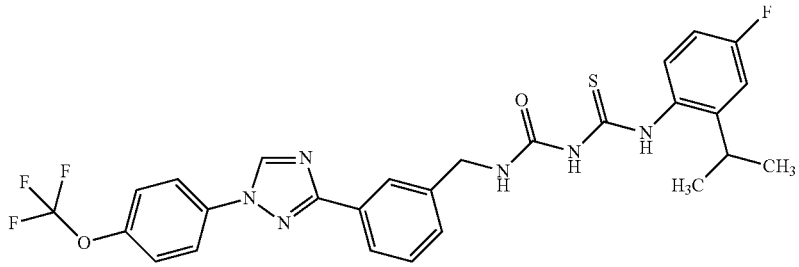 [SMILES: CC(C)c1cc(F)ccc1NC(=S)NC(=O)NCc1cccc(-c2ncn(-c3ccc(OC(F)(F)F)cc3)n2)c1]

The title compound was prepared as described in Example 75 using 3-(3-(isocyanatomethyl)phenyl)-1-(4-(trifluoromethoxy)phenyl)-1H-1,2,4-triazole (CB34) and 1-(4-fluoro-2-isopropylphenyl)thiourea and isolated as an off-white solid (0.242 g, 56%).

Preparation of 1-[(2-isopropyl-5-methyl-phenyl)carbamothioyl]-3-[[3-[1-[4-(trifluoromethoxy)phenyl]-1H-1,2,4-triazol-3-yl]phenyl]methyl]urea (FB25)

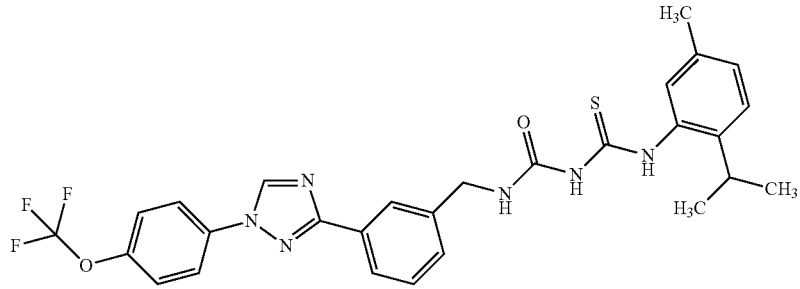 [SMILES: CC(C)c1ccc(Cl)cc1NC(=S)NC(=O)NCc1cccc(-c2ncn(-c3ccc(OC(F)(F)F)cc3)n2)c1]

The title compound was prepared as described in Example 75 using 3-(3-(isocyanatomethyl)phenyl)-1-(4-(trifluoromethoxy)phenyl)-1H-1,2,4-triazole (CB34) and 1-(2-isopropyl-5-methylphenyl)thiourea and isolated as an off-white solid (0.181 g, 42%).

Preparation of 1-[(5-chloro-2-isopropyl-phenyl)carbamothioyl]-3-[[3-[1-[4-(trifluoromethoxy)phenyl]-1H-1,2,4-triazol-3-yl]phenyl]methyl]urea (FB26)

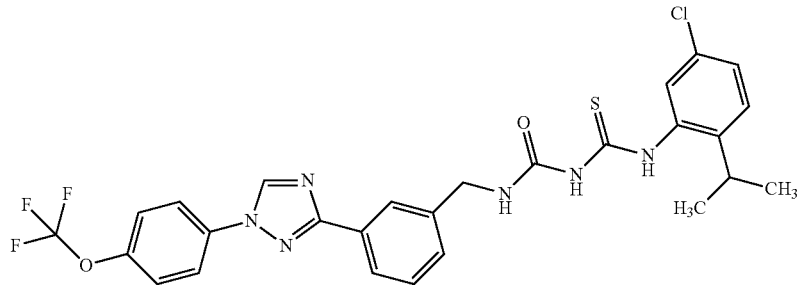

The title compound was prepared as described in Example 75 using 3-(3-(isocyanatomethyl)phenyl)-1-(4-(trifluoromethoxy)phenyl)-1H-1,2,4-triazole (CB34) and 1-(5-chloro-2-isopropylphenyl)thiourea (CB32) and isolated as an off-white solid (0.170 g, 38%).

Example 76

Preparation of 3-(3-(1-(4-(trifluoromethoxy)phenyl)-1H-1,2,4-triazol-3-yl)phenyl)propan-1-ol (CA45)

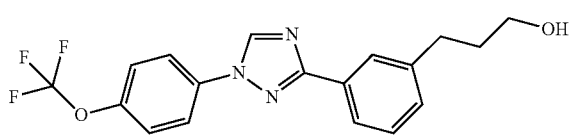 [SMILES: OCCCc1cccc(-c2ncn(-c3ccc(OC(F)(F)F)cc3)n2)c1]

In a 500 mL round bottomed flask 3-(3-(1-(4-(trifluoromethoxy)phenyl)-1H-1,2,4-triazol-3-yl)phenyl)propanoic acid (CA13) (5.68 g, 15.1 mmol) was dissolved in tetrahydrofuran (151 mL). The reaction was cooled in an ice water bath and placed under inert atmosphere. Aluminum(III) lithium hydride (2.0 M in tetrahydrofuran, 15.8 mL, 31.6 mmol) was added dropwise. The reaction was allowed to gradually warm to room temperature and stir overnight. The reaction was cooled in an ice bath and water (1.2 mL) was added dropwise to quench excess aluminum(III) lithium hydride, the reaction mixture was allowed to stir for 1 hour. Then sodium hydroxide (15 wt %, 1.2 mL) was added dropwise. The reaction was allowed to stir for 1 hour. Then water (3.6 mL) was added. The resulting precipitate was removed via filtration. The filtrate was concentrated to give a yellow solid (5.20 g). The solid was purified by flash column chromatography using 0-60% ethyl acetate/hexanes as eluent providing the title compound as a white solid (4.01 g, 72%): $^1$H NMR (400 MHz, DMSO-$d_6$) δ 9.40 (s, 1H), 8.18-8.04 (m, 2H), 7.99-7.89 (m, 2H), 7.68-7.57 (m, 2H), 7.43 (t, J=7.6 Hz, 1H), 7.32 (dt, J=7.7, 1.5 Hz, 1H), 4.51 (t, J=5.2 Hz, 1H), 3.45 (td, J=6.4, 5.1 Hz, 2H), 2.71 (dd, J=8.8, 6.7 Hz, 2H), 1.87-1.70 (m, 2H); $^{19}$F NMR (376 MHz, DMSO-$d_6$) δ −56.97; ESIMS m/z 364 ([M+H]$^+$).

Example 77

Preparation of 1-bromo-3-(but-3-en-1-yl)benzene (CA46)

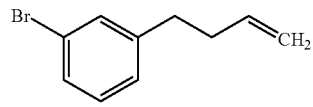

To a solution of 1-bromo-3-(bromomethyl)benzene (10.0 g, 40.0 mmol) in tetrahydrofuran (50 mL), under an inert atmosphere was added allylmagnesium bromide (1.0 M in diethyl ether, 40.0 mL, 40.0 mmol). The reaction was allowed to reflux overnight. The reaction was quenched with sulfuric acid (2 M, 45 mL). The resulting biphasic solution was solution was partitioned. The aqueous layer was extracted with diethyl ether (2×50 mL). The combined organic layers were dried over magnesium sulfate, filtered, and concentrated. The resulting residue was purified by flash column chromatography using 100% hexanes as eluent providing the title compound as a clear liquid (7.51 g, 71%, ~80% pure): $^1$H NMR (400 MHz, DMSO-d$_6$) δ 7.42 (ddd, J=2.1, 1.4, 0.7 Hz, 1H), 7.37 (dt, J=7.1, 2.1 Hz, 1H), 7.28-7.18 (m, 2H), 5.81 (ddt, J=16.9, 10.2, 6.5 Hz, 1H), 5.09-4.90 (m, 2H), 2.67 (dd, J=8.6, 6.8 Hz, 2H), 2.32 (tdt, J=7.7, 6.5, 1.5 Hz, 2H); 13C NMR (101 MHz, DMSO-d$_6$) δ 144.35, 137.61, 131.05, 130.28, 128.62, 127.44, 121.53, 115.37, 34.59, 33.91; EIMS m/z 210 ([M]$^+$).

Example 78

Preparation of 4-(3-bromophenyl)butan-1-ol (CA47)

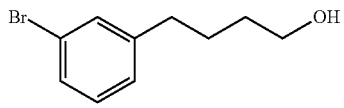 [SMILES: OCCCCc1cccc(Br)c1]

To a solution of 1-bromo-3-(but-3-en-1-yl)benzene (CA46) (7.51 g, 35.6 mmol) in hexanes (80 mL) was added (1S,5S)-9-borabicyclo[3.3.1]nonane (0.5 M in tetrahydrofuran, 74.7 mL, 37.4 mmol). The reaction was allowed to stir at room temperature overnight. To the resulting clear solution sodium hydroxide (6.0 M, 5.93 mL, 35.6 mmol) was added dropwise. The reaction was placed in an ice water bath and hydrogen peroxide (13.8 mL, 135 mmol) was added. The resulting mixture was then heated to an internal temperature of 50° C. for overnight. The reaction mixture was cooled to room temperature. The biphasic solution was partitioned, and the organic layer was washed with sodium bisulfite, and brine solution. The combined aqueous layers were made basic with saturated sodium carbonate, and extracted with diethyl ether (2×100 mL). The combined organics were dried over magnesium sulfate, filtered, and concentrated. The liquid was loaded on to silica and purified by flash column chromatography using 0-40% ethyl acetate/hexanes as eluent providing the title compound as a clear liquid (7.50 g, 90%): $^1$H NMR (400 MHz, DMSO-d$_6$) δ 7.40 (t, J=1.9 Hz, 1H), 7.37 (dt, J=7.6, 1.8 Hz, 1H), 7.28-7.17 (m, 2H), 4.39 (t, J=5.2 Hz, 1H), 3.40 (td, J=6.5, 5.2 Hz, 2H), 2.57 (t, J=7.6 Hz, 2H), 1.65-1.51 (m, 2H), 1.49-1.35 (m, 2H); EIMS m/z 228 ([M]$^+$).

Example 79

Preparation of (Z)-1-(3-(2-isopropyl-5-methylphenyl)-4-methylthiazol-2(3H)-ylidene)-3-(4-(1-(4-(trifluoromethoxy)phenyl)-1H-1,2,4-triazol-3-yl)phenethyl)urea (P65)

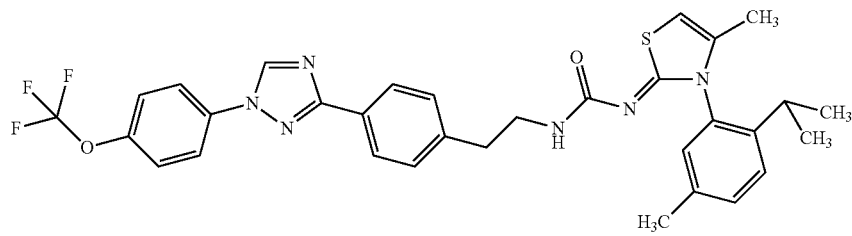 [SMILES: Cc1ccc(C(C)C)c(-n2c(C)cs/c2=N\C(=O)NCCc2ccc(-c3ncn(-c4ccc(OC(F)(F)F)cc4)n3)cc2)c1]

To N-[5-methyl-2-isopropylphenyl]-N'-[2-(4-{1-[4-(trifluoromethoxy)-phenyl]-1H-1,2,4-triazol-3-yl}phenyl)ethyl] dicarbonimidothioic diamide (F3) (0.23 g, 0.40 mmol) in butanone (4 mL) was added triethylamine (0.060 mL, 0.43 mmol) and chloroacetone (0.035 mL, 0.44 mmol) and heated at 80° C. overnight. The reaction was cooled, diluted with water, extracted dichloromethane (2×), and filtered through a phase separator. The organic layer was concentrated and loaded onto Celite® cartridge with dichloromethane. Purification by flash column chromatography using 0-100% ethyl acetate/B, where B=1:1 dichloromethane/hexanes as eluent, followed by drying in a vacuum oven provided the title compound as an orange solid (0.085 g, 34%).

The following compounds were prepared in accordance to the procedure in Example 79.

Preparation of (Z)-1-(4-hydroxy-3-(2-isopropyl-5-methylphenyl)-4-methylthiazolidin-2-ylidene)-3-(4-(1-(4-(trifluoromethoxy)phenyl)-1H-1,2,4-triazol-3-yl)phenethyl)urea (FB67)

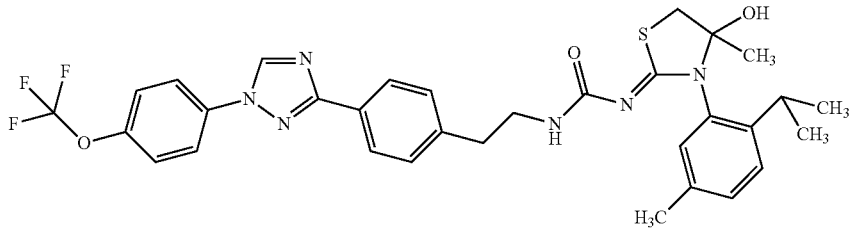 [SMILES: Cc1ccc(C(C)C)c(N2/C(=N/C(=O)NCCc3ccc(-c4ncn(-c5ccc(OC(F)(F)F)cc5)n4)cc3)SCC2(C)O)c1]

The title compound was prepared as described in Example 79 using N-[5-methyl-2-isopropylphenyl]-N'-[2-(4-{1-[4-(trifluoromethoxy)-phenyl]-1H-1,2,4-triazol-3-yl}phenyl)ethyl]dicarbonimidothioic diamide (F3) and sodium acetate as base at room temperature; purified by reverse-phase flash column chromatography using 0-100% acetonitrile/water as eluent and isolated as a clear oil (0.036 g, 33%).

Example 80

Preparation of (Z)-1-(3-(2-isopropyl-5-methylphenyl)-1,3-thiazinan-2-ylidene)-3-(4-(1-(4-(trifluoromethoxy)phenyl)-1H-1,2,4-triazol-3-yl)phenethyl)urea (P59)

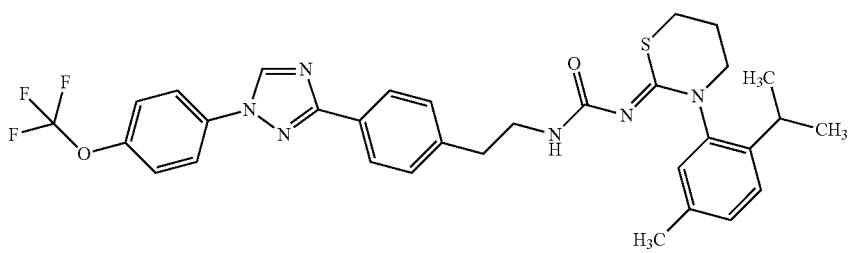 [SMILES: Cc1ccc(C(C)C)c(N2CCCS/C2=N\C(=O)NCCc2ccc(-c3ncn(-c4ccc(OC(F)(F)F)cc4)n3)cc2)c1]

To N-[5-methyl-2-isopropylphenyl]-N'-[2-(4-{1-[4-(trifluoromethoxy)-phenyl]-1H-1,2,4-triazol-3-yl}phenyl)ethyl]dicarbonimidothioic diamide (F3) (181 mg, 0.31 mmol) and potassium carbonate (0.064 g, 0.47 mmol) in butanone (3.1 mL) was added 1-bromo-3-chloropropane (0.050 mL, 0.47 mmol). The reaction was heated at 60° C. overnight. The reaction mixture was cooled, diluted with water, extracted with dichloromethane (2×), and filtered through a phase separator. The organic layer was concentrated and loaded onto a Celite® cartridge with dichloromethane. Purification by flash column chromatography using 0-100% ethyl acetate/B, where B=1:1 dichloromethane/hexanes as eluent, followed by reverse-phase flash column chromatography using 0-100% acetonitrile/water as eluent and drying in a vacuum oven provided the title compound as a white solid (0.032 g, 16%).

The following compounds were prepared in accordance to the procedure in Example 80.

Preparation of (Z)-1-(3-(2-isopropyl-5-methylphenyl)-4-methylthiazolidin-2-ylidene)-3-(4-(1-(4-(trifluoromethoxy)phenyl)-1H-1,2,4-triazol-3-yl)phenethyl)urea (P58)

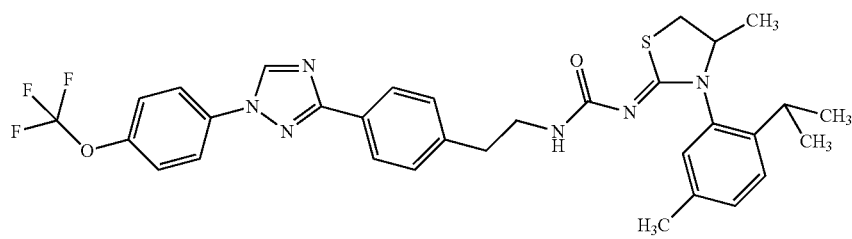 [SMILES: Cc1ccc(C(C)C)c(N2/C(=N/C(=O)NCCc3ccc(-c4ncn(-c5ccc(OC(F)(F)F)cc5)n4)cc3)SCC2C)c1]

The title compound was prepared as described in Example 80 using N-[5-methyl-2-isopropylphenyl]-N'-[2-(4-{1-[4-(trifluoromethoxy)-phenyl]-1H-1,2,4-triazol-3-yl}phenyl)ethyl]dicarbonimidothioic diamide (F3) and 1,2-dibromopropane at 80° C. and isolated as a yellow oil (0.050 g, 26%).

Preparation of (Z)-1-(3-(2-isopropyl-5-methylphenyl)-5-methyl-1,3-thiazinan-2-ylidene)-3-(4-(1-(4-(trifluoromethoxy)phenyl)-1H-1,2,4-triazol-3-yl)phenethyl)urea (P64)

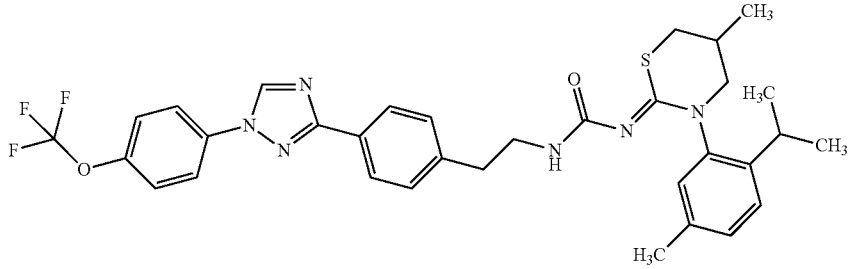 [SMILES: Cc1ccc(C(C)C)c(N2CC(C)CS/C2=N\C(=O)NCCc2ccc(-c3ncn(-c4ccc(OC(F)(F)F)cc4)n3)cc2)c1]

The title compound was prepared as described in Example 80 using N-[5-methyl-2-isopropylphenyl]-N'-[2-(4-{1-[4-(trifluoromethoxy)-phenyl]-1H-1,2,4-triazol-3-yl}phenyl)ethyl]dicarbonimidothioic diamide (F3) and 1-bromo-3-chloro-2-methylpropane and isolated as a white solid (0.061 g, 14%).

Example 80a

Preparation of (Z)-1-(3-(2-ethyl-5-methylphenyl)-4-methylthiazolidin-2-ylidene)-3-(4-(1-(4-(trifluoromethoxy)phenyl)-1H-1,2,4-triazol-3-yl)phenethyl)urea (FB55)

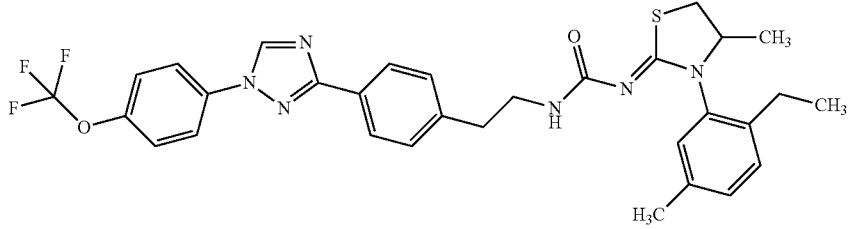 [SMILES: CCc1ccc(C)cc1N1/C(=N/C(=O)NCCc2ccc(-c3ncn(-c4ccc(OC(F)(F)F)cc4)n3)cc2)SCC1C]

3-(4-(2-Isocyanatoethyl)phenyl)-1-(4-(trifluoromethoxy)phenyl)-1H-1,2,4-triazole (C34a)(0.16 g, 0.42 mmol), 1-(2-ethyl-5-methylphenyl)thiourea (CA41) (0.081 g, 0.42 mmol), and cesium carbonate (0.13 g, 0.39 mmol) in acetonitrile (1.9 mL) was stirred at room temperature for 3 hours. The reaction was diluted with butanone (2 mL) and potassium carbonate (0.12 g, 0.83 mmol) and 1,2-dibromopropane (0.090 mL, 0.83 mmol) were added. The reaction was heated to 60° C. for 6 hours. The reaction was diluted with water and extracted with dichloromethane (2×) and the organic layers were filtered through a phase separator and concentrated. Purification by flash column chromatography using 0-100% ethyl acetate/B, where B=1:1 dichloromethane/hexanes, as eluent provided the title compound as a yellow oil (0.034 g, 13%).

The following compounds were prepared in accordance to the procedure in Example 80a.

Preparation of (Z)-1-(3-(2-ethyl-4-methylphenyl)-4-methylthiazolidin-2-ylidene)-3-(4-(1-(4-(trifluoromethoxy)phenyl)-1H-1,2,4-triazol-3-yl)phenethyl)urea (FB56)

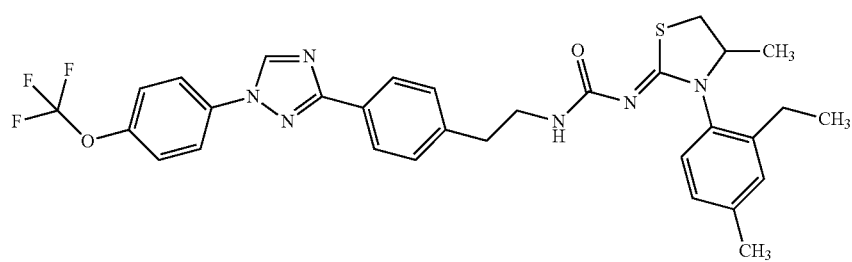 [SMILES: CCc1cc(C)ccc1N1/C(=N/C(=O)NCCc2ccc(-c3ncn(-c4ccc(OC(F)(F)F)cc4)n3)cc2)SCC1C]

The title compound was prepared as described in Example 80a using 3-(4-(2-isocyanatoethyl)phenyl)-1-(4-(trifluoromethoxy)phenyl)-1H-1,2,4-triazole (C34a) and 1-(2-ethyl-4-methylphenyl)thiourea (CA42) isolated as a yellow oil (0.040 g, 16%).

Preparation of (Z)-1-(3-(4-fluoro-2-isopropylphenyl)-4-methylthiazolidin-2-ylidene)-3-(4-(1-(4-(trifluoromethoxy)phenyl)-1H-1,2,4-triazol-3-yl)phenethyl)urea (FB57)

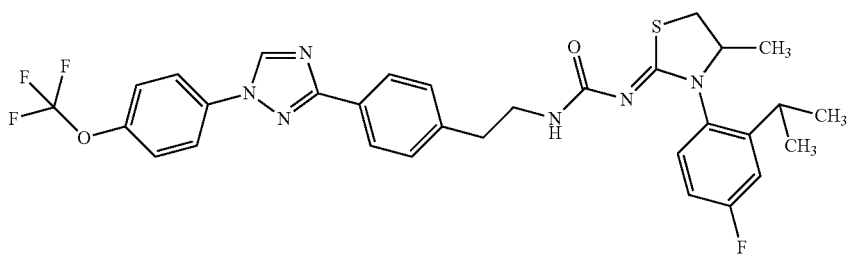 [SMILES: CC(C)c1cc(F)ccc1N1/C(=N/C(=O)NCCc2ccc(-c3ncn(-c4ccc(OC(F)(F)F)cc4)n3)cc2)SCC1C]

The title compound was prepared as described in Example 80a using 3-(4-(2-isocyanatoethyl)phenyl)-1-(4-(trifluoromethoxy)phenyl)-1H-1,2,4-triazole (C34a) and 1-(4-fluoro-2-isopropylphenyl)thiourea and isolated as a yellow oil (0.056 g, 22%).

Preparation of (Z)-1-(3-(4-methoxy-2-methylphenyl)-4-methylthiazolidin-2-ylidene)-3-(4-(1-(4-(trifluoromethoxy)phenyl)-1H-1,2,4-triazol-3-yl)phenethyl)urea (FB58)

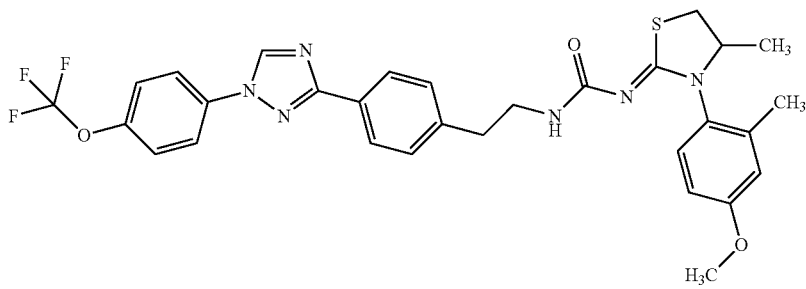 [SMILES: COc1ccc(N2/C(=N/C(=O)NCCc3ccc(-c4ncn(-c5ccc(OC(F)(F)F)cc5)n4)cc3)SCC2C)c(C)c1]

The title compound was prepared as described in Example 80a using 3-(4-(2-isocyanatoethyl)phenyl)-1-(4-(trifluoromethoxy)phenyl)-1H-1,2,4-triazole (C34a) and 1-(4-methoxy-2-methylphenyl)thiourea and isolated as a yellow oil (0.054 g, 21%).

Preparation of (Z)-1-(3-(2,6-dimethylphenyl)-4-methylthiazolidin-2-ylidene)-3-(4-(1-(4-(trifluoromethoxy)phenyl)-1H-1,2,4-triazol-3-yl)phenethyl)urea (FB59)

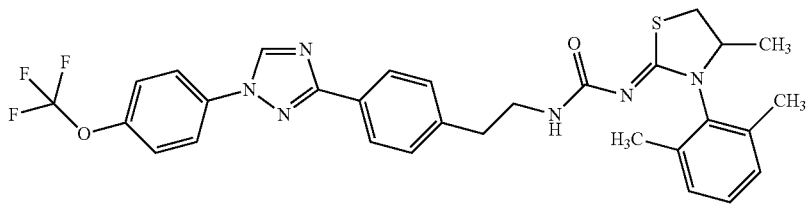 [SMILES: Cc1cccc(C)c1N1/C(=N/C(=O)NCCc2ccc(-c3ncn(-c4ccc(OC(F)(F)F)cc4)n3)cc2)SCC1C]

The title compound was prepared as described in Example 80a using 3-(4-(2-isocyanatoethyl)phenyl)-1-(4-(trifluoromethoxy)phenyl)-1H-1,2,4-triazole (C34a) and 1-(2,6-dimethylphenyl)thiourea and isolated as a clear oil (0.044 g, 18%).

Preparation of (Z)-1-(3-(2-isopropyl-4-methylphenyl)-4-methylthiazolidin-2-ylidene)-3-(4-(1-(4-(trifluoromethoxy)phenyl)-1H-1,2,4-triazol-3-yl)phenethyl)urea (FB60)

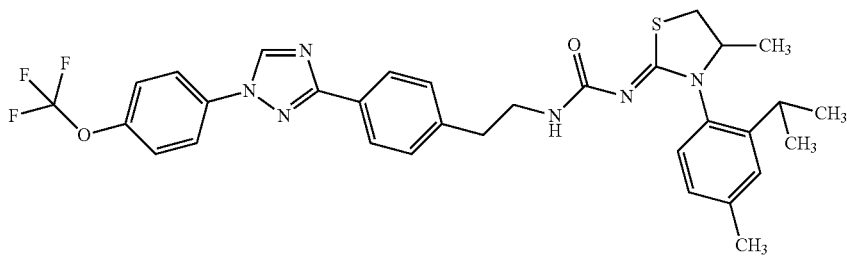 [SMILES: Cc1ccc(N2/C(=N/C(=O)NCCc3ccc(-c4ncn(-c5ccc(OC(F)(F)F)cc5)n4)cc3)SCC2C)c(C(C)C)c1]

The title compound was prepared as described in Example 80a using 3-(4-(2-isocyanatoethyl)phenyl)-1-(4-(trifluoromethoxy)phenyl)-1H-1,2,4-triazole (C34a) and 1-(2-isopropyl-4-methylphenyl)thiourea and isolated as a yellow foam (0.047 g, 17%).

Example 81

Preparation of ethyl 3-(4-(1-(4-(trifluoromethoxy)phenyl)-1H-1,2,4-triazol-3-yl)phenyl)pentanoate (CA48)

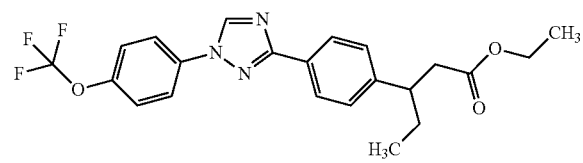 [SMILES: CCOC(=O)CC(CC)c1ccc(-c2ncn(-c3ccc(OC(F)(F)F)cc3)n2)cc1]

Sodium hydride (60% immersion in oil, 0.32 g, 7.9 mmol) was weighed into an oven-dried three neck round bottomed flask. The flask was placed under nitrogen and tetrahydrofuran (44 mL) was added. The stirring mixture was placed in an ice bath. Triethylphosphonoacetate (1.4 mL, 6.9 mmol) was added and the mixture was stirred for 2 hours. Added 1-(4-(1-(4-(trifluoromethoxy)phenyl)-1H-1,2,4-triazol-3-yl)phenyl)propan-1-one (CA7) (2.4 g, 6.5 mmol) as a solid and warmed to room temperature overnight. The reaction was diluted with water and extracted with ethyl acetate/hexanes (1:1, 2×). The organic layers were dried over sodium sulfate, filtered, and concentrated. To the crude residue was added palladium on carbon (10 wt %, 0.70 g, 0.66 mmol) and dissolved in ethyl acetate (20 mL). The reaction was stirred under hydrogen by balloon overnight. The reaction mixture was filtered through Celite® and concentrated to give the title compound as a brown liquid (2.7 g, 90%): $^1$H NMR (400 MHz, CDCl$_3$) δ 8.55 (d, J=0.6 Hz, 1H), 8.11 (dd, J=8.1, 6.0 Hz, 2H), 7.83-7.76 (m, 2H), 7.38 (dq, J=7.9, 1.0 Hz, 2H), 7.35-7.27 (m, 2H), 4.24-4.14 (m, 1H), 4.04 (qd, J=7.1, 1.6 Hz, 1H), 3.13-2.99 (m, 1H), 2.74-2.55 (m, 2H), 1.79-1.61 (m, 2H), 1.38-1.24 (m, 3H), 1.06 (dt, J=72.0, 7.2 Hz, 3H); $^{19}$F NMR (376 MHz, CDCl$_3$) δ −58.03; ESIMS m/z 434 ([M+H]$^+$).

Example 82

Preparation of para-toluenesulfonic acid salt of (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5A)

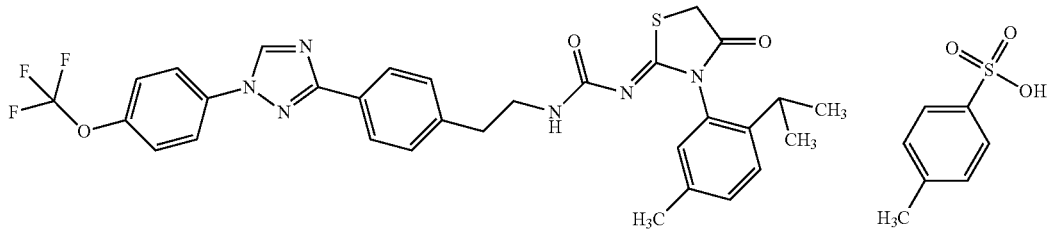 [SMILES: Cc1ccc(C(C)C)c(N2C(=O)CS/C2=N\C(=O)NCCc2ccc(-c3ncn(-c4ccc(OC(F)(F)F)cc4)n3)cc2)c1 ; Cc1ccc(S(=O)(=O)O)cc1]

To (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5) (4.82 g, 7.46 mmol) in a 250 mL round bottomed flask was added isopropanol (50 mL). The suspension was warmed to 50° C. and stirred for 20 minutes. Acetone (50 mL) was added. 4-Methylbenzenesulfonic acid hydrate (1.42 g, 7.46 mmol) dissolved in acetone (20 mL) and added to the above solution in a dropwise manner. The resulting clear light brown solution was concentrated at 50° C. The resultant residue was dried in a vacuum oven at 50° C. overnight. The brown foam was transferred to a 500 mL round bottomed flask and dissolved in acetone (200 mL). The mixture was heated to reflux for 15 hours. The solution was concentrated providing the title compound as a dark gray foam (5.90 g, 95%).

Example 83

Preparation of 2-imino-3-(2-isopropyl-5-methylphenyl)thiazolidin-4-one (CA49)

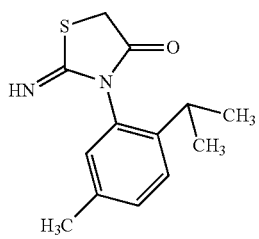

Method A.

To (1-(2-isopropyl-5-methylphenyl)thiourea (0.20 g, 0.96 mmol) in ethanol (8.0 mL) was added methyl bromoacetate (0.17 mL, 1.9 mmol) and sodium acetate (0.23 g, 2.8 mmol). The reaction was stirred overnight at room temperature. The solution was poured onto water and extracted with ethyl acetate (3×) and the organics were dried and concentrated to give the title compound as a red solid (0.24 g, 93%): $^1$H NMR (400 MHz, CDCl$_3$) δ 7.21 (d, J=7.9 Hz, 1H), 7.07 (dd, J=8.3, 1.8 Hz, 1H), 6.85 (d, J=1.6 Hz, 1H), 3.85 (d, J=0.9 Hz, 2H), 3.03 (p, J=6.9 Hz, 1H), 2.31 (t, J=0.7 Hz, 4H), 1.15 (d, J=6.9 Hz, 6H); ESIMS m/z 248 ([M]$^+$).

Method B, Step 1.

2-Isopropyl-5-methylaniline (286 g, 1.91 mol) and sodium bicarbonate (270 g, 3.22 mol) were charged in to a round bottomed flask with stirring under nitrogen atmosphere and cooled to 0-5° C. 2-Chloroacetyl chloride (218 g, 1.93 mol) was added drop wise at 0-5° C. over a period of 1 hour. The reaction was stirred at 0-5° C. for 1 hour. After completion of the reaction, purified water (2.86 L) was added and stirred at 25-30° C. for 15 minutes. The layers were then separated. The organic layer was washed with water (2×2.86 L) and with brine (1.43 L). The aqueous layers were combined and extracted with ethyl acetate (1.43 L). The organic layers were dried with sodium sulphate, filtered, and concentrated at 50-55° C. under vacuum (500-600 mm Hg) to ⅔$^{ths}$ volume. Hexanes (2.86 L) were added and the mixture was stirred at 25-30° C. for 1 hour. The solid was filtered, washed with hexanes (1.43 L), and dried at 45-50° C. under vacuum (500-600 mm Hg) to give 2-chloro-N-(2-isopropyl-5-methylphenyl)acetamide as an off-white solid (270 g, 66%): mp 97-99° C., $^1$H NMR (300 MHz, CDCl$_3$) δ 8.27 (s, 1H), 7.60 (s, 1H), 7.20 (d, J=7.95 Hz, 1H), 7.04 (d, J=7.89 Hz, 1H), 4.25 (s, 2H), 2.99 (q, J=6.78 Hz, 1H), 2.34 (s, 3H), 1.26 (d, J=6.84 Hz, 6H); $^{13}$C NMR (100 MHz, CDCl$_3$) δ 164.07, 137.28, 136.33, 132.95, 127.35, 125.62, 124.46, 43.21, 27.86, 22.98, 21.00; ESIMS m/z 226 ([M+H]$^+$).

Step 2.

2-Chloro-N-(2-isopropyl-5-methylphenyl)acetamide (290 g, 1.28 mol) and acetone (1.60 L) were charged in to a round bottomed flask with stirring under a nitrogen atmosphere. Potassium thiocyanate (250 g, 2.57 mol) was added in portions over a period of 30 minutes maintaining the temperature at 15-20° C. The reaction was stirred at 15-20° C. for 10 minutes after which time the temperature was slowly raised 53-55° C. and maintained at 53-55° C. for 3 hours. The reaction was then cooled to 20-25° C., cesium carbonate (20.9 g, 0.0641 mol) was added, and the reaction mixture was stirred at 20-25° C. for 30 minutes. After completion, the reaction mixture was filtered through Celite®, washed with acetone (1.45 L), and the filtrate collected. The filtrate was concentrated at 40-45° C. under vacuum (500-600 mm Hg) providing a syrup. The syrup was dissolved in ethyl acetate (2.90 L), washed with water (2×2.90 L) and with brine (1.45 L). The organic layers were dried with sodium sulphate, filtered, and concentrated at 50-55° C. under vacuum (500-600 mm Hg) to provide the title compound as a dark brown syrup (345 g, 99%).

Example 84

Preparation of (Z)-4-nitrophenyl (3-(2-isopropyl-5-methylphenyl)-4-oxothiazolidin-2-ylidene)carbamate (CA50)

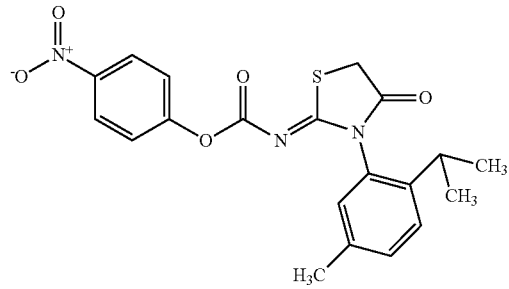

A round-bottomed flask was charged with 2-imino-3-(2-isopropyl-5-methylphenyl)thiazolidin-4-one (CA49) (1.30 g, 5.23 mmol), 4-Nitrophenyl chloroformate (1.06 g, 5.23 mmol) and cesium carbonate (1.71 g, 5.23 mmol) were dissolved in acetonitrile (13 mL). The reaction mixture was stirred at room temperature for 1.5 hours. The reaction was diluted with dichloromethane and adsorbed onto silica gel. Purification by flash column chromatography using 0-100% ethyl acetate/hexanes as eluent provided the title compound as a dark red solid (1.88 g, 86%): $^1$H NMR (400 MHz, CDCl$_3$) δ 8.31-8.18 (m, 2H), 7.39-7.27 (m, 4H), 6.92-6.83 (m, 1H), 4.14-4.00 (m, 2H), 2.61 (p, J=6.9 Hz, 1H), 2.36 (d, J=0.7 Hz, 3H), 1.30-1.10 (m, 6H); ESIMS m/z 414 ([M+H]$^+$).

Example 85

Preparation of (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5)

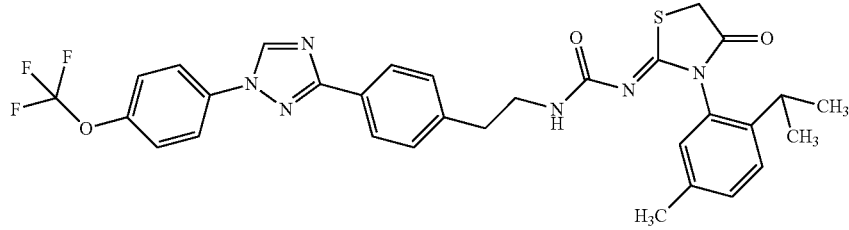 [SMILES: Cc1ccc(C(C)C)c(N2C(=O)CS/C2=N\C(=O)NCCc2ccc(-c3ncn(-c4ccc(OC(F)(F)F)cc4)n3)cc2)c1]

Method A.

To 2-(4-(1-(4-(trifluoromethoxy)phenyl)-1H-1,2,4-triazol-3-yl)phenyl)ethanamine (CA51) (0.030 g, 0.086 mmol) and cesium carbonate (0.028 g, 0.086 mmol) in anhydrous acetonitrile under nitrogen was added (Z)-4-nitrophenyl (3-(2-isopropyl-5-methylphenyl)-4-oxothiazolidin-2-ylidene) carbamate (CA50) (0.039 g, 0.095 mmol) dropwise. The reaction mixture was stirred room temperature for 3 hours. The crude mixture was concentrated in vacuo. Purification by flash column chromatography using 10-60% ethyl acetate/hexanes as eluent provided the title compound as an orange foam (0.036 g, 67%).

Method B.

To a solution of 3-(4-(2-isocyanatoethyl)phenyl)-1-(4-(trifluoromethoxy)phenyl)-1H-1,2,4-triazole (C34a) (3.00 g, 8.01 mmol) in toluene (20.0 mL) was added cesium carbonate (0.261 g, 0.801 mmol). To this was added 2-imino-3-(2-isopropyl-5-methylphenyl)thiazolidin-4-one (CA49) (1.99 g, 8.01 mmol) in acetonitrile (20.0 mL). The reaction was stirred at room temperature for 3.5 hours after which time the reaction mixture was concentrated. Acetone (200 mL) was added and the solid was filtered. The filtrate was concentrated providing a red solid. The red solid was dissolved in acetone, hexanes was added until precipitate was formed. The solid was filtered and the filtrate was concentrated. Purification by flash column chromatography using 0-20% acetone/dichloromethane as eluent provide the title compound as an off-white solid (3.10 g, 62%).

Method C.

3-(4-(2-Isocyanatoethyl)phenyl)-1-(4-(trifluoromethoxy)phenyl)-1H-1,2,4-triazole (C34a) (432 g, 1.15 mol) and acetonitrile (1.51 L) were charged in to a round bottomed flask with stirring under nitrogen atmosphere. A solution of 2-imino-3-(2-isopropyl-5-methylphenyl)thiazolidin-4-one (CA49) (320 g, 1.29 mol) in acetonitrile (1.43 L) was added at 25-30° C. The reaction was stirred at 25-30° C. for 20 hours. After completion of the reaction, the reaction mixture was filtered, washed with acetonitrile (2.16 L), heptane (464 mL), and dried at 50-55° C. under vacuum (500-600 mm Hg) to give the title compound as an off-white solid (540 g, 75%).

Example 86

Preparation of 2-methyl-4-(1-(4-(trifluoromethoxy)phenyl)-1H-1,2,4-triazol-3-yl)benzaldehyde (CB35)

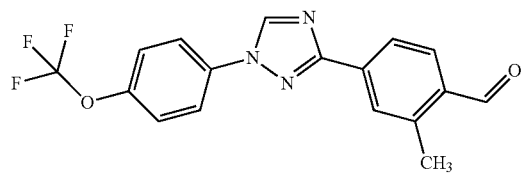

3-Bromo-1-(4-(trifluoromethoxy)phenyl)-1H-1,2,4-triazole (C1) (0.30 g, 1.0 mmol), 2-methyl-4-(4,4,5,5-tetramethyl-1,3,2-dioxaborolan-2-yl)benzaldehyde (CB4) (0.25 g, 1.0 mmol), sodium bicarbonate (0.25 g, 2.9 mmol), tetrakis (triphenylphosphine) palladium(0) (0.17 g, 0.15 mmol), dioxane (3.9 mL), and water (0.97 mL). in a 0.5-2.0 mL vial was capped and heated at 140° C. for 30 minutes in a Biotage Initiator® microwave reactor with external IR-sensor temperature monitoring from the side of the vessel. The reaction mixture was diluted with ethyl acetate and washed with water. The aqueous layer was extracted with ethyl acetate. The organic layers were poured through a phase separator and concentrated. Purification by flash column chromatography using 0-20% ethyl acetate/B, where B=1:1 dichloromethane/hexanes, as eluent provided the title compound as a white solid (0.19 g, 57%): $^1$H NMR (400 MHz, CDCl$_3$) δ 10.33 (s, 1H), 8.61 (s, 1H), 8.19 (dd, J=8.0, 1.6 Hz, 1H), 8.13 (t, J=1.1 Hz, 1H), 7.92 (d, J=8.0 Hz, 1H), 7.86-7.78 (m, 2H), 7.45-7.37 (m, 2H), 2.77 (s, 3H); $^{19}$F NMR (376 MHz, CDCl$_3$) δ −58.01; ESIMS m/z 348 ([M+H]$^+$)

The following compounds were prepared in accordance to the procedure in Example 86.

Preparation of 2-fluoro-4-(1-(4-(trifluoromethoxy) phenyl)-1H-1,2,4-triazol-3-yl)benzaldehyde (CB36)

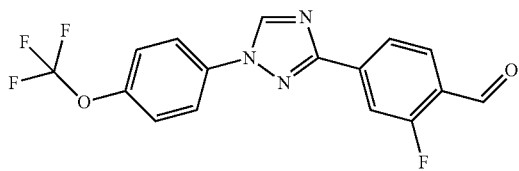 [SMILES: O=Cc1ccc(-c2ncn(-c3ccc(OC(F)(F)F)cc3)n2)cc1F]

The title compound was prepared as described in Example 86 using 3-bromo-1-(4-(trifluoromethoxy)phenyl)-1H-1,2,4-triazole (C1) and 2-fluoro-4-(4,4,5,5-tetramethyl-1,3,2-dioxaborolan-2-yl)benzaldehyde (CB5) and isolated as a white solid (0.569 g, 47%): $^1$H NMR (400 MHz, CDCl$_3$) δ 10.42 (d, J=0.7 Hz, 1H), 8.61 (s, 1H), 8.12 (ddd, J=8.1, 1.5, 0.8 Hz, 1H), 8.05-7.95 (m, 1H), 7.81 (d, J=9.0 Hz, 2H), 7.70 (d, J=9.0 Hz, 1H), 7.45-7.39 (m, 2H); ESIMS m/z 352 ([M+H]$^+$).

Example 87

Preparation of N-(2-ethylphenyl)-1,2,3,4-thiatriazol-5-amine (CB37)

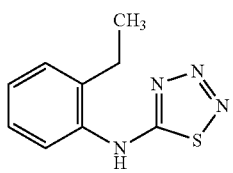

To a stirred and cooled mixture of N-(2-ethylphenyl)hydrazinecarbothioamide (0.500 g, 2.56 mmol) and acetic acid (2.00 mL, 17.5 mmol) was added sodium nitrite (0.177 g, 2.56 mmol) in water (1 mL). The mixture turned yellow upon addition and the reaction was stirred for 1 hour. The solid was filtered and the title compound was obtained as an orange solid (0.389 g, 73%): $^1$H NMR (400 MHz, CDCl$_3$) δ 9.02 (s, 1H), 7.42-7.28 (m, 4H), 2.76 (q, J=7.5 Hz, 2H), 1.25 (t, J=7.5 Hz, 3H); $^{13}$C NMR (101 MHz, CDCl$_3$) δ 138.69, 137.90, 130.38, 128.28, 128.14, 121.60, 24.73, 14.79; ESIMS m/z 179 ([M+H]−N$_2$$^+$).

The following compounds were prepared in accordance to the procedure in Example 87.

Preparation of N-(2-isopropyl-4-methoxyphenyl)-1,2,3,4-thiatriazol-5-amine (CB38)

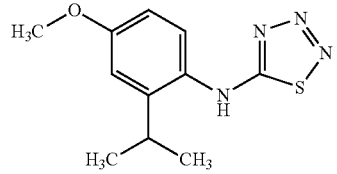

The title compound was prepared as described in Example 87 using N-(2-isopropyl-4-methoxyphenyl)hydrazinecarbothioamide (CB53) and isolated as an orange solid (0.531 g, 67%): $^1$H NMR (400 MHz, CDCl$_3$) δ 8.51 (s, 1H), 7.28 (d, J=8.7 Hz, 1H), 6.91 (d, J=2.9 Hz, 1H), 6.80 (dd, J=8.7, 2.9 Hz, 1H), 3.85 (s, 3H), 3.17 (dq, J=13.7, 6.9 Hz, 1H), 1.22 (d, J=6.9 Hz, 6H); $^{13}$C NMR (101 MHz, CDCl$_3$) δ 160.18, 146.49, 131.57, 128.24, 126.34, 113.46, 112.61, 55.95, 28.88, 23.81.

Preparation of N-(5-fluoro-2-isopropylphenyl)-1,2,3,4-thiatriazol-5-amine (CB39)

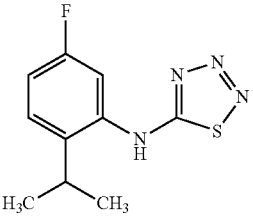

The title compound was prepared as described in Example 87 using N-(5-fluoro-2-isopropylphenyl)hydrazinecarbothioamide and isolated as a red solid (0.520 g, 64%): $^1$H NMR (400 MHz, CDCl$_3$) δ 7.37 (dd, J=8.7, 6.2 Hz, 1H), 7.13 (dd, J=9.3, 2.6 Hz, 1H), 7.04 (ddd, J=8.7, 7.9, 2.7 Hz, 1H), 3.19 (dt, J=13.7, 6.9 Hz, 2H), 1.24 (d, J=6.8 Hz, 6H); $^{19}$F NMR (376 MHz, CDCl$_3$) δ −113.32; ESIMS m/z 237 ([M−H]$^−$).

Preparation of N-(4-fluoro-2-isopropylphenyl)-1,2,3,4-thiatriazol-5-amine (CB40)

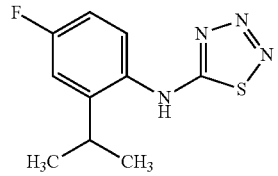 [SMILES: CC(C)c1cc(F)ccc1Nc1nnns1]

The title compound was prepared as described in Example 87 using N-(4-fluoro-2-isopropylphenyl)hydrazinecarbothioamide and isolated as a red solid (0.520 g, 64%): $^1$H NMR (400 MHz, CDCl$_3$) δ (400 MHz, CDCl$_3$) δ 8.63 (s, 1H), 7.35 (dd, J=8.7, 5.2 Hz, 1H), 7.11 (dd, J=9.8, 3.0 Hz, 1H), 7.00 (ddd, J=8.7, 7.5, 2.9 Hz, 1H), 3.20 (pd, J=6.8, 1.7 Hz, 1H), 1.23 (d, J=6.8 Hz, 6H); $^{19}$F NMR (376 MHz, CDCl$_3$) δ −111.20; ESIMS m/z 238 ([M]$^+$).

Preparation of N-(2-isopropylphenyl)-1,2,3,4-thiatriazol-5-amine (CB41)

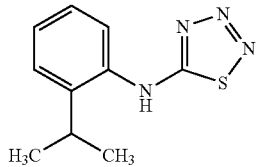

The title compound was prepared as described in Example 87 using N-(2-isopropylphenyl)hydrazinecarbothioamide and isolated as a mustard yellow solid (0.574 g, 71%): $^1$H NMR (400 MHz, CDCl$_3$) δ 8.63 (s, 1H), 7.44-7.39 (m, 1H), 7.39-7.34 (m, 2H), 7.34-7.29 (m, 1H), 3.21 (p, J=6.7 Hz, 1H), 1.26 (d, J=6.9 Hz, 6H); $^{13}$C NMR (101 MHz, CDCl$_3$) δ 179.95, 143.24, 138.10, 128.78, 128.17, 127.56, 122.85, 28.54, 23.73.

Example 88

Preparation of (Z)-1-ethyl-3-(2-ethyl-4-(2-ethylphenyl)-3-oxo-1,2,4-thiadiazolidin-5-ylidene)urea (CB42)

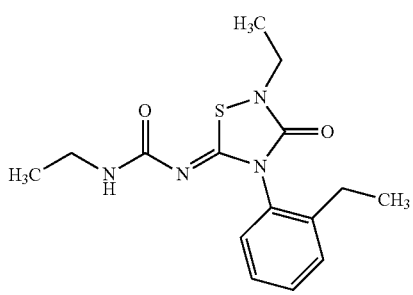 [SMILES: CCNC(=O)/N=c1\sn(CC)c(=O)n1-c1ccccc1CC]

N-(2-Ethylphenyl)-1,2,3,4-thiatriazol-5-amine (CB37) (0.350 g, 1.70 mmol) was dissolved in tetrahydrofuran (5 mL). Ethyl isocyanate (0.121 mL, 1.53 mmol) and triethylamine (5 drops) were added. The reaction was stirred at room temperature overnight. The solution was concentrated to give the title compound as an orange oil (0.484 g, 89%): $^1$H NMR (400 MHz, CDCl$_3$) δ 7.48-7.36 (m, 2H), 7.36-7.29 (m, 1H), 7.19 (dd, J=7.8, 1.4 Hz, 1H), 5.54-5.43 (m, 1H), 3.68 (q, J=7.2 Hz, 2H), 3.26 (qdd, J=7.3, 5.9, 4.8 Hz, 2H), 2.51 (qd, J=7.6, 2.9 Hz, 2H), 1.33 (t, J=7.2 Hz, 3H), 1.18 (t, J=7.6 Hz, 3H), 1.12 (t, J=7.3 Hz, 3H); ESIMS m/z 320 ([M]$^+$).

The following compounds were prepared in accordance to the procedure in Example 88.

Preparation of (Z)-1-ethyl-3-(2-ethyl-4-(2-isopropyl-4-methoxyphenyl)-3-oxo-1,2,4-thiadiazolidin-5-ylidene)urea (CB43)

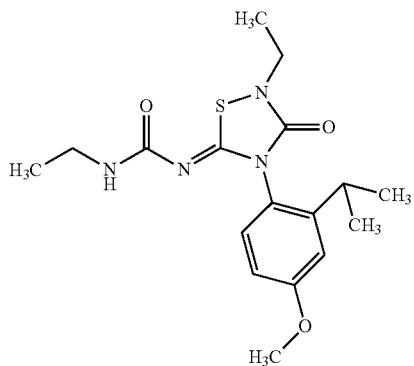

The title compound was prepared as described in Example 88 using N-(2-isopropyl-4-methoxyphenyl)-1,2,3,4-thiatriazol-5-amine (CB38) and isolated as a dark brown oil (0.693 g, 82%): $^1$H NMR (400 MHz, CDCl$_3$) δ 7.10 (d, J=8.7 Hz, 1H), 6.94 (d, J=2.8 Hz, 1H), 6.83 (dd, J=8.7, 2.8 Hz, 1H), 5.48 (t, J=5.8 Hz, 1H), 3.84 (s, 3H), 3.67 (q, J=7.3 Hz, 2H), 3.08 (q, J=7.3 Hz, 2H), 2.70 (p, J=6.9 Hz, 1H), 1.34 (dt, J=10.0, 7.3 Hz, 3H), 1.18 (t, J=6.9 Hz, 6H), 1.12 (t, J=7.3 Hz, 3H); $^{13}$C NMR (101 MHz, CDCl$_3$) δ 167.43, 165.14, 161.07, 148.57, 144.62, 129.93, 126.14, 113.06, 112.28, 55.82, 46.36, 39.68, 36.02, 29.31, 24.01, 15.31, 14.56; ESIMS m/z 364 ([M]$^+$).

Preparation of (Z)-1-ethyl-3-(2-ethyl-4-(5-fluoro-2-isopropylphenyl)-3-oxo-1,2,4-thiadiazolidin-5-ylidene)urea (CB44)

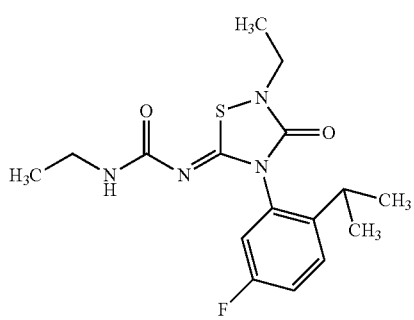

The title compound was prepared as described in Example 88 using N-(5-fluoro-2-isopropylphenyl)-1,2,3,4-thiatriazol-5-amine (CB39) and isolated as a dark brown oil (0.316 g, 37%): $^1$H NMR (400 MHz, CDCl$_3$) δ 7.41 (dd, J=8.8, 6.0 Hz, 1H), 7.21-7.13 (m, 1H), 6.92 (dd, J=8.7, 2.7 Hz, 1H), 5.46 (d, J=6.8 Hz, 1H), 3.75-3.56 (m, 2H), 3.36-3.15 (m, 2H), 2.72 (p, J=6.8 Hz, 1H), 1.34 (t, J=7.2 Hz, 3H), 1.18 (dd, J=10.9, 6.9 Hz, 6H), 1.13 (t, J=7.3 Hz, 3H); $^{19}$F NMR (376 MHz, CDCl$_3$) δ −115.44; ESIMS m/z 352 ([M]$^+$).

Preparation of (Z)-1-ethyl-3-(2-ethyl-4-(4-fluoro-2-isopropylphenyl)-3-oxo-1,2,4-thiadiazolidin-5-ylidene)urea (CB45)

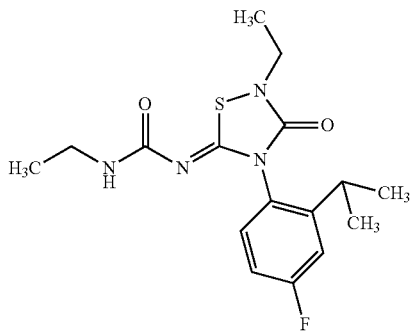 [SMILES: CCNC(=O)/N=c1\sn(CC)c(=O)n1-c1ccc(F)cc1C(C)C]

The title compound was prepared as described in Example 88 using N-(4-fluoro-2-isopropylphenyl)-1,2,3,4-thiatriazol-5-amine (CB40) and isolated as a red oil (0.340 g, 44%): $^1$H NMR (400 MHz, CDCl$_3$) δ 7.18-7.08 (m, 2H), 7.00 (ddd, J=8.7, 7.6, 2.9 Hz, 1H), 5.46 (t, J=5.8 Hz, 1H), 3.67 (q, J=7.2 Hz, 2H), 3.36-3.17 (m, 2H), 2.72 (td, J=6.8, 1.8 Hz, 1H), 1.33 (t, J=7.3 Hz, 3H), 1.22-1.07 (m, 9H); $^{19}$F NMR (376 MHz, CDCl$_3$) δ −111.31; ESIMS m/z 352 ([M]$^+$).

Preparation of (Z)-1-ethyl-3-(2-ethyl-4-(2-isopropylphenyl)-3-oxo-1,2,4-thiadiazolidin-5-ylidene)urea (CB46)

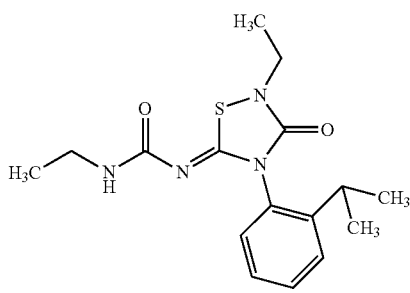 [SMILES: CCNC(=O)/N=c1\sn(CC)c(=O)n1-c1ccccc1C(C)C]

The title compound was prepared as described in Example 88 using N-(2-isopropylphenyl)-1,2,3,4-thiatriazol-5-amine (CB41) and isolated as a red oil (0.788 g, 87%): $^1$H NMR (400 MHz, CDCl$_3$) δ 7.48-7.44 (m, 2H), 7.34-7.28 (m, 1H), 7.19-7.15 (m, 1H), 3.68 (q, J=7.2 Hz, 2H), 3.34-3.19 (m, 3H), 2.75 (p, J=6.9 Hz, 1H), 1.34 (t, J=7.2 Hz, 3H), 1.20 (dd, J=7.8, 6.8 Hz, 6H), 1.12 (t, J=7.3 Hz, 3H); $^{13}$C NMR (101 MHz, CDCl$_3$) δ 167.07, 165.09, 152.63, 147.13, 133.37, 130.65, 128.95, 127.37, 127.30, 46.36, 39.67, 36.01, 29.08, 24.07, 15.32, 14.56; ESIMS m/z 334 ([M]$^+$).

Example 89

Preparation of 2-ethyl-4-(2-ethylphenyl)-5-imino-1,2,4-thiadiazolidin-3-one (CB47)

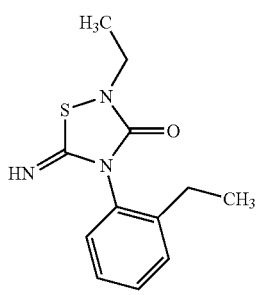

(Z)-1-Ethyl-3-(2-ethyl-4-(2-ethylphenyl)-3-oxo-1,2,4-thiadiazolidin-5-ylidene)urea (CB42) (0.484 g, 1.51 mmol) was dissolved in methanol (150 mL). Sodium hydroxide (3.36 g, 84.0 mmol) was slowly added and the reaction was stirred at room temperature. After 4 hours the solution was concentrated to ½ volume, poured onto water, and extracted with ethyl acetate. The organics were dried and concentrated to give the title compound as an orange solid (0.249 g, 65%): $^1$H NMR (400 MHz, CDCl$_3$) δ 7.35-7.32 (m, 2H), 7.30 (dd, J=5.4, 1.5 Hz, 1H), 7.25-7.20 (m, 1H), 3.65 (q, J=7.2 Hz, 2H), 3.39-3.19 (m, 1H), 2.73 (q, J=7.6 Hz, 2H), 1.26-1.13 (m, 6H); $^{13}$C NMR (101 MHz, CDCl$_3$) δ 173.32, 165.49, 141.20, 135.74, 130.42, 129.31, 127.67, 126.01, 39.50, 24.79, 15.22, 14.93; ESIMS m/z 250 ([M]$^+$).

The following compounds were prepared in accordance to the procedure in Example 89.

Preparation of 2-ethyl-5-imino-4-(2-isopropyl-4-methoxyphenyl)-1,2,4-thiadiazolidin-3-one (CB48)

The title compound was prepared as described in Example 89 using (Z)-1-ethyl-3-(2-ethyl-4-(2-isopropyl-4-methoxyphenyl)-3-oxo-1,2,4-thiadiazolidin-5-ylidene)urea (CB43) and isolated as a red oil (0.442 g, 63%): $^1$H NMR (400 MHz, CDCl$_3$) δ 7.22 (d, J=8.6 Hz, 1H), 6.90 (d, J=2.9 Hz, 1H), 6.74 (dd, J=8.7, 2.9 Hz, 1H), 3.83 (s, 3H), 3.68-3.57 (m, 2H), 3.24-3.13 (m, 2H), 1.20 (dd, J=8.5, 7.1 Hz, 9H); $^{13}$C NMR (101 MHz, CDCl$_3$) δ 165.84, 160.88, 148.76, 129.20, 126.94, 126.13, 113.50, 112.05, 55.90, 39.44, 28.90, 23.87, 15.23; ESIMS m/z 293 ([M]$^+$).

Preparation of 2-ethyl-4-(5-fluoro-2-isopropylphenyl)-5-imino-1,2,4-thiadiazolidin-3-one (CB49)

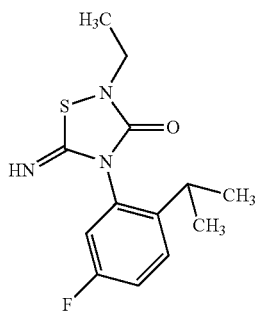

The title compound was prepared as described in Example 89 using (Z)-1-ethyl-3-(2-ethyl-4-(5-fluoro-2-isopropylphenyl)-3-oxo-1,2,4-thiadiazolidin-5-ylidene)urea (CB44) and isolated as a red solid (0.145 g, 56%): $^1$H NMR (400 MHz, CDCl$_3$) δ 7.38-7.28 (m, 1H), 7.06-6.94 (m, 2H), 3.64 (q, J=7.1 Hz, H), 3.18 (p, J=6.8 Hz, 1H), 1.30-1.05 (m, 10H); $^{19}$F NMR (376 MHz, CDCl$_3$) δ −115.44; ESIMS m/z 281 ([M]$^+$).

Preparation of 2-ethyl-4-(4-fluoro-2-isopropylphenyl)-5-imino-1,2,4-thiadiazolidin-3-one (CB50)

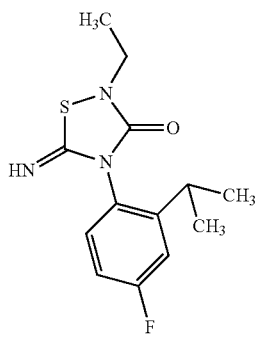 [SMILES: CCn1sc(=N)n(-c2ccc(F)cc2C(C)C)c1=O]

The title compound was prepared as described in Example 89 using (Z)-1-ethyl-3-(2-ethyl-4-(4-fluoro-2-isopropylphenyl)-3-oxo-1,2,4-thiadiazolidin-5-ylidene)urea (CB45) and isolated as a yellow oil (0.110 g, 38%): $^1$H NMR (400 MHz, CDCl$_3$) δ 7.32-7.25 (m, 1H), 7.08 (dd, J=9.9, 2.9 Hz, 1H), 6.92 (ddd, J=8.7, 7.6, 2.9 Hz, 1H), 3.75-3.57 (m, 3H), 3.32-3.13 (m, 1H), 1.23 (d, J=6.9 Hz, 6H), 1.19 (t, J=7.2 Hz, 3H); $^{19}$F NMR (376 MHz, CDCl$_3$) δ −110.83; ESIMS m/z 281 ([M]$^+$).

Preparation of 2-ethyl-5-imino-4-(2-isopropylphenyl)-1,2,4-thiadiazolidin-3-one (CB51)

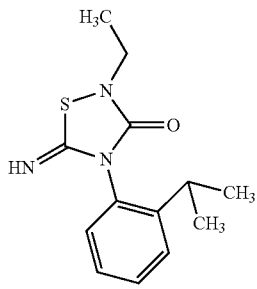 [SMILES: CCn1sc(=N)n(-c2ccccc2C(C)C)c1=O]

The title compound was prepared as described in Example 89 using (Z)-1-ethyl-3-(2-ethyl-4-(2-isopropylphenyl)-3-oxo-1,2,4-thiadiazolidin-5-ylidene)urea (CB46) and isolated as a red oil (0.421 g, 65%): $^1$H NMR (400 MHz, CDCl$_3$) δ 7.42-7.34 (m, 2H), 7.31-7.27 (m, 1H), 7.22 (dd, J=9.2, 6.5 Hz, 1H), 4.06 (s, 1H), 3.65 (d, J=8.5 Hz, 2H), 3.34-3.13 (m, 1H), 1.21 (m, 9H); ESIMS m/z 263 ([M]$^+$).

Example 90

Preparation of (Z)-1-(2-ethyl-4-(2-ethylphenyl)-3-oxo-1,2,4-thiadiazolidin-5-ylidene)-3-(4-(1-(4-(trifluoromethoxy)phenyl)-1H-1,2,4-triazol-3-yl)phenethyl)urea (FB10)

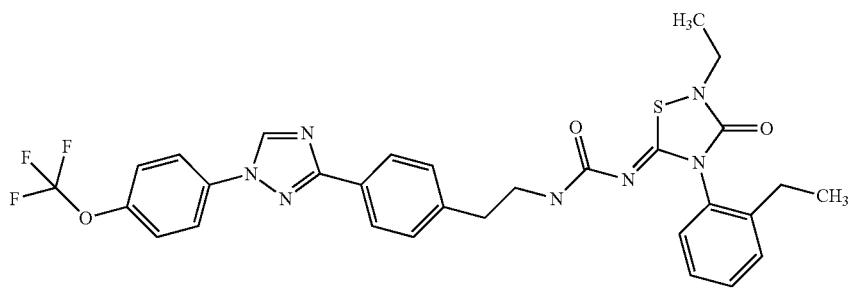 [SMILES: CCc1ccccc1-n1c(=O)n(CC)s/c1=N\C(=O)NCCc1ccc(-c2ncn(-c3ccc(OC(F)(F)F)cc3)n2)cc1]

A solution of 3-(4-(1-(4-(trifluoromethoxy)phenyl)-1H-1,2,4-triazol-3-yl)phenyl)propanoyl azide (C34) (0.100 g, 0.249 mmol) in acetonitrile (4 mL) was heated at 70° C. for 2 hours. The reaction was cooled to room temperature, and then 2-ethyl-4-(2-ethylphenyl)-5-imino-1,2,4-thiadiazolidin-3-one (CB47) (0.0660 g, 0.265 mmol) in tetrahydrofuran and triethylamine (3 drops) were added. The reaction was stirred overnight. The solution was diluted in ethyl acetate and washed with water. The organics were extracted, dried, and concentrated. Purification by reverse-phase preparative HPLC using 0-90% acetonitrile/water (0.1% acetic acid) as eluent provided the title compound as a white solid (0.045 g, 26%).

The following compounds were prepared in accordance to the procedure in Example 90.

Preparation of (Z)-1-(2-ethyl-4-(2-isopropyl-4-methoxyphenyl)-3-oxo-1,2,4-thiadiazolidin-5-ylidene)-3-(4-(1-(4-(trifluoromethoxy)phenyl)-1H-1,2,4-triazol-3-yl)phenethyl)urea (FB11)

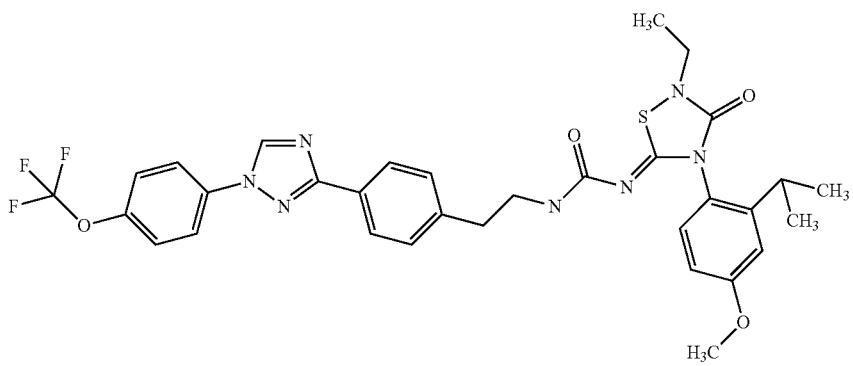 [SMILES: CCn1s/c(=N\C(=O)NCCc2ccc(-c3ncn(-c4ccc(OC(F)(F)F)cc4)n3)cc2)n(-c2ccc(OC)cc2C(C)C)c1=O]

The title compound was prepared as described in Example 90 using 3-(4-(1-(4-(trifluoromethoxy)phenyl)-1H-1,2,4-triazol-3-yl)phenyl)propanoyl azide (C34) and 2-ethyl-5-imino-4-(2-isopropyl-4-methoxyphenyl)-1,2,4-thiadiazolidin-3-one (CB48) and isolated as a yellow solid (0.016 g, 7%).

Preparation of (Z)-1-(2-ethyl-4-(5-fluoro-2-isopropylphenyl)-3-oxo-1,2,4-thiadiazolidin-5-ylidene)-3-(4-(1-(4-(trifluoromethoxy)phenyl)-1H-1,2,4-triazol-3-yl)phenethyl)urea (FB12)

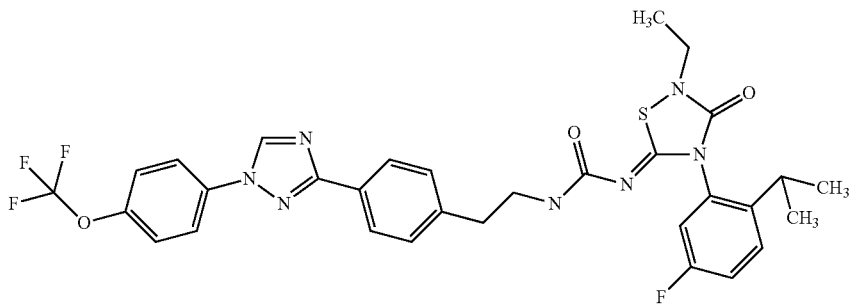 [SMILES: CCn1s/c(=N\C(=O)NCCc2ccc(-c3ncn(-c4ccc(OC(F)(F)F)cc4)n3)cc2)n(-c2cc(F)ccc2C(C)C)c1=O]

The title compound was prepared as described in Example 90 using 3-(4-(1-(4-(trifluoromethoxy)phenyl)-1H-1,2,4-triazol-3-yl)phenyl)propanoyl azide (C34) and 2-ethyl-4-(5-fluoro-2-isopropylphenyl)-5-imino-1,2,4-thiadiazolidin-3-one (CB49) and isolated as a yellow oil (0.068 g, 40%).

Preparation of (Z)-1-(2-ethyl-4-(4-fluoro-2-isopropylphenyl)-3-oxo-1,2,4-thiadiazolidin-5-ylidene)-3-(4-(1-(4-(trifluoromethoxy)phenyl)-1H-1,2,4-triazol-3-yl)phenethyl)urea (FB13)

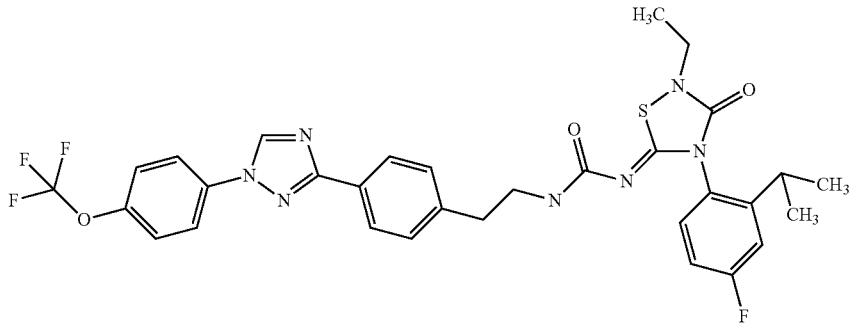 [SMILES: CCn1s/c(=N\C(=O)NCCc2ccc(-c3ncn(-c4ccc(OC(F)(F)F)cc4)n3)cc2)n(-c2ccc(F)cc2C(C)C)c1=O]

The title compound was prepared as described in Example 90 using 3-(4-(1-(4-(trifluoromethoxy)phenyl)-1H-1,2,4-triazol-3-yl)phenyl)propanoyl azide (C34) and 2-ethyl-4-(4-fluoro-2-isopropylphenyl)-5-imino-1,2,4-thiadiazolidin-3-one (CB50) and isolated as a yellow oil (0.018 g, 14%).

Preparation of (Z)-1-(2-ethyl-4-(2-isopropylphenyl)-3-oxo-1,2,4-thiadiazolidin-5-ylidene)-3-(4-(1-(4-(trifluoromethoxy)phenyl)-1H-1,2,4-triazol-3-yl)phenethyl)urea (FB14)

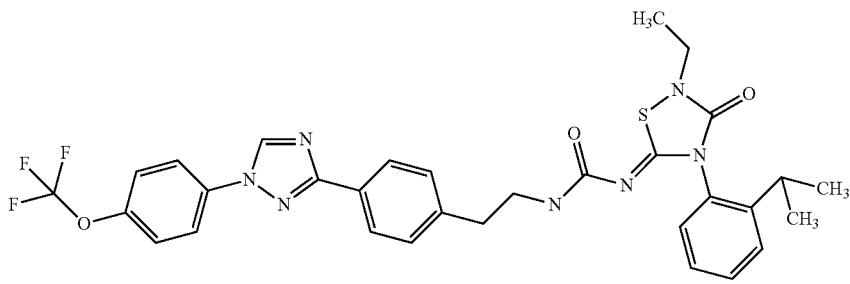 [SMILES: CCn1s/c(=N\C(=O)NCCc2ccc(-c3ncn(-c4ccc(OC(F)(F)F)cc4)n3)cc2)n(-c2ccccc2C(C)C)c1=O]

The title compound was prepared as described in Example 90 using 3-(4-(1-(4-(trifluoromethoxy)phenyl)-1H-1,2,4-triazol-3-yl)phenyl)propanoyl azide (C34) and 2-ethyl-5-imino-4-(2-isopropylphenyl)-1,2,4-thiadiazolidin-3-one (CB51) and isolated as a yellow solid (0.047 g, 23%).

Example 91

Preparation of N-(2-ethyl-4-methoxyphenyl)hydrazinecarbothioamide (CB52)

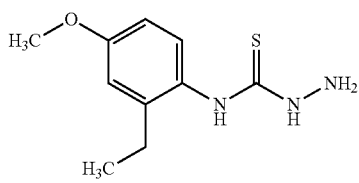

Step 1.
To solution of 2-ethyl-4-methoxyaniline (4.5 g, 30 mmol) and triethylamine (6.0 g, 60 mmol) in dichloromethane (31 mL) was added thiophosgene (3.4 g, 30 mmol) was added drop wise at 0° C. over the period of 1 hour. After completion, the reaction mixture was poured into ice-water (100 mL) and extracted with ethyl acetate (3×200 mL) and washed with ice water (2×100 mL), followed by brine (2×50 mL). The organic phase was dried over sodium sulfate, filtered, and evaporated under reduced pressure. Purification by flash column chromatography using 0-10% ethyl acetate/hexanes as eluent provided 2-ethyl-1-isothiocyanato-4-methoxybenzene as yellow oil (4.9 g, 25 mmol), which was taken onto the next step immediately.

Step 2.
To a solution of 2-ethyl-1-isothiocyanato-4-methoxybenzene (4.9 g, 25 mmol) in ethanol (22 mL), was added slowly, hydrazine hydrate (1.3 g, 28 mmol). The reaction mixture was stirred at room temperature for 18 hours. The reaction mixture was evaporated under reduced pressure and diluted with ethyl acetate (250 mL) and washed with water (2×50 mL), followed by brine (2×50 mL). The organic phase was dried over sodium sulfate, filtered, and evaporated under reduced pressure. Purification by flash column chromatography using 0-40% ethyl acetate/hexanes as eluent provided the title compound as a white solid (4.9 g, 86%): mp 113-115° C.; $^1$H NMR (400 MHz, DMSO-d$_6$) δ 9.19 (s, 1H), 8.89 (s, 1H), 7.20-7.19 (m, 1H), 6.77-6.71 (m, 2H), 4.71 (bs, 2H), 3.74 (s, 3H), 2.52-2.47 (m, 2H), 1.13-1.08 (m, 3H); ESIMS m/z 224 ([M–H]$^-$).

The following compounds were prepared in accordance to the procedure in Example 91.

Preparation of N-(2-isopropyl-4-methoxyphenyl) hydrazinecarbothioamide (CB53)

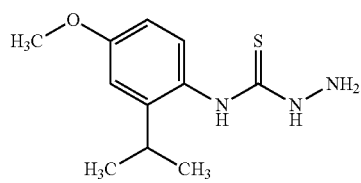 [SMILES: COc1ccc(NC(=S)NN)c(C(C)C)c1]

The title compound was prepared as described in Example 88 using 2-isopropyl-4-methoxyaniline and isolated as a white solid (9.5 g): mp 153-156° C., $^1$H NMR (400 MHz, DMSO-d$_6$) δ 9.18 (s, 1H), 8.96 (s, 1H), 7.12-7.10 (m, 1H), 6.78-6.78 (m, 2H), 4.71 (bs, 2H), 3.17 (s, 3H), 3.05-3.00 (m, 1H), 1.14 (d, J=6.6 Hz, 6H); ESIMS m/z 238 ([M–H]$^-$).

Example 92

Preparation of 3-(4-(7-oxabicyclo[4.1.0]heptan-1-yl) phenyl)-1-(4-(trifluoromethoxy)phenyl)-1H-1,2,4-triazole (CB54)

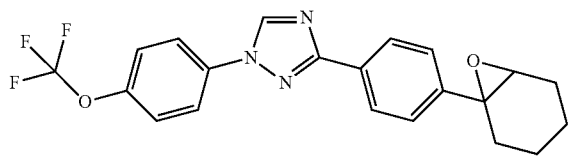 [SMILES: FC(F)(F)Oc1ccc(-n2cnc(-c3ccc(C45CCCCC4O5)cc3)n2)cc1]

To a solution of 3-(2',3',4',5'-tetrahydro-[1,1'-biphenyl]-4-yl)-1-(4-(trifluoromethoxy)phenyl)-1H-1,2,4-triazole (CB10) (3.11 g, 8.07 mmol) in diethyl ether (60 mL) was added meta-chloroperoxybenzoic acid (70%; 2.79 g, 11.3 mmol) slowly at 0° C. The reaction was stirred and allowed to gradually warm to room temperature, then stirring was continued for 18 hours. The solution was diluted in diethyl ether, washed with sodium bicarbonate, extracted with diethyl ether, washed with water, and extracted again with diethyl ether. The organics were dried, filtered, and concentrated providing the title compound as a white solid (2.5 g, 77%) which was used without further purification: $^1$H NMR (400 MHz, CDCl$_3$) δ 8.58 (s, 1H), 8.20-8.11 (m, 2H), 7.84-7.77 (m, 2H), 7.52-7.46 (m, 2H), 7.39 (dt, J=8.0, 1.0 Hz, 2H), 3.12 (dd, J=3.1, 1.7 Hz, 1H), 2.34 (ddd, J=14.9, 8.5, 5.3 Hz, 1H), 2.09-1.95 (m, 2H), 1.74-1.45 (m, 4H), 1.42-1.28 (m, 1H); $^{19}$F NMR (376 MHz, CDCl$_3$) δ –58.03; ESIMS m/z 402 ([M+H]$^+$).

Example 93

Preparation of 2-(4-(1-(4-(trifluoromethoxy)phenyl)-1H-1,2,4-triazol-3-yl)phenyl)cyclohexanone (CB55)

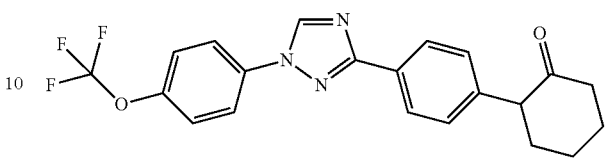

To a stirred solution of indium chloride (1.259 g, 5.69 mmol) in 15 mL of dry THF in a 100 mL flask was added a solution of 3-(4-(7-oxabicyclo[4.1.0]heptan-1-yl)phenyl)-1-(4-(trifluoromethoxy)phenyl)-1H-1,2,4-triazole (CB54) (1.14 g, 2.85 mmol) in dry tetrahydrofuran (10 mL). Stirring was continued under nitrogen for 24 hours, then the solution was diluted with diethyl ether (50 mL) and washed with water, dried, and concentrated in vacuo. Purification by flash column chromatography using 0-60% ethyl acetate/hexanes as eluent provided the title compound as a white solid (0.566 g, 35%): $^1$H NMR (400 MHz, CDCl$_3$) δ $^1$H NMR (400 MHz, CDCl$_3$) δ 8.54 (s, 1H), 8.16 (dd, J=8.6, 2.1 Hz, 2H), 7.83-7.72 (m, 2H), 7.43-7.33 (m, 2H), 7.30-7.21 (m, 2H), 3.68 (dd, J=12.2, 5.4 Hz, 1H), 2.61-2.41 (m, 2H), 2.37-2.24 (m, 1H), 2.23-1.92 (m, 3H), 1.85-1.60 (m, 2H); $^{19}$F NMR (376 MHz, CDCl$_3$) δ –58.03; ESIMS m/z 402 ([M+H]$^+$).

Example 94

Preparation of 2-(4-(1-(4-(trifluoromethoxy)phenyl)-1H-1,2,4-triazol-3-yl)phenyl)cyclohexanamine (CB56)

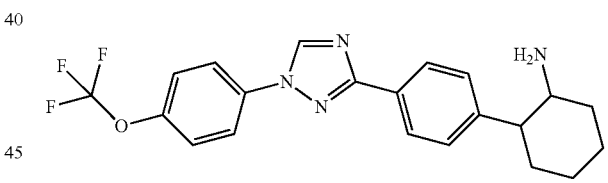

To a dry flask was added a solution of 2-(4-(1-(4-(trifluoromethoxy)phenyl)-1H-1,2,4-triazol-3-yl)phenyl)cyclohexanone (CB55) (0.98 g, 2.4 mmol) in dry methanol (30 mL). The flask was evacuated/backfilled with nitrogen and ammonium acetate (2.6 g, 34 mmol) was added, followed by sodium cyanoborohydride (0.18 g, 2.9 mmol). The reaction was stirred at room temperature overnight. The solution was quenched with water and extracted with ethyl acetate. The organics were dried, filtered, and concentrated to provide the title compound as a white solid (0.42 g, 34%): $^1$H NMR indicated the presence of 2 isomers, which were not separated. $^1$H NMR (400 MHz, DMSO-d$_6$) δ 9.41 (two s, 1H), 8.14-8.03 (m, 4H), 7.66-7.60 (m, 2H), 7.53-7.40 (m, 2H), 3.47-3.16 (br s, 2H), 3.29 (td, J=11.0, 3.8 Hz, 1H), 2.59 (td, J=11.6, 11.1, 3.7 Hz, 1H), 2.17-2.04 (m, 1H), 1.86-1.68 (m, 3H), 1.68-1.30 (m, 4H); ESIMS m/z 402 ([M]$^+$).

Example 95

Preparation of (Z)-1-(3-(2-isopropyl-5-methylphenyl)-4-oxothiazolidin-2-ylidene)-3-(2-(4-(1-(4-(trifluoromethoxy)phenyl)-1H-1,2,4-triazol-3-yl)phenyl)cyclohexyl)urea (FB15)

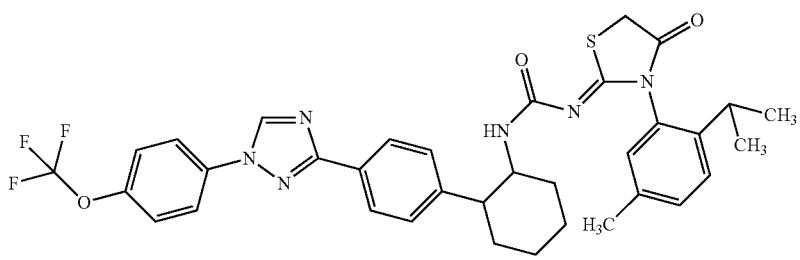 [SMILES: Cc1ccc(C(C)C)c(N2C(=O)CS/C2=N\C(=O)NC2CCCCC2c2ccc(-c3ncn(-c4ccc(OC(F)(F)F)cc4)n3)cc2)c1]

To 2-(4-(1-(4-(trifluoromethoxy)phenyl)-1H-1,2,4-triazol-3-yl)phenyl)cyclohexanamine (CB56) (0.200 g, 0.497 mmol) and (Z)-4-nitrophenyl (3-(2-isopropyl-5-methylphenyl)-4-oxothiazolidin-2-ylidene)carbamate (CA50) (0.205 g, 0.497 mmol) were dissolved in acetonitrile (10 mL) in a vial. Cesium carbonate (0.162 g, 0.497 mmol) was added, and the reaction was stirred at room temperature for 25 hours. The solution was adsorbed onto silica. Purification by reverse-phase flash column chromatography using 0-100% acetonitrile/water as eluent afforded the title compound as a red oil (0.020 g, 6%).

The following compounds were prepared in accordance to the procedure in Example 95.

Preparation of (Z)-3-(3-(2-isopropyl-5-methylphenyl)-4-oxothiazolidin-2-ylidene)-1-methyl-1-(4-(1-(4-(trifluoromethoxy)phenyl)-1H-1,2,4-triazol-3-yl)phenethyl)urea (FB51)

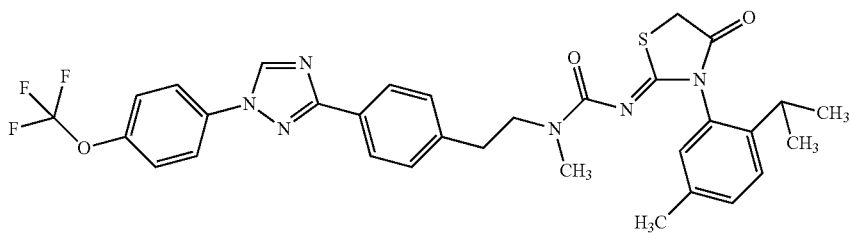 [SMILES: Cc1ccc(C(C)C)c(N2C(=O)CS/C2=N\C(=O)N(C)CCc2ccc(-c3ncn(-c4ccc(OC(F)(F)F)cc4)n3)cc2)c1]

The title compound was prepared as described in Example 95 using N-methyl-2-(4-(1-(4-(trifluoromethoxy)phenyl)-1H-1,2,4-triazol-3-yl)phenyl)ethanamine (CB24) and (Z)-4-nitrophenyl (3-(2-isopropyl-5-methylphenyl)-4-oxothiazolidin-2-ylidene)carbamate (CA50), purified by flash column chromatography using 0-100% ethyl acetate/B, where B=1:1 dichloromethane/hexanes, as eluent and isolated as a pale orange foam (0.160 g, 63%).

Preparation of (Z)-1-(3-(2-isopropyl-5-methylphenyl)-4-oxothiazolidin-2-ylidene)-3-(2-methyl-1-(4-(1-(4-(trifluoromethoxy)phenyl)-1H-1,2,4-triazol-3-yl)phenyl)propan-2-yl)urea (FB52)

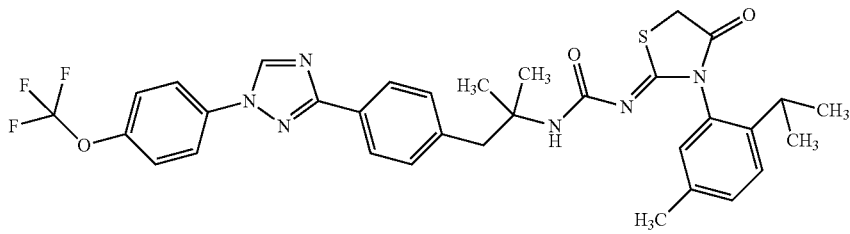 [SMILES: Cc1ccc(C(C)C)c(N2C(=O)CS/C2=N\C(=O)NC(C)(C)Cc2ccc(-c3ncn(-c4ccc(OC(F)(F)F)cc4)n3)cc2)c1]

The title compound was prepared as described in Example 95 using 2-methyl-1-(4-(1-(4-(trifluoromethoxy)phenyl)-1H-1,2,4-triazol-3-yl)phenyl)propan-2-amine (CB28) and (Z)-4-nitrophenyl (3-(2-isopropyl-5-methylphenyl)-4-oxothiazolidin-2-ylidene)carbamate (CA50), purified by flash column chromatography using 0-100% ethyl acetate/B, where B=1:1 dichloromethane/hexanes, as eluent and isolated as a brown oil (0.018 g, 9%).

Preparation of (Z)-1-(3-(2-isopropyl-5-methylphenyl)-4-oxothiazolidin-2-ylidene)-3-(2-methyl-2-(4-(1-(4-(trifluoromethoxy)phenyl)-1H-1,2,4-triazol-3-yl)phenyl)propyl)urea (FB53)

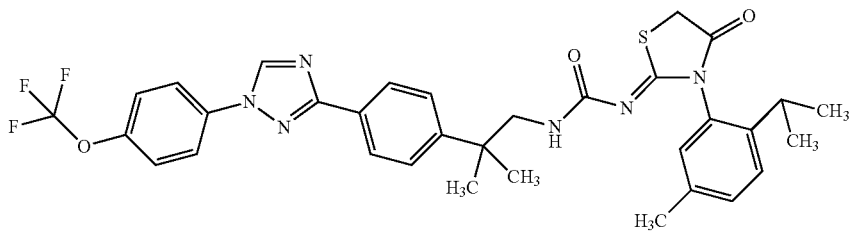 [SMILES: Cc1ccc(C(C)C)c(N2C(=O)CS/C2=N\C(=O)NCC(C)(C)c2ccc(-c3ncn(-c4ccc(OC(F)(F)F)cc4)n3)cc2)c1]

The title compound was prepared as described in Example 95 using 2-methyl-2-(4-(1-(4-(trifluoromethoxy)phenyl)-1H-1,2,4-triazol-3-yl)phenyl)propan-1-amine (CB29) and (Z)-4-nitrophenyl (3-(2-isopropyl-5-methylphenyl)-4-oxothiazolidin-2-ylidene)carbamate (CA50), purified by flash column chromatography using 0-100% ethyl acetate/B, where B=1:1 dichloromethane/hexanes, as eluent and isolated as a brown glassy foam (0.084 g, 46%).

Preparation of (Z)-1-ethyl-3-(3-(2-isopropyl-5-methylphenyl)-4-oxothiazolidin-2-ylidene)-1-(4-(1-(4-(trifluoromethoxy)phenyl)-1H-1,2,4-triazol-3-yl)phenethyl)urea (FB54)

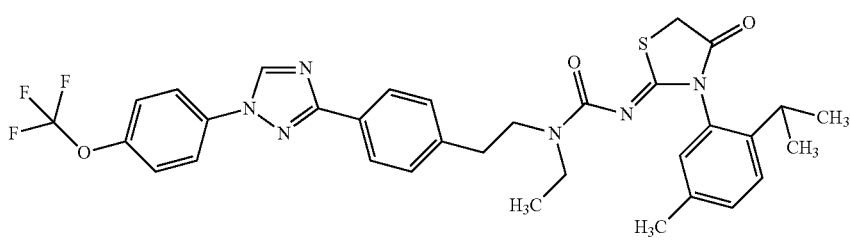 [SMILES: CCN(CCc1ccc(-c2ncn(-c3ccc(OC(F)(F)F)cc3)n2)cc1)C(=O)/N=C1\SCC(=O)N1c1cc(C)ccc1C(C)C]

The title compound was prepared as described in Example 95 using N-ethyl-2-(4-(1-(4-(trifluoromethoxy)phenyl)-1H-1,2,4-triazol-3-yl)phenyl)ethanamine (CB25) and (Z)-4-nitrophenyl (3-(2-isopropyl-5-methylphenyl)-4-oxothiazolidin-2-ylidene)carbamate (CA50), purified by flash column chromatography using 0-100% ethyl acetate/B, where B=1:1 dichloromethane/hexanes, as eluent and isolated as a red solid (0.075 g, 56%).

Preparation of (Z)-1-allyl-3-(3-(2-isopropyl-5-methylphenyl)-4-oxothiazolidin-2-ylidene)-1-(4-(1-(4-(trifluoromethoxy)phenyl)-1H-1,2,4-triazol-3-yl)phenethyl)urea (FB61)

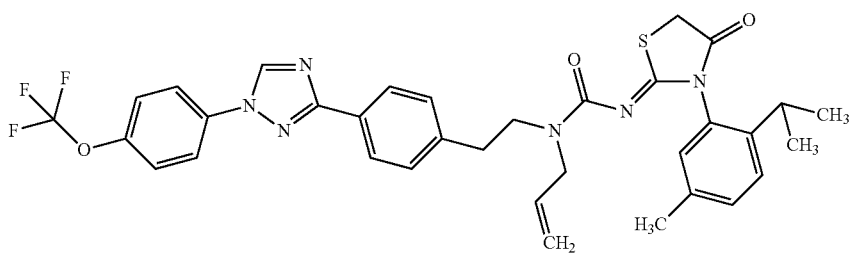 [SMILES: C=CCN(CCc1ccc(-c2ncn(-c3ccc(OC(F)(F)F)cc3)n2)cc1)C(=O)/N=C1\SCC(=O)N1c1cc(C)ccc1C(C)C]

The title compound was prepared as described in Example 95 using N-(4-(1-(4-(trifluoromethoxy)phenyl)-1H-1,2,4-triazol-3-yl)phenethyl)prop-2-en-1-amine (CB26) and (Z)-4-nitrophenyl (3-(2-isopropyl-5-methylphenyl)-4-oxothiazolidin-2-ylidene)carbamate (CA50), purified by flash column chromatography using 0-100% ethyl acetate/B, where B=1:1 dichloromethane/hexanes, as eluent and isolated as a brown oil (0.040 g, 43%).

Preparation of (Z)-1-(cyclopropylmethyl)-3-(3-(2-isopropyl-5-methylphenyl)-4-oxothiazolidin-2-ylidene)-1-(4-(1-(4-(trifluoromethoxy)phenyl)-1H-1,2,4-triazol-3-yl)phenethyl)urea (FB62)

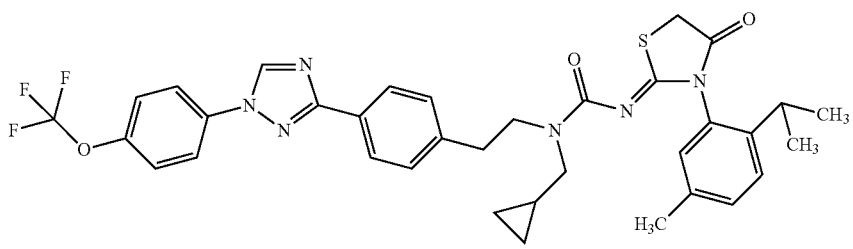 [SMILES: Cc1ccc(C(C)C)c(N2C(=O)CS/C2=N\C(=O)N(CCc2ccc(-c3ncn(-c4ccc(OC(F)(F)F)cc4)n3)cc2)CC2CC2)c1]

The title compound was prepared as described in Example 95 using N-(cyclopropylmethyl)-2-(4-(1-(4-(trifluoromethoxy)phenyl)-1H-1,2,4-triazol-3-yl)phenyl)ethanamine (CB27) and (Z)-4-nitrophenyl (3-(2-isopropyl-5-methylphenyl)-4-oxothiazolidin-2-ylidene)carbamate (CA50), purified by flash column chromatography using 0-100% ethyl acetate/B, where B=1:1 dichloromethane/hexanes, as eluent and isolated as red-orange oil (0.127 g, 60%).

Preparation of (Z)-1-(3-(2-isopropyl-5-methylphenyl)-4-oxothiazolidin-2-ylidene)-3-(1-(4-(1-(4-(trifluoromethoxy)phenyl)-1H-1,2,4-triazol-3-yl)benzyl)cyclopropyl)urea (FB63)

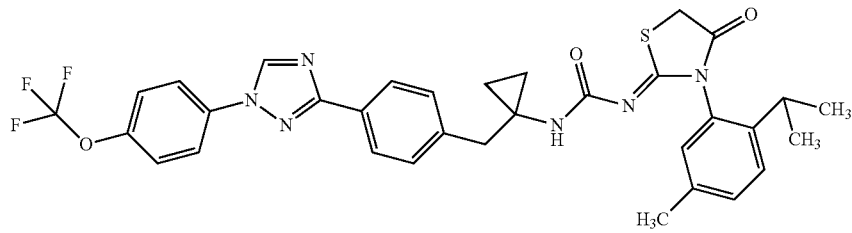 [SMILES: Cc1ccc(C(C)C)c(N2C(=O)CS/C2=N\C(=O)NC2(Cc3ccc(-c4ncn(-c5ccc(OC(F)(F)F)cc5)n4)cc3)CC2)c1]

The title compound was prepared as described in Example 95 using 1-(4-(1-(4-(trifluoromethoxy)phenyl)-1H-1,2,4-triazol-3-yl)benzyl)cyclopropanamine (CB30) and (Z)-4-nitrophenyl (3-(2-isopropyl-5-methylphenyl)-4-oxothiazolidin-2-ylidene)carbamate (CA50), purified by flash column chromatography using 0-100% ethyl acetate/B, where B=1:1 dichloromethane/hexanes, as eluent and isolated as red oil (0.104 g, 37%).

Example 96

Preparation of (Z)-1-(3-(2-isopropyl-5-methylphenyl)-4-oxo-1,3-thiazinan-2-ylidene)-3-(4-(1-(4-(trifluoromethoxy)phenyl)-1H-1,2,4-triazol-3-yl)phenethyl)urea (FB41)

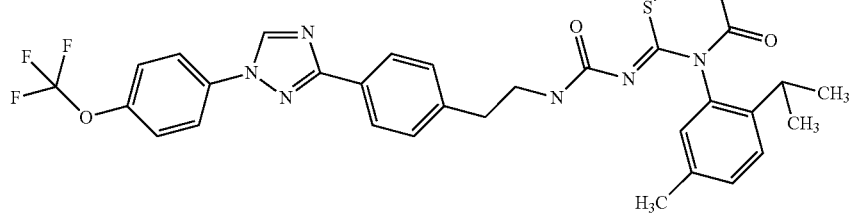

3-(4-(2-Isocyanatoethyl)phenyl)-1-(4-(trifluoromethoxy)phenyl)-1H-1,2,4-triazole (C34a) (0.18 g, 0.47 mmol), 1-(2-isopropyl-5-methylphenyl)thiourea (0.10 g, 0.50 mmol), and cesium carbonate (0.21 g, 0.63 mmol) in acetonitrile (2.3 mL) were stirred at room temperature overnight. The reaction was diluted with ethyl acetate and washed with water. The organic layers were dried over sodium sulfate, filtered, and concentrated. The crude material was dissolved in butanone (2.3 mL) followed by addition of acryloyl chloride (0.045 mL, 0.55 mmol). The reaction was heated at 40° C. for 4 hours. The reaction was cooled and concentrated. Purification by flash column chromatography using 0-100% ethyl acetate/B, where B=1:1 dichloromethane/hexanes, as eluent followed by drying in a vacuum oven provided the title compound as a yellow oil (0.13 g, 44%).

Example 97

Preparation of 1-(4-(1-(4-(trifluoromethoxy)phenyl)-1H-1,2,4-triazol-3-yl)phenyl)propan-2-one (CB57)

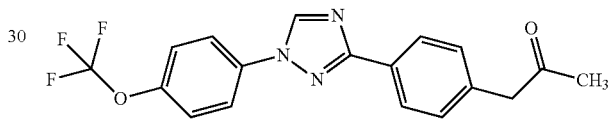

3-(4-Bromophenyl)-1-(4-(trifluoromethoxy)phenyl)-1H-1,2,4-triazole (C52) (11 g, 29 mmol), copper(I) iodide (0.55 g, 2.9 mmol), potassium phosphate (18 g, 86 mmol), and pentane-2,4-dione (8.9 mL, 86 mmol) were dissolved in dimethylsulfoxide (120 mL) in a 500 mL round bottomed flask. The reaction was heated at 110° C. for 19 hours. The solution was cooled to room temperature and then quenched with hydrogen chloride (2 N). The excess base was removed by gravity filtration and the filtrate was extracted with ethyl acetate. The organics were washed with water, extracted, dried, and concentrated. Purification by flash column chromatography using 0-30% ethyl acetate/hexanes afforded the title compound as a pure orange solid (3.7 g, 35%): $^1$H NMR (400 MHz, CDCl$_3$) δ 8.56 (s, 1H), 8.17 (d, J=8.2 Hz, 2H), 7.80 (d, J=9.0 Hz, 2H), 7.39 (dt, J=8.1, 1.0 Hz, 2H), 7.33 (dd, J=8.1, 0.6 Hz, 2H), 3.76 (s, 2H), 2.19 (s, 3H); ESIMS m/z 361 ([M]$^+$).

Example 98

Preparation of 1-(4-(1-(4-(trifluoromethoxy)phenyl)-1H-1,2,4-triazol-3-yl)phenyl)propan-2-amine (CB58)

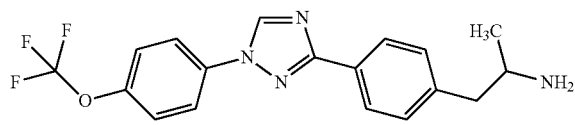

1-(4-(1-(4-(Trifluoromethoxy)phenyl)-1H-1,2,4-triazol-3-yl)phenyl)propan-2-one (CB57) (1.0 g, 2.8 mmol) and ammonium acetate (1.7 g, 22 mmol) were combined in dry methanol (22 mL) and stirred at room temperature while sodium cyanoborohydride (0.17 g, 2.7 mmol) was added in 3 equal portions over 30 minutes. The reaction was stirred overnight. The reaction was concentrated and partitioned between aqueous potassium carbonate and diethyl ether. The layers were separated, dried, filtered, and concentrated. Purification by reverse-phase flash column (C18) chromatography using 0-100% acetonitrile/water as eluent provided the title compound as a tan solid (1.0 g, 38%): mp 140-160° C.; $^1$H NMR (400 MHz, CDOD$_3$) d 9.13 (s, 1H), 8.09 (d, J=8.0 Hz, 2H), 8.00 (d, J=9.0 Hz, 2H), 7.52-7.43 (m, 2H), 7.35 (d, J=8.0 Hz, 2H), 3.40-3.33 (m, 1H), 2.86 (t, J=6.7 Hz, 1H), 2.77 (dd, J=13.3, 7.3 Hz, 1H), 1.18 (d, J=6.2 Hz, 3H) (NH$_2$ not observed); ESIMS m/z 363 ([M+H]$^+$).

Example 99

Preparation of (R)-1-(4-(1-(4-(trifluoromethoxy)phenyl)-1H-1,2,4-triazol-3-yl)phenyl)propan-2-amine (2S,3S)-2,3-dihydroxysuccinate (CB59)

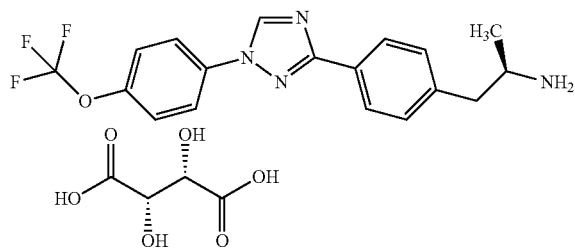

To 1-(4-(1-(4-(trifluoromethoxy)phenyl)-1H-1,2,4-triazol-3-yl)phenyl)propan-2-amine (CB58) (0.60 g, 1.7 mmol) in methanol (10 mL) was added (2S,3S)-2,3-dihydroxysuccinic acid (0.25 g, 1.7 mmol). The resultant solid was filtered and air dried overnight: mp 182-185° C. The solid was redissolved in methanol (10 mL) and heated to reflux (~65° C.). The solution was cooled to room temperature and let stand overnight. The white solid that formed was filtered and air-dried to give the title compound as a white solid (0.40 g, 46%): mp 191-194° C.; $^1$H NMR (400 MHz, CDOD$_3$) d 9.16 (s, 1H), 8.15 (d, J=8.2 Hz, 2H), 8.02 (d, J=9.1 Hz, 2H), 7.50 (dd, J=9.2, 1.0 Hz, 2H), 7.41 (d, J=8.2 Hz, 2H), 4.40 (s, 2H), 3.59 (dt, J=8.1, 6.2 Hz, 1H), 3.07 (dd, J=13.6, 6.1 Hz, 1H), 2.88 (dd, J=13.6, 8.3 Hz, 1H), 1.29 (d, J=6.5 Hz, 3H) (OH and NH$_2$ not observed).

The following compounds were prepared in accordance to the procedure in Example 99.

Preparation of (S)-1-(4-(1-(4-(trifluoromethoxy)phenyl)-1H-1,2,4-triazol-3-yl)phenyl)propan-2-amine (2R,3R)-2,3-dihydroxysuccinate (CB60)

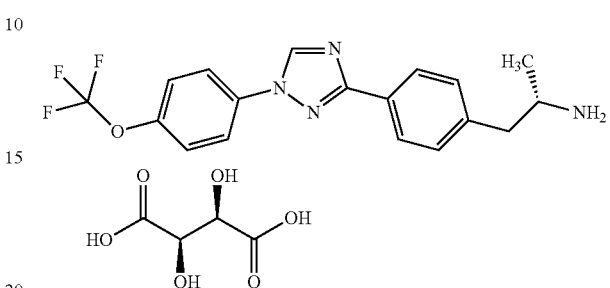

The title compound was prepared as described in Example 99 using 1-(4-(1-(4-(trifluoromethoxy)phenyl)-1H-1,2,4-triazol-3-yl)phenyl)propan-2-amine (CB58) and (2R,3R)-2,3-dihydroxysuccinic acid and isolated as a white solid (0.70 g, 49%): mp 187-191° C.; $^1$H NMR $^1$H NMR (400 MHz, DMSO-d$_6$) δ 9.40 (s, 1H), 8.08 (dd, J=8.6, 3.6 Hz, 4H), 7.63 (dt, J=8.1, 1.0 Hz, 2H), 7.49-7.32 (m, 2H), 3.81 (s, 2H), 3.47 (dt, J=8.5, 6.2 Hz, 1H), 3.01 (dd, J=13.4, 5.5 Hz, 1H), 2.74 (dd, J=13.4, 8.7 Hz, 1H), 1.13 (d, J=6.4 Hz, 3H) (OH and NH$_2$ not observed).

Example 100

Preparation of (R)-1-(4-(1-(4-(trifluoromethoxy)phenyl)-1H-1,2,4-triazol-3-yl)phenyl)propan-2-amine (CB61)

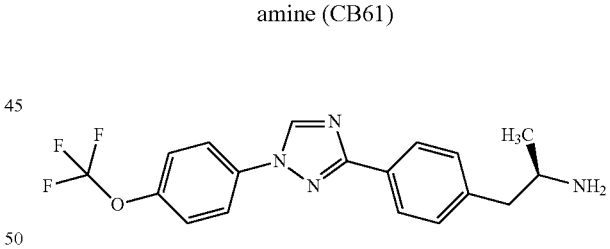

(R)-1-(4-(1-(4-(Trifluoromethoxy)phenyl)-1H-1,2,4-triazol-3-yl)phenyl)propan-2-amine (2S,3S)-2,3-dihydroxysuccinate (CB59) (0.35 g, 0.68 mmol) was slurried in methanol (20 mL) and SCX silica gel (2 g). The solution was stirred for 3 hours, filtered, and washed with methanol (20 mL). The compound was eluted from the SCX silica gel using ammonium hydroxide (5% in MeOH, 25 mL). The filtrate was concentrated providing the title compound as a white solid (0.22 g, 87%): mp 84-88° C.; $^1$H NMR (400 MHz, CDCl$_3$) δ 8.56 (s, 1H), 8.13 (d, J=8.2 Hz, 2H), 7.80 (d, J=9.0 Hz, 2H), 7.44-7.35 (m, 2H), 7.31 (d, J=8.1 Hz, 2H), 3.29-3.15 (m, 1H), 2.78 (dd, J=13.2, 5.4 Hz, 1H), 2.60 (dd, J=13.2, 8.0 Hz, 1H), 1.49 (s, 2H), 1.15 (d, J=6.3 Hz, 3H).

The following compounds were prepared in accordance to the procedure in Example 100.

Preparation of (S)-1-(4-(1-(4-(trifluoromethoxy)phenyl)-1H-1,2,4-triazol-3-yl)phenyl)propan-2-amine (CB62)

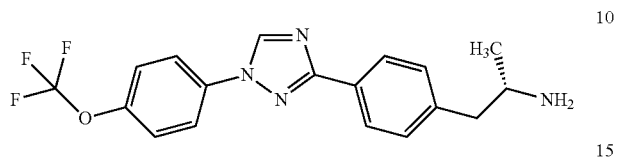

The title compound was prepared as described in Example 100 using (S)-1-(4-(1-(4-(trifluoromethoxy)phenyl)-1H-1,2,4-triazol-3-yl)phenyl)propan-2-amine (2R,3R)-2,3-dihydroxysuccinate (CB60) and isolated as a white solid (0.40 g, 94%): mp 84-86° C., $^1$H NMR (400 MHz, CDCl$_3$) δ 8.56 (s, 1H), 8.13 (d, J=8.2 Hz, 2H), 7.80 (d, J=9.0 Hz, 2H), 7.44-7.35 (m, 2H), 7.35-7.28 (m, 2H), 3.29-3.16 (m, 1H), 2.78 (dd, J=13.2, 5.3 Hz, 1H), 2.60 (dd, J=13.2, 8.0 Hz, 1H), 1.15 (d, J=6.3 Hz, 3H) (NH$_2$ not observed).

Example 101

Preparation of (R,Z)-1-(3-(2-isopropyl-5-methylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (FB45)

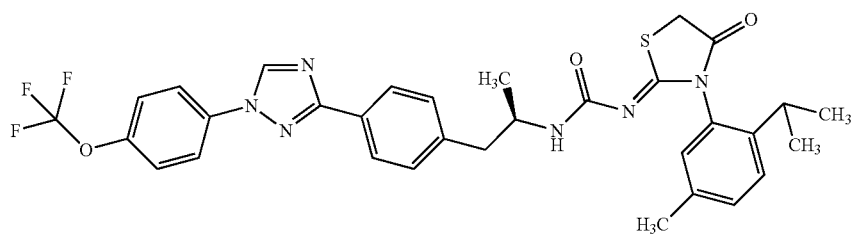 [SMILES: Cc1ccc(C(C)C)c(N2C(=O)CS/C2=N\C(=O)N[C@@H](C)Cc2ccc(-c3ncn(-c4ccc(OC(F)(F)F)cc4)n3)cc2)c1]

To (R)-1-(4-(1-(4-(trifluoromethoxy)phenyl)-1H-1,2,4-triazol-3-yl)phenyl)propan-2-amine (CB61) (0.12 g, 0.32 mmol) and sodium bicarbonate (0.10 g, 1.2 mmol) in dichloromethane/water (2:1, 3.1 mL) in an ice bath was added triphosgene (0.052 g, 0.18 mmol). The reaction was quenched with few drops of water and diluted with dichloromethane. The reaction mixture was filtered through phase separator and concentrated. The residue was dissolved in acetonitrile (2 mL) and 1-(2-isopropyl-5-methylphenyl)thiourea (0.069 g, 0.33 mmol) and cesium carbonate (0.14 g, 0.42 mmol) were added in single portions. The reaction was stirred overnight at room temperature. Additional portions of 1-(2-isopropyl-5-methylphenyl)thiourea (0.070 g, 0.33 mmol) and cesium carbonate (0.070 g, 0.21 mmol) were added and the reaction was stirred overnight. Ethanol (4 mL), methyl 2-bromoacetate (0.10 mL, 0.96 mmol), and sodium acetate (0.079 g, 0.96 mmol) were added and the reaction was heated at 60° C. for 6 hours. The reaction was cooled and stirred at room temperature over the weekend. The reaction was diluted with water and extracted with ethyl acetate (2×). The organic layers were dried with sodium sulfate, filtered, and concentrated. Purification by flash column chromatography using 0-100% ethyl acetate/B, where B=1:1 dichloromethane/hexanes, as eluent provided the title compound as a yellow oil (0.039 g, 19%).

The following compounds were prepared in accordance to the procedure in Example 101.

Preparation of (S,Z)-1-(3-(2-isopropyl-5-methylphenyl)-4-oxothiazolidin-2-ylidene)-3-(1-(4-(1-(4-(trifluoromethoxy)phenyl)-1H-1,2,4-triazol-3-yl)phenyl)propan-2-yl)urea (FB46)

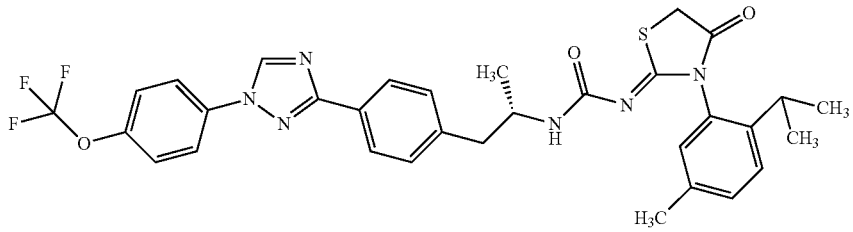

The title compound was prepared as described in Example 101 using (S)-1-(4-(1-(4-(trifluoromethoxy)phenyl)-1H-1,2,4-triazol-3-yl)phenyl)propan-2-amine (CB62) and 1-(2-isopropyl-5-methylphenyl)thiourea and isolated as an off-white foam (0.045 g, 24%).

Example 102

Preparation of tert-butyl methyl(4-(1-(4-(trifluoromethoxy)phenyl)-1H-1,2,4-triazol-3-yl)phenethyl)carbamate (CB63)

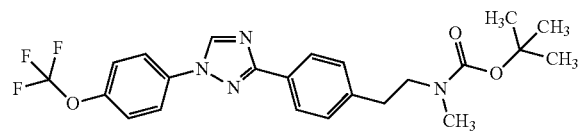 [SMILES: CN(CCc1ccc(-c2ncn(-c3ccc(OC(F)(F)F)cc3)n2)cc1)C(=O)OC(C)(C)C]

To tert-butyl 4-(1-(4-(trifluoromethoxy)phenyl)-1H-1,2,4-triazol-3-yl)phenethylcarbamate (C50) (0.021 g, 0.047 mmol) in anhydrous dimethylformamide (0.023 mL) at 0° C. was added sodium hydride (60% oil dispersion, 0.012 g, 0.30 mmol) and stirred in ice bath for 5 minutes. Iodomethane (0.013 g, 0.094 mmol) was added and the yellow solution immediately turned white. After 10 minutes, the reaction was quenched with water and extracted with dichloromethane. The organic layer was concentrated providing the title compound as a yellow oil (0.022 g, 97%): $^1$H NMR (400 MHz, CDCl$_3$) δ 8.56 (s, 1H), 8.12 (d, J=8.2 Hz, 2H), 7.80 (d, J=9.0 Hz, 2H), 7.39 (dt, J=8.0, 1.0 Hz, 2H), 7.37-7.20 (m, 2H), 3.47 (s, 2H), 2.86 (s, 2H), 1.57 (s, 3H), 1.44 (d, J=13.7 Hz, 9H); $^{19}$F NMR (376 MHz, CDCl$_3$) δ −58.03; ESIMS m/z 463 ([M+H]$^+$).

The following compounds were prepared in accordance to the procedure in Example 102.

Preparation of tert-butyl ethyl(4-(1-(4-(trifluoromethoxy)phenyl)-1H-1,2,4-triazol-3-yl)phenethyl)carbamate (CB64)

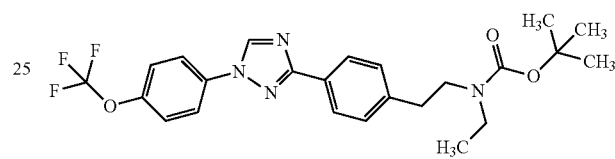

The title compound was prepared as described in Example 102 using tert-butyl 4-(1-(4-(trifluoromethoxy)phenyl)-1H-1,2,4-triazol-3-yl)phenethylcarbamate (C50) and iodoethane and isolated as a yellow oil (0.175 g, 100%): $^1$H NMR (400 MHz, CDCl$_3$) δ 8.56 (s, 1H), 8.16-8.06 (m, 2H), 7.89-7.73 (m, 2H), 7.45-7.36 (m, 2H), 7.31 (s, 2H), 3.42 (s, 2H), 3.23 (t, J=35.4 Hz, 2H), 2.96-2.84 (m, 2H), 1.47 (s, 9H), 1.08 (s, 3H); $^{19}$F NMR (376 MHz, CDCl$_3$) δ −58.03; ESIMS m/z 477 ([M+H]$^+$).

Preparation of tert-butyl allyl(4-(1-(4-(trifluoromethoxy)phenyl)-1H-1,2,4-triazol-3-yl)phenethyl)carbamate (CB65)

The title compound was prepared as described in Example 102 using tert-butyl 4-(1-(4-(trifluoromethoxy)phenyl)-1H-1,2,4-triazol-3-yl)phenethylcarbamate (C50) and allyl bromide and isolated as a yellow oil (0.144 g, 99%): $^1$H NMR (400 MHz, CDCl$_3$) δ 8.56 (s, 1H), 8.15-8.08 (m, 2H), 7.85-7.76 (m, 2H), 7.39 (dq, J=7.8, 1.0 Hz, 2H), 7.30 (s, 2H), 5.76 (s, 1H), 5.12 (s, 2H), 3.76 (d, J=45.8 Hz, 2H), 3.42 (s, 2H), 2.89 (d, J=0.7 Hz, 2H), 1.47 (s, 9H); $^{19}$F NMR (376 MHz, CDCl$_3$) δ −58.03; ESIMS m/z 489 ([M+H]$^+$).

Preparation of tert-butyl (cyclopropylmethyl)(4-(1-(4-(trifluoromethoxy)phenyl)-1H-1,2,4-triazol-3-yl)phenethyl)carbamate (CB66)

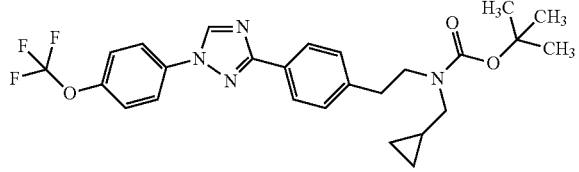 [SMILES: CC(C)(C)OC(=O)N(CCc1ccc(-c2ncn(-c3ccc(OC(F)(F)F)cc3)n2)cc1)CC1CC1]

The title compound was prepared as described in Example 102 using tert-butyl 4-(1-(4-(trifluoromethoxy)phenyl)-1H-1,2,4-triazol-3-yl)phenethylcarbamate (C50) and cyclopropylmethyl bromide and isolated as a clear oil (0.155 g, 96%): $^1$H NMR (400 MHz, CDCl$_3$) δ 8.56 (s, 1H), 8.16-8.07 (m, 2H), 7.84-7.77 (m, 2H), 7.39 (dq, J=8.0, 0.9 Hz, 2H), 7.31 (s, 2H), 3.50 (t, J=7.6 Hz, 2H), 3.17-2.86 (m, 4H), 1.48 (s, 9H), 0.87 (ddd, J=11.2, 9.0, 6.7 Hz, 1H), 0.49 (d, J=8.0 Hz, 2H), 0.21 (s, 2H); $^{19}$F NMR (376 MHz, CDCl$_3$) δ -58.03; ESIMS m/z 503 ([M+H]$^+$).

Example 103

Preparation of benzyl (2-methyl-1-(4-(1-(4-(trifluoromethoxy)phenyl)-1H-1,2,4-triazol-3-yl)phenyl)propan-2-yl)carbamate (CB67)

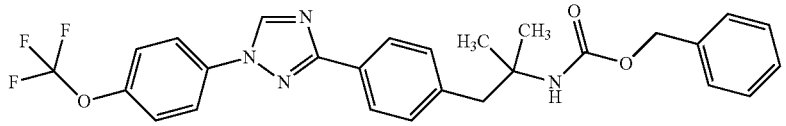 [SMILES: CC(C)(Cc1ccc(-c2ncn(-c3ccc(OC(F)(F)F)cc3)n2)cc1)NC(=O)OCc1ccccc1]

A mixture of 3-bromo-1-(4-(trifluoromethoxy)phenyl)-1H-1,2,4-triazole (C1) (4.28 g, 13.9 mmol), benzyl (2-methyl-1-(4-(4,4,5,5-tetramethyl-1,3,2-dioxaborolan-2-yl)phenyl)propan-2-yl)carbamate (CB7) (6.12 g, 15.0 mmol), tri-tert-butylphosphonium tetrafluoroborate (0.390 g, 1.40 mmol), palladium(II) acetate (0.150 g, 0.680 mmol), and cesium fluoride (4.34 g, 28.6 mmol) in dioxane/water (4:1, 90 mL) was heated at 70° C. overnight. The reaction was cooled and diluted with brine and extracted with ethyl acetate (2×). The organic layer was dried over sodium sulfate, filtered, and concentrated. Purification by flash column chromatography using 0-100% ethyl acetate/hexanes as eluent provided the title compound as a clear oil (1.16 g, 15%): $^1$H NMR (400 MHz, CDCl$_3$) δ 8.57 (s, 1H), 8.06 (d, J=8.2 Hz, 2H), 7.81 (d, J=9.0 Hz, 2H), 7.44-7.32 (m, 7H), 7.19 (d, J=8.2 Hz, 2H), 5.12 (s, 2H), 4.56 (s, 1H), 3.05 (s, 2H), 1.33 (s, 6H); $^{19}$F NMR (376 MHz, CDCl$_3$) δ -58.02; ESIMS m/z 511 ([M+H]$^+$).

The following compounds were prepared in accordance to the procedure in Example 103.

Preparation of benzyl (2-methyl-2-(4-(1-(4-(trifluoromethoxy)phenyl)-1H-1,2,4-triazol-3-yl)phenyl)propyl)carbamate (CB68)

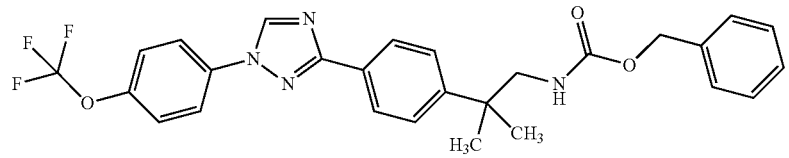 [SMILES: CC(C)(CNC(=O)OCc1ccccc1)c1ccc(-c2ncn(-c3ccc(OC(F)(F)F)cc3)n2)cc1]

The title compound was prepared as described in Example 103 using benzyl (2-methyl-2-(4-(4,4,5,5-tetramethyl-1,3,2-dioxaborolan-2-yl)phenyl)propyl)carbamate (CB8) and isolated as a clear oil (0.045 g, 24%): $^1$H NMR (400 MHz, CDCl$_3$) δ 8.57 (s, 1H), 8.18-8.10 (m, 2H), 7.84-7.75 (m, 2H), 7.49-7.42 (m, 2H), 7.39 (dq, J=9.0, 0.9 Hz, 2H), 7.31 (q, J=6.8, 6.4 Hz, 5H), 5.06 (s, 2H), 4.52 (s, 1H), 3.45 (d, J=6.3 Hz, 2H), 1.38 (s, 6H); $^{19}$F NMR (376 MHz, CDCl$_3$) δ -58.03; ESIMS m/z 511 ([M+H]$^+$).

Preparation of benzyl (1-(4-(1-(4-(trifluoromethoxy)phenyl)-1H-1,2,4-triazol-3-yl)benzyl)cyclopropyl)carbamate (CB69)

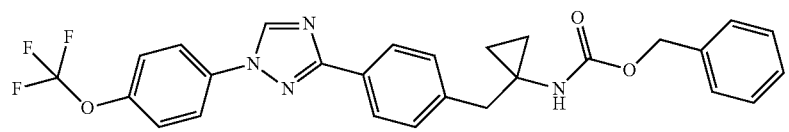 [SMILES: O=C(NC1(Cc2ccc(-c3ncn(-c4ccc(OC(F)(F)F)cc4)n3)cc2)CC1)OCc1ccccc1]

The title compound was prepared as described in Example 103 using benzyl (1-(4-(4,4,5,5-tetramethyl-1,3,2-dioxaborolan-2-yl)benzyl)cyclopropyl)carbamate (CB9) and isolated as a tan solid (2.19 g, 68%): mp 156-158° C., $^1$H NMR (400 MHz, CDCl$_3$) δ 8.56 (s, 1H), 8.10 (d, J=8.1 Hz, 2H), 7.84-7.73 (m, 2H), 7.42-7.30 (m, 6H), 7.26-7.25 (m, 3H), 5.10 (s, 2H), 4.96 (s, 1H), 2.94 (s, 2H), 0.85 (s, 4H); $^{19}$F NMR (376 MHz, CDCl$_3$) δ −58.03; ESIMS m/z 509 ([M+H]$^+$).

Example 104

Preparation of (Z)-1-(5-fluoro-3-(2-isopropyl-5-methylphenyl)-4-oxothiazolidin-2-ylidene)-3-(4-(1-(4-(trifluoromethoxy)phenyl)-1H-1,2,4-triazol-3-yl) phenethyl)urea (FB64)

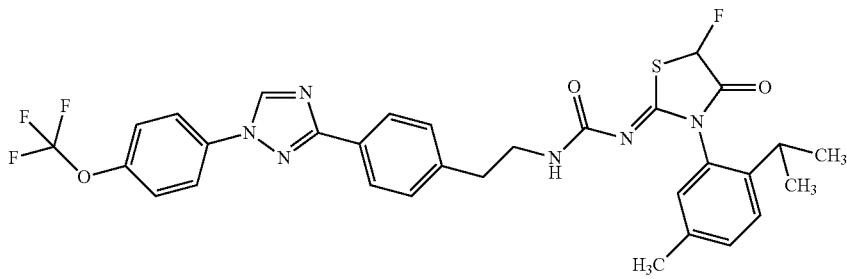 [SMILES: Cc1ccc(C(C)C)c(N2C(=O)C(F)S/C2=N\C(=O)NCCc2ccc(-c3ncn(-c4ccc(OC(F)(F)F)cc4)n3)cc2)c1]

To (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5) (0.050 g, 0.080 mmol) and 2-fluorenone (0.0080 g, 0.044 mmol) in anhydrous acetonitrile (0.80 mL) was added Selectfluor® (0.062 g, 0.18 mmol). The reaction was stirred at room temperature overnight. Purification by flash column chromatography using 0-100% ethyl acetate/B, where B=1:1 dichloromethane/hexanes, as eluent provided the title compound as a yellow oil (0.033 g, 63%).

Example 105

Preparation of (Z)-methyl N-(2-isopropyl-5-methylphenyl)-N'-((4-(1-(4-(trifluoromethoxy)phenyl)-1H-1,2,4-triazol-3-yl)phenethyl)carbamoyl)carbamimidothioate (FB65)

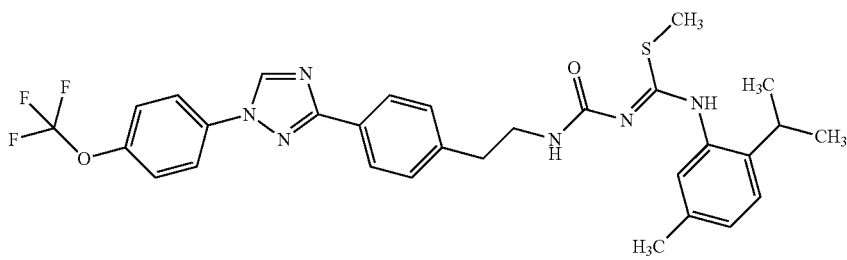 [SMILES: CS/C(=N\C(=O)NCCc1ccc(-c2ncn(-c3ccc(OC(F)(F)F)cc3)n2)cc1)Nc1cc(C)ccc1C(C)C]

To N-[5-methyl-2-isopropylphenyl]-N'-[2-(4-{1-[4-(trifluoromethoxy)-phenyl]-1H-1,2,4-triazol-3-yl}phenyl)ethyl] dicarbonimidothioic diamide (F3) (0.15 g, 0.26 mmol) and sodium acetate (0.053 g, 0.65 mmol) in ethanol (1 mL) was added iodomethane (0.020 mL, 0.32 mmol). The reaction was stirred at room temperature overnight. The reaction mixture was diluted with water and the water was decanted off to leave white solid, which was dried under vacuum for 3 hours. Purification by flash column chromatography using 0-100% ethyl acetate/B, where B=1:1 dichloromethane/hexanes, as eluent provided the title compound as a clear oil (0.081 g, 49%).

The following compounds were prepared in accordance to the procedure in Example 105.

Preparation of (Z)-ethyl N-(2-isopropyl-5-methylphenyl)-N'-((4-(1-(4-(trifluoromethoxy)phenyl)-1H-1,2,4-triazol-3-yl)phenethyl)carbamoyl)carbamimidothioate (FB66)

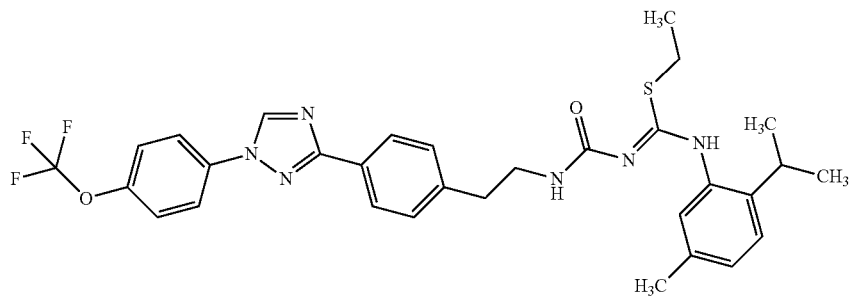 [SMILES: CCS/C(=N\C(=O)NCCc1ccc(-c2ncn(-c3ccc(OC(F)(F)F)cc3)n2)cc1)Nc1cc(C)ccc1C(C)C]

The title compound was prepared as described in Example 105 using N-[5-methyl-2-isopropylphenyl]-N'-[2-(4-{1-[4-(trifluoromethoxy)-phenyl]-1H-1,2,4-triazol-3-yl}phenyl) ethyl]dicarbonimidothioic diamide (F3) and iodoethane, purified by reverse-phase flash column chromatography using 0-100% acetonitrile/water as eluent, and isolated as a clear oil (0.050 g, 43%).

Example 106

Preparation of (Z)-1-(3-(2-isopropyl-5-methylphenyl)-5,5-dimethyl-4-oxothiazolidin-2-ylidene)-3-(4-(1-(4-(trifluoromethoxy)phenyl)-1H-1,2,4-triazol-3-yl)phenethyl)urea (FB68)

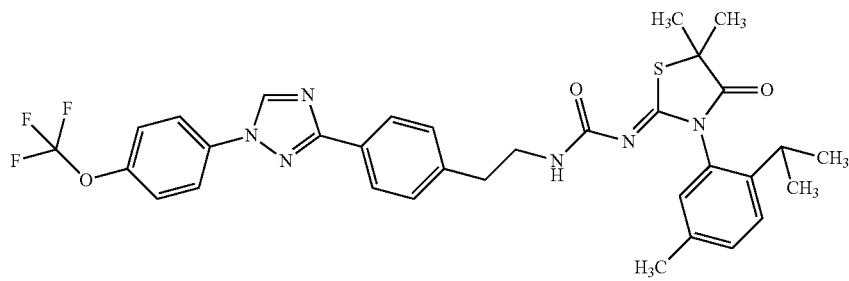 [SMILES: Cc1ccc(C(C)C)c(N2C(=O)C(C)(C)S/C2=N\C(=O)NCCc2ccc(-c3ncn(-c4ccc(OC(F)(F)F)cc4)n3)cc2)c1]

To a dry 2 dram vial equipped with magnetic stirrer was added (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5) (0.10 g, 0.16 mmol) and anhydrous dimethylformamide (0.5 mL). To this solution was added sodium hydride (60% oil dispersion, 0.0064 g, 0.16 mmol) followed by iodomethane (0.022 g, 0.16 mmol). The reaction was stirred overnight at room temperature. Purification by flash column chromatography using 0-100% ethyl acetate/hexanes as eluent provided the title compound as a pale yellow foam (0.054 g, 52%).

The following compounds were prepared in accordance to the procedure in Example 106.

Preparation of (Z)-1-(6-(2-isopropyl-5-methylphenyl)-7-oxo-4-thia-6-azaspiro[2.4]heptan-5-ylidene)-3-(4-(1-(4-(trifluoromethoxy)phenyl)-1H-1,2,4-triazol-3-yl)phenethyl)urea (FB69)

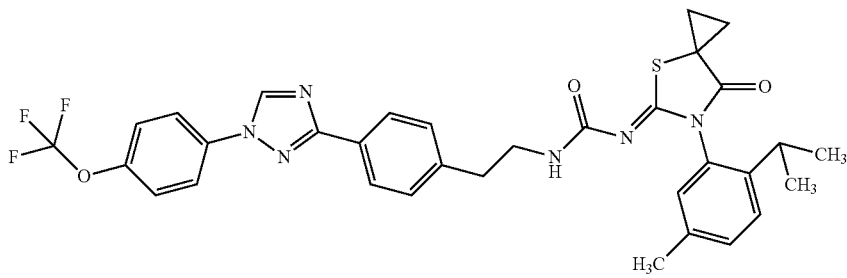 [SMILES: Cc1ccc(C(C)C)c(N2C(=O)C3(CC3)S/C2=N\C(=O)NCCc2ccc(-c3ncn(-c4ccc(OC(F)(F)F)cc4)n3)cc2)c1]

The title compound was prepared as described in Example 106 using N-[5-methyl-2-isopropylphenyl]-N'-[2-(4-{1-[4-(trifluoromethoxy)-phenyl]-1H-1,2,4-triazol-3-yl}phenyl)ethyl]dicarbonimidothioic diamide (F3) and 1,2-dibromoethane and isolated as a white foam (0.023 g, 22%).

column chromatography using 0-100% ethyl acetate/hexanes as eluent provided the title compound as a clear colorless oil (0.041 g, 18%).

Example 107

Preparation of (Z)-1-(5-bromo-3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (FB70)

Example 108

Preparation of (Z)-1-(2-bromo-2-(4-(1-(4-(trifluoromethoxy)phenyl)-1H-1,2,4-triazol-3-yl)phenyl)ethyl)-3-(3-(2-isopropyl-5-methylphenyl)-4-oxothiazolidin-2-ylidene)urea (FB71)

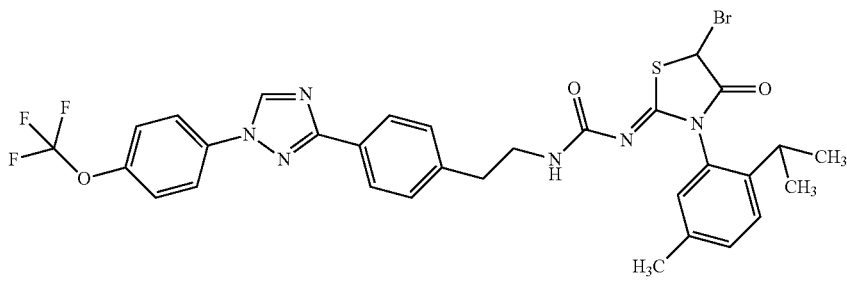 [SMILES: Cc1ccc(C(C)C)c(N2C(=O)C(Br)S/C2=N\C(=O)NCCc2ccc(-c3ncn(-c4ccc(OC(F)(F)F)cc4)n3)cc2)c1]

To a dry 2 dram vial equipped with magnetic stirrer was added (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5) (0.20 g, 0.32 mmol)

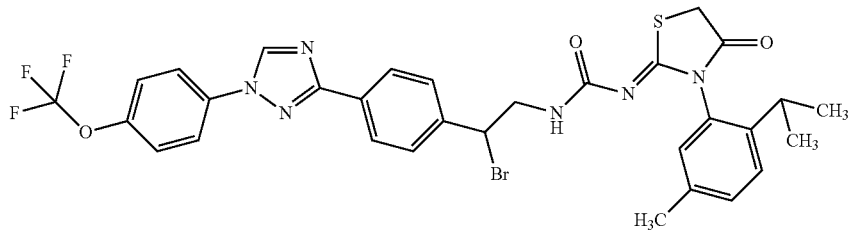 [SMILES: Cc1ccc(C(C)C)c(N2C(=O)CS/C2=N\C(=O)NCC(Br)c2ccc(-c3ncn(-c4ccc(OC(F)(F)F)cc4)n3)cc2)c1]

and anhydrous dichloromethane (0.5 mL). To this solution was added bromine (0.033 mL, 0.64 mmol). The reaction was stirred overnight at room temperature. Purification by flash To a dry round-bottomed flask (20 mL) equipped with a magnetic stirrer and a reflux condenser were added (Z)-1-(3-(2-isopropyl-5-methylphenyl)-4-oxothiazolidin-2-ylidene)-

3-(4-(1-(4-(trifluoromethoxy)phenyl)-1H-1,2,4-triazol-3-yl) phenethyl)urea (F5) (0.20 g, 0.32 mmol), carbon tetrachloride (1 mL), N-bromosuccinimide (0.057 g, 0.32 mmol), and azobisisobutyronitrile (0.0053 g, 0.032 mmol). The reaction was heated to reflux for 2 hours. The reaction was cooled. Purification by flash column chromatography using 0-100% ethyl acetate/hexanes as eluent provided the title compound as a yellow oil (0.049 g, 21%).

Example 109

Preparation of (Z)-1-(5-(2-hydroxypropan-2-yl)-3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (FB72)

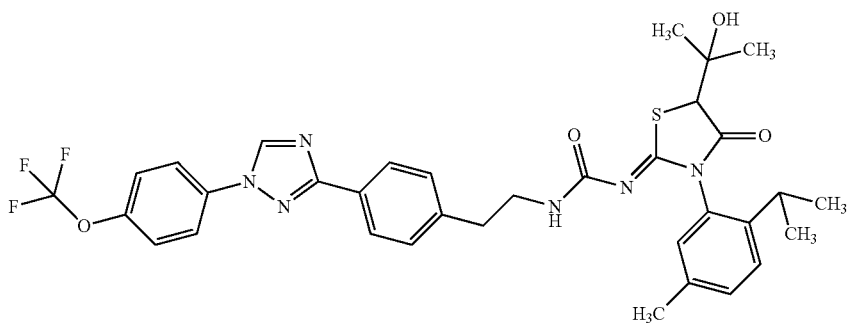 [SMILES: Cc1ccc(C(C)C)c(N2C(=O)C(C(C)(C)O)S/C2=N\C(=O)NCCc2ccc(-c3ncn(-c4ccc(OC(F)(F)F)cc4)n3)cc2)c1]

To (Z)-1-(3-(2-isopropyl-5-methylphenyl)-4-oxothiazolidin-2-ylidene)-3-(4-(1-(4-(trifluoromethoxy)phenyl)-1H-1,2,4-triazol-3-yl)phenethyl)urea (F5) (0.40 g, 0.64 mmol) in acetone (30 mL) was added saturated aqueous sodium bicarbonate (3 mL). The reaction was heated to reflux for 12 hours, cooled, and concentrated. The reaction mixture was partitioned between ethyl acetate and water. The organic layer was dried and concentrated. Purification by flash column chromatography using 100-40% A/B, where A=1:1 dichloromethane/hexanes and B=3:1 ethyl acetate/acetone, as eluent provided the title compound as a white solid (0.095 g, 19%).

Using the procedures disclosed herein the following list of prophetic molecules having a structure according to Formula One may be made (Table P-One).

TABLE P-One

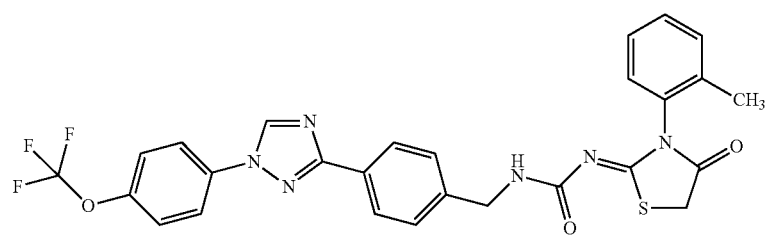 [SMILES: Cc1ccccc1N1C(=O)CS/C1=N\C(=O)NCc1ccc(-c2ncn(-c3ccc(OC(F)(F)F)cc3)n2)cc1]

P1

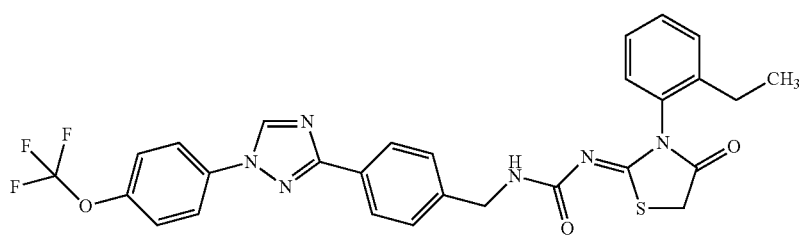 [SMILES: CCc1ccccc1N1C(=O)CS/C1=N\C(=O)NCc1ccc(-c2ncn(-c3ccc(OC(F)(F)F)cc3)n2)cc1]

P2

TABLE P-One-continued
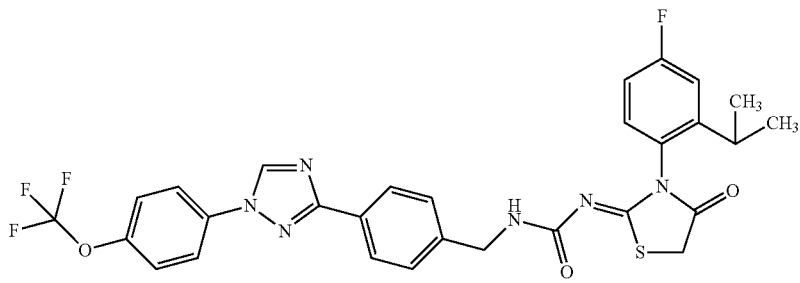 [SMILES: CC(C)c1cc(F)ccc1N1C(=O)CS/C1=N\C(=O)NCc1ccc(-c2ncn(-c3ccc(OC(F)(F)F)cc3)n2)cc1]
P3
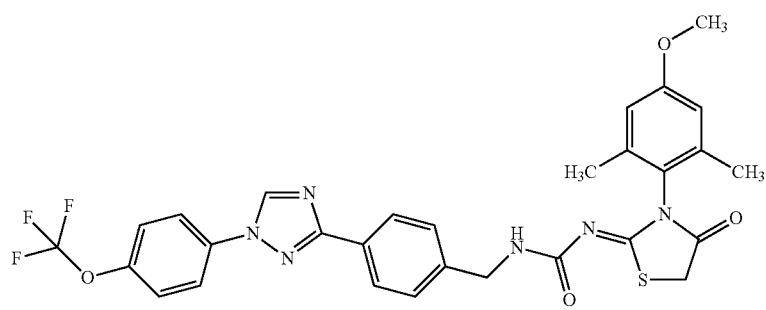 [SMILES: COc1cc(C)c(N2C(=O)CS/C2=N\C(=O)NCc2ccc(-c3ncn(-c4ccc(OC(F)(F)F)cc4)n3)cc2)c(C)c1]
P4
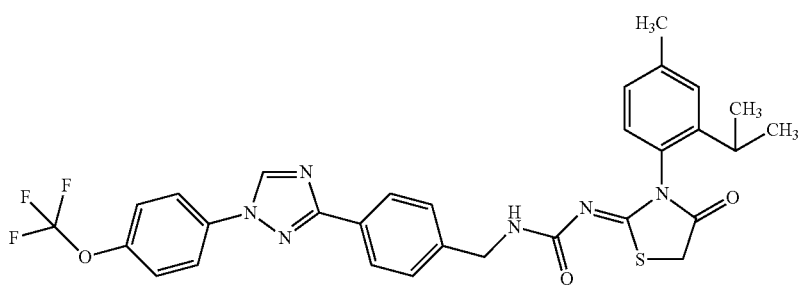 [SMILES: Cc1ccc(N2C(=O)CS/C2=N\C(=O)NCc2ccc(-c3ncn(-c4ccc(OC(F)(F)F)cc4)n3)cc2)c(C(C)C)c1]
P5
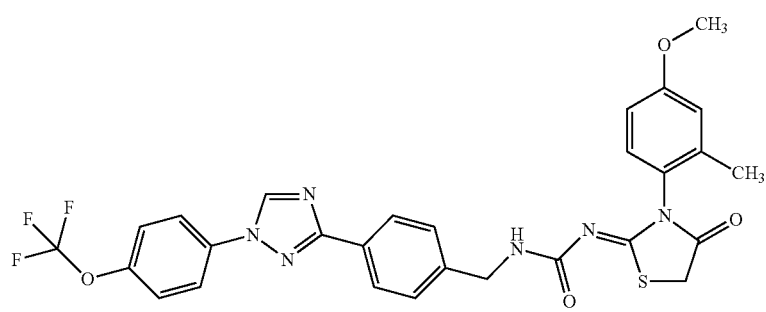 [SMILES: COc1ccc(N2C(=O)CS/C2=N\C(=O)NCc2ccc(-c3ncn(-c4ccc(OC(F)(F)F)cc4)n3)cc2)c(C)c1]
P6
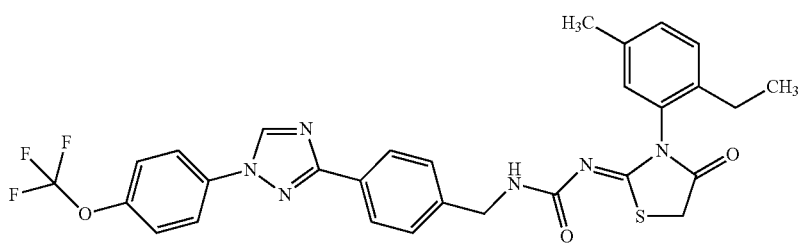 [SMILES: CCc1ccc(C)cc1N1C(=O)CS/C1=N\C(=O)NCc1ccc(-c2ncn(-c3ccc(OC(F)(F)F)cc3)n2)cc1]
P7

TABLE P-One-continued
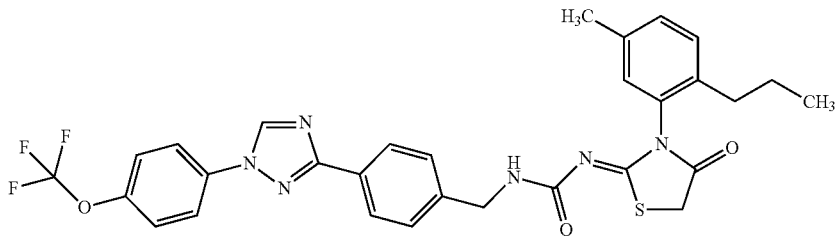 [SMILES: CCCc1ccc(C)cc1N1C(=O)CS/C1=N\C(=O)NCc1ccc(-c2ncn(-c3ccc(OC(F)(F)F)cc3)n2)cc1]
P8
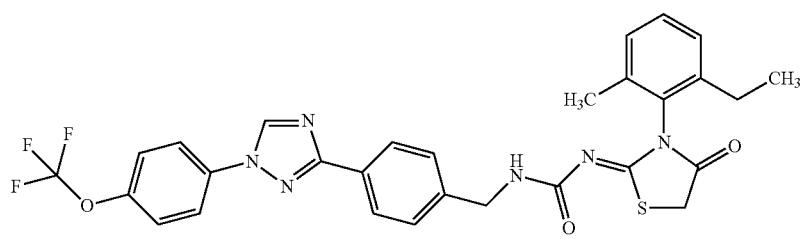 [SMILES: CCc1cccc(C)c1N1C(=O)CS/C1=N\C(=O)NCc1ccc(-c2ncn(-c3ccc(OC(F)(F)F)cc3)n2)cc1]
P9
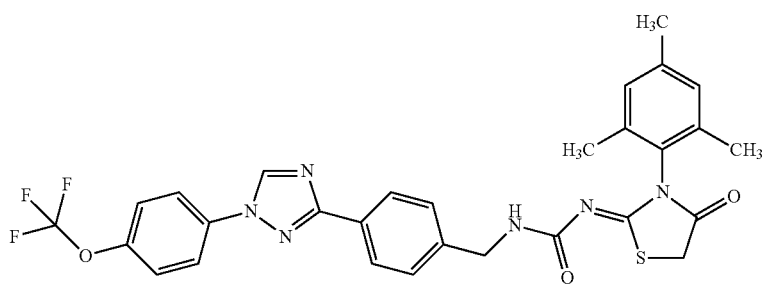 [SMILES: Cc1cc(C)c(N2C(=O)CS/C2=N\C(=O)NCc2ccc(-c3ncn(-c4ccc(OC(F)(F)F)cc4)n3)cc2)c(C)c1]
P10
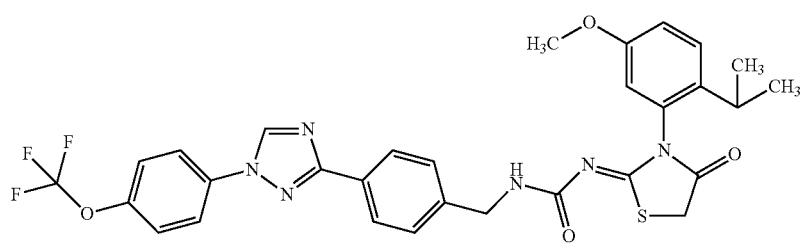 [SMILES: COc1ccc(C(C)C)c(N2C(=O)CS/C2=N\C(=O)NCc2ccc(-c3ncn(-c4ccc(OC(F)(F)F)cc4)n3)cc2)c1]
P11
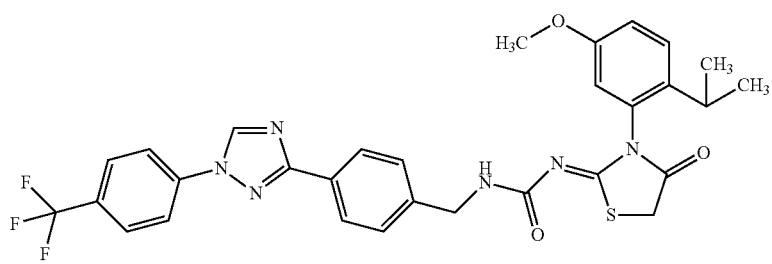 [SMILES: COc1ccc(C(C)C)c(N2C(=O)CS/C2=N\C(=O)NCc2ccc(-c3ncn(-c4ccc(C(F)(F)F)cc4)n3)cc2)c1]
P12
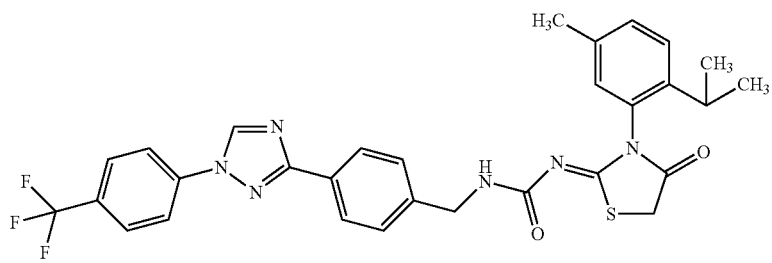 [SMILES: Cc1ccc(C(C)C)c(N2C(=O)CS/C2=N\C(=O)NCc2ccc(-c3ncn(-c4ccc(C(F)(F)F)cc4)n3)cc2)c1]
P13

TABLE P-One-continued
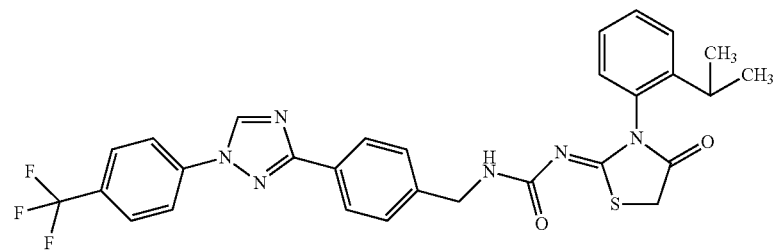 [SMILES: CC(C)c1ccccc1N1C(=O)CS/C1=N\C(=O)NCc1ccc(-c2ncn(-c3ccc(C(F)(F)F)cc3)n2)cc1]
P14
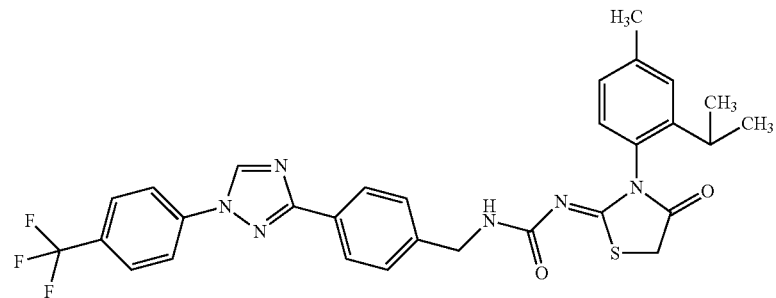 [SMILES: Cc1ccc(N2C(=O)CS/C2=N\C(=O)NCc2ccc(-c3ncn(-c4ccc(C(F)(F)F)cc4)n3)cc2)c(C(C)C)c1]
P15
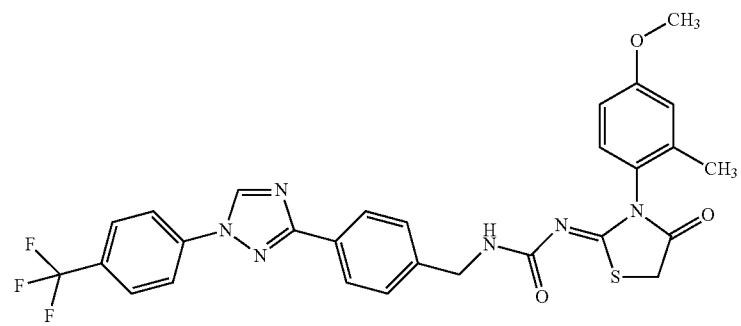 [SMILES: COc1ccc(N2C(=O)CS/C2=N\C(=O)NCc2ccc(-c3ncn(-c4ccc(C(F)(F)F)cc4)n3)cc2)c(C)c1]
P16
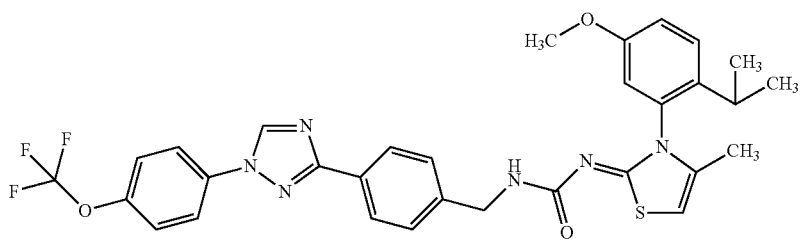 [SMILES: COc1ccc(C(C)C)c(-n2c(C)cs/c2=N\C(=O)NCc2ccc(-c3ncn(-c4ccc(OC(F)(F)F)cc4)n3)cc2)c1]
P17
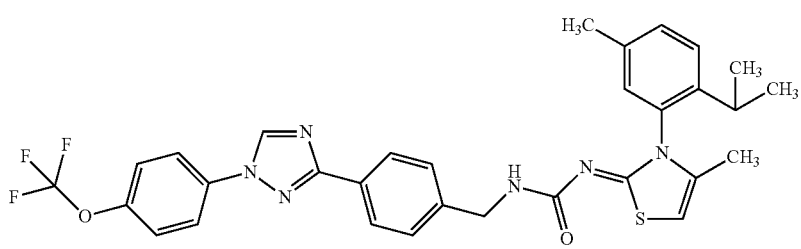 [SMILES: Cc1ccc(C(C)C)c(-n2c(C)cs/c2=N\C(=O)NCc2ccc(-c3ncn(-c4ccc(OC(F)(F)F)cc4)n3)cc2)c1]
P18
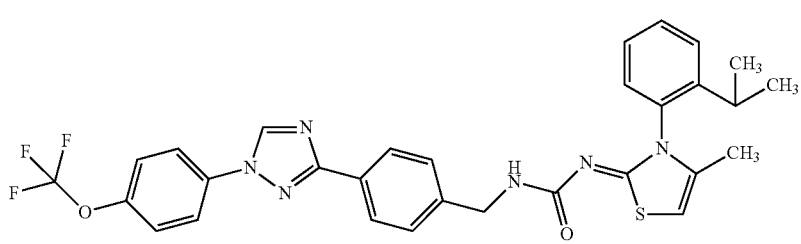 [SMILES: Cc1cs/c(=N\C(=O)NCc2ccc(-c3ncn(-c4ccc(OC(F)(F)F)cc4)n3)cc2)n1-c1ccccc1C(C)C]
P19

TABLE P-One-continued
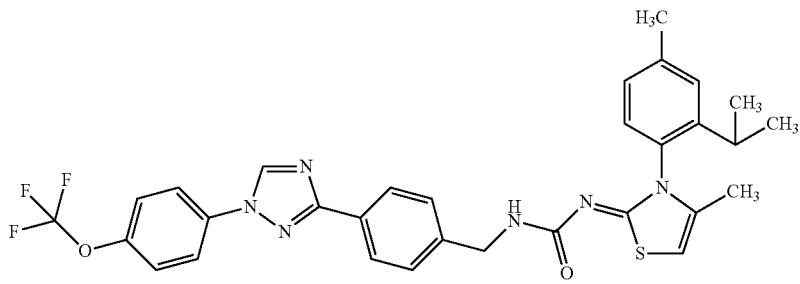 [SMILES: Cc1ccc(-n2c(C)cs/c2=N\C(=O)NCc2ccc(-c3ncn(-c4ccc(OC(F)(F)F)cc4)n3)cc2)c(C(C)C)c1]
P20
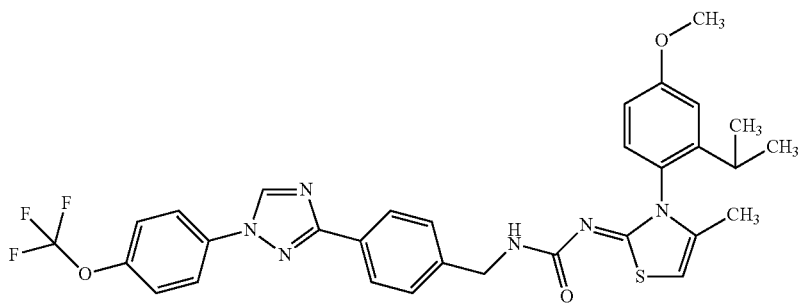 [SMILES: COc1ccc(-n2c(C)cs/c2=N\C(=O)NCc2ccc(-c3ncn(-c4ccc(OC(F)(F)F)cc4)n3)cc2)c(C(C)C)c1]
P21
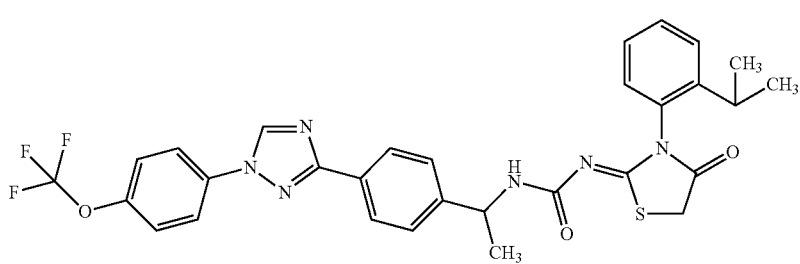 [SMILES: CC(C)c1ccccc1N1C(=O)CS/C1=N\C(=O)NC(C)c1ccc(-c2ncn(-c3ccc(OC(F)(F)F)cc3)n2)cc1]
P22
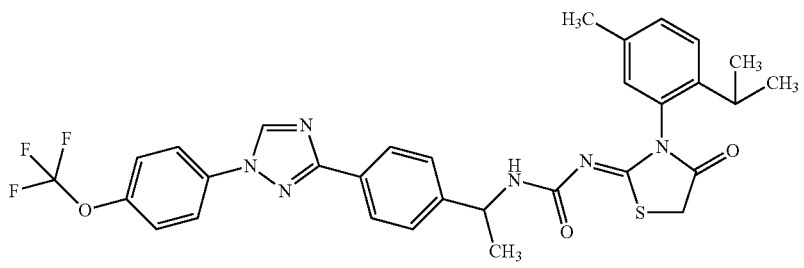 [SMILES: Cc1ccc(C(C)C)c(N2C(=O)CS/C2=N\C(=O)NC(C)c2ccc(-c3ncn(-c4ccc(OC(F)(F)F)cc4)n3)cc2)c1]
P23
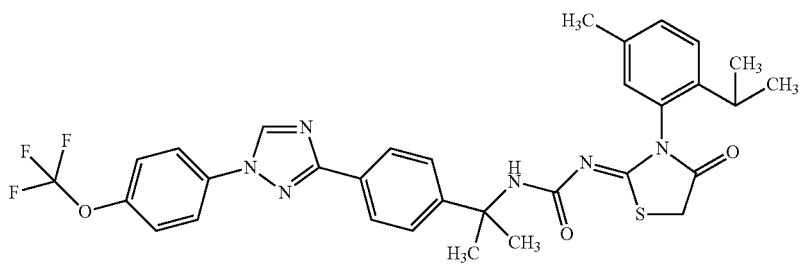 [SMILES: Cc1ccc(C(C)C)c(N2C(=O)CS/C2=N\C(=O)NC(C)(C)c2ccc(-c3ncn(-c4ccc(OC(F)(F)F)cc4)n3)cc2)c1]
P24
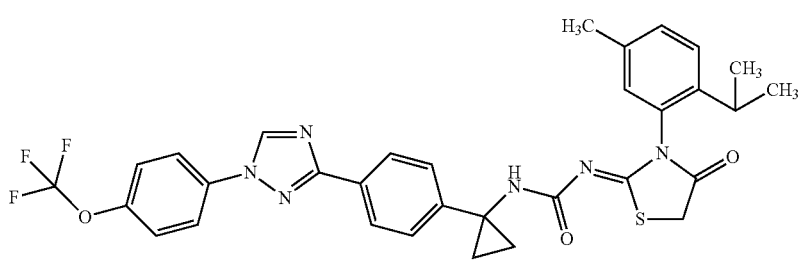 [SMILES: Cc1ccc(C(C)C)c(N2C(=O)CS/C2=N\C(=O)NC2(c3ccc(-c4ncn(-c5ccc(OC(F)(F)F)cc5)n4)cc3)CC2)c1]
P25

TABLE P-One-continued
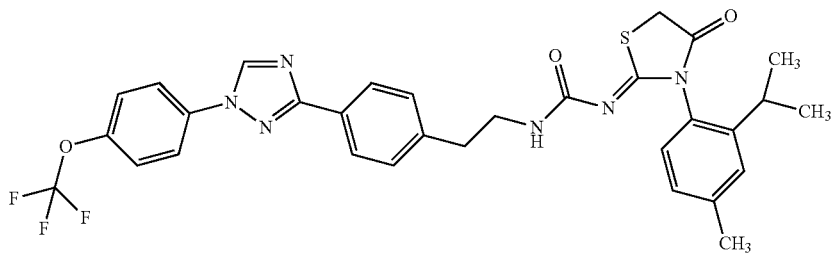 P26
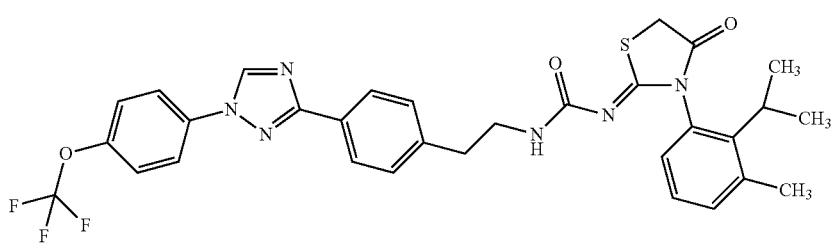 [SMILES: Cc1cccc(N2C(=O)CS/C2=N\C(=O)NCCc2ccc(-c3ncn(-c4ccc(OC(F)(F)F)cc4)n3)cc2)c1C(C)C] P27
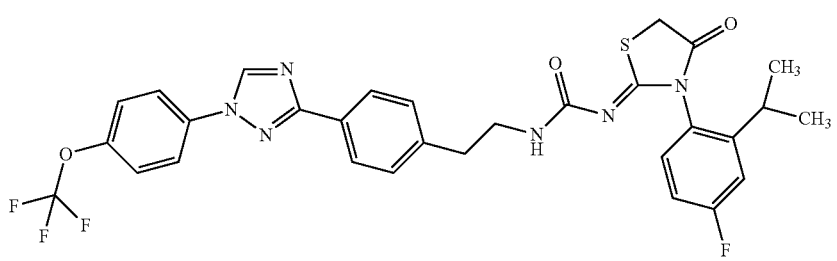 [SMILES: CC(C)c1cc(F)ccc1N1C(=O)CS/C1=N\C(=O)NCCc1ccc(-c2ncn(-c3ccc(OC(F)(F)F)cc3)n2)cc1] P28
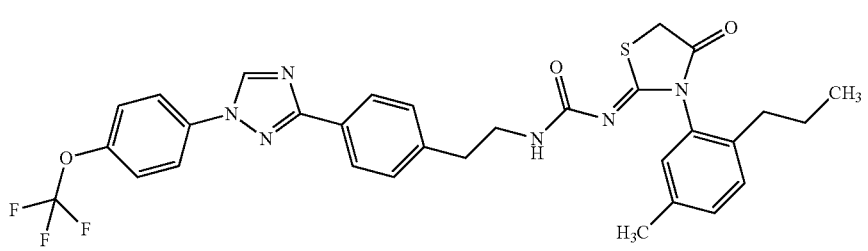 [SMILES: CCCc1ccc(C)cc1N1C(=O)CS/C1=N\C(=O)NCCc1ccc(-c2ncn(-c3ccc(OC(F)(F)F)cc3)n2)cc1] P29
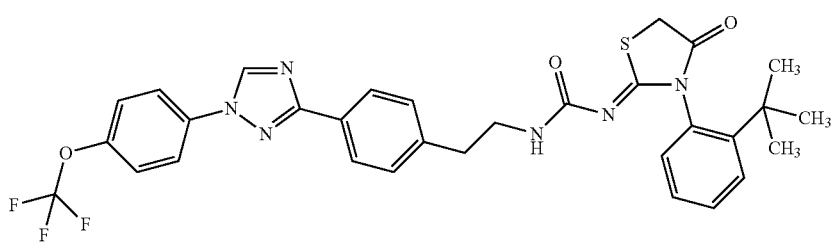 P30
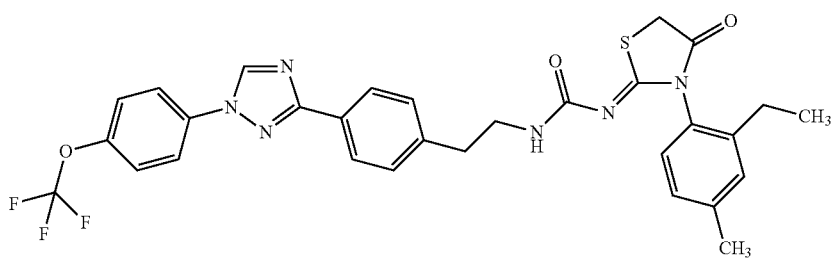 P31

TABLE P-One-continued
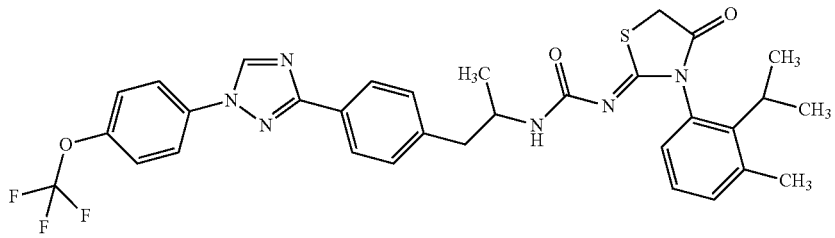 [SMILES: Cc1cccc(N2C(=O)CS/C2=N\C(=O)NC(C)Cc2ccc(-c3ncn(-c4ccc(OC(F)(F)F)cc4)n3)cc2)c1C(C)C] P32
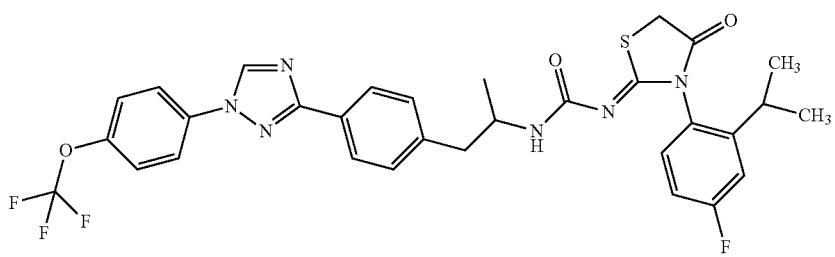 [SMILES: CC(Cc1ccc(-c2ncn(-c3ccc(OC(F)(F)F)cc3)n2)cc1)NC(=O)/N=C1\SCC(=O)N1c1ccc(F)cc1C(C)C] P33
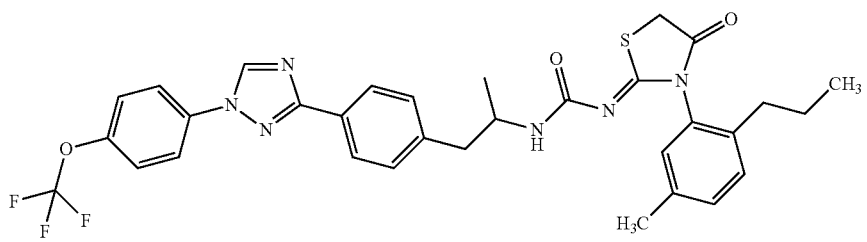 P34
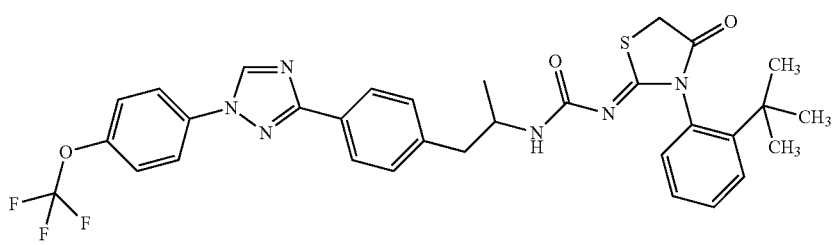 P35
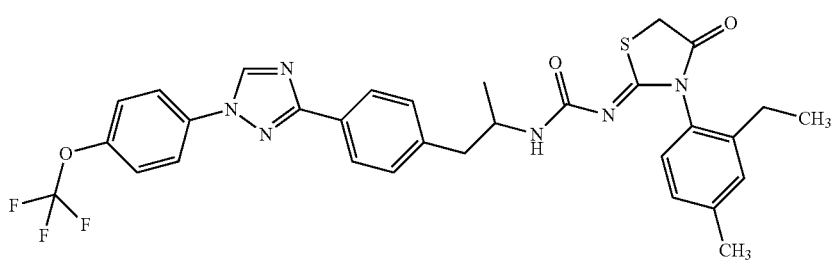 [SMILES: CCc1cc(C)ccc1N1C(=O)CS/C1=N\C(=O)NC(C)Cc1ccc(-c2ncn(-c3ccc(OC(F)(F)F)cc3)n2)cc1] P36
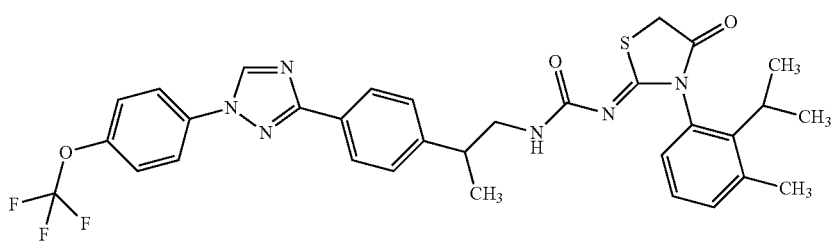 [SMILES: Cc1cccc(N2C(=O)CS/C2=N\C(=O)NCC(C)c2ccc(-c3ncn(-c4ccc(OC(F)(F)F)cc4)n3)cc2)c1C(C)C] P37

TABLE P-One-continued
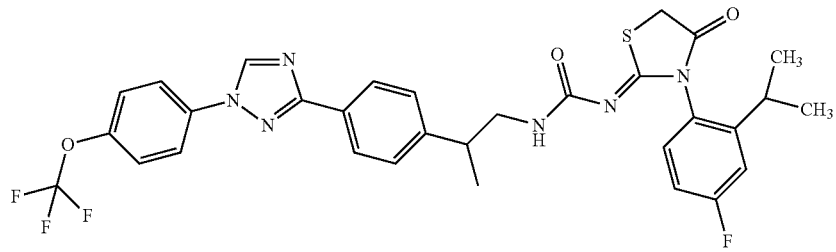 [SMILES: CC(C)c1cc(F)ccc1N1C(=O)CS/C1=N\C(=O)NCC(C)c1ccc(-c2ncn(-c3ccc(OC(F)(F)F)cc3)n2)cc1] P38
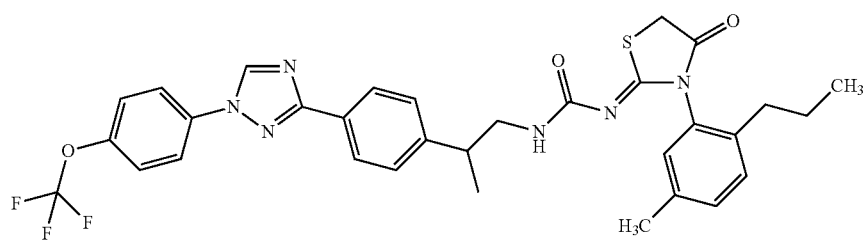 [SMILES: CCCc1ccc(C)cc1N1C(=O)CS/C1=N\C(=O)NCC(C)c1ccc(-c2ncn(-c3ccc(OC(F)(F)F)cc3)n2)cc1] P39
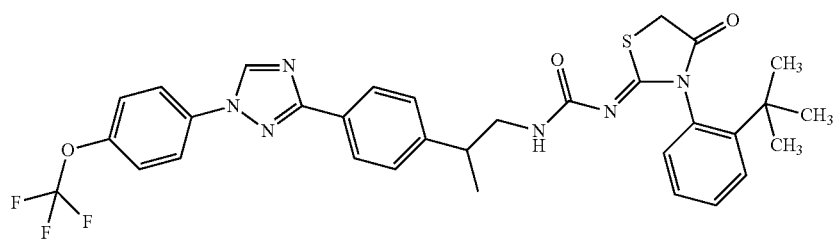 [SMILES: CC(CNC(=O)/N=C1\SCC(=O)N1c1ccccc1C(C)(C)C)c1ccc(-c2ncn(-c3ccc(OC(F)(F)F)cc3)n2)cc1] P40
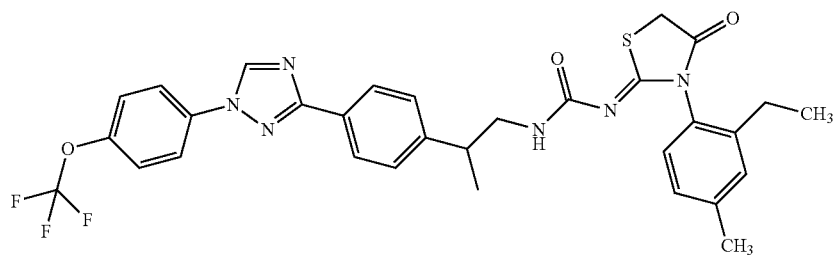 [SMILES: CCc1cc(C)ccc1N1C(=O)CS/C1=N\C(=O)NCC(C)c1ccc(-c2ncn(-c3ccc(OC(F)(F)F)cc3)n2)cc1] P41
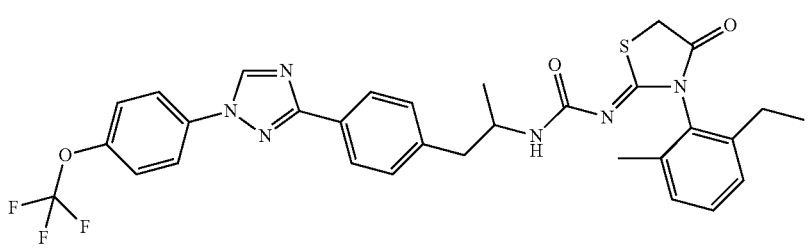 [SMILES: CCc1cccc(C)c1N1C(=O)CS/C1=N\C(=O)NC(C)Cc1ccc(-c2ncn(-c3ccc(OC(F)(F)F)cc3)n2)cc1] P42
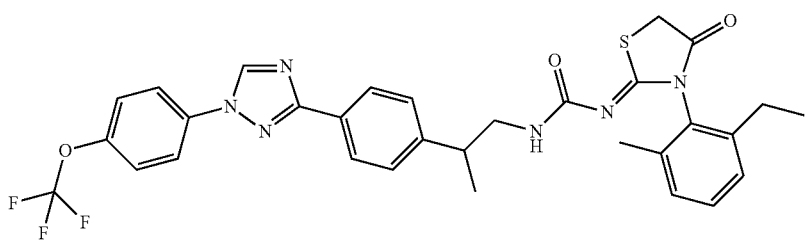 [SMILES: CCc1cccc(C)c1N1C(=O)CS/C1=N\C(=O)NCC(C)c1ccc(-c2ncn(-c3ccc(OC(F)(F)F)cc3)n2)cc1] P43

TABLE P-One-continued
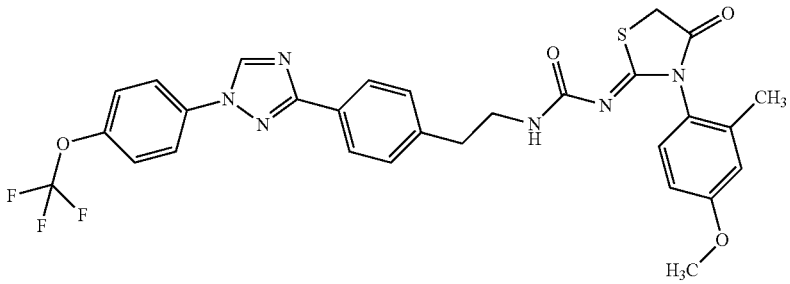 [SMILES: COc1ccc(N2C(=O)CS/C2=N\C(=O)NCC(C)c2ccc(-c3ncn(-c4ccc(OC(F)(F)F)cc4)n3)cc2)c(C)c1]
P44
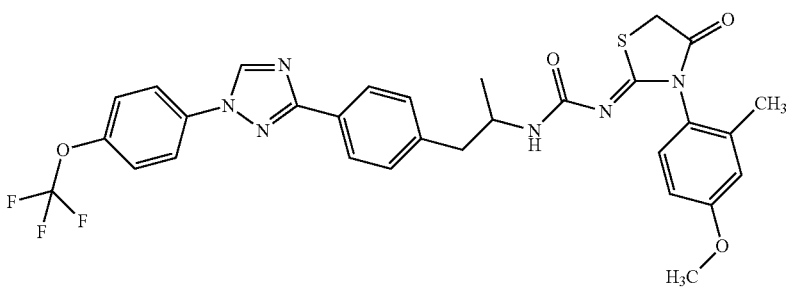
P45
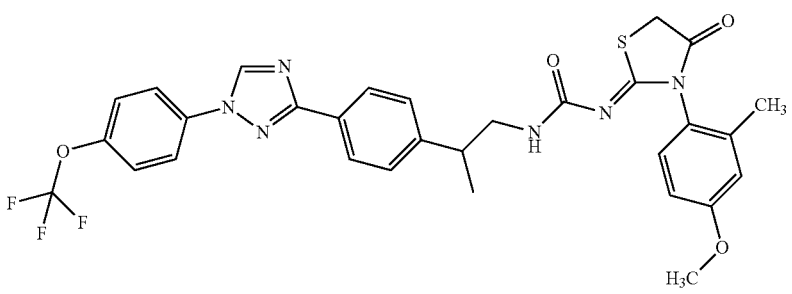
P46
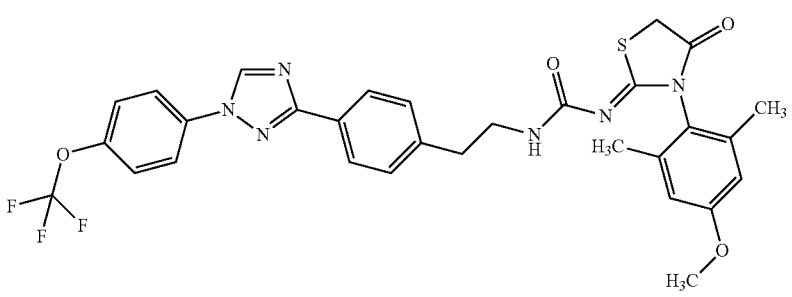 [SMILES: COc1cc(C)c(N2C(=O)CS/C2=N\C(=O)NCCc2ccc(-c3ncn(-c4ccc(OC(F)(F)F)cc4)n3)cc2)c(C)c1]
P47
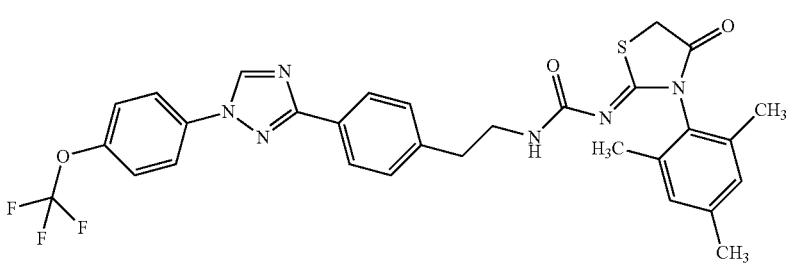 [SMILES: Cc1cc(C)c(N2C(=O)CS/C2=N\C(=O)NCCc2ccc(-c3ncn(-c4ccc(OC(F)(F)F)cc4)n3)cc2)c(C)c1]
P48

TABLE P-One-continued
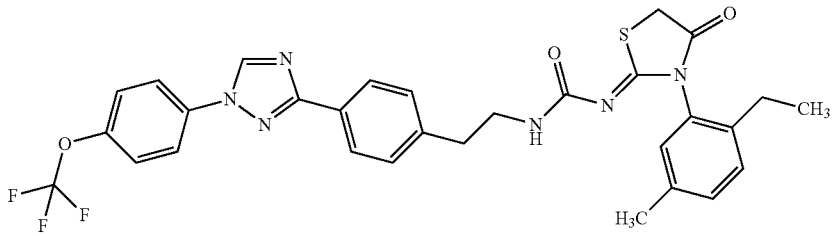 [SMILES: CCc1ccc(C)cc1N1C(=O)CS/C1=N\C(=O)NCCc1ccc(-c2ncn(-c3ccc(OC(F)(F)F)cc3)n2)cc1]
P49
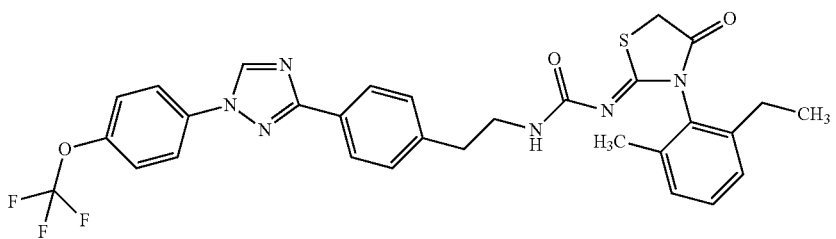 [SMILES: CCc1cccc(C)c1N1C(=O)CS/C1=N\C(=O)NCCc1ccc(-c2ncn(-c3ccc(OC(F)(F)F)cc3)n2)cc1]
P50
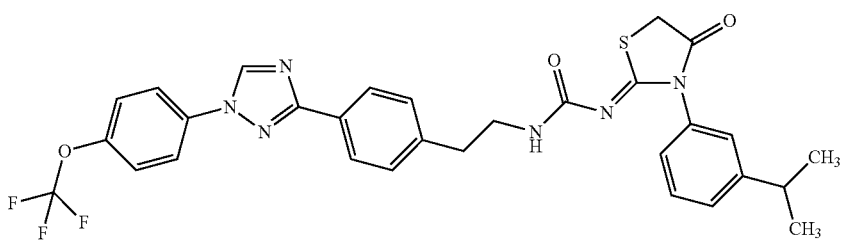 [SMILES: CC(C)c1cccc(N2C(=O)CS/C2=N\C(=O)NCCc2ccc(-c3ncn(-c4ccc(OC(F)(F)F)cc4)n3)cc2)c1]
P51
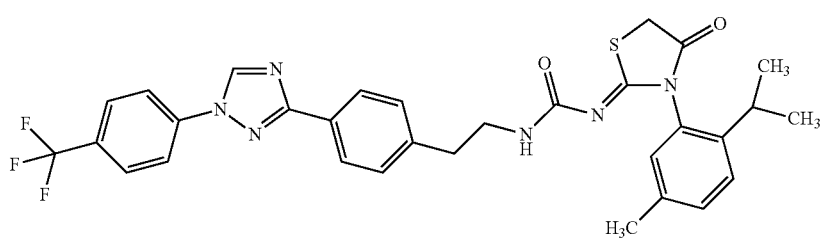 [SMILES: Cc1ccc(C(C)C)c(N2C(=O)CS/C2=N\C(=O)NCCc2ccc(-c3ncn(-c4ccc(C(F)(F)F)cc4)n3)cc2)c1]
P52
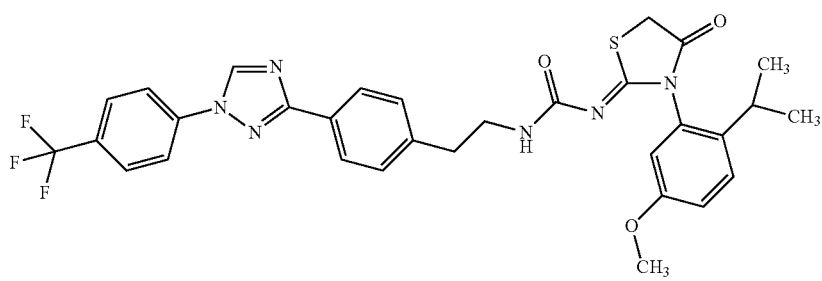 [SMILES: COc1ccc(C(C)C)c(N2C(=O)CS/C2=N\C(=O)NCCc2ccc(-c3ncn(-c4ccc(C(F)(F)F)cc4)n3)cc2)c1]
P53
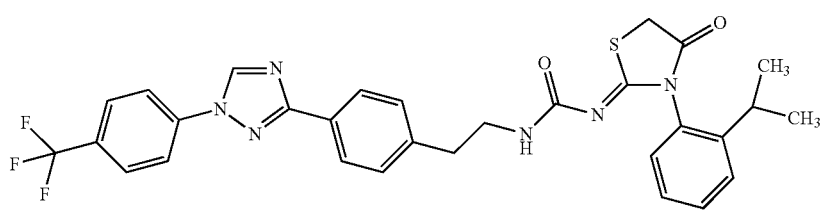 [SMILES: CC(C)c1ccccc1N1C(=O)CS/C1=N\C(=O)NCCc1ccc(-c2ncn(-c3ccc(C(F)(F)F)cc3)n2)cc1]
P54

TABLE P-One-continued
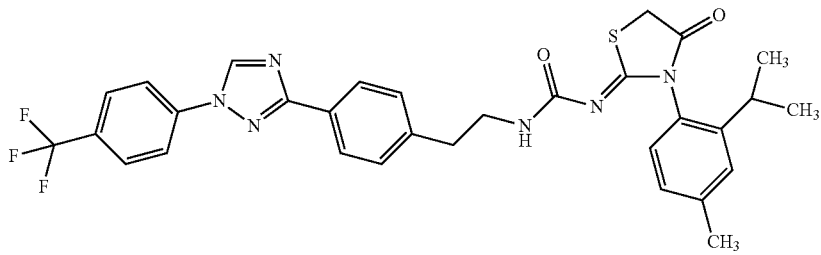 [SMILES: Cc1ccc(N2C(=O)CS/C2=N\C(=O)NCCc2ccc(-c3ncn(-c4ccc(C(F)(F)F)cc4)n3)cc2)c(C(C)C)c1] P55
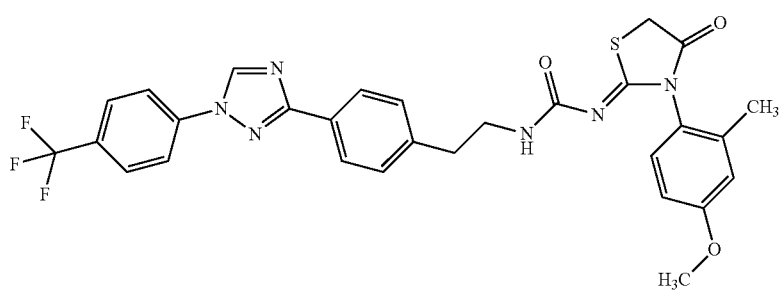 [SMILES: COc1ccc(N2C(=O)CS/C2=N\C(=O)NCCc2ccc(-c3ncn(-c4ccc(C(F)(F)F)cc4)n3)cc2)c(C)c1] P56
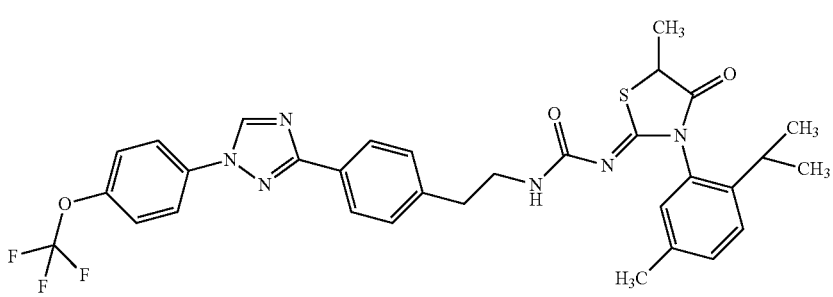 [SMILES: Cc1ccc(C(C)C)c(N2C(=O)C(C)S/C2=N\C(=O)NCCc2ccc(-c3ncn(-c4ccc(OC(F)(F)F)cc4)n3)cc2)c1] P57
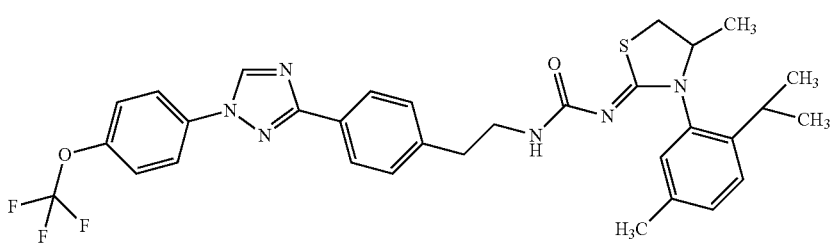 [SMILES: Cc1ccc(C(C)C)c(N2/C(=N/C(=O)NCCc3ccc(-c4ncn(-c5ccc(OC(F)(F)F)cc5)n4)cc3)SCC2C)c1] P58
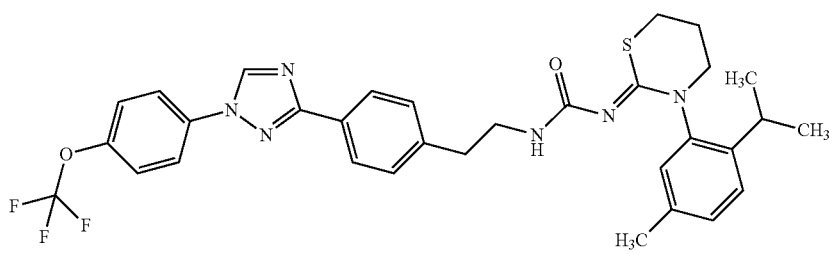 P59
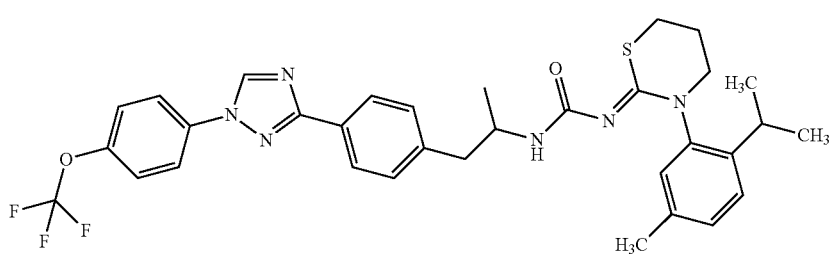 P60

TABLE P-One-continued
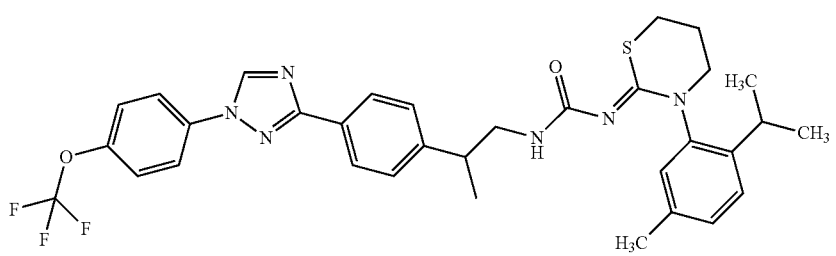 [SMILES: Cc1ccc(C(C)C)c(N2CCCS/C2=N\C(=O)NCCc2ccc(-c3ncn(-c4ccc(OC(F)(F)F)cc4)n3)cc2)c1]
P61
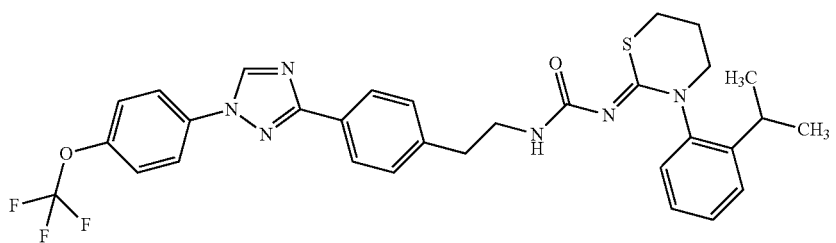 [SMILES: CC(C)c1ccccc1N1CCCS/C1=N\C(=O)NCCc1ccc(-c2ncn(-c3ccc(OC(F)(F)F)cc3)n2)cc1]
P62
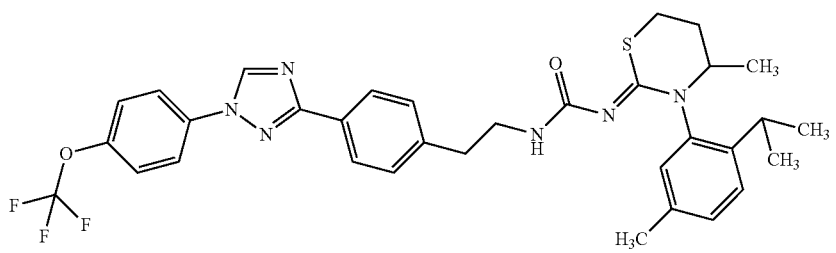 [SMILES: Cc1ccc(C(C)C)c(N2/C(=N/C(=O)NCCc3ccc(-c4ncn(-c5ccc(OC(F)(F)F)cc5)n4)cc3)SCCC2C)c1]
P63
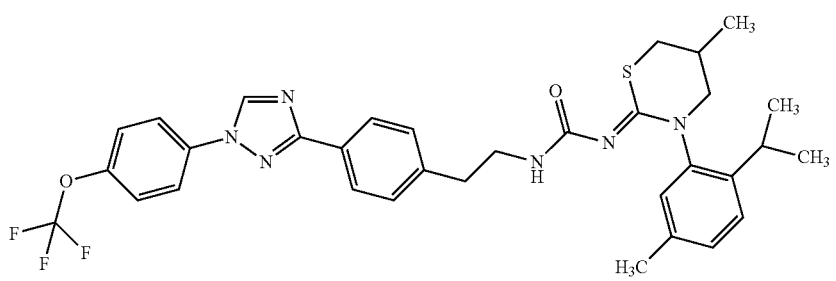 [SMILES: Cc1ccc(C(C)C)c(N2CC(C)CS/C2=N\C(=O)NCCc2ccc(-c3ncn(-c4ccc(OC(F)(F)F)cc4)n3)cc2)c1]
P64
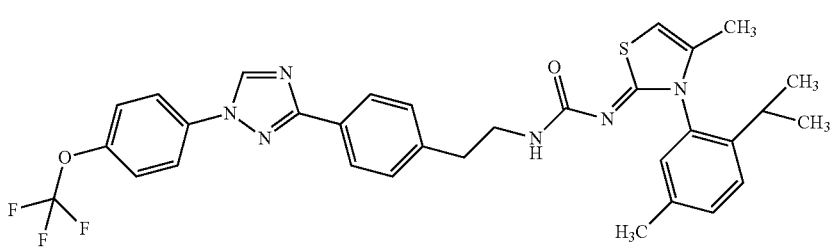 [SMILES: Cc1ccc(C(C)C)c(-n2c(C)cs/c2=N\C(=O)NCCc2ccc(-c3ncn(-c4ccc(OC(F)(F)F)cc4)n3)cc2)c1]
P65
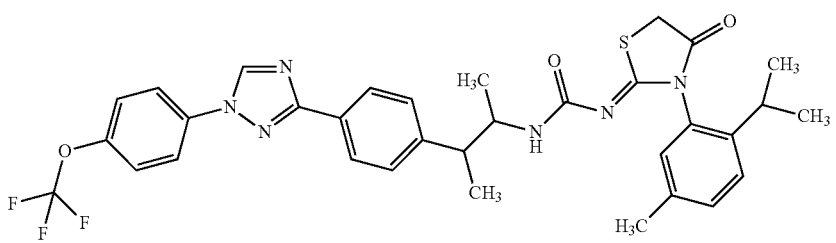 [SMILES: Cc1ccc(C(C)C)c(N2C(=O)CS/C2=N\C(=O)NC(C)C(C)c2ccc(-c3ncn(-c4ccc(OC(F)(F)F)cc4)n3)cc2)c1]
P66

TABLE P-One-continued
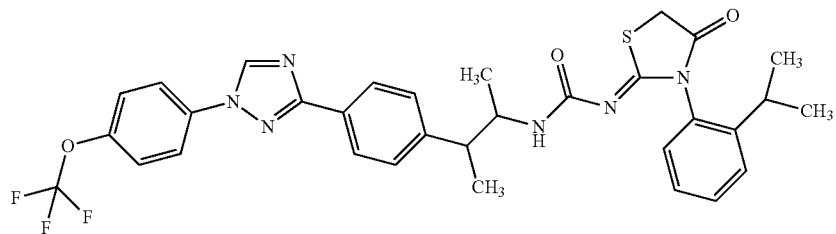 [SMILES: CC(C)c1ccccc1N1C(=O)CS/C1=N\C(=O)NC(C)C(C)c1ccc(-c2ncn(-c3ccc(OC(F)(F)F)cc3)n2)cc1]
P67
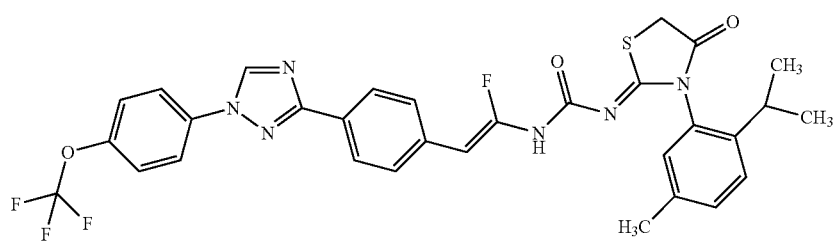 [SMILES: Cc1ccc(C(C)C)c(N2C(=O)CS/C2=N\C(=O)N/C(F)=C/c2ccc(-c3ncn(-c4ccc(OC(F)(F)F)cc4)n3)cc2)c1]
P68
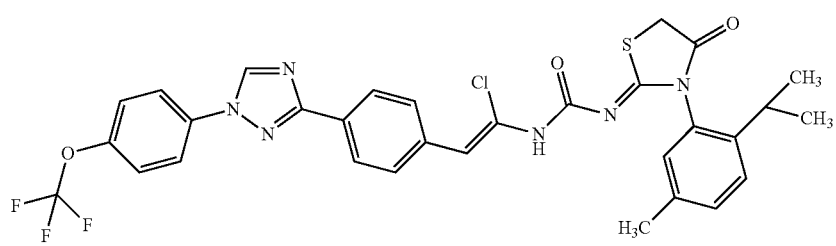 [SMILES: Cc1ccc(C(C)C)c(N2C(=O)CS/C2=N\C(=O)N/C(Cl)=C/c2ccc(-c3ncn(-c4ccc(OC(F)(F)F)cc4)n3)cc2)c1]
P69
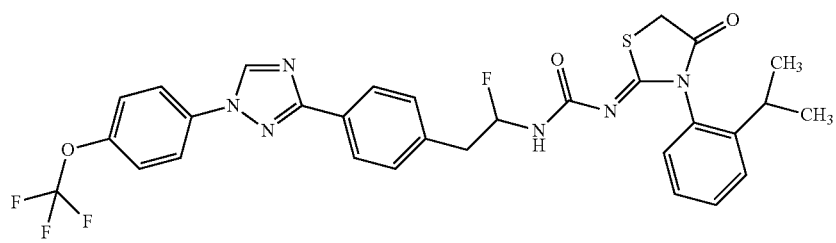 [SMILES: CC(C)c1ccccc1N1C(=O)CS/C1=N\C(=O)NC(F)Cc1ccc(-c2ncn(-c3ccc(OC(F)(F)F)cc3)n2)cc1]
P70
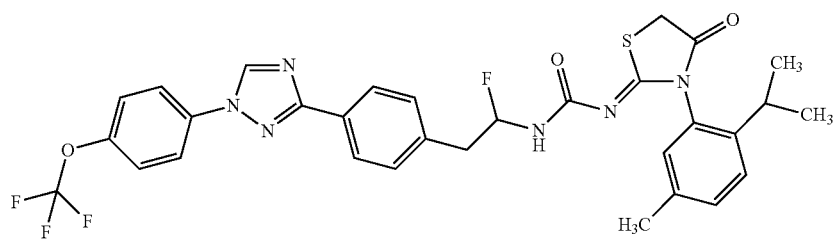 [SMILES: Cc1ccc(C(C)C)c(N2C(=O)CS/C2=N\C(=O)NC(F)Cc2ccc(-c3ncn(-c4ccc(OC(F)(F)F)cc4)n3)cc2)c1]
P71
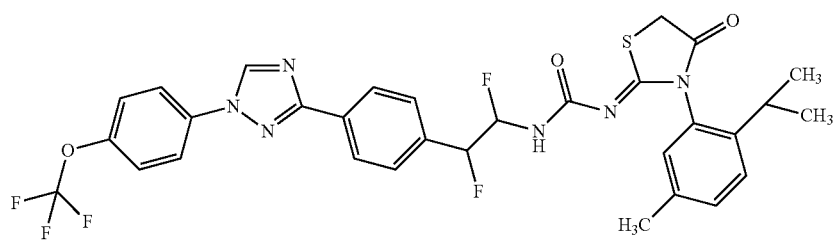 [SMILES: Cc1ccc(C(C)C)c(N2C(=O)CS/C2=N\C(=O)NC(F)C(F)c2ccc(-c3ncn(-c4ccc(OC(F)(F)F)cc4)n3)cc2)c1]
P72

TABLE P-One-continued
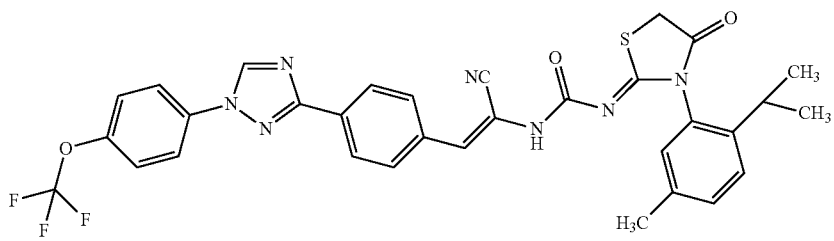 P73
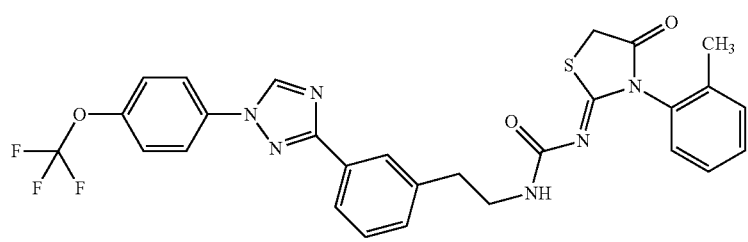 [SMILES: Cc1ccccc1N1C(=O)CS/C1=N\C(=O)NCCc1cccc(-c2ncn(-c3ccc(OC(F)(F)F)cc3)n2)c1] P74
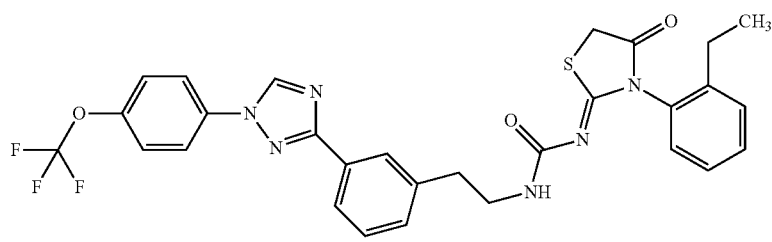 [SMILES: CCc1ccccc1N1C(=O)CS/C1=N\C(=O)NCCc1cccc(-c2ncn(-c3ccc(OC(F)(F)F)cc3)n2)c1] P75
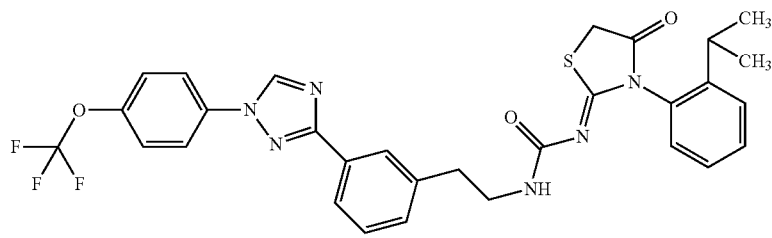 [SMILES: CC(C)c1ccccc1N1C(=O)CS/C1=N\C(=O)NCCc1cccc(-c2ncn(-c3ccc(OC(F)(F)F)cc3)n2)c1] P76
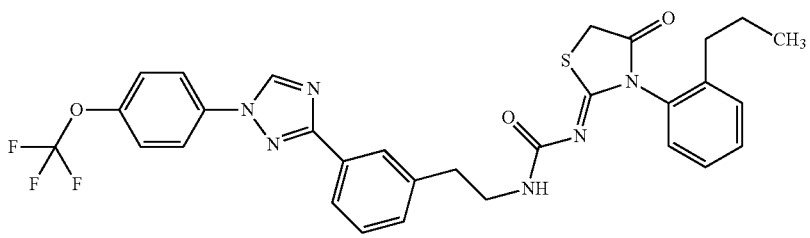 [SMILES: CCCc1ccccc1N1C(=O)CS/C1=N\C(=O)NCCc1cccc(-c2ncn(-c3ccc(OC(F)(F)F)cc3)n2)c1] P77
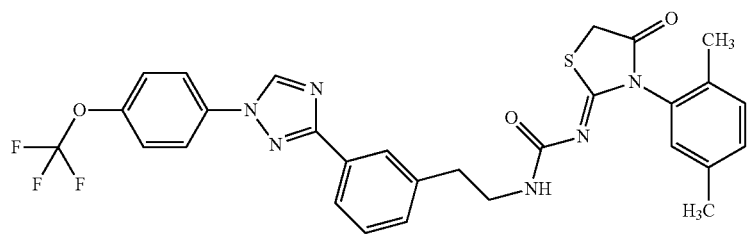 [SMILES: Cc1ccc(C)c(N2C(=O)CS/C2=N\C(=O)NCCc2cccc(-c3ncn(-c4ccc(OC(F)(F)F)cc4)n3)c2)c1] P78

TABLE P-One-continued
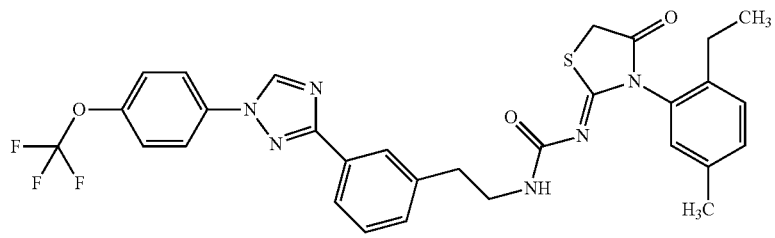 [SMILES: CCc1ccc(C)cc1N1C(=O)CS/C1=N\C(=O)NCCc1cccc(-c2ncn(-c3ccc(OC(F)(F)F)cc3)n2)c1] P79
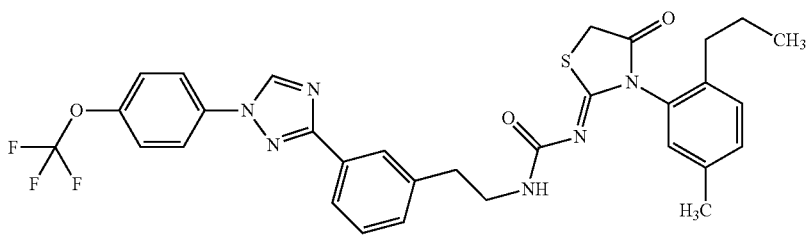 [SMILES: CCCc1ccc(C)cc1N1C(=O)CS/C1=N\C(=O)NCCc1cccc(-c2ncn(-c3ccc(OC(F)(F)F)cc3)n2)c1] P80
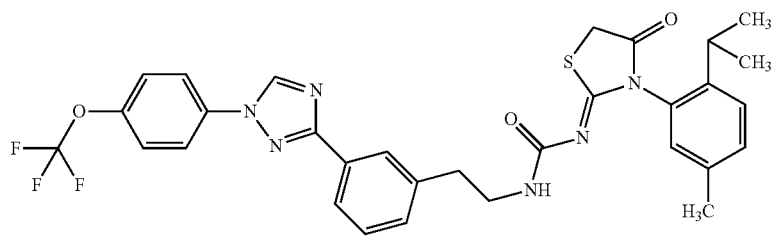 [SMILES: Cc1ccc(C(C)C)c(N2C(=O)CS/C2=N\C(=O)NCCc2cccc(-c3ncn(-c4ccc(OC(F)(F)F)cc4)n3)c2)c1] P81
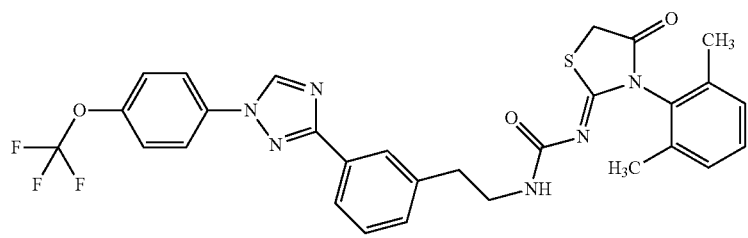 [SMILES: Cc1cccc(C)c1N1C(=O)CS/C1=N\C(=O)NCCc1cccc(-c2ncn(-c3ccc(OC(F)(F)F)cc3)n2)c1] P82
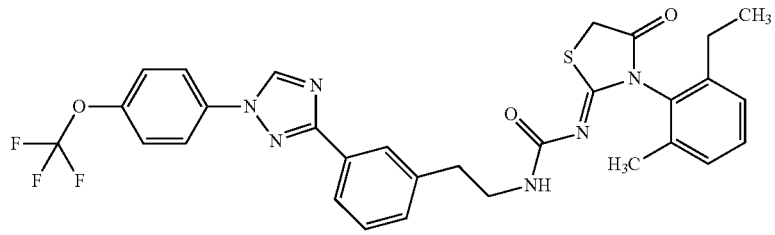 [SMILES: CCc1cccc(C)c1N1C(=O)CS/C1=N\C(=O)NCCc1cccc(-c2ncn(-c3ccc(OC(F)(F)F)cc3)n2)c1] P83
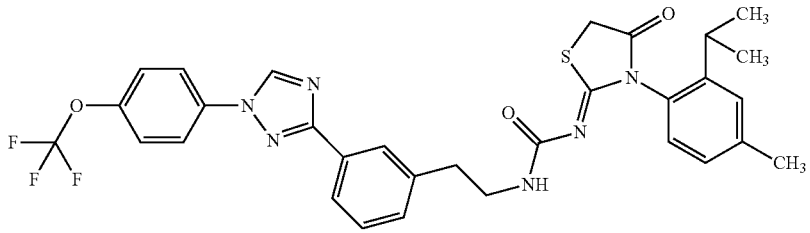 [SMILES: Cc1ccc(N2C(=O)CS/C2=N\C(=O)NCCc2cccc(-c3ncn(-c4ccc(OC(F)(F)F)cc4)n3)c2)c(C(C)C)c1] P84

TABLE P-One-continued
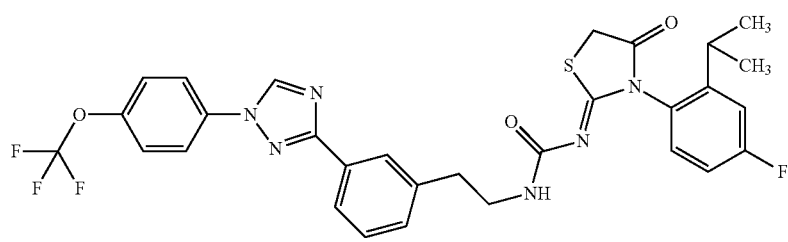 [SMILES: CC(C)c1cc(F)ccc1N1C(=O)CS/C1=N\C(=O)NCCc1cccc(-c2ncn(-c3ccc(OC(F)(F)F)cc3)n2)c1]
P85
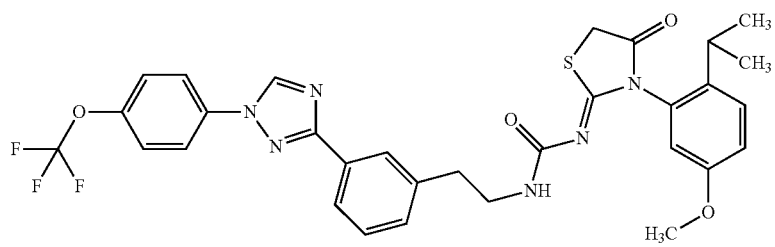 [SMILES: COc1ccc(C(C)C)c(N2C(=O)CS/C2=N\C(=O)NCCc2cccc(-c3ncn(-c4ccc(OC(F)(F)F)cc4)n3)c2)c1]
P86
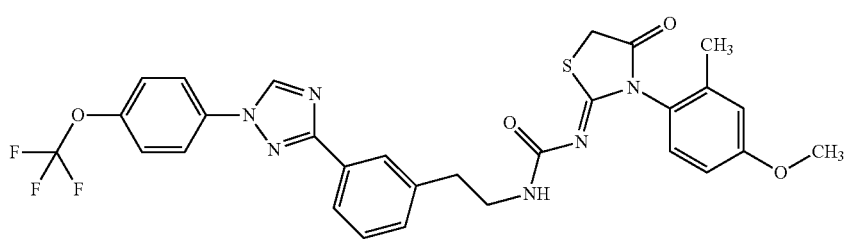 [SMILES: COc1ccc(N2C(=O)CS/C2=N\C(=O)NCCc2cccc(-c3ncn(-c4ccc(OC(F)(F)F)cc4)n3)c2)c(C)c1]
P87
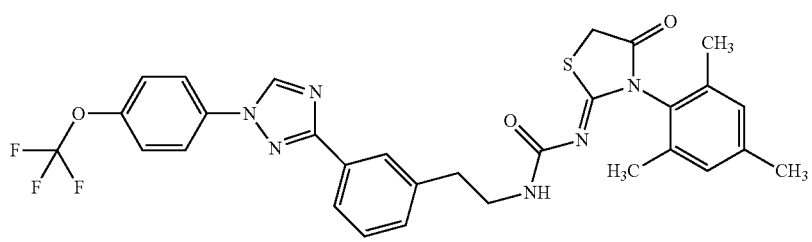 [SMILES: Cc1cc(C)c(N2C(=O)CS/C2=N\C(=O)NCCc2cccc(-c3ncn(-c4ccc(OC(F)(F)F)cc4)n3)c2)c(C)c1]
P88
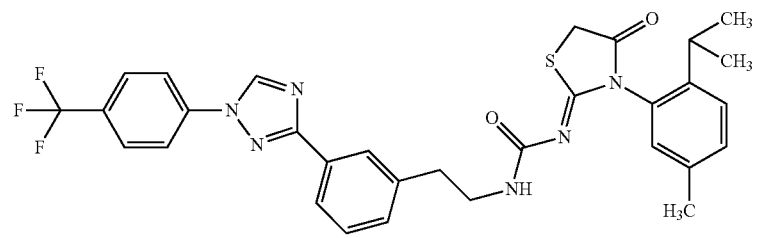 [SMILES: Cc1ccc(C(C)C)c(N2C(=O)CS/C2=N\C(=O)NCCc2cccc(-c3ncn(-c4ccc(C(F)(F)F)cc4)n3)c2)c1]
P89
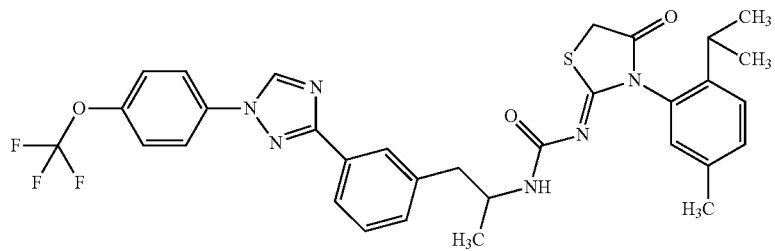 [SMILES: Cc1ccc(C(C)C)c(N2C(=O)CS/C2=N\C(=O)NC(C)Cc2cccc(-c3ncn(-c4ccc(OC(F)(F)F)cc4)n3)c2)c1]
P90

TABLE P-One-continued
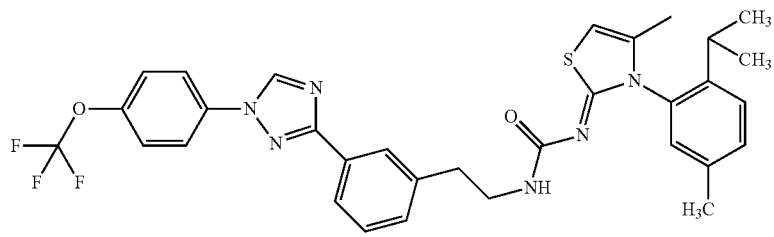 [SMILES: Cc1ccc(C(C)C)c(-n2c(C)cs/c2=N\C(=O)NCCc2cccc(-c3ncn(-c4ccc(OC(F)(F)F)cc4)n3)c2)c1]
P91
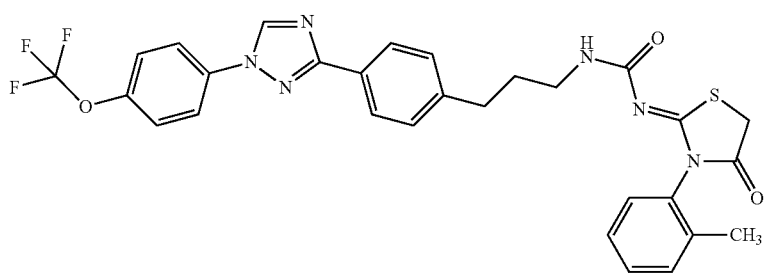 [SMILES: Cc1ccccc1N1C(=O)CS/C1=N\C(=O)NCCCc1ccc(-c2ncn(-c3ccc(OC(F)(F)F)cc3)n2)cc1]
P92
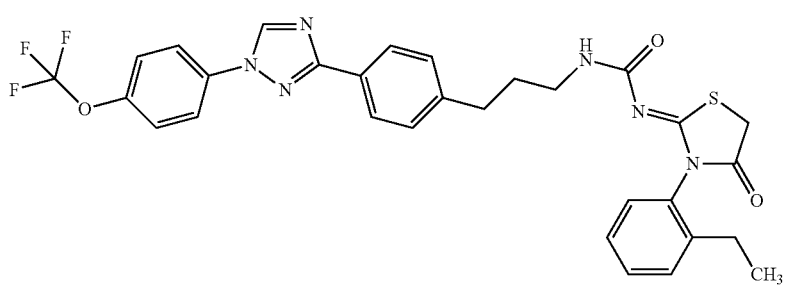 [SMILES: CCc1ccccc1N1C(=O)CS/C1=N\C(=O)NCCCc1ccc(-c2ncn(-c3ccc(OC(F)(F)F)cc3)n2)cc1]
P93
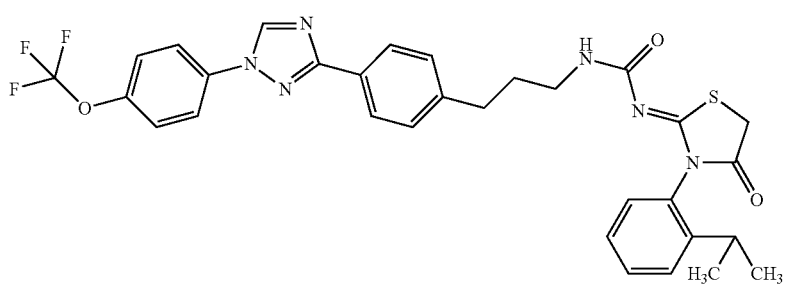 [SMILES: CC(C)c1ccccc1N1C(=O)CS/C1=N\C(=O)NCCCc1ccc(-c2ncn(-c3ccc(OC(F)(F)F)cc3)n2)cc1]
P94
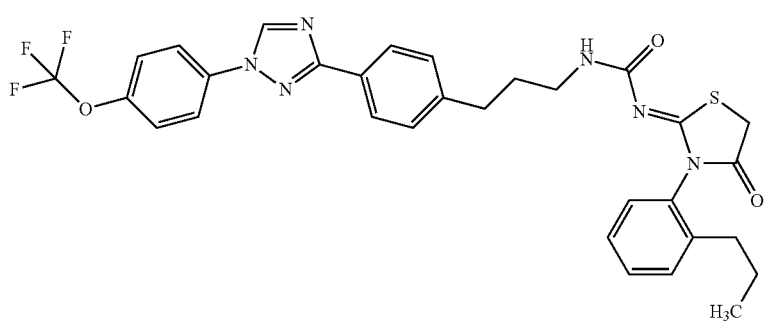 [SMILES: CCCc1ccccc1N1C(=O)CS/C1=N\C(=O)NCCCc1ccc(-c2ncn(-c3ccc(OC(F)(F)F)cc3)n2)cc1]
P95

TABLE P-One-continued
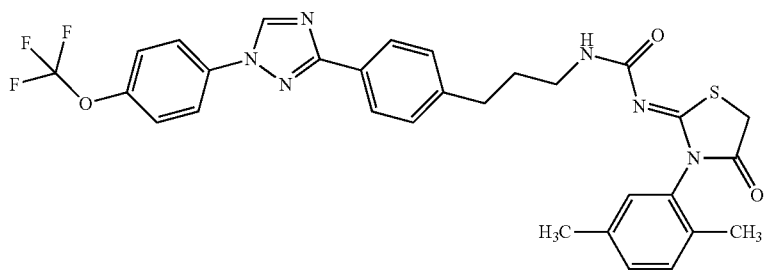 [SMILES: Cc1ccc(C)c(N2C(=O)CS/C2=N\C(=O)NCCCc2ccc(-c3ncn(-c4ccc(OC(F)(F)F)cc4)n3)cc2)c1]
P96
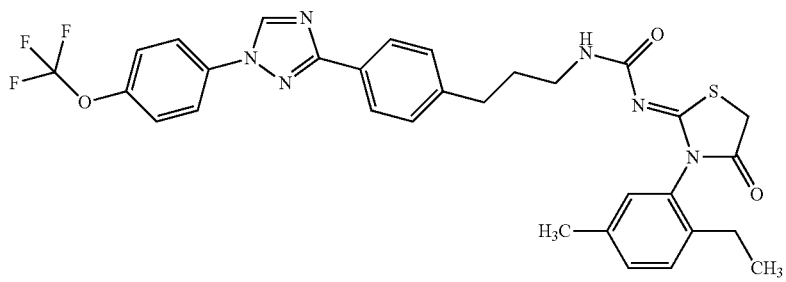 [SMILES: CCc1ccc(C)cc1N1C(=O)CS/C1=N\C(=O)NCCCc1ccc(-c2ncn(-c3ccc(OC(F)(F)F)cc3)n2)cc1]
P97
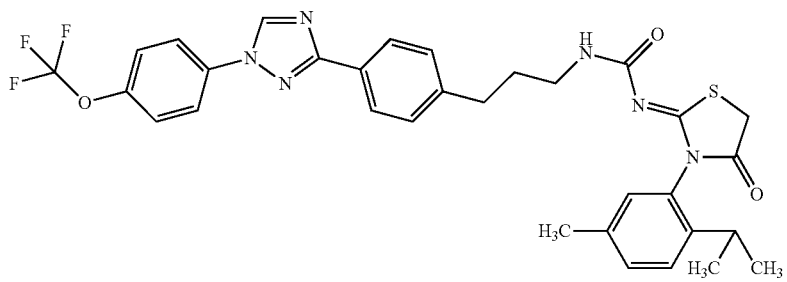 [SMILES: Cc1ccc(C(C)C)c(N2C(=O)CS/C2=N\C(=O)NCCCc2ccc(-c3ncn(-c4ccc(OC(F)(F)F)cc4)n3)cc2)c1]
P98
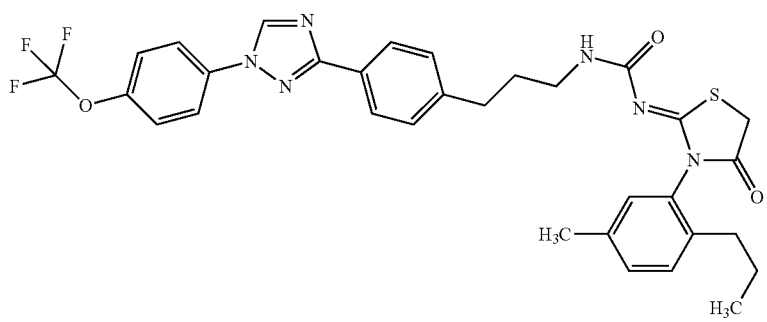 [SMILES: CCCc1ccc(C)cc1N1C(=O)CS/C1=N\C(=O)NCCCc1ccc(-c2ncn(-c3ccc(OC(F)(F)F)cc3)n2)cc1]
P99
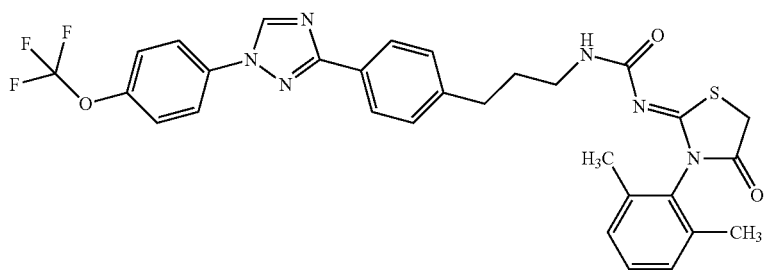 [SMILES: Cc1cccc(C)c1N1C(=O)CS/C1=N\C(=O)NCCCc1ccc(-c2ncn(-c3ccc(OC(F)(F)F)cc3)n2)cc1]
P100

TABLE P-One-continued
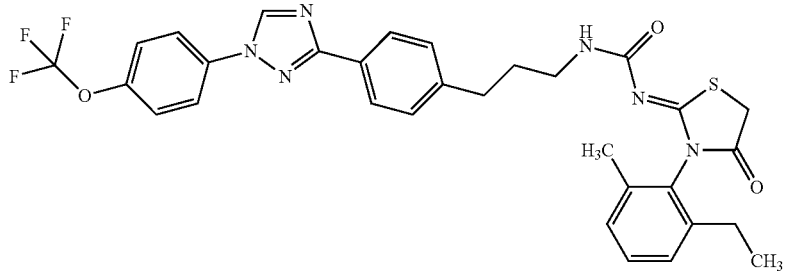 [SMILES: CCc1cccc(C)c1N1C(=O)CS/C1=N\C(=O)NCCCc1ccc(-c2ncn(-c3ccc(OC(F)(F)F)cc3)n2)cc1]
P101
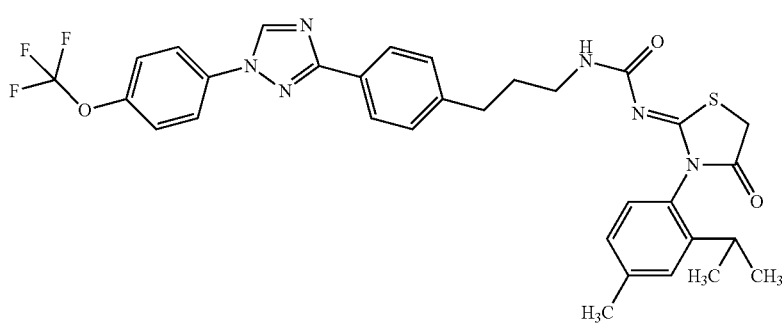 [SMILES: Cc1ccc(N2C(=O)CS/C2=N\C(=O)NCCCc2ccc(-c3ncn(-c4ccc(OC(F)(F)F)cc4)n3)cc2)c(C(C)C)c1]
P102
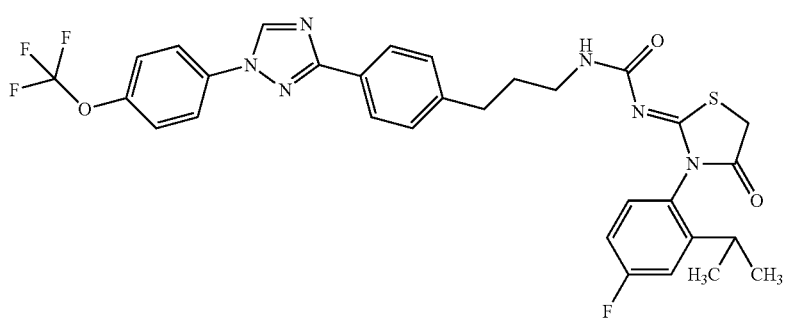 [SMILES: CC(C)c1cc(F)ccc1N1C(=O)CS/C1=N\C(=O)NCCCc1ccc(-c2ncn(-c3ccc(OC(F)(F)F)cc3)n2)cc1]
P103
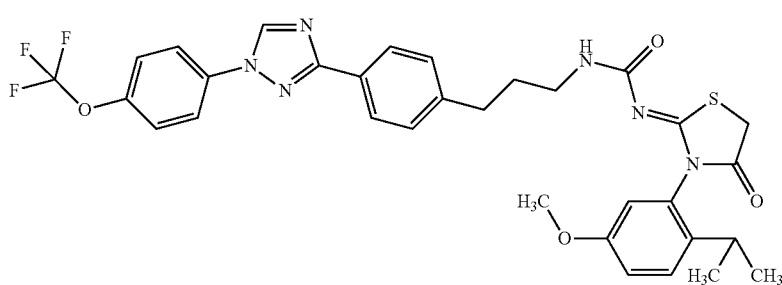 [SMILES: COc1ccc(C(C)C)c(N2C(=O)CS/C2=N\C(=O)NCCCc2ccc(-c3ncn(-c4ccc(OC(F)(F)F)cc4)n3)cc2)c1]
P104
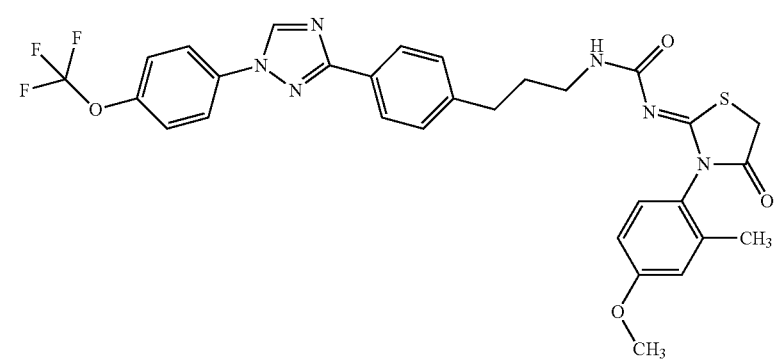 [SMILES: COc1ccc(N2C(=O)CS/C2=N\C(=O)NCCCc2ccc(-c3ncn(-c4ccc(OC(F)(F)F)cc4)n3)cc2)c(C)c1]
P105

TABLE P-One-continued
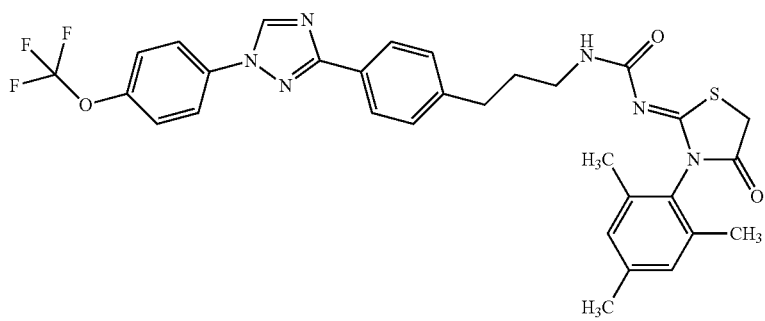 [SMILES: Cc1cc(C)c(N2C(=O)CS/C2=N\C(=O)NCCCc2ccc(-c3ncn(-c4ccc(OC(F)(F)F)cc4)n3)cc2)c(C)c1]
P106
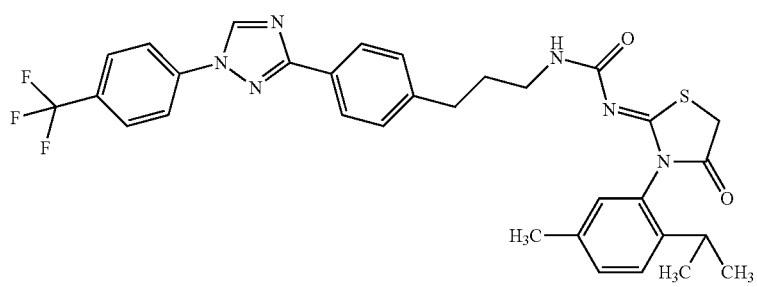 [SMILES: Cc1ccc(C(C)C)c(N2C(=O)CS/C2=N\C(=O)NCCCc2ccc(-c3ncn(-c4ccc(C(F)(F)F)cc4)n3)cc2)c1]
P107
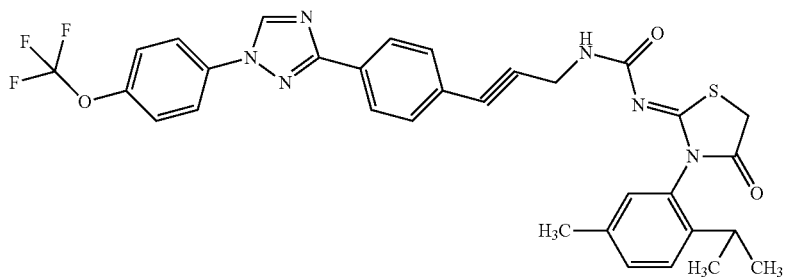
P108
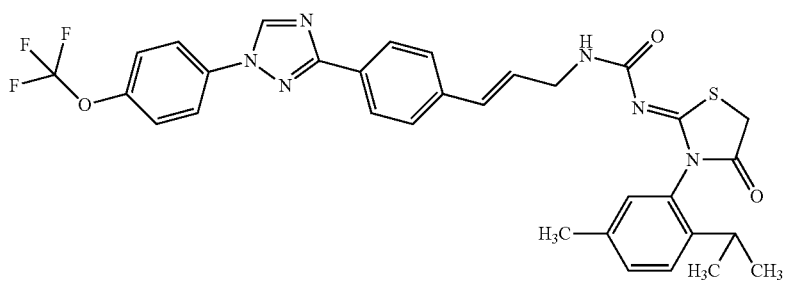 [SMILES: Cc1ccc(C(C)C)c(N2C(=O)CS/C2=N\C(=O)NC/C=C/c2ccc(-c3ncn(-c4ccc(OC(F)(F)F)cc4)n3)cc2)c1]
P109
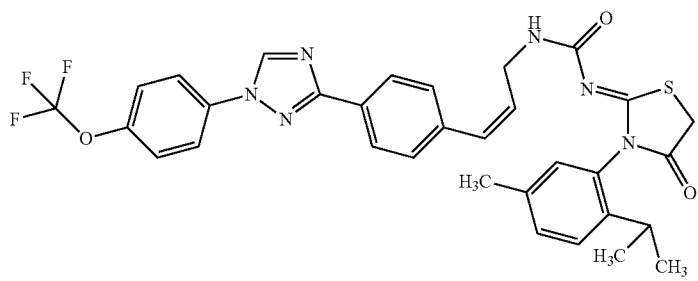 [SMILES: Cc1ccc(C(C)C)c(N2C(=O)CS/C2=N\C(=O)NC/C=C\c2ccc(-c3ncn(-c4ccc(OC(F)(F)F)cc4)n3)cc2)c1]
P110

TABLE P-One-continued
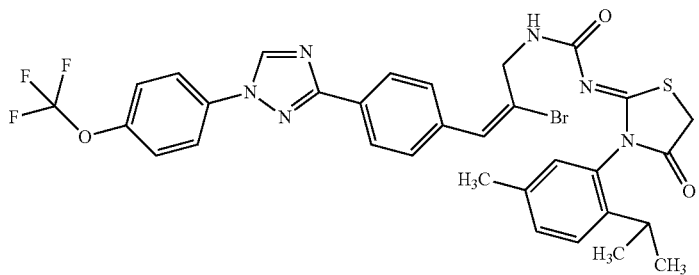 P111
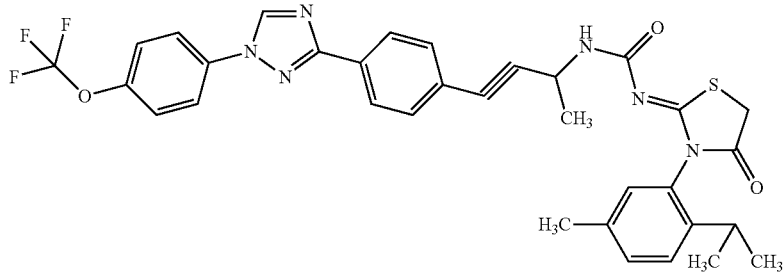 [SMILES: Cc1ccc(C(C)C)c(N2C(=O)CS/C2=N\C(=O)NC(C)C#Cc2ccc(-c3ncn(-c4ccc(OC(F)(F)F)cc4)n3)cc2)c1] P112
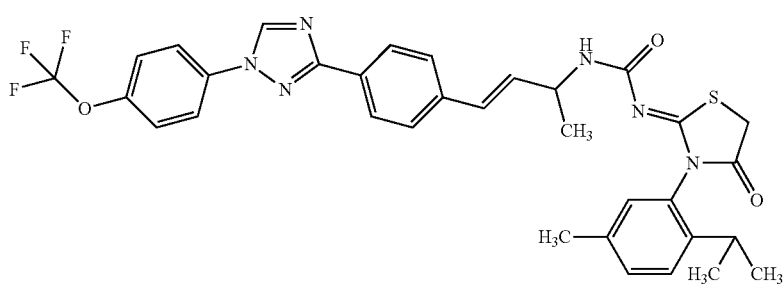 P113
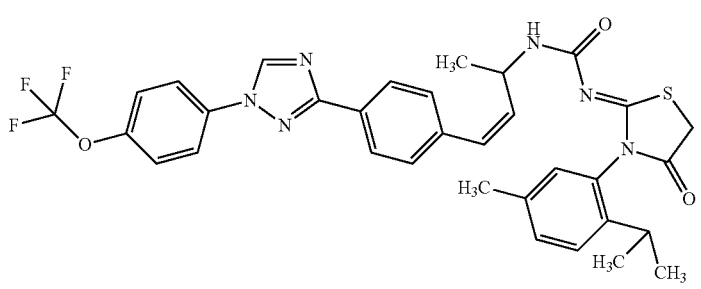 [SMILES: Cc1ccc(C(C)C)c(N2C(=O)CS/C2=N\C(=O)NC(C)/C=C\c2ccc(-c3ncn(-c4ccc(OC(F)(F)F)cc4)n3)cc2)c1] P114
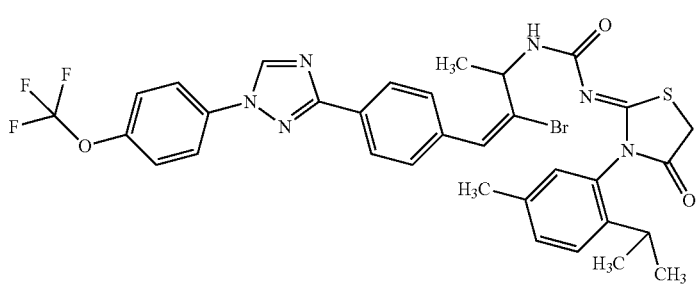 [SMILES: Cc1ccc(C(C)C)c(N2C(=O)CS/C2=N\C(=O)NC(C)/C(Br)=C\c2ccc(-c3ncn(-c4ccc(OC(F)(F)F)cc4)n3)cc2)c1] P115

TABLE P-One-continued
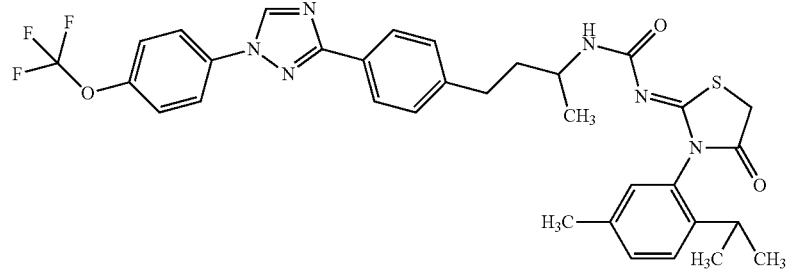 [SMILES: Cc1ccc(C(C)C)c(N2C(=O)CS/C2=N\C(=O)NC(C)CCc2ccc(-c3ncn(-c4ccc(OC(F)(F)F)cc4)n3)cc2)c1]
P116
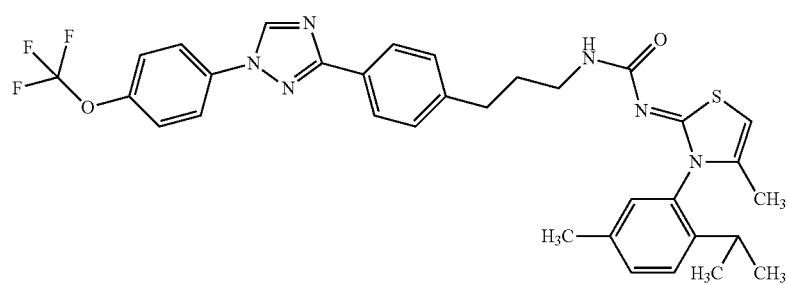 [SMILES: Cc1ccc(C(C)C)c(-n2c(C)cs/c2=N\C(=O)NCCCc2ccc(-c3ncn(-c4ccc(OC(F)(F)F)cc4)n3)cc2)c1]
P117
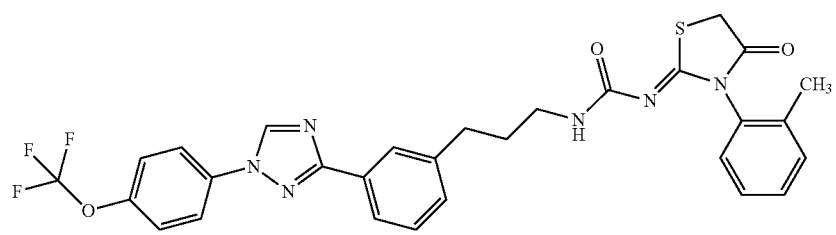 [SMILES: Cc1ccccc1N1C(=O)CS/C1=N\C(=O)NCCCc1cccc(-c2ncn(-c3ccc(OC(F)(F)F)cc3)n2)c1]
P118
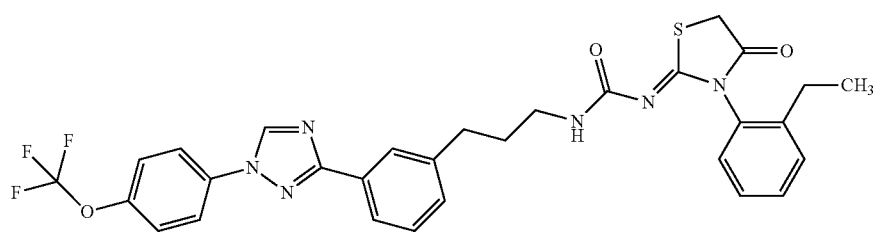 [SMILES: CCc1ccccc1N1C(=O)CS/C1=N\C(=O)NCCCc1cccc(-c2ncn(-c3ccc(OC(F)(F)F)cc3)n2)c1]
P119
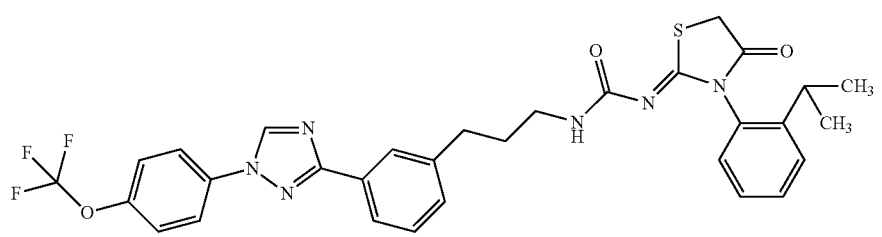 [SMILES: CC(C)c1ccccc1N1C(=O)CS/C1=N\C(=O)NCCCc1cccc(-c2ncn(-c3ccc(OC(F)(F)F)cc3)n2)c1]
P120
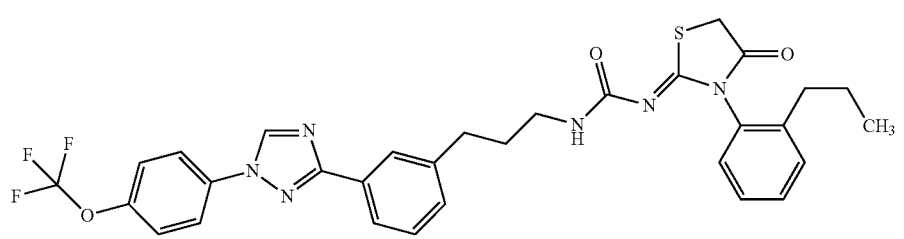 [SMILES: CCCc1ccccc1N1C(=O)CS/C1=N\C(=O)NCCCc1cccc(-c2ncn(-c3ccc(OC(F)(F)F)cc3)n2)c1]
P121

TABLE P-One-continued
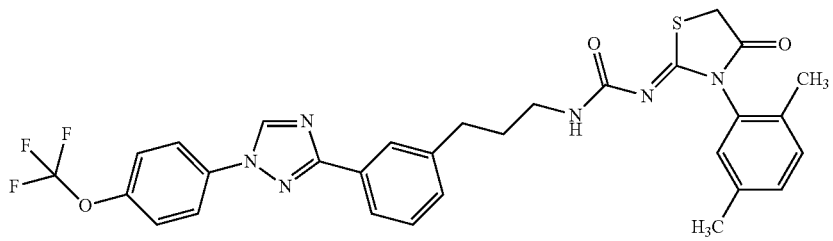 [SMILES: Cc1ccc(C)c(N2C(=O)CS/C2=N\C(=O)NCCCc2cccc(-c3ncn(-c4ccc(OC(F)(F)F)cc4)n3)c2)c1]
P122
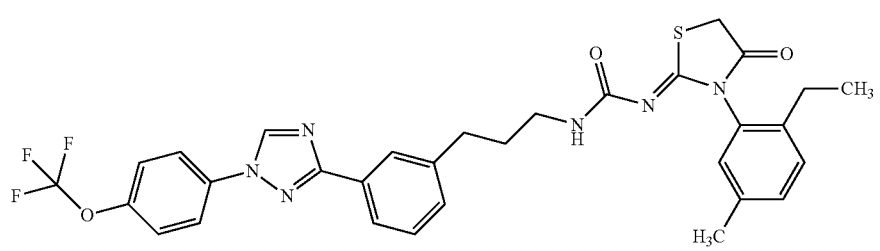 [SMILES: CCc1ccc(C)cc1N1C(=O)CS/C1=N\C(=O)NCCCc1cccc(-c2ncn(-c3ccc(OC(F)(F)F)cc3)n2)c1]
P123
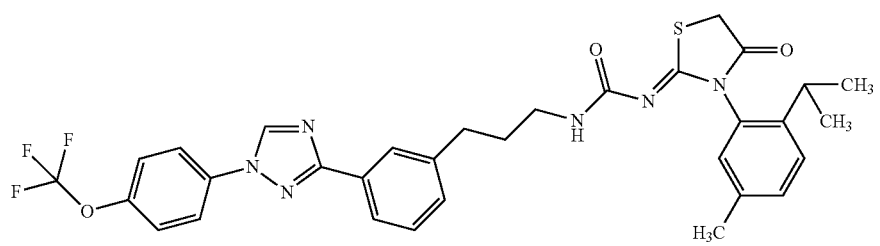
P124
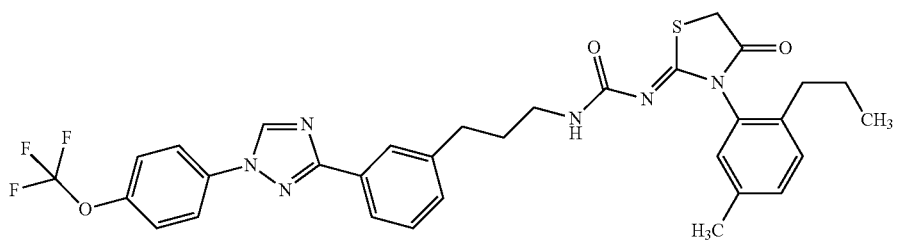 [SMILES: CCCc1ccc(C)cc1N1C(=O)CS/C1=N\C(=O)NCCCc1cccc(-c2ncn(-c3ccc(OC(F)(F)F)cc3)n2)c1]
P125
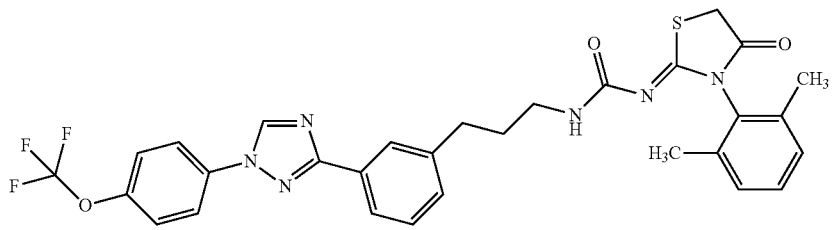
P126
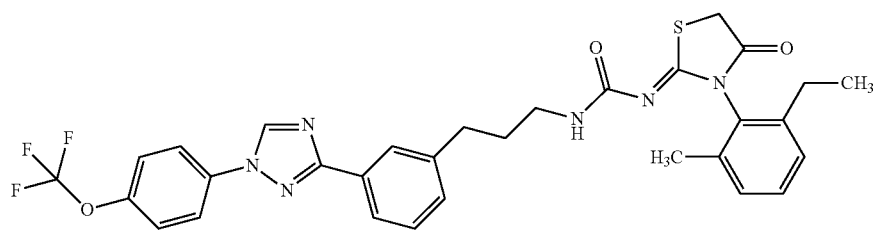 [SMILES: CCc1cccc(C)c1N1C(=O)CS/C1=N\C(=O)NCCCc1cccc(-c2ncn(-c3ccc(OC(F)(F)F)cc3)n2)c1]
P127

TABLE P-One-continued
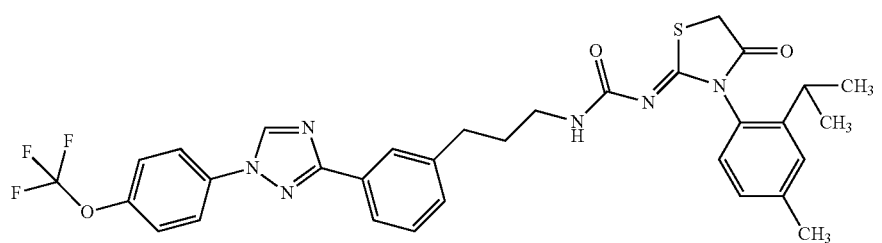 [SMILES: Cc1ccc(N2C(=O)CS/C2=N\C(=O)NCCCc2cccc(-c3ncn(-c4ccc(OC(F)(F)F)cc4)n3)c2)c(C(C)C)c1]
P128
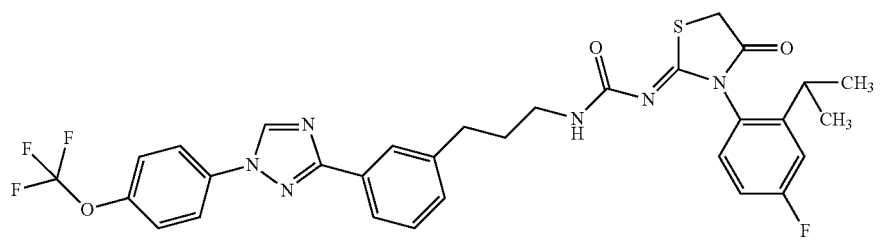 [SMILES: CC(C)c1cc(F)ccc1N1C(=O)CS/C1=N\C(=O)NCCCc1cccc(-c2ncn(-c3ccc(OC(F)(F)F)cc3)n2)c1]
P129
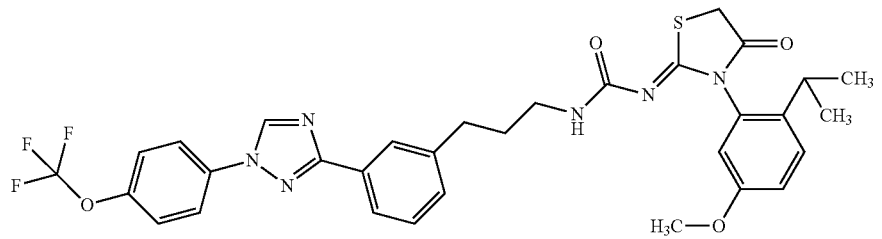 [SMILES: COc1ccc(C(C)C)c(N2C(=O)CS/C2=N\C(=O)NCCCc2cccc(-c3ncn(-c4ccc(OC(F)(F)F)cc4)n3)c2)c1]
P130
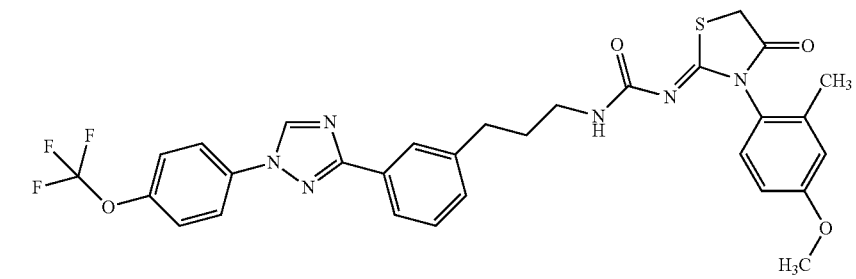 [SMILES: COc1ccc(N2C(=O)CS/C2=N\C(=O)NCCCc2cccc(-c3ncn(-c4ccc(OC(F)(F)F)cc4)n3)c2)c(C)c1]
P131
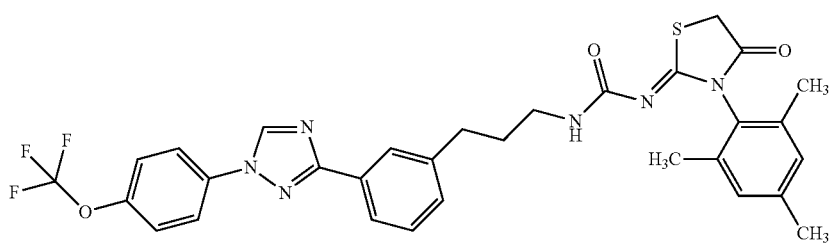 [SMILES: Cc1cc(C)c(N2C(=O)CS/C2=N\C(=O)NCCCc2cccc(-c3ncn(-c4ccc(OC(F)(F)F)cc4)n3)c2)c(C)c1]
P132
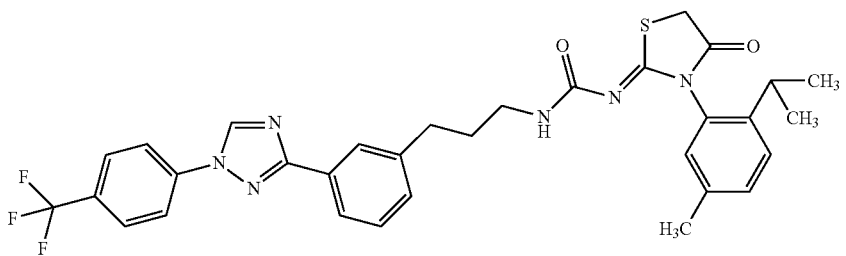 [SMILES: Cc1ccc(C(C)C)c(N2C(=O)CS/C2=N\C(=O)NCCCc2cccc(-c3ncn(-c4ccc(C(F)(F)F)cc4)n3)c2)c1]
P133

TABLE P-One-continued
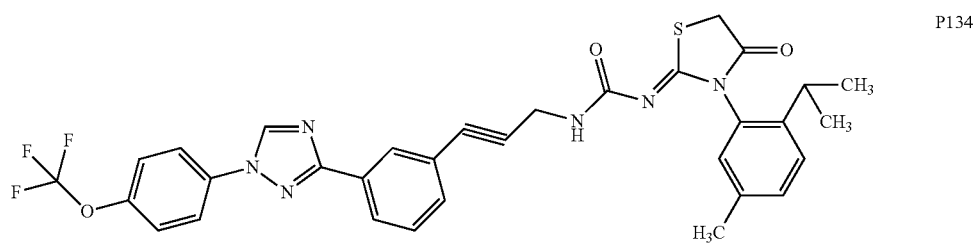 P134
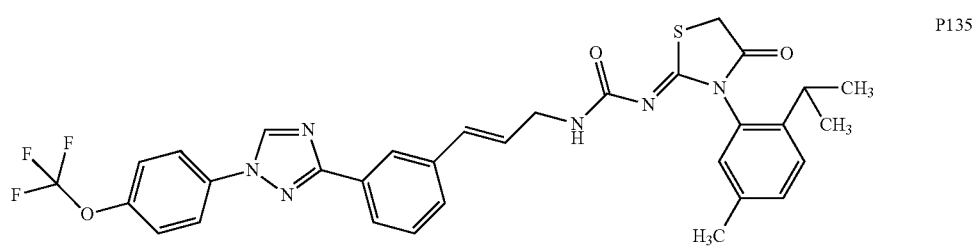 P135
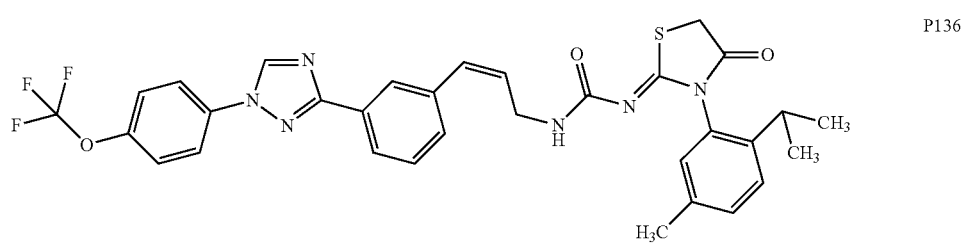 P136
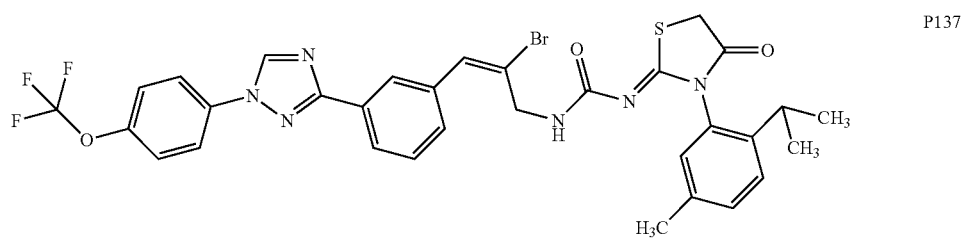 P137
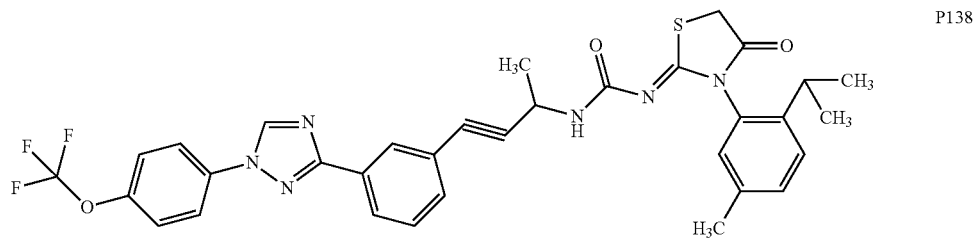 P138
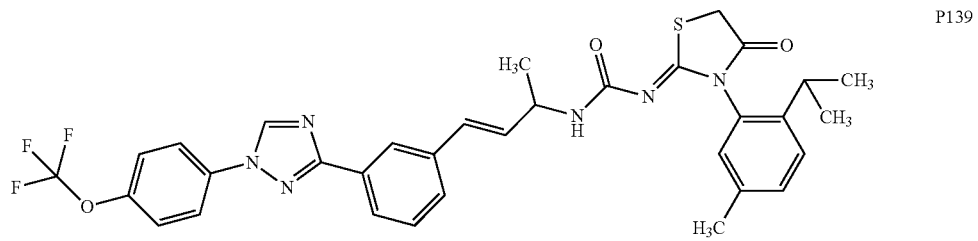 P139

TABLE P-One-continued
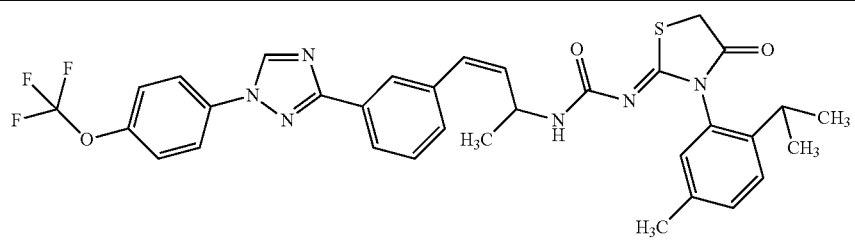 P140
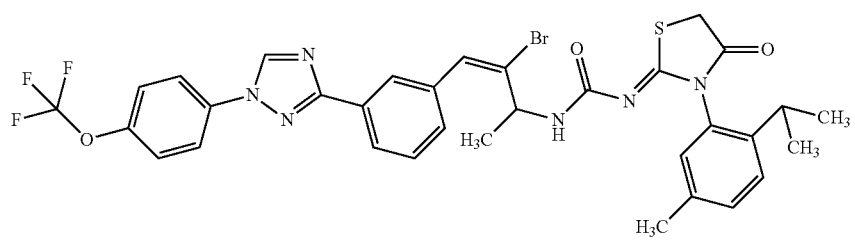 P141
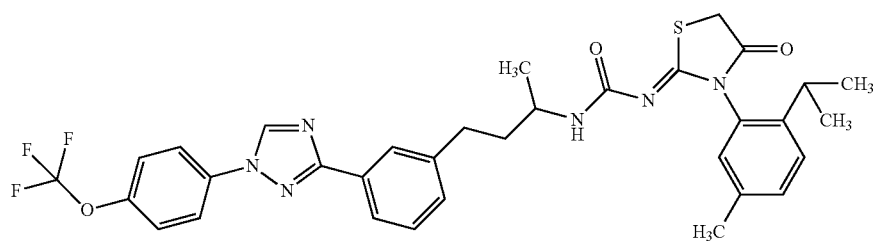 [SMILES: Cc1ccc(C(C)C)c(N2C(=O)CS/C2=N\C(=O)NC(C)C#Cc2cccc(-c3ncn(-c4ccc(OC(F)(F)F)cc4)n3)c2)c1] P142
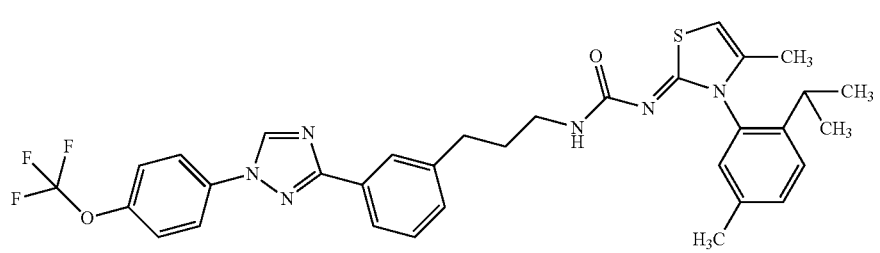 P143
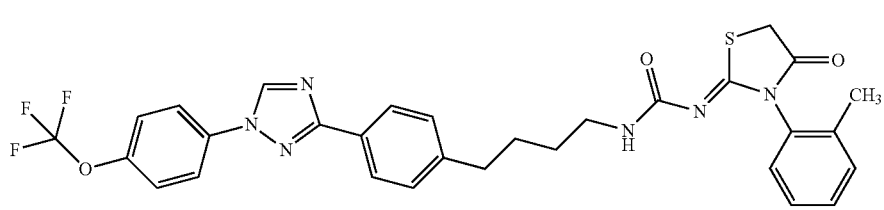 [SMILES: Cc1ccccc1N1C(=O)CS/C1=N\C(=O)NCCCCc1ccc(-c2ncn(-c3ccc(OC(F)(F)F)cc3)n2)cc1] P144
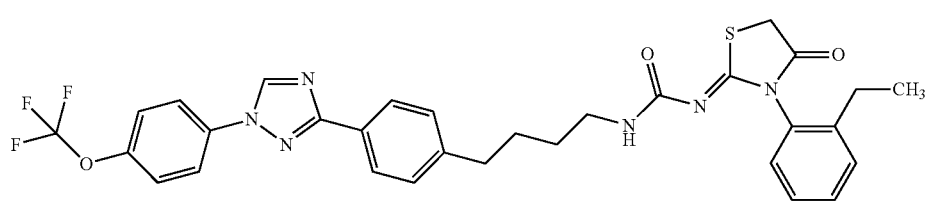 [SMILES: CCc1ccccc1N1C(=O)CS/C1=N\C(=O)NCCCCc1ccc(-c2ncn(-c3ccc(OC(F)(F)F)cc3)n2)cc1] P145
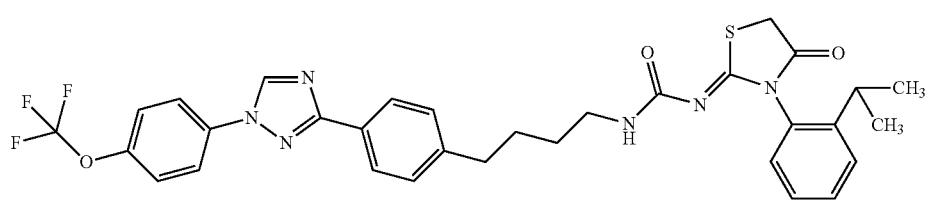 [SMILES: CC(C)c1ccccc1N1C(=O)CS/C1=N\C(=O)NCCCCc1ccc(-c2ncn(-c3ccc(OC(F)(F)F)cc3)n2)cc1] P146

TABLE P-One-continued
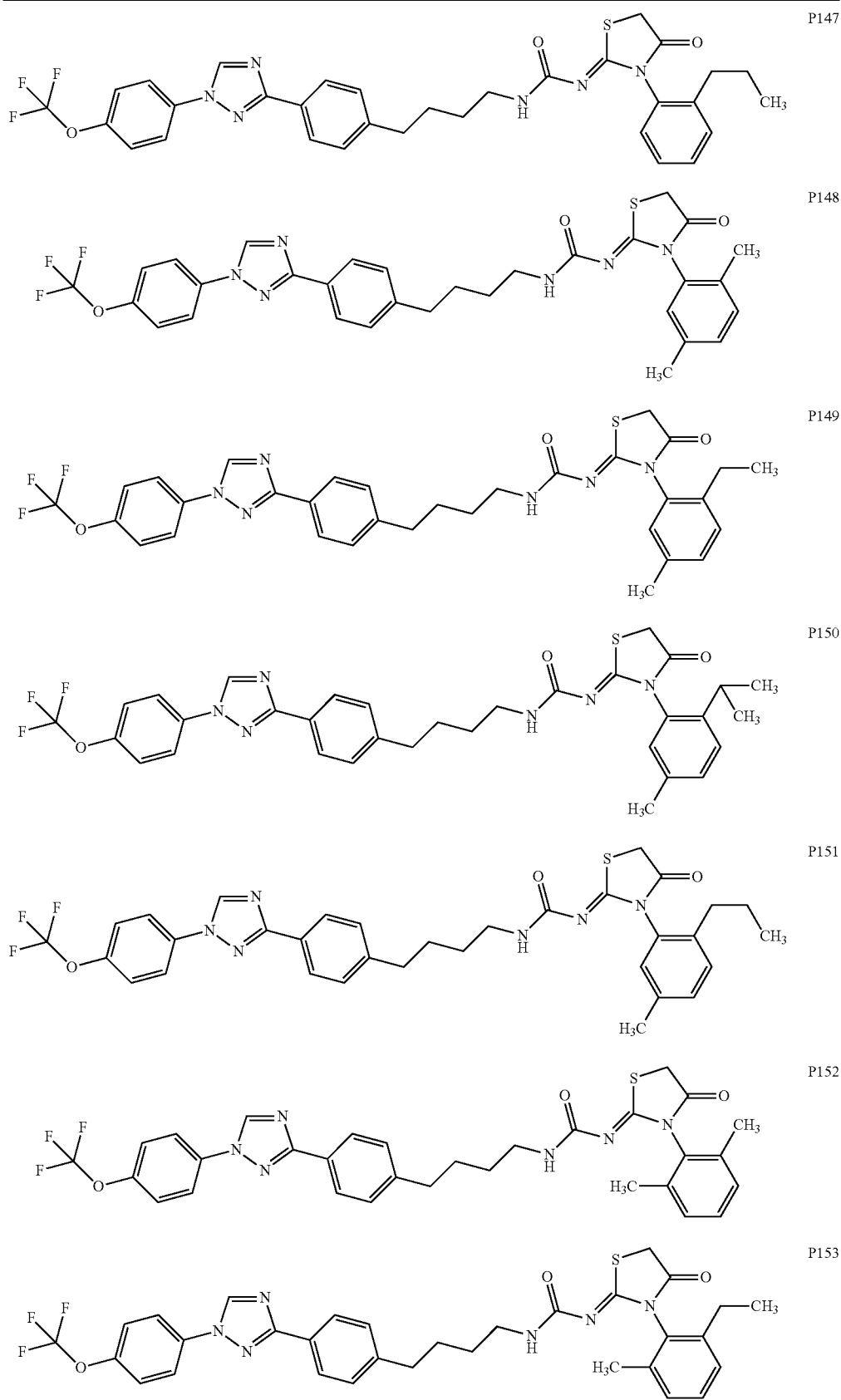

TABLE P-One-continued
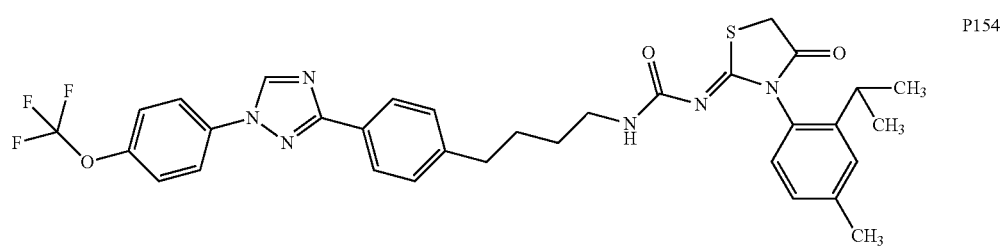 P154
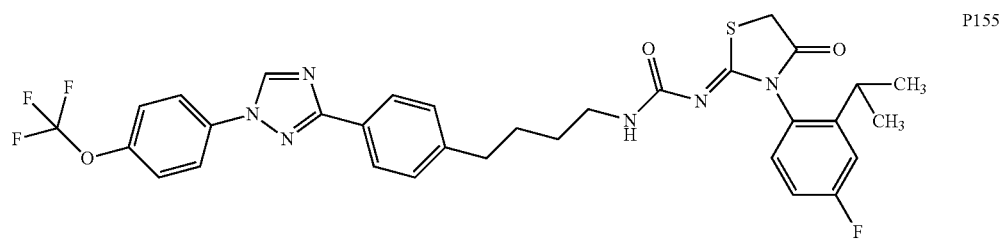 P155
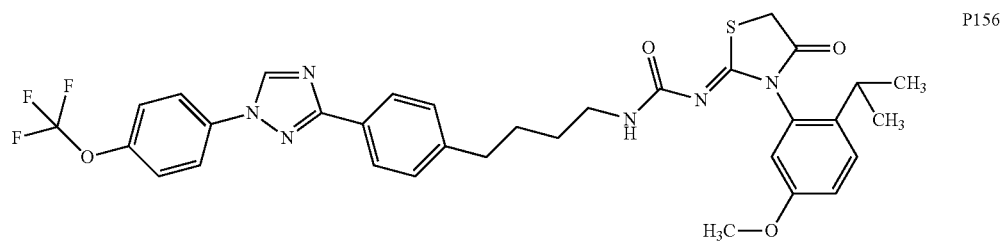 P156
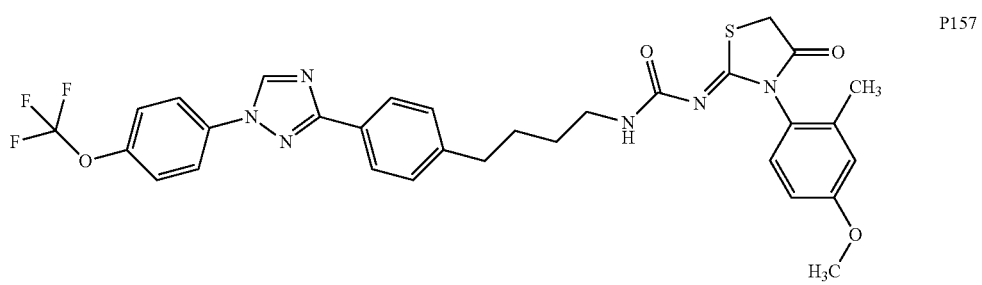 P157
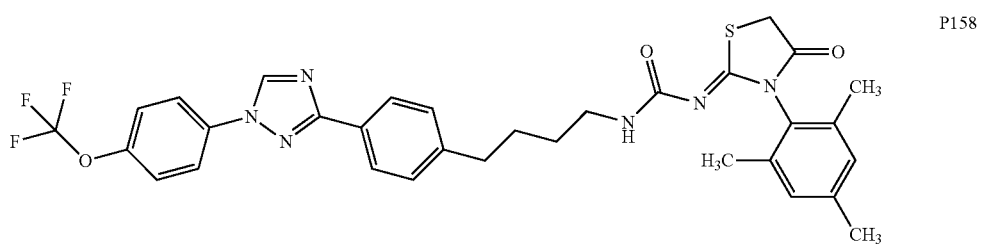 P158
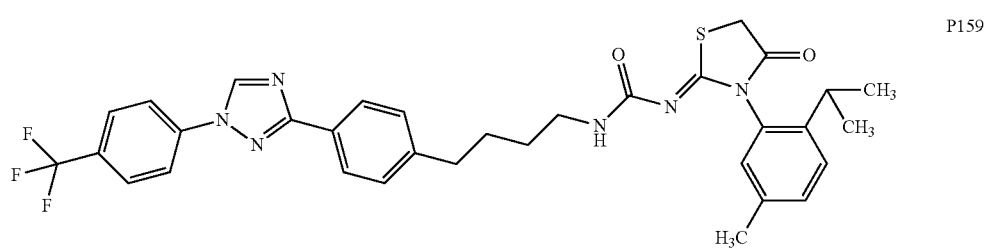 P159

TABLE P-One-continued
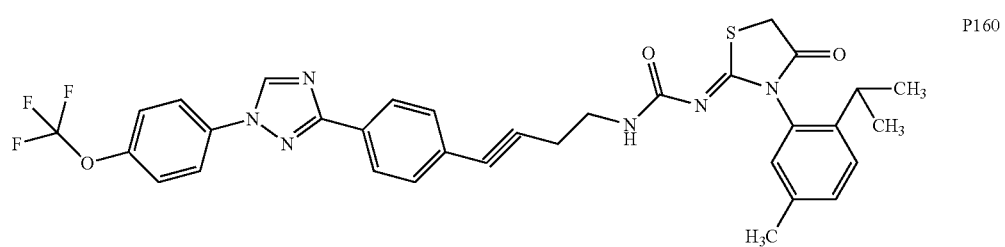
P160
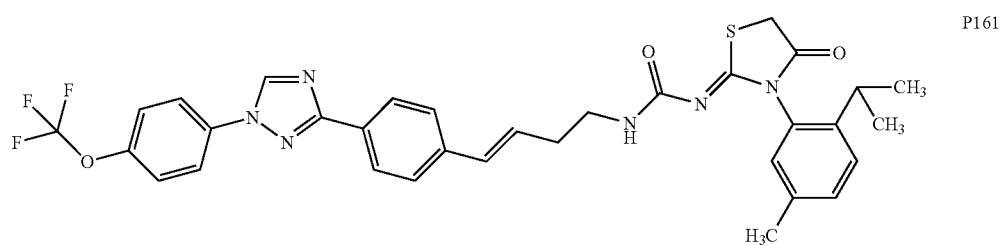
P161
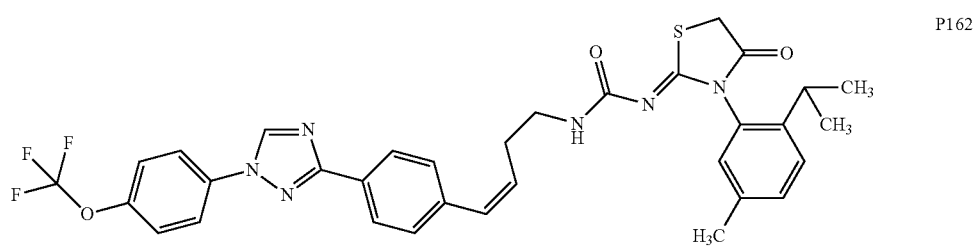
P162
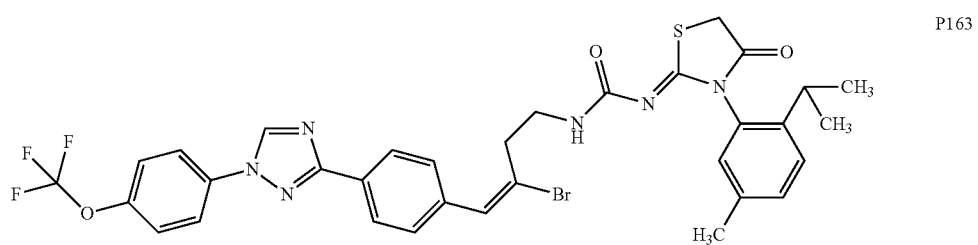
P163
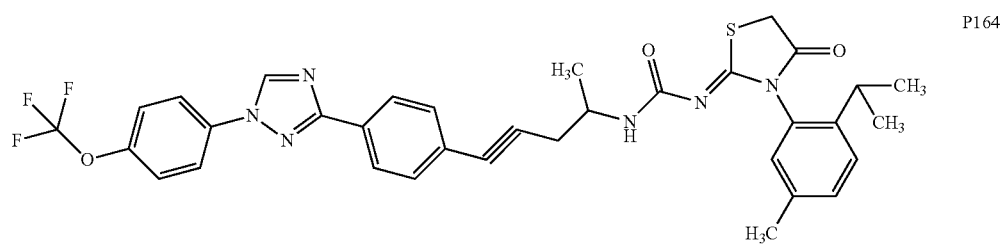
P164
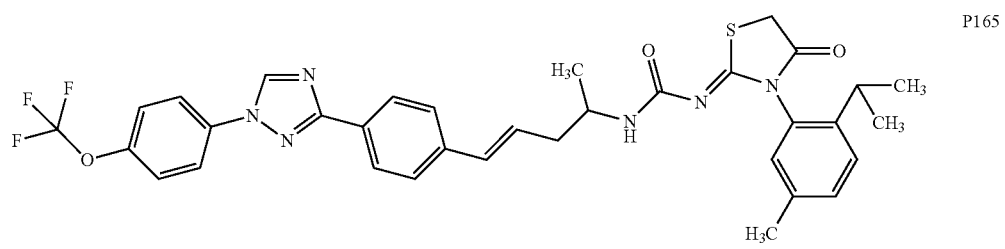
P165

TABLE P-One-continued
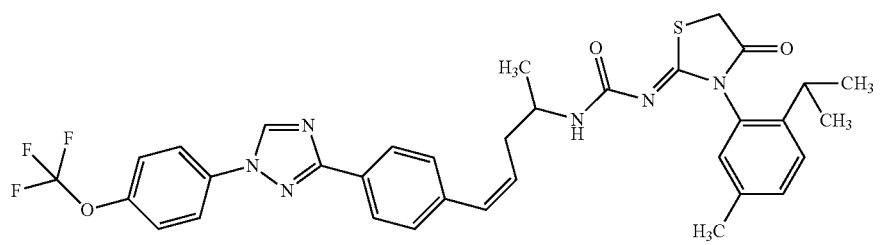 [SMILES: Cc1ccc(C(C)C)c(N2C(=O)CS/C2=N\C(=O)NCC/C=C\c2ccc(-c3ncn(-c4ccc(OC(F)(F)F)cc4)n3)cc2)c1] P166
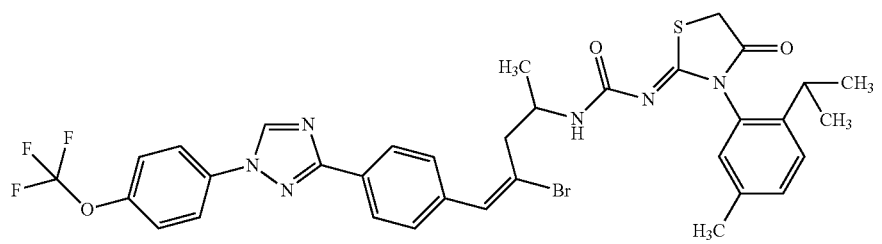 [SMILES: Cc1ccc(C(C)C)c(N2C(=O)CS/C2=N\C(=O)NC(C)C/C(Br)=C\c2ccc(-c3ncn(-c4ccc(OC(F)(F)F)cc4)n3)cc2)c1] P167
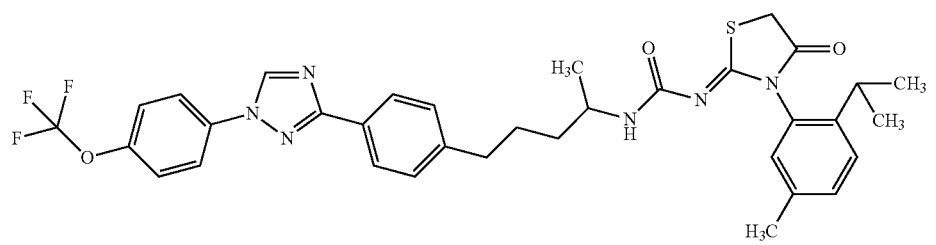 [SMILES: Cc1ccc(C(C)C)c(N2C(=O)CS/C2=N\C(=O)NC(C)CCCc2ccc(-c3ncn(-c4ccc(OC(F)(F)F)cc4)n3)cc2)c1] P168
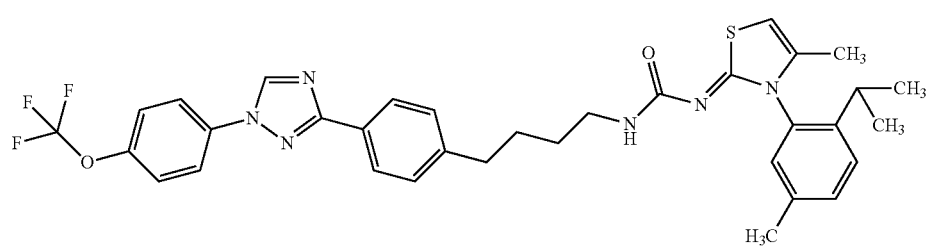 [SMILES: Cc1ccc(C(C)C)c(-n2c(C)cs/c2=N\C(=O)NCCCCc2ccc(-c3ncn(-c4ccc(OC(F)(F)F)cc4)n3)cc2)c1] P169
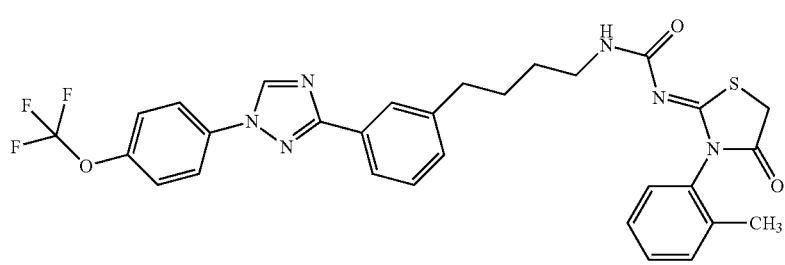 [SMILES: Cc1ccccc1N1C(=O)CS/C1=N\C(=O)NCCCCc1cccc(-c2ncn(-c3ccc(OC(F)(F)F)cc3)n2)c1] P170
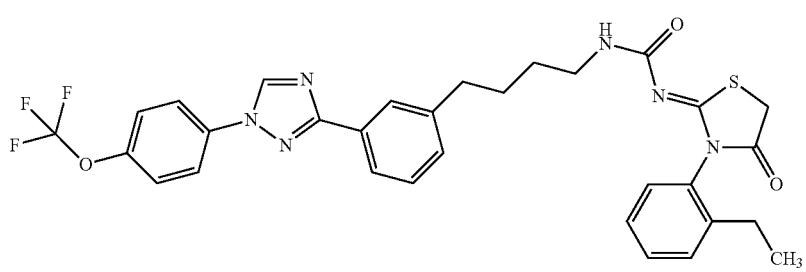 [SMILES: CCc1ccccc1N1C(=O)CS/C1=N\C(=O)NCCCCc1cccc(-c2ncn(-c3ccc(OC(F)(F)F)cc3)n2)c1] P171

TABLE P-One-continued
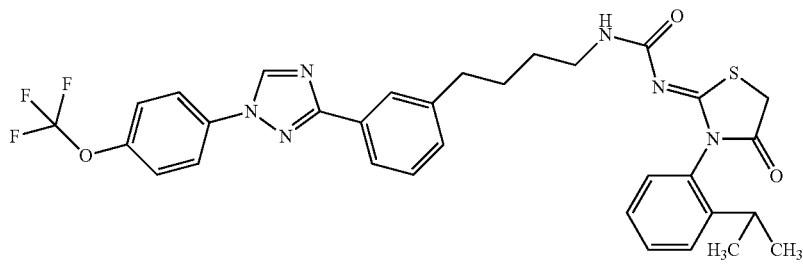 [SMILES: CC(C)c1ccccc1N1C(=O)CS/C1=N\C(=O)NCCCCc1cccc(-c2ncn(-c3ccc(OC(F)(F)F)cc3)n2)c1]
P172
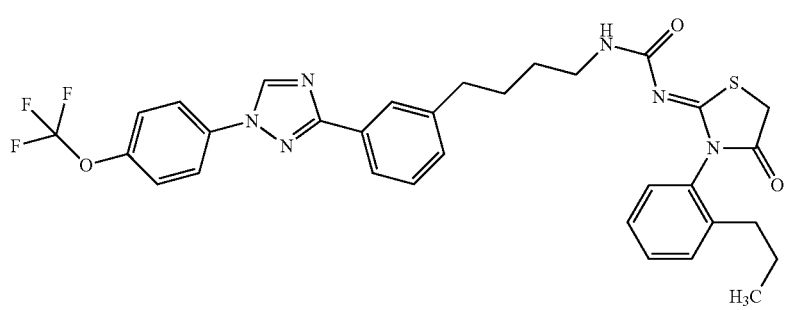 [SMILES: CCCc1ccccc1N1C(=O)CS/C1=N\C(=O)NCCCCc1cccc(-c2ncn(-c3ccc(OC(F)(F)F)cc3)n2)c1]
P173
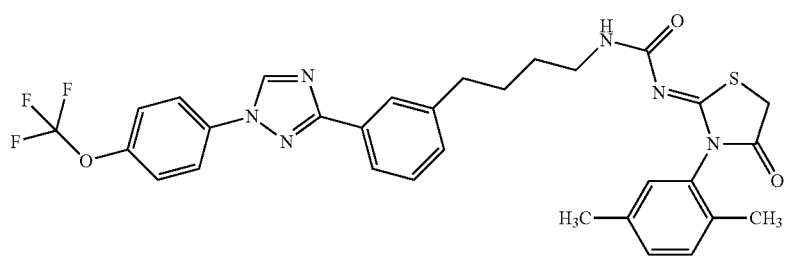 [SMILES: Cc1ccc(C)c(N2C(=O)CS/C2=N\C(=O)NCCCCc2cccc(-c3ncn(-c4ccc(OC(F)(F)F)cc4)n3)c2)c1]
P174
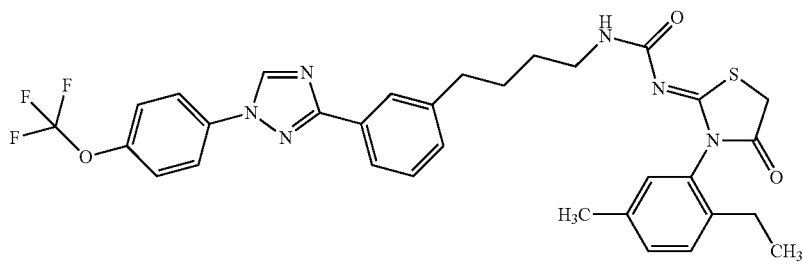 [SMILES: CCc1ccc(C)cc1N1C(=O)CS/C1=N\C(=O)NCCCCc1cccc(-c2ncn(-c3ccc(OC(F)(F)F)cc3)n2)c1]
P175
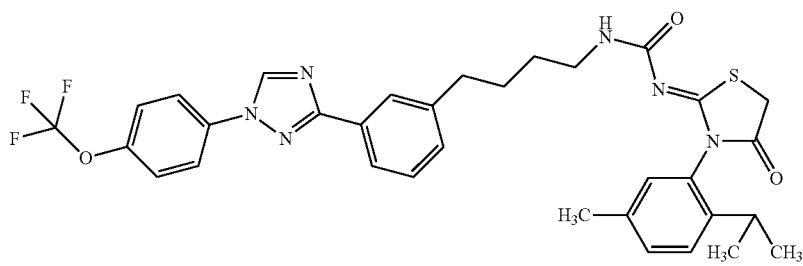 [SMILES: Cc1ccc(C(C)C)c(N2C(=O)CS/C2=N\C(=O)NCCCCc2cccc(-c3ncn(-c4ccc(OC(F)(F)F)cc4)n3)c2)c1]
P176

TABLE P-One-continued
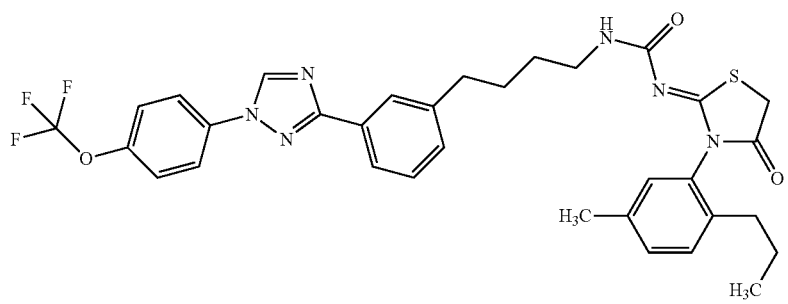 [SMILES: CCCc1ccc(C)cc1N1C(=O)CS/C1=N\C(=O)NCCCCc1cccc(-c2ncn(-c3ccc(OC(F)(F)F)cc3)n2)c1]
P177
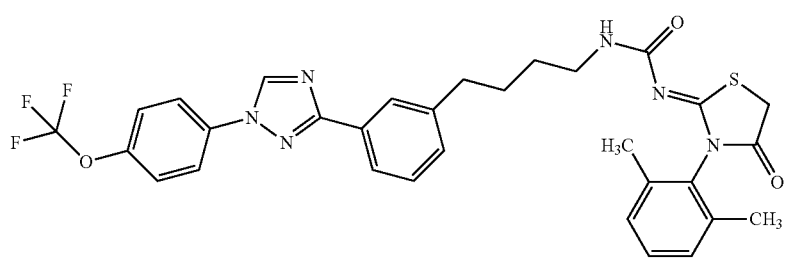 [SMILES: Cc1cccc(C)c1N1C(=O)CS/C1=N\C(=O)NCCCCc1cccc(-c2ncn(-c3ccc(OC(F)(F)F)cc3)n2)c1]
P178
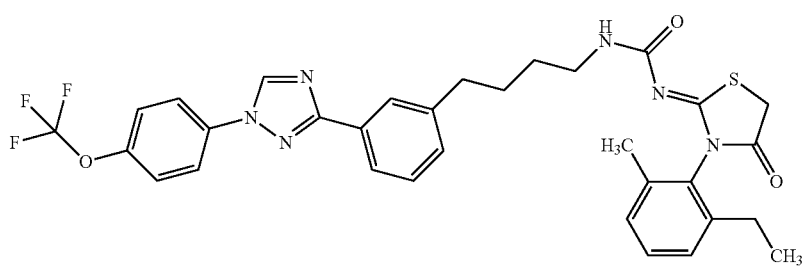 [SMILES: CCc1cccc(C)c1N1C(=O)CS/C1=N\C(=O)NCCCCc1cccc(-c2ncn(-c3ccc(OC(F)(F)F)cc3)n2)c1]
P179
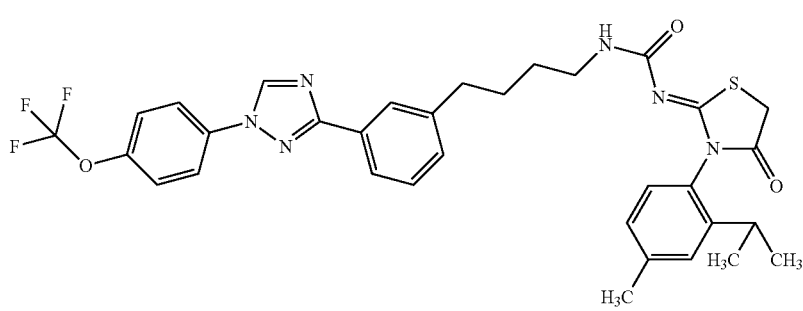 [SMILES: Cc1ccc(N2C(=O)CS/C2=N\C(=O)NCCCCc2cccc(-c3ncn(-c4ccc(OC(F)(F)F)cc4)n3)c2)c(C(C)C)c1]
P180
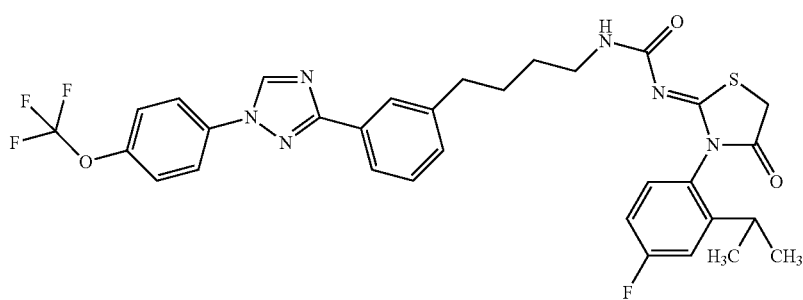 [SMILES: CC(C)c1cc(F)ccc1N1C(=O)CS/C1=N\C(=O)NCCCCc1cccc(-c2ncn(-c3ccc(OC(F)(F)F)cc3)n2)c1]
P181

TABLE P-One-continued
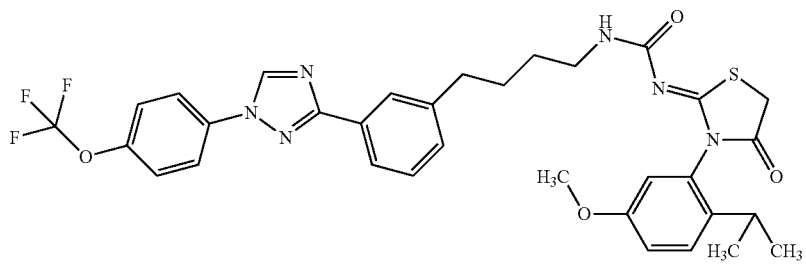 [SMILES: COc1ccc(C(C)C)c(N2C(=O)CS/C2=N\C(=O)NCCCCc2cccc(-c3ncn(-c4ccc(OC(F)(F)F)cc4)n3)c2)c1] P182
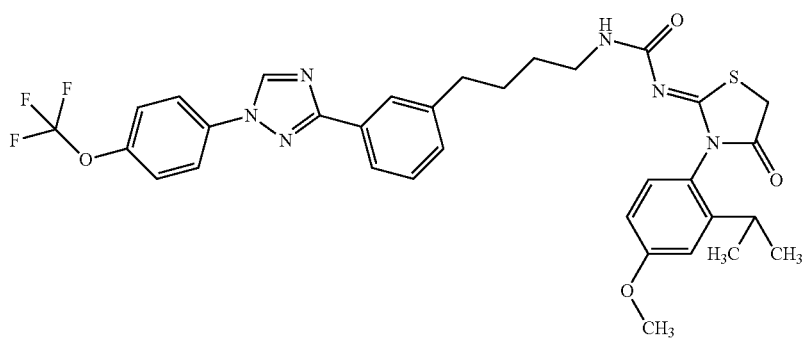 [SMILES: COc1ccc(N2C(=O)CS/C2=N\C(=O)NCCCCc2cccc(-c3ncn(-c4ccc(OC(F)(F)F)cc4)n3)c2)c(C(C)C)c1] P183
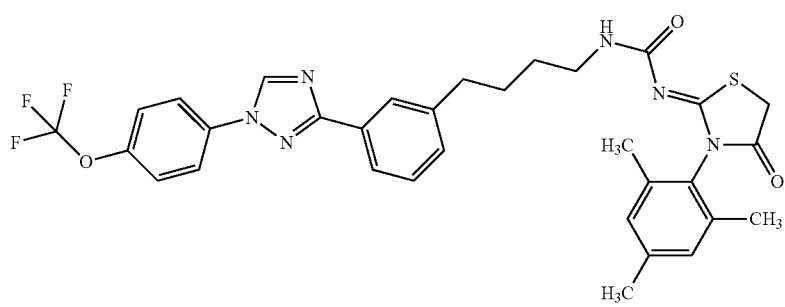 [SMILES: Cc1cc(C)c(N2C(=O)CS/C2=N\C(=O)NCCCCc2cccc(-c3ncn(-c4ccc(OC(F)(F)F)cc4)n3)c2)c(C)c1] P184
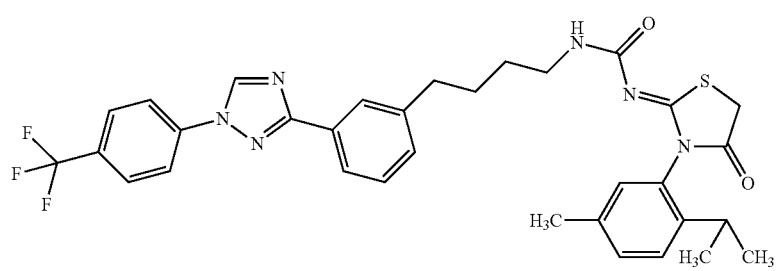 [SMILES: Cc1ccc(C(C)C)c(N2C(=O)CS/C2=N\C(=O)NCCCCc2cccc(-c3ncn(-c4ccc(C(F)(F)F)cc4)n3)c2)c1] P185
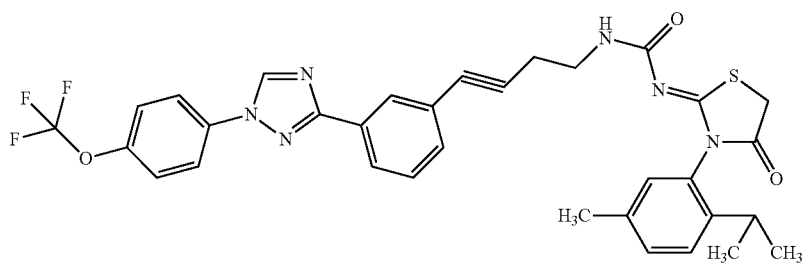 [SMILES: Cc1ccc(C(C)C)c(N2C(=O)CS/C2=N\C(=O)NCCC#Cc2cccc(-c3ncn(-c4ccc(OC(F)(F)F)cc4)n3)c2)c1] P186

TABLE P-One-continued
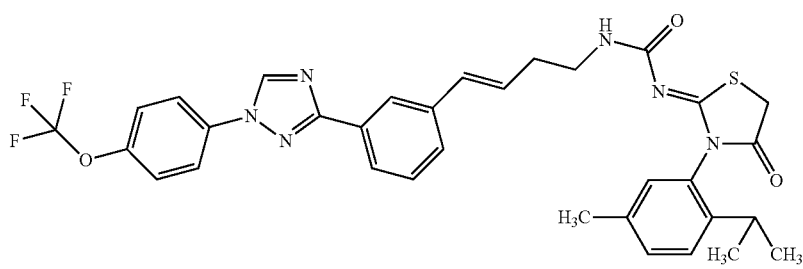 [SMILES: Cc1ccc(C(C)C)c(N2C(=O)CS/C2=N\C(=O)NCC/C=C/c2cccc(-c3ncn(-c4ccc(OC(F)(F)F)cc4)n3)c2)c1]
P187
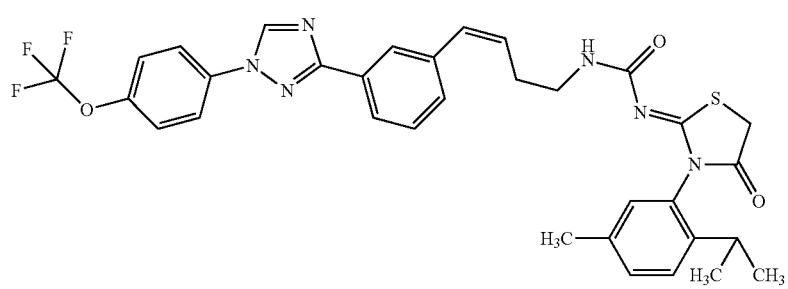 [SMILES: Cc1ccc(C(C)C)c(N2C(=O)CS/C2=N\C(=O)NCC/C=C\c2cccc(-c3ncn(-c4ccc(OC(F)(F)F)cc4)n3)c2)c1]
P188
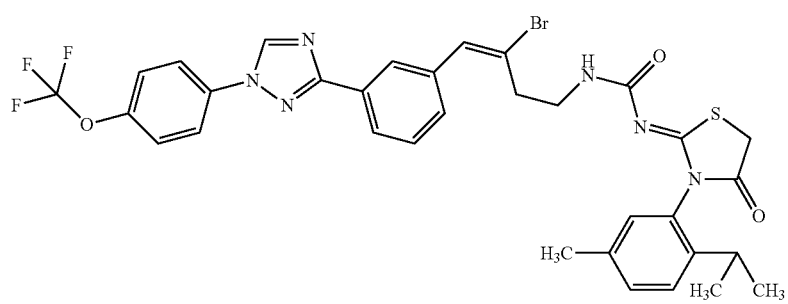 [SMILES: Cc1ccc(C(C)C)c(N2C(=O)CS/C2=N\C(=O)NCC/C(Br)=C\c2cccc(-c3ncn(-c4ccc(OC(F)(F)F)cc4)n3)c2)c1]
P189
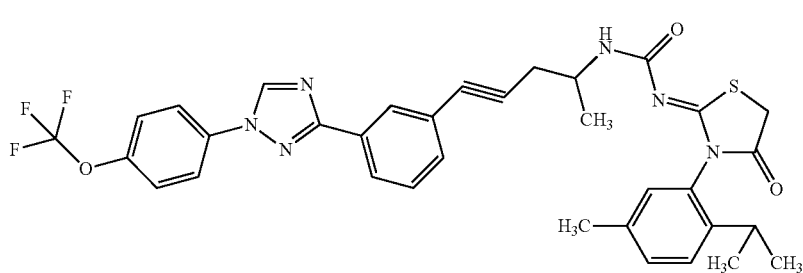 [SMILES: Cc1ccc(C(C)C)c(N2C(=O)CS/C2=N\C(=O)NC(C)CC#Cc2cccc(-c3ncn(-c4ccc(OC(F)(F)F)cc4)n3)c2)c1]
P190
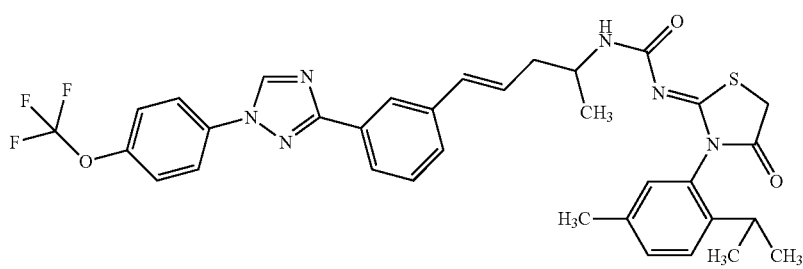
P191

TABLE P-One-continued
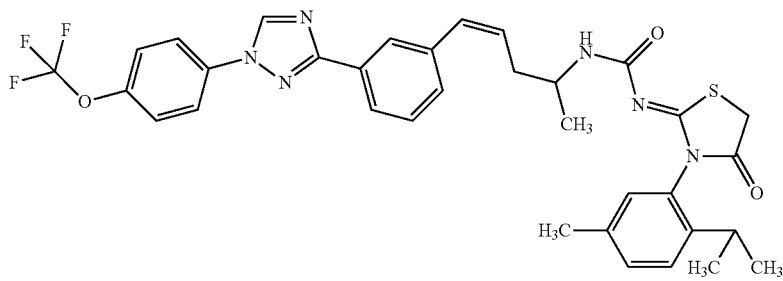 [SMILES: Cc1ccc(C(C)C)c(N2C(=O)CS/C2=N\C(=O)NC(C)C/C=C\c2cccc(-c3ncn(-c4ccc(OC(F)(F)F)cc4)n3)c2)c1]
P192
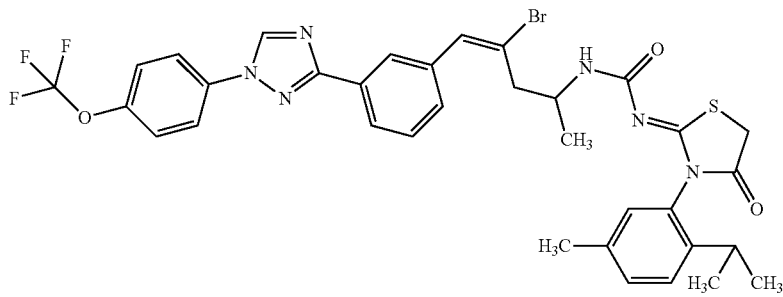
P193
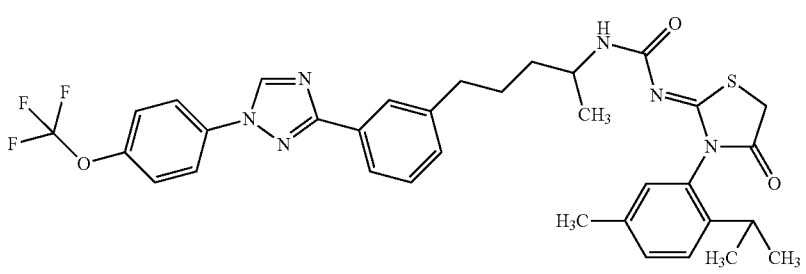 [SMILES: Cc1ccc(C(C)C)c(N2C(=O)CS/C2=N\C(=O)NC(C)CCCc2cccc(-c3ncn(-c4ccc(OC(F)(F)F)cc4)n3)c2)c1]
P194
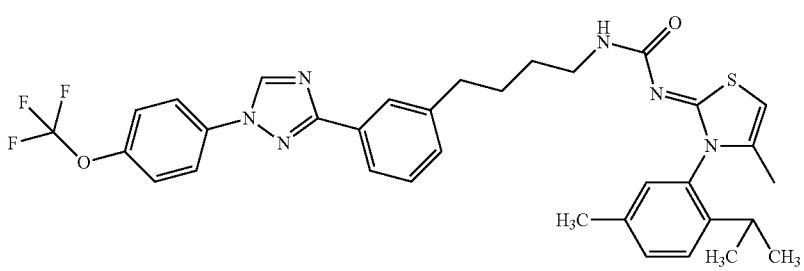 [SMILES: Cc1ccc(C(C)C)c(-n2c(C)cs/c2=N\C(=O)NCCCCc2cccc(-c3ncn(-c4ccc(OC(F)(F)F)cc4)n3)c2)c1]
P195
Additionally using the procedures disclosed herein the following list of prophetic molecules having a structure according to Formula One may be made (Table P-Two).
TABLE P-Two
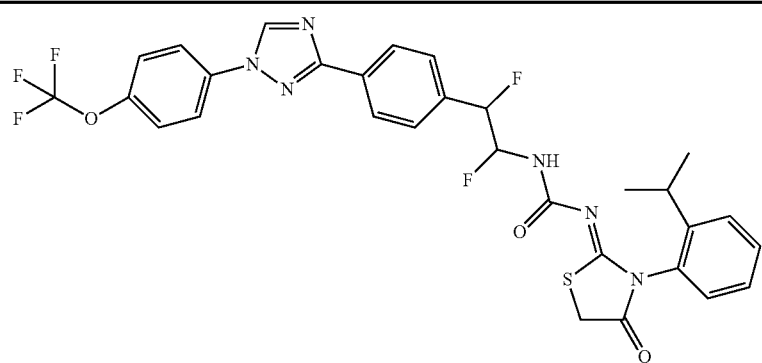
P196

TABLE P-Two-continued
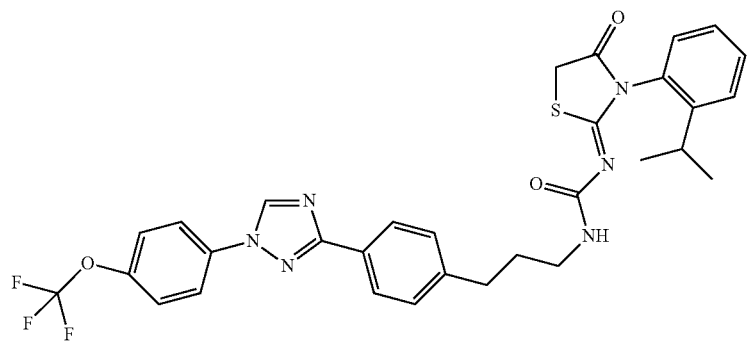 [SMILES: CC(C)c1ccccc1N1C(=O)CS/C1=N\C(=O)NCCCc1ccc(-c2ncn(-c3ccc(OC(F)(F)F)cc3)n2)cc1]
P197
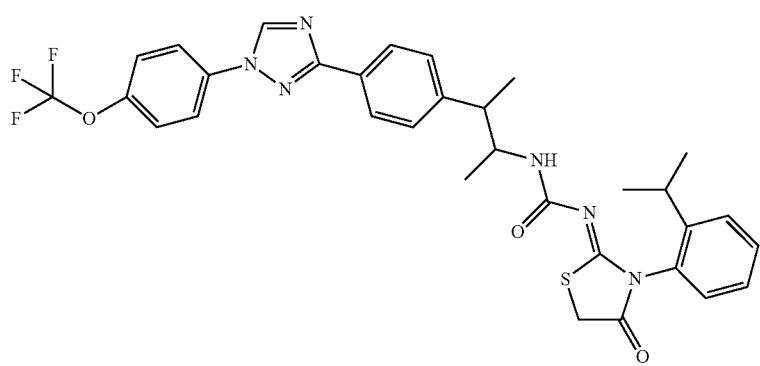
P198
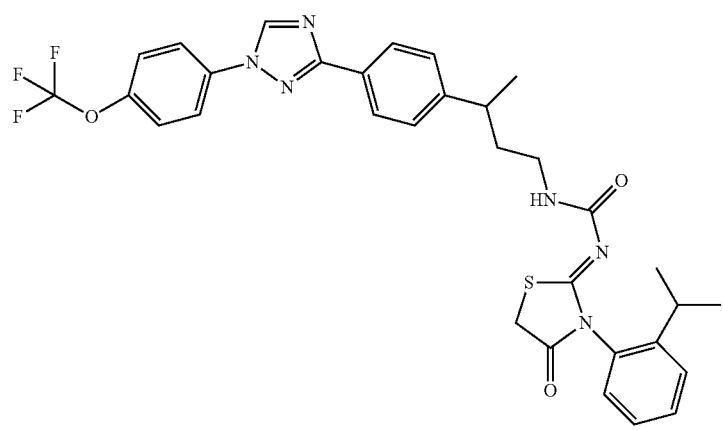 [SMILES: CC(C)c1ccccc1N1C(=O)CS/C1=N\C(=O)NCCC(C)c1ccc(-c2ncn(-c3ccc(OC(F)(F)F)cc3)n2)cc1]
P199
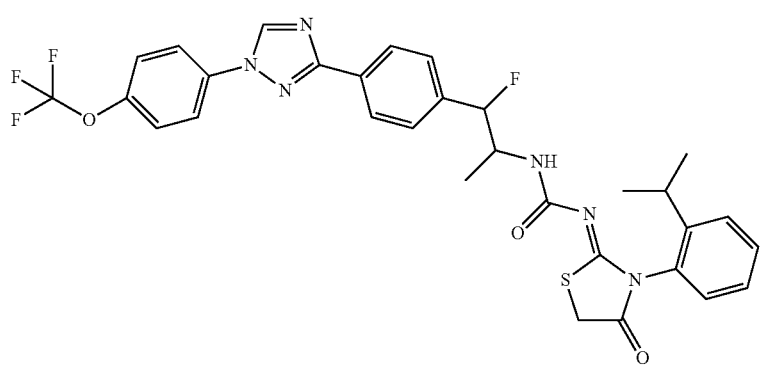 [SMILES: CC(C)c1ccccc1N1C(=O)CS/C1=N\C(=O)NC(C)C(F)c1ccc(-c2ncn(-c3ccc(OC(F)(F)F)cc3)n2)cc1]
P200

TABLE P-Two-continued
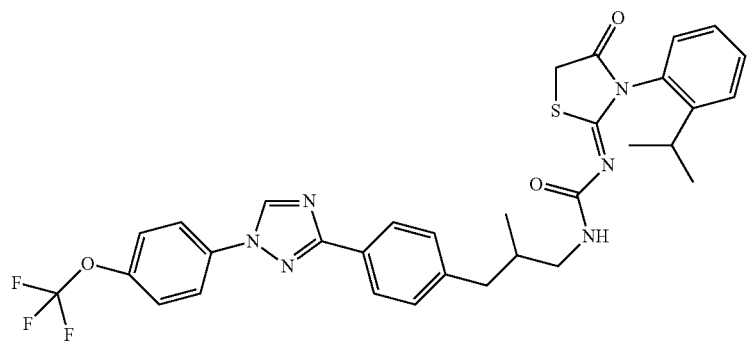 [SMILES: CC(CNC(=O)/N=C1\SCC(=O)N1c1ccccc1C(C)C)Cc1ccc(-c2ncn(-c3ccc(OC(F)(F)F)cc3)n2)cc1]
P201
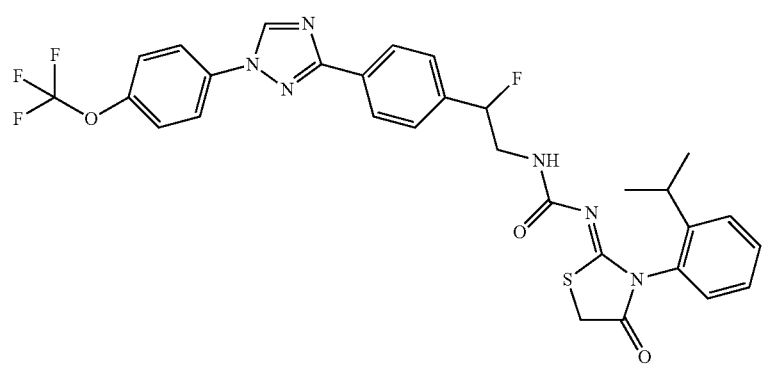 [SMILES: CC(C)c1ccccc1N1C(=O)CS/C1=N\C(=O)NCC(F)c1ccc(-c2ncn(-c3ccc(OC(F)(F)F)cc3)n2)cc1]
P202
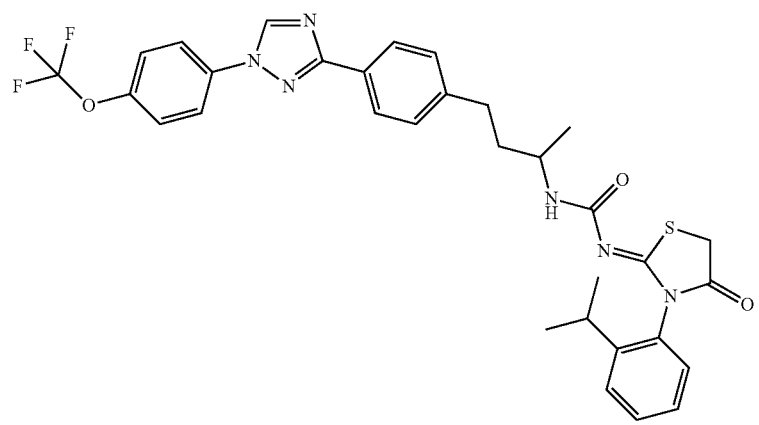 [SMILES: CC(CCc1ccc(-c2ncn(-c3ccc(OC(F)(F)F)cc3)n2)cc1)NC(=O)/N=C1\SCC(=O)N1c1ccccc1C(C)C]
P203
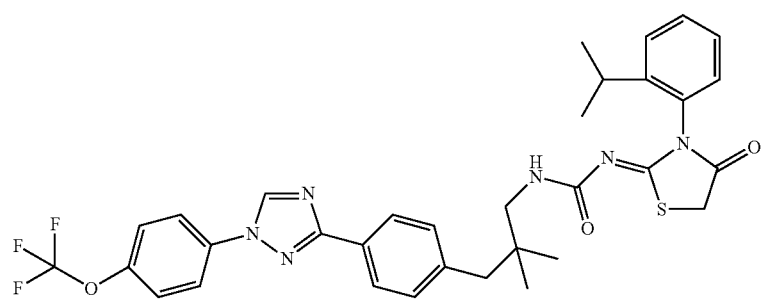 [SMILES: CC(C)c1ccccc1N1C(=O)CS/C1=N\C(=O)NCC(C)(C)Cc1ccc(-c2ncn(-c3ccc(OC(F)(F)F)cc3)n2)cc1]
P204

TABLE P-Two-continued
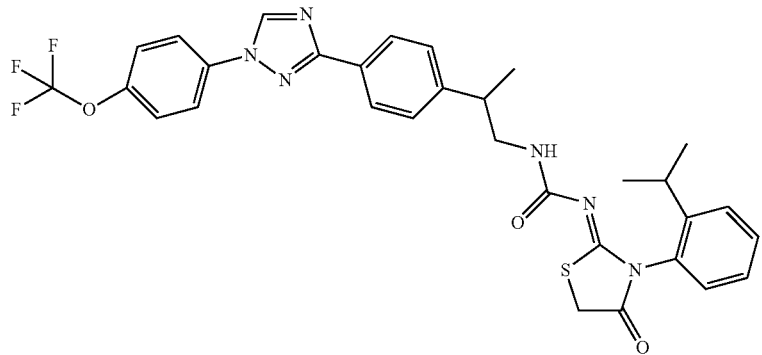 [SMILES: CC(C)c1ccccc1N1C(=O)CS/C1=N\C(=O)NCC(C)c1ccc(-c2ncn(-c3ccc(OC(F)(F)F)cc3)n2)cc1]
P205
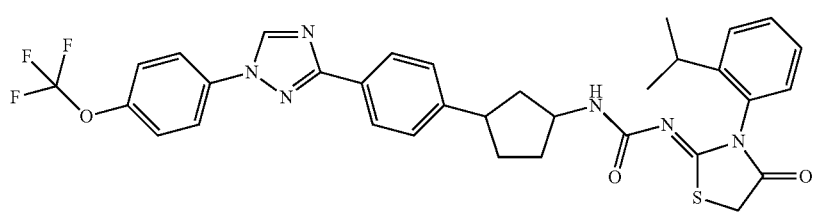 [SMILES: CC(C)c1ccccc1N1C(=O)CS/C1=N\C(=O)NC1CCC(c2ccc(-c3ncn(-c4ccc(OC(F)(F)F)cc4)n3)cc2)C1]
P206
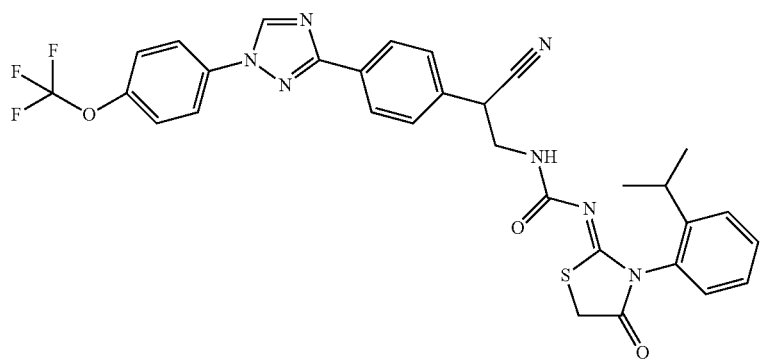 [SMILES: CC(C)c1ccccc1N1C(=O)CS/C1=N\C(=O)NCC(C#N)c1ccc(-c2ncn(-c3ccc(OC(F)(F)F)cc3)n2)cc1]
P207
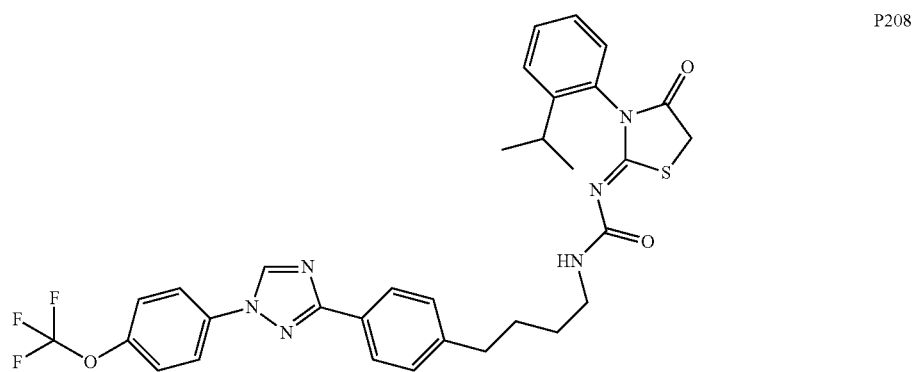
P208

TABLE P-Two-continued
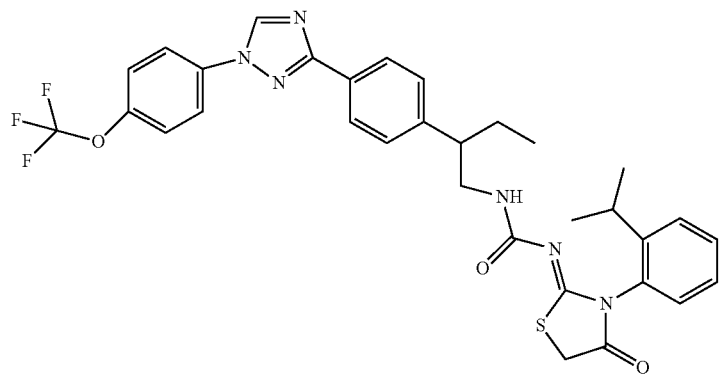 [SMILES: CCC(CNC(=O)/N=C1\SCC(=O)N1c1ccccc1C(C)C)c1ccc(-c2ncn(-c3ccc(OC(F)(F)F)cc3)n2)cc1]
P209
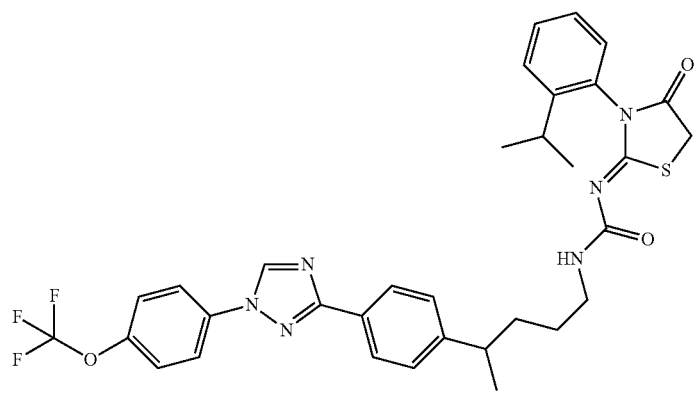 [SMILES: CC(C)c1ccccc1N1C(=O)CS/C1=N\C(=O)NCCCC(C)c1ccc(-c2ncn(-c3ccc(OC(F)(F)F)cc3)n2)cc1]
P210
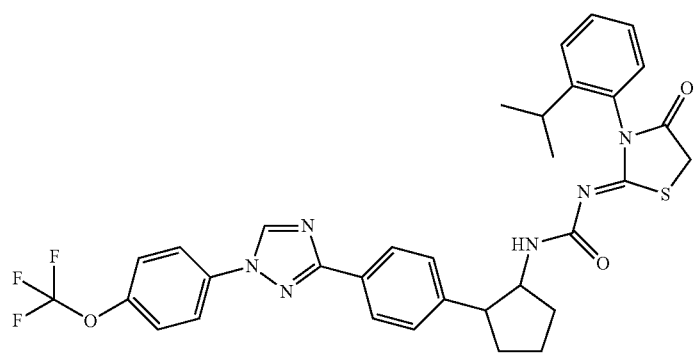 [SMILES: CC(C)c1ccccc1N1C(=O)CS/C1=N\C(=O)NC1CCCC1c1ccc(-c2ncn(-c3ccc(OC(F)(F)F)cc3)n2)cc1]
P211
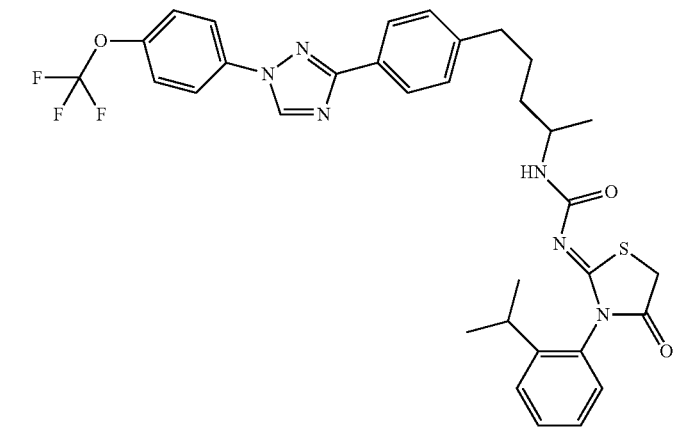 [SMILES: CC(CCCc1ccc(-c2ncn(-c3ccc(OC(F)(F)F)cc3)n2)cc1)NC(=O)/N=C1\SCC(=O)N1c1ccccc1C(C)C]
P212

TABLE P-Two-continued
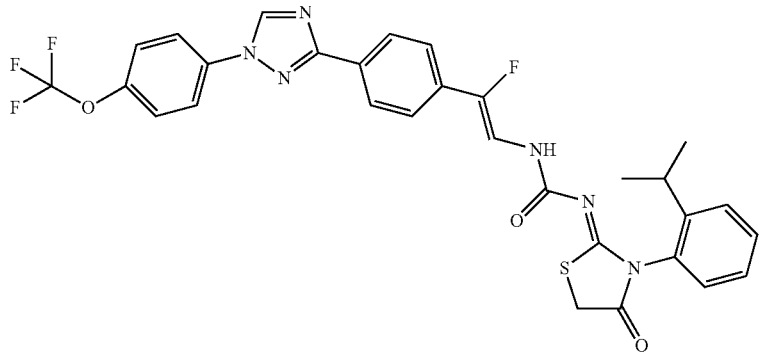 [SMILES: CC(C)c1ccccc1N1C(=O)CS/C1=N\C(=O)N/C=C(\F)c1ccc(-c2ncn(-c3ccc(OC(F)(F)F)cc3)n2)cc1]
P213
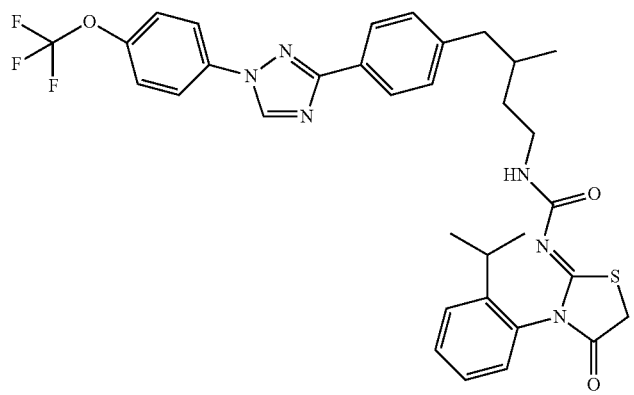 [SMILES: CC(CCNC(=O)/N=C1\SCC(=O)N1c1ccccc1C(C)C)Cc1ccc(-c2ncn(-c3ccc(OC(F)(F)F)cc3)n2)cc1]
P214
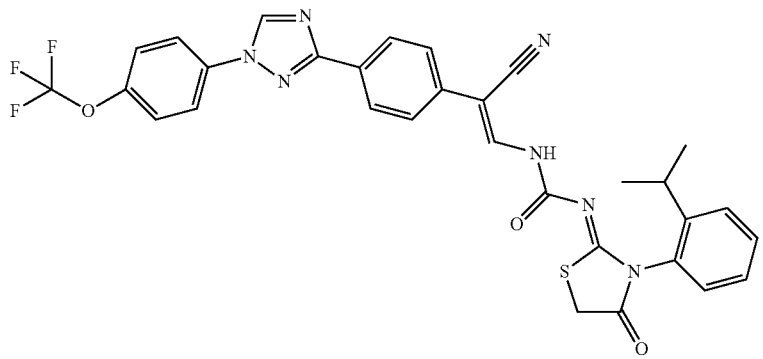 [SMILES: CC(C)c1ccccc1N1C(=O)CS/C1=N\C(=O)N/C=C(\C#N)c1ccc(-c2ncn(-c3ccc(OC(F)(F)F)cc3)n2)cc1]
P215
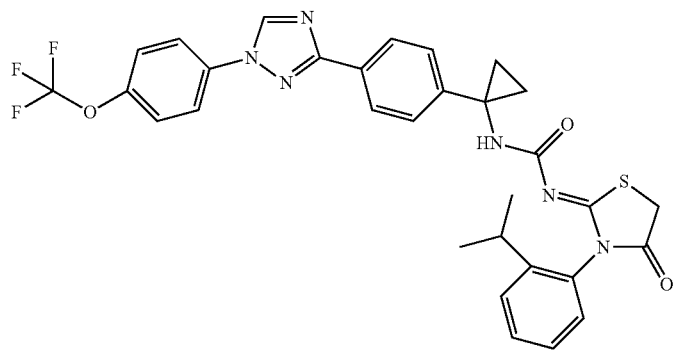 [SMILES: CC(C)c1ccccc1N1C(=O)CS/C1=N\C(=O)NC1(c2ccc(-c3ncn(-c4ccc(OC(F)(F)F)cc4)n3)cc2)CC1]
P216

TABLE P-Two-continued
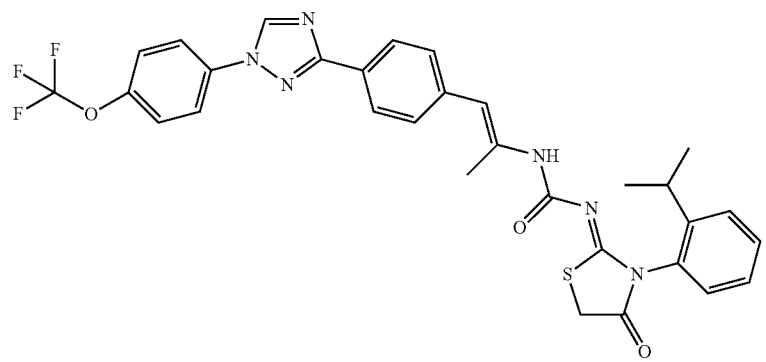 [SMILES: C/C(=C\c1ccc(-c2ncn(-c3ccc(OC(F)(F)F)cc3)n2)cc1)NC(=O)/N=C1\SCC(=O)N1c1ccccc1C(C)C]
P217
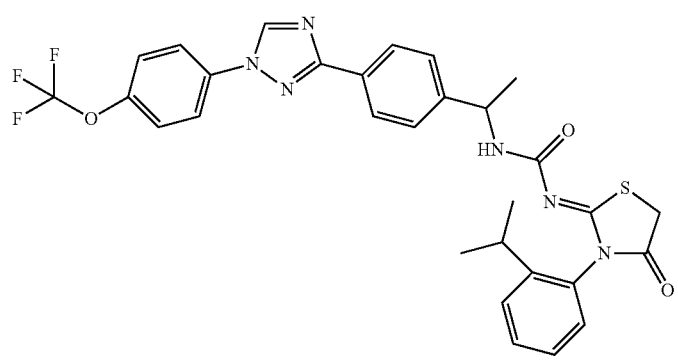 [SMILES: CC(C)c1ccccc1N1C(=O)CS/C1=N\C(=O)NC(C)c1ccc(-c2ncn(-c3ccc(OC(F)(F)F)cc3)n2)cc1]
P218
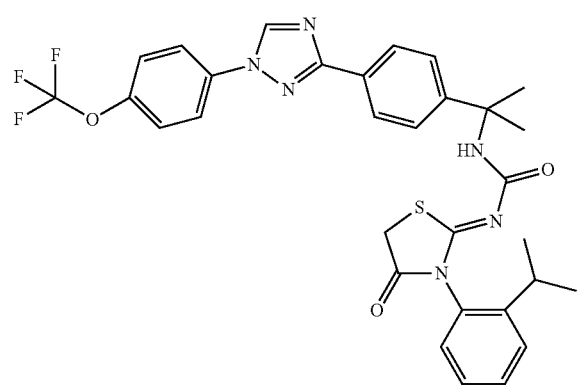 [SMILES: CC(C)c1ccccc1N1C(=O)CS/C1=N\C(=O)NC(C)(C)c1ccc(-c2ncn(-c3ccc(OC(F)(F)F)cc3)n2)cc1]
P219
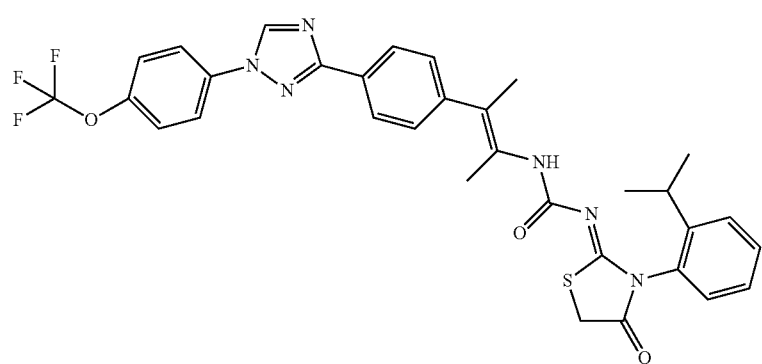 [SMILES: C/C(NC(=O)/N=C1\SCC(=O)N1c1ccccc1C(C)C)=C(/C)c1ccc(-c2ncn(-c3ccc(OC(F)(F)F)cc3)n2)cc1]
P220

TABLE P-Two-continued
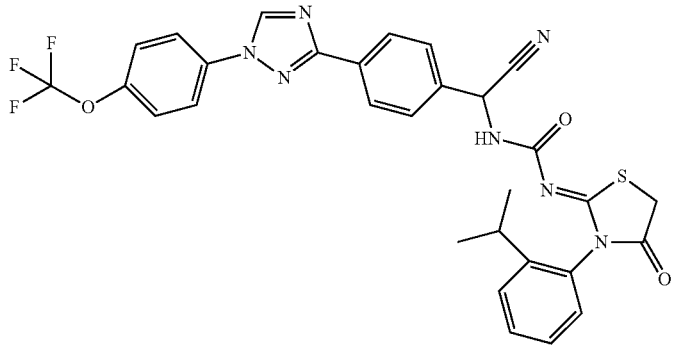 [SMILES: CC(C)c1ccccc1N1C(=O)CS/C1=N\C(=O)NC(C#N)c1ccc(-c2ncn(-c3ccc(OC(F)(F)F)cc3)n2)cc1]
P221
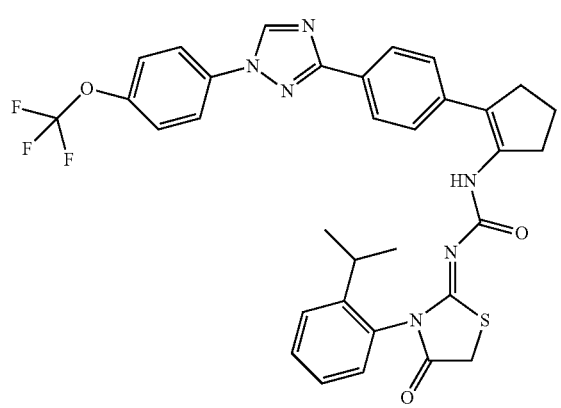 [SMILES: CC(C)c1ccccc1N1C(=O)CS/C1=N\C(=O)NC1=C(c2ccc(-c3ncn(-c4ccc(OC(F)(F)F)cc4)n3)cc2)CCC1]
P222
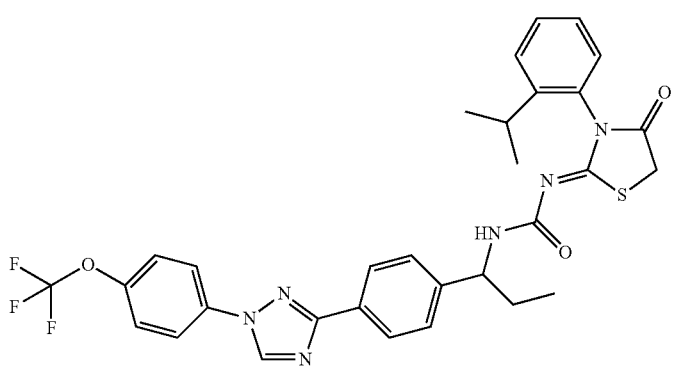 [SMILES: CCC(NC(=O)/N=C1\SCC(=O)N1c1ccccc1C(C)C)c1ccc(-c2ncn(-c3ccc(OC(F)(F)F)cc3)n2)cc1]
P223
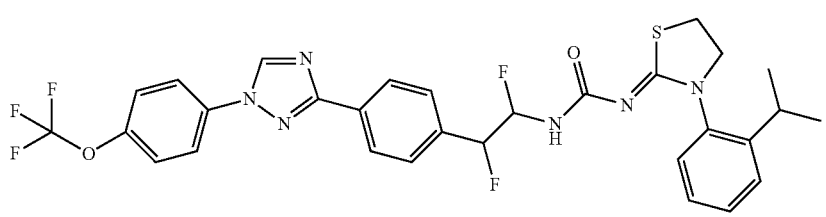 [SMILES: CC(C)c1ccccc1N1CCS/C1=N\C(=O)NC(F)C(F)c1ccc(-c2ncn(-c3ccc(OC(F)(F)F)cc3)n2)cc1]
P224
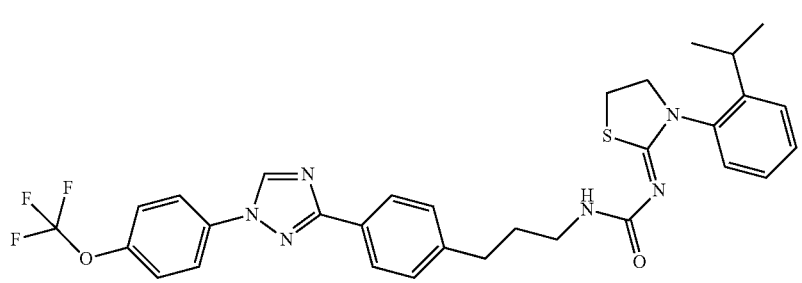 [SMILES: CC(C)c1ccccc1N1CCS/C1=N\C(=O)NCCCc1ccc(-c2ncn(-c3ccc(OC(F)(F)F)cc3)n2)cc1]
P225

TABLE P-Two-continued
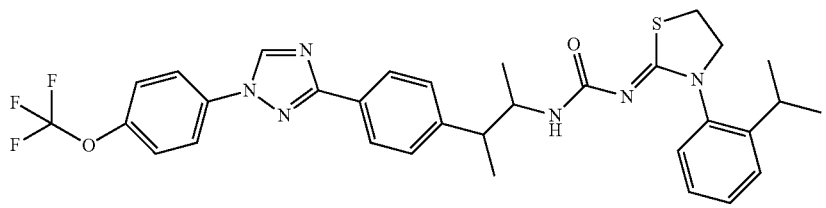 [SMILES: CC(C)c1ccccc1N1CCS/C1=N\C(=O)NC(C)C(C)c1ccc(-c2ncn(-c3ccc(OC(F)(F)F)cc3)n2)cc1]
P226
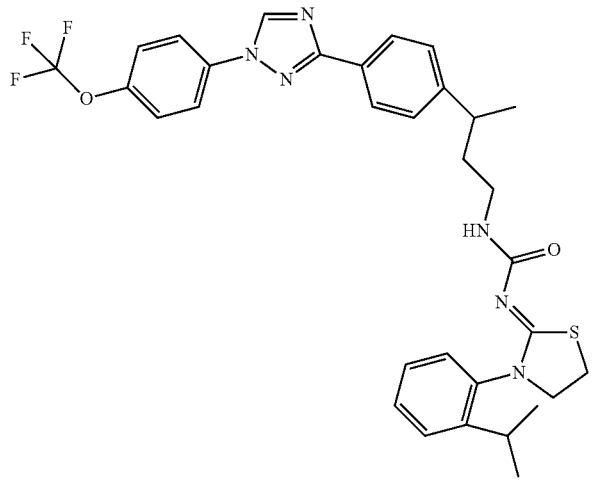 [SMILES: CC(C)c1ccccc1N1CCS/C1=N\C(=O)NCCC(C)c1ccc(-c2ncn(-c3ccc(OC(F)(F)F)cc3)n2)cc1]
P227
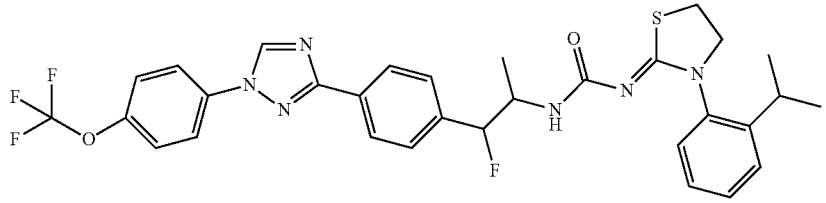 [SMILES: CC(C)c1ccccc1N1CCS/C1=N\C(=O)NC(C)C(F)c1ccc(-c2ncn(-c3ccc(OC(F)(F)F)cc3)n2)cc1]
P228
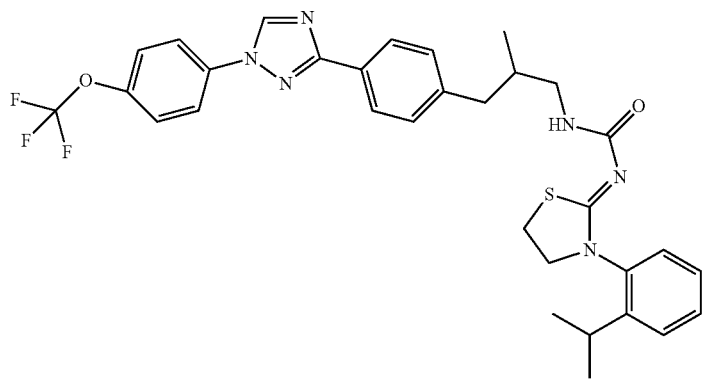 [SMILES: CC(CNC(=O)/N=C1\SCCN1c1ccccc1C(C)C)Cc1ccc(-c2ncn(-c3ccc(OC(F)(F)F)cc3)n2)cc1]
P229
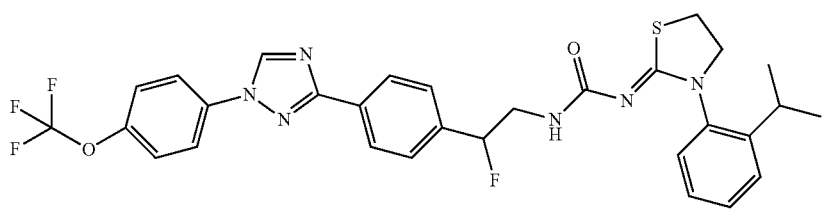 [SMILES: CC(C)c1ccccc1N1CCS/C1=N\C(=O)NCC(F)c1ccc(-c2ncn(-c3ccc(OC(F)(F)F)cc3)n2)cc1]
P230

TABLE P-Two-continued
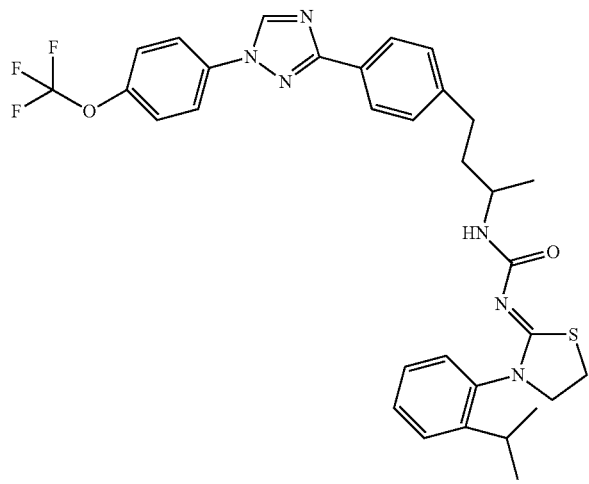 [SMILES: CC(CCc1ccc(-c2ncn(-c3ccc(OC(F)(F)F)cc3)n2)cc1)NC(=O)/N=C1\SCCN1c1ccccc1C(C)C]
P231
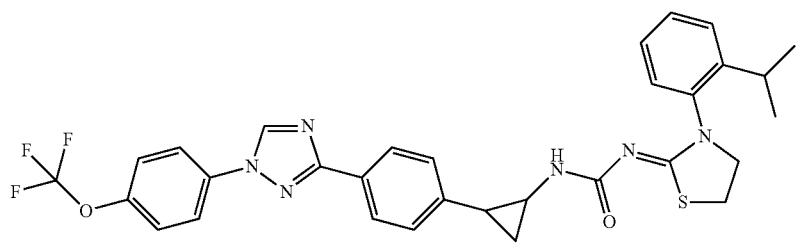 [SMILES: CC(C)c1ccccc1N1CCS/C1=N\C(=O)NC1CC1c1ccc(-c2ncn(-c3ccc(OC(F)(F)F)cc3)n2)cc1]
P232
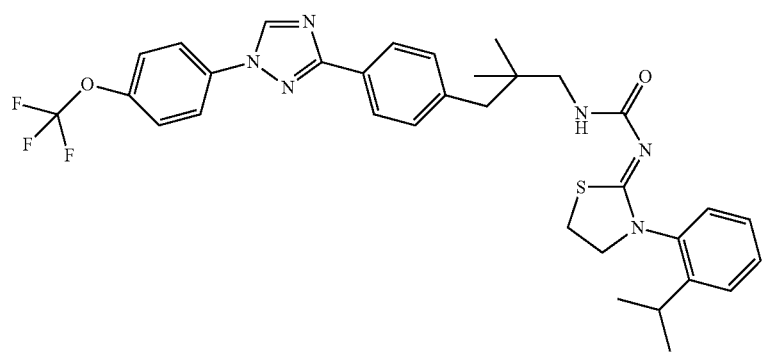 [SMILES: CC(C)c1ccccc1N1CCS/C1=N\C(=O)NCC(C)(C)Cc1ccc(-c2ncn(-c3ccc(OC(F)(F)F)cc3)n2)cc1]
P233
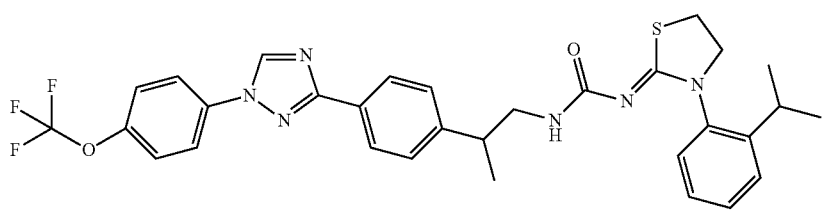 [SMILES: CC(C)c1ccccc1N1CCS/C1=N\C(=O)NCC(C)c1ccc(-c2ncn(-c3ccc(OC(F)(F)F)cc3)n2)cc1]
P234
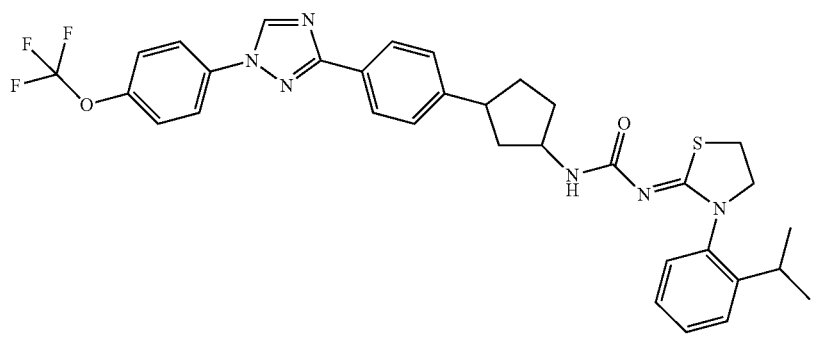 [SMILES: CC(C)c1ccccc1N1CCS/C1=N\C(=O)NC1CCC(c2ccc(-c3ncn(-c4ccc(OC(F)(F)F)cc4)n3)cc2)C1]
P235

TABLE P-Two-continued
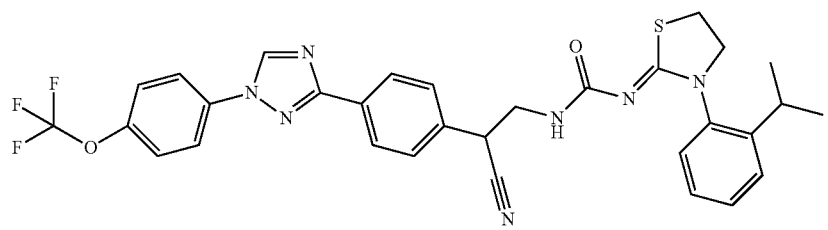 [SMILES: CC(C)c1ccccc1N1CCS/C1=N\C(=O)NCC(C#N)c1ccc(-c2ncn(-c3ccc(OC(F)(F)F)cc3)n2)cc1]
P236
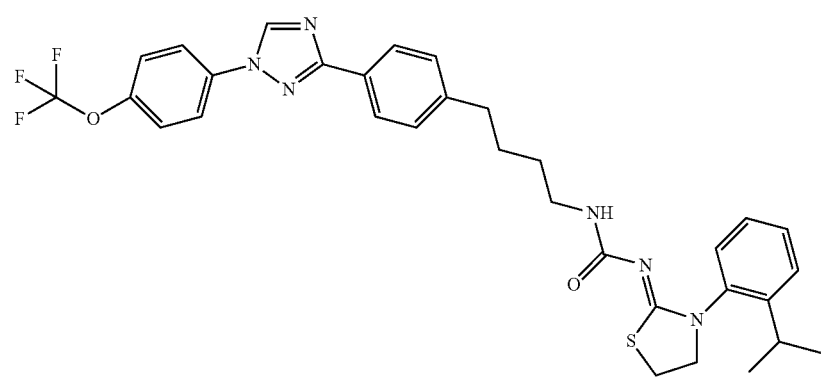 [SMILES: CC(C)c1ccccc1N1CCS/C1=N\C(=O)NCCCCc1ccc(-c2ncn(-c3ccc(OC(F)(F)F)cc3)n2)cc1]
P237
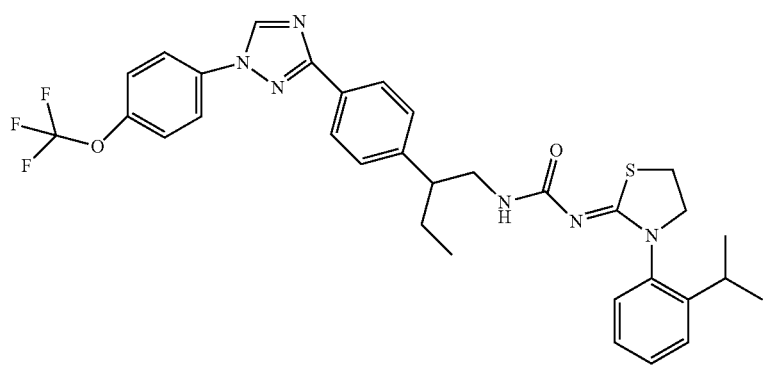 [SMILES: CCC(CNC(=O)/N=C1\SCCN1c1ccccc1C(C)C)c1ccc(-c2ncn(-c3ccc(OC(F)(F)F)cc3)n2)cc1]
P238
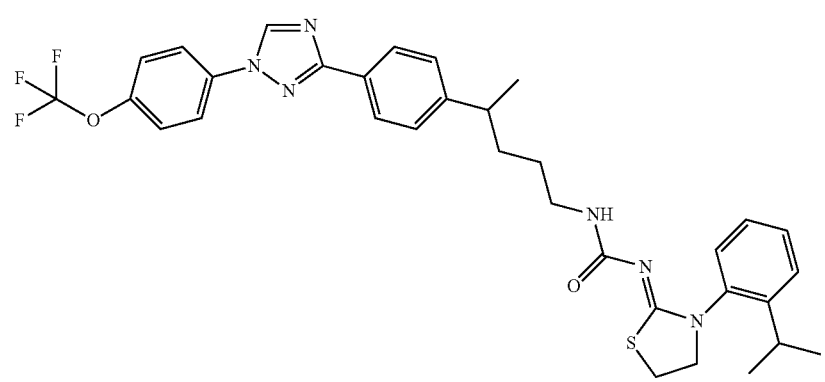 [SMILES: CC(C)c1ccccc1N1CCS/C1=N\C(=O)NCCCC(C)c1ccc(-c2ncn(-c3ccc(OC(F)(F)F)cc3)n2)cc1]
P239

TABLE P-Two-continued
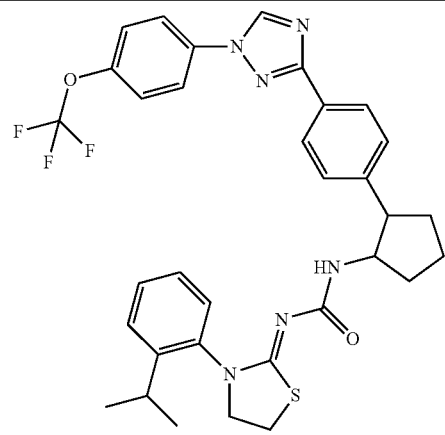
P240
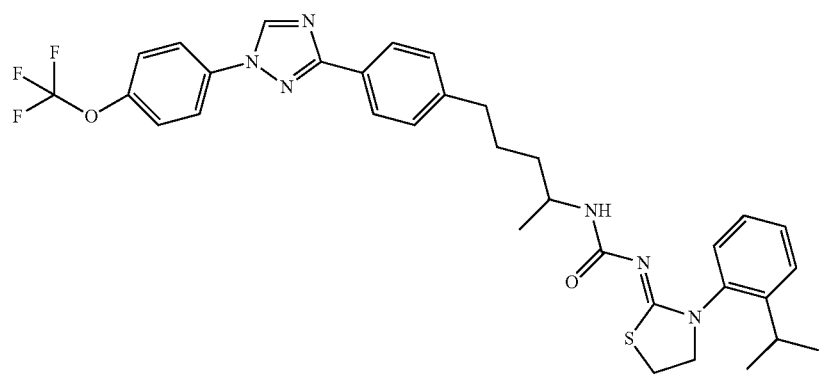 [SMILES: CC(CCCc1ccc(-c2ncn(-c3ccc(OC(F)(F)F)cc3)n2)cc1)NC(=O)/N=C1\SCCN1c1ccccc1C(C)C]
P241
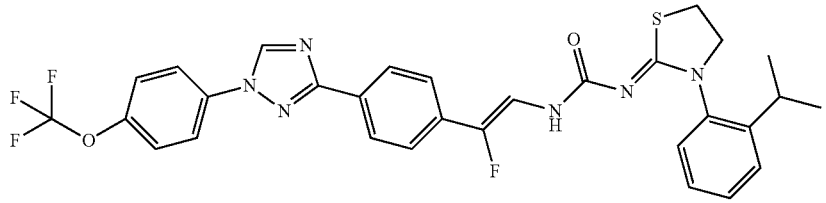
P242
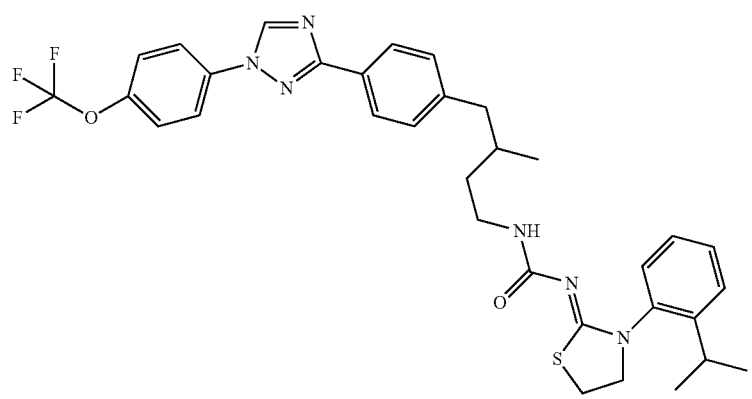 [SMILES: CC(CCNC(=O)/N=C1\SCCN1c1ccccc1C(C)C)Cc1ccc(-c2ncn(-c3ccc(OC(F)(F)F)cc3)n2)cc1]
P243
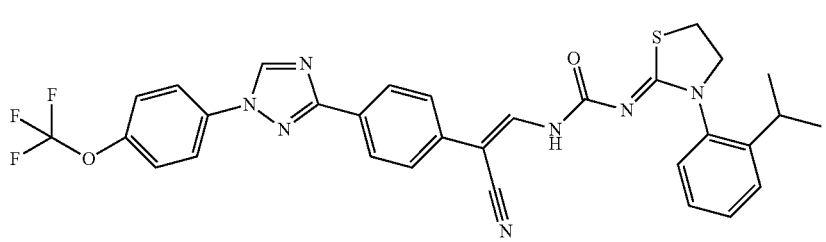 [SMILES: CC(C)c1ccccc1N1CCS/C1=N\C(=O)N/C=C(\C#N)c1ccc(-c2ncn(-c3ccc(OC(F)(F)F)cc3)n2)cc1]
P244

TABLE P-Two-continued
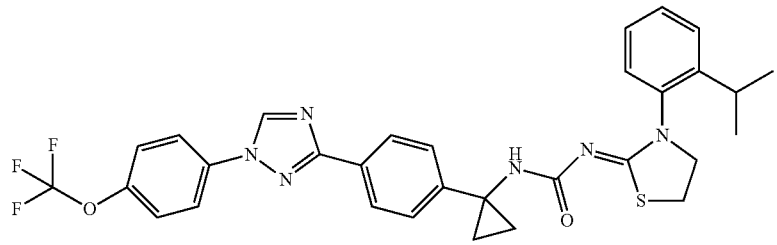 [SMILES: CC(C)c1ccccc1N1CCS/C1=N\C(=O)NC1(c2ccc(-c3ncn(-c4ccc(OC(F)(F)F)cc4)n3)cc2)CC1] P245
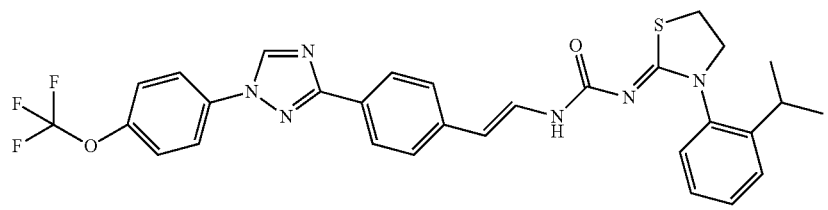 [SMILES: CC(C)c1ccccc1N1CCS/C1=N\C(=O)N/C=C/c1ccc(-c2ncn(-c3ccc(OC(F)(F)F)cc3)n2)cc1] P246
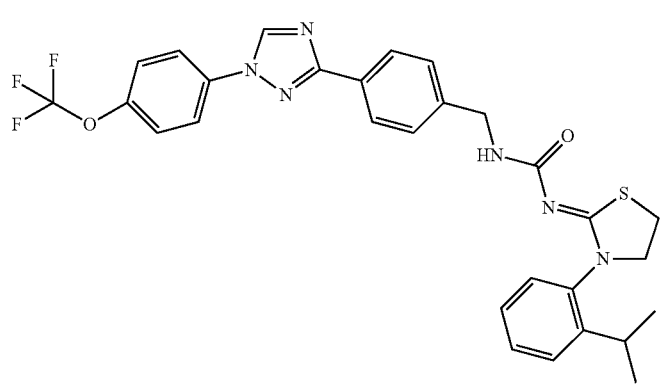 [SMILES: CC(C)c1ccccc1N1CCS/C1=N\C(=O)NCc1ccc(-c2ncn(-c3ccc(OC(F)(F)F)cc3)n2)cc1] P247
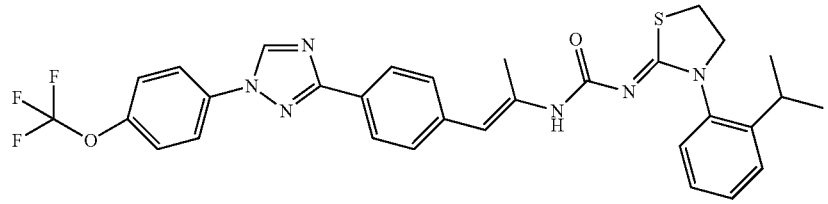 [SMILES: C/C(=C\c1ccc(-c2ncn(-c3ccc(OC(F)(F)F)cc3)n2)cc1)NC(=O)/N=C1\SCCN1c1ccccc1C(C)C] P248
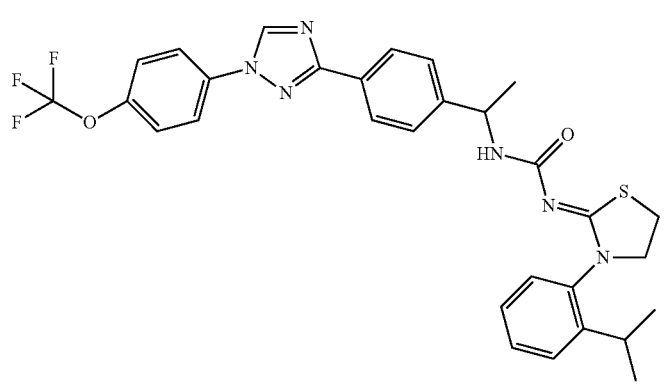 [SMILES: CC(C)c1ccccc1N1CCS/C1=N\C(=O)NC(C)c1ccc(-c2ncn(-c3ccc(OC(F)(F)F)cc3)n2)cc1] P249
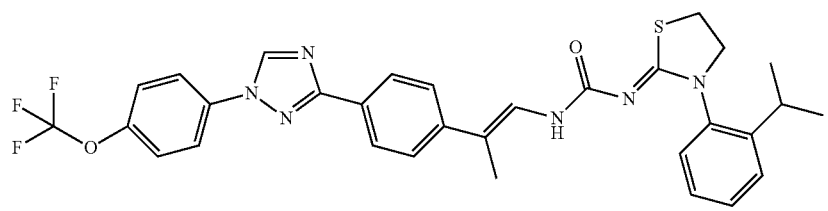 [SMILES: C/C(=C\NC(=O)/N=C1\SCCN1c1ccccc1C(C)C)c1ccc(-c2ncn(-c3ccc(OC(F)(F)F)cc3)n2)cc1] P250

TABLE P-Two-continued
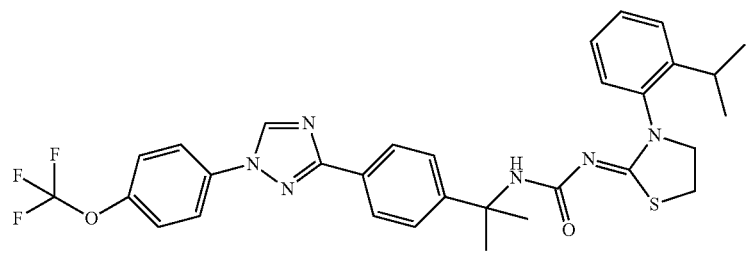 [SMILES: CC(C)c1ccccc1N1CCS/C1=N\C(=O)NC(C)(C)c1ccc(-c2ncn(-c3ccc(OC(F)(F)F)cc3)n2)cc1]
P251
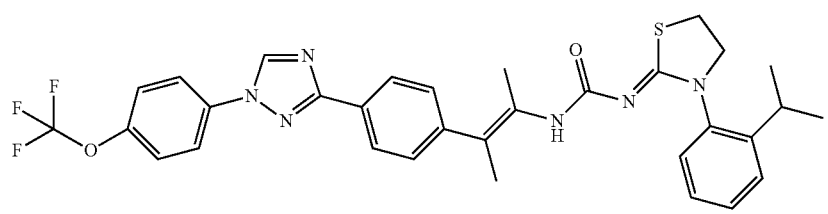 [SMILES: C/C(NC(=O)/N=C1\SCCN1c1ccccc1C(C)C)=C(/C)c1ccc(-c2ncn(-c3ccc(OC(F)(F)F)cc3)n2)cc1]
P252
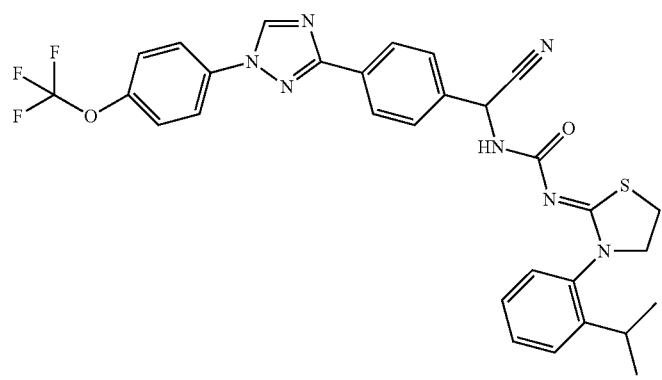 [SMILES: CC(C)c1ccccc1N1CCS/C1=N\C(=O)NC(C#N)c1ccc(-c2ncn(-c3ccc(OC(F)(F)F)cc3)n2)cc1]
P253
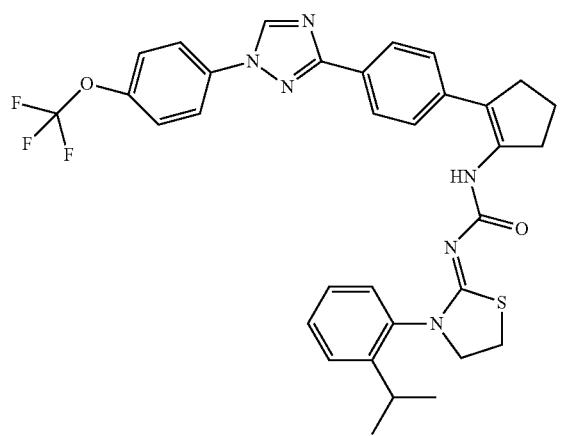 [SMILES: CC(C)c1ccccc1N1CCS/C1=N\C(=O)NC1=C(c2ccc(-c3ncn(-c4ccc(OC(F)(F)F)cc4)n3)cc2)CCC1]
P254

TABLE P-Two-continued
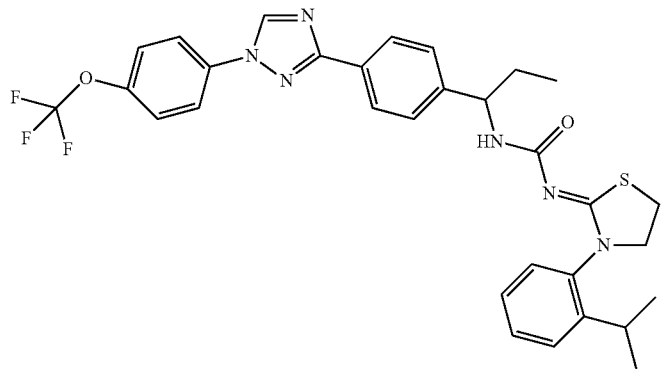 [SMILES: CCC(NC(=O)/N=C1\SCCN1c1ccccc1C(C)C)c1ccc(-c2ncn(-c3ccc(OC(F)(F)F)cc3)n2)cc1]
P255
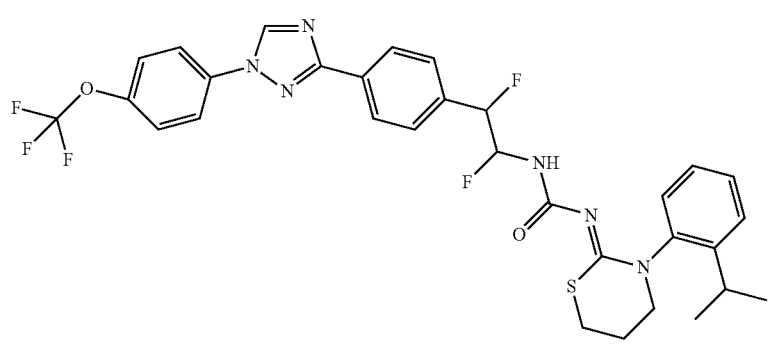
P256
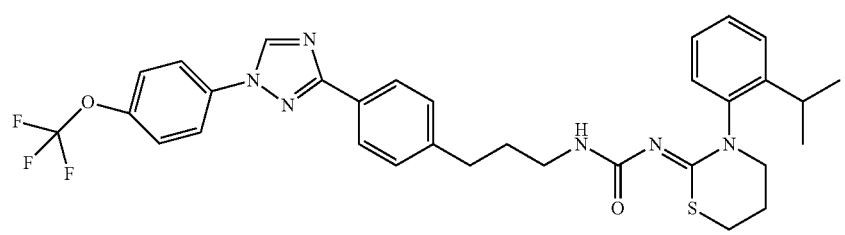 [SMILES: CC(C)c1ccccc1N1CCCS/C1=N\C(=O)NCCCc1ccc(-c2ncn(-c3ccc(OC(F)(F)F)cc3)n2)cc1]
P257
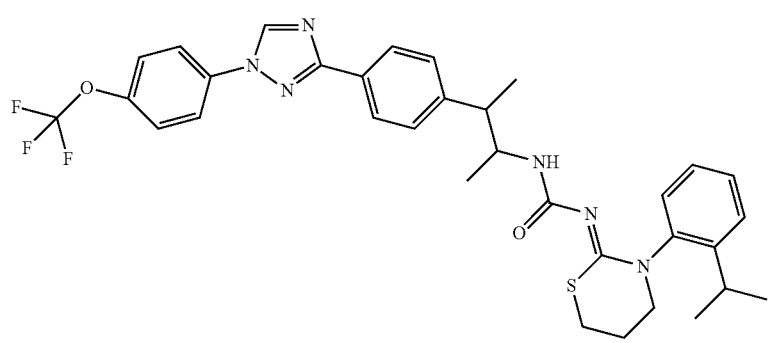 [SMILES: CC(C)c1ccccc1N1CCCS/C1=N\C(=O)NC(C)C(C)c1ccc(-c2ncn(-c3ccc(OC(F)(F)F)cc3)n2)cc1]
P258

TABLE P-Two-continued
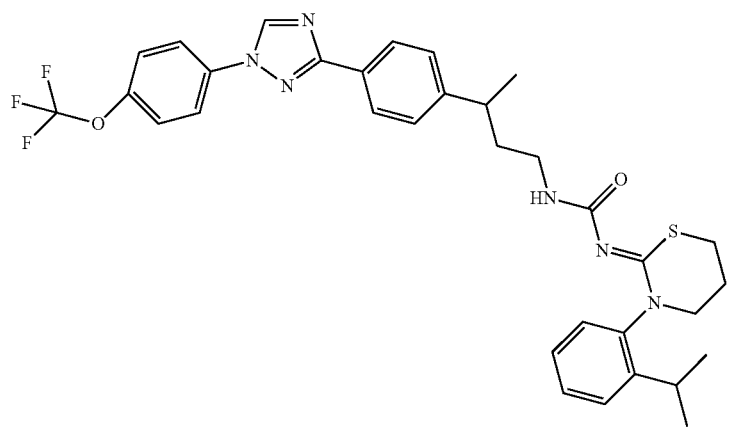 [SMILES: CC(C)c1ccccc1N1CCCS/C1=N\C(=O)NCCC(C)c1ccc(-c2ncn(-c3ccc(OC(F)(F)F)cc3)n2)cc1]
P259
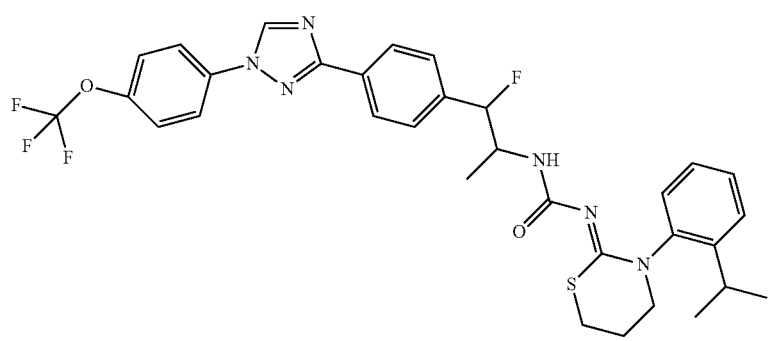 [SMILES: CC(C)c1ccccc1N1CCCS/C1=N\C(=O)NC(C)C(F)c1ccc(-c2ncn(-c3ccc(OC(F)(F)F)cc3)n2)cc1]
P260
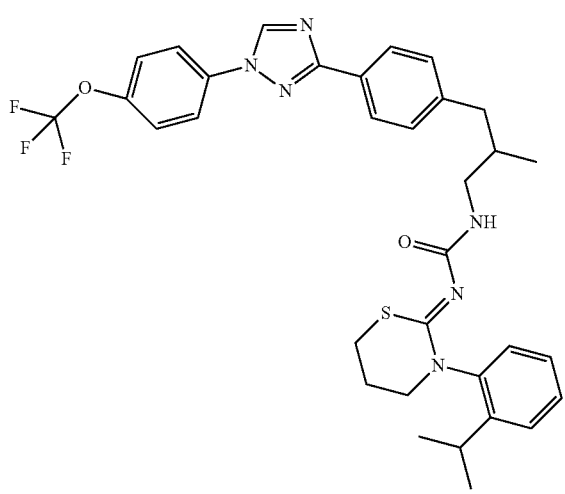 [SMILES: CC(CNC(=O)/N=C1\SCCCN1c1ccccc1C(C)C)Cc1ccc(-c2ncn(-c3ccc(OC(F)(F)F)cc3)n2)cc1]
P261
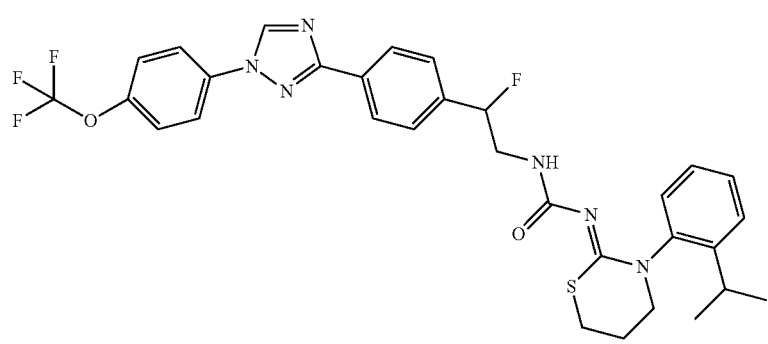 [SMILES: CC(C)c1ccccc1N1CCCS/C1=N\C(=O)NCC(F)c1ccc(-c2ncn(-c3ccc(OC(F)(F)F)cc3)n2)cc1]
P262

TABLE P-Two-continued
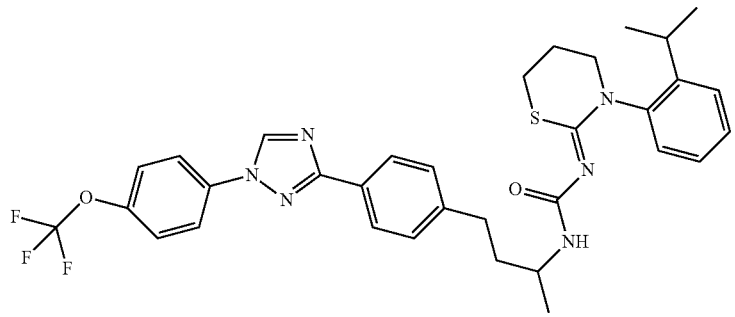 [SMILES: CC(CCc1ccc(-c2ncn(-c3ccc(OC(F)(F)F)cc3)n2)cc1)NC(=O)/N=C1\SCCCN1c1ccccc1C(C)C]
P263
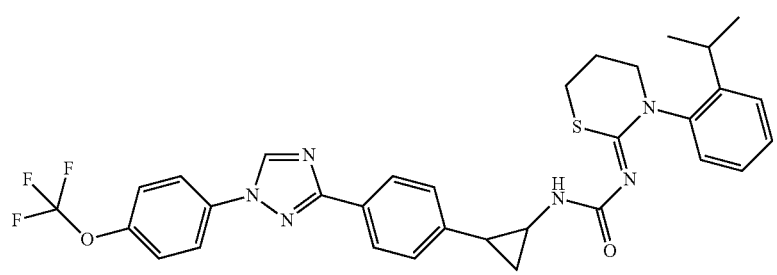 [SMILES: CC(C)c1ccccc1N1CCCS/C1=N\C(=O)NC1CC1c1ccc(-c2ncn(-c3ccc(OC(F)(F)F)cc3)n2)cc1]
P264
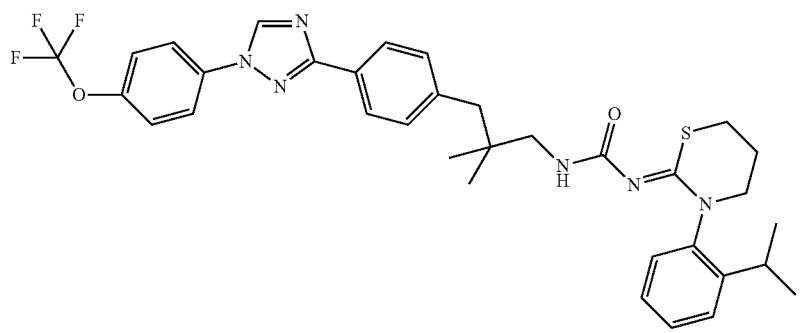 [SMILES: CC(C)c1ccccc1N1CCCS/C1=N\C(=O)NCC(C)(C)Cc1ccc(-c2ncn(-c3ccc(OC(F)(F)F)cc3)n2)cc1]
P265
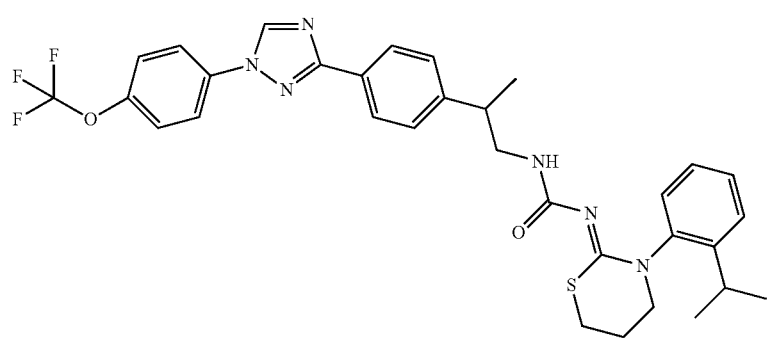 [SMILES: CC(C)c1ccccc1N1CCCS/C1=N\C(=O)NCC(C)c1ccc(-c2ncn(-c3ccc(OC(F)(F)F)cc3)n2)cc1]
P266

TABLE P-Two-continued
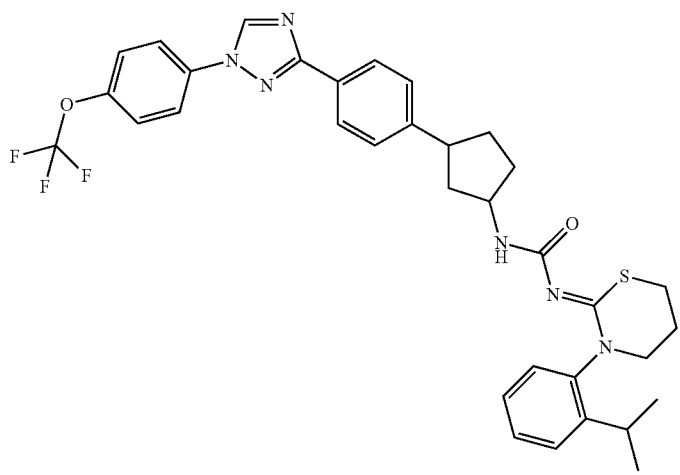 [SMILES: CC(C)c1ccccc1N1CCCS/C1=N\C(=O)NC1CCC(c2ccc(-c3ncn(-c4ccc(OC(F)(F)F)cc4)n3)cc2)C1]
P267
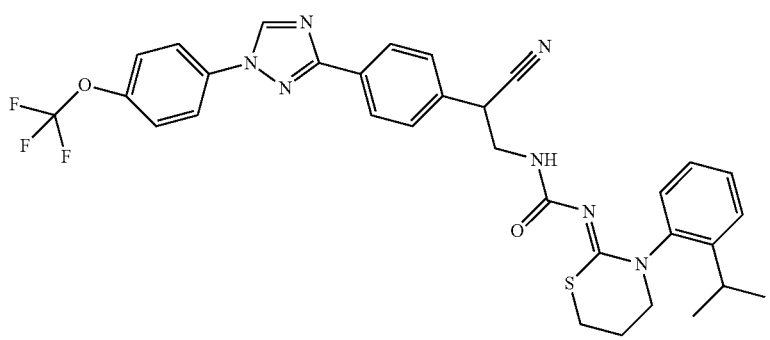 [SMILES: CC(C)c1ccccc1N1CCCS/C1=N\C(=O)NCC(C#N)c1ccc(-c2ncn(-c3ccc(OC(F)(F)F)cc3)n2)cc1]
P268
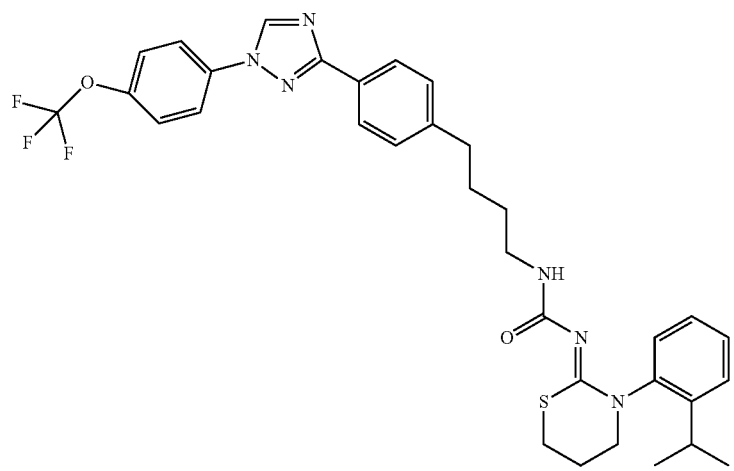 [SMILES: CC(C)c1ccccc1N1CCCS/C1=N\C(=O)NCCCCc1ccc(-c2ncn(-c3ccc(OC(F)(F)F)cc3)n2)cc1]
P269
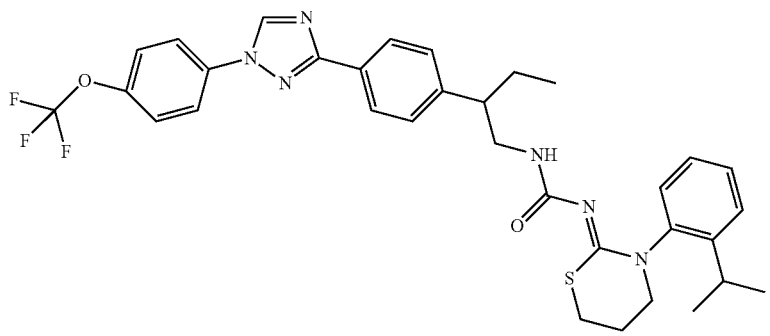 [SMILES: CCC(CNC(=O)/N=C1\SCCCN1c1ccccc1C(C)C)c1ccc(-c2ncn(-c3ccc(OC(F)(F)F)cc3)n2)cc1]
P270

TABLE P-Two-continued
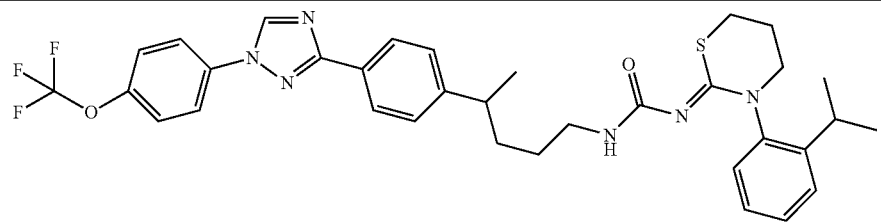
P271
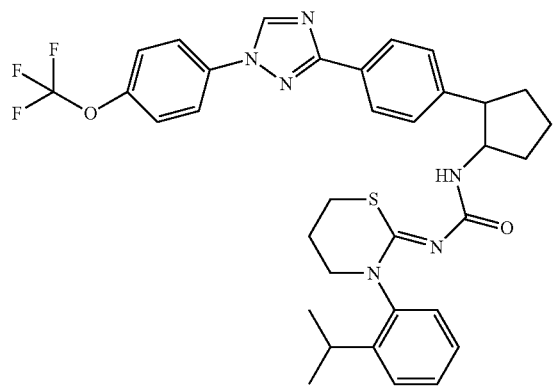 [SMILES: CC(C)c1ccccc1N1CCCS/C1=N\C(=O)NC1CCCC1c1ccc(-c2ncn(-c3ccc(OC(F)(F)F)cc3)n2)cc1]
P272
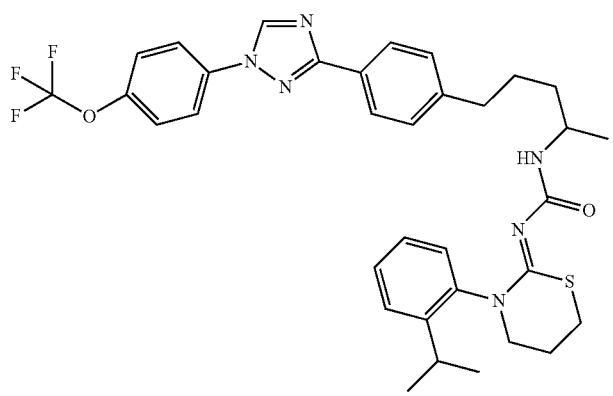 [SMILES: CC(CCCc1ccc(-c2ncn(-c3ccc(OC(F)(F)F)cc3)n2)cc1)NC(=O)/N=C1\SCCCN1c1ccccc1C(C)C]
P273
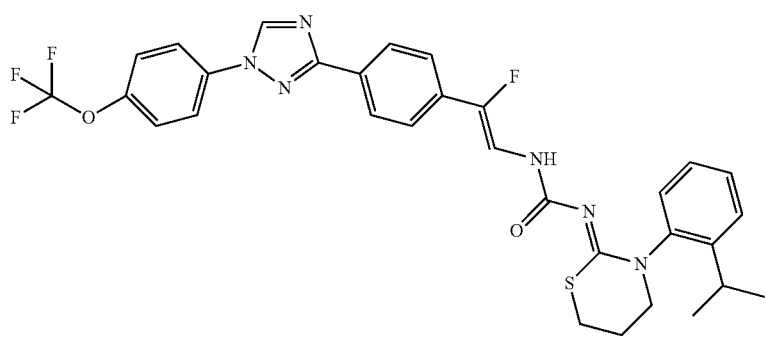 [SMILES: CC(C)c1ccccc1N1CCCS/C1=N\C(=O)N/C=C(\F)c1ccc(-c2ncn(-c3ccc(OC(F)(F)F)cc3)n2)cc1]
P274
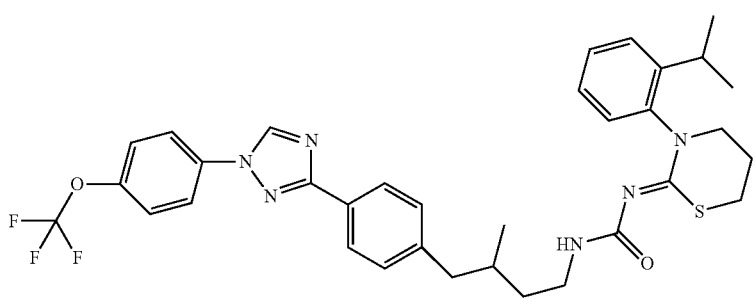 [SMILES: CC(CCNC(=O)/N=C1\SCCCN1c1ccccc1C(C)C)Cc1ccc(-c2ncn(-c3ccc(OC(F)(F)F)cc3)n2)cc1]
P275

TABLE P-Two-continued
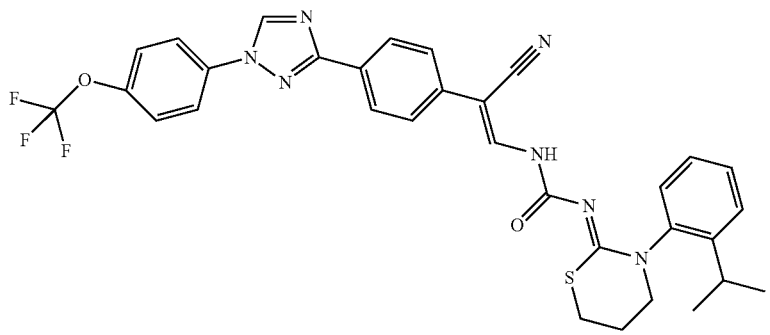 [SMILES: CC(C)c1ccccc1N1CCCS/C1=N\C(=O)N/C=C(\C#N)c1ccc(-c2ncn(-c3ccc(OC(F)(F)F)cc3)n2)cc1]
P276
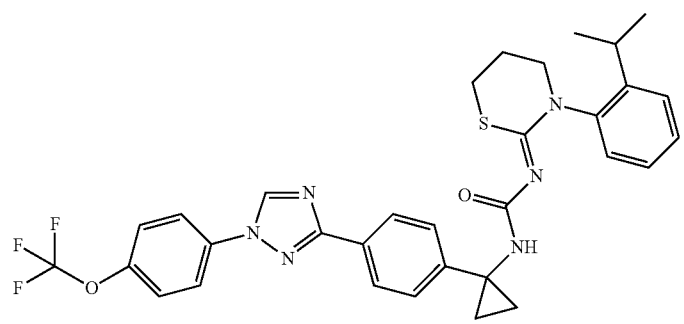 [SMILES: CC(C)c1ccccc1N1CCCS/C1=N\C(=O)NC1(c2ccc(-c3ncn(-c4ccc(OC(F)(F)F)cc4)n3)cc2)CC1]
P277
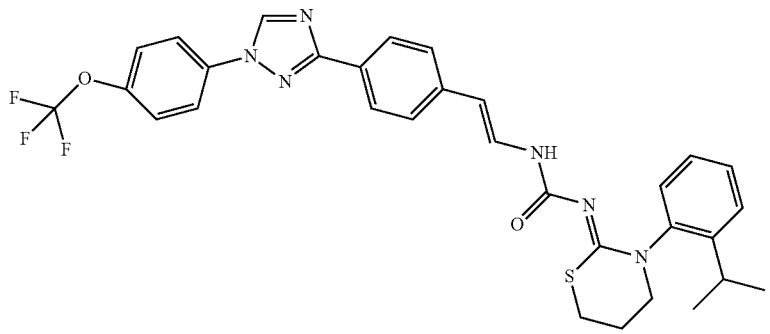 [SMILES: CC(C)c1ccccc1N1CCCS/C1=N\C(=O)N/C=C/c1ccc(-c2ncn(-c3ccc(OC(F)(F)F)cc3)n2)cc1]
P278
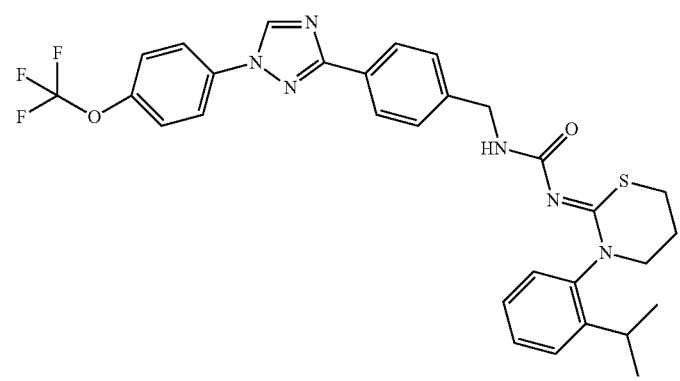 [SMILES: CC(C)c1ccccc1N1CCCS/C1=N\C(=O)NCc1ccc(-c2ncn(-c3ccc(OC(F)(F)F)cc3)n2)cc1]
P279

TABLE P-Two-continued
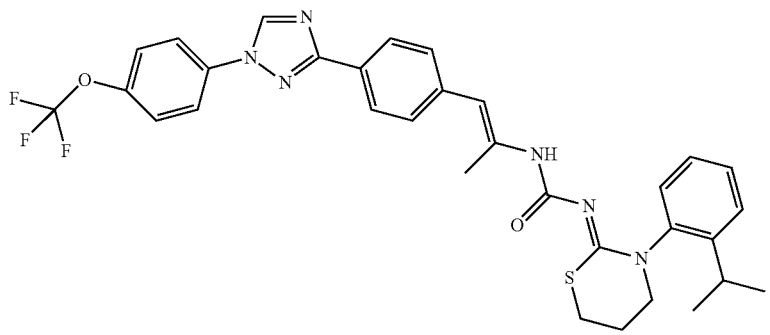 [SMILES: C/C(=C\c1ccc(-c2ncn(-c3ccc(OC(F)(F)F)cc3)n2)cc1)NC(=O)/N=C1\SCCCN1c1ccccc1C(C)C]
P280
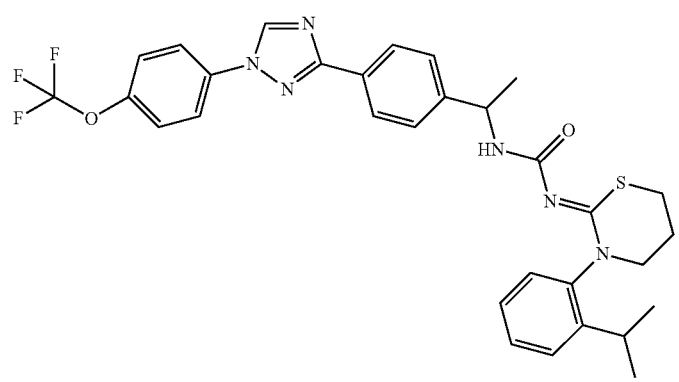 [SMILES: CC(C)c1ccccc1N1CCCS/C1=N\C(=O)NC(C)c1ccc(-c2ncn(-c3ccc(OC(F)(F)F)cc3)n2)cc1]
P281
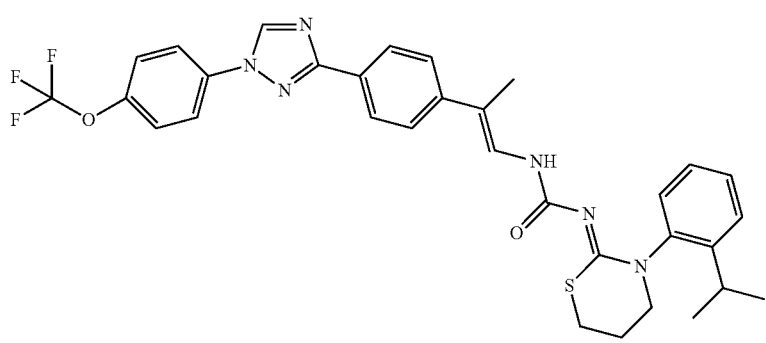 [SMILES: C/C(=C\NC(=O)/N=C1\SCCCN1c1ccccc1C(C)C)c1ccc(-c2ncn(-c3ccc(OC(F)(F)F)cc3)n2)cc1]
P282
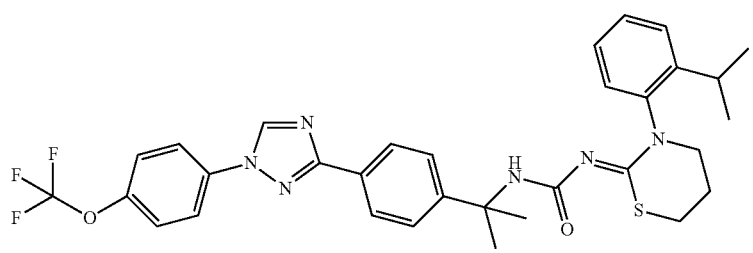 [SMILES: CC(C)c1ccccc1N1CCCS/C1=N\C(=O)NC(C)(C)c1ccc(-c2ncn(-c3ccc(OC(F)(F)F)cc3)n2)cc1]
P283
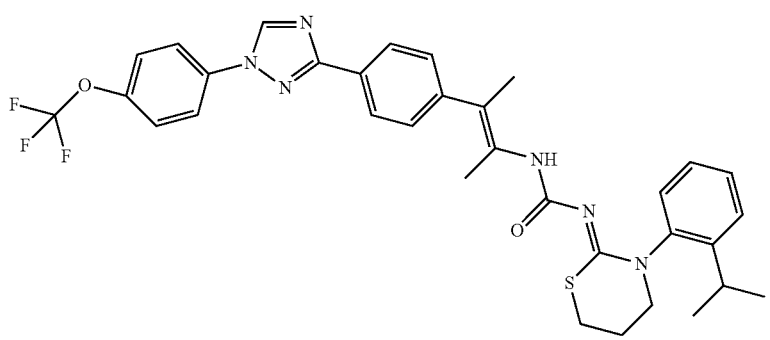 [SMILES: C/C(NC(=O)/N=C1\SCCCN1c1ccccc1C(C)C)=C(/C)c1ccc(-c2ncn(-c3ccc(OC(F)(F)F)cc3)n2)cc1]
P284

TABLE P-Two-continued
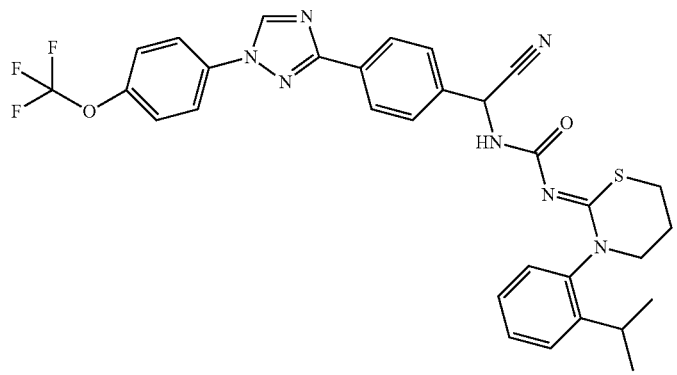 [SMILES: CC(C)c1ccccc1N1CCCS/C1=N\C(=O)NC(C#N)c1ccc(-c2ncn(-c3ccc(OC(F)(F)F)cc3)n2)cc1]
P285
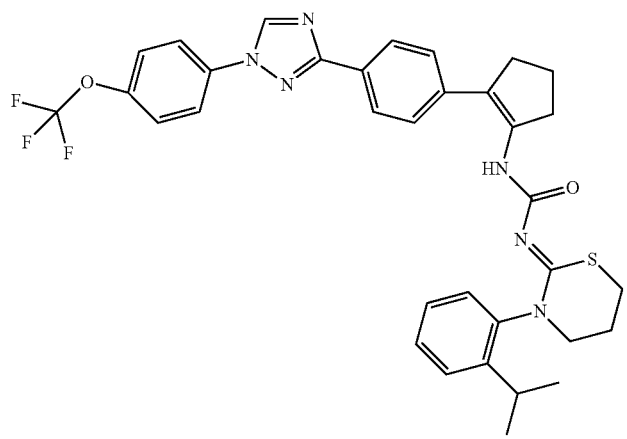 [SMILES: CC(C)c1ccccc1N1CCCS/C1=N\C(=O)NC1=C(c2ccc(-c3ncn(-c4ccc(OC(F)(F)F)cc4)n3)cc2)CCC1]
P286
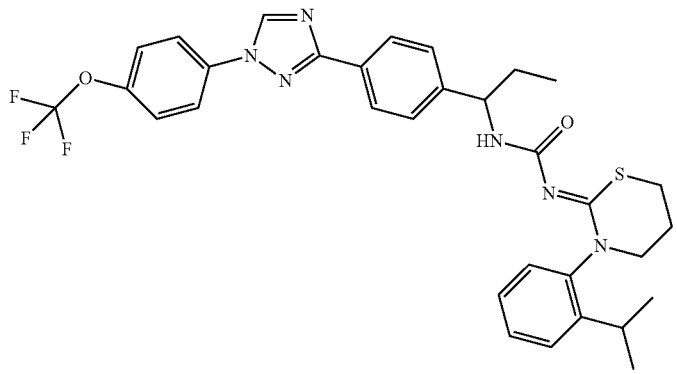 [SMILES: CCC(NC(=O)/N=C1\SCCCN1c1ccccc1C(C)C)c1ccc(-c2ncn(-c3ccc(OC(F)(F)F)cc3)n2)cc1]
P287
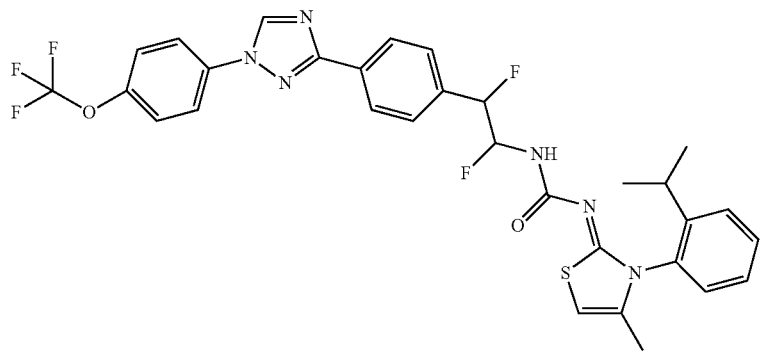
P288

TABLE P-Two-continued
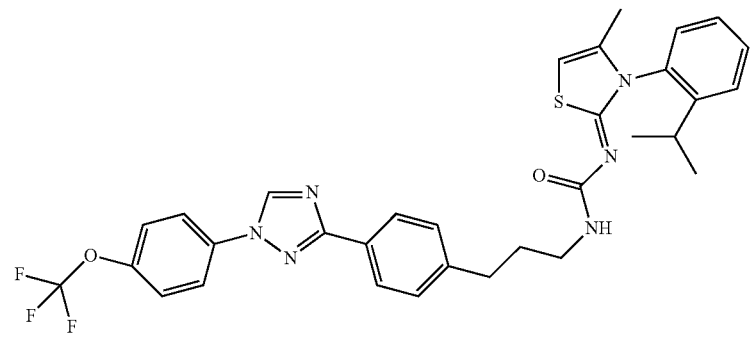 [SMILES: Cc1cs/c(=N\C(=O)NCCCc2ccc(-c3ncn(-c4ccc(OC(F)(F)F)cc4)n3)cc2)n1-c1ccccc1C(C)C]
P289
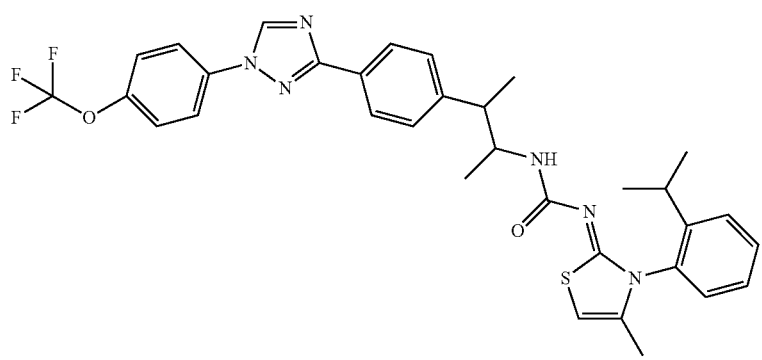 [SMILES: Cc1cs/c(=N\C(=O)NC(C)C(C)c2ccc(-c3ncn(-c4ccc(OC(F)(F)F)cc4)n3)cc2)n1-c1ccccc1C(C)C]
P290
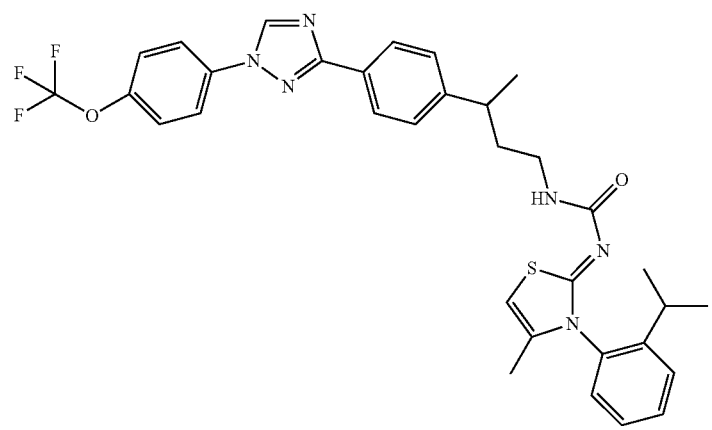 [SMILES: Cc1cs/c(=N\C(=O)NCCC(C)c2ccc(-c3ncn(-c4ccc(OC(F)(F)F)cc4)n3)cc2)n1-c1ccccc1C(C)C]
P291
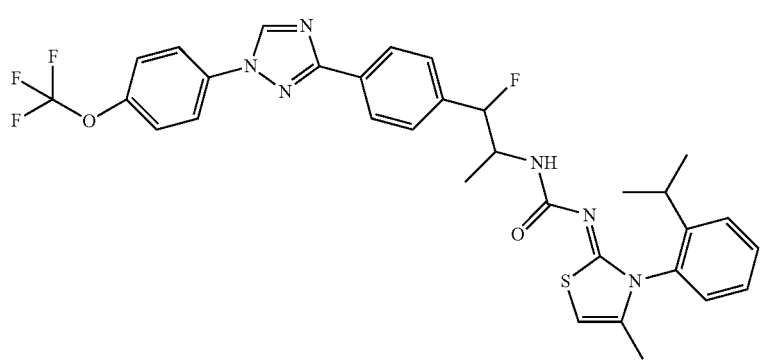 [SMILES: Cc1cs/c(=N\C(=O)NC(C)C(F)c2ccc(-c3ncn(-c4ccc(OC(F)(F)F)cc4)n3)cc2)n1-c1ccccc1C(C)C]
P292

TABLE P-Two-continued
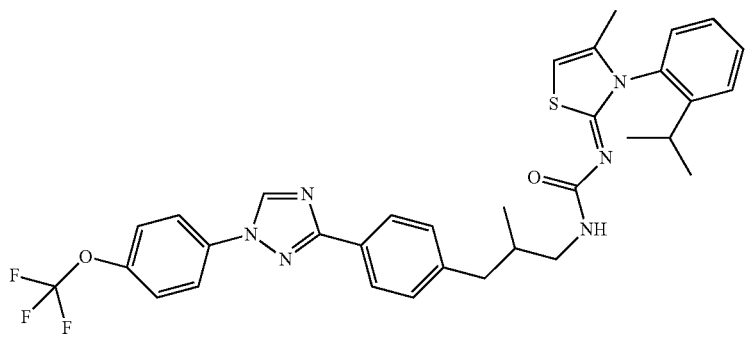 [SMILES: Cc1cs/c(=N\C(=O)NCC(C)Cc2ccc(-c3ncn(-c4ccc(OC(F)(F)F)cc4)n3)cc2)n1-c1ccccc1C(C)C]
P293
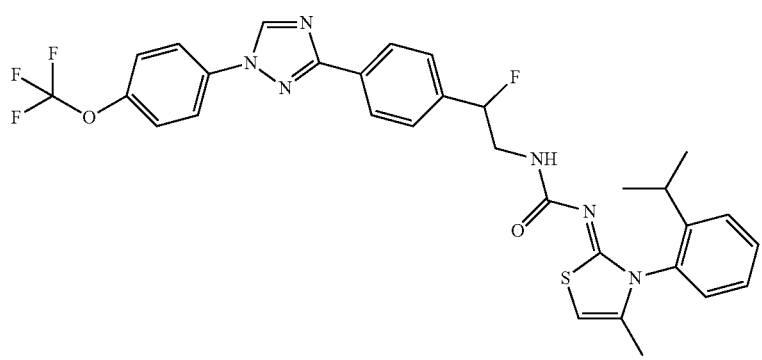 [SMILES: Cc1cs/c(=N\C(=O)NCC(F)c2ccc(-c3ncn(-c4ccc(OC(F)(F)F)cc4)n3)cc2)n1-c1ccccc1C(C)C]
P294
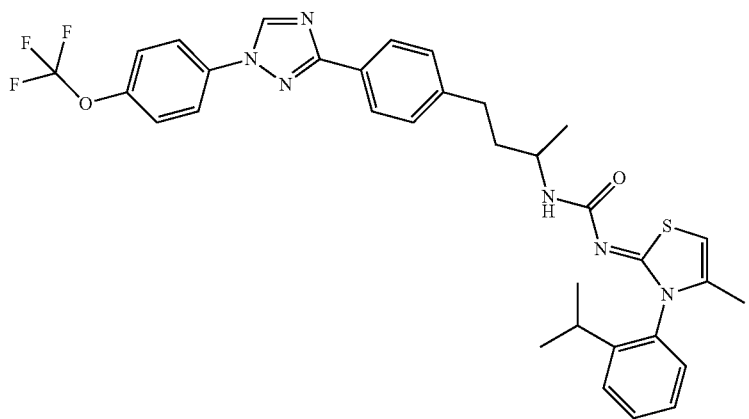 [SMILES: Cc1cs/c(=N\C(=O)NC(C)CCc2ccc(-c3ncn(-c4ccc(OC(F)(F)F)cc4)n3)cc2)n1-c1ccccc1C(C)C]
P295
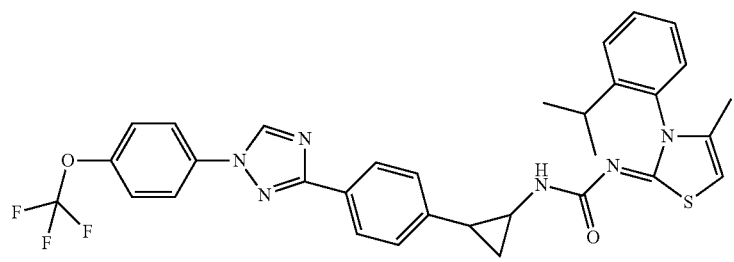 [SMILES: Cc1cs/c(=N\C(=O)NC2CC2c2ccc(-c3ncn(-c4ccc(OC(F)(F)F)cc4)n3)cc2)n1-c1ccccc1C(C)C]
P296

TABLE P-Two-continued
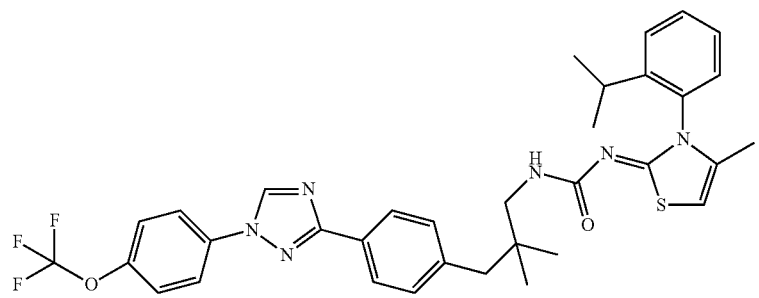 [SMILES: Cc1cs/c(=N\C(=O)NCC(C)(C)Cc2ccc(-c3ncn(-c4ccc(OC(F)(F)F)cc4)n3)cc2)n1-c1ccccc1C(C)C]
P297
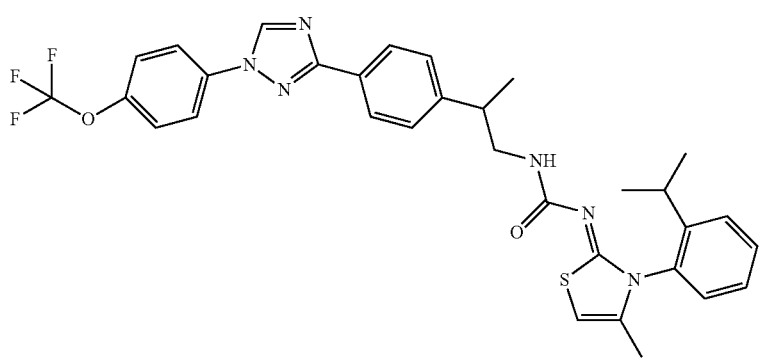 [SMILES: Cc1cs/c(=N\C(=O)NCC(C)c2ccc(-c3ncn(-c4ccc(OC(F)(F)F)cc4)n3)cc2)n1-c1ccccc1C(C)C]
P298
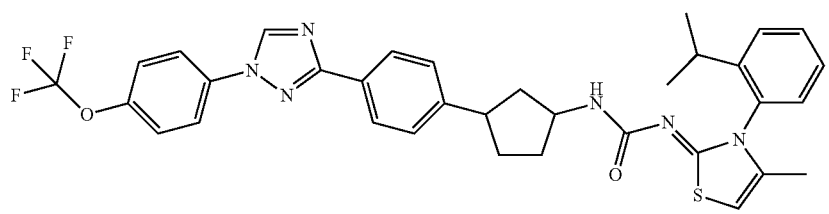 [SMILES: Cc1cs/c(=N\C(=O)NC2CCC(c3ccc(-c4ncn(-c5ccc(OC(F)(F)F)cc5)n4)cc3)C2)n1-c1ccccc1C(C)C]
P299
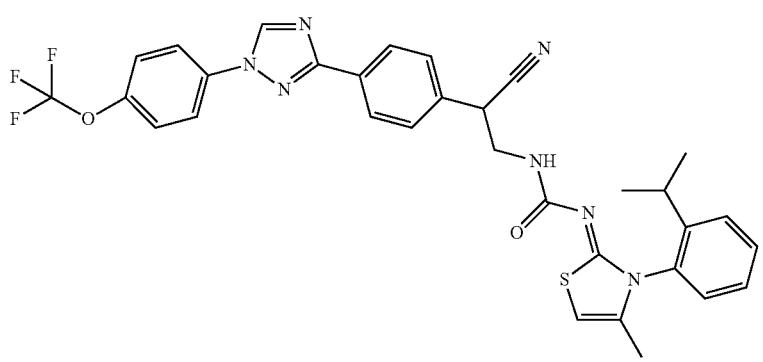 [SMILES: Cc1cs/c(=N\C(=O)NCC(C#N)c2ccc(-c3ncn(-c4ccc(OC(F)(F)F)cc4)n3)cc2)n1-c1ccccc1C(C)C]
P300
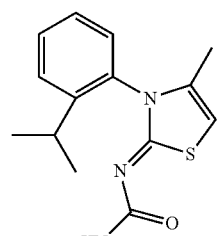
P301
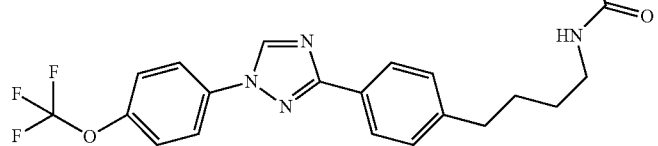

TABLE P-Two-continued
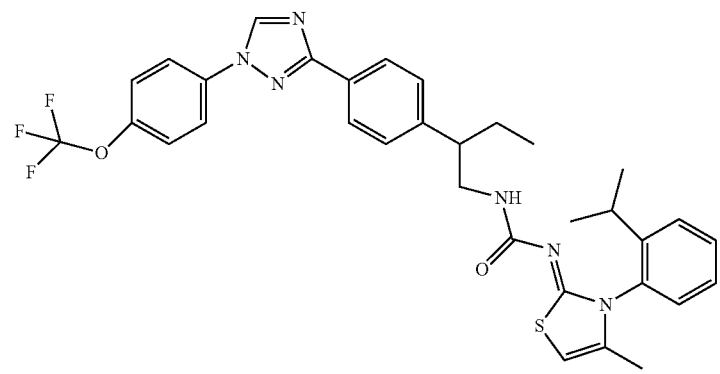 [SMILES: CCC(CNC(=O)/N=c1\scc(C)n1-c1ccccc1C(C)C)c1ccc(-c2ncn(-c3ccc(OC(F)(F)F)cc3)n2)cc1]
P302
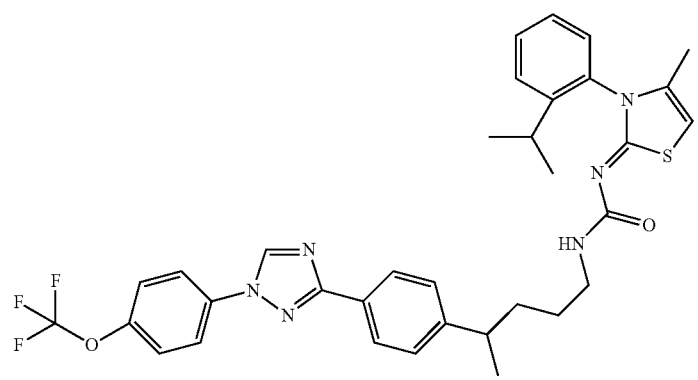 [SMILES: Cc1cs/c(=N\C(=O)NCCCC(C)c2ccc(-c3ncn(-c4ccc(OC(F)(F)F)cc4)n3)cc2)n1-c1ccccc1C(C)C]
P303
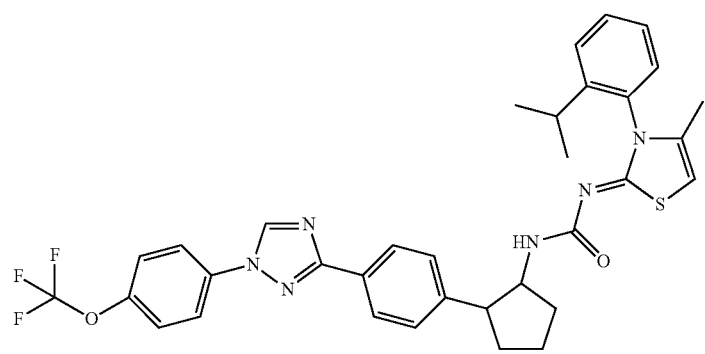 [SMILES: Cc1cs/c(=N\C(=O)NC2CCCC2c2ccc(-c3ncn(-c4ccc(OC(F)(F)F)cc4)n3)cc2)n1-c1ccccc1C(C)C]
P304
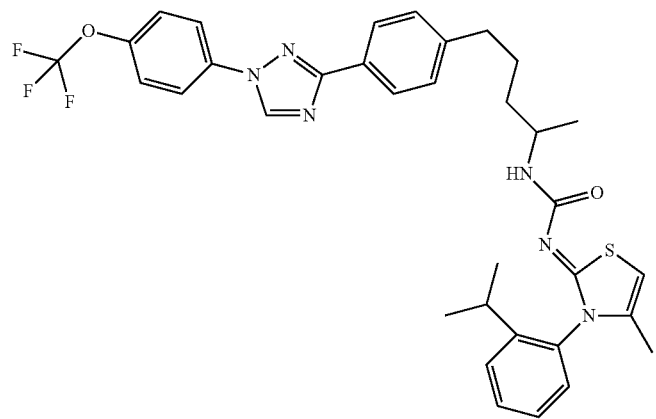 [SMILES: Cc1cs/c(=N\C(=O)NC(C)CCCc2ccc(-c3ncn(-c4ccc(OC(F)(F)F)cc4)n3)cc2)n1-c1ccccc1C(C)C]
P305

TABLE P-Two-continued
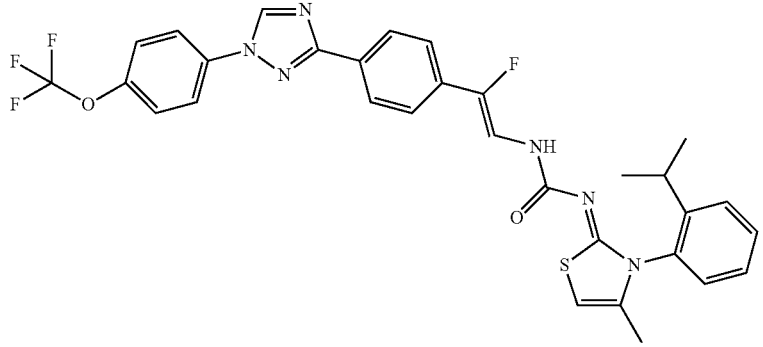 [SMILES: Cc1cs/c(=N\C(=O)N/C=C(\F)c2ccc(-c3ncn(-c4ccc(OC(F)(F)F)cc4)n3)cc2)n1-c1ccccc1C(C)C]
P306
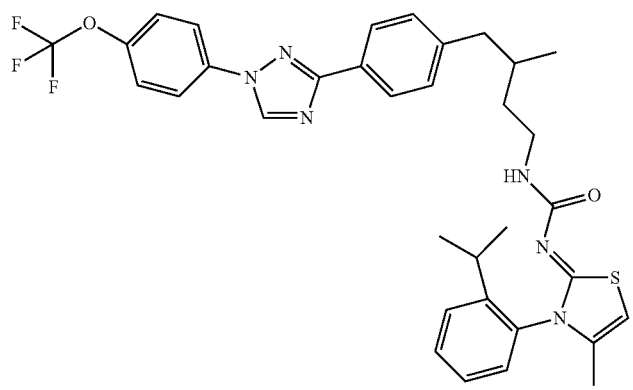 [SMILES: Cc1cs/c(=N\C(=O)NCCC(C)Cc2ccc(-c3ncn(-c4ccc(OC(F)(F)F)cc4)n3)cc2)n1-c1ccccc1C(C)C]
P307
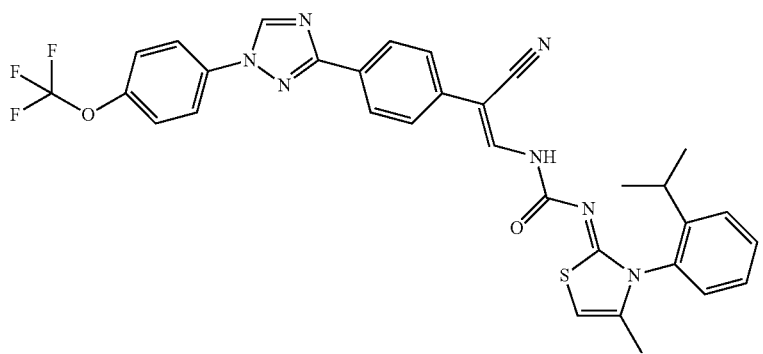 [SMILES: Cc1cs/c(=N\C(=O)N/C=C(\C#N)c2ccc(-c3ncn(-c4ccc(OC(F)(F)F)cc4)n3)cc2)n1-c1ccccc1C(C)C]
P308
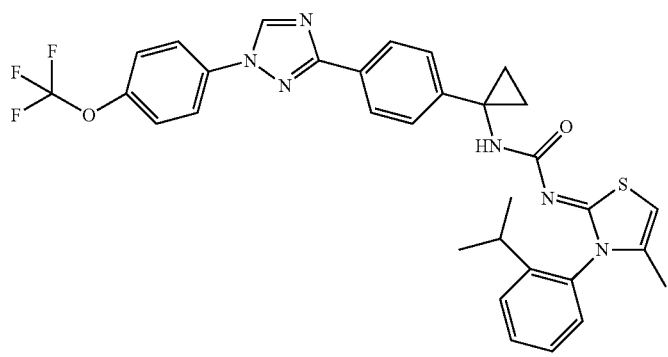 [SMILES: Cc1cs/c(=N\C(=O)NC2(c3ccc(-c4ncn(-c5ccc(OC(F)(F)F)cc5)n4)cc3)CC2)n1-c1ccccc1C(C)C]
P309

TABLE P-Two-continued
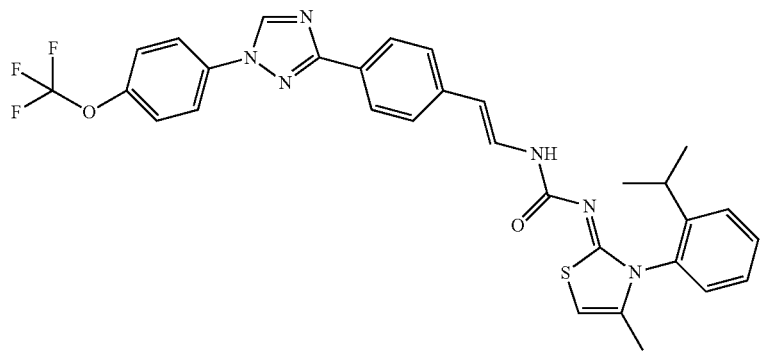 [SMILES: Cc1cs/c(=N\C(=O)N/C=C/c2ccc(-c3ncn(-c4ccc(OC(F)(F)F)cc4)n3)cc2)n1-c1ccccc1C(C)C]
P310
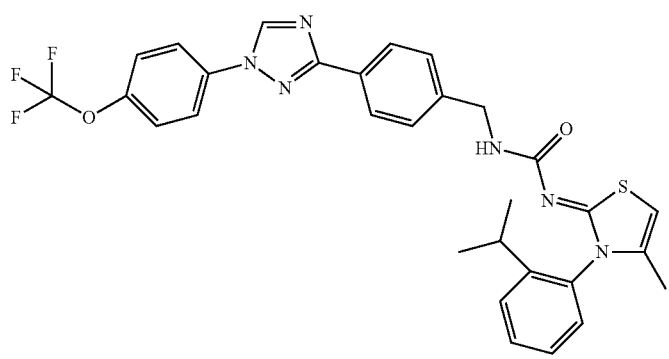 [SMILES: Cc1cs/c(=N\C(=O)NCc2ccc(-c3ncn(-c4ccc(OC(F)(F)F)cc4)n3)cc2)n1-c1ccccc1C(C)C]
P311
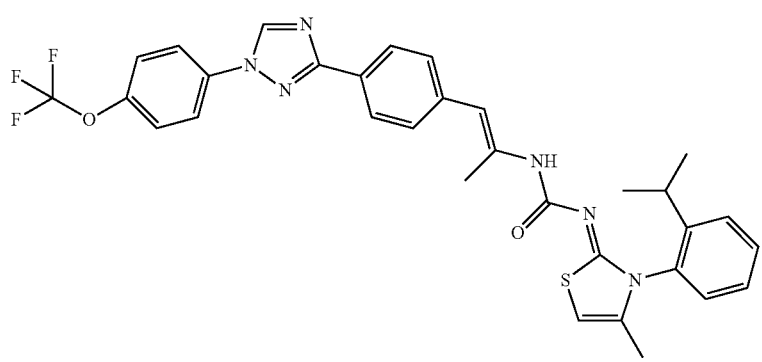 [SMILES: C/C(=C\c1ccc(-c2ncn(-c3ccc(OC(F)(F)F)cc3)n2)cc1)NC(=O)/N=c1\scc(C)n1-c1ccccc1C(C)C]
P312
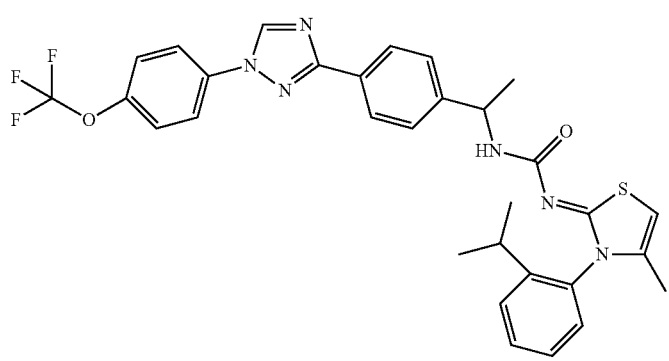 [SMILES: Cc1cs/c(=N\C(=O)NC(C)c2ccc(-c3ncn(-c4ccc(OC(F)(F)F)cc4)n3)cc2)n1-c1ccccc1C(C)C]
P313

TABLE P-Two-continued
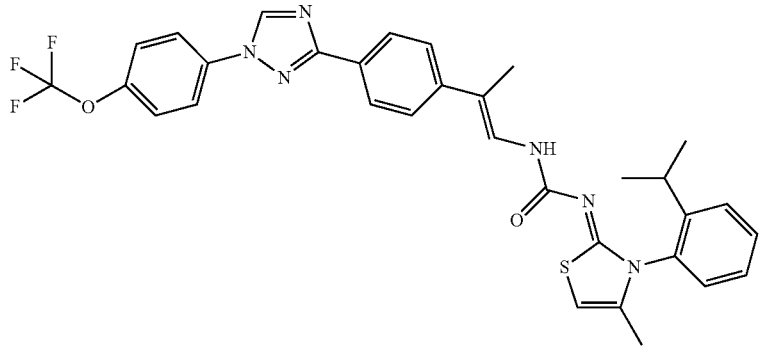 [SMILES: C/C(=C\NC(=O)/N=c1\scc(C)n1-c1ccccc1C(C)C)c1ccc(-c2ncn(-c3ccc(OC(F)(F)F)cc3)n2)cc1]
P314
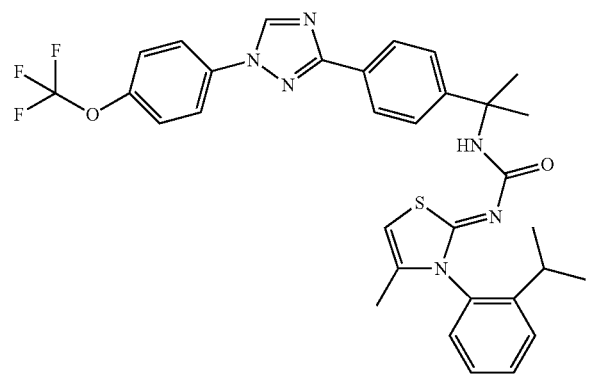 [SMILES: Cc1cs/c(=N\C(=O)NC(C)(C)c2ccc(-c3ncn(-c4ccc(OC(F)(F)F)cc4)n3)cc2)n1-c1ccccc1C(C)C]
P315
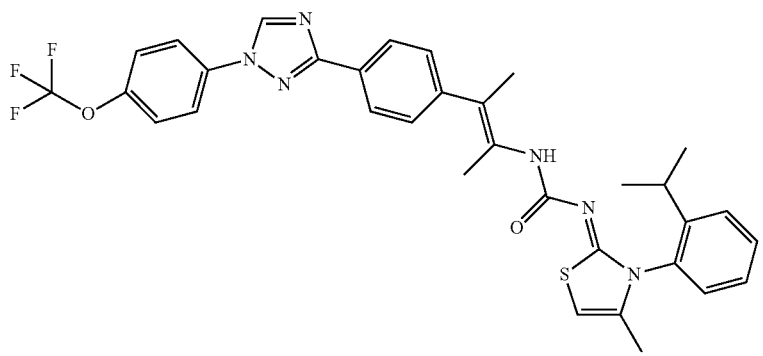 [SMILES: C/C(NC(=O)/N=c1\scc(C)n1-c1ccccc1C(C)C)=C(/C)c1ccc(-c2ncn(-c3ccc(OC(F)(F)F)cc3)n2)cc1]
P316
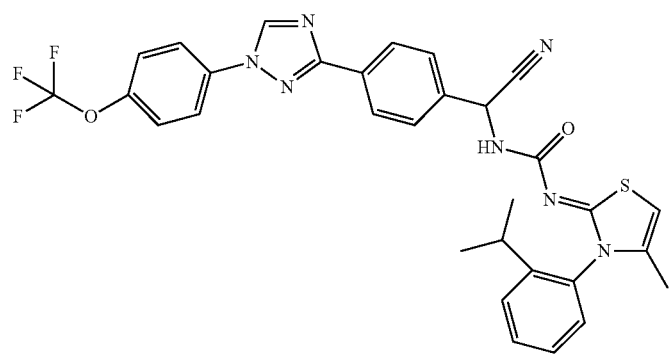 [SMILES: Cc1cs/c(=N\C(=O)NC(C#N)c2ccc(-c3ncn(-c4ccc(OC(F)(F)F)cc4)n3)cc2)n1-c1ccccc1C(C)C]
P317

TABLE P-Two-continued
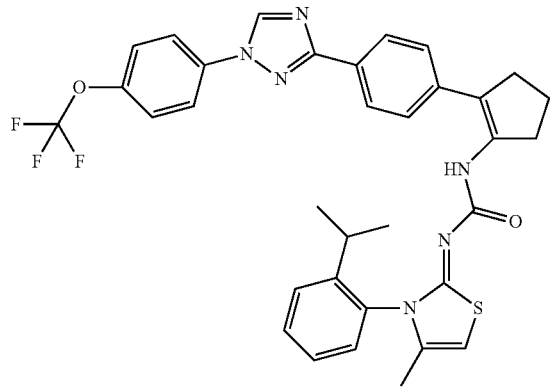 [SMILES: Cc1cs/c(=N\C(=O)NC2=C(c3ccc(-c4ncn(-c5ccc(OC(F)(F)F)cc5)n4)cc3)CCC2)n1-c1ccccc1C(C)C]
P318
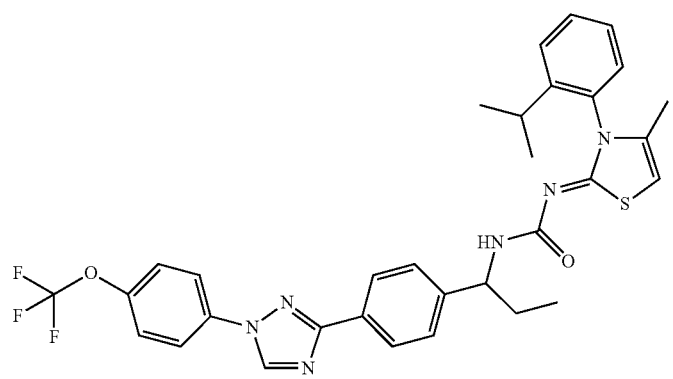 [SMILES: CCC(NC(=O)/N=c1\scc(C)n1-c1ccccc1C(C)C)c1ccc(-c2ncn(-c3ccc(OC(F)(F)F)cc3)n2)cc1]
P319
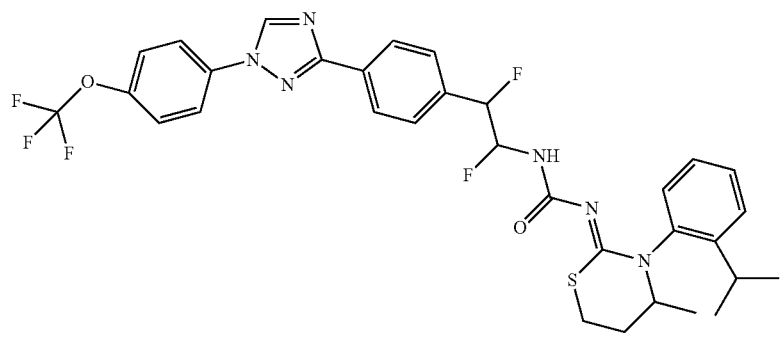 [SMILES: CC(C)c1ccccc1N1/C(=N/C(=O)NC(F)C(F)c2ccc(-c3ncn(-c4ccc(OC(F)(F)F)cc4)n3)cc2)SCCC1C]
P320
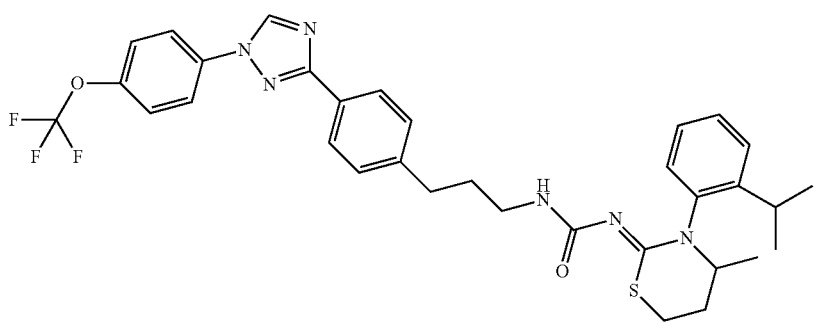 [SMILES: CC(C)c1ccccc1N1/C(=N/C(=O)NCCCc2ccc(-c3ncn(-c4ccc(OC(F)(F)F)cc4)n3)cc2)SCCC1C]
P321

TABLE P-Two-continued
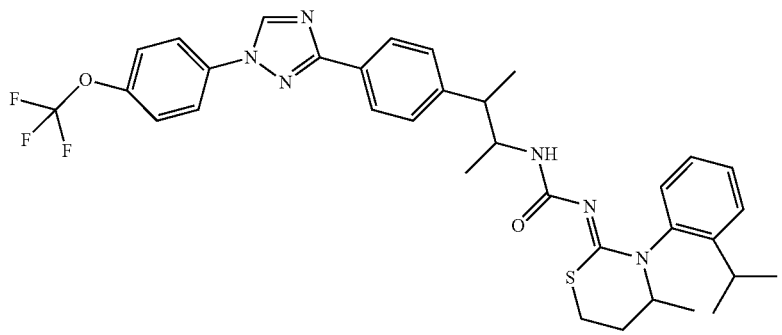 [SMILES: CC(C)c1ccccc1N1/C(=N/C(=O)NC(C)C(C)c2ccc(-c3ncn(-c4ccc(OC(F)(F)F)cc4)n3)cc2)SCCC1C]
P322
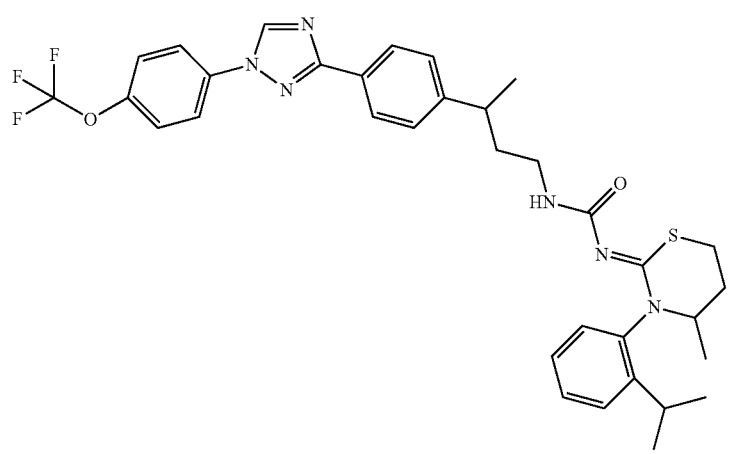 [SMILES: CC(C)c1ccccc1N1/C(=N/C(=O)NCCC(C)c2ccc(-c3ncn(-c4ccc(OC(F)(F)F)cc4)n3)cc2)SCCC1C]
P323
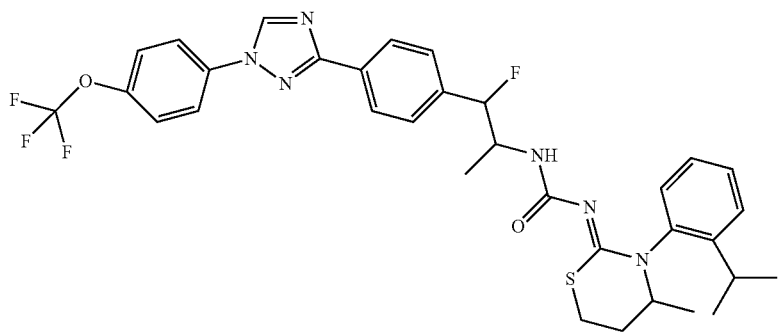 [SMILES: CC(C)c1ccccc1N1/C(=N/C(=O)NC(C)C(F)c2ccc(-c3ncn(-c4ccc(OC(F)(F)F)cc4)n3)cc2)SCCC1C]
P324
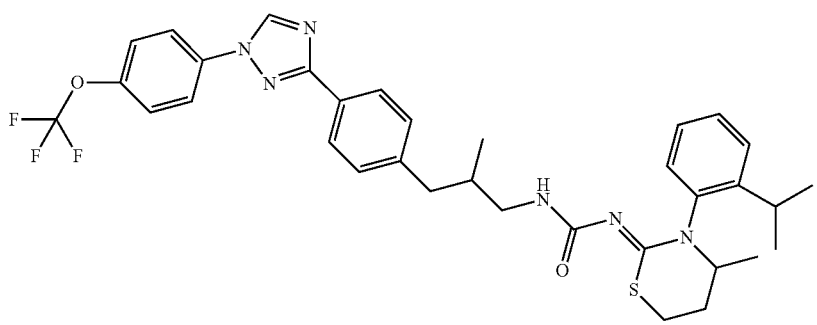 [SMILES: CC(CNC(=O)/N=C1\SCCC(C)N1c1ccccc1C(C)C)Cc1ccc(-c2ncn(-c3ccc(OC(F)(F)F)cc3)n2)cc1]
P325

TABLE P-Two-continued
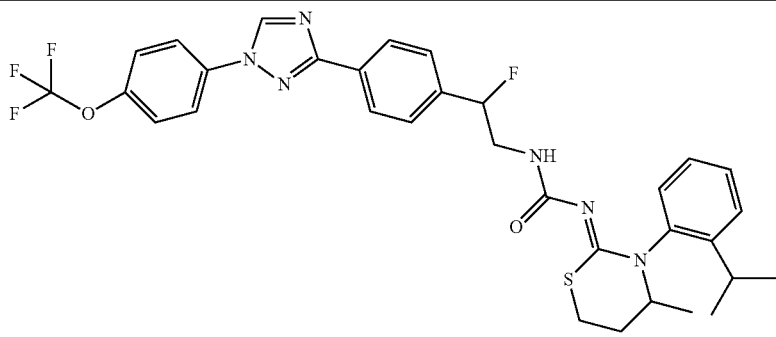
P326
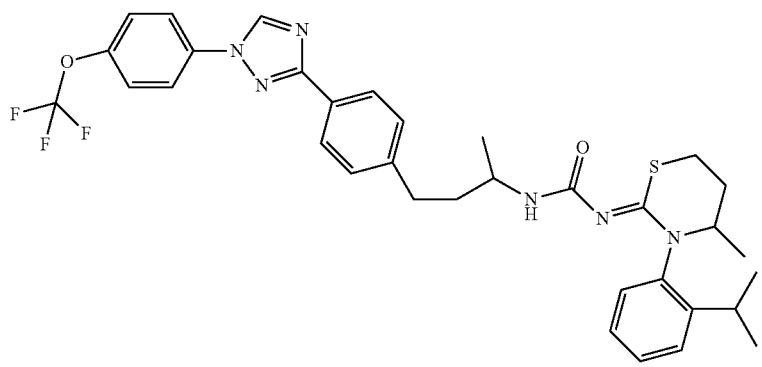 [SMILES: CC(CCc1ccc(-c2ncn(-c3ccc(OC(F)(F)F)cc3)n2)cc1)NC(=O)/N=C1\SCCC(C)N1c1ccccc1C(C)C]
P327
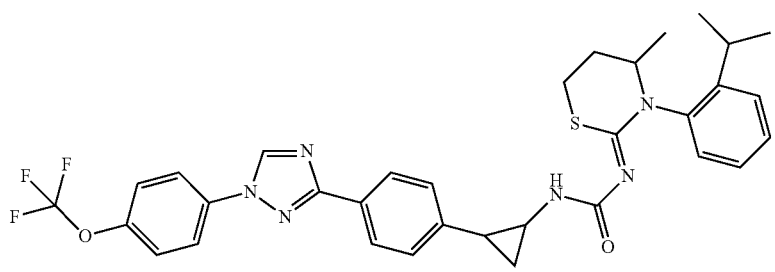 [SMILES: CC(C)c1ccccc1N1/C(=N/C(=O)NC2CC2c2ccc(-c3ncn(-c4ccc(OC(F)(F)F)cc4)n3)cc2)SCCC1C]
P328
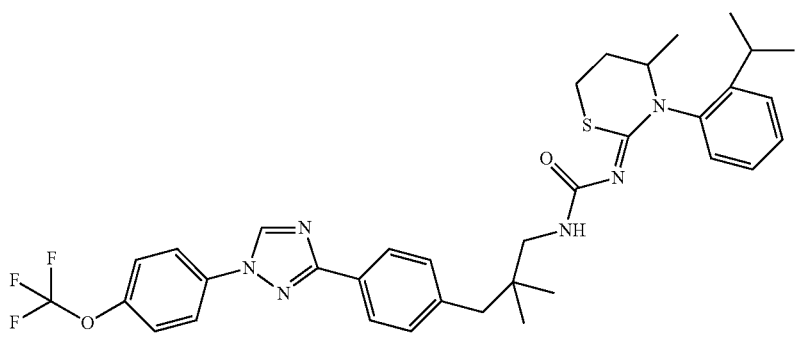 [SMILES: CC(C)c1ccccc1N1/C(=N/C(=O)NCC(C)(C)Cc2ccc(-c3ncn(-c4ccc(OC(F)(F)F)cc4)n3)cc2)SCCC1C]
P329
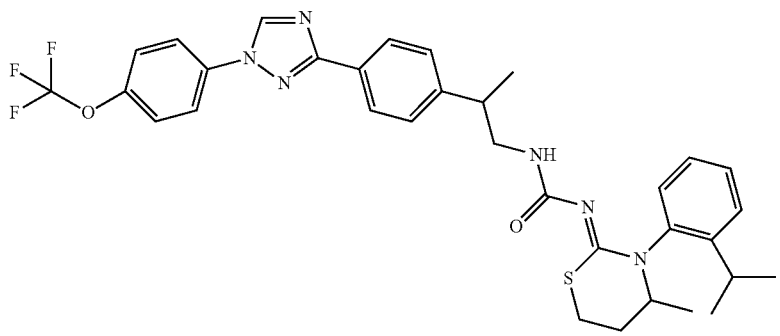 [SMILES: CC(C)c1ccccc1N1/C(=N/C(=O)NCC(C)c2ccc(-c3ncn(-c4ccc(OC(F)(F)F)cc4)n3)cc2)SCCC1C]
P330

TABLE P-Two-continued
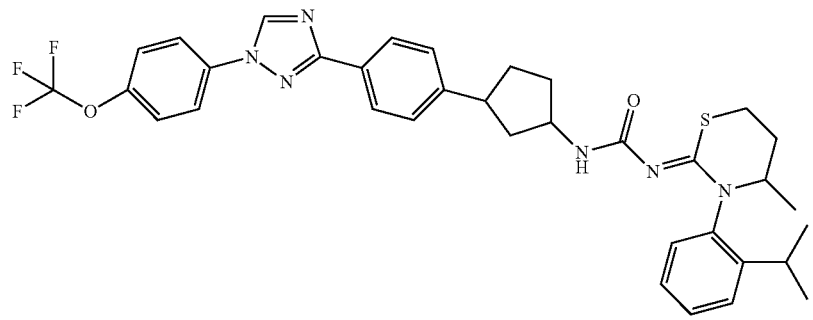 [SMILES: CC(C)c1ccccc1N1/C(=N/C(=O)NC2CCC(c3ccc(-c4ncn(-c5ccc(OC(F)(F)F)cc5)n4)cc3)C2)SCCC1C]
P331
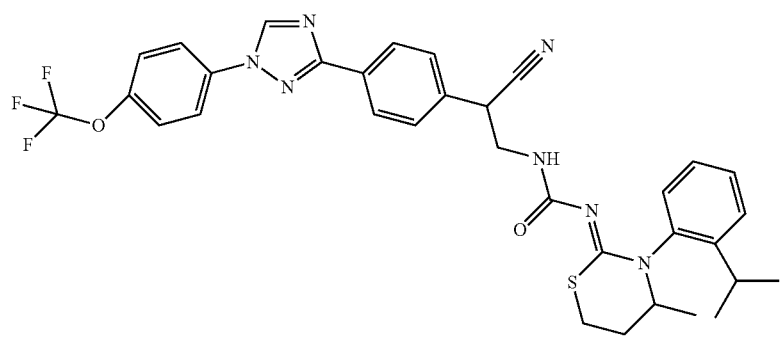 [SMILES: CC(C)c1ccccc1N1/C(=N/C(=O)NCC(C#N)c2ccc(-c3ncn(-c4ccc(OC(F)(F)F)cc4)n3)cc2)SCCC1C]
P332
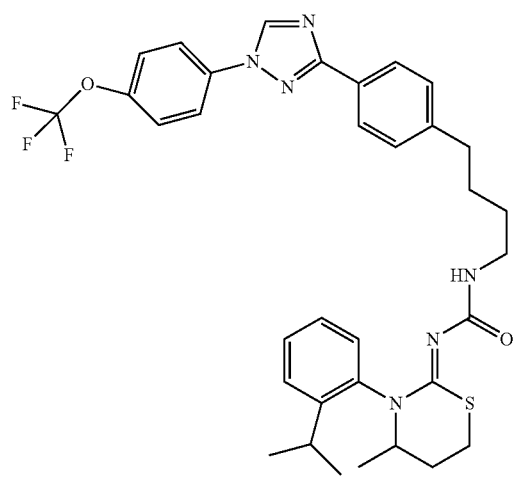 [SMILES: CC(C)c1ccccc1N1/C(=N/C(=O)NCCCCc2ccc(-c3ncn(-c4ccc(OC(F)(F)F)cc4)n3)cc2)SCCC1C]
P333
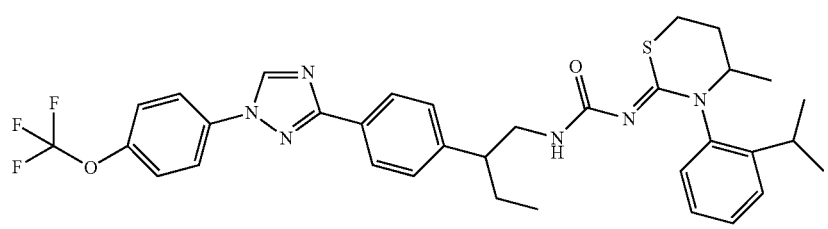 [SMILES: CCC(CNC(=O)/N=C1\SCCC(C)N1c1ccccc1C(C)C)c1ccc(-c2ncn(-c3ccc(OC(F)(F)F)cc3)n2)cc1]
P334
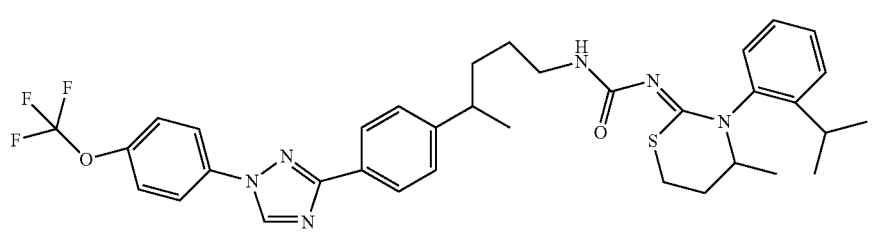 [SMILES: CC(C)c1ccccc1N1/C(=N/C(=O)NCCCC(C)c2ccc(-c3ncn(-c4ccc(OC(F)(F)F)cc4)n3)cc2)SCCC1C]
P335

TABLE P-Two-continued
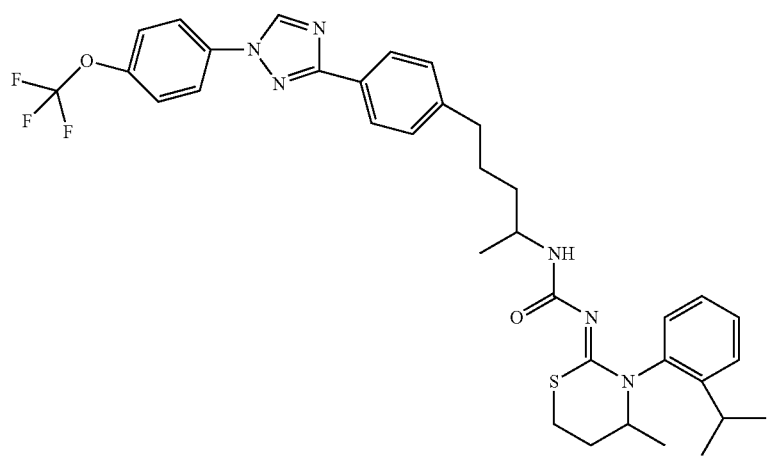 [SMILES: CC(CCCc1ccc(-c2ncn(-c3ccc(OC(F)(F)F)cc3)n2)cc1)NC(=O)/N=C1\SCCC(C)N1c1ccccc1C(C)C]
P336
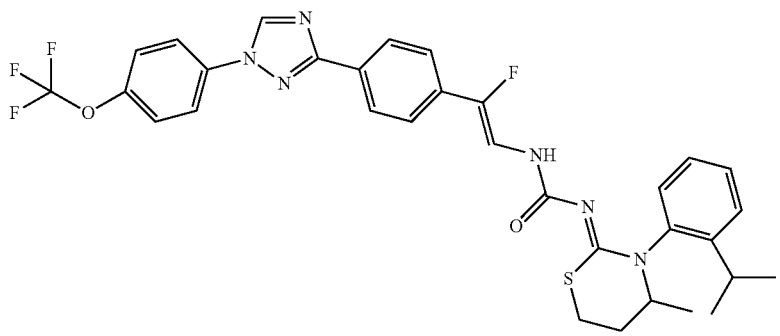 [SMILES: CC(C)c1ccccc1N1/C(=N/C(=O)N/C=C(\F)c2ccc(-c3ncn(-c4ccc(OC(F)(F)F)cc4)n3)cc2)SCCC1C]
P337
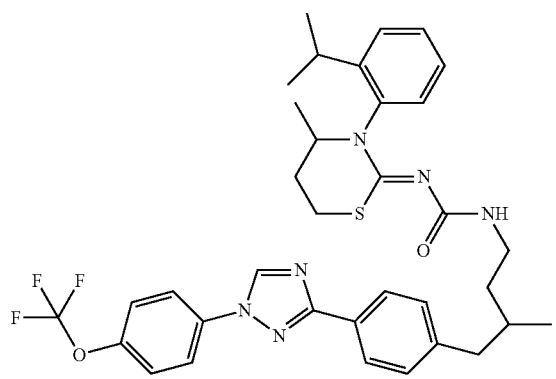 [SMILES: CC(CCNC(=O)/N=C1\SCCC(C)N1c1ccccc1C(C)C)Cc1ccc(-c2ncn(-c3ccc(OC(F)(F)F)cc3)n2)cc1]
P338
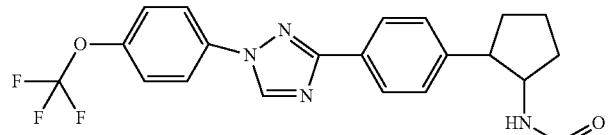
P339

TABLE P-Two-continued
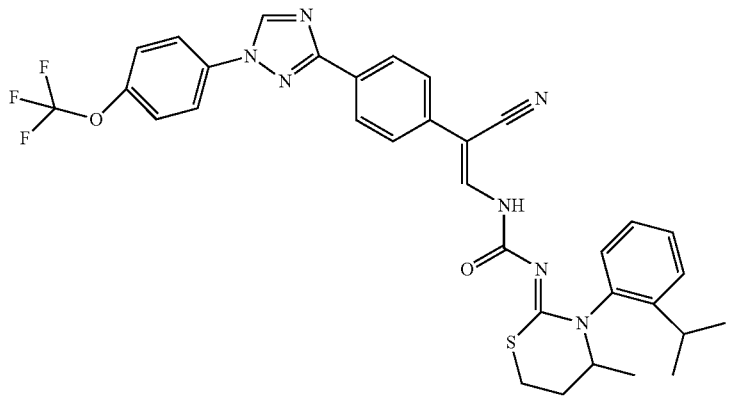 [SMILES: CC(C)c1ccccc1N1/C(=N/C(=O)N/C=C(\C#N)c2ccc(-c3ncn(-c4ccc(OC(F)(F)F)cc4)n3)cc2)SCCC1C]
P340
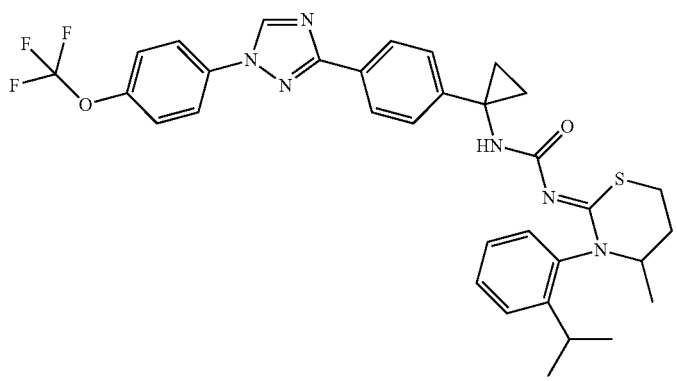 [SMILES: CC(C)c1ccccc1N1/C(=N/C(=O)NC2(c3ccc(-c4ncn(-c5ccc(OC(F)(F)F)cc5)n4)cc3)CC2)SCCC1C]
P341
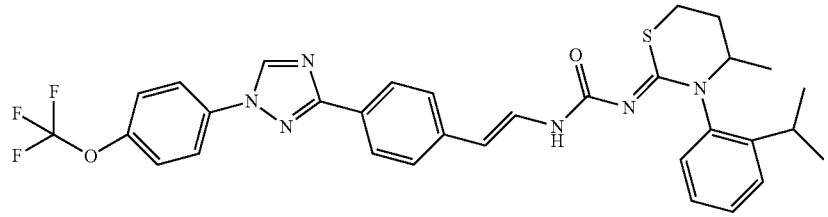 [SMILES: CC(C)c1ccccc1N1/C(=N/C(=O)N/C=C/c2ccc(-c3ncn(-c4ccc(OC(F)(F)F)cc4)n3)cc2)SCCC1C]
P342
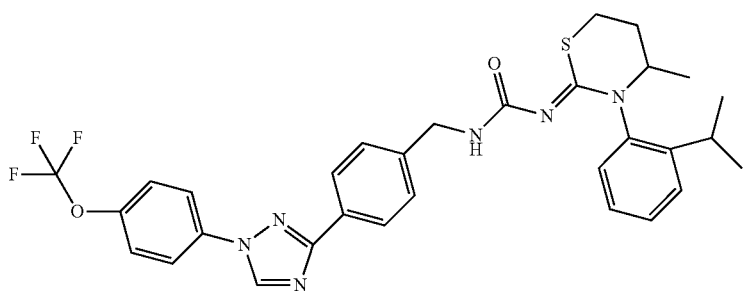 [SMILES: CC(C)c1ccccc1N1/C(=N/C(=O)NCc2ccc(-c3ncn(-c4ccc(OC(F)(F)F)cc4)n3)cc2)SCCC1C]
P343
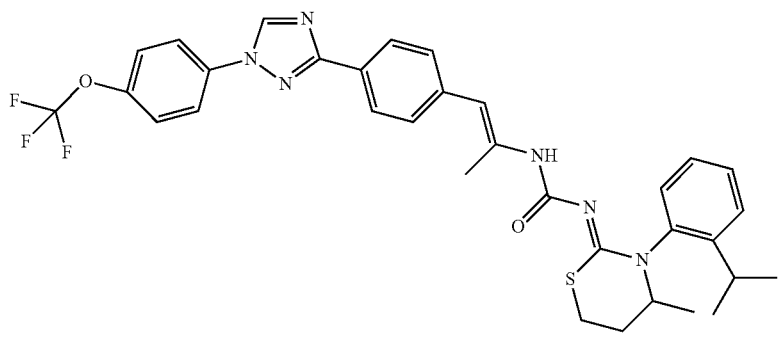 [SMILES: C/C(=C\c1ccc(-c2ncn(-c3ccc(OC(F)(F)F)cc3)n2)cc1)NC(=O)/N=C1\SCCC(C)N1c1ccccc1C(C)C]
P344

TABLE P-Two-continued
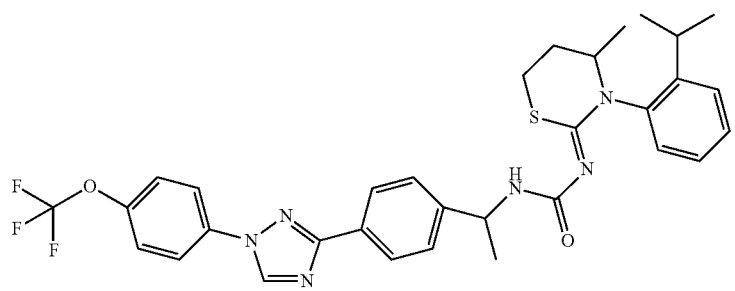 [SMILES: CC(C)c1ccccc1N1/C(=N/C(=O)NC(C)c2ccc(-c3ncn(-c4ccc(OC(F)(F)F)cc4)n3)cc2)SCCC1C] P345
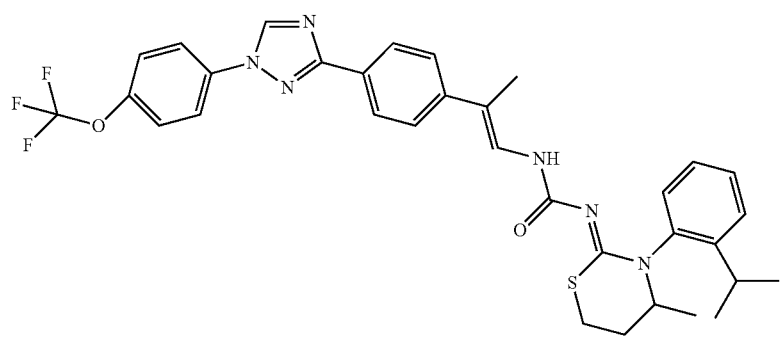 [SMILES: C/C(=C\NC(=O)/N=C1\SCCC(C)N1c1ccccc1C(C)C)c1ccc(-c2ncn(-c3ccc(OC(F)(F)F)cc3)n2)cc1] P346
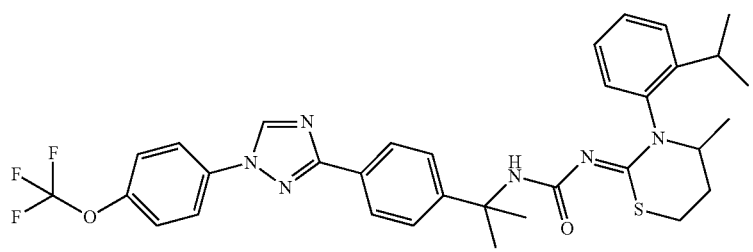 [SMILES: CC(C)c1ccccc1N1/C(=N/C(=O)NC(C)(C)c2ccc(-c3ncn(-c4ccc(OC(F)(F)F)cc4)n3)cc2)SCCC1C] P347
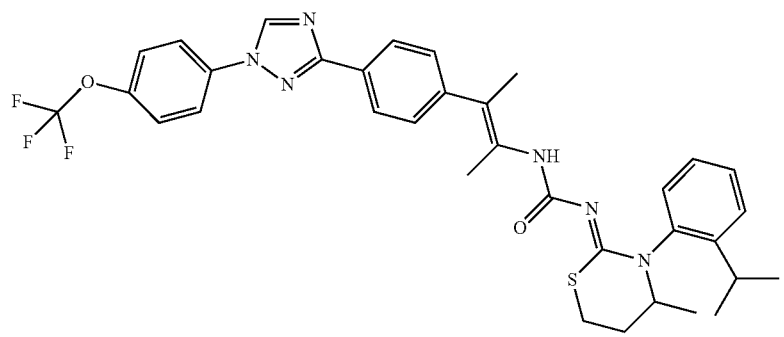 [SMILES: C/C(NC(=O)/N=C1\SCCC(C)N1c1ccccc1C(C)C)=C(/C)c1ccc(-c2ncn(-c3ccc(OC(F)(F)F)cc3)n2)cc1] P348
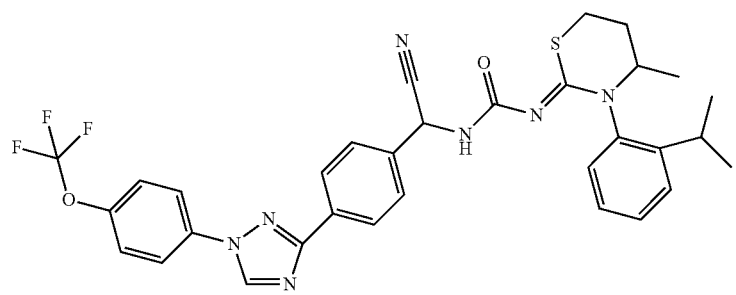 [SMILES: CC(C)c1ccccc1N1/C(=N/C(=O)NC(C#N)c2ccc(-c3ncn(-c4ccc(OC(F)(F)F)cc4)n3)cc2)SCCC1C] P349

TABLE P-Two-continued
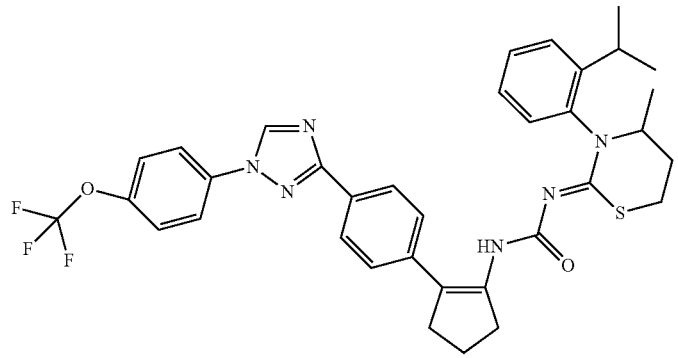 [SMILES: CC(C)c1ccccc1N1/C(=N/C(=O)NC2=C(c3ccc(-c4ncn(-c5ccc(OC(F)(F)F)cc5)n4)cc3)CCC2)SCCC1C]
P350
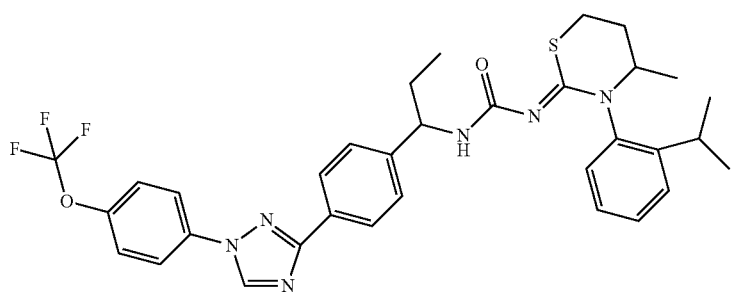 [SMILES: CCC(NC(=O)/N=C1\SCCC(C)N1c1ccccc1C(C)C)c1ccc(-c2ncn(-c3ccc(OC(F)(F)F)cc3)n2)cc1]
P351
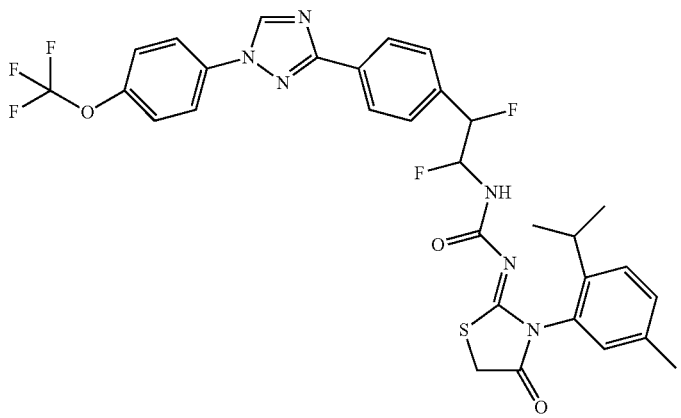 [SMILES: Cc1ccc(C(C)C)c(N2C(=O)CS/C2=N\C(=O)NC(F)C(F)c2ccc(-c3ncn(-c4ccc(OC(F)(F)F)cc4)n3)cc2)c1]
P352
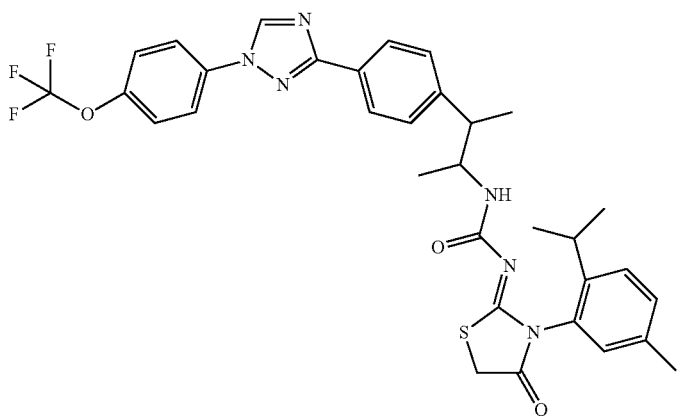 [SMILES: Cc1ccc(C(C)C)c(N2C(=O)CS/C2=N\C(=O)NC(C)C(C)c2ccc(-c3ncn(-c4ccc(OC(F)(F)F)cc4)n3)cc2)c1]
P353

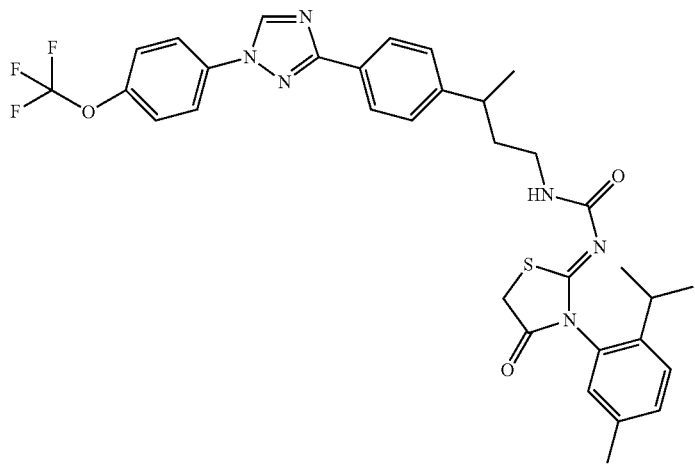 [SMILES: Cc1ccc(C(C)C)c(N2C(=O)CS/C2=N\C(=O)NCCC(C)c2ccc(-c3ncn(-c4ccc(OC(F)(F)F)cc4)n3)cc2)c1]
P354
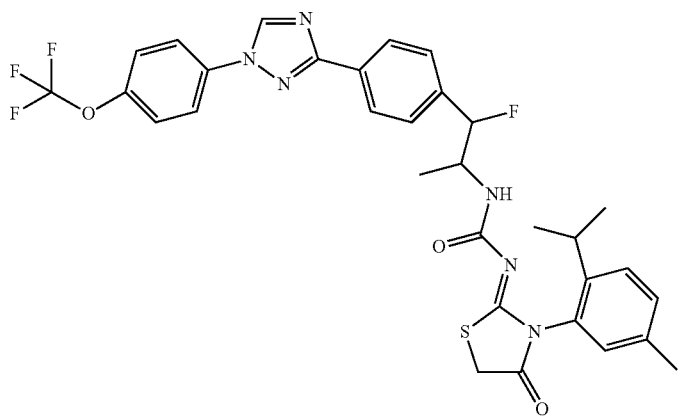
P355
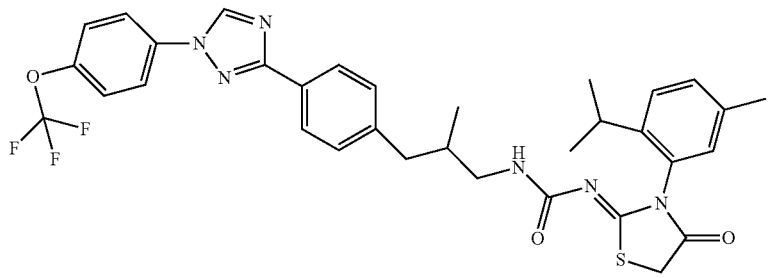 [SMILES: Cc1ccc(C(C)C)c(N2C(=O)CS/C2=N\C(=O)NCC(C)Cc2ccc(-c3ncn(-c4ccc(OC(F)(F)F)cc4)n3)cc2)c1]
P356
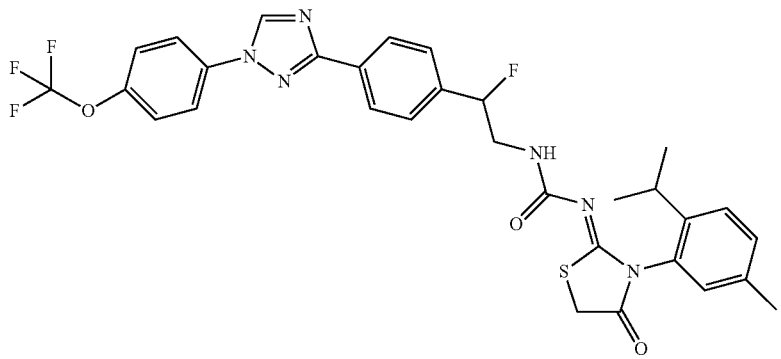 [SMILES: Cc1ccc(C(C)C)c(N2C(=O)CS/C2=N\C(=O)NCC(F)c2ccc(-c3ncn(-c4ccc(OC(F)(F)F)cc4)n3)cc2)c1]
P357

TABLE P-Two-continued
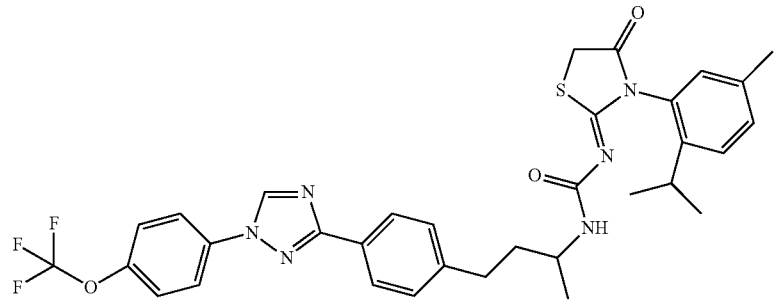 [SMILES: Cc1ccc(C(C)C)c(N2C(=O)CS/C2=N\C(=O)NC(C)CCc2ccc(-c3ncn(-c4ccc(OC(F)(F)F)cc4)n3)cc2)c1]
P358
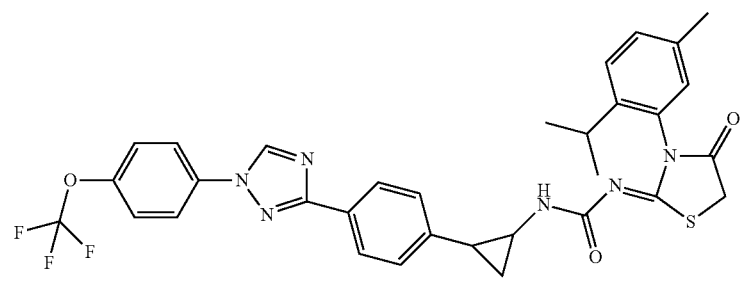 [SMILES: Cc1ccc(C(C)C)c(N2C(=O)CS/C2=N\C(=O)NC2CC2c2ccc(-c3ncn(-c4ccc(OC(F)(F)F)cc4)n3)cc2)c1]
P359
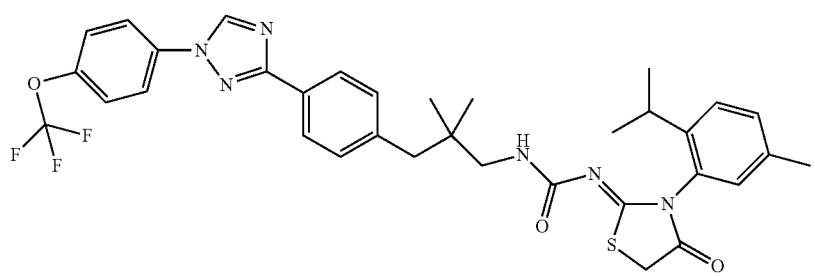 [SMILES: Cc1ccc(C(C)C)c(N2C(=O)CS/C2=N\C(=O)NCC(C)(C)Cc2ccc(-c3ncn(-c4ccc(OC(F)(F)F)cc4)n3)cc2)c1]
P360
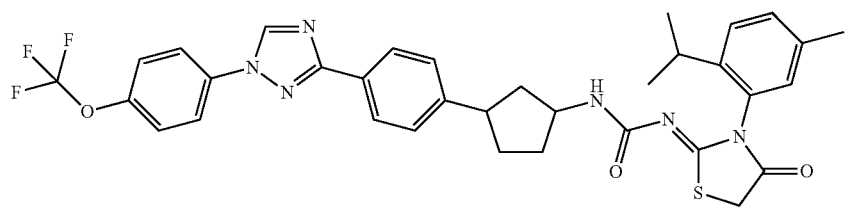 [SMILES: Cc1ccc(C(C)C)c(N2C(=O)CS/C2=N\C(=O)NC2CCC(c3ccc(-c4ncn(-c5ccc(OC(F)(F)F)cc5)n4)cc3)C2)c1]
P361
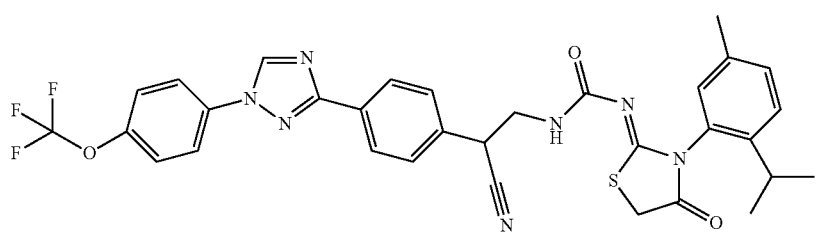 [SMILES: Cc1ccc(C(C)C)c(N2C(=O)CS/C2=N\C(=O)NCC(C#N)c2ccc(-c3ncn(-c4ccc(OC(F)(F)F)cc4)n3)cc2)c1]
P362

TABLE P-Two-continued
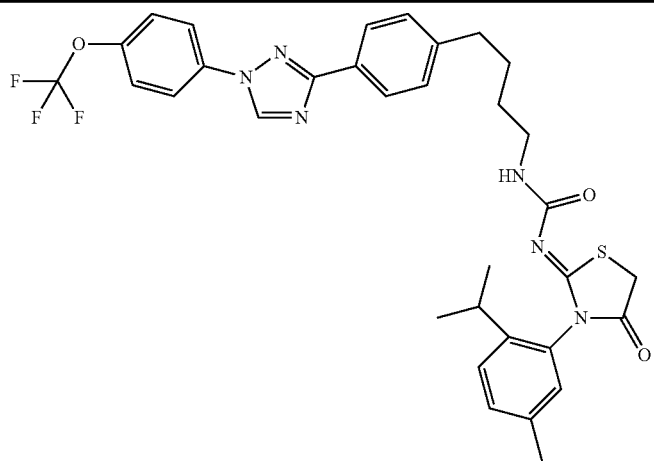
P363
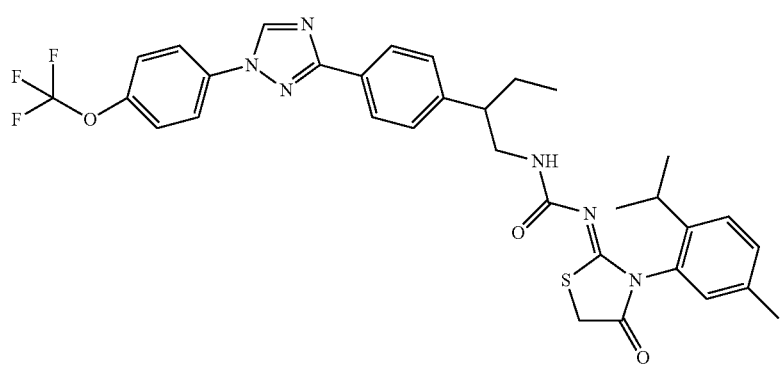 [SMILES: CCC(CNC(=O)/N=C1\SCC(=O)N1c1cc(C)ccc1C(C)C)c1ccc(-c2ncn(-c3ccc(OC(F)(F)F)cc3)n2)cc1]
P364
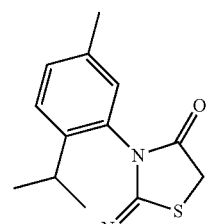
P365
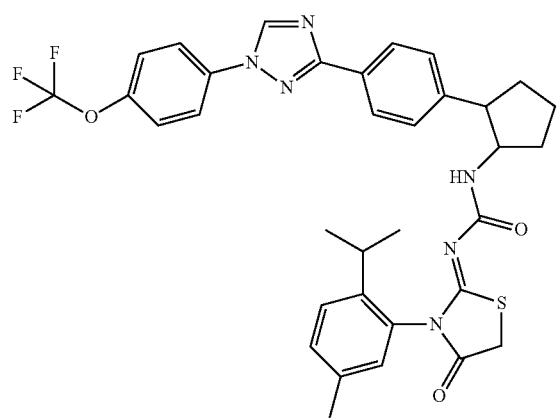 [SMILES: Cc1ccc(C(C)C)c(N2C(=O)CS/C2=N\C(=O)NC2CCCC2c2ccc(-c3ncn(-c4ccc(OC(F)(F)F)cc4)n3)cc2)c1]
P366

TABLE P-Two-continued
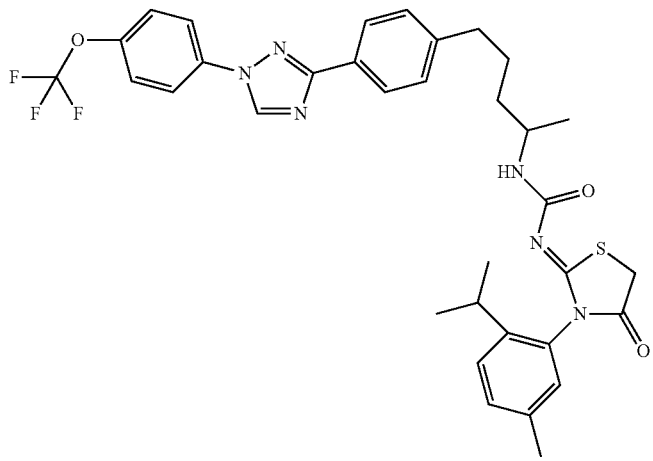 [SMILES: Cc1ccc(C(C)C)c(N2C(=O)CS/C2=N\C(=O)NC(C)CCCc2ccc(-c3ncn(-c4ccc(OC(F)(F)F)cc4)n3)cc2)c1]
P367
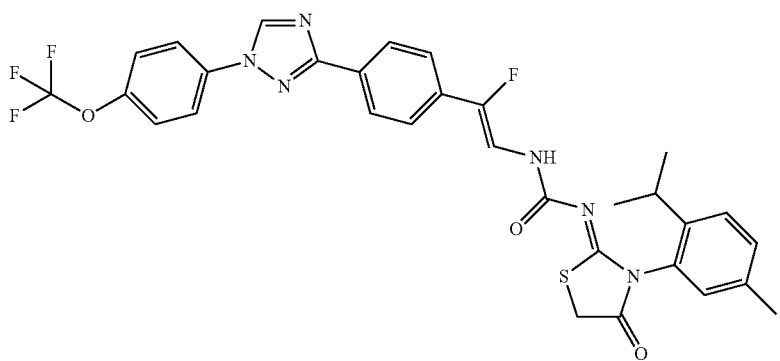 [SMILES: Cc1ccc(C(C)C)c(N2C(=O)CS/C2=N\C(=O)N/C=C(\F)c2ccc(-c3ncn(-c4ccc(OC(F)(F)F)cc4)n3)cc2)c1]
P368
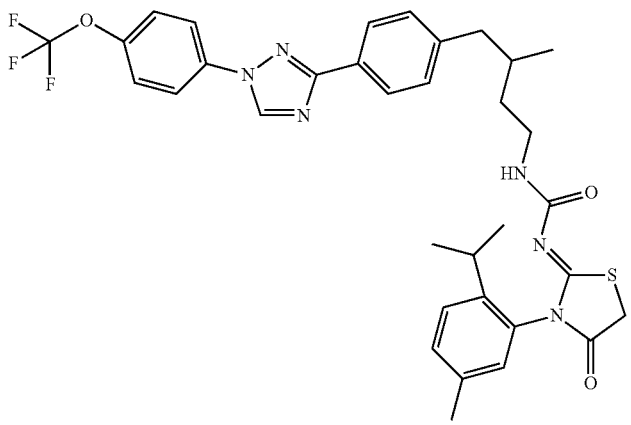 [SMILES: Cc1ccc(C(C)C)c(N2C(=O)CS/C2=N\C(=O)NCCC(C)Cc2ccc(-c3ncn(-c4ccc(OC(F)(F)F)cc4)n3)cc2)c1]
P369
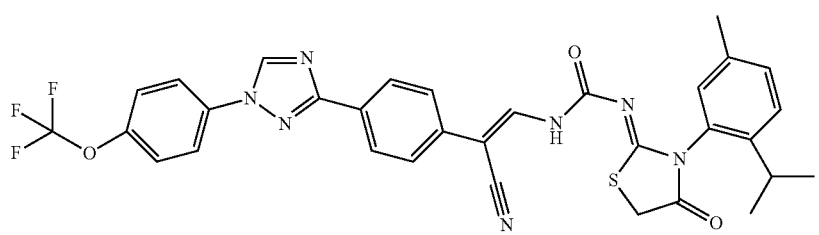 [SMILES: Cc1ccc(C(C)C)c(N2C(=O)CS/C2=N\C(=O)N/C=C(\C#N)c2ccc(-c3ncn(-c4ccc(OC(F)(F)F)cc4)n3)cc2)c1]
P370

TABLE P-Two-continued
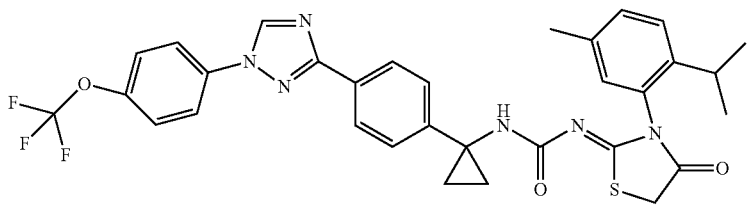 [SMILES: Cc1ccc(C(C)C)c(N2C(=O)CS/C2=N\C(=O)NC2(c3ccc(-c4ncn(-c5ccc(OC(F)(F)F)cc5)n4)cc3)CC2)c1]
P371
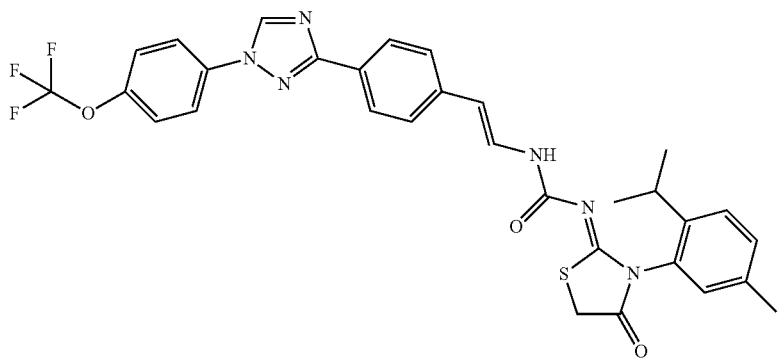 [SMILES: Cc1ccc(C(C)C)c(N2C(=O)CS/C2=N\C(=O)N/C=C/c2ccc(-c3ncn(-c4ccc(OC(F)(F)F)cc4)n3)cc2)c1]
P372
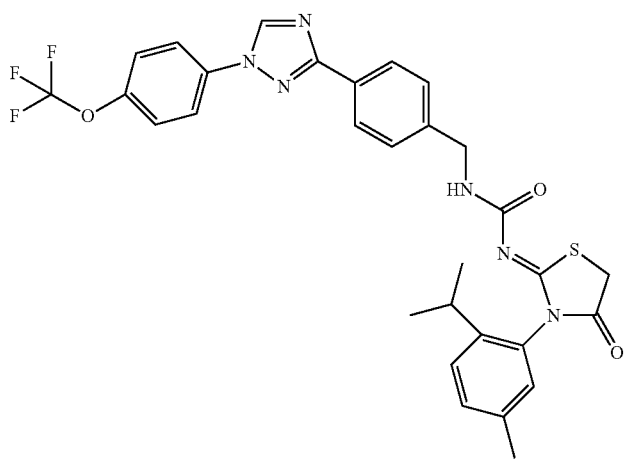 [SMILES: Cc1ccc(C(C)C)c(N2C(=O)CS/C2=N\C(=O)NCc2ccc(-c3ncn(-c4ccc(OC(F)(F)F)cc4)n3)cc2)c1]
P373
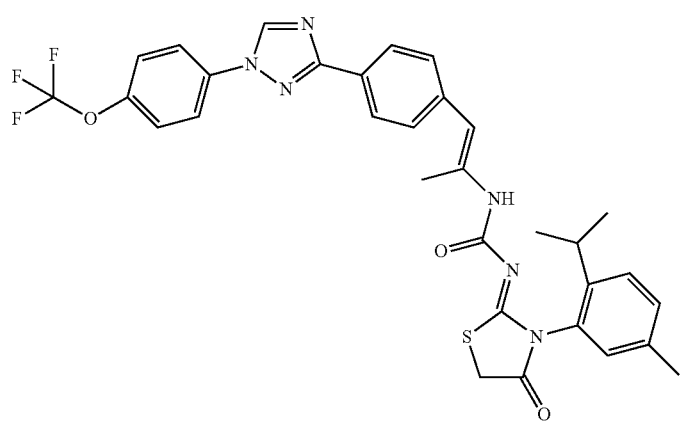 [SMILES: C/C(=C\c1ccc(-c2ncn(-c3ccc(OC(F)(F)F)cc3)n2)cc1)NC(=O)/N=C1\SCC(=O)N1c1cc(C)ccc1C(C)C]
P374

TABLE P-Two-continued
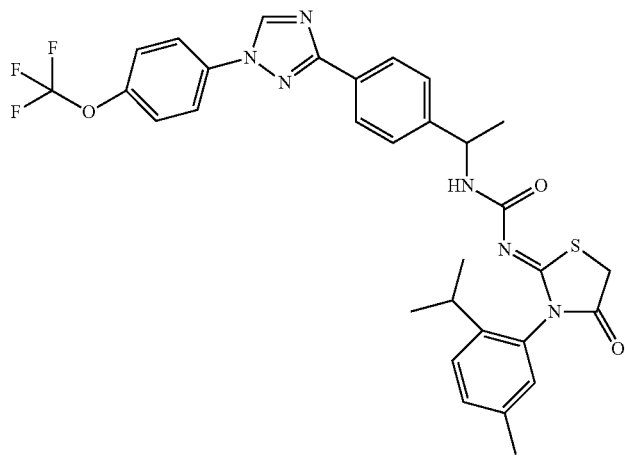 [SMILES: Cc1ccc(C(C)C)c(N2C(=O)CS/C2=N\C(=O)NC(C)c2ccc(-c3ncn(-c4ccc(OC(F)(F)F)cc4)n3)cc2)c1]
P375
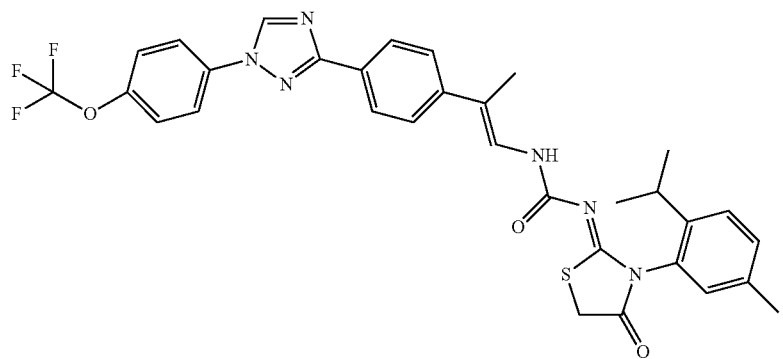
P376
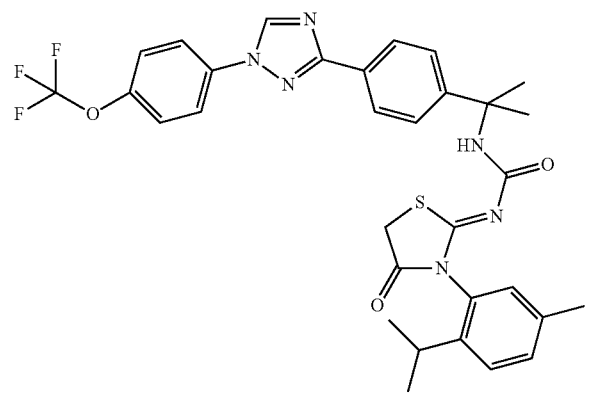 [SMILES: Cc1ccc(C(C)C)c(N2C(=O)CS/C2=N\C(=O)NC(C)(C)c2ccc(-c3ncn(-c4ccc(OC(F)(F)F)cc4)n3)cc2)c1]
P377
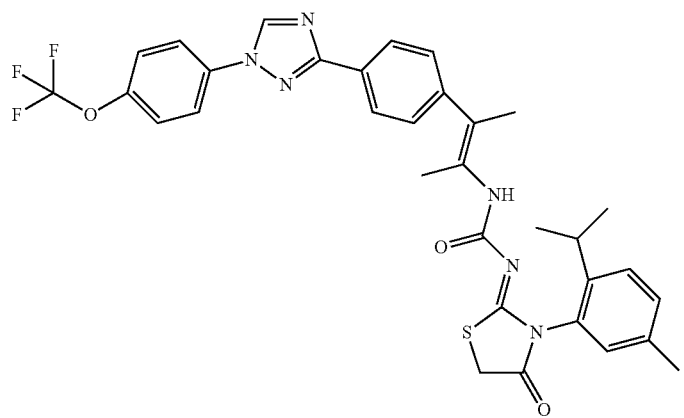 [SMILES: C/C(NC(=O)/N=C1\SCC(=O)N1c1cc(C)ccc1C(C)C)=C(/C)c1ccc(-c2ncn(-c3ccc(OC(F)(F)F)cc3)n2)cc1]
P378

TABLE P-Two-continued
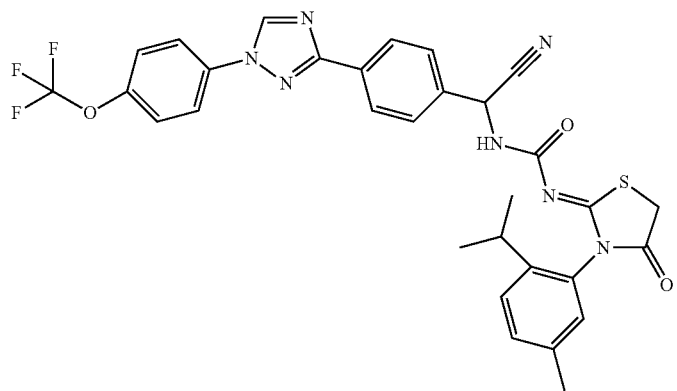 [SMILES: Cc1ccc(C(C)C)c(N2C(=O)CS/C2=N\C(=O)NC(C#N)c2ccc(-c3ncn(-c4ccc(OC(F)(F)F)cc4)n3)cc2)c1]
P379
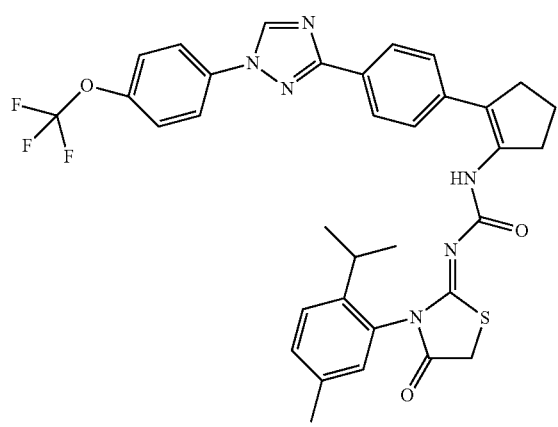 [SMILES: Cc1ccc(C(C)C)c(N2C(=O)CS/C2=N\C(=O)NC2=C(c3ccc(-c4ncn(-c5ccc(OC(F)(F)F)cc5)n4)cc3)CCC2)c1]
P380
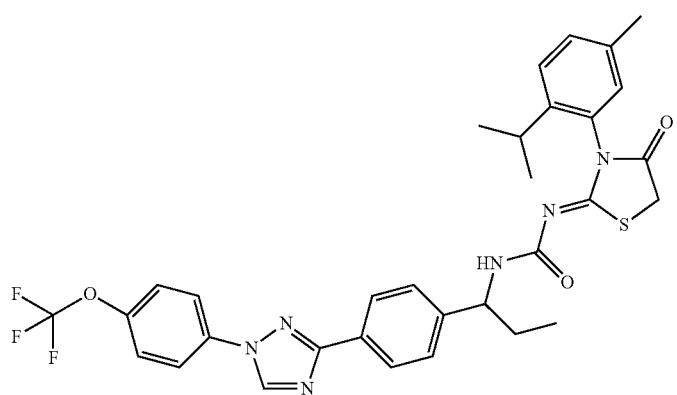 [SMILES: CCC(NC(=O)/N=C1\SCC(=O)N1c1cc(C)ccc1C(C)C)c1ccc(-c2ncn(-c3ccc(OC(F)(F)F)cc3)n2)cc1]
P381
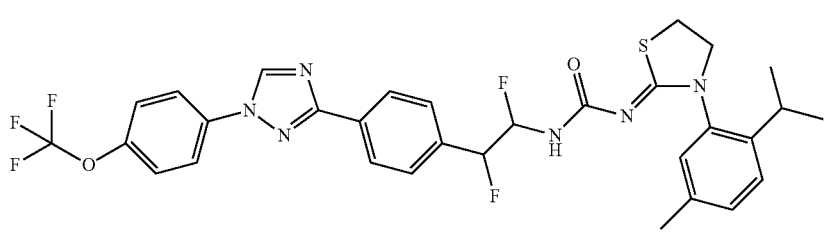 [SMILES: Cc1ccc(C(C)C)c(N2CCS/C2=N\C(=O)NC(F)C(F)c2ccc(-c3ncn(-c4ccc(OC(F)(F)F)cc4)n3)cc2)c1]
P382

TABLE P-Two-continued
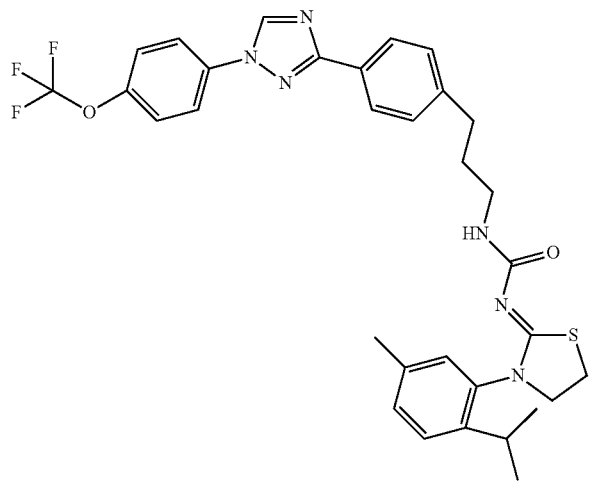 [SMILES: Cc1ccc(C(C)C)c(N2CCS/C2=N\C(=O)NCCCc2ccc(-c3ncn(-c4ccc(OC(F)(F)F)cc4)n3)cc2)c1]
P383
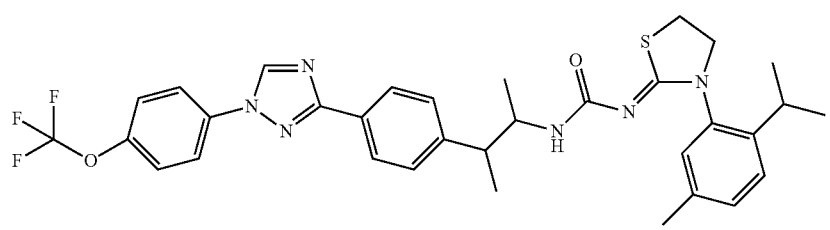 [SMILES: Cc1ccc(C(C)C)c(N2CCS/C2=N\C(=O)NC(C)C(C)c2ccc(-c3ncn(-c4ccc(OC(F)(F)F)cc4)n3)cc2)c1]
P384
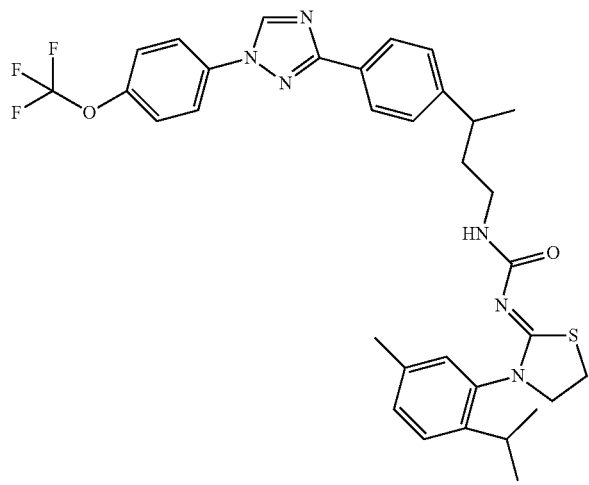 [SMILES: Cc1ccc(C(C)C)c(N2CCS/C2=N\C(=O)NCCC(C)c2ccc(-c3ncn(-c4ccc(OC(F)(F)F)cc4)n3)cc2)c1]
P385
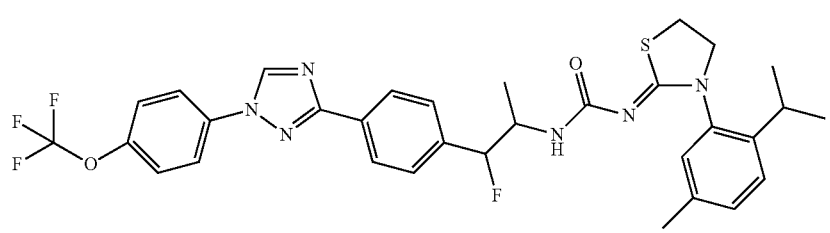 [SMILES: Cc1ccc(C(C)C)c(N2CCS/C2=N\C(=O)NC(C)C(F)c2ccc(-c3ncn(-c4ccc(OC(F)(F)F)cc4)n3)cc2)c1]
P386

TABLE P-Two-continued
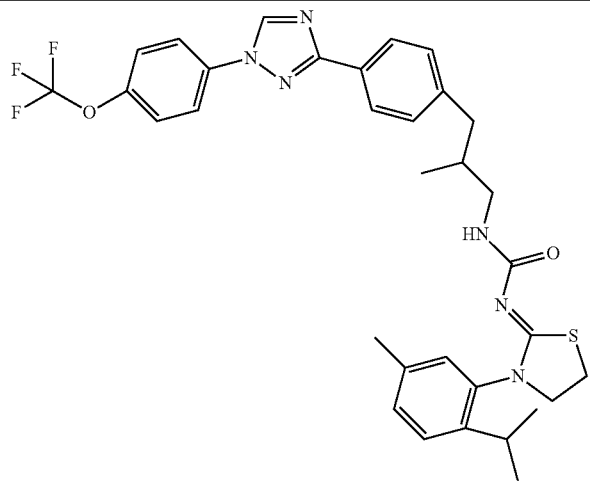
P387
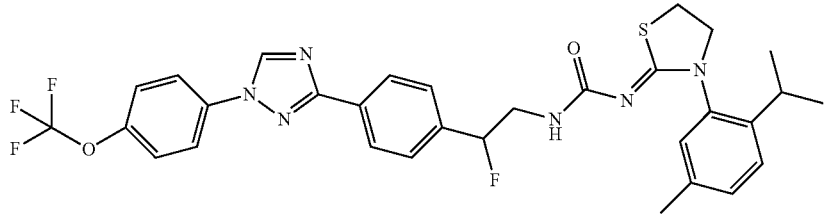
P388
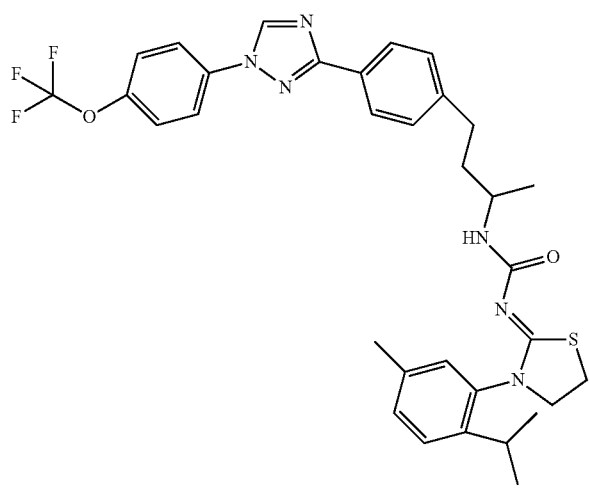 [SMILES: Cc1ccc(C(C)C)c(N2CCS/C2=N\C(=O)NC(C)CCc2ccc(-c3ncn(-c4ccc(OC(F)(F)F)cc4)n3)cc2)c1]
P389
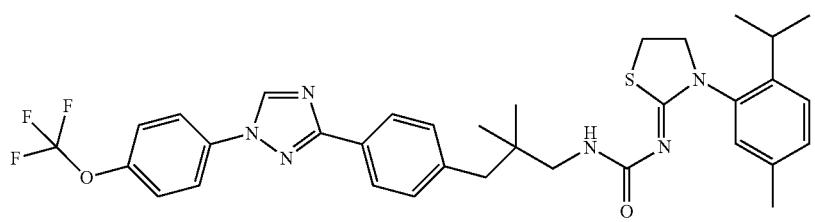 [SMILES: Cc1ccc(C(C)C)c(N2CCS/C2=N\C(=O)NCC(C)(C)Cc2ccc(-c3ncn(-c4ccc(OC(F)(F)F)cc4)n3)cc2)c1]
P390
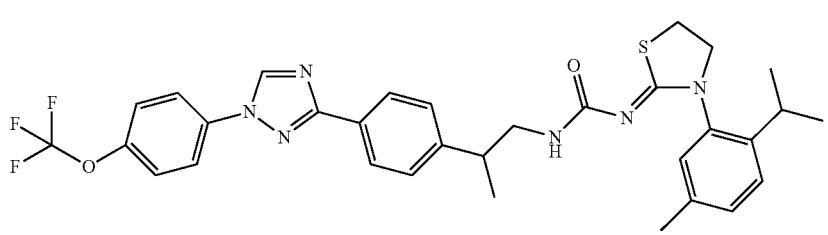 [SMILES: Cc1ccc(C(C)C)c(N2CCS/C2=N\C(=O)NCC(C)c2ccc(-c3ncn(-c4ccc(OC(F)(F)F)cc4)n3)cc2)c1]
P391

TABLE P-Two-continued
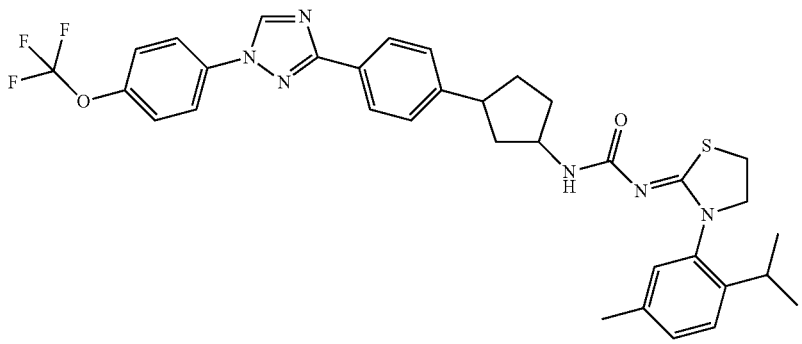 [SMILES: Cc1ccc(C(C)C)c(N2CCS/C2=N\C(=O)NC2CCC(c3ccc(-c4ncn(-c5ccc(OC(F)(F)F)cc5)n4)cc3)C2)c1]
P392
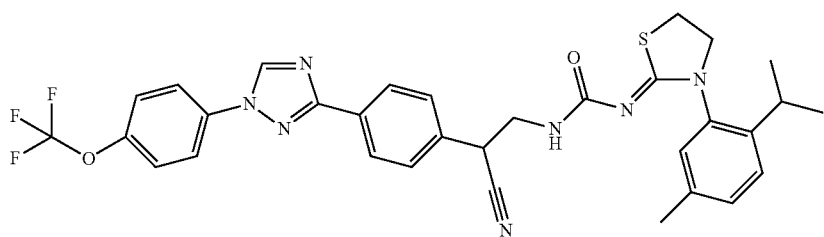 [SMILES: Cc1ccc(C(C)C)c(N2CCS/C2=N\C(=O)NCC(C#N)c2ccc(-c3ncn(-c4ccc(OC(F)(F)F)cc4)n3)cc2)c1]
P393
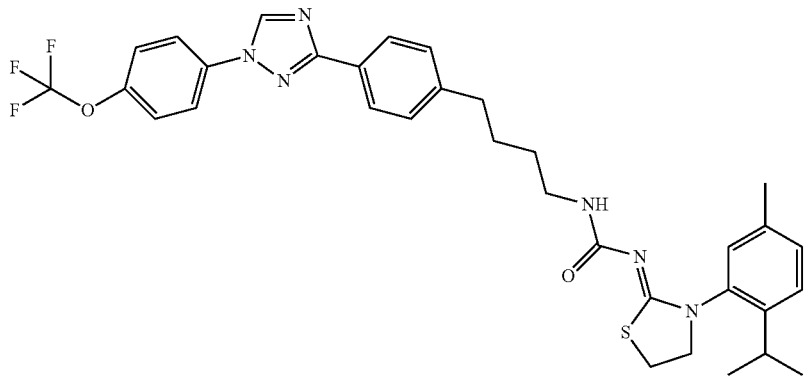 [SMILES: Cc1ccc(C(C)C)c(N2CCS/C2=N\C(=O)NCCCCc2ccc(-c3ncn(-c4ccc(OC(F)(F)F)cc4)n3)cc2)c1]
P394
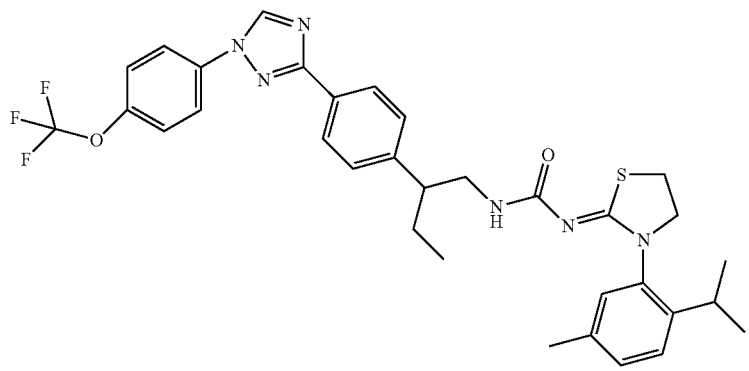 [SMILES: CCC(CNC(=O)/N=C1\SCCN1c1cc(C)ccc1C(C)C)c1ccc(-c2ncn(-c3ccc(OC(F)(F)F)cc3)n2)cc1]
P395

TABLE P-Two-continued
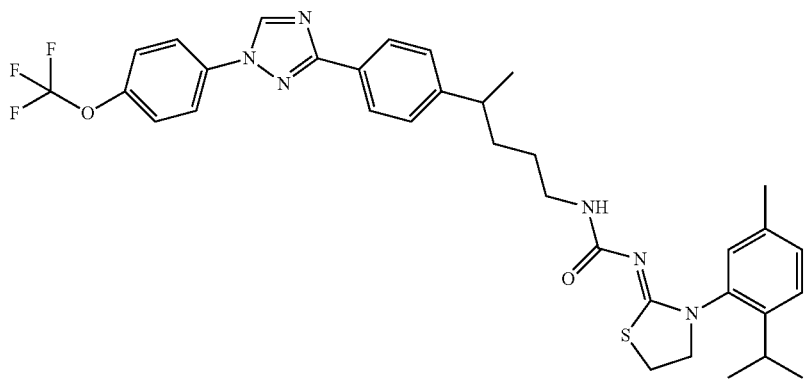 [SMILES: Cc1ccc(C(C)C)c(N2CCS/C2=N\C(=O)NCCCC(C)c2ccc(-c3ncn(-c4ccc(OC(F)(F)F)cc4)n3)cc2)c1]
P396
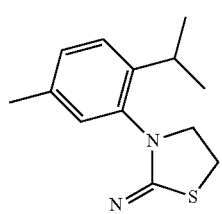
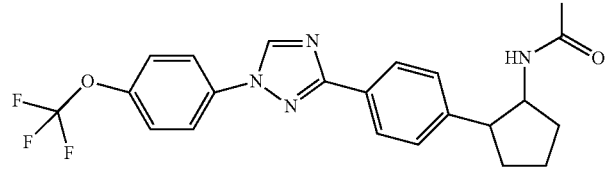
P397
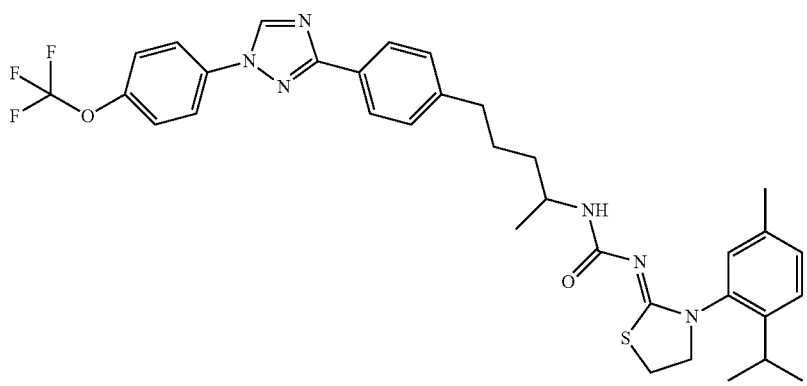 [SMILES: Cc1ccc(C(C)C)c(N2CCS/C2=N\C(=O)NC(C)CCCc2ccc(-c3ncn(-c4ccc(OC(F)(F)F)cc4)n3)cc2)c1]
P398
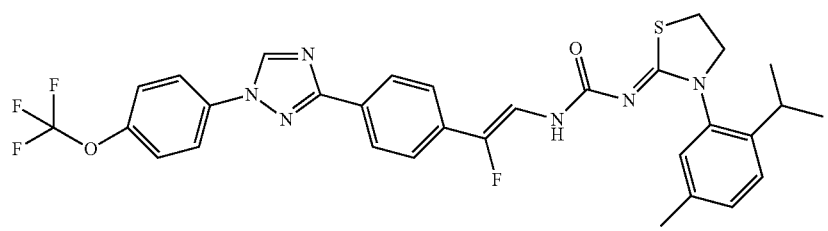 [SMILES: Cc1ccc(C(C)C)c(N2CCS/C2=N\C(=O)N/C=C(\F)c2ccc(-c3ncn(-c4ccc(OC(F)(F)F)cc4)n3)cc2)c1]
P399
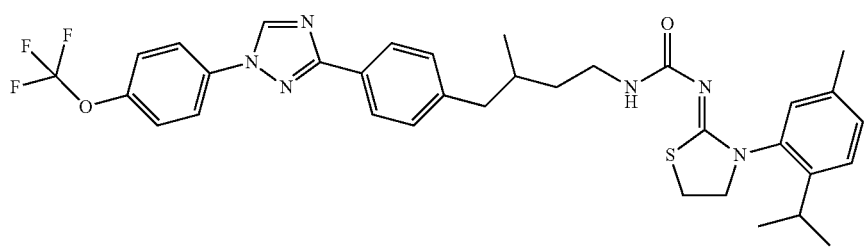 [SMILES: Cc1ccc(C(C)C)c(N2CCS/C2=N\C(=O)NCCC(C)Cc2ccc(-c3ncn(-c4ccc(OC(F)(F)F)cc4)n3)cc2)c1]
P400

TABLE P-Two-continued
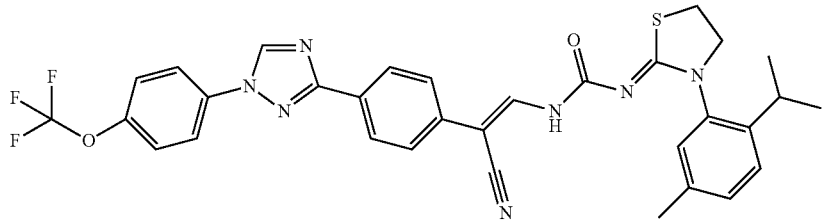 [SMILES: Cc1ccc(C(C)C)c(N2CCS/C2=N\C(=O)N/C=C(\C#N)c2ccc(-c3ncn(-c4ccc(OC(F)(F)F)cc4)n3)cc2)c1]
P401
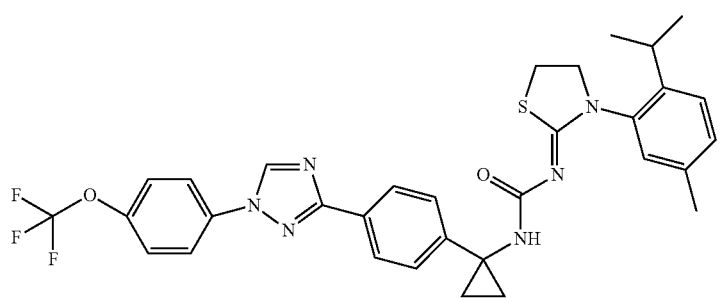 [SMILES: Cc1ccc(C(C)C)c(N2CCS/C2=N\C(=O)NC2(c3ccc(-c4ncn(-c5ccc(OC(F)(F)F)cc5)n4)cc3)CC2)c1]
P402
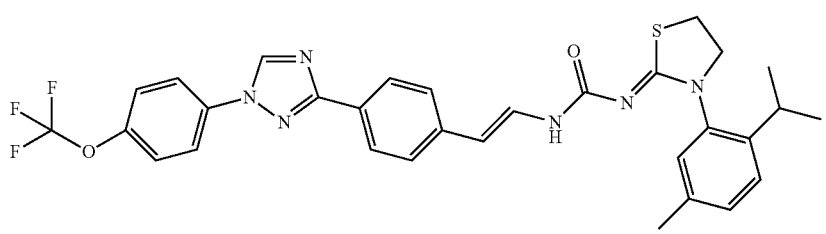 [SMILES: Cc1ccc(C(C)C)c(N2CCS/C2=N\C(=O)N/C=C/c2ccc(-c3ncn(-c4ccc(OC(F)(F)F)cc4)n3)cc2)c1]
P403
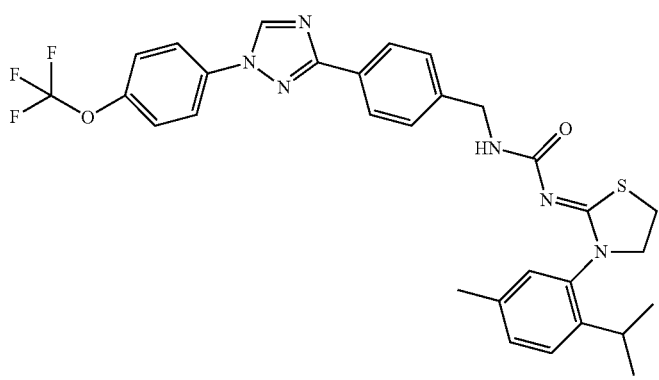 [SMILES: Cc1ccc(C(C)C)c(N2CCS/C2=N\C(=O)NCc2ccc(-c3ncn(-c4ccc(OC(F)(F)F)cc4)n3)cc2)c1]
P404
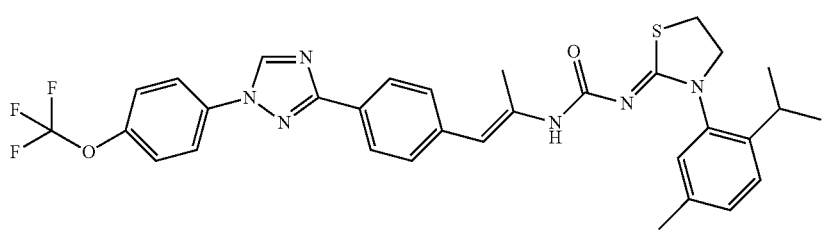 [SMILES: C/C(=C\c1ccc(-c2ncn(-c3ccc(OC(F)(F)F)cc3)n2)cc1)NC(=O)/N=C1\SCCN1c1cc(C)ccc1C(C)C]
P405

TABLE P-Two-continued
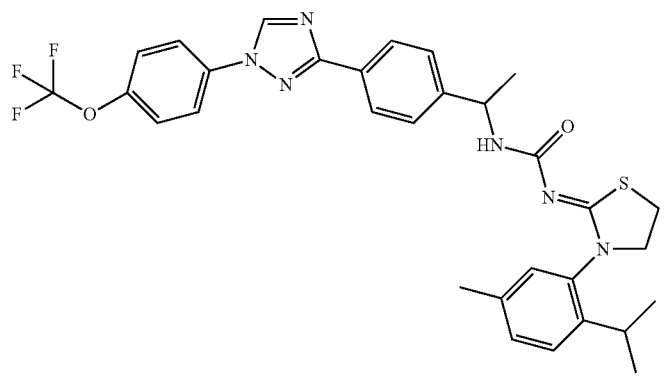 [SMILES: Cc1ccc(C(C)C)c(N2CCS/C2=N\C(=O)NC(C)c2ccc(-c3ncn(-c4ccc(OC(F)(F)F)cc4)n3)cc2)c1]
P406
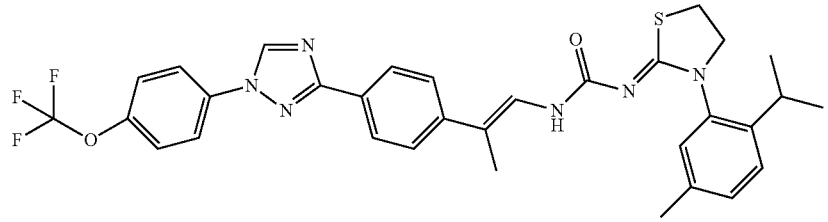 [SMILES: C/C(=C\NC(=O)/N=C1\SCCN1c1cc(C)ccc1C(C)C)c1ccc(-c2ncn(-c3ccc(OC(F)(F)F)cc3)n2)cc1]
P407
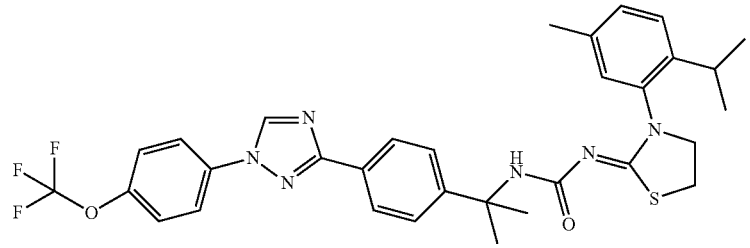 [SMILES: Cc1ccc(C(C)C)c(N2CCS/C2=N\C(=O)NC(C)(C)c2ccc(-c3ncn(-c4ccc(OC(F)(F)F)cc4)n3)cc2)c1]
P408
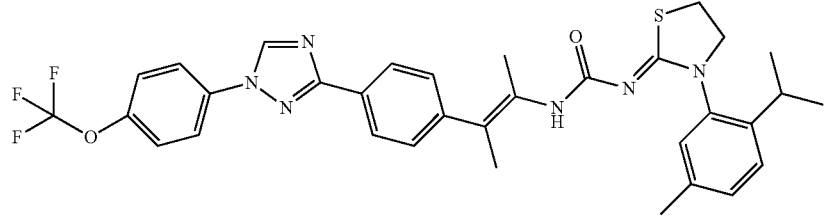 [SMILES: C/C(NC(=O)/N=C1\SCCN1c1cc(C)ccc1C(C)C)=C(/C)c1ccc(-c2ncn(-c3ccc(OC(F)(F)F)cc3)n2)cc1]
P409
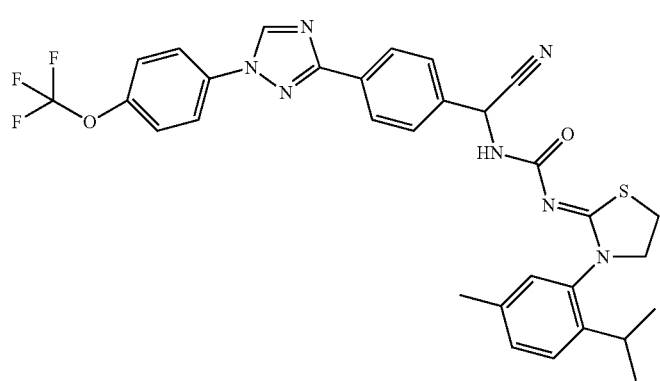 [SMILES: Cc1ccc(C(C)C)c(N2CCS/C2=N\C(=O)NC(C#N)c2ccc(-c3ncn(-c4ccc(OC(F)(F)F)cc4)n3)cc2)c1]
P410

TABLE P-Two-continued
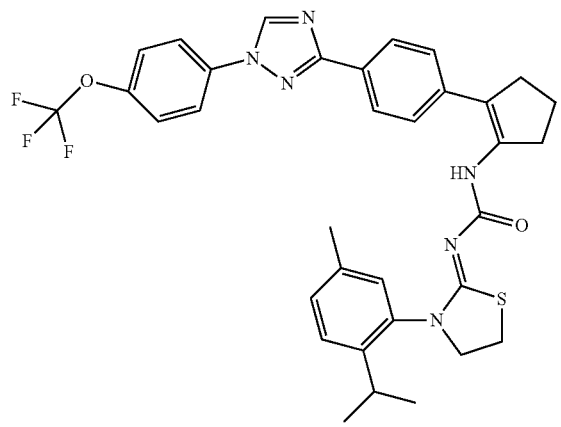 [SMILES: Cc1ccc(C(C)C)c(N2CCS/C2=N\C(=O)NC2=C(c3ccc(-c4ncn(-c5ccc(OC(F)(F)F)cc5)n4)cc3)CCC2)c1]
P411
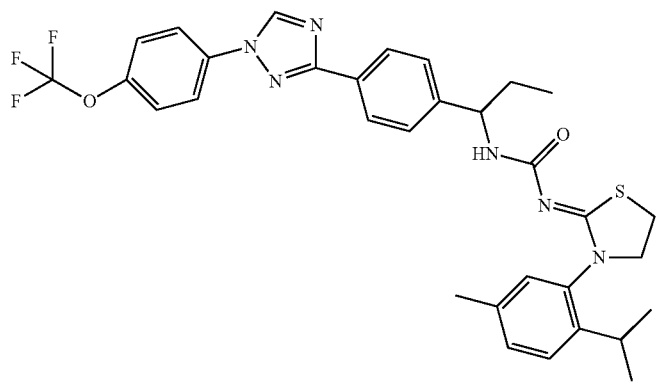 [SMILES: CCC(NC(=O)/N=C1\SCCN1c1cc(C)ccc1C(C)C)c1ccc(-c2ncn(-c3ccc(OC(F)(F)F)cc3)n2)cc1]
P412
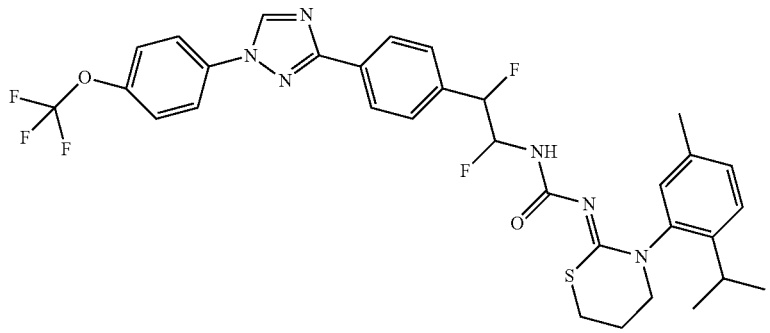 [SMILES: Cc1ccc(C(C)C)c(N2CCCS/C2=N\C(=O)NC(F)C(F)c2ccc(-c3ncn(-c4ccc(OC(F)(F)F)cc4)n3)cc2)c1]
P413
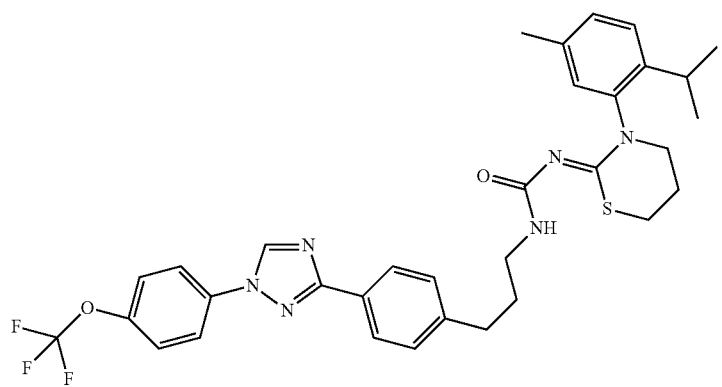 [SMILES: Cc1ccc(C(C)C)c(N2CCCS/C2=N\C(=O)NCCCc2ccc(-c3ncn(-c4ccc(OC(F)(F)F)cc4)n3)cc2)c1]
P414

TABLE P-Two-continued
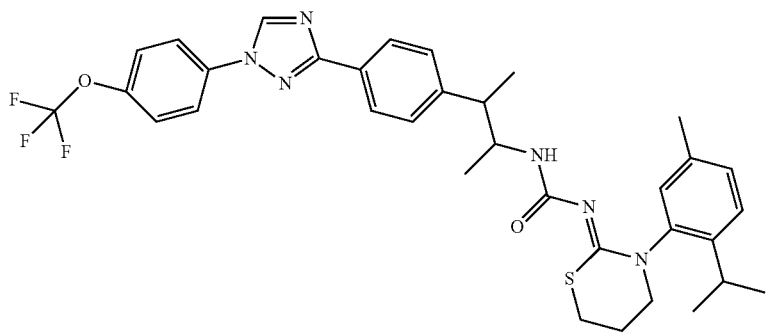 [SMILES: Cc1ccc(C(C)C)c(N2CCCS/C2=N\C(=O)NC(C)C(C)c2ccc(-c3ncn(-c4ccc(OC(F)(F)F)cc4)n3)cc2)c1]
P415
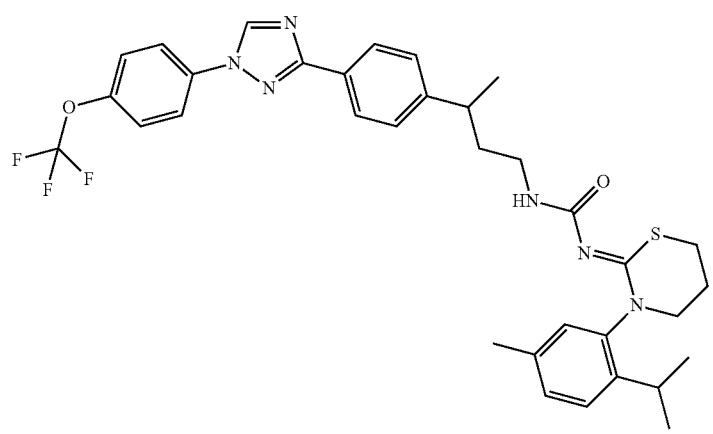 [SMILES: Cc1ccc(C(C)C)c(N2CCCS/C2=N\C(=O)NCCC(C)c2ccc(-c3ncn(-c4ccc(OC(F)(F)F)cc4)n3)cc2)c1]
P416
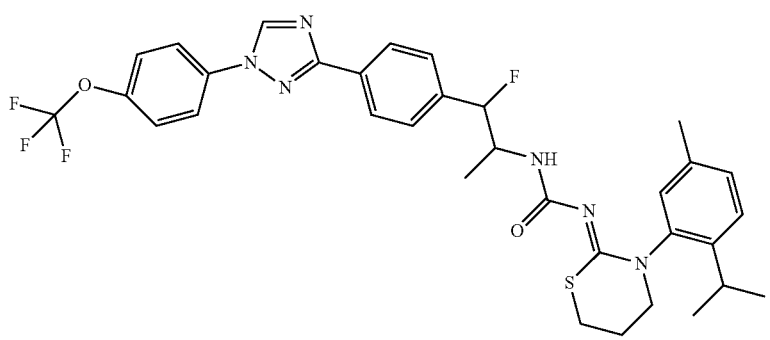
P417
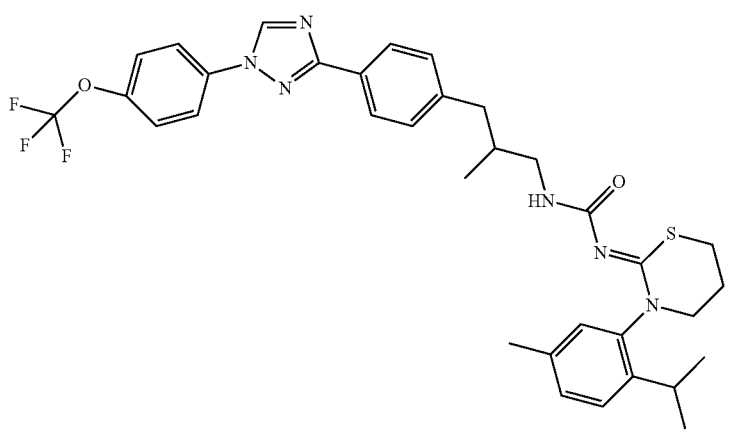 [SMILES: Cc1ccc(C(C)C)c(N2CCCS/C2=N\C(=O)NCC(C)Cc2ccc(-c3ncn(-c4ccc(OC(F)(F)F)cc4)n3)cc2)c1]
P418

TABLE P-Two-continued
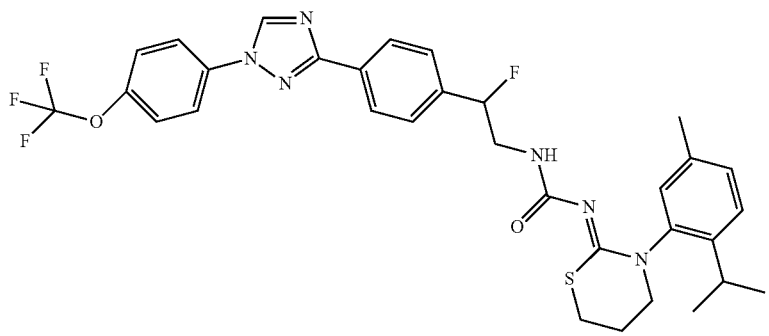 [SMILES: Cc1ccc(C(C)C)c(N2CCCS/C2=N\C(=O)NCC(F)c2ccc(-c3ncn(-c4ccc(OC(F)(F)F)cc4)n3)cc2)c1]
P419
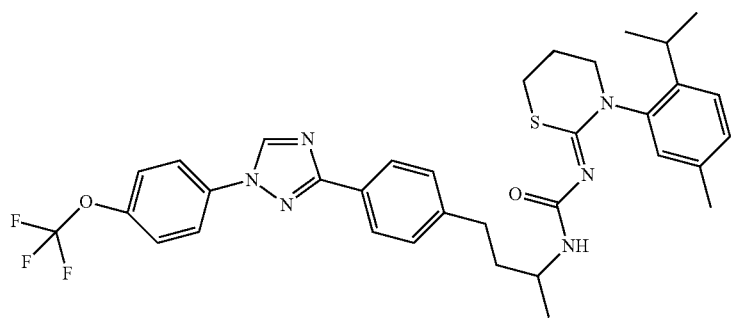 [SMILES: Cc1ccc(C(C)C)c(N2CCCS/C2=N\C(=O)NC(C)CCc2ccc(-c3ncn(-c4ccc(OC(F)(F)F)cc4)n3)cc2)c1]
P420
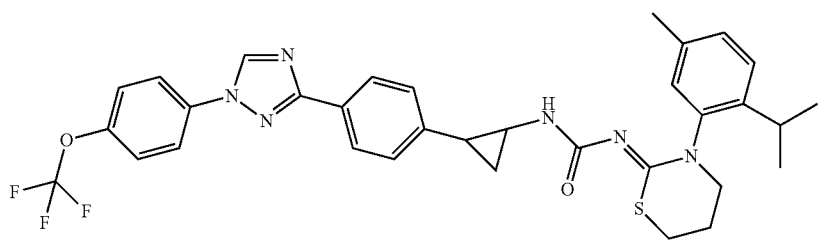 [SMILES: Cc1ccc(C(C)C)c(N2CCCS/C2=N\C(=O)NC2CC2c2ccc(-c3ncn(-c4ccc(OC(F)(F)F)cc4)n3)cc2)c1]
P421
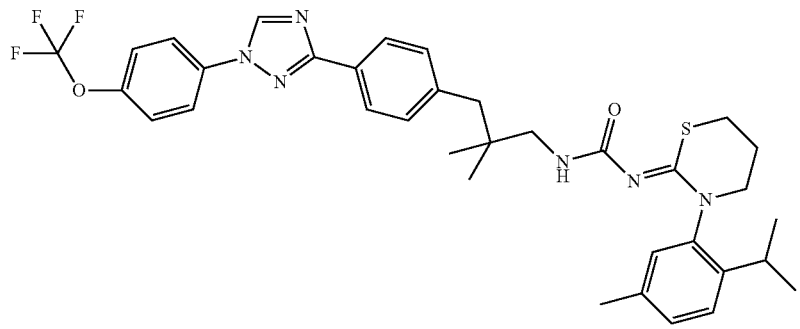 [SMILES: Cc1ccc(C(C)C)c(N2CCCS/C2=N\C(=O)NCC(C)(C)Cc2ccc(-c3ncn(-c4ccc(OC(F)(F)F)cc4)n3)cc2)c1]
P422
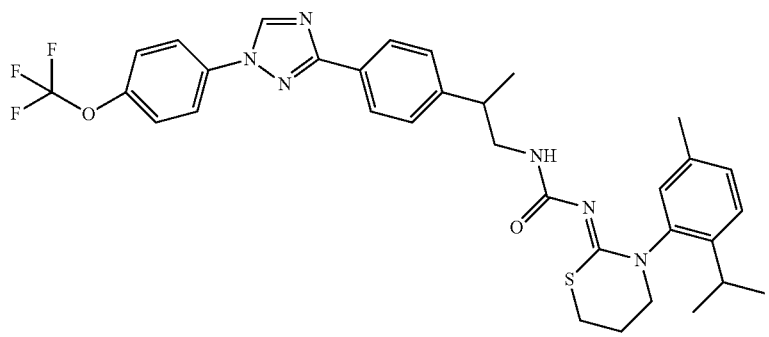 [SMILES: Cc1ccc(C(C)C)c(N2CCCS/C2=N\C(=O)NCC(C)c2ccc(-c3ncn(-c4ccc(OC(F)(F)F)cc4)n3)cc2)c1]
P423

TABLE P-Two-continued
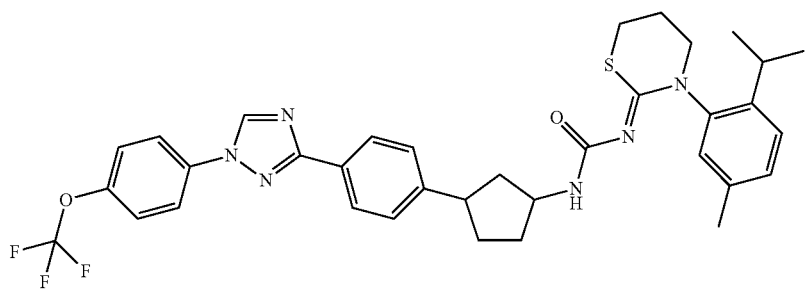 [SMILES: Cc1ccc(C(C)C)c(N2CCCS/C2=N\C(=O)NC2CCC(c3ccc(-c4ncn(-c5ccc(OC(F)(F)F)cc5)n4)cc3)C2)c1]
P424
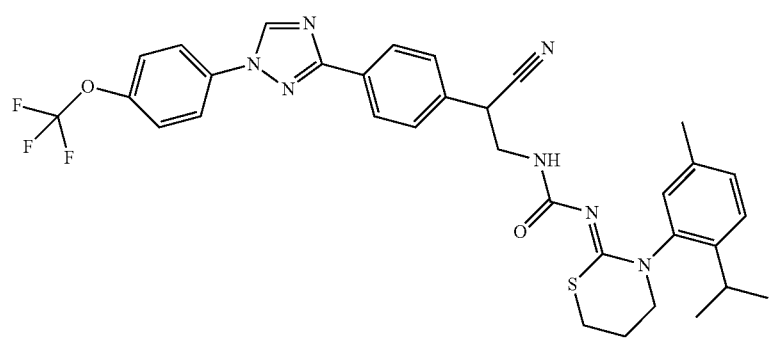
P425
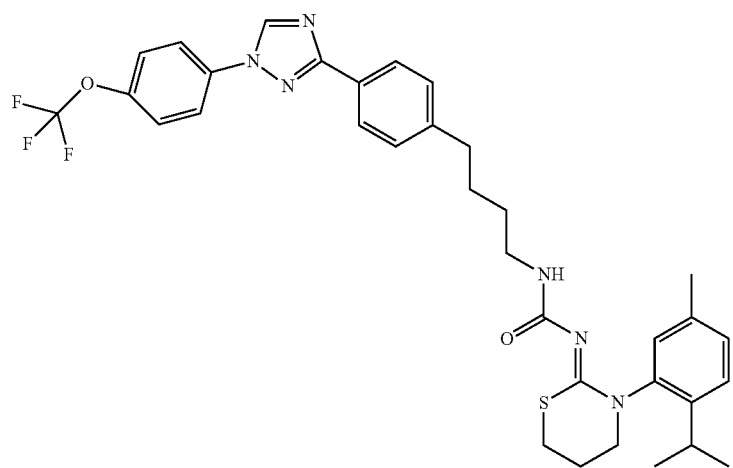 [SMILES: Cc1ccc(C(C)C)c(N2CCCS/C2=N\C(=O)NCCCCc2ccc(-c3ncn(-c4ccc(OC(F)(F)F)cc4)n3)cc2)c1]
P426
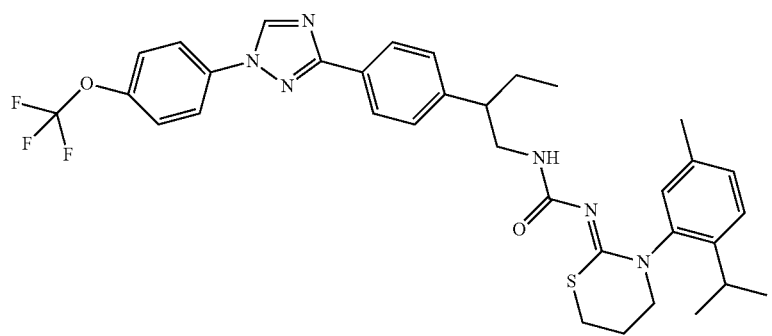 [SMILES: CCC(CNC(=O)/N=C1\SCCCN1c1cc(C)ccc1C(C)C)c1ccc(-c2ncn(-c3ccc(OC(F)(F)F)cc3)n2)cc1]
P427

TABLE P-Two-continued
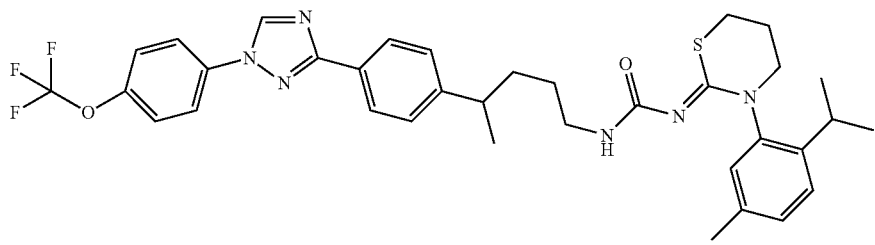 [SMILES: Cc1ccc(C(C)C)c(N2CCCS/C2=N\C(=O)NCCCC(C)c2ccc(-c3ncn(-c4ccc(OC(F)(F)F)cc4)n3)cc2)c1]
P428
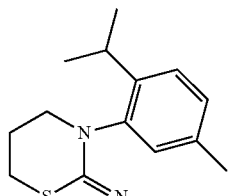
P429
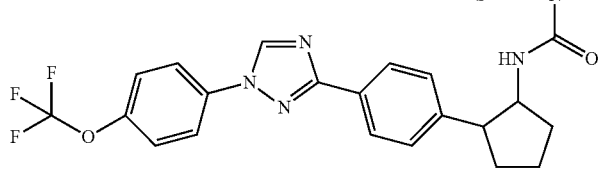
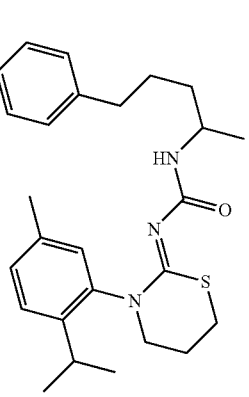
P430
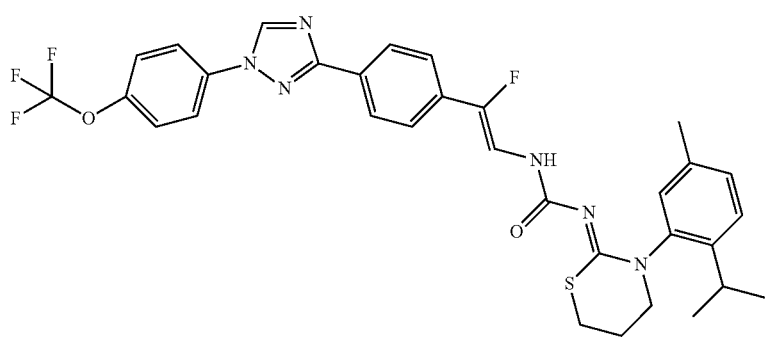
P431
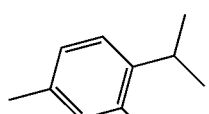
P432
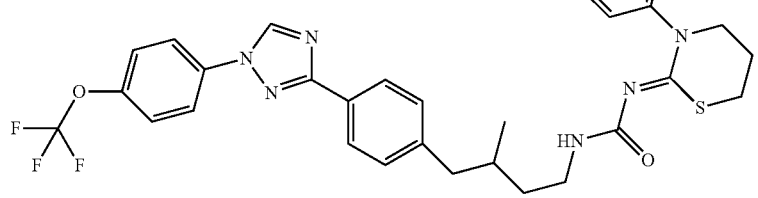

TABLE P-Two-continued
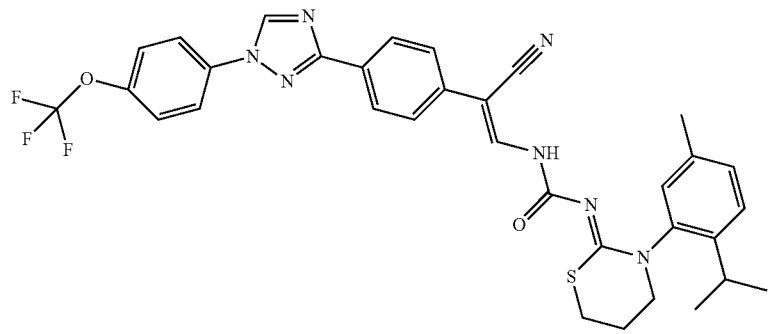 [SMILES: Cc1ccc(C(C)C)c(N2CCCS/C2=N\C(=O)N/C=C(\C#N)c2ccc(-c3ncn(-c4ccc(OC(F)(F)F)cc4)n3)cc2)c1]
P433
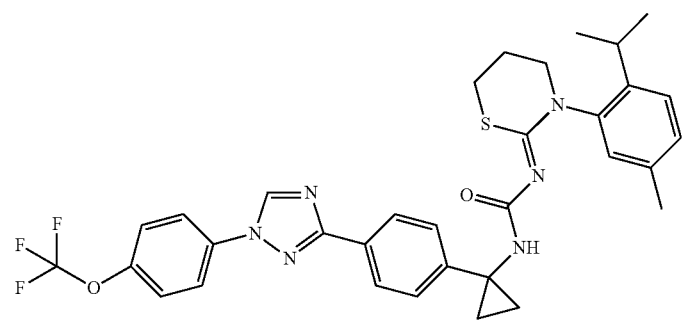 [SMILES: Cc1ccc(C(C)C)c(N2CCCS/C2=N\C(=O)NC2(c3ccc(-c4ncn(-c5ccc(OC(F)(F)F)cc5)n4)cc3)CC2)c1]
P434
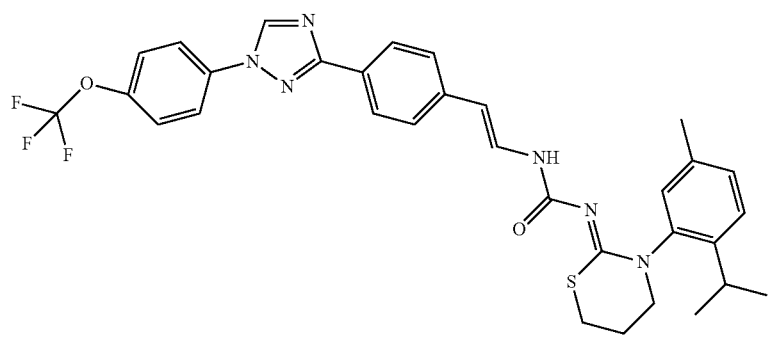 [SMILES: Cc1ccc(C(C)C)c(N2CCCS/C2=N\C(=O)N/C=C/c2ccc(-c3ncn(-c4ccc(OC(F)(F)F)cc4)n3)cc2)c1]
P435
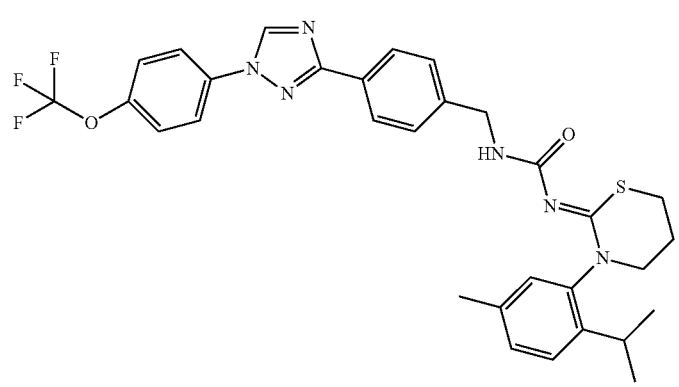 [SMILES: Cc1ccc(C(C)C)c(N2CCCS/C2=N\C(=O)NCc2ccc(-c3ncn(-c4ccc(OC(F)(F)F)cc4)n3)cc2)c1]
P436

TABLE P-Two-continued
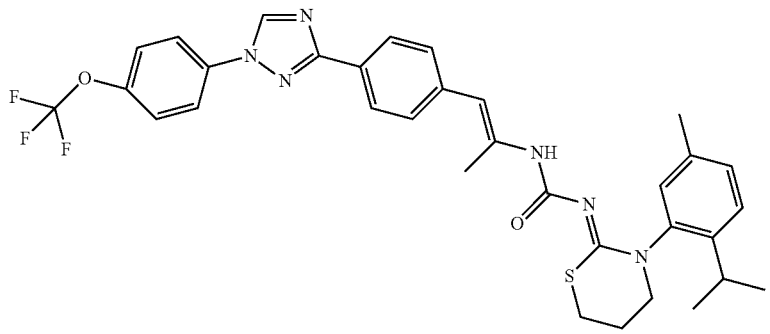 [SMILES: C/C(=C\c1ccc(-c2ncn(-c3ccc(OC(F)(F)F)cc3)n2)cc1)NC(=O)/N=C1\SCCCN1c1cc(C)ccc1C(C)C]
P437
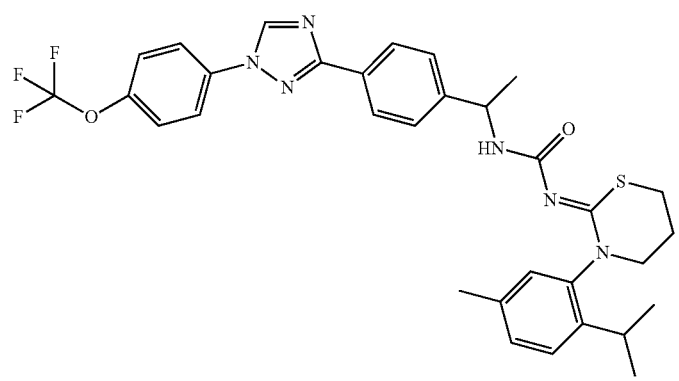
P438
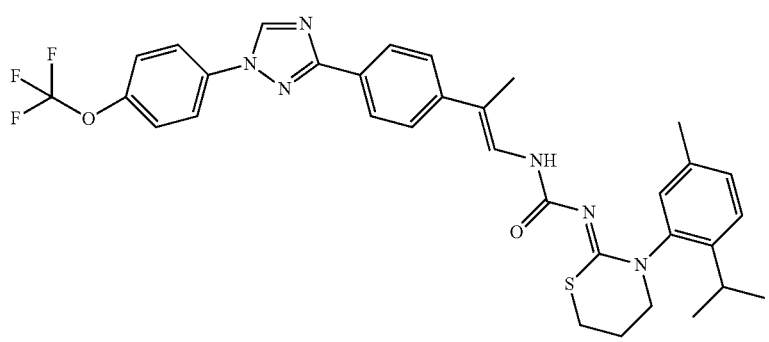 [SMILES: C/C(=C\NC(=O)/N=C1\SCCCN1c1cc(C)ccc1C(C)C)c1ccc(-c2ncn(-c3ccc(OC(F)(F)F)cc3)n2)cc1]
P439
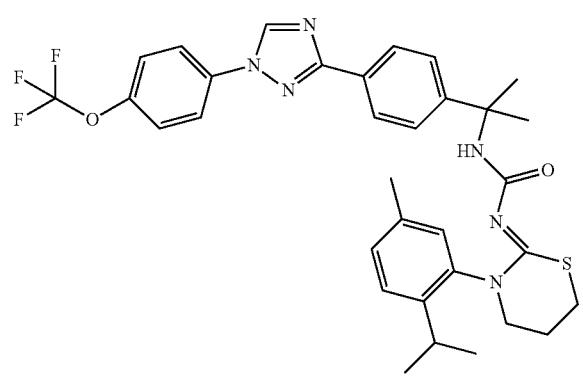 [SMILES: Cc1ccc(C(C)C)c(N2CCCS/C2=N\C(=O)NC(C)(C)c2ccc(-c3ncn(-c4ccc(OC(F)(F)F)cc4)n3)cc2)c1]
P440

TABLE P-Two-continued
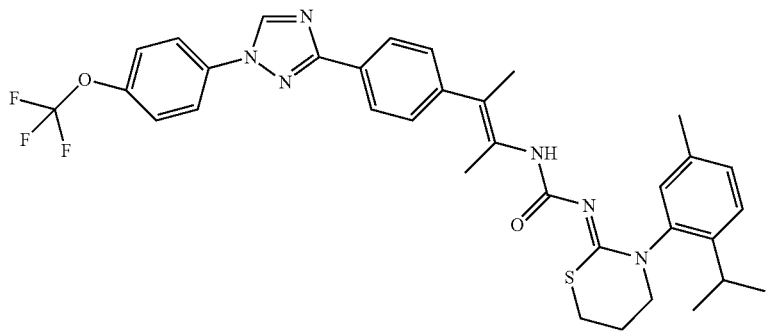 [SMILES: C/C(NC(=O)/N=C1\SCCCN1c1cc(C)ccc1C(C)C)=C(/C)c1ccc(-c2ncn(-c3ccc(OC(F)(F)F)cc3)n2)cc1]
P441
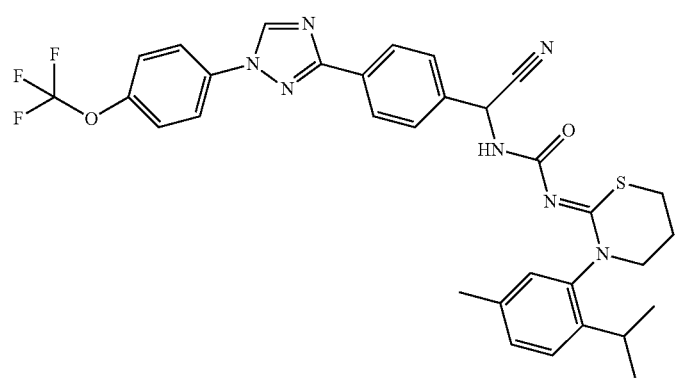 [SMILES: Cc1ccc(C(C)C)c(N2CCCS/C2=N\C(=O)NC(C#N)c2ccc(-c3ncn(-c4ccc(OC(F)(F)F)cc4)n3)cc2)c1]
P442
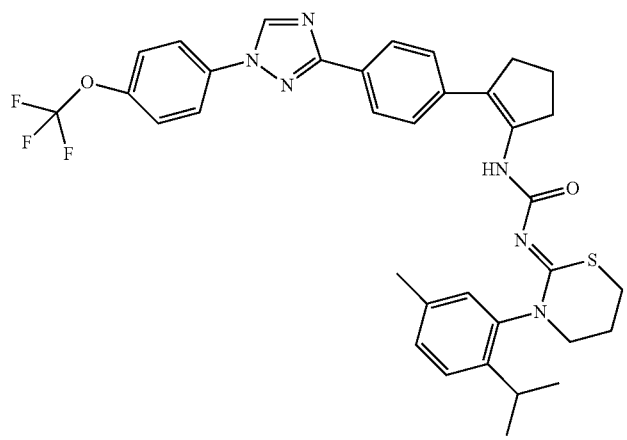 [SMILES: Cc1ccc(C(C)C)c(N2CCCS/C2=N\C(=O)NC2=C(c3ccc(-c4ncn(-c5ccc(OC(F)(F)F)cc5)n4)cc3)CCC2)c1]
P443
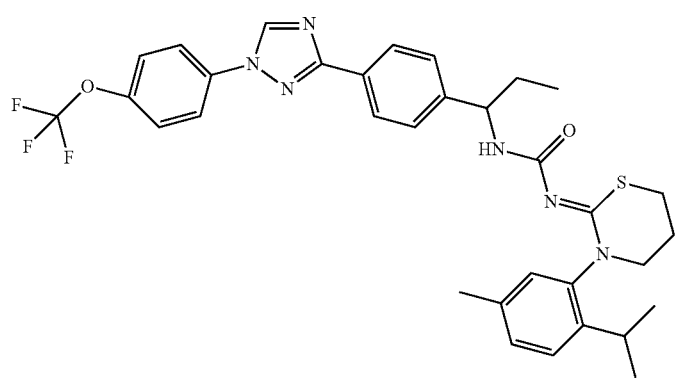 [SMILES: CCC(NC(=O)/N=C1\SCCCN1c1cc(C)ccc1C(C)C)c1ccc(-c2ncn(-c3ccc(OC(F)(F)F)cc3)n2)cc1]
P444

TABLE P-Two-continued
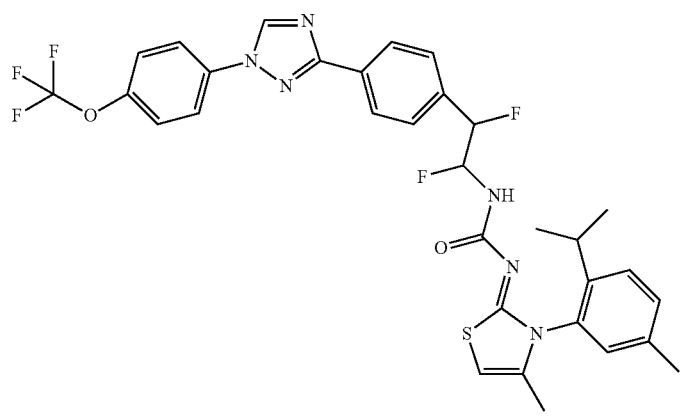 [SMILES: Cc1ccc(C(C)C)c(-n2c(C)cs/c2=N\C(=O)NC(F)C(F)c2ccc(-c3ncn(-c4ccc(OC(F)(F)F)cc4)n3)cc2)c1]
P445
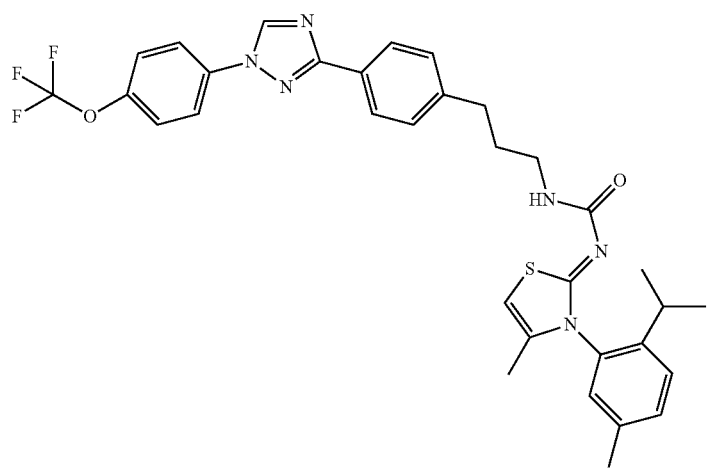 [SMILES: Cc1ccc(C(C)C)c(-n2c(C)cs/c2=N\C(=O)NCCCc2ccc(-c3ncn(-c4ccc(OC(F)(F)F)cc4)n3)cc2)c1]
P446
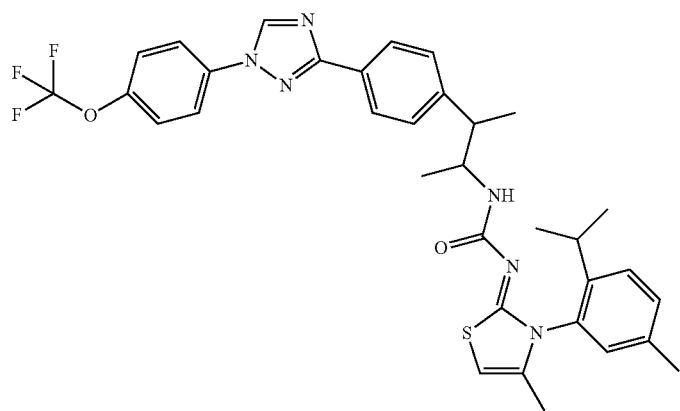 [SMILES: Cc1ccc(C(C)C)c(-n2c(C)cs/c2=N\C(=O)NC(C)C(C)c2ccc(-c3ncn(-c4ccc(OC(F)(F)F)cc4)n3)cc2)c1]
P447

TABLE P-Two-continued
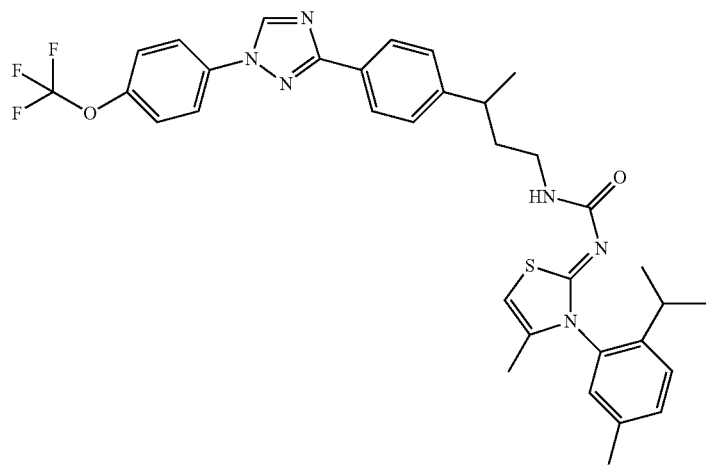 [SMILES: Cc1ccc(C(C)C)c(-n2c(C)cs/c2=N\C(=O)NCCC(C)c2ccc(-c3ncn(-c4ccc(OC(F)(F)F)cc4)n3)cc2)c1]
P448
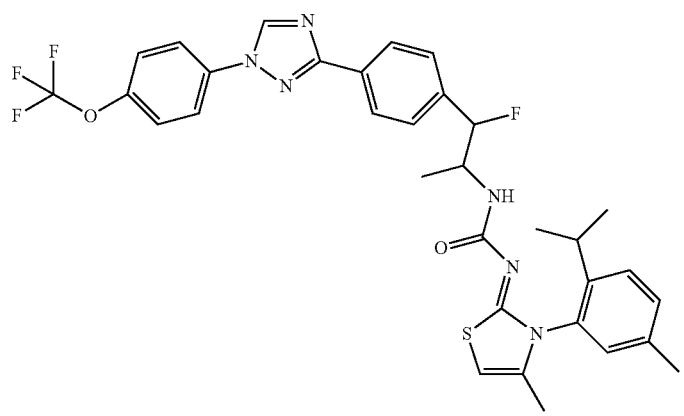 [SMILES: Cc1ccc(C(C)C)c(-n2c(C)cs/c2=N\C(=O)NC(C)C(F)c2ccc(-c3ncn(-c4ccc(OC(F)(F)F)cc4)n3)cc2)c1]
P449
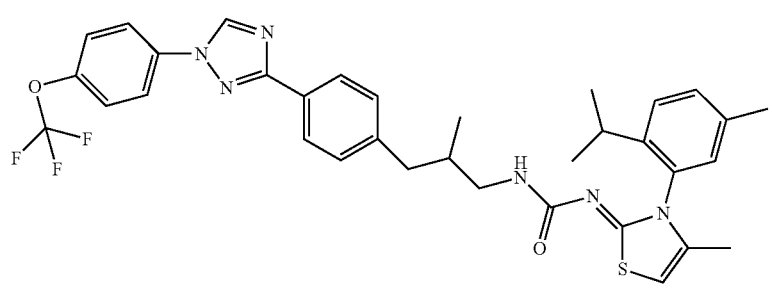 [SMILES: Cc1ccc(C(C)C)c(-n2c(C)cs/c2=N\C(=O)NCC(C)Cc2ccc(-c3ncn(-c4ccc(OC(F)(F)F)cc4)n3)cc2)c1]
P450
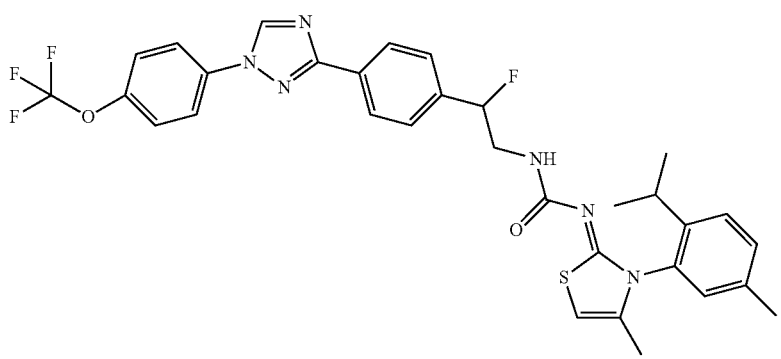
P451

TABLE P-Two-continued
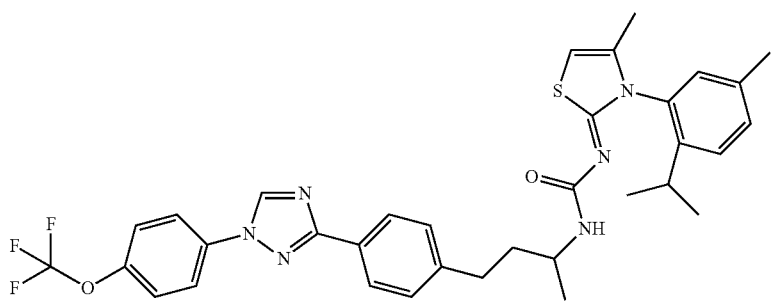 [SMILES: Cc1ccc(C(C)C)c(-n2c(C)cs/c2=N\C(=O)NC(C)CCc2ccc(-c3ncn(-c4ccc(OC(F)(F)F)cc4)n3)cc2)c1]
P452
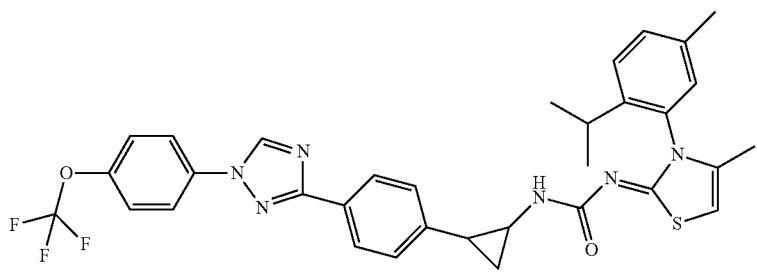 [SMILES: Cc1ccc(C(C)C)c(-n2c(C)cs/c2=N\C(=O)NC2CC2c2ccc(-c3ncn(-c4ccc(OC(F)(F)F)cc4)n3)cc2)c1]
P453
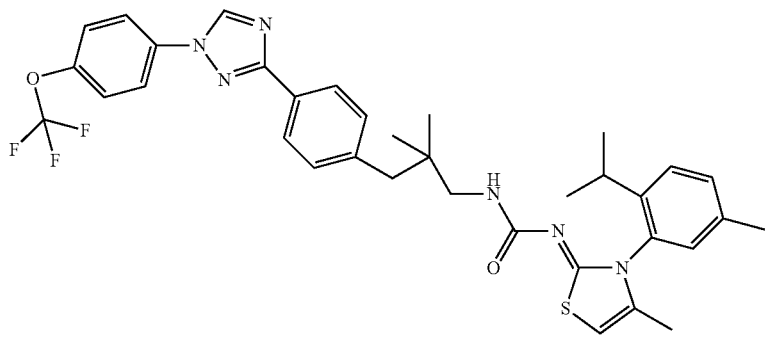 [SMILES: Cc1ccc(C(C)C)c(-n2c(C)cs/c2=N\C(=O)NCC(C)(C)Cc2ccc(-c3ncn(-c4ccc(OC(F)(F)F)cc4)n3)cc2)c1]
P454
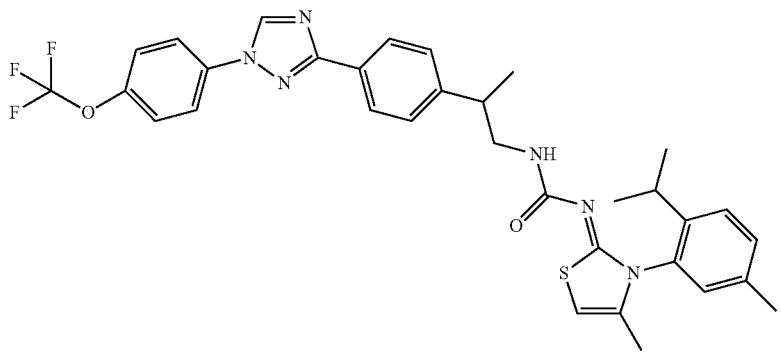 [SMILES: Cc1ccc(C(C)C)c(-n2c(C)cs/c2=N\C(=O)NCC(C)c2ccc(-c3ncn(-c4ccc(OC(F)(F)F)cc4)n3)cc2)c1]
P455
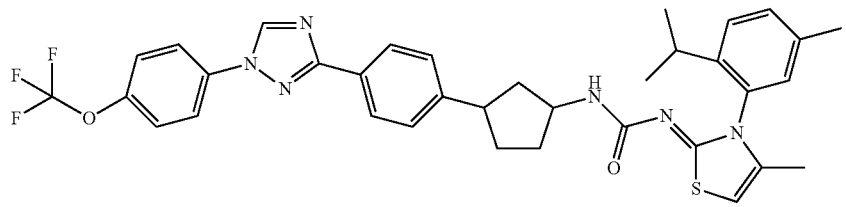 [SMILES: Cc1ccc(C(C)C)c(-n2c(C)cs/c2=N\C(=O)NC2CCC(c3ccc(-c4ncn(-c5ccc(OC(F)(F)F)cc5)n4)cc3)C2)c1]
P456

TABLE P-Two-continued
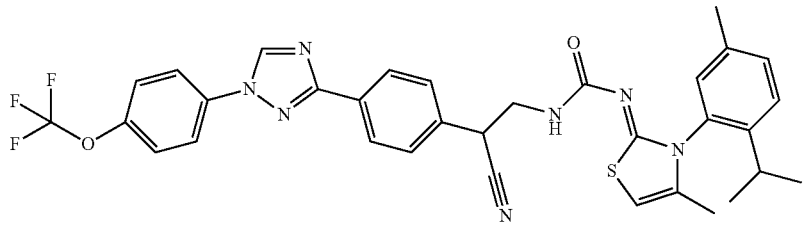 [SMILES: Cc1ccc(C(C)C)c(-n2c(C)cs/c2=N\C(=O)NCC(C#N)c2ccc(-c3ncn(-c4ccc(OC(F)(F)F)cc4)n3)cc2)c1]
P457
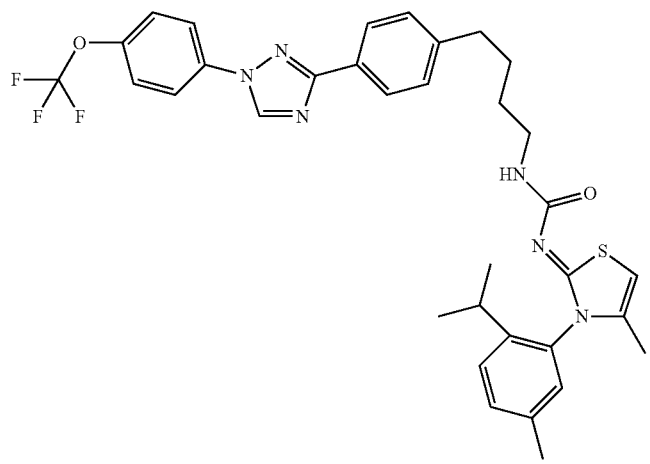 [SMILES: Cc1ccc(C(C)C)c(-n2c(C)cs/c2=N\C(=O)NCCCCc2ccc(-c3ncn(-c4ccc(OC(F)(F)F)cc4)n3)cc2)c1]
P458
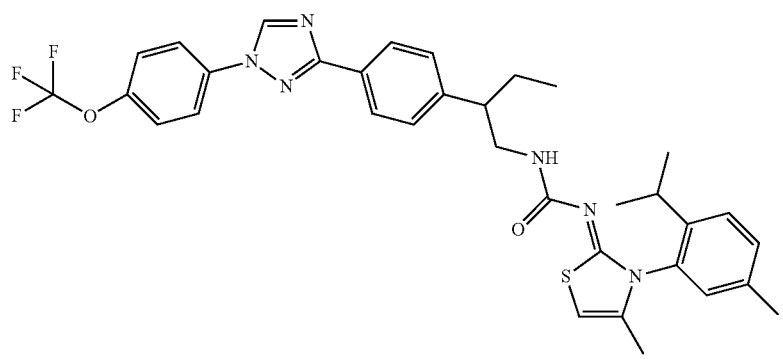 [SMILES: CCC(CNC(=O)/N=c1\scc(C)n1-c1cc(C)ccc1C(C)C)c1ccc(-c2ncn(-c3ccc(OC(F)(F)F)cc3)n2)cc1]
P459
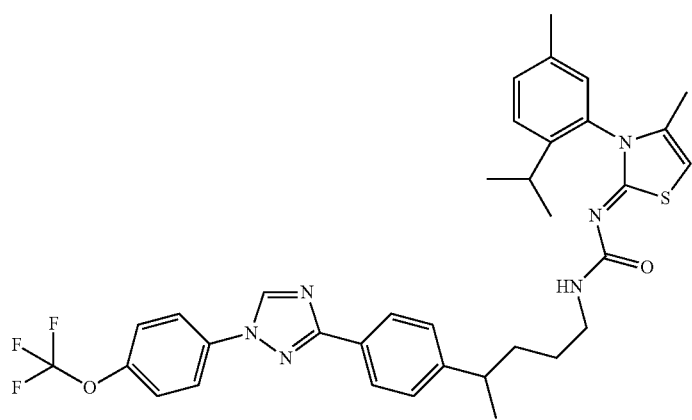 [SMILES: Cc1ccc(C(C)C)c(-n2c(C)cs/c2=N\C(=O)NCCCC(C)c2ccc(-c3ncn(-c4ccc(OC(F)(F)F)cc4)n3)cc2)c1]
P460

TABLE P-Two-continued
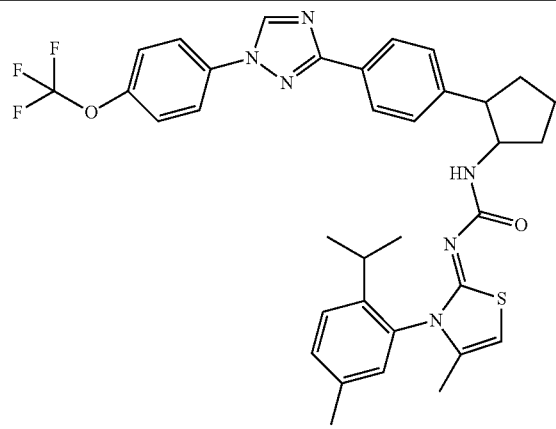
P461
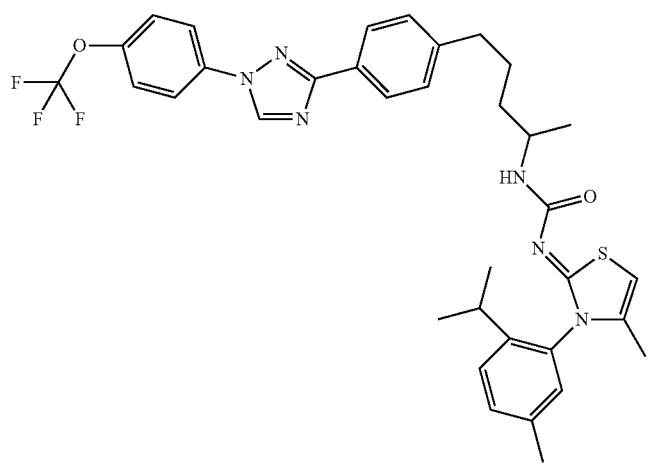 [SMILES: Cc1ccc(C(C)C)c(-n2c(C)cs/c2=N\C(=O)NC(C)CCCc2ccc(-c3ncn(-c4ccc(OC(F)(F)F)cc4)n3)cc2)c1]
P462
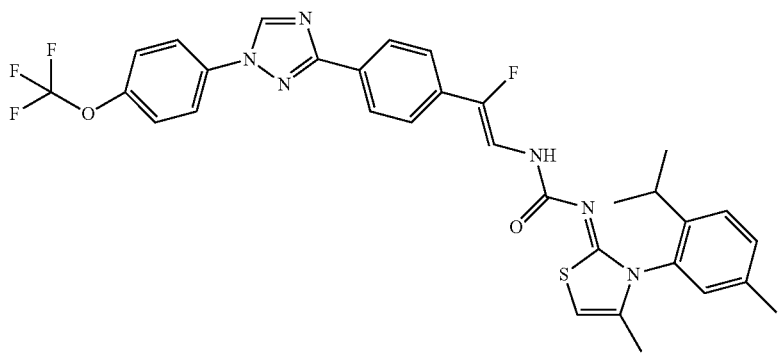
P463
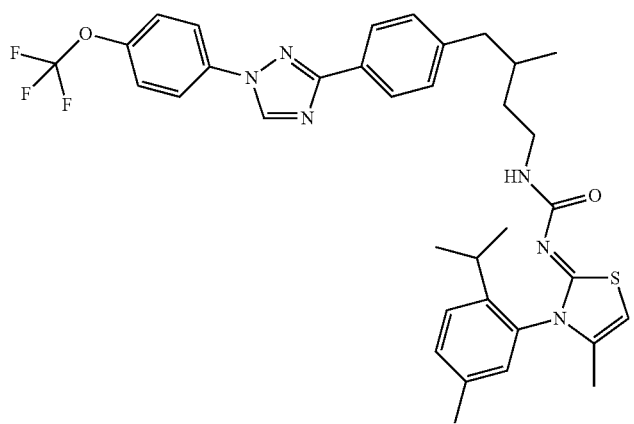 [SMILES: Cc1ccc(C(C)C)c(-n2c(C)cs/c2=N\C(=O)NCCC(C)Cc2ccc(-c3ncn(-c4ccc(OC(F)(F)F)cc4)n3)cc2)c1]
P464

TABLE P-Two-continued
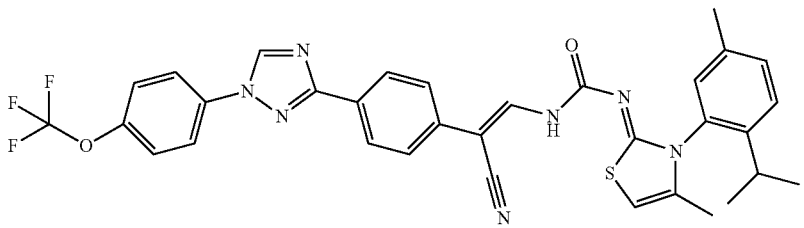 [SMILES: Cc1ccc(C(C)C)c(-n2c(C)cs/c2=N\C(=O)N/C=C(\C#N)c2ccc(-c3ncn(-c4ccc(OC(F)(F)F)cc4)n3)cc2)c1]
P465
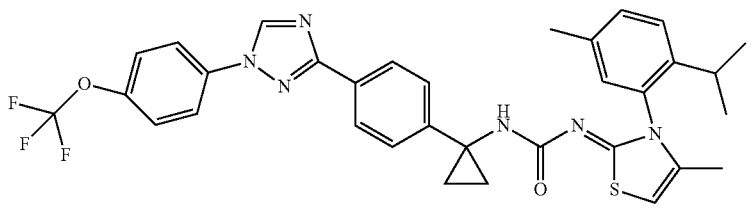 [SMILES: Cc1ccc(C(C)C)c(-n2c(C)cs/c2=N\C(=O)NC2(c3ccc(-c4ncn(-c5ccc(OC(F)(F)F)cc5)n4)cc3)CC2)c1]
P466
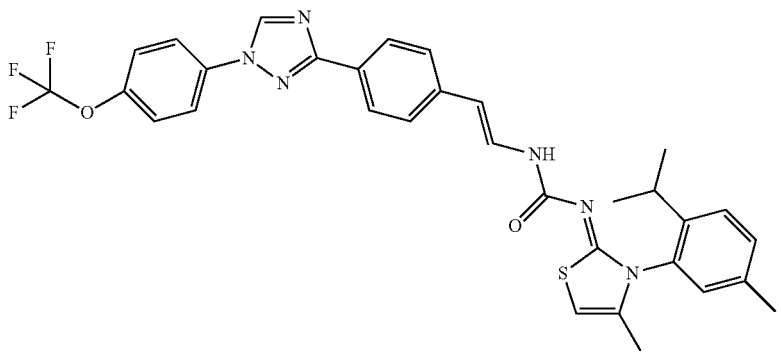 [SMILES: Cc1ccc(C(C)C)c(-n2c(C)cs/c2=N\C(=O)N/C=C/c2ccc(-c3ncn(-c4ccc(OC(F)(F)F)cc4)n3)cc2)c1]
P467
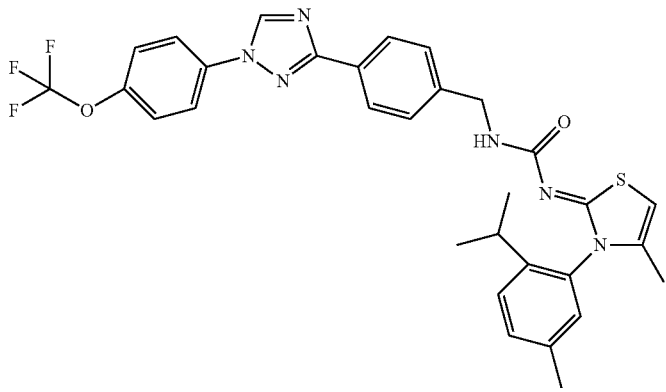 [SMILES: Cc1ccc(C(C)C)c(-n2c(C)cs/c2=N\C(=O)NCc2ccc(-c3ncn(-c4ccc(OC(F)(F)F)cc4)n3)cc2)c1]
P468
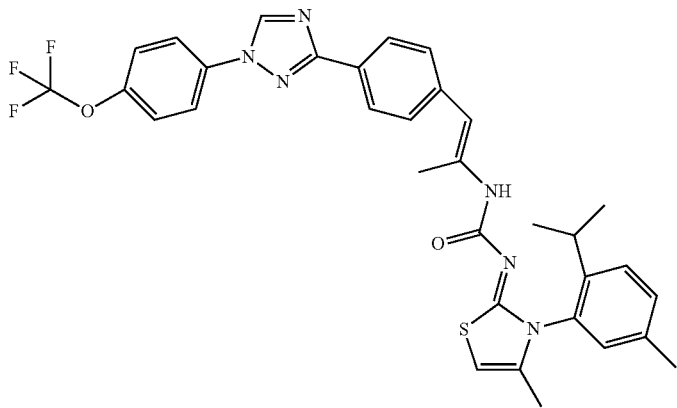 [SMILES: C/C(=C\c1ccc(-c2ncn(-c3ccc(OC(F)(F)F)cc3)n2)cc1)NC(=O)/N=c1\scc(C)n1-c1cc(C)ccc1C(C)C]
P469

TABLE P-Two-continued
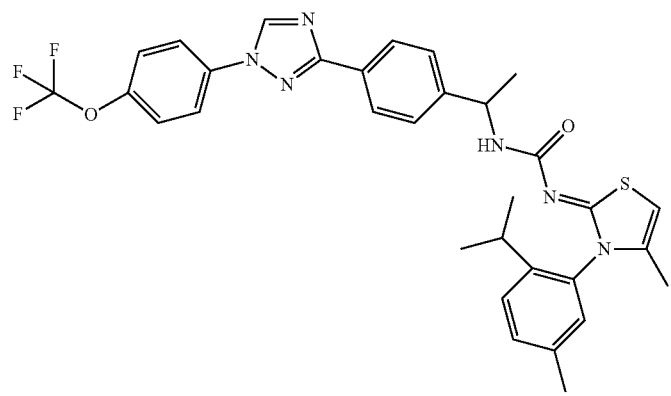 [SMILES: Cc1ccc(C(C)C)c(-n2c(C)cs/c2=N\C(=O)NC(C)c2ccc(-c3ncn(-c4ccc(OC(F)(F)F)cc4)n3)cc2)c1]
P470
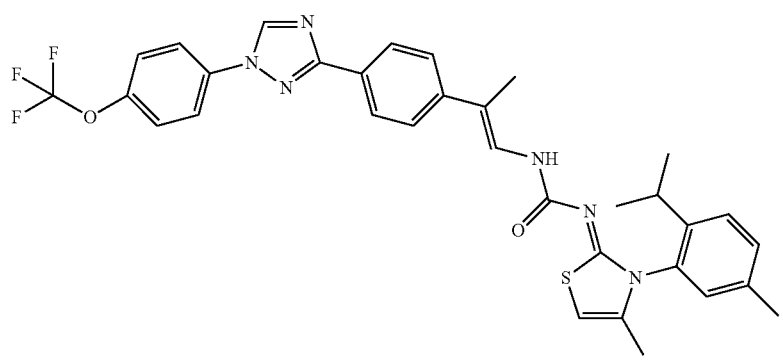 [SMILES: C/C(=C\NC(=O)/N=c1\scc(C)n1-c1cc(C)ccc1C(C)C)c1ccc(-c2ncn(-c3ccc(OC(F)(F)F)cc3)n2)cc1]
P471
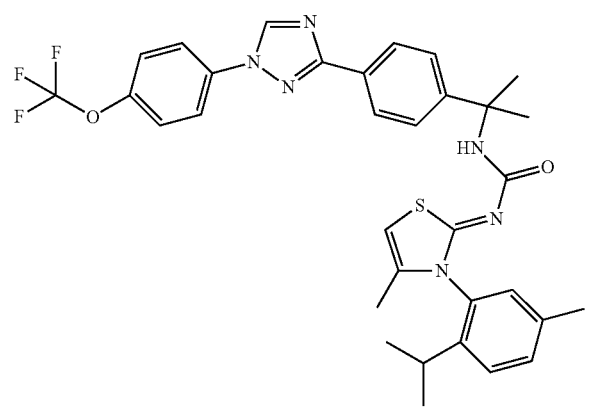 [SMILES: Cc1ccc(C(C)C)c(-n2c(C)cs/c2=N\C(=O)NC(C)(C)c2ccc(-c3ncn(-c4ccc(OC(F)(F)F)cc4)n3)cc2)c1]
P472
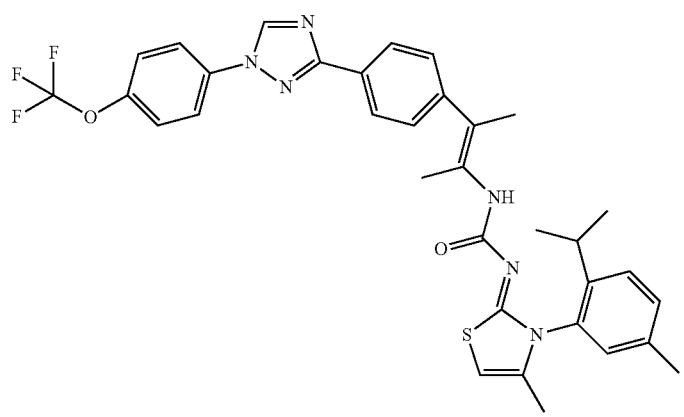 [SMILES: C/C(NC(=O)/N=c1\scc(C)n1-c1cc(C)ccc1C(C)C)=C(/C)c1ccc(-c2ncn(-c3ccc(OC(F)(F)F)cc3)n2)cc1]
P473

TABLE P-Two-continued
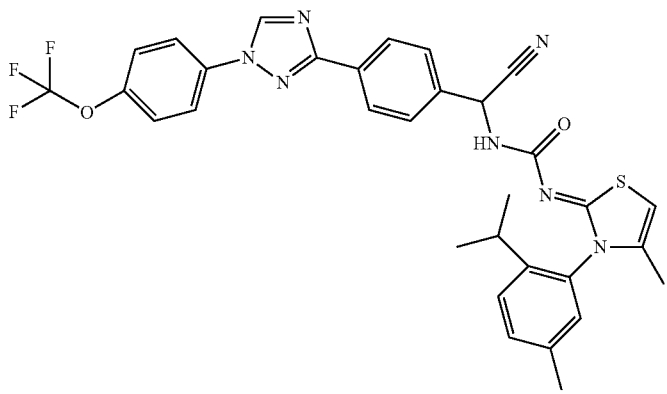 [SMILES: Cc1ccc(C(C)C)c(-n2c(C)cs/c2=N\C(=O)NC(C#N)c2ccc(-c3ncn(-c4ccc(OC(F)(F)F)cc4)n3)cc2)c1]
P474
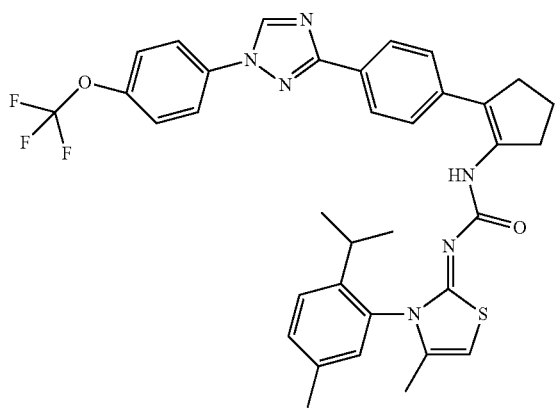 [SMILES: Cc1ccc(C(C)C)c(-n2c(C)cs/c2=N\C(=O)NC2=C(c3ccc(-c4ncn(-c5ccc(OC(F)(F)F)cc5)n4)cc3)CCC2)c1]
P475
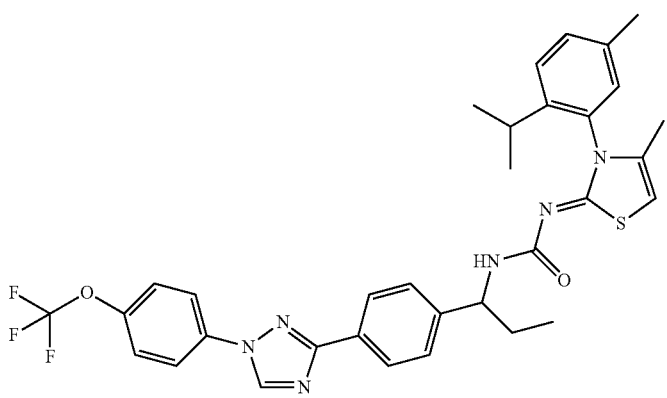 [SMILES: CCC(NC(=O)/N=c1\scc(C)n1-c1cc(C)ccc1C(C)C)c1ccc(-c2ncn(-c3ccc(OC(F)(F)F)cc3)n2)cc1]
P476
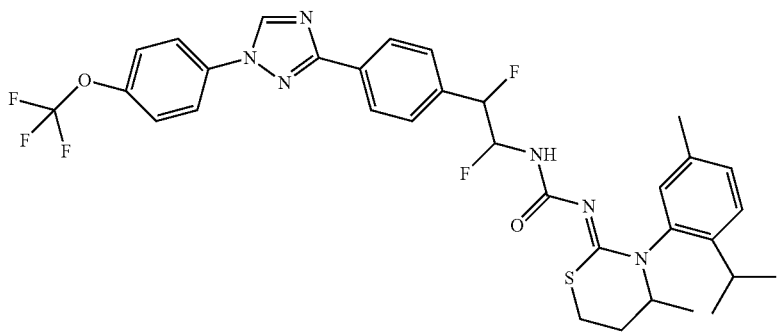 [SMILES: Cc1ccc(C(C)C)c(N2/C(=N/C(=O)NC(F)C(F)c3ccc(-c4ncn(-c5ccc(OC(F)(F)F)cc5)n4)cc3)SCCC2C)c1]
P477

TABLE P-Two-continued
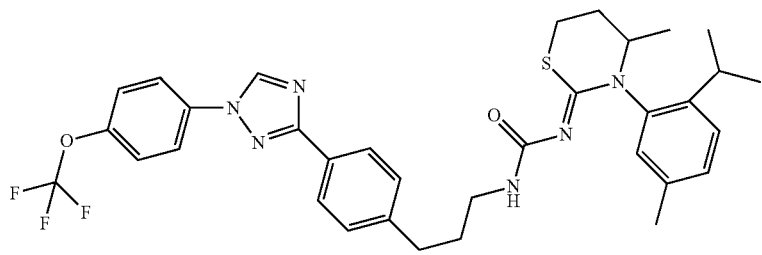 [SMILES: Cc1ccc(C(C)C)c(N2/C(=N/C(=O)NCCCc3ccc(-c4ncn(-c5ccc(OC(F)(F)F)cc5)n4)cc3)SCCC2C)c1]
P478
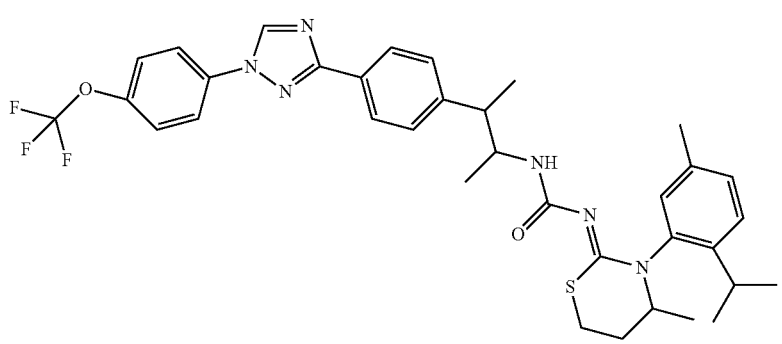 [SMILES: Cc1ccc(C(C)C)c(N2/C(=N/C(=O)NC(C)C(C)c3ccc(-c4ncn(-c5ccc(OC(F)(F)F)cc5)n4)cc3)SCCC2C)c1]
P479
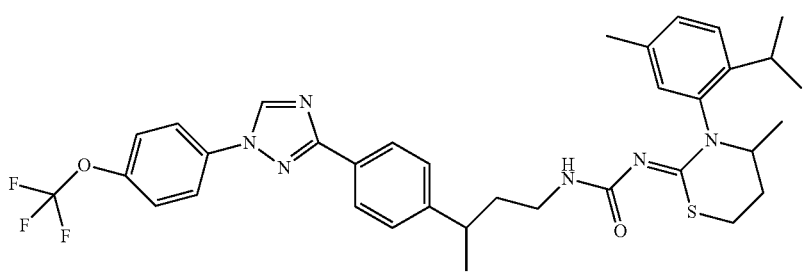 [SMILES: Cc1ccc(C(C)C)c(N2/C(=N/C(=O)NCCC(C)c3ccc(-c4ncn(-c5ccc(OC(F)(F)F)cc5)n4)cc3)SCCC2C)c1]
P480
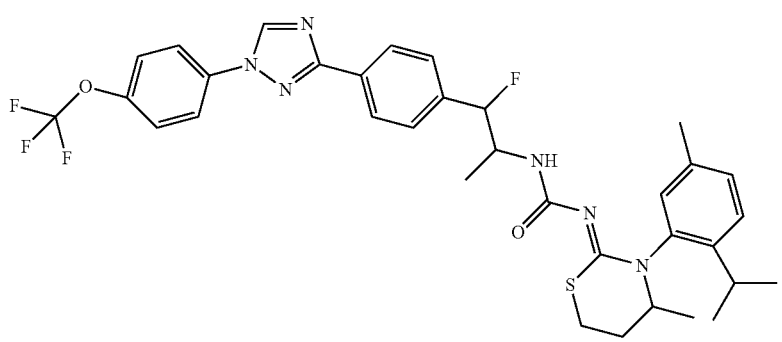 [SMILES: Cc1ccc(C(C)C)c(N2/C(=N/C(=O)NC(C)C(F)c3ccc(-c4ncn(-c5ccc(OC(F)(F)F)cc5)n4)cc3)SCCC2C)c1]
P481
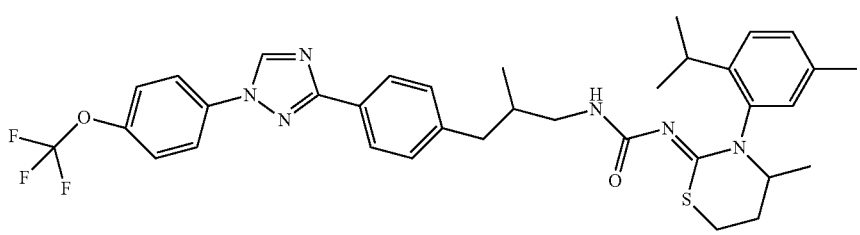 [SMILES: Cc1ccc(C(C)C)c(N2/C(=N/C(=O)NCC(C)Cc3ccc(-c4ncn(-c5ccc(OC(F)(F)F)cc5)n4)cc3)SCCC2C)c1]
P482

TABLE P-Two-continued
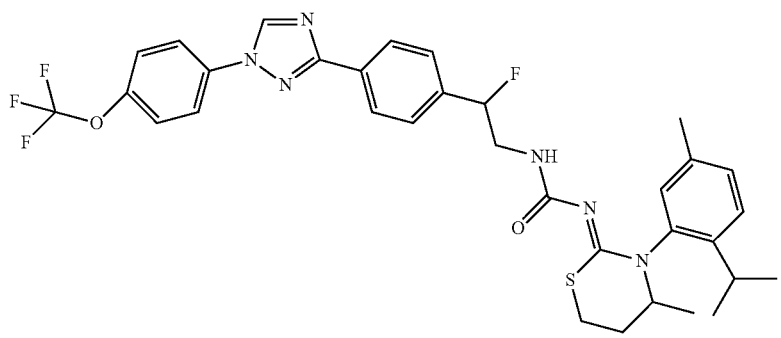 [SMILES: Cc1ccc(C(C)C)c(N2/C(=N/C(=O)NCC(F)c3ccc(-c4ncn(-c5ccc(OC(F)(F)F)cc5)n4)cc3)SCCC2C)c1]
P483
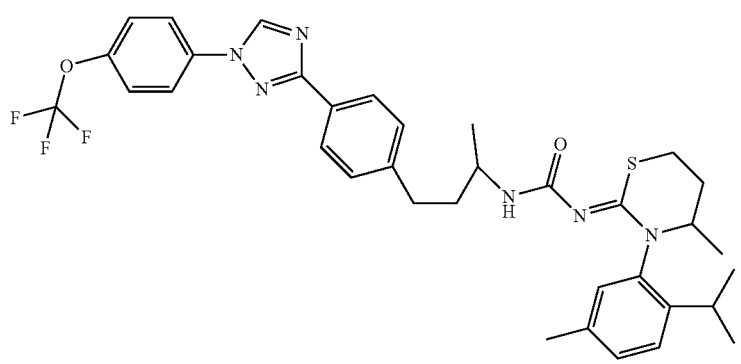 [SMILES: Cc1ccc(C(C)C)c(N2/C(=N/C(=O)NC(C)CCc3ccc(-c4ncn(-c5ccc(OC(F)(F)F)cc5)n4)cc3)SCCC2C)c1]
P484
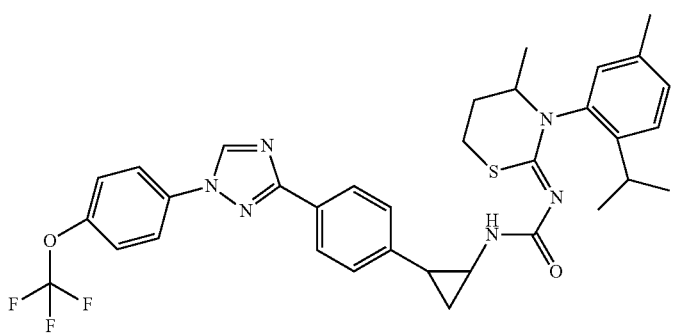 [SMILES: Cc1ccc(C(C)C)c(N2/C(=N/C(=O)NC3CC3c3ccc(-c4ncn(-c5ccc(OC(F)(F)F)cc5)n4)cc3)SCCC2C)c1]
P485
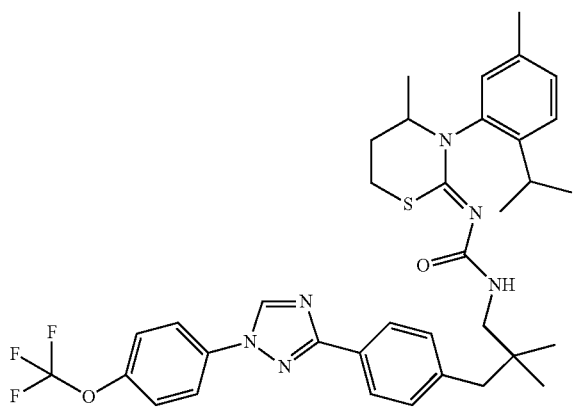 [SMILES: Cc1ccc(C(C)C)c(N2/C(=N/C(=O)NCC(C)(C)Cc3ccc(-c4ncn(-c5ccc(OC(F)(F)F)cc5)n4)cc3)SCCC2C)c1]
P486

TABLE P-Two-continued
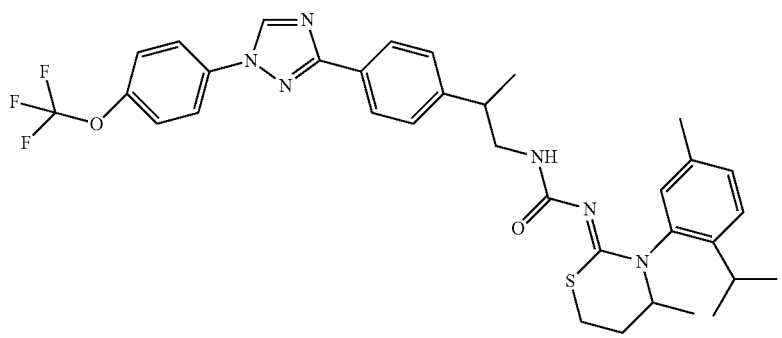 [SMILES: Cc1ccc(C(C)C)c(N2/C(=N/C(=O)NCC(C)c3ccc(-c4ncn(-c5ccc(OC(F)(F)F)cc5)n4)cc3)SCCC2C)c1]
P487
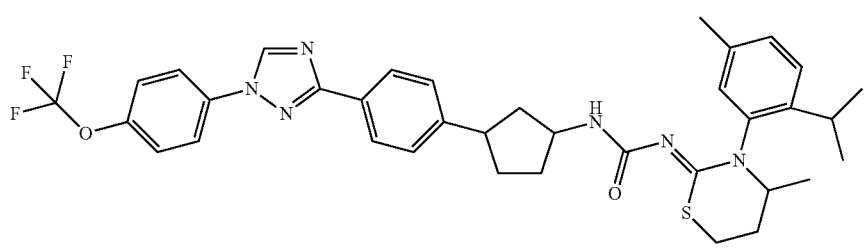 [SMILES: Cc1ccc(C(C)C)c(N2/C(=N/C(=O)NC3CCC(c4ccc(-c5ncn(-c6ccc(OC(F)(F)F)cc6)n5)cc4)C3)SCCC2C)c1]
P488
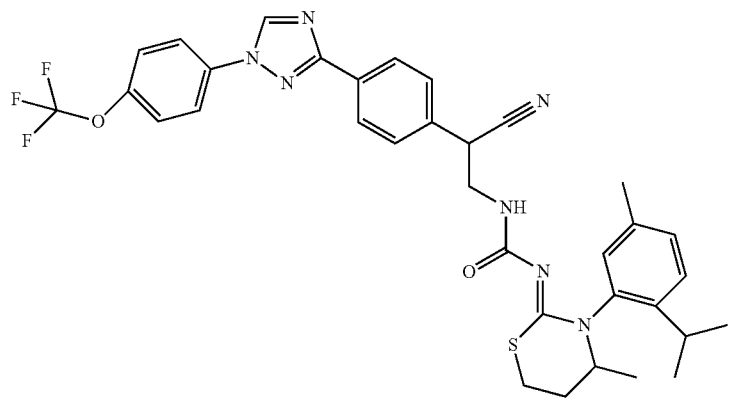 [SMILES: Cc1ccc(C(C)C)c(N2/C(=N/C(=O)NCC(C#N)c3ccc(-c4ncn(-c5ccc(OC(F)(F)F)cc5)n4)cc3)SCCC2C)c1]
P489
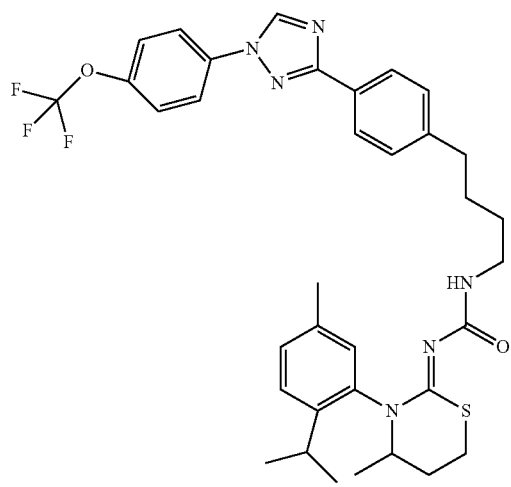 [SMILES: Cc1ccc(C(C)C)c(N2/C(=N/C(=O)NCCCCc3ccc(-c4ncn(-c5ccc(OC(F)(F)F)cc5)n4)cc3)SCCC2C)c1]
P490

TABLE P-Two-continued
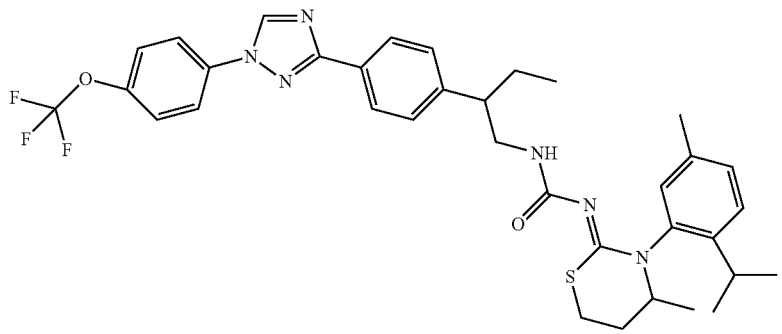 [SMILES: CCC(CNC(=O)/N=C1\SCCC(C)N1c1cc(C)ccc1C(C)C)c1ccc(-c2ncn(-c3ccc(OC(F)(F)F)cc3)n2)cc1]
P491
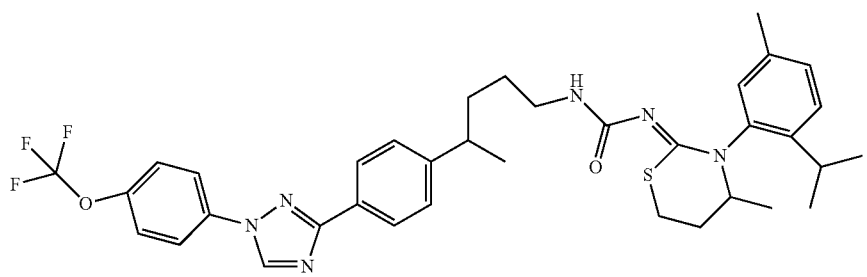 [SMILES: Cc1ccc(C(C)C)c(N2/C(=N/C(=O)NCCCC(C)c3ccc(-c4ncn(-c5ccc(OC(F)(F)F)cc5)n4)cc3)SCCC2C)c1]
P492
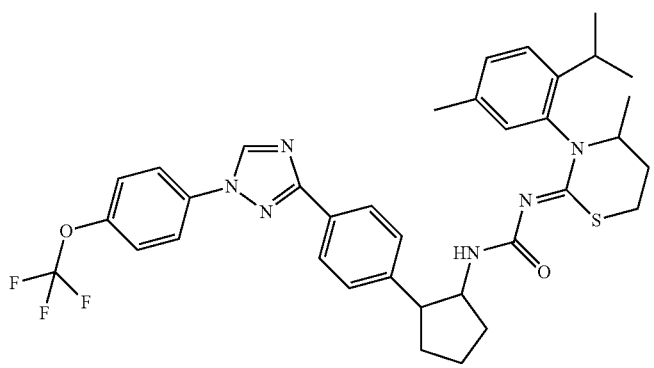 [SMILES: Cc1ccc(C(C)C)c(N2/C(=N/C(=O)NC3CCCC3c3ccc(-c4ncn(-c5ccc(OC(F)(F)F)cc5)n4)cc3)SCCC2C)c1]
P493
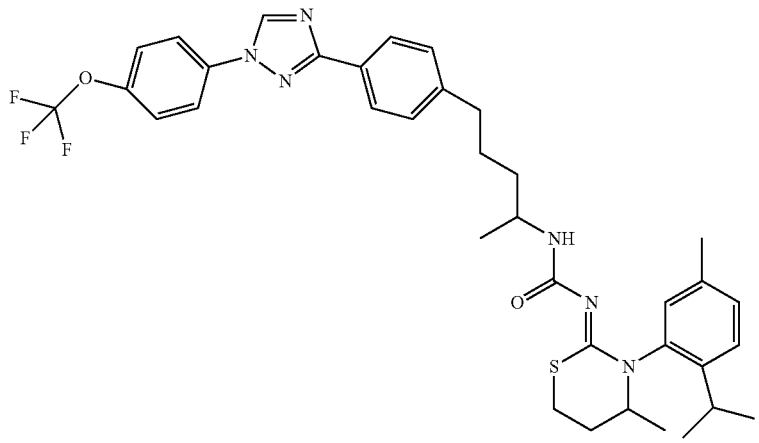 [SMILES: Cc1ccc(C(C)C)c(N2/C(=N/C(=O)NC(C)CCCc3ccc(-c4ncn(-c5ccc(OC(F)(F)F)cc5)n4)cc3)SCCC2C)c1]
P494

TABLE P-Two-continued
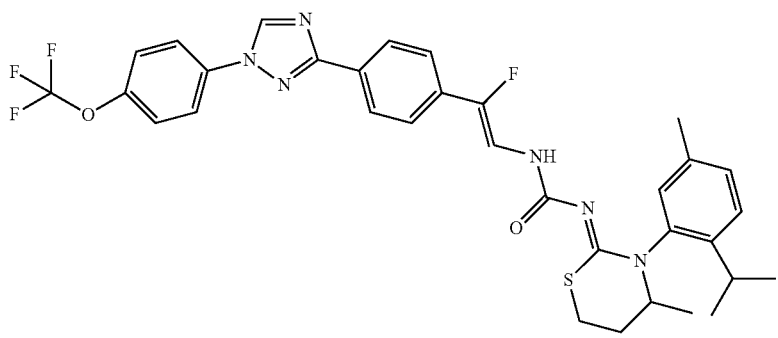 [SMILES: Cc1ccc(C(C)C)c(N2/C(=N/C(=O)N/C=C(\F)c3ccc(-c4ncn(-c5ccc(OC(F)(F)F)cc5)n4)cc3)SCCC2C)c1]
P495
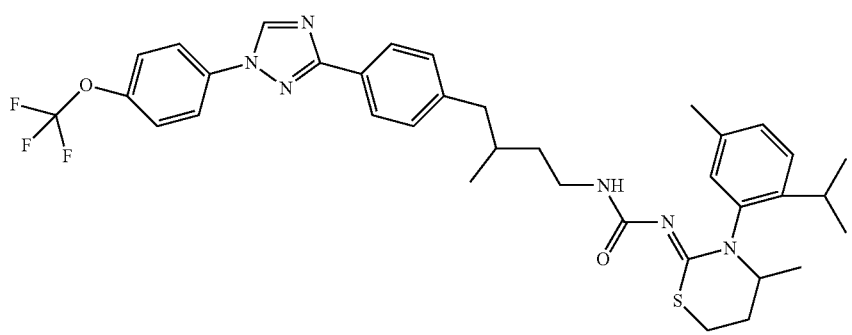 [SMILES: Cc1ccc(C(C)C)c(N2/C(=N/C(=O)NCCC(C)Cc3ccc(-c4ncn(-c5ccc(OC(F)(F)F)cc5)n4)cc3)SCCC2C)c1]
P496
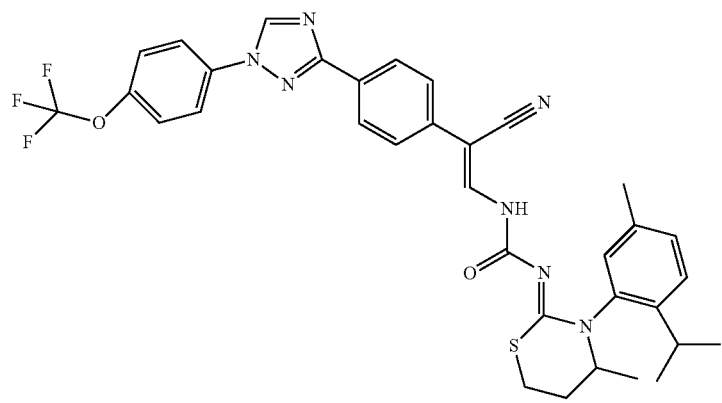 [SMILES: Cc1ccc(C(C)C)c(N2/C(=N/C(=O)N/C=C(\C#N)c3ccc(-c4ncn(-c5ccc(OC(F)(F)F)cc5)n4)cc3)SCCC2C)c1]
P497
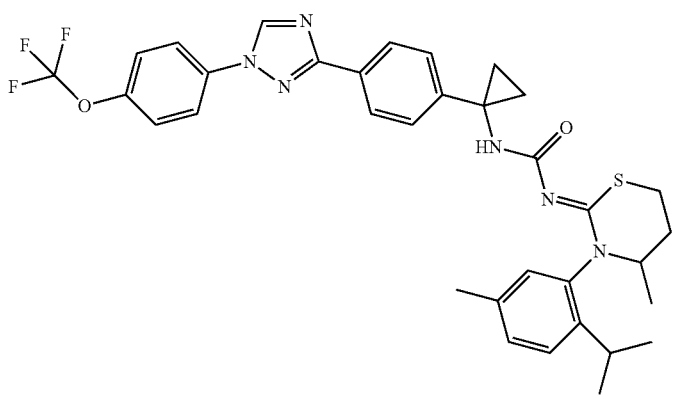 [SMILES: Cc1ccc(C(C)C)c(N2/C(=N/C(=O)NC3(c4ccc(-c5ncn(-c6ccc(OC(F)(F)F)cc6)n5)cc4)CC3)SCCC2C)c1]
P498

TABLE P-Two-continued
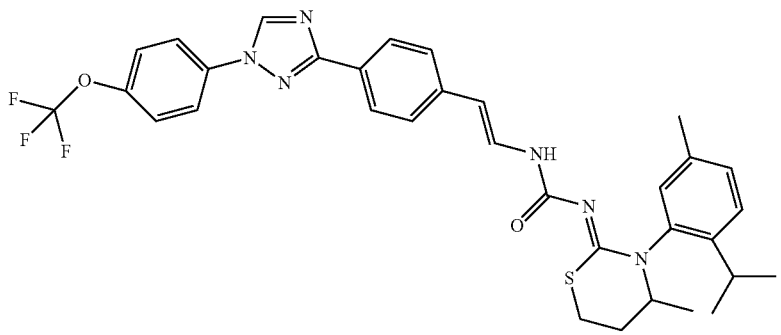 [SMILES: Cc1ccc(C(C)C)c(N2/C(=N/C(=O)N/C=C/c3ccc(-c4ncn(-c5ccc(OC(F)(F)F)cc5)n4)cc3)SCCC2C)c1]
P499
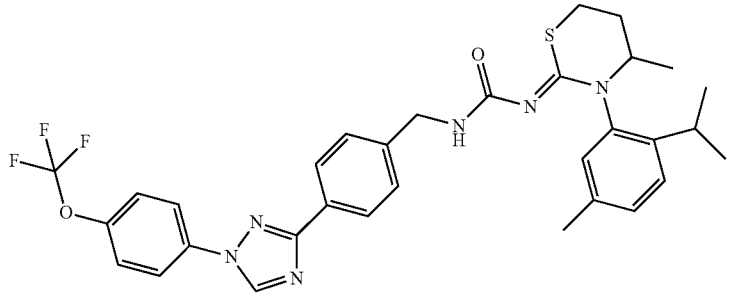 [SMILES: Cc1ccc(C(C)C)c(N2/C(=N/C(=O)NCc3ccc(-c4ncn(-c5ccc(OC(F)(F)F)cc5)n4)cc3)SCCC2C)c1]
P500
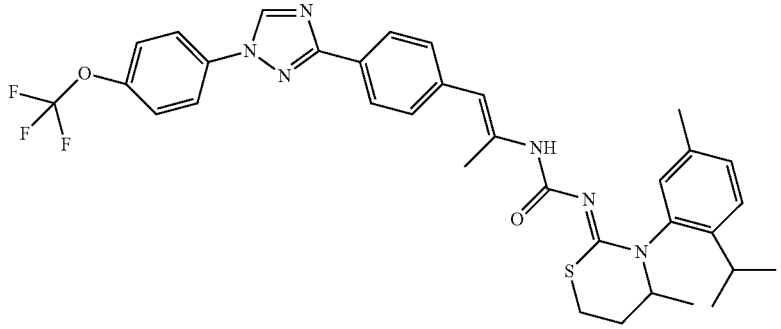 [SMILES: C/C(=C\c1ccc(-c2ncn(-c3ccc(OC(F)(F)F)cc3)n2)cc1)NC(=O)/N=C1\SCCC(C)N1c1cc(C)ccc1C(C)C]
P501
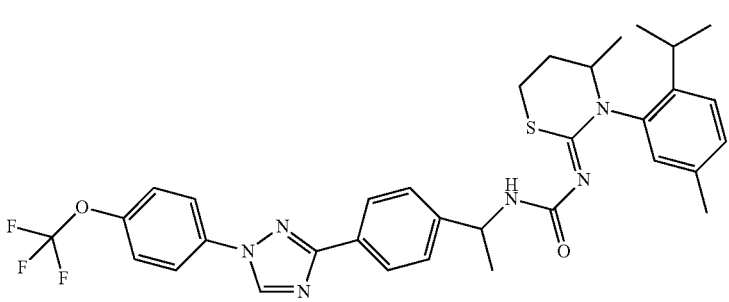 [SMILES: Cc1ccc(C(C)C)c(N2/C(=N/C(=O)NC(C)c3ccc(-c4ncn(-c5ccc(OC(F)(F)F)cc5)n4)cc3)SCCC2C)c1]
P502
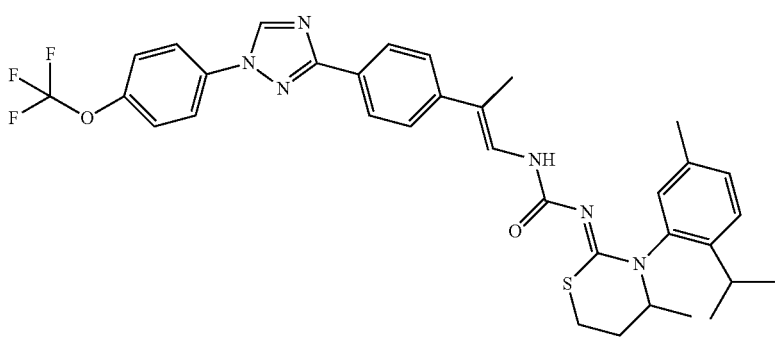 [SMILES: C/C(=C\NC(=O)/N=C1\SCCC(C)N1c1cc(C)ccc1C(C)C)c1ccc(-c2ncn(-c3ccc(OC(F)(F)F)cc3)n2)cc1]
P503

TABLE P-Two-continued
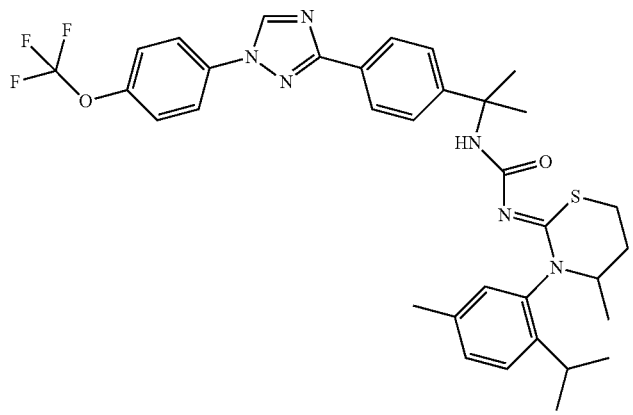 [SMILES: Cc1ccc(C(C)C)c(N2/C(=N/C(=O)NC(C)(C)c3ccc(-c4ncn(-c5ccc(OC(F)(F)F)cc5)n4)cc3)SCCC2C)c1]
P504
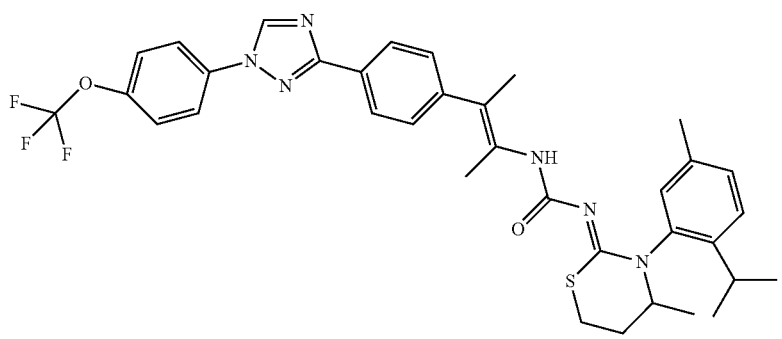 [SMILES: C/C(NC(=O)/N=C1\SCCC(C)N1c1cc(C)ccc1C(C)C)=C(/C)c1ccc(-c2ncn(-c3ccc(OC(F)(F)F)cc3)n2)cc1]
P505
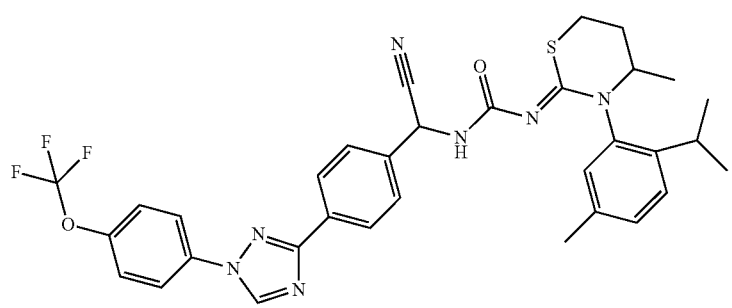 [SMILES: Cc1ccc(C(C)C)c(N2/C(=N/C(=O)NC(C#N)c3ccc(-c4ncn(-c5ccc(OC(F)(F)F)cc5)n4)cc3)SCCC2C)c1]
P506
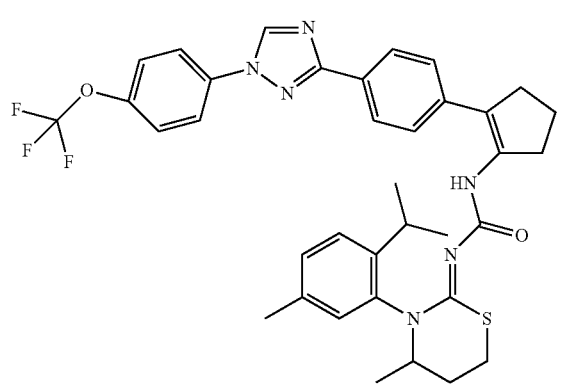 [SMILES: Cc1ccc(C(C)C)c(N2/C(=N/C(=O)NC3=C(c4ccc(-c5ncn(-c6ccc(OC(F)(F)F)cc6)n5)cc4)CCC3)SCCC2C)c1]
P507

TABLE P-Two-continued
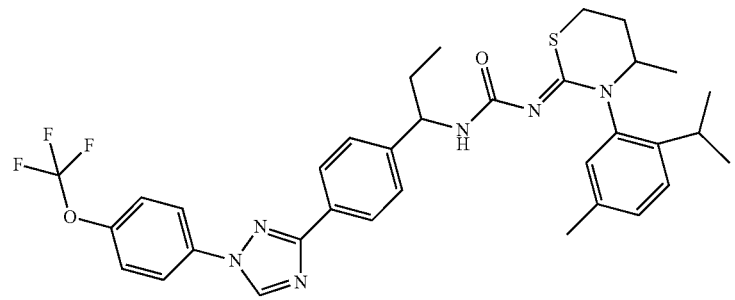 [SMILES: CCC(NC(=O)/N=C1\SCCC(C)N1c1cc(C)ccc1C(C)C)c1ccc(-c2ncn(-c3ccc(OC(F)(F)F)cc3)n2)cc1]
P508
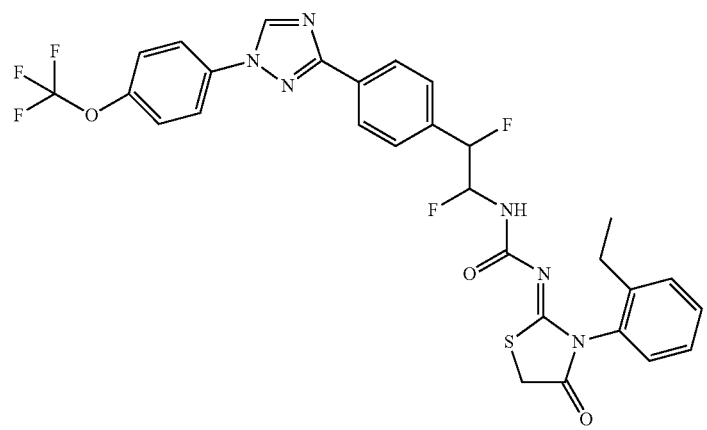 [SMILES: CCc1ccccc1N1C(=O)CS/C1=N\C(=O)NC(F)C(F)c1ccc(-c2ncn(-c3ccc(OC(F)(F)F)cc3)n2)cc1]
P509
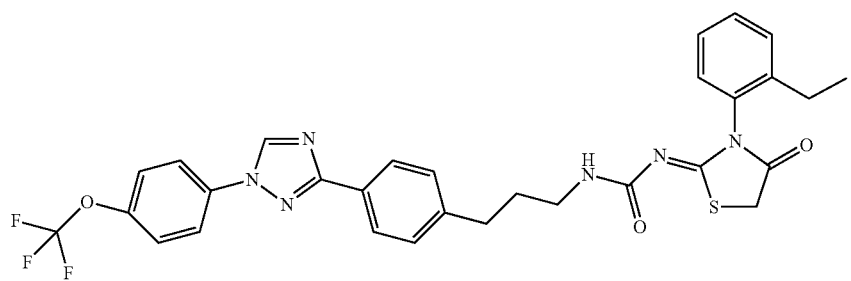 [SMILES: CCc1ccccc1N1C(=O)CS/C1=N\C(=O)NCCCc1ccc(-c2ncn(-c3ccc(OC(F)(F)F)cc3)n2)cc1]
P510
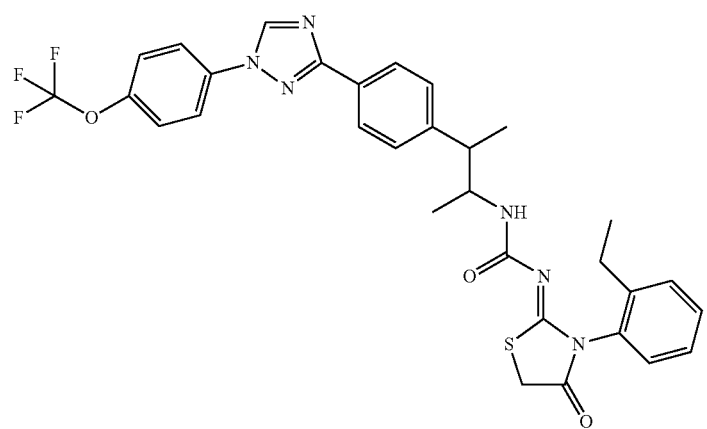 [SMILES: CCc1ccccc1N1C(=O)CS/C1=N\C(=O)NC(C)C(C)c1ccc(-c2ncn(-c3ccc(OC(F)(F)F)cc3)n2)cc1]
P511

TABLE P-Two-continued
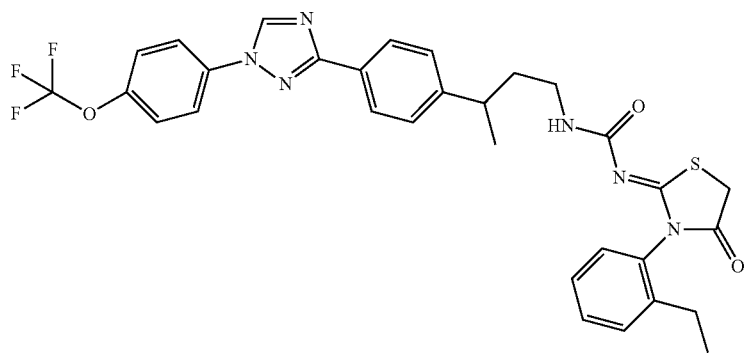 [SMILES: CCc1ccccc1N1C(=O)CS/C1=N\C(=O)NCCC(C)c1ccc(-c2ncn(-c3ccc(OC(F)(F)F)cc3)n2)cc1]
P512
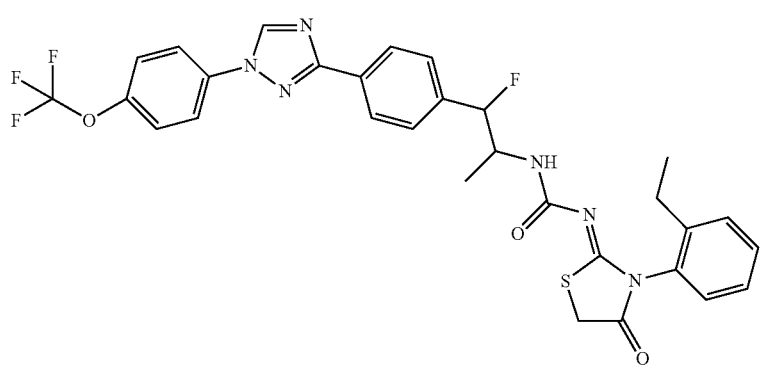 [SMILES: CCc1ccccc1N1C(=O)CS/C1=N\C(=O)NC(C)C(F)c1ccc(-c2ncn(-c3ccc(OC(F)(F)F)cc3)n2)cc1]
P513
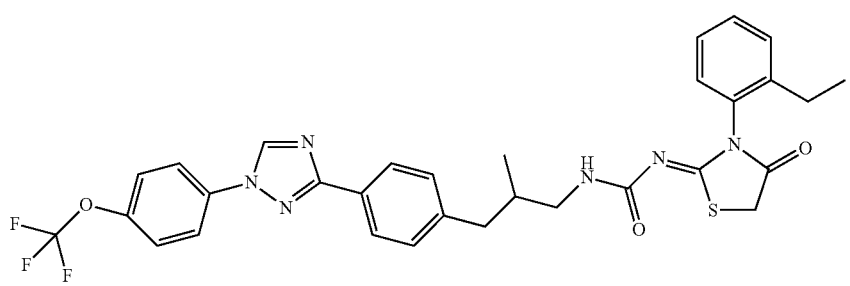 [SMILES: CCc1ccccc1N1C(=O)CS/C1=N\C(=O)NCC(C)Cc1ccc(-c2ncn(-c3ccc(OC(F)(F)F)cc3)n2)cc1]
P514
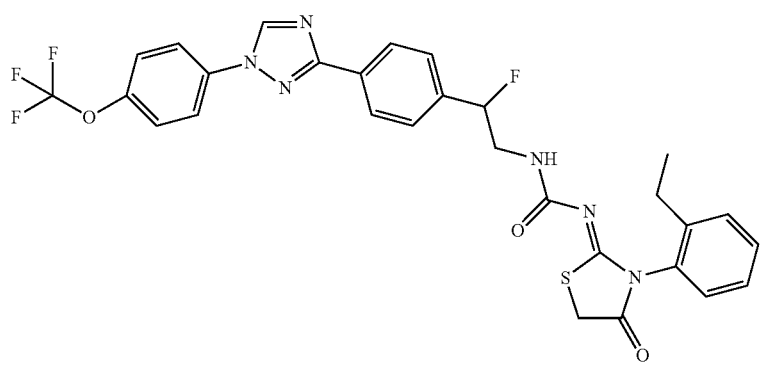 [SMILES: CCc1ccccc1N1C(=O)CS/C1=N\C(=O)NCC(F)c1ccc(-c2ncn(-c3ccc(OC(F)(F)F)cc3)n2)cc1]
P515

TABLE P-Two-continued
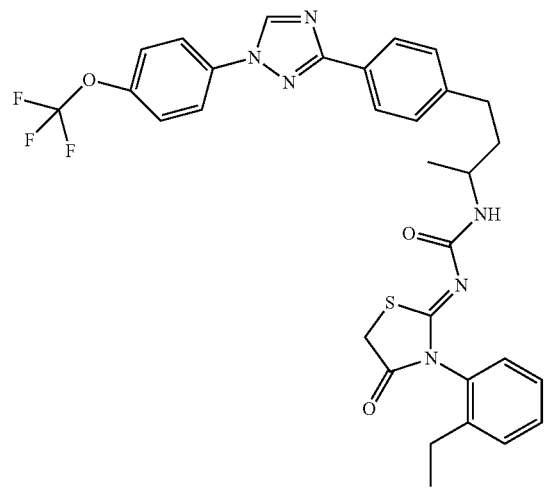 [SMILES: CCc1ccccc1N1C(=O)CS/C1=N\C(=O)NC(C)CCc1ccc(-c2ncn(-c3ccc(OC(F)(F)F)cc3)n2)cc1]
P516
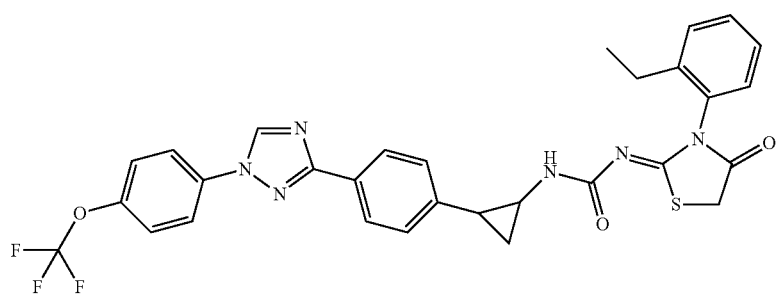 [SMILES: CCc1ccccc1N1C(=O)CS/C1=N\C(=O)NC1CC1c1ccc(-c2ncn(-c3ccc(OC(F)(F)F)cc3)n2)cc1]
P517
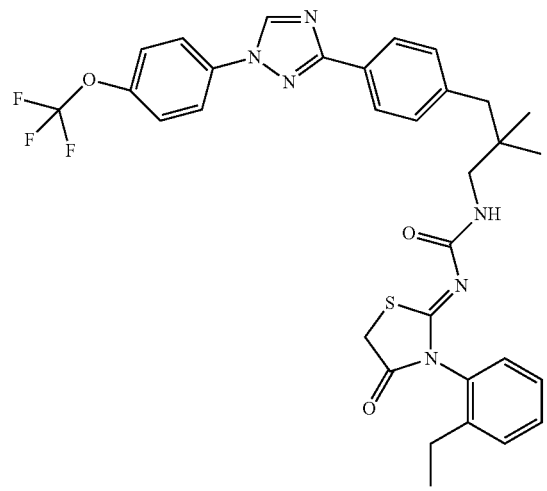 [SMILES: CCc1ccccc1N1C(=O)CS/C1=N\C(=O)NCC(C)(C)Cc1ccc(-c2ncn(-c3ccc(OC(F)(F)F)cc3)n2)cc1]
P518
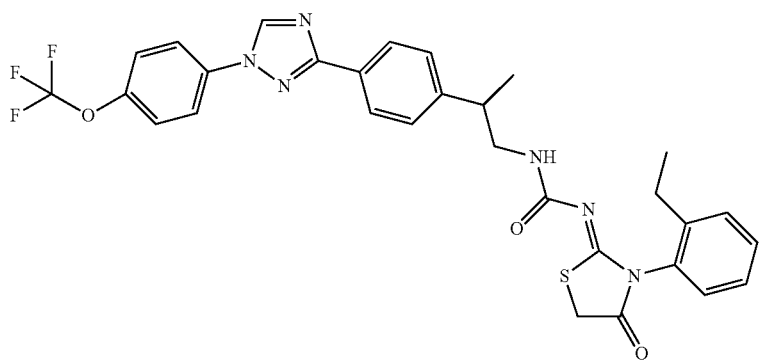 [SMILES: CCc1ccccc1N1C(=O)CS/C1=N\C(=O)NCC(C)c1ccc(-c2ncn(-c3ccc(OC(F)(F)F)cc3)n2)cc1]
P519

TABLE P-Two-continued
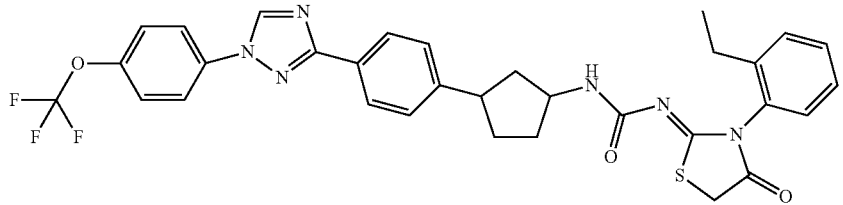 [SMILES: CCc1ccccc1N1C(=O)CS/C1=N\C(=O)NC1CCC(c2ccc(-c3ncn(-c4ccc(OC(F)(F)F)cc4)n3)cc2)C1] P520
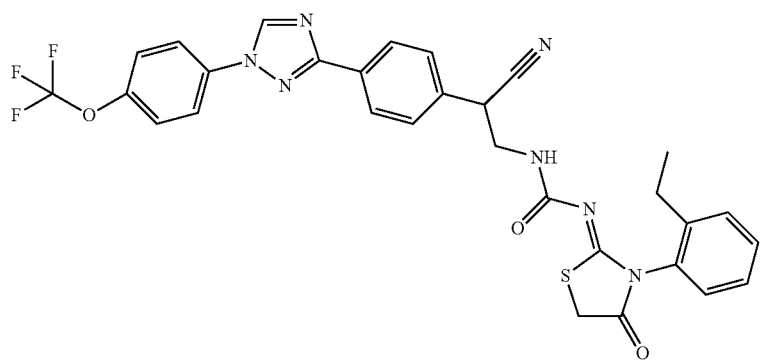 [SMILES: CCc1ccccc1N1C(=O)CS/C1=N\C(=O)NCC(C#N)c1ccc(-c2ncn(-c3ccc(OC(F)(F)F)cc3)n2)cc1] P521
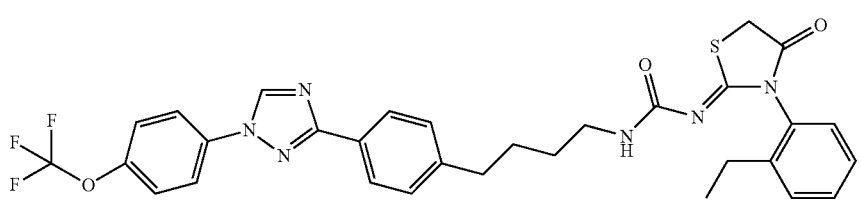 [SMILES: CCc1ccccc1N1C(=O)CS/C1=N\C(=O)NCCCCc1ccc(-c2ncn(-c3ccc(OC(F)(F)F)cc3)n2)cc1] P522
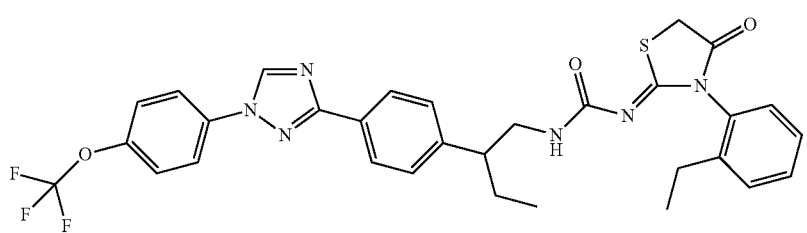 [SMILES: CCc1ccccc1N1C(=O)CS/C1=N\C(=O)NCC(CC)c1ccc(-c2ncn(-c3ccc(OC(F)(F)F)cc3)n2)cc1] P523
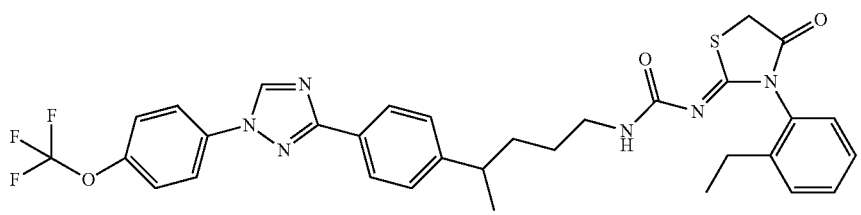 [SMILES: CCc1ccccc1N1C(=O)CS/C1=N\C(=O)NCCCC(C)c1ccc(-c2ncn(-c3ccc(OC(F)(F)F)cc3)n2)cc1] P524
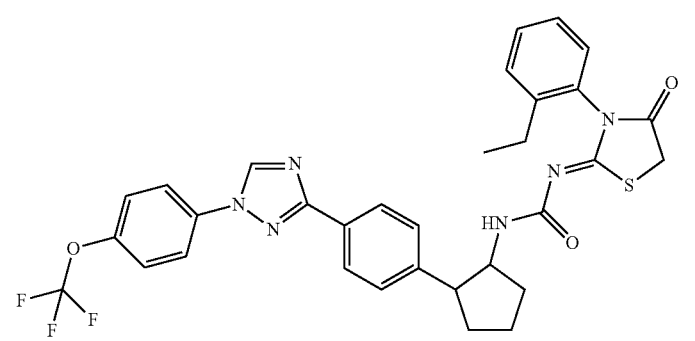 [SMILES: CCc1ccccc1N1C(=O)CS/C1=N\C(=O)NC1CCCC1c1ccc(-c2ncn(-c3ccc(OC(F)(F)F)cc3)n2)cc1] P525

TABLE P-Two-continued
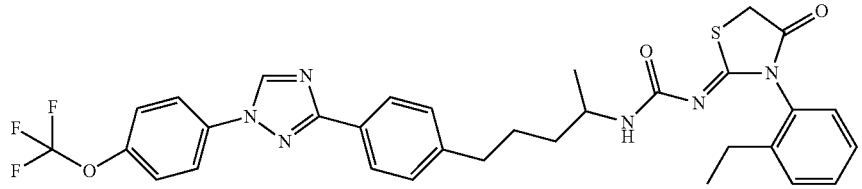 [SMILES: CCc1ccccc1N1C(=O)CS/C1=N\C(=O)NC(C)CCCc1ccc(-c2ncn(-c3ccc(OC(F)(F)F)cc3)n2)cc1]
P526
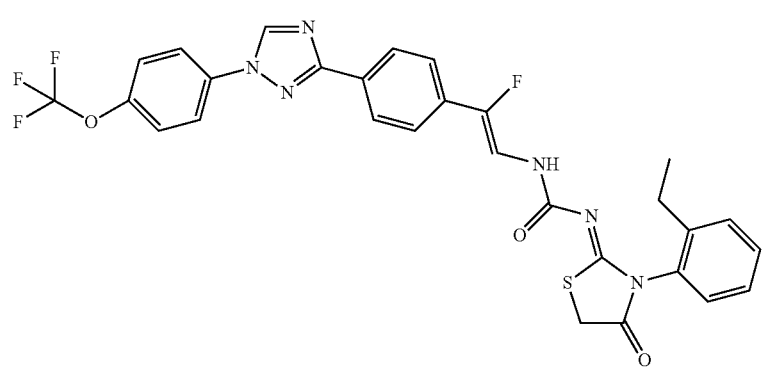 [SMILES: CCc1ccccc1N1C(=O)CS/C1=N\C(=O)N/C=C(\F)c1ccc(-c2ncn(-c3ccc(OC(F)(F)F)cc3)n2)cc1]
P527
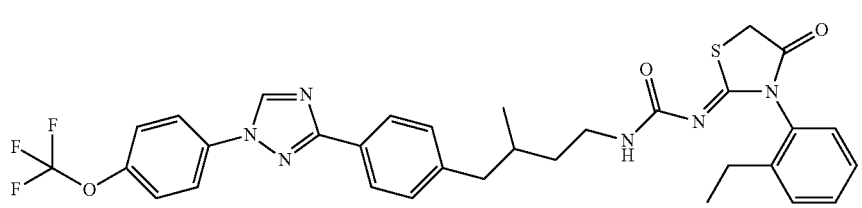
P528
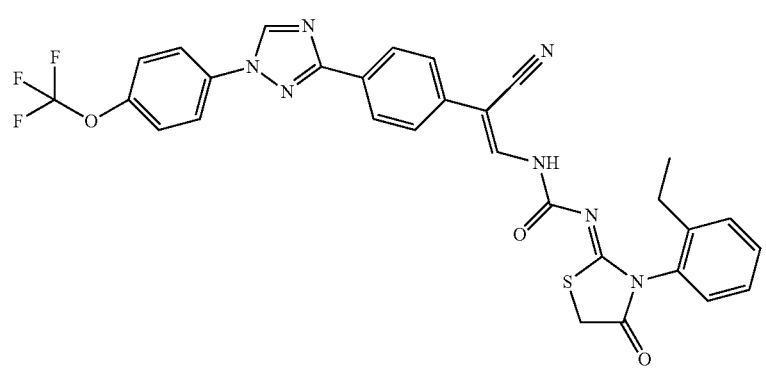 [SMILES: CCc1ccccc1N1C(=O)CS/C1=N\C(=O)N/C=C(\C#N)c1ccc(-c2ncn(-c3ccc(OC(F)(F)F)cc3)n2)cc1]
P529
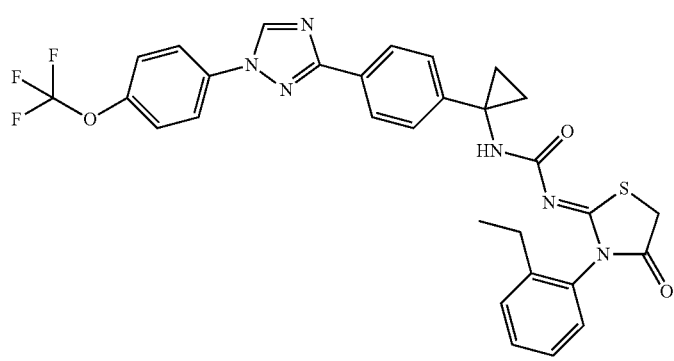 [SMILES: CCc1ccccc1N1C(=O)CS/C1=N\C(=O)NC1(c2ccc(-c3ncn(-c4ccc(OC(F)(F)F)cc4)n3)cc2)CC1]
P530

TABLE P-Two-continued
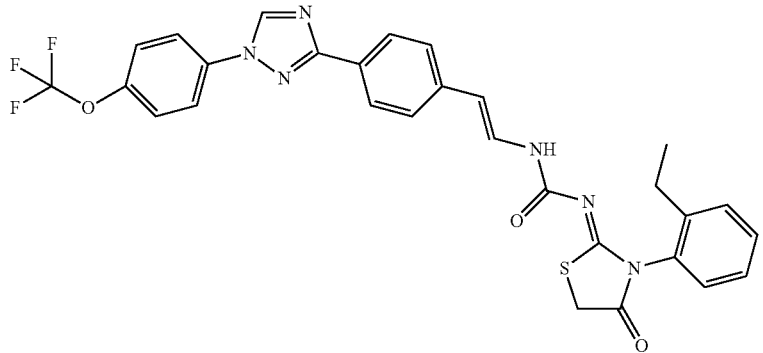 [SMILES: CCc1ccccc1N1C(=O)CS/C1=N\C(=O)N/C=C/c1ccc(-c2ncn(-c3ccc(OC(F)(F)F)cc3)n2)cc1]
P531
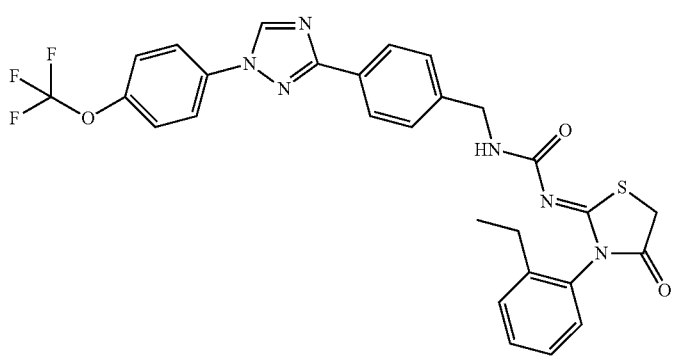 [SMILES: CCc1ccccc1N1C(=O)CS/C1=N\C(=O)NCc1ccc(-c2ncn(-c3ccc(OC(F)(F)F)cc3)n2)cc1]
P532
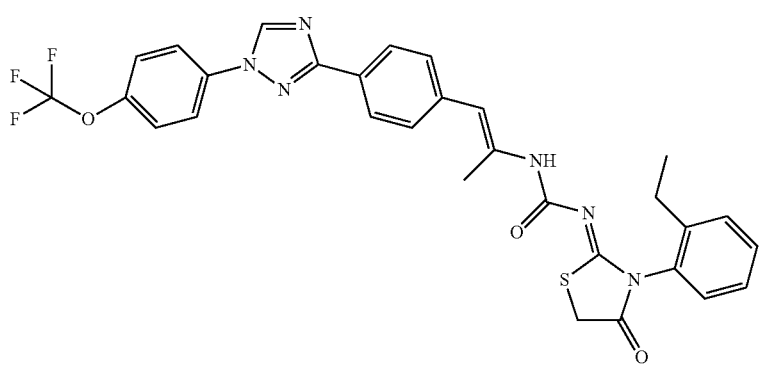 [SMILES: CCc1ccccc1N1C(=O)CS/C1=N\C(=O)N/C(C)=C/c1ccc(-c2ncn(-c3ccc(OC(F)(F)F)cc3)n2)cc1]
P533
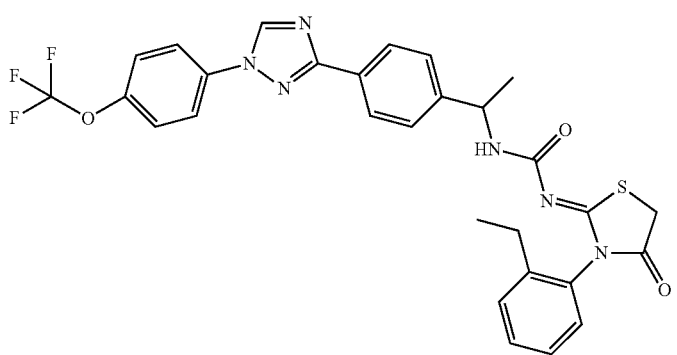 [SMILES: CCc1ccccc1N1C(=O)CS/C1=N\C(=O)NC(C)c1ccc(-c2ncn(-c3ccc(OC(F)(F)F)cc3)n2)cc1]
P534

TABLE P-Two-continued
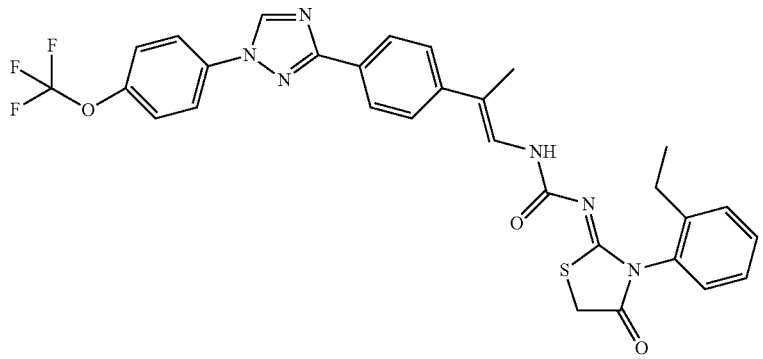 [SMILES: CCc1ccccc1N1C(=O)CS/C1=N\C(=O)N/C=C(\C)c1ccc(-c2ncn(-c3ccc(OC(F)(F)F)cc3)n2)cc1]
P535
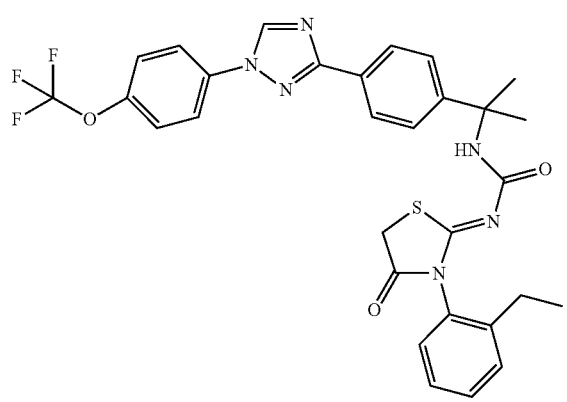 [SMILES: CCc1ccccc1N1C(=O)CS/C1=N\C(=O)NC(C)(C)c1ccc(-c2ncn(-c3ccc(OC(F)(F)F)cc3)n2)cc1]
P536
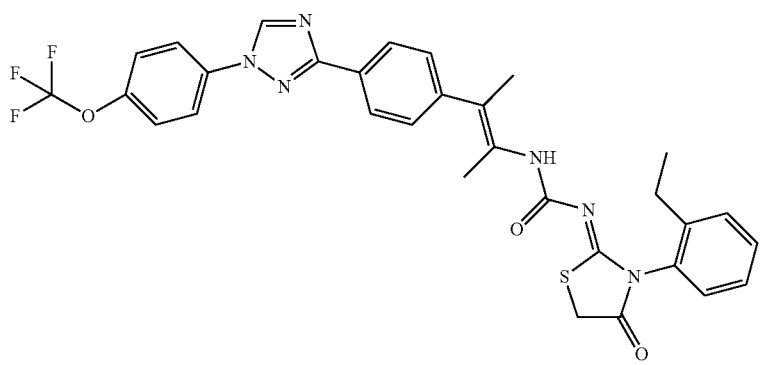 [SMILES: CCc1ccccc1N1C(=O)CS/C1=N\C(=O)N/C(C)=C(\C)c1ccc(-c2ncn(-c3ccc(OC(F)(F)F)cc3)n2)cc1]
P537
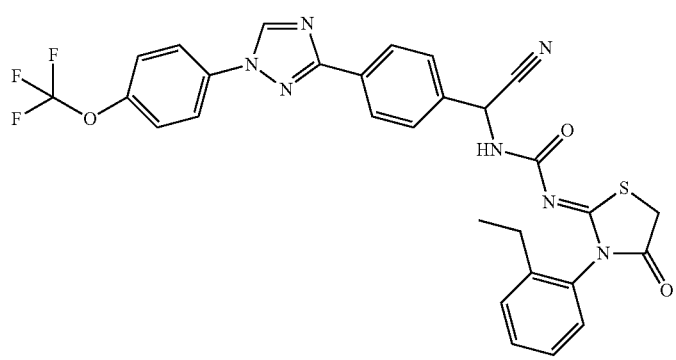 [SMILES: CCc1ccccc1N1C(=O)CS/C1=N\C(=O)NC(C#N)c1ccc(-c2ncn(-c3ccc(OC(F)(F)F)cc3)n2)cc1]
P538

TABLE P-Two-continued
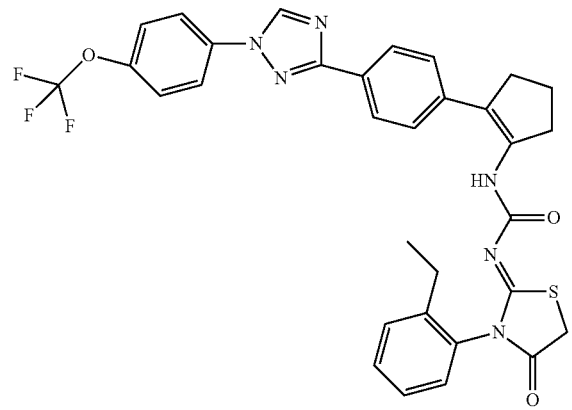 [SMILES: CCc1ccccc1N1C(=O)CS/C1=N\C(=O)NC1=C(c2ccc(-c3ncn(-c4ccc(OC(F)(F)F)cc4)n3)cc2)CCC1]
P539
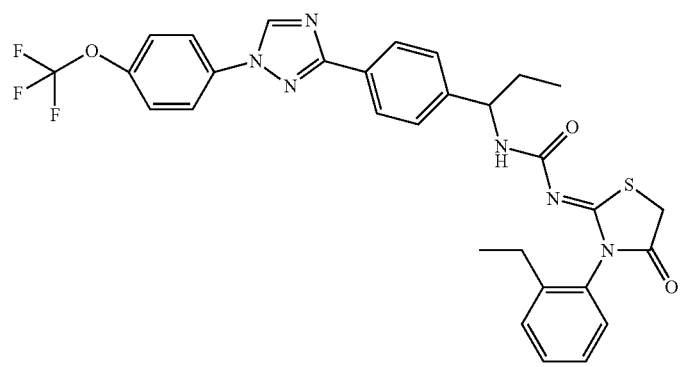 [SMILES: CCc1ccccc1N1C(=O)CS/C1=N\C(=O)NC(CC)c1ccc(-c2ncn(-c3ccc(OC(F)(F)F)cc3)n2)cc1]
P540
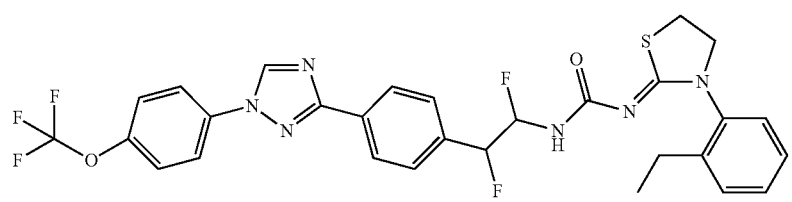 [SMILES: CCc1ccccc1N1CCS/C1=N\C(=O)NC(F)C(F)c1ccc(-c2ncn(-c3ccc(OC(F)(F)F)cc3)n2)cc1]
P541
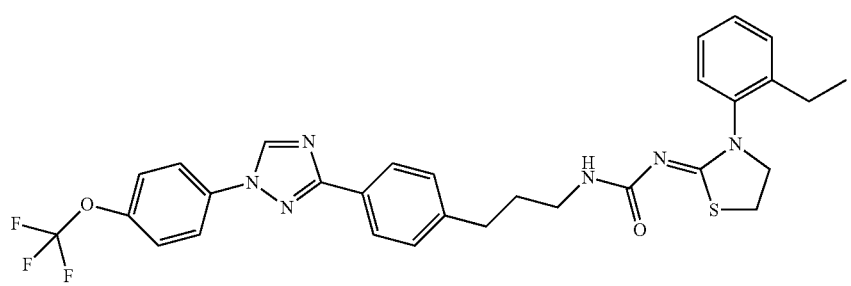 [SMILES: CCc1ccccc1N1CCS/C1=N\C(=O)NCCCc1ccc(-c2ncn(-c3ccc(OC(F)(F)F)cc3)n2)cc1]
P542
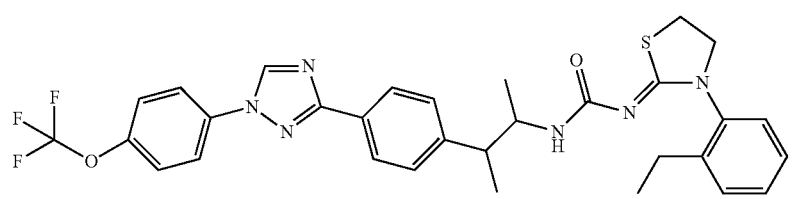 [SMILES: CCc1ccccc1N1CCS/C1=N\C(=O)NC(C)C(C)c1ccc(-c2ncn(-c3ccc(OC(F)(F)F)cc3)n2)cc1]
P543

TABLE P-Two-continued
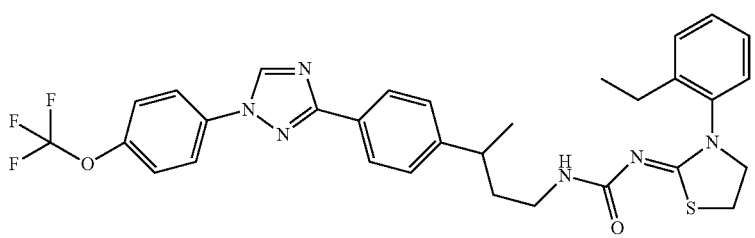 [SMILES: CCc1ccccc1N1CCS/C1=N\C(=O)NCCC(C)c1ccc(-c2ncn(-c3ccc(OC(F)(F)F)cc3)n2)cc1]
P544
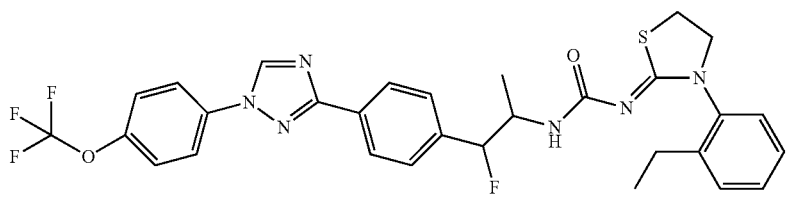 [SMILES: CCc1ccccc1N1CCS/C1=N\C(=O)NC(C)C(F)c1ccc(-c2ncn(-c3ccc(OC(F)(F)F)cc3)n2)cc1]
P545
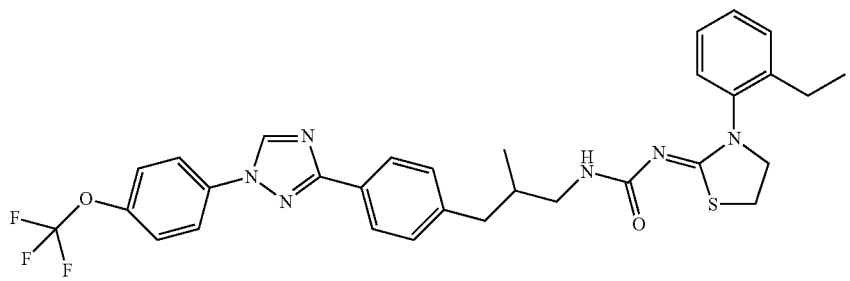 [SMILES: CCc1ccccc1N1CCS/C1=N\C(=O)NCC(C)Cc1ccc(-c2ncn(-c3ccc(OC(F)(F)F)cc3)n2)cc1]
P546
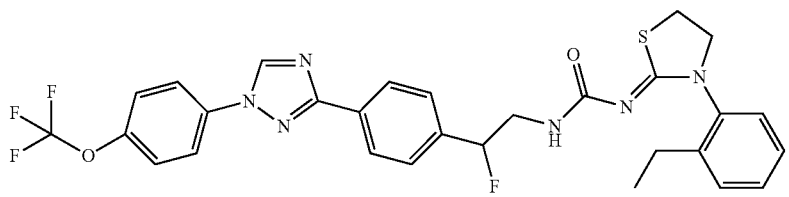 [SMILES: CCc1ccccc1N1CCS/C1=N\C(=O)NCC(F)c1ccc(-c2ncn(-c3ccc(OC(F)(F)F)cc3)n2)cc1]
P547
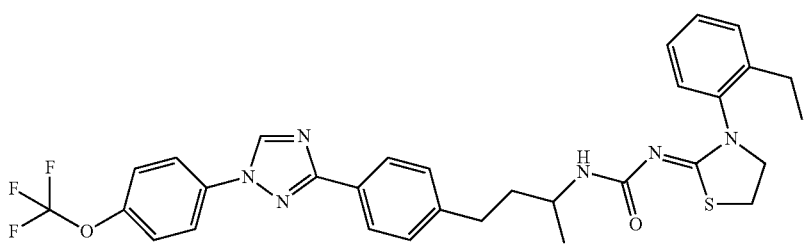 [SMILES: CCc1ccccc1N1CCS/C1=N\C(=O)NC(C)CCc1ccc(-c2ncn(-c3ccc(OC(F)(F)F)cc3)n2)cc1]
P548
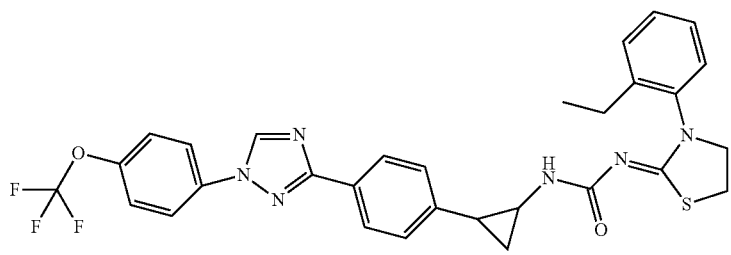 [SMILES: CCc1ccccc1N1CCS/C1=N\C(=O)NC1CC1c1ccc(-c2ncn(-c3ccc(OC(F)(F)F)cc3)n2)cc1]
P549

TABLE P-Two-continued
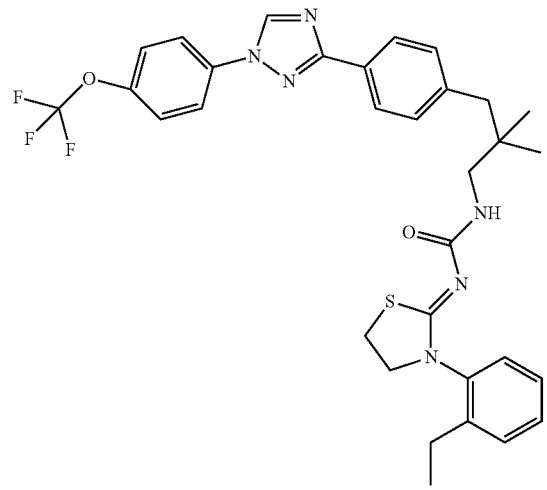 [SMILES: CCc1ccccc1N1CCS/C1=N\C(=O)NCC(C)(C)Cc1ccc(-c2ncn(-c3ccc(OC(F)(F)F)cc3)n2)cc1]
P550
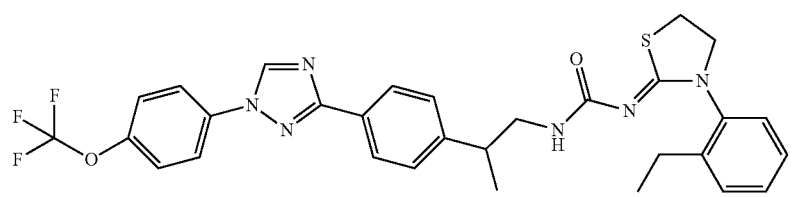 [SMILES: CCc1ccccc1N1CCS/C1=N\C(=O)NCC(C)c1ccc(-c2ncn(-c3ccc(OC(F)(F)F)cc3)n2)cc1]
P551
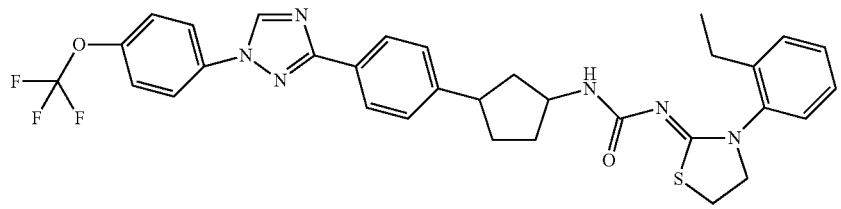 [SMILES: CCc1ccccc1N1CCS/C1=N\C(=O)NC1CCC(c2ccc(-c3ncn(-c4ccc(OC(F)(F)F)cc4)n3)cc2)C1]
P552
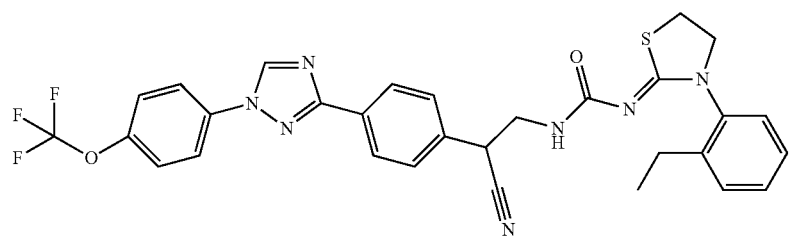 [SMILES: CCc1ccccc1N1CCS/C1=N\C(=O)NCC(C#N)c1ccc(-c2ncn(-c3ccc(OC(F)(F)F)cc3)n2)cc1]
P553
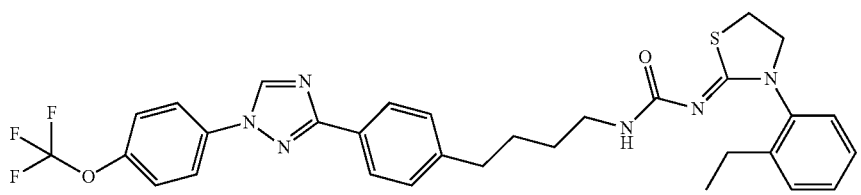 [SMILES: CCc1ccccc1N1CCS/C1=N\C(=O)NCCCCc1ccc(-c2ncn(-c3ccc(OC(F)(F)F)cc3)n2)cc1]
P554

TABLE P-Two-continued
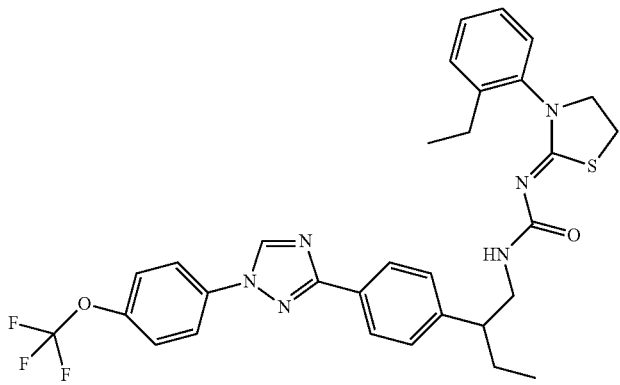 [SMILES: CCc1ccccc1N1CCS/C1=N\C(=O)NCC(CC)c1ccc(-c2ncn(-c3ccc(OC(F)(F)F)cc3)n2)cc1]
P555
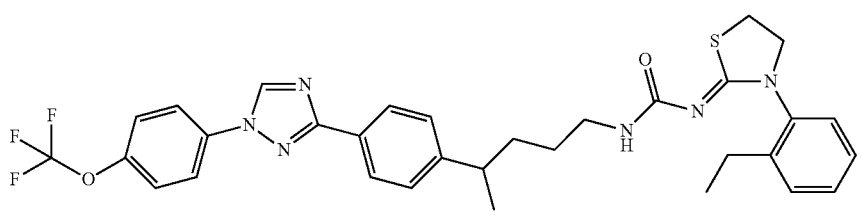 [SMILES: CCc1ccccc1N1CCS/C1=N\C(=O)NCCCC(C)c1ccc(-c2ncn(-c3ccc(OC(F)(F)F)cc3)n2)cc1]
P556
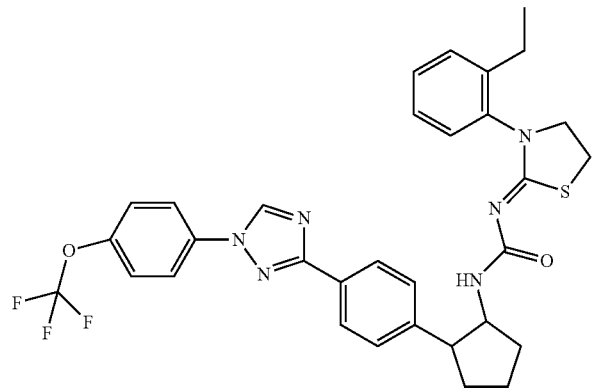 [SMILES: CCc1ccccc1N1CCS/C1=N\C(=O)NC1CCCC1c1ccc(-c2ncn(-c3ccc(OC(F)(F)F)cc3)n2)cc1]
P557
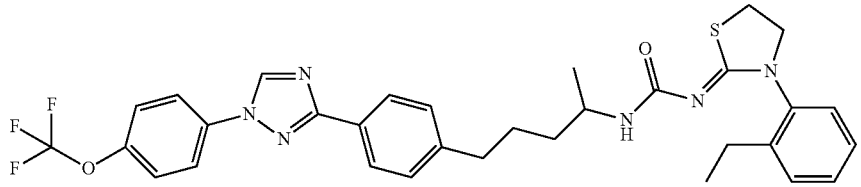 [SMILES: CCc1ccccc1N1CCS/C1=N\C(=O)NC(C)CCCc1ccc(-c2ncn(-c3ccc(OC(F)(F)F)cc3)n2)cc1]
P558
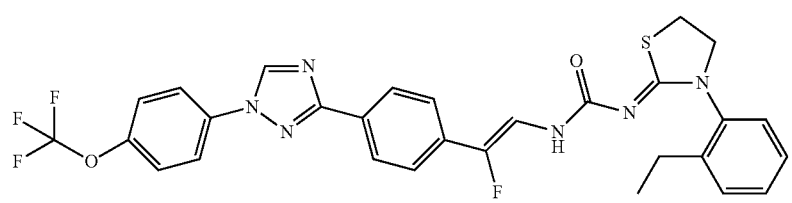 [SMILES: CCc1ccccc1N1CCS/C1=N\C(=O)N/C=C(\F)c1ccc(-c2ncn(-c3ccc(OC(F)(F)F)cc3)n2)cc1]
P559
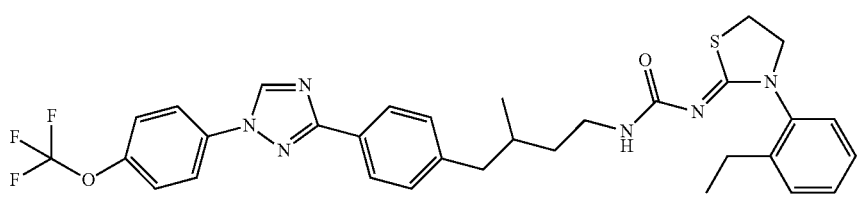 [SMILES: CCc1ccccc1N1CCS/C1=N\C(=O)NCCC(C)Cc1ccc(-c2ncn(-c3ccc(OC(F)(F)F)cc3)n2)cc1]
P560

TABLE P-Two-continued
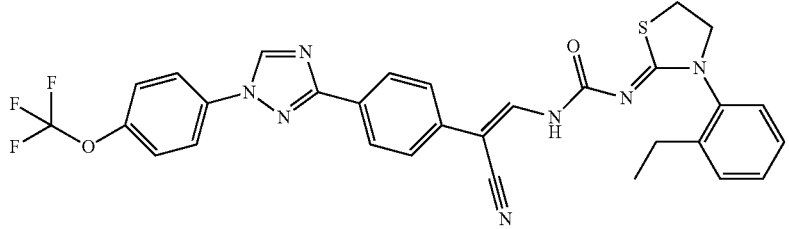 [SMILES: CCc1ccccc1N1CCS/C1=N\C(=O)N/C=C(\C#N)c1ccc(-c2ncn(-c3ccc(OC(F)(F)F)cc3)n2)cc1]
P561
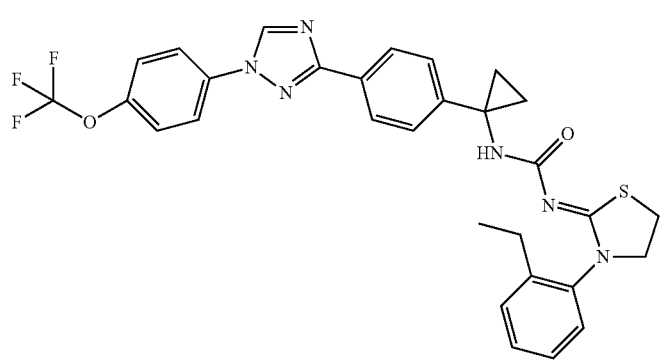 [SMILES: CCc1ccccc1N1CCS/C1=N\C(=O)NC1(c2ccc(-c3ncn(-c4ccc(OC(F)(F)F)cc4)n3)cc2)CC1]
P562
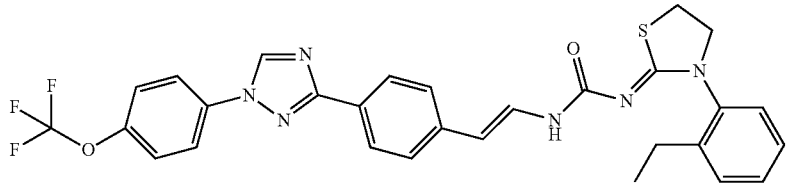 [SMILES: CCc1ccccc1N1CCS/C1=N\C(=O)N/C=C/c1ccc(-c2ncn(-c3ccc(OC(F)(F)F)cc3)n2)cc1]
P563
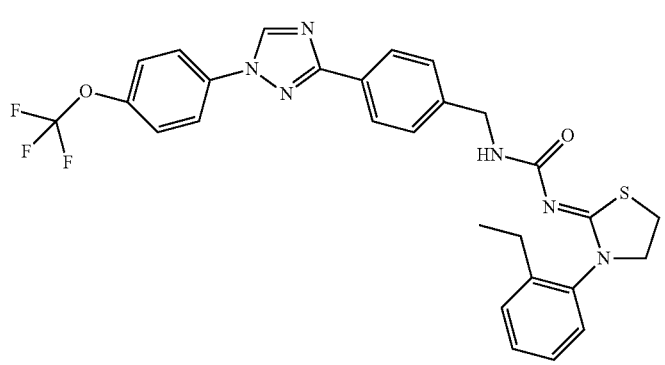 [SMILES: CCc1ccccc1N1CCS/C1=N\C(=O)NCc1ccc(-c2ncn(-c3ccc(OC(F)(F)F)cc3)n2)cc1]
P564
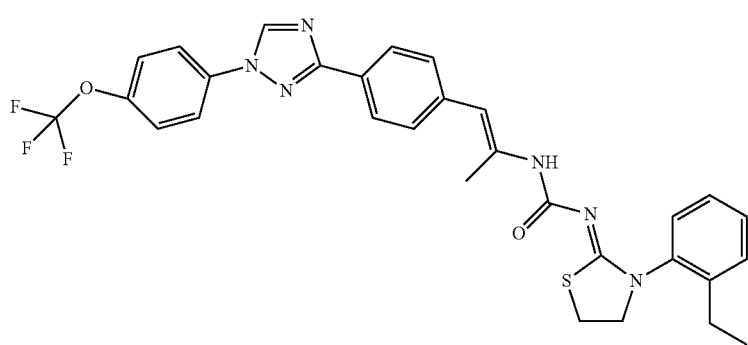 [SMILES: CCc1ccccc1N1CCS/C1=N\C(=O)N/C(C)=C/c1ccc(-c2ncn(-c3ccc(OC(F)(F)F)cc3)n2)cc1]
P565

TABLE P-Two-continued
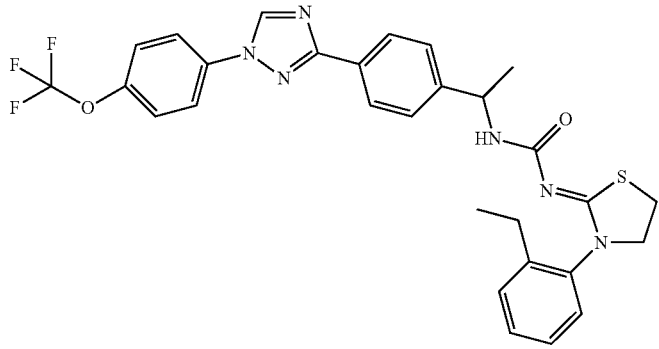 [SMILES: CCc1ccccc1N1CCS/C1=N\C(=O)NC(C)c1ccc(-c2ncn(-c3ccc(OC(F)(F)F)cc3)n2)cc1]
P566
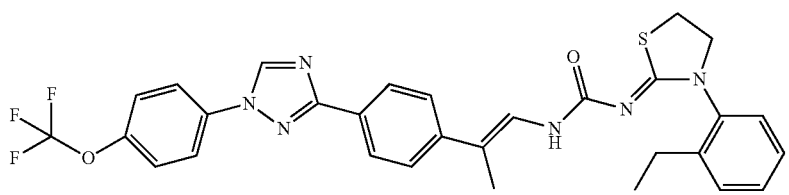 [SMILES: CCc1ccccc1N1CCS/C1=N\C(=O)N/C=C(\C)c1ccc(-c2ncn(-c3ccc(OC(F)(F)F)cc3)n2)cc1]
P567
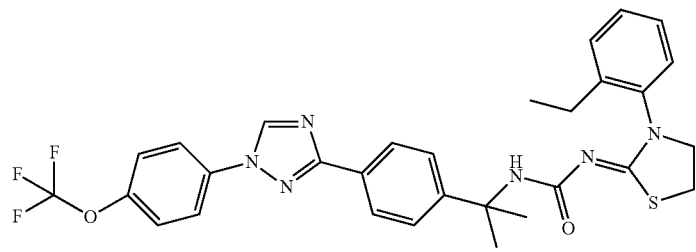 [SMILES: CCc1ccccc1N1CCS/C1=N\C(=O)NC(C)(C)c1ccc(-c2ncn(-c3ccc(OC(F)(F)F)cc3)n2)cc1]
P568
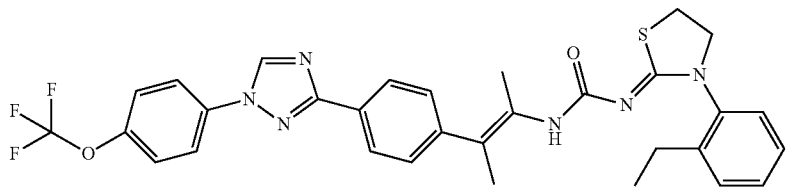 [SMILES: CCc1ccccc1N1CCS/C1=N\C(=O)N/C(C)=C(\C)c1ccc(-c2ncn(-c3ccc(OC(F)(F)F)cc3)n2)cc1]
P569
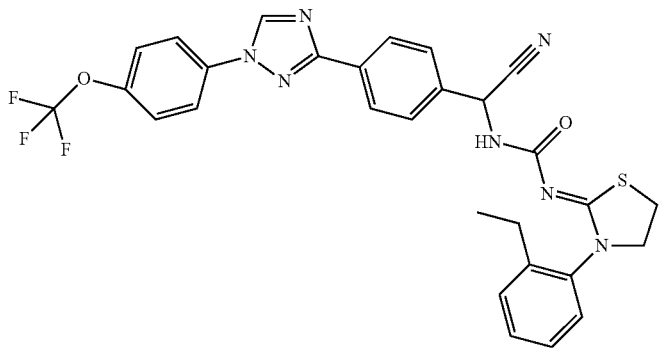 [SMILES: CCc1ccccc1N1CCS/C1=N\C(=O)NC(C#N)c1ccc(-c2ncn(-c3ccc(OC(F)(F)F)cc3)n2)cc1]
P570

TABLE P-Two-continued
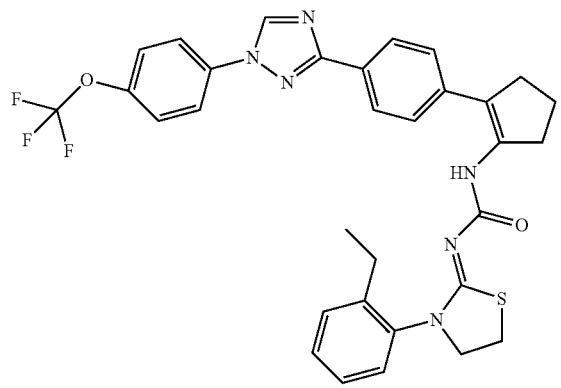 [SMILES: CCc1ccccc1N1CCS/C1=N\C(=O)NC1=C(c2ccc(-c3ncn(-c4ccc(OC(F)(F)F)cc4)n3)cc2)CCC1]
P571
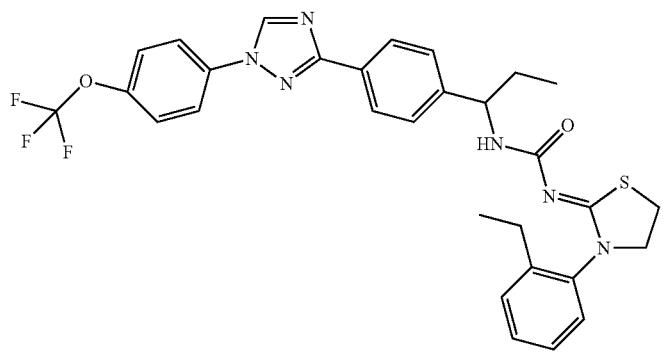 [SMILES: CCc1ccccc1N1CCS/C1=N\C(=O)NC(CC)c1ccc(-c2ncn(-c3ccc(OC(F)(F)F)cc3)n2)cc1]
P572
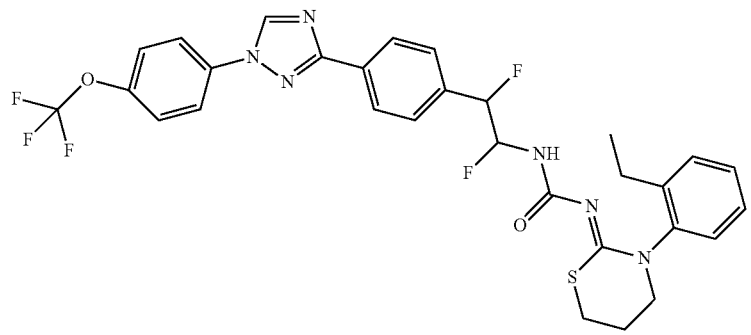 [SMILES: CCc1ccccc1N1CCCS/C1=N\C(=O)NC(F)C(F)c1ccc(-c2ncn(-c3ccc(OC(F)(F)F)cc3)n2)cc1]
P573
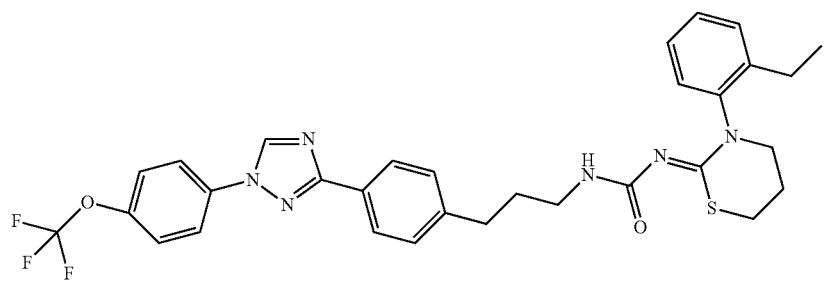 [SMILES: CCc1ccccc1N1CCCS/C1=N\C(=O)NCCCc1ccc(-c2ncn(-c3ccc(OC(F)(F)F)cc3)n2)cc1]
P574

TABLE P-Two-continued
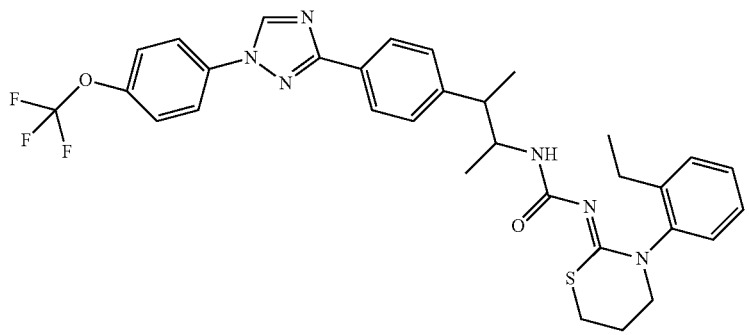 [SMILES: CCc1ccccc1N1CCCS/C1=N\C(=O)NC(C)C(C)c1ccc(-c2ncn(-c3ccc(OC(F)(F)F)cc3)n2)cc1]
P575
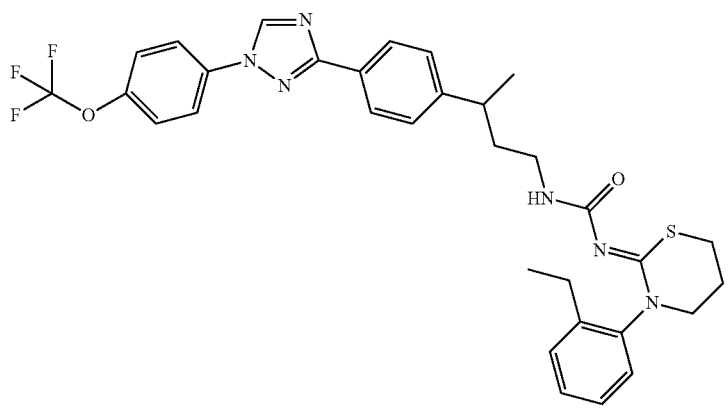 [SMILES: CCc1ccccc1N1CCCS/C1=N\C(=O)NCCC(C)c1ccc(-c2ncn(-c3ccc(OC(F)(F)F)cc3)n2)cc1]
P576
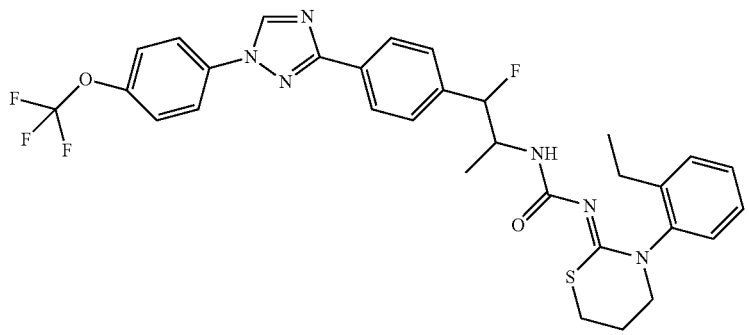 [SMILES: CCc1ccccc1N1CCCS/C1=N\C(=O)NC(C)C(F)c1ccc(-c2ncn(-c3ccc(OC(F)(F)F)cc3)n2)cc1]
P577
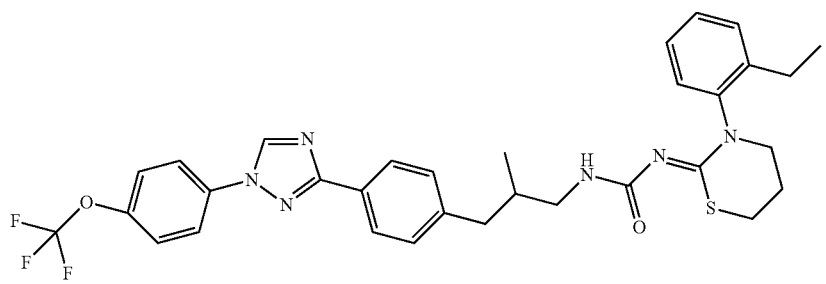 [SMILES: CCc1ccccc1N1CCCS/C1=N\C(=O)NCC(C)Cc1ccc(-c2ncn(-c3ccc(OC(F)(F)F)cc3)n2)cc1]
P578

TABLE P-Two-continued
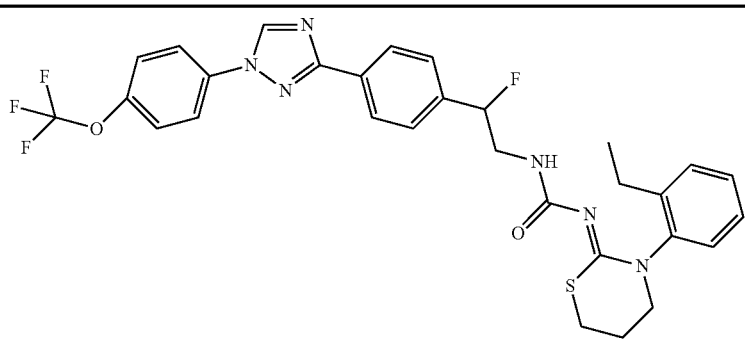
P579
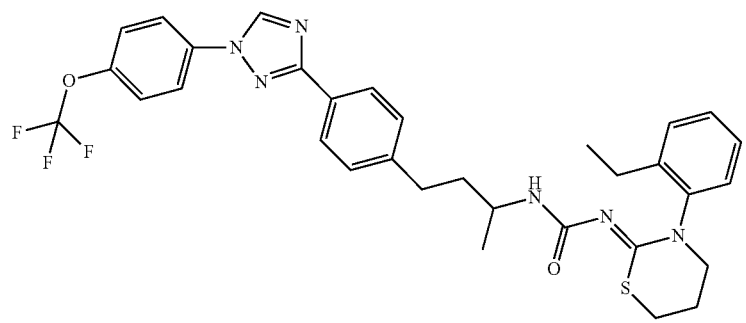 [SMILES: CCc1ccccc1N1CCCS/C1=N\C(=O)NC(C)CCc1ccc(-c2ncn(-c3ccc(OC(F)(F)F)cc3)n2)cc1]
P580
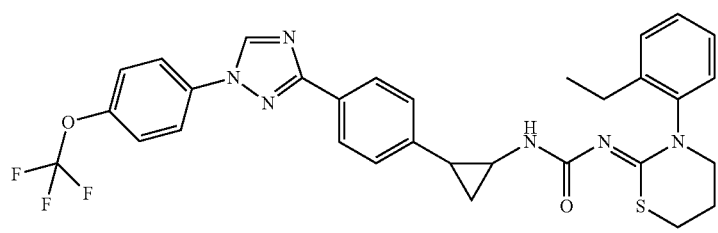 [SMILES: CCc1ccccc1N1CCCS/C1=N\C(=O)NC1CC1c1ccc(-c2ncn(-c3ccc(OC(F)(F)F)cc3)n2)cc1]
P581
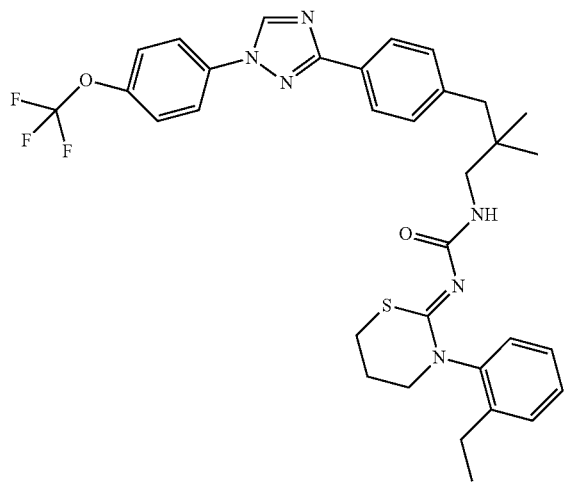 [SMILES: CCc1ccccc1N1CCCS/C1=N\C(=O)NCC(C)(C)Cc1ccc(-c2ncn(-c3ccc(OC(F)(F)F)cc3)n2)cc1]
P582

TABLE P-Two-continued
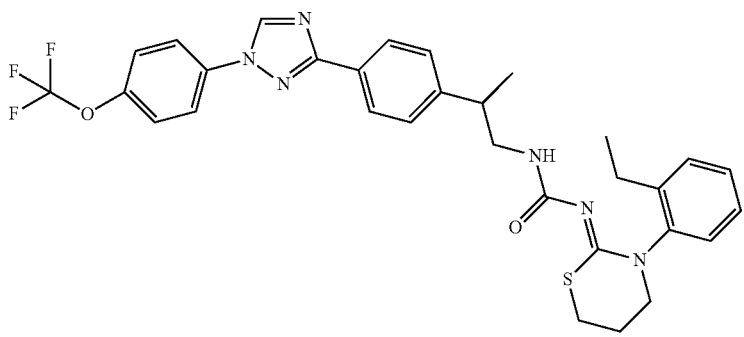 [SMILES: CCc1ccccc1N1CCCS/C1=N\C(=O)NCC(C)c1ccc(-c2ncn(-c3ccc(OC(F)(F)F)cc3)n2)cc1]
P583
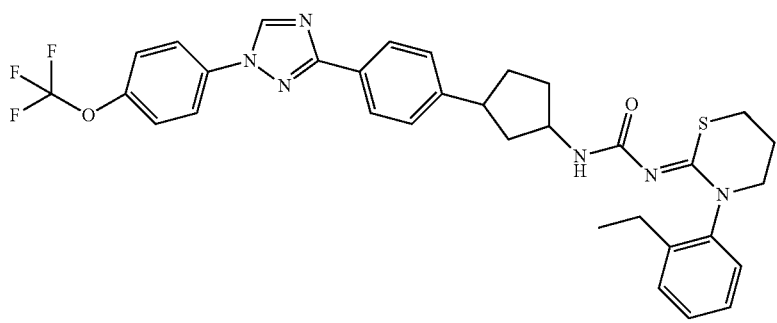 [SMILES: CCc1ccccc1N1CCCS/C1=N\C(=O)NC1CCC(c2ccc(-c3ncn(-c4ccc(OC(F)(F)F)cc4)n3)cc2)C1]
P584
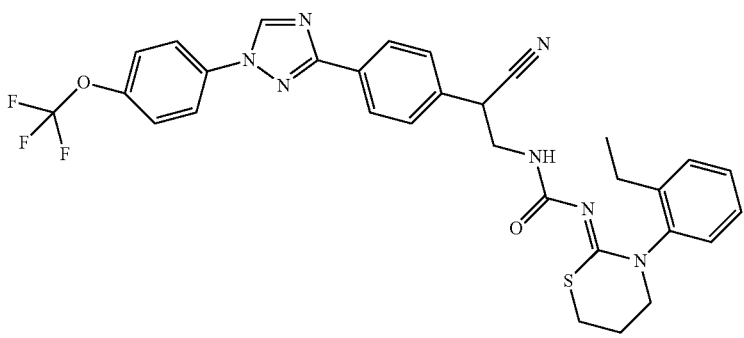 [SMILES: CCc1ccccc1N1CCCS/C1=N\C(=O)NCC(C#N)c1ccc(-c2ncn(-c3ccc(OC(F)(F)F)cc3)n2)cc1]
P585
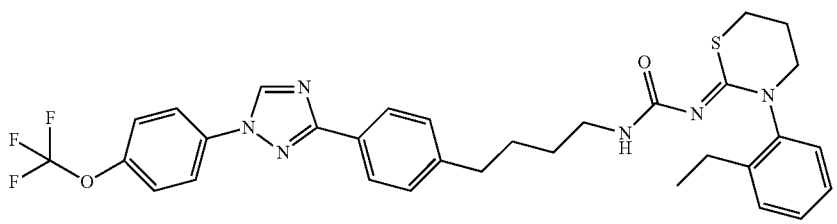 [SMILES: CCc1ccccc1N1CCCS/C1=N\C(=O)NCCCCc1ccc(-c2ncn(-c3ccc(OC(F)(F)F)cc3)n2)cc1]
P586
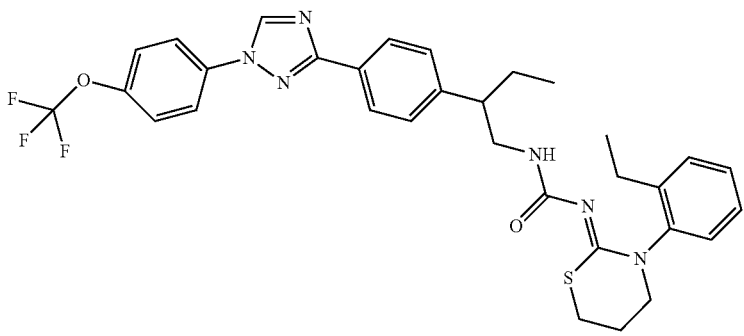 [SMILES: CCc1ccccc1N1CCCS/C1=N\C(=O)NCC(CC)c1ccc(-c2ncn(-c3ccc(OC(F)(F)F)cc3)n2)cc1]
P587

TABLE P-Two-continued
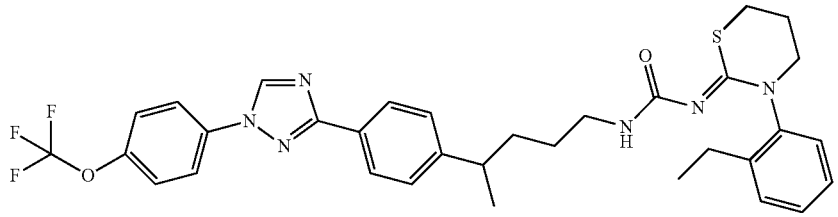 [SMILES: CCc1ccccc1N1CCCS/C1=N\C(=O)NCCCC(C)c1ccc(-c2ncn(-c3ccc(OC(F)(F)F)cc3)n2)cc1]
P588
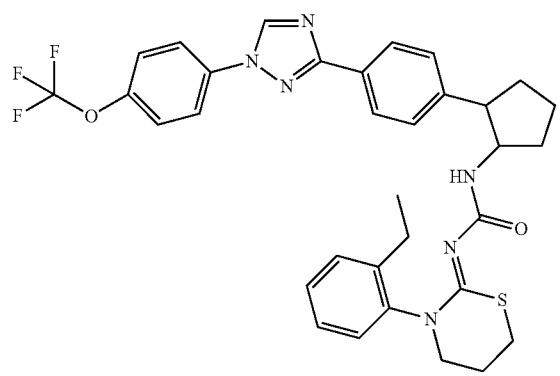 [SMILES: CCc1ccccc1N1CCCS/C1=N\C(=O)NC1CCCC1c1ccc(-c2ncn(-c3ccc(OC(F)(F)F)cc3)n2)cc1]
P589
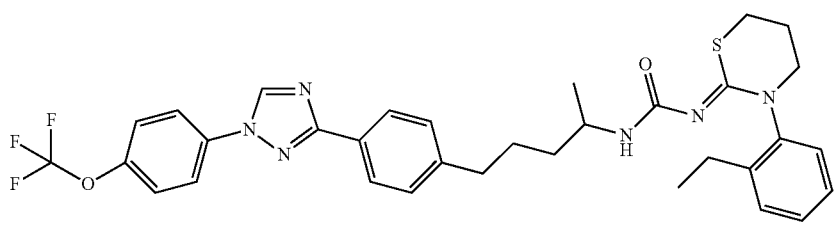 [SMILES: CCc1ccccc1N1CCCS/C1=N\C(=O)NC(C)CCCc1ccc(-c2ncn(-c3ccc(OC(F)(F)F)cc3)n2)cc1]
P590
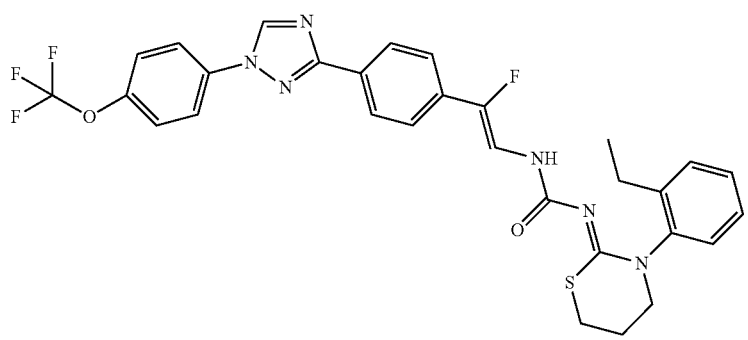
P591
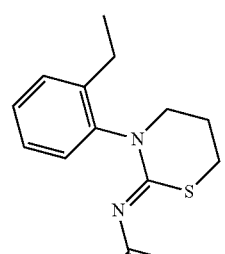
P592
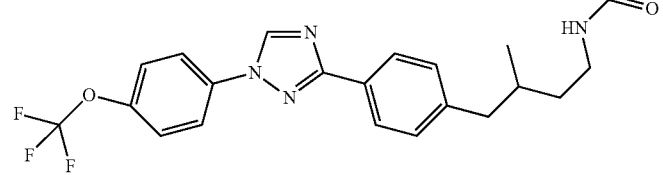

TABLE P-Two-continued
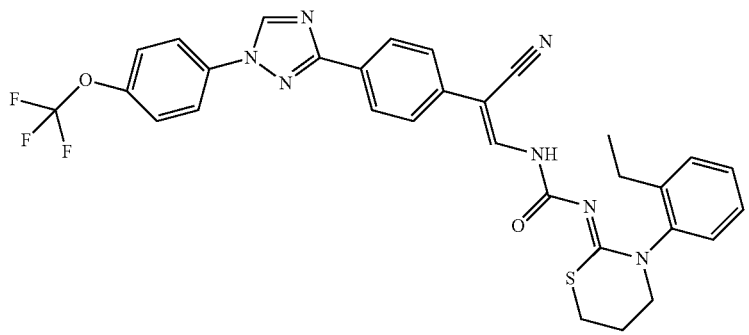 [SMILES: CCc1ccccc1N1CCCS/C1=N\C(=O)N/C=C(\C#N)c1ccc(-c2ncn(-c3ccc(OC(F)(F)F)cc3)n2)cc1]
P593
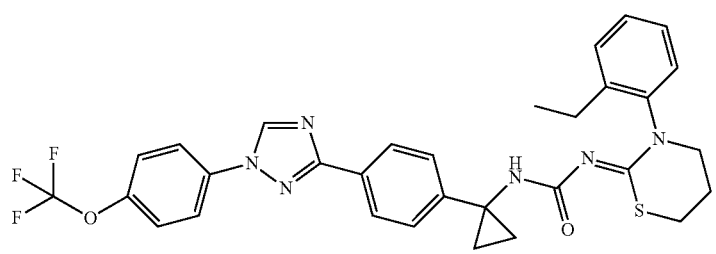 [SMILES: CCc1ccccc1N1CCCS/C1=N\C(=O)NC1(c2ccc(-c3ncn(-c4ccc(OC(F)(F)F)cc4)n3)cc2)CC1]
P594
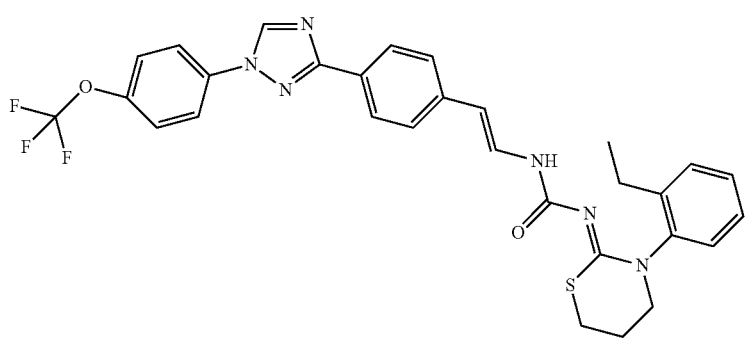 [SMILES: CCc1ccccc1N1CCCS/C1=N\C(=O)N/C=C/c1ccc(-c2ncn(-c3ccc(OC(F)(F)F)cc3)n2)cc1]
P595
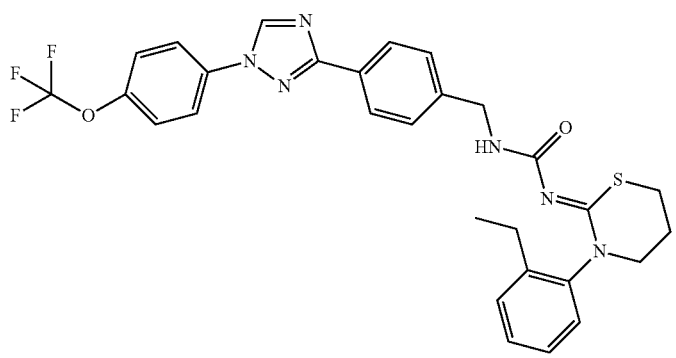 [SMILES: CCc1ccccc1N1CCCS/C1=N\C(=O)NCc1ccc(-c2ncn(-c3ccc(OC(F)(F)F)cc3)n2)cc1]
P596
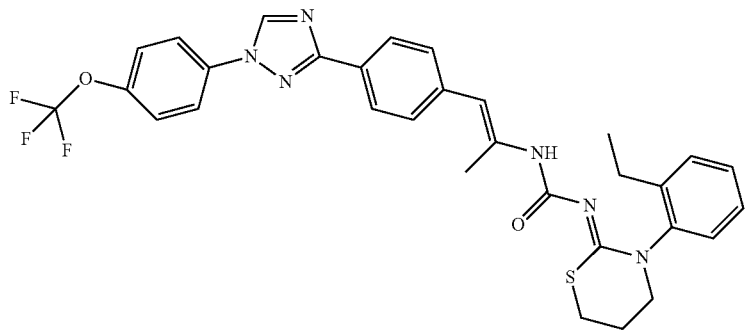 [SMILES: CCc1ccccc1N1CCCS/C1=N\C(=O)N/C(C)=C/c1ccc(-c2ncn(-c3ccc(OC(F)(F)F)cc3)n2)cc1]
P597

TABLE P-Two-continued
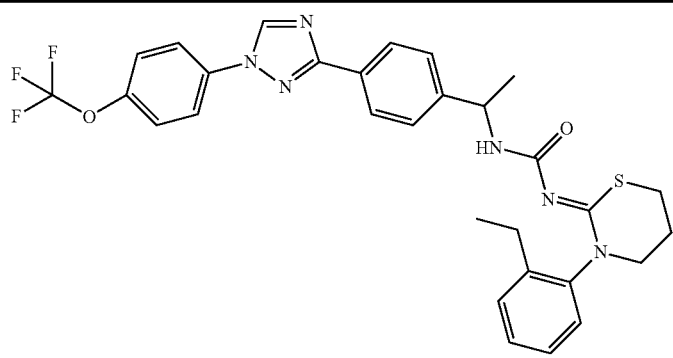
P598
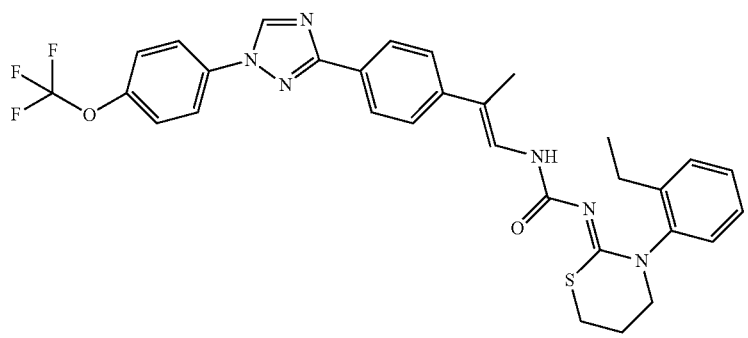 [SMILES: CCc1ccccc1N1CCCS/C1=N\C(=O)N/C=C(\C)c1ccc(-c2ncn(-c3ccc(OC(F)(F)F)cc3)n2)cc1]
P599
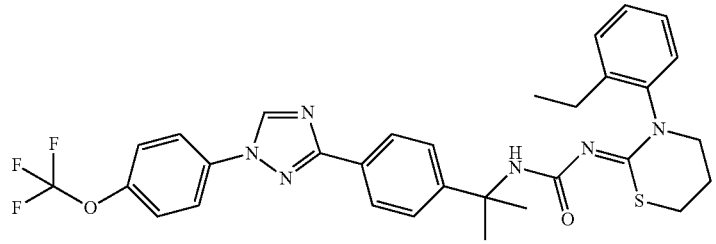 [SMILES: CCc1ccccc1N1CCCS/C1=N\C(=O)NC(C)(C)c1ccc(-c2ncn(-c3ccc(OC(F)(F)F)cc3)n2)cc1]
P600
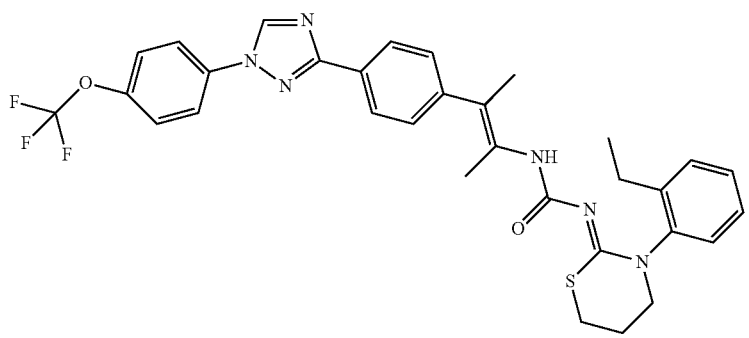 [SMILES: CCc1ccccc1N1CCCS/C1=N\C(=O)N/C(C)=C(\C)c1ccc(-c2ncn(-c3ccc(OC(F)(F)F)cc3)n2)cc1]
P601
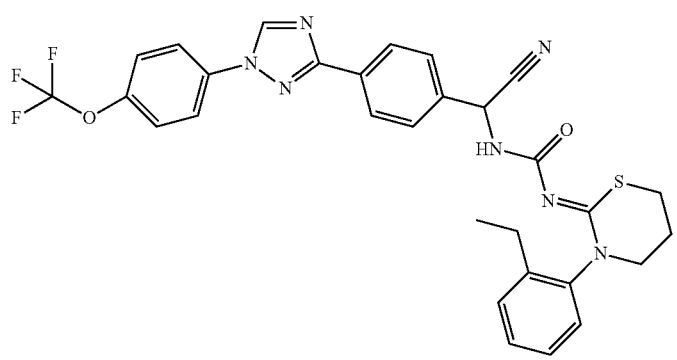 [SMILES: CCc1ccccc1N1CCCS/C1=N\C(=O)NC(C#N)c1ccc(-c2ncn(-c3ccc(OC(F)(F)F)cc3)n2)cc1]
P602

TABLE P-Two-continued
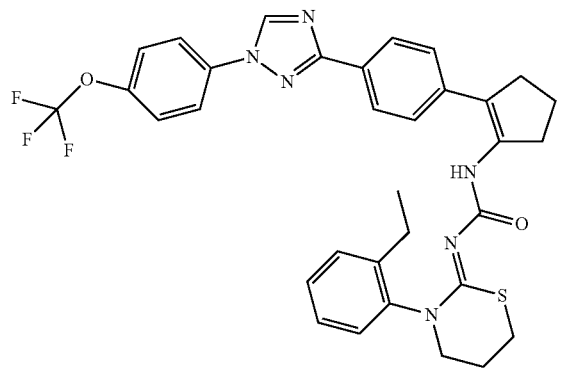 [SMILES: CCc1ccccc1N1CCCS/C1=N\C(=O)NC1=C(c2ccc(-c3ncn(-c4ccc(OC(F)(F)F)cc4)n3)cc2)CCC1]
P603
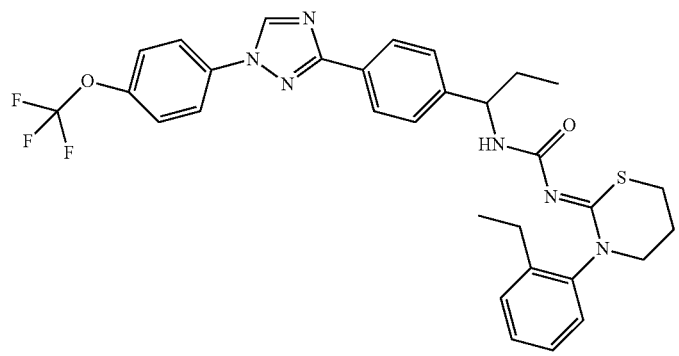 [SMILES: CCc1ccccc1N1CCCS/C1=N\C(=O)NC(CC)c1ccc(-c2ncn(-c3ccc(OC(F)(F)F)cc3)n2)cc1]
P604
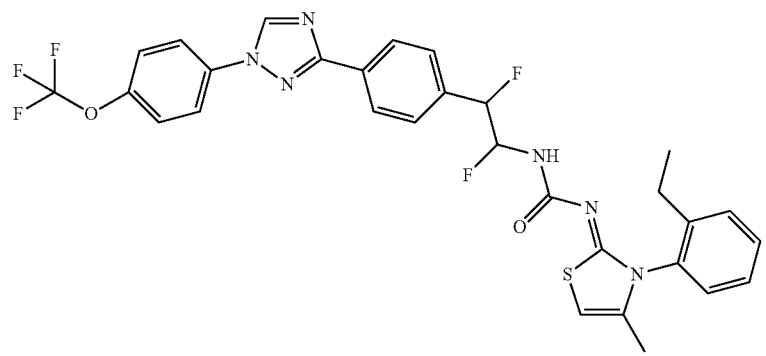 [SMILES: CCc1ccccc1-n1c(C)cs/c1=N\C(=O)NC(F)C(F)c1ccc(-c2ncn(-c3ccc(OC(F)(F)F)cc3)n2)cc1]
P605
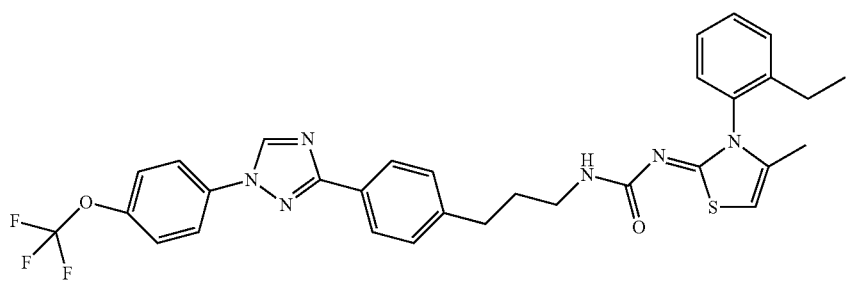 [SMILES: CCc1ccccc1-n1c(C)cs/c1=N\C(=O)NCCCc1ccc(-c2ncn(-c3ccc(OC(F)(F)F)cc3)n2)cc1]
P606

TABLE P-Two-continued
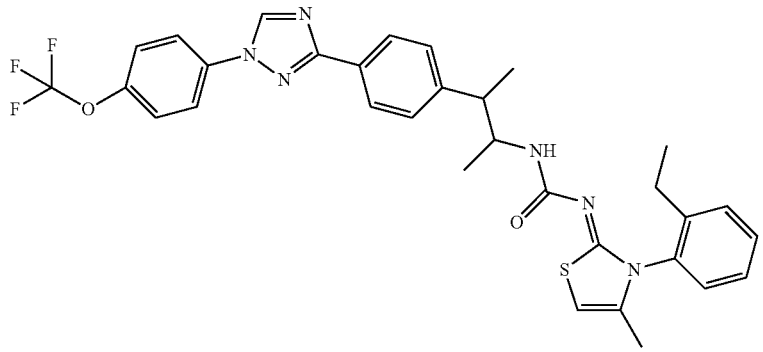
P607
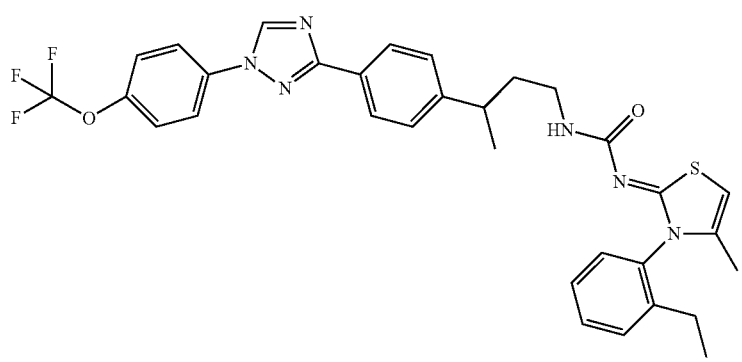 [SMILES: CCc1ccccc1-n1c(C)cs/c1=N\C(=O)NCCC(C)c1ccc(-c2ncn(-c3ccc(OC(F)(F)F)cc3)n2)cc1]
P608
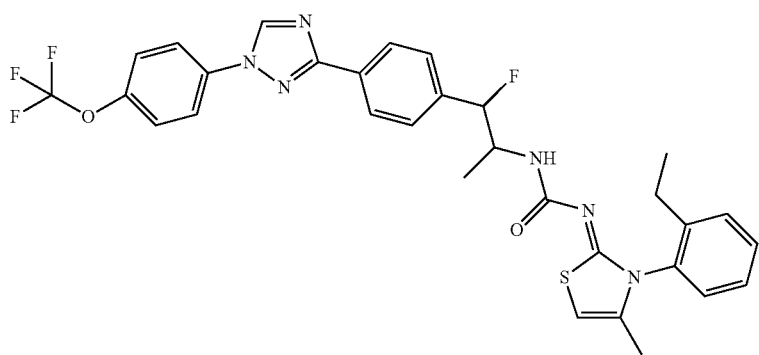
P609
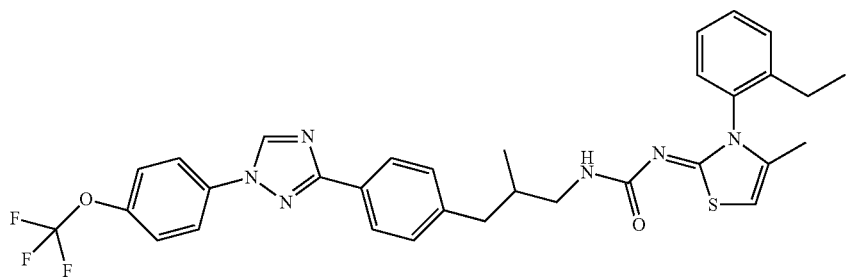 [SMILES: CCc1ccccc1-n1c(C)cs/c1=N\C(=O)NCC(C)Cc1ccc(-c2ncn(-c3ccc(OC(F)(F)F)cc3)n2)cc1]
P610

TABLE P-Two-continued
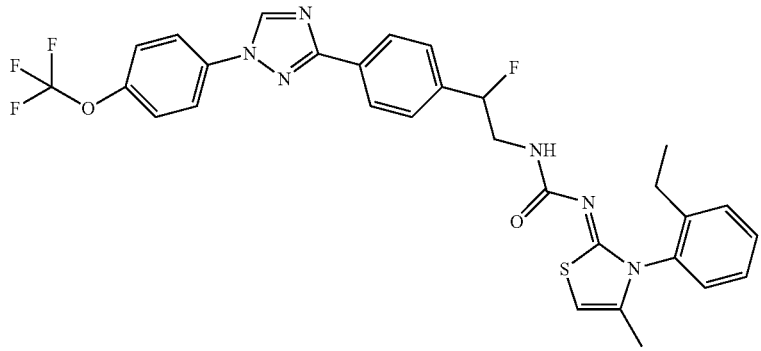 [SMILES: CCc1ccccc1-n1c(C)cs/c1=N\C(=O)NCC(F)c1ccc(-c2ncn(-c3ccc(OC(F)(F)F)cc3)n2)cc1]
P611
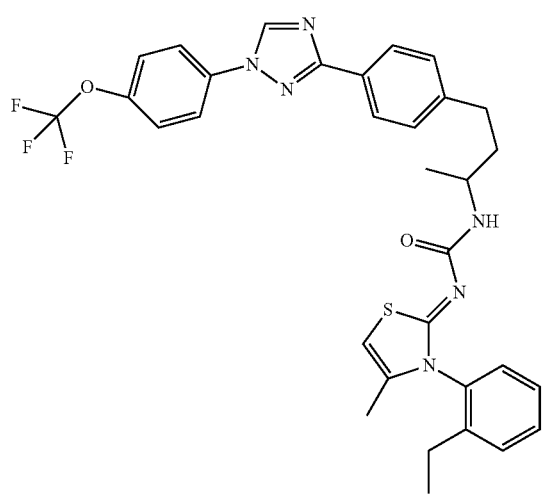 [SMILES: CCc1ccccc1-n1c(C)cs/c1=N\C(=O)NC(C)CCc1ccc(-c2ncn(-c3ccc(OC(F)(F)F)cc3)n2)cc1]
P612
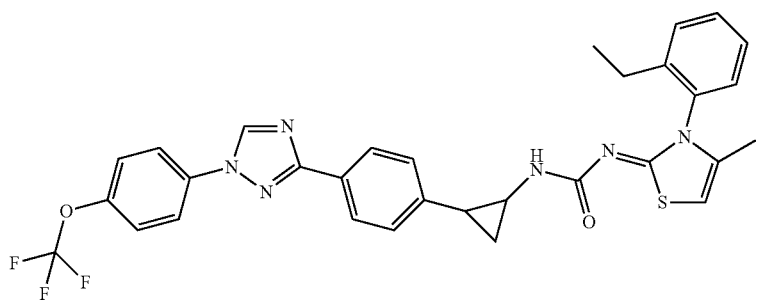 [SMILES: CCc1ccccc1-n1c(C)cs/c1=N\C(=O)NC1CC1c1ccc(-c2ncn(-c3ccc(OC(F)(F)F)cc3)n2)cc1]
P613
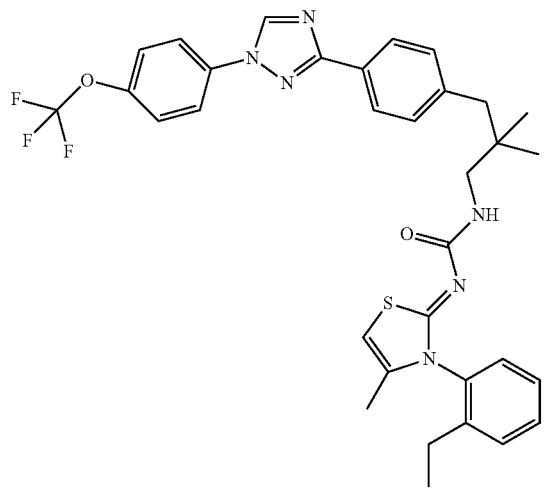 [SMILES: CCc1ccccc1-n1c(C)cs/c1=N\C(=O)NCC(C)(C)Cc1ccc(-c2ncn(-c3ccc(OC(F)(F)F)cc3)n2)cc1]
P614

TABLE P-Two-continued
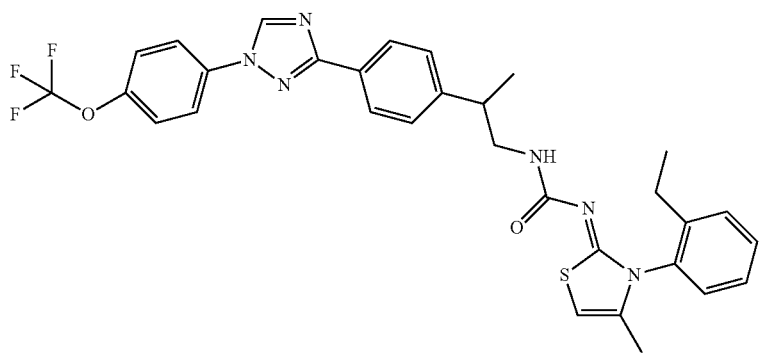
P615
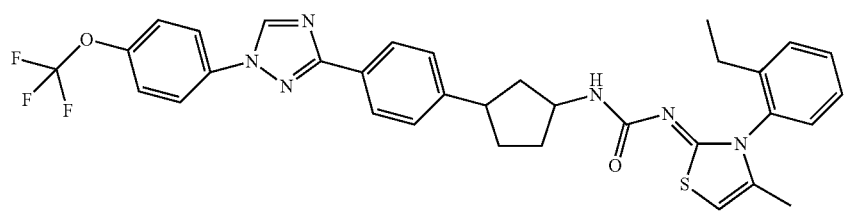 [SMILES: CCc1ccccc1-n1c(C)cs/c1=N\C(=O)NC1CCC(c2ccc(-c3ncn(-c4ccc(OC(F)(F)F)cc4)n3)cc2)C1]
P616
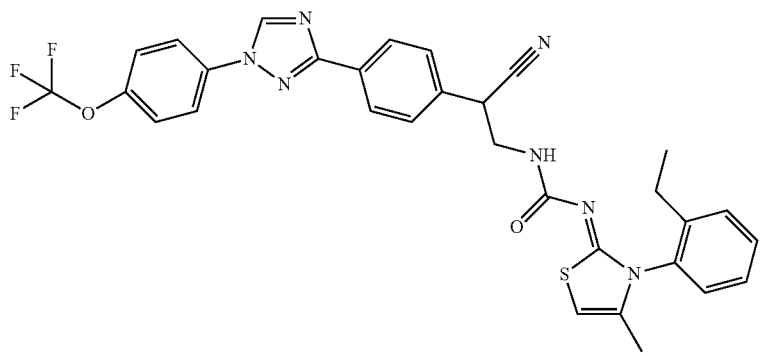 [SMILES: CCc1ccccc1-n1c(C)cs/c1=N\C(=O)NCC(C#N)c1ccc(-c2ncn(-c3ccc(OC(F)(F)F)cc3)n2)cc1]
P617
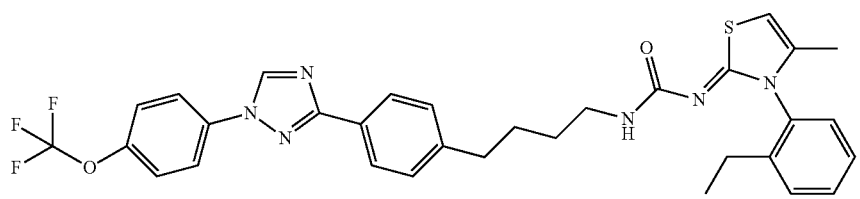 [SMILES: CCc1ccccc1-n1c(C)cs/c1=N\C(=O)NCCCCc1ccc(-c2ncn(-c3ccc(OC(F)(F)F)cc3)n2)cc1]
P618
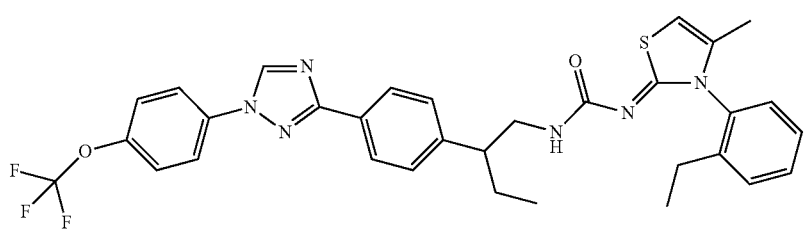 [SMILES: CCc1ccccc1-n1c(C)cs/c1=N\C(=O)NCC(CC)c1ccc(-c2ncn(-c3ccc(OC(F)(F)F)cc3)n2)cc1]
P619
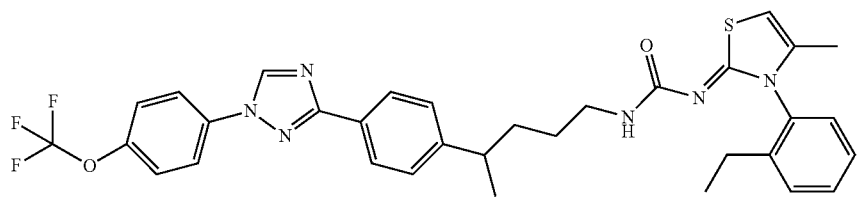 [SMILES: CCc1ccccc1-n1c(C)cs/c1=N\C(=O)NCCCC(C)c1ccc(-c2ncn(-c3ccc(OC(F)(F)F)cc3)n2)cc1]
P620

TABLE P-Two-continued
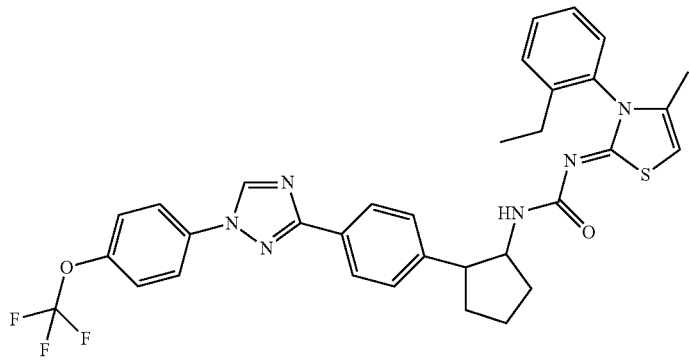 [SMILES: CCc1ccccc1-n1c(C)cs/c1=N\C(=O)NC1CCCC1c1ccc(-c2ncn(-c3ccc(OC(F)(F)F)cc3)n2)cc1]
P621
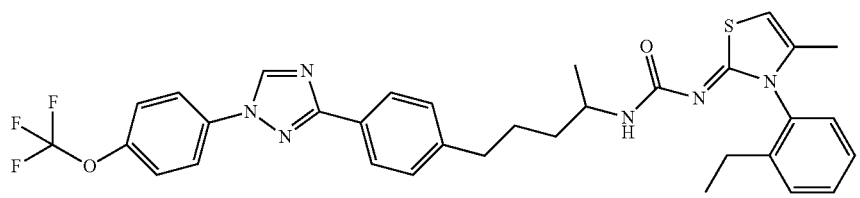 [SMILES: CCc1ccccc1-n1c(C)cs/c1=N\C(=O)NC(C)CCCc1ccc(-c2ncn(-c3ccc(OC(F)(F)F)cc3)n2)cc1]
P622
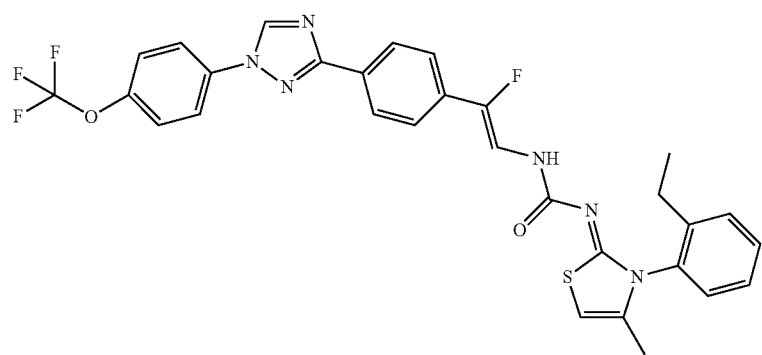 [SMILES: CCc1ccccc1-n1c(C)cs/c1=N\C(=O)N/C=C(\F)c1ccc(-c2ncn(-c3ccc(OC(F)(F)F)cc3)n2)cc1]
P623
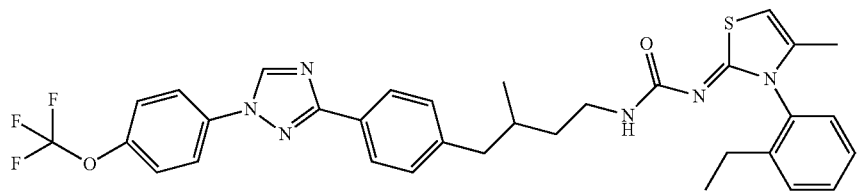 [SMILES: CCc1ccccc1-n1c(C)cs/c1=N\C(=O)NCCC(C)Cc1ccc(-c2ncn(-c3ccc(OC(F)(F)F)cc3)n2)cc1]
P624
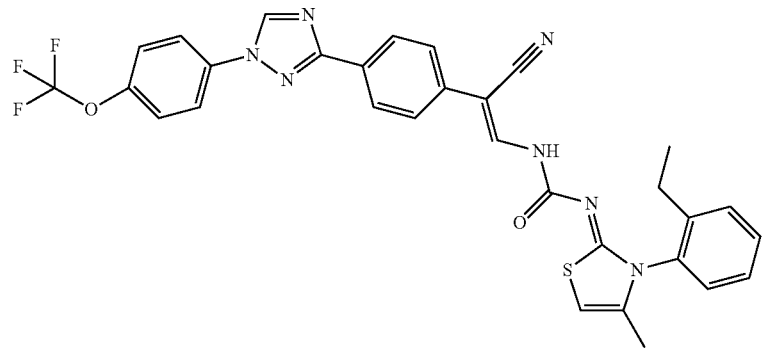 [SMILES: CCc1ccccc1-n1c(C)cs/c1=N\C(=O)N/C=C(\C#N)c1ccc(-c2ncn(-c3ccc(OC(F)(F)F)cc3)n2)cc1]
P625

TABLE P-Two-continued
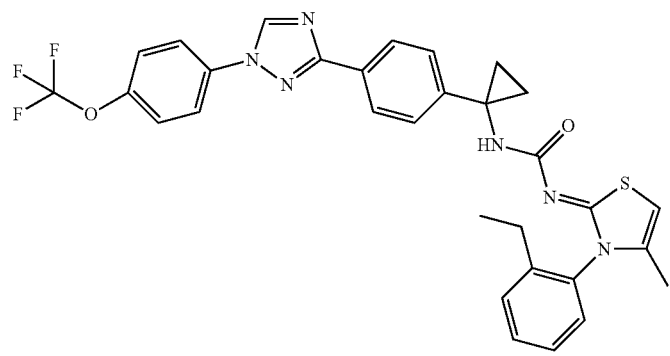 [SMILES: CCc1ccccc1-n1c(C)cs/c1=N\C(=O)NC1(c2ccc(-c3ncn(-c4ccc(OC(F)(F)F)cc4)n3)cc2)CC1]
P626
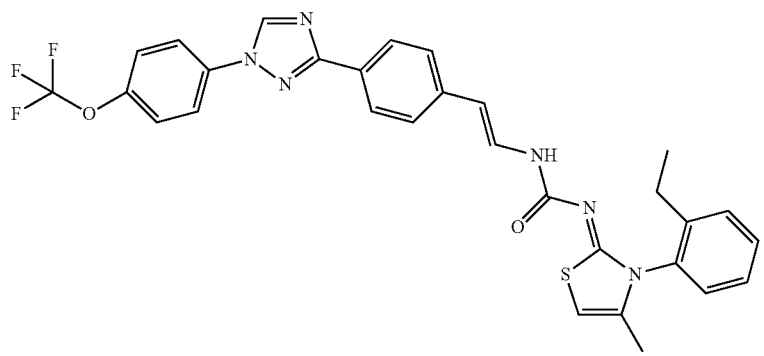 [SMILES: CCc1ccccc1-n1c(C)cs/c1=N\C(=O)N/C=C/c1ccc(-c2ncn(-c3ccc(OC(F)(F)F)cc3)n2)cc1]
P627
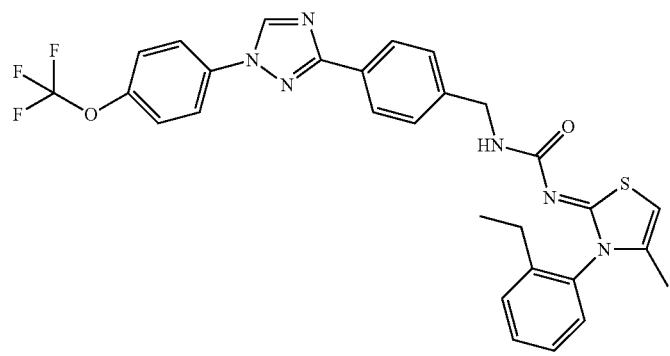 [SMILES: CCc1ccccc1-n1c(C)cs/c1=N\C(=O)NCc1ccc(-c2ncn(-c3ccc(OC(F)(F)F)cc3)n2)cc1]
P628
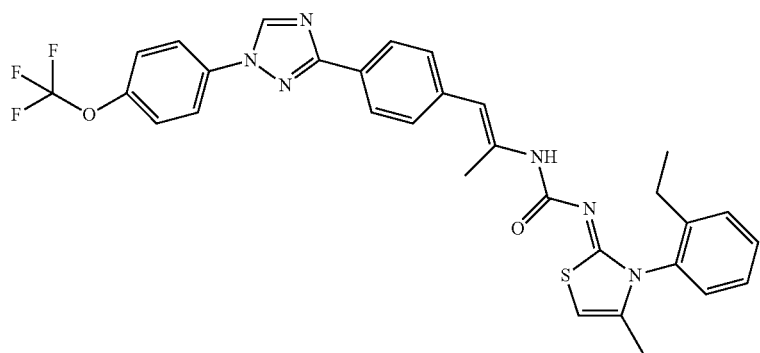 [SMILES: CCc1ccccc1-n1c(C)cs/c1=N\C(=O)N/C(C)=C/c1ccc(-c2ncn(-c3ccc(OC(F)(F)F)cc3)n2)cc1]
P629

TABLE P-Two-continued
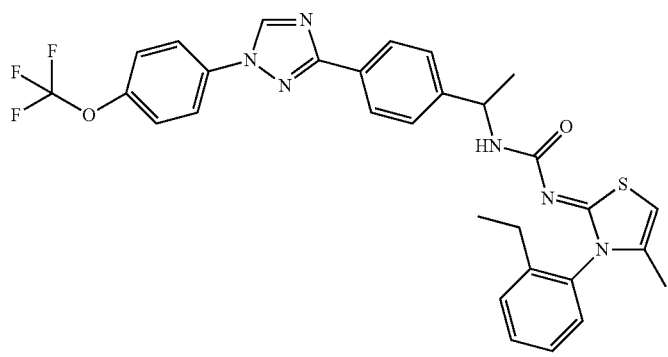 [SMILES: CCc1ccccc1-n1c(C)cs/c1=N\C(=O)NC(C)c1ccc(-c2ncn(-c3ccc(OC(F)(F)F)cc3)n2)cc1]
P630
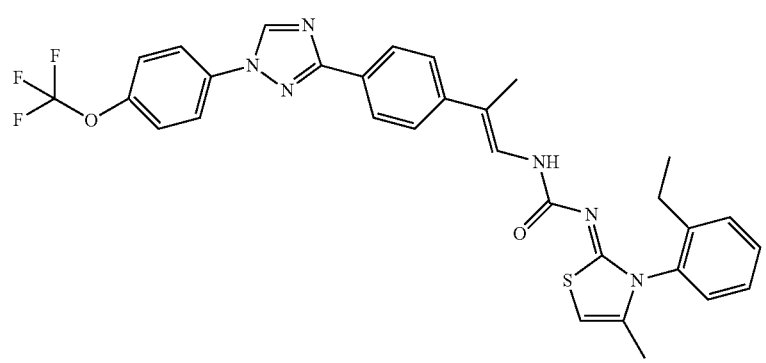 [SMILES: CCc1ccccc1-n1c(C)cs/c1=N\C(=O)N/C=C(\C)c1ccc(-c2ncn(-c3ccc(OC(F)(F)F)cc3)n2)cc1]
P631
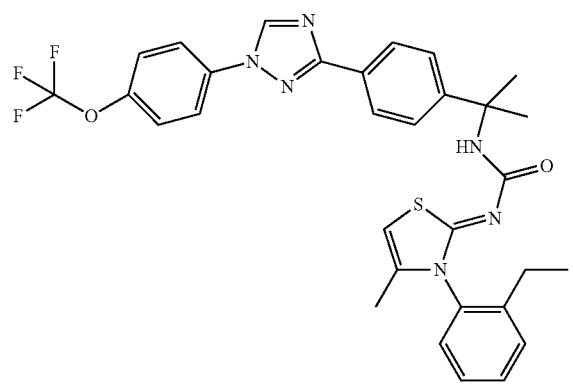 [SMILES: CCc1ccccc1-n1c(C)cs/c1=N\C(=O)NC(C)(C)c1ccc(-c2ncn(-c3ccc(OC(F)(F)F)cc3)n2)cc1]
P632
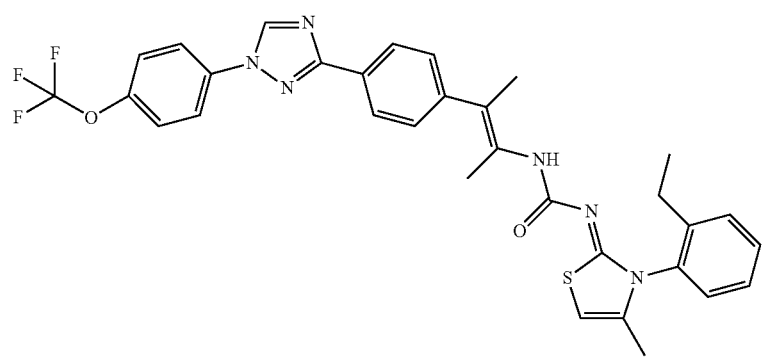
P633

TABLE P-Two-continued
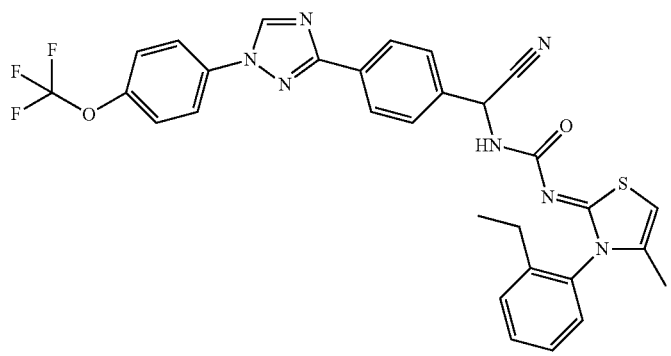 [SMILES: CCc1ccccc1-n1c(C)cs/c1=N\C(=O)NC(C#N)c1ccc(-c2ncn(-c3ccc(OC(F)(F)F)cc3)n2)cc1]
P634
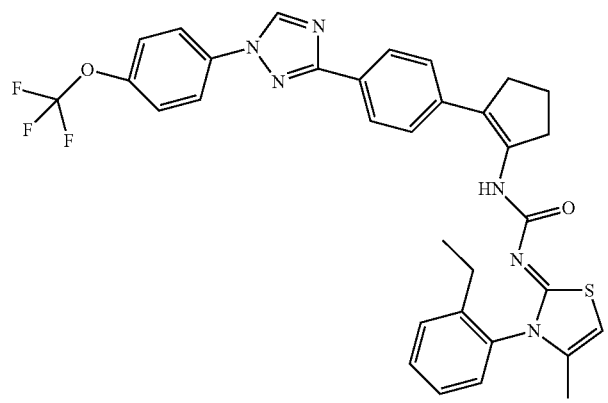 [SMILES: CCc1ccccc1-n1c(C)cs/c1=N\C(=O)NC1=C(c2ccc(-c3ncn(-c4ccc(OC(F)(F)F)cc4)n3)cc2)CCC1]
P635
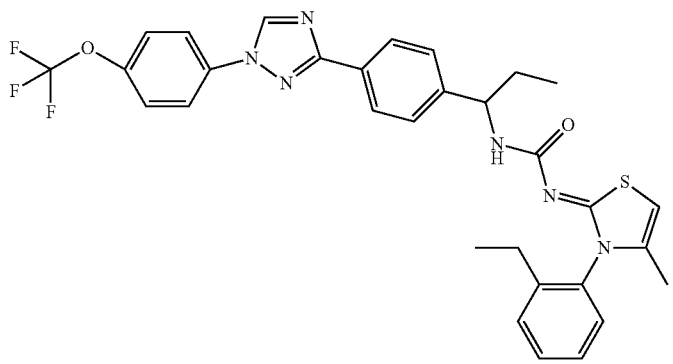 [SMILES: CCc1ccccc1-n1c(C)cs/c1=N\C(=O)NC(CC)c1ccc(-c2ncn(-c3ccc(OC(F)(F)F)cc3)n2)cc1]
P636
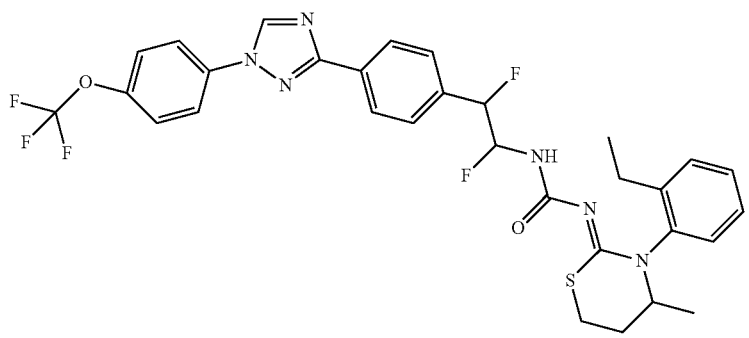 [SMILES: CCc1ccccc1N1/C(=N/C(=O)NC(F)C(F)c2ccc(-c3ncn(-c4ccc(OC(F)(F)F)cc4)n3)cc2)SCCC1C]
P637

TABLE P-Two-continued
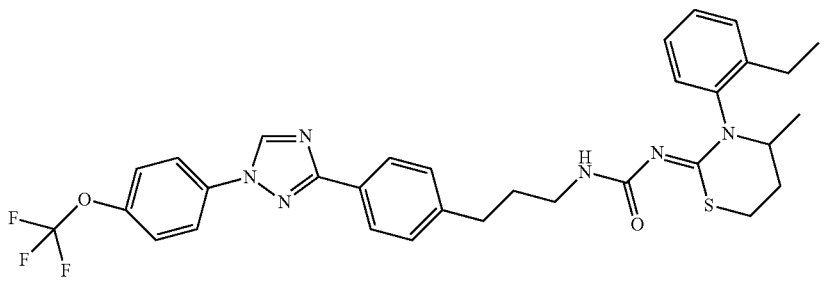 [SMILES: CCc1ccccc1N1/C(=N/C(=O)NCCCc2ccc(-c3ncn(-c4ccc(OC(F)(F)F)cc4)n3)cc2)SCCC1C]
P638
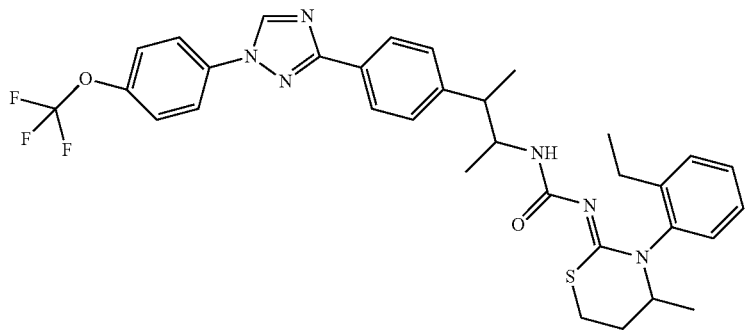 [SMILES: CCc1ccccc1N1/C(=N/C(=O)NC(C)C(C)c2ccc(-c3ncn(-c4ccc(OC(F)(F)F)cc4)n3)cc2)SCCC1C]
P639
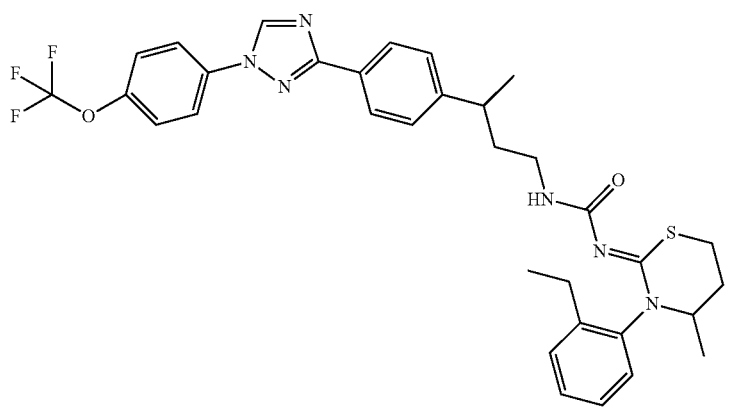 [SMILES: CCc1ccccc1N1/C(=N/C(=O)NCCC(C)c2ccc(-c3ncn(-c4ccc(OC(F)(F)F)cc4)n3)cc2)SCCC1C]
P640
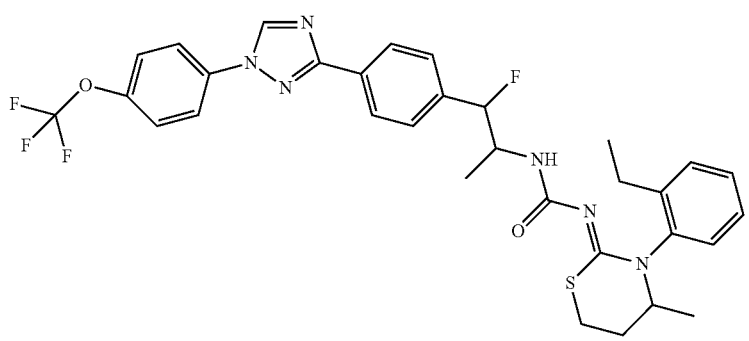 [SMILES: CCc1ccccc1N1/C(=N/C(=O)NC(C)C(F)c2ccc(-c3ncn(-c4ccc(OC(F)(F)F)cc4)n3)cc2)SCCC1C]
P641
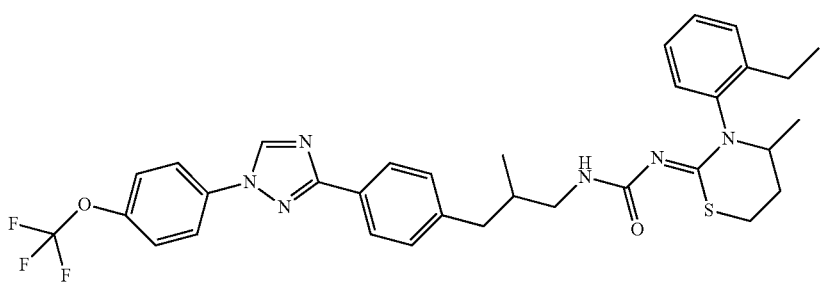 [SMILES: CCc1ccccc1N1/C(=N/C(=O)NCC(C)Cc2ccc(-c3ncn(-c4ccc(OC(F)(F)F)cc4)n3)cc2)SCCC1C]
P642

TABLE P-Two-continued
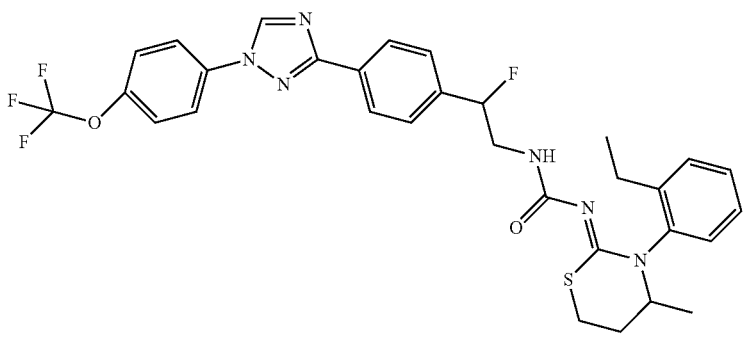 [SMILES: CCc1ccccc1N1/C(=N/C(=O)NCC(F)c2ccc(-c3ncn(-c4ccc(OC(F)(F)F)cc4)n3)cc2)SCCC1C] P643
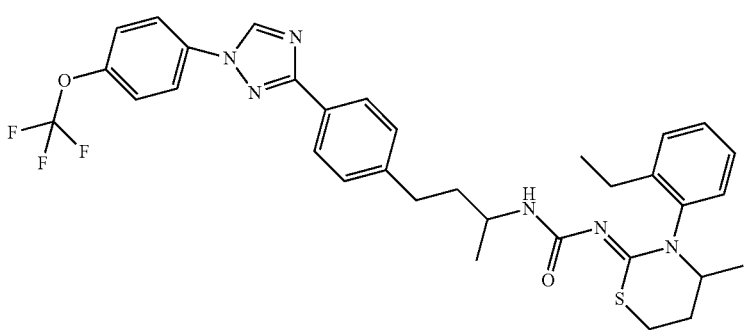 [SMILES: CCc1ccccc1N1/C(=N/C(=O)NC(C)CCc2ccc(-c3ncn(-c4ccc(OC(F)(F)F)cc4)n3)cc2)SCCC1C] P644
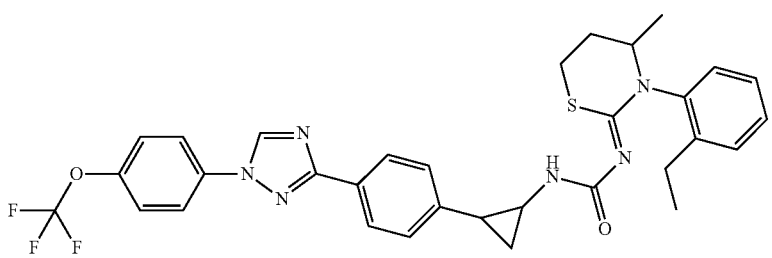 [SMILES: CCc1ccccc1N1/C(=N/C(=O)NC2CC2c2ccc(-c3ncn(-c4ccc(OC(F)(F)F)cc4)n3)cc2)SCCC1C] P645
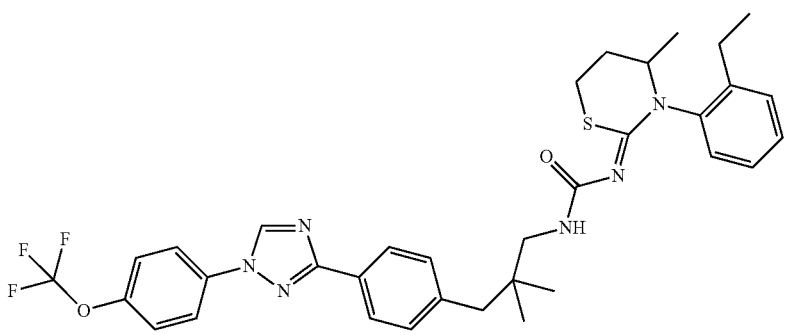 [SMILES: CCc1ccccc1N1/C(=N/C(=O)NCC(C)(C)Cc2ccc(-c3ncn(-c4ccc(OC(F)(F)F)cc4)n3)cc2)SCCC1C] P646
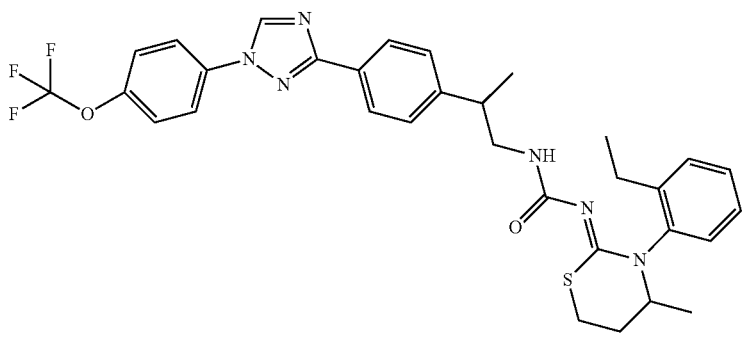 [SMILES: CCc1ccccc1N1/C(=N/C(=O)NCC(C)c2ccc(-c3ncn(-c4ccc(OC(F)(F)F)cc4)n3)cc2)SCCC1C] P647

TABLE P-Two-continued
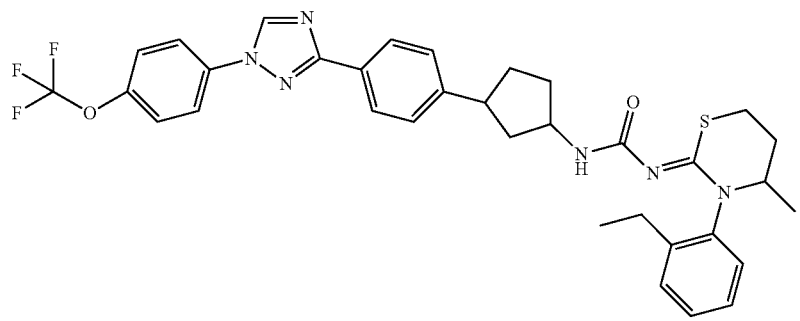 [SMILES: CCc1ccccc1N1/C(=N/C(=O)NC2CCC(c3ccc(-c4ncn(-c5ccc(OC(F)(F)F)cc5)n4)cc3)C2)SCCC1C]
P648
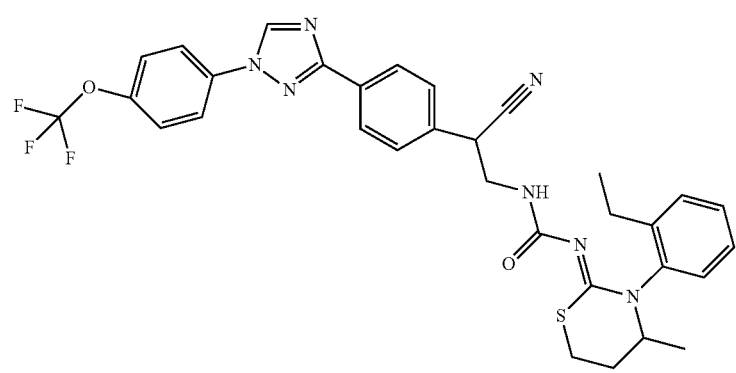 [SMILES: CCc1ccccc1N1/C(=N/C(=O)NCC(C#N)c2ccc(-c3ncn(-c4ccc(OC(F)(F)F)cc4)n3)cc2)SCCC1C]
P649
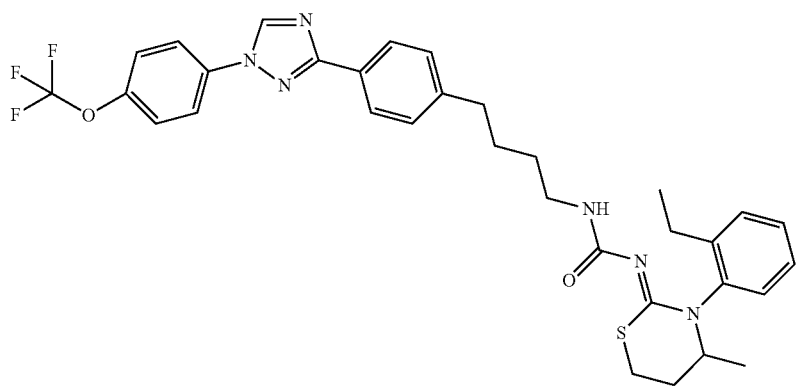 [SMILES: CCc1ccccc1N1/C(=N/C(=O)NCCCCc2ccc(-c3ncn(-c4ccc(OC(F)(F)F)cc4)n3)cc2)SCCC1C]
P650
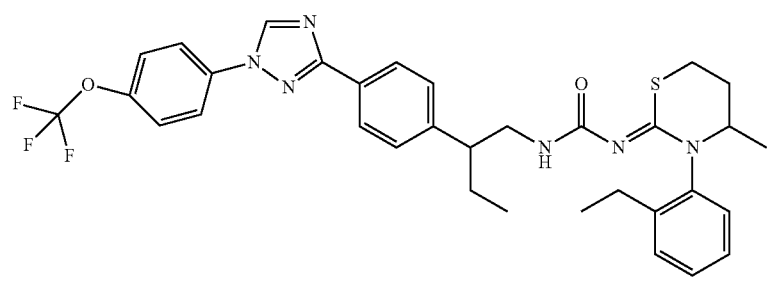 [SMILES: CCc1ccccc1N1/C(=N/C(=O)NCC(CC)c2ccc(-c3ncn(-c4ccc(OC(F)(F)F)cc4)n3)cc2)SCCC1C]
P651

TABLE P-Two-continued
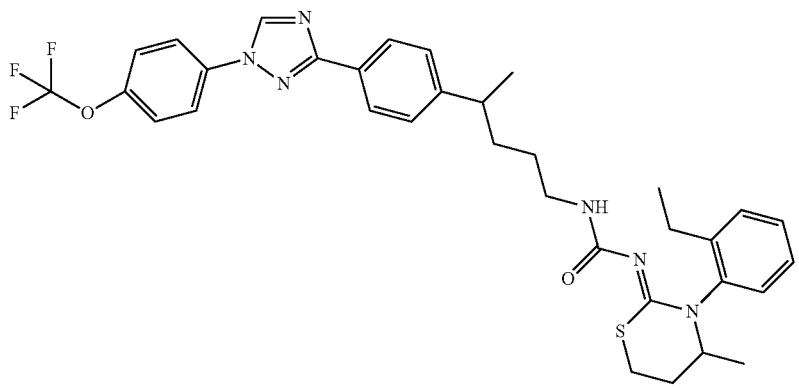 [SMILES: CCc1ccccc1N1/C(=N/C(=O)NCCCC(C)c2ccc(-c3ncn(-c4ccc(OC(F)(F)F)cc4)n3)cc2)SCCC1C]
P652
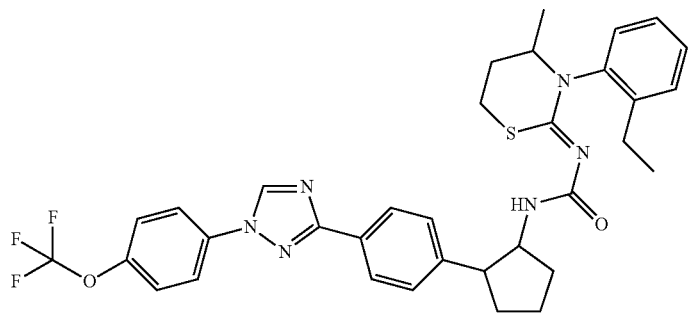 [SMILES: CCc1ccccc1N1/C(=N/C(=O)NC2CCCC2c2ccc(-c3ncn(-c4ccc(OC(F)(F)F)cc4)n3)cc2)SCCC1C]
P653
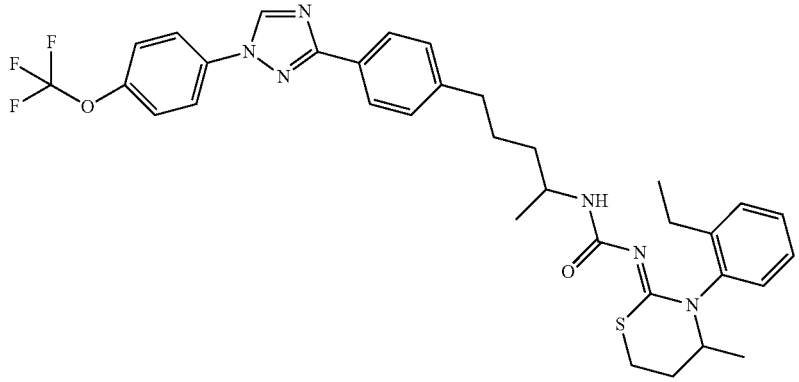 [SMILES: CCc1ccccc1N1/C(=N/C(=O)NC(C)CCCc2ccc(-c3ncn(-c4ccc(OC(F)(F)F)cc4)n3)cc2)SCCC1C]
P654
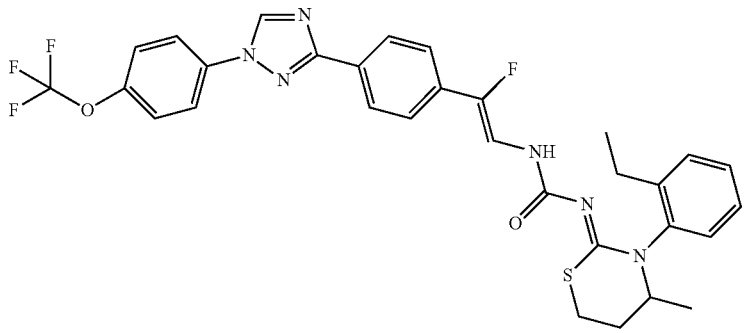 [SMILES: CCc1ccccc1N1/C(=N/C(=O)N/C=C(\F)c2ccc(-c3ncn(-c4ccc(OC(F)(F)F)cc4)n3)cc2)SCCC1C]
P655

TABLE P-Two-continued
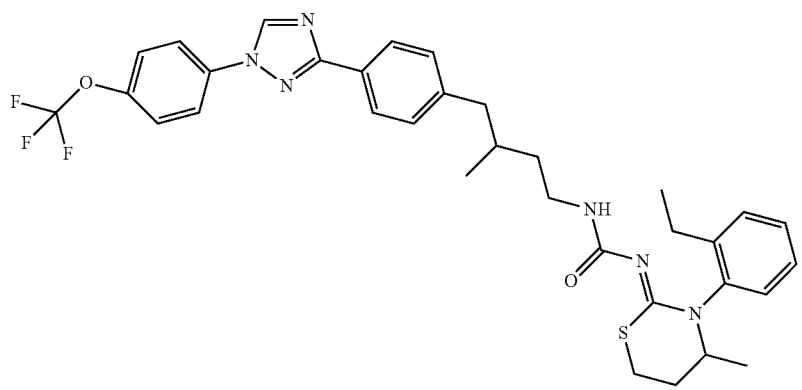 [SMILES: CCc1ccccc1N1/C(=N/C(=O)NCCC(C)Cc2ccc(-c3ncn(-c4ccc(OC(F)(F)F)cc4)n3)cc2)SCCC1C] P656
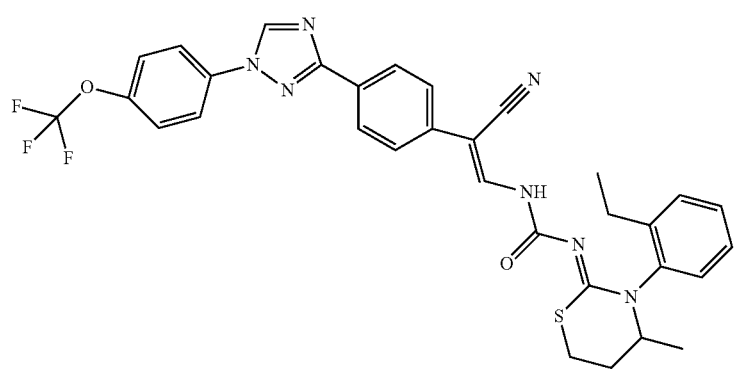 [SMILES: CCc1ccccc1N1/C(=N/C(=O)N/C=C(\C#N)c2ccc(-c3ncn(-c4ccc(OC(F)(F)F)cc4)n3)cc2)SCCC1C] P657
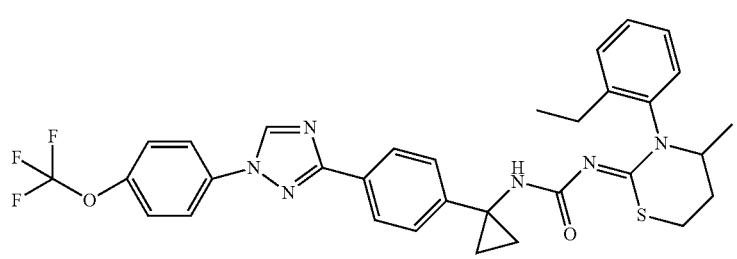 [SMILES: CCc1ccccc1N1/C(=N/C(=O)NC2(c3ccc(-c4ncn(-c5ccc(OC(F)(F)F)cc5)n4)cc3)CC2)SCCC1C] P658
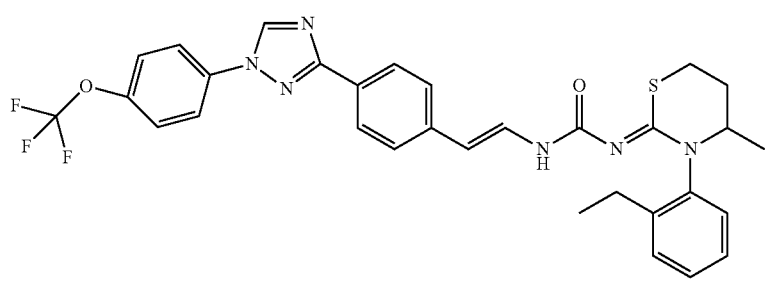 [SMILES: CCc1ccccc1N1/C(=N/C(=O)N/C=C/c2ccc(-c3ncn(-c4ccc(OC(F)(F)F)cc4)n3)cc2)SCCC1C] P659
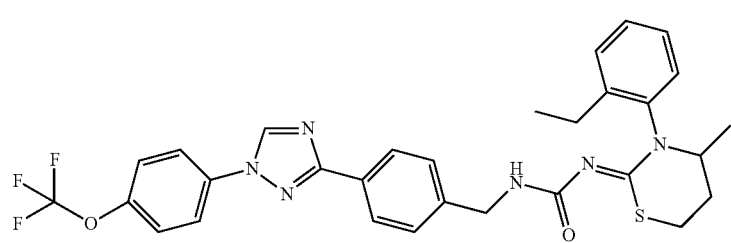 [SMILES: CCc1ccccc1N1/C(=N/C(=O)NCc2ccc(-c3ncn(-c4ccc(OC(F)(F)F)cc4)n3)cc2)SCCC1C] P660

TABLE P-Two-continued
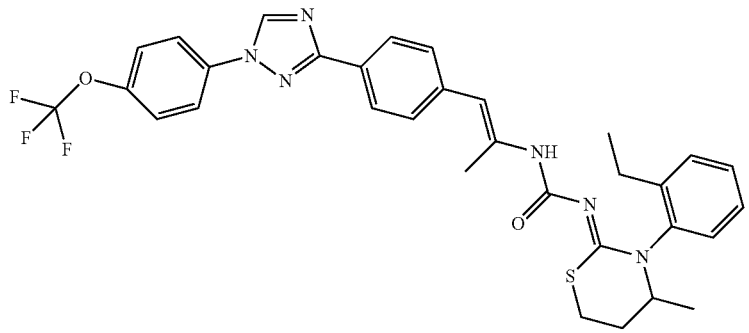 [SMILES: CCc1ccccc1N1/C(=N/C(=O)N/C(C)=C/c2ccc(-c3ncn(-c4ccc(OC(F)(F)F)cc4)n3)cc2)SCCC1C]
P661
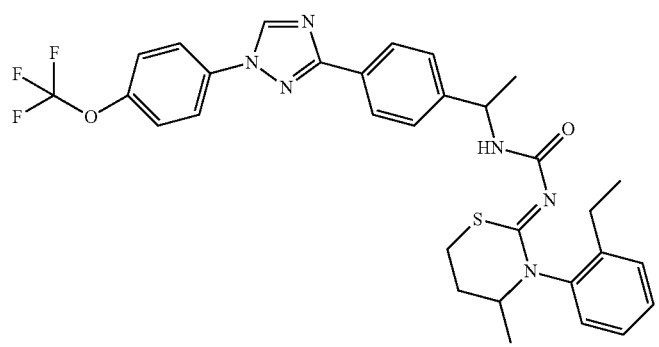 [SMILES: CCc1ccccc1N1/C(=N/C(=O)NC(C)c2ccc(-c3ncn(-c4ccc(OC(F)(F)F)cc4)n3)cc2)SCCC1C]
P662
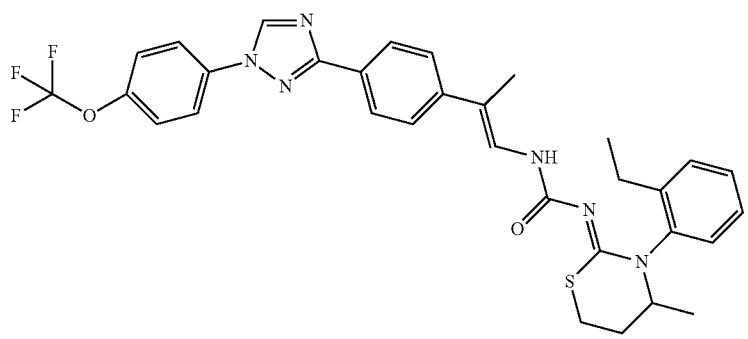 [SMILES: CCc1ccccc1N1/C(=N/C(=O)N/C=C(\C)c2ccc(-c3ncn(-c4ccc(OC(F)(F)F)cc4)n3)cc2)SCCC1C]
P663
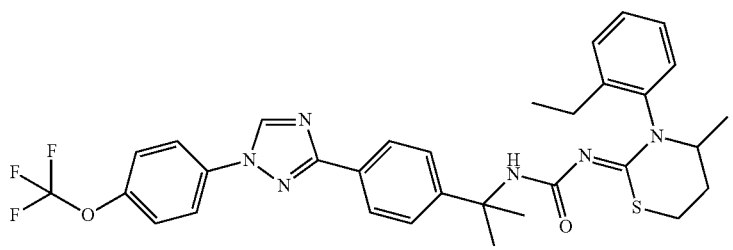 [SMILES: CCc1ccccc1N1/C(=N/C(=O)NC(C)(C)c2ccc(-c3ncn(-c4ccc(OC(F)(F)F)cc4)n3)cc2)SCCC1C]
P664
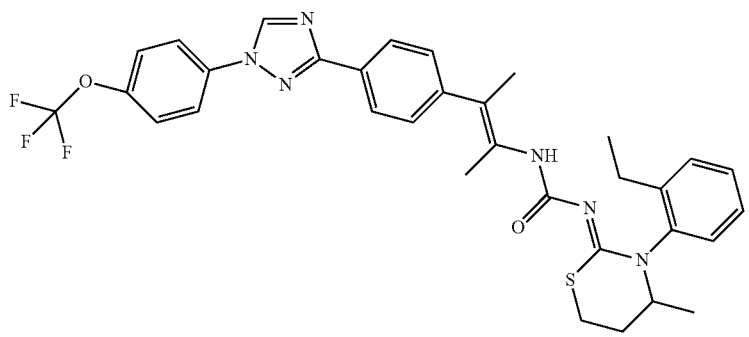 [SMILES: CCc1ccccc1N1/C(=N/C(=O)N/C(C)=C(\C)c2ccc(-c3ncn(-c4ccc(OC(F)(F)F)cc4)n3)cc2)SCCC1C]
P665

TABLE P-Two-continued
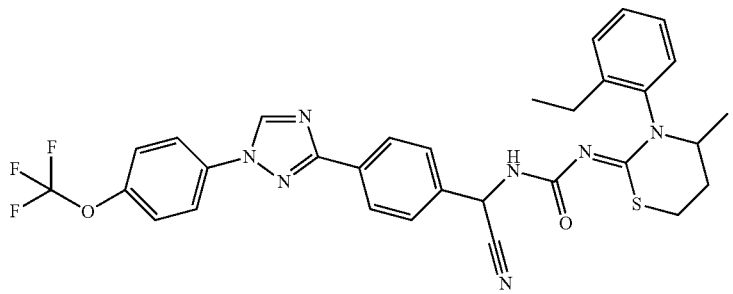 [SMILES: CCc1ccccc1N1/C(=N/C(=O)NC(C#N)c2ccc(-c3ncn(-c4ccc(OC(F)(F)F)cc4)n3)cc2)SCCC1C]
P666
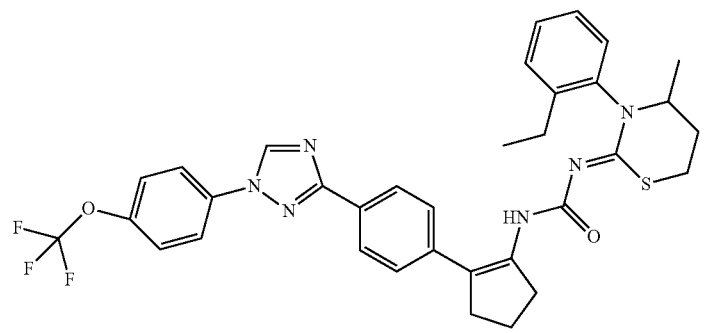 [SMILES: CCc1ccccc1N1/C(=N/C(=O)NC2=C(c3ccc(-c4ncn(-c5ccc(OC(F)(F)F)cc5)n4)cc3)CCC2)SCCC1C]
P667
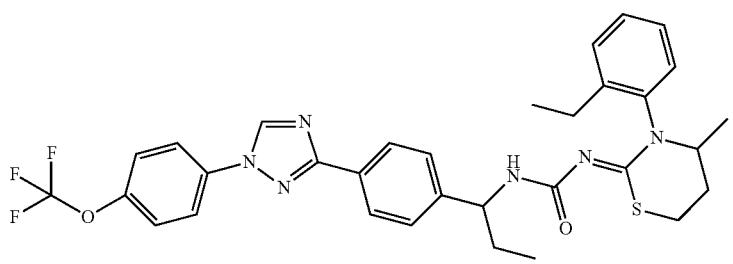 [SMILES: CCc1ccccc1N1/C(=N/C(=O)NC(CC)c2ccc(-c3ncn(-c4ccc(OC(F)(F)F)cc4)n3)cc2)SCCC1C]
P668
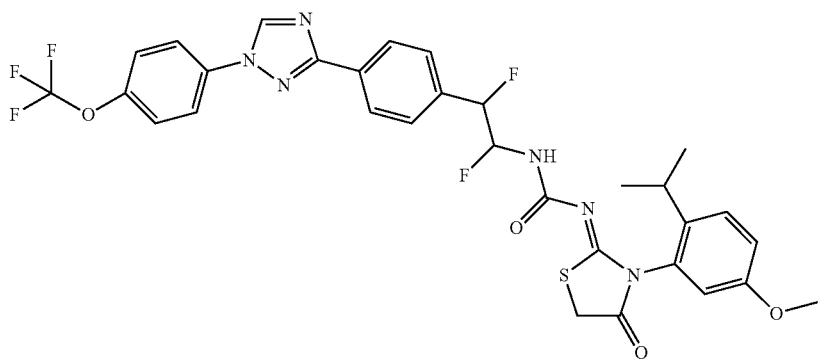 [SMILES: COc1ccc(C(C)C)c(N2C(=O)CS/C2=N\C(=O)NC(F)C(F)c2ccc(-c3ncn(-c4ccc(OC(F)(F)F)cc4)n3)cc2)c1]
P669
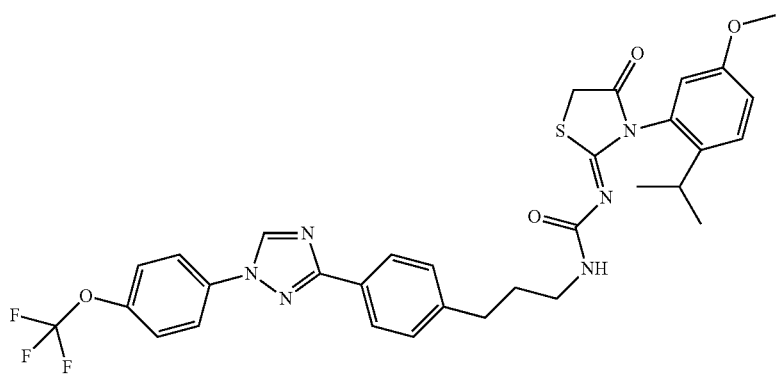 [SMILES: COc1ccc(C(C)C)c(N2C(=O)CS/C2=N\C(=O)NCCCc2ccc(-c3ncn(-c4ccc(OC(F)(F)F)cc4)n3)cc2)c1]
P670

TABLE P-Two-continued
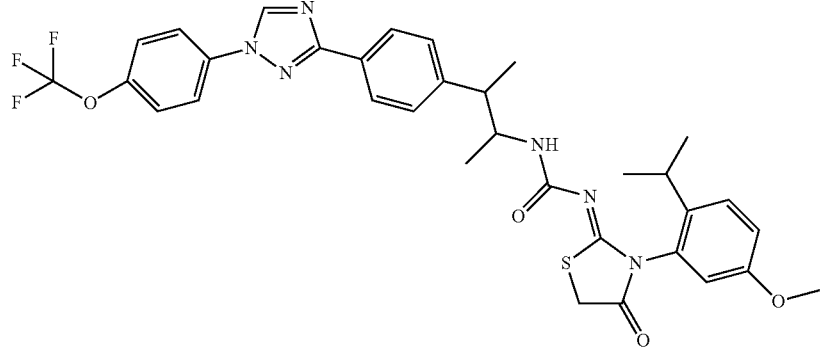 [SMILES: COc1ccc(C(C)C)c(N2C(=O)CS/C2=N\C(=O)NC(C)C(C)c2ccc(-c3ncn(-c4ccc(OC(F)(F)F)cc4)n3)cc2)c1]
P671
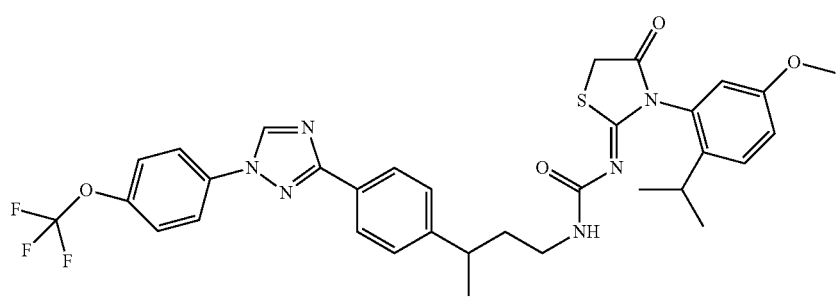 [SMILES: COc1ccc(C(C)C)c(N2C(=O)CS/C2=N\C(=O)NCCC(C)c2ccc(-c3ncn(-c4ccc(OC(F)(F)F)cc4)n3)cc2)c1]
P672
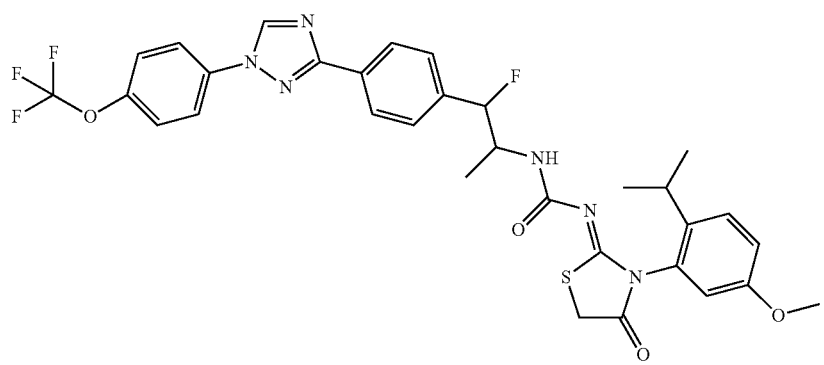 [SMILES: COc1ccc(C(C)C)c(N2C(=O)CS/C2=N\C(=O)NC(C)C(F)c2ccc(-c3ncn(-c4ccc(OC(F)(F)F)cc4)n3)cc2)c1]
P673
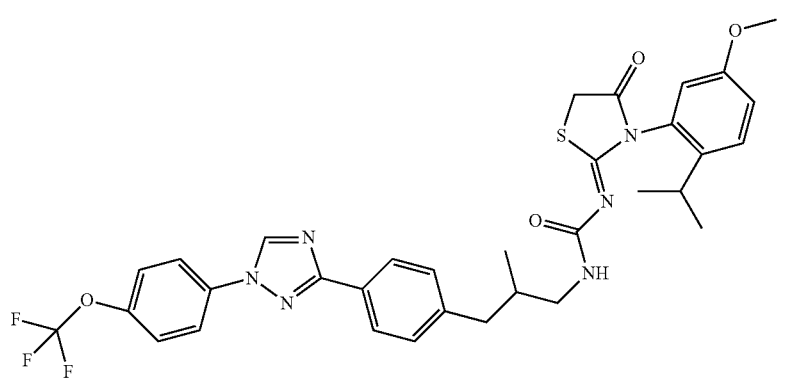 [SMILES: COc1ccc(C(C)C)c(N2C(=O)CS/C2=N\C(=O)NCC(C)Cc2ccc(-c3ncn(-c4ccc(OC(F)(F)F)cc4)n3)cc2)c1]
P674

TABLE P-Two-continued
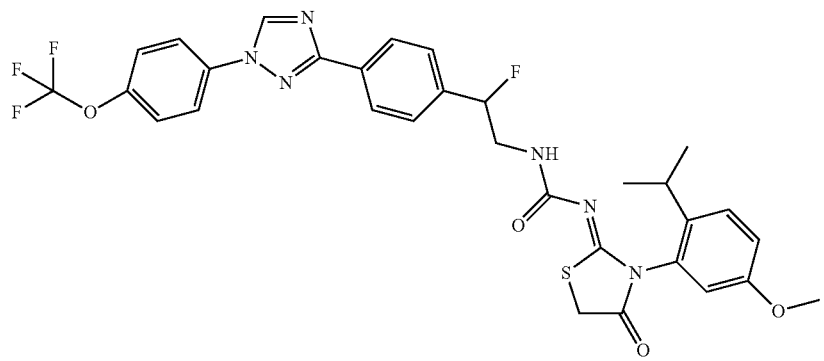 [SMILES: COc1ccc(C(C)C)c(N2C(=O)CS/C2=N\C(=O)NCC(F)c2ccc(-c3ncn(-c4ccc(OC(F)(F)F)cc4)n3)cc2)c1]
P675
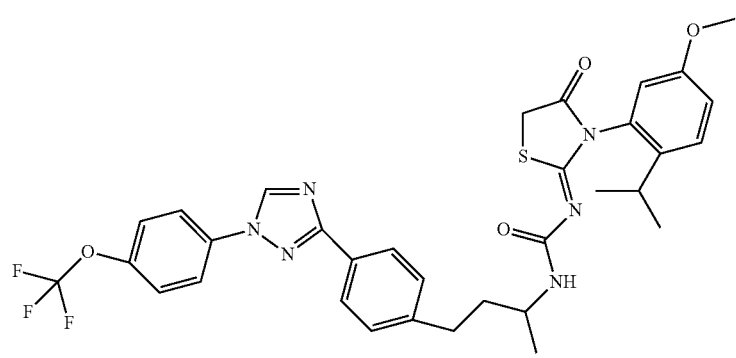 [SMILES: COc1ccc(C(C)C)c(N2C(=O)CS/C2=N\C(=O)NC(C)CCc2ccc(-c3ncn(-c4ccc(OC(F)(F)F)cc4)n3)cc2)c1]
P676
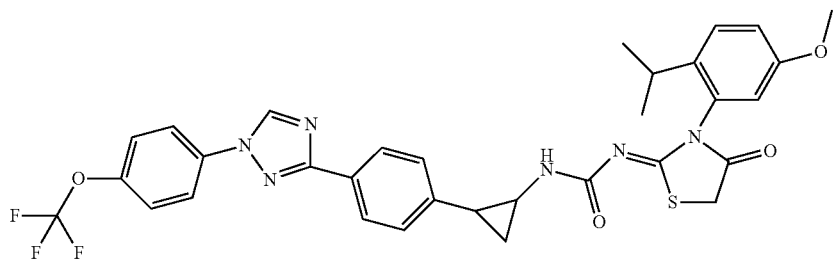 [SMILES: COc1ccc(C(C)C)c(N2C(=O)CS/C2=N\C(=O)NC2CC2c2ccc(-c3ncn(-c4ccc(OC(F)(F)F)cc4)n3)cc2)c1]
P677
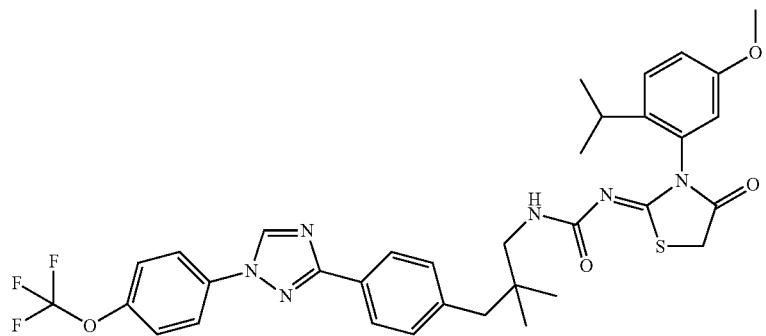 [SMILES: COc1ccc(C(C)C)c(N2C(=O)CS/C2=N\C(=O)NCC(C)(C)Cc2ccc(-c3ncn(-c4ccc(OC(F)(F)F)cc4)n3)cc2)c1]
P678

TABLE P-Two-continued
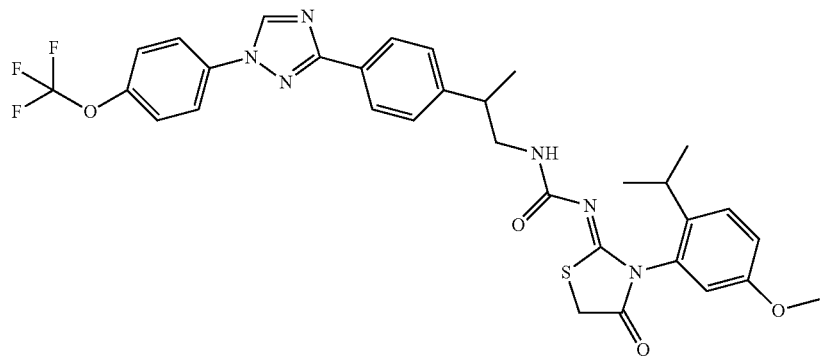 [SMILES: COc1ccc(C(C)C)c(N2C(=O)CS/C2=N\C(=O)NCC(C)c2ccc(-c3ncn(-c4ccc(OC(F)(F)F)cc4)n3)cc2)c1]
P679
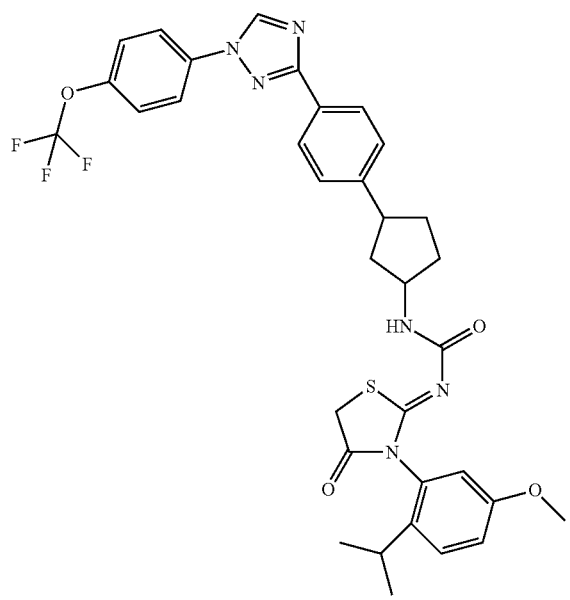 [SMILES: COc1ccc(C(C)C)c(N2C(=O)CS/C2=N\C(=O)NC2CCC(c3ccc(-c4ncn(-c5ccc(OC(F)(F)F)cc5)n4)cc3)C2)c1]
P680
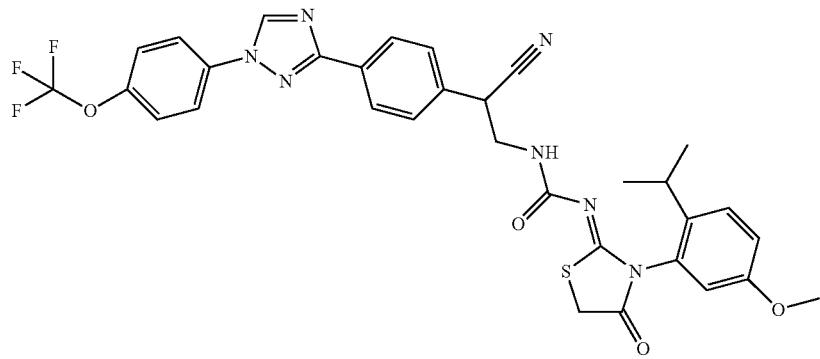 [SMILES: COc1ccc(C(C)C)c(N2C(=O)CS/C2=N\C(=O)NCC(C#N)c2ccc(-c3ncn(-c4ccc(OC(F)(F)F)cc4)n3)cc2)c1]
P681

TABLE P-Two-continued
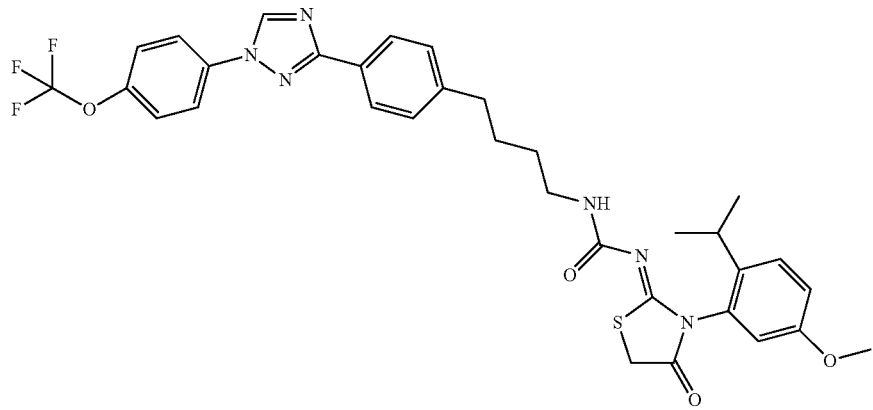 [SMILES: COc1ccc(C(C)C)c(N2C(=O)CS/C2=N\C(=O)NCCCCc2ccc(-c3ncn(-c4ccc(OC(F)(F)F)cc4)n3)cc2)c1]
P682
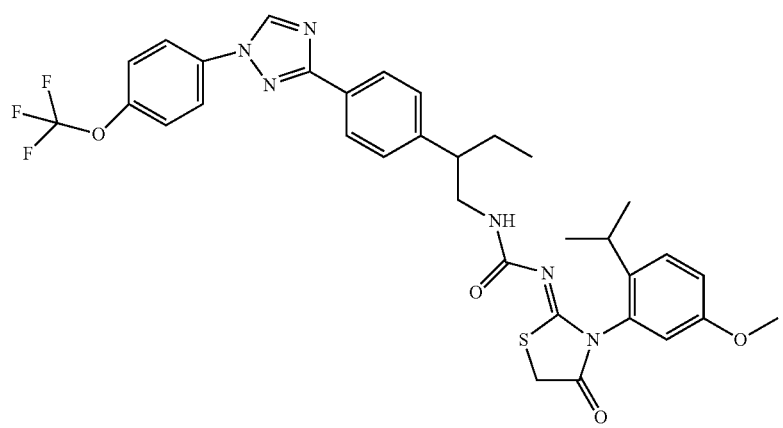 [SMILES: CCC(CNC(=O)/N=C1\SCC(=O)N1c1cc(OC)ccc1C(C)C)c1ccc(-c2ncn(-c3ccc(OC(F)(F)F)cc3)n2)cc1]
P683
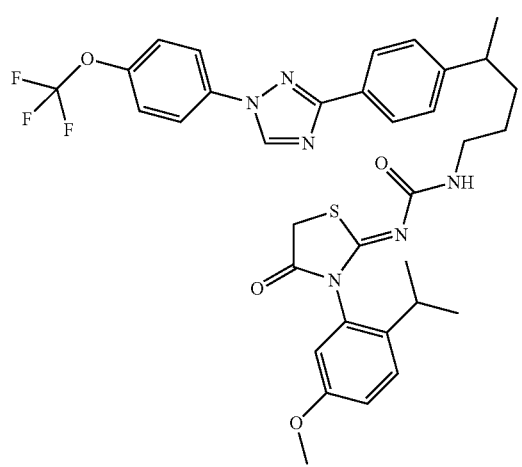 [SMILES: COc1ccc(C(C)C)c(N2C(=O)CS/C2=N\C(=O)NCCCC(C)c2ccc(-c3ncn(-c4ccc(OC(F)(F)F)cc4)n3)cc2)c1]
P684

TABLE P-Two-continued
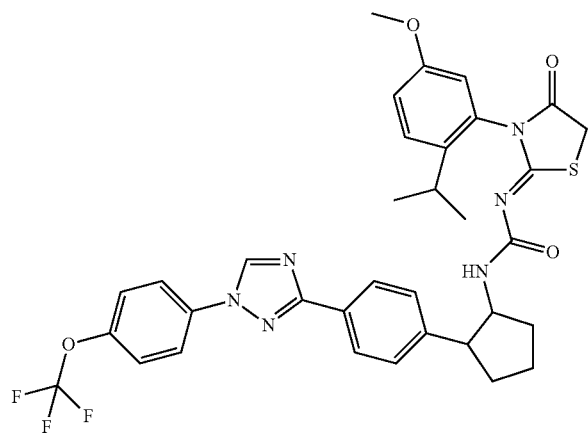 [SMILES: COc1ccc(C(C)C)c(N2C(=O)CS/C2=N\C(=O)NC2CCCC2c2ccc(-c3ncn(-c4ccc(OC(F)(F)F)cc4)n3)cc2)c1]
P685
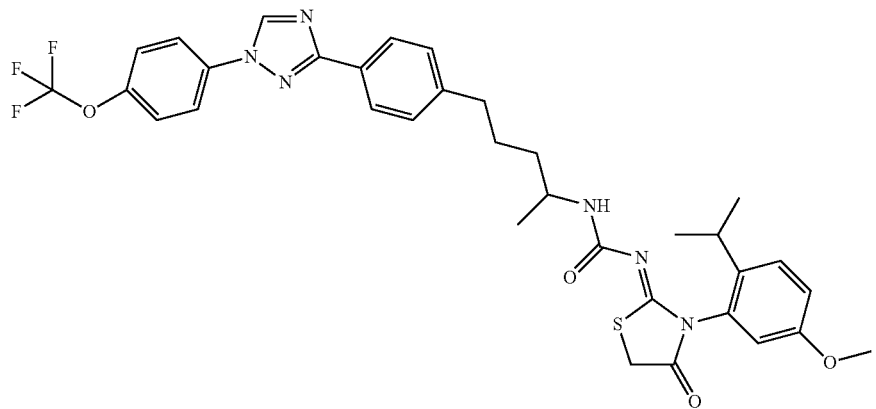 [SMILES: COc1ccc(C(C)C)c(N2C(=O)CS/C2=N\C(=O)NC(C)CCCc2ccc(-c3ncn(-c4ccc(OC(F)(F)F)cc4)n3)cc2)c1]
P686
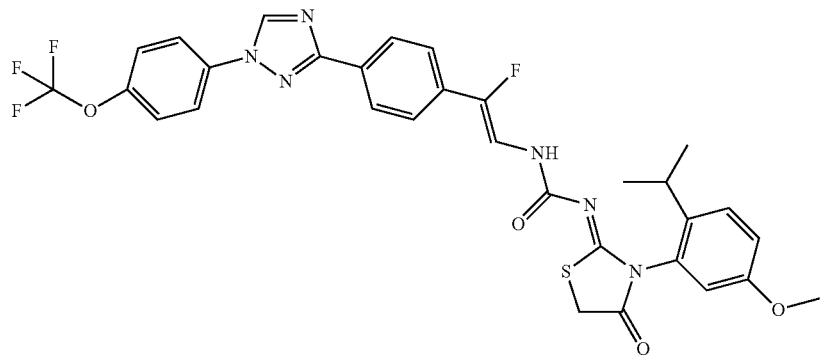 [SMILES: COc1ccc(C(C)C)c(N2C(=O)CS/C2=N\C(=O)N/C=C(\F)c2ccc(-c3ncn(-c4ccc(OC(F)(F)F)cc4)n3)cc2)c1]
P687
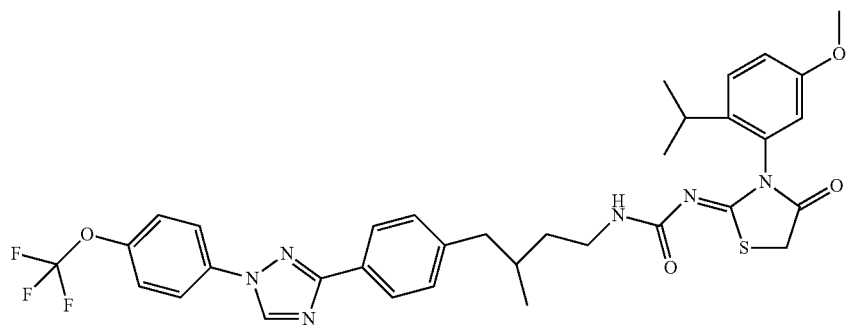 [SMILES: COc1ccc(C(C)C)c(N2C(=O)CS/C2=N\C(=O)NCCC(C)Cc2ccc(-c3ncn(-c4ccc(OC(F)(F)F)cc4)n3)cc2)c1]
P688

TABLE P-Two-continued
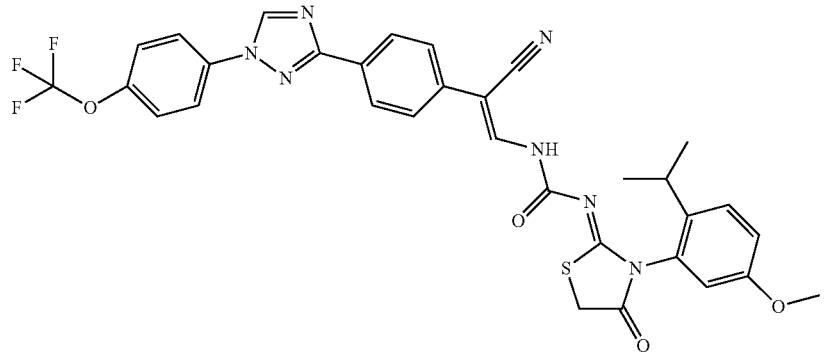 [SMILES: COc1ccc(C(C)C)c(N2C(=O)CS/C2=N\C(=O)N/C=C(\C#N)c2ccc(-c3ncn(-c4ccc(OC(F)(F)F)cc4)n3)cc2)c1]

TABLE P-Two-continued
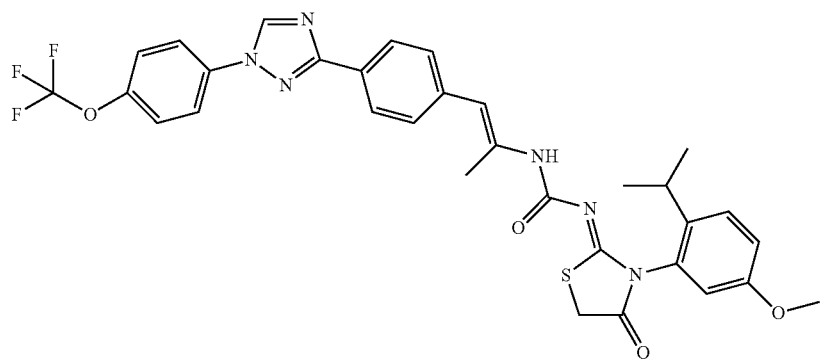 [SMILES: COc1ccc(C(C)C)c(N2C(=O)CS/C2=N\C(=O)N/C(C)=C/c2ccc(-c3ncn(-c4ccc(OC(F)(F)F)cc4)n3)cc2)c1]
P693
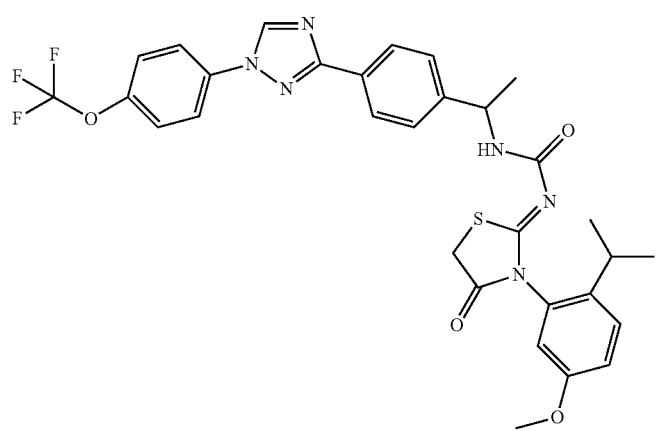 [SMILES: COc1ccc(C(C)C)c(N2C(=O)CS/C2=N\C(=O)NC(C)c2ccc(-c3ncn(-c4ccc(OC(F)(F)F)cc4)n3)cc2)c1]
P694
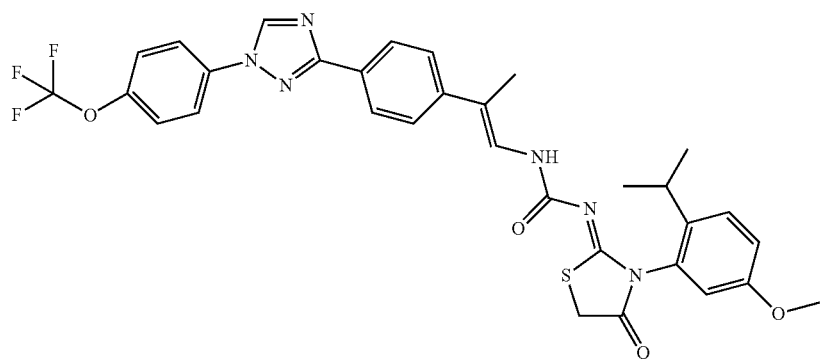 [SMILES: COc1ccc(C(C)C)c(N2C(=O)CS/C2=N\C(=O)N/C=C(\C)c2ccc(-c3ncn(-c4ccc(OC(F)(F)F)cc4)n3)cc2)c1]
P695
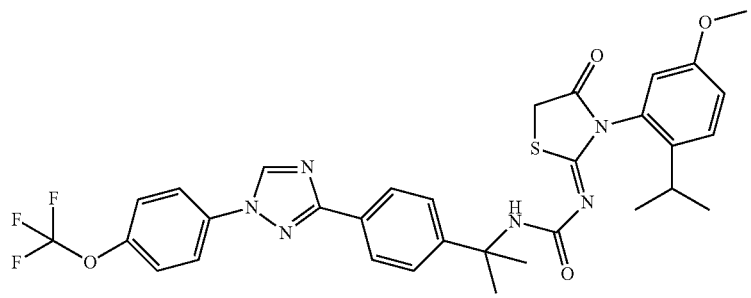 [SMILES: COc1ccc(C(C)C)c(N2C(=O)CS/C2=N\C(=O)NC(C)(C)c2ccc(-c3ncn(-c4ccc(OC(F)(F)F)cc4)n3)cc2)c1]
P696

TABLE P-Two-continued
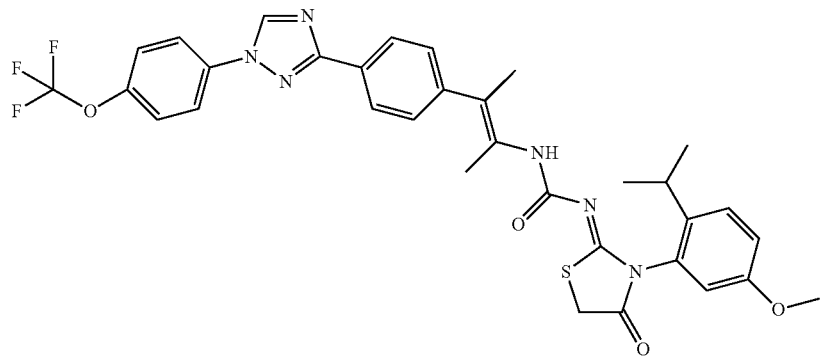 [SMILES: COc1ccc(C(C)C)c(N2C(=O)CS/C2=N\C(=O)N/C(C)=C(\C)c2ccc(-c3ncn(-c4ccc(OC(F)(F)F)cc4)n3)cc2)c1]
P697
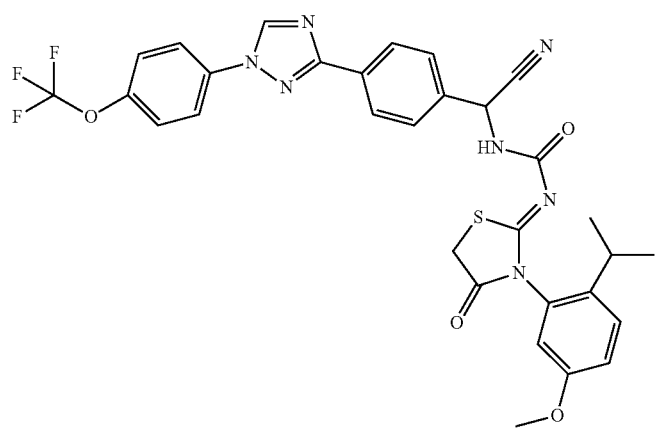 [SMILES: COc1ccc(C(C)C)c(N2C(=O)CS/C2=N\C(=O)NC(C#N)c2ccc(-c3ncn(-c4ccc(OC(F)(F)F)cc4)n3)cc2)c1]
P698
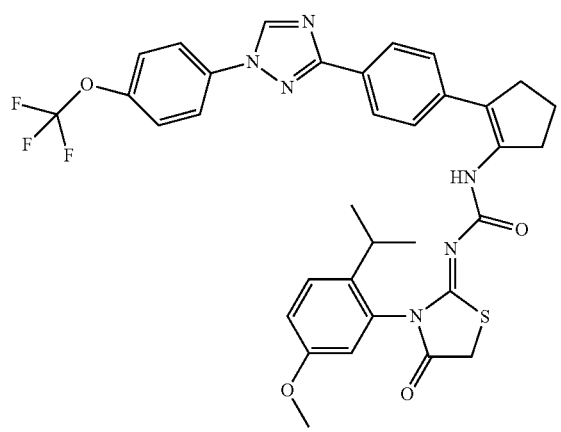 [SMILES: COc1ccc(C(C)C)c(N2C(=O)CS/C2=N\C(=O)NC2=C(c3ccc(-c4ncn(-c5ccc(OC(F)(F)F)cc5)n4)cc3)CCC2)c1]
P699
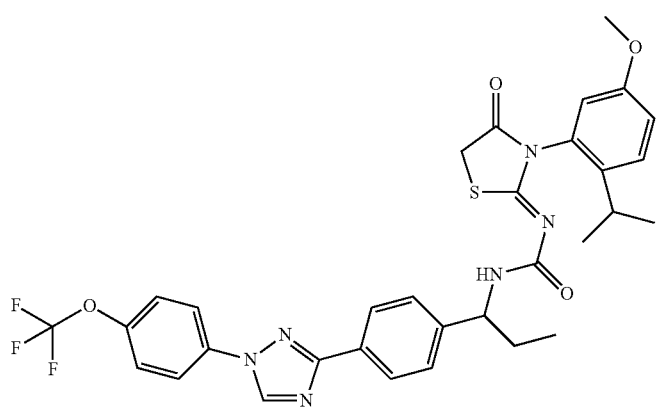 [SMILES: CCC(NC(=O)/N=C1\SCC(=O)N1c1cc(OC)ccc1C(C)C)c1ccc(-c2ncn(-c3ccc(OC(F)(F)F)cc3)n2)cc1]
P700

TABLE P-Two-continued
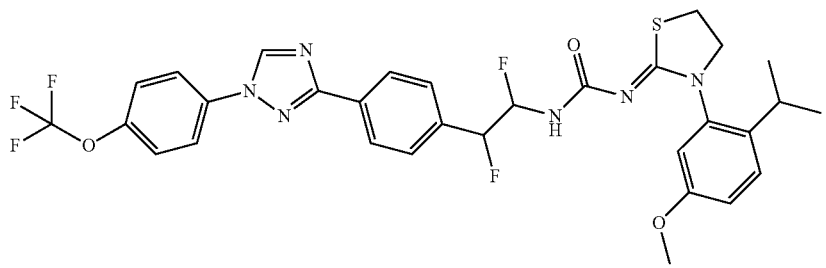 [SMILES: COc1ccc(C(C)C)c(N2CCS/C2=N\C(=O)NC(F)C(F)c2ccc(-c3ncn(-c4ccc(OC(F)(F)F)cc4)n3)cc2)c1]
P701
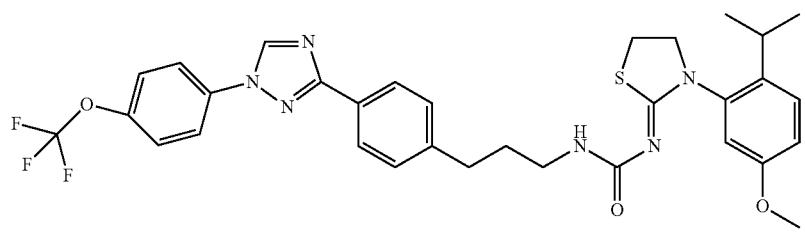 [SMILES: COc1ccc(C(C)C)c(N2CCS/C2=N\C(=O)NCCCc2ccc(-c3ncn(-c4ccc(OC(F)(F)F)cc4)n3)cc2)c1]
P702
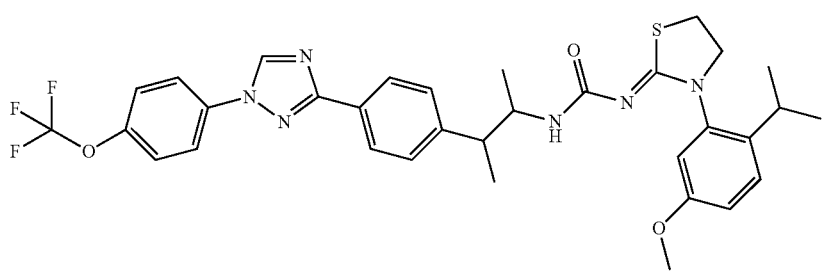 [SMILES: COc1ccc(C(C)C)c(N2CCS/C2=N\C(=O)NC(C)C(C)c2ccc(-c3ncn(-c4ccc(OC(F)(F)F)cc4)n3)cc2)c1]
P703
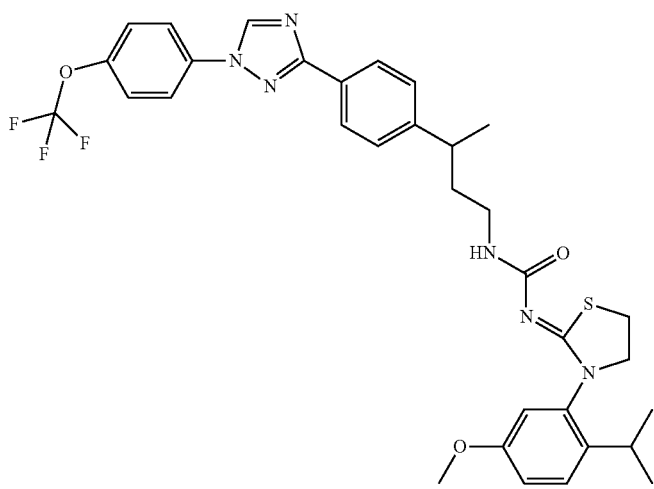 [SMILES: COc1ccc(C(C)C)c(N2CCS/C2=N\C(=O)NCCC(C)c2ccc(-c3ncn(-c4ccc(OC(F)(F)F)cc4)n3)cc2)c1]
P704
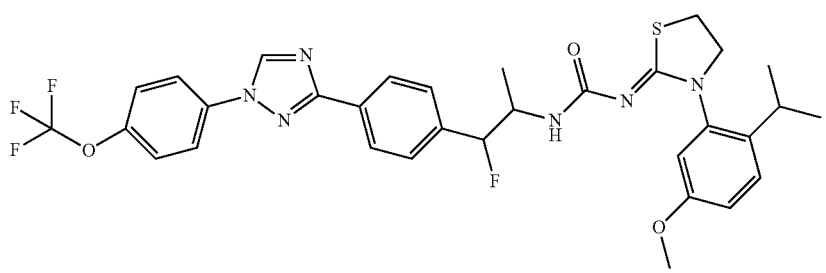 [SMILES: COc1ccc(C(C)C)c(N2CCS/C2=N\C(=O)NC(C)C(F)c2ccc(-c3ncn(-c4ccc(OC(F)(F)F)cc4)n3)cc2)c1]
P705

TABLE P-Two-continued
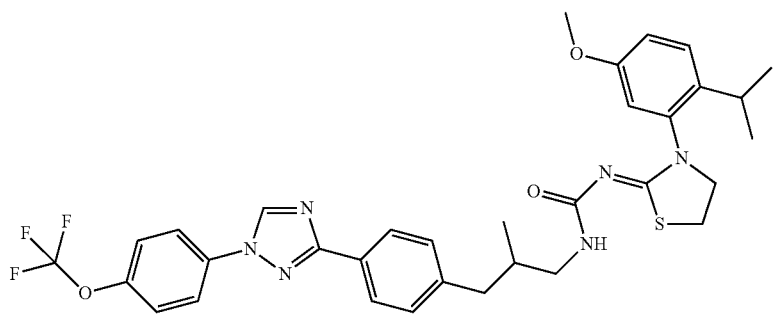 [SMILES: COc1ccc(C(C)C)c(N2CCS/C2=N\C(=O)NCC(C)Cc2ccc(-c3ncn(-c4ccc(OC(F)(F)F)cc4)n3)cc2)c1]
P706
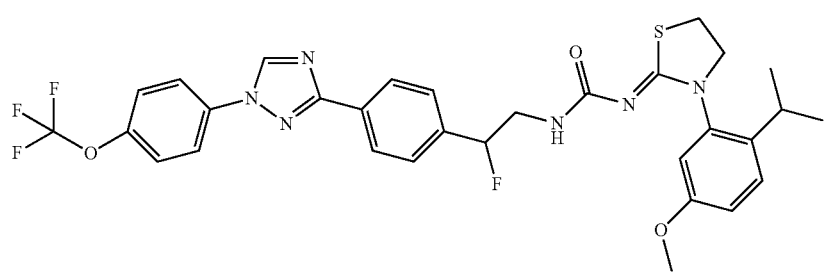 [SMILES: COc1ccc(C(C)C)c(N2CCS/C2=N\C(=O)NCC(F)c2ccc(-c3ncn(-c4ccc(OC(F)(F)F)cc4)n3)cc2)c1]
P707
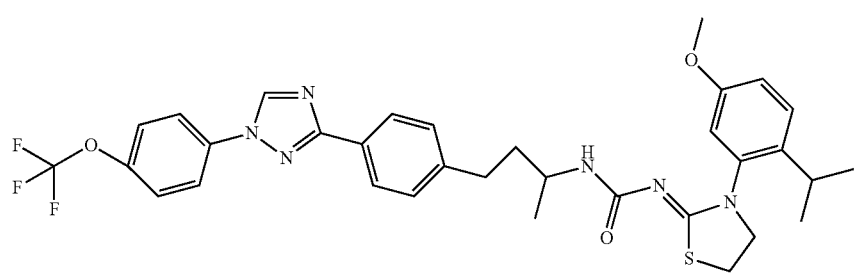 [SMILES: COc1ccc(C(C)C)c(N2CCS/C2=N\C(=O)NC(C)CCc2ccc(-c3ncn(-c4ccc(OC(F)(F)F)cc4)n3)cc2)c1]
P708
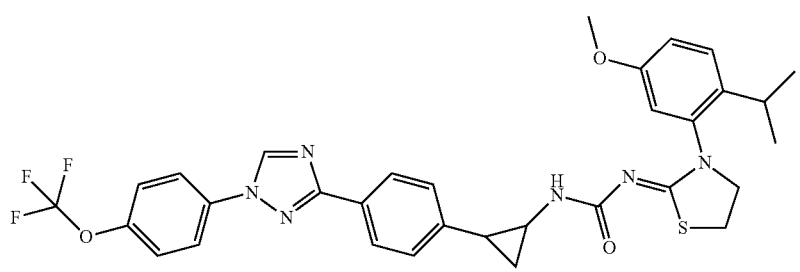 [SMILES: COc1ccc(C(C)C)c(N2CCS/C2=N\C(=O)NC2CC2c2ccc(-c3ncn(-c4ccc(OC(F)(F)F)cc4)n3)cc2)c1]
P709
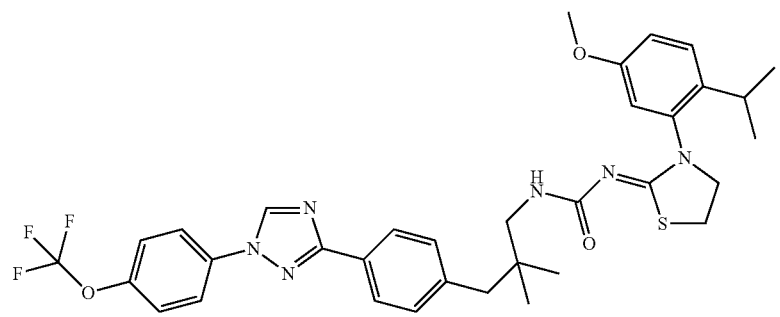 [SMILES: COc1ccc(C(C)C)c(N2CCS/C2=N\C(=O)NCC(C)(C)Cc2ccc(-c3ncn(-c4ccc(OC(F)(F)F)cc4)n3)cc2)c1]
P710

TABLE P-Two-continued
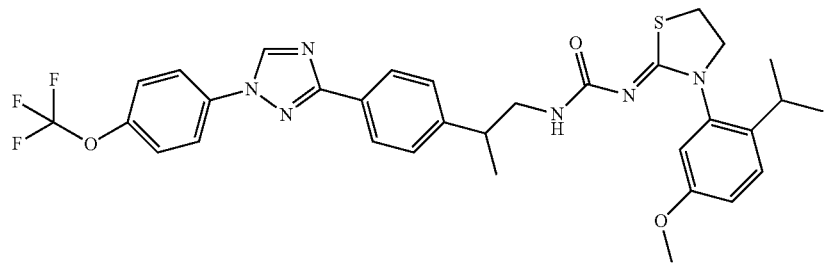 [SMILES: COc1ccc(C(C)C)c(N2CCS/C2=N\C(=O)NCC(C)c2ccc(-c3ncn(-c4ccc(OC(F)(F)F)cc4)n3)cc2)c1]
P711
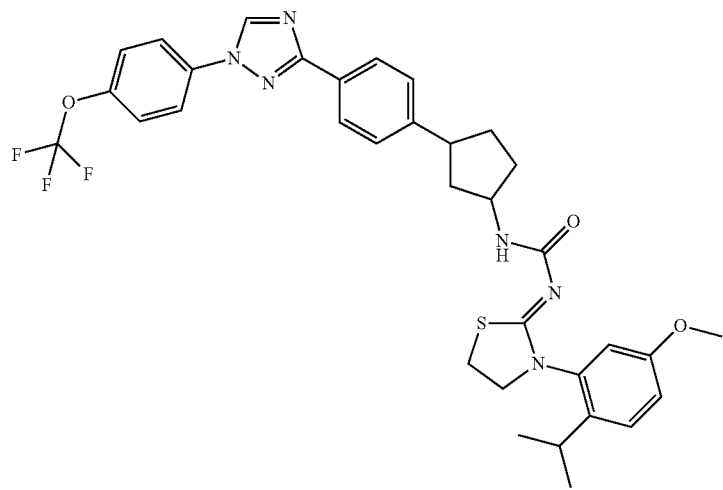 [SMILES: COc1ccc(C(C)C)c(N2CCS/C2=N\C(=O)NC2CCC(c3ccc(-c4ncn(-c5ccc(OC(F)(F)F)cc5)n4)cc3)C2)c1]
P712
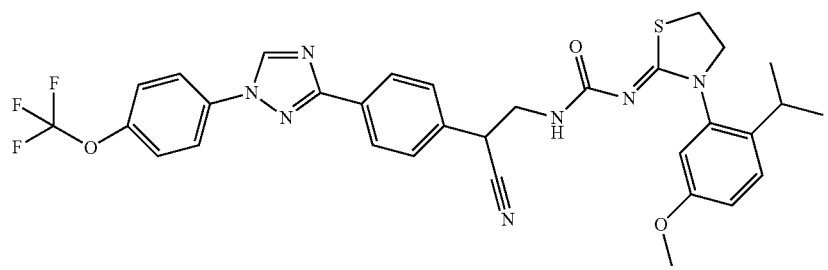 [SMILES: COc1ccc(C(C)C)c(N2CCS/C2=N\C(=O)NCC(C#N)c2ccc(-c3ncn(-c4ccc(OC(F)(F)F)cc4)n3)cc2)c1]
P713
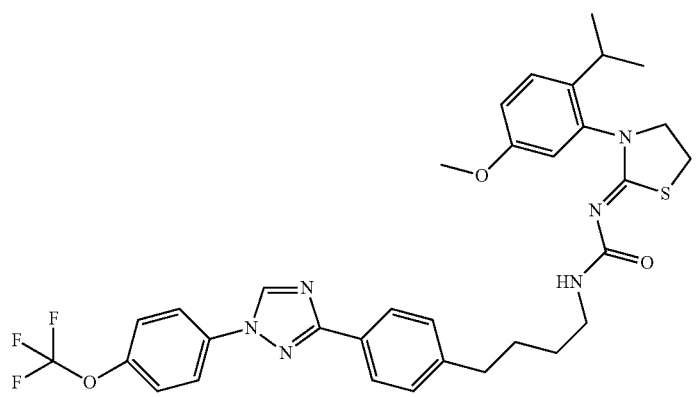 [SMILES: COc1ccc(C(C)C)c(N2CCS/C2=N\C(=O)NCCCCc2ccc(-c3ncn(-c4ccc(OC(F)(F)F)cc4)n3)cc2)c1]
P714

TABLE P-Two-continued
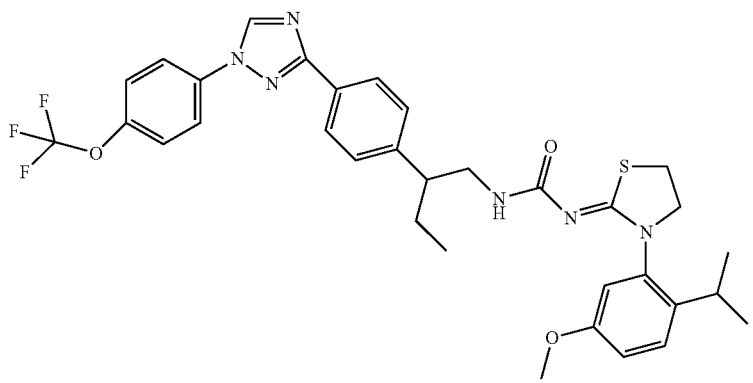 [SMILES: CCC(CNC(=O)/N=C1\SCCN1c1cc(OC)ccc1C(C)C)c1ccc(-c2ncn(-c3ccc(OC(F)(F)F)cc3)n2)cc1]
P715
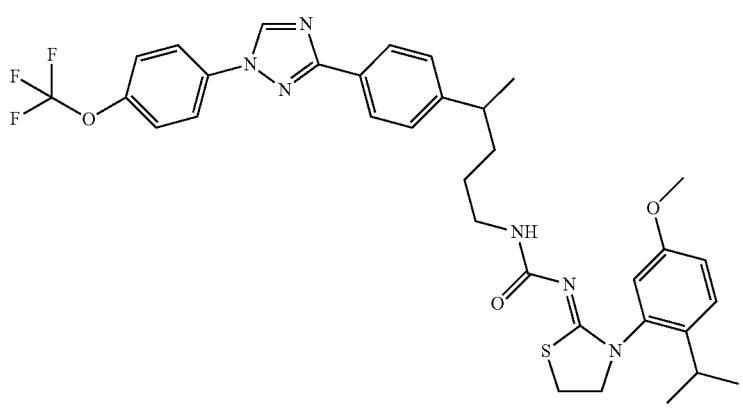 [SMILES: COc1ccc(C(C)C)c(N2CCS/C2=N\C(=O)NCCCC(C)c2ccc(-c3ncn(-c4ccc(OC(F)(F)F)cc4)n3)cc2)c1]
P716
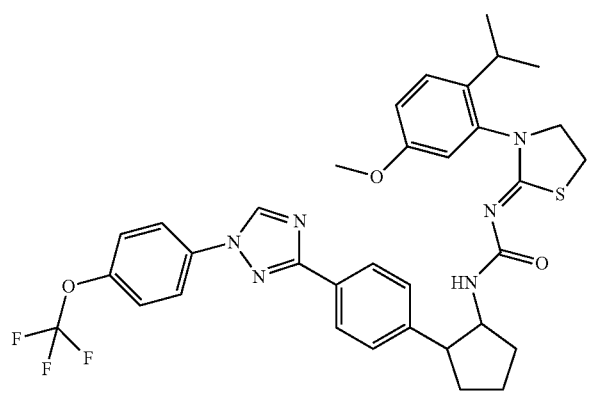 [SMILES: COc1ccc(C(C)C)c(N2CCS/C2=N\C(=O)NC2CCCC2c2ccc(-c3ncn(-c4ccc(OC(F)(F)F)cc4)n3)cc2)c1]
P717
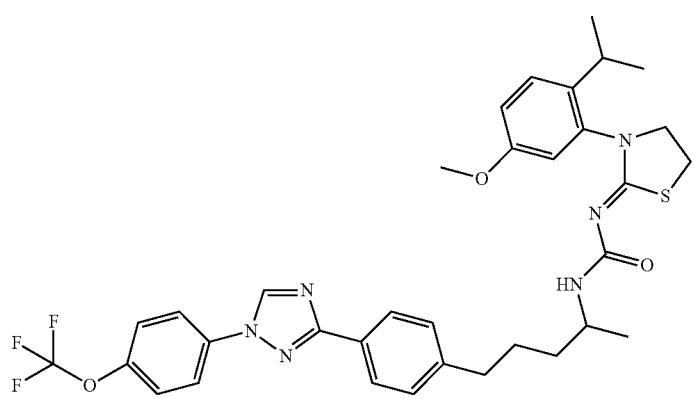 [SMILES: COc1ccc(C(C)C)c(N2CCS/C2=N\C(=O)NC(C)CCCc2ccc(-c3ncn(-c4ccc(OC(F)(F)F)cc4)n3)cc2)c1]
P718

TABLE P-Two-continued
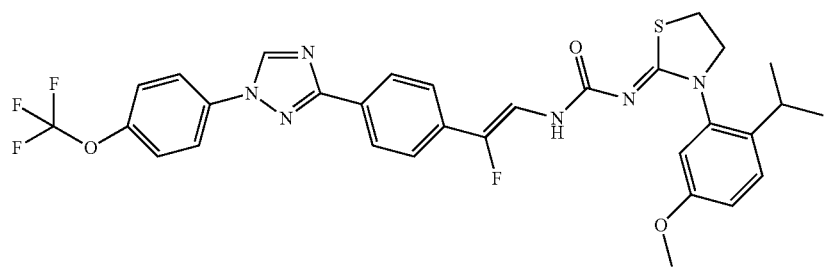 [SMILES: COc1ccc(C(C)C)c(N2CCS/C2=N\C(=O)N/C=C(\F)c2ccc(-c3ncn(-c4ccc(OC(F)(F)F)cc4)n3)cc2)c1]
P719
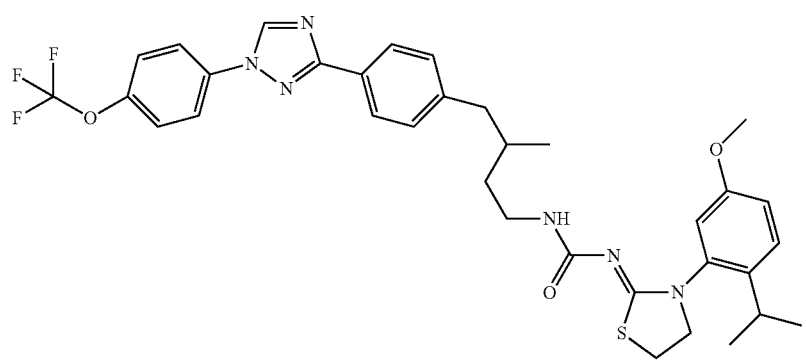 [SMILES: COc1ccc(C(C)C)c(N2CCS/C2=N\C(=O)NCCC(C)Cc2ccc(-c3ncn(-c4ccc(OC(F)(F)F)cc4)n3)cc2)c1]
P720
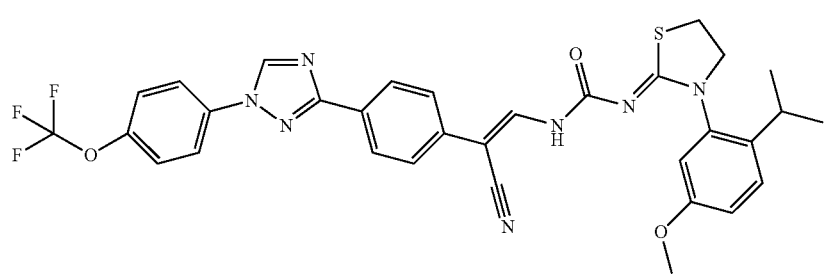 [SMILES: COc1ccc(C(C)C)c(N2CCS/C2=N\C(=O)N/C=C(\C#N)c2ccc(-c3ncn(-c4ccc(OC(F)(F)F)cc4)n3)cc2)c1]
P721
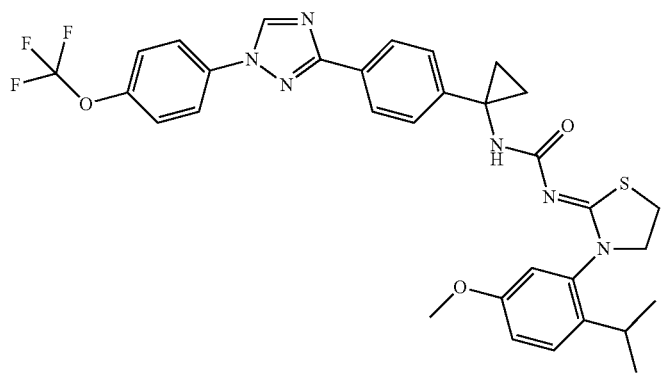 [SMILES: COc1ccc(C(C)C)c(N2CCS/C2=N\C(=O)NC2(c3ccc(-c4ncn(-c5ccc(OC(F)(F)F)cc5)n4)cc3)CC2)c1]
P722
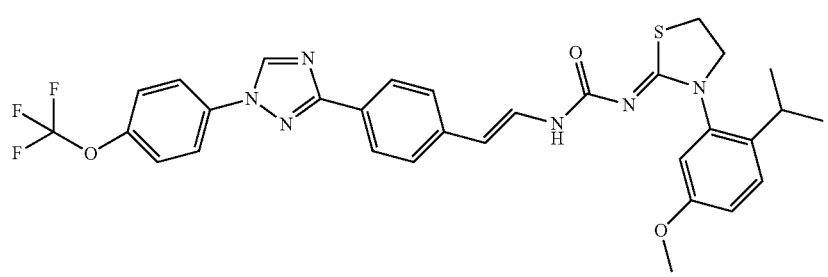 [SMILES: COc1ccc(C(C)C)c(N2CCS/C2=N\C(=O)N/C=C/c2ccc(-c3ncn(-c4ccc(OC(F)(F)F)cc4)n3)cc2)c1]
P723

TABLE P-Two-continued
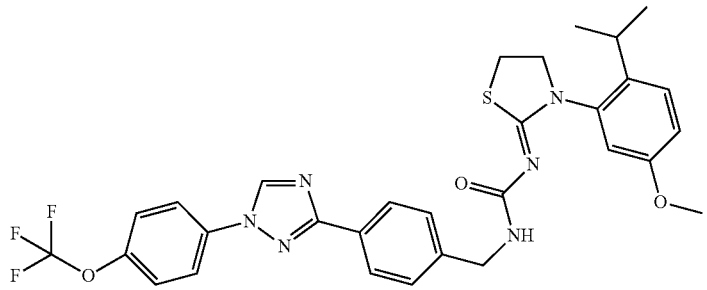 [SMILES: COc1ccc(C(C)C)c(N2CCS/C2=N\C(=O)NCc2ccc(-c3ncn(-c4ccc(OC(F)(F)F)cc4)n3)cc2)c1]
P724
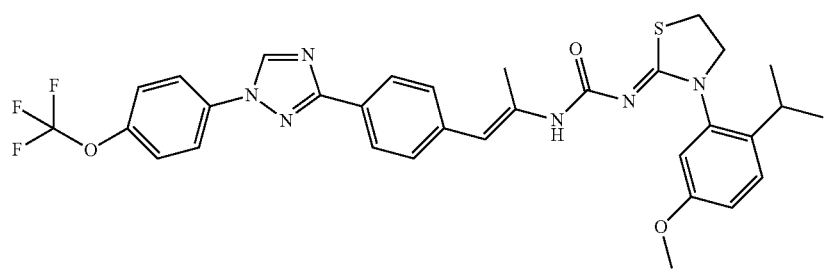 [SMILES: COc1ccc(C(C)C)c(N2CCS/C2=N\C(=O)N/C(C)=C/c2ccc(-c3ncn(-c4ccc(OC(F)(F)F)cc4)n3)cc2)c1]
P725
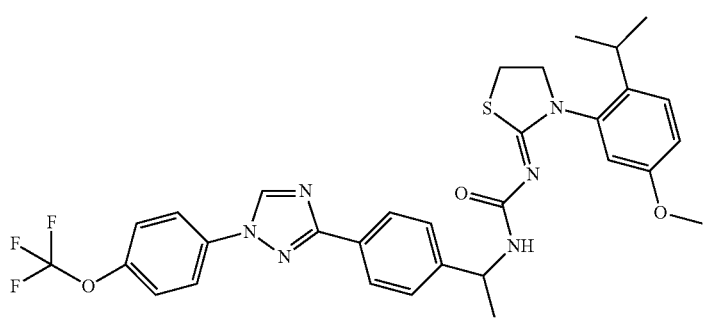 [SMILES: COc1ccc(C(C)C)c(N2CCS/C2=N\C(=O)NC(C)c2ccc(-c3ncn(-c4ccc(OC(F)(F)F)cc4)n3)cc2)c1]
P726
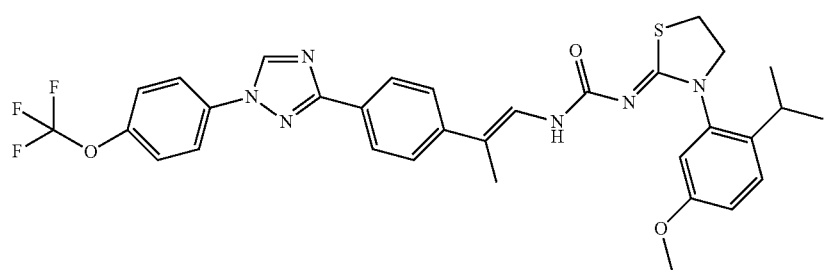 [SMILES: COc1ccc(C(C)C)c(N2CCS/C2=N\C(=O)N/C=C(\C)c2ccc(-c3ncn(-c4ccc(OC(F)(F)F)cc4)n3)cc2)c1]
P727
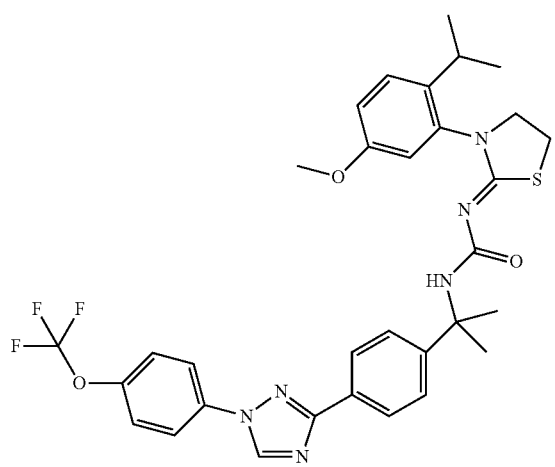 [SMILES: COc1ccc(C(C)C)c(N2CCS/C2=N\C(=O)NC(C)(C)c2ccc(-c3ncn(-c4ccc(OC(F)(F)F)cc4)n3)cc2)c1]
P728

TABLE P-Two-continued
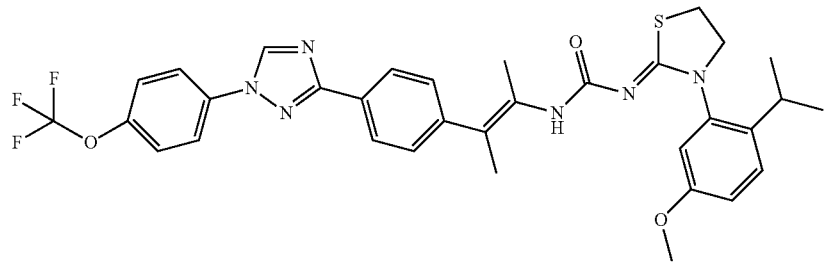 [SMILES: COc1ccc(C(C)C)c(N2CCS/C2=N\C(=O)N/C(C)=C(\C)c2ccc(-c3ncn(-c4ccc(OC(F)(F)F)cc4)n3)cc2)c1]
P729
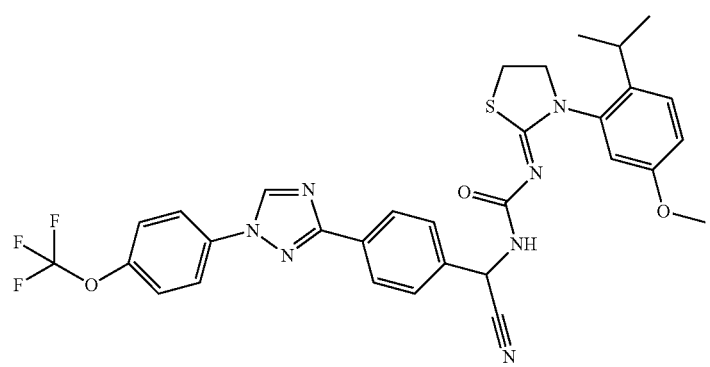 [SMILES: COc1ccc(C(C)C)c(N2CCS/C2=N\C(=O)NC(C#N)c2ccc(-c3ncn(-c4ccc(OC(F)(F)F)cc4)n3)cc2)c1]
P730
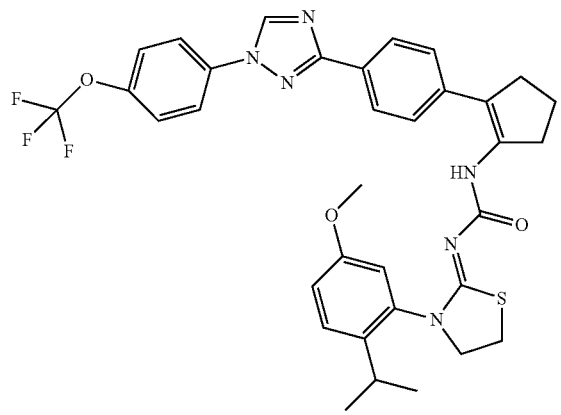 [SMILES: COc1ccc(C(C)C)c(N2CCS/C2=N\C(=O)NC2=C(c3ccc(-c4ncn(-c5ccc(OC(F)(F)F)cc5)n4)cc3)CCC2)c1]
P731
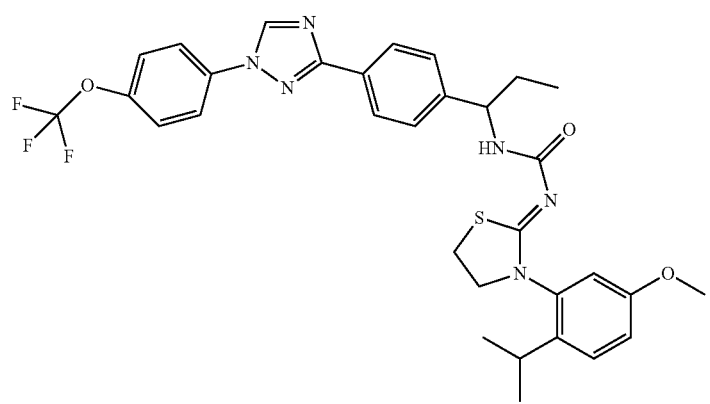 [SMILES: CCC(NC(=O)/N=C1\SCCN1c1cc(OC)ccc1C(C)C)c1ccc(-c2ncn(-c3ccc(OC(F)(F)F)cc3)n2)cc1]
P732

TABLE P-Two-continued
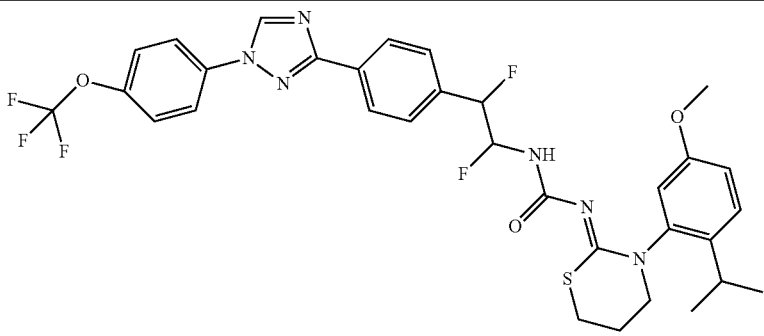
P733
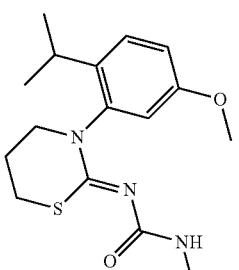
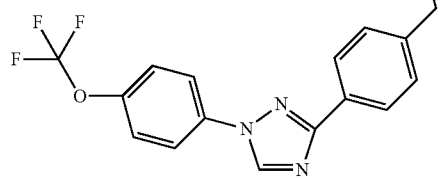
P734
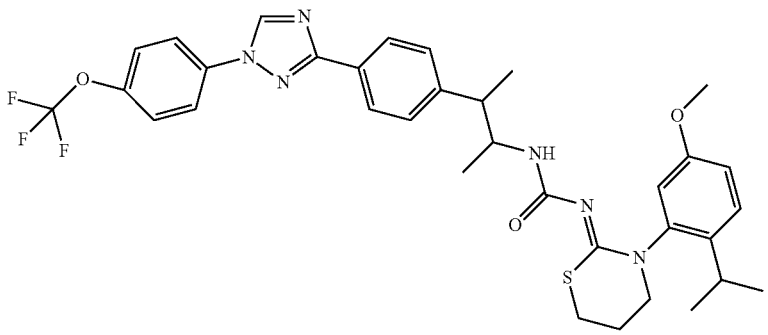 [SMILES: COc1ccc(C(C)C)c(N2CCCS/C2=N\C(=O)NC(C)C(C)c2ccc(-c3ncn(-c4ccc(OC(F)(F)F)cc4)n3)cc2)c1]
P735
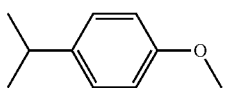
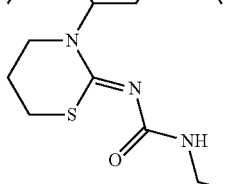
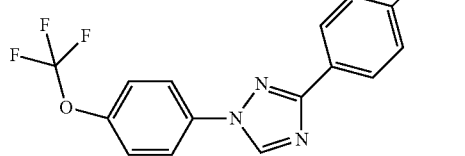
P736

TABLE P-Two-continued
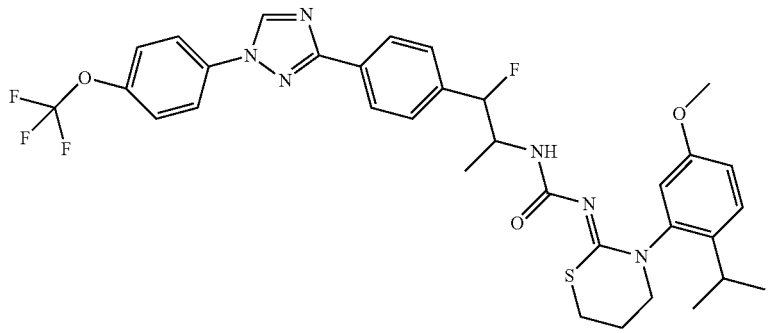 [SMILES: COc1ccc(C(C)C)c(N2CCCS/C2=N\C(=O)NC(C)C(F)c2ccc(-c3ncn(-c4ccc(OC(F)(F)F)cc4)n3)cc2)c1]
P737
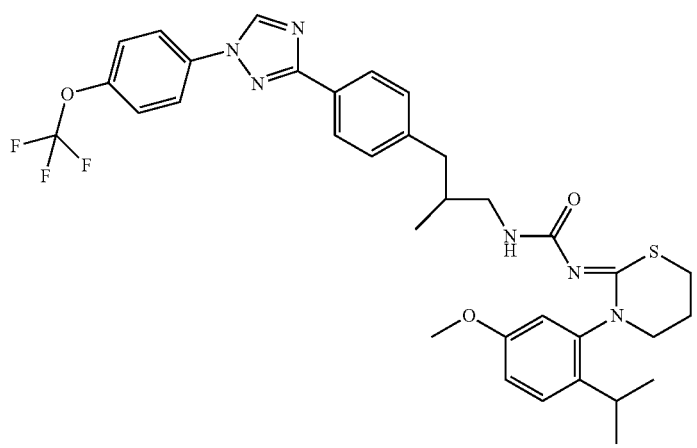 [SMILES: COc1ccc(C(C)C)c(N2CCCS/C2=N\C(=O)NCC(C)Cc2ccc(-c3ncn(-c4ccc(OC(F)(F)F)cc4)n3)cc2)c1]
P738
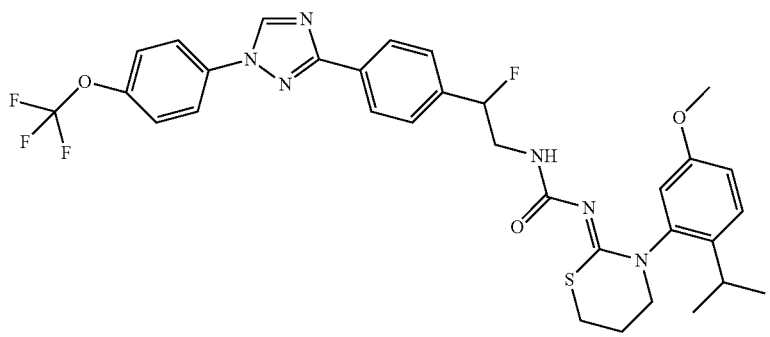 [SMILES: COc1ccc(C(C)C)c(N2CCCS/C2=N\C(=O)NCC(F)c2ccc(-c3ncn(-c4ccc(OC(F)(F)F)cc4)n3)cc2)c1]
P739
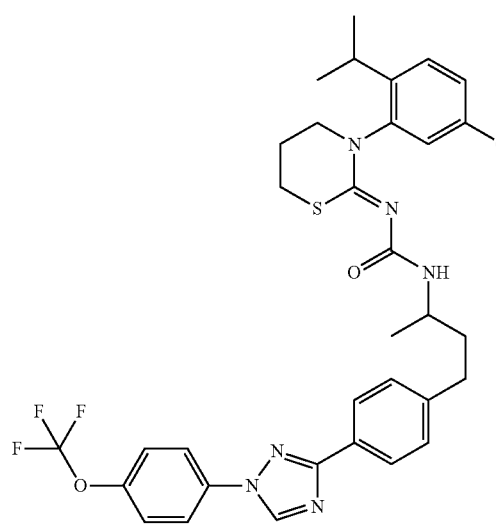
P740

TABLE P-Two-continued
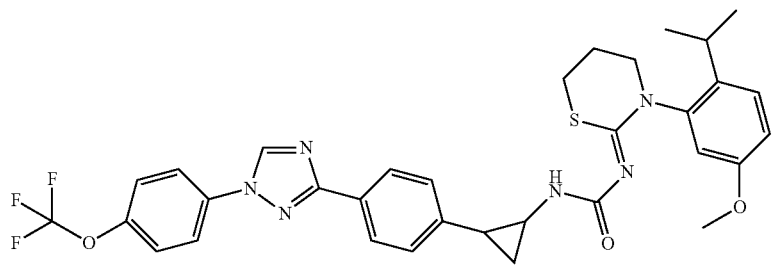 [SMILES: COc1ccc(C(C)C)c(N2CCCS/C2=N\C(=O)NC2CC2c2ccc(-c3ncn(-c4ccc(OC(F)(F)F)cc4)n3)cc2)c1]
P741
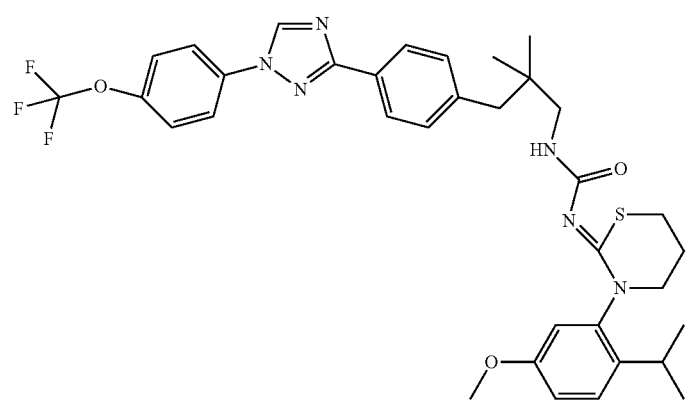 [SMILES: COc1ccc(C(C)C)c(N2CCCS/C2=N\C(=O)NCC(C)(C)Cc2ccc(-c3ncn(-c4ccc(OC(F)(F)F)cc4)n3)cc2)c1]
P742
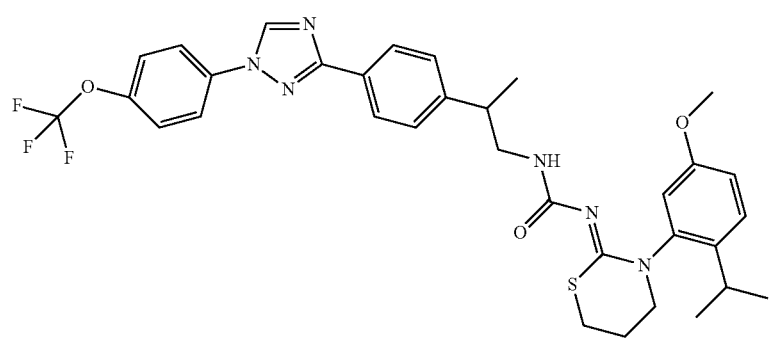 [SMILES: COc1ccc(C(C)C)c(N2CCCS/C2=N\C(=O)NCC(C)c2ccc(-c3ncn(-c4ccc(OC(F)(F)F)cc4)n3)cc2)c1]
P743
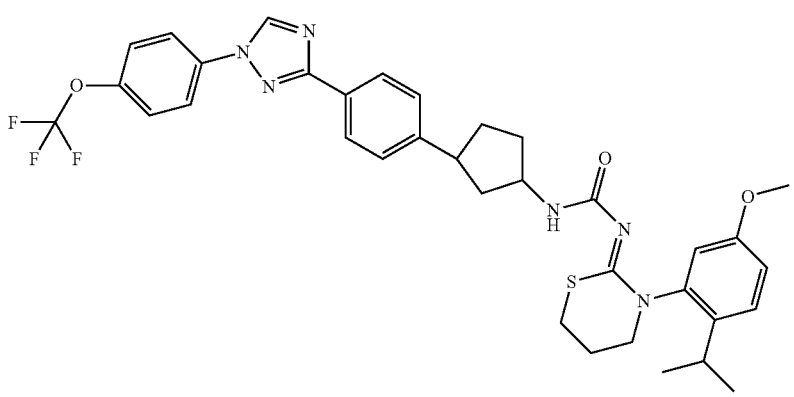 [SMILES: COc1ccc(C(C)C)c(N2CCCS/C2=N\C(=O)NC2CCC(c3ccc(-c4ncn(-c5ccc(OC(F)(F)F)cc5)n4)cc3)C2)c1]
P744

TABLE P-Two-continued
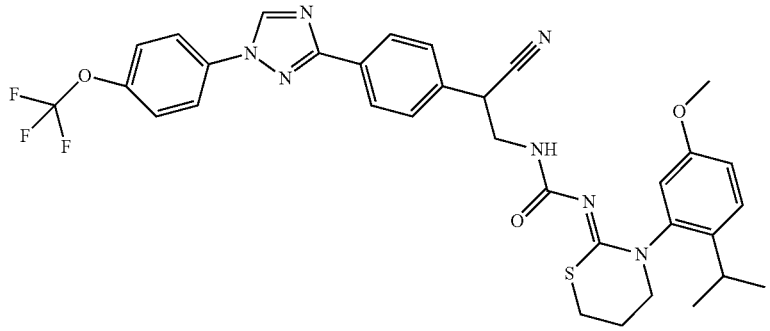 [SMILES: COc1ccc(C(C)C)c(N2CCCS/C2=N\C(=O)NCC(C#N)c2ccc(-c3ncn(-c4ccc(OC(F)(F)F)cc4)n3)cc2)c1]
P745
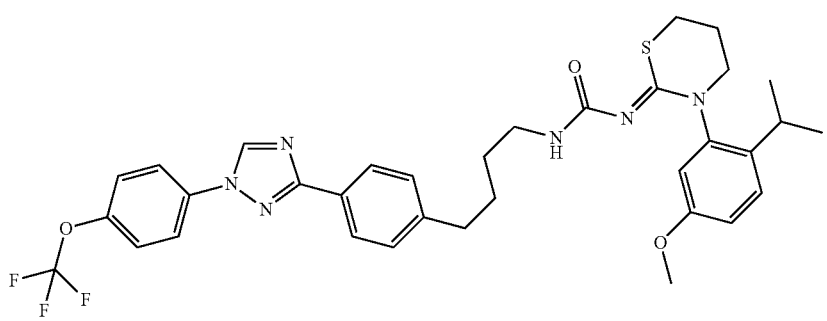 [SMILES: COc1ccc(C(C)C)c(N2CCCS/C2=N\C(=O)NCCCCc2ccc(-c3ncn(-c4ccc(OC(F)(F)F)cc4)n3)cc2)c1]
P746
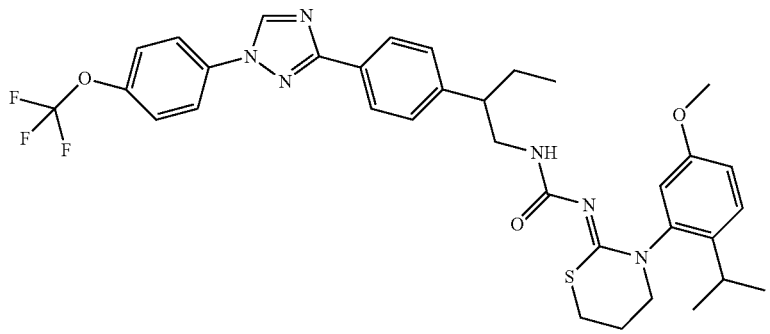 [SMILES: CCC(CNC(=O)/N=C1\SCCCN1c1cc(OC)ccc1C(C)C)c1ccc(-c2ncn(-c3ccc(OC(F)(F)F)cc3)n2)cc1]
P747
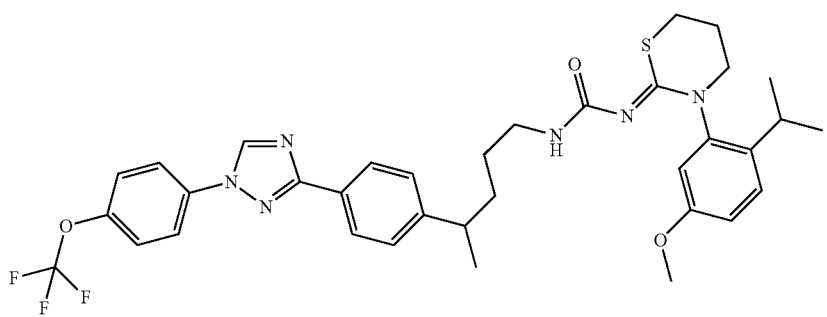 [SMILES: COc1ccc(C(C)C)c(N2CCCS/C2=N\C(=O)NCCCC(C)c2ccc(-c3ncn(-c4ccc(OC(F)(F)F)cc4)n3)cc2)c1]
P748

TABLE P-Two-continued
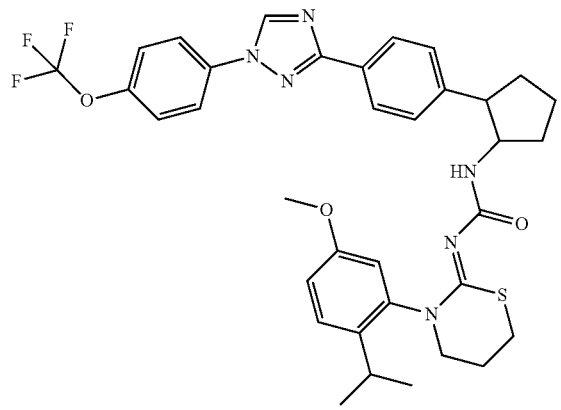 [SMILES: COc1ccc(C(C)C)c(N2CCCS/C2=N\C(=O)NC2CCCC2c2ccc(-c3ncn(-c4ccc(OC(F)(F)F)cc4)n3)cc2)c1]
P749
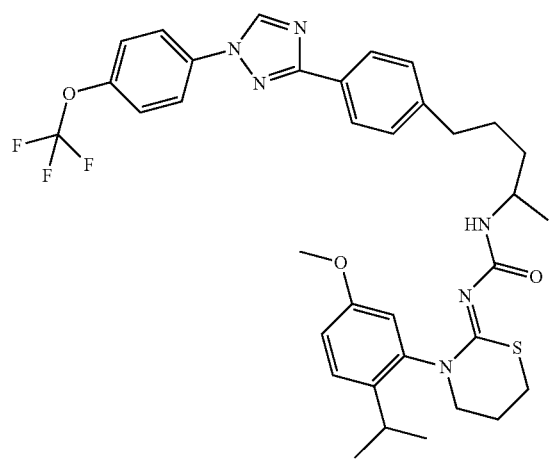 [SMILES: COc1ccc(C(C)C)c(N2CCCS/C2=N\C(=O)NC(C)CCCc2ccc(-c3ncn(-c4ccc(OC(F)(F)F)cc4)n3)cc2)c1]
P750
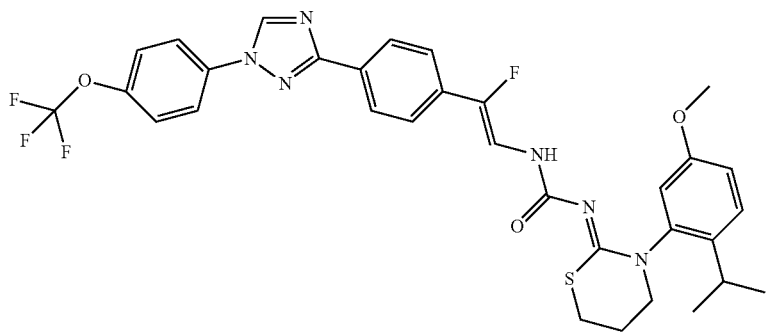 [SMILES: COc1ccc(C(C)C)c(N2CCCS/C2=N\C(=O)N/C=C(\F)c2ccc(-c3ncn(-c4ccc(OC(F)(F)F)cc4)n3)cc2)c1]
P751
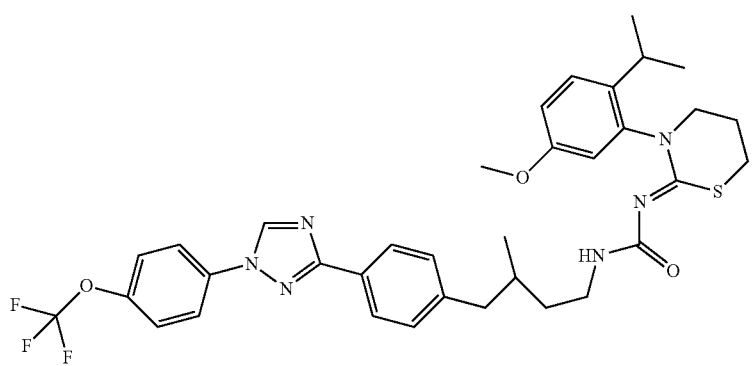 [SMILES: COc1ccc(C(C)C)c(N2CCCS/C2=N\C(=O)NCCC(C)Cc2ccc(-c3ncn(-c4ccc(OC(F)(F)F)cc4)n3)cc2)c1]
P752

TABLE P-Two-continued
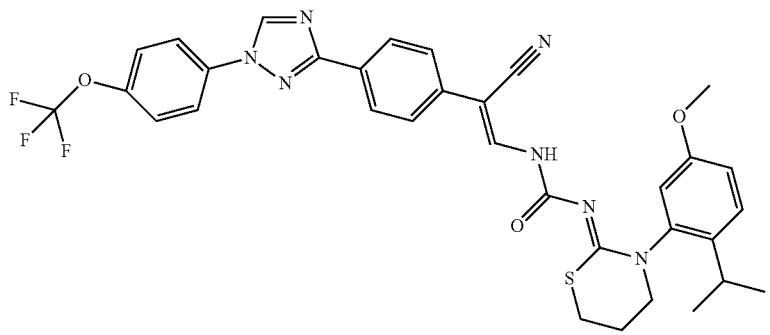 [SMILES: COc1ccc(C(C)C)c(N2CCCS/C2=N\C(=O)N/C=C(\C#N)c2ccc(-c3ncn(-c4ccc(OC(F)(F)F)cc4)n3)cc2)c1]
P753
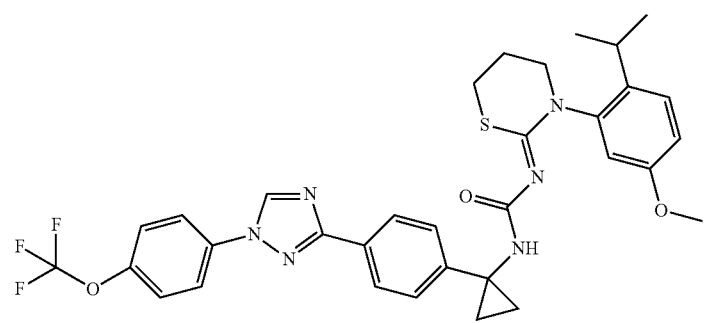 [SMILES: COc1ccc(C(C)C)c(N2CCCS/C2=N\C(=O)NC2(c3ccc(-c4ncn(-c5ccc(OC(F)(F)F)cc5)n4)cc3)CC2)c1]
P754
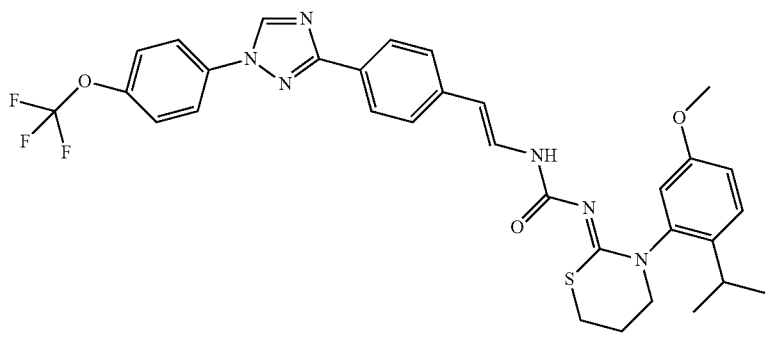 [SMILES: COc1ccc(C(C)C)c(N2CCCS/C2=N\C(=O)N/C=C/c2ccc(-c3ncn(-c4ccc(OC(F)(F)F)cc4)n3)cc2)c1]
P755
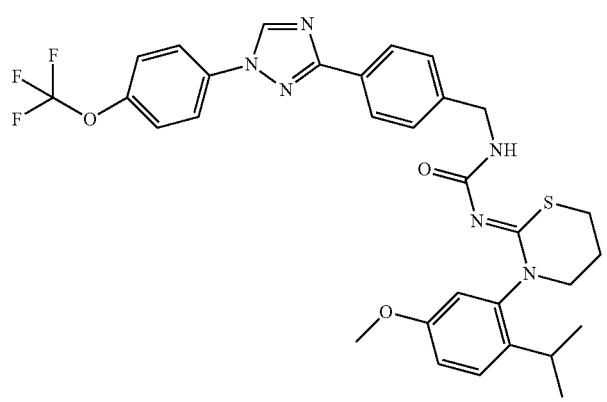 [SMILES: COc1ccc(C(C)C)c(N2CCCS/C2=N\C(=O)NCc2ccc(-c3ncn(-c4ccc(OC(F)(F)F)cc4)n3)cc2)c1]
P756

TABLE P-Two-continued
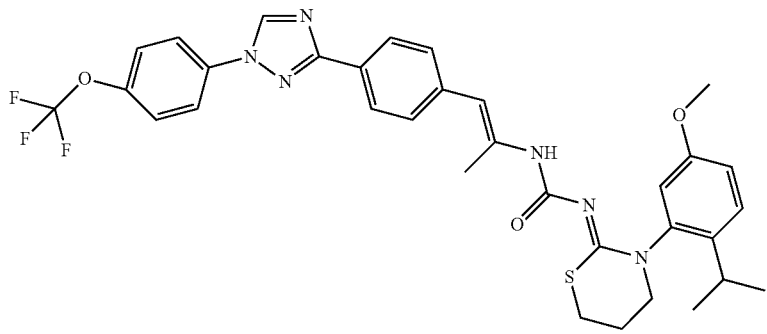 [SMILES: COc1ccc(C(C)C)c(N2CCCS/C2=N\C(=O)N/C(C)=C/c2ccc(-c3ncn(-c4ccc(OC(F)(F)F)cc4)n3)cc2)c1]
P757
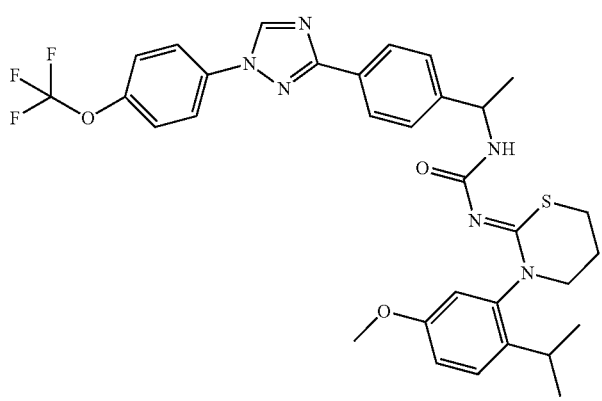 [SMILES: COc1ccc(C(C)C)c(N2CCCS/C2=N\C(=O)NC(C)c2ccc(-c3ncn(-c4ccc(OC(F)(F)F)cc4)n3)cc2)c1]
P758
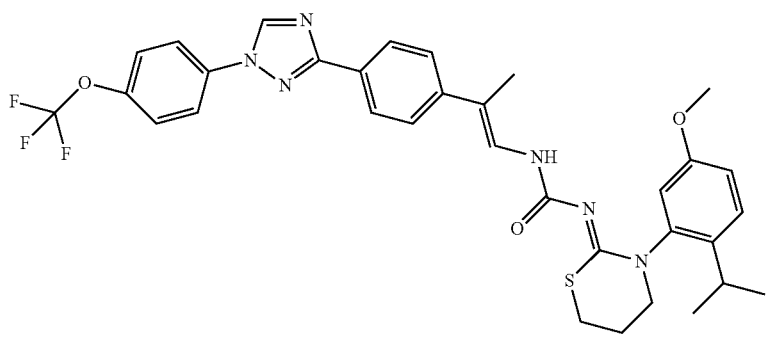 [SMILES: COc1ccc(C(C)C)c(N2CCCS/C2=N\C(=O)N/C=C(\C)c2ccc(-c3ncn(-c4ccc(OC(F)(F)F)cc4)n3)cc2)c1]
P759
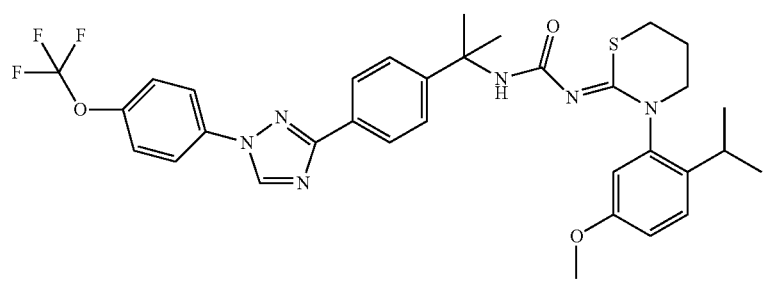 [SMILES: COc1ccc(C(C)C)c(N2CCCS/C2=N\C(=O)NC(C)(C)c2ccc(-c3ncn(-c4ccc(OC(F)(F)F)cc4)n3)cc2)c1]
P760

TABLE P-Two-continued
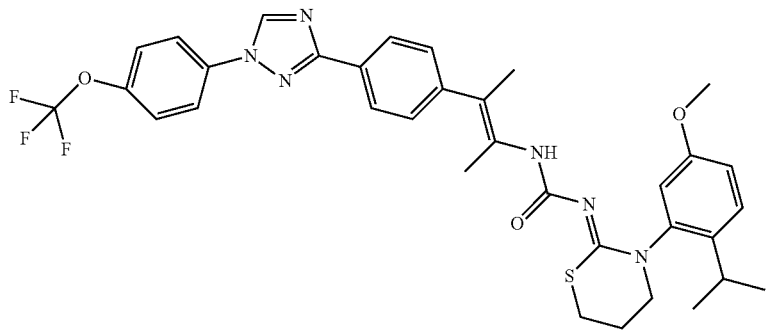 [SMILES: COc1ccc(C(C)C)c(N2CCCS/C2=N\C(=O)N/C(C)=C(\C)c2ccc(-c3ncn(-c4ccc(OC(F)(F)F)cc4)n3)cc2)c1]
P761
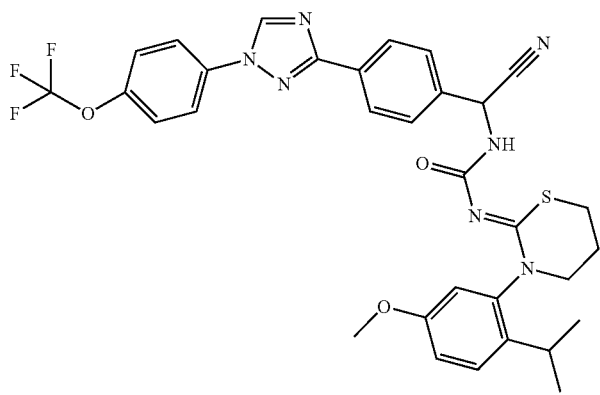 [SMILES: COc1ccc(C(C)C)c(N2CCCS/C2=N\C(=O)NC(C#N)c2ccc(-c3ncn(-c4ccc(OC(F)(F)F)cc4)n3)cc2)c1]
P762
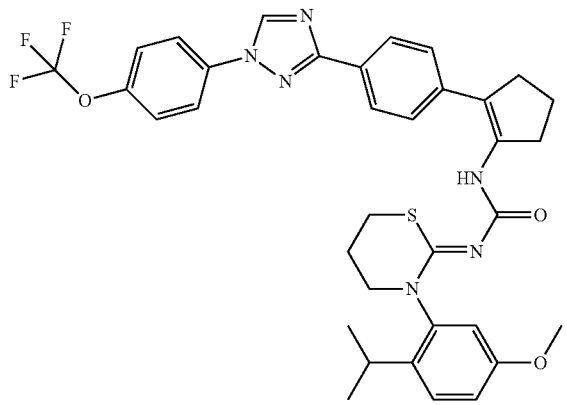 [SMILES: COc1ccc(C(C)C)c(N2CCCS/C2=N\C(=O)NC2=C(c3ccc(-c4ncn(-c5ccc(OC(F)(F)F)cc5)n4)cc3)CCC2)c1]
P763
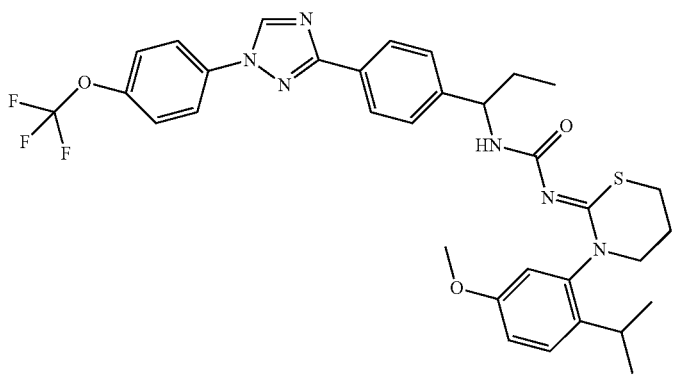 [SMILES: CCC(NC(=O)/N=C1\SCCCN1c1cc(OC)ccc1C(C)C)c1ccc(-c2ncn(-c3ccc(OC(F)(F)F)cc3)n2)cc1]
P764

TABLE P-Two-continued
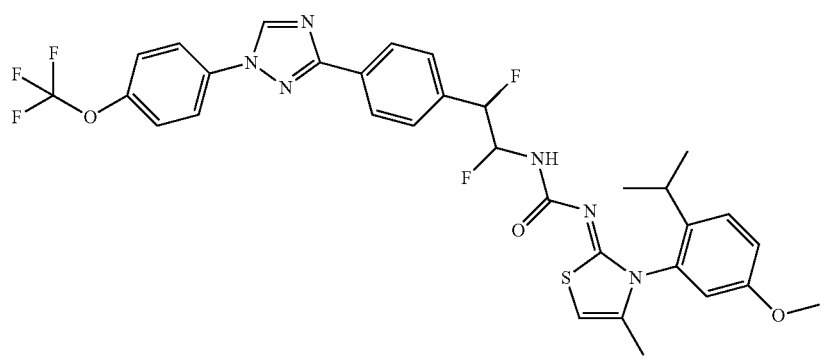 [SMILES: COc1ccc(C(C)C)c(-n2c(C)cs/c2=N\C(=O)NC(F)C(F)c2ccc(-c3ncn(-c4ccc(OC(F)(F)F)cc4)n3)cc2)c1]
P765
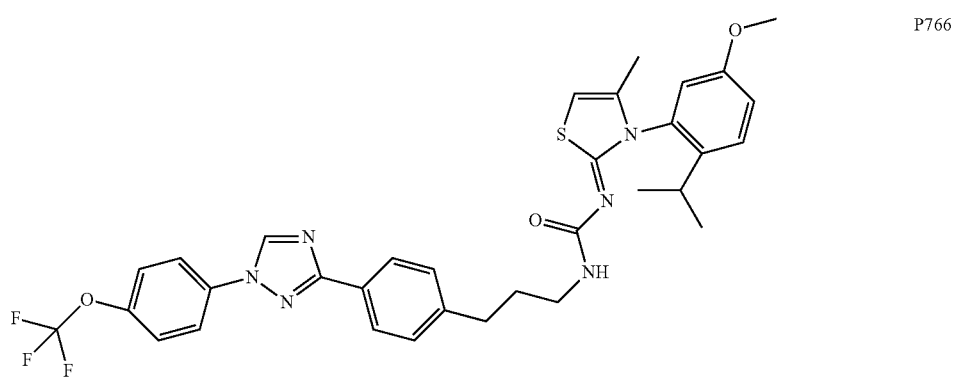
P766
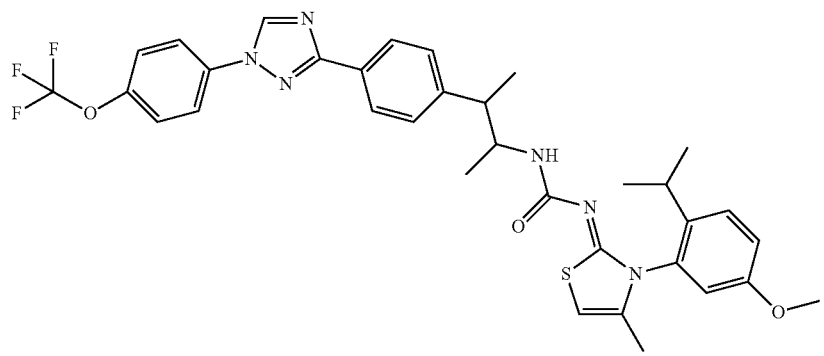
P767
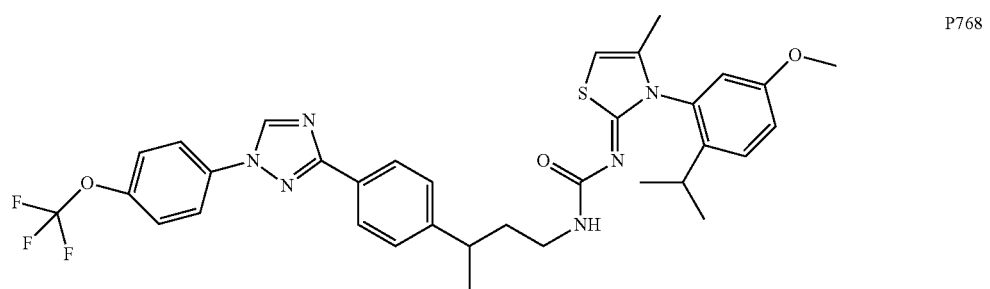
P768

TABLE P-Two-continued
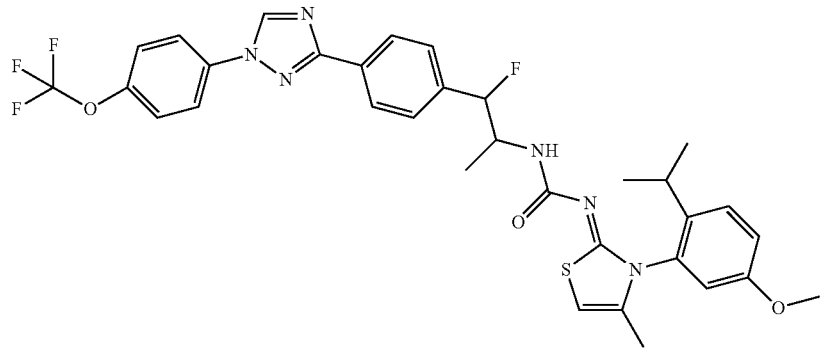 [SMILES: COc1ccc(C(C)C)c(-n2c(C)cs/c2=N\C(=O)NC(C)C(C)c2ccc(-c3ncn(-c4ccc(OC(F)(F)F)cc4)n3)cc2)c1]
P769
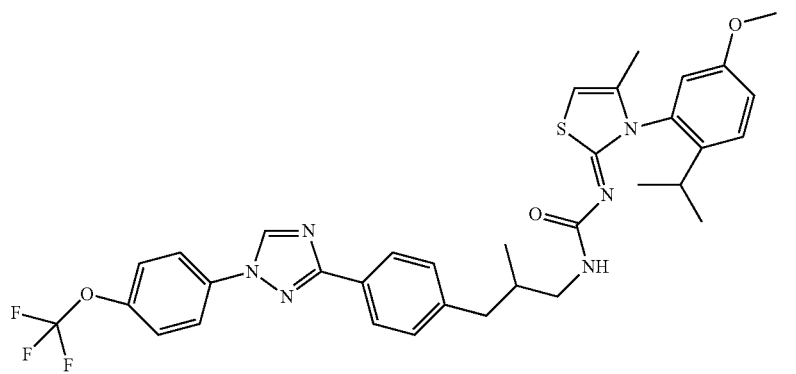 [SMILES: COc1ccc(C(C)C)c(-n2c(C)cs/c2=N\C(=O)NCC(C)Cc2ccc(-c3ncn(-c4ccc(OC(F)(F)F)cc4)n3)cc2)c1]
P770
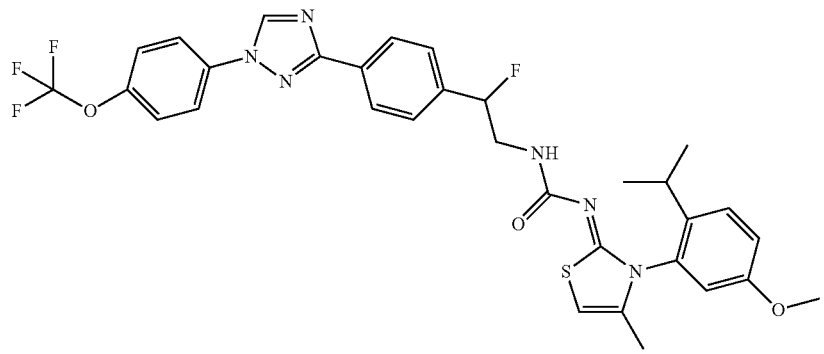 [SMILES: COc1ccc(C(C)C)c(-n2c(C)cs/c2=N\C(=O)NCC(F)c2ccc(-c3ncn(-c4ccc(OC(F)(F)F)cc4)n3)cc2)c1]
P771
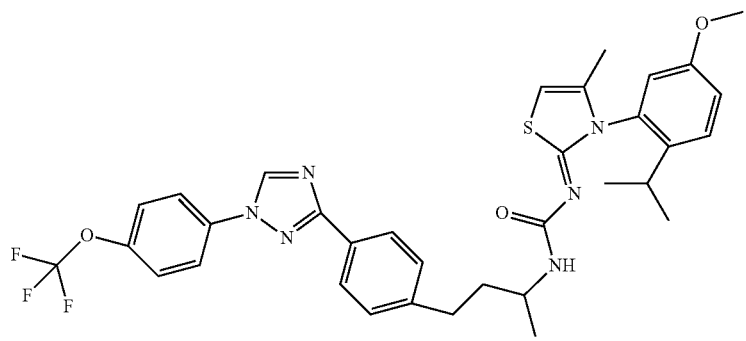 [SMILES: COc1ccc(C(C)C)c(-n2c(C)cs/c2=N\C(=O)NC(C)CCc2ccc(-c3ncn(-c4ccc(OC(F)(F)F)cc4)n3)cc2)c1]
P772

TABLE P-Two-continued
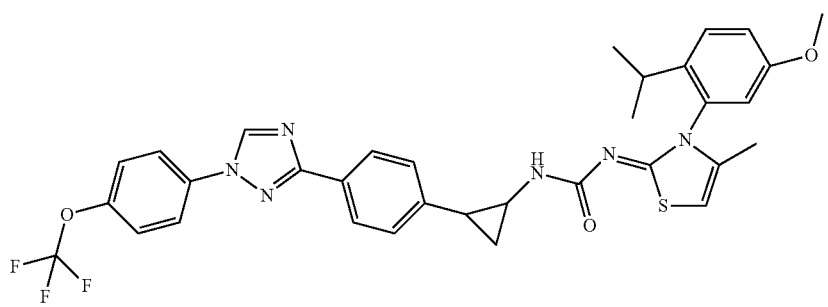 [SMILES: COc1ccc(C(C)C)c(-n2c(C)cs/c2=N\C(=O)NC2CC2c2ccc(-c3ncn(-c4ccc(OC(F)(F)F)cc4)n3)cc2)c1]
P773
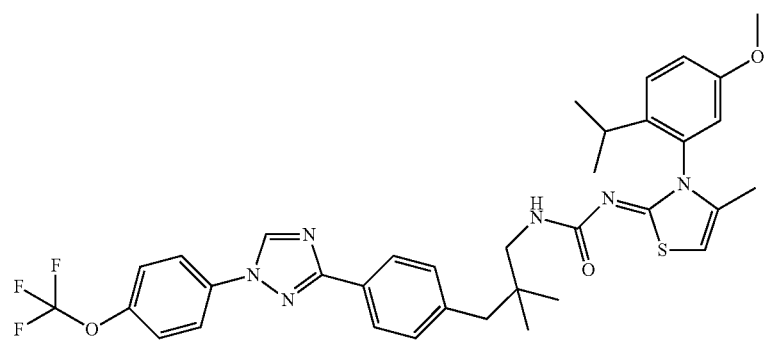 [SMILES: COc1ccc(C(C)C)c(-n2c(C)cs/c2=N\C(=O)NCC(C)(C)Cc2ccc(-c3ncn(-c4ccc(OC(F)(F)F)cc4)n3)cc2)c1]
P774
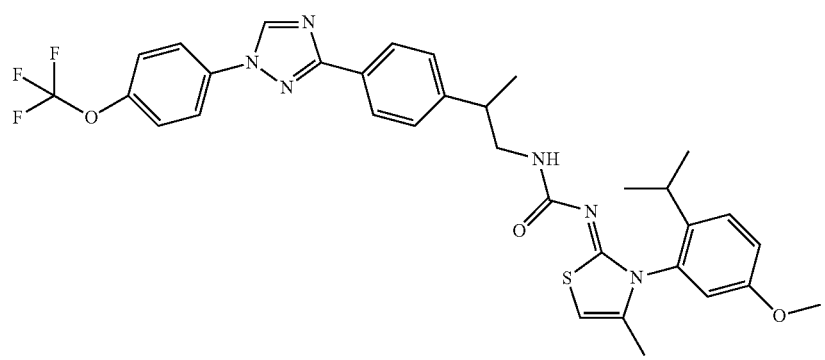 [SMILES: COc1ccc(C(C)C)c(-n2c(C)cs/c2=N\C(=O)NCC(C)c2ccc(-c3ncn(-c4ccc(OC(F)(F)F)cc4)n3)cc2)c1]
P775
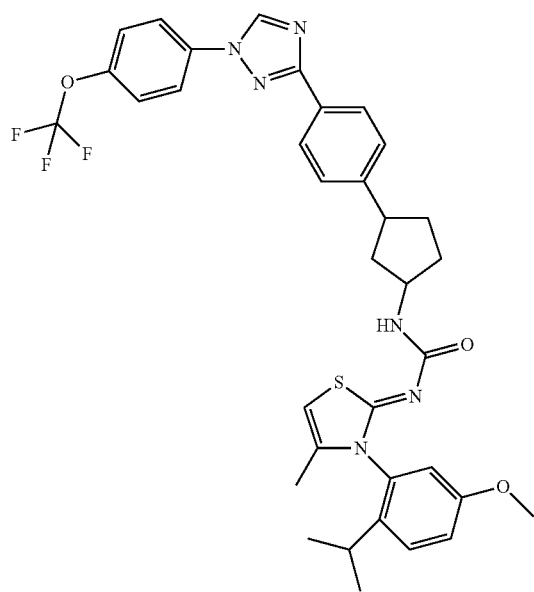 [SMILES: COc1ccc(C(C)C)c(-n2c(C)cs/c2=N\C(=O)NC2CCC(c3ccc(-c4ncn(-c5ccc(OC(F)(F)F)cc5)n4)cc3)C2)c1]
P776

TABLE P-Two-continued
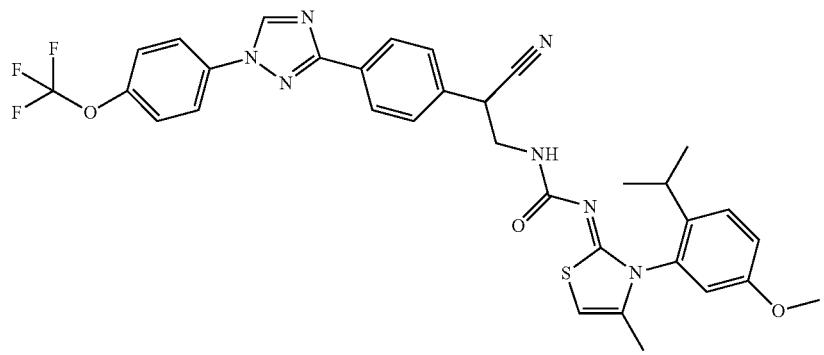 [SMILES: COc1ccc(C(C)C)c(-n2c(C)cs/c2=N\C(=O)NCC(C#N)c2ccc(-c3ncn(-c4ccc(OC(F)(F)F)cc4)n3)cc2)c1]
P777
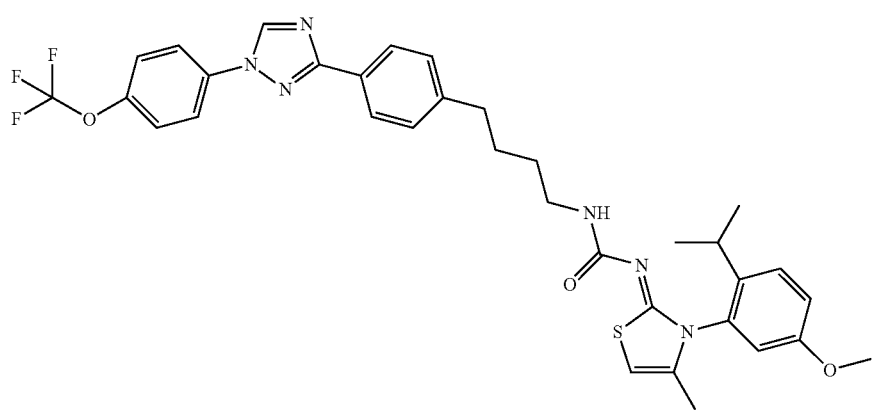 [SMILES: COc1ccc(C(C)C)c(-n2c(C)cs/c2=N\C(=O)NCCCCc2ccc(-c3ncn(-c4ccc(OC(F)(F)F)cc4)n3)cc2)c1]
P778
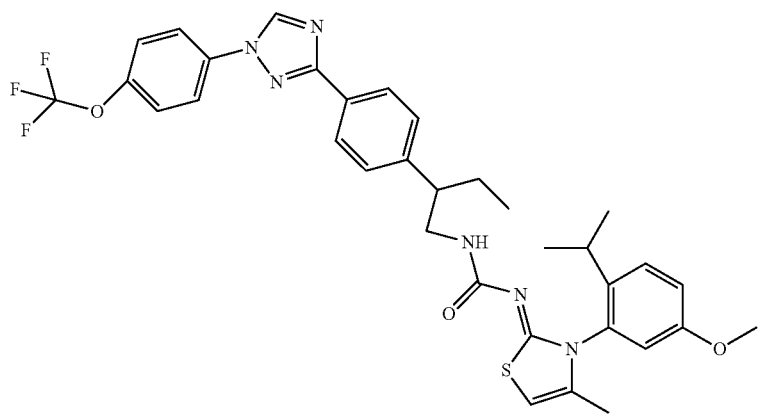 [SMILES: CCC(CNC(=O)/N=c1\scc(C)n1-c1cc(OC)ccc1C(C)C)c1ccc(-c2ncn(-c3ccc(OC(F)(F)F)cc3)n2)cc1]
P779
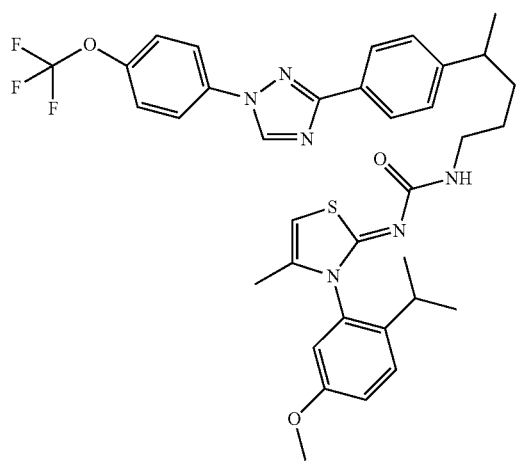 [SMILES: COc1ccc(C(C)C)c(-n2c(C)cs/c2=N\C(=O)NCCCC(C)c2ccc(-c3ncn(-c4ccc(OC(F)(F)F)cc4)n3)cc2)c1]
P780

TABLE P-Two-continued
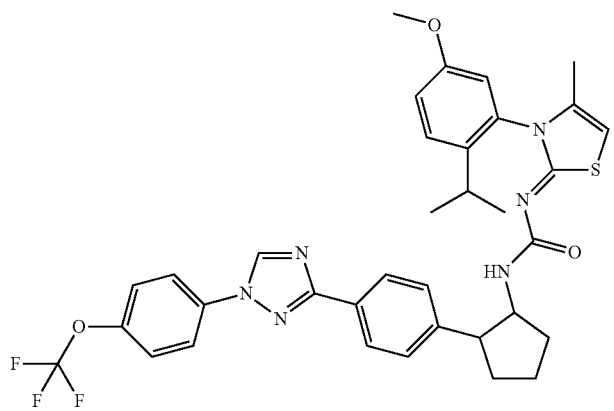 [SMILES: COc1ccc(C(C)C)c(-n2c(C)cs/c2=N\C(=O)NC2CCCC2c2ccc(-c3ncn(-c4ccc(OC(F)(F)F)cc4)n3)cc2)c1]
P781
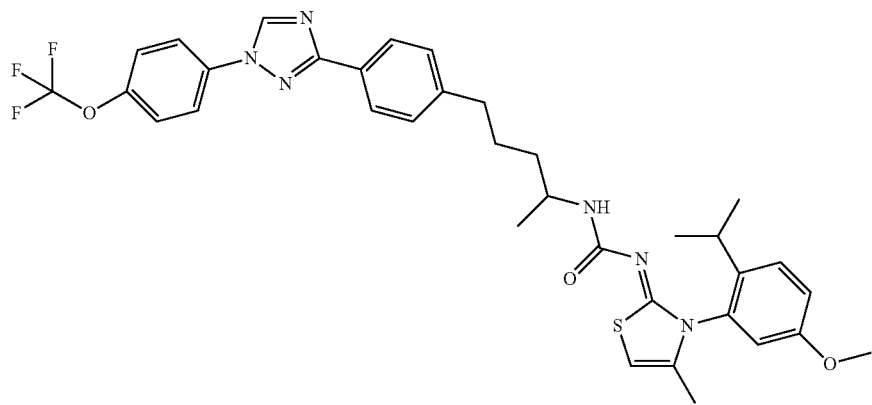 [SMILES: COc1ccc(C(C)C)c(-n2c(C)cs/c2=N\C(=O)NC(C)CCCc2ccc(-c3ncn(-c4ccc(OC(F)(F)F)cc4)n3)cc2)c1]
P782
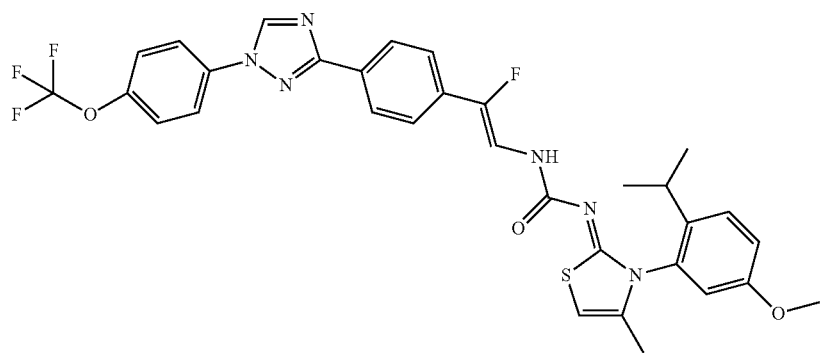 [SMILES: COc1ccc(C(C)C)c(-n2c(C)cs/c2=N\C(=O)N/C=C(\F)c2ccc(-c3ncn(-c4ccc(OC(F)(F)F)cc4)n3)cc2)c1]
P783
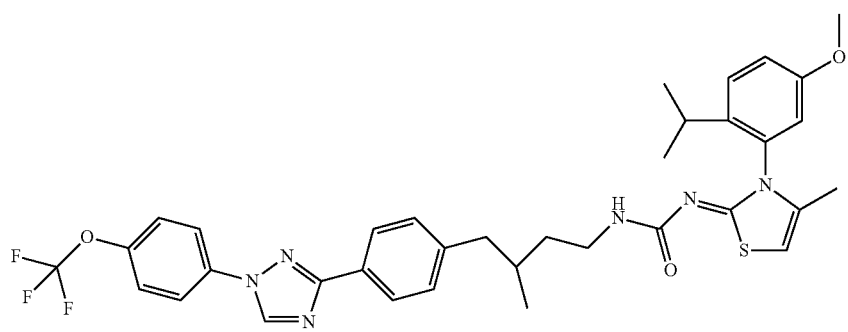 [SMILES: COc1ccc(C(C)C)c(-n2c(C)cs/c2=N\C(=O)NCCC(C)Cc2ccc(-c3ncn(-c4ccc(OC(F)(F)F)cc4)n3)cc2)c1]
P784

TABLE P-Two-continued
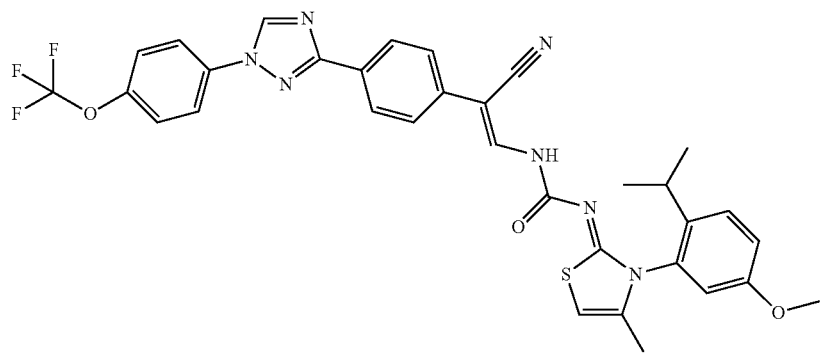 [SMILES: COc1ccc(C(C)C)c(-n2c(C)cs/c2=N\C(=O)N/C=C(\C#N)c2ccc(-c3ncn(-c4ccc(OC(F)(F)F)cc4)n3)cc2)c1]
P785
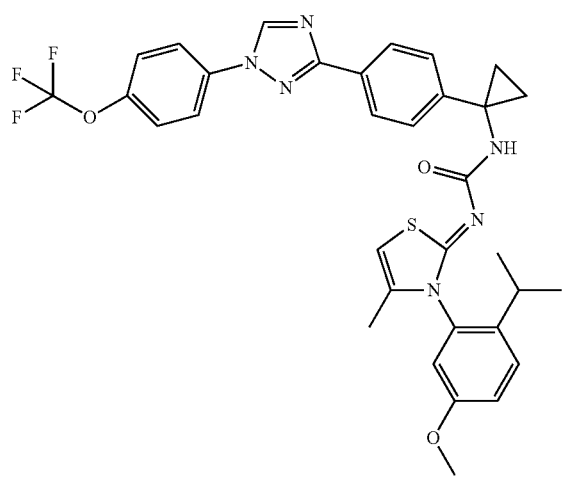 [SMILES: COc1ccc(C(C)C)c(-n2c(C)cs/c2=N\C(=O)NC2(c3ccc(-c4ncn(-c5ccc(OC(F)(F)F)cc5)n4)cc3)CC2)c1]
P786
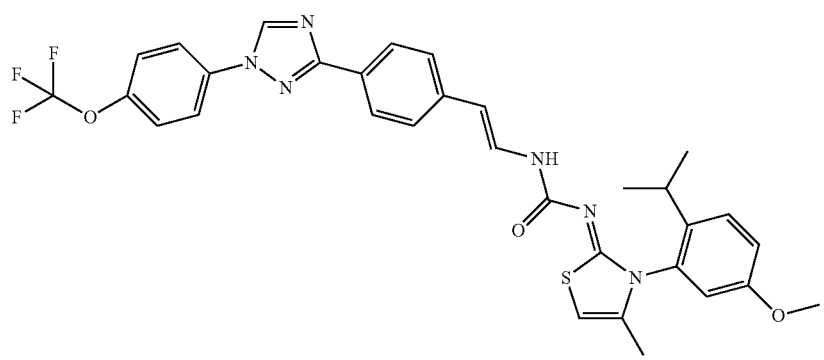 [SMILES: COc1ccc(C(C)C)c(-n2c(C)cs/c2=N\C(=O)N/C=C/c2ccc(-c3ncn(-c4ccc(OC(F)(F)F)cc4)n3)cc2)c1]
P787
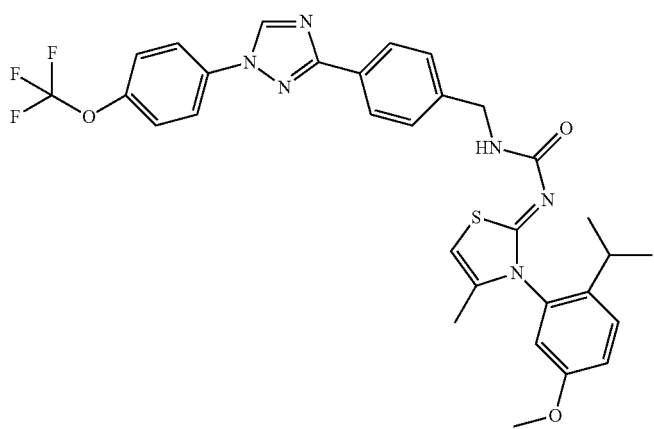 [SMILES: COc1ccc(C(C)C)c(-n2c(C)cs/c2=N\C(=O)NCc2ccc(-c3ncn(-c4ccc(OC(F)(F)F)cc4)n3)cc2)c1]
P788

TABLE P-Two-continued
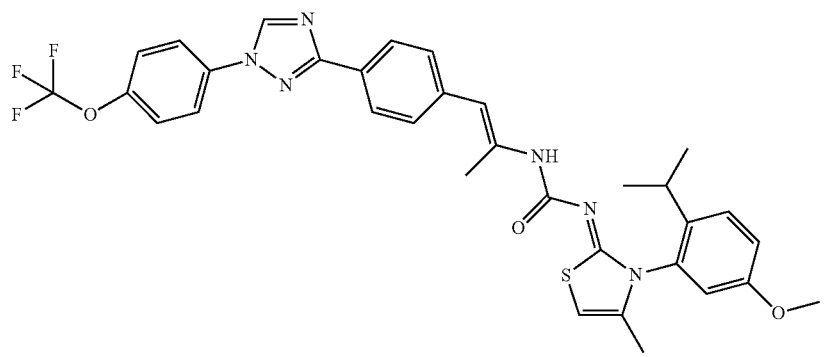 [SMILES: COc1ccc(C(C)C)c(-n2c(C)cs/c2=N\C(=O)N/C(C)=C/c2ccc(-c3ncn(-c4ccc(OC(F)(F)F)cc4)n3)cc2)c1]
P789
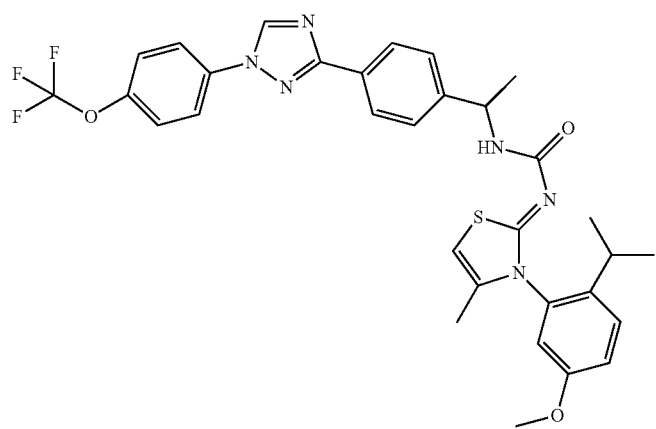 [SMILES: COc1ccc(C(C)C)c(-n2c(C)cs/c2=N\C(=O)NC(C)c2ccc(-c3ncn(-c4ccc(OC(F)(F)F)cc4)n3)cc2)c1]
P790
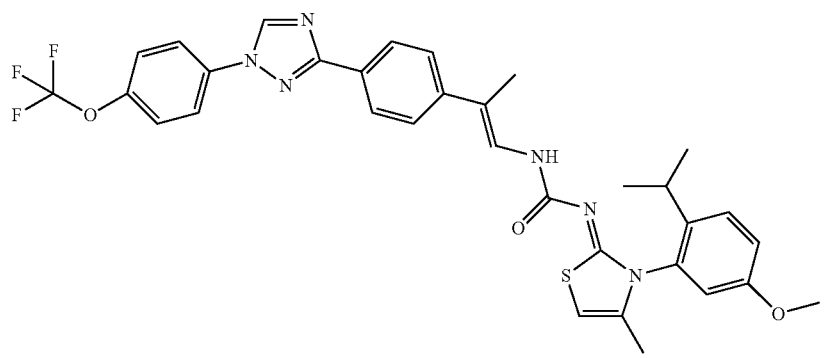 [SMILES: COc1ccc(C(C)C)c(-n2c(C)cs/c2=N\C(=O)N/C=C(\C)c2ccc(-c3ncn(-c4ccc(OC(F)(F)F)cc4)n3)cc2)c1]
P791
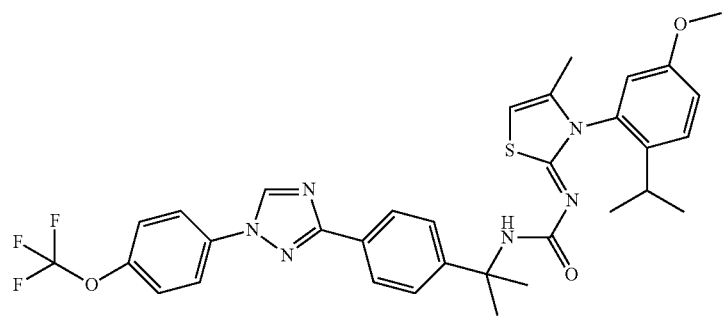 [SMILES: COc1ccc(C(C)C)c(-n2c(C)cs/c2=N\C(=O)NC(C)(C)c2ccc(-c3ncn(-c4ccc(OC(F)(F)F)cc4)n3)cc2)c1]
P792

TABLE P-Two-continued
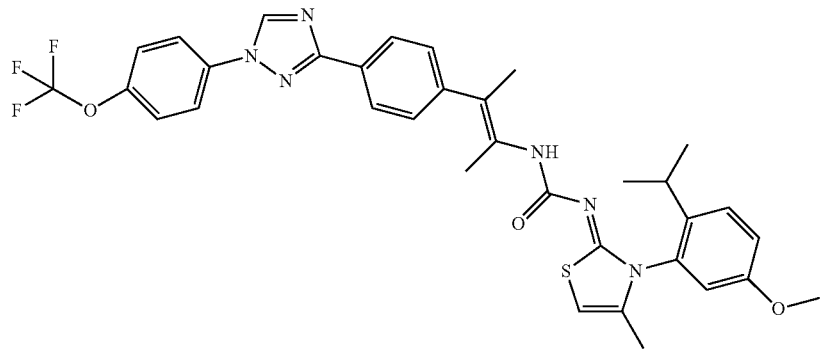 [SMILES: COc1ccc(C(C)C)c(-n2c(C)cs/c2=N\C(=O)N/C(C)=C(\C)c2ccc(-c3ncn(-c4ccc(OC(F)(F)F)cc4)n3)cc2)c1]
P793
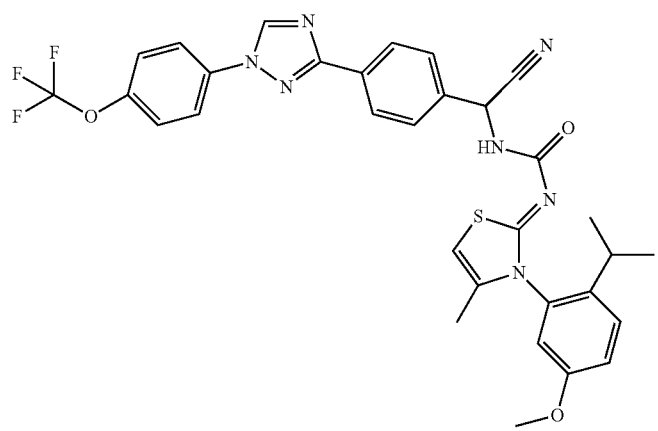 [SMILES: COc1ccc(C(C)C)c(-n2c(C)cs/c2=N\C(=O)NC(C#N)c2ccc(-c3ncn(-c4ccc(OC(F)(F)F)cc4)n3)cc2)c1]
P794
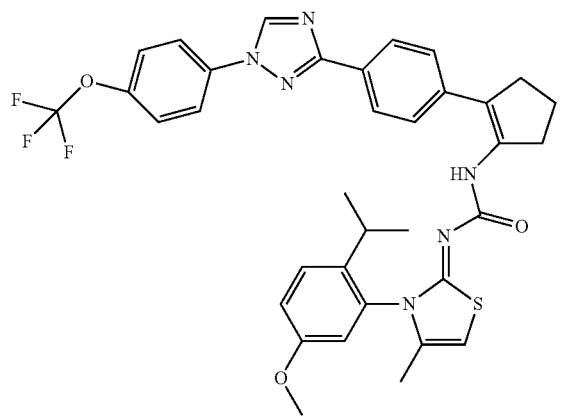 [SMILES: COc1ccc(C(C)C)c(-n2c(C)cs/c2=N\C(=O)NC2=C(c3ccc(-c4ncn(-c5ccc(OC(F)(F)F)cc5)n4)cc3)CCC2)c1]
P795
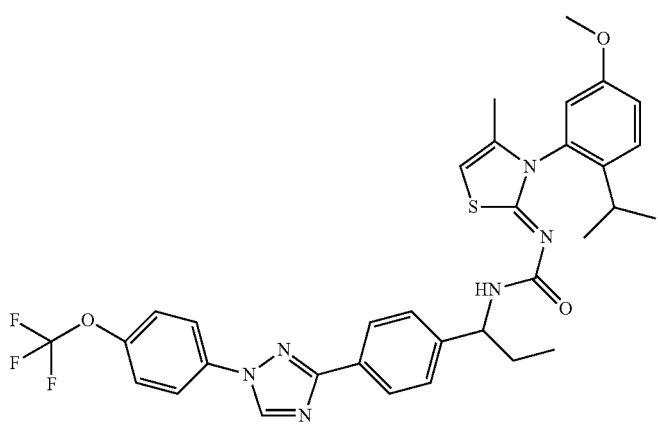 [SMILES: CCC(NC(=O)/N=c1\scc(C)n1-c1cc(OC)ccc1C(C)C)c1ccc(-c2ncn(-c3ccc(OC(F)(F)F)cc3)n2)cc1]
P796

TABLE P-Two-continued
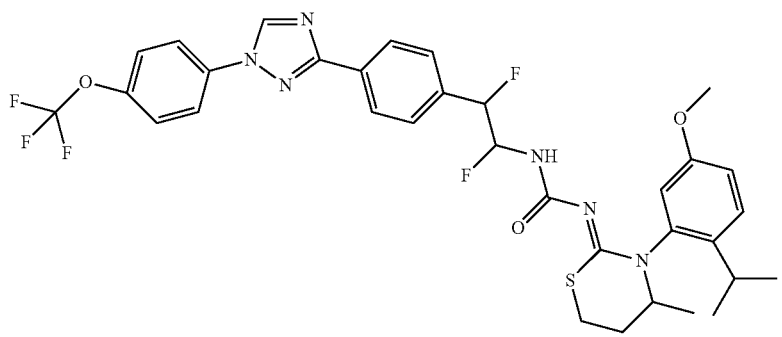 [SMILES: COc1ccc(C(C)C)c(N2/C(=N/C(=O)NC(F)C(F)c3ccc(-c4ncn(-c5ccc(OC(F)(F)F)cc5)n4)cc3)SCCC2C)c1]
P797
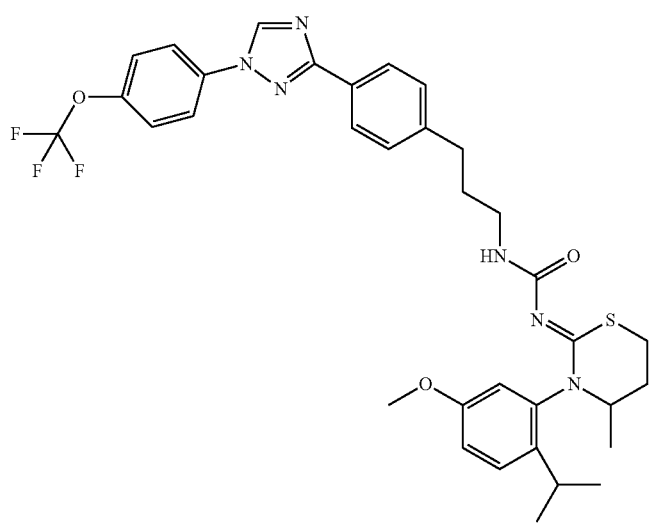 [SMILES: COc1ccc(C(C)C)c(N2/C(=N/C(=O)NCCCc3ccc(-c4ncn(-c5ccc(OC(F)(F)F)cc5)n4)cc3)SCCC2C)c1]
P798
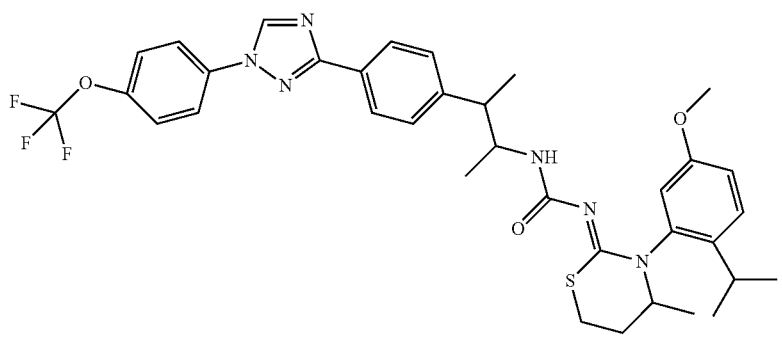 [SMILES: COc1ccc(C(C)C)c(N2/C(=N/C(=O)NC(C)C(C)c3ccc(-c4ncn(-c5ccc(OC(F)(F)F)cc5)n4)cc3)SCCC2C)c1]
P799

TABLE P-Two-continued
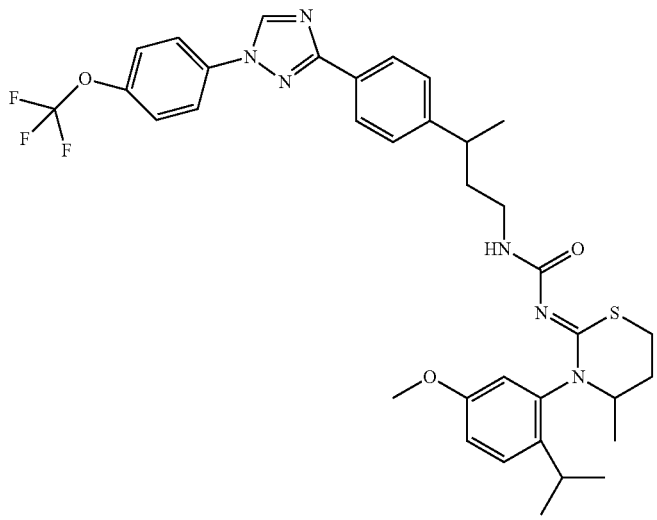 [SMILES: COc1ccc(C(C)C)c(N2/C(=N/C(=O)NCCC(C)c3ccc(-c4ncn(-c5ccc(OC(F)(F)F)cc5)n4)cc3)SCCC2C)c1]
P800
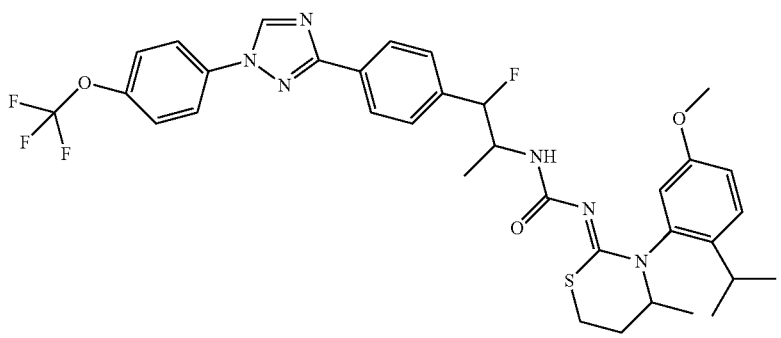 [SMILES: COc1ccc(C(C)C)c(N2/C(=N/C(=O)NC(C)C(F)c3ccc(-c4ncn(-c5ccc(OC(F)(F)F)cc5)n4)cc3)SCCC2C)c1]
P801
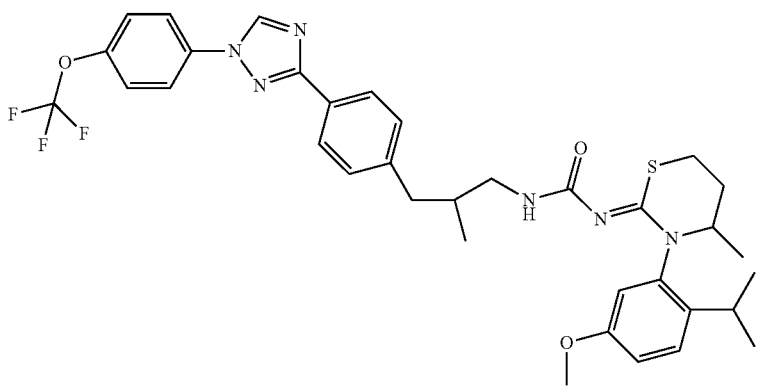 [SMILES: COc1ccc(C(C)C)c(N2/C(=N/C(=O)NCC(C)Cc3ccc(-c4ncn(-c5ccc(OC(F)(F)F)cc5)n4)cc3)SCCC2C)c1]
P802
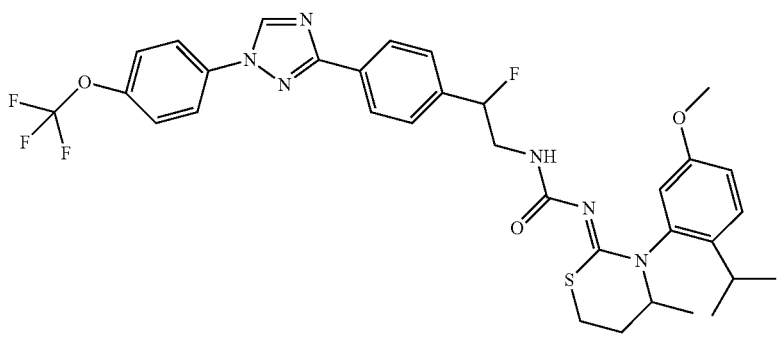 [SMILES: COc1ccc(C(C)C)c(N2/C(=N/C(=O)NCC(F)c3ccc(-c4ncn(-c5ccc(OC(F)(F)F)cc5)n4)cc3)SCCC2C)c1]
P803

TABLE P-Two-continued
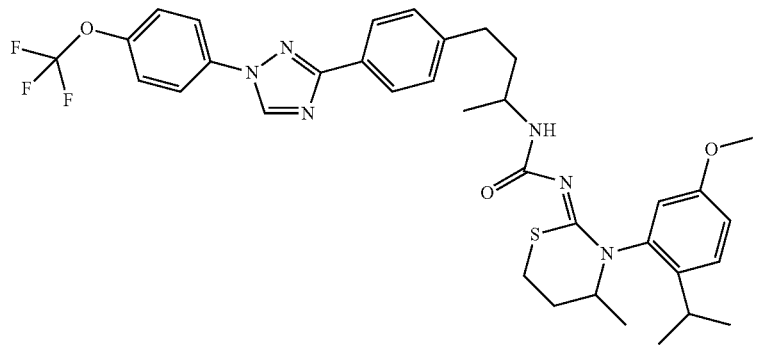 [SMILES: COc1ccc(C(C)C)c(N2/C(=N/C(=O)NC(C)CCc3ccc(-c4ncn(-c5ccc(OC(F)(F)F)cc5)n4)cc3)SCCC2C)c1]
P804
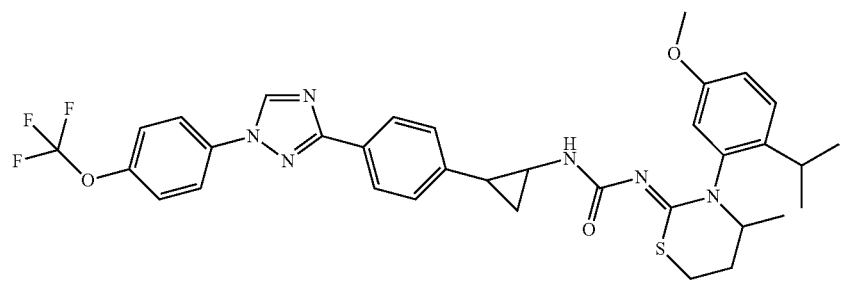 [SMILES: COc1ccc(C(C)C)c(N2/C(=N/C(=O)NC3CC3c3ccc(-c4ncn(-c5ccc(OC(F)(F)F)cc5)n4)cc3)SCCC2C)c1]
P805
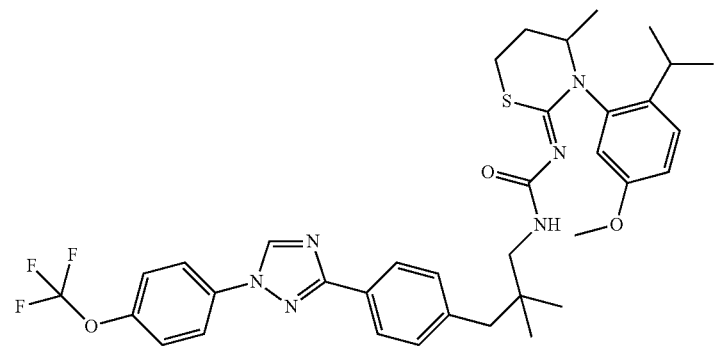 [SMILES: COc1ccc(C(C)C)c(N2/C(=N/C(=O)NCC(C)(C)Cc3ccc(-c4ncn(-c5ccc(OC(F)(F)F)cc5)n4)cc3)SCCC2C)c1]
P806
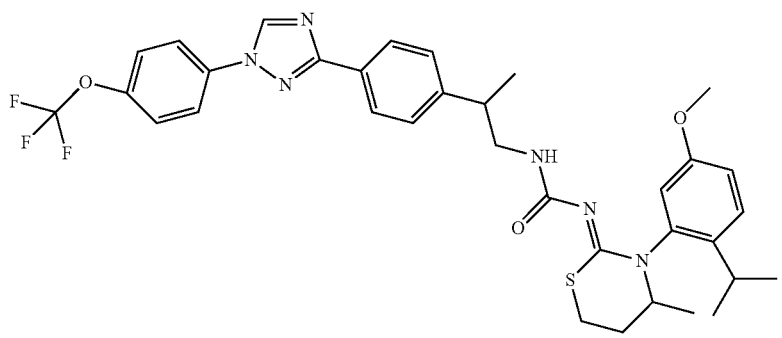 [SMILES: COc1ccc(C(C)C)c(N2/C(=N/C(=O)NCC(C)c3ccc(-c4ncn(-c5ccc(OC(F)(F)F)cc5)n4)cc3)SCCC2C)c1]
P807

TABLE P-Two-continued
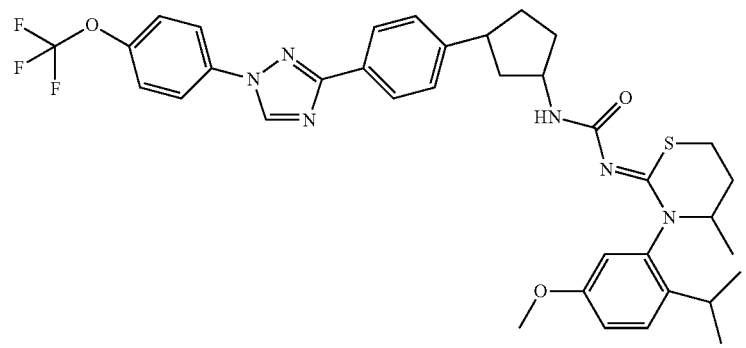 [SMILES: COc1ccc(C(C)C)c(N2/C(=N/C(=O)NC3CCC(c4ccc(-c5ncn(-c6ccc(OC(F)(F)F)cc6)n5)cc4)C3)SCCC2C)c1]
P808
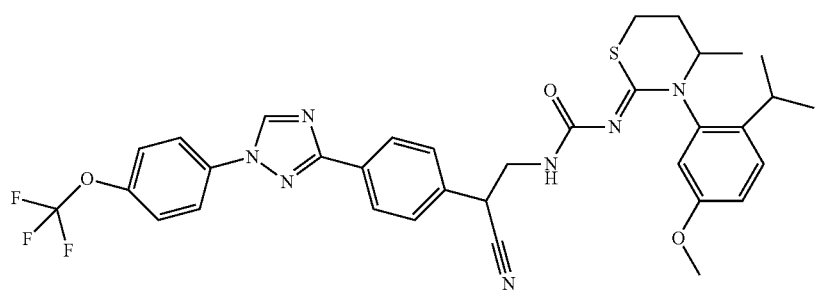 [SMILES: COc1ccc(C(C)C)c(N2/C(=N/C(=O)NCC(C#N)c3ccc(-c4ncn(-c5ccc(OC(F)(F)F)cc5)n4)cc3)SCCC2C)c1]
P809
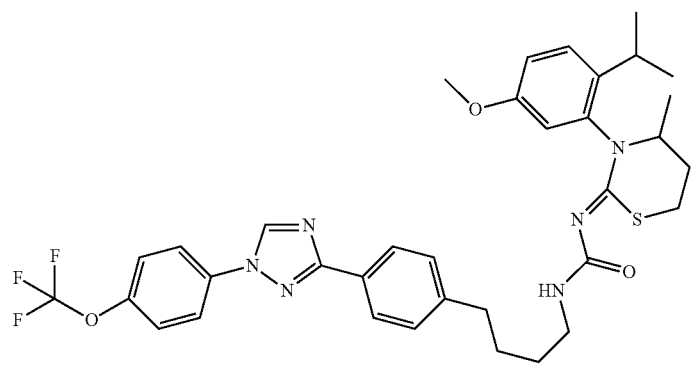 [SMILES: COc1ccc(C(C)C)c(N2/C(=N/C(=O)NCCCCc3ccc(-c4ncn(-c5ccc(OC(F)(F)F)cc5)n4)cc3)SCCC2C)c1]
P810
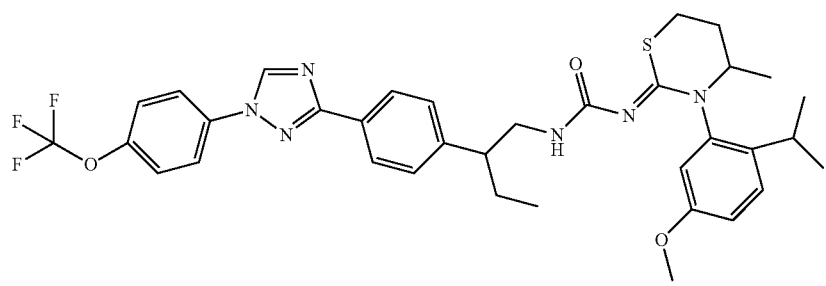 [SMILES: CCC(CNC(=O)/N=C1\SCCC(C)N1c1cc(OC)ccc1C(C)C)c1ccc(-c2ncn(-c3ccc(OC(F)(F)F)cc3)n2)cc1]
P811

TABLE P-Two-continued
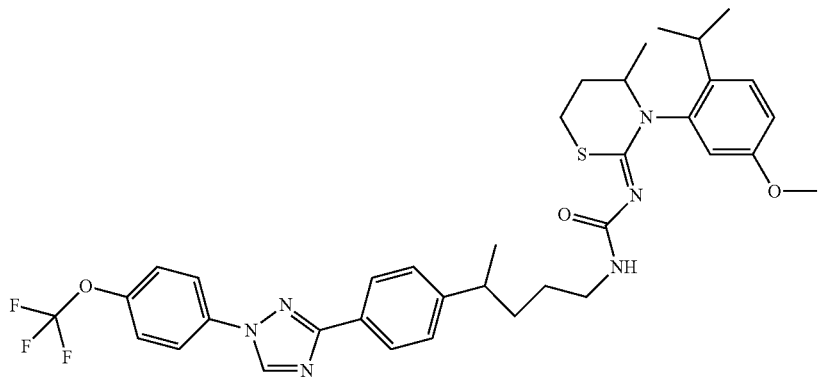 [SMILES: COc1ccc(C(C)C)c(N2/C(=N/C(=O)NCCCC(C)c3ccc(-c4ncn(-c5ccc(OC(F)(F)F)cc5)n4)cc3)SCCC2C)c1]
P812
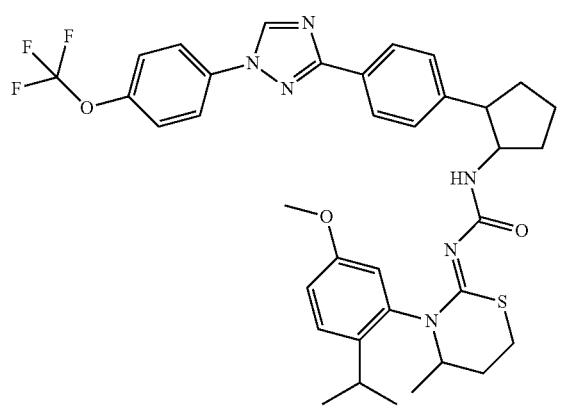 [SMILES: COc1ccc(C(C)C)c(N2/C(=N/C(=O)NC3CCCC3c3ccc(-c4ncn(-c5ccc(OC(F)(F)F)cc5)n4)cc3)SCCC2C)c1]
P813
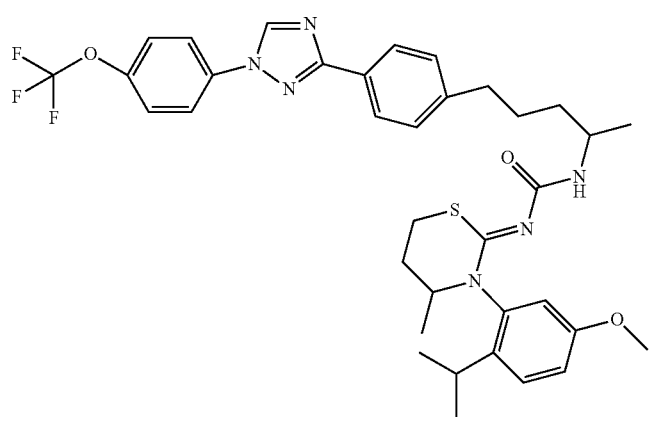 [SMILES: COc1ccc(C(C)C)c(N2/C(=N/C(=O)NC(C)CCCc3ccc(-c4ncn(-c5ccc(OC(F)(F)F)cc5)n4)cc3)SCCC2C)c1]
P814
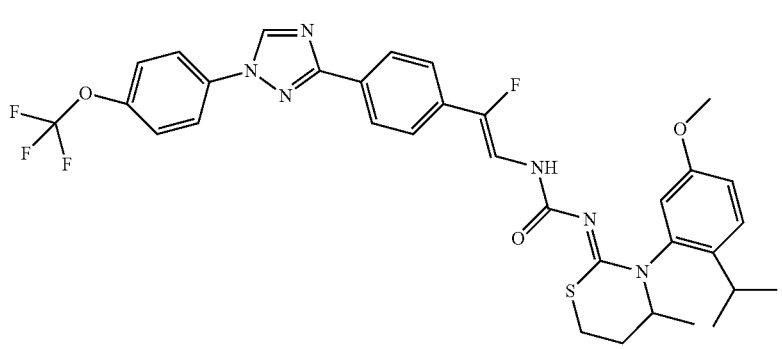 [SMILES: COc1ccc(C(C)C)c(N2/C(=N/C(=O)N/C=C(\F)c3ccc(-c4ncn(-c5ccc(OC(F)(F)F)cc5)n4)cc3)SCCC2C)c1]
P815

TABLE P-Two-continued
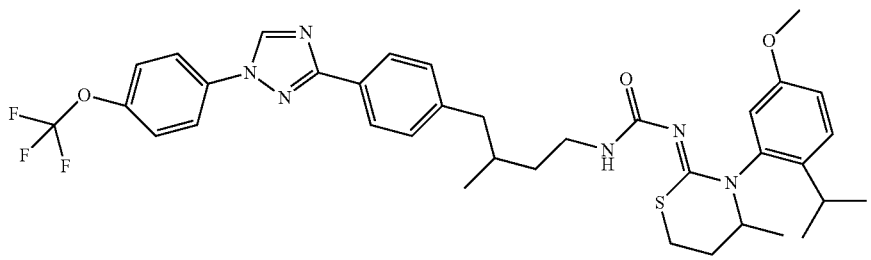 [SMILES: COc1ccc(C(C)C)c(N2/C(=N/C(=O)NCCC(C)Cc3ccc(-c4ncn(-c5ccc(OC(F)(F)F)cc5)n4)cc3)SCCC2C)c1]
P816
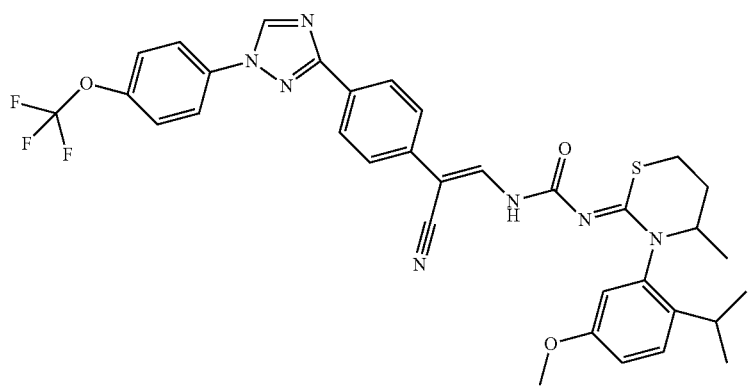 [SMILES: COc1ccc(C(C)C)c(N2/C(=N/C(=O)N/C=C(\C#N)c3ccc(-c4ncn(-c5ccc(OC(F)(F)F)cc5)n4)cc3)SCCC2C)c1]
P817
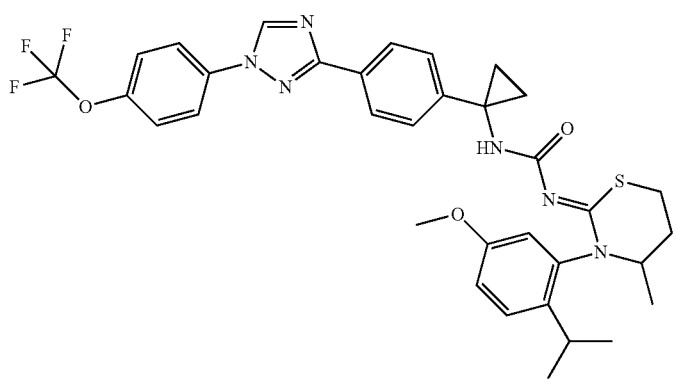 [SMILES: COc1ccc(C(C)C)c(N2/C(=N/C(=O)NC3(c4ccc(-c5ncn(-c6ccc(OC(F)(F)F)cc6)n5)cc4)CC3)SCCC2C)c1]
P818
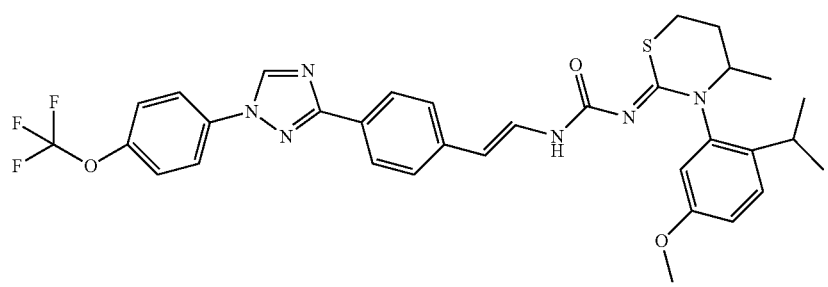 [SMILES: COc1ccc(C(C)C)c(N2/C(=N/C(=O)N/C=C/c3ccc(-c4ncn(-c5ccc(OC(F)(F)F)cc5)n4)cc3)SCCC2C)c1]
P819
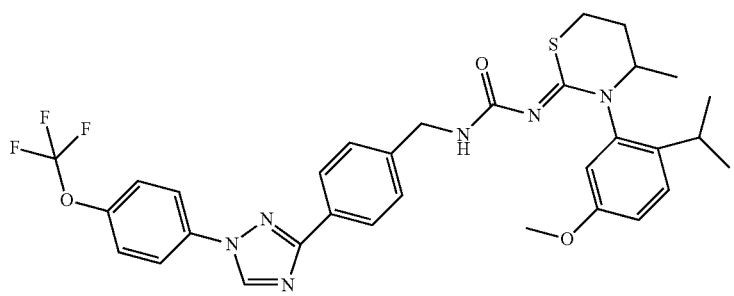 [SMILES: COc1ccc(C(C)C)c(N2/C(=N/C(=O)NCc3ccc(-c4ncn(-c5ccc(OC(F)(F)F)cc5)n4)cc3)SCCC2C)c1]
P820

TABLE P-Two-continued
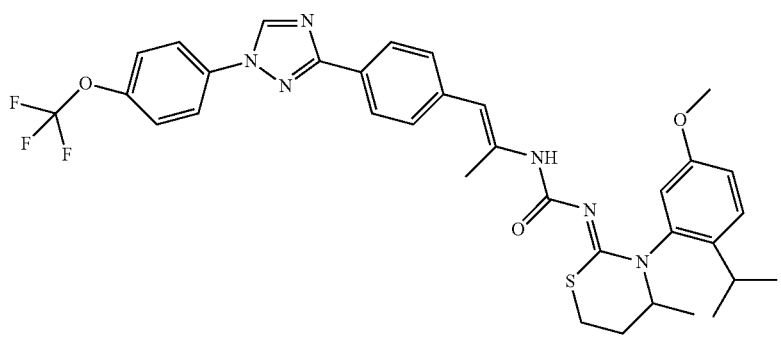 [SMILES: COc1ccc(C(C)C)c(N2/C(=N/C(=O)N/C(C)=C/c3ccc(-c4ncn(-c5ccc(OC(F)(F)F)cc5)n4)cc3)SCCC2C)c1]
P821
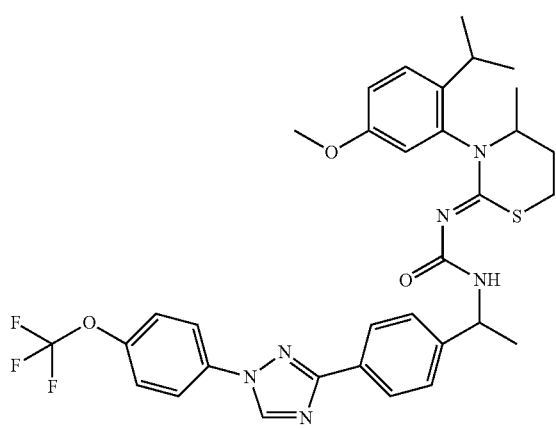 [SMILES: COc1ccc(C(C)C)c(N2/C(=N/C(=O)NC(C)c3ccc(-c4ncn(-c5ccc(OC(F)(F)F)cc5)n4)cc3)SCCC2C)c1]
P822
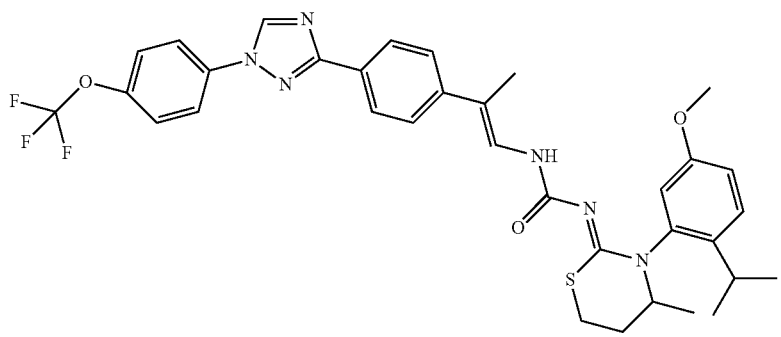 [SMILES: COc1ccc(C(C)C)c(N2/C(=N/C(=O)N/C=C(\C)c3ccc(-c4ncn(-c5ccc(OC(F)(F)F)cc5)n4)cc3)SCCC2C)c1]
P823
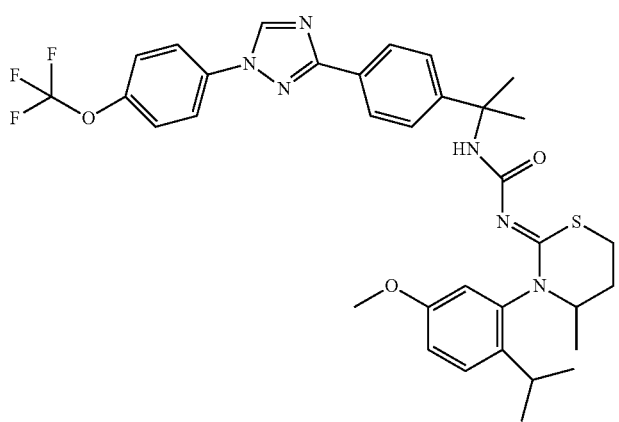 [SMILES: COc1ccc(C(C)C)c(N2/C(=N/C(=O)NC(C)(C)c3ccc(-c4ncn(-c5ccc(OC(F)(F)F)cc5)n4)cc3)SCCC2C)c1]
P824

TABLE P-Two-continued
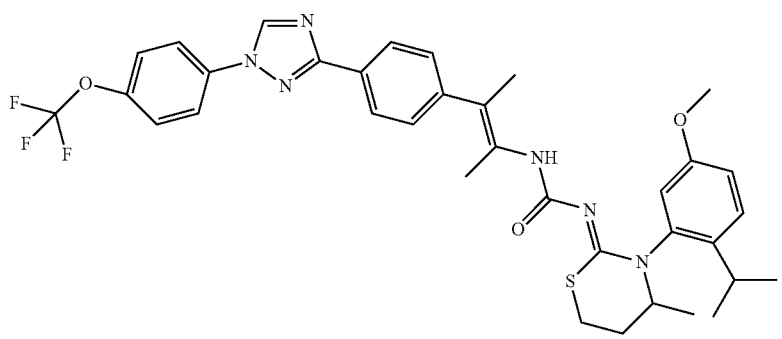 [SMILES: COc1ccc(C(C)C)c(N2/C(=N/C(=O)N/C(C)=C(\C)c3ccc(-c4ncn(-c5ccc(OC(F)(F)F)cc5)n4)cc3)SCCC2C)c1]
P825
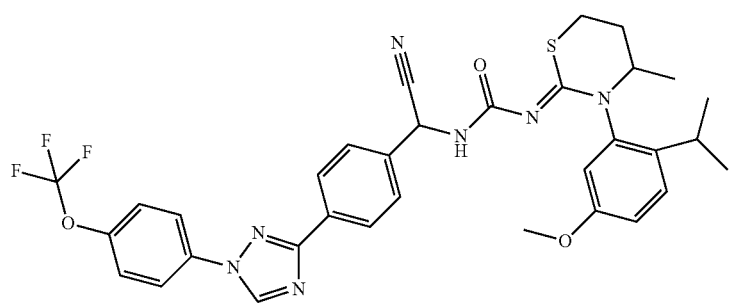 [SMILES: COc1ccc(C(C)C)c(N2/C(=N/C(=O)NC(C#N)c3ccc(-c4ncn(-c5ccc(OC(F)(F)F)cc5)n4)cc3)SCCC2C)c1]
P826
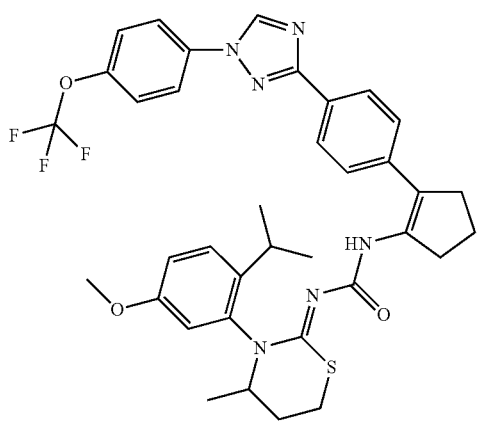 [SMILES: COc1ccc(C(C)C)c(N2/C(=N/C(=O)NC3=C(c4ccc(-c5ncn(-c6ccc(OC(F)(F)F)cc6)n5)cc4)CCC3)SCCC2C)c1]
P827
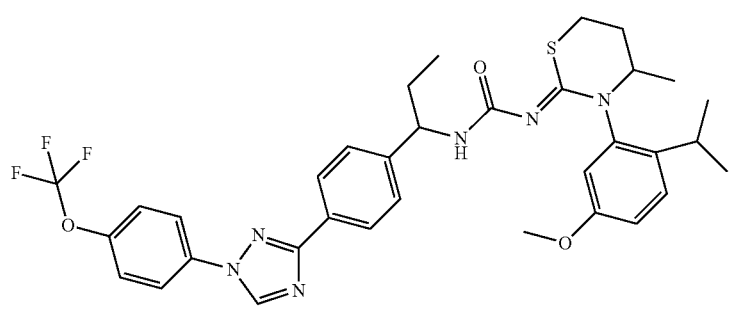 [SMILES: CCC(NC(=O)/N=C1\SCCC(C)N1c1cc(OC)ccc1C(C)C)c1ccc(-c2ncn(-c3ccc(OC(F)(F)F)cc3)n2)cc1]
P828

TABLE P-Two-continued
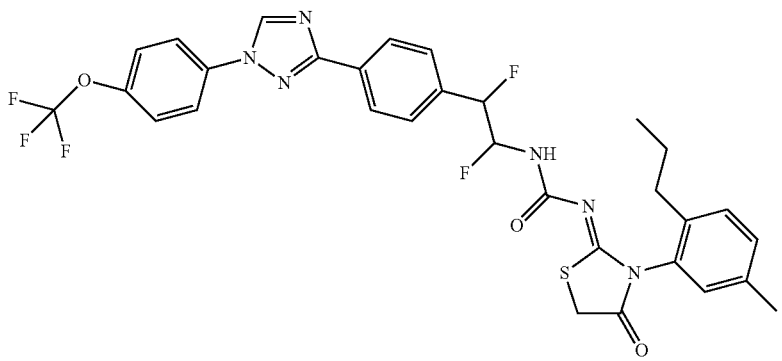 [SMILES: CCCc1ccc(C)cc1N1C(=O)CS/C1=N\C(=O)NC(F)C(F)c1ccc(-c2ncn(-c3ccc(OC(F)(F)F)cc3)n2)cc1]
P829
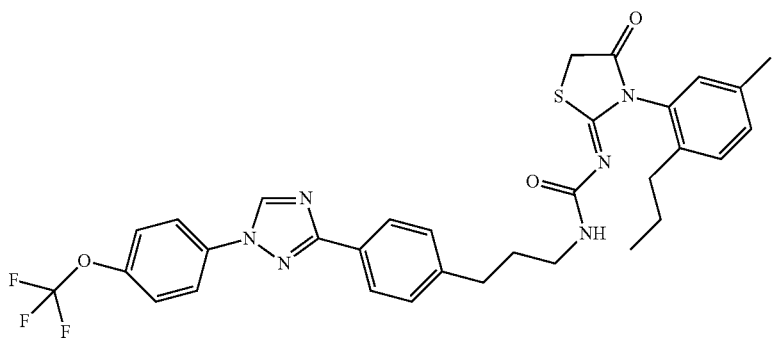 [SMILES: CCCc1ccc(C)cc1N1C(=O)CS/C1=N\C(=O)NCCCc1ccc(-c2ncn(-c3ccc(OC(F)(F)F)cc3)n2)cc1]
P830
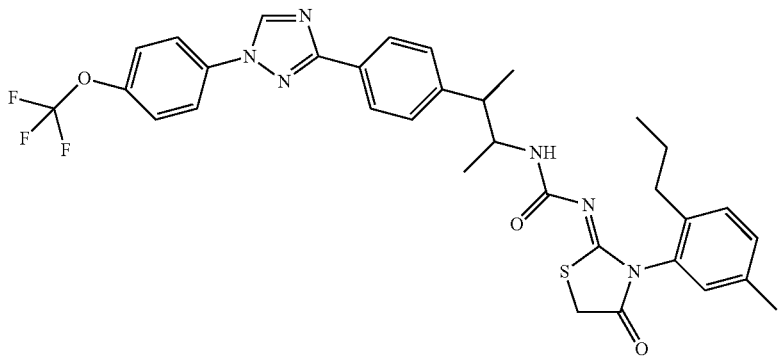 [SMILES: CCCc1ccc(C)cc1N1C(=O)CS/C1=N\C(=O)NC(C)C(C)c1ccc(-c2ncn(-c3ccc(OC(F)(F)F)cc3)n2)cc1]
P831
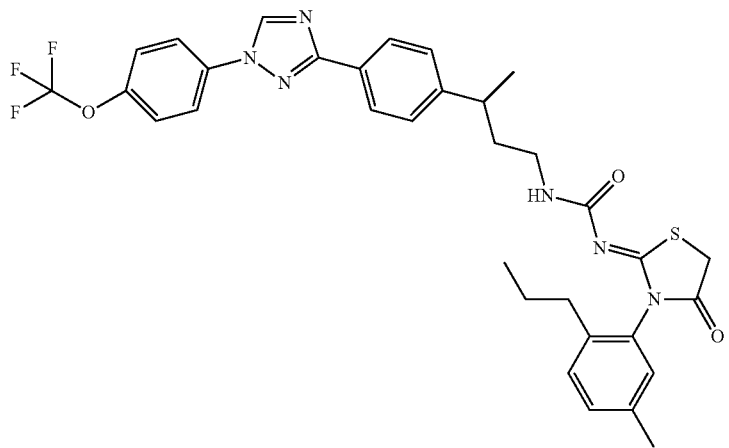 [SMILES: CCCc1ccc(C)cc1N1C(=O)CS/C1=N\C(=O)NCCC(C)c1ccc(-c2ncn(-c3ccc(OC(F)(F)F)cc3)n2)cc1]
P832

TABLE P-Two-continued
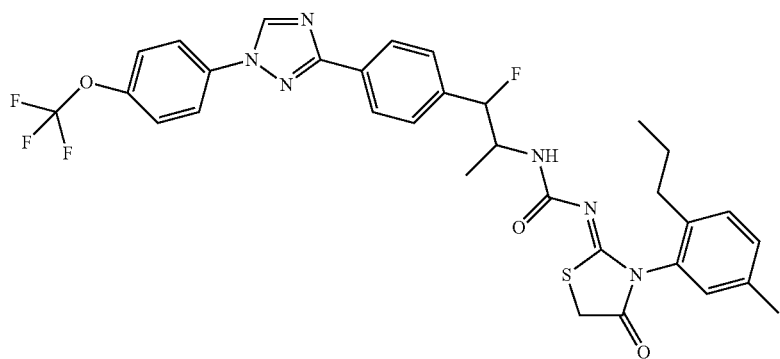 [SMILES: CCCc1ccc(C)cc1N1C(=O)CS/C1=N\C(=O)NC(C)C(F)c1ccc(-c2ncn(-c3ccc(OC(F)(F)F)cc3)n2)cc1]
P833
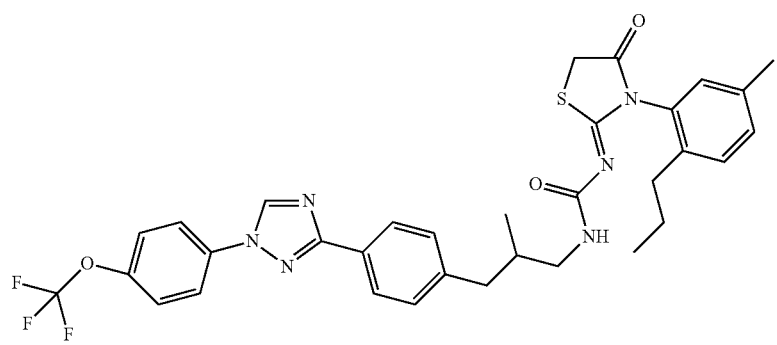 [SMILES: CCCc1ccc(C)cc1N1C(=O)CS/C1=N\C(=O)NCC(C)Cc1ccc(-c2ncn(-c3ccc(OC(F)(F)F)cc3)n2)cc1]
P834
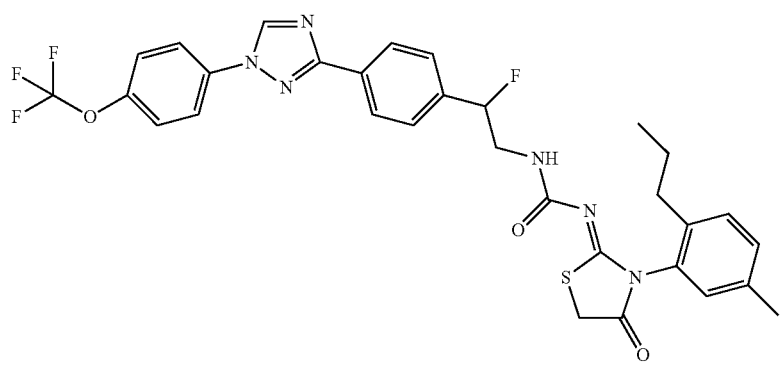 [SMILES: CCCc1ccc(C)cc1N1C(=O)CS/C1=N\C(=O)NCC(F)c1ccc(-c2ncn(-c3ccc(OC(F)(F)F)cc3)n2)cc1]
P835
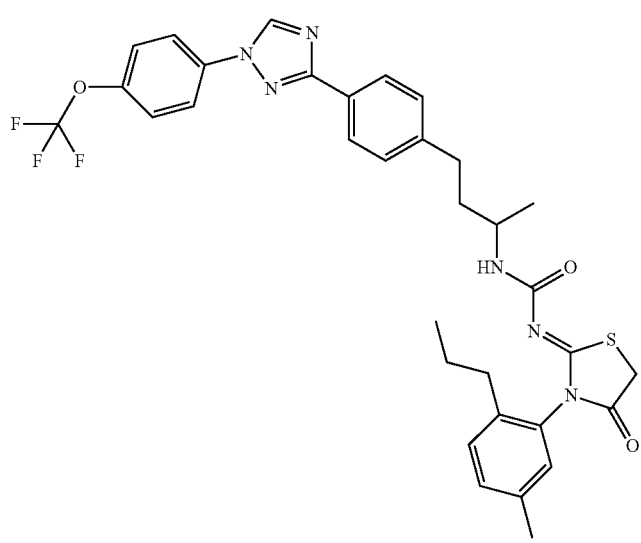 [SMILES: CCCc1ccc(C)cc1N1C(=O)CS/C1=N\C(=O)NC(C)CCc1ccc(-c2ncn(-c3ccc(OC(F)(F)F)cc3)n2)cc1]
P836

TABLE P-Two-continued
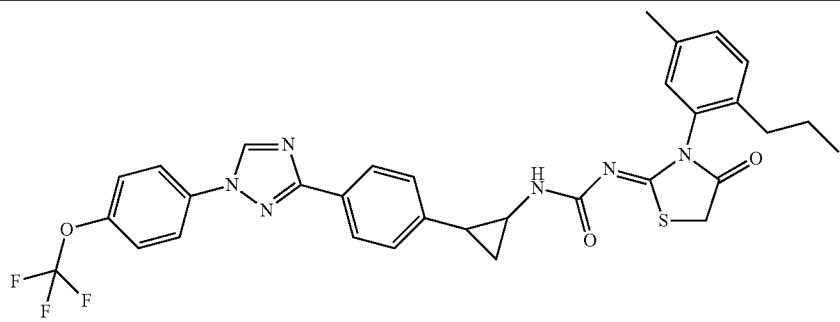
P837
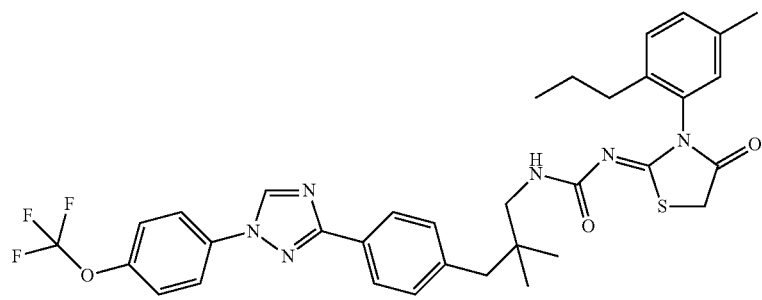 [SMILES: CCCc1ccc(C)cc1N1C(=O)CS/C1=N\C(=O)NCC(C)(C)Cc1ccc(-c2ncn(-c3ccc(OC(F)(F)F)cc3)n2)cc1]
P838
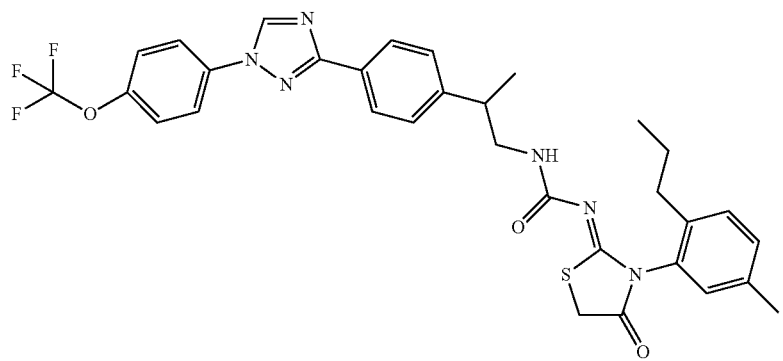 [SMILES: CCCc1ccc(C)cc1N1C(=O)CS/C1=N\C(=O)NCC(C)c1ccc(-c2ncn(-c3ccc(OC(F)(F)F)cc3)n2)cc1]
P839
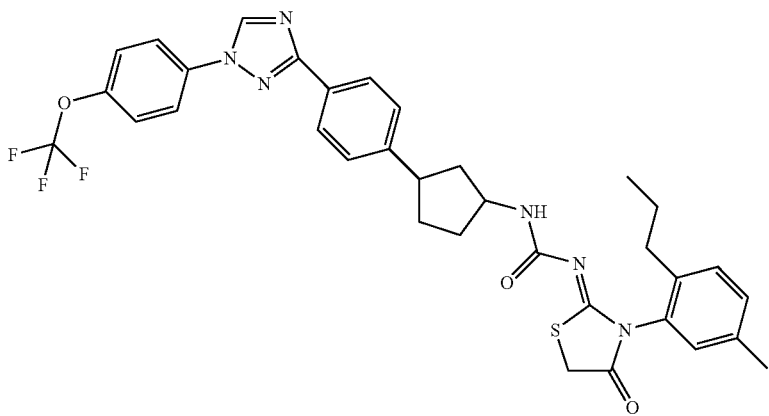 [SMILES: CCCc1ccc(C)cc1N1C(=O)CS/C1=N\C(=O)NC1CCC(c2ccc(-c3ncn(-c4ccc(OC(F)(F)F)cc4)n3)cc2)C1]
P840

TABLE P-Two-continued
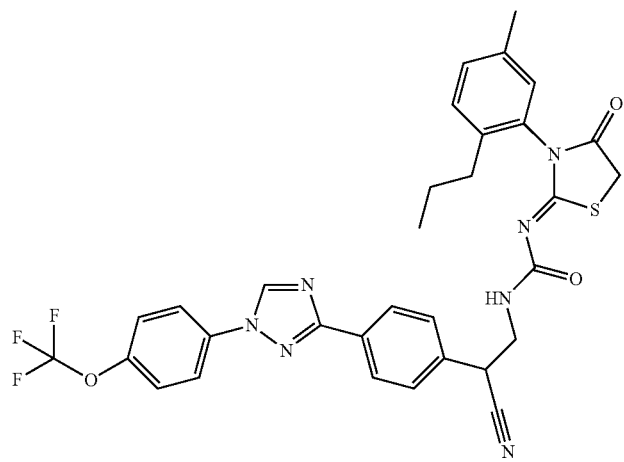 [SMILES: CCCc1ccc(C)cc1N1C(=O)CS/C1=N\C(=O)NCC(C#N)c1ccc(-c2ncn(-c3ccc(OC(F)(F)F)cc3)n2)cc1]
P841
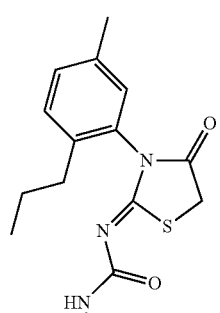
P842
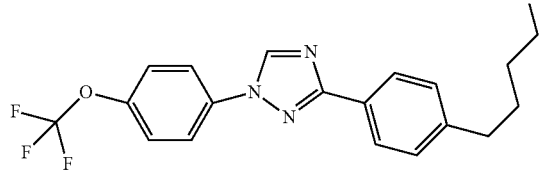
P843
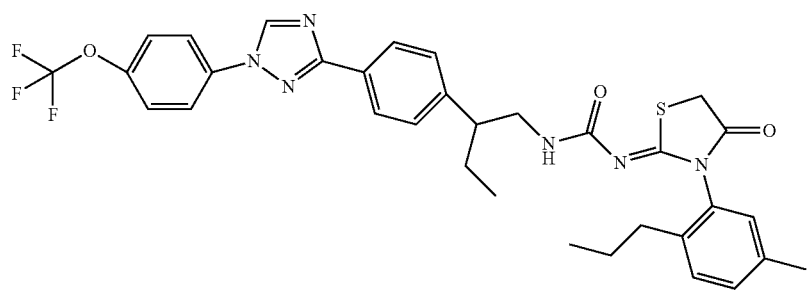 [SMILES: CCCc1ccc(C)cc1N1C(=O)CS/C1=N\C(=O)NCC(CC)c1ccc(-c2ncn(-c3ccc(OC(F)(F)F)cc3)n2)cc1]
P844
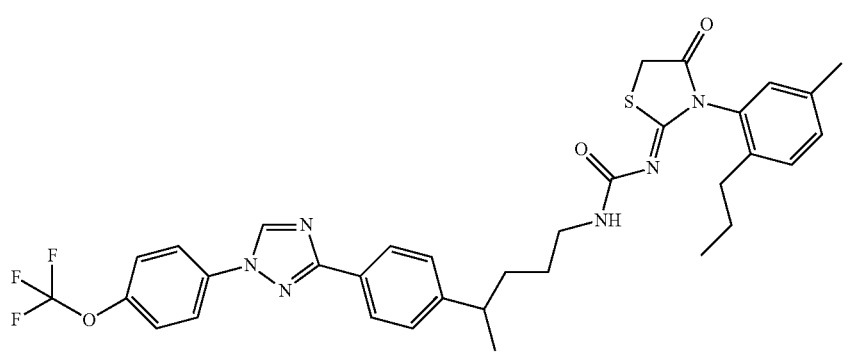 [SMILES: CCCc1ccc(C)cc1N1C(=O)CS/C1=N\C(=O)NCCCC(C)c1ccc(-c2ncn(-c3ccc(OC(F)(F)F)cc3)n2)cc1]

TABLE P-Two-continued
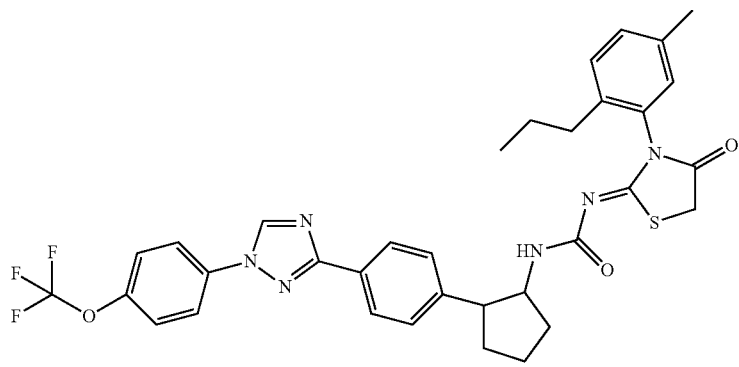 [SMILES: CCCc1ccc(C)cc1N1C(=O)CS/C1=N\C(=O)NC1CCCC1c1ccc(-c2ncn(-c3ccc(OC(F)(F)F)cc3)n2)cc1]
P845
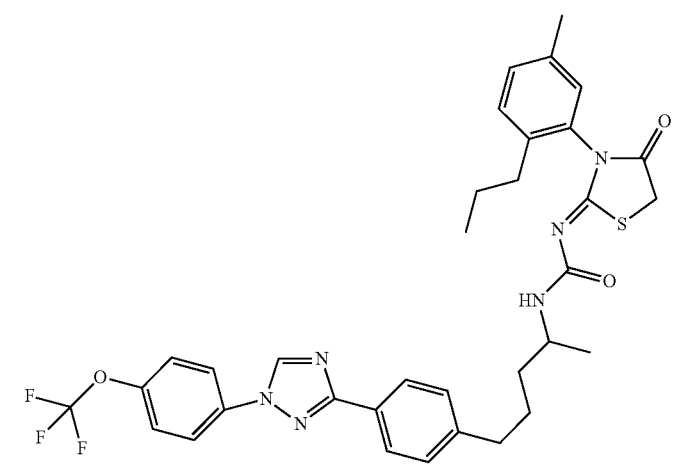 [SMILES: CCCc1ccc(C)cc1N1C(=O)CS/C1=N\C(=O)NC(C)CCCc1ccc(-c2ncn(-c3ccc(OC(F)(F)F)cc3)n2)cc1]
P846
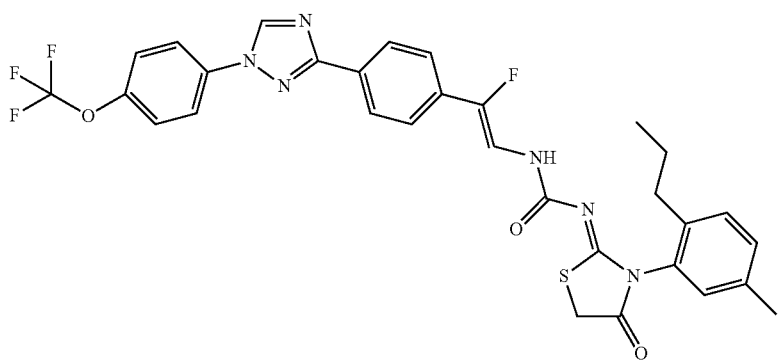 [SMILES: CCCc1ccc(C)cc1N1C(=O)CS/C1=N\C(=O)N/C=C(\F)c1ccc(-c2ncn(-c3ccc(OC(F)(F)F)cc3)n2)cc1]
P847
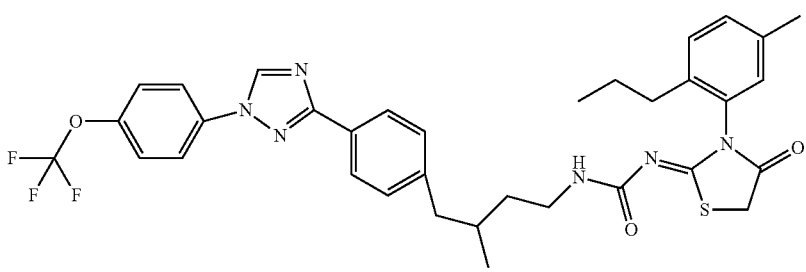 [SMILES: CCCc1ccc(C)cc1N1C(=O)CS/C1=N\C(=O)NCCC(C)Cc1ccc(-c2ncn(-c3ccc(OC(F)(F)F)cc3)n2)cc1]
P848

TABLE P-Two-continued
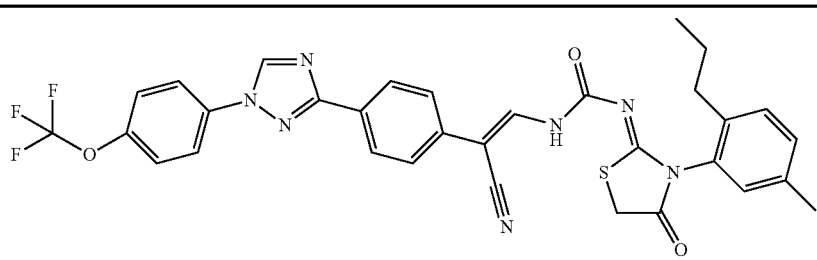
P849
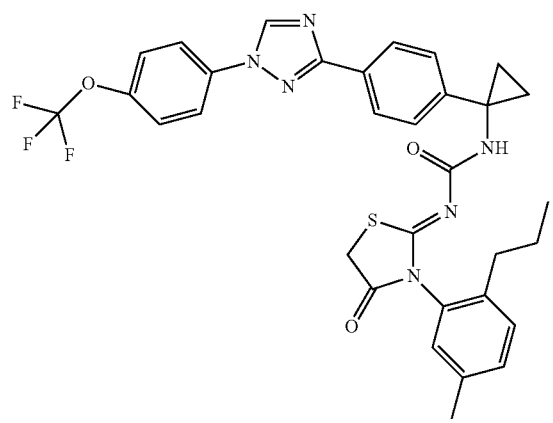 [SMILES: CCCc1ccc(C)cc1N1C(=O)CS/C1=N\C(=O)NC1(c2ccc(-c3ncn(-c4ccc(OC(F)(F)F)cc4)n3)cc2)CC1]
P850
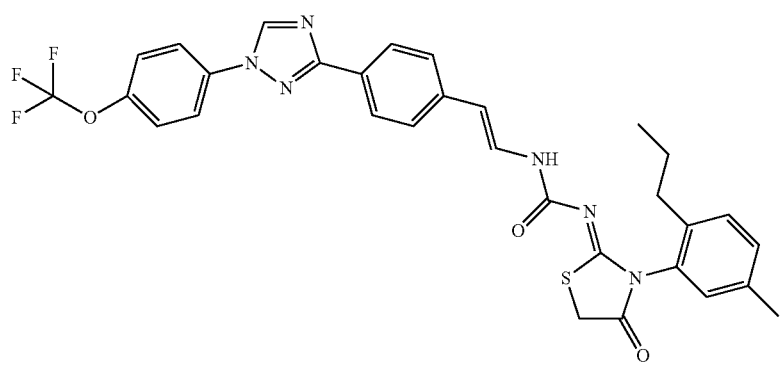 [SMILES: CCCc1ccc(C)cc1N1C(=O)CS/C1=N\C(=O)N/C=C/c1ccc(-c2ncn(-c3ccc(OC(F)(F)F)cc3)n2)cc1]
P851
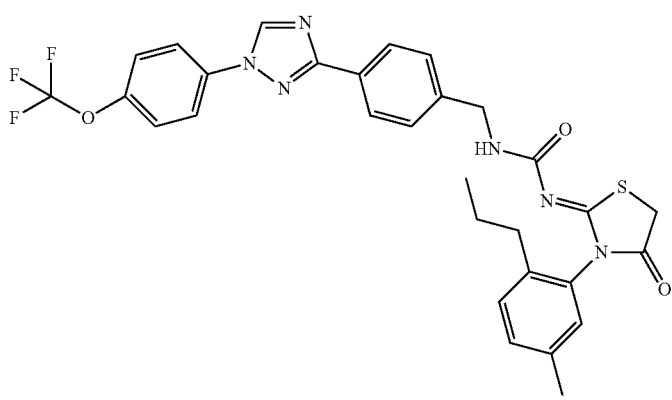 [SMILES: CCCc1ccc(C)cc1N1C(=O)CS/C1=N\C(=O)NCc1ccc(-c2ncn(-c3ccc(OC(F)(F)F)cc3)n2)cc1]
P852
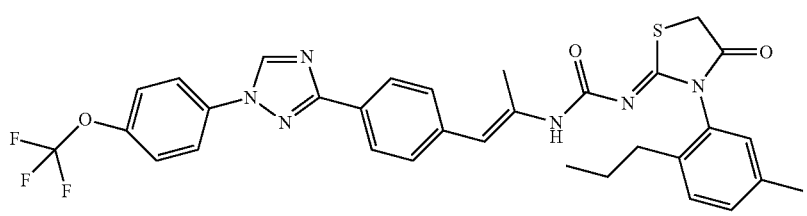 [SMILES: CCCc1ccc(C)cc1N1C(=O)CS/C1=N\C(=O)N/C(C)=C/c1ccc(-c2ncn(-c3ccc(OC(F)(F)F)cc3)n2)cc1]
P853

TABLE P-Two-continued
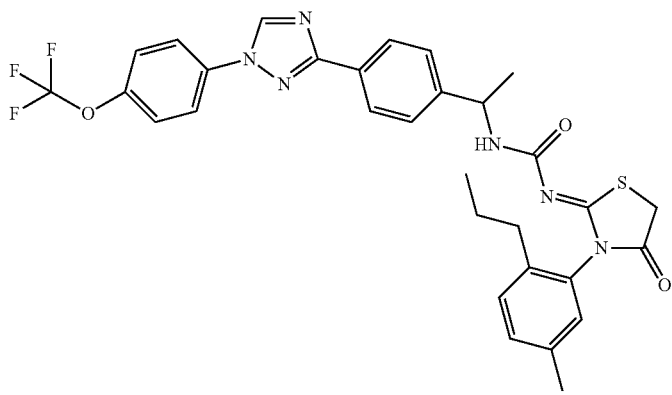 [SMILES: CCCc1ccc(C)cc1N1C(=O)CS/C1=N\C(=O)NC(C)c1ccc(-c2ncn(-c3ccc(OC(F)(F)F)cc3)n2)cc1]
P854
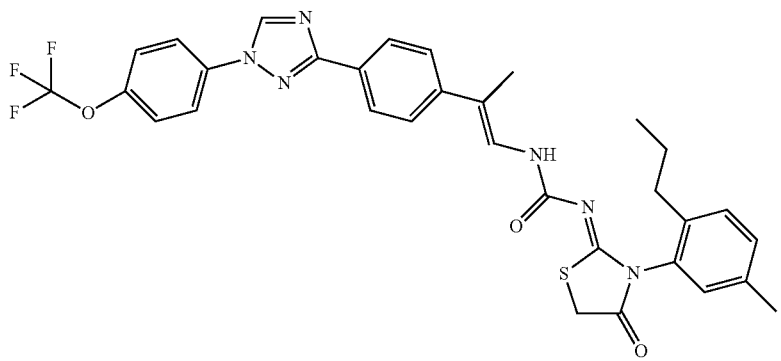 [SMILES: CCCc1ccc(C)cc1N1C(=O)CS/C1=N\C(=O)N/C=C(\C)c1ccc(-c2ncn(-c3ccc(OC(F)(F)F)cc3)n2)cc1]
P855
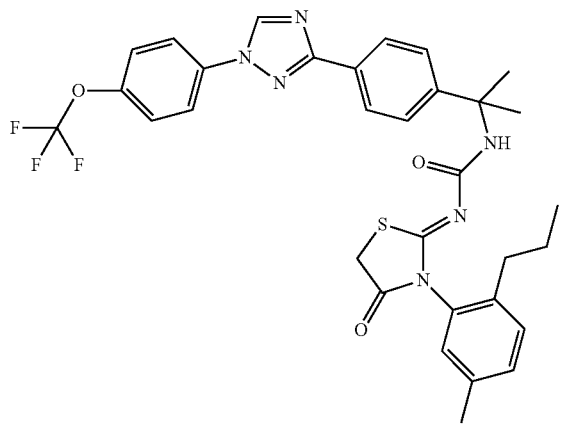 [SMILES: CCCc1ccc(C)cc1N1C(=O)CS/C1=N\C(=O)NC(C)(C)c1ccc(-c2ncn(-c3ccc(OC(F)(F)F)cc3)n2)cc1]
P856
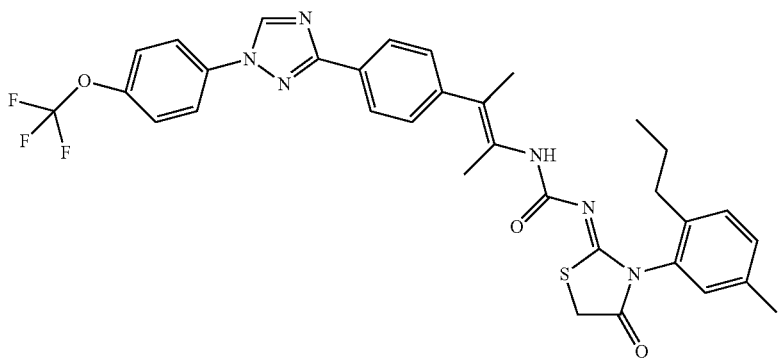 [SMILES: CCCc1ccc(C)cc1N1C(=O)CS/C1=N\C(=O)N/C(C)=C(\C)c1ccc(-c2ncn(-c3ccc(OC(F)(F)F)cc3)n2)cc1]
P857

TABLE P-Two-continued
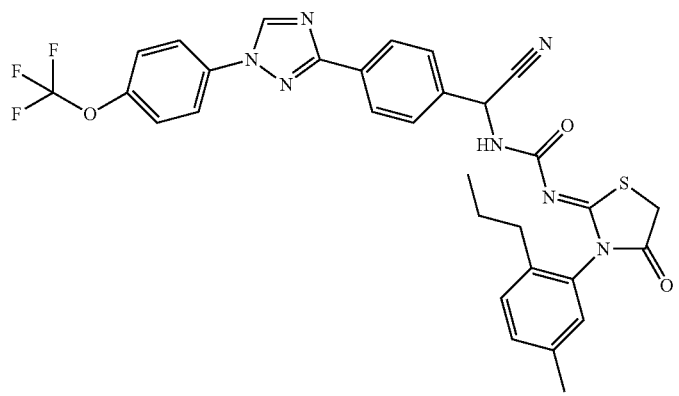 [SMILES: CCCc1ccc(C)cc1N1C(=O)CS/C1=N\C(=O)NC(C#N)c1ccc(-c2ncn(-c3ccc(OC(F)(F)F)cc3)n2)cc1]
P858
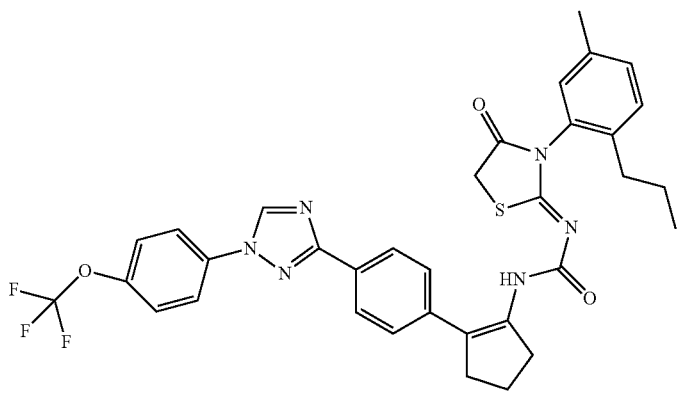 [SMILES: CCCc1ccc(C)cc1N1C(=O)CS/C1=N\C(=O)NC1=C(c2ccc(-c3ncn(-c4ccc(OC(F)(F)F)cc4)n3)cc2)CCC1]
P859
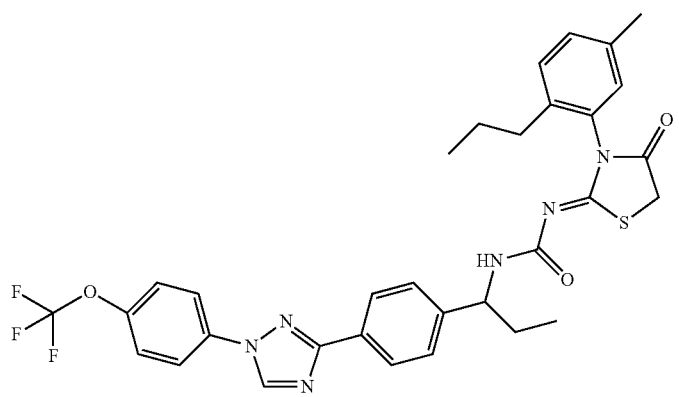 [SMILES: CCCc1ccc(C)cc1N1C(=O)CS/C1=N\C(=O)NC(CC)c1ccc(-c2ncn(-c3ccc(OC(F)(F)F)cc3)n2)cc1]
P860
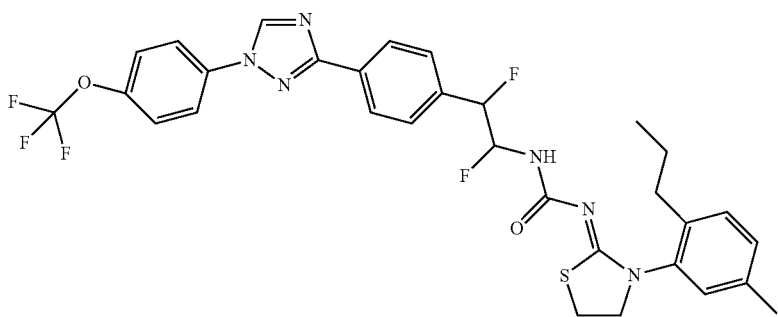 [SMILES: CCCc1ccc(C)cc1N1CCS/C1=N\C(=O)NC(F)C(F)c1ccc(-c2ncn(-c3ccc(OC(F)(F)F)cc3)n2)cc1]
P861

TABLE P-Two-continued
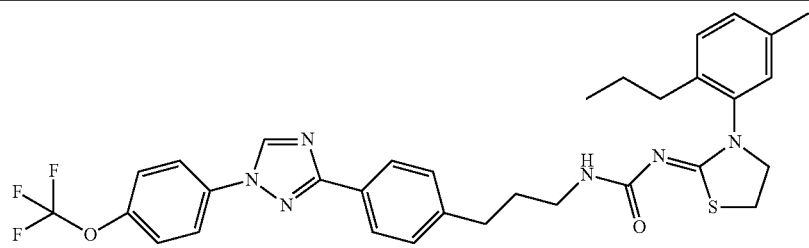
P862
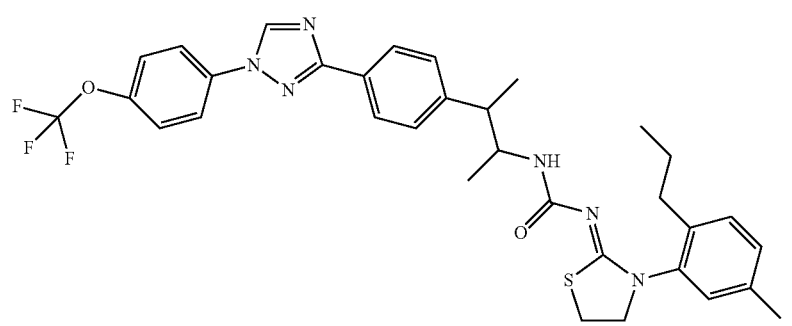 [SMILES: CCCc1ccc(C)cc1N1CCS/C1=N\C(=O)NC(C)C(C)c1ccc(-c2ncn(-c3ccc(OC(F)(F)F)cc3)n2)cc1]
P863
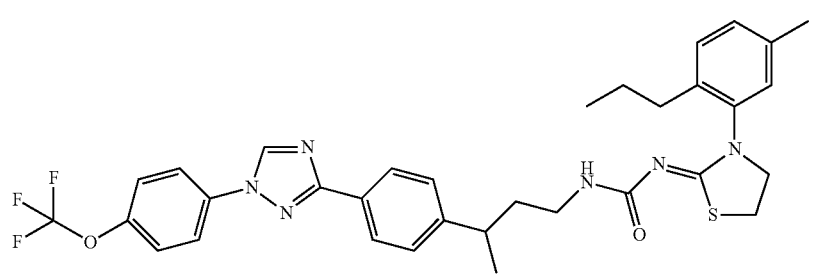 [SMILES: CCCc1ccc(C)cc1N1CCS/C1=N\C(=O)NCCC(C)c1ccc(-c2ncn(-c3ccc(OC(F)(F)F)cc3)n2)cc1]
P864
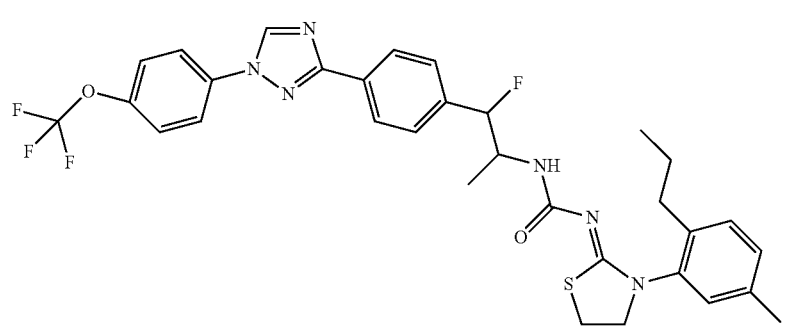 [SMILES: CCCc1ccc(C)cc1N1CCS/C1=N\C(=O)NC(C)C(F)c1ccc(-c2ncn(-c3ccc(OC(F)(F)F)cc3)n2)cc1]
P865
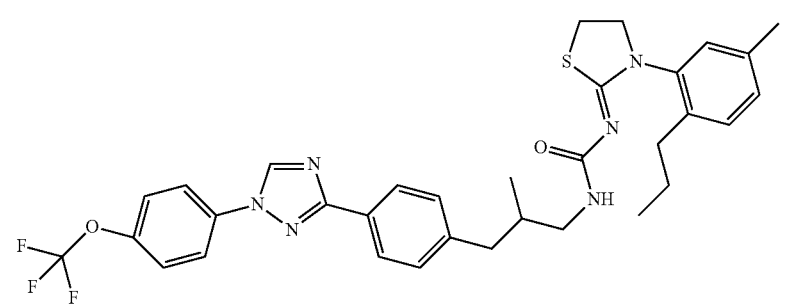 [SMILES: CCCc1ccc(C)cc1N1CCS/C1=N\C(=O)NCC(C)Cc1ccc(-c2ncn(-c3ccc(OC(F)(F)F)cc3)n2)cc1]
P866
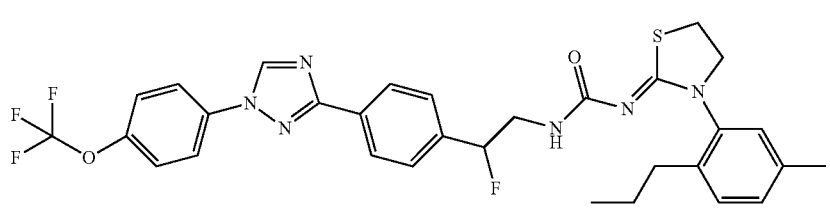 [SMILES: CCCc1ccc(C)cc1N1CCS/C1=N\C(=O)NCC(F)c1ccc(-c2ncn(-c3ccc(OC(F)(F)F)cc3)n2)cc1]
P867

| | |
|---|---|
| 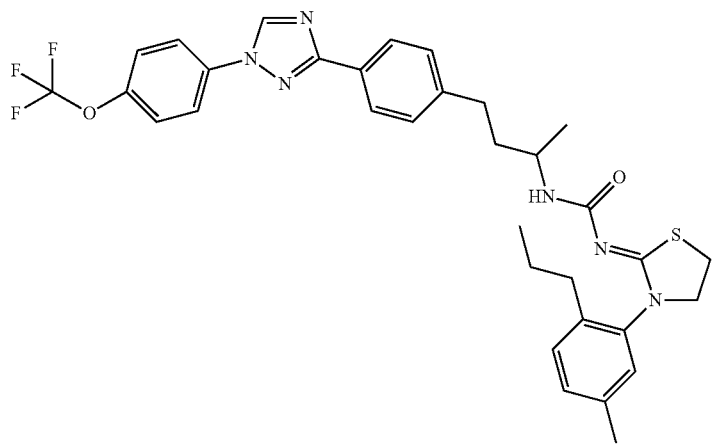 [SMILES: CCCc1ccc(C)cc1N1CCS/C1=N\C(=O)NC(C)CCc1ccc(-c2ncn(-c3ccc(OC(F)(F)F)cc3)n2)cc1] | P868 |
| 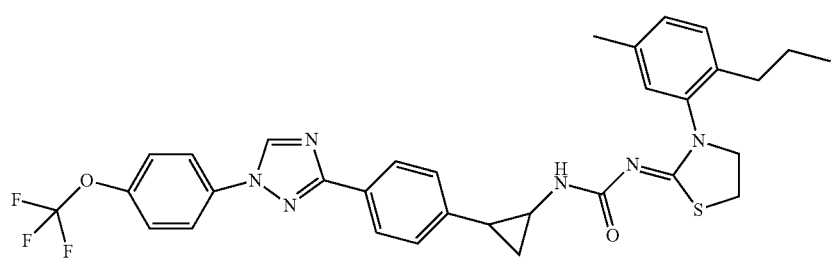 [SMILES: CCCc1ccc(C)cc1N1CCS/C1=N\C(=O)NC1CC1c1ccc(-c2ncn(-c3ccc(OC(F)(F)F)cc3)n2)cc1] | P869 |
| 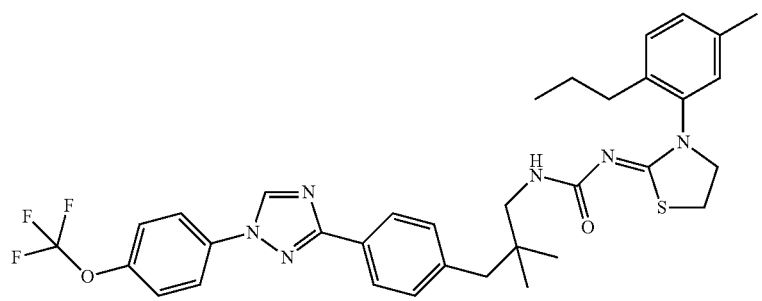 [SMILES: CCCc1ccc(C)cc1N1CCS/C1=N\C(=O)NCC(C)(C)Cc1ccc(-c2ncn(-c3ccc(OC(F)(F)F)cc3)n2)cc1] | P870 |
| 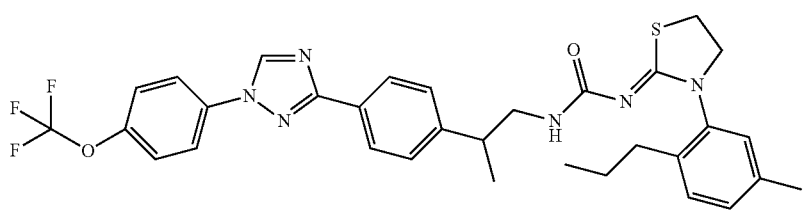 [SMILES: CCCc1ccc(C)cc1N1CCS/C1=N\C(=O)NCC(C)c1ccc(-c2ncn(-c3ccc(OC(F)(F)F)cc3)n2)cc1] | P871 |
| 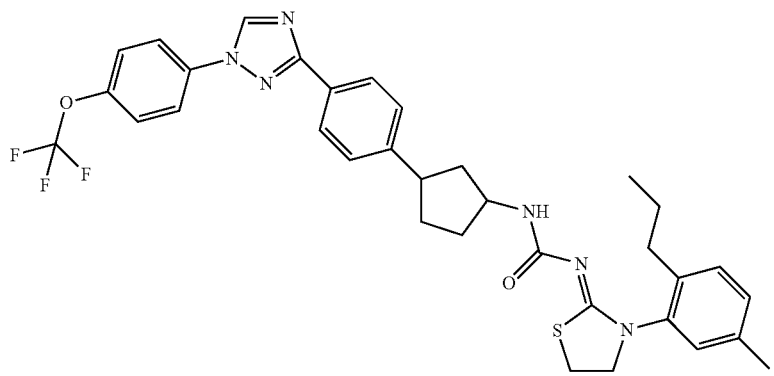 [SMILES: CCCc1ccc(C)cc1N1CCS/C1=N\C(=O)NC1CCC(c2ccc(-c3ncn(-c4ccc(OC(F)(F)F)cc4)n3)cc2)C1] | P872 |

TABLE P-Two-continued
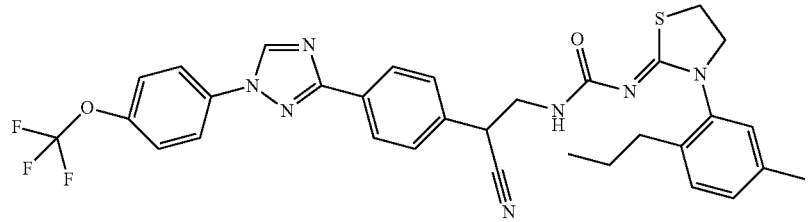
P873
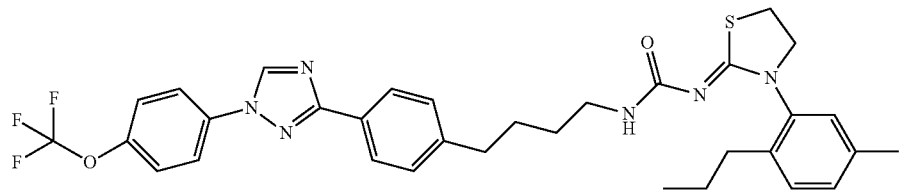 [SMILES: CCCc1ccc(C)cc1N1CCS/C1=N\C(=O)NCCCCc1ccc(-c2ncn(-c3ccc(OC(F)(F)F)cc3)n2)cc1]
P874
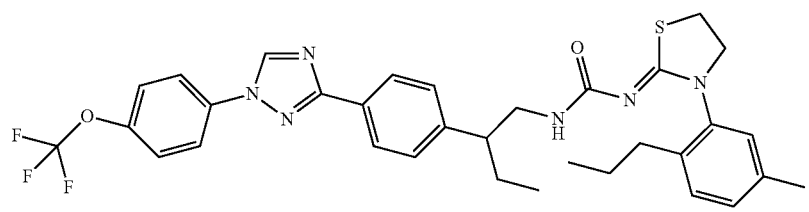 [SMILES: CCCc1ccc(C)cc1N1CCS/C1=N\C(=O)NCC(CC)c1ccc(-c2ncn(-c3ccc(OC(F)(F)F)cc3)n2)cc1]
P875
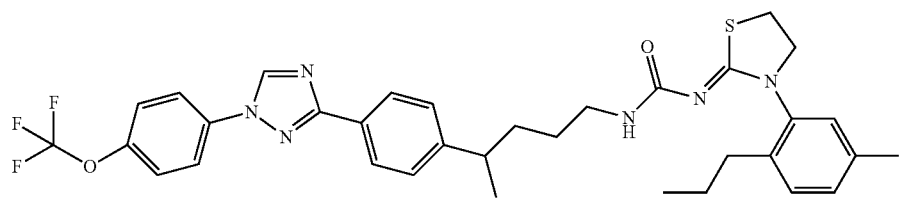 [SMILES: CCCc1ccc(C)cc1N1CCS/C1=N\C(=O)NCCCC(C)c1ccc(-c2ncn(-c3ccc(OC(F)(F)F)cc3)n2)cc1]
P876
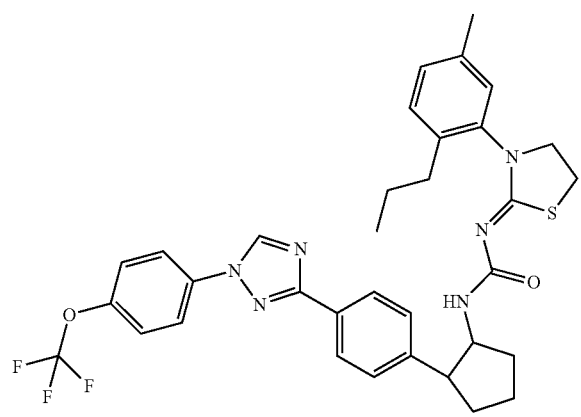 [SMILES: CCCc1ccc(C)cc1N1CCS/C1=N\C(=O)NC1CCCC1c1ccc(-c2ncn(-c3ccc(OC(F)(F)F)cc3)n2)cc1]
P877

TABLE P-Two-continued

| | |
|---|---|
| (structure) | P878 |
| (structure) | P879 |
| (structure) | P880 |
| (structure) | P881 |

TABLE P-Two-continued
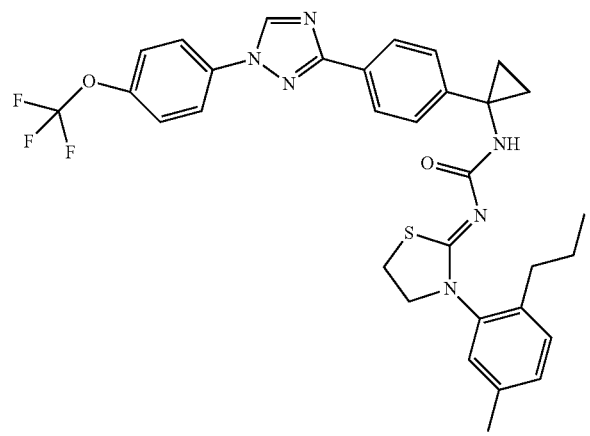 [SMILES: CCCc1ccc(C)cc1N1CCS/C1=N\C(=O)NC1(c2ccc(-c3ncn(-c4ccc(OC(F)(F)F)cc4)n3)cc2)CC1]
P882
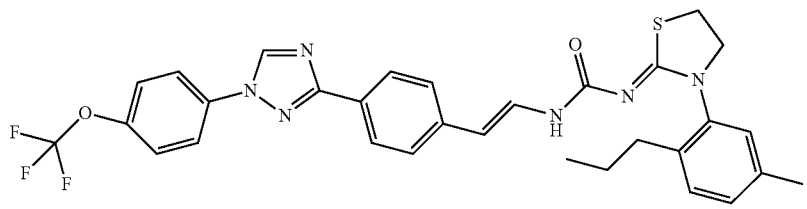 [SMILES: CCCc1ccc(C)cc1N1CCS/C1=N\C(=O)N/C=C/c1ccc(-c2ncn(-c3ccc(OC(F)(F)F)cc3)n2)cc1]
P883
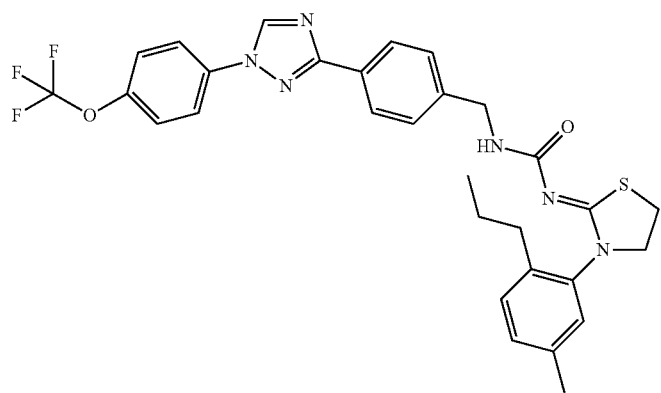 [SMILES: CCCc1ccc(C)cc1N1CCS/C1=N\C(=O)NCc1ccc(-c2ncn(-c3ccc(OC(F)(F)F)cc3)n2)cc1]
P884
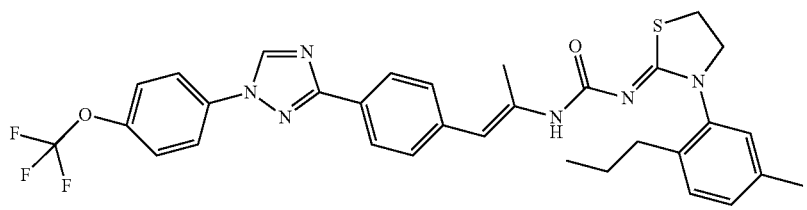 [SMILES: CCCc1ccc(C)cc1N1CCS/C1=N\C(=O)N/C(C)=C/c1ccc(-c2ncn(-c3ccc(OC(F)(F)F)cc3)n2)cc1]
P885
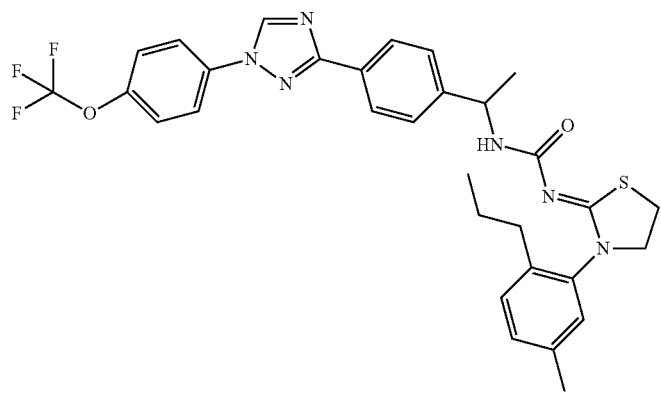 [SMILES: CCCc1ccc(C)cc1N1CCS/C1=N\C(=O)NC(C)c1ccc(-c2ncn(-c3ccc(OC(F)(F)F)cc3)n2)cc1]
P886

TABLE P-Two-continued
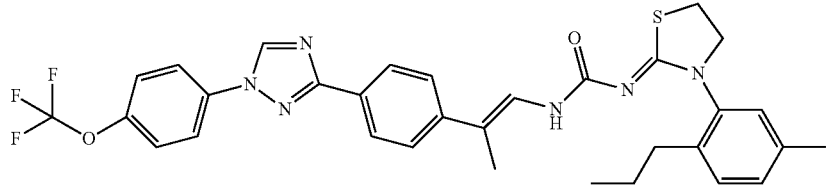 [SMILES: CCCc1ccc(C)cc1N1CCS/C1=N\C(=O)N/C=C(\C)c1ccc(-c2ncn(-c3ccc(OC(F)(F)F)cc3)n2)cc1]
P887
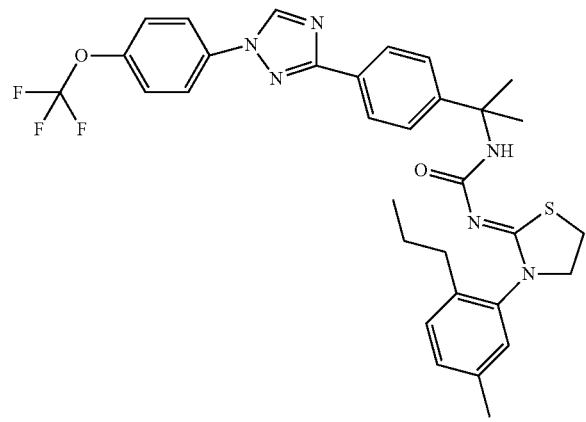 [SMILES: CCCc1ccc(C)cc1N1CCS/C1=N\C(=O)NC(C)(C)c1ccc(-c2ncn(-c3ccc(OC(F)(F)F)cc3)n2)cc1]
P888
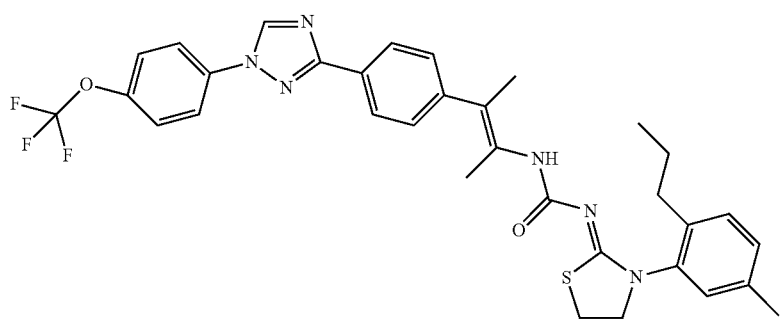 [SMILES: CCCc1ccc(C)cc1N1CCS/C1=N\C(=O)N/C(C)=C(\C)c1ccc(-c2ncn(-c3ccc(OC(F)(F)F)cc3)n2)cc1]
P889
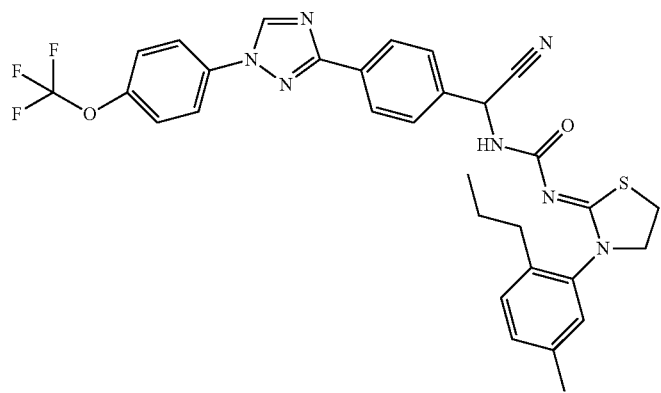 [SMILES: CCCc1ccc(C)cc1N1CCS/C1=N\C(=O)NC(C#N)c1ccc(-c2ncn(-c3ccc(OC(F)(F)F)cc3)n2)cc1]
P890

TABLE P-Two-continued

TABLE P-Two-continued
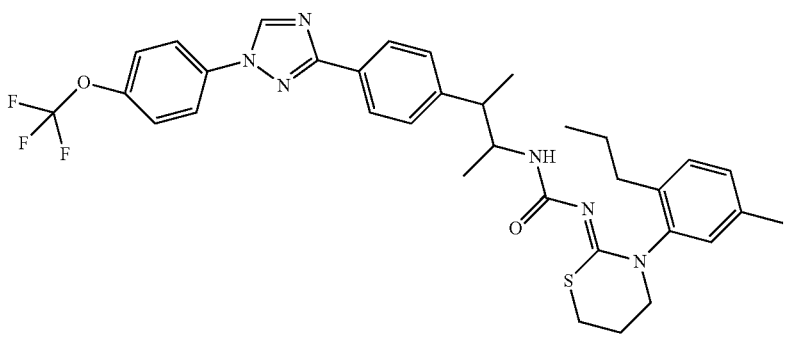 [SMILES: CCCc1ccc(C)cc1N1CCCS/C1=N\C(=O)NC(C)C(C)c1ccc(-c2ncn(-c3ccc(OC(F)(F)F)cc3)n2)cc1]
P895
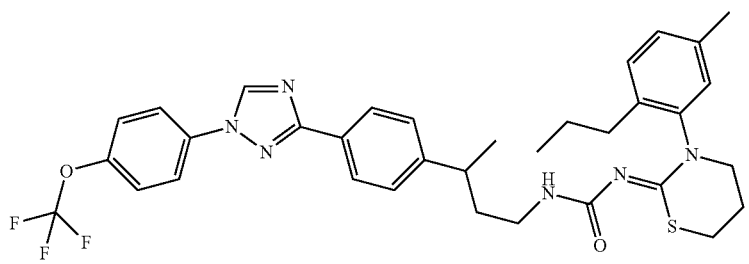 [SMILES: CCCc1ccc(C)cc1N1CCCS/C1=N\C(=O)NCCC(C)c1ccc(-c2ncn(-c3ccc(OC(F)(F)F)cc3)n2)cc1]
P896
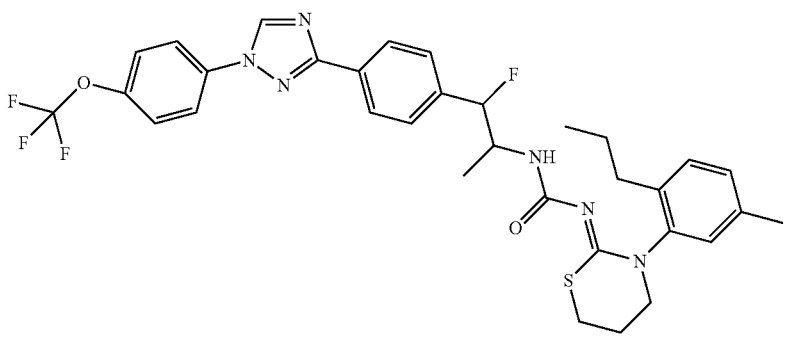 [SMILES: CCCc1ccc(C)cc1N1CCCS/C1=N\C(=O)NC(C)C(F)c1ccc(-c2ncn(-c3ccc(OC(F)(F)F)cc3)n2)cc1]
P897
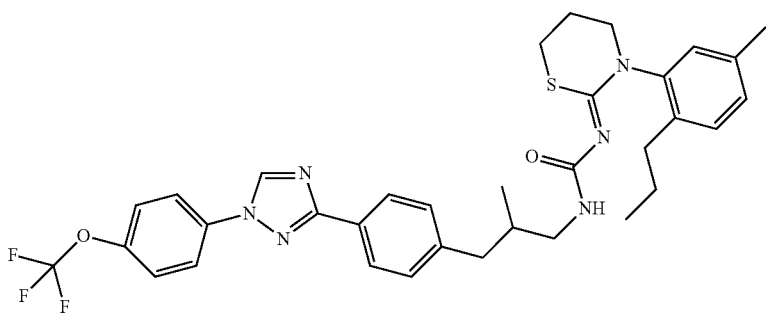 [SMILES: CCCc1ccc(C)cc1N1CCCS/C1=N\C(=O)NCC(C)Cc1ccc(-c2ncn(-c3ccc(OC(F)(F)F)cc3)n2)cc1]
P898
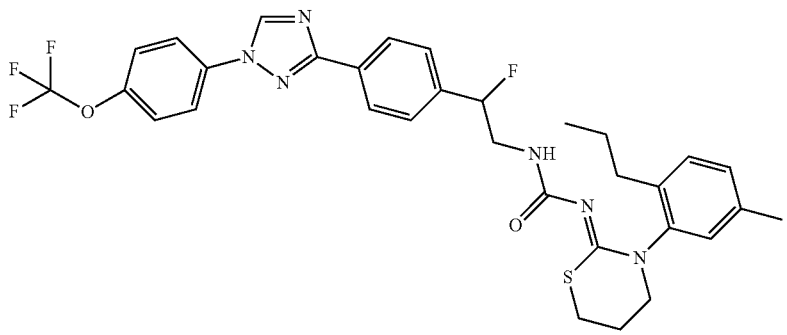 [SMILES: CCCc1ccc(C)cc1N1CCCS/C1=N\C(=O)NCC(F)c1ccc(-c2ncn(-c3ccc(OC(F)(F)F)cc3)n2)cc1]
P899

TABLE P-Two-continued
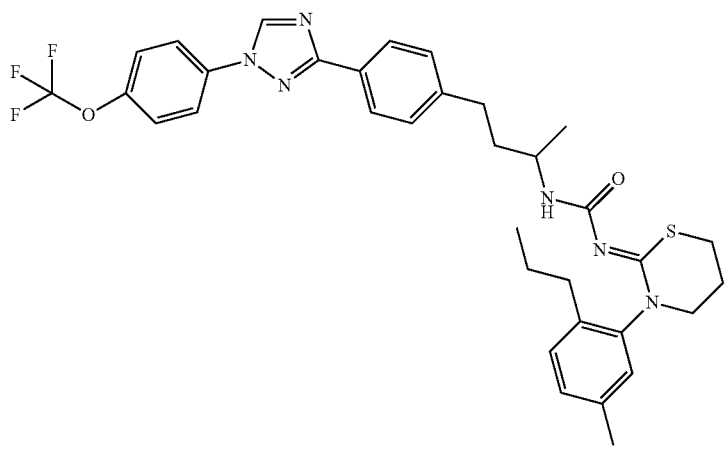 [SMILES: CCCc1ccc(C)cc1N1CCCS/C1=N\C(=O)NC(C)CCc1ccc(-c2ncn(-c3ccc(OC(F)(F)F)cc3)n2)cc1]
P900
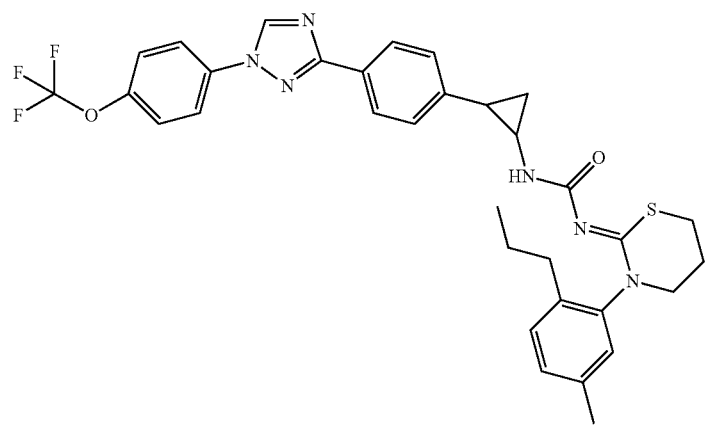 [SMILES: CCCc1ccc(C)cc1N1CCCS/C1=N\C(=O)NC1CC1c1ccc(-c2ncn(-c3ccc(OC(F)(F)F)cc3)n2)cc1]
P901
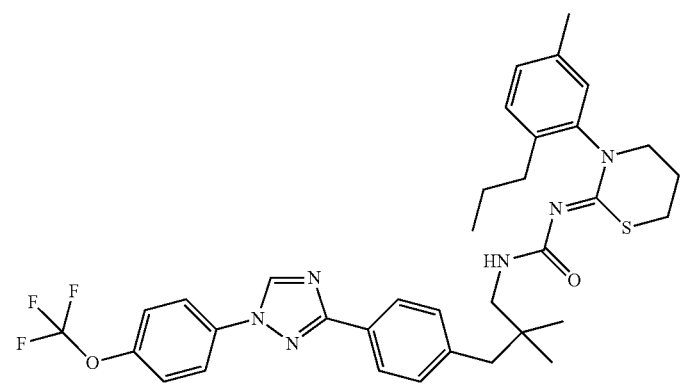 [SMILES: CCCc1ccc(C)cc1N1CCCS/C1=N\C(=O)NCC(C)(C)Cc1ccc(-c2ncn(-c3ccc(OC(F)(F)F)cc3)n2)cc1]
P902
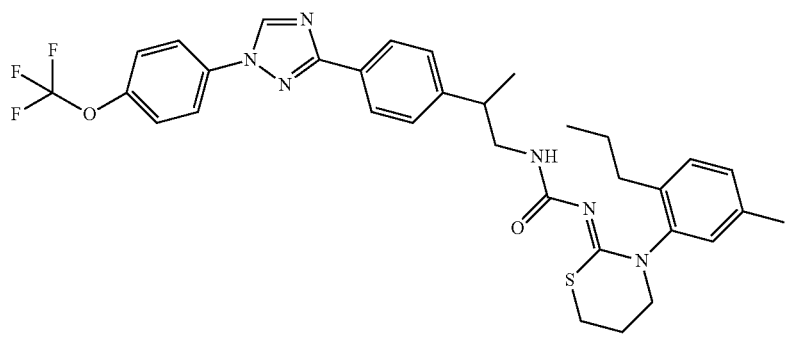 [SMILES: CCCc1ccc(C)cc1N1CCCS/C1=N\C(=O)NCC(C)c1ccc(-c2ncn(-c3ccc(OC(F)(F)F)cc3)n2)cc1]
P903

TABLE P-Two-continued
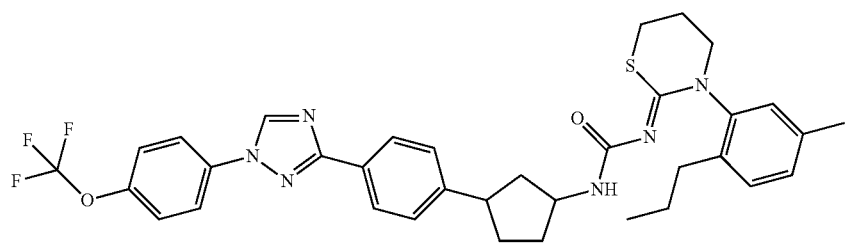 [SMILES: CCCc1ccc(C)cc1N1CCCS/C1=N\C(=O)NC1CCC(c2ccc(-c3ncn(-c4ccc(OC(F)(F)F)cc4)n3)cc2)C1]
P904
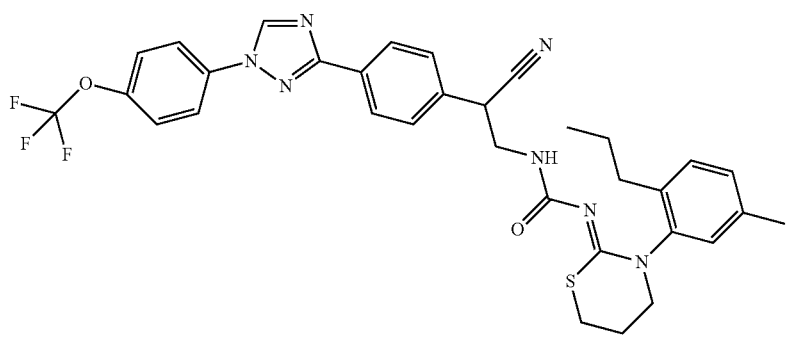 [SMILES: CCCc1ccc(C)cc1N1CCCS/C1=N\C(=O)NCC(C#N)c1ccc(-c2ncn(-c3ccc(OC(F)(F)F)cc3)n2)cc1]
P905
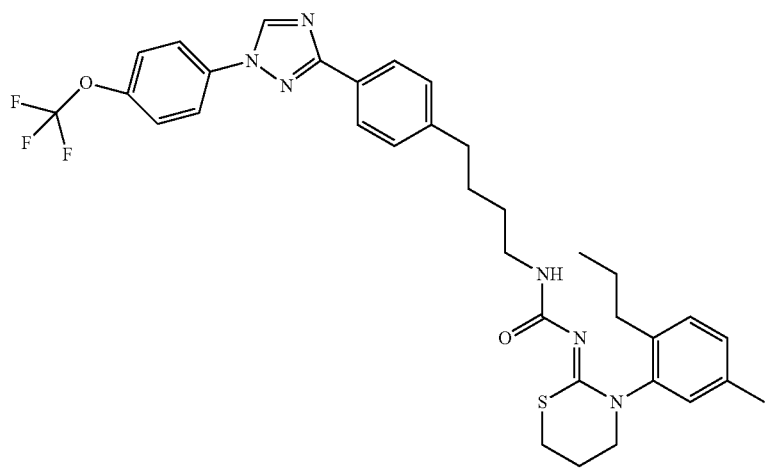 [SMILES: CCCc1ccc(C)cc1N1CCCS/C1=N\C(=O)NCCCCc1ccc(-c2ncn(-c3ccc(OC(F)(F)F)cc3)n2)cc1]
P906
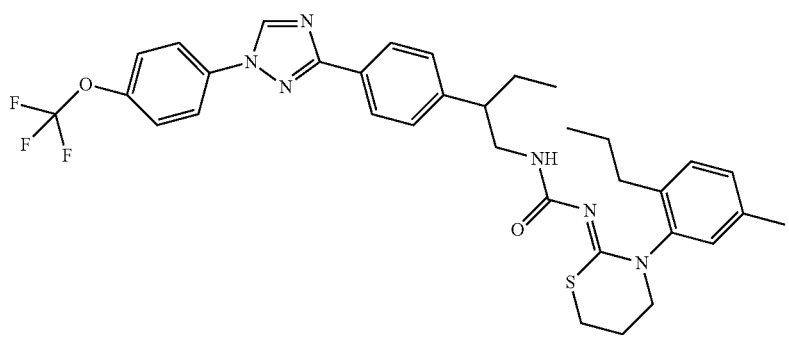 [SMILES: CCCc1ccc(C)cc1N1CCCS/C1=N\C(=O)NCC(CC)c1ccc(-c2ncn(-c3ccc(OC(F)(F)F)cc3)n2)cc1]
P907
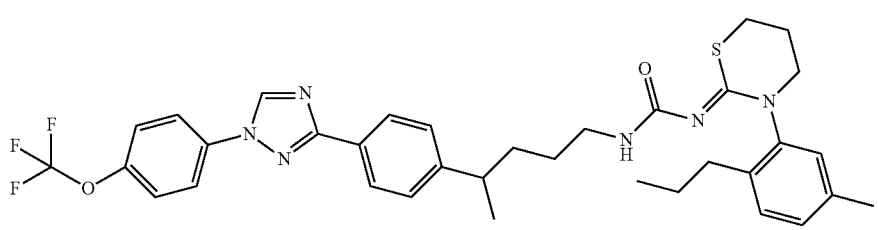 [SMILES: CCCc1ccc(C)cc1N1CCCS/C1=N\C(=O)NCCCC(C)c1ccc(-c2ncn(-c3ccc(OC(F)(F)F)cc3)n2)cc1]
P908

TABLE P-Two-continued
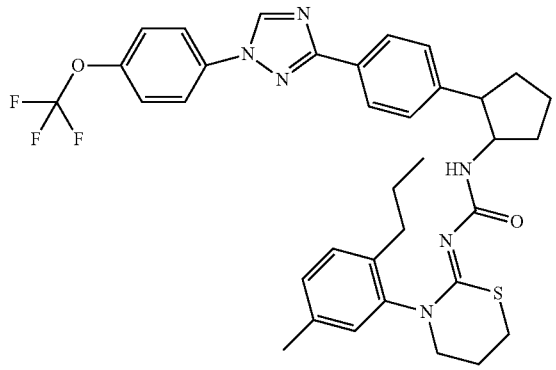 [SMILES: CCCc1ccc(C)cc1N1CCCS/C1=N\C(=O)NC1CCCC1c1ccc(-c2ncn(-c3ccc(OC(F)(F)F)cc3)n2)cc1]
P909
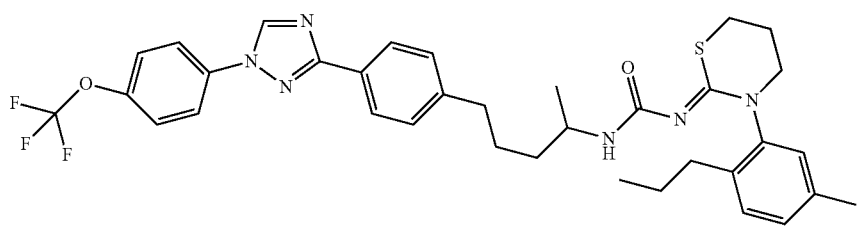 [SMILES: CCCc1ccc(C)cc1N1CCCS/C1=N\C(=O)NC(C)CCCc1ccc(-c2ncn(-c3ccc(OC(F)(F)F)cc3)n2)cc1]
P910
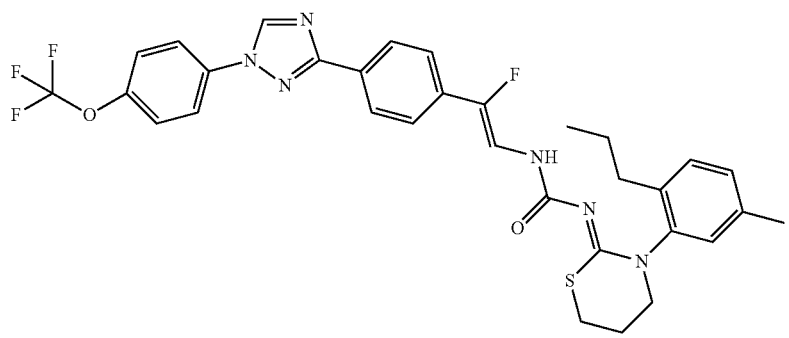 [SMILES: CCCc1ccc(C)cc1N1CCCS/C1=N\C(=O)N/C=C(\F)c1ccc(-c2ncn(-c3ccc(OC(F)(F)F)cc3)n2)cc1]
P911
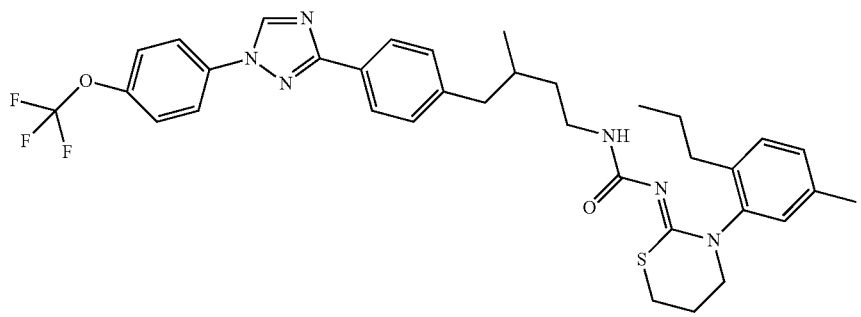 [SMILES: CCCc1ccc(C)cc1N1CCCS/C1=N\C(=O)NCCC(C)Cc1ccc(-c2ncn(-c3ccc(OC(F)(F)F)cc3)n2)cc1]
P912
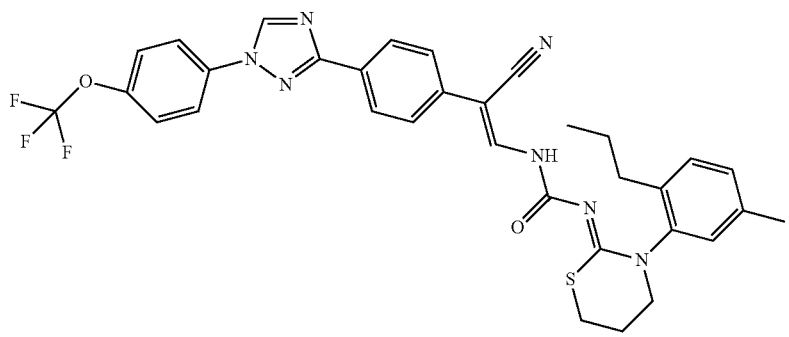 [SMILES: CCCc1ccc(C)cc1N1CCCS/C1=N\C(=O)N/C=C(\C#N)c1ccc(-c2ncn(-c3ccc(OC(F)(F)F)cc3)n2)cc1]
P913

TABLE P-Two-continued
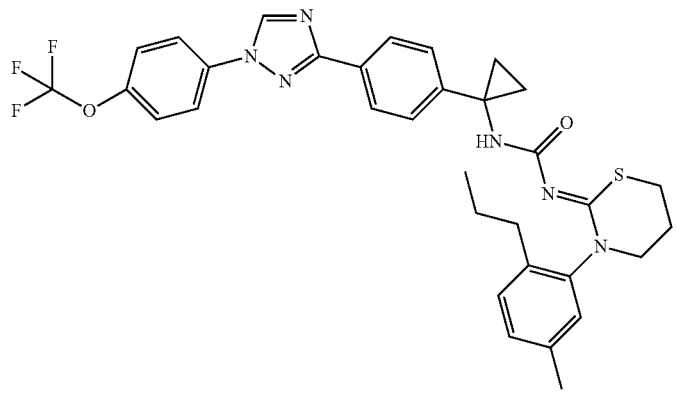 [SMILES: CCCc1ccc(C)cc1N1CCCS/C1=N\C(=O)NC1(c2ccc(-c3ncn(-c4ccc(OC(F)(F)F)cc4)n3)cc2)CC1]
P914
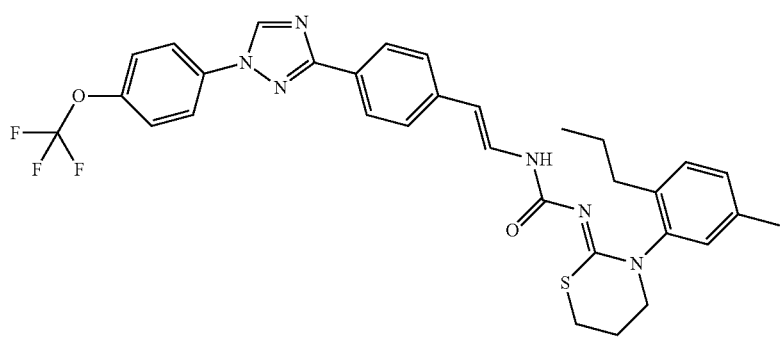 [SMILES: CCCc1ccc(C)cc1N1CCCS/C1=N\C(=O)N/C=C/c1ccc(-c2ncn(-c3ccc(OC(F)(F)F)cc3)n2)cc1]
P915
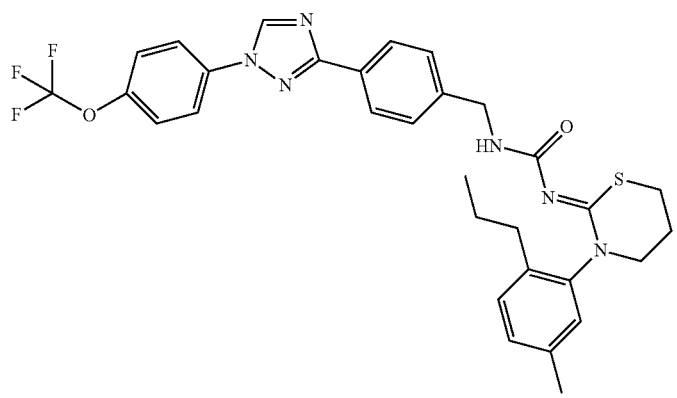 [SMILES: CCCc1ccc(C)cc1N1CCCS/C1=N\C(=O)NCc1ccc(-c2ncn(-c3ccc(OC(F)(F)F)cc3)n2)cc1]
P916
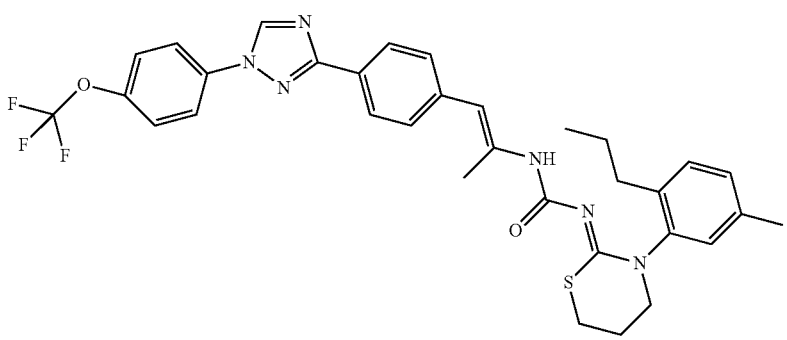 [SMILES: CCCc1ccc(C)cc1N1CCCS/C1=N\C(=O)N/C(C)=C/c1ccc(-c2ncn(-c3ccc(OC(F)(F)F)cc3)n2)cc1]
P917

TABLE P-Two-continued
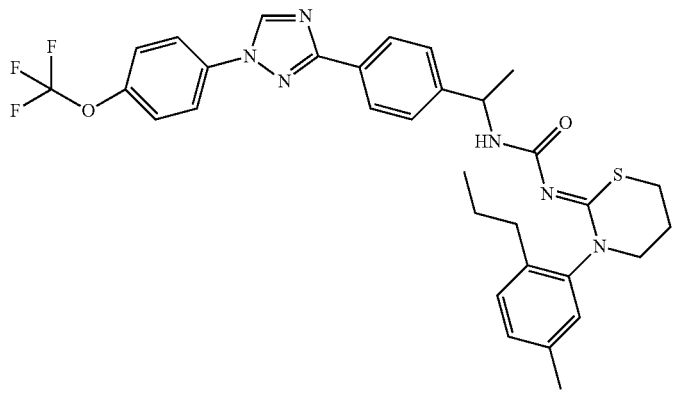 [SMILES: CCCc1ccc(C)cc1N1CCCS/C1=N\C(=O)NC(C)c1ccc(-c2ncn(-c3ccc(OC(F)(F)F)cc3)n2)cc1]
P918
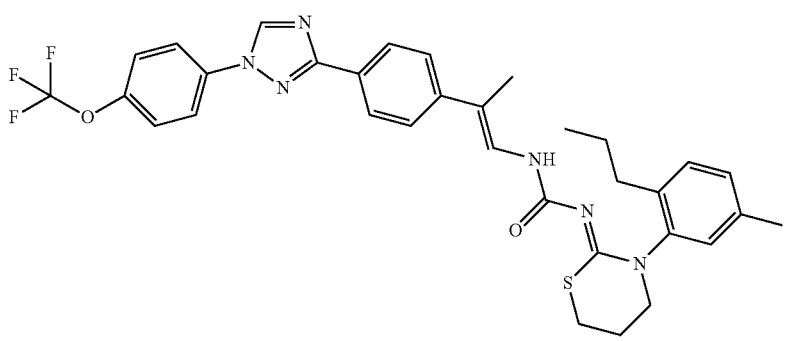 [SMILES: CCCc1ccc(C)cc1N1CCCS/C1=N\C(=O)N/C=C(\C)c1ccc(-c2ncn(-c3ccc(OC(F)(F)F)cc3)n2)cc1]
P919
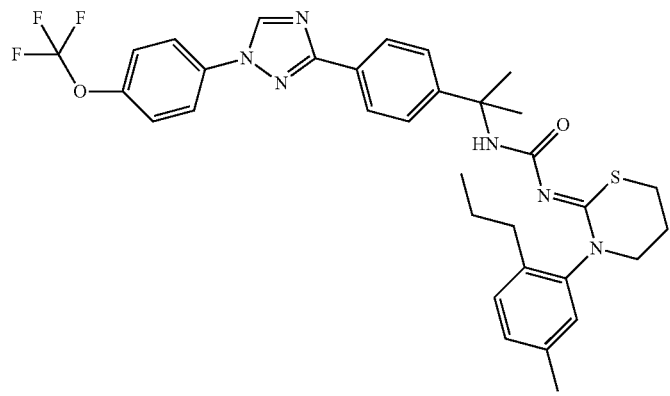 [SMILES: CCCc1ccc(C)cc1N1CCCS/C1=N\C(=O)NC(C)(C)c1ccc(-c2ncn(-c3ccc(OC(F)(F)F)cc3)n2)cc1]
P920
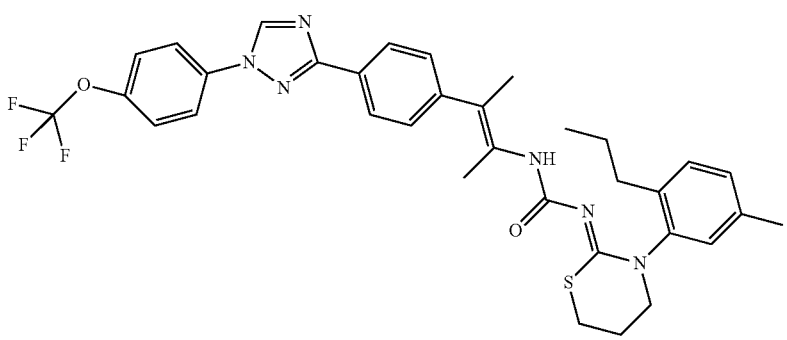 [SMILES: CCCc1ccc(C)cc1N1CCCS/C1=N\C(=O)N/C(C)=C(\C)c1ccc(-c2ncn(-c3ccc(OC(F)(F)F)cc3)n2)cc1]
P921

TABLE P-Two-continued
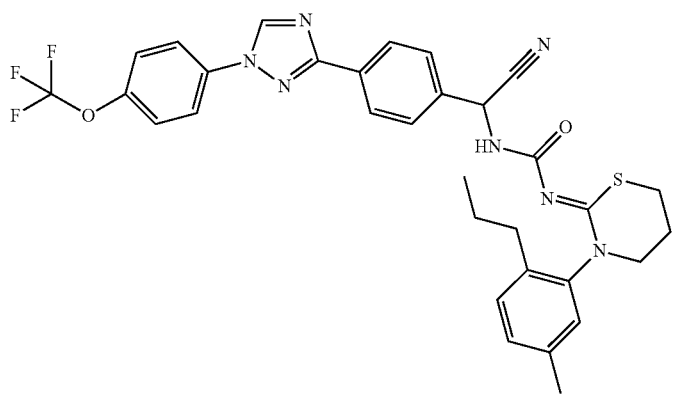 [SMILES: CCCc1ccc(C)cc1N1CCCS/C1=N\C(=O)NC(C#N)c1ccc(-c2ncn(-c3ccc(OC(F)(F)F)cc3)n2)cc1]
P922
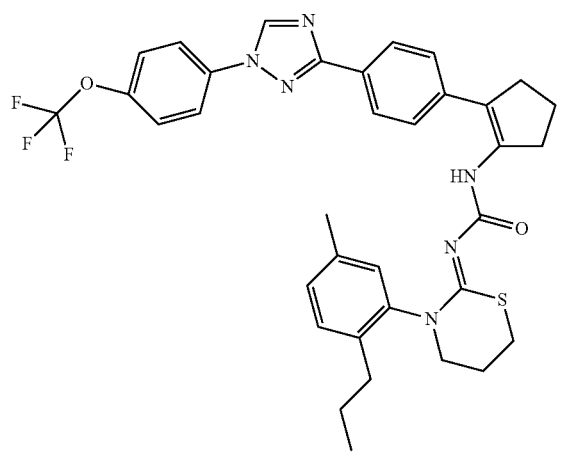 [SMILES: CCCc1ccc(C)cc1N1CCCS/C1=N\C(=O)NC1=C(c2ccc(-c3ncn(-c4ccc(OC(F)(F)F)cc4)n3)cc2)CCC1]
P923
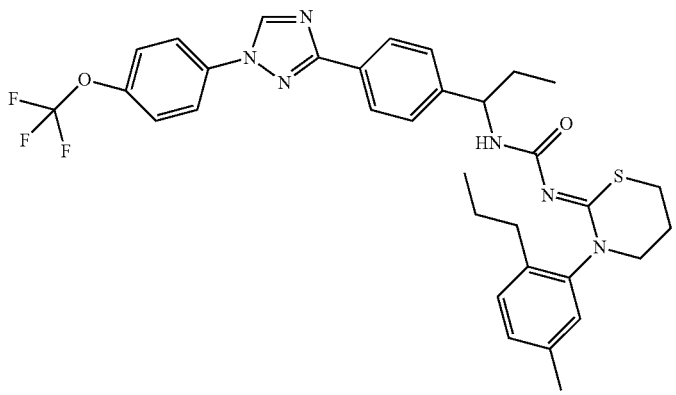 [SMILES: CCCc1ccc(C)cc1N1CCCS/C1=N\C(=O)NC(CC)c1ccc(-c2ncn(-c3ccc(OC(F)(F)F)cc3)n2)cc1]
P924
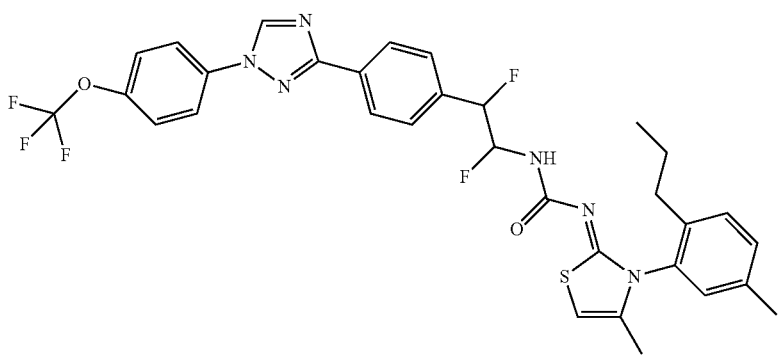 [SMILES: CCCc1ccc(C)cc1-n1c(C)cs/c1=N\C(=O)NC(F)C(F)c1ccc(-c2ncn(-c3ccc(OC(F)(F)F)cc3)n2)cc1]
P925

TABLE P-Two-continued
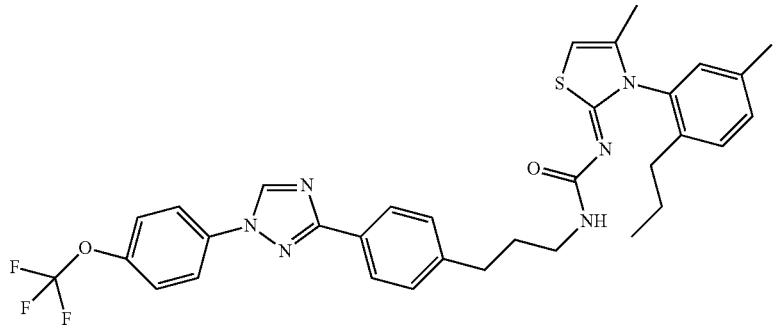 [SMILES: CCCc1ccc(C)cc1-n1c(C)cs/c1=N\C(=O)NCCCc1ccc(-c2ncn(-c3ccc(OC(F)(F)F)cc3)n2)cc1]
P926
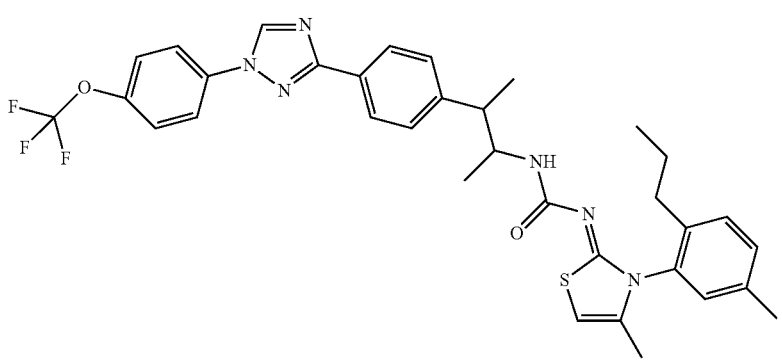 [SMILES: CCCc1ccc(C)cc1-n1c(C)cs/c1=N\C(=O)NC(C)C(C)c1ccc(-c2ncn(-c3ccc(OC(F)(F)F)cc3)n2)cc1]
P927
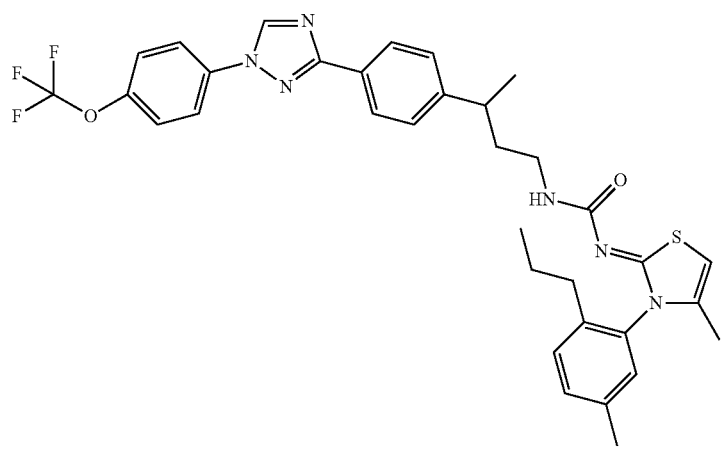 [SMILES: CCCc1ccc(C)cc1-n1c(C)cs/c1=N\C(=O)NCCC(C)c1ccc(-c2ncn(-c3ccc(OC(F)(F)F)cc3)n2)cc1]
P928
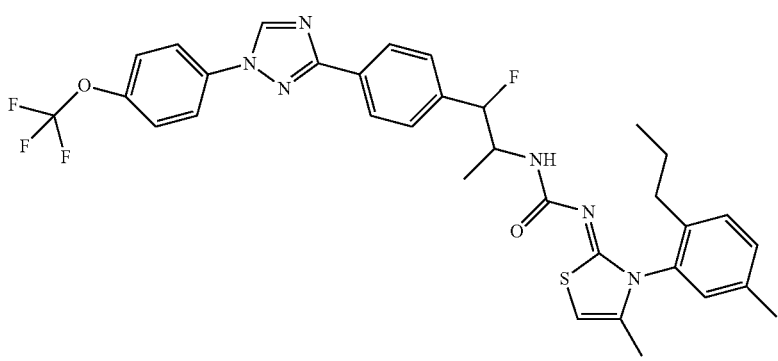 [SMILES: CCCc1ccc(C)cc1-n1c(C)cs/c1=N\C(=O)NC(C)C(F)c1ccc(-c2ncn(-c3ccc(OC(F)(F)F)cc3)n2)cc1]
P929

| | |
|---|---|
| 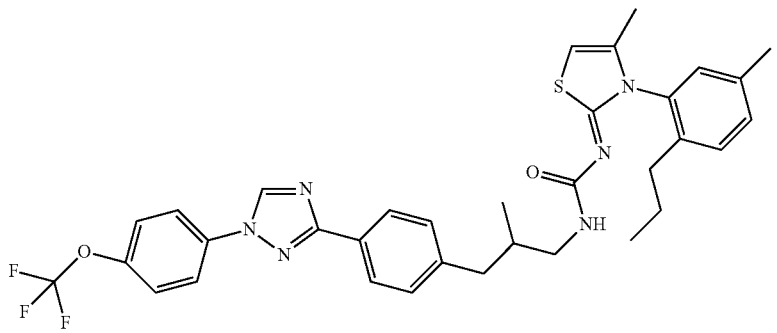 [SMILES: CCCc1ccc(C)cc1-n1c(C)cs/c1=N\C(=O)NCC(C)Cc1ccc(-c2ncn(-c3ccc(OC(F)(F)F)cc3)n2)cc1] | P930 |
| 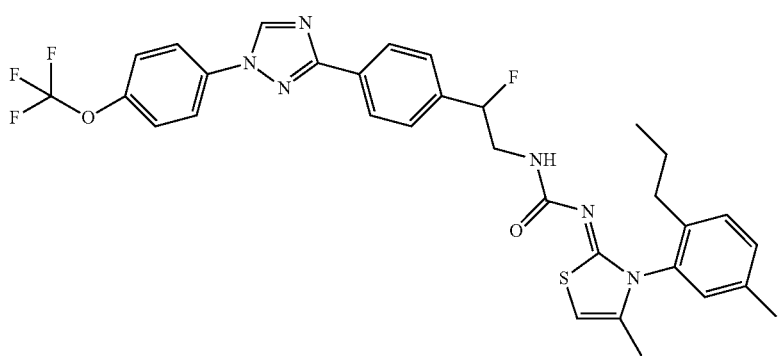 [SMILES: CCCc1ccc(C)cc1-n1c(C)cs/c1=N\C(=O)NCC(F)c1ccc(-c2ncn(-c3ccc(OC(F)(F)F)cc3)n2)cc1] | P931 |
| 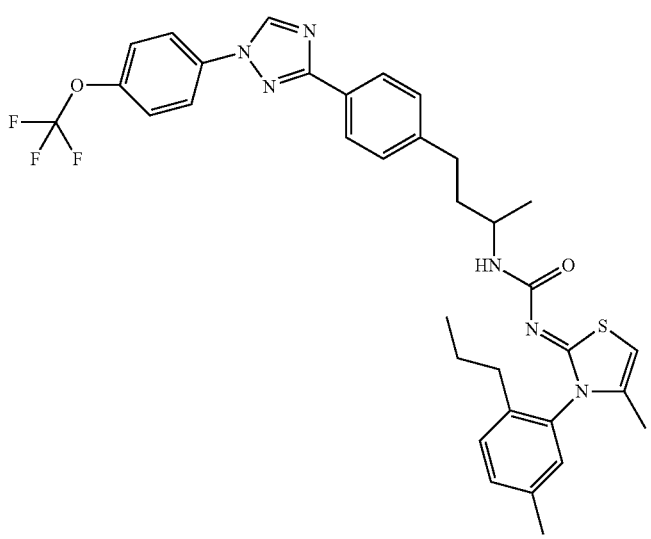 [SMILES: CCCc1ccc(C)cc1-n1c(C)cs/c1=N\C(=O)NC(C)CCc1ccc(-c2ncn(-c3ccc(OC(F)(F)F)cc3)n2)cc1] | P932 |
| 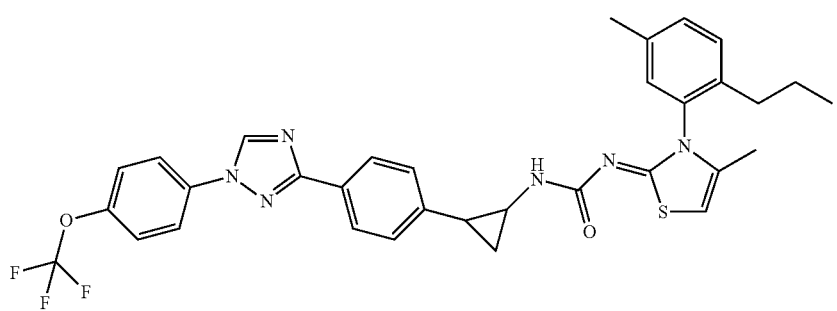 [SMILES: CCCc1ccc(C)cc1-n1c(C)cs/c1=N\C(=O)NC1CC1c1ccc(-c2ncn(-c3ccc(OC(F)(F)F)cc3)n2)cc1] | P933 |

TABLE P-Two-continued
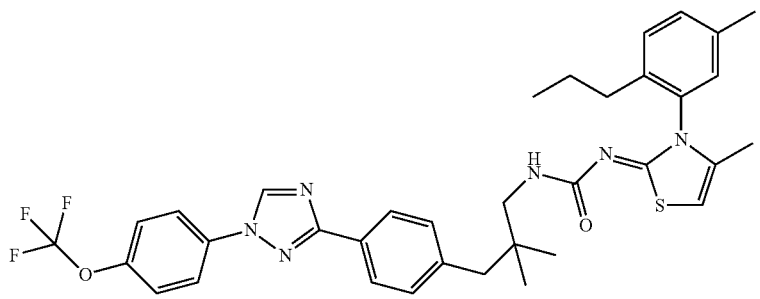 [SMILES: CCCc1ccc(C)cc1-n1c(C)cs/c1=N\C(=O)NCC(C)(C)Cc1ccc(-c2ncn(-c3ccc(OC(F)(F)F)cc3)n2)cc1]
P934
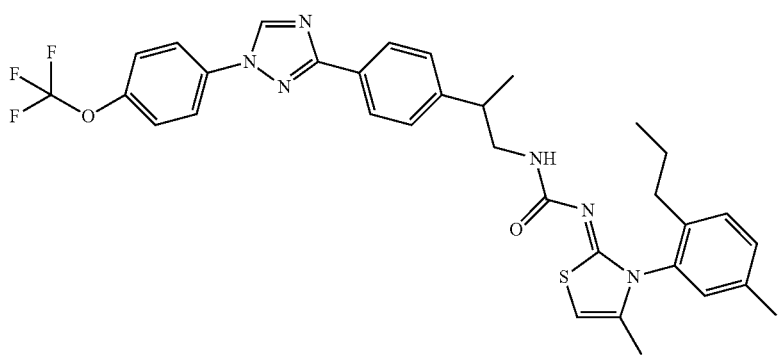 [SMILES: CCCc1ccc(C)cc1-n1c(C)cs/c1=N\C(=O)NCC(C)c1ccc(-c2ncn(-c3ccc(OC(F)(F)F)cc3)n2)cc1]
P935
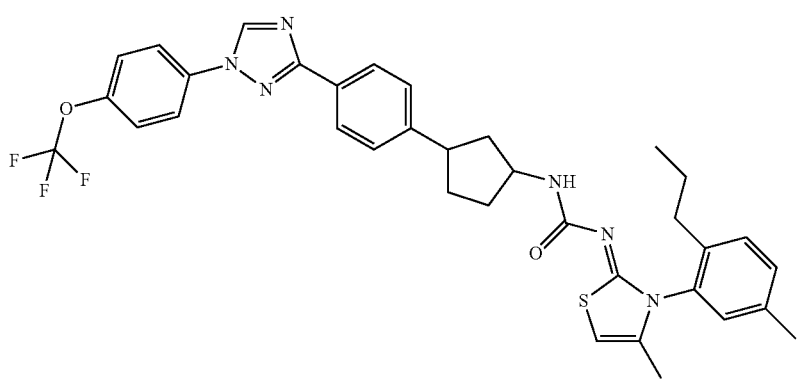 [SMILES: CCCc1ccc(C)cc1-n1c(C)cs/c1=N\C(=O)NC1CCC(c2ccc(-c3ncn(-c4ccc(OC(F)(F)F)cc4)n3)cc2)C1]
P936
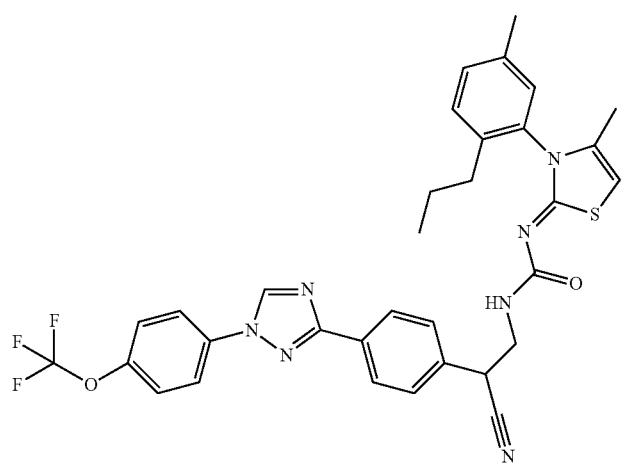 [SMILES: CCCc1ccc(C)cc1-n1c(C)cs/c1=N\C(=O)NCC(C#N)c1ccc(-c2ncn(-c3ccc(OC(F)(F)F)cc3)n2)cc1]
P937

TABLE P-Two-continued
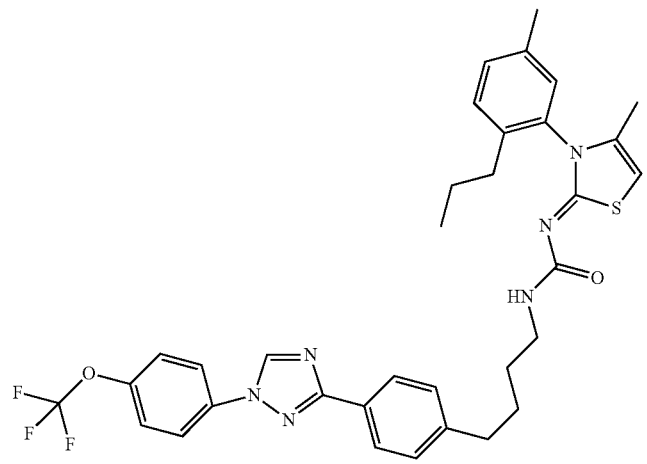 [SMILES: CCCc1ccc(C)cc1-n1c(C)cs/c1=N\C(=O)NCCCCc1ccc(-c2ncn(-c3ccc(OC(F)(F)F)cc3)n2)cc1]
P938
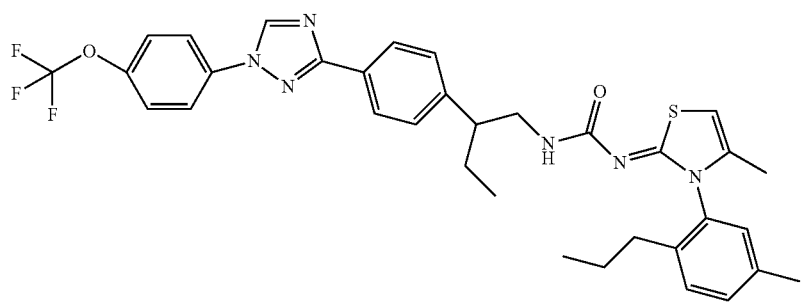 [SMILES: CCCc1ccc(C)cc1-n1c(C)cs/c1=N\C(=O)NCC(CC)c1ccc(-c2ncn(-c3ccc(OC(F)(F)F)cc3)n2)cc1]
P939
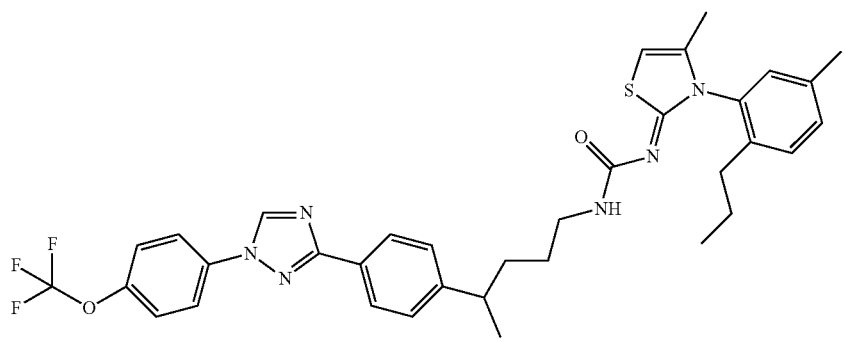 [SMILES: CCCc1ccc(C)cc1-n1c(C)cs/c1=N\C(=O)NCCCC(C)c1ccc(-c2ncn(-c3ccc(OC(F)(F)F)cc3)n2)cc1]
P940
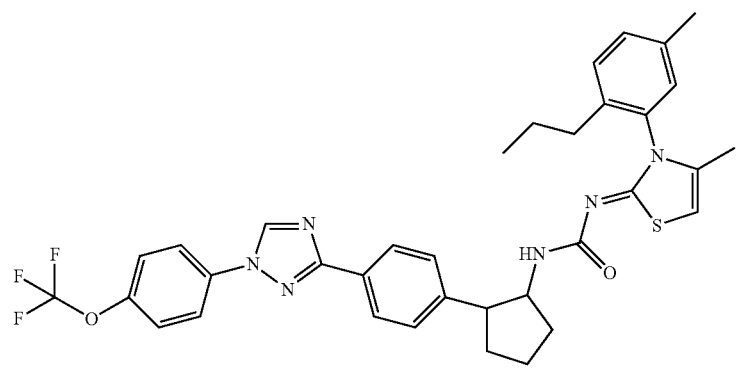 [SMILES: CCCc1ccc(C)cc1-n1c(C)cs/c1=N\C(=O)NC1CCCC1c1ccc(-c2ncn(-c3ccc(OC(F)(F)F)cc3)n2)cc1]
P941

TABLE P-Two-continued
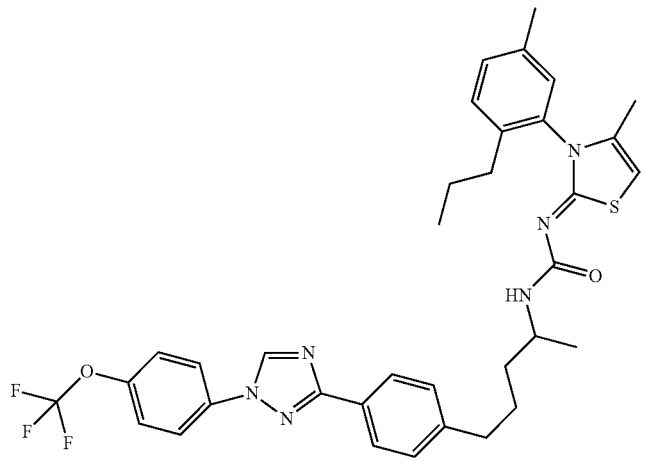 [SMILES: CCCc1ccc(C)cc1-n1c(C)cs/c1=N\C(=O)NC(C)CCCc1ccc(-c2ncn(-c3ccc(OC(F)(F)F)cc3)n2)cc1]
P942
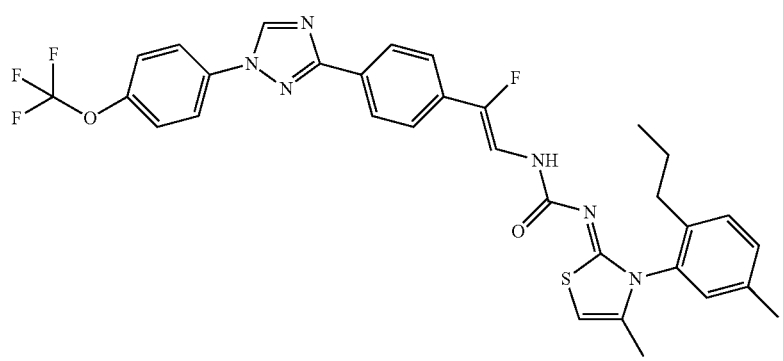 [SMILES: CCCc1ccc(C)cc1-n1c(C)cs/c1=N\C(=O)N/C=C(\F)c1ccc(-c2ncn(-c3ccc(OC(F)(F)F)cc3)n2)cc1]
P943
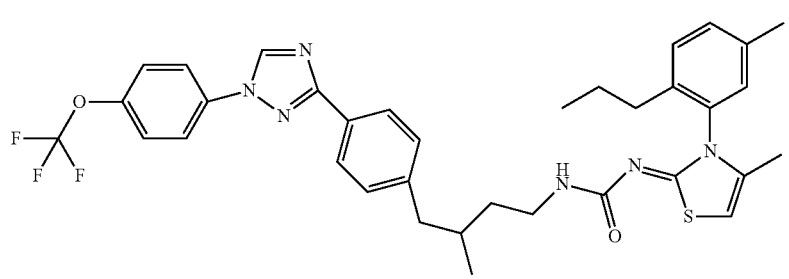 [SMILES: CCCc1ccc(C)cc1-n1c(C)cs/c1=N\C(=O)NCCC(C)Cc1ccc(-c2ncn(-c3ccc(OC(F)(F)F)cc3)n2)cc1]
P944
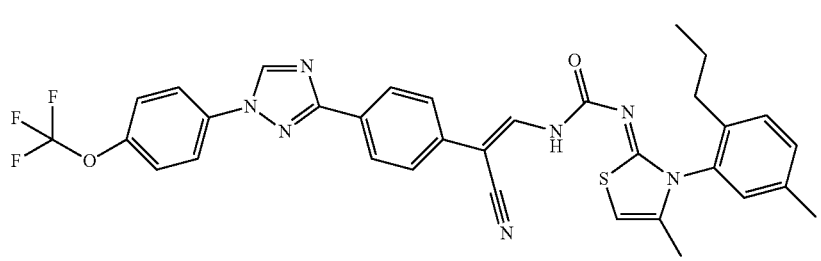 [SMILES: CCCc1ccc(C)cc1-n1c(C)cs/c1=N\C(=O)N/C=C(\C#N)c1ccc(-c2ncn(-c3ccc(OC(F)(F)F)cc3)n2)cc1]
P945

TABLE P-Two-continued
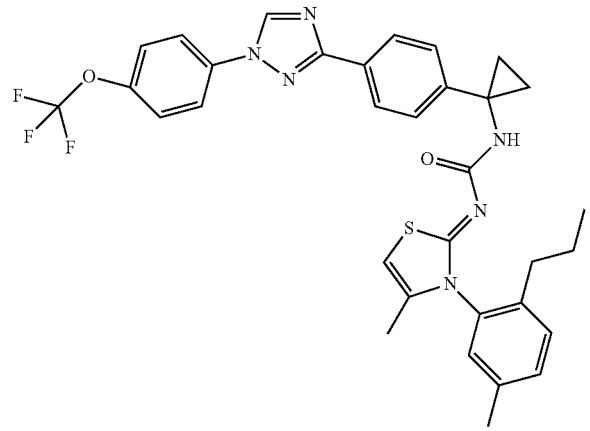 [SMILES: CCCc1ccc(C)cc1-n1c(C)cs/c1=N\C(=O)NC1(c2ccc(-c3ncn(-c4ccc(OC(F)(F)F)cc4)n3)cc2)CC1]
P946
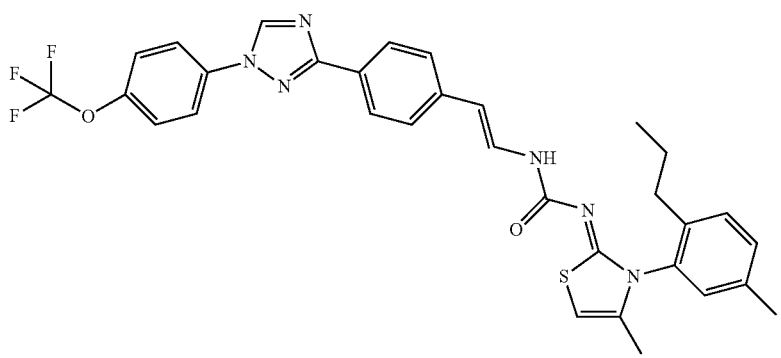 [SMILES: CCCc1ccc(C)cc1-n1c(C)cs/c1=N\C(=O)N/C=C/c1ccc(-c2ncn(-c3ccc(OC(F)(F)F)cc3)n2)cc1]
P947
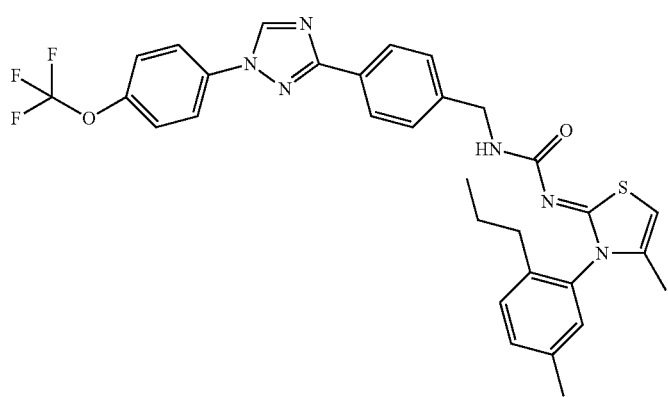 [SMILES: CCCc1ccc(C)cc1-n1c(C)cs/c1=N\C(=O)NCc1ccc(-c2ncn(-c3ccc(OC(F)(F)F)cc3)n2)cc1]
P948
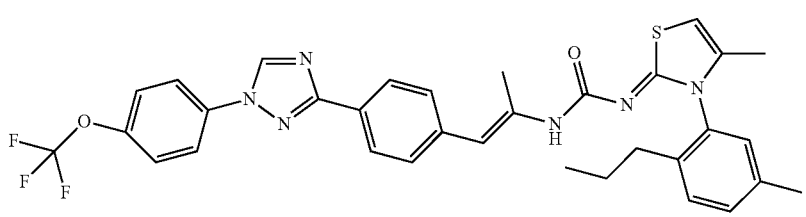 [SMILES: CCCc1ccc(C)cc1-n1c(C)cs/c1=N\C(=O)N/C(C)=C/c1ccc(-c2ncn(-c3ccc(OC(F)(F)F)cc3)n2)cc1]
P949

TABLE P-Two-continued
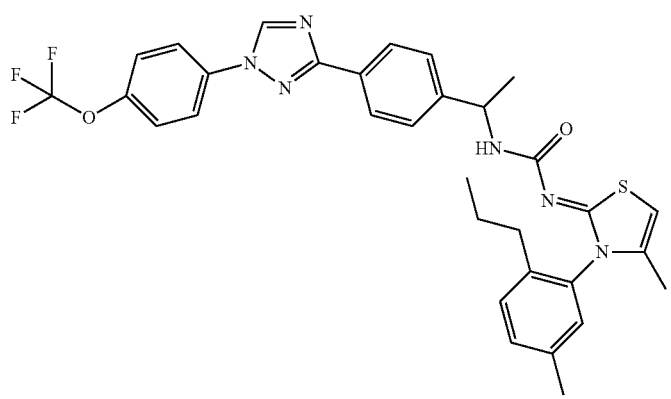 [SMILES: CCCc1ccc(C)cc1-n1c(C)cs/c1=N\C(=O)NC(C)c1ccc(-c2ncn(-c3ccc(OC(F)(F)F)cc3)n2)cc1]
P950
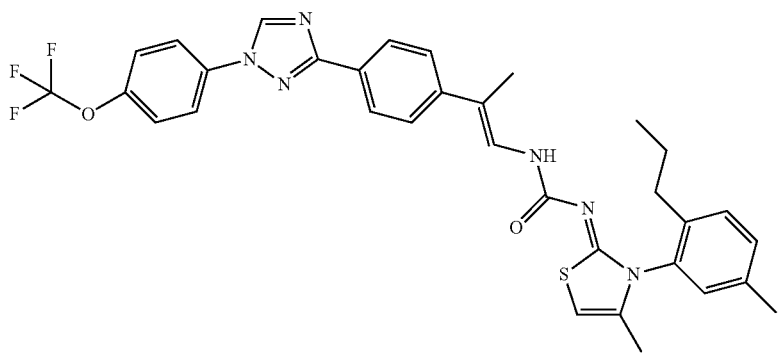 [SMILES: CCCc1ccc(C)cc1-n1c(C)cs/c1=N\C(=O)N/C=C(\C)c1ccc(-c2ncn(-c3ccc(OC(F)(F)F)cc3)n2)cc1]
P951
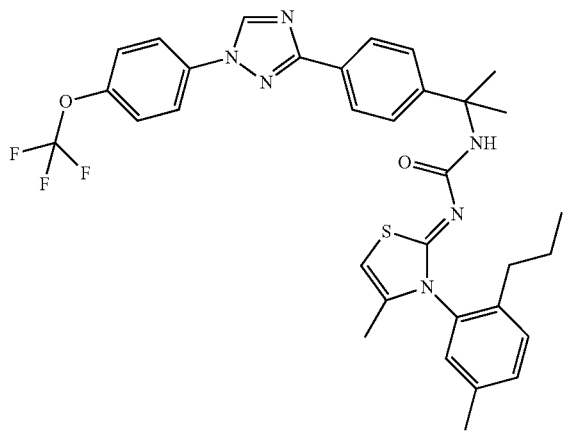 [SMILES: CCCc1ccc(C)cc1-n1c(C)cs/c1=N\C(=O)NC(C)(C)c1ccc(-c2ncn(-c3ccc(OC(F)(F)F)cc3)n2)cc1]
P952
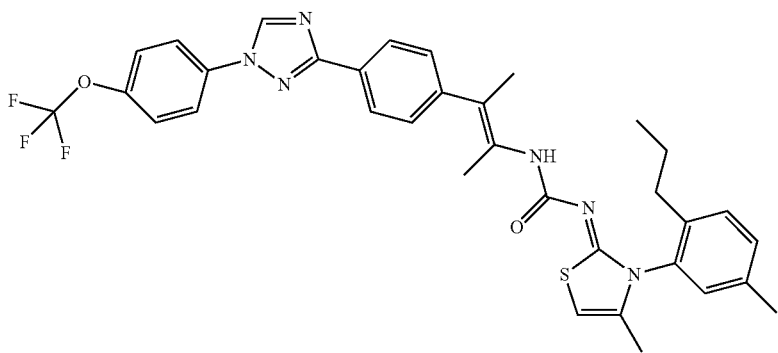 [SMILES: CCCc1ccc(C)cc1-n1c(C)cs/c1=N\C(=O)N/C(C)=C(\C)c1ccc(-c2ncn(-c3ccc(OC(F)(F)F)cc3)n2)cc1]
P953

TABLE P-Two-continued
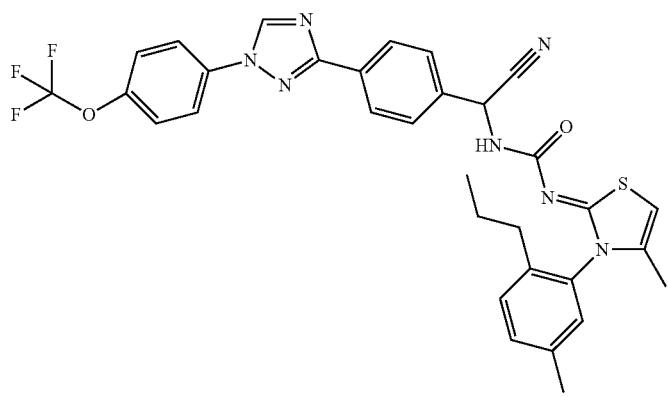 [SMILES: CCCc1ccc(C)cc1-n1c(C)cs/c1=N\C(=O)NC(C#N)c1ccc(-c2ncn(-c3ccc(OC(F)(F)F)cc3)n2)cc1]
P954
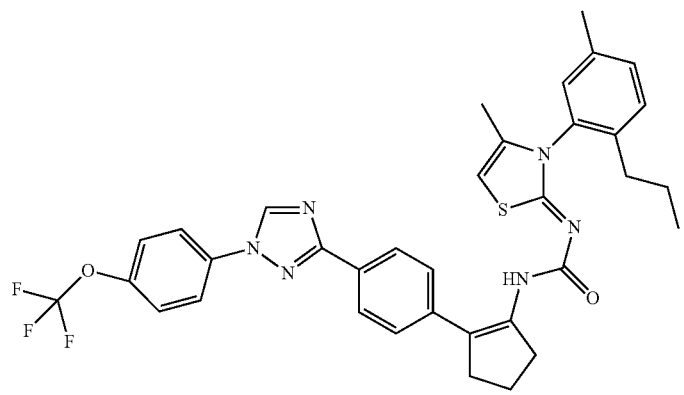 [SMILES: CCCc1ccc(C)cc1-n1c(C)cs/c1=N\C(=O)NC1=C(c2ccc(-c3ncn(-c4ccc(OC(F)(F)F)cc4)n3)cc2)CCC1]
P955
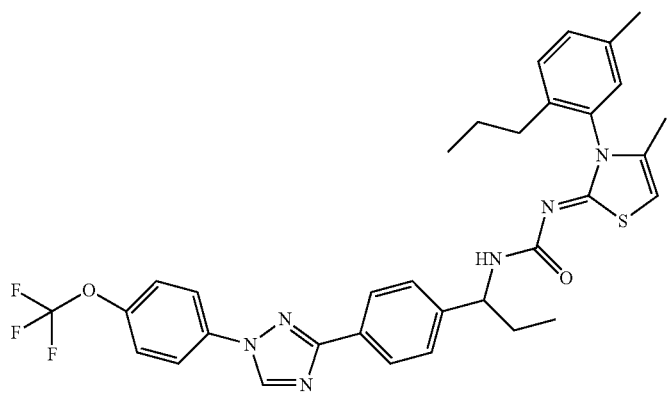 [SMILES: CCCc1ccc(C)cc1-n1c(C)cs/c1=N\C(=O)NC(CC)c1ccc(-c2ncn(-c3ccc(OC(F)(F)F)cc3)n2)cc1]
P956
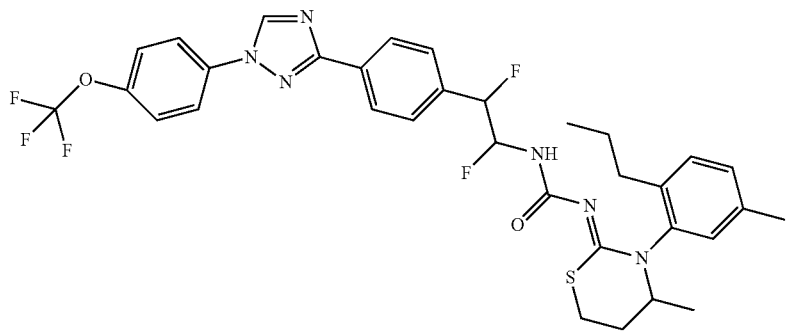 [SMILES: CCCc1ccc(C)cc1N1/C(=N/C(=O)NC(F)C(F)c2ccc(-c3ncn(-c4ccc(OC(F)(F)F)cc4)n3)cc2)SCCC1C]
P957

TABLE P-Two-continued
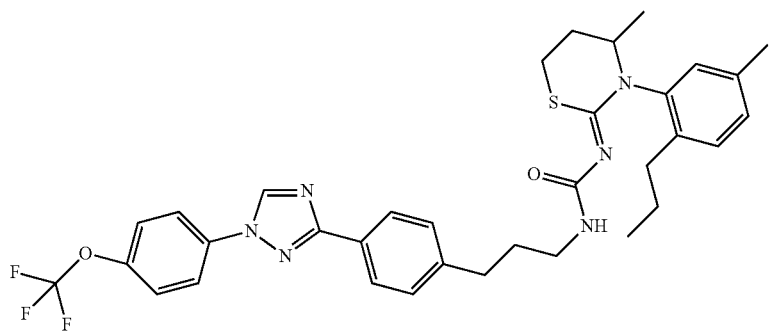 [SMILES: CCCc1ccc(C)cc1N1/C(=N/C(=O)NCCCc2ccc(-c3ncn(-c4ccc(OC(F)(F)F)cc4)n3)cc2)SCCC1C]
P958
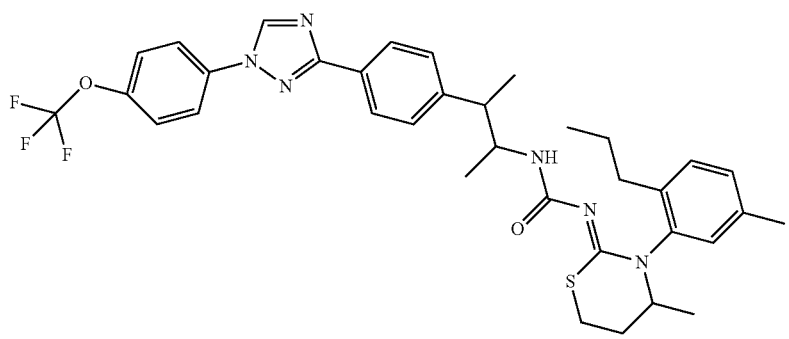 [SMILES: CCCc1ccc(C)cc1N1/C(=N/C(=O)NC(C)C(C)c2ccc(-c3ncn(-c4ccc(OC(F)(F)F)cc4)n3)cc2)SCCC1C]
P959
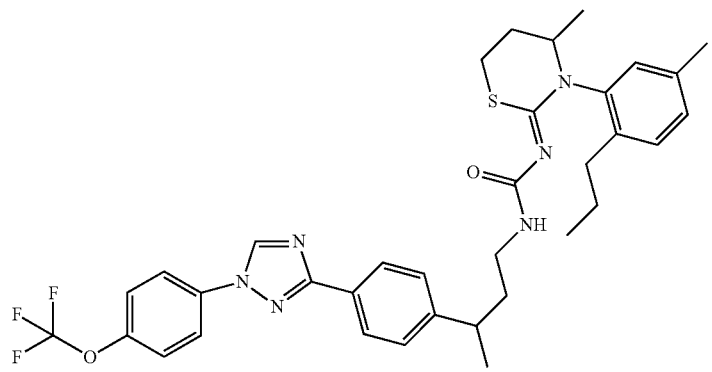 [SMILES: CCCc1ccc(C)cc1N1/C(=N/C(=O)NCCC(C)c2ccc(-c3ncn(-c4ccc(OC(F)(F)F)cc4)n3)cc2)SCCC1C]
P960
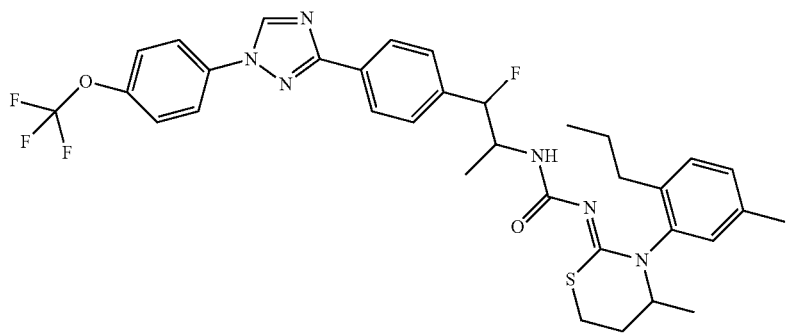
P961

TABLE P-Two-continued
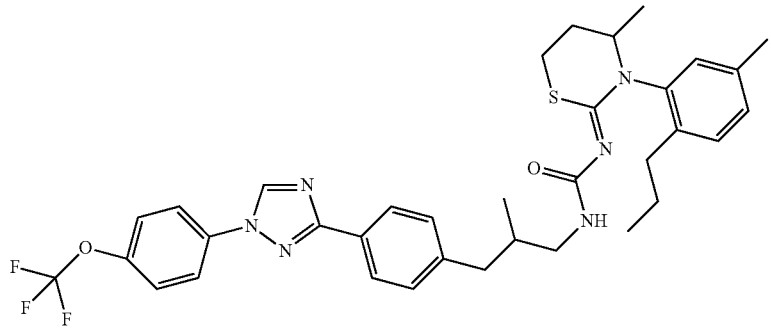 [SMILES: CCCc1ccc(C)cc1N1/C(=N/C(=O)NCC(C)Cc2ccc(-c3ncn(-c4ccc(OC(F)(F)F)cc4)n3)cc2)SCCC1C]
P962
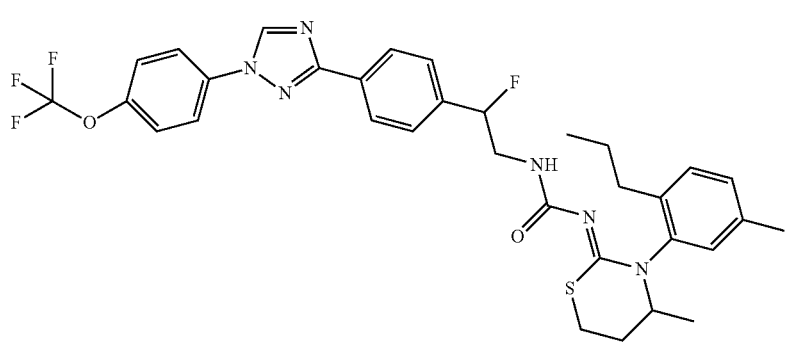 [SMILES: CCCc1ccc(C)cc1N1/C(=N/C(=O)NCC(F)c2ccc(-c3ncn(-c4ccc(OC(F)(F)F)cc4)n3)cc2)SCCC1C]
P963
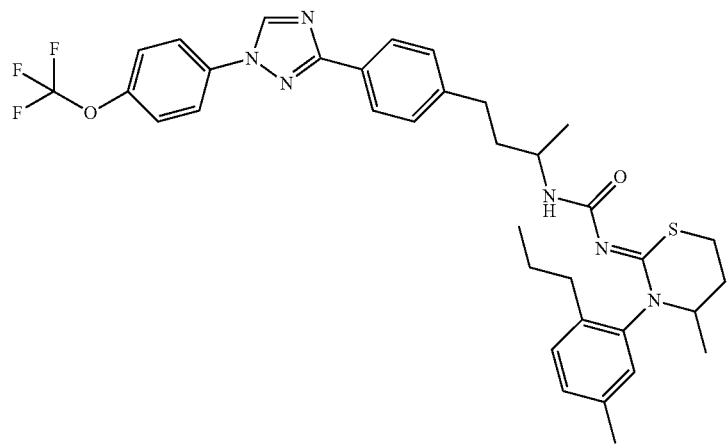 [SMILES: CCCc1ccc(C)cc1N1/C(=N/C(=O)NC(C)CCc2ccc(-c3ncn(-c4ccc(OC(F)(F)F)cc4)n3)cc2)SCCC1C]
P964
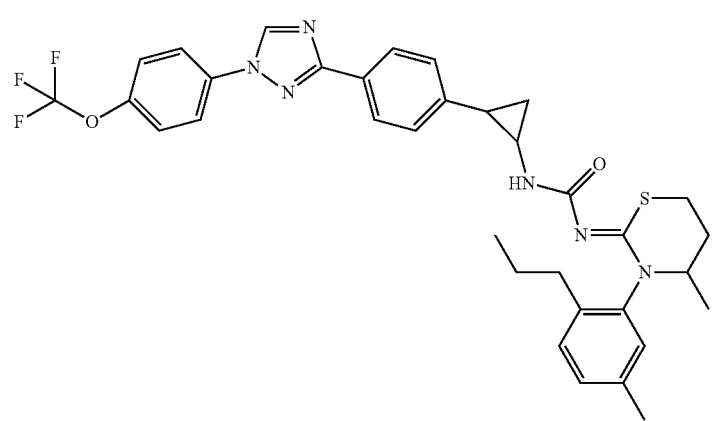 [SMILES: CCCc1ccc(C)cc1N1/C(=N/C(=O)NC2CC2c2ccc(-c3ncn(-c4ccc(OC(F)(F)F)cc4)n3)cc2)SCCC1C]
P965

TABLE P-Two-continued
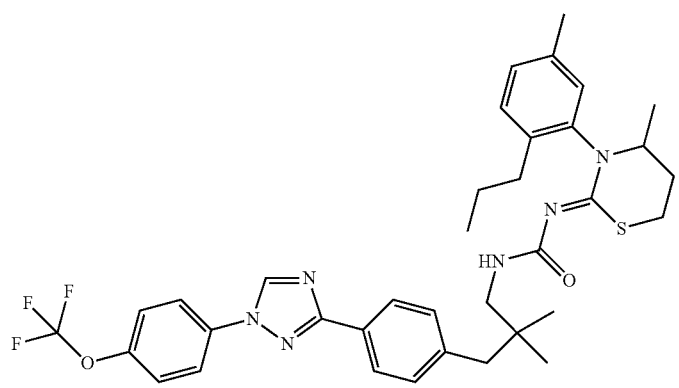 [SMILES: CCCc1ccc(C)cc1N1/C(=N/C(=O)NCC(C)(C)Cc2ccc(-c3ncn(-c4ccc(OC(F)(F)F)cc4)n3)cc2)SCCC1C]
P966
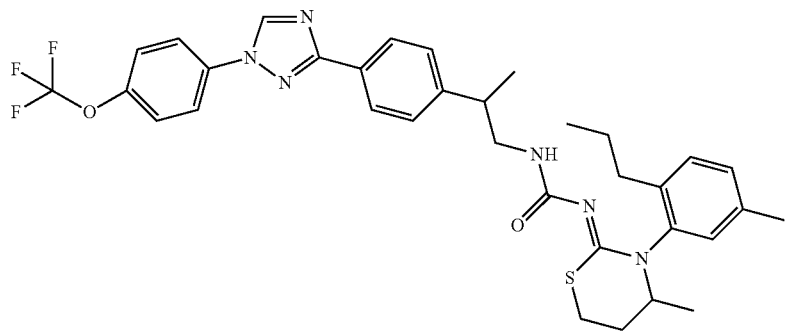 [SMILES: CCCc1ccc(C)cc1N1/C(=N/C(=O)NCC(C)c2ccc(-c3ncn(-c4ccc(OC(F)(F)F)cc4)n3)cc2)SCCC1C]
P967
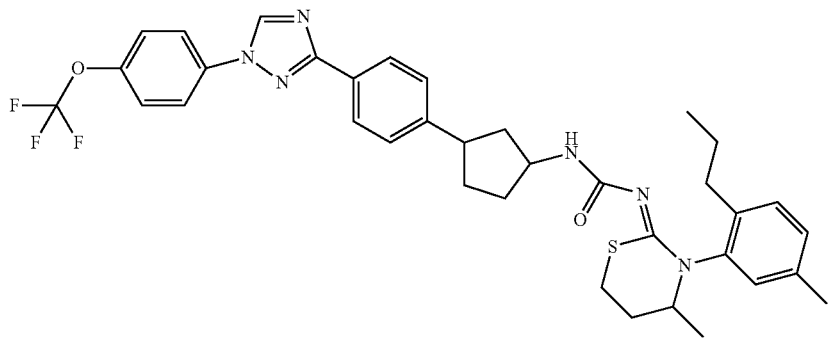 [SMILES: CCCc1ccc(C)cc1N1/C(=N/C(=O)NC2CCC(c3ccc(-c4ncn(-c5ccc(OC(F)(F)F)cc5)n4)cc3)C2)SCCC1C]
P968
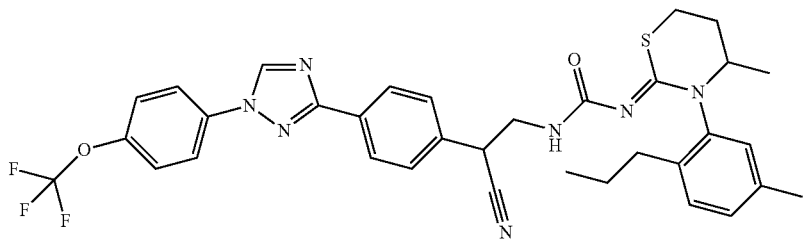 [SMILES: CCCc1ccc(C)cc1N1/C(=N/C(=O)NCC(C#N)c2ccc(-c3ncn(-c4ccc(OC(F)(F)F)cc4)n3)cc2)SCCC1C]
P969

TABLE P-Two-continued
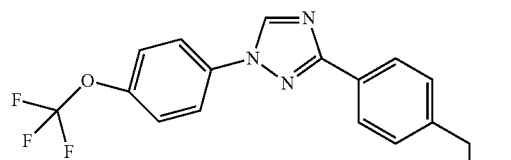
P970
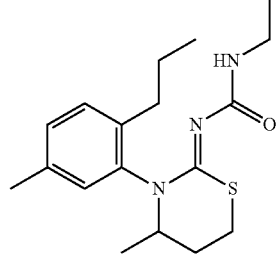
P971
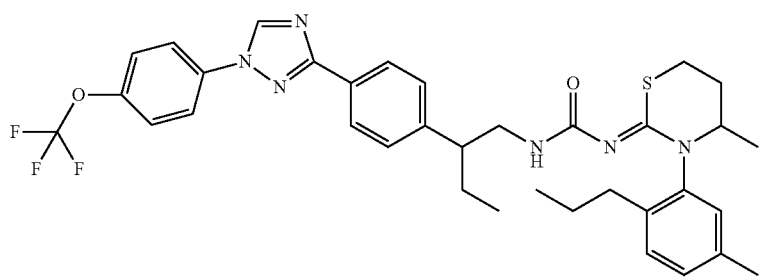 [SMILES: CCCc1ccc(C)cc1N1/C(=N/C(=O)NCC(CC)c2ccc(-c3ncn(-c4ccc(OC(F)(F)F)cc4)n3)cc2)SCCC1C]
P972
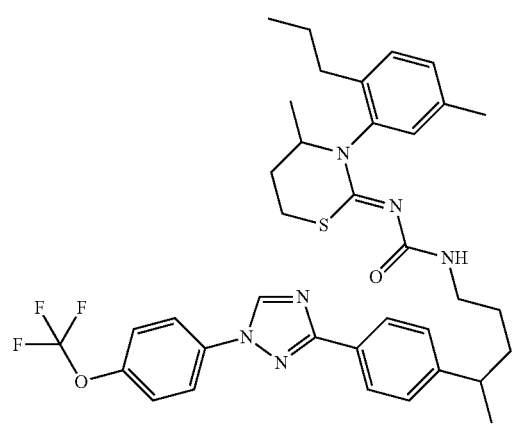 [SMILES: CCCc1ccc(C)cc1N1/C(=N/C(=O)NCCCC(C)c2ccc(-c3ncn(-c4ccc(OC(F)(F)F)cc4)n3)cc2)SCCC1C]
P973
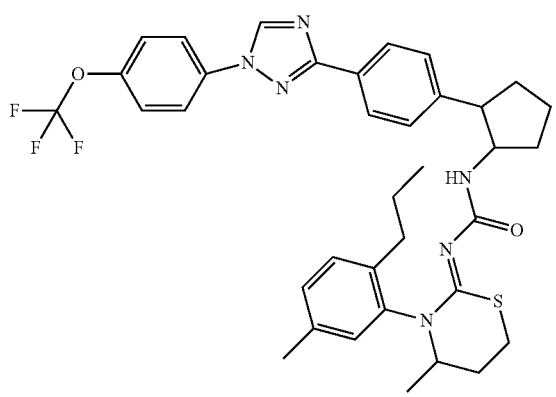 [SMILES: CCCc1ccc(C)cc1N1/C(=N/C(=O)NC2CCCC2c2ccc(-c3ncn(-c4ccc(OC(F)(F)F)cc4)n3)cc2)SCCC1C]

TABLE P-Two-continued
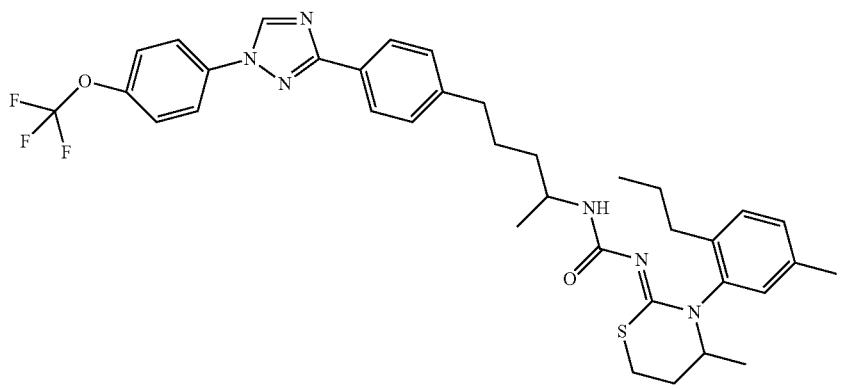 [SMILES: CCCc1ccc(C)cc1N1/C(=N/C(=O)NC(C)CCCc2ccc(-c3ncn(-c4ccc(OC(F)(F)F)cc4)n3)cc2)SCCC1C]
P974
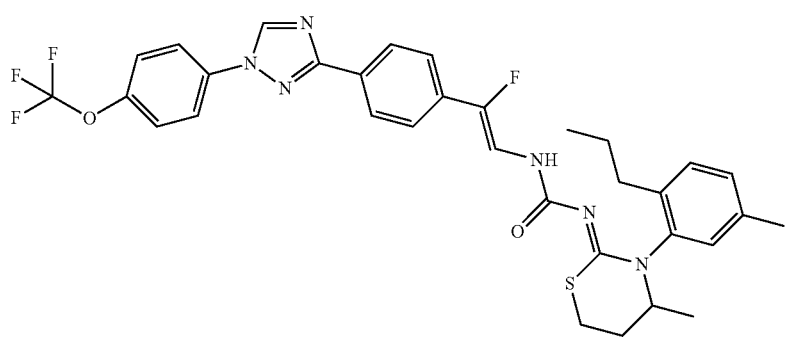 [SMILES: CCCc1ccc(C)cc1N1/C(=N/C(=O)N/C=C(\F)c2ccc(-c3ncn(-c4ccc(OC(F)(F)F)cc4)n3)cc2)SCCC1C]
P975
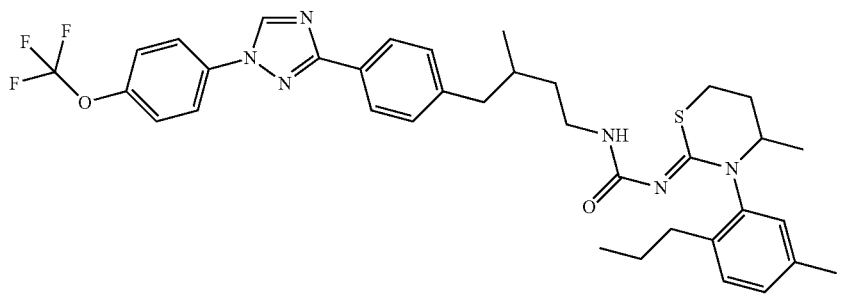 [SMILES: CCCc1ccc(C)cc1N1/C(=N/C(=O)NCCC(C)Cc2ccc(-c3ncn(-c4ccc(OC(F)(F)F)cc4)n3)cc2)SCCC1C]
P976
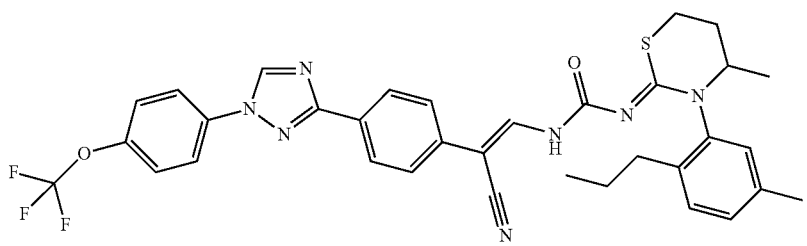 [SMILES: CCCc1ccc(C)cc1N1/C(=N/C(=O)N/C=C(\C#N)c2ccc(-c3ncn(-c4ccc(OC(F)(F)F)cc4)n3)cc2)SCCC1C]
P977
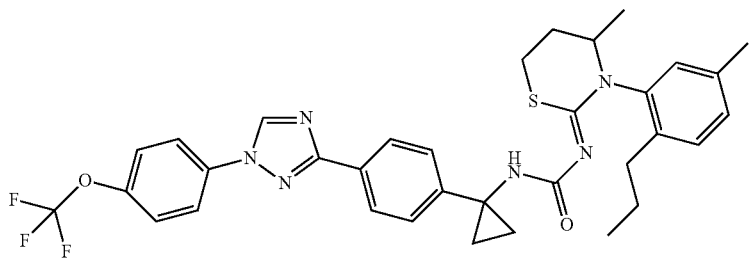 [SMILES: CCCc1ccc(C)cc1N1/C(=N/C(=O)NC2(c3ccc(-c4ncn(-c5ccc(OC(F)(F)F)cc5)n4)cc3)CC2)SCCC1C]
P978

TABLE P-Two-continued
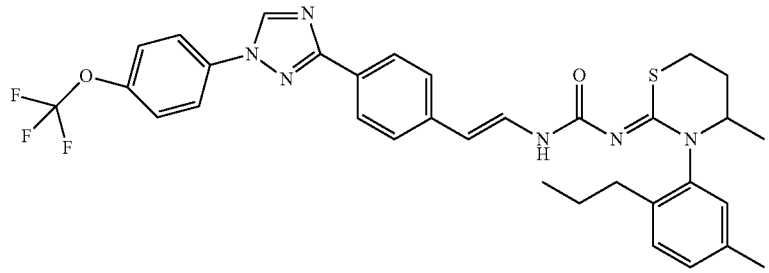 [SMILES: CCCc1ccc(C)cc1N1/C(=N/C(=O)N/C=C/c2ccc(-c3ncn(-c4ccc(OC(F)(F)F)cc4)n3)cc2)SCCC1C]
P979
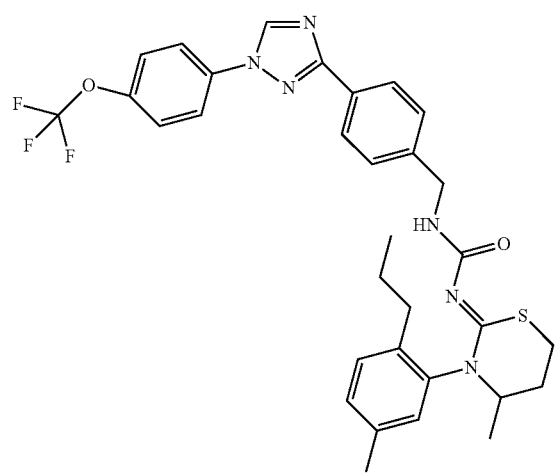 [SMILES: CCCc1ccc(C)cc1N1/C(=N/C(=O)NCc2ccc(-c3ncn(-c4ccc(OC(F)(F)F)cc4)n3)cc2)SCCC1C]
P980
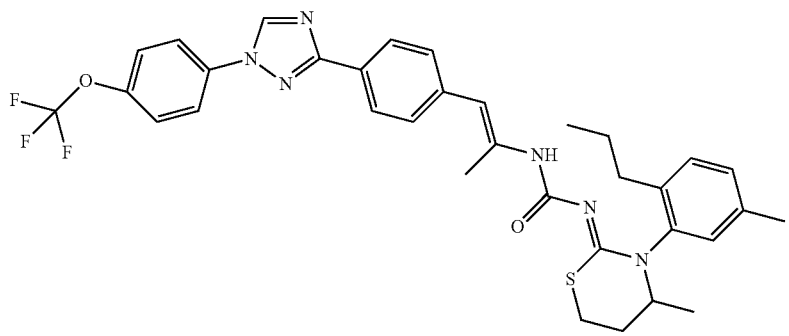 [SMILES: CCCc1ccc(C)cc1N1/C(=N/C(=O)N/C(C)=C/c2ccc(-c3ncn(-c4ccc(OC(F)(F)F)cc4)n3)cc2)SCCC1C]
P981
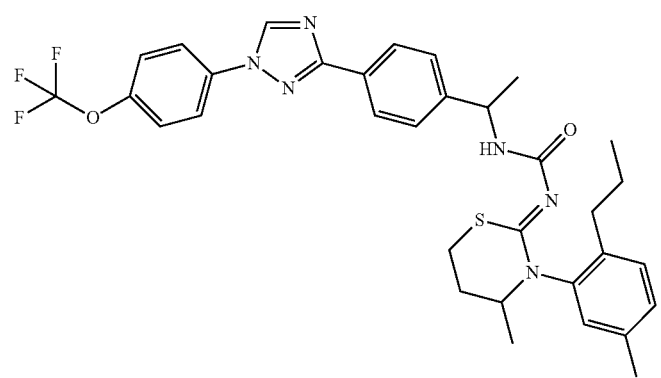 [SMILES: CCCc1ccc(C)cc1N1/C(=N/C(=O)NC(C)c2ccc(-c3ncn(-c4ccc(OC(F)(F)F)cc4)n3)cc2)SCCC1C]
P982

TABLE P-Two-continued
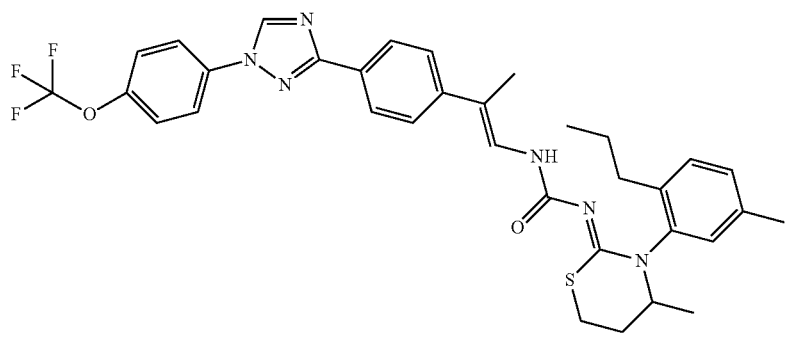 [SMILES: CCCc1ccc(C)cc1N1/C(=N/C(=O)N/C=C(\C)c2ccc(-c3ncn(-c4ccc(OC(F)(F)F)cc4)n3)cc2)SCCC1C]
P983
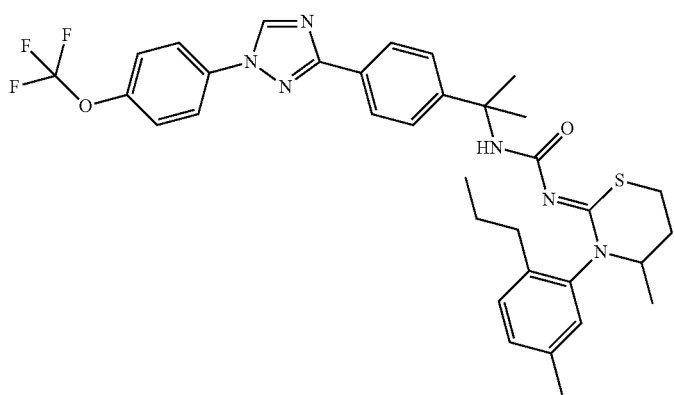 [SMILES: CCCc1ccc(C)cc1N1/C(=N/C(=O)NC(C)(C)c2ccc(-c3ncn(-c4ccc(OC(F)(F)F)cc4)n3)cc2)SCCC1C]
P984
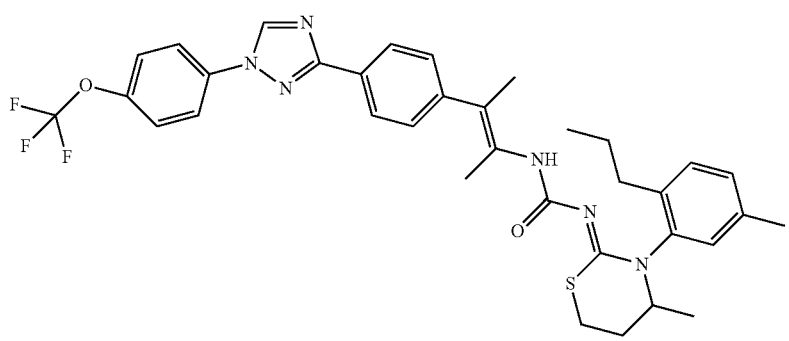 [SMILES: CCCc1ccc(C)cc1N1/C(=N/C(=O)N/C(C)=C(\C)c2ccc(-c3ncn(-c4ccc(OC(F)(F)F)cc4)n3)cc2)SCCC1C]
P985
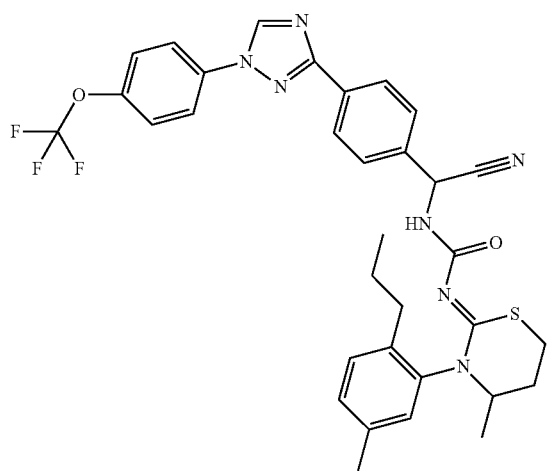 [SMILES: CCCc1ccc(C)cc1N1/C(=N/C(=O)NC(C#N)c2ccc(-c3ncn(-c4ccc(OC(F)(F)F)cc4)n3)cc2)SCCC1C]
P986

TABLE P-Two-continued
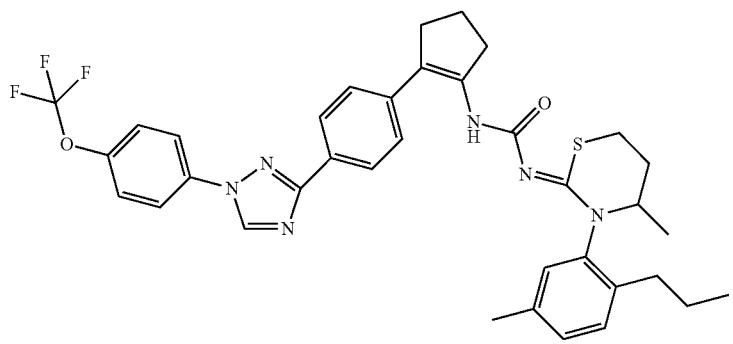 [SMILES: CCCc1ccc(C)cc1N1/C(=N/C(=O)NC2=C(c3ccc(-c4ncn(-c5ccc(OC(F)(F)F)cc5)n4)cc3)CCC2)SCCC1C]
P987
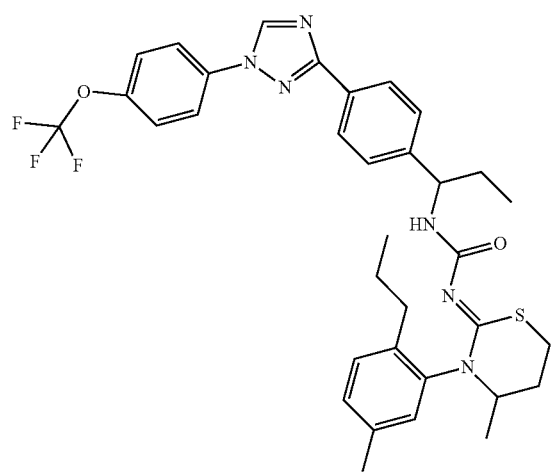 [SMILES: CCCc1ccc(C)cc1N1/C(=N/C(=O)NC(CC)c2ccc(-c3ncn(-c4ccc(OC(F)(F)F)cc4)n3)cc2)SCCC1C]
P988
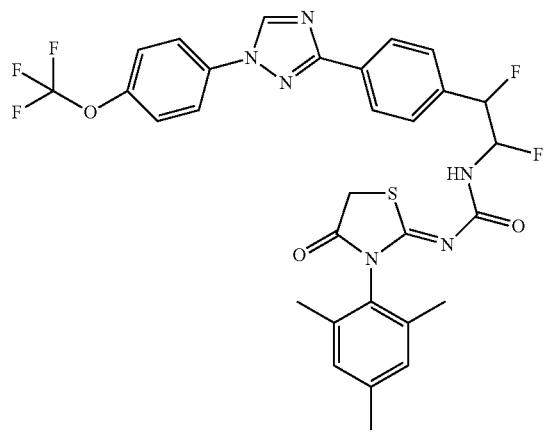 [SMILES: Cc1cc(C)c(N2C(=O)CS/C2=N\C(=O)NC(F)C(F)c2ccc(-c3ncn(-c4ccc(OC(F)(F)F)cc4)n3)cc2)c(C)c1]
P989
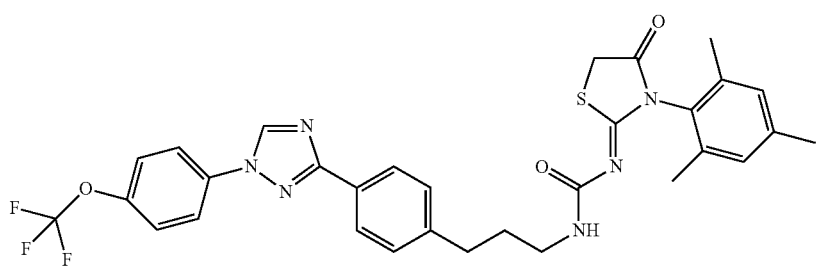 [SMILES: Cc1cc(C)c(N2C(=O)CS/C2=N\C(=O)NCCCc2ccc(-c3ncn(-c4ccc(OC(F)(F)F)cc4)n3)cc2)c(C)c1]
P990

TABLE P-Two-continued
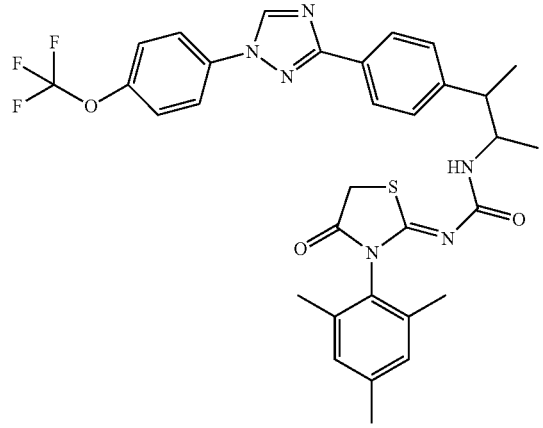 [SMILES: Cc1cc(C)c(N2C(=O)CS/C2=N\C(=O)NC(C)C(C)c2ccc(-c3ncn(-c4ccc(OC(F)(F)F)cc4)n3)cc2)c(C)c1]
P991
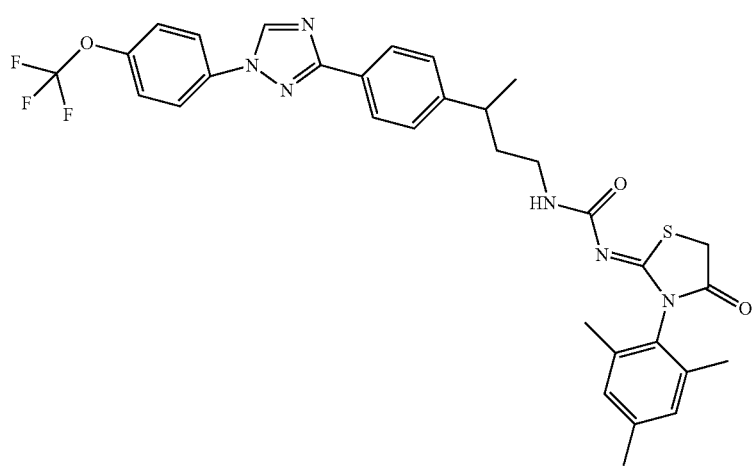 [SMILES: Cc1cc(C)c(N2C(=O)CS/C2=N\C(=O)NCCC(C)c2ccc(-c3ncn(-c4ccc(OC(F)(F)F)cc4)n3)cc2)c(C)c1]
P992
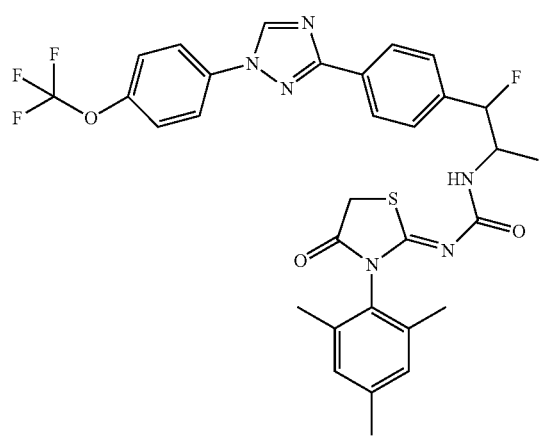 [SMILES: Cc1cc(C)c(N2C(=O)CS/C2=N\C(=O)NC(C)C(F)c2ccc(-c3ncn(-c4ccc(OC(F)(F)F)cc4)n3)cc2)c(C)c1]
P993
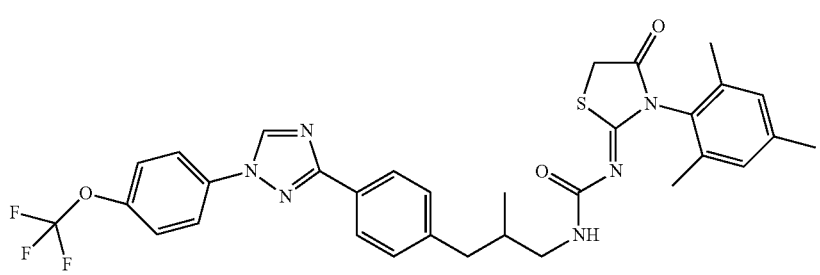 [SMILES: Cc1cc(C)c(N2C(=O)CS/C2=N\C(=O)NCC(C)Cc2ccc(-c3ncn(-c4ccc(OC(F)(F)F)cc4)n3)cc2)c(C)c1]
P994

| | |
|---|---|
| 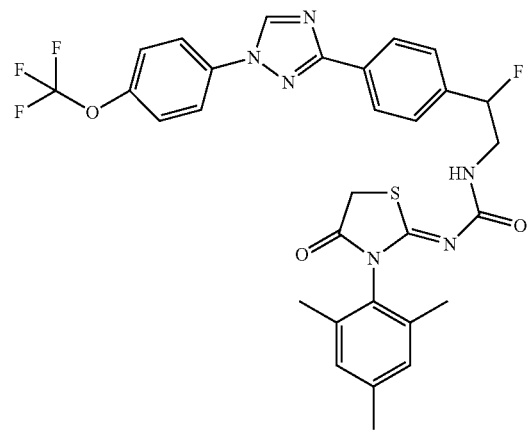 [SMILES: Cc1cc(C)c(N2C(=O)CS/C2=N\C(=O)NCC(F)c2ccc(-c3ncn(-c4ccc(OC(F)(F)F)cc4)n3)cc2)c(C)c1] | P995 |
| 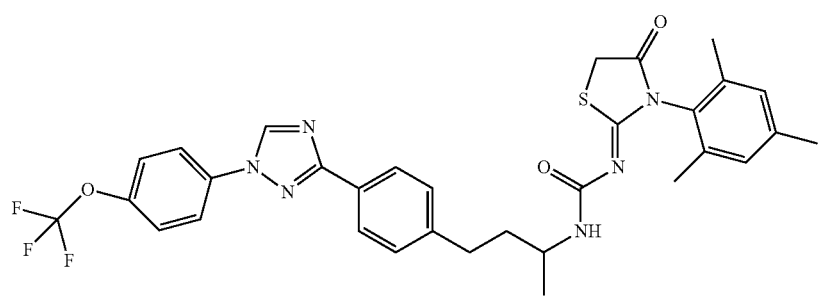 [SMILES: Cc1cc(C)c(N2C(=O)CS/C2=N\C(=O)NC(C)CCc2ccc(-c3ncn(-c4ccc(OC(F)(F)F)cc4)n3)cc2)c(C)c1] | P996 |
| 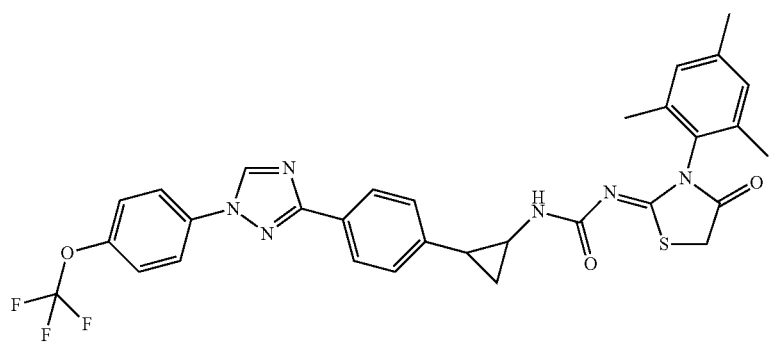 [SMILES: Cc1cc(C)c(N2C(=O)CS/C2=N\C(=O)NC2CC2c2ccc(-c3ncn(-c4ccc(OC(F)(F)F)cc4)n3)cc2)c(C)c1] | P997 |
| 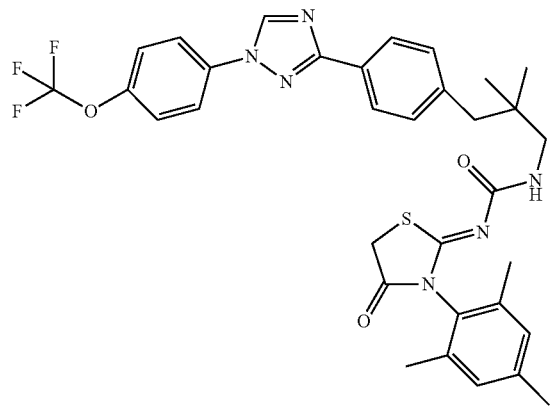 [SMILES: Cc1cc(C)c(N2C(=O)CS/C2=N\C(=O)NCC(C)(C)Cc2ccc(-c3ncn(-c4ccc(OC(F)(F)F)cc4)n3)cc2)c(C)c1] | P998 |

TABLE P-Two-continued
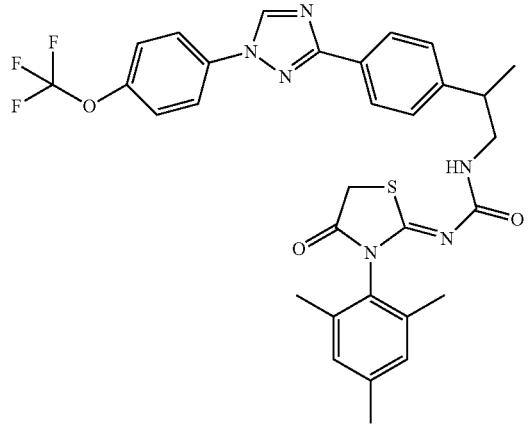 [SMILES: Cc1cc(C)c(N2C(=O)CS/C2=N\C(=O)NCC(C)c2ccc(-c3ncn(-c4ccc(OC(F)(F)F)cc4)n3)cc2)c(C)c1]
P999
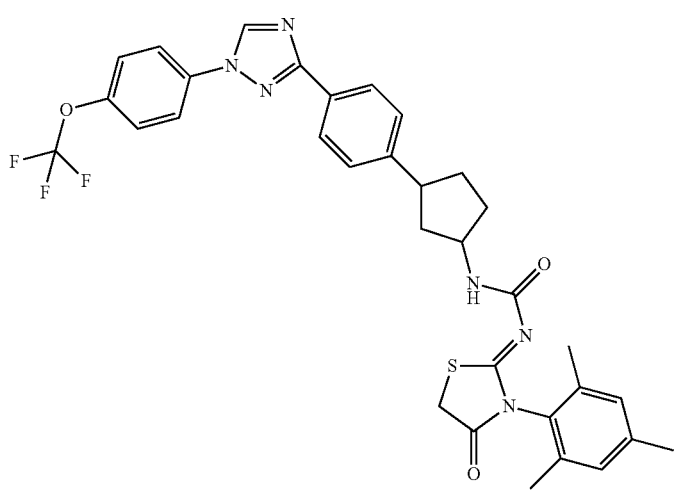 [SMILES: Cc1cc(C)c(N2C(=O)CS/C2=N\C(=O)NC2CCC(c3ccc(-c4ncn(-c5ccc(OC(F)(F)F)cc5)n4)cc3)C2)c(C)c1]
P1000
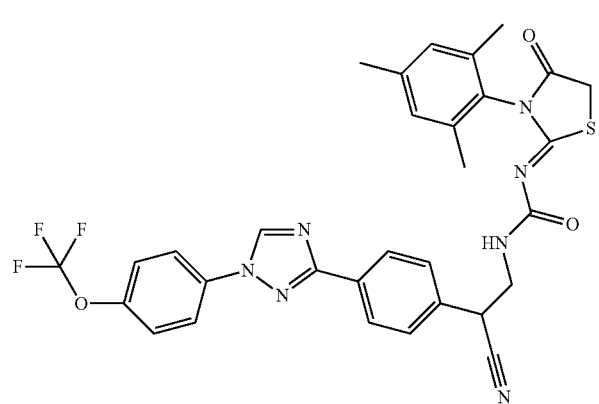 [SMILES: Cc1cc(C)c(N2C(=O)CS/C2=N\C(=O)NCC(C#N)c2ccc(-c3ncn(-c4ccc(OC(F)(F)F)cc4)n3)cc2)c(C)c1]
P1001

TABLE P-Two-continued
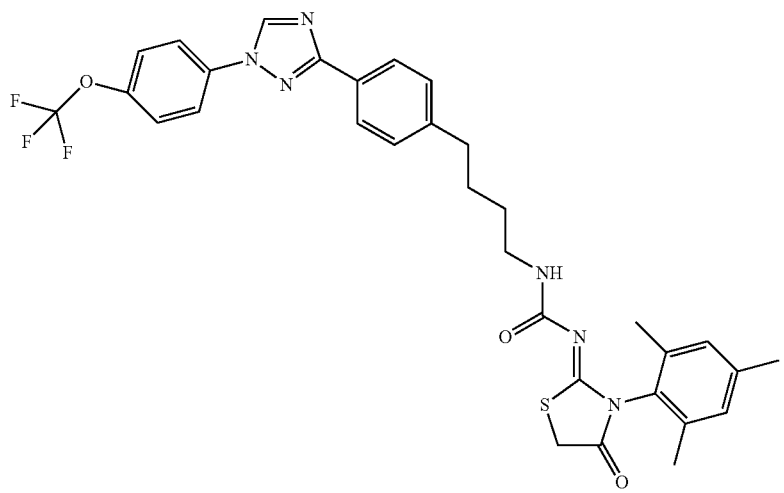 [SMILES: Cc1cc(C)c(N2C(=O)CS/C2=N\C(=O)NCCCCc2ccc(-c3ncn(-c4ccc(OC(F)(F)F)cc4)n3)cc2)c(C)c1]
P1002
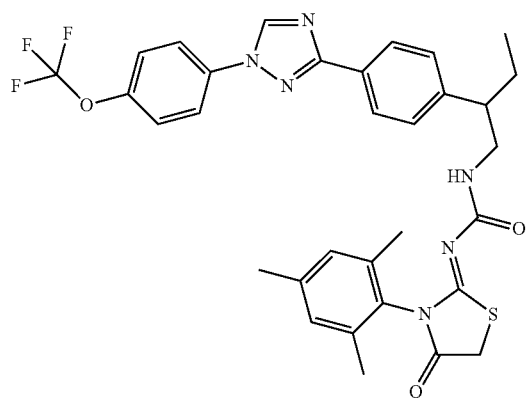 [SMILES: CCC(CNC(=O)/N=C1\SCC(=O)N1c1c(C)cc(C)cc1C)c1ccc(-c2ncn(-c3ccc(OC(F)(F)F)cc3)n2)cc1]
P1003
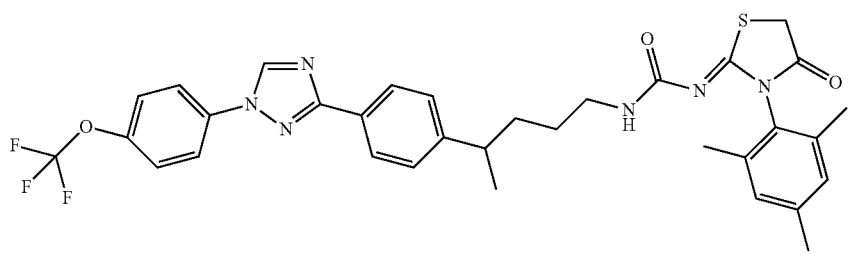 [SMILES: Cc1cc(C)c(N2C(=O)CS/C2=N\C(=O)NCCCC(C)c2ccc(-c3ncn(-c4ccc(OC(F)(F)F)cc4)n3)cc2)c(C)c1]
P1004
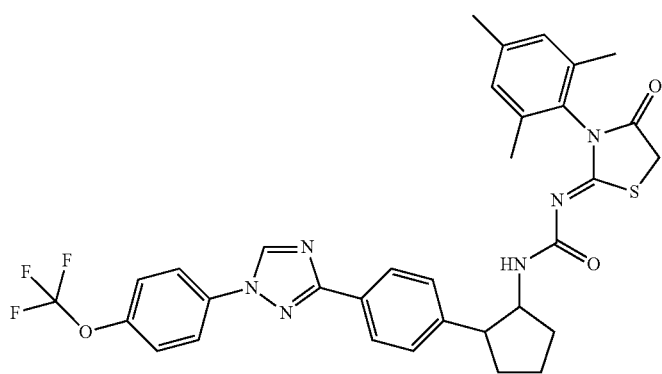 [SMILES: Cc1cc(C)c(N2C(=O)CS/C2=N\C(=O)NC2CCCC2c2ccc(-c3ncn(-c4ccc(OC(F)(F)F)cc4)n3)cc2)c(C)c1]
P1005

TABLE P-Two-continued
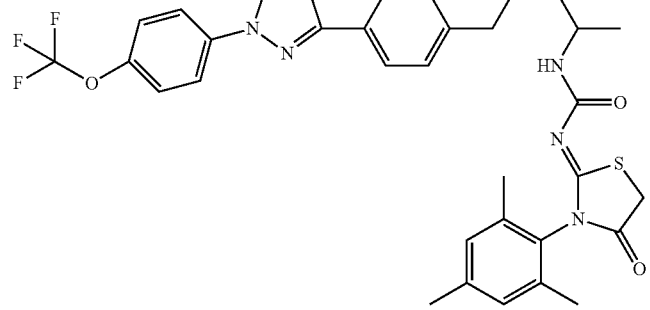
P1006
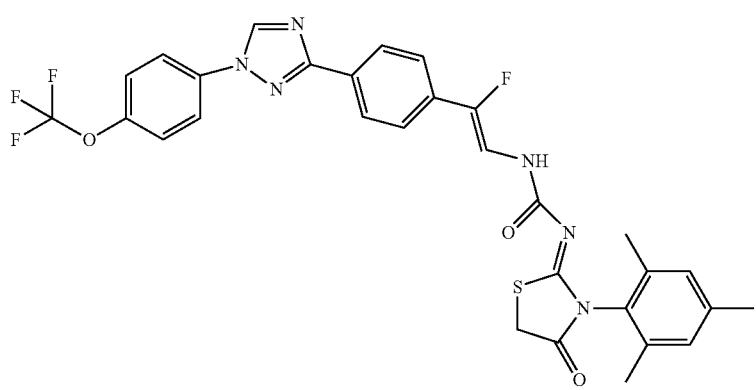 [SMILES: Cc1cc(C)c(N2C(=O)CS/C2=N\C(=O)N/C=C(\F)c2ccc(-c3ncn(-c4ccc(OC(F)(F)F)cc4)n3)cc2)c(C)c1]
P1007
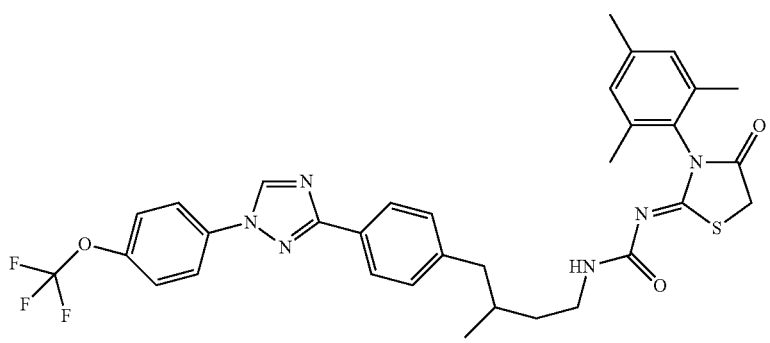 [SMILES: Cc1cc(C)c(N2C(=O)CS/C2=N\C(=O)NCCC(C)Cc2ccc(-c3ncn(-c4ccc(OC(F)(F)F)cc4)n3)cc2)c(C)c1]
P1008
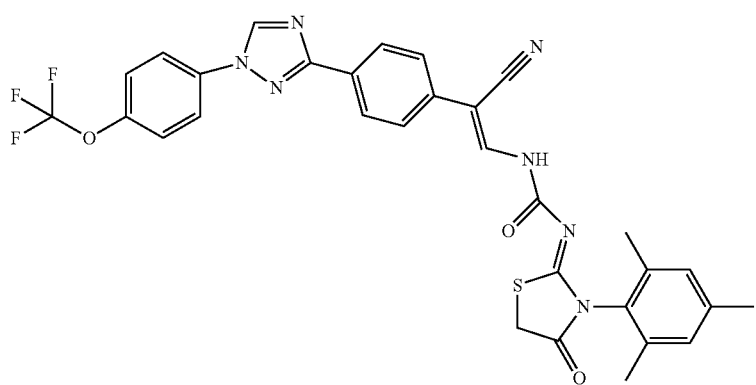 [SMILES: Cc1cc(C)c(N2C(=O)CS/C2=N\C(=O)N/C=C(\C#N)c2ccc(-c3ncn(-c4ccc(OC(F)(F)F)cc4)n3)cc2)c(C)c1]
P1009

TABLE P-Two-continued
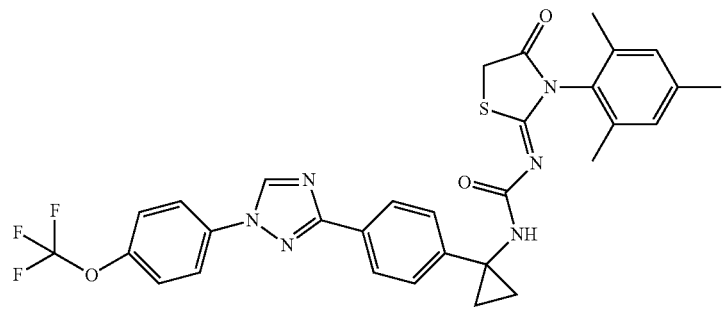 [SMILES: Cc1cc(C)c(N2C(=O)CS/C2=N\C(=O)NC2(c3ccc(-c4ncn(-c5ccc(OC(F)(F)F)cc5)n4)cc3)CC2)c(C)c1]
P1010
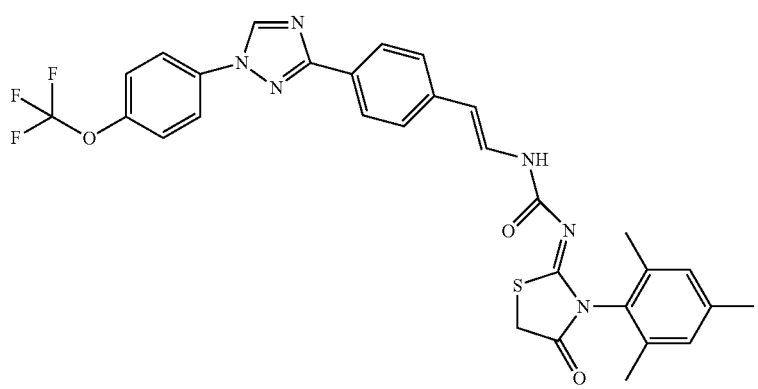 [SMILES: Cc1cc(C)c(N2C(=O)CS/C2=N\C(=O)N/C=C/c2ccc(-c3ncn(-c4ccc(OC(F)(F)F)cc4)n3)cc2)c(C)c1]
P1011
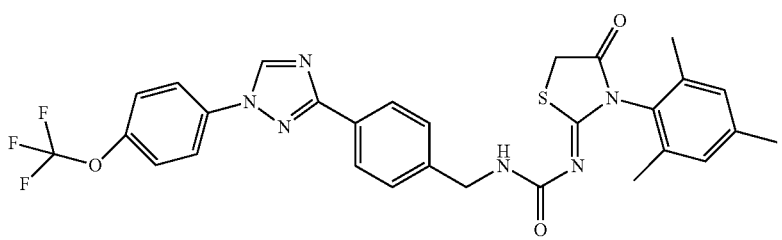 [SMILES: Cc1cc(C)c(N2C(=O)CS/C2=N\C(=O)NCc2ccc(-c3ncn(-c4ccc(OC(F)(F)F)cc4)n3)cc2)c(C)c1]
P1012
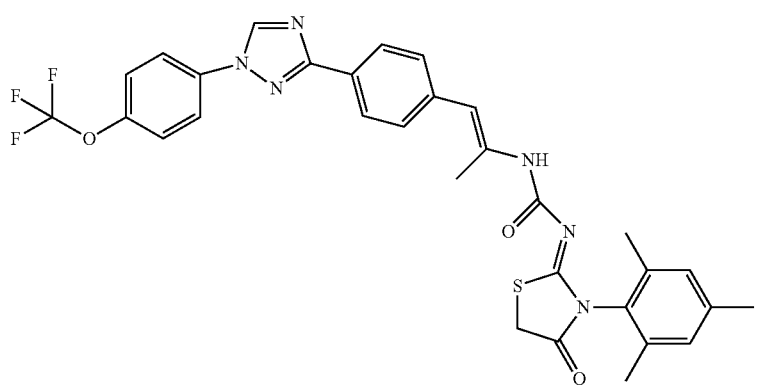 [SMILES: C/C(=C\c1ccc(-c2ncn(-c3ccc(OC(F)(F)F)cc3)n2)cc1)NC(=O)/N=C1\SCC(=O)N1c1c(C)cc(C)cc1C]
P1013
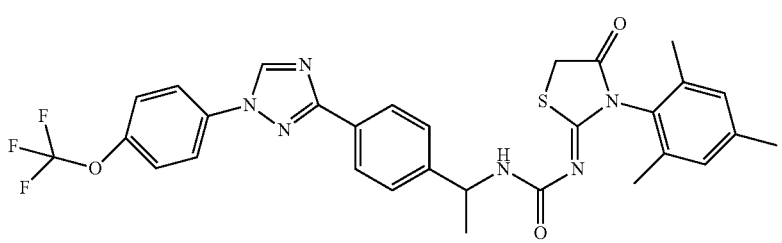 [SMILES: Cc1cc(C)c(N2C(=O)CS/C2=N\C(=O)NC(C)c2ccc(-c3ncn(-c4ccc(OC(F)(F)F)cc4)n3)cc2)c(C)c1]
P1014

TABLE P-Two-continued
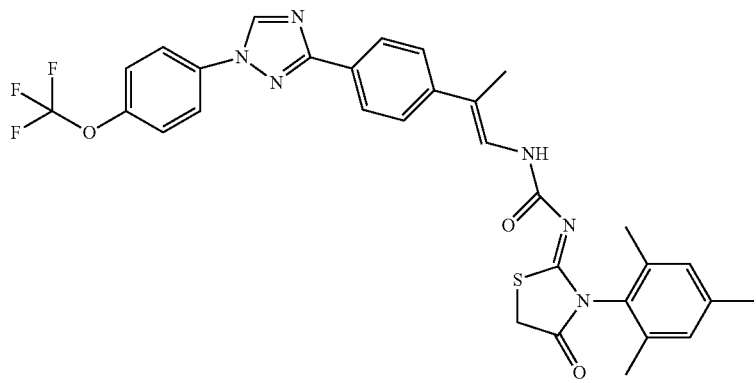 [SMILES: C/C(=C\NC(=O)/N=C1\SCC(=O)N1c1c(C)cc(C)cc1C)c1ccc(-c2ncn(-c3ccc(OC(F)(F)F)cc3)n2)cc1]
P1015
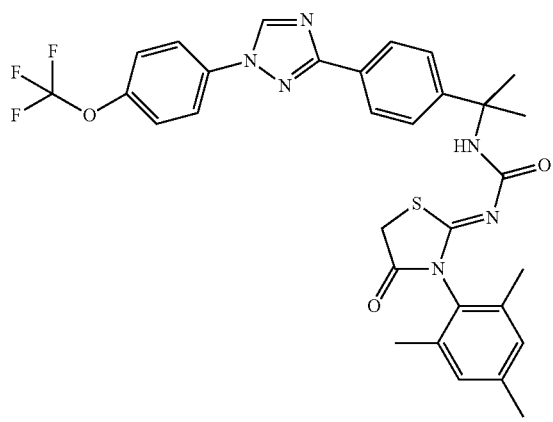 [SMILES: Cc1cc(C)c(N2C(=O)CS/C2=N\C(=O)NC(C)(C)c2ccc(-c3ncn(-c4ccc(OC(F)(F)F)cc4)n3)cc2)c(C)c1]
P1016
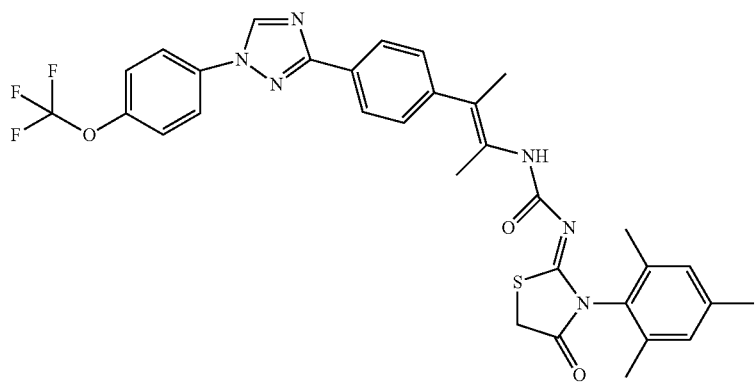 [SMILES: C/C(NC(=O)/N=C1\SCC(=O)N1c1c(C)cc(C)cc1C)=C(/C)c1ccc(-c2ncn(-c3ccc(OC(F)(F)F)cc3)n2)cc1]
P1017
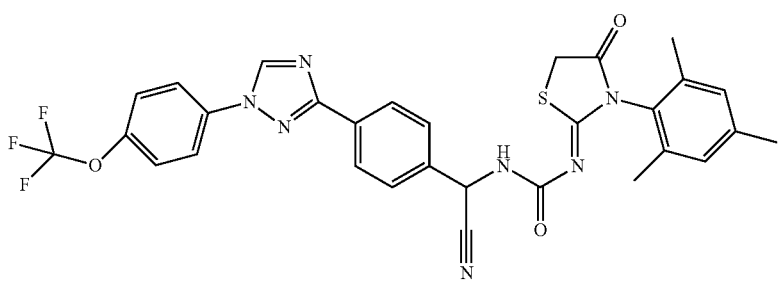 [SMILES: Cc1cc(C)c(N2C(=O)CS/C2=N\C(=O)NC(C#N)c2ccc(-c3ncn(-c4ccc(OC(F)(F)F)cc4)n3)cc2)c(C)c1]
P1018

TABLE P-Two-continued
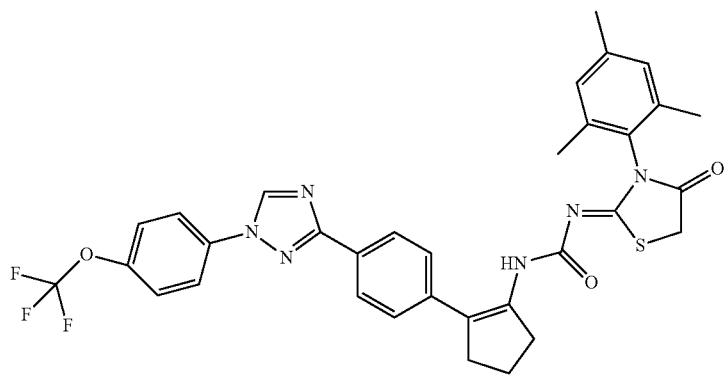 [SMILES: Cc1cc(C)c(N2C(=O)CS/C2=N\C(=O)NC2=C(c3ccc(-c4ncn(-c5ccc(OC(F)(F)F)cc5)n4)cc3)CCC2)c(C)c1]
P1019
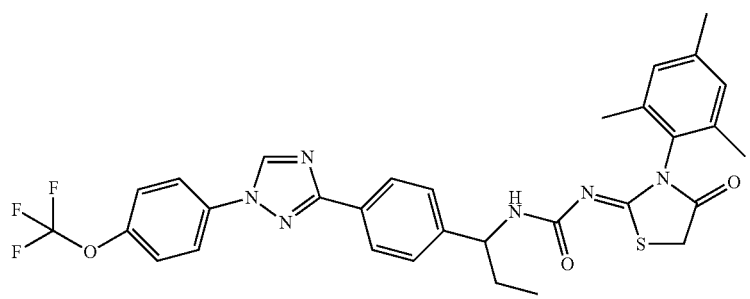 [SMILES: CCC(NC(=O)/N=C1\SCC(=O)N1c1c(C)cc(C)cc1C)c1ccc(-c2ncn(-c3ccc(OC(F)(F)F)cc3)n2)cc1]
P1020
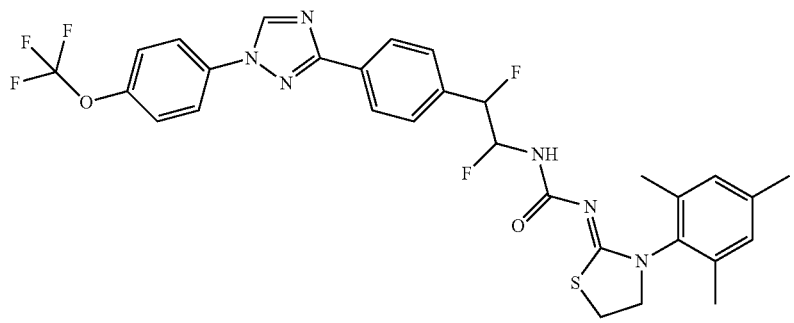 [SMILES: Cc1cc(C)c(N2CCS/C2=N\C(=O)NC(F)C(F)c2ccc(-c3ncn(-c4ccc(OC(F)(F)F)cc4)n3)cc2)c(C)c1]
P1021
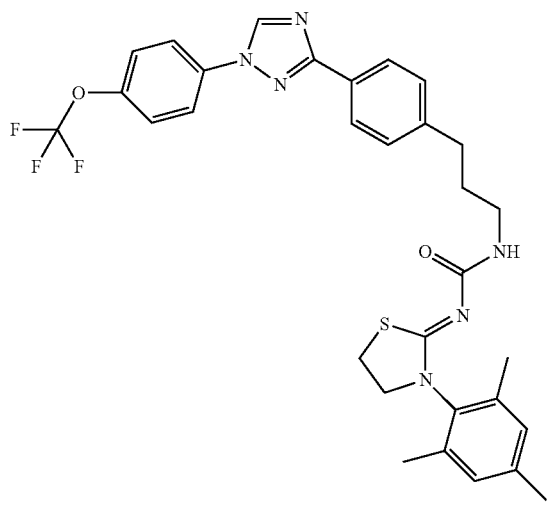 [SMILES: Cc1cc(C)c(N2CCS/C2=N\C(=O)NCCCc2ccc(-c3ncn(-c4ccc(OC(F)(F)F)cc4)n3)cc2)c(C)c1]
P1022

TABLE P-Two-continued
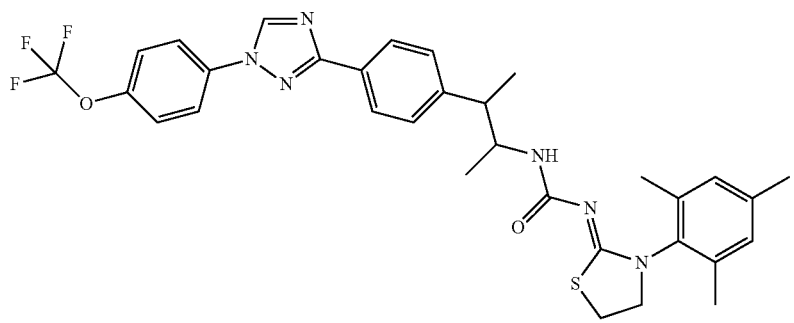 [SMILES: Cc1cc(C)c(N2CCS/C2=N\C(=O)NC(C)C(C)c2ccc(-c3ncn(-c4ccc(OC(F)(F)F)cc4)n3)cc2)c(C)c1]
P1023
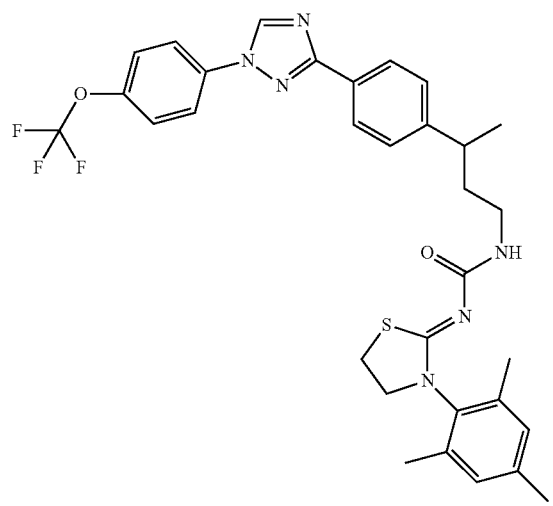 [SMILES: Cc1cc(C)c(N2CCS/C2=N\C(=O)NCCC(C)c2ccc(-c3ncn(-c4ccc(OC(F)(F)F)cc4)n3)cc2)c(C)c1]
P1024
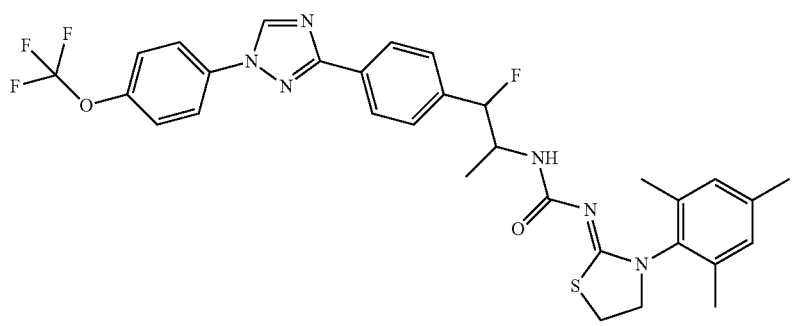 [SMILES: Cc1cc(C)c(N2CCS/C2=N\C(=O)NC(C)C(F)c2ccc(-c3ncn(-c4ccc(OC(F)(F)F)cc4)n3)cc2)c(C)c1]
P1025
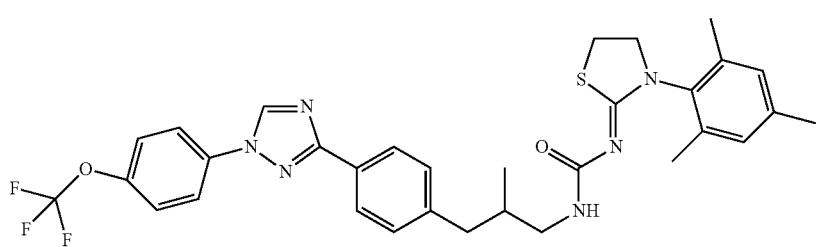 [SMILES: Cc1cc(C)c(N2CCS/C2=N\C(=O)NCC(C)Cc2ccc(-c3ncn(-c4ccc(OC(F)(F)F)cc4)n3)cc2)c(C)c1]
P1026

TABLE P-Two-continued
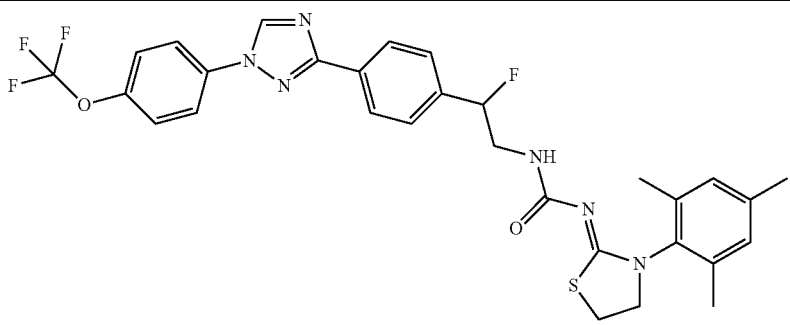
P1027
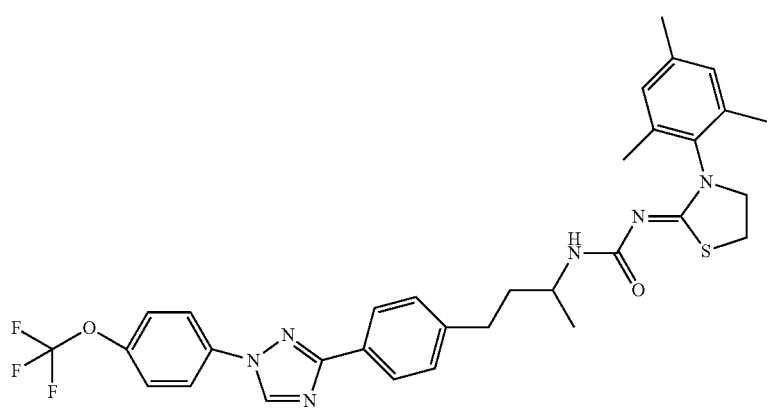 [SMILES: Cc1cc(C)c(N2CCS/C2=N\C(=O)NC(C)CCc2ccc(-c3ncn(-c4ccc(OC(F)(F)F)cc4)n3)cc2)c(C)c1]
P1028
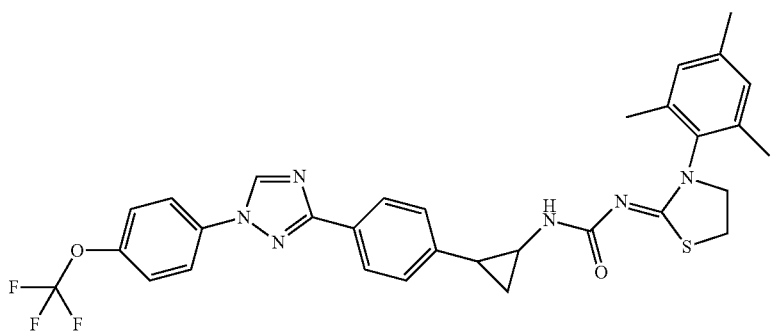 [SMILES: Cc1cc(C)c(N2CCS/C2=N\C(=O)NC2CC2c2ccc(-c3ncn(-c4ccc(OC(F)(F)F)cc4)n3)cc2)c(C)c1]
P1029
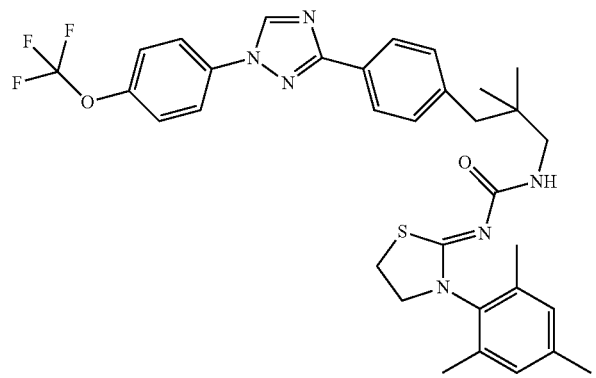 [SMILES: Cc1cc(C)c(N2CCS/C2=N\C(=O)NCC(C)(C)Cc2ccc(-c3ncn(-c4ccc(OC(F)(F)F)cc4)n3)cc2)c(C)c1]
P1030

TABLE P-Two-continued
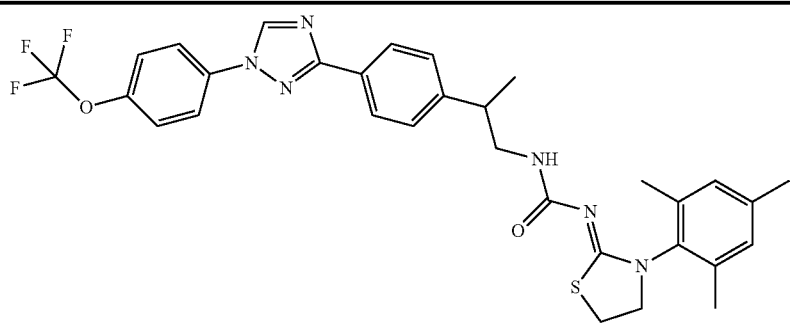
P1031
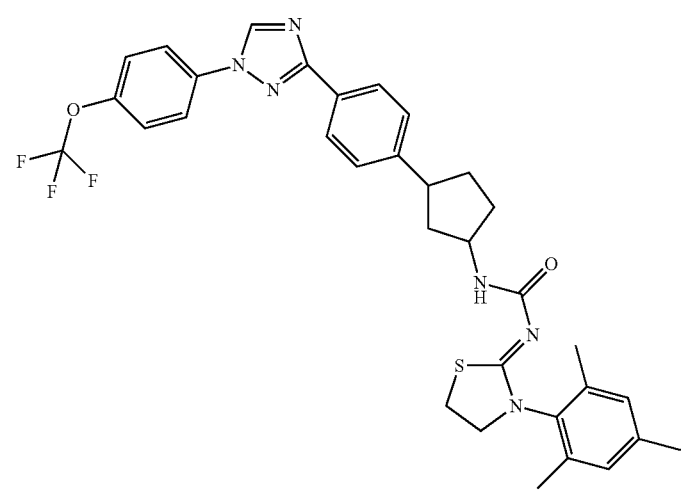 [SMILES: Cc1cc(C)c(N2CCS/C2=N\C(=O)NC2CCC(c3ccc(-c4ncn(-c5ccc(OC(F)(F)F)cc5)n4)cc3)C2)c(C)c1]
P1032
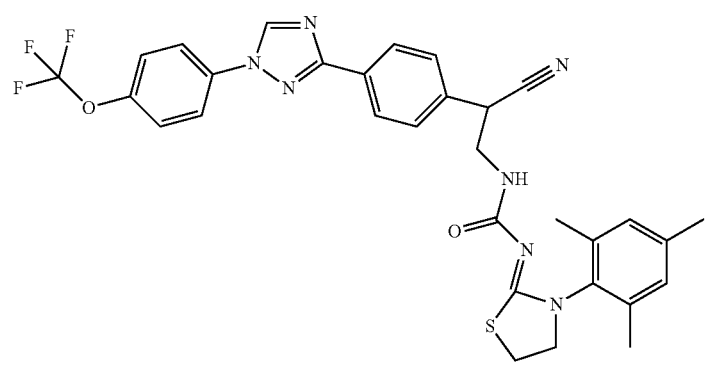 [SMILES: Cc1cc(C)c(N2CCS/C2=N\C(=O)NCC(C#N)c2ccc(-c3ncn(-c4ccc(OC(F)(F)F)cc4)n3)cc2)c(C)c1]
P1033
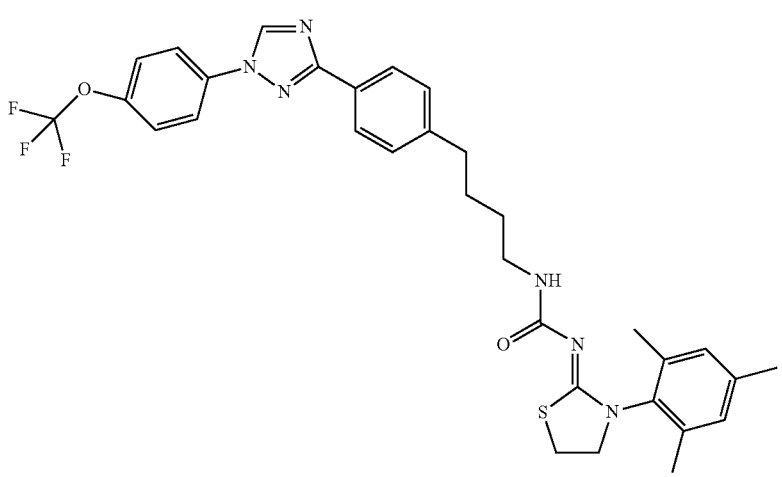 [SMILES: Cc1cc(C)c(N2CCS/C2=N\C(=O)NCCCCc2ccc(-c3ncn(-c4ccc(OC(F)(F)F)cc4)n3)cc2)c(C)c1]
P1034

TABLE P-Two-continued
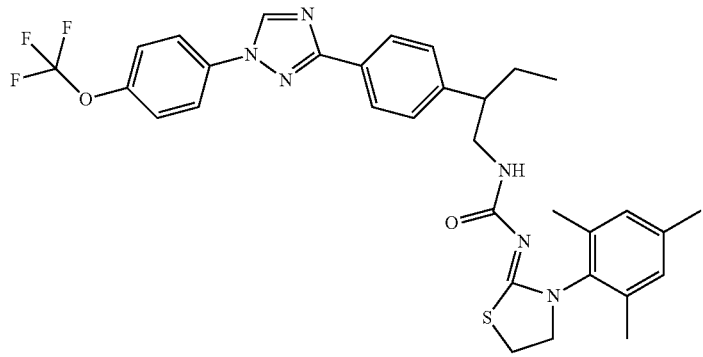 [SMILES: CCC(CNC(=O)/N=C1\SCCN1c1c(C)cc(C)cc1C)c1ccc(-c2ncn(-c3ccc(OC(F)(F)F)cc3)n2)cc1]
P1035
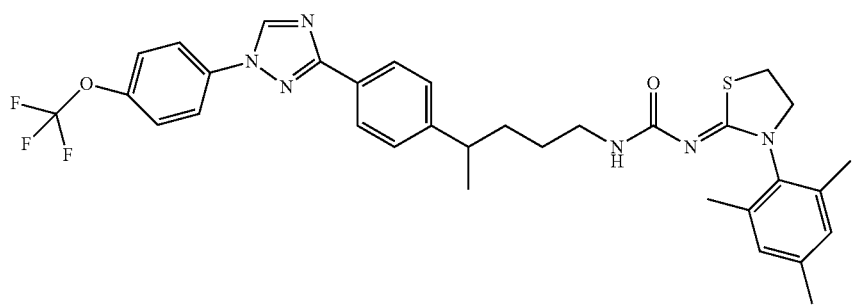 [SMILES: Cc1cc(C)c(N2CCS/C2=N\C(=O)NCCCC(C)c2ccc(-c3ncn(-c4ccc(OC(F)(F)F)cc4)n3)cc2)c(C)c1]
P1036
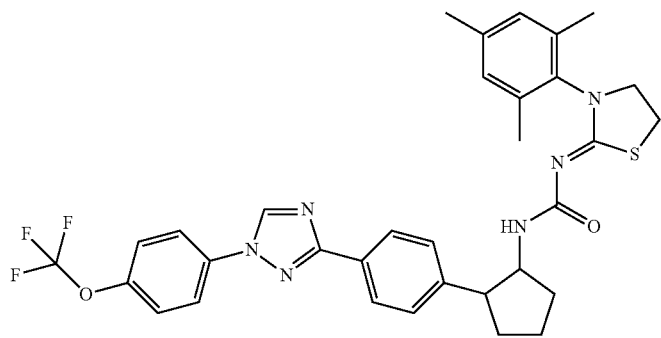 [SMILES: Cc1cc(C)c(N2CCS/C2=N\C(=O)NC2CCCC2c2ccc(-c3ncn(-c4ccc(OC(F)(F)F)cc4)n3)cc2)c(C)c1]
P1037
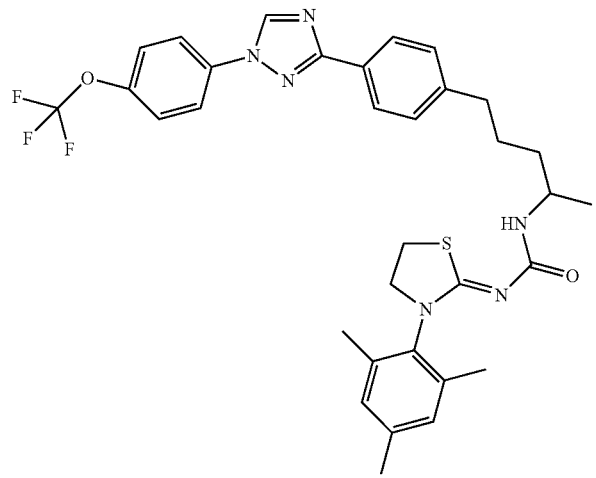 [SMILES: Cc1cc(C)c(N2CCS/C2=N\C(=O)NC(C)CCCc2ccc(-c3ncn(-c4ccc(OC(F)(F)F)cc4)n3)cc2)c(C)c1]
P1038

TABLE P-Two-continued
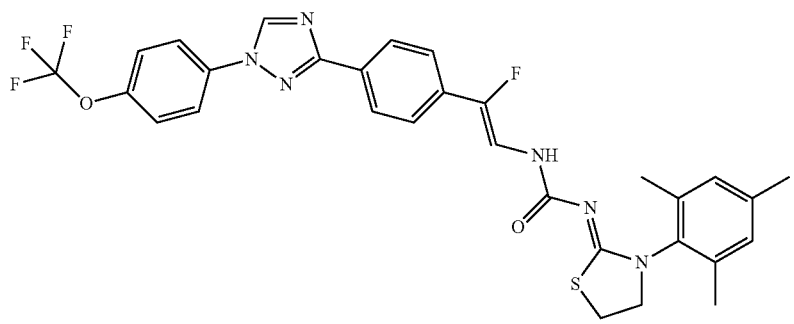 [SMILES: Cc1cc(C)c(N2CCS/C2=N\C(=O)N/C=C(\F)c2ccc(-c3ncn(-c4ccc(OC(F)(F)F)cc4)n3)cc2)c(C)c1]
P1039
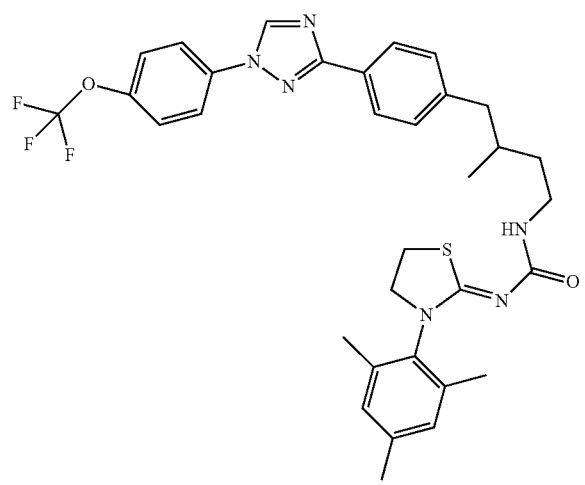 [SMILES: Cc1cc(C)c(N2CCS/C2=N\C(=O)NCCC(C)Cc2ccc(-c3ncn(-c4ccc(OC(F)(F)F)cc4)n3)cc2)c(C)c1]
P1040
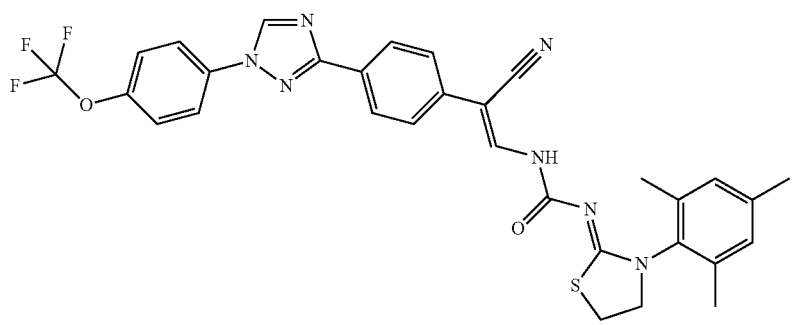 [SMILES: Cc1cc(C)c(N2CCS/C2=N\C(=O)N/C=C(\C#N)c2ccc(-c3ncn(-c4ccc(OC(F)(F)F)cc4)n3)cc2)c(C)c1]
P1041
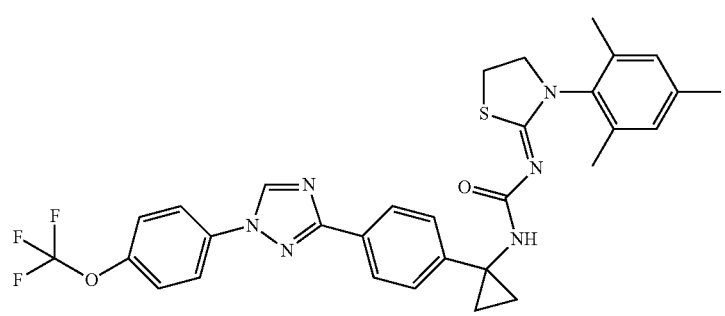 [SMILES: Cc1cc(C)c(N2CCS/C2=N\C(=O)NC2(c3ccc(-c4ncn(-c5ccc(OC(F)(F)F)cc5)n4)cc3)CC2)c(C)c1]
P1042

TABLE P-Two-continued
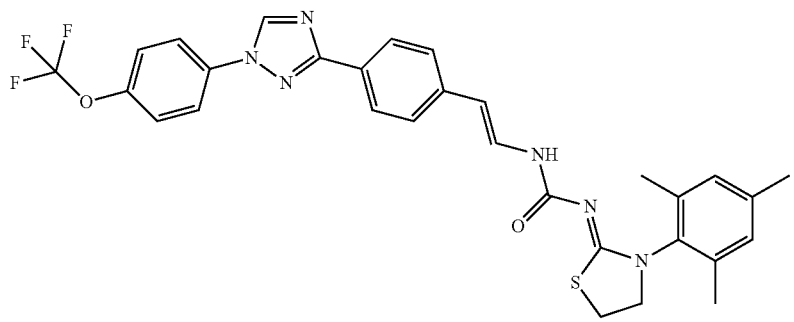 [SMILES: Cc1cc(C)c(N2CCS/C2=N\C(=O)N/C=C/c2ccc(-c3ncn(-c4ccc(OC(F)(F)F)cc4)n3)cc2)c(C)c1]
P1043
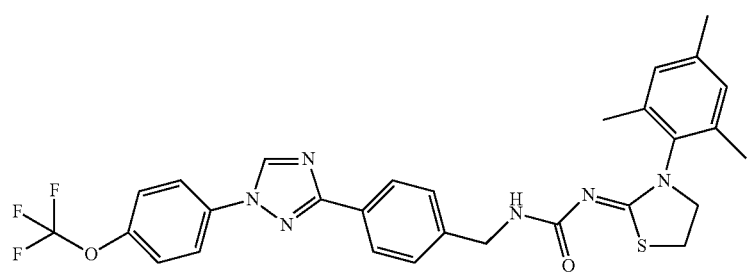 [SMILES: Cc1cc(C)c(N2CCS/C2=N\C(=O)NCc2ccc(-c3ncn(-c4ccc(OC(F)(F)F)cc4)n3)cc2)c(C)c1]
P1044
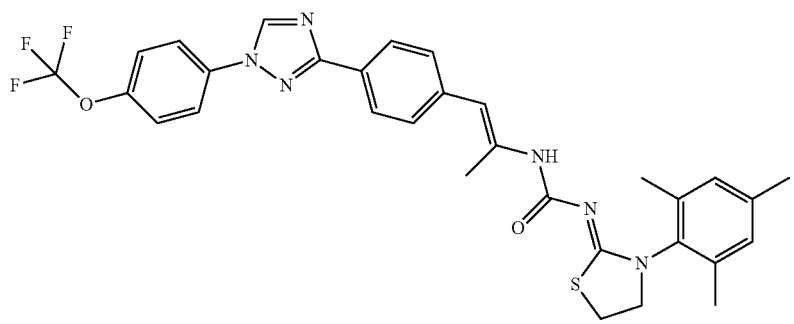 [SMILES: C/C(=C\c1ccc(-c2ncn(-c3ccc(OC(F)(F)F)cc3)n2)cc1)NC(=O)/N=C1\SCCN1c1c(C)cc(C)cc1C]
P1045
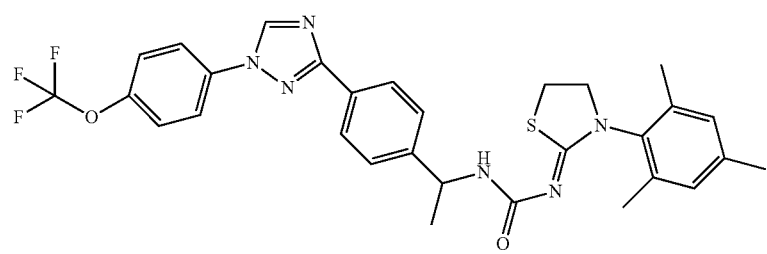 [SMILES: Cc1cc(C)c(N2CCS/C2=N\C(=O)NC(C)c2ccc(-c3ncn(-c4ccc(OC(F)(F)F)cc4)n3)cc2)c(C)c1]
P1046
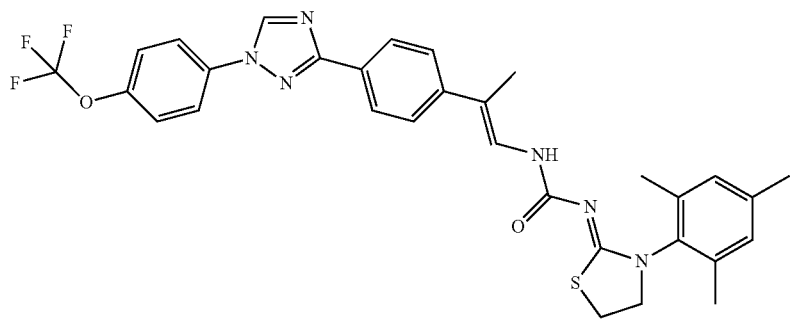 [SMILES: C/C(=C\NC(=O)/N=C1\SCCN1c1c(C)cc(C)cc1C)c1ccc(-c2ncn(-c3ccc(OC(F)(F)F)cc3)n2)cc1]
P1047

TABLE P-Two-continued
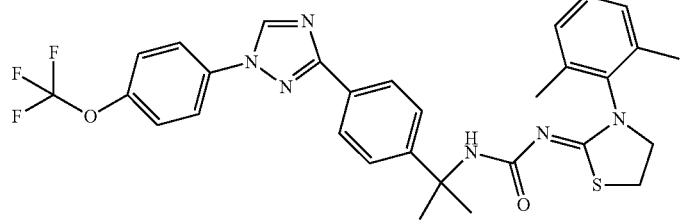
P1048
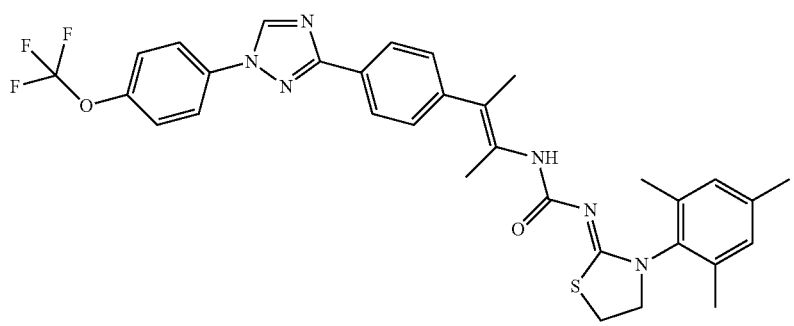 [SMILES: C/C(NC(=O)/N=C1\SCCN1c1c(C)cc(C)cc1C)=C(/C)c1ccc(-c2ncn(-c3ccc(OC(F)(F)F)cc3)n2)cc1]
P1049
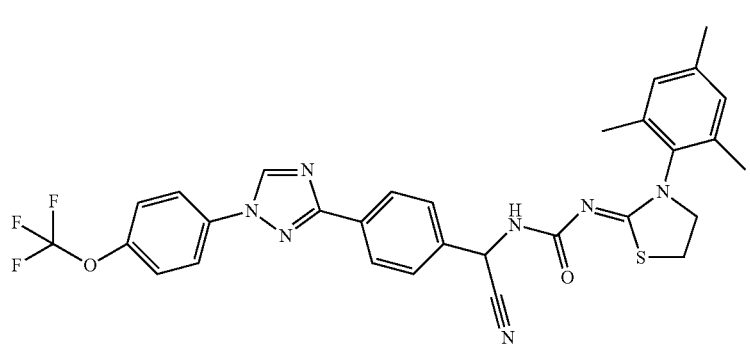 [SMILES: Cc1cc(C)c(N2CCS/C2=N\C(=O)NC(C#N)c2ccc(-c3ncn(-c4ccc(OC(F)(F)F)cc4)n3)cc2)c(C)c1]
P1050
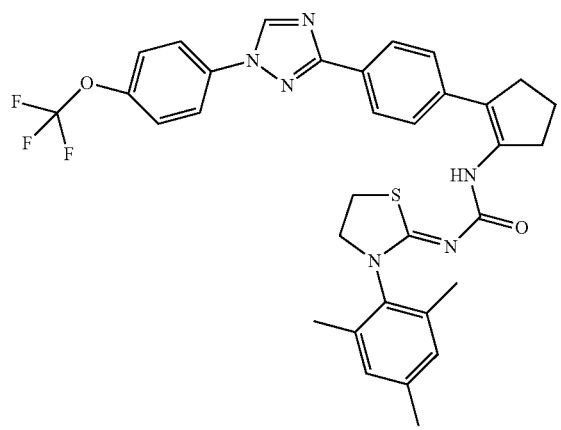 [SMILES: Cc1cc(C)c(N2CCS/C2=N\C(=O)NC2=C(c3ccc(-c4ncn(-c5ccc(OC(F)(F)F)cc5)n4)cc3)CCC2)c(C)c1]
P1051
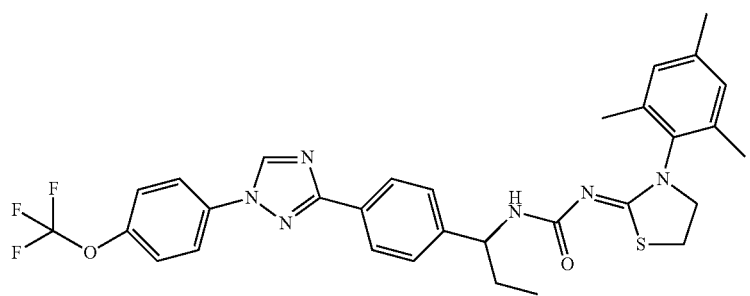 [SMILES: CCC(NC(=O)/N=C1\SCCN1c1c(C)cc(C)cc1C)c1ccc(-c2ncn(-c3ccc(OC(F)(F)F)cc3)n2)cc1]
P1052

TABLE P-Two-continued
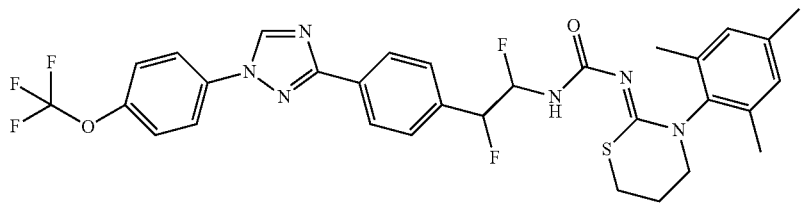 [SMILES: Cc1cc(C)c(N2CCCS/C2=N\C(=O)NC(F)C(F)c2ccc(-c3ncn(-c4ccc(OC(F)(F)F)cc4)n3)cc2)c(C)c1]
P1053
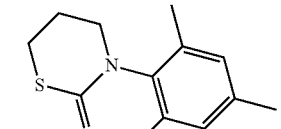
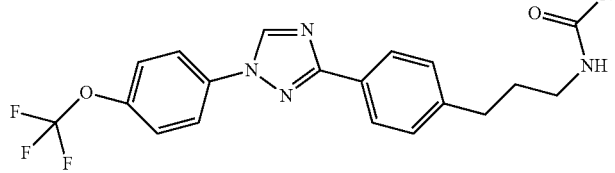
P1054
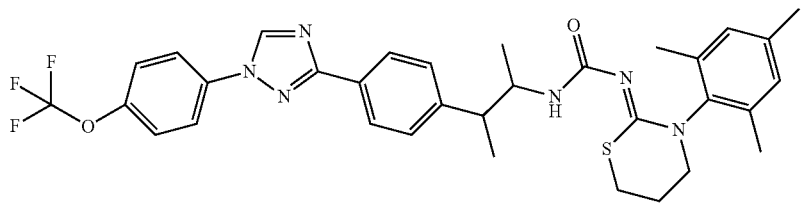 [SMILES: Cc1cc(C)c(N2CCCS/C2=N\C(=O)NC(C)C(C)c2ccc(-c3ncn(-c4ccc(OC(F)(F)F)cc4)n3)cc2)c(C)c1]
P1055
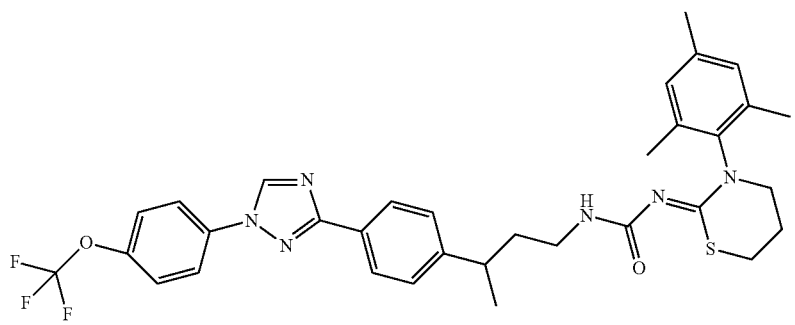 [SMILES: Cc1cc(C)c(N2CCCS/C2=N\C(=O)NCCC(C)c2ccc(-c3ncn(-c4ccc(OC(F)(F)F)cc4)n3)cc2)c(C)c1]
P1056
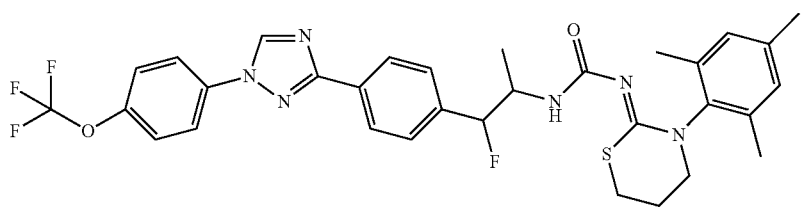 [SMILES: Cc1cc(C)c(N2CCCS/C2=N\C(=O)NC(C)C(F)c2ccc(-c3ncn(-c4ccc(OC(F)(F)F)cc4)n3)cc2)c(C)c1]
P1057
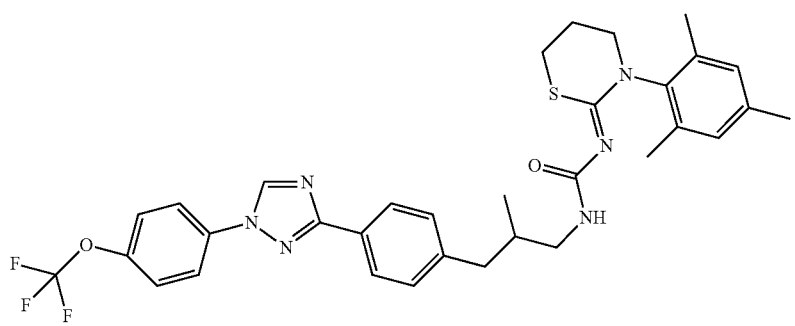 [SMILES: Cc1cc(C)c(N2CCCS/C2=N\C(=O)NCC(C)Cc2ccc(-c3ncn(-c4ccc(OC(F)(F)F)cc4)n3)cc2)c(C)c1]
P1058

TABLE P-Two-continued
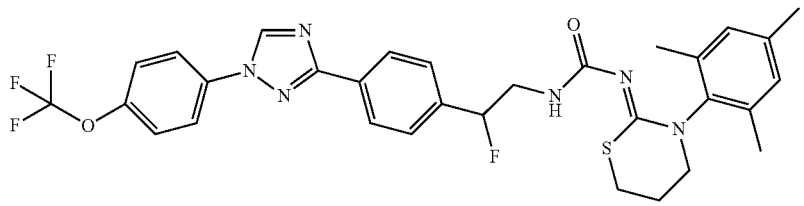 [SMILES: Cc1cc(C)c(N2CCCS/C2=N\C(=O)NCC(F)c2ccc(-c3ncn(-c4ccc(OC(F)(F)F)cc4)n3)cc2)c(C)c1] P1059
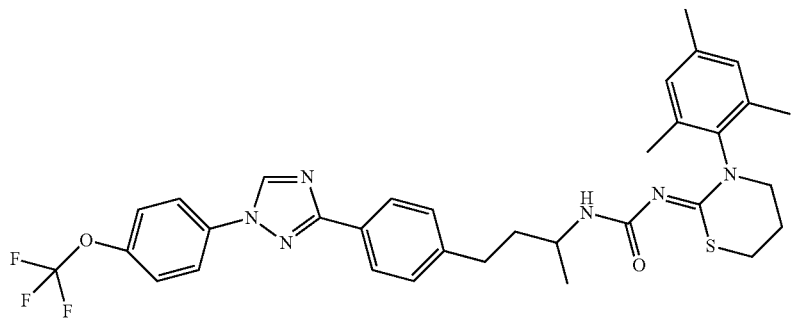 [SMILES: Cc1cc(C)c(N2CCCS/C2=N\C(=O)NC(C)CCc2ccc(-c3ncn(-c4ccc(OC(F)(F)F)cc4)n3)cc2)c(C)c1] P1060
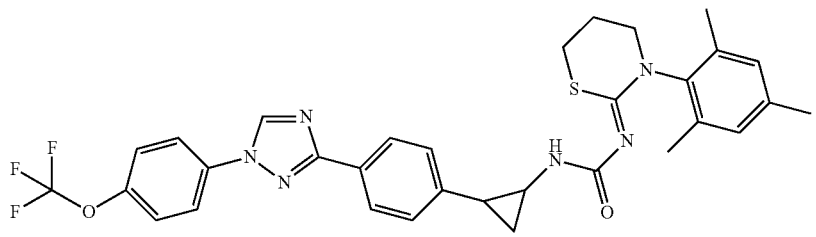 [SMILES: Cc1cc(C)c(N2CCCS/C2=N\C(=O)NC2CC2c2ccc(-c3ncn(-c4ccc(OC(F)(F)F)cc4)n3)cc2)c(C)c1] P1061
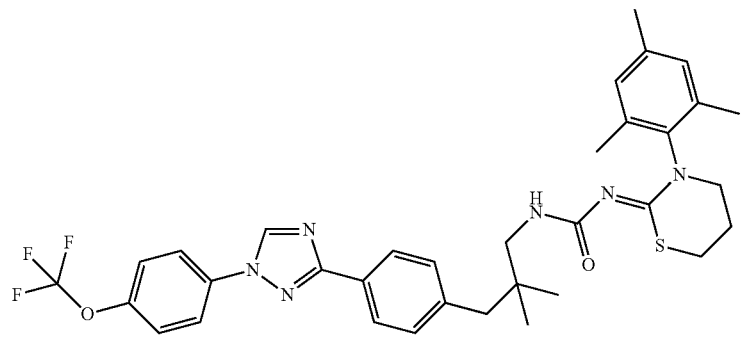 [SMILES: Cc1cc(C)c(N2CCCS/C2=N\C(=O)NCC(C)(C)Cc2ccc(-c3ncn(-c4ccc(OC(F)(F)F)cc4)n3)cc2)c(C)c1] P1062
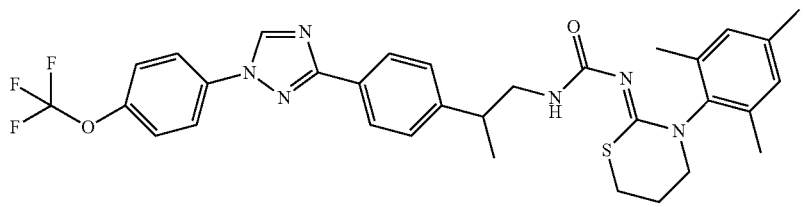 [SMILES: Cc1cc(C)c(N2CCCS/C2=N\C(=O)NCC(C)c2ccc(-c3ncn(-c4ccc(OC(F)(F)F)cc4)n3)cc2)c(C)c1] P1063
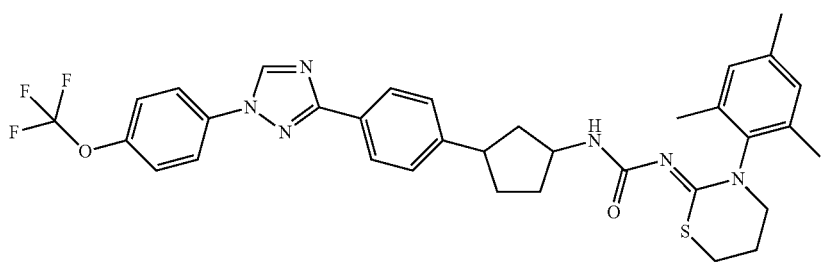 [SMILES: Cc1cc(C)c(N2CCCS/C2=N\C(=O)NC2CCC(c3ccc(-c4ncn(-c5ccc(OC(F)(F)F)cc5)n4)cc3)C2)c(C)c1] P1064

TABLE P-Two-continued
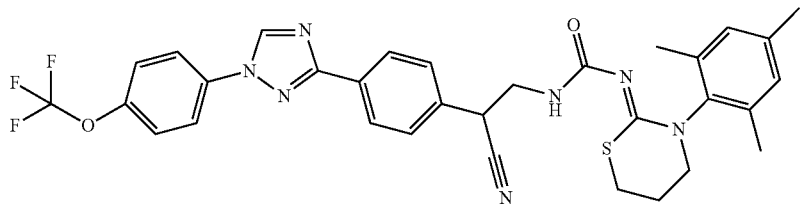 [SMILES: Cc1cc(C)c(N2CCCS/C2=N\C(=O)NCC(C#N)c2ccc(-c3ncn(-c4ccc(OC(F)(F)F)cc4)n3)cc2)c(C)c1]
P1065
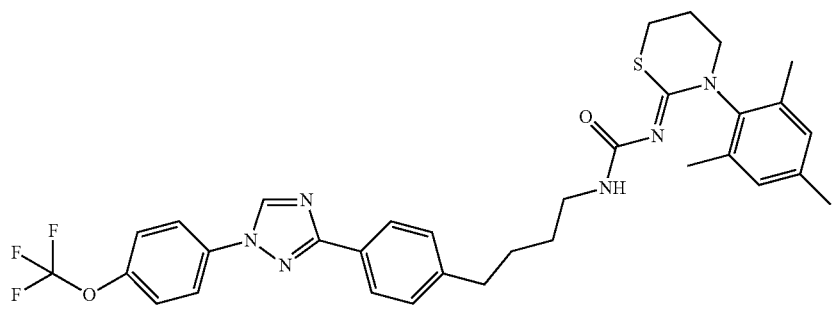 [SMILES: Cc1cc(C)c(N2CCCS/C2=N\C(=O)NCCCCc2ccc(-c3ncn(-c4ccc(OC(F)(F)F)cc4)n3)cc2)c(C)c1]
P1066
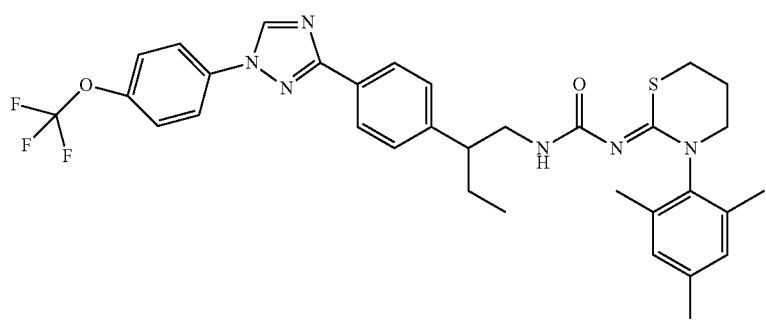 [SMILES: CCC(CNC(=O)/N=C1\SCCCN1c1c(C)cc(C)cc1C)c1ccc(-c2ncn(-c3ccc(OC(F)(F)F)cc3)n2)cc1]
P1067
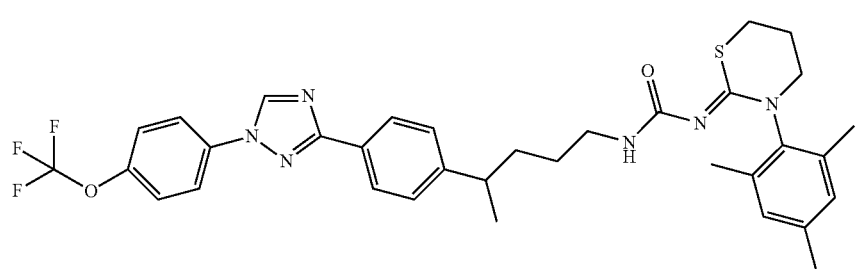 [SMILES: Cc1cc(C)c(N2CCCS/C2=N\C(=O)NCCCC(C)c2ccc(-c3ncn(-c4ccc(OC(F)(F)F)cc4)n3)cc2)c(C)c1]
P1068
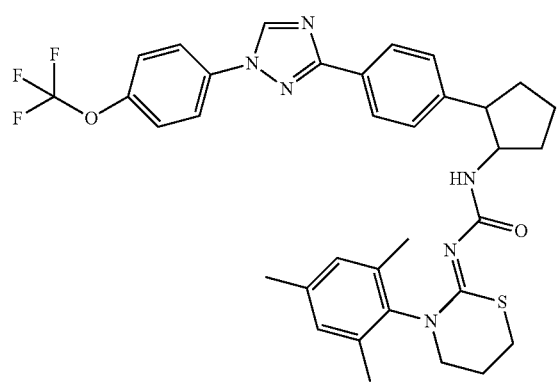 [SMILES: Cc1cc(C)c(N2CCCS/C2=N\C(=O)NC2CCCC2c2ccc(-c3ncn(-c4ccc(OC(F)(F)F)cc4)n3)cc2)c(C)c1]
P1069

TABLE P-Two-continued
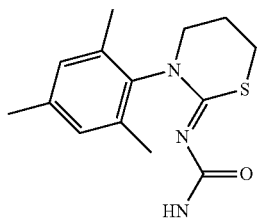
P1070
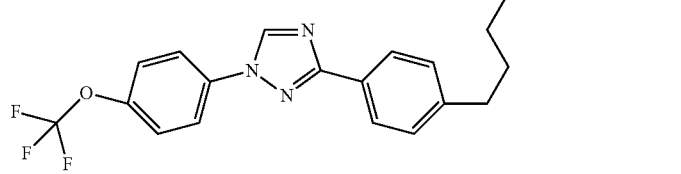
P1071
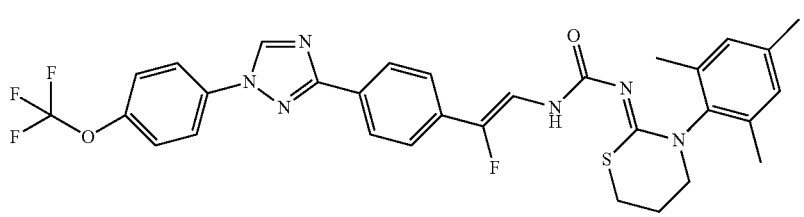
P1072
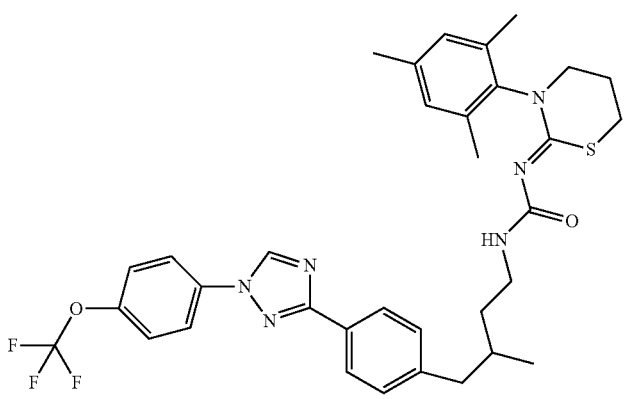 [SMILES: Cc1cc(C)c(N2CCCS/C2=N\C(=O)NCCC(C)Cc2ccc(-c3ncn(-c4ccc(OC(F)(F)F)cc4)n3)cc2)c(C)c1]
P1073
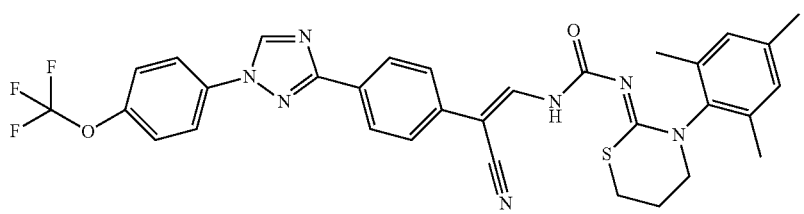 [SMILES: Cc1cc(C)c(N2CCCS/C2=N\C(=O)N/C=C(\C#N)c2ccc(-c3ncn(-c4ccc(OC(F)(F)F)cc4)n3)cc2)c(C)c1]
P1074
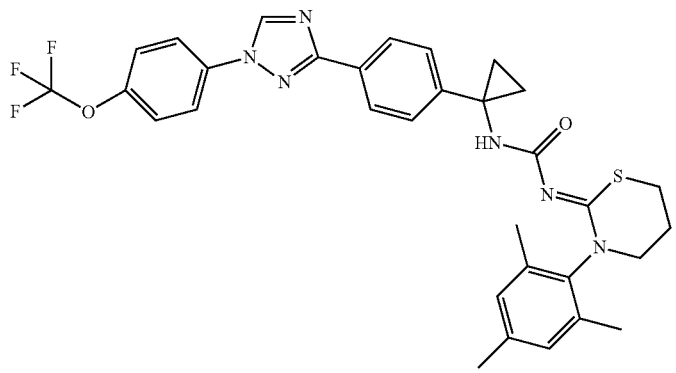 [SMILES: Cc1cc(C)c(N2CCCS/C2=N\C(=O)NC2(c3ccc(-c4ncn(-c5ccc(OC(F)(F)F)cc5)n4)cc3)CC2)c(C)c1]

TABLE P-Two-continued
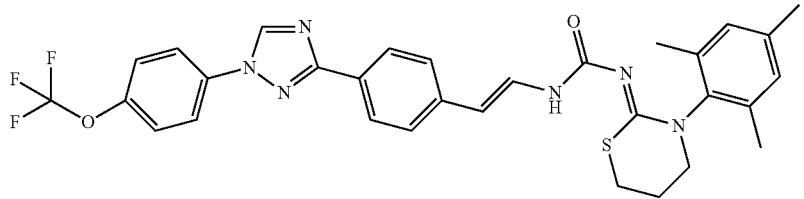 [SMILES: Cc1cc(C)c(N2CCCS/C2=N\C(=O)N/C=C/c2ccc(-c3ncn(-c4ccc(OC(F)(F)F)cc4)n3)cc2)c(C)c1]
P1075
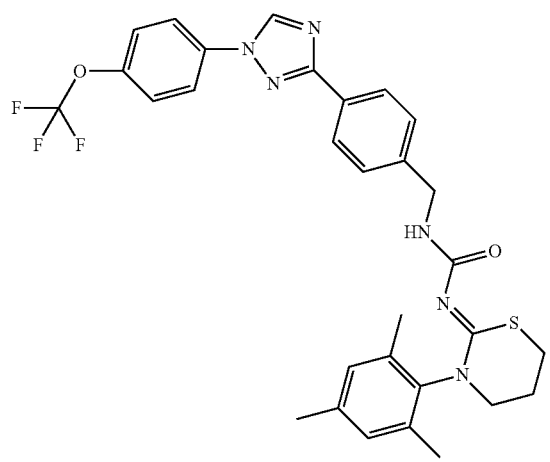 [SMILES: Cc1cc(C)c(N2CCCS/C2=N\C(=O)NCc2ccc(-c3ncn(-c4ccc(OC(F)(F)F)cc4)n3)cc2)c(C)c1]
P1076
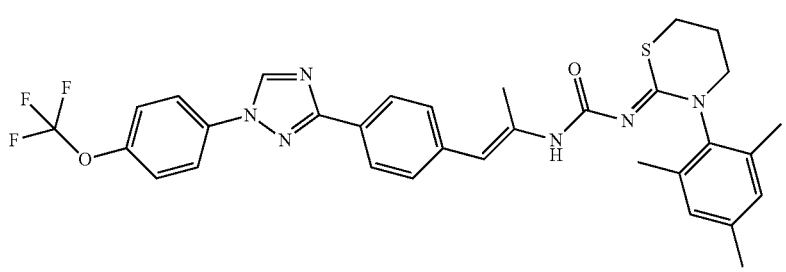 [SMILES: C/C(=C\c1ccc(-c2ncn(-c3ccc(OC(F)(F)F)cc3)n2)cc1)NC(=O)/N=C1\SCCCN1c1c(C)cc(C)cc1C]
P1077
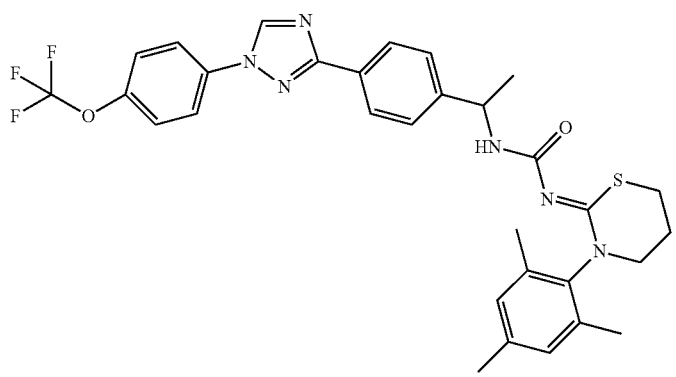 [SMILES: Cc1cc(C)c(N2CCCS/C2=N\C(=O)NC(C)c2ccc(-c3ncn(-c4ccc(OC(F)(F)F)cc4)n3)cc2)c(C)c1]
P1078
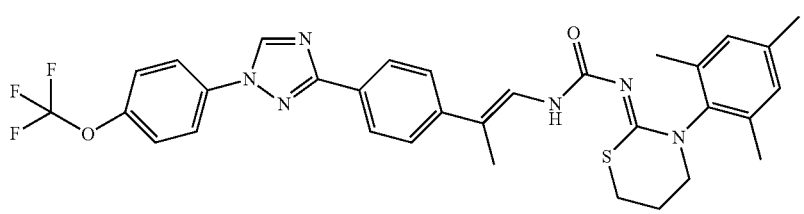 [SMILES: C/C(=C\NC(=O)/N=C1\SCCCN1c1c(C)cc(C)cc1C)c1ccc(-c2ncn(-c3ccc(OC(F)(F)F)cc3)n2)cc1]
P1079

TABLE P-Two-continued
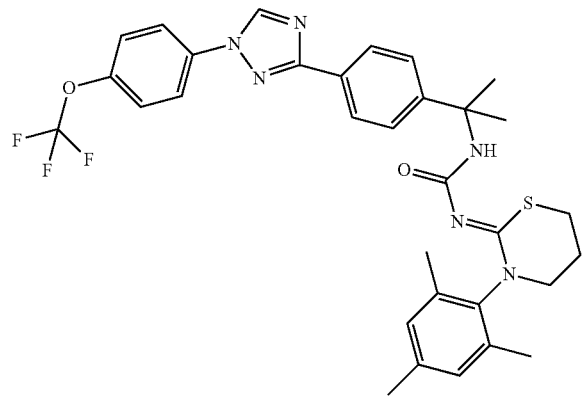 [SMILES: Cc1cc(C)c(N2CCCS/C2=N\C(=O)NC(C)(C)c2ccc(-c3ncn(-c4ccc(OC(F)(F)F)cc4)n3)cc2)c(C)c1]
P1080
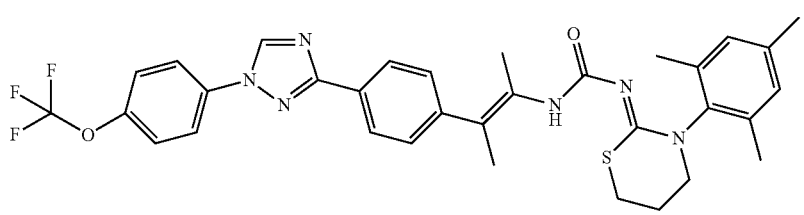 [SMILES: C/C(NC(=O)/N=C1\SCCCN1c1c(C)cc(C)cc1C)=C(/C)c1ccc(-c2ncn(-c3ccc(OC(F)(F)F)cc3)n2)cc1]
P1081
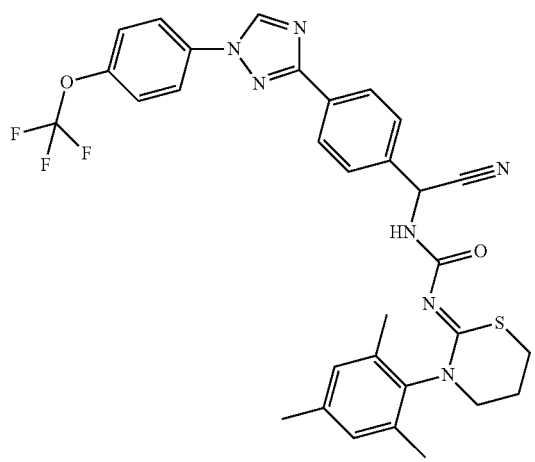 [SMILES: Cc1cc(C)c(N2CCCS/C2=N\C(=O)NC(C#N)c2ccc(-c3ncn(-c4ccc(OC(F)(F)F)cc4)n3)cc2)c(C)c1]
P1082
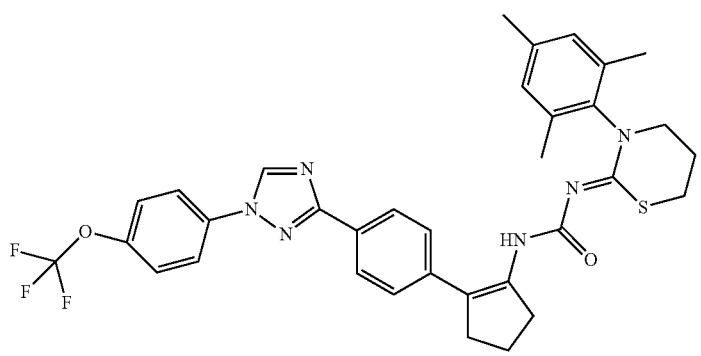 [SMILES: Cc1cc(C)c(N2CCCS/C2=N\C(=O)NC2=C(c3ccc(-c4ncn(-c5ccc(OC(F)(F)F)cc5)n4)cc3)CCC2)c(C)c1]
P1083

TABLE P-Two-continued
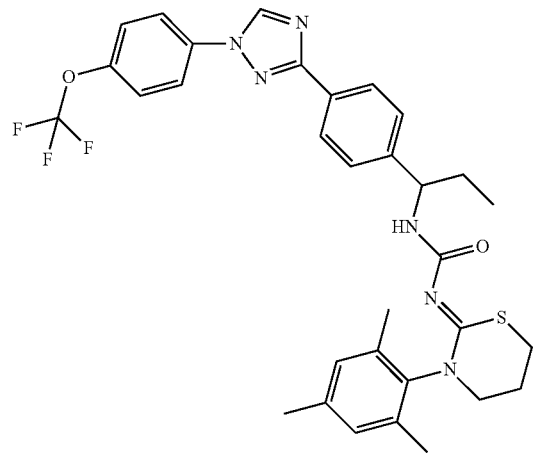 [SMILES: CCC(NC(=O)/N=C1\SCCCN1c1c(C)cc(C)cc1C)c1ccc(-c2ncn(-c3ccc(OC(F)(F)F)cc3)n2)cc1]
P1084
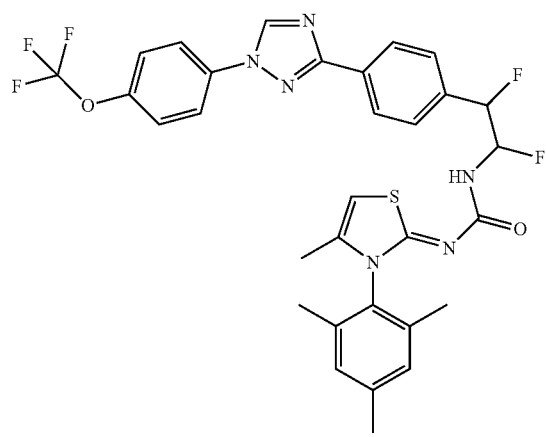 [SMILES: Cc1cc(C)c(-n2c(C)cs/c2=N\C(=O)NC(F)C(F)c2ccc(-c3ncn(-c4ccc(OC(F)(F)F)cc4)n3)cc2)c(C)c1]
P1085
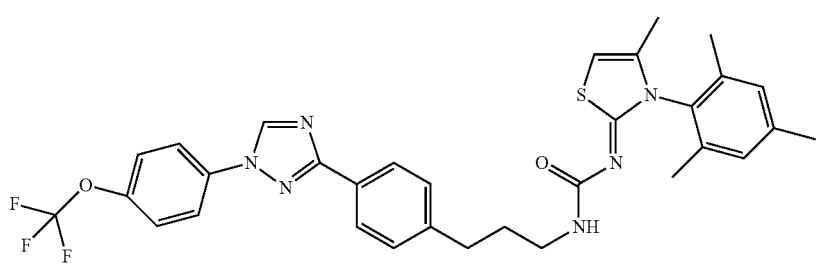 [SMILES: Cc1cc(C)c(-n2c(C)cs/c2=N\C(=O)NCCCc2ccc(-c3ncn(-c4ccc(OC(F)(F)F)cc4)n3)cc2)c(C)c1]
P1086
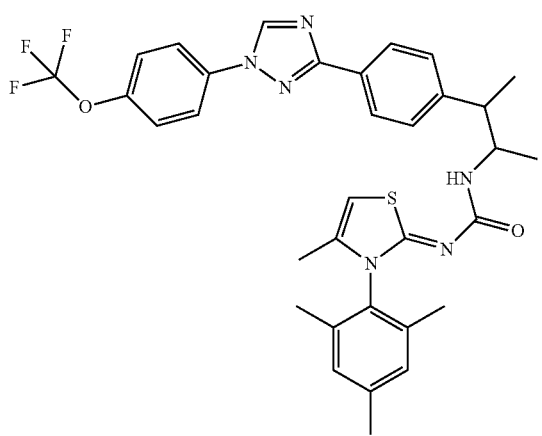 [SMILES: Cc1cc(C)c(-n2c(C)cs/c2=N\C(=O)NC(C)C(C)c2ccc(-c3ncn(-c4ccc(OC(F)(F)F)cc4)n3)cc2)c(C)c1]
P1087

TABLE P-Two-continued
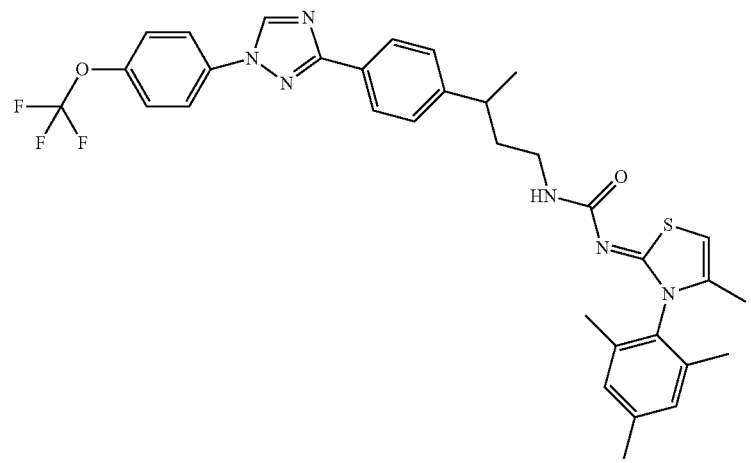 [SMILES: Cc1cc(C)c(-n2c(C)cs/c2=N\C(=O)NCCC(C)c2ccc(-c3ncn(-c4ccc(OC(F)(F)F)cc4)n3)cc2)c(C)c1]
P1088
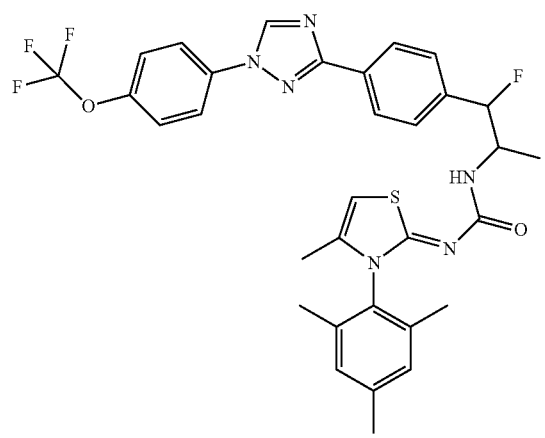 [SMILES: Cc1cc(C)c(-n2c(C)cs/c2=N\C(=O)NC(C)C(F)c2ccc(-c3ncn(-c4ccc(OC(F)(F)F)cc4)n3)cc2)c(C)c1]
P1089
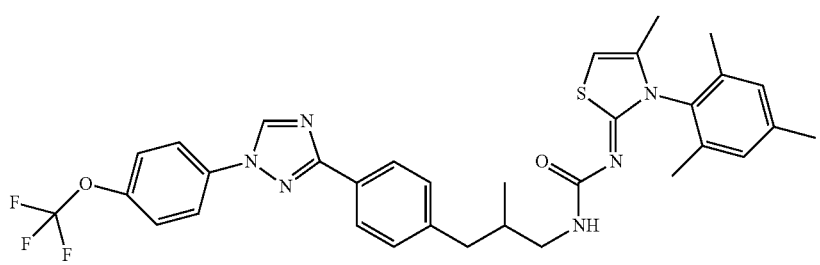 [SMILES: Cc1cc(C)c(-n2c(C)cs/c2=N\C(=O)NCC(C)Cc2ccc(-c3ncn(-c4ccc(OC(F)(F)F)cc4)n3)cc2)c(C)c1]
P1090
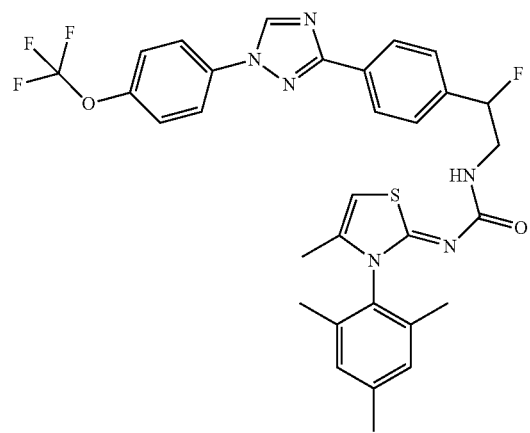 [SMILES: Cc1cc(C)c(-n2c(C)cs/c2=N\C(=O)NCC(F)c2ccc(-c3ncn(-c4ccc(OC(F)(F)F)cc4)n3)cc2)c(C)c1]
P1091

TABLE P-Two-continued
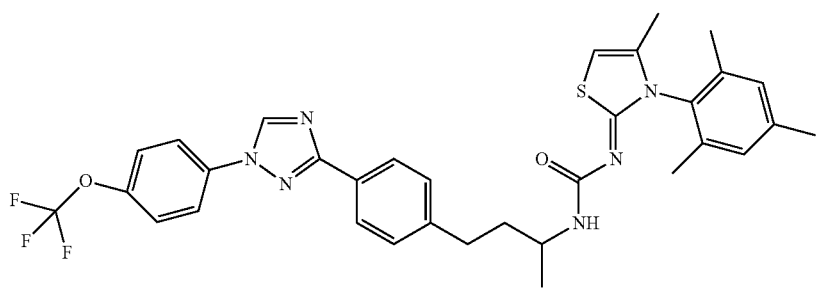 [SMILES: Cc1cc(C)c(-n2c(C)cs/c2=N\C(=O)NC(C)CCc2ccc(-c3ncn(-c4ccc(OC(F)(F)F)cc4)n3)cc2)c(C)c1]
P1092
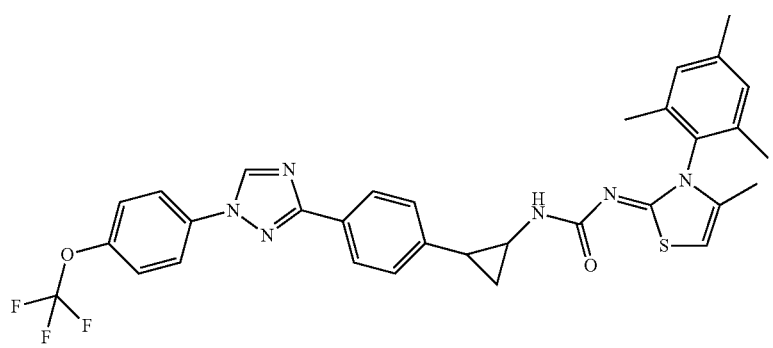 [SMILES: Cc1cc(C)c(-n2c(C)cs/c2=N\C(=O)NC2CC2c2ccc(-c3ncn(-c4ccc(OC(F)(F)F)cc4)n3)cc2)c(C)c1]
P1093
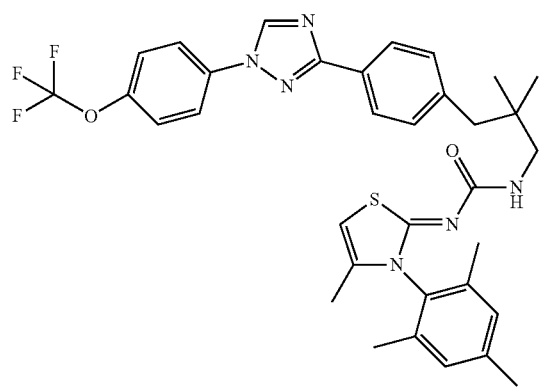 [SMILES: Cc1cc(C)c(-n2c(C)cs/c2=N\C(=O)NCC(C)(C)Cc2ccc(-c3ncn(-c4ccc(OC(F)(F)F)cc4)n3)cc2)c(C)c1]
P1094
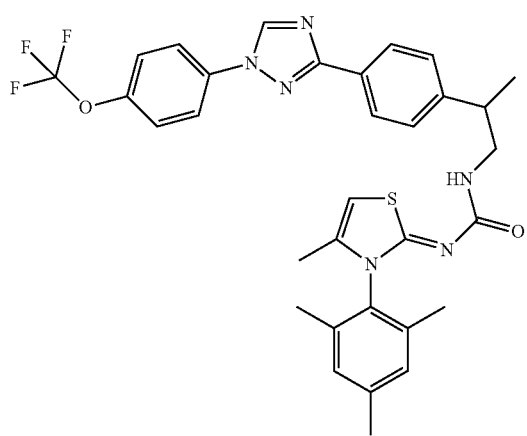 [SMILES: Cc1cc(C)c(-n2c(C)cs/c2=N\C(=O)NCC(C)c2ccc(-c3ncn(-c4ccc(OC(F)(F)F)cc4)n3)cc2)c(C)c1]
P1095

TABLE P-Two-continued
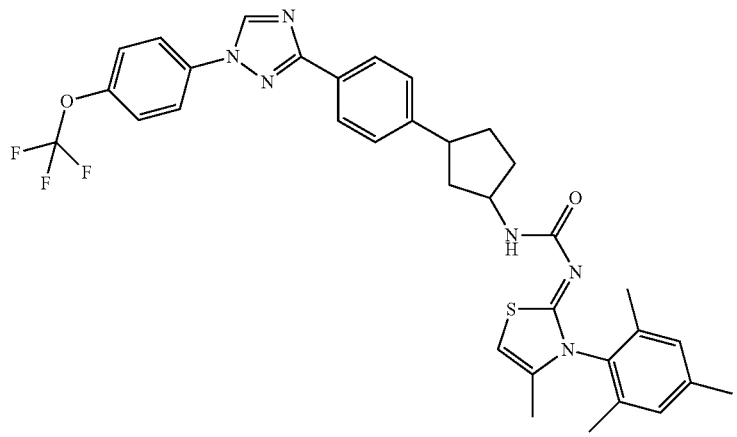 [SMILES: Cc1cc(C)c(-n2c(C)cs/c2=N\C(=O)NC2CCC(c3ccc(-c4ncn(-c5ccc(OC(F)(F)F)cc5)n4)cc3)C2)c(C)c1]
P1096
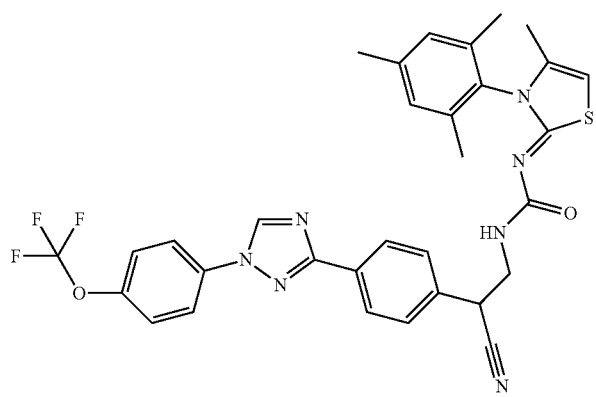 [SMILES: Cc1cc(C)c(-n2c(C)cs/c2=N\C(=O)NCC(C#N)c2ccc(-c3ncn(-c4ccc(OC(F)(F)F)cc4)n3)cc2)c(C)c1]
P1097
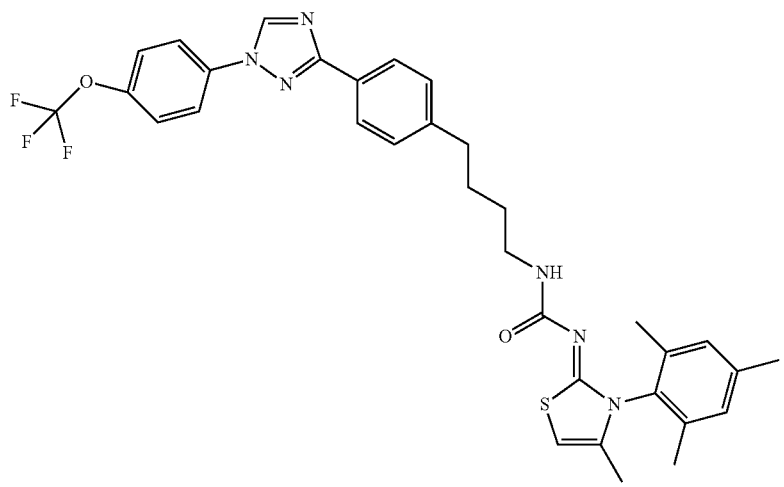 [SMILES: Cc1cc(C)c(-n2c(C)cs/c2=N\C(=O)NCCCCc2ccc(-c3ncn(-c4ccc(OC(F)(F)F)cc4)n3)cc2)c(C)c1]
P1098

TABLE P-Two-continued
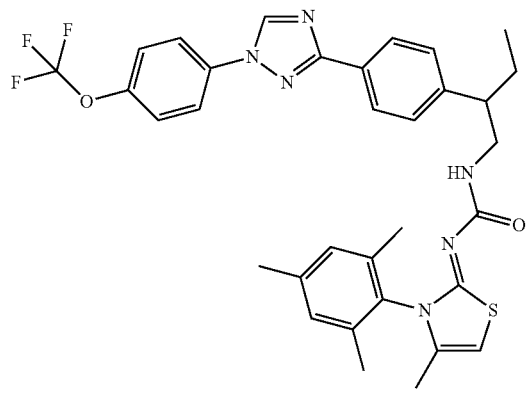 [SMILES: CCC(CNC(=O)/N=c1\scc(C)n1-c1c(C)cc(C)cc1C)c1ccc(-c2ncn(-c3ccc(OC(F)(F)F)cc3)n2)cc1]
P1099
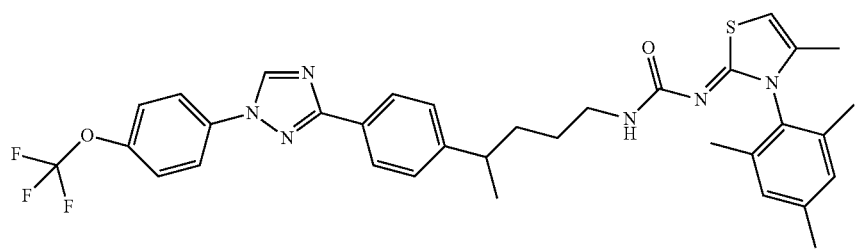 [SMILES: Cc1cc(C)c(-n2c(C)cs/c2=N\C(=O)NCCCC(C)c2ccc(-c3ncn(-c4ccc(OC(F)(F)F)cc4)n3)cc2)c(C)c1]
P1100
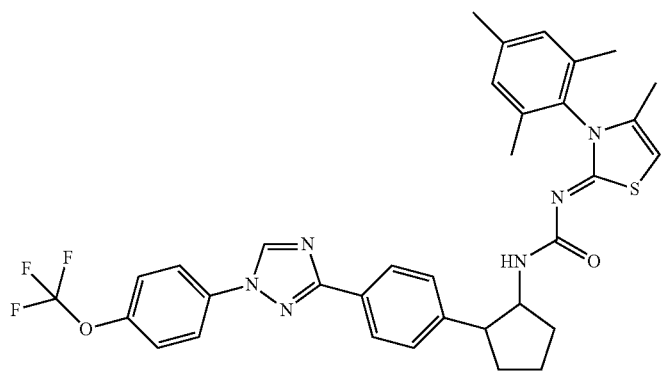 [SMILES: Cc1cc(C)c(-n2c(C)cs/c2=N\C(=O)NC2CCCC2c2ccc(-c3ncn(-c4ccc(OC(F)(F)F)cc4)n3)cc2)c(C)c1]
P1101
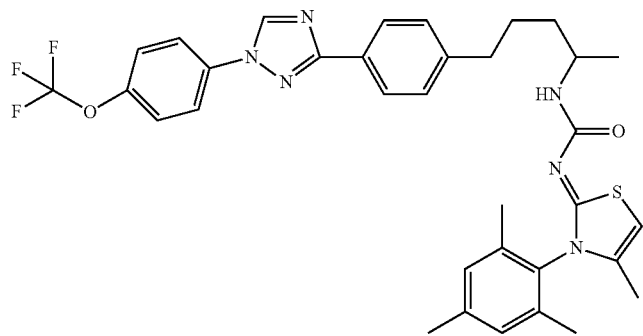 [SMILES: Cc1cc(C)c(-n2c(C)cs/c2=N\C(=O)NC(C)CCCc2ccc(-c3ncn(-c4ccc(OC(F)(F)F)cc4)n3)cc2)c(C)c1]
P1102

TABLE P-Two-continued
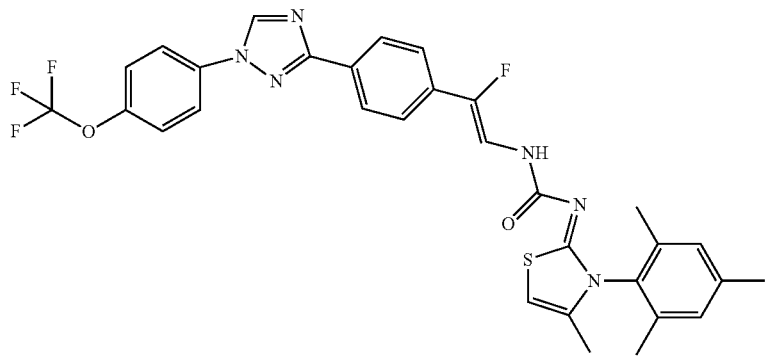
P1103
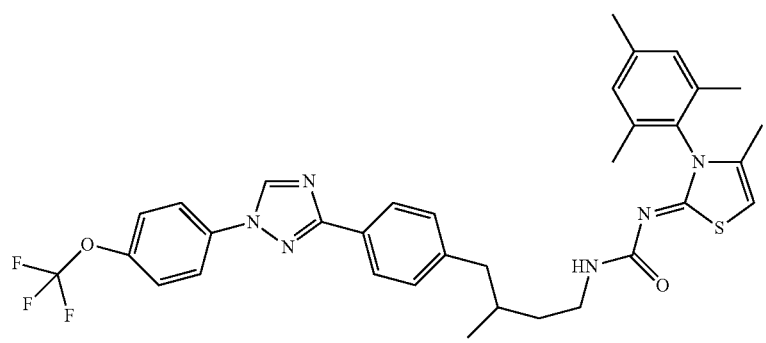 [SMILES: Cc1cc(C)c(-n2c(C)cs/c2=N\C(=O)NCCC(C)Cc2ccc(-c3ncn(-c4ccc(OC(F)(F)F)cc4)n3)cc2)c(C)c1]
P1104
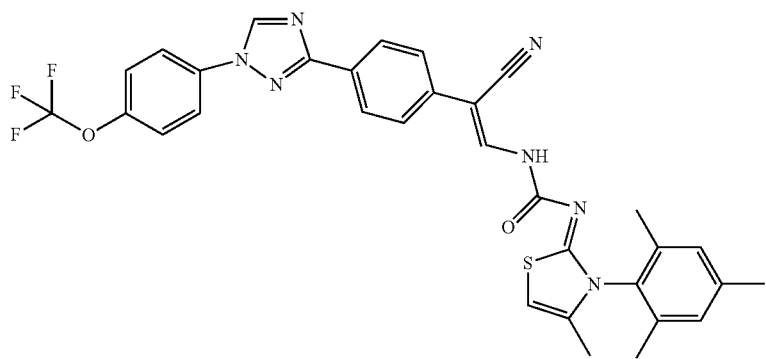 [SMILES: Cc1cc(C)c(-n2c(C)cs/c2=N\C(=O)N/C=C(\C#N)c2ccc(-c3ncn(-c4ccc(OC(F)(F)F)cc4)n3)cc2)c(C)c1]
P1105
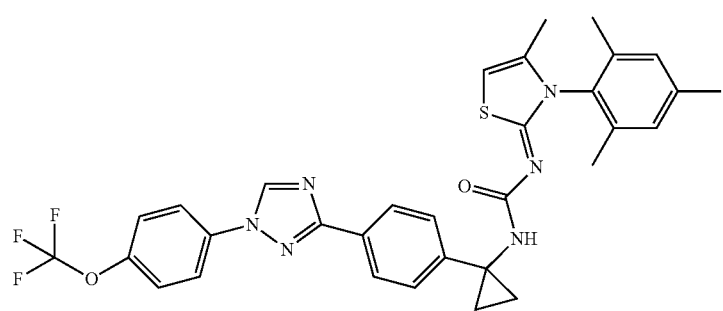 [SMILES: Cc1cc(C)c(-n2c(C)cs/c2=N\C(=O)NC2(c3ccc(-c4ncn(-c5ccc(OC(F)(F)F)cc5)n4)cc3)CC2)c(C)c1]
P1106

TABLE P-Two-continued
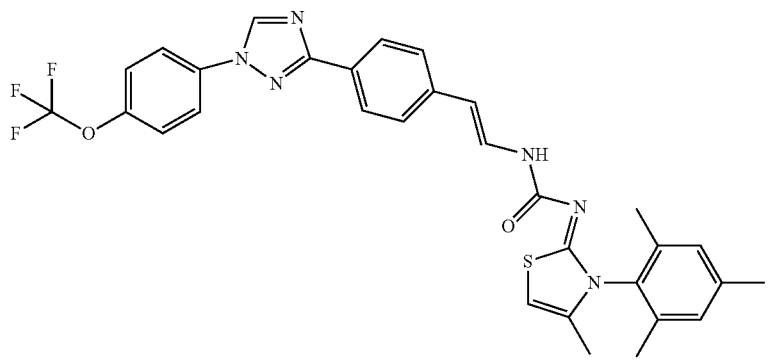 [SMILES: Cc1cc(C)c(-n2c(C)cs/c2=N\C(=O)N/C=C/c2ccc(-c3ncn(-c4ccc(OC(F)(F)F)cc4)n3)cc2)c(C)c1]
P1107
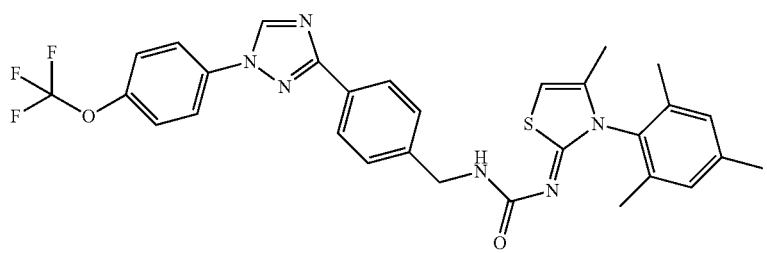 [SMILES: Cc1cc(C)c(-n2c(C)cs/c2=N\C(=O)NCc2ccc(-c3ncn(-c4ccc(OC(F)(F)F)cc4)n3)cc2)c(C)c1]
P1108
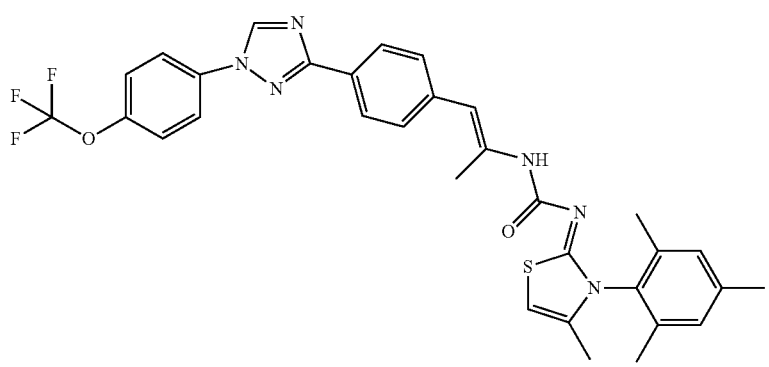 [SMILES: C/C(=C\c1ccc(-c2ncn(-c3ccc(OC(F)(F)F)cc3)n2)cc1)NC(=O)/N=c1\scc(C)n1-c1c(C)cc(C)cc1C]
P1109
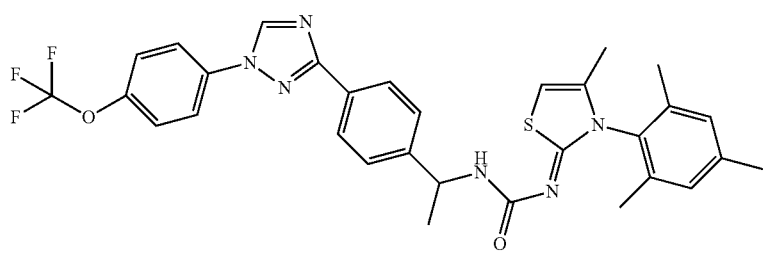 [SMILES: Cc1cc(C)c(-n2c(C)cs/c2=N\C(=O)NC(C)c2ccc(-c3ncn(-c4ccc(OC(F)(F)F)cc4)n3)cc2)c(C)c1]
P1110
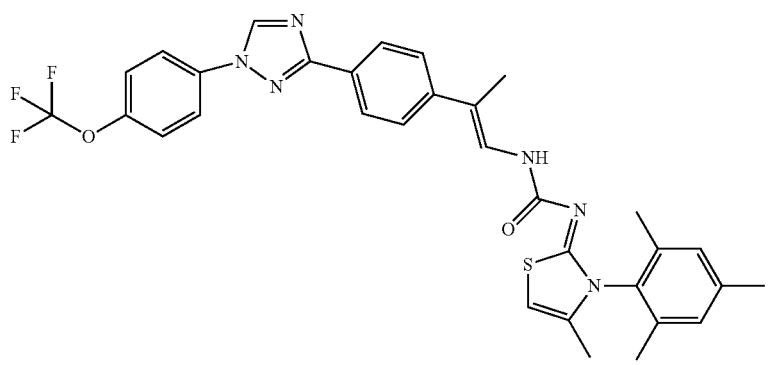 [SMILES: C/C(=C\NC(=O)/N=c1\scc(C)n1-c1c(C)cc(C)cc1C)c1ccc(-c2ncn(-c3ccc(OC(F)(F)F)cc3)n2)cc1]
P1111

TABLE P-Two-continued
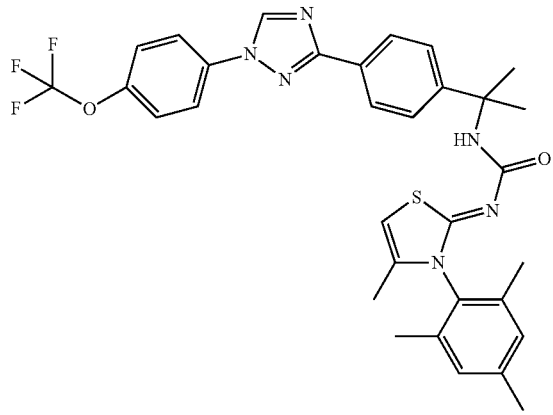 [SMILES: Cc1cc(C)c(-n2c(C)cs/c2=N\C(=O)NC(C)(C)c2ccc(-c3ncn(-c4ccc(OC(F)(F)F)cc4)n3)cc2)c(C)c1]
P1112
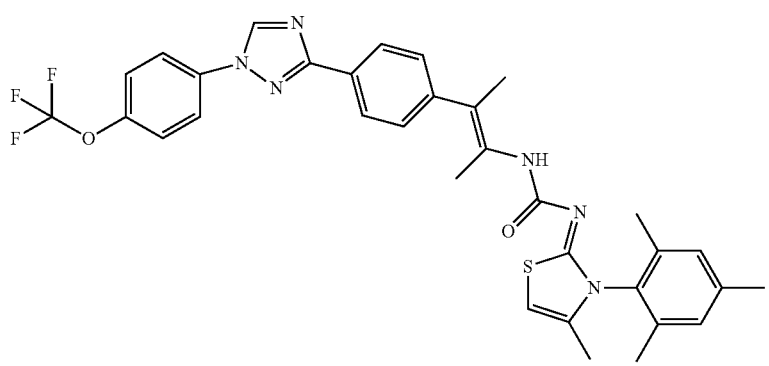 [SMILES: C/C(NC(=O)/N=c1\scc(C)n1-c1c(C)cc(C)cc1C)=C(/C)c1ccc(-c2ncn(-c3ccc(OC(F)(F)F)cc3)n2)cc1]
P1113
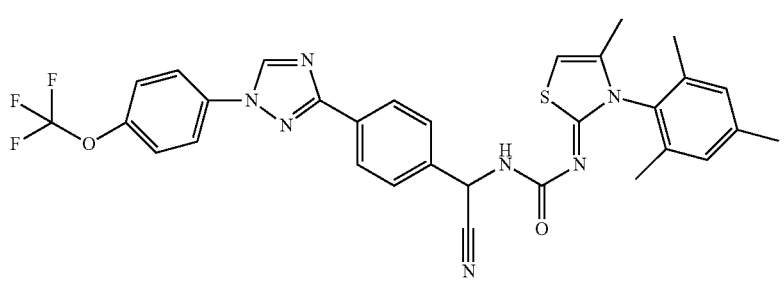 [SMILES: Cc1cc(C)c(-n2c(C)cs/c2=N\C(=O)NC(C#N)c2ccc(-c3ncn(-c4ccc(OC(F)(F)F)cc4)n3)cc2)c(C)c1]
P1114
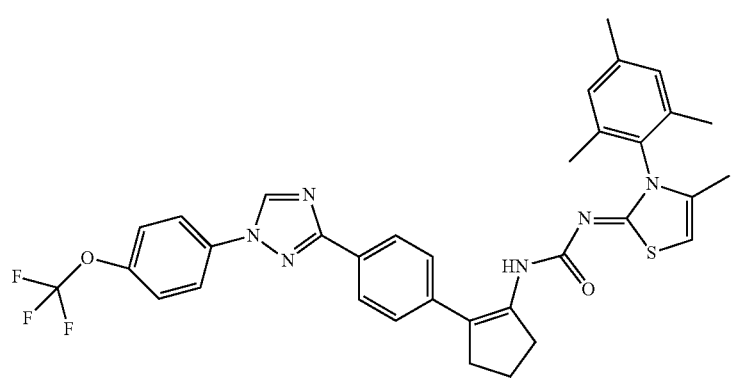 [SMILES: Cc1cc(C)c(-n2c(C)cs/c2=N\C(=O)NC2=C(c3ccc(-c4ncn(-c5ccc(OC(F)(F)F)cc5)n4)cc3)CCC2)c(C)c1]
P1115

TABLE P-Two-continued
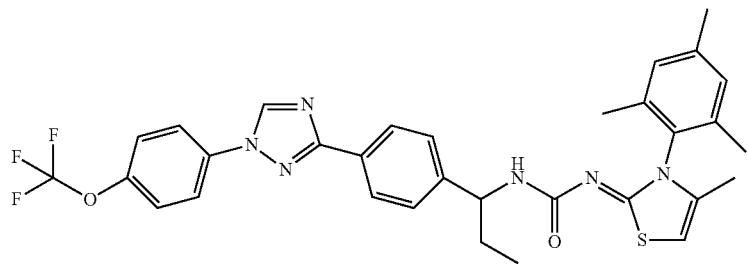 [SMILES: CCC(NC(=O)/N=c1\scc(C)n1-c1c(C)cc(C)cc1C)c1ccc(-c2ncn(-c3ccc(OC(F)(F)F)cc3)n2)cc1]
P1116
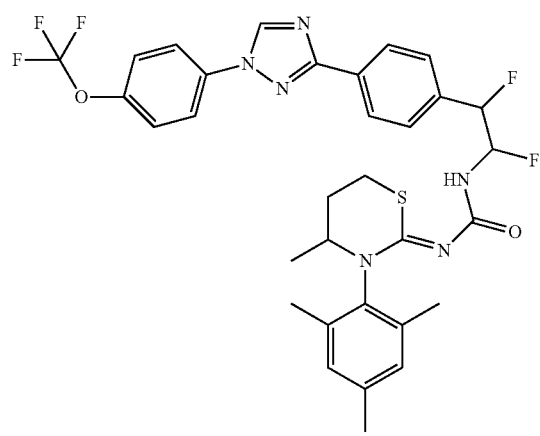 [SMILES: Cc1cc(C)c(N2/C(=N/C(=O)NC(F)C(F)c3ccc(-c4ncn(-c5ccc(OC(F)(F)F)cc5)n4)cc3)SCCC2C)c(C)c1]
P1117
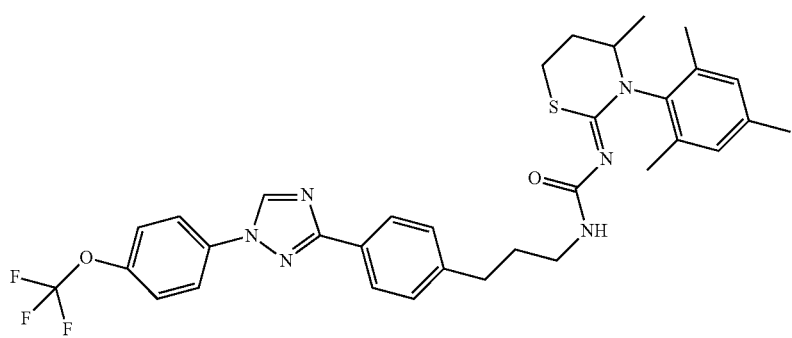 [SMILES: Cc1cc(C)c(N2/C(=N/C(=O)NCCCc3ccc(-c4ncn(-c5ccc(OC(F)(F)F)cc5)n4)cc3)SCCC2C)c(C)c1]
P1118
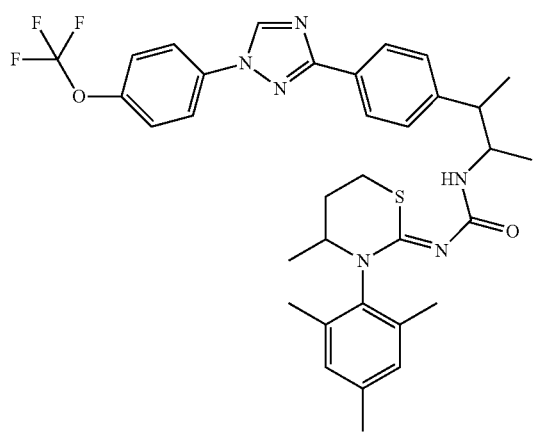 [SMILES: Cc1cc(C)c(N2/C(=N/C(=O)NC(C)C(C)c3ccc(-c4ncn(-c5ccc(OC(F)(F)F)cc5)n4)cc3)SCCC2C)c(C)c1]
P1119

TABLE P-Two-continued
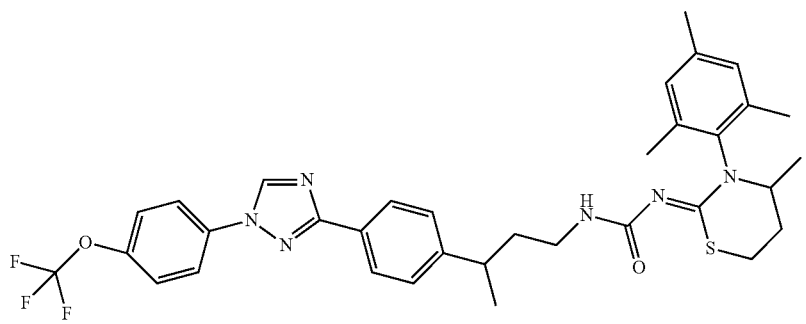 [SMILES: Cc1cc(C)c(N2/C(=N/C(=O)NCCC(C)c3ccc(-c4ncn(-c5ccc(OC(F)(F)F)cc5)n4)cc3)SCCC2C)c(C)c1]
P1120
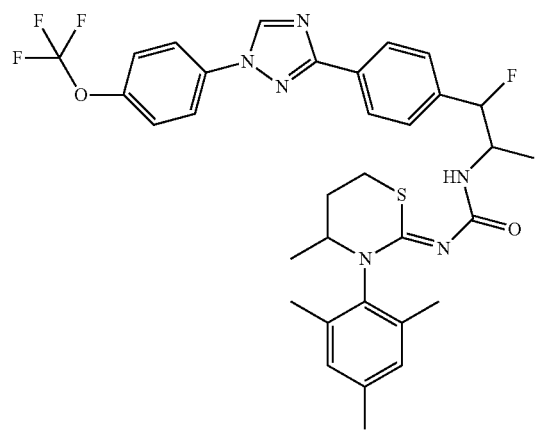 [SMILES: Cc1cc(C)c(N2/C(=N/C(=O)NC(C)C(F)c3ccc(-c4ncn(-c5ccc(OC(F)(F)F)cc5)n4)cc3)SCCC2C)c(C)c1]
P1121
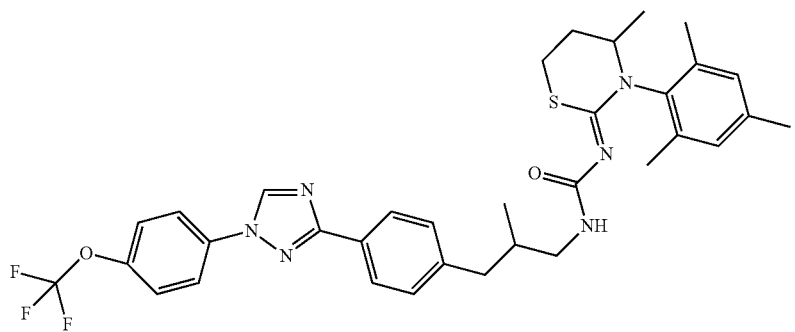 [SMILES: Cc1cc(C)c(N2/C(=N/C(=O)NCC(C)Cc3ccc(-c4ncn(-c5ccc(OC(F)(F)F)cc5)n4)cc3)SCCC2C)c(C)c1]
P1122
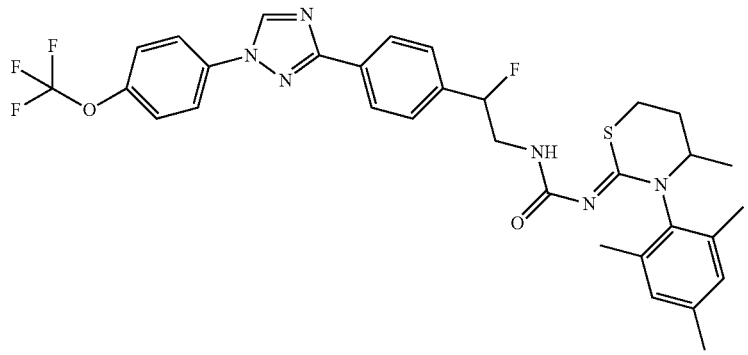
P1123

TABLE P-Two-continued
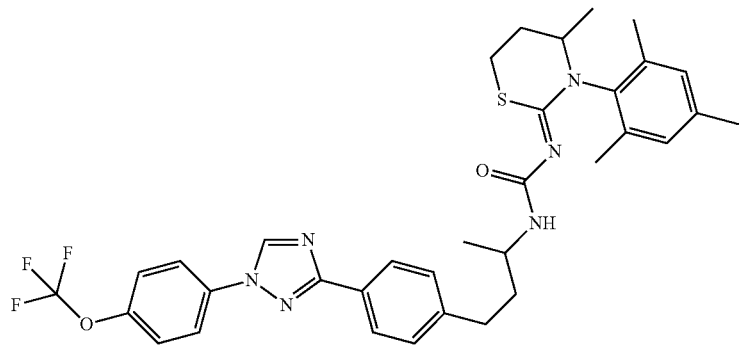 [SMILES: Cc1cc(C)c(N2/C(=N/C(=O)NC(C)CCc3ccc(-c4ncn(-c5ccc(OC(F)(F)F)cc5)n4)cc3)SCCC2C)c(C)c1]
P1124
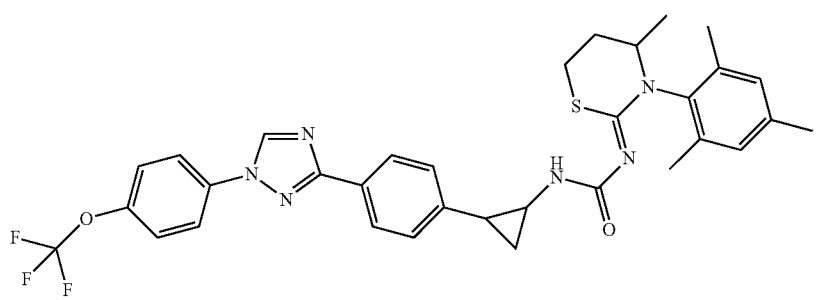 [SMILES: Cc1cc(C)c(N2/C(=N/C(=O)NC3CC3c3ccc(-c4ncn(-c5ccc(OC(F)(F)F)cc5)n4)cc3)SCCC2C)c(C)c1]
P1125
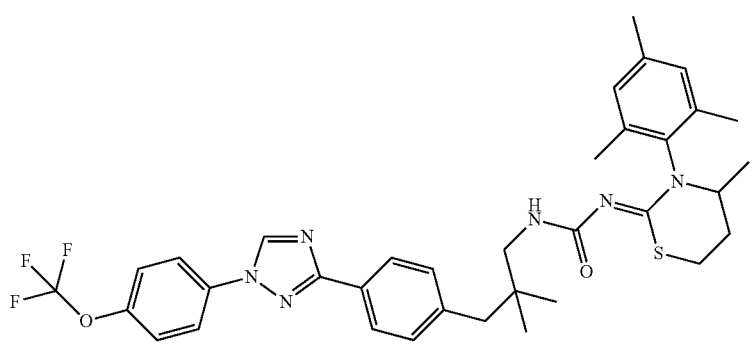 [SMILES: Cc1cc(C)c(N2/C(=N/C(=O)NCC(C)(C)Cc3ccc(-c4ncn(-c5ccc(OC(F)(F)F)cc5)n4)cc3)SCCC2C)c(C)c1]
P1126
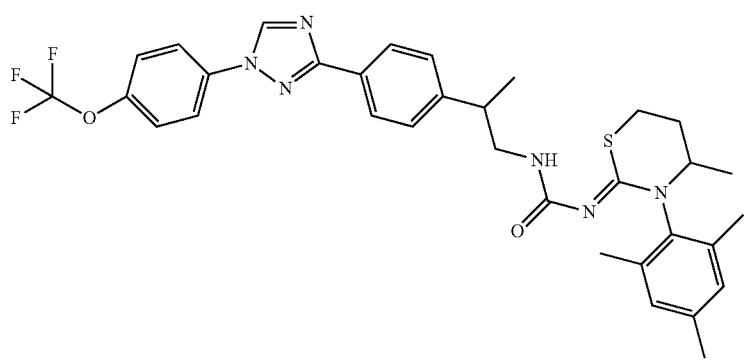 [SMILES: Cc1cc(C)c(N2/C(=N/C(=O)NCC(C)c3ccc(-c4ncn(-c5ccc(OC(F)(F)F)cc5)n4)cc3)SCCC2C)c(C)c1]
P1127

TABLE P-Two-continued
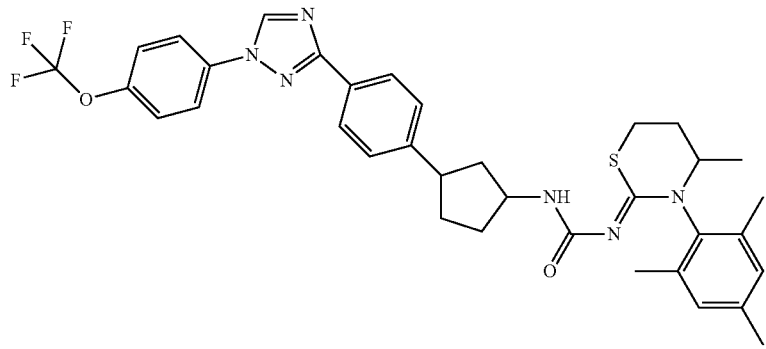 [SMILES: Cc1cc(C)c(N2/C(=N/C(=O)NC3CCC(c4ccc(-c5ncn(-c6ccc(OC(F)(F)F)cc6)n5)cc4)C3)SCCC2C)c(C)c1]
P1128
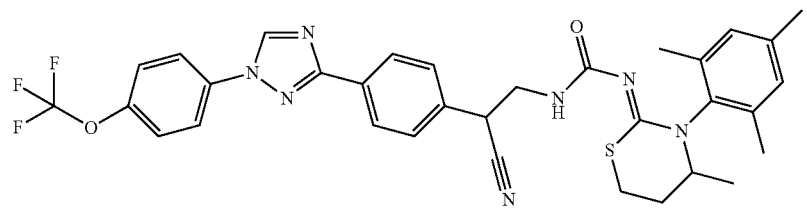
P1129
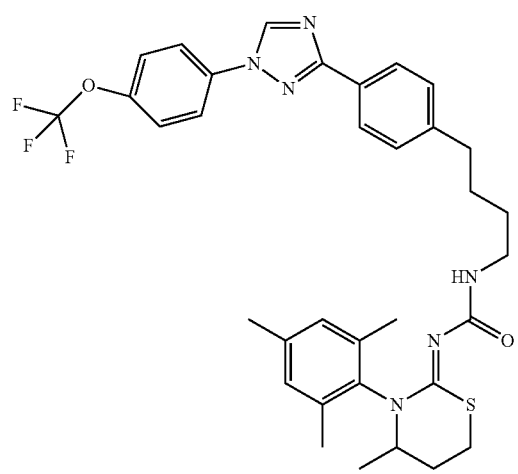 [SMILES: Cc1cc(C)c(N2/C(=N/C(=O)NCCCCc3ccc(-c4ncn(-c5ccc(OC(F)(F)F)cc5)n4)cc3)SCCC2C)c(C)c1]
P1130
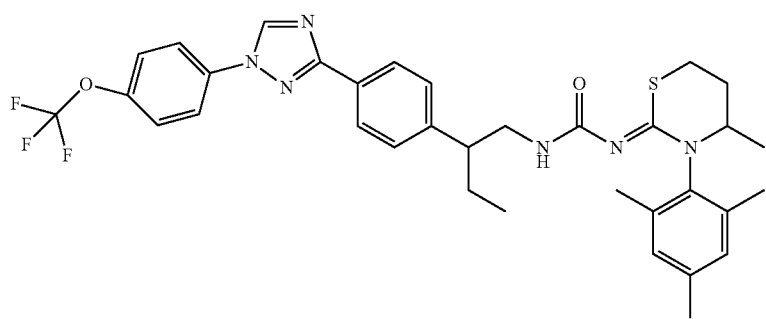 [SMILES: CCC(CNC(=O)/N=C1\SCCC(C)N1c1c(C)cc(C)cc1C)c1ccc(-c2ncn(-c3ccc(OC(F)(F)F)cc3)n2)cc1]
P1131

TABLE P-Two-continued
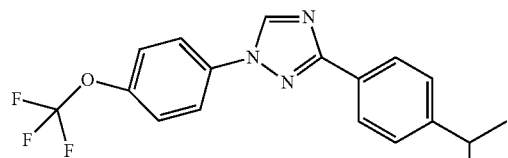
P1132
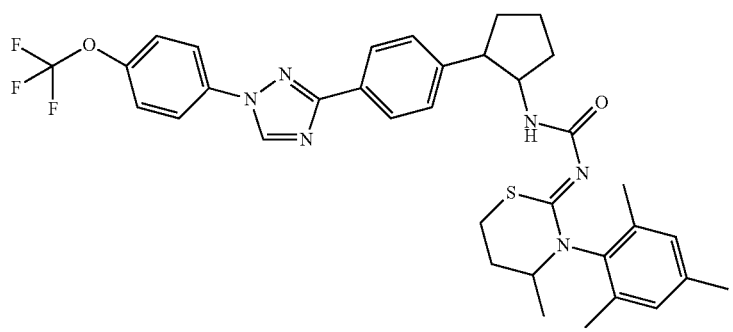 [SMILES: Cc1cc(C)c(N2/C(=N/C(=O)NC3CCCC3c3ccc(-c4ncn(-c5ccc(OC(F)(F)F)cc5)n4)cc3)SCCC2C)c(C)c1]
P1133
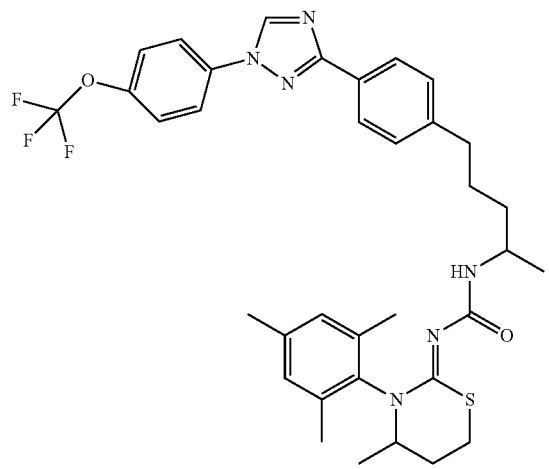 [SMILES: Cc1cc(C)c(N2/C(=N/C(=O)NC(C)CCCc3ccc(-c4ncn(-c5ccc(OC(F)(F)F)cc5)n4)cc3)SCCC2C)c(C)c1]
P1134
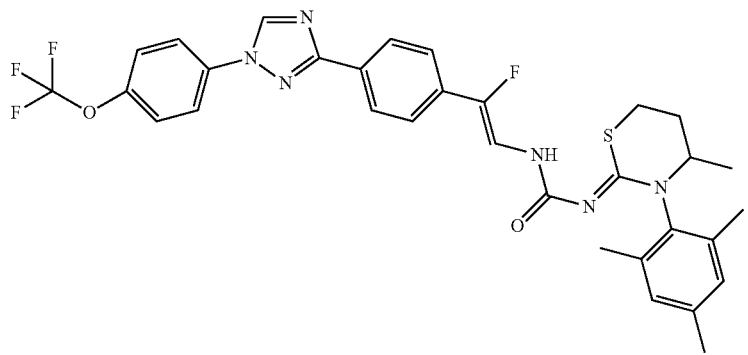 [SMILES: Cc1cc(C)c(N2/C(=N/C(=O)N/C=C(\F)c3ccc(-c4ncn(-c5ccc(OC(F)(F)F)cc5)n4)cc3)SCCC2C)c(C)c1]
P1135

TABLE P-Two-continued
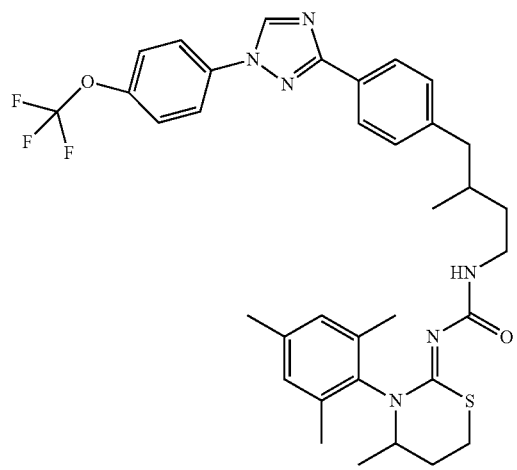 [SMILES: Cc1cc(C)c(N2/C(=N/C(=O)NCCC(C)Cc3ccc(-c4ncn(-c5ccc(OC(F)(F)F)cc5)n4)cc3)SCCC2C)c(C)c1]
P1136
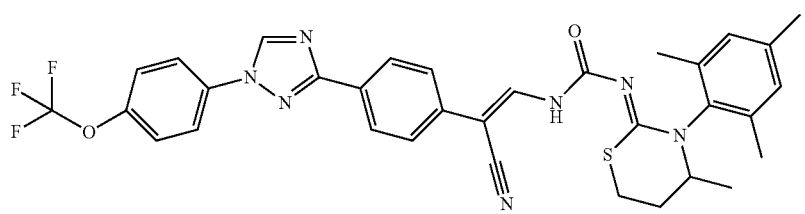
P1137
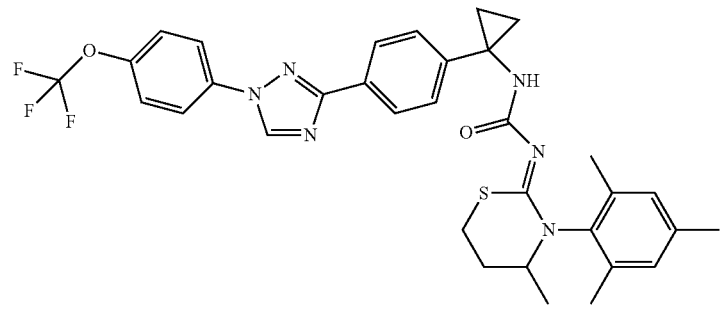 [SMILES: Cc1cc(C)c(N2/C(=N/C(=O)NC3(c4ccc(-c5ncn(-c6ccc(OC(F)(F)F)cc6)n5)cc4)CC3)SCCC2C)c(C)c1]
P1138
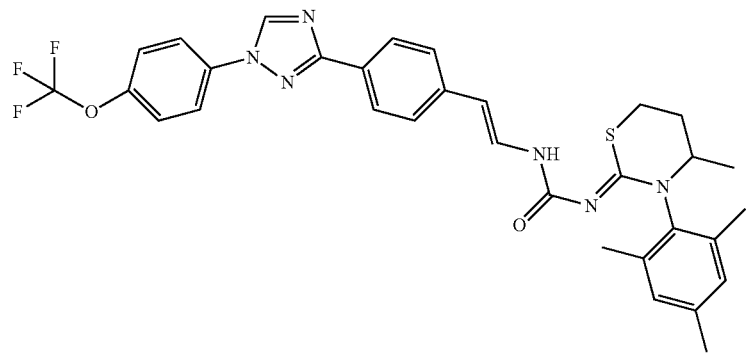 [SMILES: Cc1cc(C)c(N2/C(=N/C(=O)N/C=C/c3ccc(-c4ncn(-c5ccc(OC(F)(F)F)cc5)n4)cc3)SCCC2C)c(C)c1]
P1139

TABLE P-Two-continued
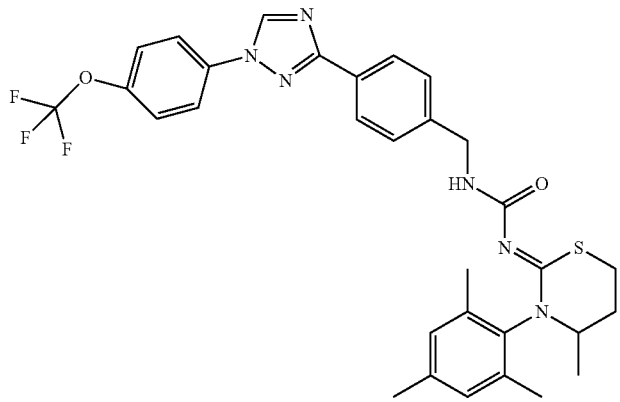 [SMILES: Cc1cc(C)c(N2/C(=N/C(=O)NCc3ccc(-c4ncn(-c5ccc(OC(F)(F)F)cc5)n4)cc3)SCCC2C)c(C)c1]
P1140
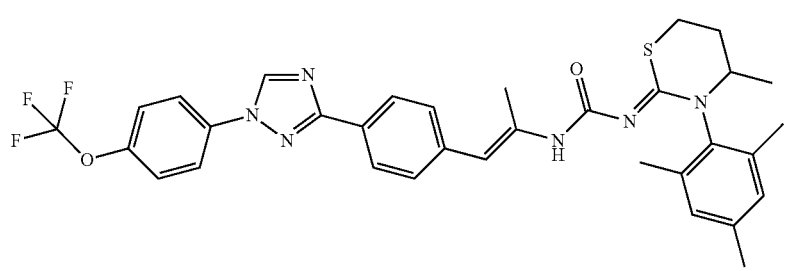 [SMILES: C/C(=C\c1ccc(-c2ncn(-c3ccc(OC(F)(F)F)cc3)n2)cc1)NC(=O)/N=C1\SCCC(C)N1c1c(C)cc(C)cc1C]
P1141
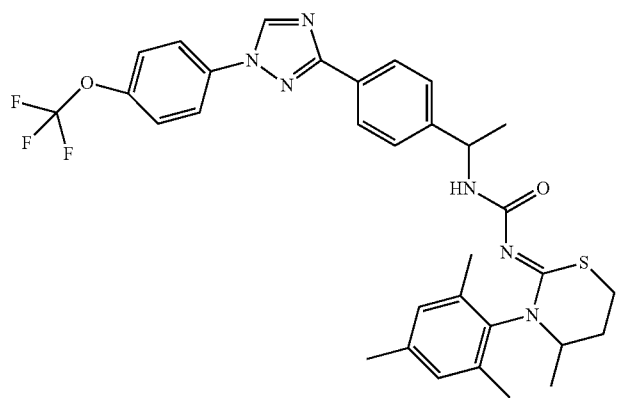 [SMILES: Cc1cc(C)c(N2/C(=N/C(=O)NC(C)c3ccc(-c4ncn(-c5ccc(OC(F)(F)F)cc5)n4)cc3)SCCC2C)c(C)c1]
P1142
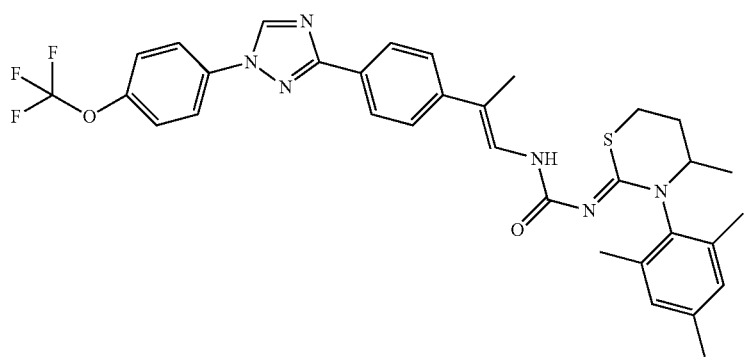 [SMILES: C/C(=C\NC(=O)/N=C1\SCCC(C)N1c1c(C)cc(C)cc1C)c1ccc(-c2ncn(-c3ccc(OC(F)(F)F)cc3)n2)cc1]
P1143

TABLE P-Two-continued
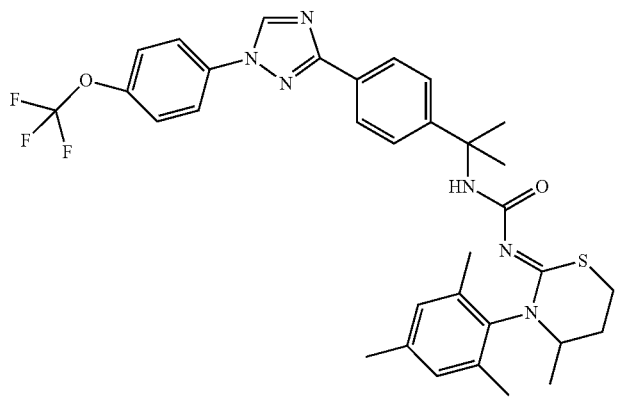 [SMILES: Cc1cc(C)c(N2/C(=N/C(=O)NC(C)(C)c3ccc(-c4ncn(-c5ccc(OC(F)(F)F)cc5)n4)cc3)SCCC2C)c(C)c1]
P1144
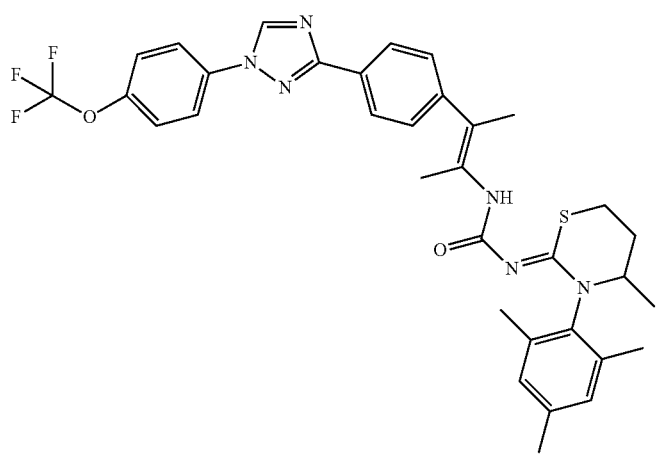 [SMILES: C/C(NC(=O)/N=C1\SCCC(C)N1c1c(C)cc(C)cc1C)=C(/C)c1ccc(-c2ncn(-c3ccc(OC(F)(F)F)cc3)n2)cc1]
P1145
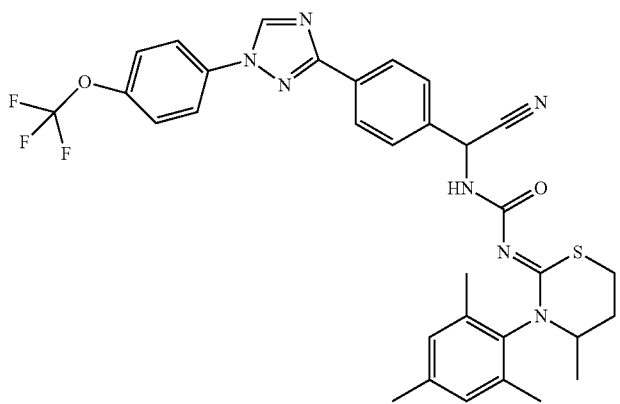 [SMILES: Cc1cc(C)c(N2/C(=N/C(=O)NC(C#N)c3ccc(-c4ncn(-c5ccc(OC(F)(F)F)cc5)n4)cc3)SCCC2C)c(C)c1]
P1146
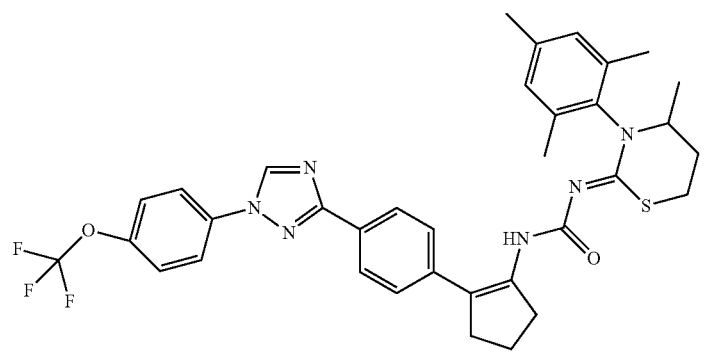 [SMILES: Cc1cc(C)c(N2/C(=N/C(=O)NC3=C(c4ccc(-c5ncn(-c6ccc(OC(F)(F)F)cc6)n5)cc4)CCC3)SCCC2C)c(C)c1]
P1147

TABLE P-Two-continued
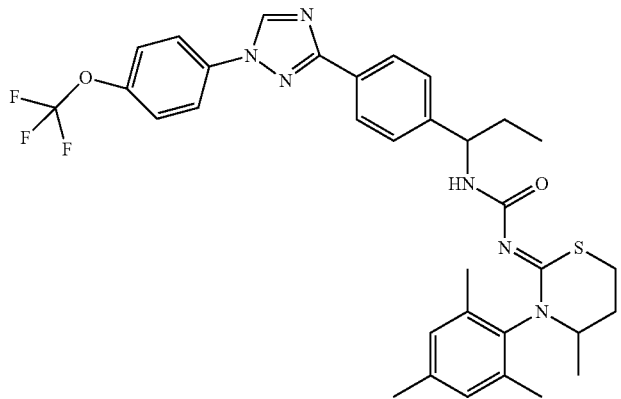 [SMILES: CCC(NC(=O)/N=C1\SCCC(C)N1c1c(C)cc(C)cc1C)c1ccc(-c2ncn(-c3ccc(OC(F)(F)F)cc3)n2)cc1]
P1148
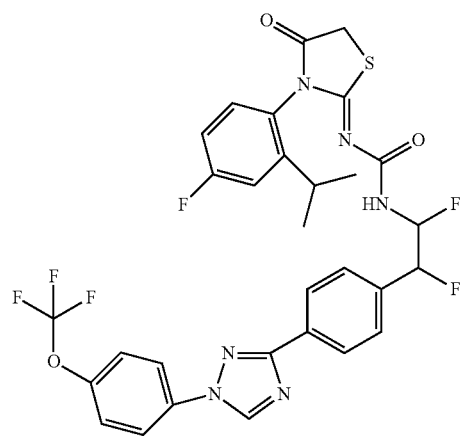 [SMILES: CC(C)c1cc(F)ccc1N1C(=O)CS/C1=N\C(=O)NC(F)C(F)c1ccc(-c2ncn(-c3ccc(OC(F)(F)F)cc3)n2)cc1]
P1149
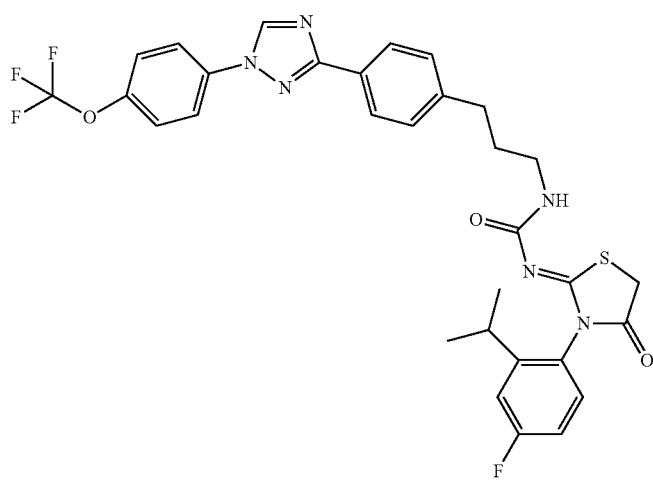 [SMILES: CC(C)c1cc(F)ccc1N1C(=O)CS/C1=N\C(=O)NCCCc1ccc(-c2ncn(-c3ccc(OC(F)(F)F)cc3)n2)cc1]
P1150

TABLE P-Two-continued
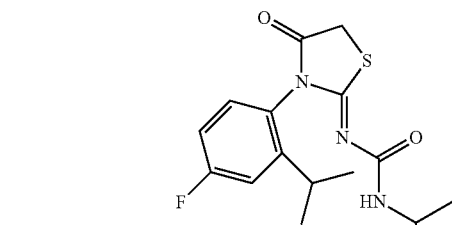
P1151
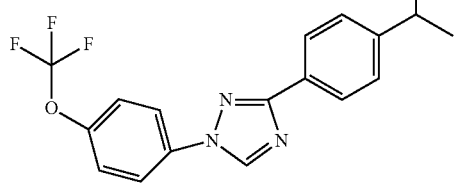
P1152
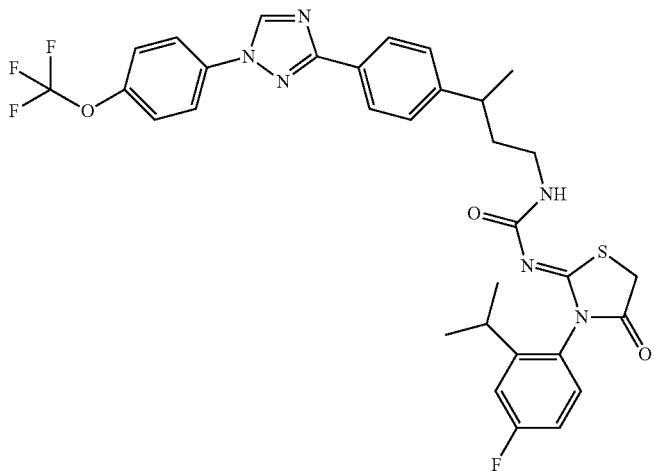 [SMILES: CC(C)c1cc(F)ccc1N1C(=O)CS/C1=N\C(=O)NCCC(C)c1ccc(-c2ncn(-c3ccc(OC(F)(F)F)cc3)n2)cc1]
P1153
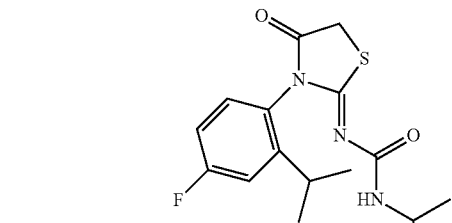
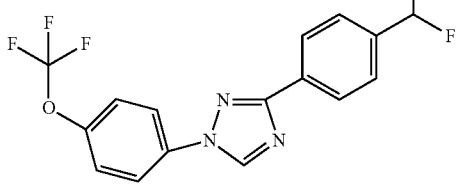
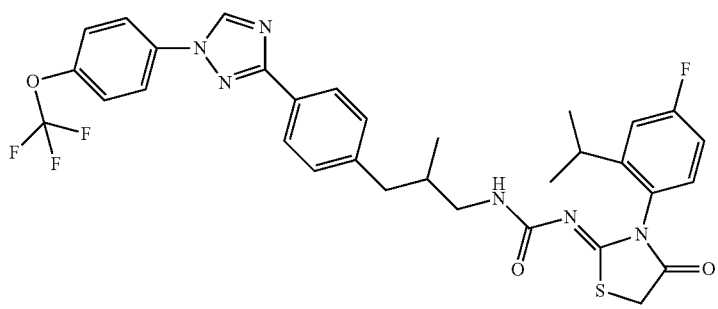 [SMILES: CC(CNC(=O)/N=C1\SCC(=O)N1c1ccc(F)cc1C(C)C)Cc1ccc(-c2ncn(-c3ccc(OC(F)(F)F)cc3)n2)cc1]
P1154

TABLE P-Two-continued
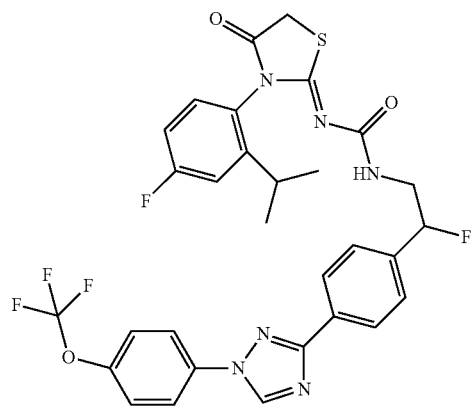 [SMILES: CC(C)c1cc(F)ccc1N1C(=O)CS/C1=N\C(=O)NCC(F)c1ccc(-c2ncn(-c3ccc(OC(F)(F)F)cc3)n2)cc1] P1155
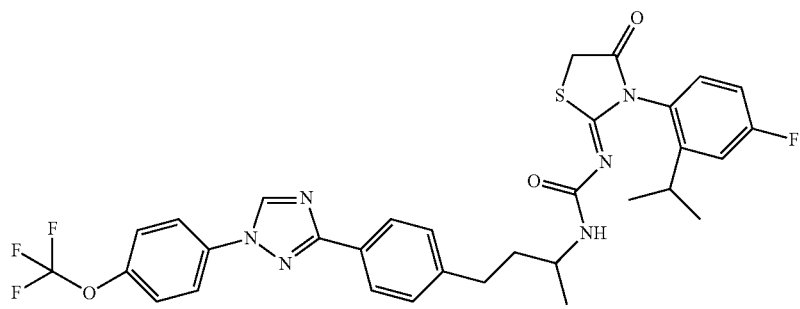 [SMILES: CC(CCc1ccc(-c2ncn(-c3ccc(OC(F)(F)F)cc3)n2)cc1)NC(=O)/N=C1\SCC(=O)N1c1ccc(F)cc1C(C)C] P1156
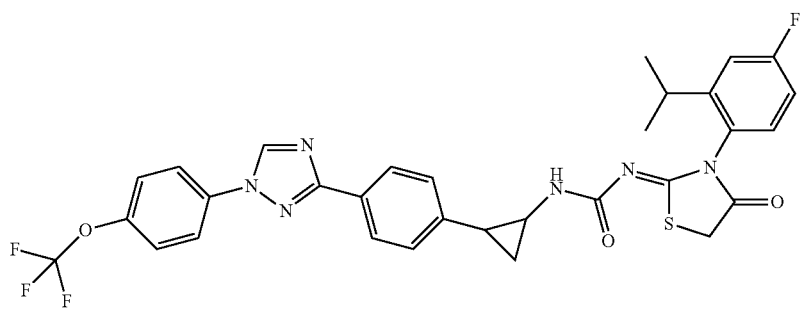 [SMILES: CC(C)c1cc(F)ccc1N1C(=O)CS/C1=N\C(=O)NC1CC1c1ccc(-c2ncn(-c3ccc(OC(F)(F)F)cc3)n2)cc1] P1157
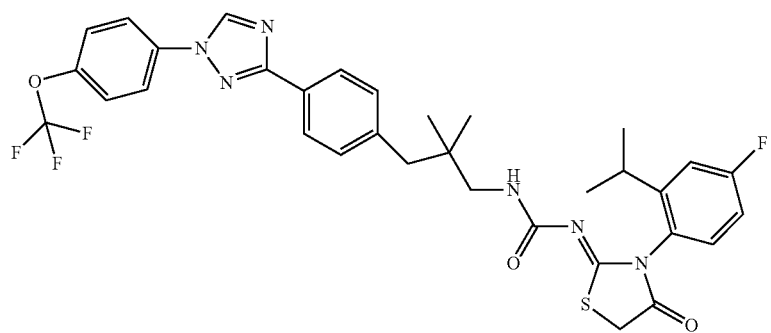 [SMILES: CC(C)c1cc(F)ccc1N1C(=O)CS/C1=N\C(=O)NCC(C)(C)Cc1ccc(-c2ncn(-c3ccc(OC(F)(F)F)cc3)n2)cc1] P1158

TABLE P-Two-continued
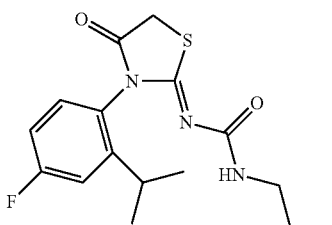
P1159
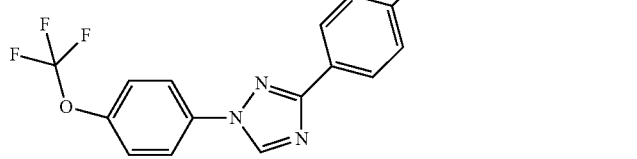
P1160
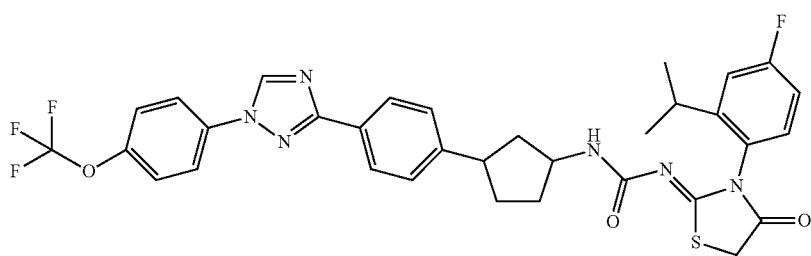 [SMILES: CC(C)c1cc(F)ccc1N1C(=O)CS/C1=N\C(=O)NC1CCC(c2ccc(-c3ncn(-c4ccc(OC(F)(F)F)cc4)n3)cc2)C1]
P1161
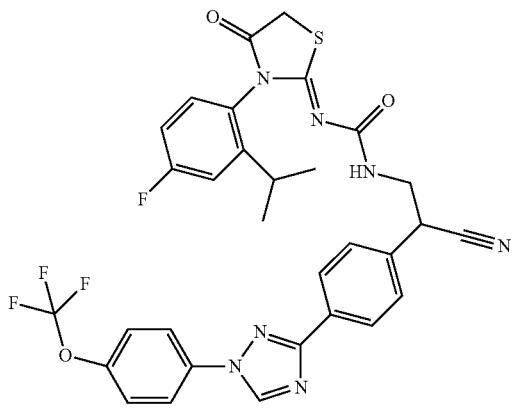 [SMILES: CC(C)c1cc(F)ccc1N1C(=O)CS/C1=N\C(=O)NCC(C#N)c1ccc(-c2ncn(-c3ccc(OC(F)(F)F)cc3)n2)cc1]
P1162

TABLE P-Two-continued
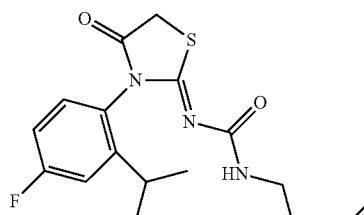
P1163
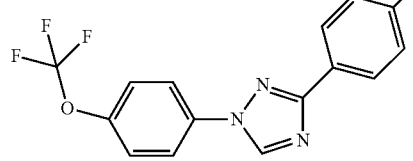
P1164
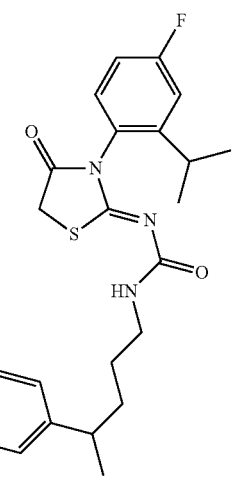
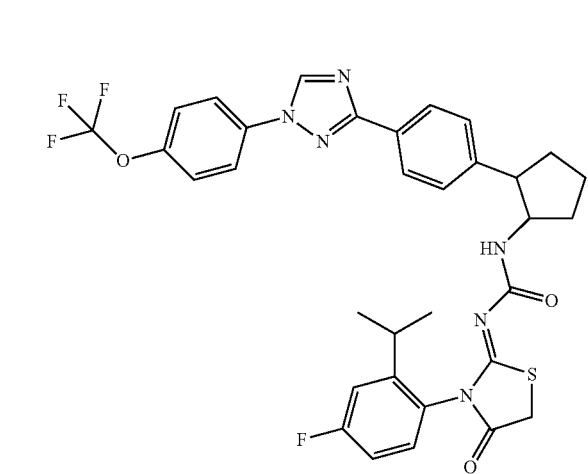 [SMILES: CC(C)c1cc(F)ccc1N1C(=O)CS/C1=N\C(=O)NC1CCCC1c1ccc(-c2ncn(-c3ccc(OC(F)(F)F)cc3)n2)cc1]
P1165

TABLE P-Two-continued
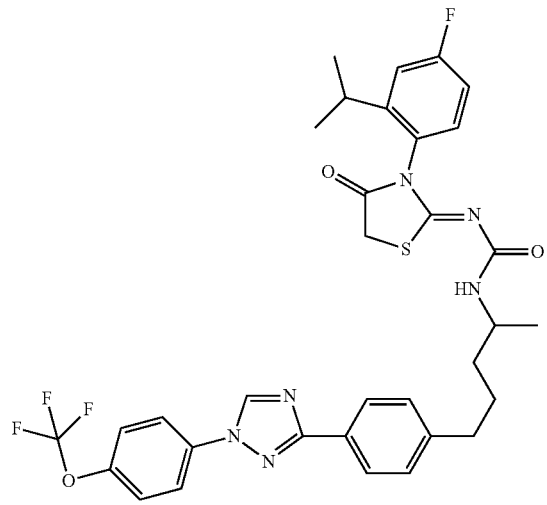 [SMILES: CC(CCCc1ccc(-c2ncn(-c3ccc(OC(F)(F)F)cc3)n2)cc1)NC(=O)/N=C1\SCC(=O)N1c1ccc(F)cc1C(C)C]
P1166
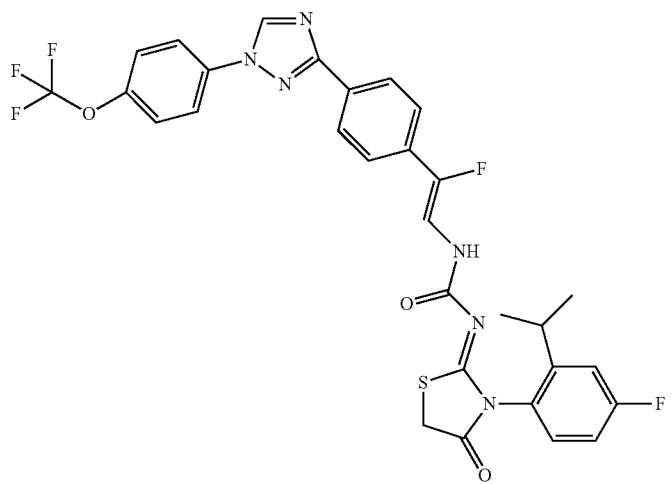 [SMILES: CC(C)c1cc(F)ccc1N1C(=O)CS/C1=N\C(=O)N/C=C(\F)c1ccc(-c2ncn(-c3ccc(OC(F)(F)F)cc3)n2)cc1]
P1167
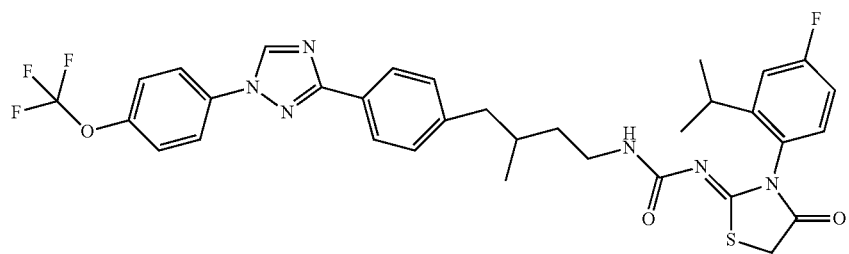 [SMILES: CC(CCNC(=O)/N=C1\SCC(=O)N1c1ccc(F)cc1C(C)C)Cc1ccc(-c2ncn(-c3ccc(OC(F)(F)F)cc3)n2)cc1]
P1168

TABLE P-Two-continued
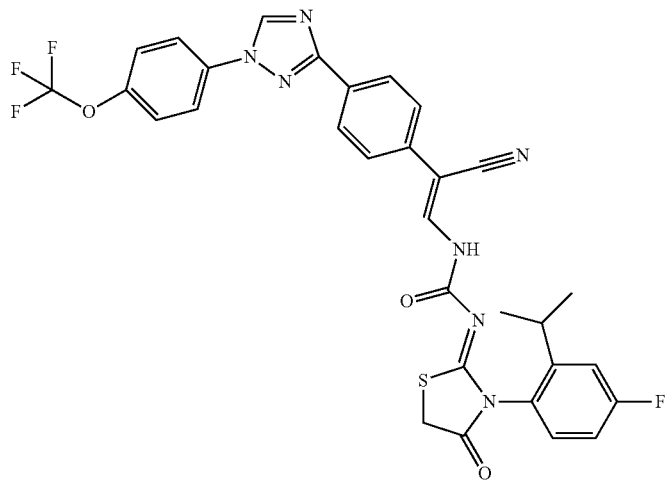 [SMILES: CC(C)c1cc(F)ccc1N1C(=O)CS/C1=N\C(=O)N/C=C(\C#N)c1ccc(-c2ncn(-c3ccc(OC(F)(F)F)cc3)n2)cc1]
P1169
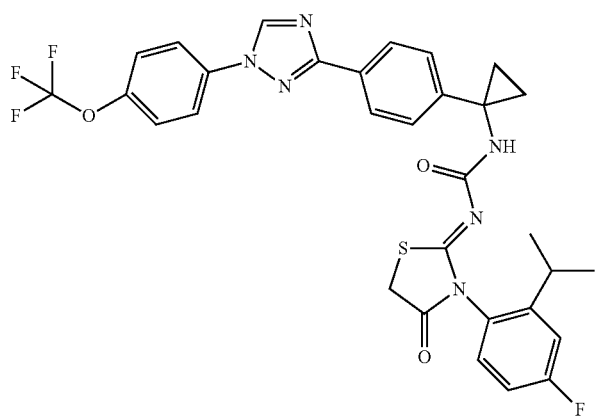 [SMILES: CC(C)c1cc(F)ccc1N1C(=O)CS/C1=N\C(=O)NC1(c2ccc(-c3ncn(-c4ccc(OC(F)(F)F)cc4)n3)cc2)CC1]
P1170
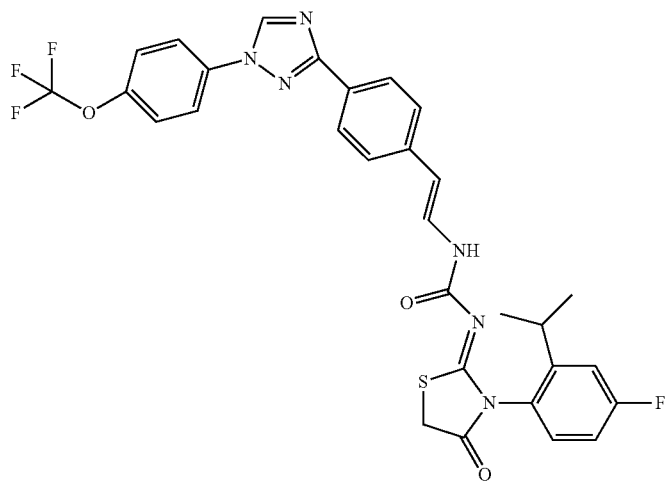 [SMILES: CC(C)c1cc(F)ccc1N1C(=O)CS/C1=N\C(=O)N/C=C/c1ccc(-c2ncn(-c3ccc(OC(F)(F)F)cc3)n2)cc1]
P1171

TABLE P-Two-continued
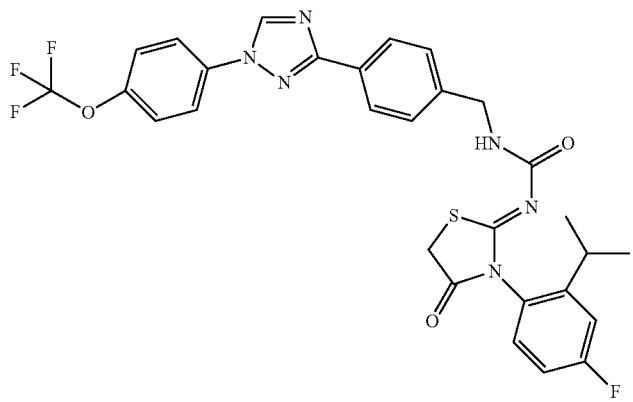 [SMILES: CC(C)c1cc(F)ccc1N1C(=O)CS/C1=N\C(=O)NCc1ccc(-c2ncn(-c3ccc(OC(F)(F)F)cc3)n2)cc1]
P1172
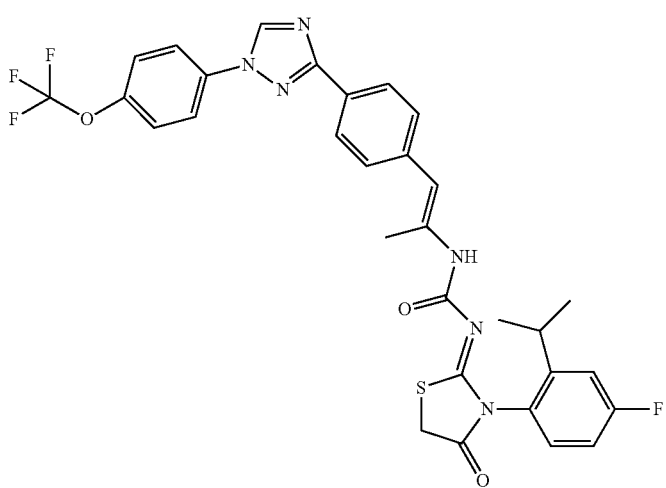 [SMILES: C/C(=C\c1ccc(-c2ncn(-c3ccc(OC(F)(F)F)cc3)n2)cc1)NC(=O)/N=C1\SCC(=O)N1c1ccc(F)cc1C(C)C]
P1173
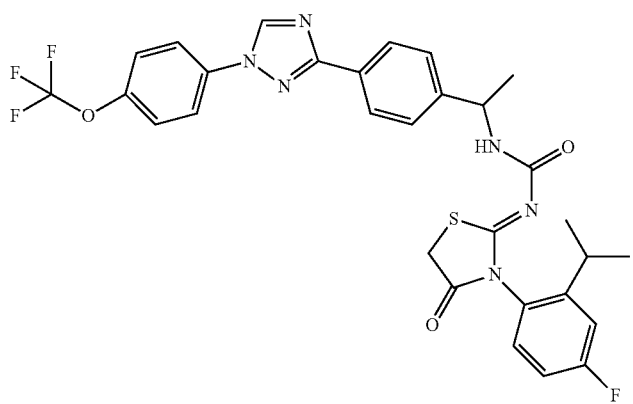 [SMILES: CC(C)c1cc(F)ccc1N1C(=O)CS/C1=N\C(=O)NC(C)c1ccc(-c2ncn(-c3ccc(OC(F)(F)F)cc3)n2)cc1]
P1174

TABLE P-Two-continued
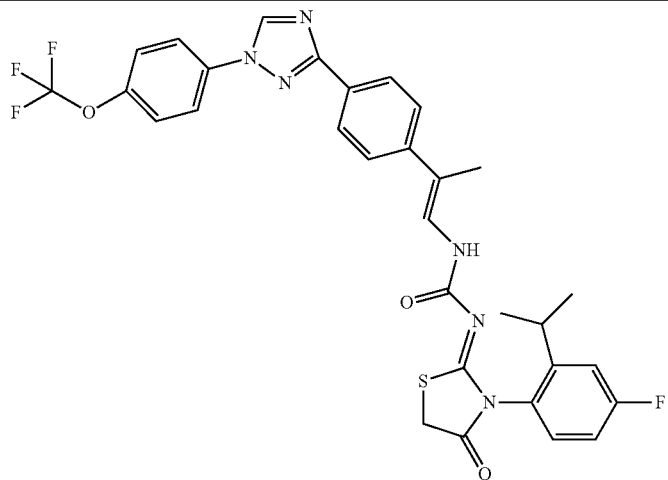
P1175
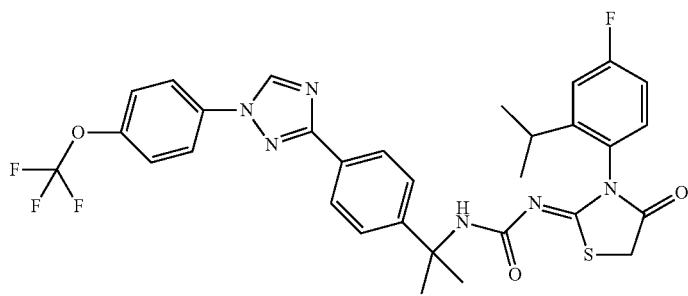 [SMILES: CC(C)c1cc(F)ccc1N1C(=O)CS/C1=N\C(=O)NC(C)(C)c1ccc(-c2ncn(-c3ccc(OC(F)(F)F)cc3)n2)cc1]
P1176
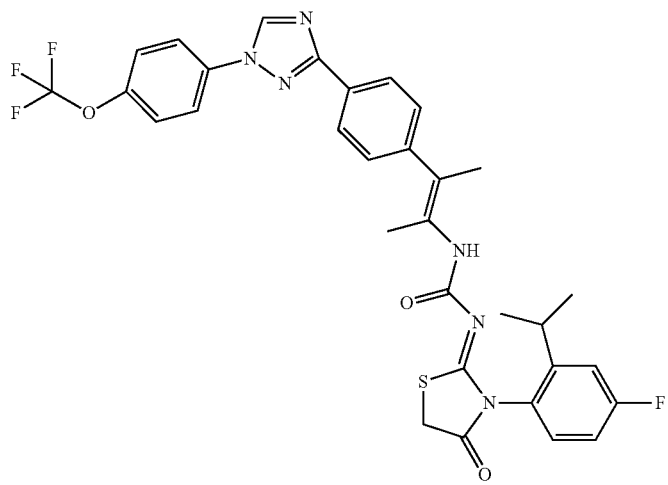 [SMILES: C/C(NC(=O)/N=C1\SCC(=O)N1c1ccc(F)cc1C(C)C)=C(/C)c1ccc(-c2ncn(-c3ccc(OC(F)(F)F)cc3)n2)cc1]
P1177
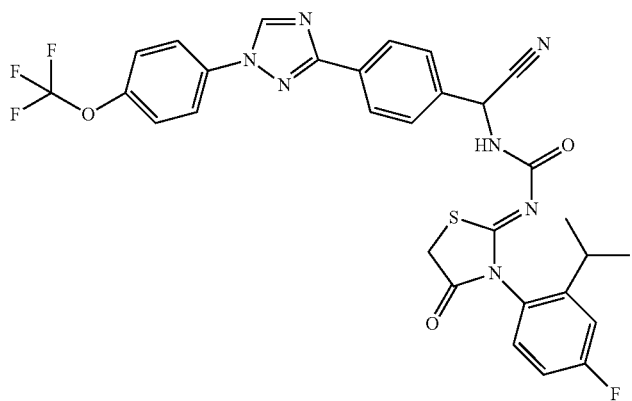 [SMILES: CC(C)c1cc(F)ccc1N1C(=O)CS/C1=N\C(=O)NC(C#N)c1ccc(-c2ncn(-c3ccc(OC(F)(F)F)cc3)n2)cc1]
P1178

TABLE P-Two-continued
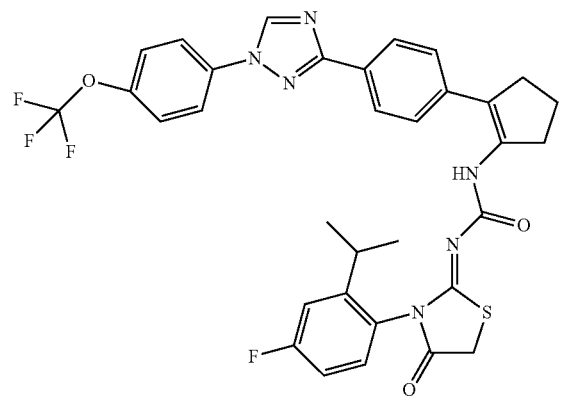 [SMILES: CC(C)c1cc(F)ccc1N1C(=O)CS/C1=N\C(=O)NC1=C(c2ccc(-c3ncn(-c4ccc(OC(F)(F)F)cc4)n3)cc2)CCC1]
P1179
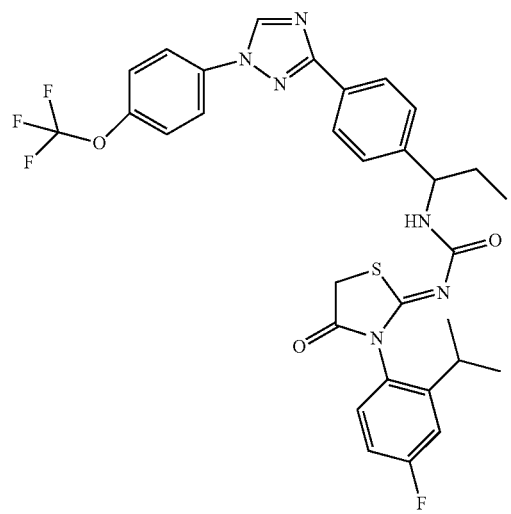 [SMILES: CCC(NC(=O)/N=C1\SCC(=O)N1c1ccc(F)cc1C(C)C)c1ccc(-c2ncn(-c3ccc(OC(F)(F)F)cc3)n2)cc1]
P1180
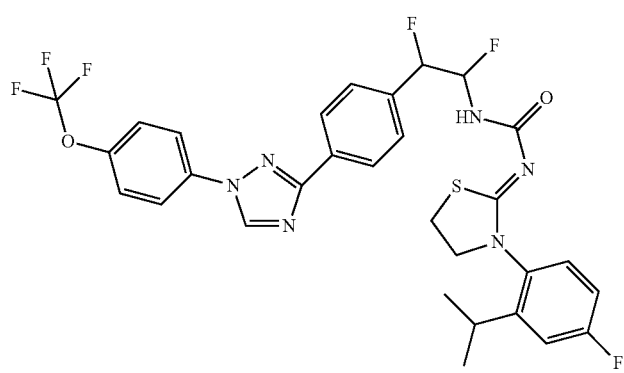 [SMILES: CC(C)c1cc(F)ccc1N1CCS/C1=N\C(=O)NC(F)C(F)c1ccc(-c2ncn(-c3ccc(OC(F)(F)F)cc3)n2)cc1]
P1181
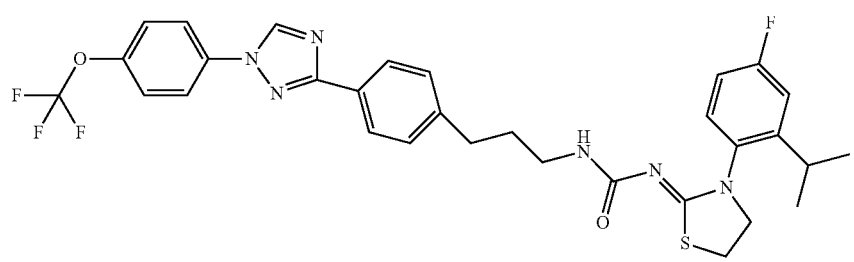 [SMILES: CC(C)c1cc(F)ccc1N1CCS/C1=N\C(=O)NCCCc1ccc(-c2ncn(-c3ccc(OC(F)(F)F)cc3)n2)cc1]
P1182

TABLE P-Two-continued
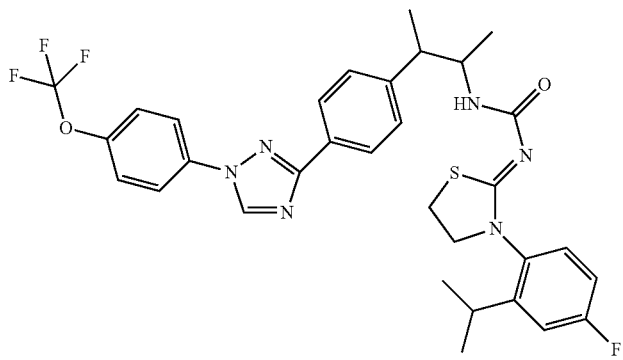 [SMILES: CC(C)c1cc(F)ccc1N1CCS/C1=N\C(=O)NC(C)C(C)c1ccc(-c2ncn(-c3ccc(OC(F)(F)F)cc3)n2)cc1]
P1183
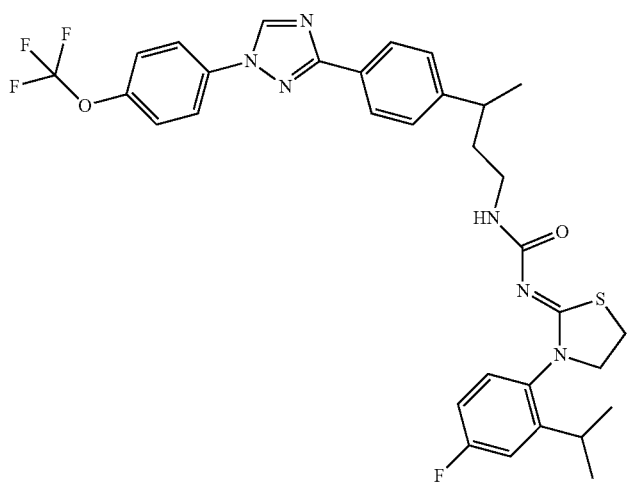 [SMILES: CC(C)c1cc(F)ccc1N1CCS/C1=N\C(=O)NCCC(C)c1ccc(-c2ncn(-c3ccc(OC(F)(F)F)cc3)n2)cc1]
P1184
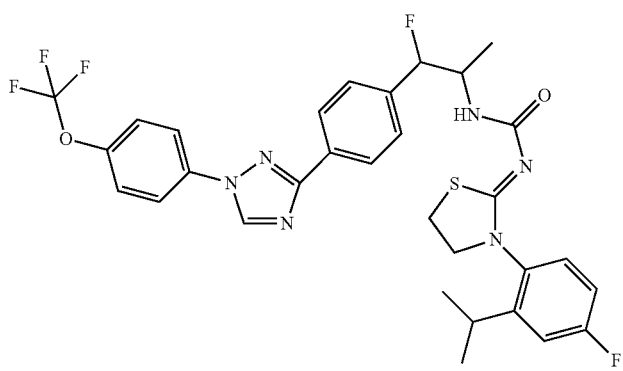 [SMILES: CC(C)c1cc(F)ccc1N1CCS/C1=N\C(=O)NC(C)C(F)c1ccc(-c2ncn(-c3ccc(OC(F)(F)F)cc3)n2)cc1]
P1185
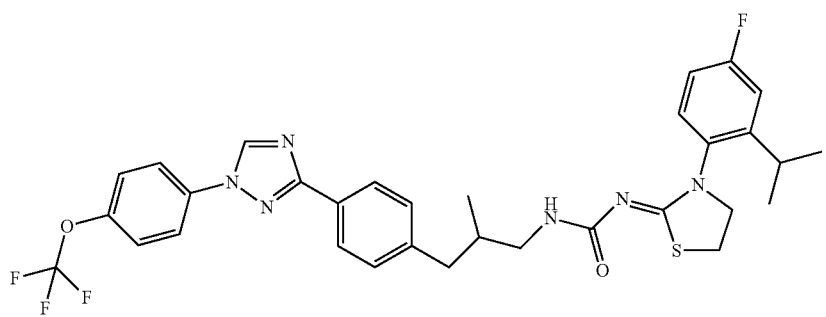 [SMILES: CC(CNC(=O)/N=C1\SCCN1c1ccc(F)cc1C(C)C)Cc1ccc(-c2ncn(-c3ccc(OC(F)(F)F)cc3)n2)cc1]
P1186

TABLE P-Two-continued
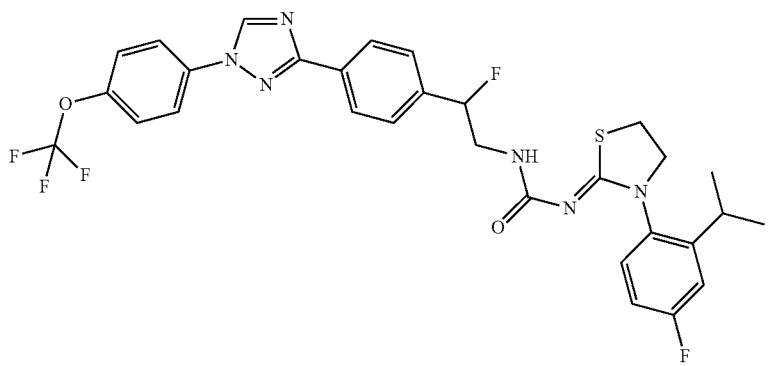 [SMILES: CC(C)c1cc(F)ccc1N1CCS/C1=N\C(=O)NCC(F)c1ccc(-c2ncn(-c3ccc(OC(F)(F)F)cc3)n2)cc1] P1187
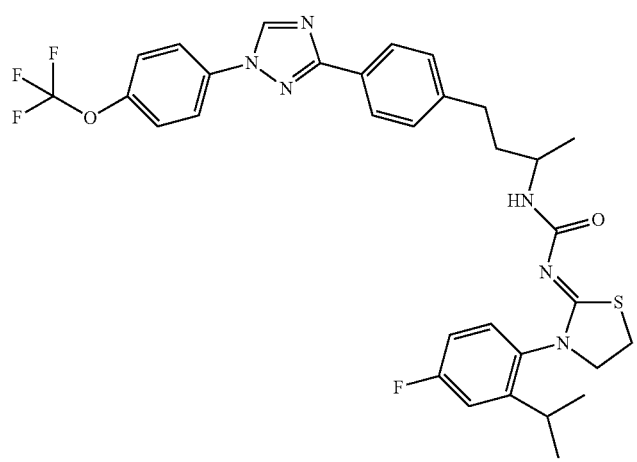 [SMILES: CC(CCc1ccc(-c2ncn(-c3ccc(OC(F)(F)F)cc3)n2)cc1)NC(=O)/N=C1\SCCN1c1ccc(F)cc1C(C)C] P1188
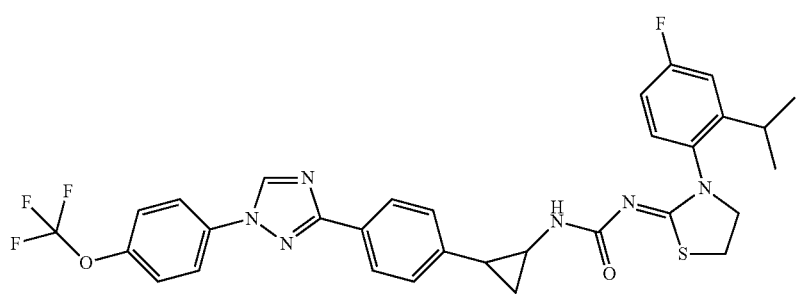 [SMILES: CC(C)c1cc(F)ccc1N1CCS/C1=N\C(=O)NC1CC1c1ccc(-c2ncn(-c3ccc(OC(F)(F)F)cc3)n2)cc1] P1189
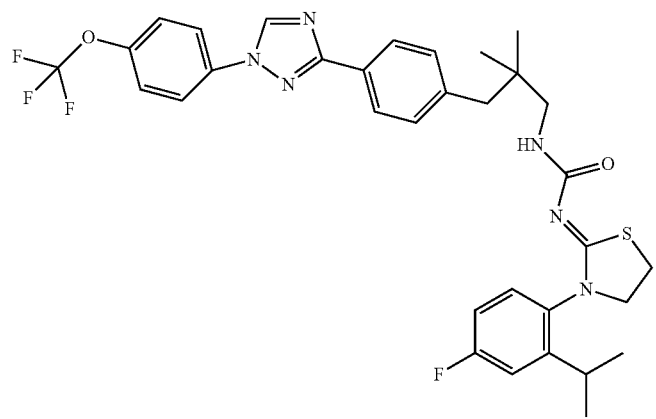 [SMILES: CC(C)c1cc(F)ccc1N1CCS/C1=N\C(=O)NCC(C)(C)Cc1ccc(-c2ncn(-c3ccc(OC(F)(F)F)cc3)n2)cc1] P1190

TABLE P-Two-continued
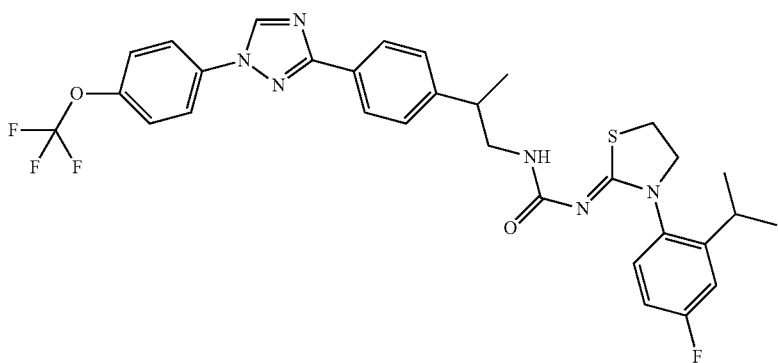 [SMILES: CC(C)c1cc(F)ccc1N1CCS/C1=N\C(=O)NCC(C)c1ccc(-c2ncn(-c3ccc(OC(F)(F)F)cc3)n2)cc1]
P1191
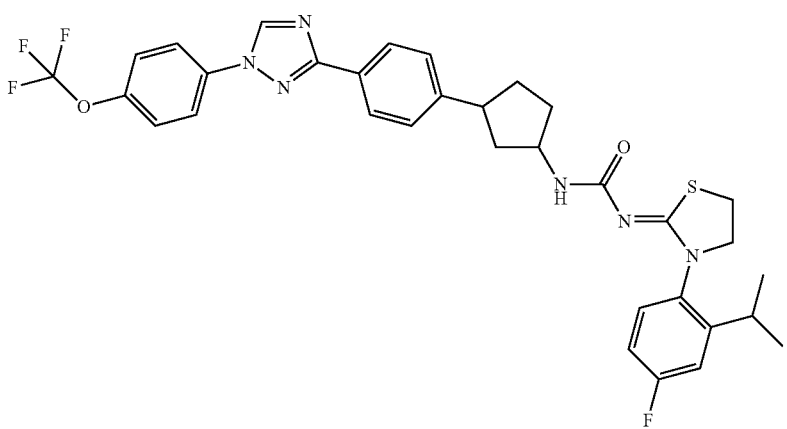 [SMILES: CC(C)c1cc(F)ccc1N1CCS/C1=N\C(=O)NC1CCC(c2ccc(-c3ncn(-c4ccc(OC(F)(F)F)cc4)n3)cc2)C1]
P1192
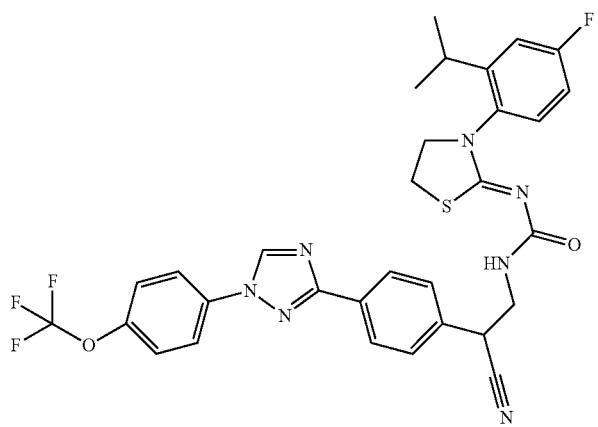 [SMILES: CC(C)c1cc(F)ccc1N1CCS/C1=N\C(=O)NCC(C#N)c1ccc(-c2ncn(-c3ccc(OC(F)(F)F)cc3)n2)cc1]
P1193
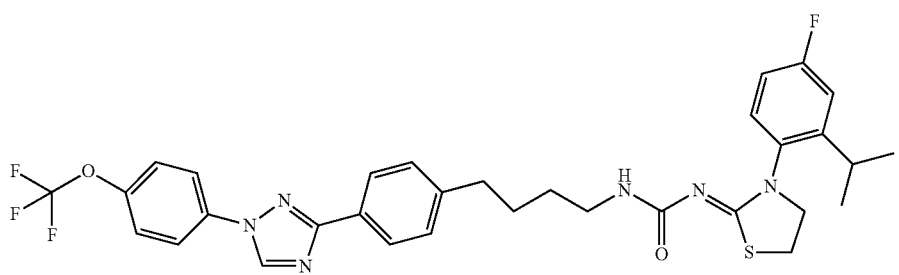 [SMILES: CC(C)c1cc(F)ccc1N1CCS/C1=N\C(=O)NCCCCc1ccc(-c2ncn(-c3ccc(OC(F)(F)F)cc3)n2)cc1]
P1194

TABLE P-Two-continued
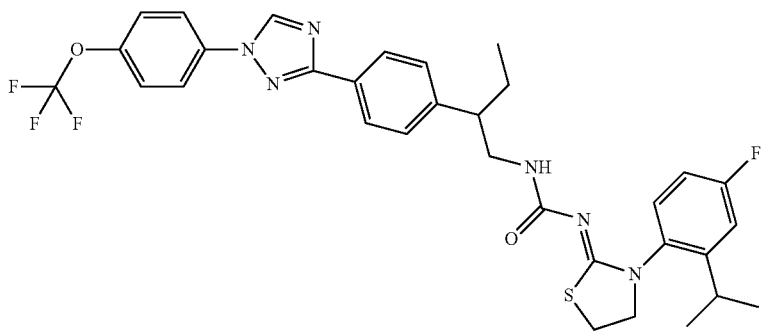 [SMILES: CCC(CNC(=O)/N=C1\SCCN1c1ccc(F)cc1C(C)C)c1ccc(-c2ncn(-c3ccc(OC(F)(F)F)cc3)n2)cc1]
P1195
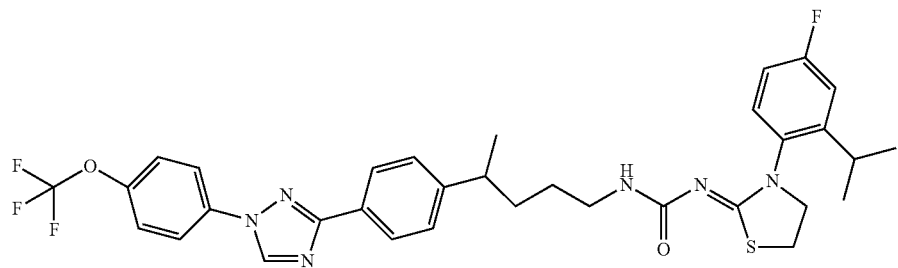 [SMILES: CC(C)c1cc(F)ccc1N1CCS/C1=N\C(=O)NCCCC(C)c1ccc(-c2ncn(-c3ccc(OC(F)(F)F)cc3)n2)cc1]
P1196
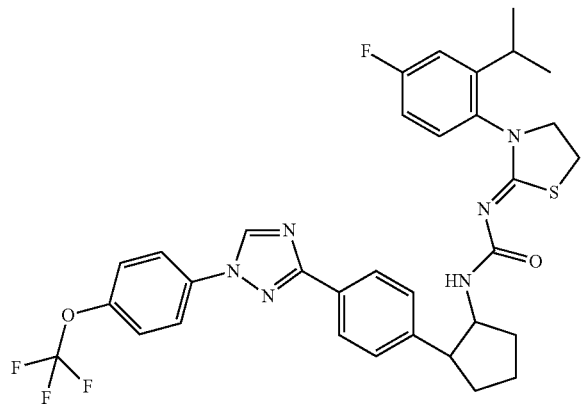 [SMILES: CC(C)c1cc(F)ccc1N1CCS/C1=N\C(=O)NC1CCCC1c1ccc(-c2ncn(-c3ccc(OC(F)(F)F)cc3)n2)cc1]
P1197
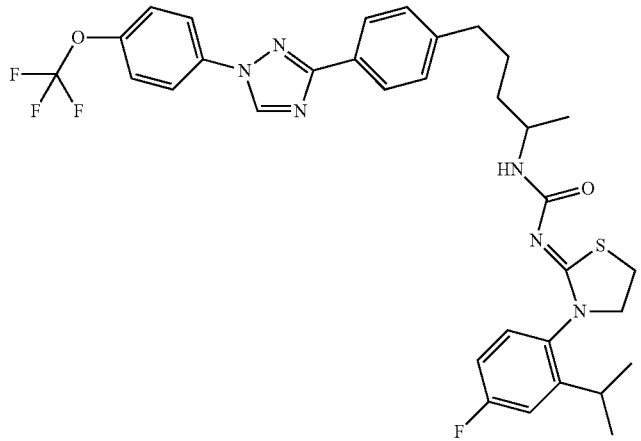 [SMILES: CC(CCCc1ccc(-c2ncn(-c3ccc(OC(F)(F)F)cc3)n2)cc1)NC(=O)/N=C1\SCCN1c1ccc(F)cc1C(C)C]
P1198

TABLE P-Two-continued
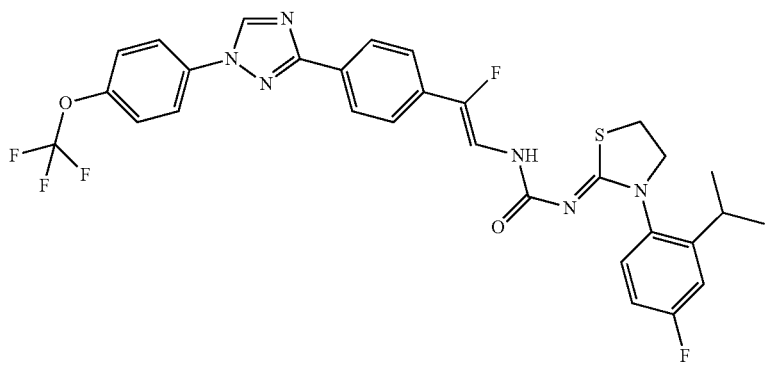 [SMILES: CC(C)c1cc(F)ccc1N1CCS/C1=N\C(=O)N/C=C(\F)c1ccc(-c2ncn(-c3ccc(OC(F)(F)F)cc3)n2)cc1]
P1199
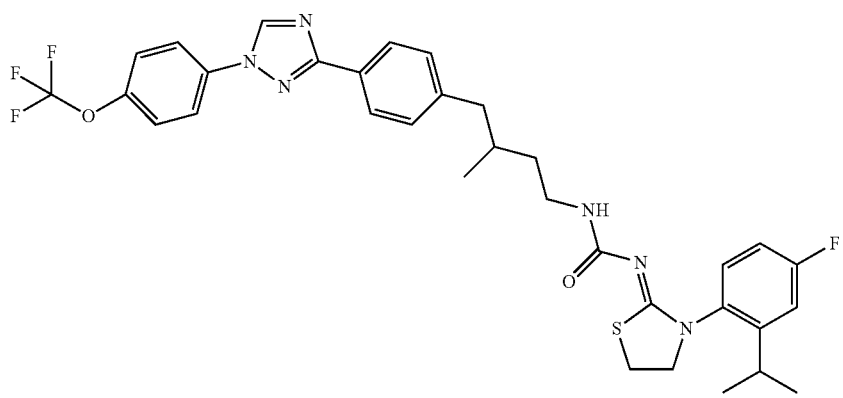 [SMILES: CC(CCNC(=O)/N=C1\SCCN1c1ccc(F)cc1C(C)C)Cc1ccc(-c2ncn(-c3ccc(OC(F)(F)F)cc3)n2)cc1]
P1200
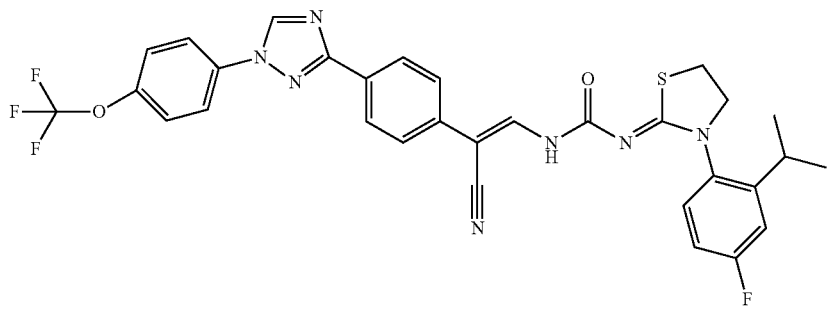 [SMILES: CC(C)c1cc(F)ccc1N1CCS/C1=N\C(=O)N/C=C(\C#N)c1ccc(-c2ncn(-c3ccc(OC(F)(F)F)cc3)n2)cc1]
P1201
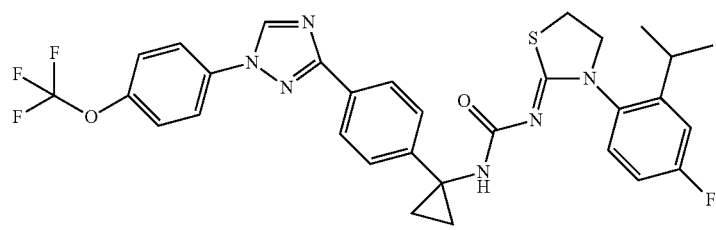 [SMILES: CC(C)c1cc(F)ccc1N1CCS/C1=N\C(=O)NC1(c2ccc(-c3ncn(-c4ccc(OC(F)(F)F)cc4)n3)cc2)CC1]
P1202
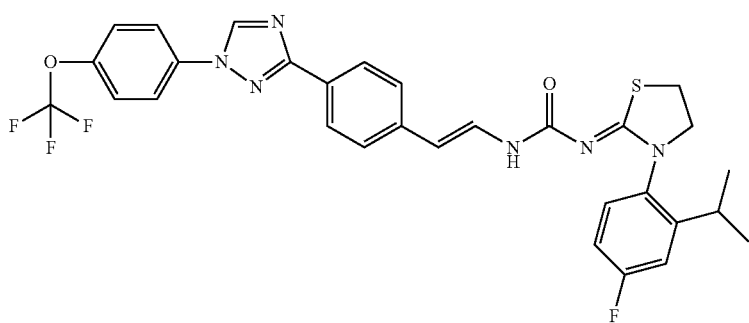 [SMILES: CC(C)c1cc(F)ccc1N1CCS/C1=N\C(=O)N/C=C/c1ccc(-c2ncn(-c3ccc(OC(F)(F)F)cc3)n2)cc1]
P1203

TABLE P-Two-continued
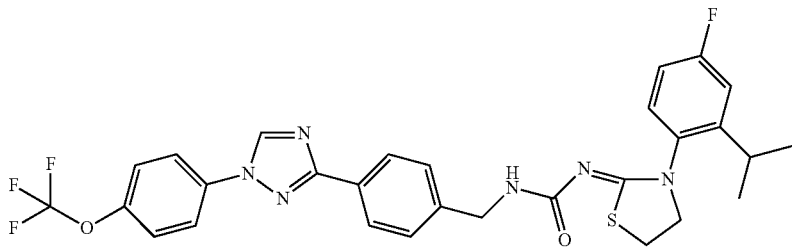 [SMILES: CC(C)c1cc(F)ccc1N1CCS/C1=N\C(=O)NCc1ccc(-c2ncn(-c3ccc(OC(F)(F)F)cc3)n2)cc1]
P1204
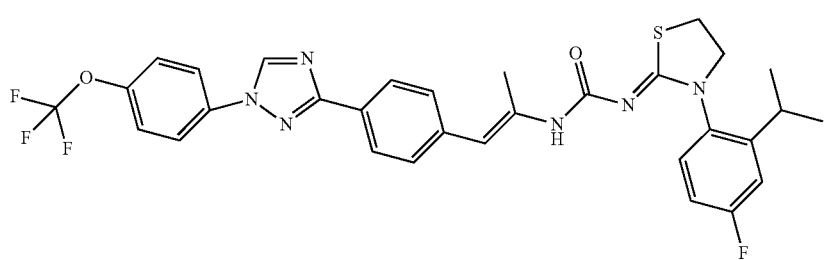 [SMILES: C/C(=C\c1ccc(-c2ncn(-c3ccc(OC(F)(F)F)cc3)n2)cc1)NC(=O)/N=C1\SCCN1c1ccc(F)cc1C(C)C]
P1205
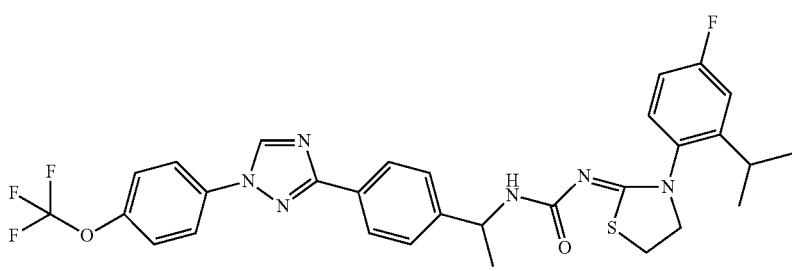 [SMILES: CC(C)c1cc(F)ccc1N1CCS/C1=N\C(=O)NC(C)c1ccc(-c2ncn(-c3ccc(OC(F)(F)F)cc3)n2)cc1]
P1206
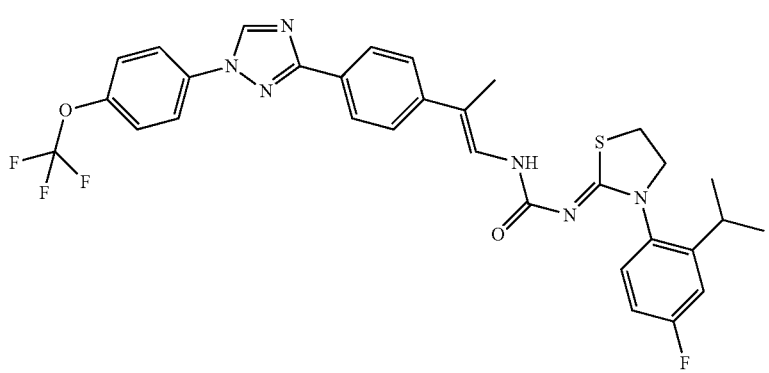 [SMILES: C/C(=C\NC(=O)/N=C1\SCCN1c1ccc(F)cc1C(C)C)c1ccc(-c2ncn(-c3ccc(OC(F)(F)F)cc3)n2)cc1]
P1207
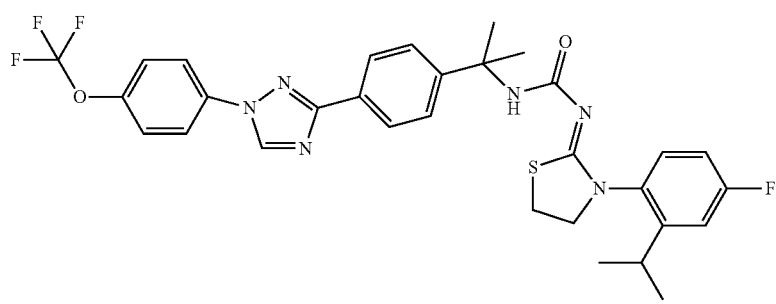 [SMILES: CC(C)c1cc(F)ccc1N1CCS/C1=N\C(=O)NC(C)(C)c1ccc(-c2ncn(-c3ccc(OC(F)(F)F)cc3)n2)cc1]
P1208

TABLE P-Two-continued
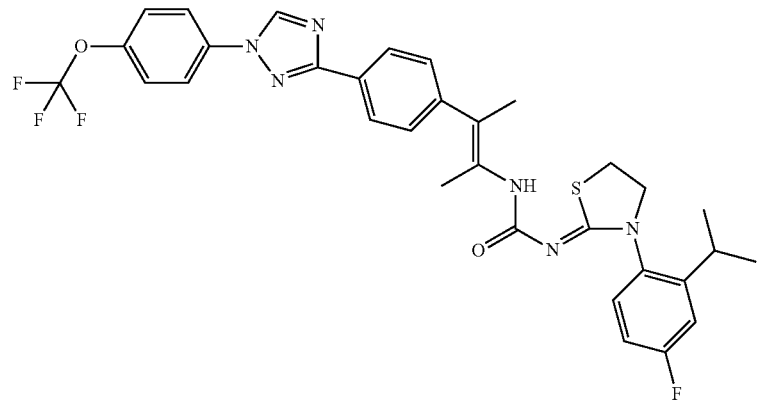 [SMILES: C/C(NC(=O)/N=C1\SCCN1c1ccc(F)cc1C(C)C)=C(/C)c1ccc(-c2ncn(-c3ccc(OC(F)(F)F)cc3)n2)cc1]
P1209
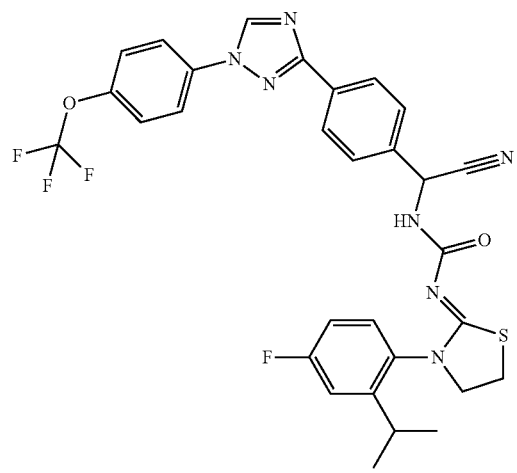 [SMILES: CC(C)c1cc(F)ccc1N1CCS/C1=N\C(=O)NC(C#N)c1ccc(-c2ncn(-c3ccc(OC(F)(F)F)cc3)n2)cc1]
P1210
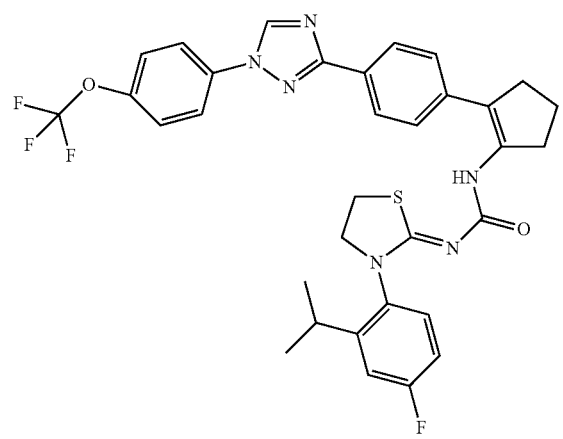 [SMILES: CC(C)c1cc(F)ccc1N1CCS/C1=N\C(=O)NC1=C(c2ccc(-c3ncn(-c4ccc(OC(F)(F)F)cc4)n3)cc2)CCC1]
P1211

TABLE P-Two-continued
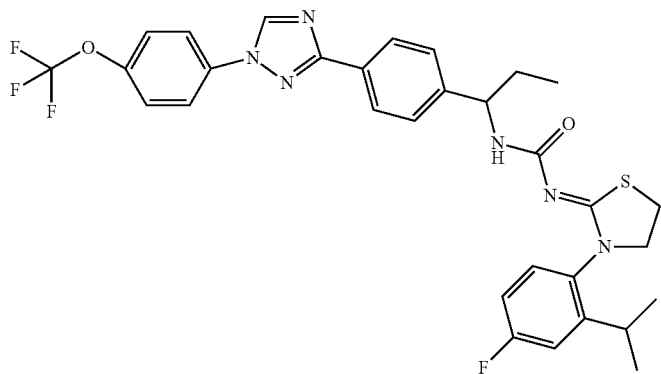 [SMILES: CCC(NC(=O)/N=C1\SCCN1c1ccc(F)cc1C(C)C)c1ccc(-c2ncn(-c3ccc(OC(F)(F)F)cc3)n2)cc1]
P1212
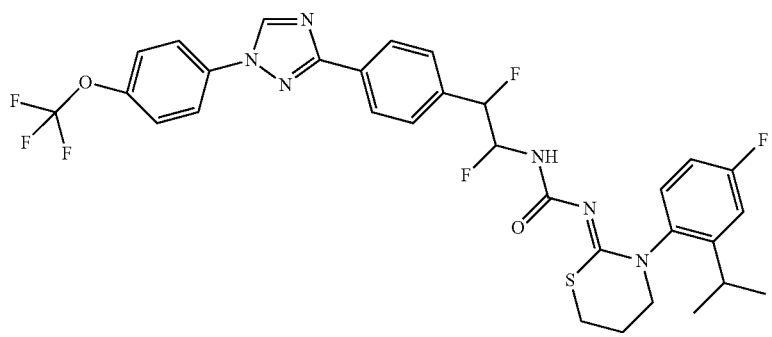 [SMILES: CC(C)c1cc(F)ccc1N1CCCS/C1=N\C(=O)NC(F)C(F)c1ccc(-c2ncn(-c3ccc(OC(F)(F)F)cc3)n2)cc1]
P1213
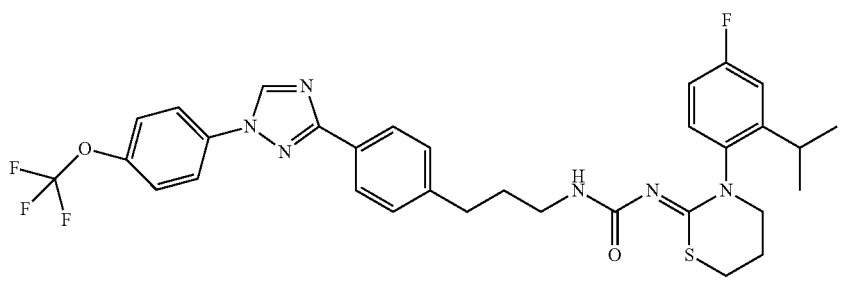 [SMILES: CC(C)c1cc(F)ccc1N1CCCS/C1=N\C(=O)NCCCc1ccc(-c2ncn(-c3ccc(OC(F)(F)F)cc3)n2)cc1]
P1214
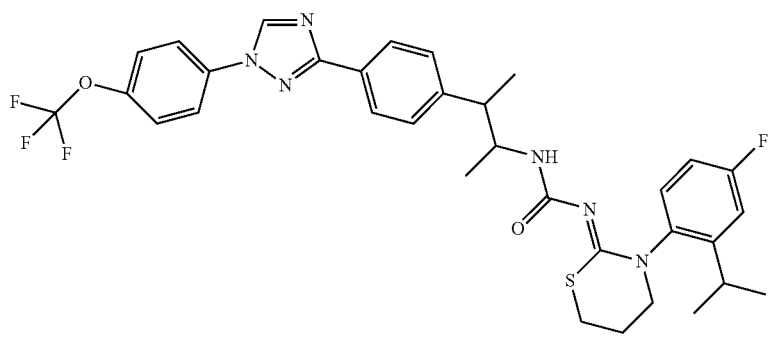 [SMILES: CC(C)c1cc(F)ccc1N1CCCS/C1=N\C(=O)NC(C)C(C)c1ccc(-c2ncn(-c3ccc(OC(F)(F)F)cc3)n2)cc1]
P1215

TABLE P-Two-continued
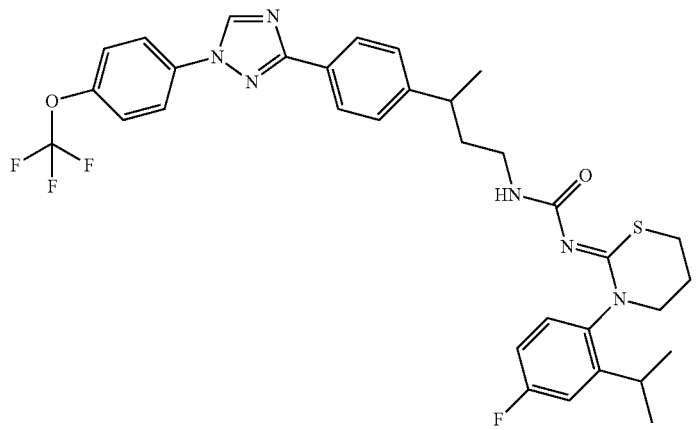 [SMILES: CC(C)c1cc(F)ccc1N1CCCS/C1=N\C(=O)NCCC(C)c1ccc(-c2ncn(-c3ccc(OC(F)(F)F)cc3)n2)cc1]
P1216
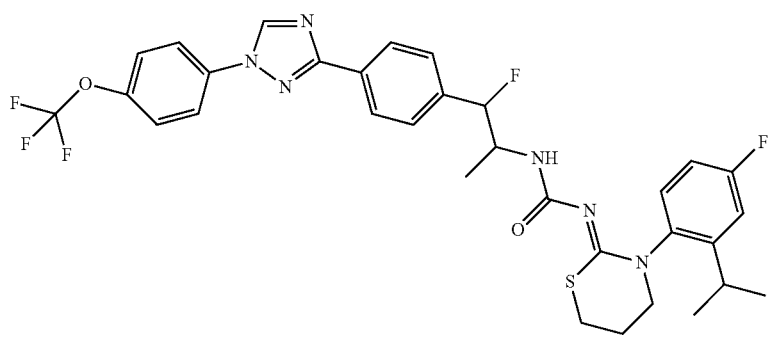 [SMILES: CC(C)c1cc(F)ccc1N1CCCS/C1=N\C(=O)NC(C)C(F)c1ccc(-c2ncn(-c3ccc(OC(F)(F)F)cc3)n2)cc1]
P1217
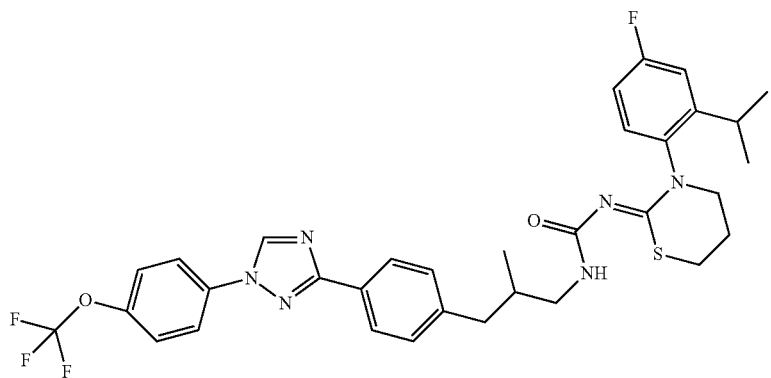 [SMILES: CC(CNC(=O)/N=C1\SCCCN1c1ccc(F)cc1C(C)C)Cc1ccc(-c2ncn(-c3ccc(OC(F)(F)F)cc3)n2)cc1]
P1218
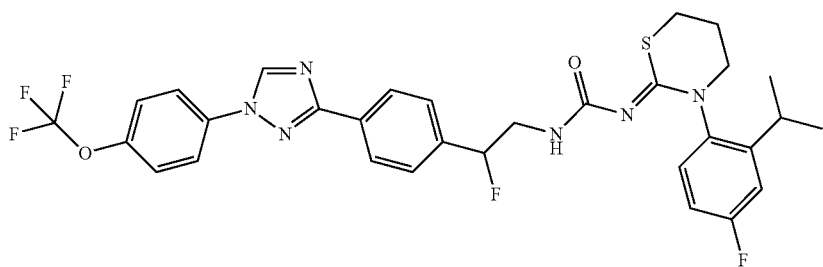
P1219

TABLE P-Two-continued
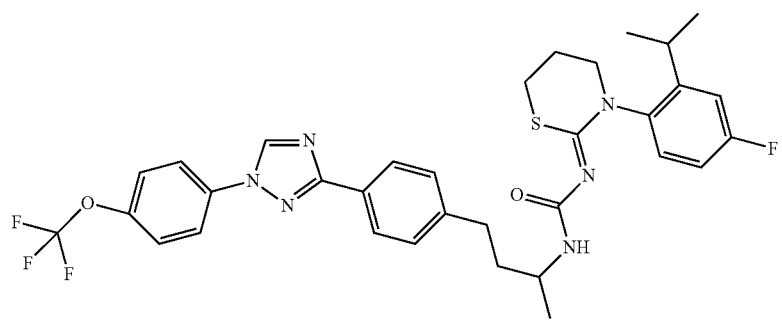 [SMILES: CC(CCc1ccc(-c2ncn(-c3ccc(OC(F)(F)F)cc3)n2)cc1)NC(=O)/N=C1\SCCCN1c1ccc(F)cc1C(C)C]
P1220
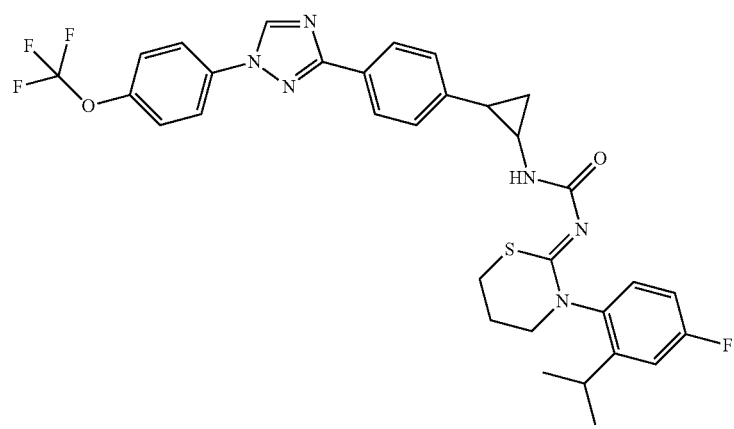 [SMILES: CC(C)c1cc(F)ccc1N1CCCS/C1=N\C(=O)NC1CC1c1ccc(-c2ncn(-c3ccc(OC(F)(F)F)cc3)n2)cc1]
P1221
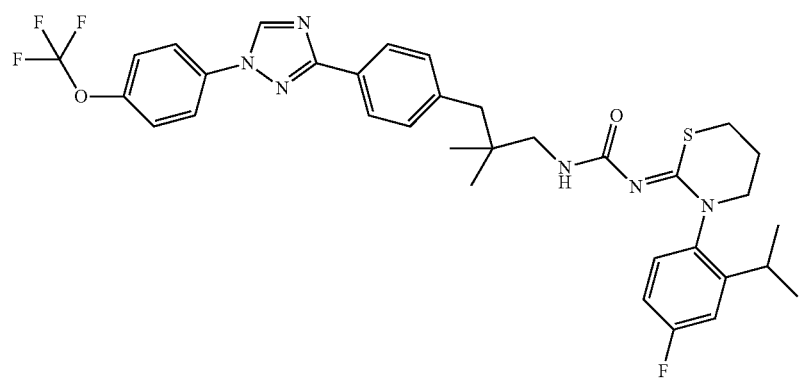 [SMILES: CC(C)c1cc(F)ccc1N1CCCS/C1=N\C(=O)NCC(C)(C)Cc1ccc(-c2ncn(-c3ccc(OC(F)(F)F)cc3)n2)cc1]
P1222
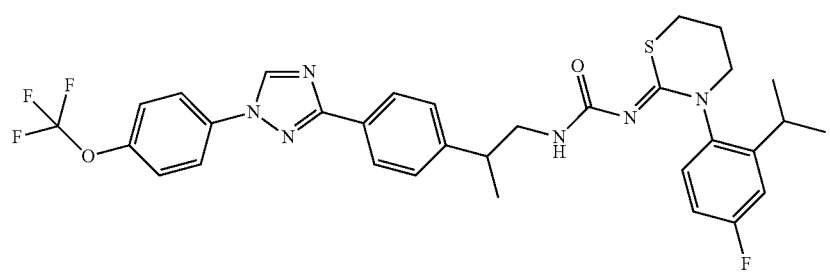 [SMILES: CC(C)c1cc(F)ccc1N1CCCS/C1=N\C(=O)NCC(C)c1ccc(-c2ncn(-c3ccc(OC(F)(F)F)cc3)n2)cc1]
P1223

TABLE P-Two-continued
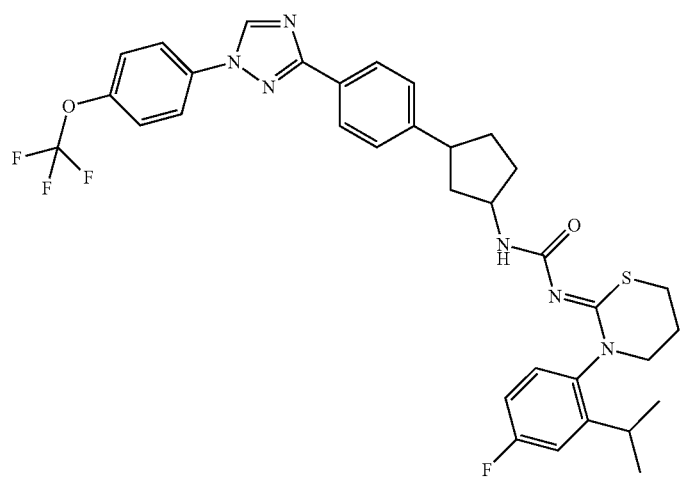 [SMILES: CC(C)c1cc(F)ccc1N1CCCS/C1=N\C(=O)NC1CCC(c2ccc(-c3ncn(-c4ccc(OC(F)(F)F)cc4)n3)cc2)C1]
P1224
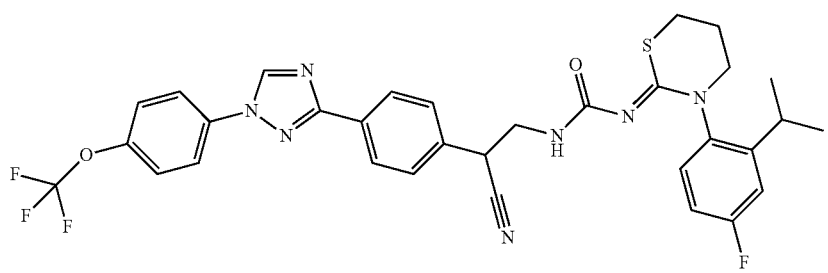 [SMILES: CC(C)c1cc(F)ccc1N1CCCS/C1=N\C(=O)NCC(C#N)c1ccc(-c2ncn(-c3ccc(OC(F)(F)F)cc3)n2)cc1]
P1225
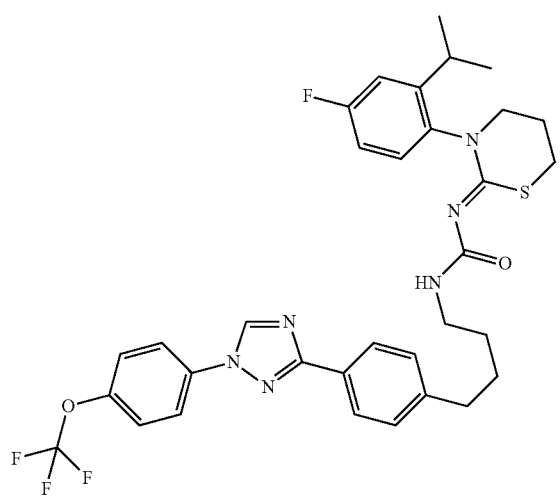 [SMILES: CC(C)c1cc(F)ccc1N1CCCS/C1=N\C(=O)NCCCCc1ccc(-c2ncn(-c3ccc(OC(F)(F)F)cc3)n2)cc1]
P1226
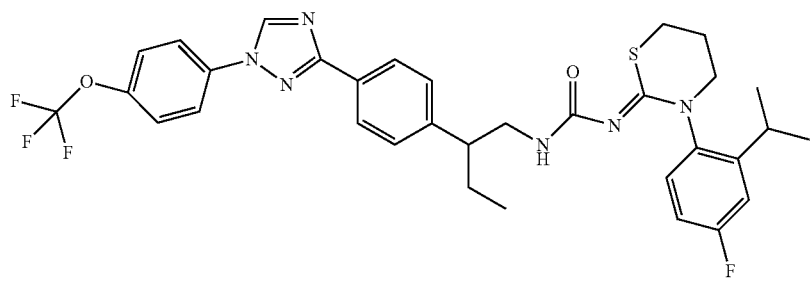 [SMILES: CCC(CNC(=O)/N=C1\SCCCN1c1ccc(F)cc1C(C)C)c1ccc(-c2ncn(-c3ccc(OC(F)(F)F)cc3)n2)cc1]
P1227

TABLE P-Two-continued
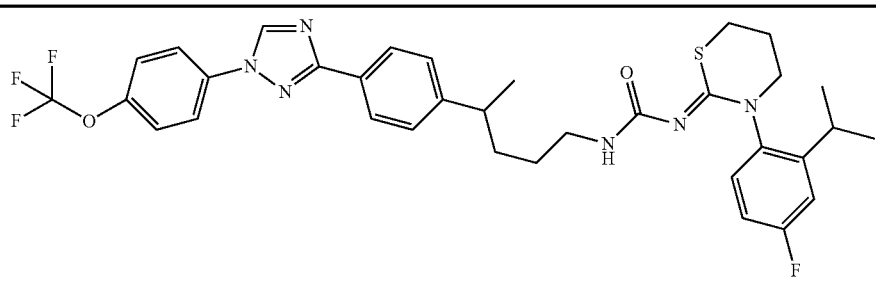
P1228
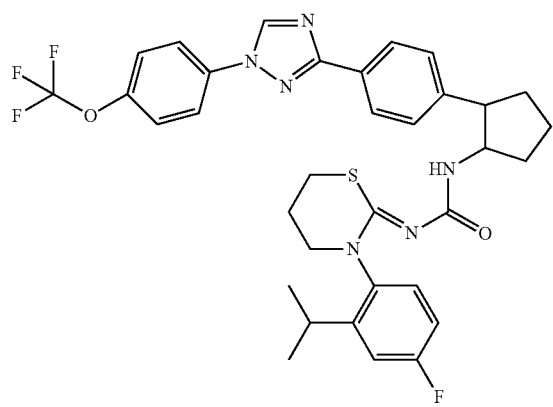 [SMILES: CC(C)c1cc(F)ccc1N1CCCS/C1=N\C(=O)NC1CCCC1c1ccc(-c2ncn(-c3ccc(OC(F)(F)F)cc3)n2)cc1]
P1229
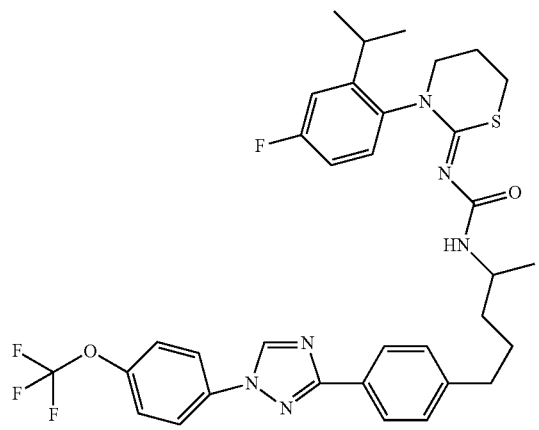 [SMILES: CC(CCCc1ccc(-c2ncn(-c3ccc(OC(F)(F)F)cc3)n2)cc1)NC(=O)/N=C1\SCCCN1c1ccc(F)cc1C(C)C]
P1230
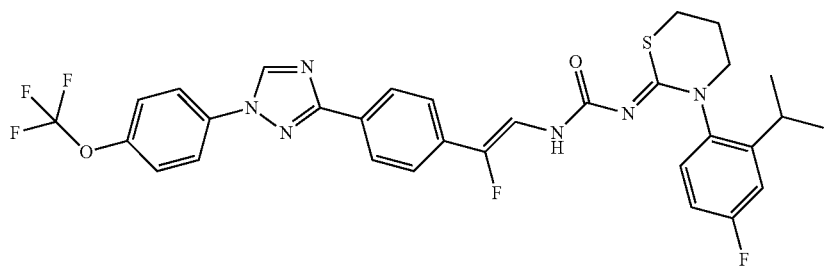
P1231

TABLE P-Two-continued
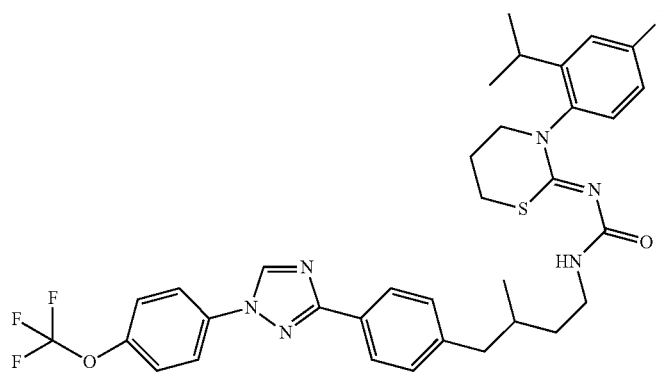
P1232
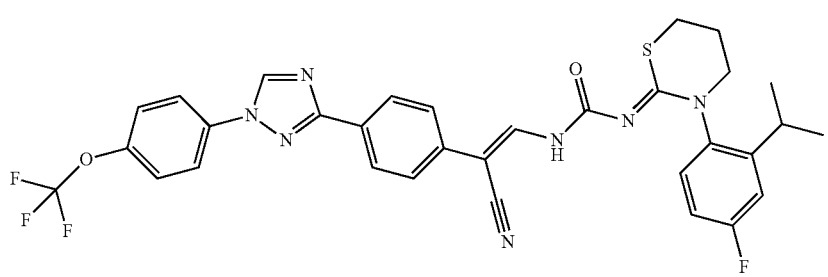 [SMILES: CC(C)c1cc(F)ccc1N1CCCS/C1=N\C(=O)N/C=C(\C#N)c1ccc(-c2ncn(-c3ccc(OC(F)(F)F)cc3)n2)cc1]
P1233
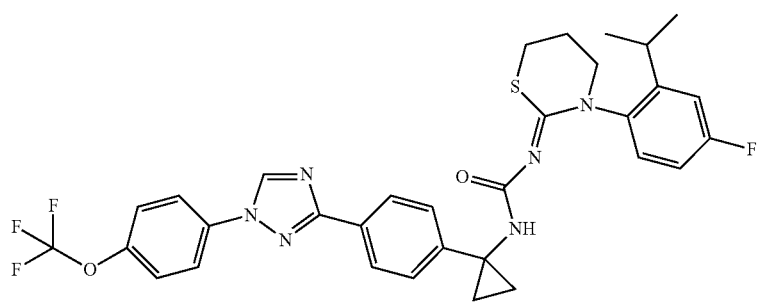 [SMILES: CC(C)c1cc(F)ccc1N1CCCS/C1=N\C(=O)NC1(c2ccc(-c3ncn(-c4ccc(OC(F)(F)F)cc4)n3)cc2)CC1]
P1234
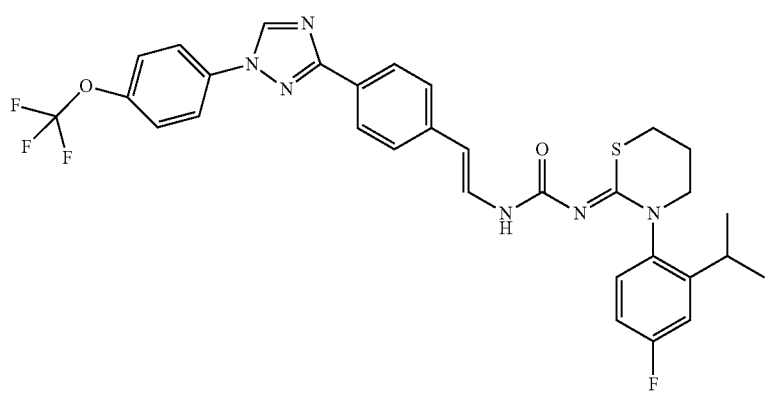 [SMILES: CC(C)c1cc(F)ccc1N1CCCS/C1=N\C(=O)N/C=C/c1ccc(-c2ncn(-c3ccc(OC(F)(F)F)cc3)n2)cc1]
P1235

TABLE P-Two-continued
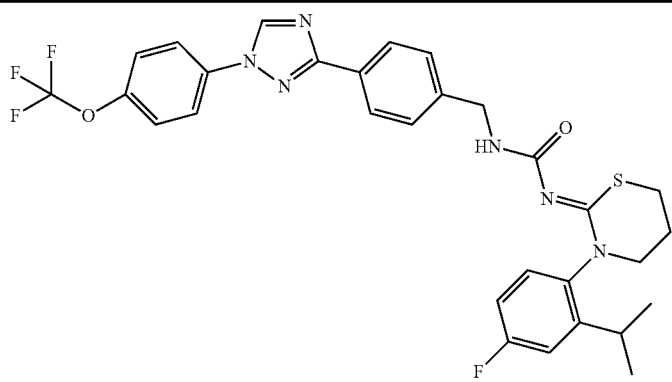 P1236
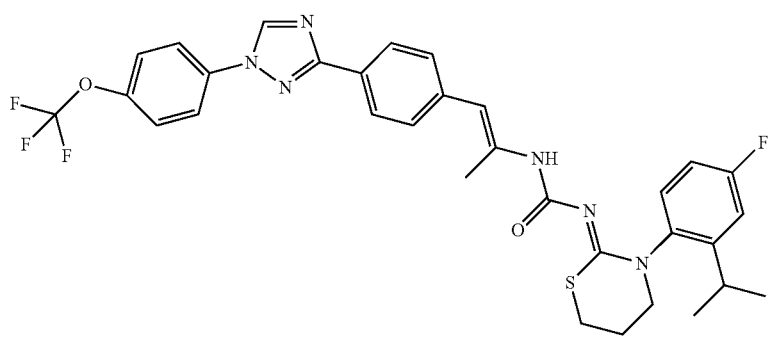 [SMILES: C/C(=C\c1ccc(-c2ncn(-c3ccc(OC(F)(F)F)cc3)n2)cc1)NC(=O)/N=C1\SCCCN1c1ccc(F)cc1C(C)C] P1237
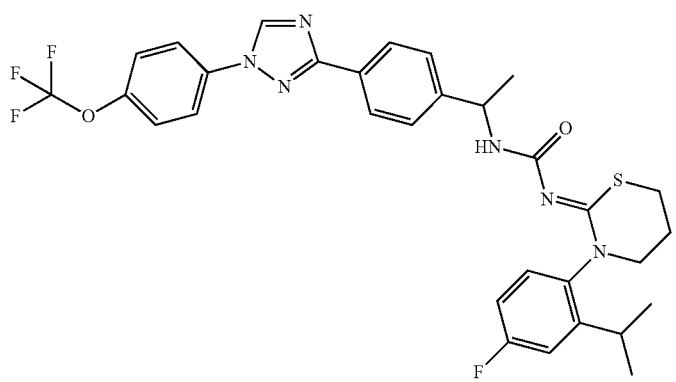 [SMILES: CC(C)c1cc(F)ccc1N1CCCS/C1=N\C(=O)NC(C)c1ccc(-c2ncn(-c3ccc(OC(F)(F)F)cc3)n2)cc1] P1238
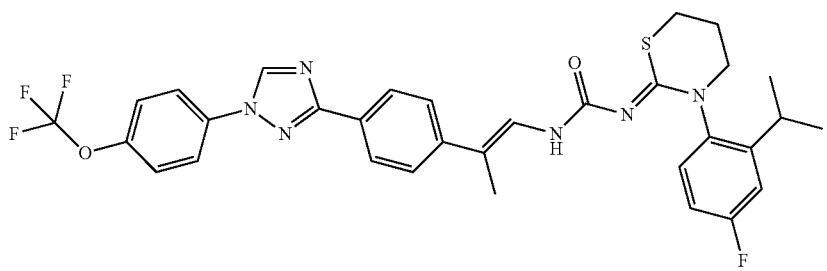 [SMILES: C/C(=C\NC(=O)/N=C1\SCCCN1c1ccc(F)cc1C(C)C)c1ccc(-c2ncn(-c3ccc(OC(F)(F)F)cc3)n2)cc1] P1239
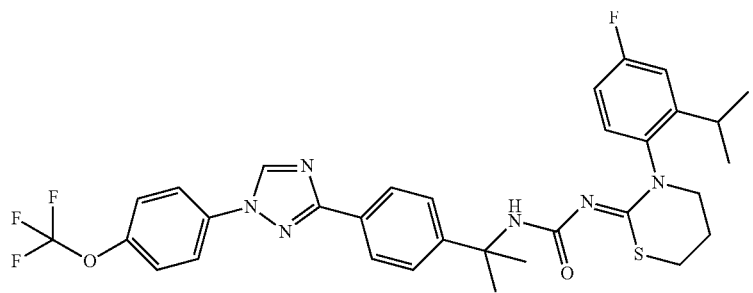 [SMILES: CC(C)c1cc(F)ccc1N1CCCS/C1=N\C(=O)NC(C)(C)c1ccc(-c2ncn(-c3ccc(OC(F)(F)F)cc3)n2)cc1] P1240

TABLE P-Two-continued
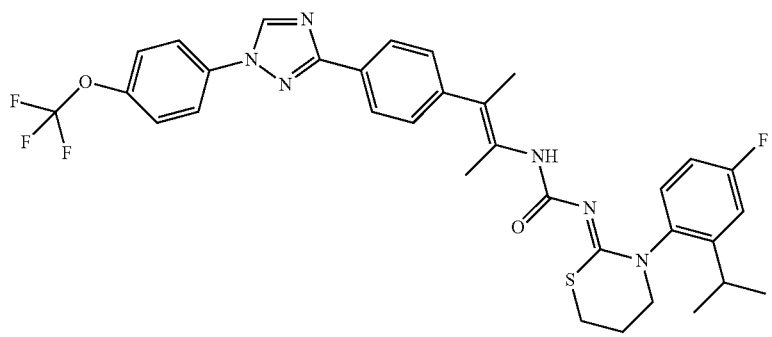 [SMILES: C/C(NC(=O)/N=C1\SCCCN1c1ccc(F)cc1C(C)C)=C(/C)c1ccc(-c2ncn(-c3ccc(OC(F)(F)F)cc3)n2)cc1] P1241
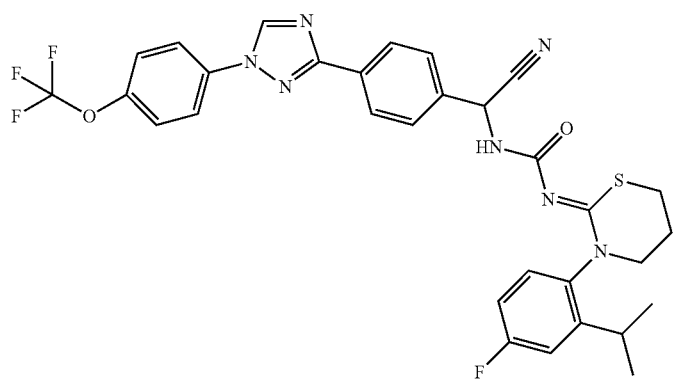 [SMILES: CC(C)c1cc(F)ccc1N1CCCS/C1=N\C(=O)NC(C#N)c1ccc(-c2ncn(-c3ccc(OC(F)(F)F)cc3)n2)cc1] P1242
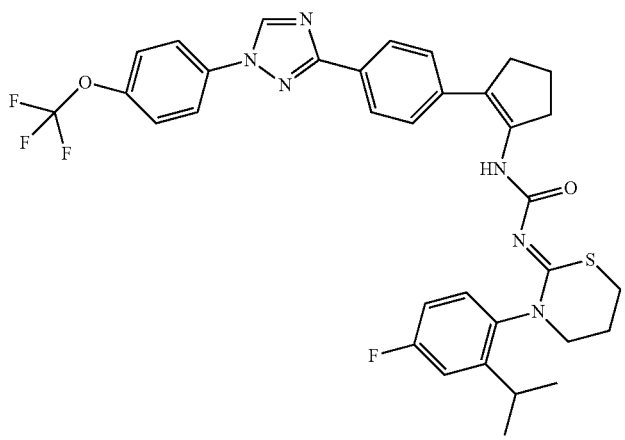 [SMILES: CC(C)c1cc(F)ccc1N1CCCS/C1=N\C(=O)NC1=C(c2ccc(-c3ncn(-c4ccc(OC(F)(F)F)cc4)n3)cc2)CCC1] P1243
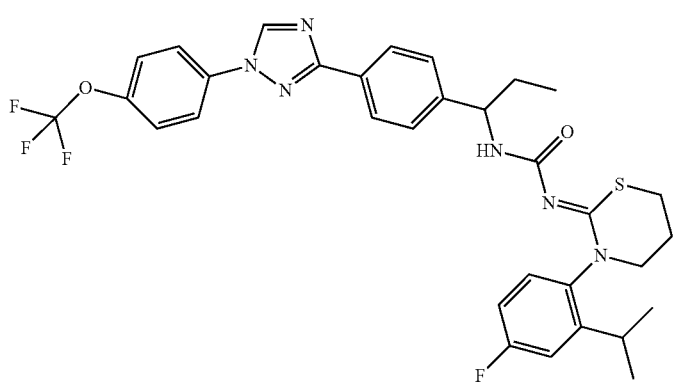 [SMILES: CCC(NC(=O)/N=C1\SCCCN1c1ccc(F)cc1C(C)C)c1ccc(-c2ncn(-c3ccc(OC(F)(F)F)cc3)n2)cc1] P1244

TABLE P-Two-continued
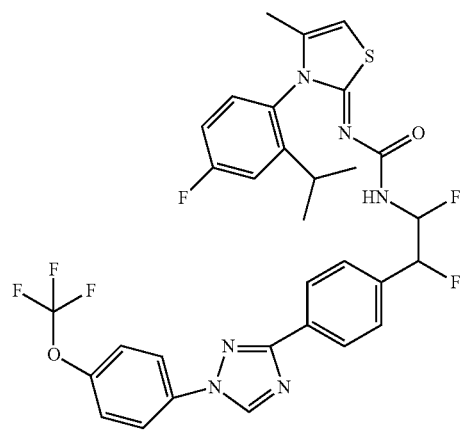 [SMILES: Cc1cs/c(=N\C(=O)NC(F)C(F)c2ccc(-c3ncn(-c4ccc(OC(F)(F)F)cc4)n3)cc2)n1-c1ccc(F)cc1C(C)C]
P1245
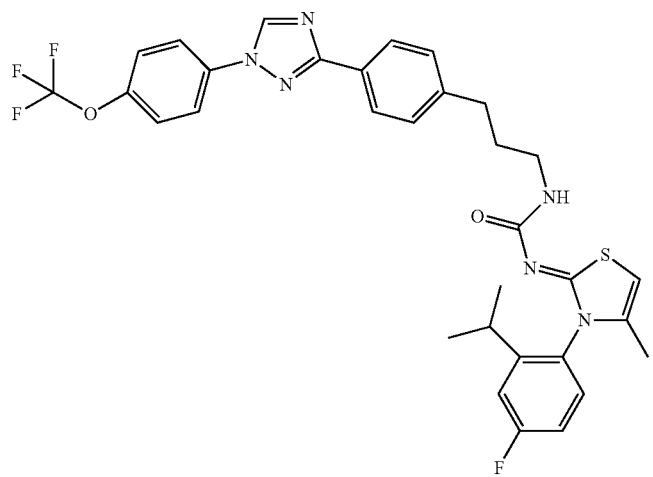 [SMILES: Cc1cs/c(=N\C(=O)NCCCc2ccc(-c3ncn(-c4ccc(OC(F)(F)F)cc4)n3)cc2)n1-c1ccc(F)cc1C(C)C]
P1246
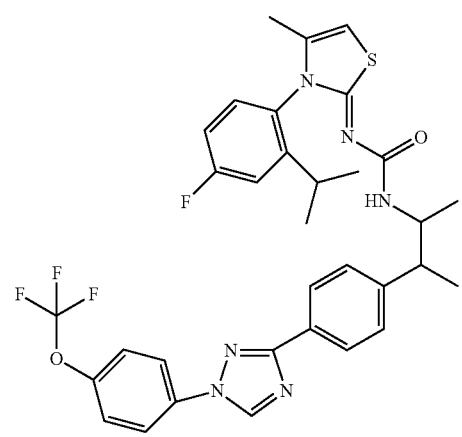
P1247

TABLE P-Two-continued
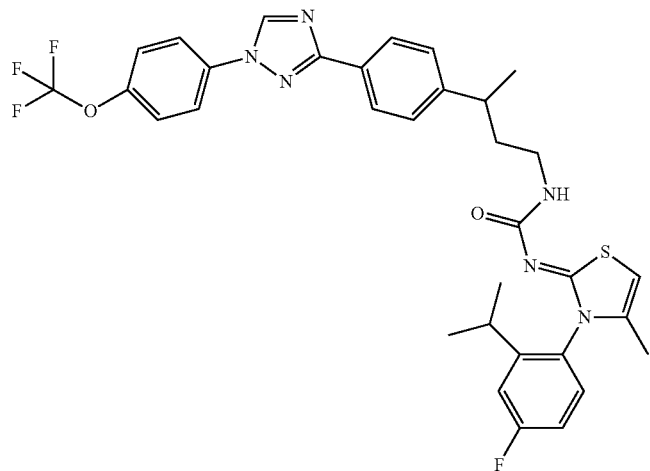 [SMILES: Cc1cs/c(=N\C(=O)NCCC(C)c2ccc(-c3ncn(-c4ccc(OC(F)(F)F)cc4)n3)cc2)n1-c1ccc(F)cc1C(C)C]
P1248
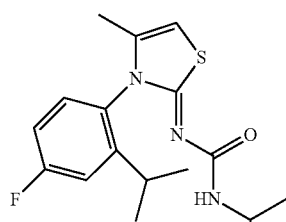
P1249
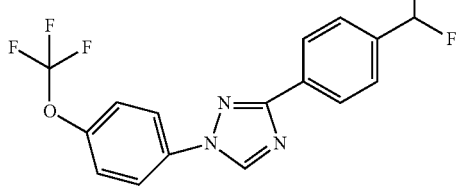
P1250
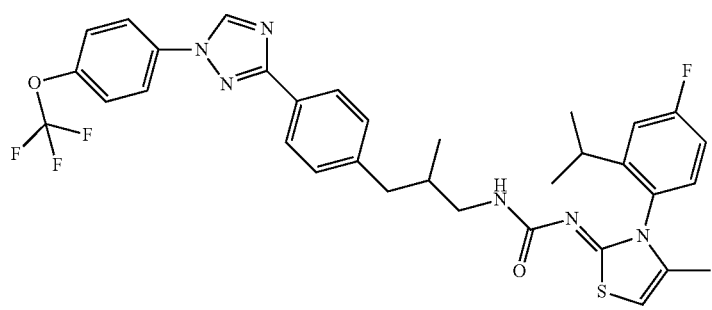 [SMILES: Cc1cs/c(=N\C(=O)NCC(C)Cc2ccc(-c3ncn(-c4ccc(OC(F)(F)F)cc4)n3)cc2)n1-c1ccc(F)cc1C(C)C]
P1251
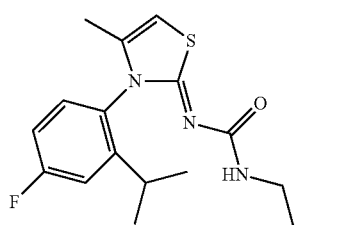
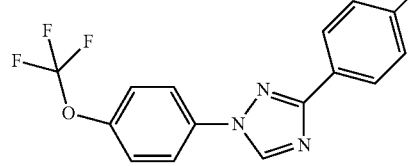

TABLE P-Two-continued
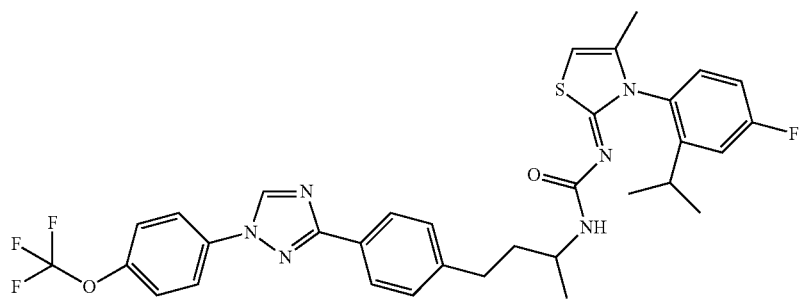 [SMILES: Cc1cs/c(=N\C(=O)NC(C)CCc2ccc(-c3ncn(-c4ccc(OC(F)(F)F)cc4)n3)cc2)n1-c1ccc(F)cc1C(C)C]
P1252
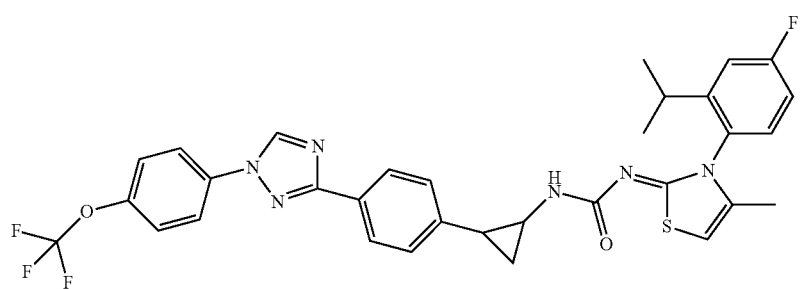 [SMILES: Cc1cs/c(=N\C(=O)NC2CC2c2ccc(-c3ncn(-c4ccc(OC(F)(F)F)cc4)n3)cc2)n1-c1ccc(F)cc1C(C)C]
P1253
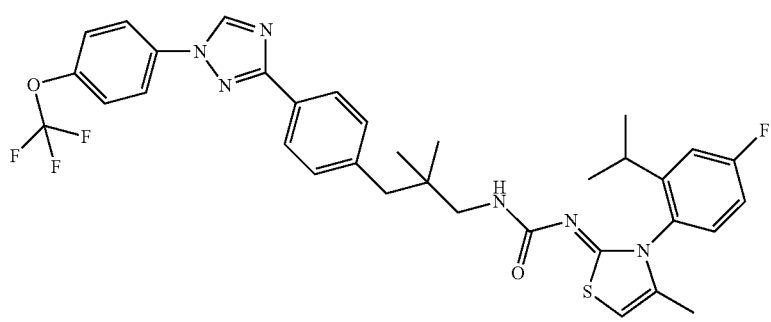 [SMILES: Cc1cs/c(=N\C(=O)NCC(C)(C)Cc2ccc(-c3ncn(-c4ccc(OC(F)(F)F)cc4)n3)cc2)n1-c1ccc(F)cc1C(C)C]
P1254
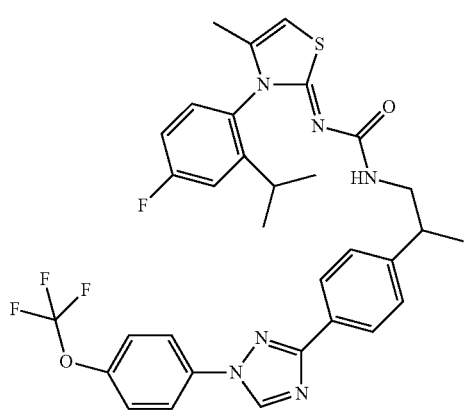 [SMILES: Cc1cs/c(=N\C(=O)NCC(C)c2ccc(-c3ncn(-c4ccc(OC(F)(F)F)cc4)n3)cc2)n1-c1ccc(F)cc1C(C)C]
P1255
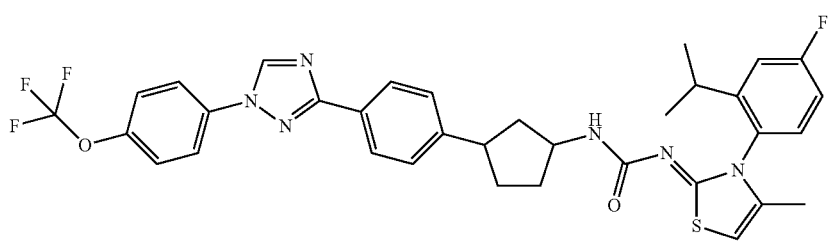 [SMILES: Cc1cs/c(=N\C(=O)NC2CCC(c3ccc(-c4ncn(-c5ccc(OC(F)(F)F)cc5)n4)cc3)C2)n1-c1ccc(F)cc1C(C)C]
P1256

TABLE P-Two-continued
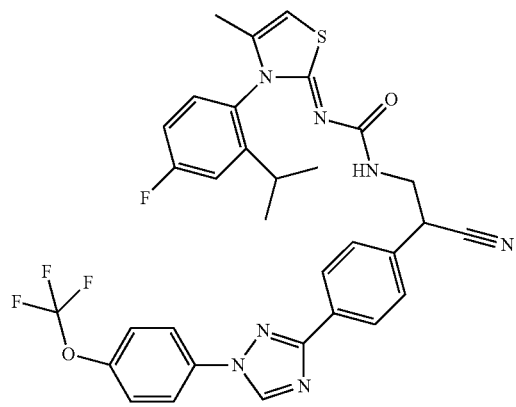 [SMILES: Cc1cs/c(=N\C(=O)NCC(C#N)c2ccc(-c3ncn(-c4ccc(OC(F)(F)F)cc4)n3)cc2)n1-c1ccc(F)cc1C(C)C]
P1257
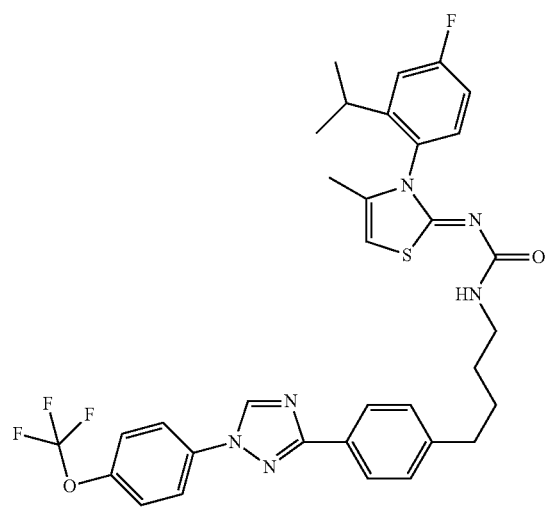 [SMILES: Cc1cs/c(=N\C(=O)NCCCCc2ccc(-c3ncn(-c4ccc(OC(F)(F)F)cc4)n3)cc2)n1-c1ccc(F)cc1C(C)C]
P1258
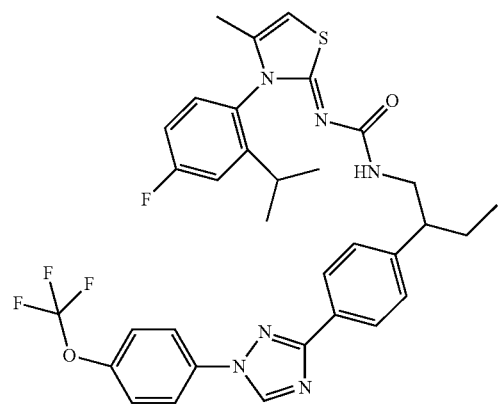 [SMILES: CCC(CNC(=O)/N=c1\scc(C)n1-c1ccc(F)cc1C(C)C)c1ccc(-c2ncn(-c3ccc(OC(F)(F)F)cc3)n2)cc1]
P1259

TABLE P-Two-continued
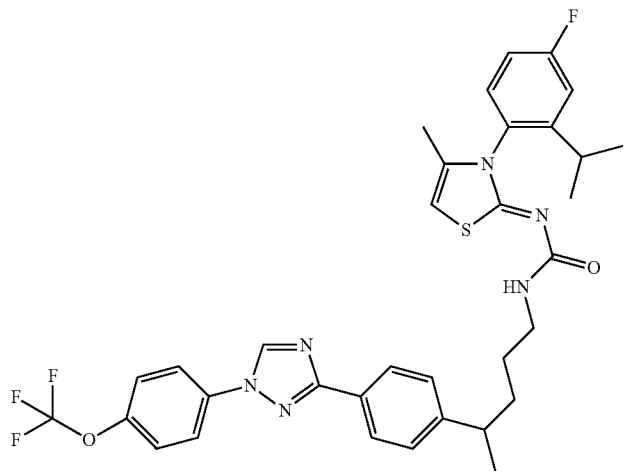 [SMILES: Cc1cs/c(=N\C(=O)NCCCC(C)c2ccc(-c3ncn(-c4ccc(OC(F)(F)F)cc4)n3)cc2)n1-c1ccc(F)cc1C(C)C]
P1260
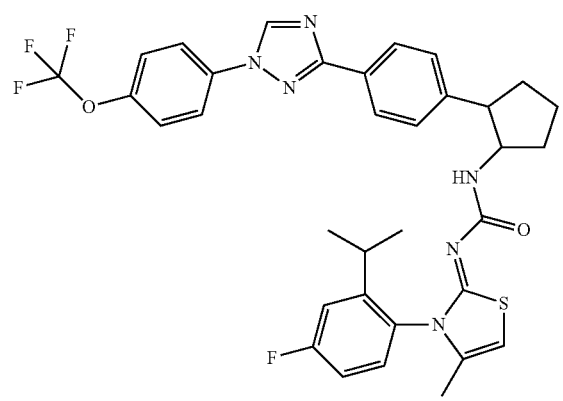 [SMILES: Cc1cs/c(=N\C(=O)NC2CCCC2c2ccc(-c3ncn(-c4ccc(OC(F)(F)F)cc4)n3)cc2)n1-c1ccc(F)cc1C(C)C]
P1261
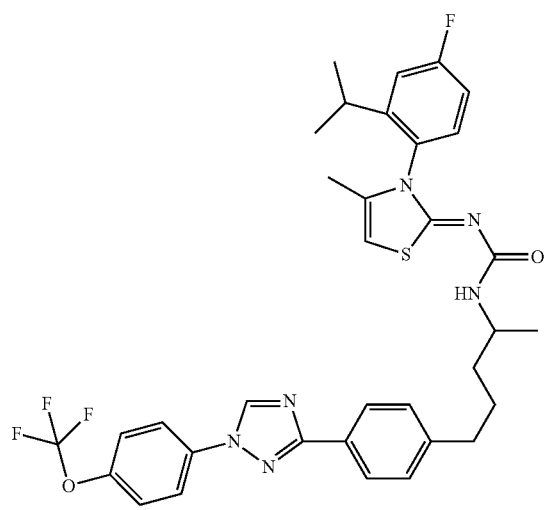 [SMILES: Cc1cs/c(=N\C(=O)NC(C)CCCc2ccc(-c3ncn(-c4ccc(OC(F)(F)F)cc4)n3)cc2)n1-c1ccc(F)cc1C(C)C]
P1262

TABLE P-Two-continued
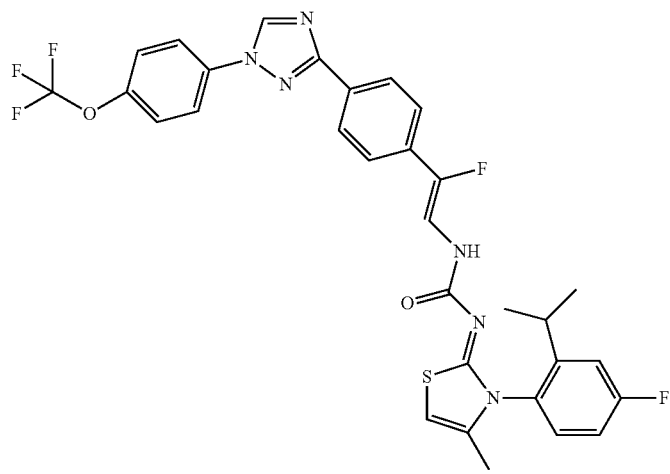 [SMILES: Cc1cs/c(=N\C(=O)N/C=C(\F)c2ccc(-c3ncn(-c4ccc(OC(F)(F)F)cc4)n3)cc2)n1-c1ccc(F)cc1C(C)C]
P1263
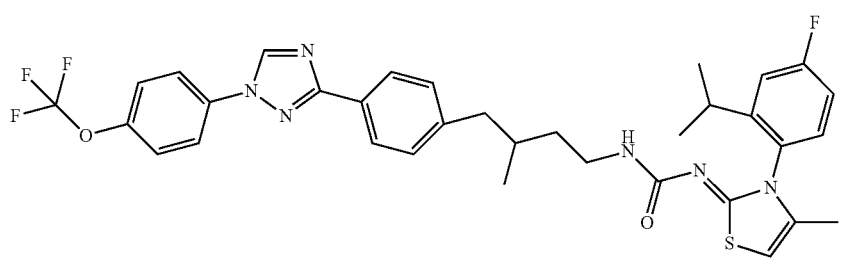 [SMILES: Cc1cs/c(=N\C(=O)NCCC(C)Cc2ccc(-c3ncn(-c4ccc(OC(F)(F)F)cc4)n3)cc2)n1-c1ccc(F)cc1C(C)C]
P1264
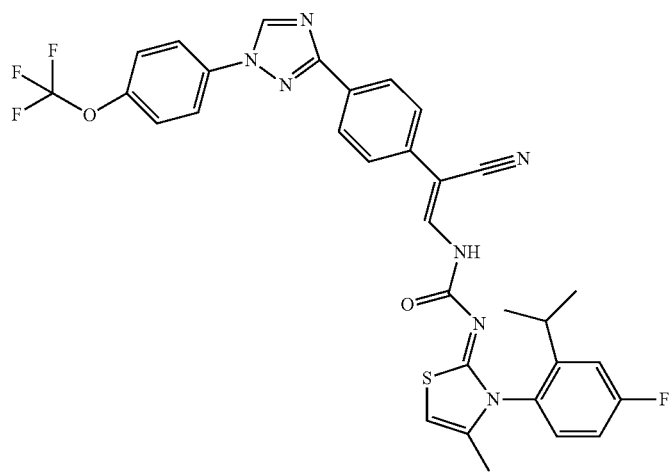 [SMILES: Cc1cs/c(=N\C(=O)N/C=C(\C#N)c2ccc(-c3ncn(-c4ccc(OC(F)(F)F)cc4)n3)cc2)n1-c1ccc(F)cc1C(C)C]
P1265
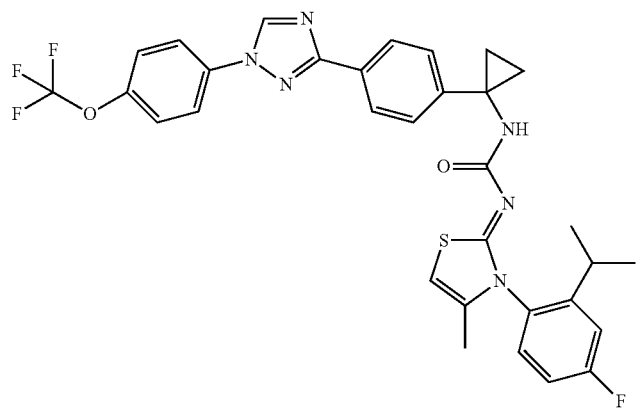 [SMILES: Cc1cs/c(=N\C(=O)NC2(c3ccc(-c4ncn(-c5ccc(OC(F)(F)F)cc5)n4)cc3)CC2)n1-c1ccc(F)cc1C(C)C]
P1266

TABLE P-Two-continued
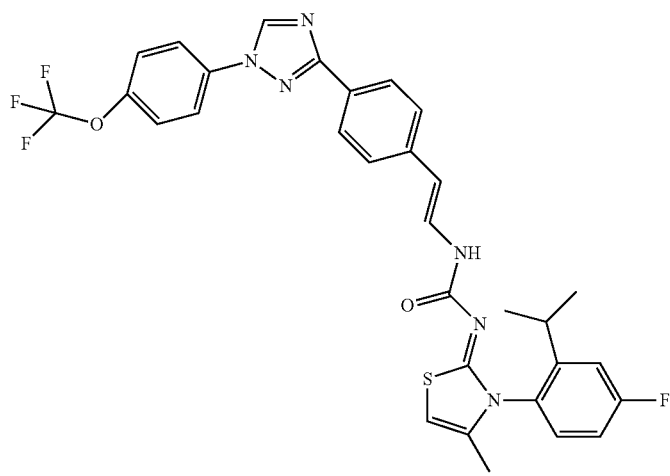 [SMILES: Cc1cs/c(=N\C(=O)N/C=C/c2ccc(-c3ncn(-c4ccc(OC(F)(F)F)cc4)n3)cc2)n1-c1ccc(F)cc1C(C)C]
P1267
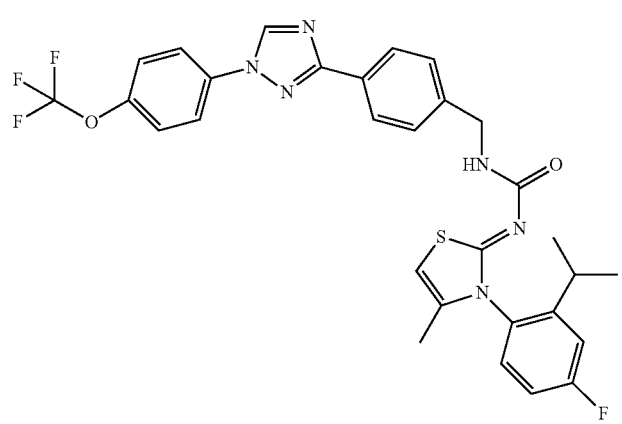 [SMILES: Cc1cs/c(=N\C(=O)NCc2ccc(-c3ncn(-c4ccc(OC(F)(F)F)cc4)n3)cc2)n1-c1ccc(F)cc1C(C)C]
P1268
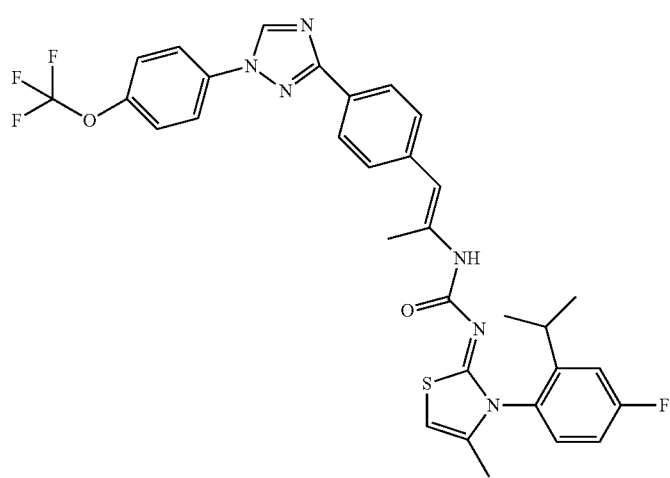 [SMILES: C/C(=C\c1ccc(-c2ncn(-c3ccc(OC(F)(F)F)cc3)n2)cc1)NC(=O)/N=c1\scc(C)n1-c1ccc(F)cc1C(C)C]
P1269

TABLE P-Two-continued
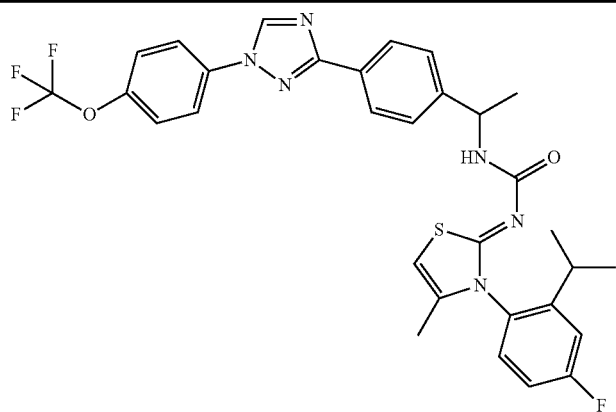
P1270
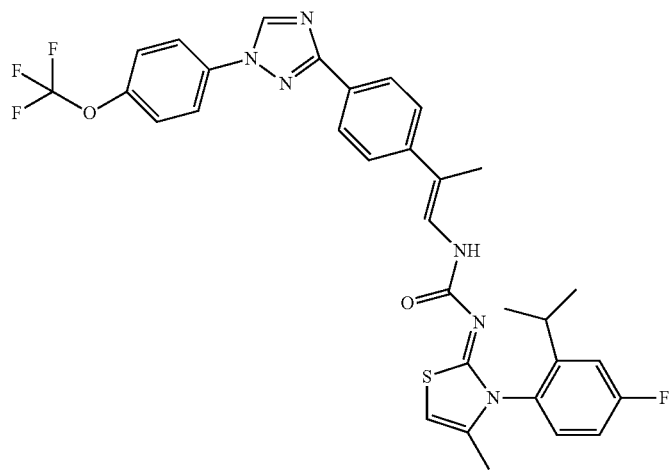 [SMILES: C/C(=C\NC(=O)/N=c1\scc(C)n1-c1ccc(F)cc1C(C)C)c1ccc(-c2ncn(-c3ccc(OC(F)(F)F)cc3)n2)cc1]
P1271
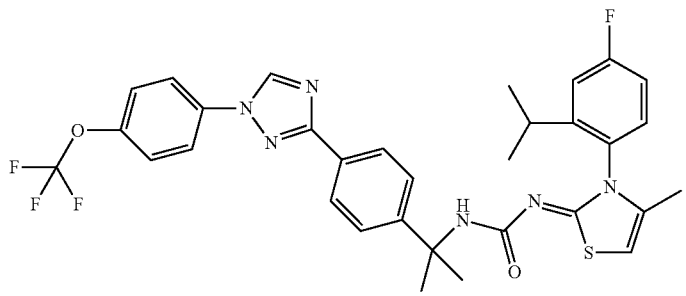 [SMILES: Cc1cs/c(=N\C(=O)NC(C)(C)c2ccc(-c3ncn(-c4ccc(OC(F)(F)F)cc4)n3)cc2)n1-c1ccc(F)cc1C(C)C]
P1272
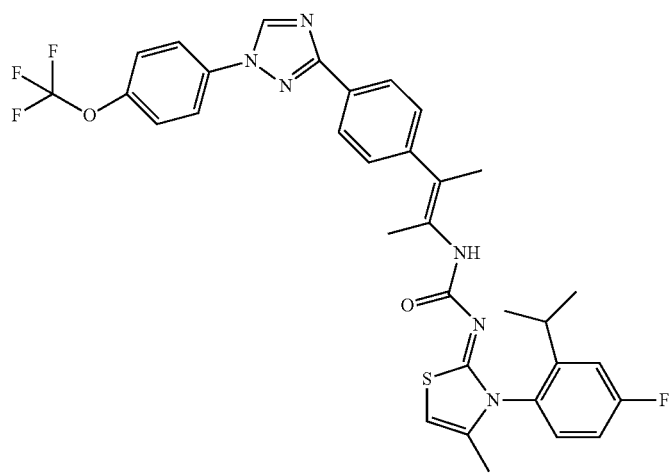 [SMILES: C/C(NC(=O)/N=c1\scc(C)n1-c1ccc(F)cc1C(C)C)=C(/C)c1ccc(-c2ncn(-c3ccc(OC(F)(F)F)cc3)n2)cc1]
P1273

TABLE P-Two-continued
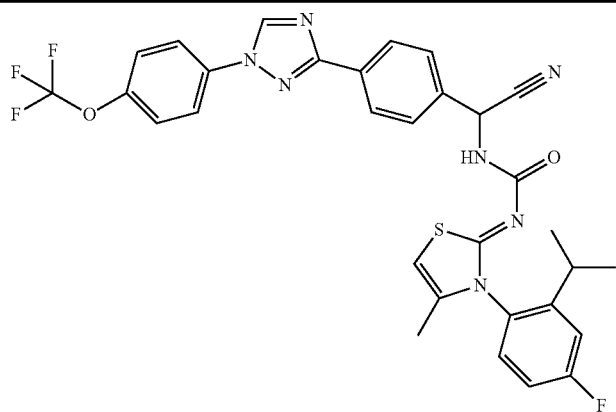
P1274
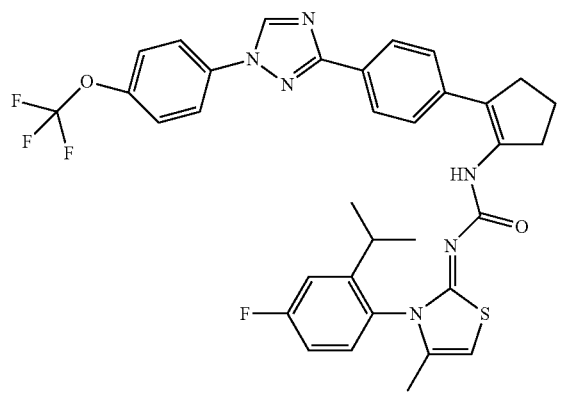 [SMILES: Cc1cs/c(=N\C(=O)NC2=C(c3ccc(-c4ncn(-c5ccc(OC(F)(F)F)cc5)n4)cc3)CCC2)n1-c1ccc(F)cc1C(C)C]
P1275
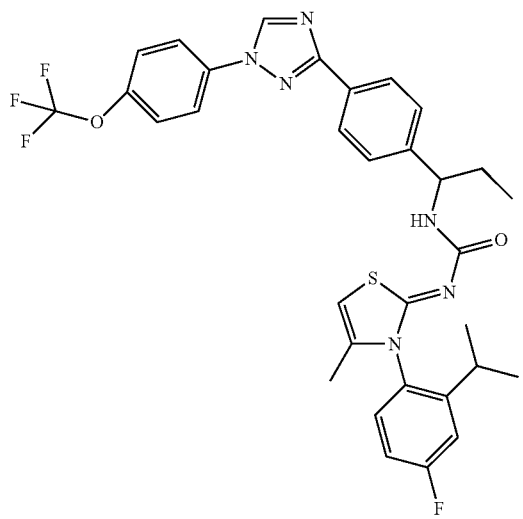 [SMILES: CCC(NC(=O)/N=c1\scc(C)n1-c1ccc(F)cc1C(C)C)c1ccc(-c2ncn(-c3ccc(OC(F)(F)F)cc3)n2)cc1]
P1276
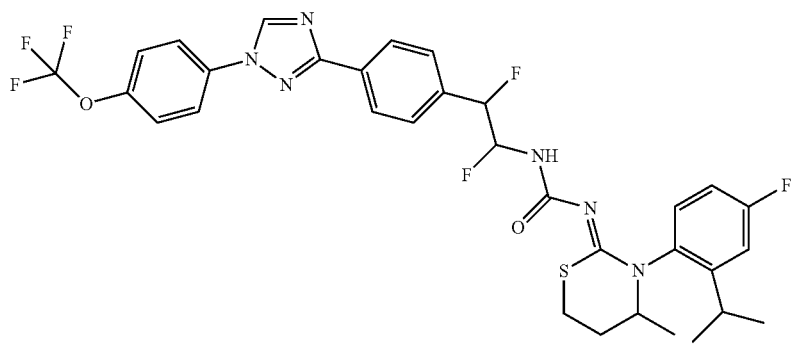 [SMILES: CC(C)c1cc(F)ccc1N1/C(=N/C(=O)NC(F)C(F)c2ccc(-c3ncn(-c4ccc(OC(F)(F)F)cc4)n3)cc2)SCCC1C]
P1277

TABLE P-Two-continued
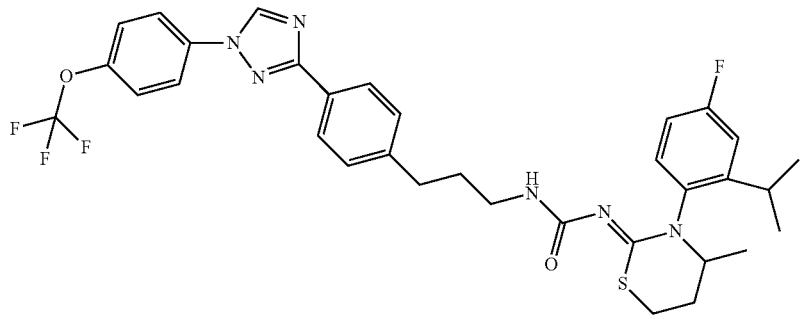 [SMILES: CC(C)c1cc(F)ccc1N1/C(=N/C(=O)NCCCc2ccc(-c3ncn(-c4ccc(OC(F)(F)F)cc4)n3)cc2)SCCC1C]
P1278
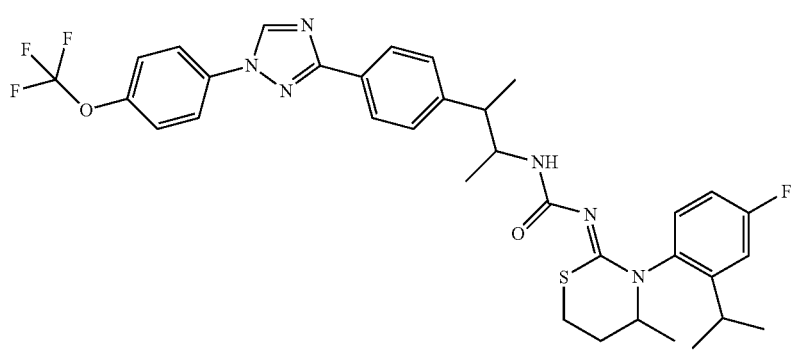 [SMILES: CC(C)c1cc(F)ccc1N1/C(=N/C(=O)NC(C)C(C)c2ccc(-c3ncn(-c4ccc(OC(F)(F)F)cc4)n3)cc2)SCCC1C]
P1279
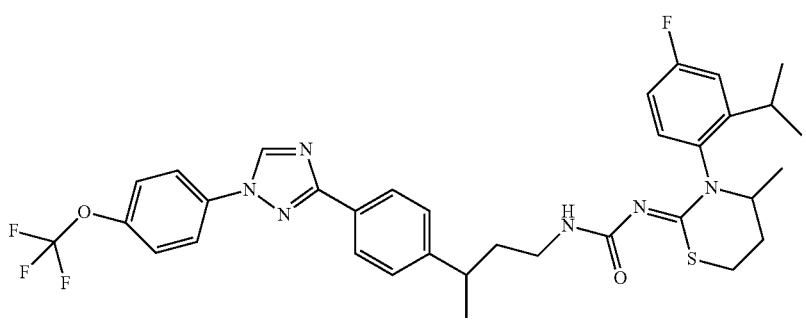 [SMILES: CC(C)c1cc(F)ccc1N1/C(=N/C(=O)NCCC(C)c2ccc(-c3ncn(-c4ccc(OC(F)(F)F)cc4)n3)cc2)SCCC1C]
P1280
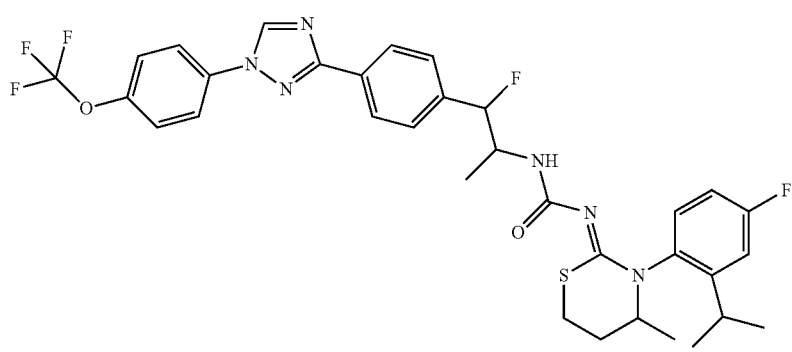 [SMILES: CC(C)c1cc(F)ccc1N1/C(=N/C(=O)NC(C)C(F)c2ccc(-c3ncn(-c4ccc(OC(F)(F)F)cc4)n3)cc2)SCCC1C]
P1281
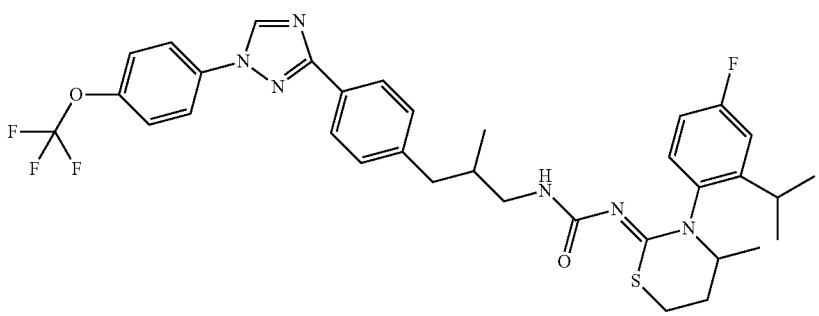 [SMILES: CC(CNC(=O)/N=C1\SCCC(C)N1c1ccc(F)cc1C(C)C)Cc1ccc(-c2ncn(-c3ccc(OC(F)(F)F)cc3)n2)cc1]
P1282

TABLE P-Two-continued
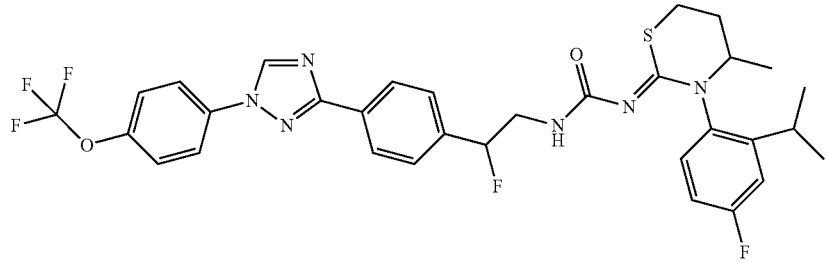
P1283
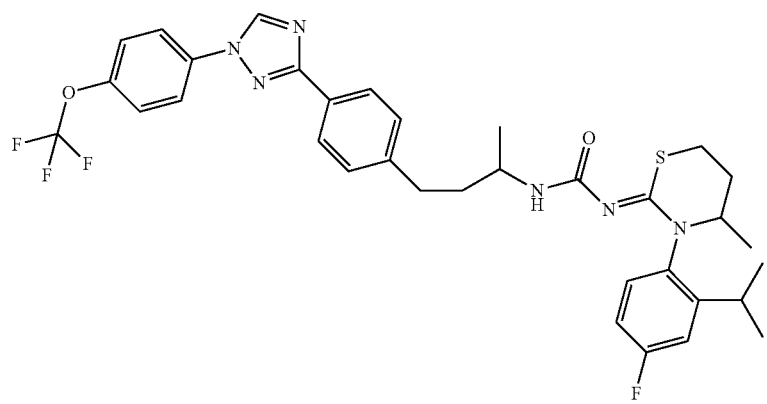 [SMILES: CC(CCc1ccc(-c2ncn(-c3ccc(OC(F)(F)F)cc3)n2)cc1)NC(=O)/N=C1\SCCC(C)N1c1ccc(F)cc1C(C)C]
P1284
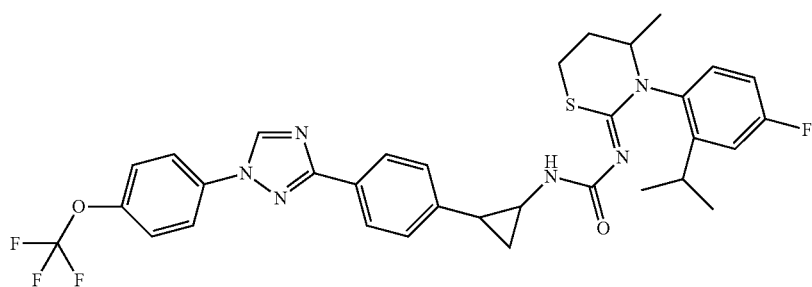 [SMILES: CC(C)c1cc(F)ccc1N1/C(=N/C(=O)NC2CC2c2ccc(-c3ncn(-c4ccc(OC(F)(F)F)cc4)n3)cc2)SCCC1C]
P1285
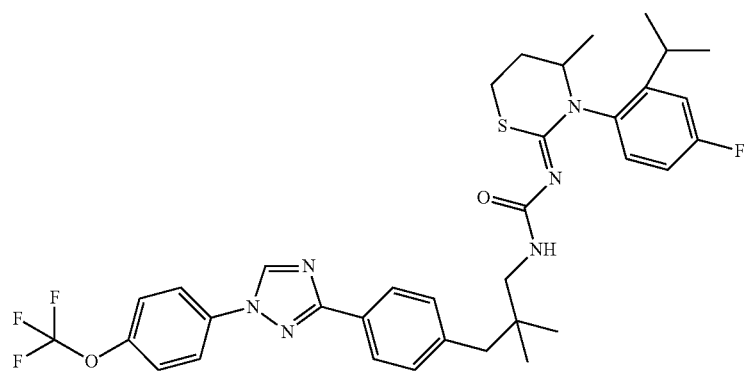 [SMILES: CC(C)c1cc(F)ccc1N1/C(=N/C(=O)NCC(C)(C)Cc2ccc(-c3ncn(-c4ccc(OC(F)(F)F)cc4)n3)cc2)SCCC1C]
P1286
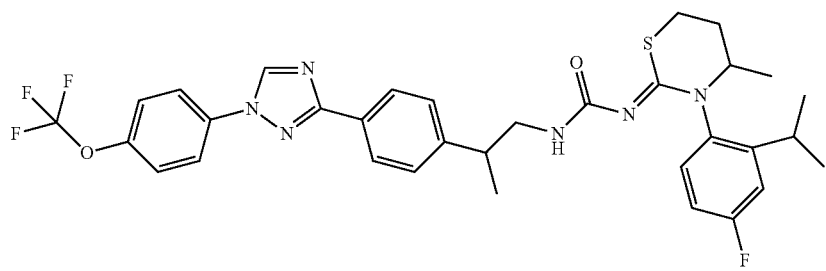 [SMILES: CC(C)c1cc(F)ccc1N1/C(=N/C(=O)NCC(C)c2ccc(-c3ncn(-c4ccc(OC(F)(F)F)cc4)n3)cc2)SCCC1C]
P1287

TABLE P-Two-continued
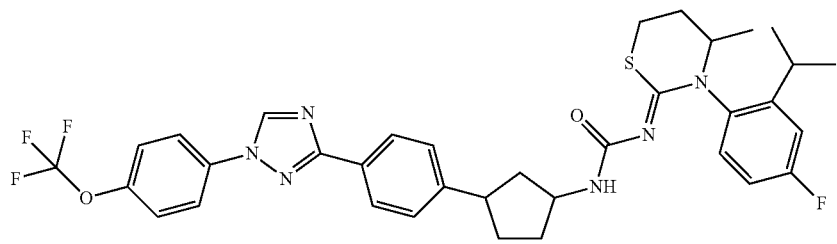 [SMILES: CC(C)c1cc(F)ccc1N1/C(=N/C(=O)NC2CCC(c3ccc(-c4ncn(-c5ccc(OC(F)(F)F)cc5)n4)cc3)C2)SCCC1C]
P1288
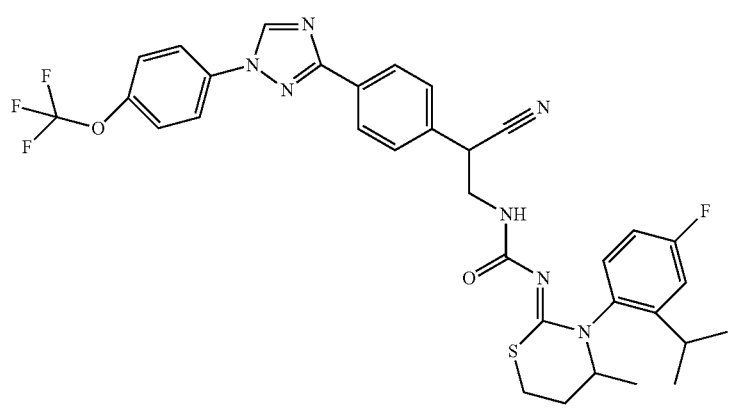 [SMILES: CC(C)c1cc(F)ccc1N1/C(=N/C(=O)NCC(C#N)c2ccc(-c3ncn(-c4ccc(OC(F)(F)F)cc4)n3)cc2)SCCC1C]
P1289
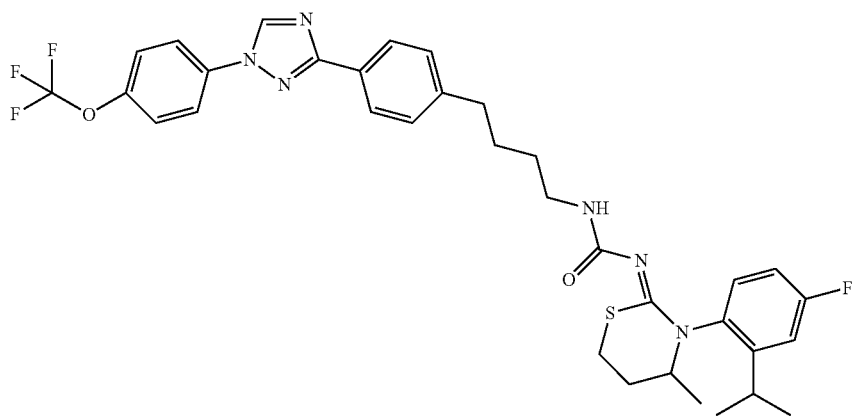 [SMILES: CC(C)c1cc(F)ccc1N1/C(=N/C(=O)NCCCCc2ccc(-c3ncn(-c4ccc(OC(F)(F)F)cc4)n3)cc2)SCCC1C]
P1290
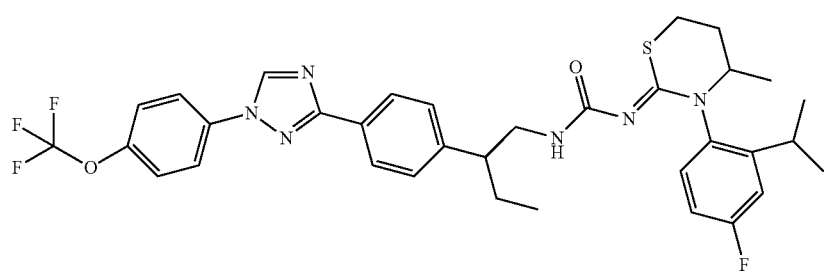 [SMILES: CCC(CNC(=O)/N=C1\SCCC(C)N1c1ccc(F)cc1C(C)C)c1ccc(-c2ncn(-c3ccc(OC(F)(F)F)cc3)n2)cc1]
P1291

TABLE P-Two-continued
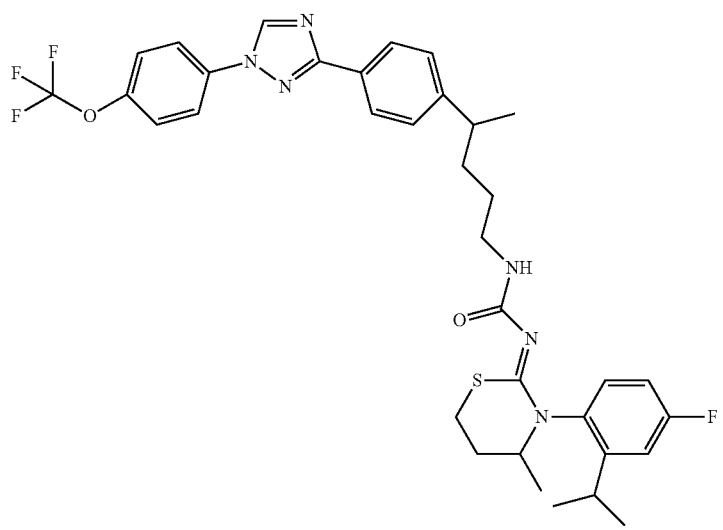 [SMILES: CC(C)c1cc(F)ccc1N1/C(=N/C(=O)NCCCC(C)c2ccc(-c3ncn(-c4ccc(OC(F)(F)F)cc4)n3)cc2)SCCC1C]
P1292
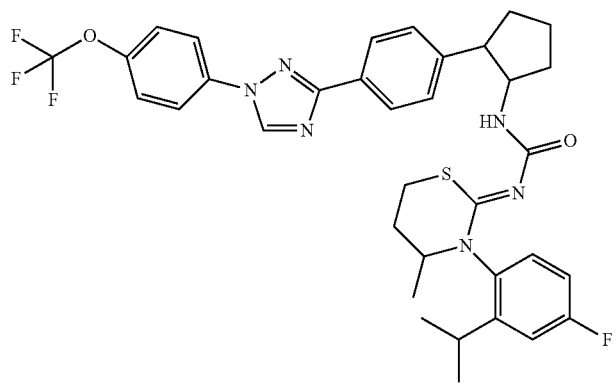 [SMILES: CC(C)c1cc(F)ccc1N1/C(=N/C(=O)NC2CCCC2c2ccc(-c3ncn(-c4ccc(OC(F)(F)F)cc4)n3)cc2)SCCC1C]
P1293
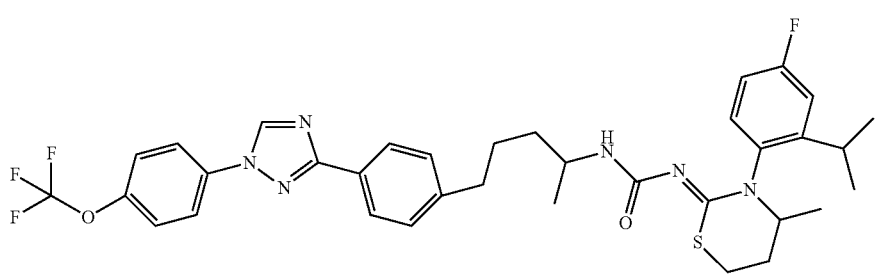 [SMILES: CC(CCCc1ccc(-c2ncn(-c3ccc(OC(F)(F)F)cc3)n2)cc1)NC(=O)/N=C1\SCCC(C)N1c1ccc(F)cc1C(C)C]
P1294
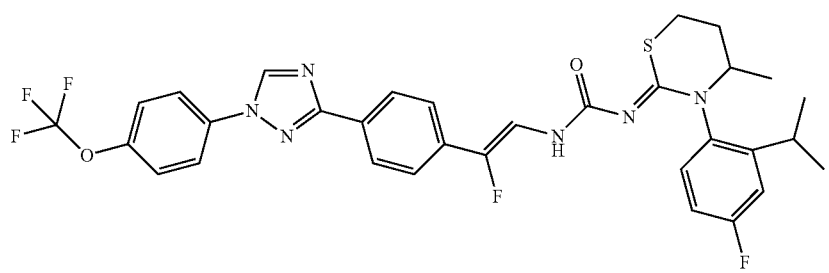
P1295

TABLE P-Two-continued
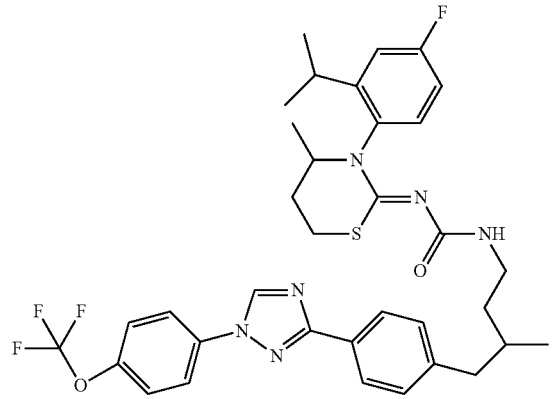 [SMILES: CC(CCNC(=O)/N=C1\SCCC(C)N1c1ccc(F)cc1C(C)C)Cc1ccc(-c2ncn(-c3ccc(OC(F)(F)F)cc3)n2)cc1]
P1296
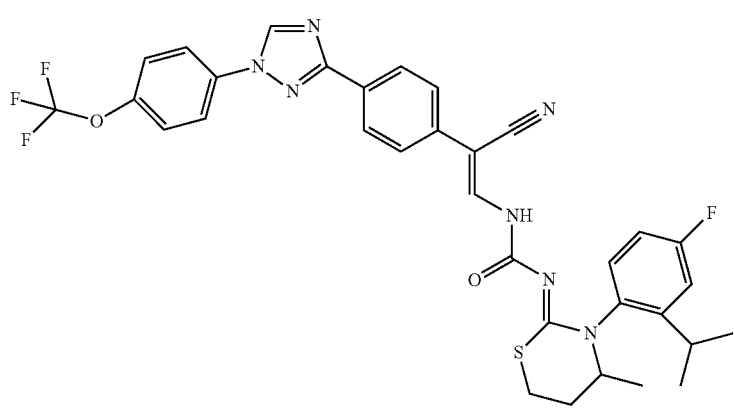 [SMILES: CC(C)c1cc(F)ccc1N1/C(=N/C(=O)N/C=C(\C#N)c2ccc(-c3ncn(-c4ccc(OC(F)(F)F)cc4)n3)cc2)SCCC1C]
P1297
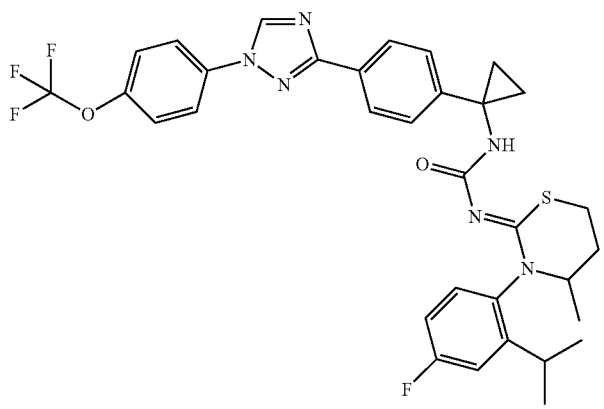 [SMILES: CC(C)c1cc(F)ccc1N1/C(=N/C(=O)NC2(c3ccc(-c4ncn(-c5ccc(OC(F)(F)F)cc5)n4)cc3)CC2)SCCC1C]
P1298
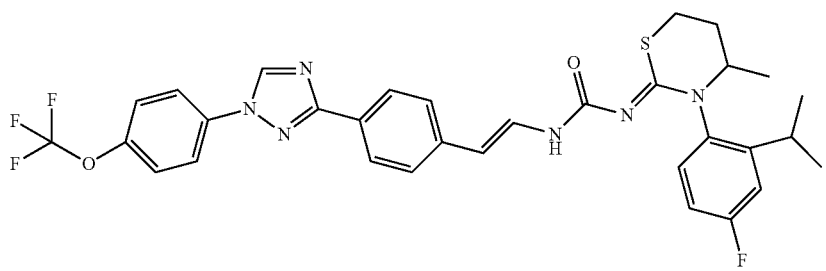 [SMILES: CC(C)c1cc(F)ccc1N1/C(=N/C(=O)N/C=C/c2ccc(-c3ncn(-c4ccc(OC(F)(F)F)cc4)n3)cc2)SCCC1C]
P1299

TABLE P-Two-continued
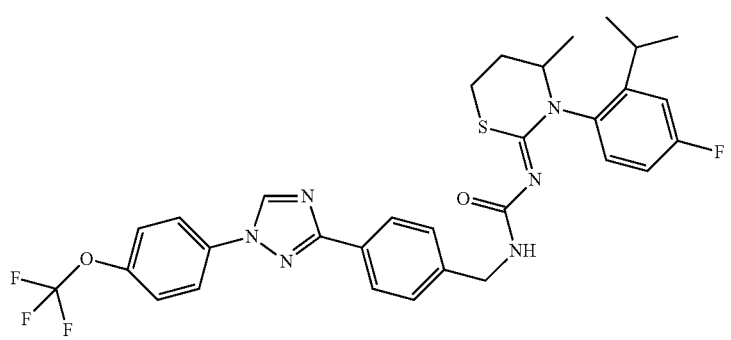 [SMILES: CC(C)c1cc(F)ccc1N1/C(=N/C(=O)NCc2ccc(-c3ncn(-c4ccc(OC(F)(F)F)cc4)n3)cc2)SCCC1C]
P1300
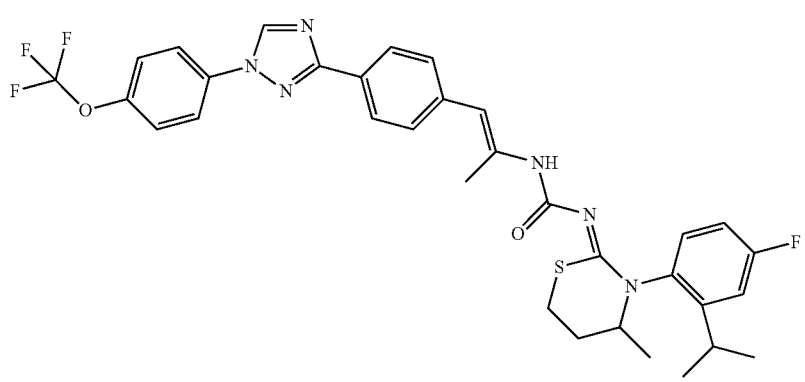 [SMILES: C/C(=C\c1ccc(-c2ncn(-c3ccc(OC(F)(F)F)cc3)n2)cc1)NC(=O)/N=C1\SCCC(C)N1c1ccc(F)cc1C(C)C]
P1301
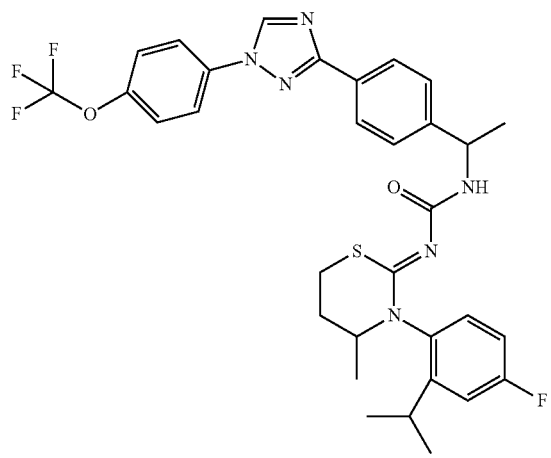 [SMILES: CC(C)c1cc(F)ccc1N1/C(=N/C(=O)NC(C)c2ccc(-c3ncn(-c4ccc(OC(F)(F)F)cc4)n3)cc2)SCCC1C]
P1302
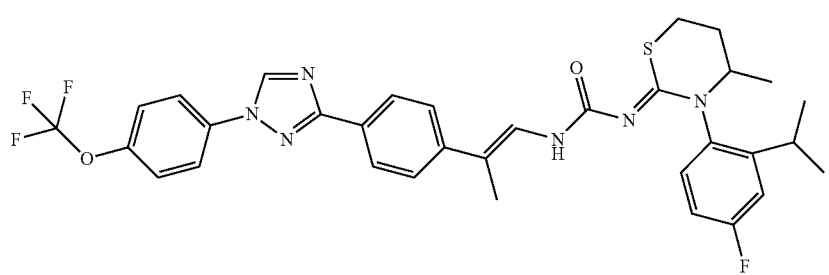 [SMILES: C/C(=C\NC(=O)/N=C1\SCCC(C)N1c1ccc(F)cc1C(C)C)c1ccc(-c2ncn(-c3ccc(OC(F)(F)F)cc3)n2)cc1]
P1303

TABLE P-Two-continued
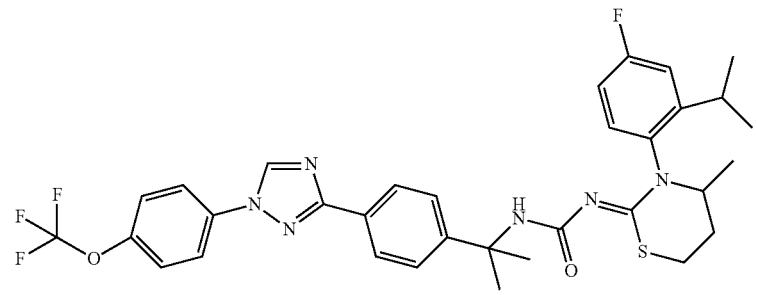 [SMILES: CC(C)c1cc(F)ccc1N1/C(=N/C(=O)NC(C)(C)c2ccc(-c3ncn(-c4ccc(OC(F)(F)F)cc4)n3)cc2)SCCC1C]
P1304
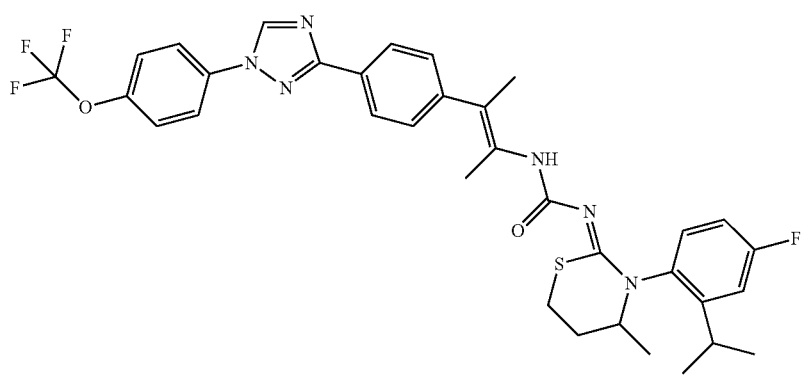 [SMILES: C/C(NC(=O)/N=C1\SCCC(C)N1c1ccc(F)cc1C(C)C)=C(/C)c1ccc(-c2ncn(-c3ccc(OC(F)(F)F)cc3)n2)cc1]
P1305
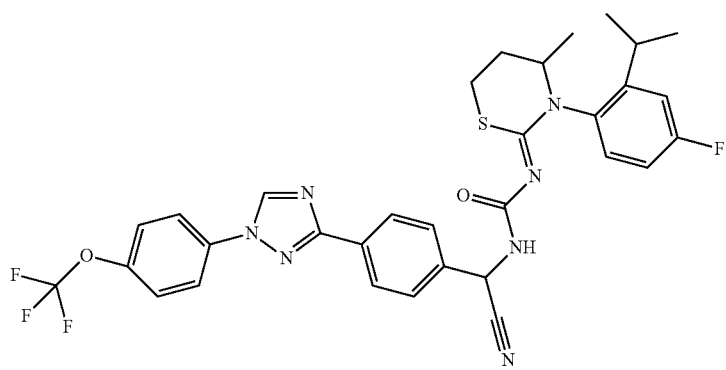 [SMILES: CC(C)c1cc(F)ccc1N1/C(=N/C(=O)NC(C#N)c2ccc(-c3ncn(-c4ccc(OC(F)(F)F)cc4)n3)cc2)SCCC1C]
P1306
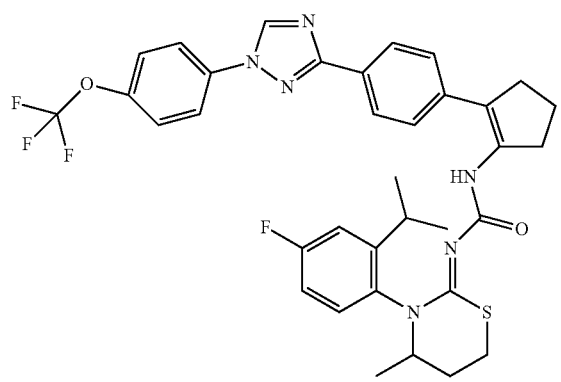 [SMILES: CC(C)c1cc(F)ccc1N1/C(=N/C(=O)NC2=C(c3ccc(-c4ncn(-c5ccc(OC(F)(F)F)cc5)n4)cc3)CCC2)SCCC1C]
P1307

TABLE P-Two-continued
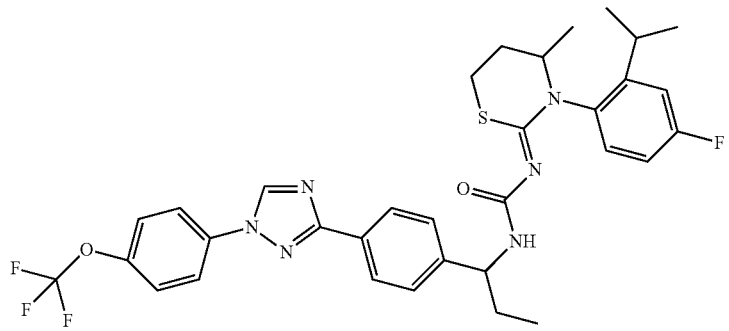 [SMILES: CCC(NC(=O)/N=C1\SCCC(C)N1c1ccc(F)cc1C(C)C)c1ccc(-c2ncn(-c3ccc(OC(F)(F)F)cc3)n2)cc1]
P1308
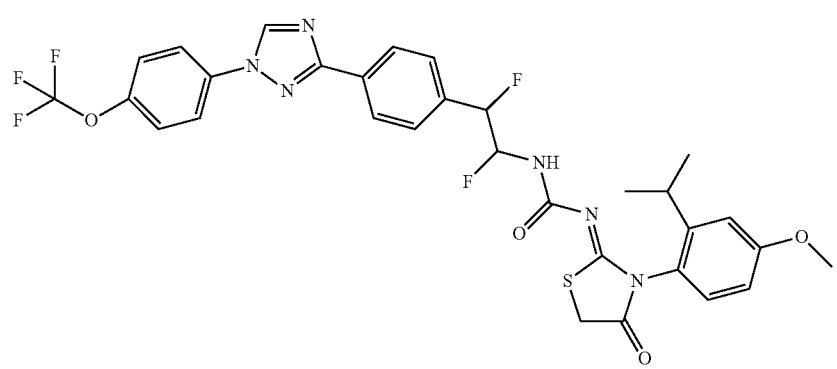 [SMILES: COc1ccc(N2C(=O)CS/C2=N\C(=O)NC(F)C(F)c2ccc(-c3ncn(-c4ccc(OC(F)(F)F)cc4)n3)cc2)c(C(C)C)c1]
P1309
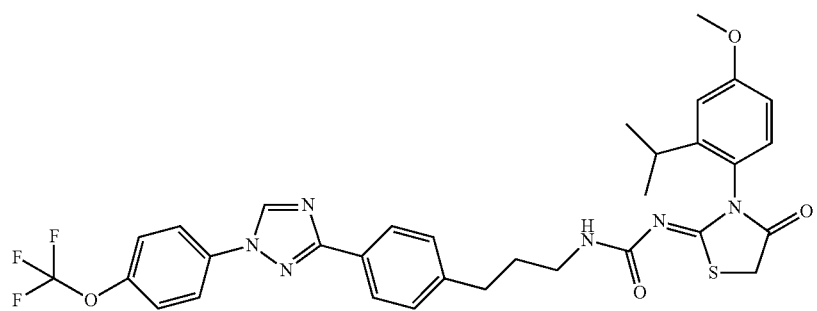 [SMILES: COc1ccc(N2C(=O)CS/C2=N\C(=O)NCCCc2ccc(-c3ncn(-c4ccc(OC(F)(F)F)cc4)n3)cc2)c(C(C)C)c1]
P1310
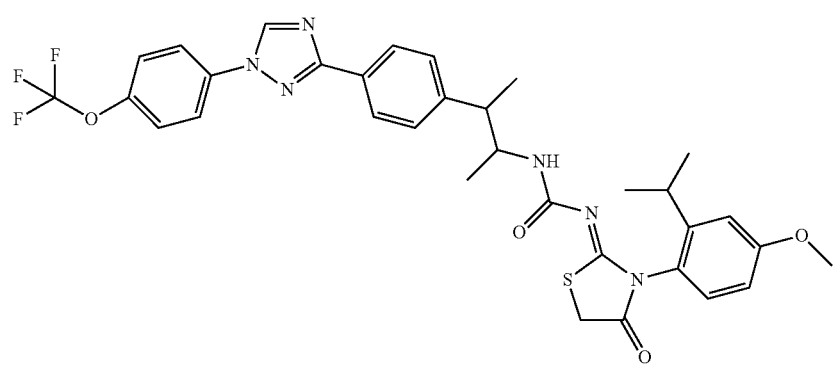 [SMILES: COc1ccc(N2C(=O)CS/C2=N\C(=O)NC(C)C(C)c2ccc(-c3ncn(-c4ccc(OC(F)(F)F)cc4)n3)cc2)c(C(C)C)c1]
P1311

TABLE P-Two-continued
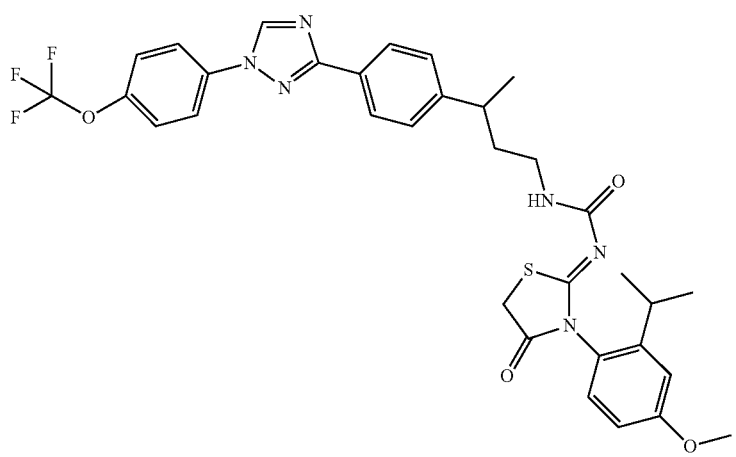 [SMILES: COc1ccc(N2C(=O)CS/C2=N\C(=O)NCCC(C)c2ccc(-c3ncn(-c4ccc(OC(F)(F)F)cc4)n3)cc2)c(C(C)C)c1]
P1312
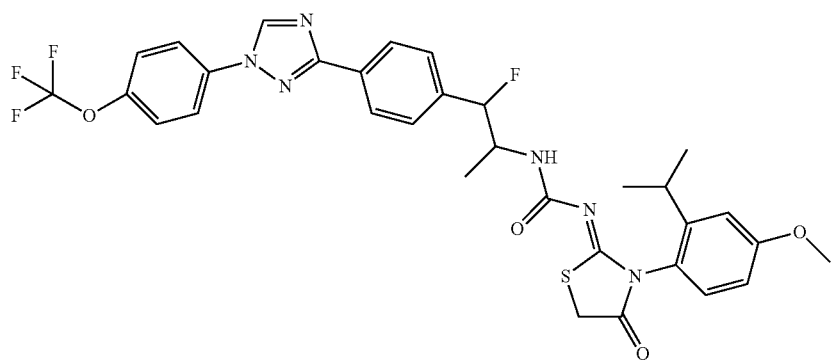 [SMILES: COc1ccc(N2C(=O)CS/C2=N\C(=O)NC(C)C(F)c2ccc(-c3ncn(-c4ccc(OC(F)(F)F)cc4)n3)cc2)c(C(C)C)c1]
P1313
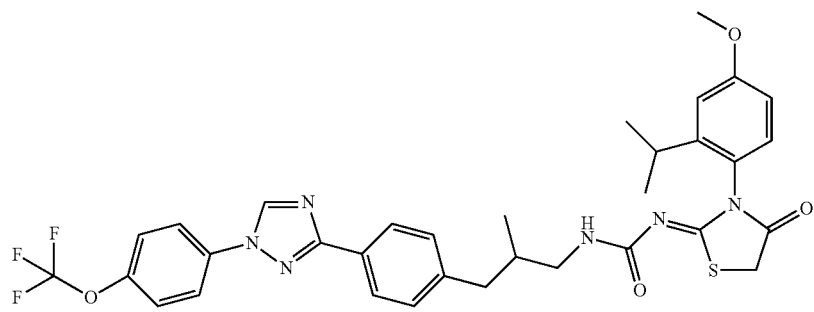 [SMILES: COc1ccc(N2C(=O)CS/C2=N\C(=O)NCC(C)Cc2ccc(-c3ncn(-c4ccc(OC(F)(F)F)cc4)n3)cc2)c(C(C)C)c1]
P1314
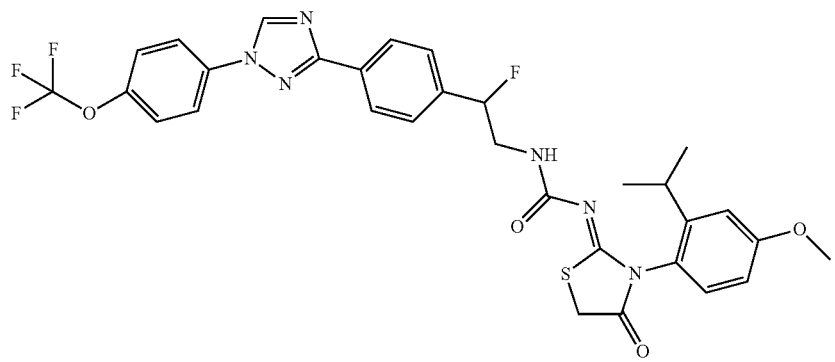 [SMILES: COc1ccc(N2C(=O)CS/C2=N\C(=O)NCC(F)c2ccc(-c3ncn(-c4ccc(OC(F)(F)F)cc4)n3)cc2)c(C(C)C)c1]
P1315

TABLE P-Two-continued
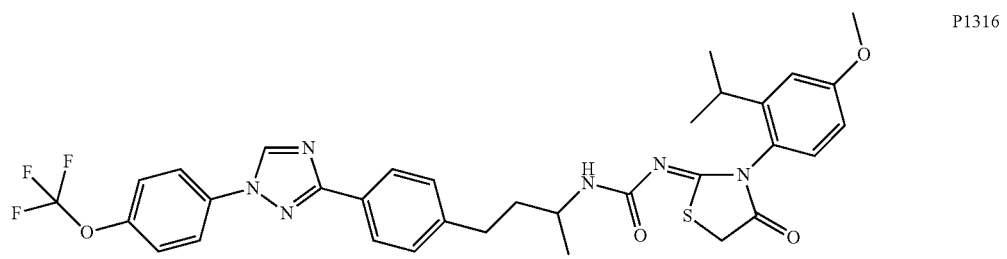
P1316
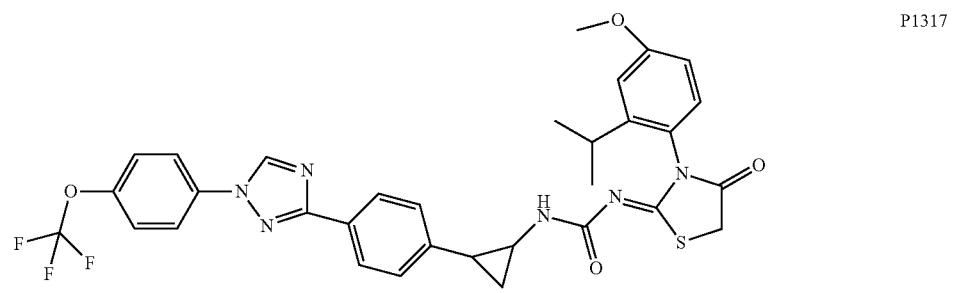
P1317
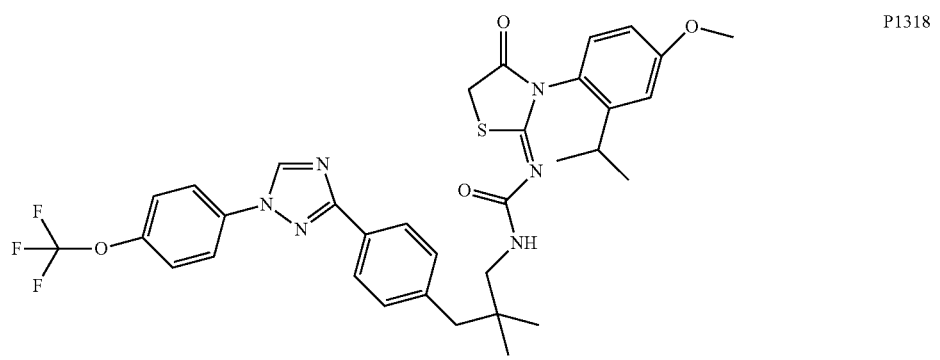
P1318
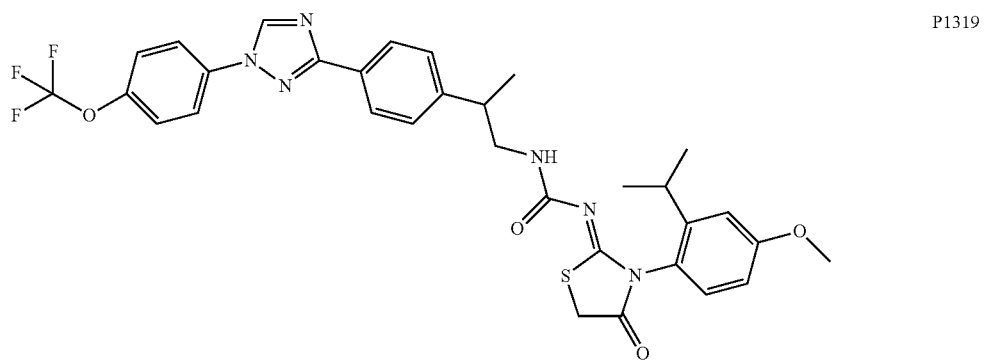
P1319
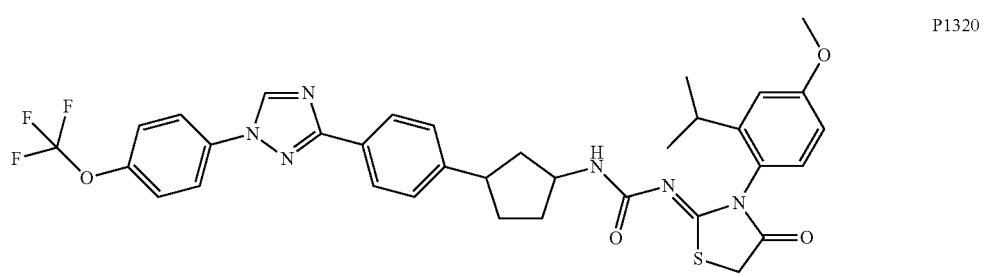
P1320

TABLE P-Two-continued
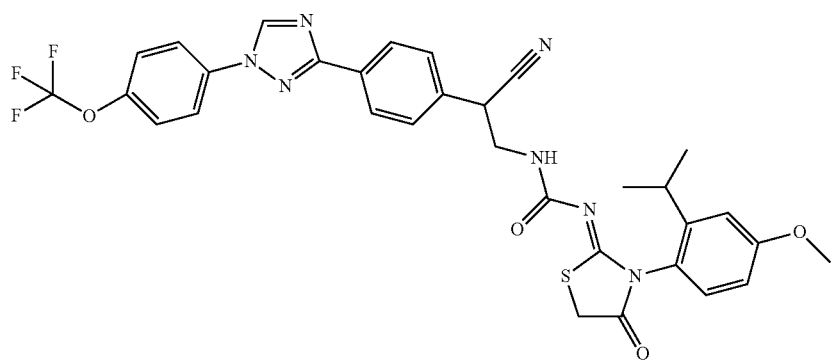 [SMILES: COc1ccc(N2C(=O)CS/C2=N\C(=O)NCC(C#N)c2ccc(-c3ncn(-c4ccc(OC(F)(F)F)cc4)n3)cc2)c(C(C)C)c1]
P1321
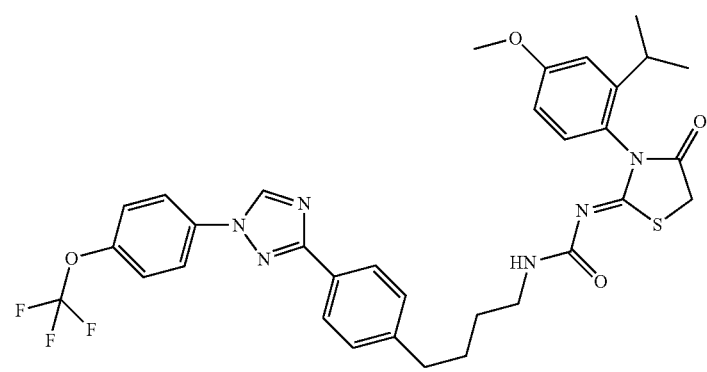 [SMILES: COc1ccc(N2C(=O)CS/C2=N\C(=O)NCCCCc2ccc(-c3ncn(-c4ccc(OC(F)(F)F)cc4)n3)cc2)c(C(C)C)c1]
P1322
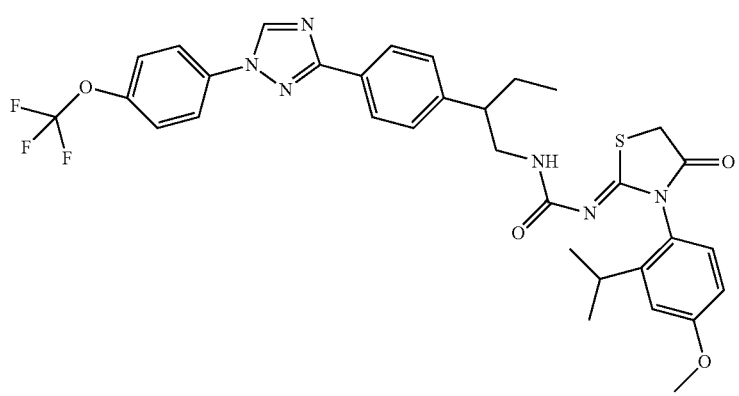 [SMILES: CCC(CNC(=O)/N=C1\SCC(=O)N1c1ccc(OC)cc1C(C)C)c1ccc(-c2ncn(-c3ccc(OC(F)(F)F)cc3)n2)cc1]
P1323
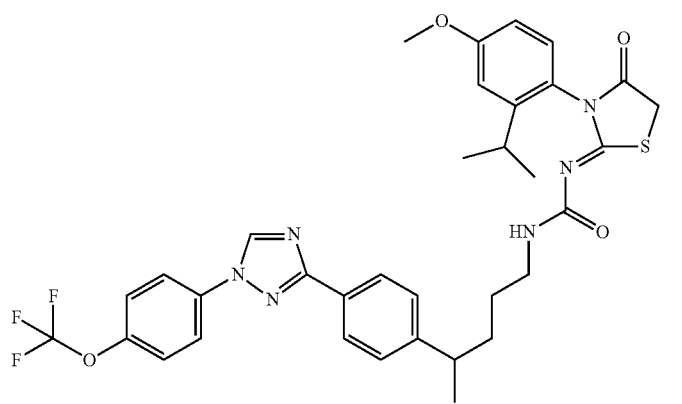 [SMILES: COc1ccc(N2C(=O)CS/C2=N\C(=O)NCCCC(C)c2ccc(-c3ncn(-c4ccc(OC(F)(F)F)cc4)n3)cc2)c(C(C)C)c1]
P1324

TABLE P-Two-continued
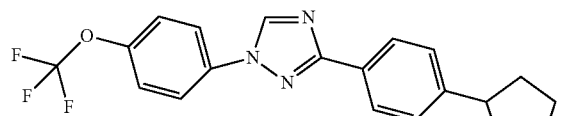
P1325
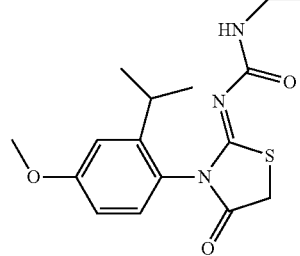
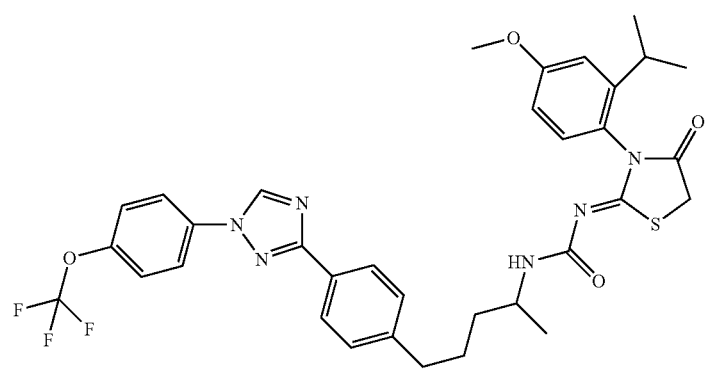 [SMILES: COc1ccc(N2C(=O)CS/C2=N\C(=O)NC(C)CCCc2ccc(-c3ncn(-c4ccc(OC(F)(F)F)cc4)n3)cc2)c(C(C)C)c1]
P1326
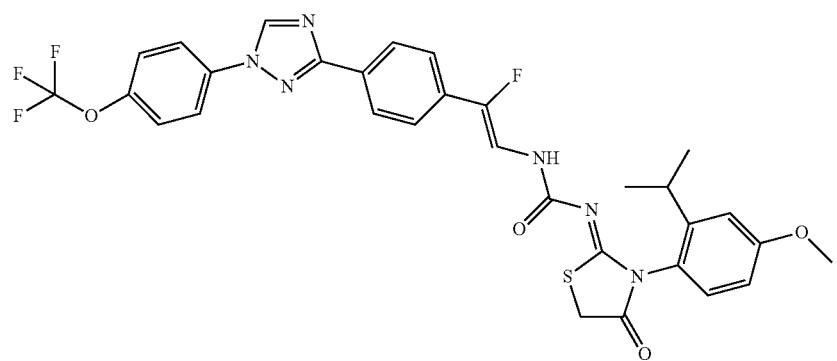 [SMILES: COc1ccc(N2C(=O)CS/C2=N\C(=O)N/C=C(\F)c2ccc(-c3ncn(-c4ccc(OC(F)(F)F)cc4)n3)cc2)c(C(C)C)c1]
P1327
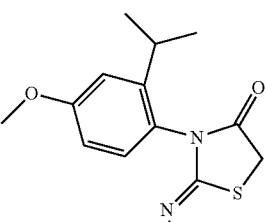
P1328
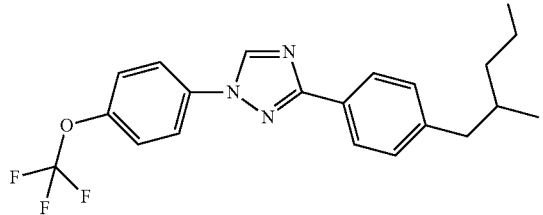

TABLE P-Two-continued
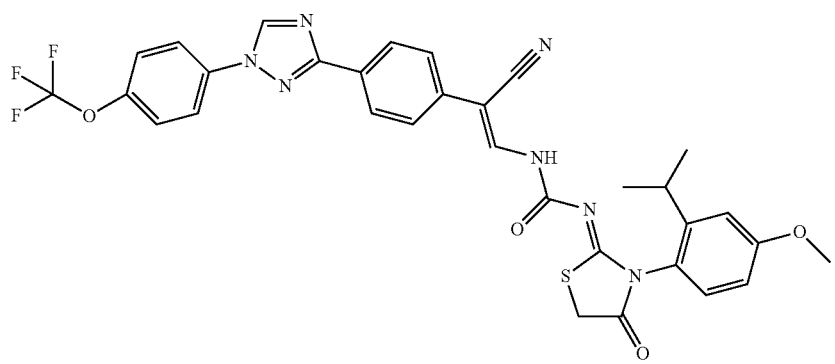 [SMILES: COc1ccc(N2C(=O)CS/C2=N\C(=O)N/C=C(\C#N)c2ccc(-c3ncn(-c4ccc(OC(F)(F)F)cc4)n3)cc2)c(C(C)C)c1]
P1329
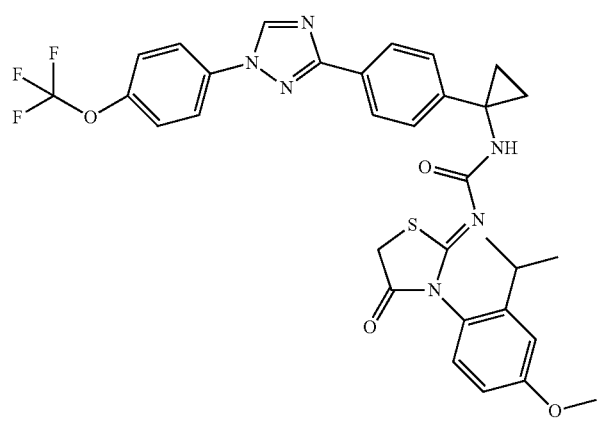 [SMILES: COc1ccc(N2C(=O)CS/C2=N\C(=O)NC2(c3ccc(-c4ncn(-c5ccc(OC(F)(F)F)cc5)n4)cc3)CC2)c(C(C)C)c1]
P1330
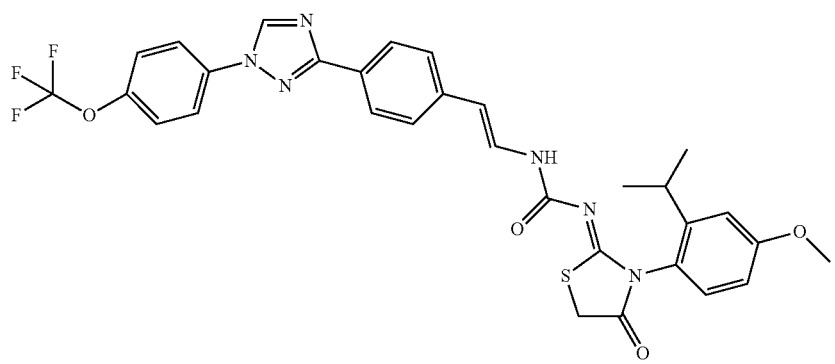 [SMILES: COc1ccc(N2C(=O)CS/C2=N\C(=O)N/C=C/c2ccc(-c3ncn(-c4ccc(OC(F)(F)F)cc4)n3)cc2)c(C(C)C)c1]
P1331
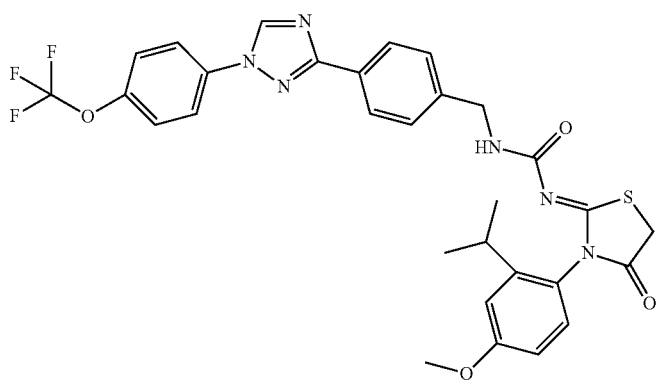 [SMILES: COc1ccc(N2C(=O)CS/C2=N\C(=O)NCc2ccc(-c3ncn(-c4ccc(OC(F)(F)F)cc4)n3)cc2)c(C(C)C)c1]
P1332

TABLE P-Two-continued
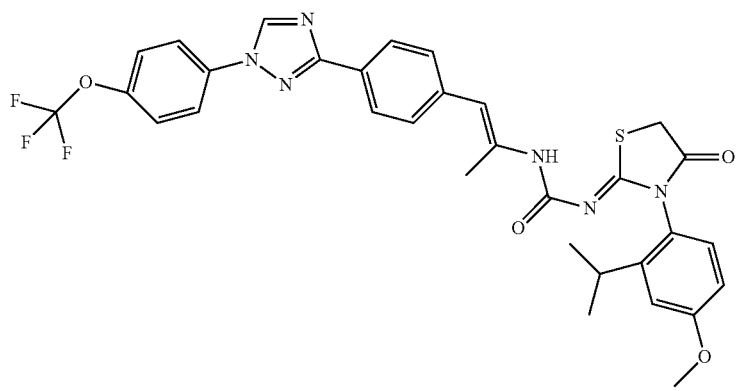 [SMILES: COc1ccc(N2C(=O)CS/C2=N\C(=O)N/C(C)=C/c2ccc(-c3ncn(-c4ccc(OC(F)(F)F)cc4)n3)cc2)c(C(C)C)c1]
P1333
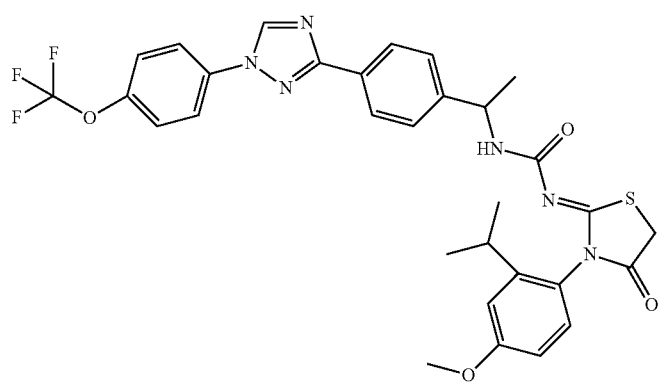 [SMILES: COc1ccc(N2C(=O)CS/C2=N\C(=O)NC(C)c2ccc(-c3ncn(-c4ccc(OC(F)(F)F)cc4)n3)cc2)c(C(C)C)c1]
P1334
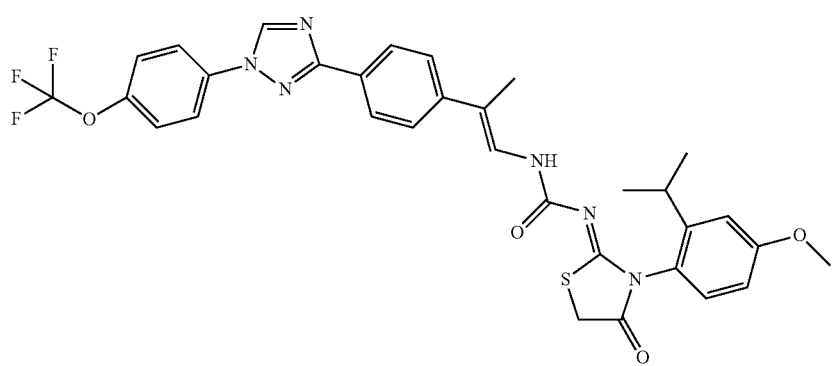 [SMILES: COc1ccc(N2C(=O)CS/C2=N\C(=O)N/C=C(\C)c2ccc(-c3ncn(-c4ccc(OC(F)(F)F)cc4)n3)cc2)c(C(C)C)c1]
P1335
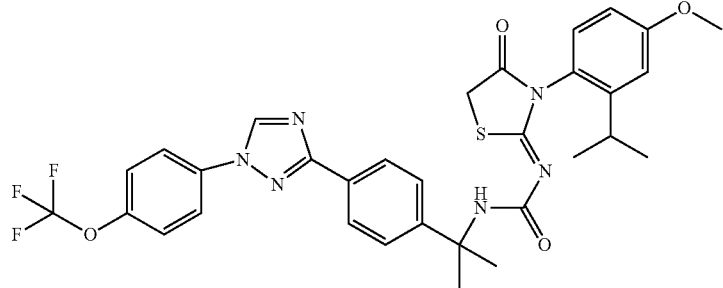 [SMILES: COc1ccc(N2C(=O)CS/C2=N\C(=O)NC(C)(C)c2ccc(-c3ncn(-c4ccc(OC(F)(F)F)cc4)n3)cc2)c(C(C)C)c1]
P1336

TABLE P-Two-continued
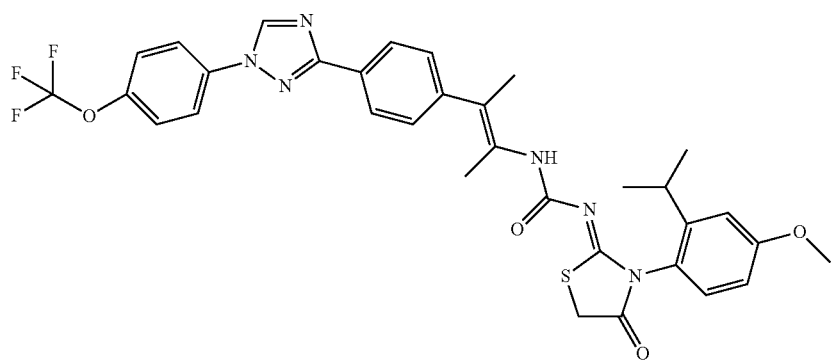 [SMILES: COc1ccc(N2C(=O)CS/C2=N\C(=O)N/C(C)=C(\C)c2ccc(-c3ncn(-c4ccc(OC(F)(F)F)cc4)n3)cc2)c(C(C)C)c1]
P1337
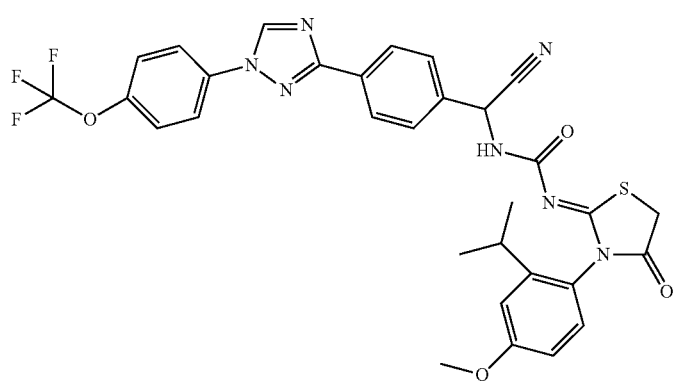 [SMILES: COc1ccc(N2C(=O)CS/C2=N\C(=O)NC(C#N)c2ccc(-c3ncn(-c4ccc(OC(F)(F)F)cc4)n3)cc2)c(C(C)C)c1]
P1338
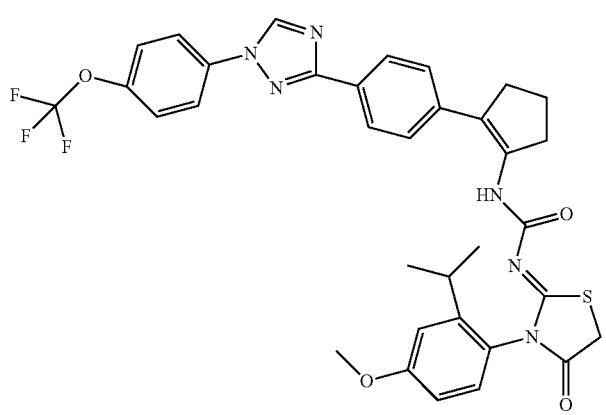 [SMILES: COc1ccc(N2C(=O)CS/C2=N\C(=O)NC2=C(c3ccc(-c4ncn(-c5ccc(OC(F)(F)F)cc5)n4)cc3)CCC2)c(C(C)C)c1]
P1339
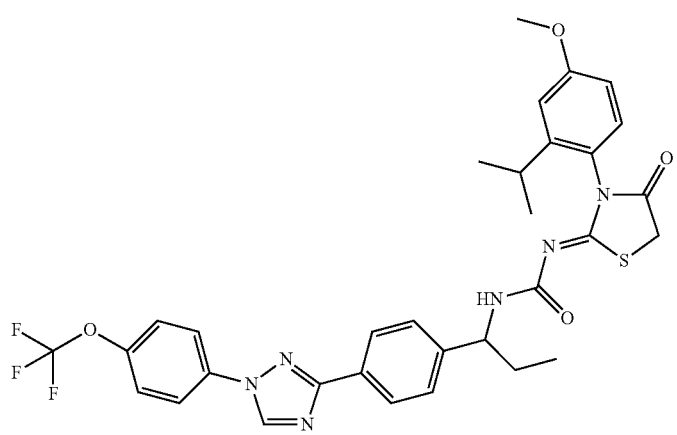 [SMILES: CCC(NC(=O)/N=C1\SCC(=O)N1c1ccc(OC)cc1C(C)C)c1ccc(-c2ncn(-c3ccc(OC(F)(F)F)cc3)n2)cc1]
P1340

TABLE P-Two-continued
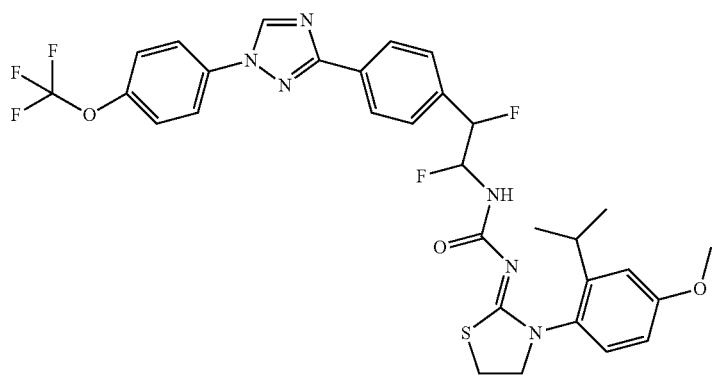 [SMILES: COc1ccc(N2CCS/C2=N\C(=O)NC(F)C(F)c2ccc(-c3ncn(-c4ccc(OC(F)(F)F)cc4)n3)cc2)c(C(C)C)c1]
P1341
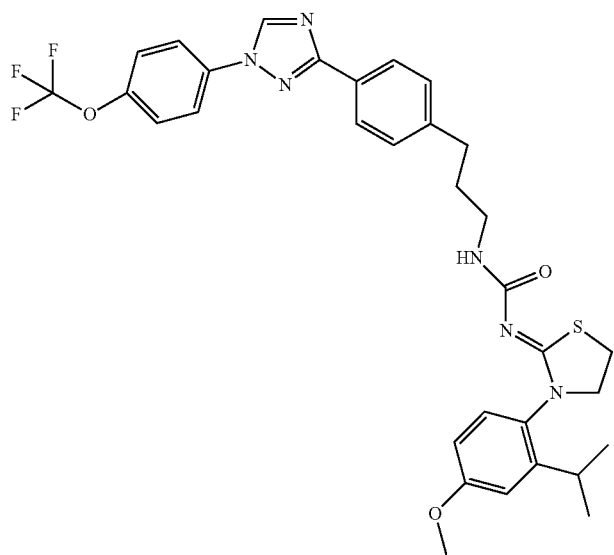 [SMILES: COc1ccc(N2CCS/C2=N\C(=O)NCCCc2ccc(-c3ncn(-c4ccc(OC(F)(F)F)cc4)n3)cc2)c(C(C)C)c1]
P1342
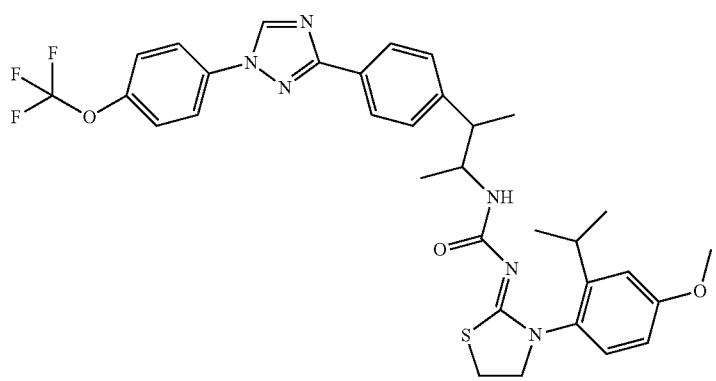 [SMILES: COc1ccc(N2CCS/C2=N\C(=O)NC(C)C(C)c2ccc(-c3ncn(-c4ccc(OC(F)(F)F)cc4)n3)cc2)c(C(C)C)c1]
P1343

TABLE P-Two-continued
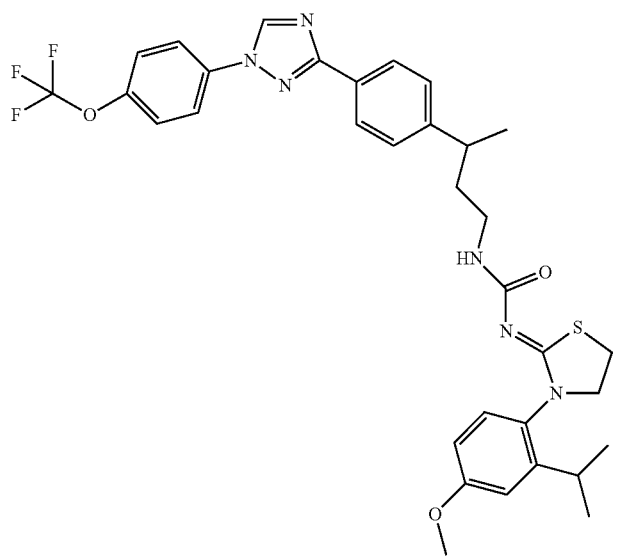 [SMILES: COc1ccc(N2CCS/C2=N\C(=O)NCCC(C)c2ccc(-c3ncn(-c4ccc(OC(F)(F)F)cc4)n3)cc2)c(C(C)C)c1]
P1344
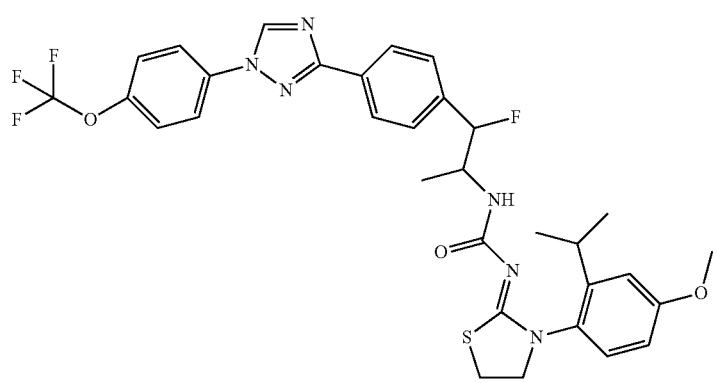 [SMILES: COc1ccc(N2CCS/C2=N\C(=O)NC(C)C(F)c2ccc(-c3ncn(-c4ccc(OC(F)(F)F)cc4)n3)cc2)c(C(C)C)c1]
P1345
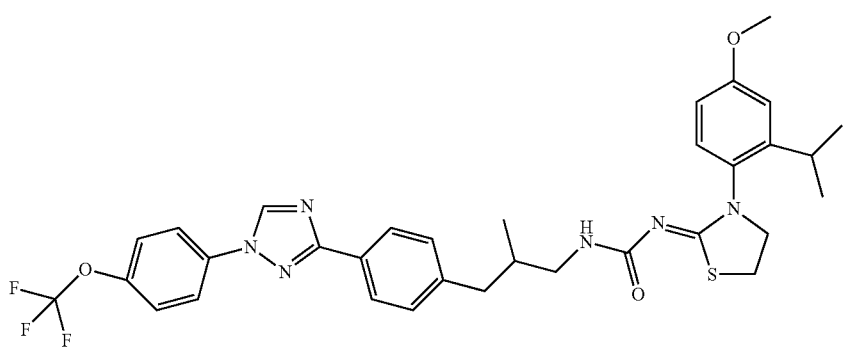 [SMILES: COc1ccc(N2CCS/C2=N\C(=O)NCC(C)Cc2ccc(-c3ncn(-c4ccc(OC(F)(F)F)cc4)n3)cc2)c(C(C)C)c1]
P1346
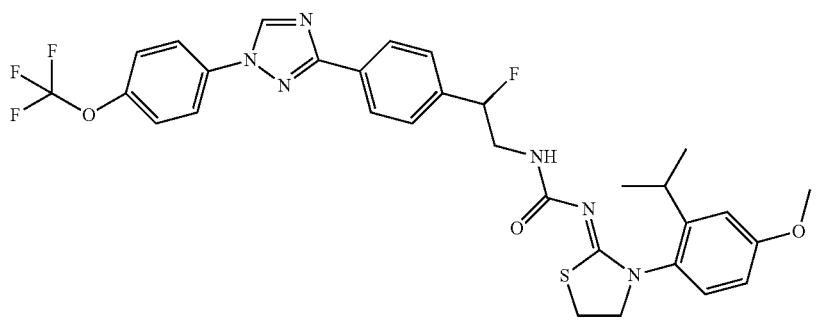 [SMILES: COc1ccc(N2CCS/C2=N\C(=O)NCC(F)c2ccc(-c3ncn(-c4ccc(OC(F)(F)F)cc4)n3)cc2)c(C(C)C)c1]
P1347

TABLE P-Two-continued
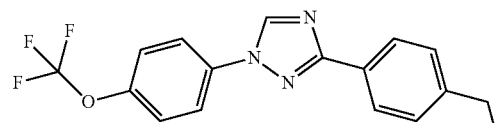
P1348
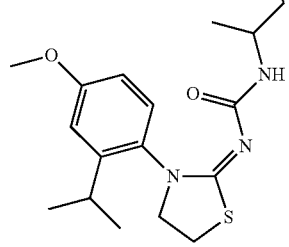
P1349
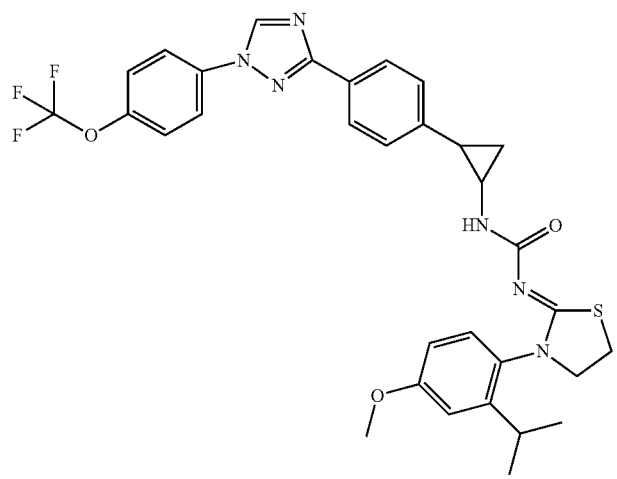 [SMILES: COc1ccc(N2CCS/C2=N\C(=O)NC2CC2c2ccc(-c3ncn(-c4ccc(OC(F)(F)F)cc4)n3)cc2)c(C(C)C)c1]
P1350
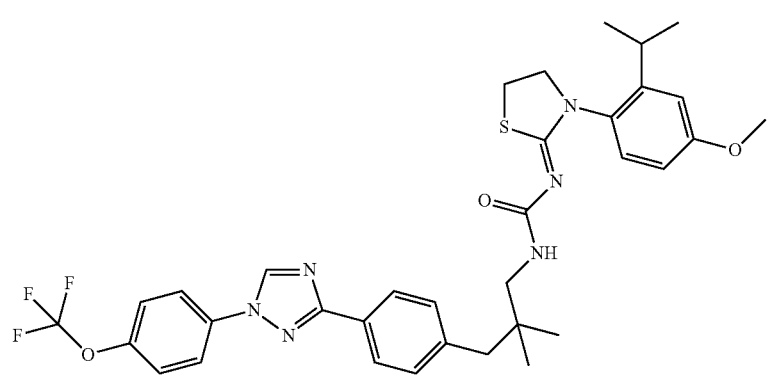 [SMILES: COc1ccc(N2CCS/C2=N\C(=O)NCC(C)(C)Cc2ccc(-c3ncn(-c4ccc(OC(F)(F)F)cc4)n3)cc2)c(C(C)C)c1]
P1351

TABLE P-Two-continued
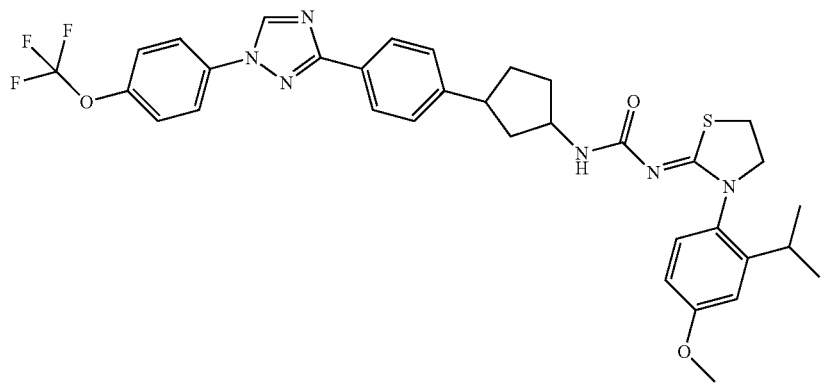 [SMILES: COc1ccc(N2CCS/C2=N\C(=O)NC2CCC(c3ccc(-c4ncn(-c5ccc(OC(F)(F)F)cc5)n4)cc3)C2)c(C(C)C)c1]
P1352
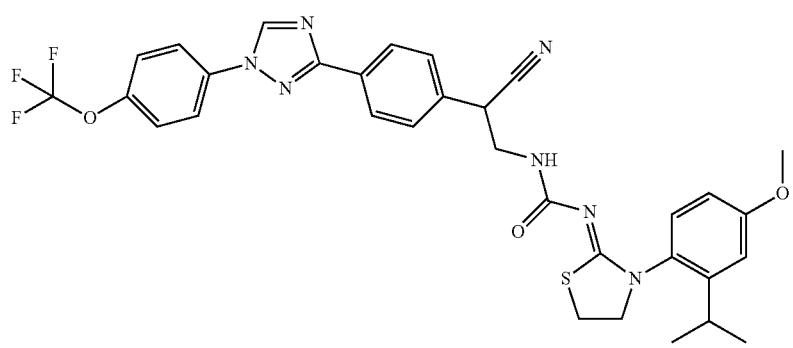 [SMILES: COc1ccc(N2CCS/C2=N\C(=O)NCC(C#N)c2ccc(-c3ncn(-c4ccc(OC(F)(F)F)cc4)n3)cc2)c(C(C)C)c1]
P1353
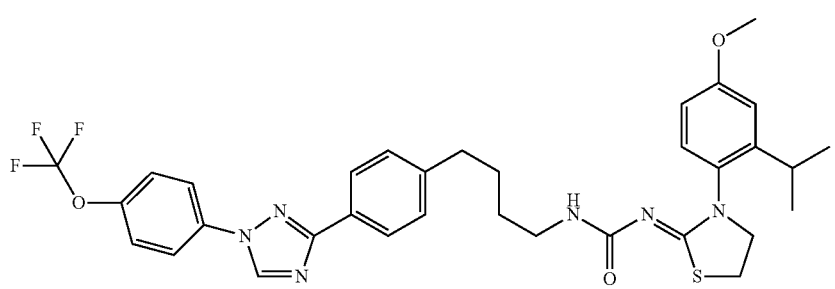 [SMILES: COc1ccc(N2CCS/C2=N\C(=O)NCCCCc2ccc(-c3ncn(-c4ccc(OC(F)(F)F)cc4)n3)cc2)c(C(C)C)c1]
P1354
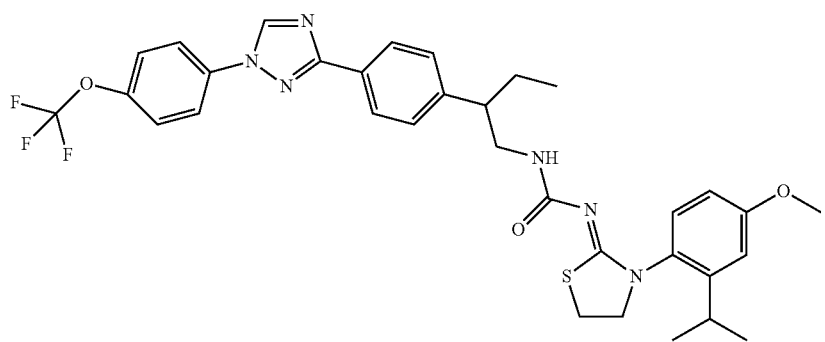 [SMILES: CCC(CNC(=O)/N=C1\SCCN1c1ccc(OC)cc1C(C)C)c1ccc(-c2ncn(-c3ccc(OC(F)(F)F)cc3)n2)cc1]
P1355

TABLE P-Two-continued
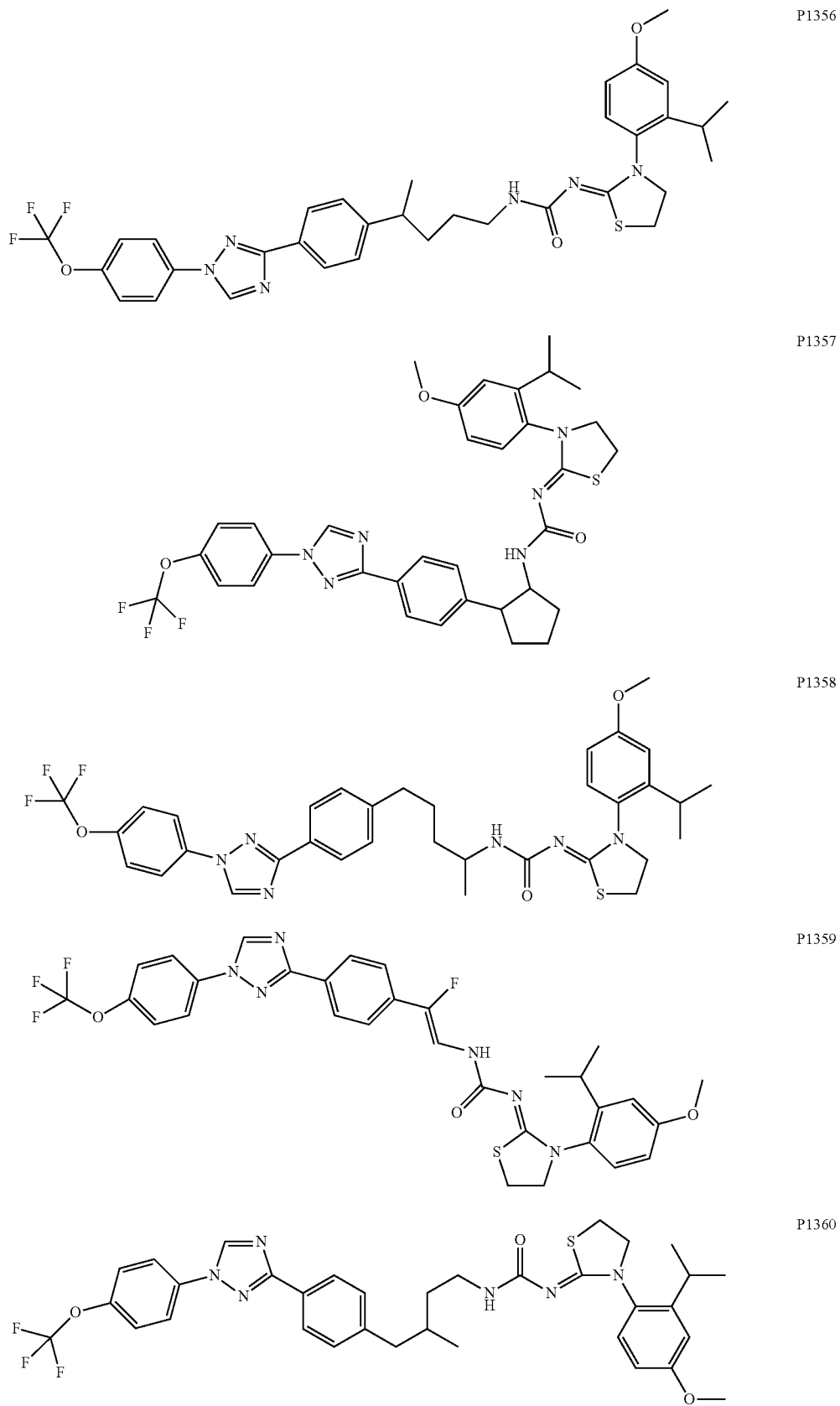

| | |
|---|---|
| 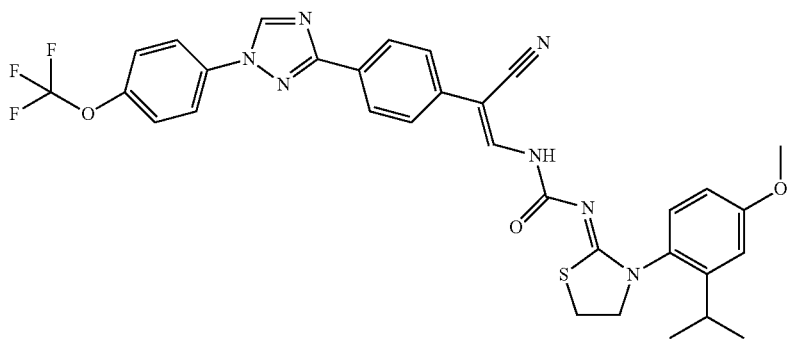 [SMILES: COc1ccc(N2CCS/C2=N\C(=O)N/C=C(\C#N)c2ccc(-c3ncn(-c4ccc(OC(F)(F)F)cc4)n3)cc2)c(C(C)C)c1] | P1361 |
| 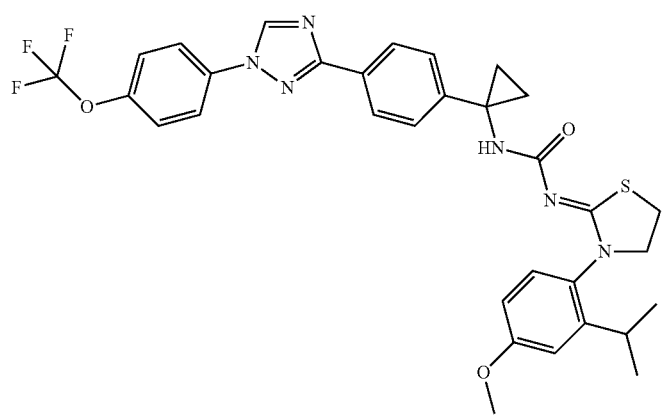 [SMILES: COc1ccc(N2CCS/C2=N\C(=O)NC2(c3ccc(-c4ncn(-c5ccc(OC(F)(F)F)cc5)n4)cc3)CC2)c(C(C)C)c1] | P1362 |
| 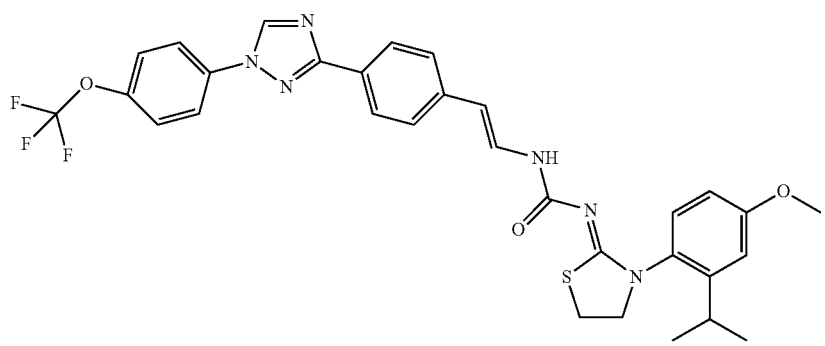 [SMILES: COc1ccc(N2CCS/C2=N\C(=O)N/C=C/c2ccc(-c3ncn(-c4ccc(OC(F)(F)F)cc4)n3)cc2)c(C(C)C)c1] | P1363 |
| 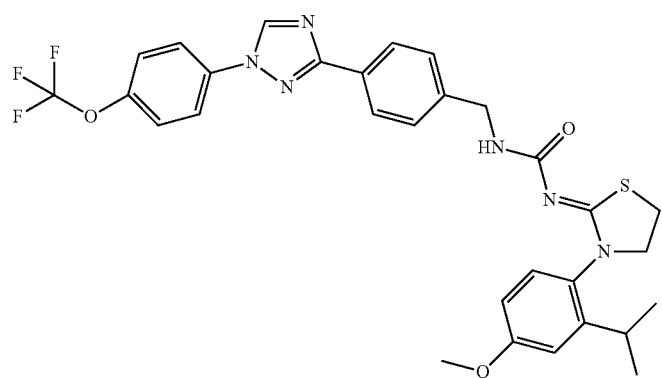 [SMILES: COc1ccc(N2CCS/C2=N\C(=O)NCc2ccc(-c3ncn(-c4ccc(OC(F)(F)F)cc4)n3)cc2)c(C(C)C)c1] | P1364 |

TABLE P-Two-continued
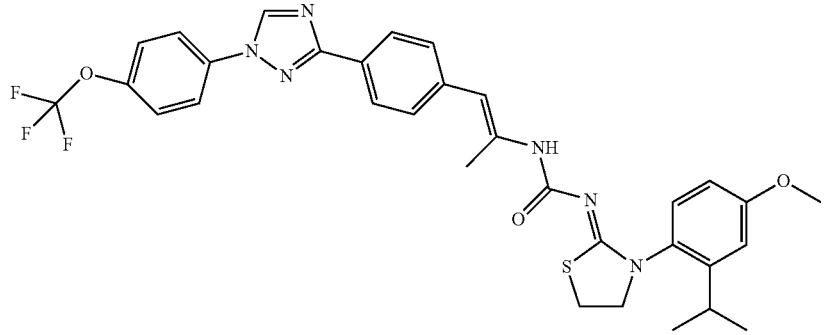 [SMILES: COc1ccc(N2CCS/C2=N\C(=O)N/C(C)=C/c2ccc(-c3ncn(-c4ccc(OC(F)(F)F)cc4)n3)cc2)c(C(C)C)c1]
P1365
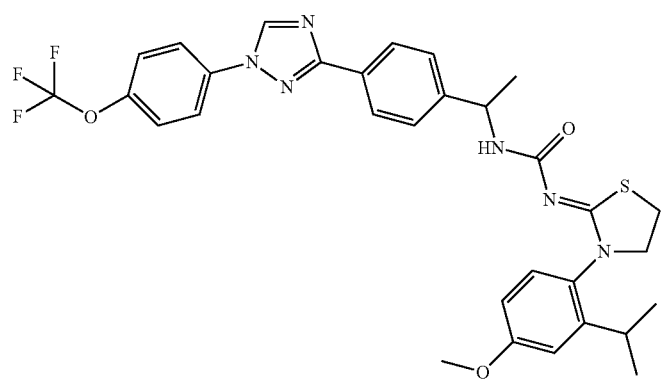 [SMILES: COc1ccc(N2CCS/C2=N\C(=O)NC(C)c2ccc(-c3ncn(-c4ccc(OC(F)(F)F)cc4)n3)cc2)c(C(C)C)c1]
P1366
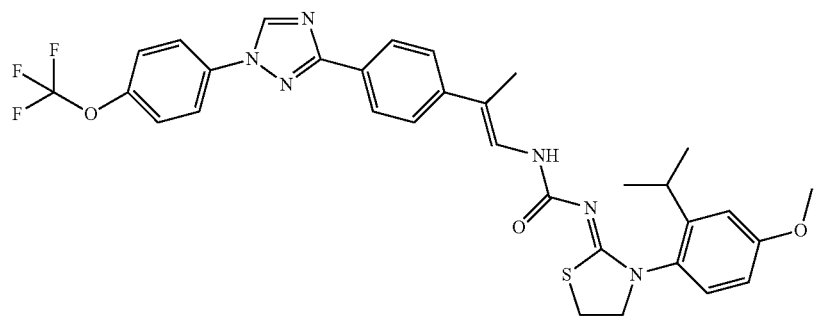 [SMILES: COc1ccc(N2CCS/C2=N\C(=O)N/C=C(\C)c2ccc(-c3ncn(-c4ccc(OC(F)(F)F)cc4)n3)cc2)c(C(C)C)c1]
P1367
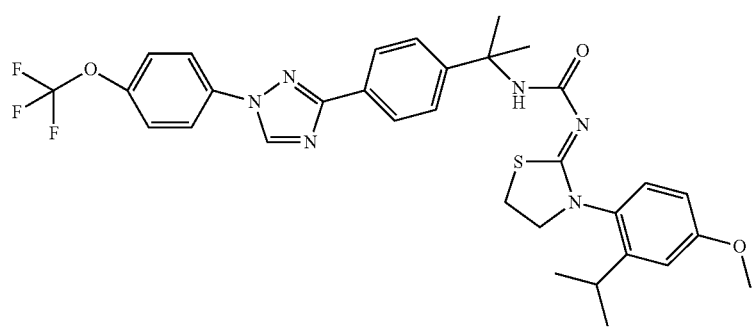 [SMILES: COc1ccc(N2CCS/C2=N\C(=O)NC(C)(C)c2ccc(-c3ncn(-c4ccc(OC(F)(F)F)cc4)n3)cc2)c(C(C)C)c1]
P1368

TABLE P-Two-continued
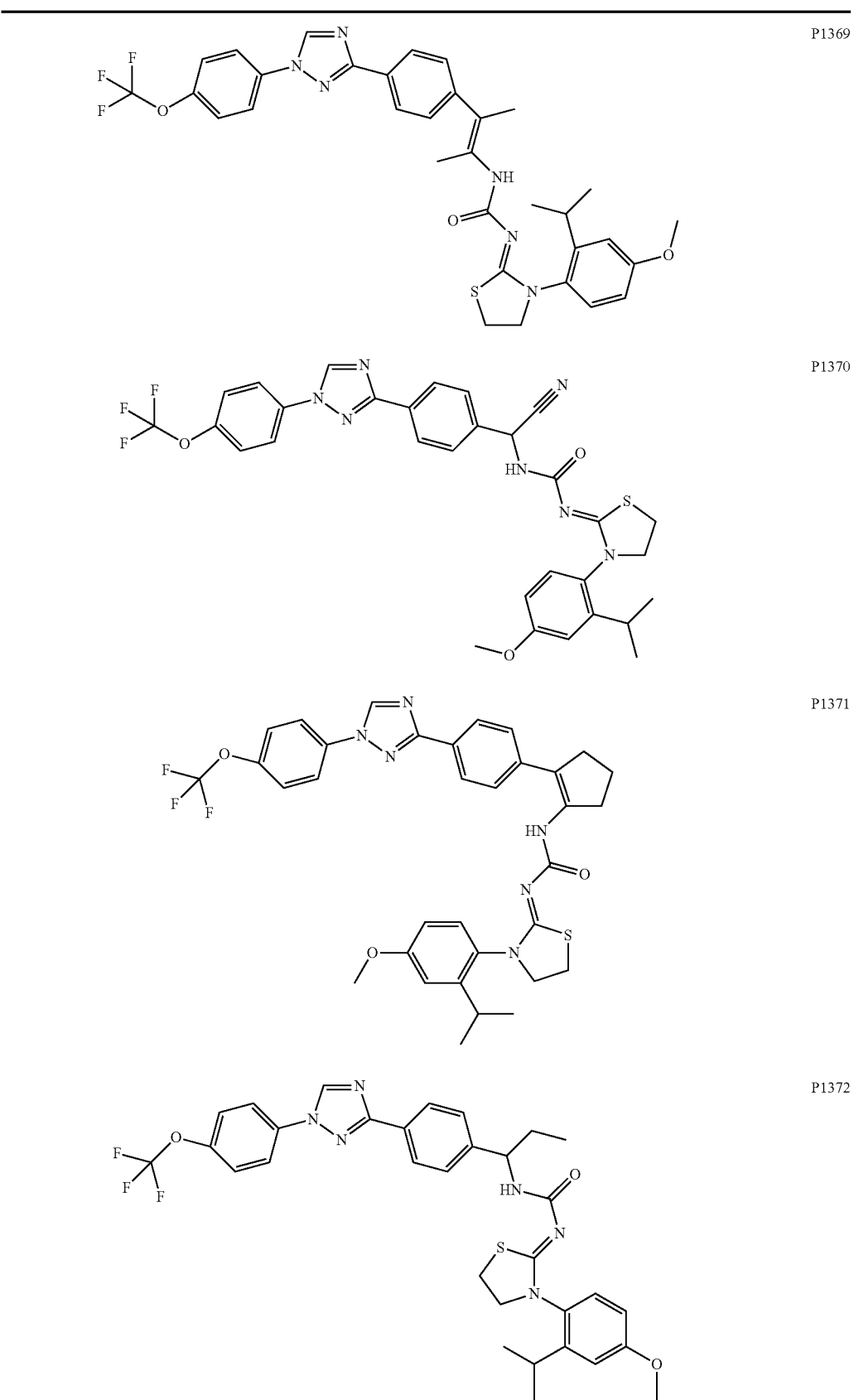
P1369
P1370
P1371
P1372

TABLE P-Two-continued
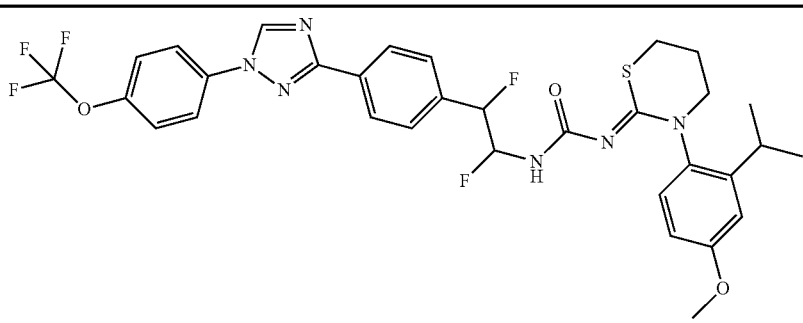
P1373
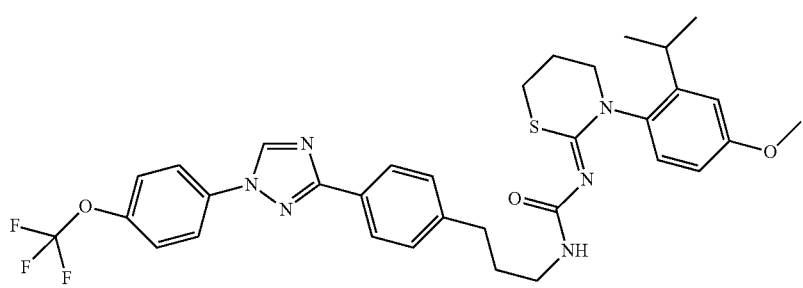 [SMILES: COc1ccc(N2CCCS/C2=N\C(=O)NCCCc2ccc(-c3ncn(-c4ccc(OC(F)(F)F)cc4)n3)cc2)c(C(C)C)c1]
P1374
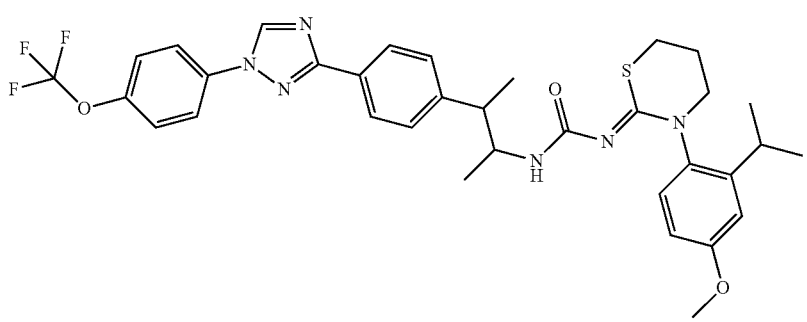 [SMILES: COc1ccc(N2CCCS/C2=N\C(=O)NC(C)C(C)c2ccc(-c3ncn(-c4ccc(OC(F)(F)F)cc4)n3)cc2)c(C(C)C)c1]
P1375
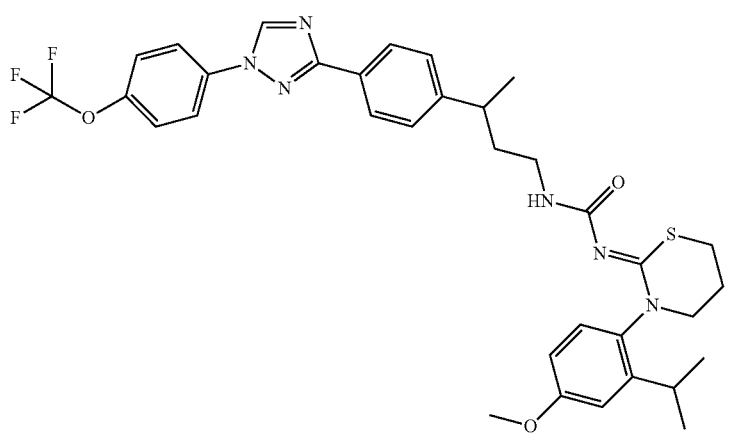 [SMILES: COc1ccc(N2CCCS/C2=N\C(=O)NCCC(C)c2ccc(-c3ncn(-c4ccc(OC(F)(F)F)cc4)n3)cc2)c(C(C)C)c1]
P1376
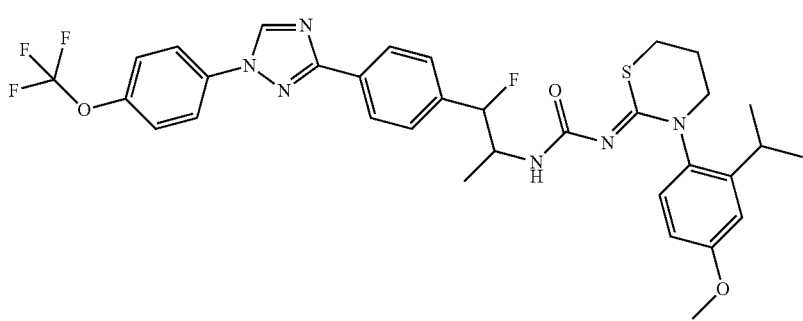 [SMILES: COc1ccc(N2CCCS/C2=N\C(=O)NC(C)C(F)c2ccc(-c3ncn(-c4ccc(OC(F)(F)F)cc4)n3)cc2)c(C(C)C)c1]
P1377

TABLE P-Two-continued
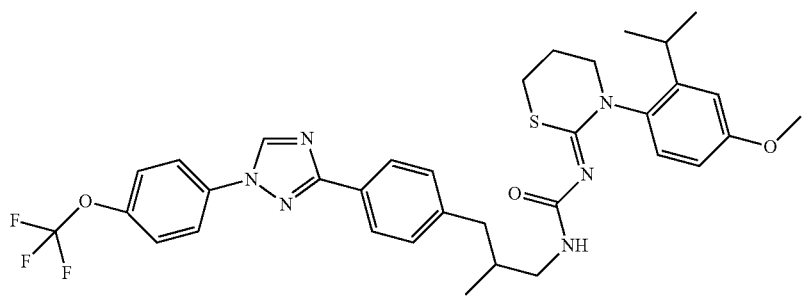 [SMILES: COc1ccc(N2CCCS/C2=N\C(=O)NCC(C)Cc2ccc(-c3ncn(-c4ccc(OC(F)(F)F)cc4)n3)cc2)c(C(C)C)c1] P1378
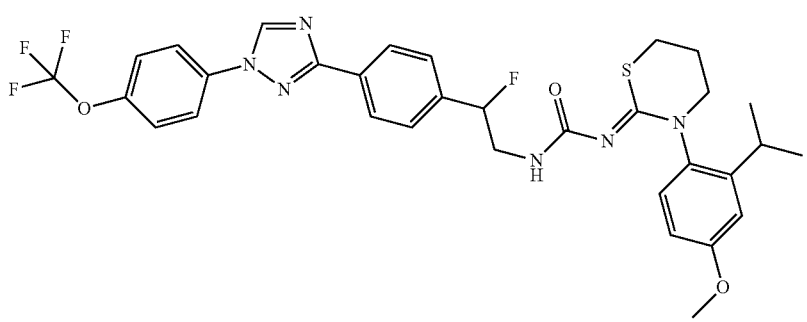 [SMILES: COc1ccc(N2CCCS/C2=N\C(=O)NCC(F)c2ccc(-c3ncn(-c4ccc(OC(F)(F)F)cc4)n3)cc2)c(C(C)C)c1] P1379
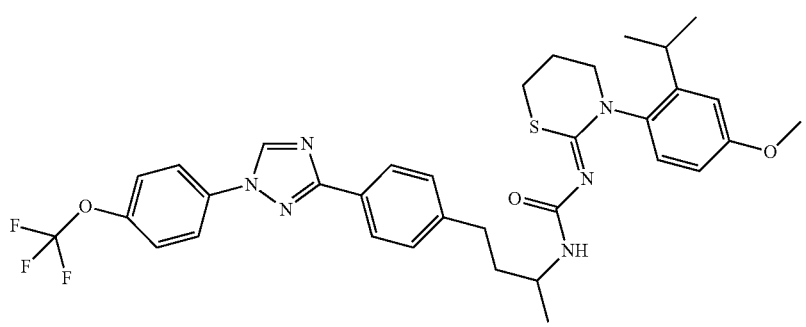 [SMILES: COc1ccc(N2CCCS/C2=N\C(=O)NC(C)CCc2ccc(-c3ncn(-c4ccc(OC(F)(F)F)cc4)n3)cc2)c(C(C)C)c1] P1380
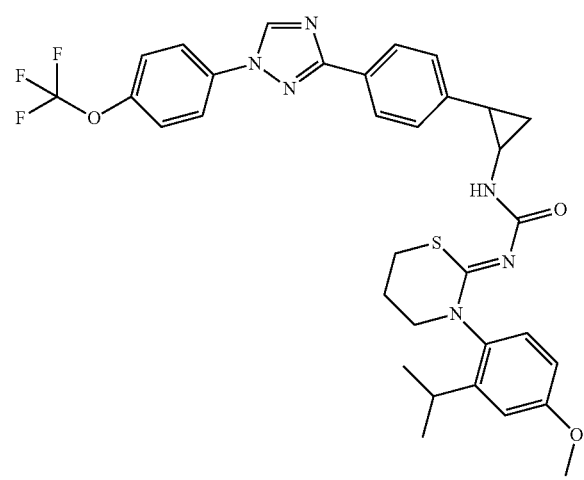 [SMILES: COc1ccc(N2CCCS/C2=N\C(=O)NC2CC2c2ccc(-c3ncn(-c4ccc(OC(F)(F)F)cc4)n3)cc2)c(C(C)C)c1] P1381

TABLE P-Two-continued
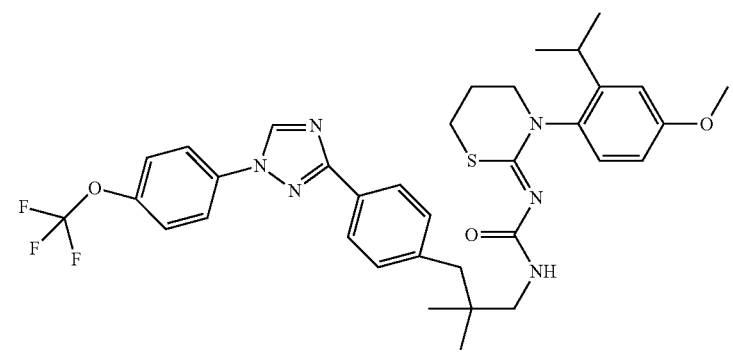 [SMILES: COc1ccc(N2CCCS/C2=N\C(=O)NCC(C)(C)Cc2ccc(-c3ncn(-c4ccc(OC(F)(F)F)cc4)n3)cc2)c(C(C)C)c1]
P1382
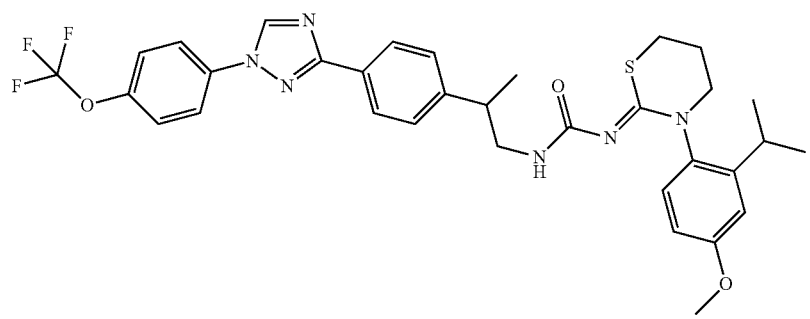 [SMILES: COc1ccc(N2CCCS/C2=N\C(=O)NCC(C)c2ccc(-c3ncn(-c4ccc(OC(F)(F)F)cc4)n3)cc2)c(C(C)C)c1]
P1383
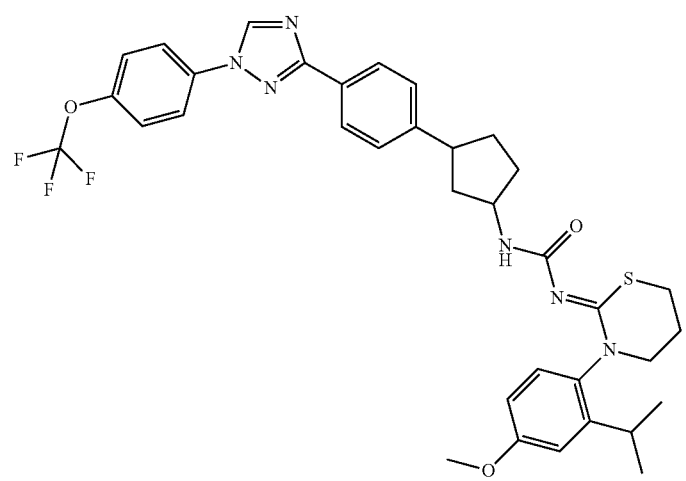 [SMILES: COc1ccc(N2CCCS/C2=N\C(=O)NC2CCC(c3ccc(-c4ncn(-c5ccc(OC(F)(F)F)cc5)n4)cc3)C2)c(C(C)C)c1]
P1384
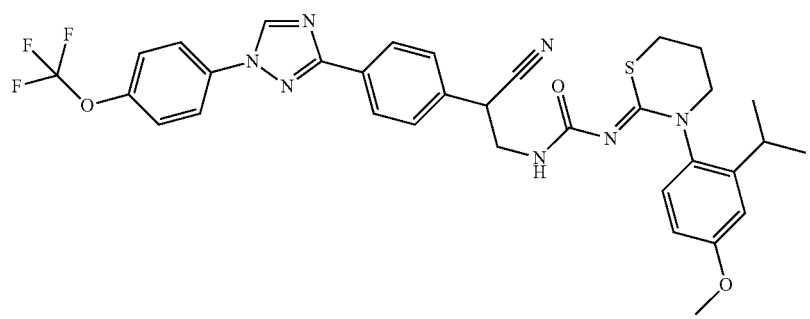 [SMILES: COc1ccc(N2CCCS/C2=N\C(=O)NCC(C#N)c2ccc(-c3ncn(-c4ccc(OC(F)(F)F)cc4)n3)cc2)c(C(C)C)c1]
P1385

TABLE P-Two-continued
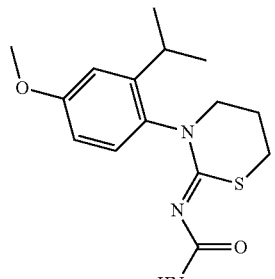
P1386
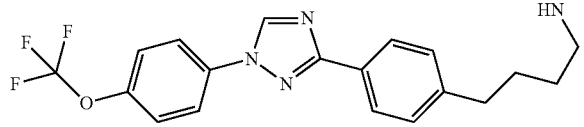
P1387
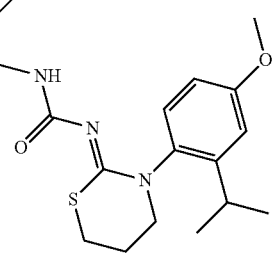
P1388
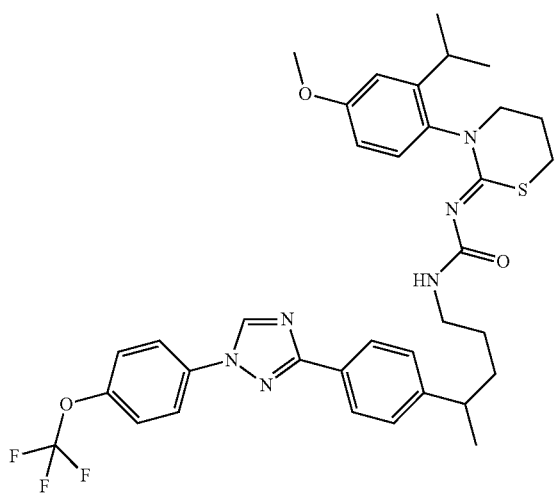 [SMILES: COc1ccc(N2CCCS/C2=N\C(=O)NCCCC(C)c2ccc(-c3ncn(-c4ccc(OC(F)(F)F)cc4)n3)cc2)c(C(C)C)c1]
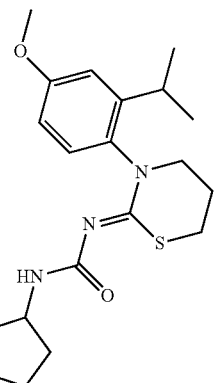
P1389

TABLE P-Two-continued
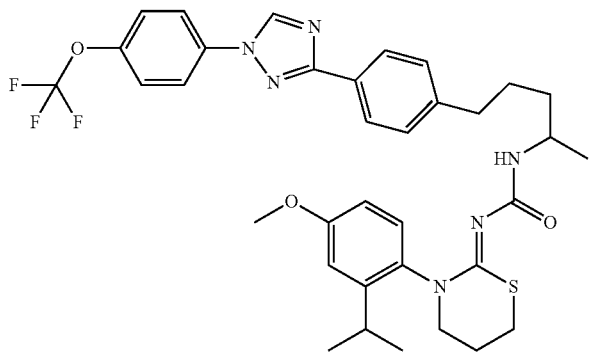 [SMILES: COc1ccc(N2CCCS/C2=N\C(=O)NC(C)CCCc2ccc(-c3ncn(-c4ccc(OC(F)(F)F)cc4)n3)cc2)c(C(C)C)c1]
P1390
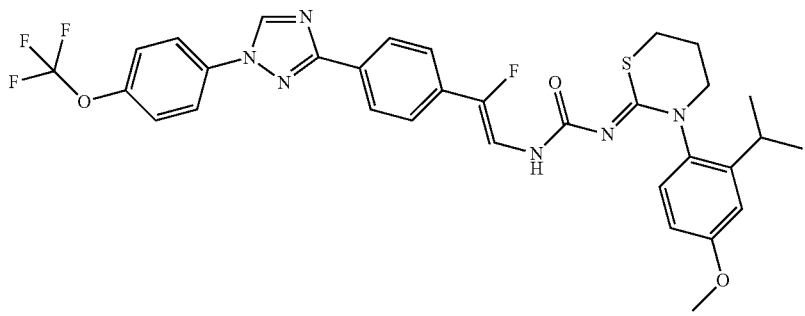 [SMILES: COc1ccc(N2CCCS/C2=N\C(=O)N/C=C(\F)c2ccc(-c3ncn(-c4ccc(OC(F)(F)F)cc4)n3)cc2)c(C(C)C)c1]
P1391
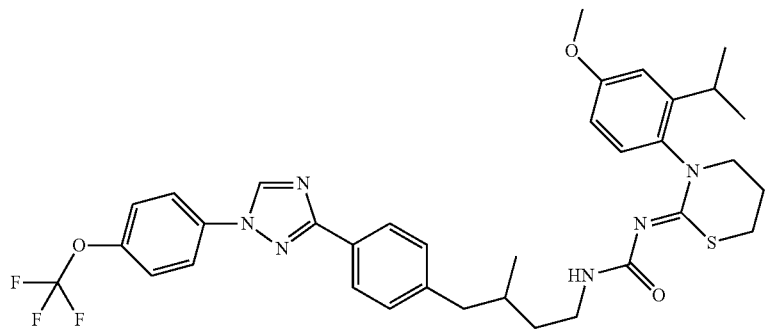 [SMILES: COc1ccc(N2CCCS/C2=N\C(=O)NCCC(C)Cc2ccc(-c3ncn(-c4ccc(OC(F)(F)F)cc4)n3)cc2)c(C(C)C)c1]
P1392
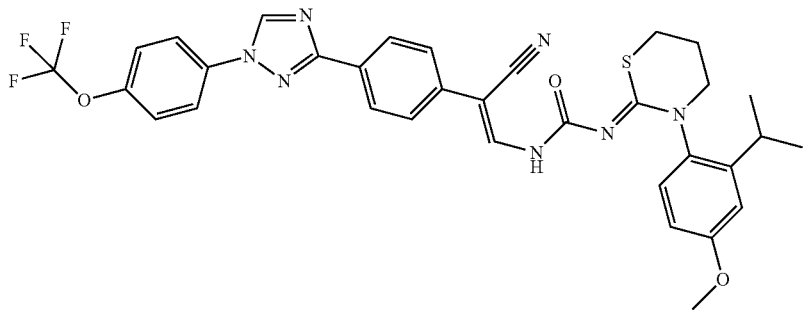 [SMILES: COc1ccc(N2CCCS/C2=N\C(=O)N/C=C(\C#N)c2ccc(-c3ncn(-c4ccc(OC(F)(F)F)cc4)n3)cc2)c(C(C)C)c1]
P1393
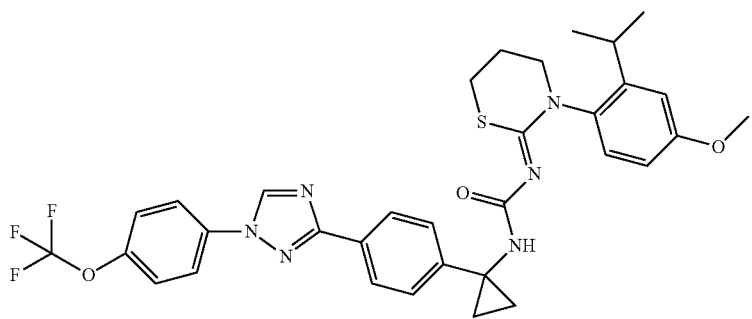 [SMILES: COc1ccc(N2CCCS/C2=N\C(=O)NC2(c3ccc(-c4ncn(-c5ccc(OC(F)(F)F)cc5)n4)cc3)CC2)c(C(C)C)c1]
P1394

TABLE P-Two-continued
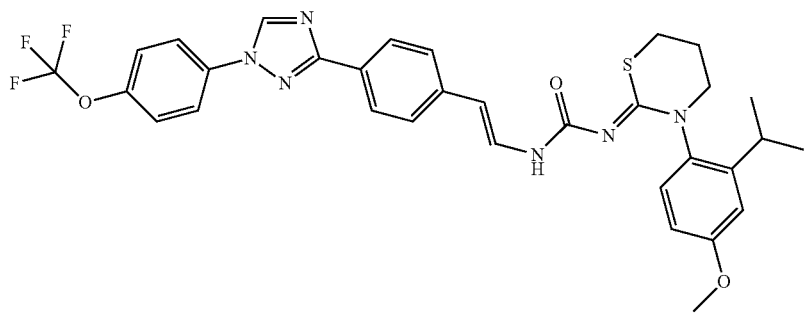 [SMILES: COc1ccc(N2CCCS/C2=N\C(=O)N/C=C/c2ccc(-c3ncn(-c4ccc(OC(F)(F)F)cc4)n3)cc2)c(C(C)C)c1]
P1395
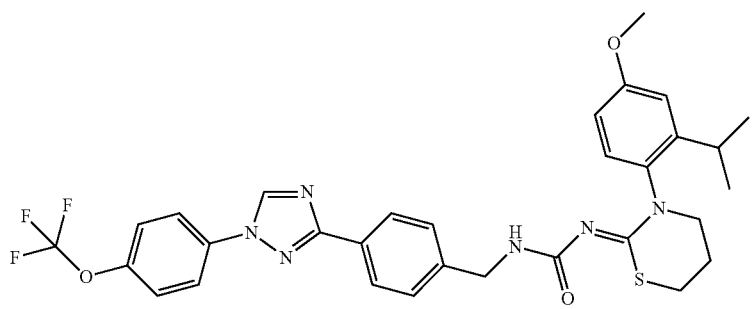 [SMILES: COc1ccc(N2CCCS/C2=N\C(=O)NCc2ccc(-c3ncn(-c4ccc(OC(F)(F)F)cc4)n3)cc2)c(C(C)C)c1]
P1396
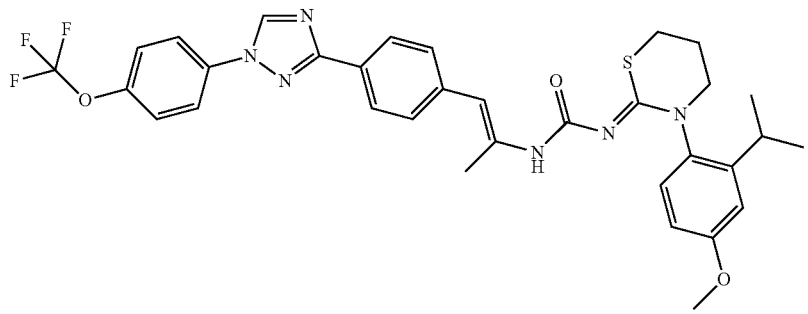 [SMILES: COc1ccc(N2CCCS/C2=N\C(=O)N/C(C)=C/c2ccc(-c3ncn(-c4ccc(OC(F)(F)F)cc4)n3)cc2)c(C(C)C)c1]
P1397
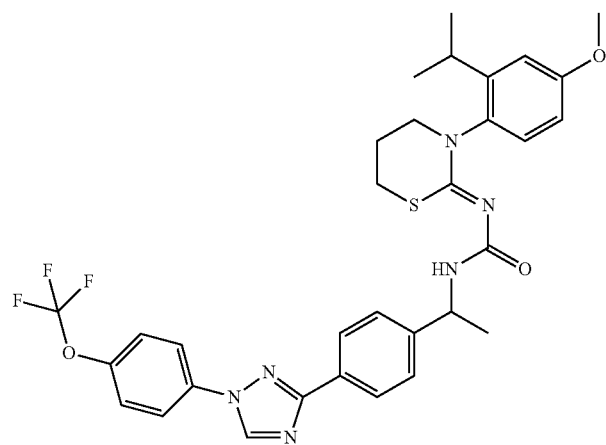 [SMILES: COc1ccc(N2CCCS/C2=N\C(=O)NC(C)c2ccc(-c3ncn(-c4ccc(OC(F)(F)F)cc4)n3)cc2)c(C(C)C)c1]
P1398

TABLE P-Two-continued
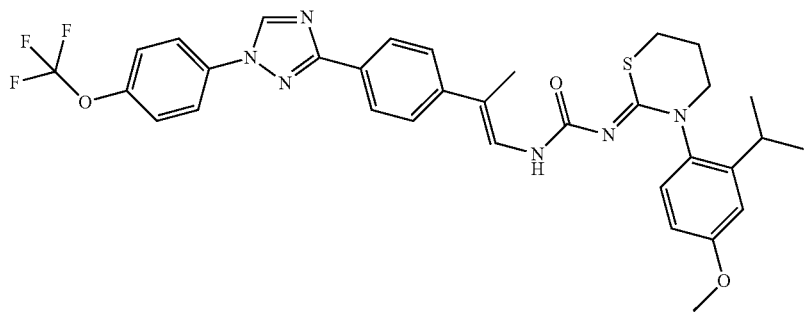 [SMILES: COc1ccc(N2CCCS/C2=N\C(=O)N/C=C(\C)c2ccc(-c3ncn(-c4ccc(OC(F)(F)F)cc4)n3)cc2)c(C(C)C)c1]
P1399
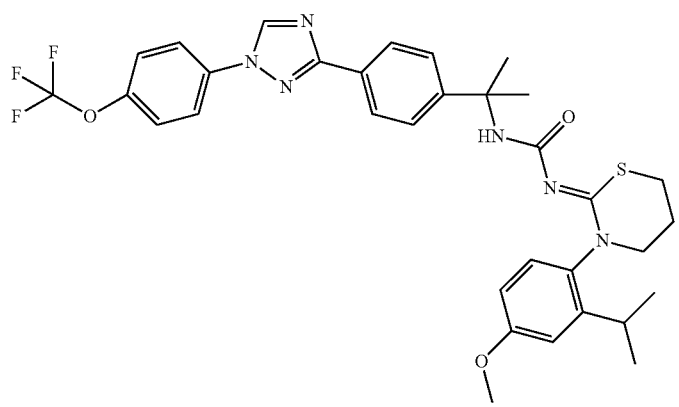 [SMILES: COc1ccc(N2CCCS/C2=N\C(=O)NC(C)(C)c2ccc(-c3ncn(-c4ccc(OC(F)(F)F)cc4)n3)cc2)c(C(C)C)c1]
P1400
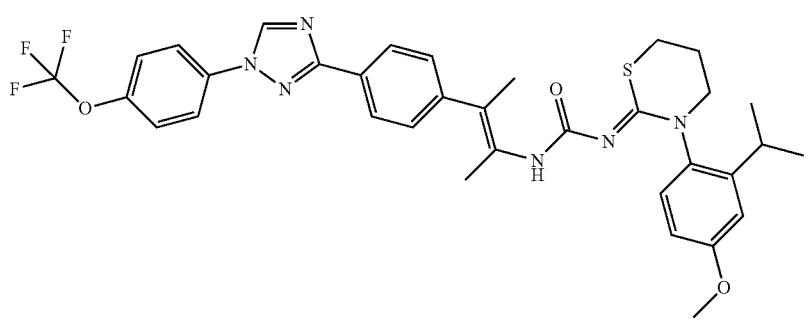 [SMILES: COc1ccc(N2CCCS/C2=N\C(=O)N/C(C)=C(\C)c2ccc(-c3ncn(-c4ccc(OC(F)(F)F)cc4)n3)cc2)c(C(C)C)c1]
P1401
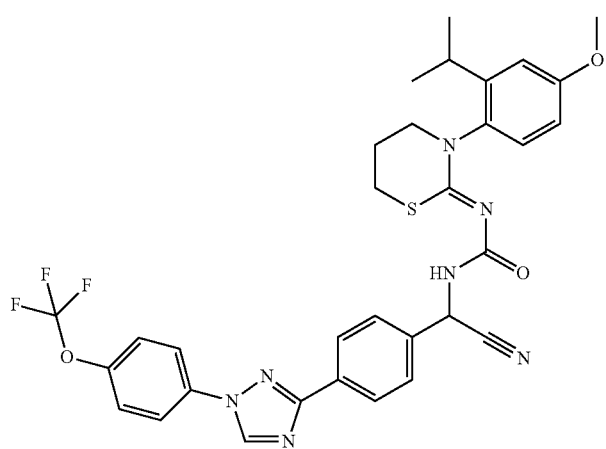 [SMILES: COc1ccc(N2CCCS/C2=N\C(=O)NC(C#N)c2ccc(-c3ncn(-c4ccc(OC(F)(F)F)cc4)n3)cc2)c(C(C)C)c1]
P1402

TABLE P-Two-continued
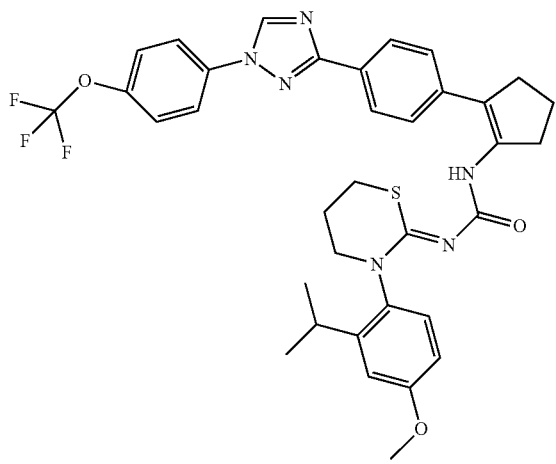 [SMILES: COc1ccc(N2CCCS/C2=N\C(=O)NC2=C(c3ccc(-c4ncn(-c5ccc(OC(F)(F)F)cc5)n4)cc3)CCC2)c(C(C)C)c1]
P1403
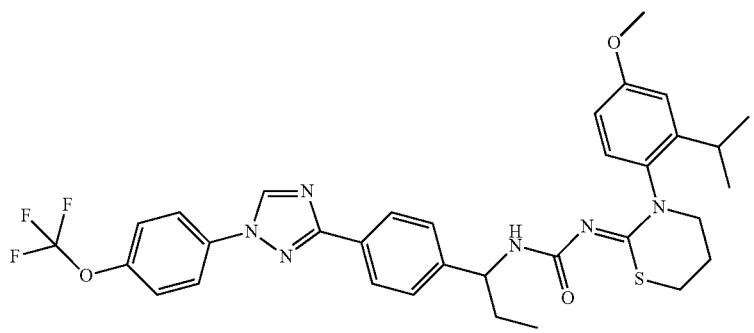 [SMILES: CCC(NC(=O)/N=C1\SCCCN1c1ccc(OC)cc1C(C)C)c1ccc(-c2ncn(-c3ccc(OC(F)(F)F)cc3)n2)cc1]
P1404
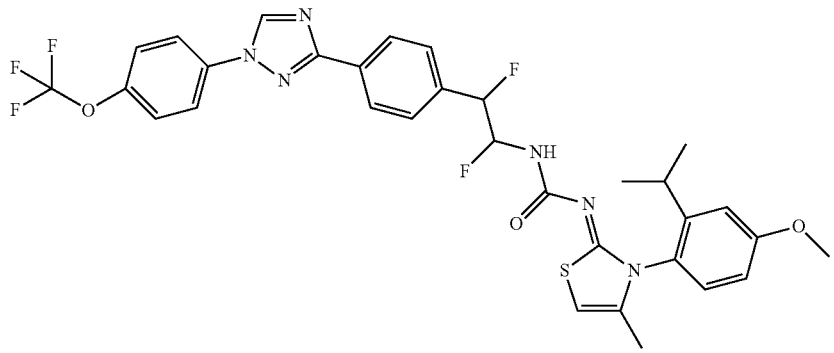 [SMILES: COc1ccc(-n2c(C)cs/c2=N\C(=O)NC(F)C(F)c2ccc(-c3ncn(-c4ccc(OC(F)(F)F)cc4)n3)cc2)c(C(C)C)c1]
P1405
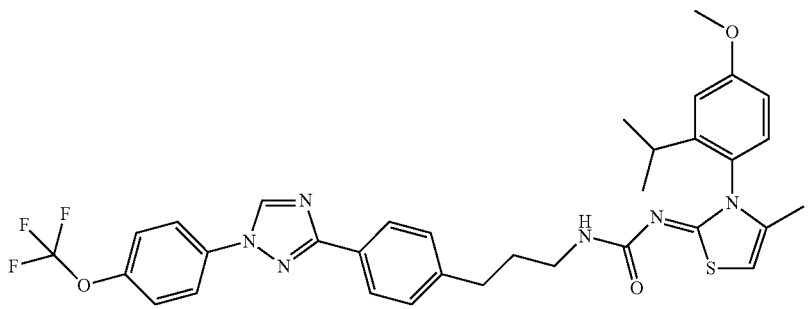 [SMILES: COc1ccc(-n2c(C)cs/c2=N\C(=O)NCCCc2ccc(-c3ncn(-c4ccc(OC(F)(F)F)cc4)n3)cc2)c(C(C)C)c1]
P1406

TABLE P-Two-continued
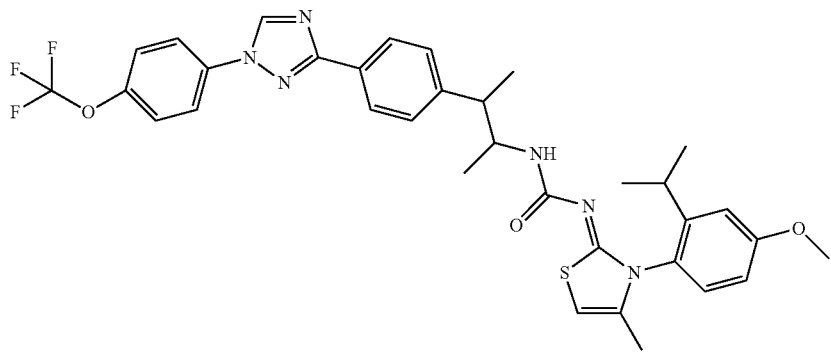 [SMILES: COc1ccc(-n2c(C)cs/c2=N\C(=O)NC(C)C(C)c2ccc(-c3ncn(-c4ccc(OC(F)(F)F)cc4)n3)cc2)c(C(C)C)c1]
P1407
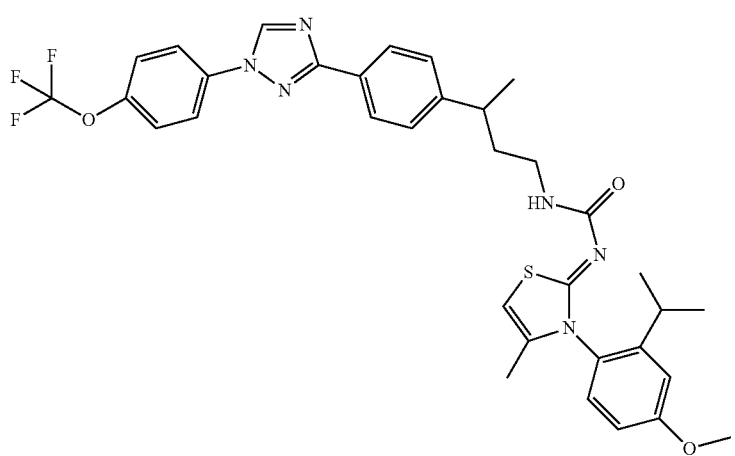 [SMILES: COc1ccc(-n2c(C)cs/c2=N\C(=O)NCCC(C)c2ccc(-c3ncn(-c4ccc(OC(F)(F)F)cc4)n3)cc2)c(C(C)C)c1]
P1408
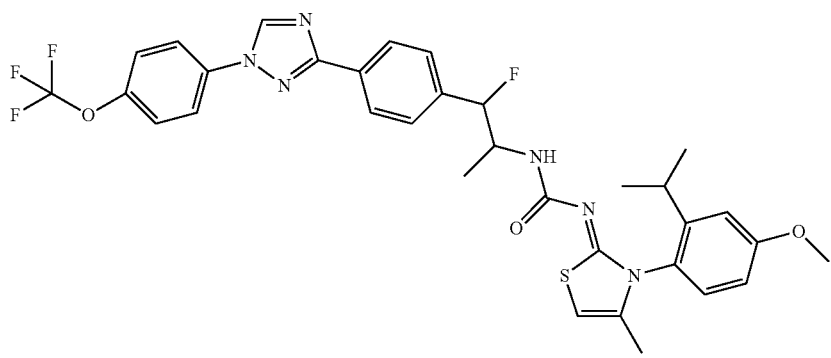 [SMILES: COc1ccc(-n2c(C)cs/c2=N\C(=O)NC(C)C(F)c2ccc(-c3ncn(-c4ccc(OC(F)(F)F)cc4)n3)cc2)c(C(C)C)c1]
P1409
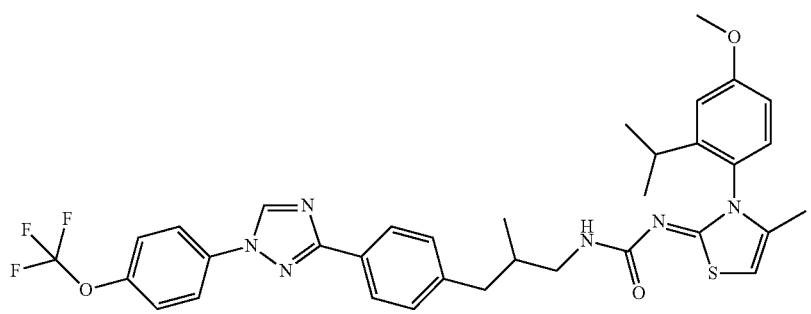 [SMILES: COc1ccc(-n2c(C)cs/c2=N\C(=O)NCC(C)Cc2ccc(-c3ncn(-c4ccc(OC(F)(F)F)cc4)n3)cc2)c(C(C)C)c1]
P1410

TABLE P-Two-continued
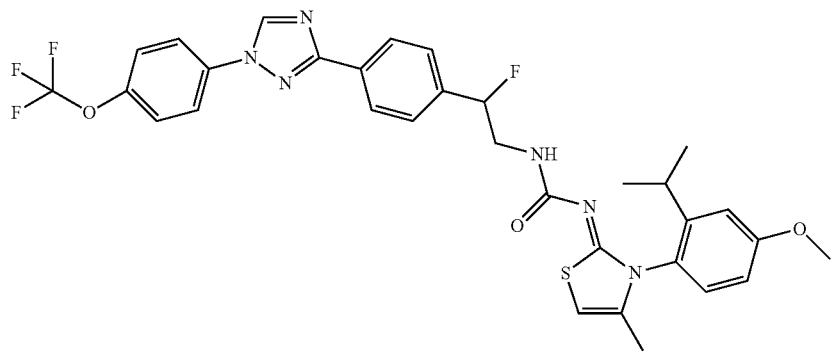 [SMILES: COc1ccc(-n2c(C)cs/c2=N\C(=O)NCC(F)c2ccc(-c3ncn(-c4ccc(OC(F)(F)F)cc4)n3)cc2)c(C(C)C)c1]
P1411
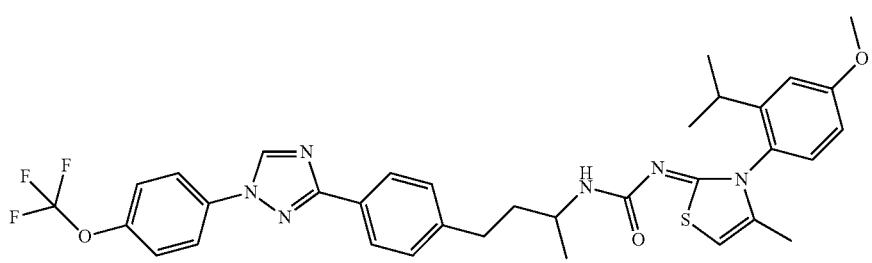 [SMILES: COc1ccc(-n2c(C)cs/c2=N\C(=O)NC(C)CCc2ccc(-c3ncn(-c4ccc(OC(F)(F)F)cc4)n3)cc2)c(C(C)C)c1]
P1412
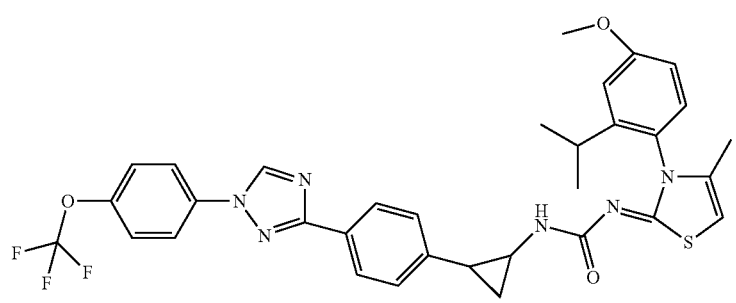 [SMILES: COc1ccc(-n2c(C)cs/c2=N\C(=O)NC2CC2c2ccc(-c3ncn(-c4ccc(OC(F)(F)F)cc4)n3)cc2)c(C(C)C)c1]
P1413
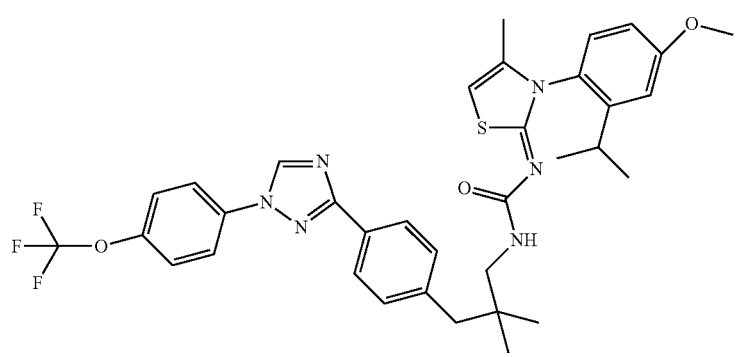 [SMILES: COc1ccc(-n2c(C)cs/c2=N\C(=O)NCC(C)(C)Cc2ccc(-c3ncn(-c4ccc(OC(F)(F)F)cc4)n3)cc2)c(C(C)C)c1]
P1414
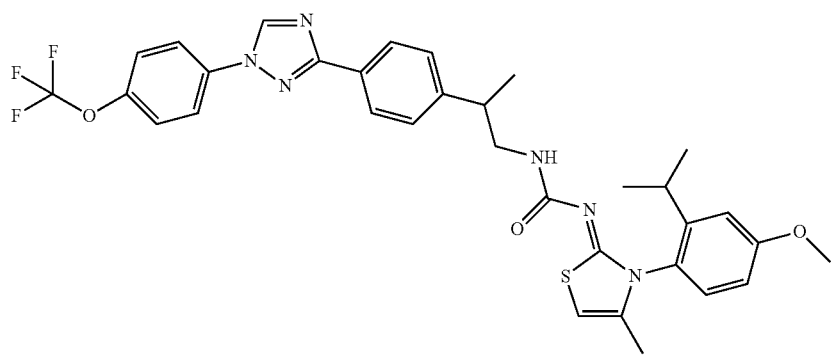 [SMILES: COc1ccc(-n2c(C)cs/c2=N\C(=O)NCC(C)c2ccc(-c3ncn(-c4ccc(OC(F)(F)F)cc4)n3)cc2)c(C(C)C)c1]
P1415

TABLE P-Two-continued
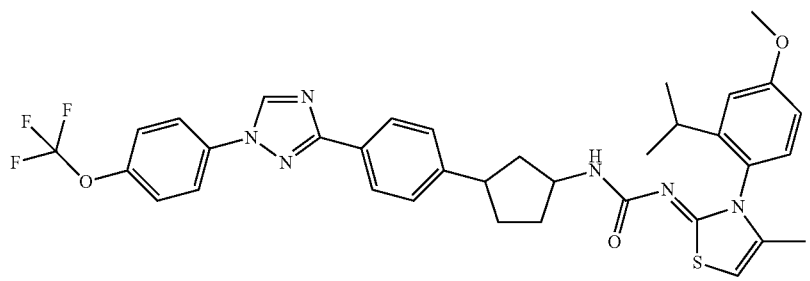 [SMILES: COc1ccc(-n2c(C)cs/c2=N\C(=O)NC2CCC(c3ccc(-c4ncn(-c5ccc(OC(F)(F)F)cc5)n4)cc3)C2)c(C(C)C)c1]
P1416
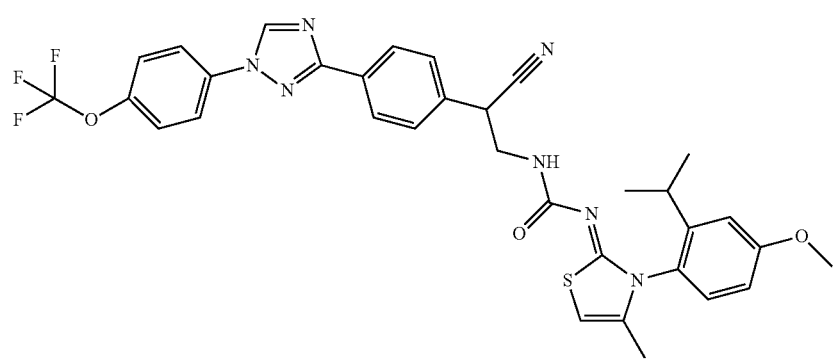 [SMILES: COc1ccc(-n2c(C)cs/c2=N\C(=O)NCC(C#N)c2ccc(-c3ncn(-c4ccc(OC(F)(F)F)cc4)n3)cc2)c(C(C)C)c1]
P1417
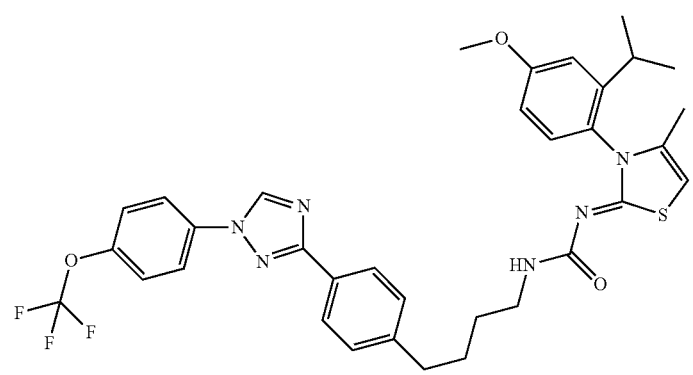 [SMILES: COc1ccc(-n2c(C)cs/c2=N\C(=O)NCCCCc2ccc(-c3ncn(-c4ccc(OC(F)(F)F)cc4)n3)cc2)c(C(C)C)c1]
P1418
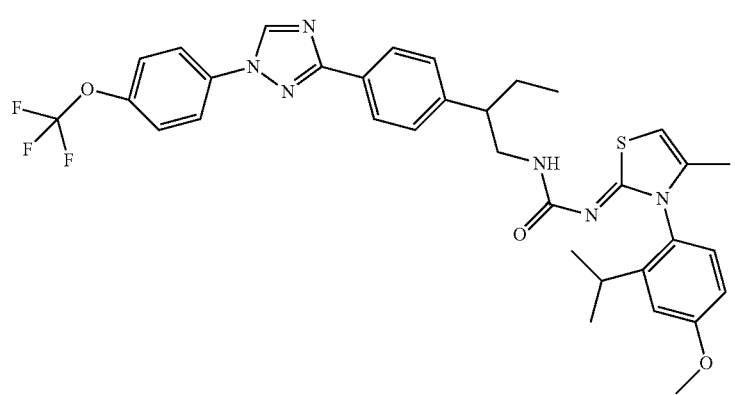 [SMILES: CCC(CNC(=O)/N=c1\scc(C)n1-c1ccc(OC)cc1C(C)C)c1ccc(-c2ncn(-c3ccc(OC(F)(F)F)cc3)n2)cc1]
P1419

TABLE P-Two-continued
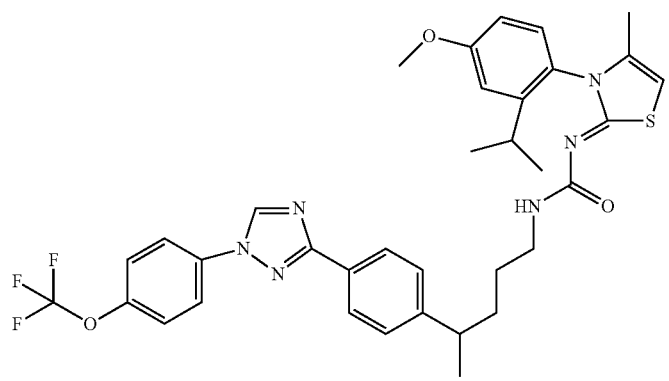 [SMILES: COc1ccc(-n2c(C)cs/c2=N\C(=O)NCCCC(C)c2ccc(-c3ncn(-c4ccc(OC(F)(F)F)cc4)n3)cc2)c(C(C)C)c1]
P1420
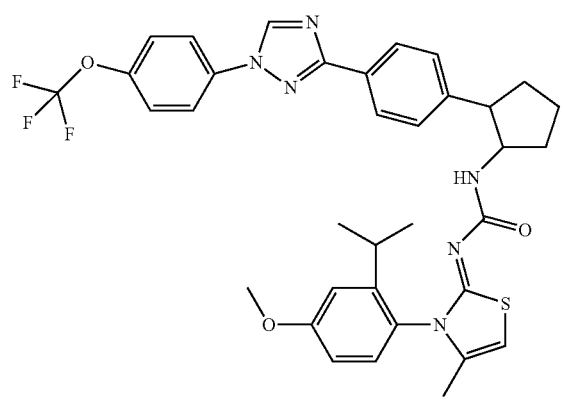 [SMILES: COc1ccc(-n2c(C)cs/c2=N\C(=O)NC2CCCC2c2ccc(-c3ncn(-c4ccc(OC(F)(F)F)cc4)n3)cc2)c(C(C)C)c1]
P1421
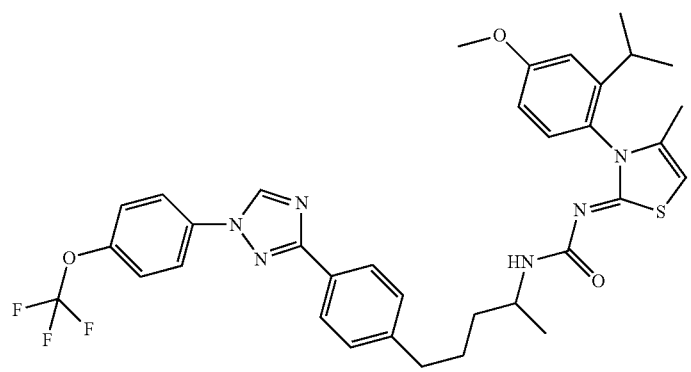 [SMILES: COc1ccc(-n2c(C)cs/c2=N\C(=O)NC(C)CCCc2ccc(-c3ncn(-c4ccc(OC(F)(F)F)cc4)n3)cc2)c(C(C)C)c1]
P1422
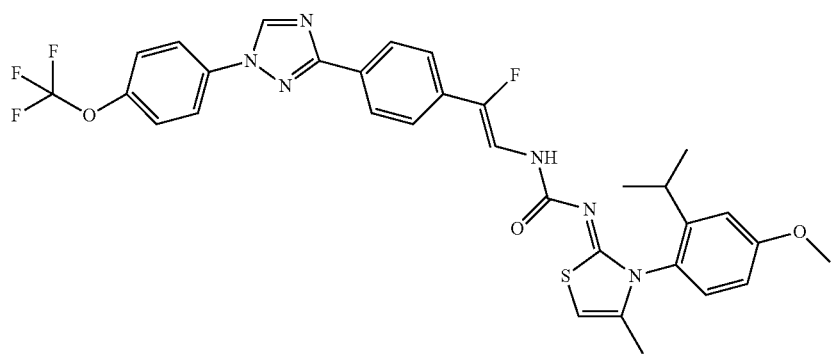 [SMILES: COc1ccc(-n2c(C)cs/c2=N\C(=O)N/C=C(\F)c2ccc(-c3ncn(-c4ccc(OC(F)(F)F)cc4)n3)cc2)c(C(C)C)c1]
P1423

TABLE P-Two-continued
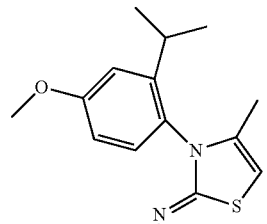
P1424
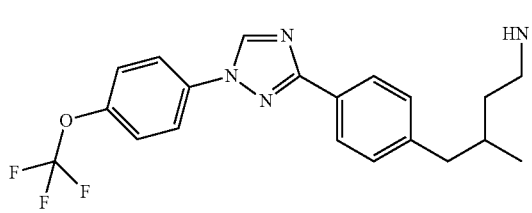
P1425
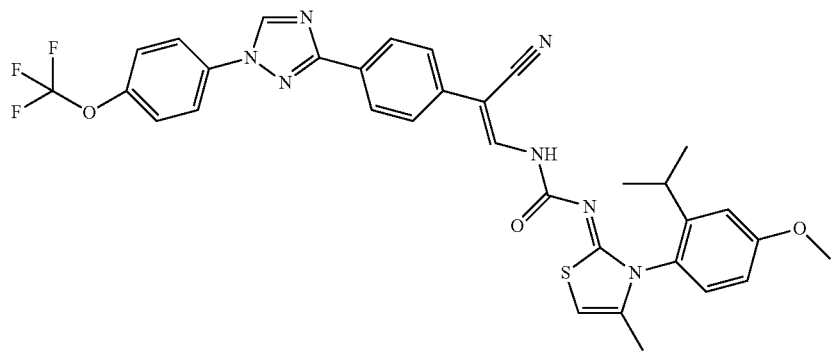 [SMILES: COc1ccc(-n2c(C)cs/c2=N\C(=O)N/C=C(\C#N)c2ccc(-c3ncn(-c4ccc(OC(F)(F)F)cc4)n3)cc2)c(C(C)C)c1]
P1426
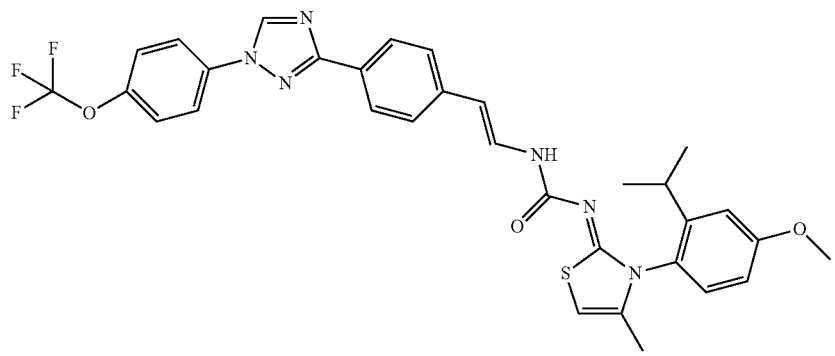 [SMILES: COc1ccc(-n2c(C)cs/c2=N\C(=O)N/C=C/c2ccc(-c3ncn(-c4ccc(OC(F)(F)F)cc4)n3)cc2)c(C(C)C)c1]
P1427

TABLE P-Two-continued
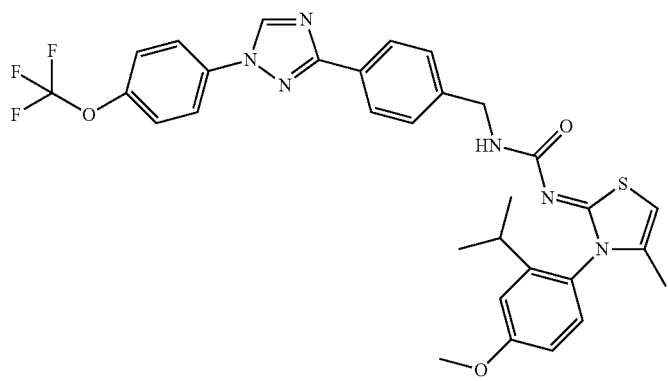 [SMILES: COc1ccc(-n2c(C)cs/c2=N\C(=O)NCc2ccc(-c3ncn(-c4ccc(OC(F)(F)F)cc4)n3)cc2)c(C(C)C)c1]
P1428
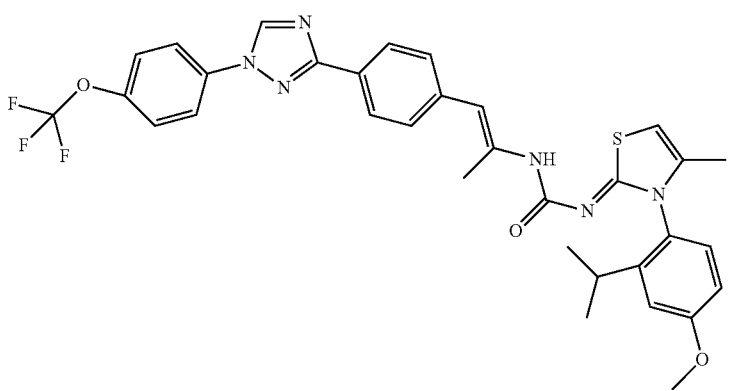 [SMILES: COc1ccc(-n2c(C)cs/c2=N\C(=O)N/C(C)=C/c2ccc(-c3ncn(-c4ccc(OC(F)(F)F)cc4)n3)cc2)c(C(C)C)c1]
P1429
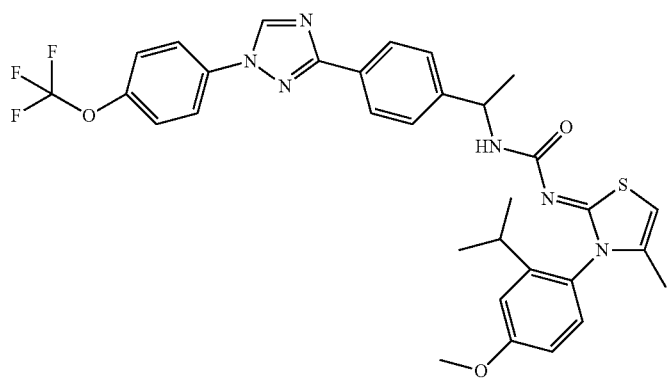 [SMILES: COc1ccc(-n2c(C)cs/c2=N\C(=O)NC(C)c2ccc(-c3ncn(-c4ccc(OC(F)(F)F)cc4)n3)cc2)c(C(C)C)c1]
P1430
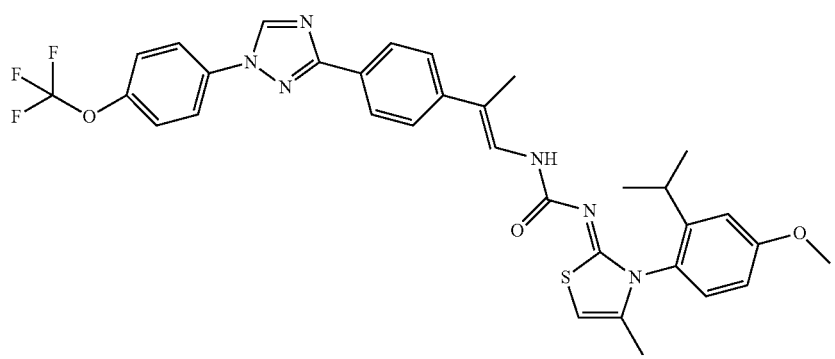 [SMILES: COc1ccc(-n2c(C)cs/c2=N\C(=O)N/C=C(\C)c2ccc(-c3ncn(-c4ccc(OC(F)(F)F)cc4)n3)cc2)c(C(C)C)c1]
P1431

TABLE P-Two-continued
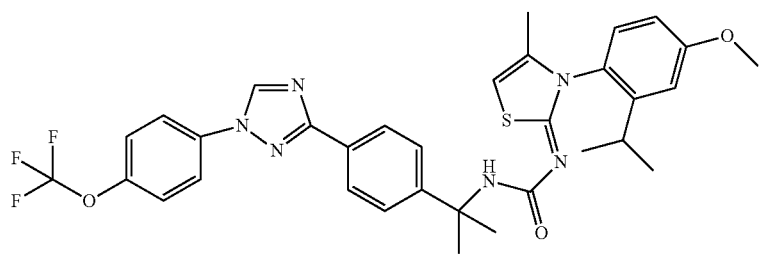 [SMILES: COc1ccc(-n2c(C)cs/c2=N\C(=O)NC(C)(C)c2ccc(-c3ncn(-c4ccc(OC(F)(F)F)cc4)n3)cc2)c(C(C)C)c1]
P1432
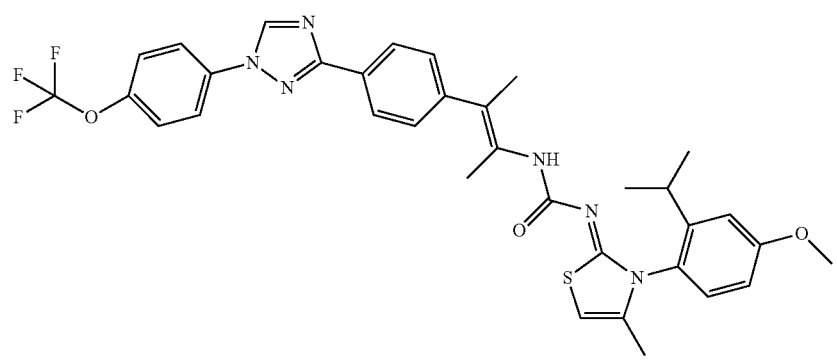 [SMILES: COc1ccc(-n2c(C)cs/c2=N\C(=O)N/C(C)=C(\C)c2ccc(-c3ncn(-c4ccc(OC(F)(F)F)cc4)n3)cc2)c(C(C)C)c1]
P1433
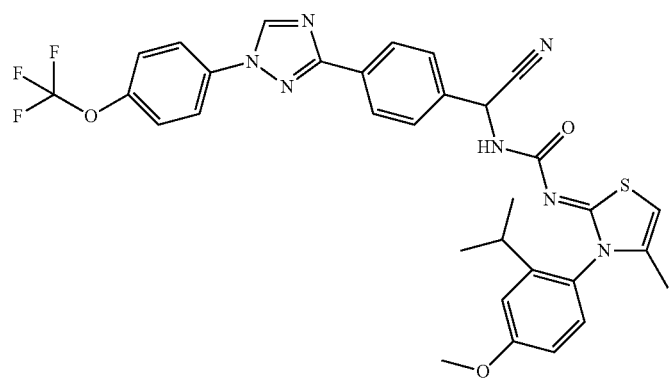 [SMILES: COc1ccc(-n2c(C)cs/c2=N\C(=O)NC(C#N)c2ccc(-c3ncn(-c4ccc(OC(F)(F)F)cc4)n3)cc2)c(C(C)C)c1]
P1434
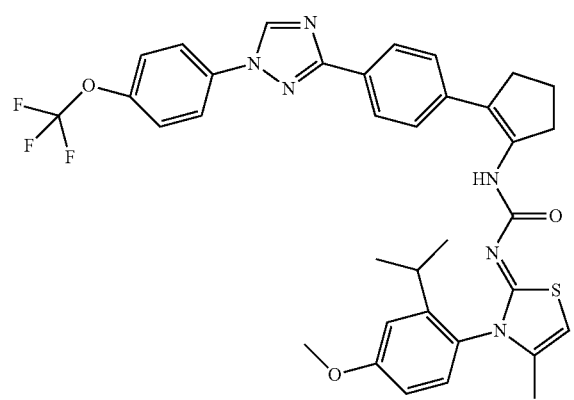 [SMILES: COc1ccc(-n2c(C)cs/c2=N\C(=O)NC2=C(c3ccc(-c4ncn(-c5ccc(OC(F)(F)F)cc5)n4)cc3)CCC2)c(C(C)C)c1]
P1435

TABLE P-Two-continued
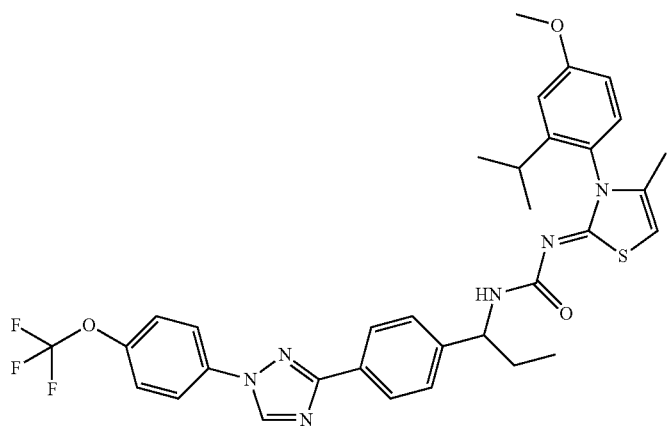 [SMILES: CCC(NC(=O)/N=c1\scc(C)n1-c1ccc(OC)cc1C(C)C)c1ccc(-c2ncn(-c3ccc(OC(F)(F)F)cc3)n2)cc1]
P1436
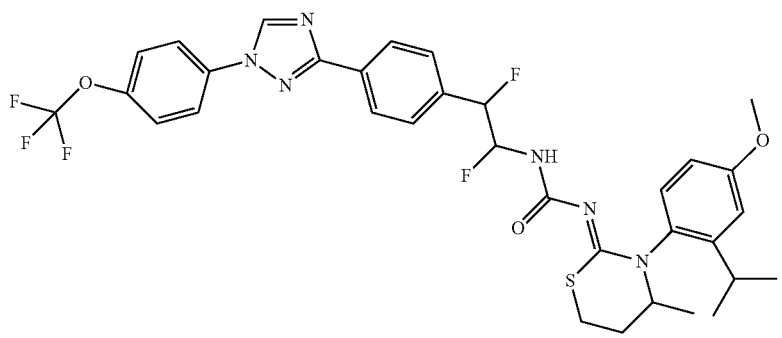 [SMILES: COc1ccc(N2/C(=N/C(=O)NC(F)C(F)c3ccc(-c4ncn(-c5ccc(OC(F)(F)F)cc5)n4)cc3)SCCC2C)c(C(C)C)c1]
P1437
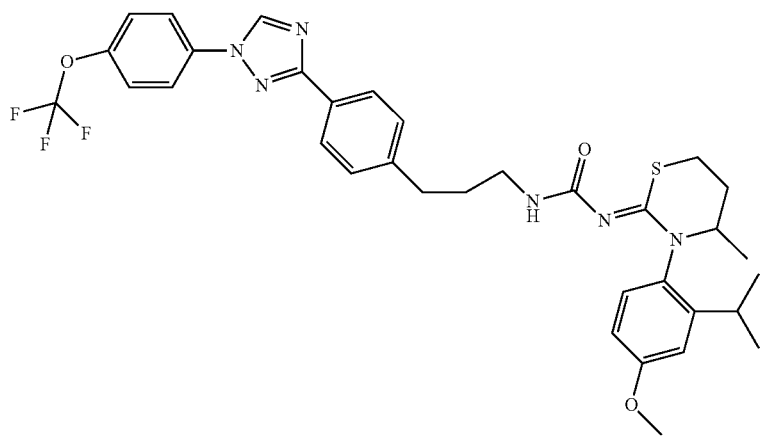 [SMILES: COc1ccc(N2/C(=N/C(=O)NCCCc3ccc(-c4ncn(-c5ccc(OC(F)(F)F)cc5)n4)cc3)SCCC2C)c(C(C)C)c1]
P1438
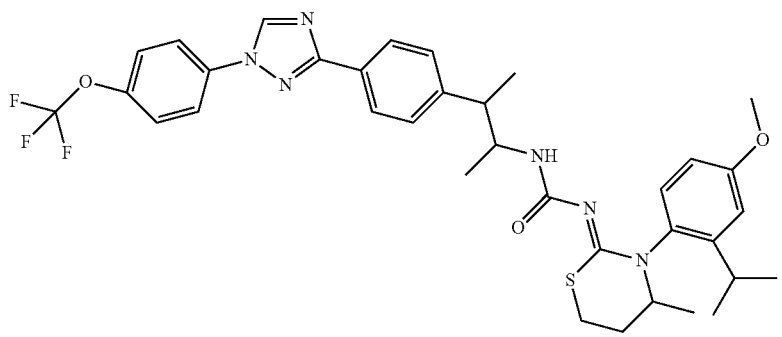 [SMILES: COc1ccc(N2/C(=N/C(=O)NC(C)C(C)c3ccc(-c4ncn(-c5ccc(OC(F)(F)F)cc5)n4)cc3)SCCC2C)c(C(C)C)c1]
P1439

TABLE P-Two-continued
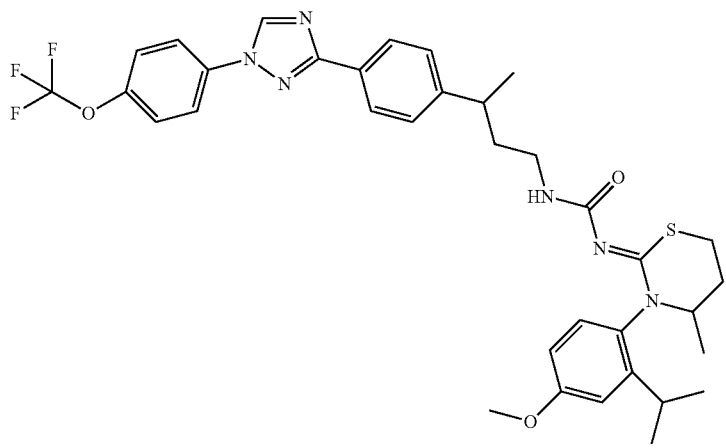 [SMILES: COc1ccc(N2/C(=N/C(=O)NCCC(C)c3ccc(-c4ncn(-c5ccc(OC(F)(F)F)cc5)n4)cc3)SCCC2C)c(C(C)C)c1]
P1440
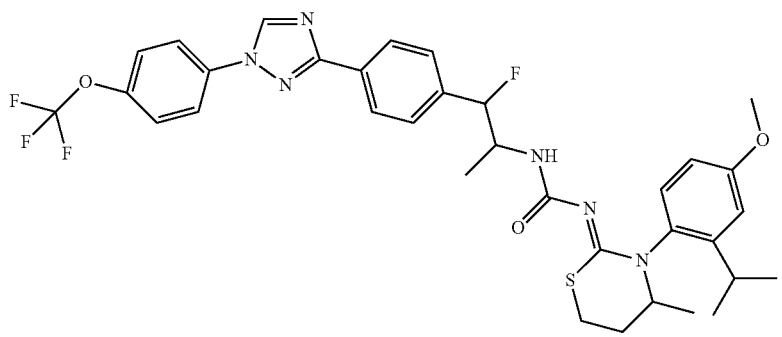
P1441
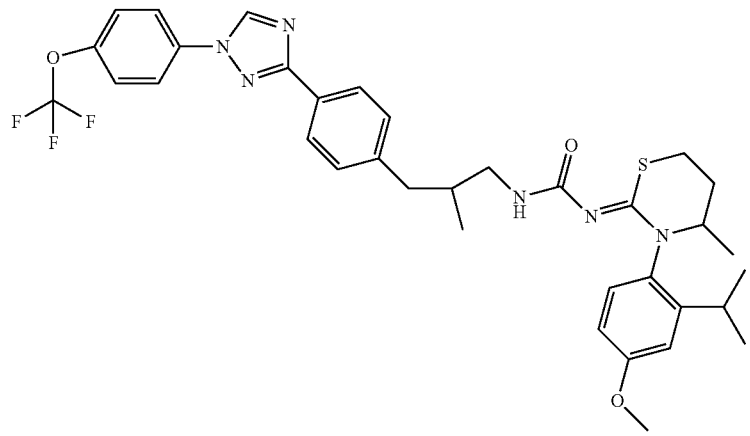 [SMILES: COc1ccc(N2/C(=N/C(=O)NCC(C)Cc3ccc(-c4ncn(-c5ccc(OC(F)(F)F)cc5)n4)cc3)SCCC2C)c(C(C)C)c1]
P1442
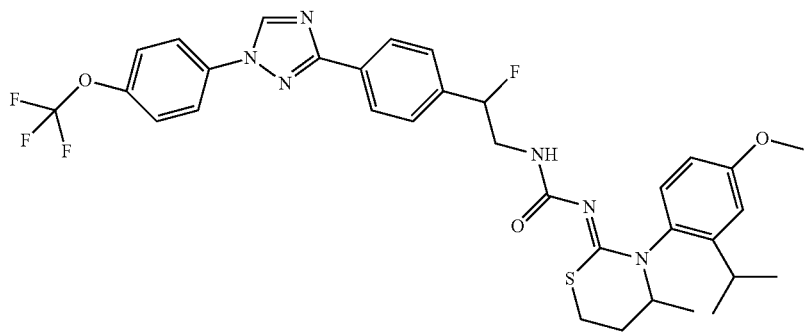 [SMILES: COc1ccc(N2/C(=N/C(=O)NCC(F)c3ccc(-c4ncn(-c5ccc(OC(F)(F)F)cc5)n4)cc3)SCCC2C)c(C(C)C)c1]
P1443

TABLE P-Two-continued
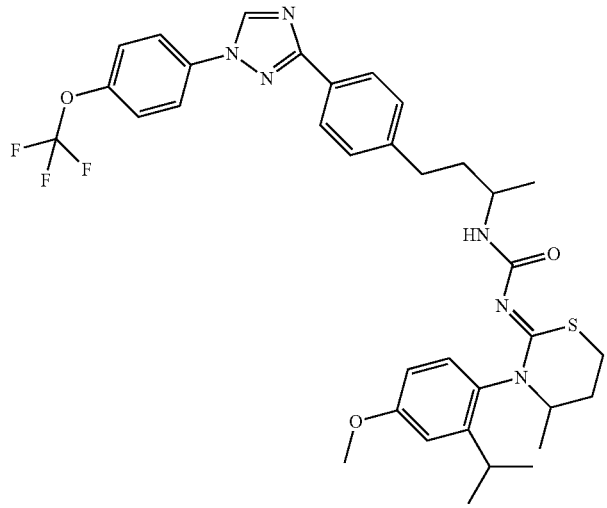 [SMILES: COc1ccc(N2/C(=N/C(=O)NC(C)CCc3ccc(-c4ncn(-c5ccc(OC(F)(F)F)cc5)n4)cc3)SCCC2C)c(C(C)C)c1]
P1444
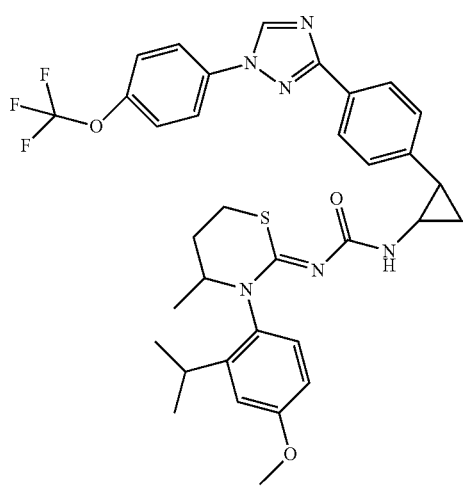 [SMILES: COc1ccc(N2/C(=N/C(=O)NC3CC3c3ccc(-c4ncn(-c5ccc(OC(F)(F)F)cc5)n4)cc3)SCCC2C)c(C(C)C)c1]
P1445
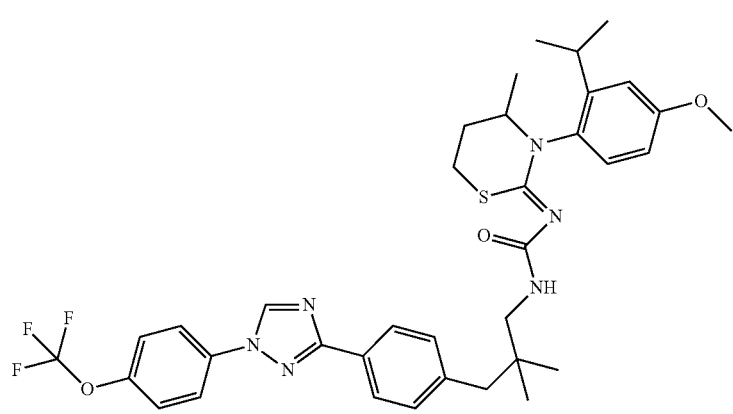 [SMILES: COc1ccc(N2/C(=N/C(=O)NCC(C)(C)Cc3ccc(-c4ncn(-c5ccc(OC(F)(F)F)cc5)n4)cc3)SCCC2C)c(C(C)C)c1]
P1446

TABLE P-Two-continued
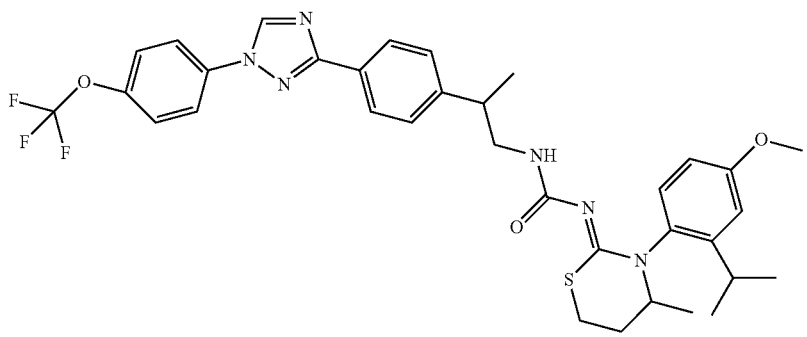 [SMILES: COc1ccc(N2/C(=N/C(=O)NCC(C)c3ccc(-c4ncn(-c5ccc(OC(F)(F)F)cc5)n4)cc3)SCCC2C)c(C(C)C)c1]
P1447
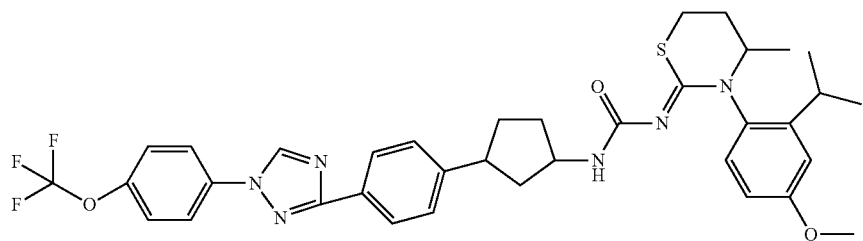 [SMILES: COc1ccc(N2/C(=N/C(=O)NC3CCC(c4ccc(-c5ncn(-c6ccc(OC(F)(F)F)cc6)n5)cc4)C3)SCCC2C)c(C(C)C)c1]
P1448
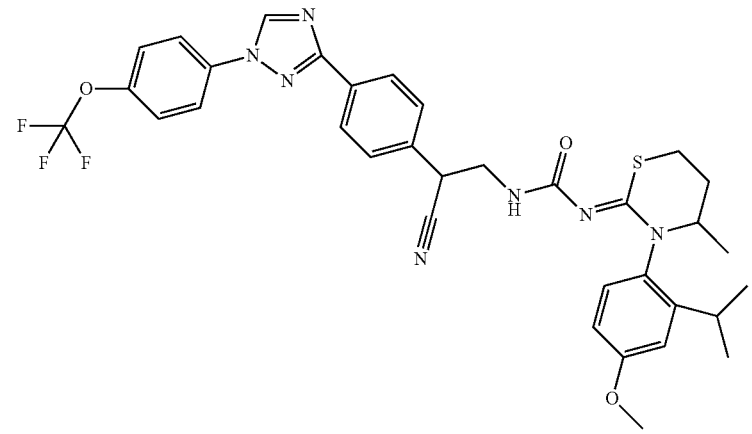 [SMILES: COc1ccc(N2/C(=N/C(=O)NCC(C#N)c3ccc(-c4ncn(-c5ccc(OC(F)(F)F)cc5)n4)cc3)SCCC2C)c(C(C)C)c1]
P1449
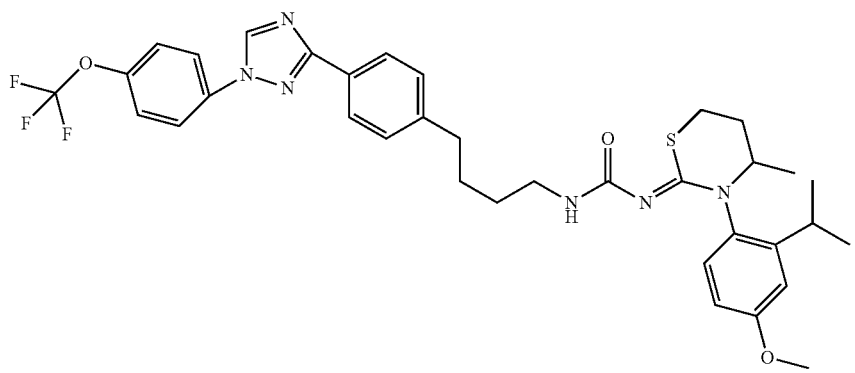 [SMILES: COc1ccc(N2/C(=N/C(=O)NCCCCc3ccc(-c4ncn(-c5ccc(OC(F)(F)F)cc5)n4)cc3)SCCC2C)c(C(C)C)c1]
P1450

TABLE P-Two-continued
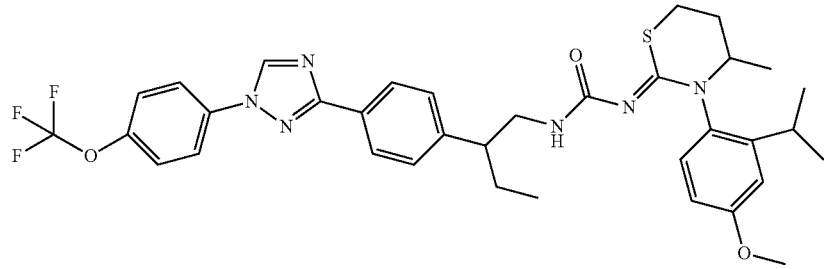 [SMILES: CCC(CNC(=O)/N=C1\SCCC(C)N1c1ccc(OC)cc1C(C)C)c1ccc(-c2ncn(-c3ccc(OC(F)(F)F)cc3)n2)cc1]
P1451
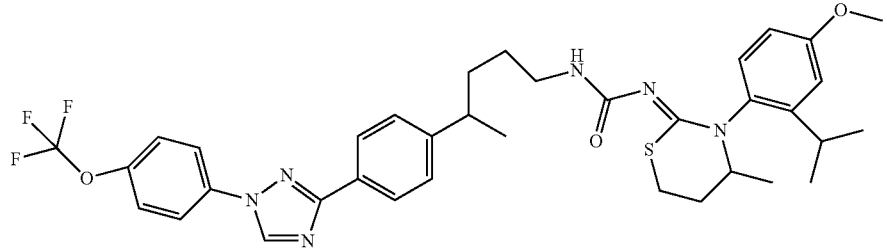 [SMILES: COc1ccc(N2/C(=N/C(=O)NCCCC(C)c3ccc(-c4ncn(-c5ccc(OC(F)(F)F)cc5)n4)cc3)SCCC2C)c(C(C)C)c1]
P1452
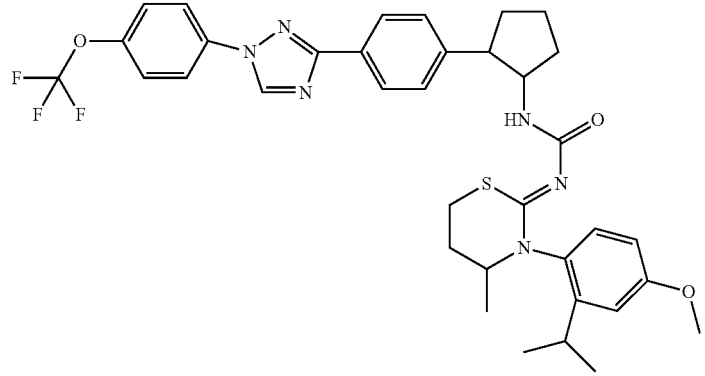 [SMILES: COc1ccc(N2/C(=N/C(=O)NC3CCCC3c3ccc(-c4ncn(-c5ccc(OC(F)(F)F)cc5)n4)cc3)SCCC2C)c(C(C)C)c1]
P1453
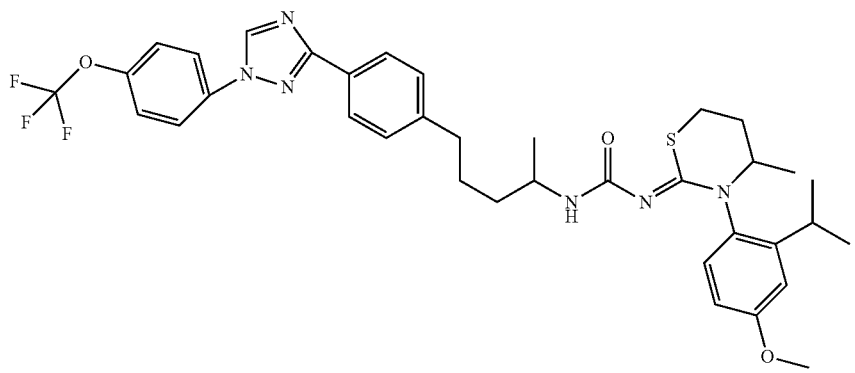 [SMILES: COc1ccc(N2/C(=N/C(=O)NC(C)CCCc3ccc(-c4ncn(-c5ccc(OC(F)(F)F)cc5)n4)cc3)SCCC2C)c(C(C)C)c1]
P1454
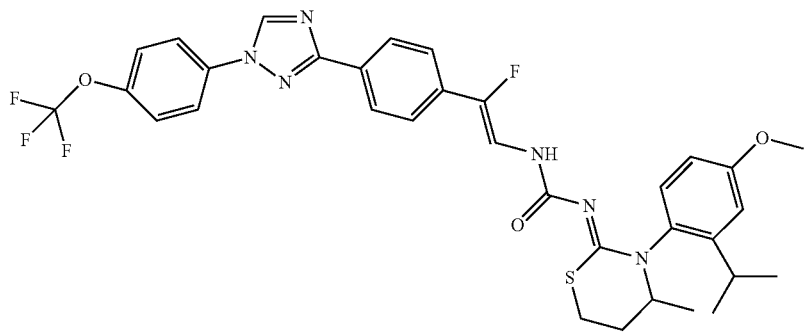 [SMILES: COc1ccc(N2/C(=N/C(=O)N/C=C(\F)c3ccc(-c4ncn(-c5ccc(OC(F)(F)F)cc5)n4)cc3)SCCC2C)c(C(C)C)c1]
P1455

TABLE P-Two-continued
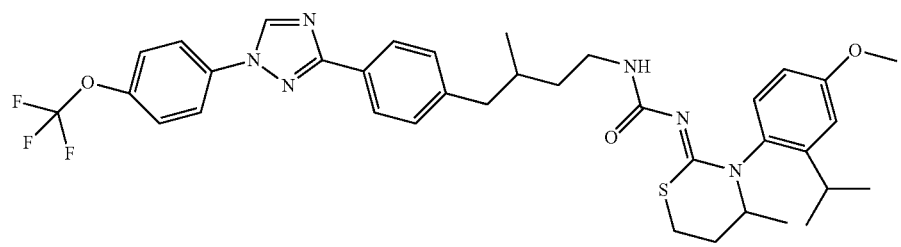 [SMILES: COc1ccc(N2/C(=N/C(=O)NCCC(C)Cc3ccc(-c4ncn(-c5ccc(OC(F)(F)F)cc5)n4)cc3)SCCC2C)c(C(C)C)c1]
P1456
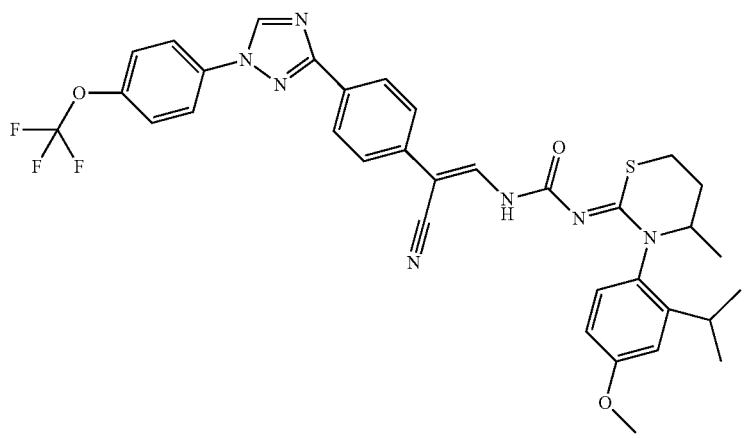 [SMILES: COc1ccc(N2/C(=N/C(=O)N/C=C(\C#N)c3ccc(-c4ncn(-c5ccc(OC(F)(F)F)cc5)n4)cc3)SCCC2C)c(C(C)C)c1]
P1457
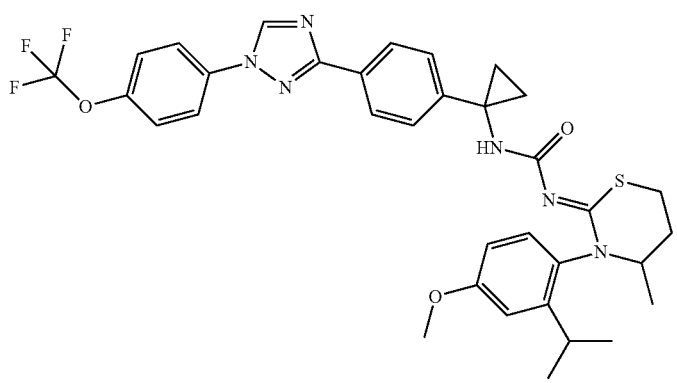 [SMILES: COc1ccc(N2/C(=N/C(=O)NC3(c4ccc(-c5ncn(-c6ccc(OC(F)(F)F)cc6)n5)cc4)CC3)SCCC2C)c(C(C)C)c1]
P1458
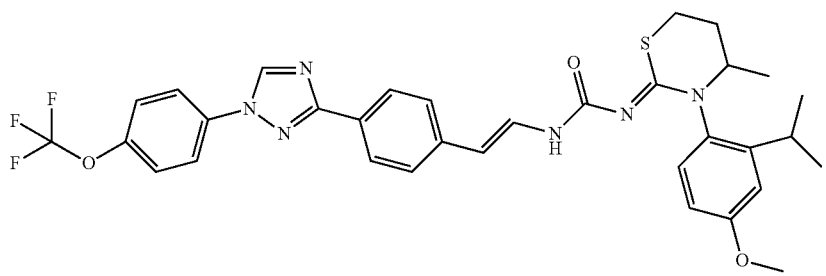 [SMILES: COc1ccc(N2/C(=N/C(=O)N/C=C/c3ccc(-c4ncn(-c5ccc(OC(F)(F)F)cc5)n4)cc3)SCCC2C)c(C(C)C)c1]
P1459
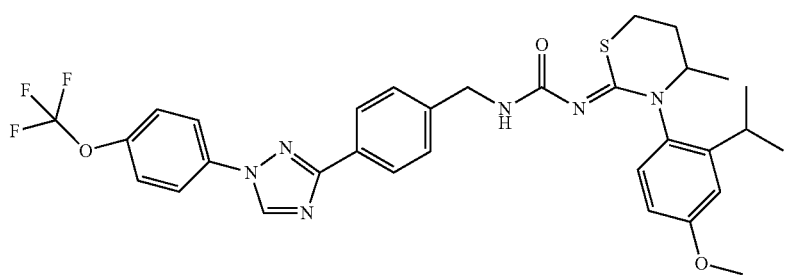 [SMILES: COc1ccc(N2/C(=N/C(=O)NCc3ccc(-c4ncn(-c5ccc(OC(F)(F)F)cc5)n4)cc3)SCCC2C)c(C(C)C)c1]
P1460

TABLE P-Two-continued
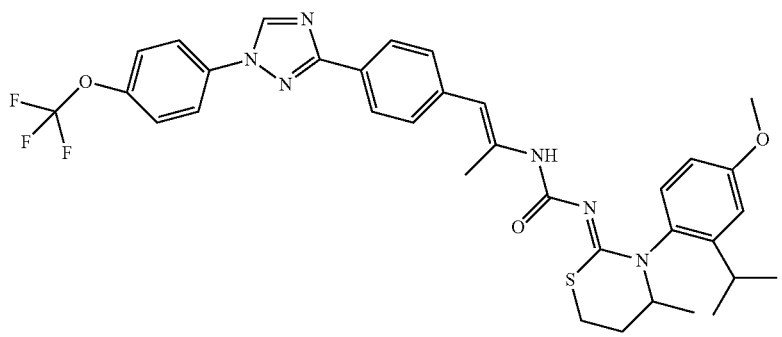 [SMILES: COc1ccc(N2/C(=N/C(=O)N/C(C)=C/c3ccc(-c4ncn(-c5ccc(OC(F)(F)F)cc5)n4)cc3)SCCC2C)c(C(C)C)c1]
P1461
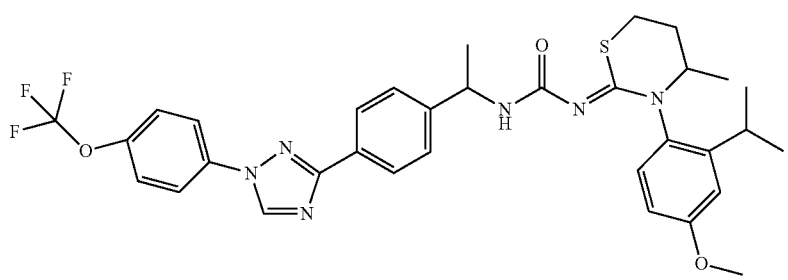 [SMILES: COc1ccc(N2/C(=N/C(=O)NC(C)c3ccc(-c4ncn(-c5ccc(OC(F)(F)F)cc5)n4)cc3)SCCC2C)c(C(C)C)c1]
P1462
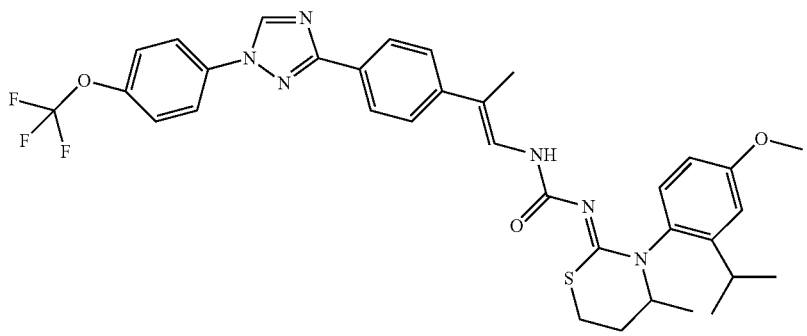 [SMILES: COc1ccc(N2/C(=N/C(=O)N/C=C(\C)c3ccc(-c4ncn(-c5ccc(OC(F)(F)F)cc5)n4)cc3)SCCC2C)c(C(C)C)c1]
P1463
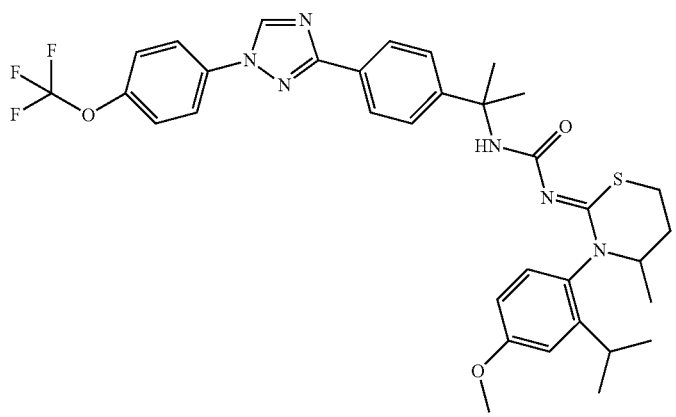 [SMILES: COc1ccc(N2/C(=N/C(=O)NC(C)(C)c3ccc(-c4ncn(-c5ccc(OC(F)(F)F)cc5)n4)cc3)SCCC2C)c(C(C)C)c1]
P1464

TABLE P-Two-continued
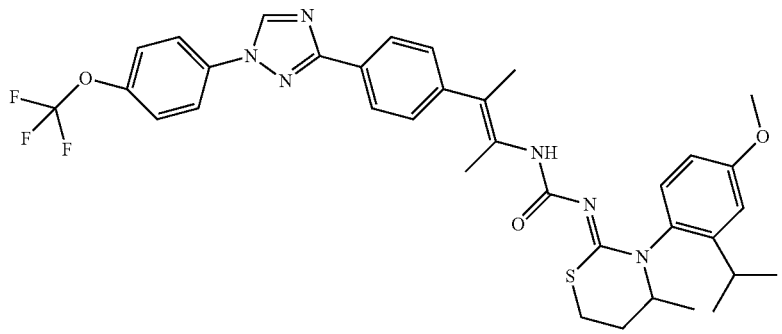 [SMILES: COc1ccc(N2/C(=N/C(=O)N/C(C)=C(\C)c3ccc(-c4ncn(-c5ccc(OC(F)(F)F)cc5)n4)cc3)SCCC2C)c(C(C)C)c1]
P1465
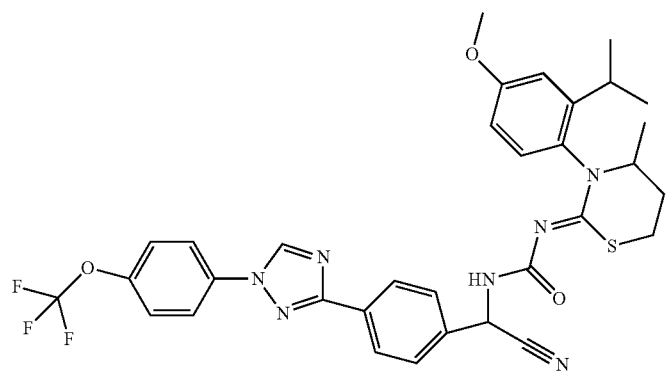 [SMILES: COc1ccc(N2/C(=N/C(=O)NC(C#N)c3ccc(-c4ncn(-c5ccc(OC(F)(F)F)cc5)n4)cc3)SCCC2C)c(C(C)C)c1]
P1466
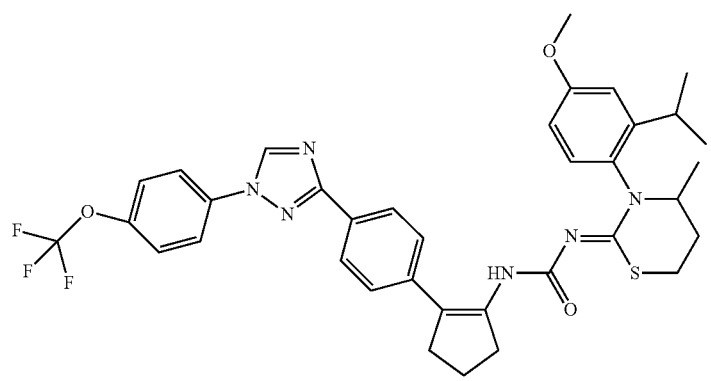 [SMILES: COc1ccc(N2/C(=N/C(=O)NC3=C(c4ccc(-c5ncn(-c6ccc(OC(F)(F)F)cc6)n5)cc4)CCC3)SCCC2C)c(C(C)C)c1]
P1467
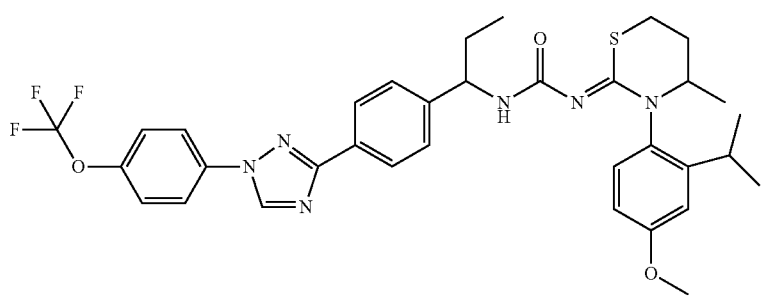 [SMILES: CCC(NC(=O)/N=C1\SCCC(C)N1c1ccc(OC)cc1C(C)C)c1ccc(-c2ncn(-c3ccc(OC(F)(F)F)cc3)n2)cc1]
P1468
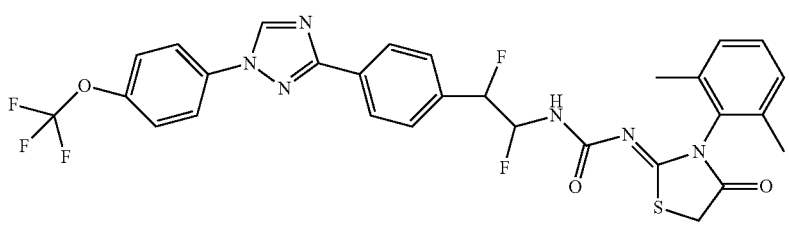
P1469

TABLE P-Two-continued
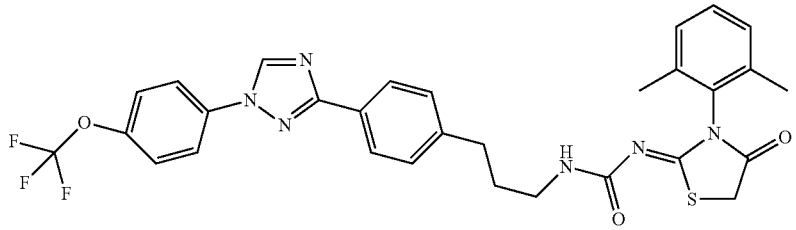 [SMILES: Cc1cccc(C)c1N1C(=O)CS/C1=N\C(=O)NCCCc1ccc(-c2ncn(-c3ccc(OC(F)(F)F)cc3)n2)cc1] P1470
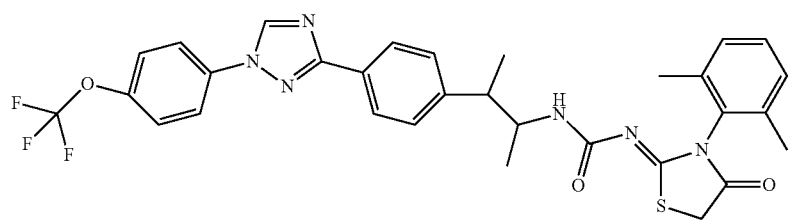 [SMILES: Cc1cccc(C)c1N1C(=O)CS/C1=N\C(=O)NC(C)C(C)c1ccc(-c2ncn(-c3ccc(OC(F)(F)F)cc3)n2)cc1] P1471
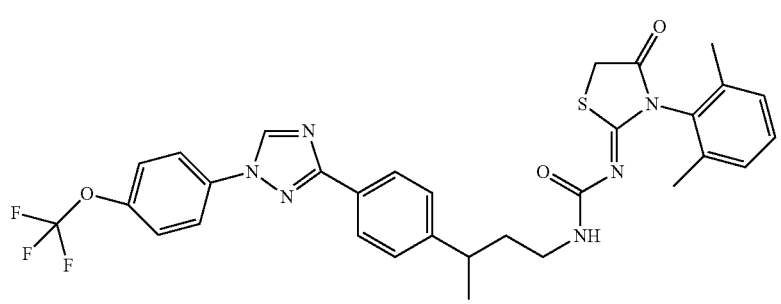 [SMILES: Cc1cccc(C)c1N1C(=O)CS/C1=N\C(=O)NCCC(C)c1ccc(-c2ncn(-c3ccc(OC(F)(F)F)cc3)n2)cc1] P1472
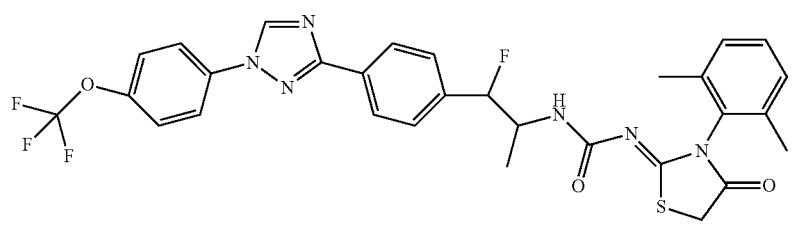 [SMILES: Cc1cccc(C)c1N1C(=O)CS/C1=N\C(=O)NC(C)C(F)c1ccc(-c2ncn(-c3ccc(OC(F)(F)F)cc3)n2)cc1] P1473
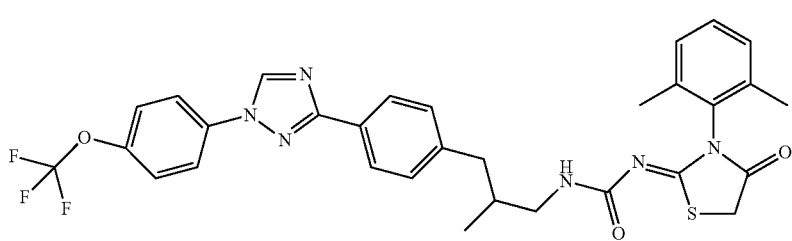 [SMILES: Cc1cccc(C)c1N1C(=O)CS/C1=N\C(=O)NCC(C)Cc1ccc(-c2ncn(-c3ccc(OC(F)(F)F)cc3)n2)cc1] P1474
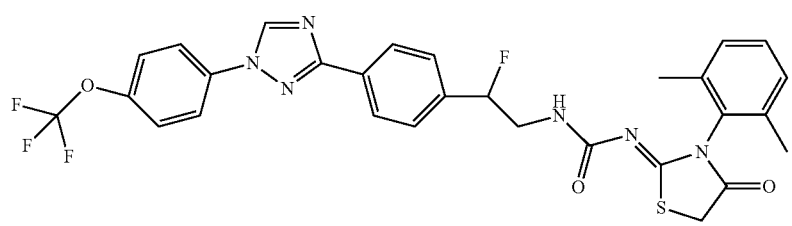 [SMILES: Cc1cccc(C)c1N1C(=O)CS/C1=N\C(=O)NCC(F)c1ccc(-c2ncn(-c3ccc(OC(F)(F)F)cc3)n2)cc1] P1475

TABLE P-Two-continued
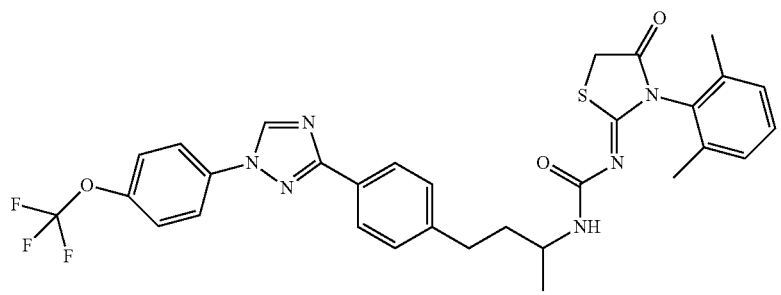 [SMILES: Cc1cccc(C)c1N1C(=O)CS/C1=N\C(=O)NC(C)CCc1ccc(-c2ncn(-c3ccc(OC(F)(F)F)cc3)n2)cc1] P1476
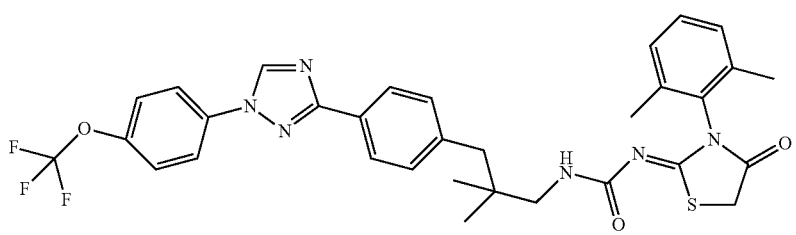 [SMILES: Cc1cccc(C)c1N1C(=O)CS/C1=N\C(=O)NCC(C)(C)Cc1ccc(-c2ncn(-c3ccc(OC(F)(F)F)cc3)n2)cc1] P1477
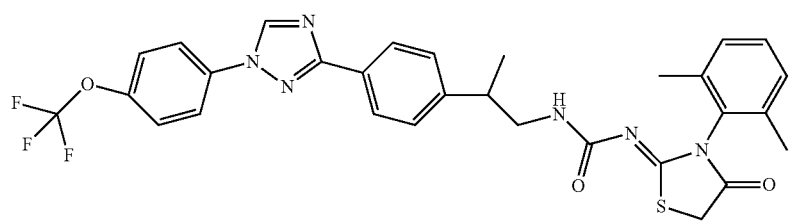 [SMILES: Cc1cccc(C)c1N1C(=O)CS/C1=N\C(=O)NCC(C)c1ccc(-c2ncn(-c3ccc(OC(F)(F)F)cc3)n2)cc1] P1478
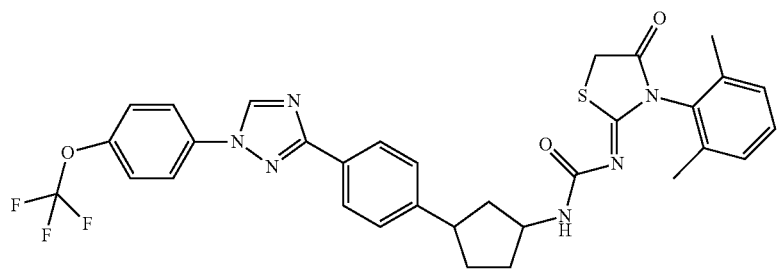 [SMILES: Cc1cccc(C)c1N1C(=O)CS/C1=N\C(=O)NC1CCC(c2ccc(-c3ncn(-c4ccc(OC(F)(F)F)cc4)n3)cc2)C1] P1479
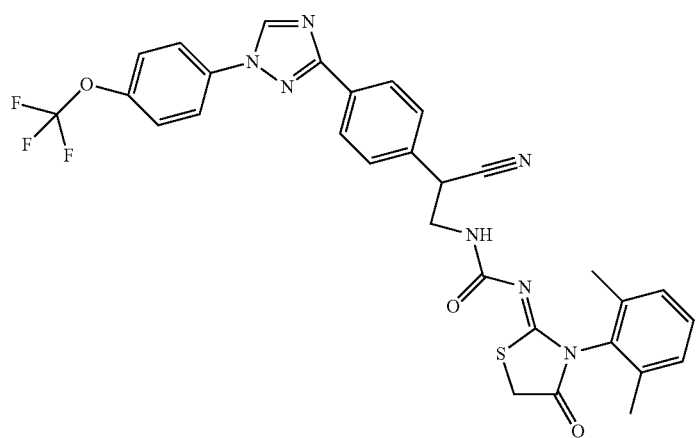 [SMILES: Cc1cccc(C)c1N1C(=O)CS/C1=N\C(=O)NCC(C#N)c1ccc(-c2ncn(-c3ccc(OC(F)(F)F)cc3)n2)cc1] P1480

TABLE P-Two-continued
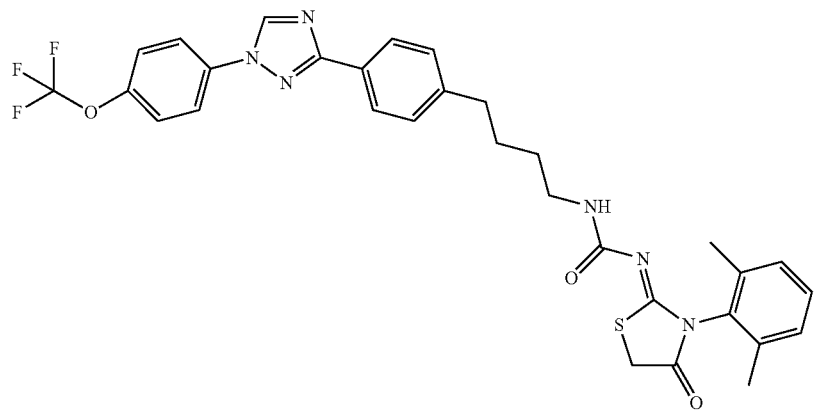 [SMILES: Cc1cccc(C)c1N1C(=O)CS/C1=N\C(=O)NCCCCc1ccc(-c2ncn(-c3ccc(OC(F)(F)F)cc3)n2)cc1]
P1481
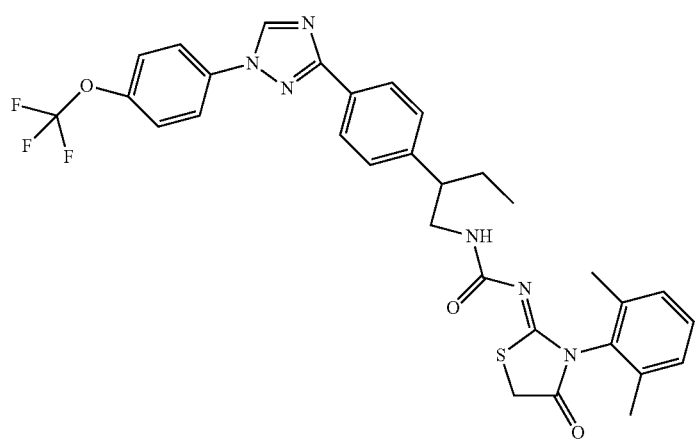 [SMILES: CCC(CNC(=O)/N=C1\SCC(=O)N1c1c(C)cccc1C)c1ccc(-c2ncn(-c3ccc(OC(F)(F)F)cc3)n2)cc1]
P1482
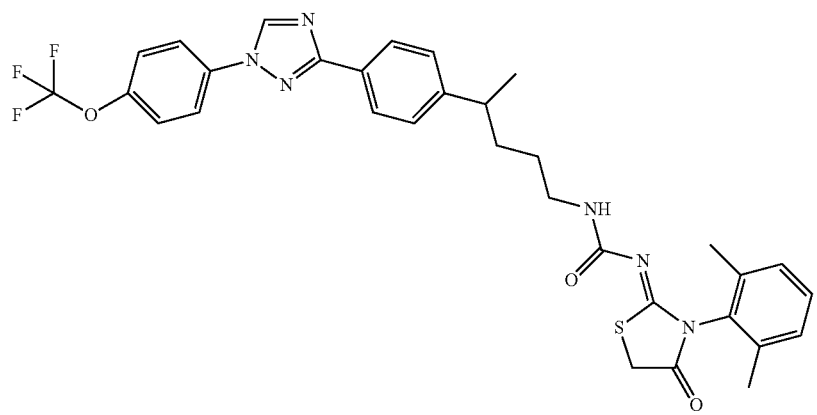 [SMILES: Cc1cccc(C)c1N1C(=O)CS/C1=N\C(=O)NCCCC(C)c1ccc(-c2ncn(-c3ccc(OC(F)(F)F)cc3)n2)cc1]
P1483
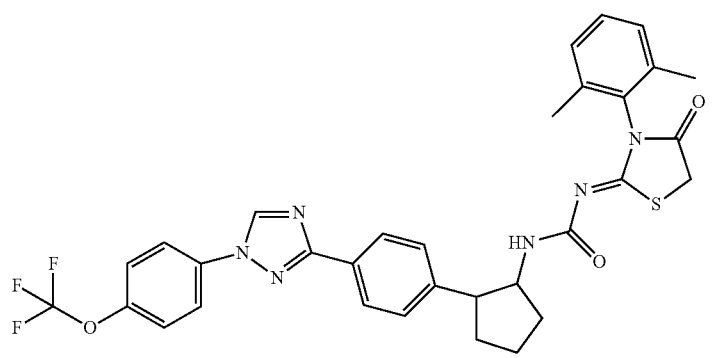 [SMILES: Cc1cccc(C)c1N1C(=O)CS/C1=N\C(=O)NC1CCCC1c1ccc(-c2ncn(-c3ccc(OC(F)(F)F)cc3)n2)cc1]
P1484

TABLE P-Two-continued
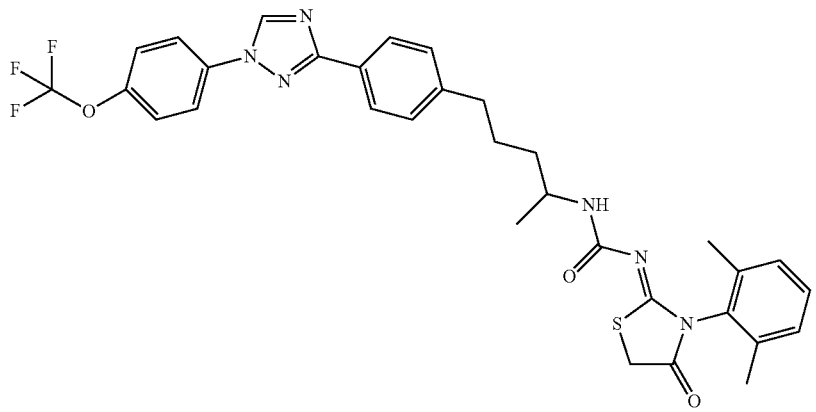 [SMILES: Cc1cccc(C)c1N1C(=O)CS/C1=N\C(=O)NC(C)CCCc1ccc(-c2ncn(-c3ccc(OC(F)(F)F)cc3)n2)cc1]
P1485
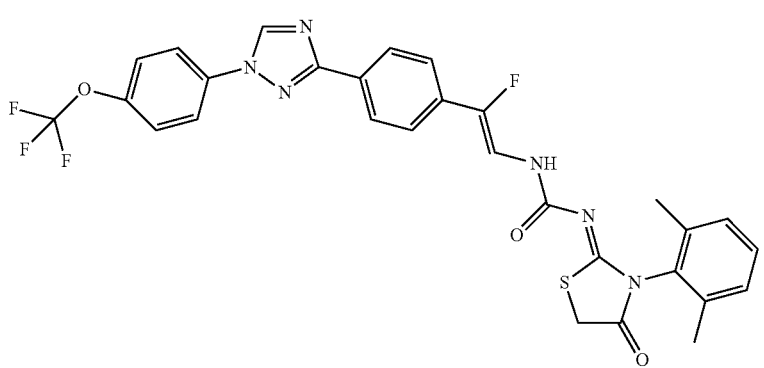 [SMILES: Cc1cccc(C)c1N1C(=O)CS/C1=N\C(=O)N/C=C(\F)c1ccc(-c2ncn(-c3ccc(OC(F)(F)F)cc3)n2)cc1]
P1486
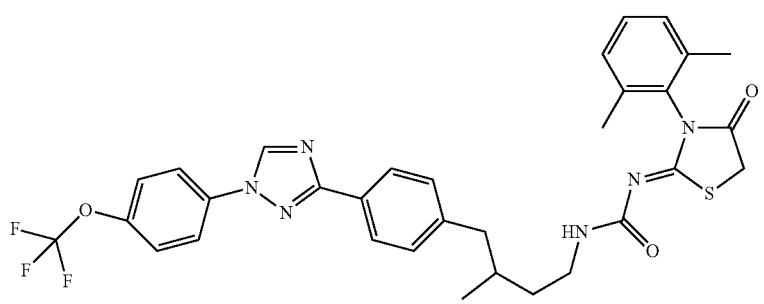 [SMILES: Cc1cccc(C)c1N1C(=O)CS/C1=N\C(=O)NCCC(C)Cc1ccc(-c2ncn(-c3ccc(OC(F)(F)F)cc3)n2)cc1]
P1487
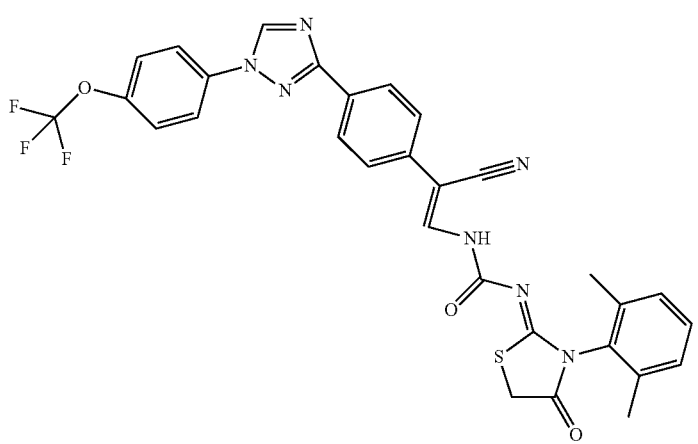 [SMILES: Cc1cccc(C)c1N1C(=O)CS/C1=N\C(=O)N/C=C(\C#N)c1ccc(-c2ncn(-c3ccc(OC(F)(F)F)cc3)n2)cc1]
P1488

TABLE P-Two-continued
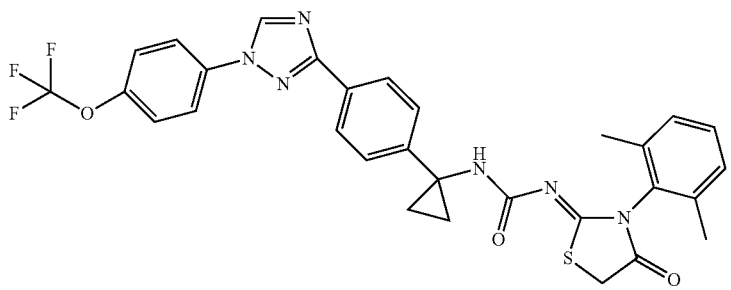 [SMILES: Cc1cccc(C)c1N1C(=O)CS/C1=N\C(=O)NC1(c2ccc(-c3ncn(-c4ccc(OC(F)(F)F)cc4)n3)cc2)CC1]
P1489
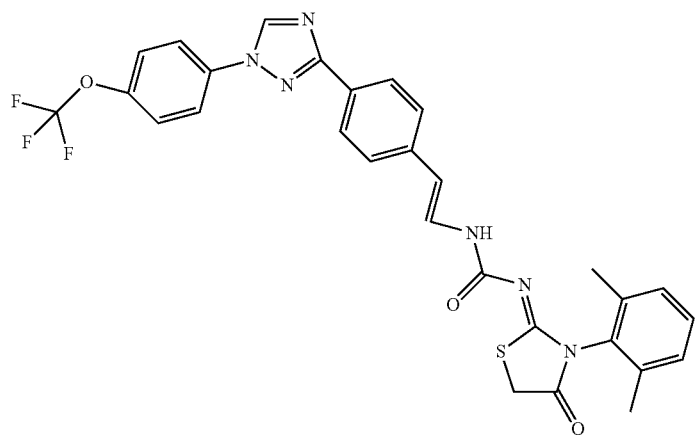 [SMILES: Cc1cccc(C)c1N1C(=O)CS/C1=N\C(=O)N/C=C/c1ccc(-c2ncn(-c3ccc(OC(F)(F)F)cc3)n2)cc1]
P1490
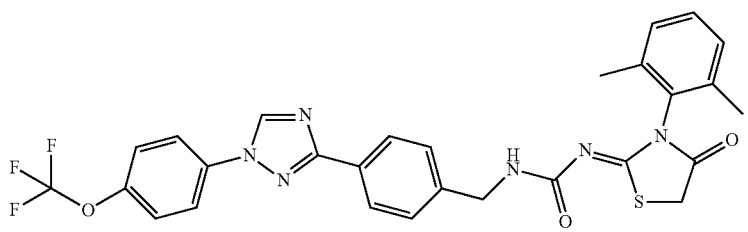 [SMILES: Cc1cccc(C)c1N1C(=O)CS/C1=N\C(=O)NCc1ccc(-c2ncn(-c3ccc(OC(F)(F)F)cc3)n2)cc1]
P1491
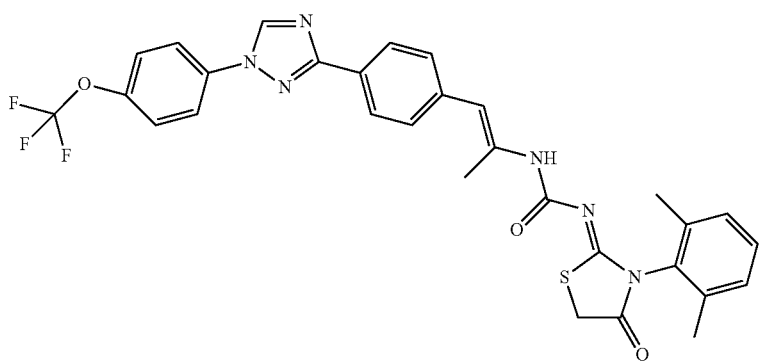 [SMILES: C/C(=C\c1ccc(-c2ncn(-c3ccc(OC(F)(F)F)cc3)n2)cc1)NC(=O)/N=C1\SCC(=O)N1c1c(C)cccc1C]
P1492
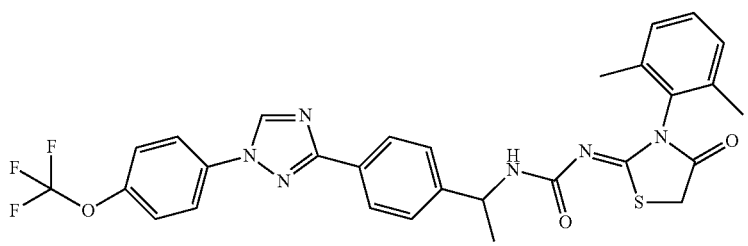 [SMILES: Cc1cccc(C)c1N1C(=O)CS/C1=N\C(=O)NC(C)c1ccc(-c2ncn(-c3ccc(OC(F)(F)F)cc3)n2)cc1]
P1493

TABLE P-Two-continued
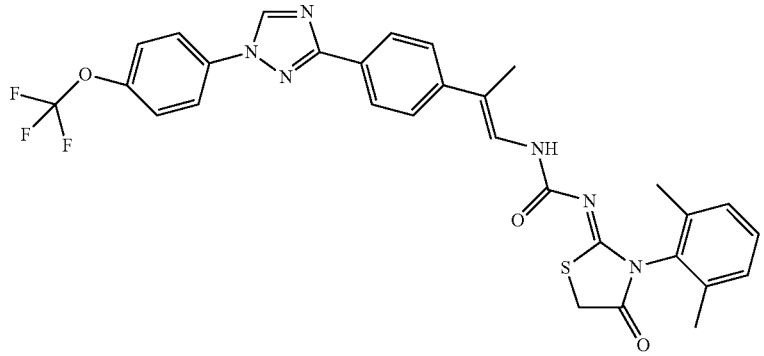 [SMILES: C/C(=C\NC(=O)/N=C1\SCC(=O)N1c1c(C)cccc1C)c1ccc(-c2ncn(-c3ccc(OC(F)(F)F)cc3)n2)cc1]
P1494
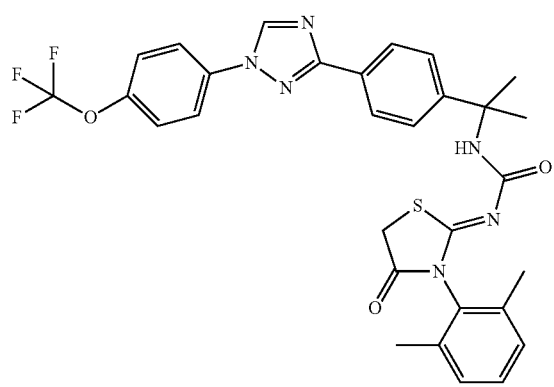 [SMILES: Cc1cccc(C)c1N1C(=O)CS/C1=N\C(=O)NC(C)(C)c1ccc(-c2ncn(-c3ccc(OC(F)(F)F)cc3)n2)cc1]
P1495
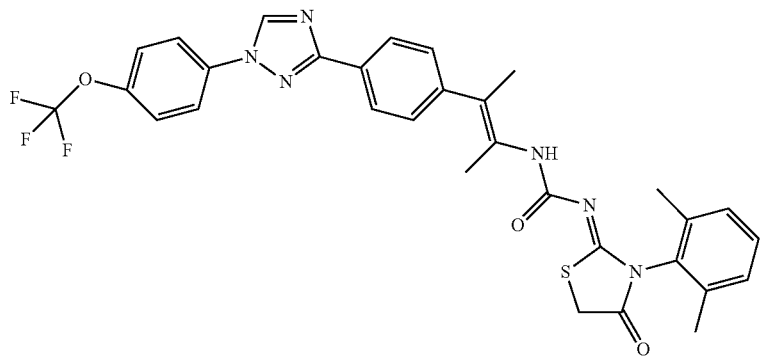 [SMILES: C/C(NC(=O)/N=C1\SCC(=O)N1c1c(C)cccc1C)=C(/C)c1ccc(-c2ncn(-c3ccc(OC(F)(F)F)cc3)n2)cc1]
P1496
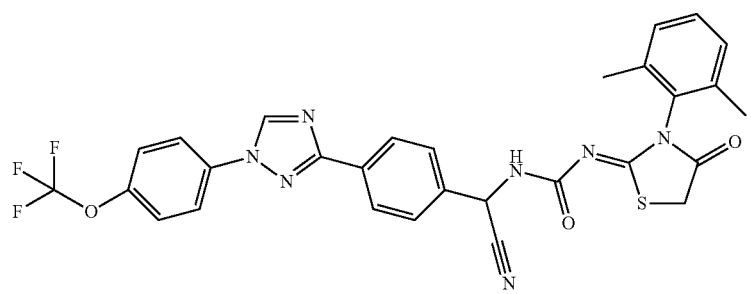 [SMILES: Cc1cccc(C)c1N1C(=O)CS/C1=N\C(=O)NC(C#N)c1ccc(-c2ncn(-c3ccc(OC(F)(F)F)cc3)n2)cc1]
P1497

TABLE P-Two-continued
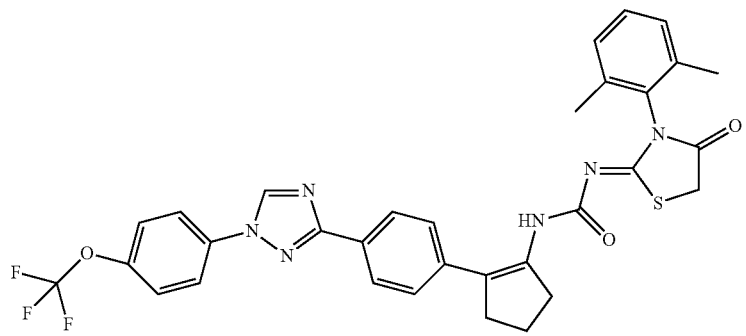 [SMILES: Cc1cccc(C)c1N1C(=O)CS/C1=N\C(=O)NC1=C(c2ccc(-c3ncn(-c4ccc(OC(F)(F)F)cc4)n3)cc2)CCC1]
P1498
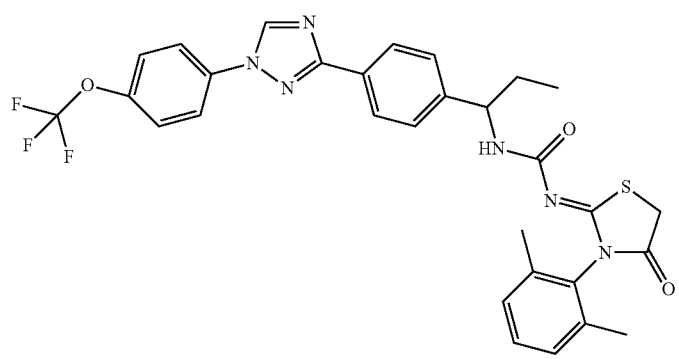 [SMILES: CCC(NC(=O)/N=C1\SCC(=O)N1c1c(C)cccc1C)c1ccc(-c2ncn(-c3ccc(OC(F)(F)F)cc3)n2)cc1]
P1499
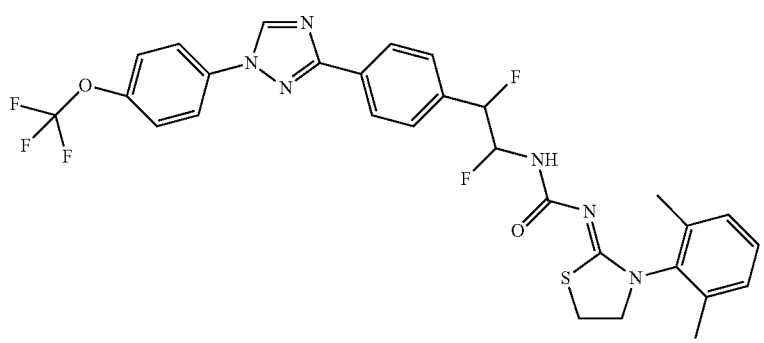 [SMILES: Cc1cccc(C)c1N1CCS/C1=N\C(=O)NC(F)C(F)c1ccc(-c2ncn(-c3ccc(OC(F)(F)F)cc3)n2)cc1]
P1500
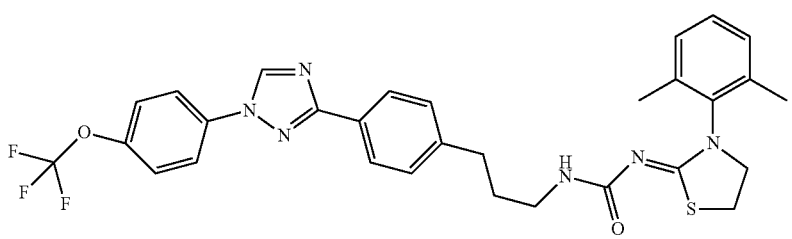 [SMILES: Cc1cccc(C)c1N1CCS/C1=N\C(=O)NCCCc1ccc(-c2ncn(-c3ccc(OC(F)(F)F)cc3)n2)cc1]
P1501
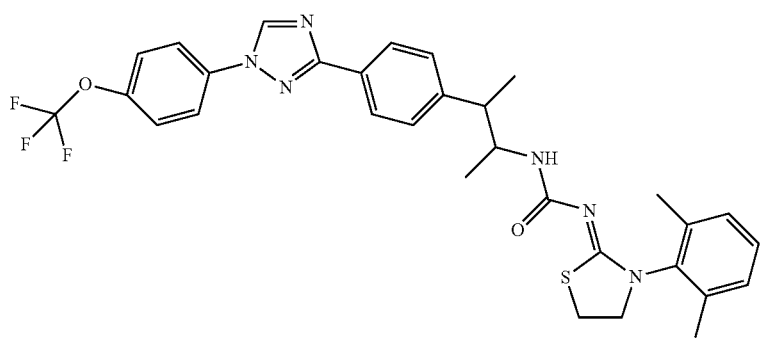 [SMILES: Cc1cccc(C)c1N1CCS/C1=N\C(=O)NC(C)C(C)c1ccc(-c2ncn(-c3ccc(OC(F)(F)F)cc3)n2)cc1]
P1502

TABLE P-Two-continued
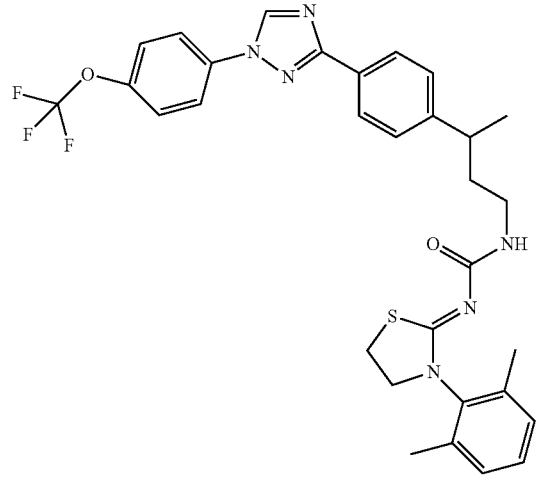 [SMILES: Cc1cccc(C)c1N1CCS/C1=N\C(=O)NCCC(C)c1ccc(-c2ncn(-c3ccc(OC(F)(F)F)cc3)n2)cc1]
P1503
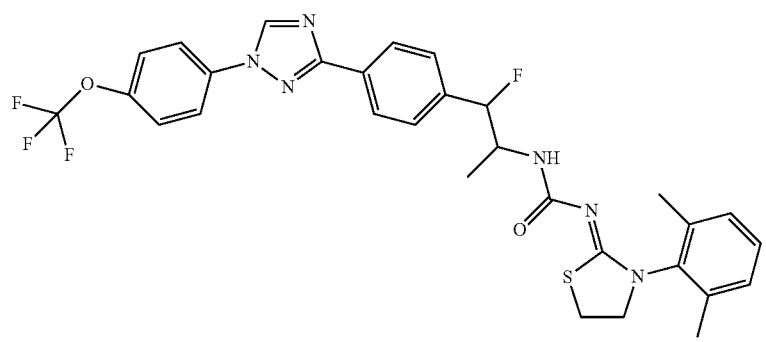
P1504
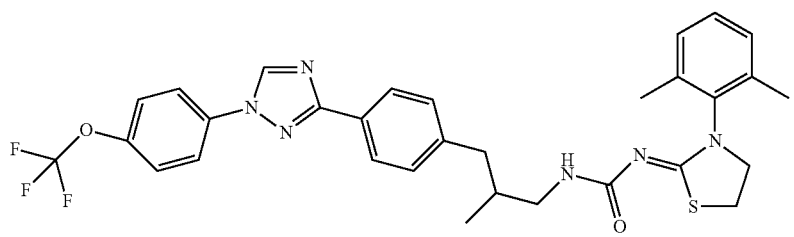 [SMILES: Cc1cccc(C)c1N1CCS/C1=N\C(=O)NCC(C)Cc1ccc(-c2ncn(-c3ccc(OC(F)(F)F)cc3)n2)cc1]
P1505
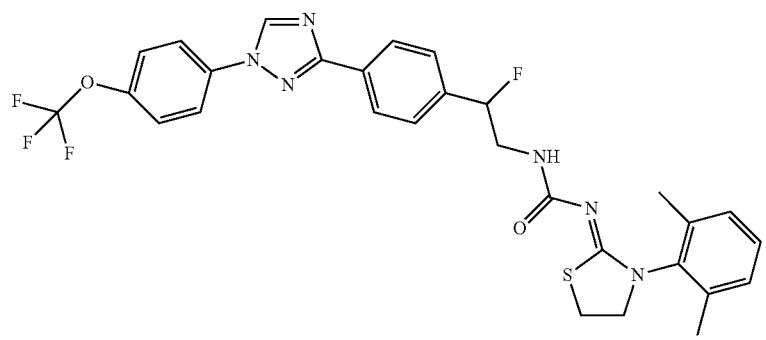 [SMILES: Cc1cccc(C)c1N1CCS/C1=N\C(=O)NCC(F)c1ccc(-c2ncn(-c3ccc(OC(F)(F)F)cc3)n2)cc1]
P1506

TABLE P-Two-continued
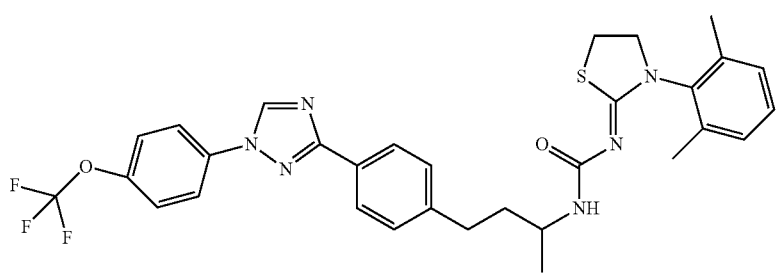 [SMILES: Cc1cccc(C)c1N1CCS/C1=N\C(=O)NC(C)CCc1ccc(-c2ncn(-c3ccc(OC(F)(F)F)cc3)n2)cc1]
P1507
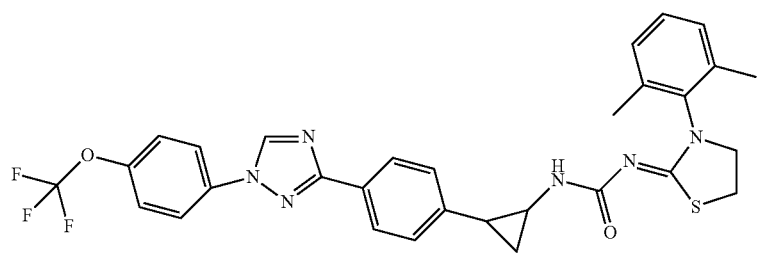 [SMILES: Cc1cccc(C)c1N1CCS/C1=N\C(=O)NC1CC1c1ccc(-c2ncn(-c3ccc(OC(F)(F)F)cc3)n2)cc1]
P1508
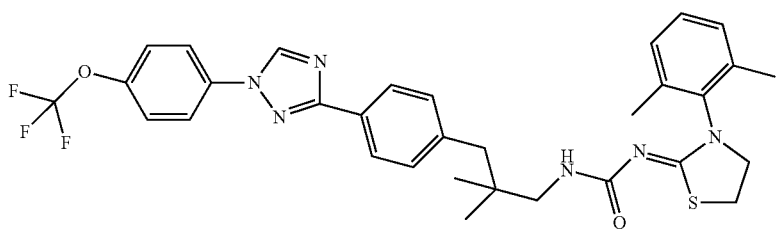 [SMILES: Cc1cccc(C)c1N1CCS/C1=N\C(=O)NCC(C)(C)Cc1ccc(-c2ncn(-c3ccc(OC(F)(F)F)cc3)n2)cc1]
P1509
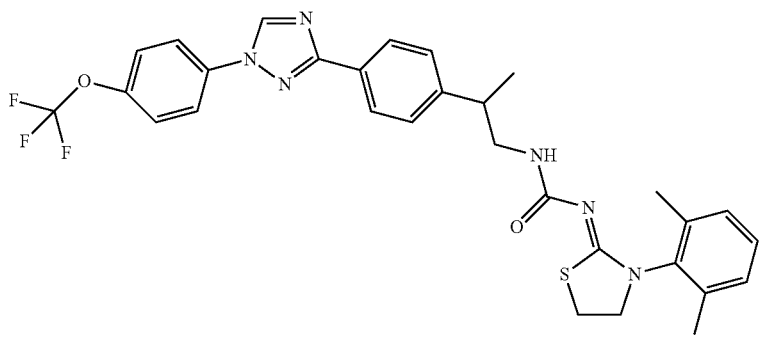 [SMILES: Cc1cccc(C)c1N1CCS/C1=N\C(=O)NCC(C)c1ccc(-c2ncn(-c3ccc(OC(F)(F)F)cc3)n2)cc1]
P1510
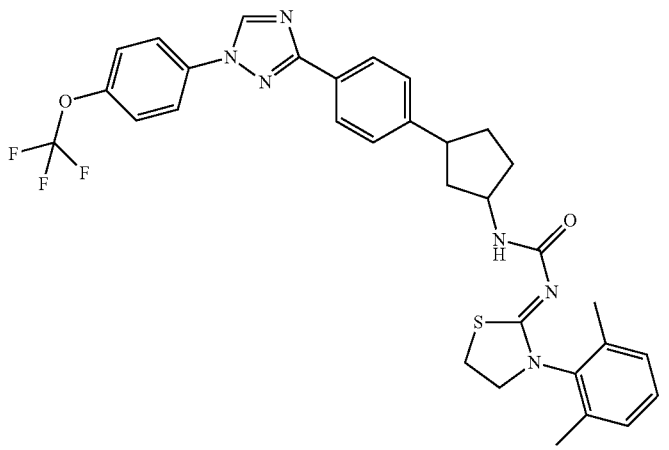 [SMILES: Cc1cccc(C)c1N1CCS/C1=N\C(=O)NC1CCC(c2ccc(-c3ncn(-c4ccc(OC(F)(F)F)cc4)n3)cc2)C1]
P1511

TABLE P-Two-continued
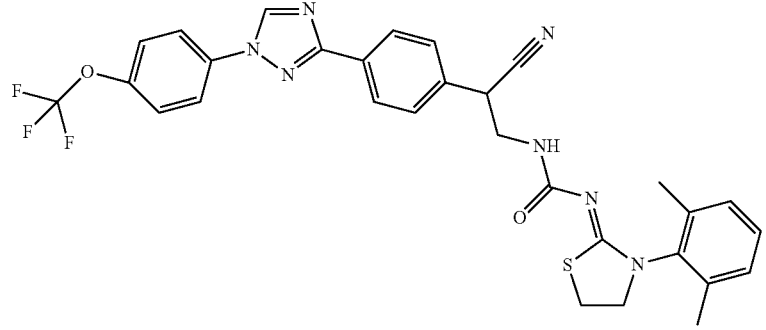 [SMILES: Cc1cccc(C)c1N1CCS/C1=N\C(=O)NCC(C#N)c1ccc(-c2ncn(-c3ccc(OC(F)(F)F)cc3)n2)cc1]
P1512
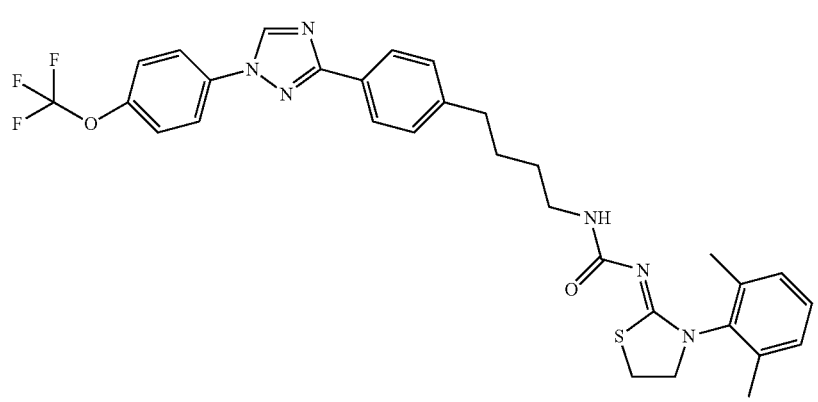 [SMILES: Cc1cccc(C)c1N1CCS/C1=N\C(=O)NCCCCc1ccc(-c2ncn(-c3ccc(OC(F)(F)F)cc3)n2)cc1]
P1513
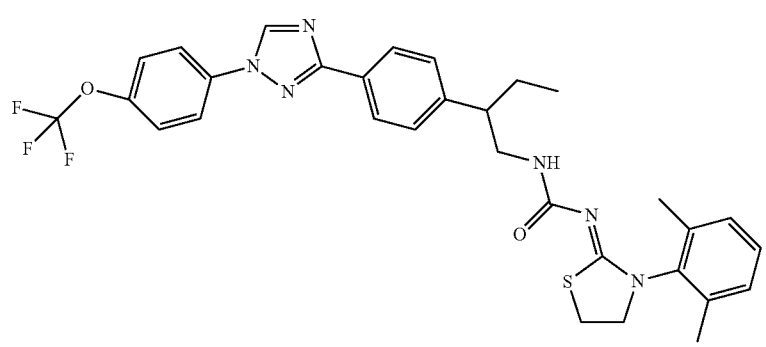 [SMILES: CCC(CNC(=O)/N=C1\SCCN1c1c(C)cccc1C)c1ccc(-c2ncn(-c3ccc(OC(F)(F)F)cc3)n2)cc1]
P1514
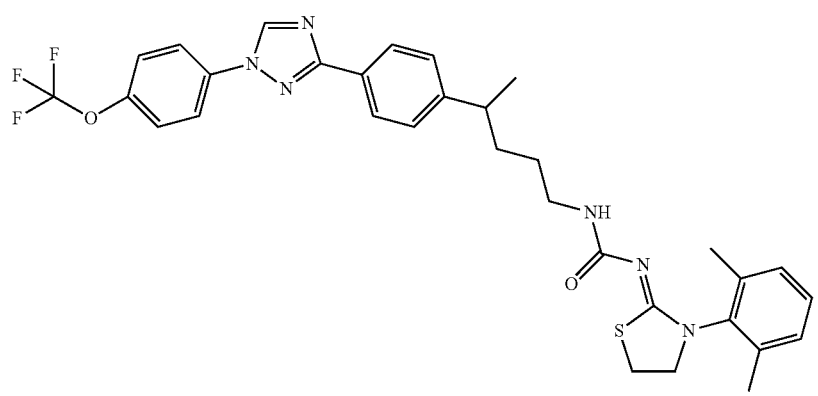 [SMILES: Cc1cccc(C)c1N1CCS/C1=N\C(=O)NCCCC(C)c1ccc(-c2ncn(-c3ccc(OC(F)(F)F)cc3)n2)cc1]
P1515

TABLE P-Two-continued
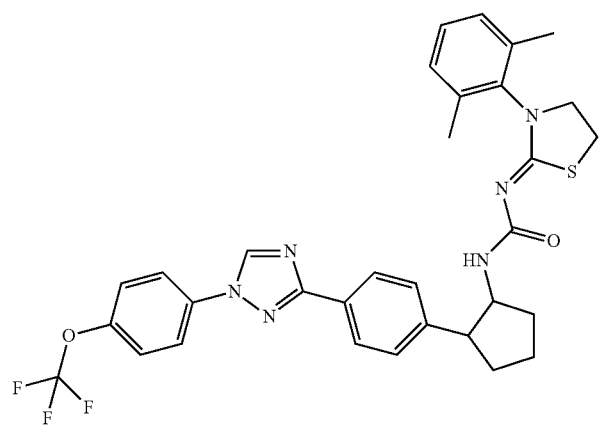 [SMILES: Cc1cccc(C)c1N1CCS/C1=N\C(=O)NC1CCCC1c1ccc(-c2ncn(-c3ccc(OC(F)(F)F)cc3)n2)cc1]
P1516
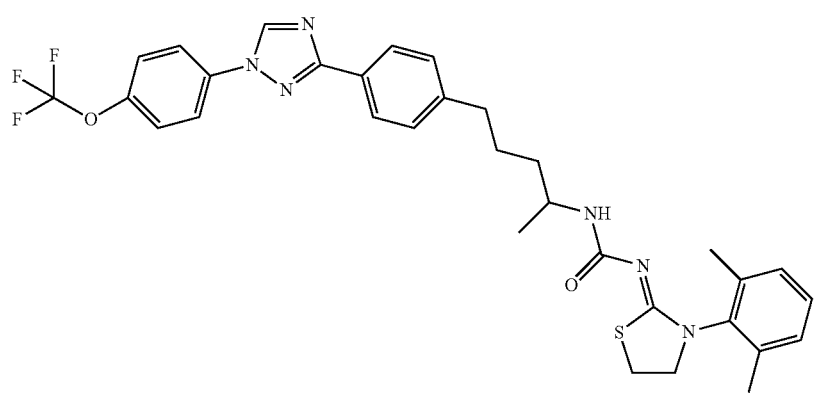 [SMILES: Cc1cccc(C)c1N1CCS/C1=N\C(=O)NC(C)CCCc1ccc(-c2ncn(-c3ccc(OC(F)(F)F)cc3)n2)cc1]
P1517
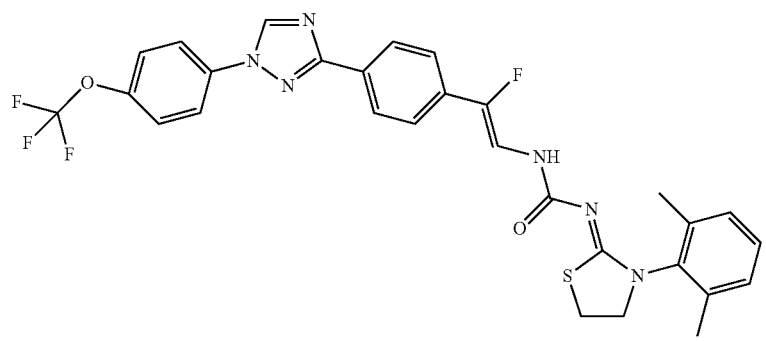
P1518
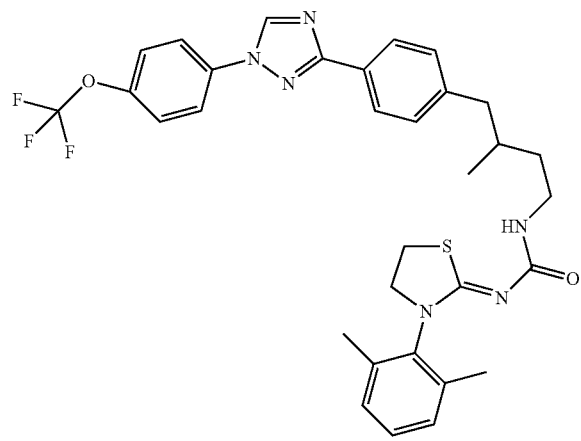 [SMILES: Cc1cccc(C)c1N1CCS/C1=N\C(=O)NCCC(C)Cc1ccc(-c2ncn(-c3ccc(OC(F)(F)F)cc3)n2)cc1]
P1519

TABLE P-Two-continued
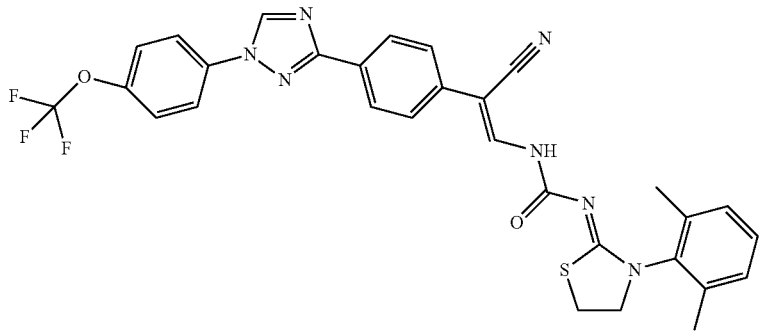 [SMILES: Cc1cccc(C)c1N1CCS/C1=N\C(=O)N/C=C(\C#N)c1ccc(-c2ncn(-c3ccc(OC(F)(F)F)cc3)n2)cc1]
P1520
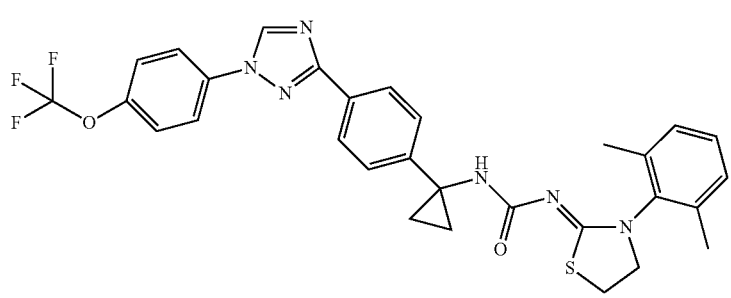 [SMILES: Cc1cccc(C)c1N1CCS/C1=N\C(=O)NC1(c2ccc(-c3ncn(-c4ccc(OC(F)(F)F)cc4)n3)cc2)CC1]
P1521
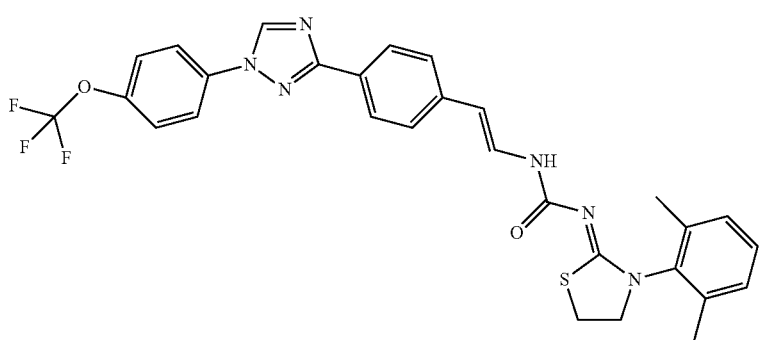 [SMILES: Cc1cccc(C)c1N1CCS/C1=N\C(=O)N/C=C/c1ccc(-c2ncn(-c3ccc(OC(F)(F)F)cc3)n2)cc1]
P1522
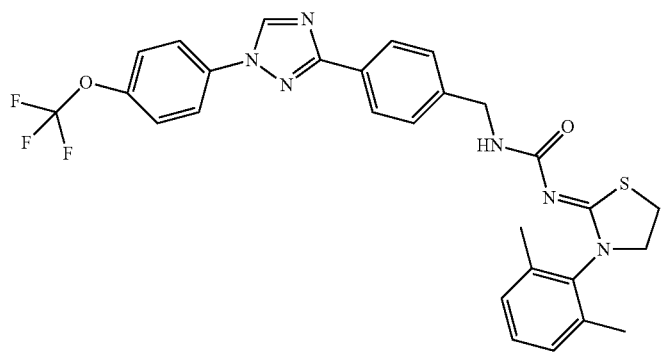 [SMILES: Cc1cccc(C)c1N1CCS/C1=N\C(=O)NCc1ccc(-c2ncn(-c3ccc(OC(F)(F)F)cc3)n2)cc1]
P1523
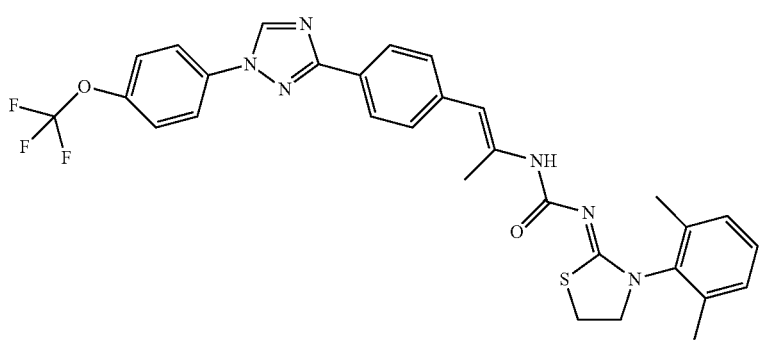 [SMILES: C/C(=C\c1ccc(-c2ncn(-c3ccc(OC(F)(F)F)cc3)n2)cc1)NC(=O)/N=C1\SCCN1c1c(C)cccc1C]
P1524

TABLE P-Two-continued
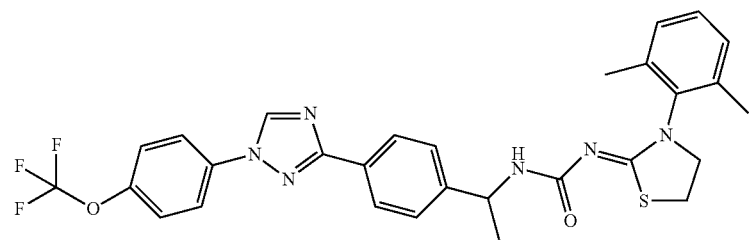 [SMILES: Cc1cccc(C)c1N1CCS/C1=N\C(=O)NC(C)c1ccc(-c2ncn(-c3ccc(OC(F)(F)F)cc3)n2)cc1]
P1525
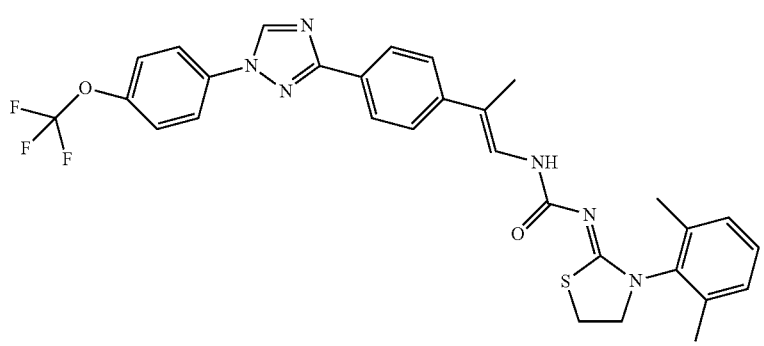 [SMILES: C/C(=C\NC(=O)/N=C1\SCCN1c1c(C)cccc1C)c1ccc(-c2ncn(-c3ccc(OC(F)(F)F)cc3)n2)cc1]
P1526
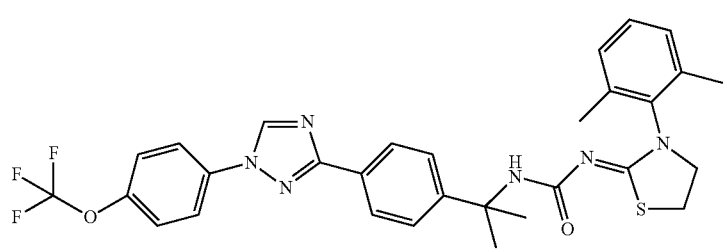 [SMILES: Cc1cccc(C)c1N1CCS/C1=N\C(=O)NC(C)(C)c1ccc(-c2ncn(-c3ccc(OC(F)(F)F)cc3)n2)cc1]
P1527
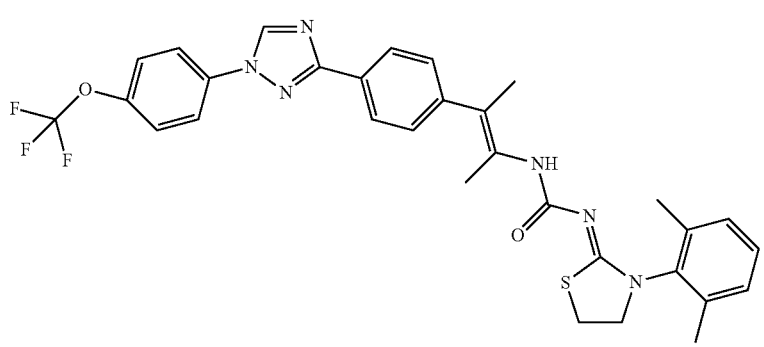 [SMILES: C/C(NC(=O)/N=C1\SCCN1c1c(C)cccc1C)=C(/C)c1ccc(-c2ncn(-c3ccc(OC(F)(F)F)cc3)n2)cc1]
P1528
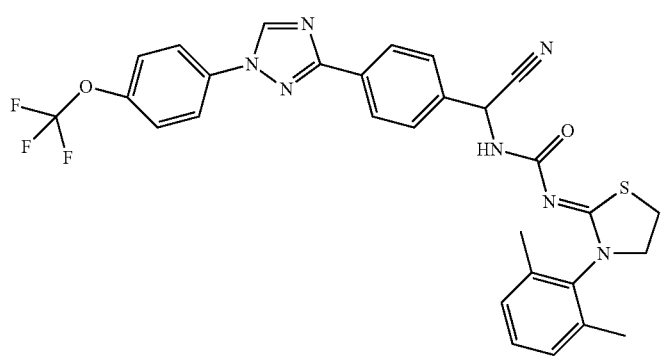 [SMILES: Cc1cccc(C)c1N1CCS/C1=N\C(=O)NC(C#N)c1ccc(-c2ncn(-c3ccc(OC(F)(F)F)cc3)n2)cc1]
P1529

TABLE P-Two-continued
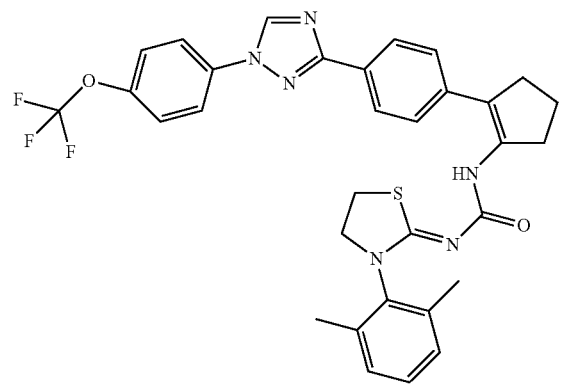 [SMILES: Cc1cccc(C)c1N1CCS/C1=N\C(=O)NC1=C(c2ccc(-c3ncn(-c4ccc(OC(F)(F)F)cc4)n3)cc2)CCC1]
P1530
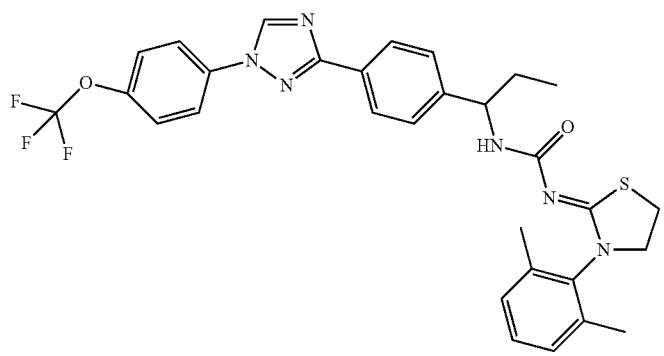 [SMILES: CCC(NC(=O)/N=C1\SCCN1c1c(C)cccc1C)c1ccc(-c2ncn(-c3ccc(OC(F)(F)F)cc3)n2)cc1]
P1531
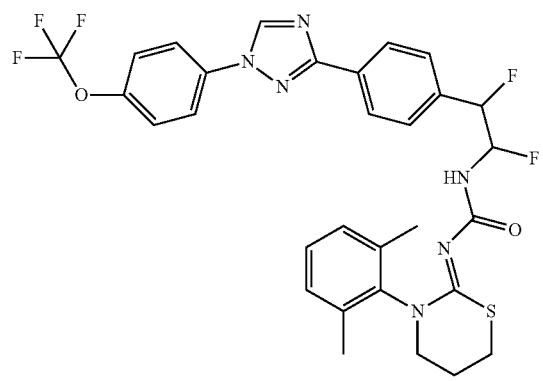 [SMILES: Cc1cccc(C)c1N1CCCS/C1=N\C(=O)NC(F)C(F)c1ccc(-c2ncn(-c3ccc(OC(F)(F)F)cc3)n2)cc1]
P1532
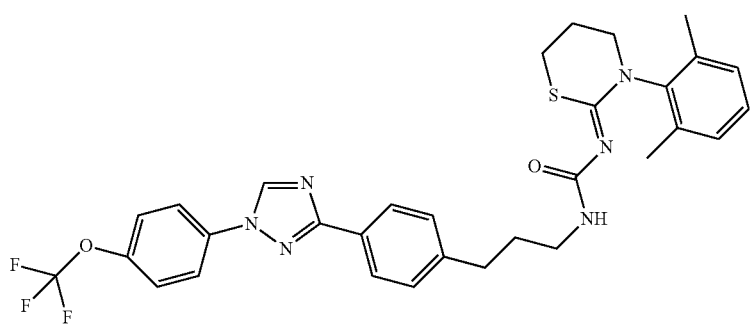 [SMILES: Cc1cccc(C)c1N1CCCS/C1=N\C(=O)NCCCc1ccc(-c2ncn(-c3ccc(OC(F)(F)F)cc3)n2)cc1]
P1533

TABLE P-Two-continued
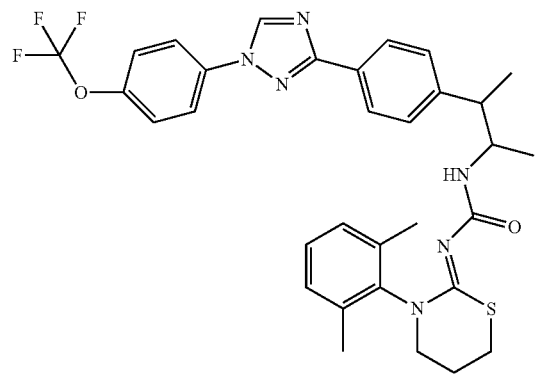 [SMILES: Cc1cccc(C)c1N1CCCS/C1=N\C(=O)NC(C)C(C)c1ccc(-c2ncn(-c3ccc(OC(F)(F)F)cc3)n2)cc1]
P1534
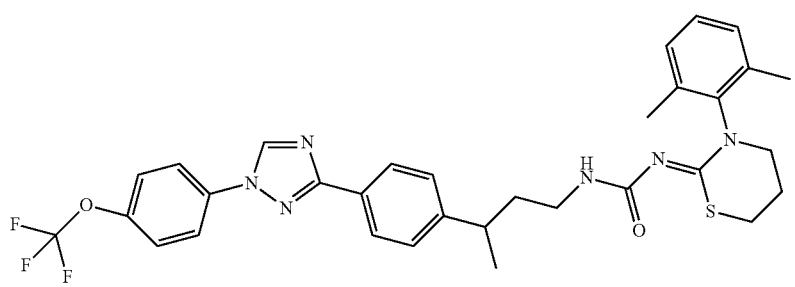 [SMILES: Cc1cccc(C)c1N1CCCS/C1=N\C(=O)NCCC(C)c1ccc(-c2ncn(-c3ccc(OC(F)(F)F)cc3)n2)cc1]
P1535
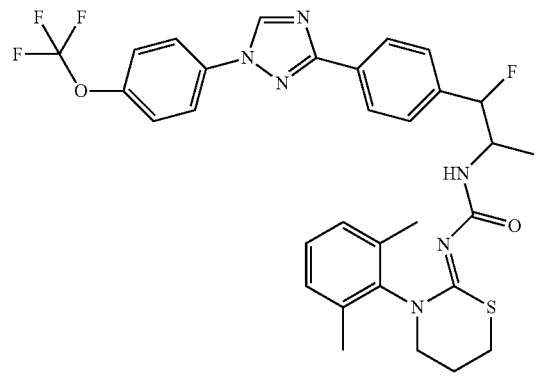 [SMILES: Cc1cccc(C)c1N1CCCS/C1=N\C(=O)NC(C)C(F)c1ccc(-c2ncn(-c3ccc(OC(F)(F)F)cc3)n2)cc1]
P1536
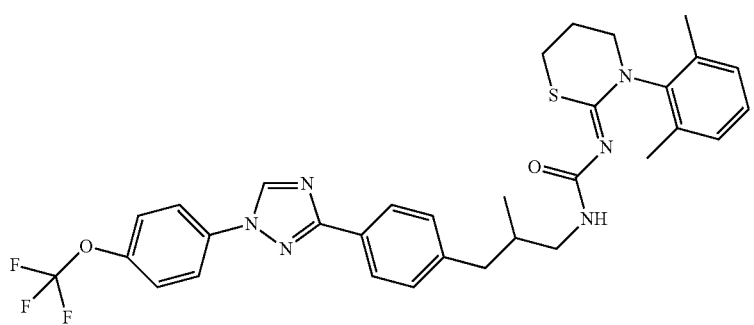 [SMILES: Cc1cccc(C)c1N1CCCS/C1=N\C(=O)NCC(C)Cc1ccc(-c2ncn(-c3ccc(OC(F)(F)F)cc3)n2)cc1]
P1537

TABLE P-Two-continued

| | |
|---|---|
| (structure) | P1538 |
| (structure) | P1539 |
| (structure) | P1540 |
| (structure) | P1541 |
| (structure) | P1542 |

TABLE P-Two-continued
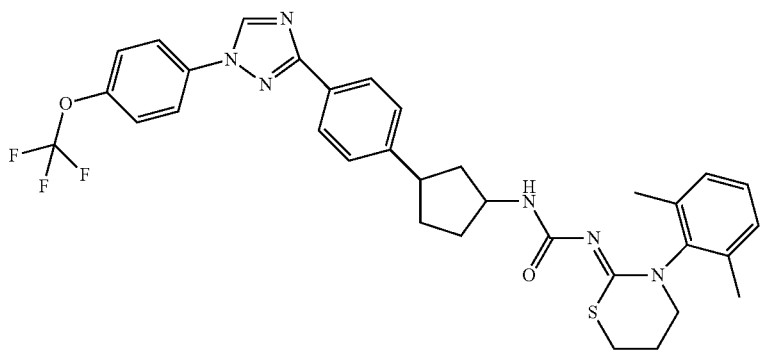 [SMILES: Cc1cccc(C)c1N1CCCS/C1=N\C(=O)NC1CCC(c2ccc(-c3ncn(-c4ccc(OC(F)(F)F)cc4)n3)cc2)C1]
P1543
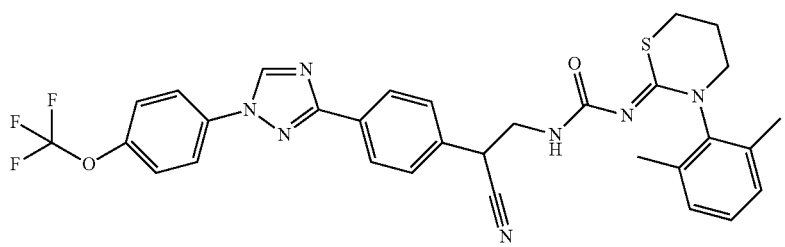 [SMILES: Cc1cccc(C)c1N1CCCS/C1=N\C(=O)NCC(C#N)c1ccc(-c2ncn(-c3ccc(OC(F)(F)F)cc3)n2)cc1]
P1544
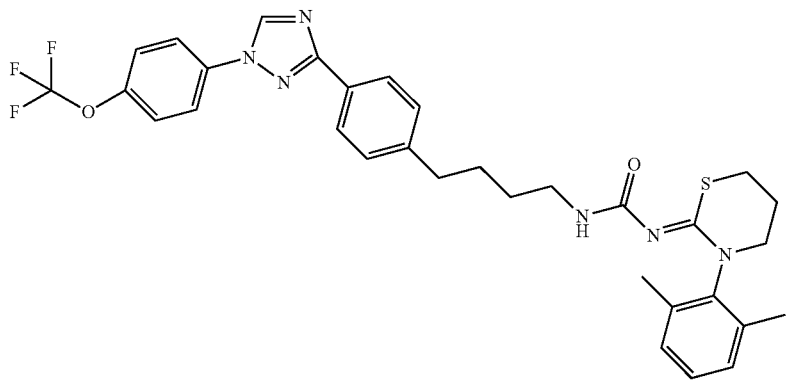 [SMILES: Cc1cccc(C)c1N1CCCS/C1=N\C(=O)NCCCCc1ccc(-c2ncn(-c3ccc(OC(F)(F)F)cc3)n2)cc1]
P1545
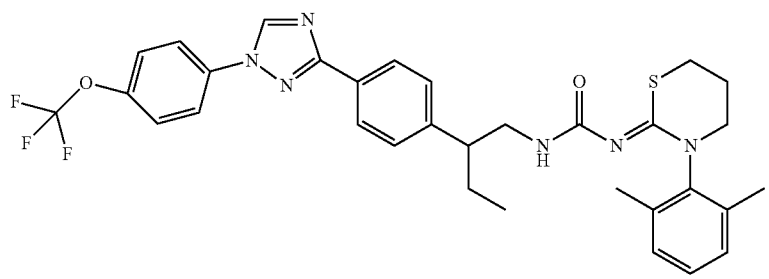 [SMILES: CCC(CNC(=O)/N=C1\SCCCN1c1c(C)cccc1C)c1ccc(-c2ncn(-c3ccc(OC(F)(F)F)cc3)n2)cc1]
P1546
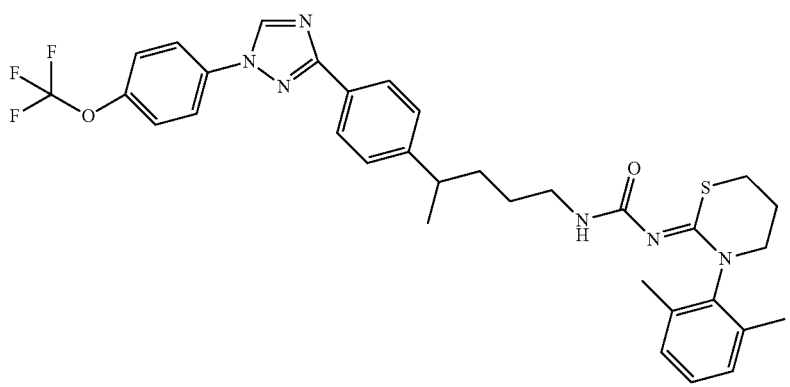 [SMILES: Cc1cccc(C)c1N1CCCS/C1=N\C(=O)NCCCC(C)c1ccc(-c2ncn(-c3ccc(OC(F)(F)F)cc3)n2)cc1]
P1547

TABLE P-Two-continued

P1548

P1549

P1550

P1551

TABLE P-Two-continued
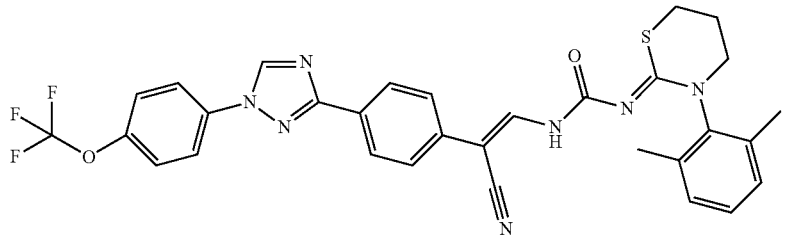 [SMILES: Cc1cccc(C)c1N1CCCS/C1=N\C(=O)N/C=C(\C#N)c1ccc(-c2ncn(-c3ccc(OC(F)(F)F)cc3)n2)cc1]
P1552
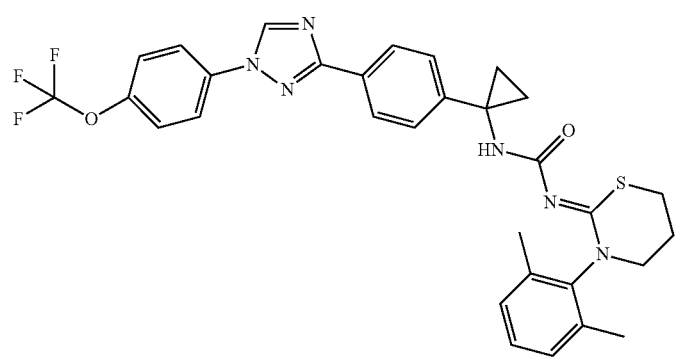 [SMILES: Cc1cccc(C)c1N1CCCS/C1=N\C(=O)NC1(c2ccc(-c3ncn(-c4ccc(OC(F)(F)F)cc4)n3)cc2)CC1]
P1553
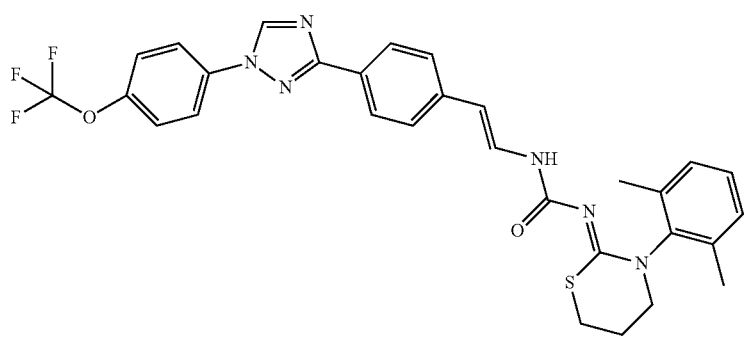 [SMILES: Cc1cccc(C)c1N1CCCS/C1=N\C(=O)N/C=C/c1ccc(-c2ncn(-c3ccc(OC(F)(F)F)cc3)n2)cc1]
P1554
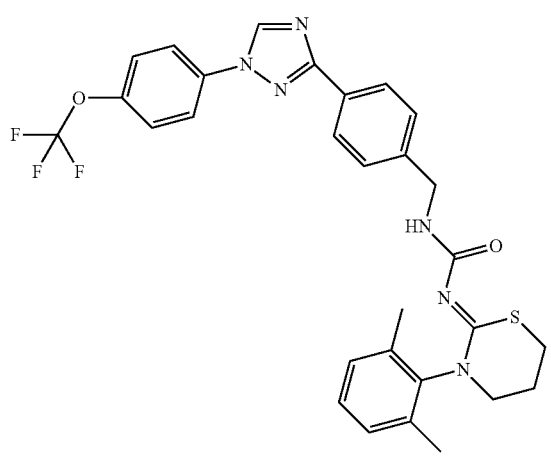 [SMILES: Cc1cccc(C)c1N1CCCS/C1=N\C(=O)NCc1ccc(-c2ncn(-c3ccc(OC(F)(F)F)cc3)n2)cc1]
P1555

TABLE P-Two-continued
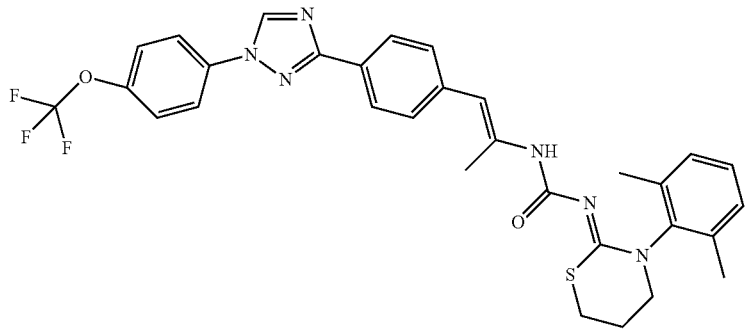 [SMILES: C/C(=C\c1ccc(-c2ncn(-c3ccc(OC(F)(F)F)cc3)n2)cc1)NC(=O)/N=C1\SCCCN1c1c(C)cccc1C]
P1556
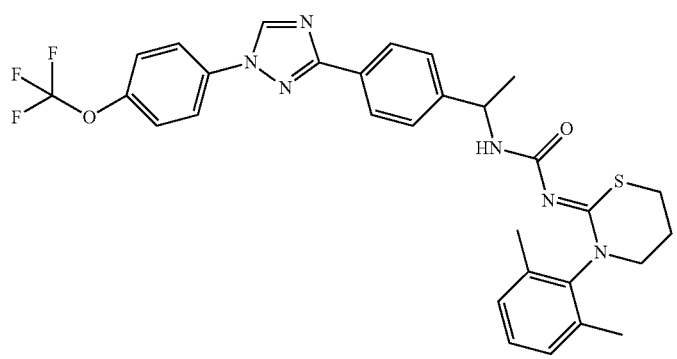 [SMILES: Cc1cccc(C)c1N1CCCS/C1=N\C(=O)NC(C)c1ccc(-c2ncn(-c3ccc(OC(F)(F)F)cc3)n2)cc1]
P1557
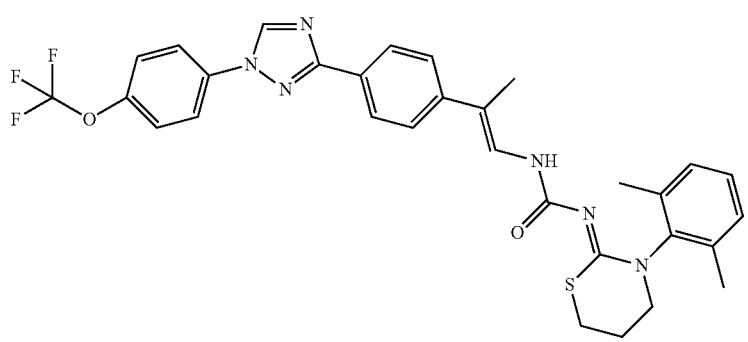 [SMILES: C/C(=C\NC(=O)/N=C1\SCCCN1c1c(C)cccc1C)c1ccc(-c2ncn(-c3ccc(OC(F)(F)F)cc3)n2)cc1]
P1558
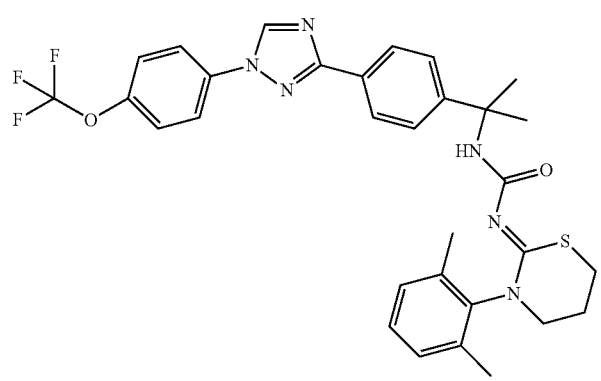 [SMILES: Cc1cccc(C)c1N1CCCS/C1=N\C(=O)NC(C)(C)c1ccc(-c2ncn(-c3ccc(OC(F)(F)F)cc3)n2)cc1]
P1559

TABLE P-Two-continued
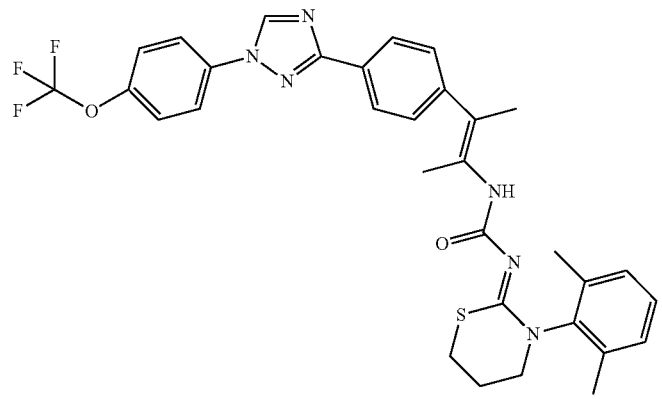 [SMILES: C/C(NC(=O)/N=C1\SCCCN1c1c(C)cccc1C)=C(/C)c1ccc(-c2ncn(-c3ccc(OC(F)(F)F)cc3)n2)cc1]
P1560
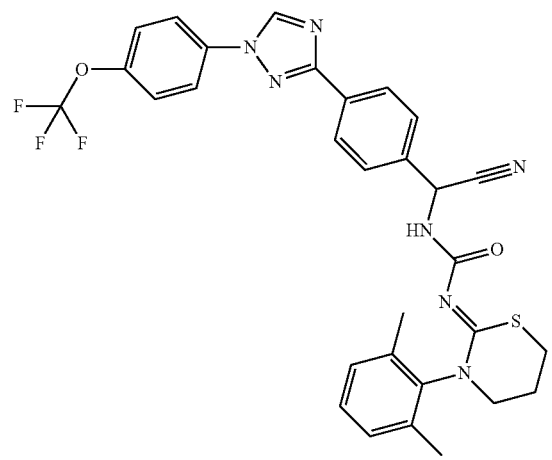 [SMILES: Cc1cccc(C)c1N1CCCS/C1=N\C(=O)NC(C#N)c1ccc(-c2ncn(-c3ccc(OC(F)(F)F)cc3)n2)cc1]
P1561
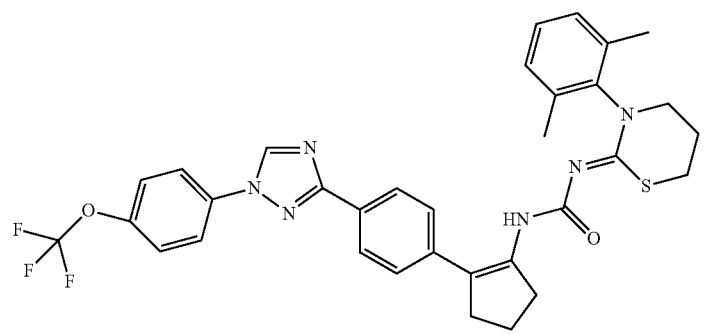 [SMILES: Cc1cccc(C)c1N1CCCS/C1=N\C(=O)NC1=C(c2ccc(-c3ncn(-c4ccc(OC(F)(F)F)cc4)n3)cc2)CCC1]
P1562
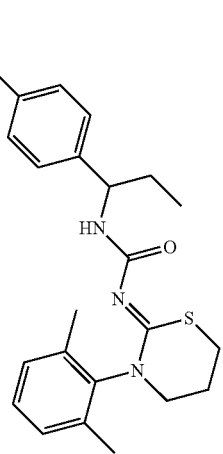
P1563

TABLE P-Two-continued
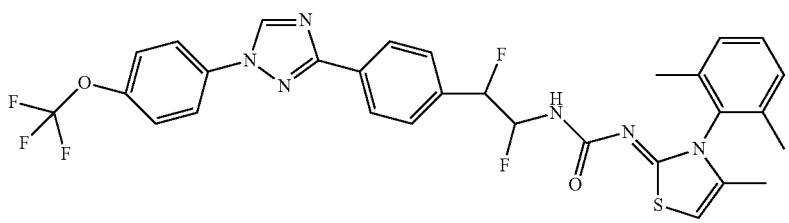 P1564
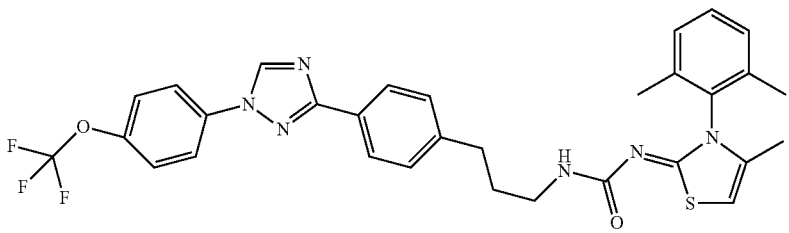 [SMILES: Cc1cccc(C)c1-n1c(C)cs/c1=N\C(=O)NCCCc1ccc(-c2ncn(-c3ccc(OC(F)(F)F)cc3)n2)cc1] P1565
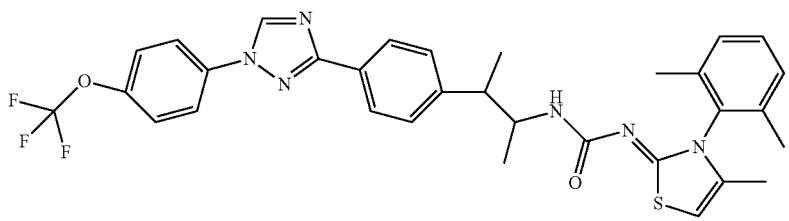 [SMILES: Cc1cccc(C)c1-n1c(C)cs/c1=N\C(=O)NC(C)C(C)c1ccc(-c2ncn(-c3ccc(OC(F)(F)F)cc3)n2)cc1] P1566
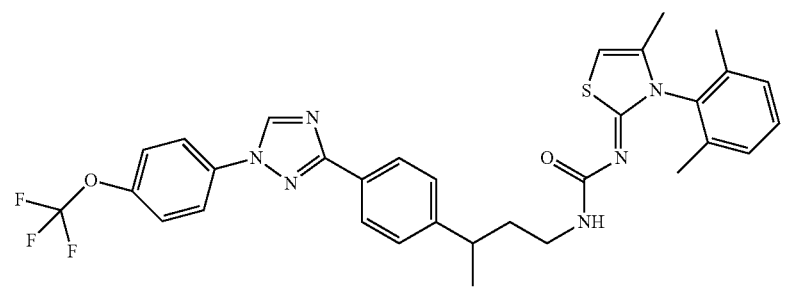 [SMILES: Cc1cccc(C)c1-n1c(C)cs/c1=N\C(=O)NCCC(C)c1ccc(-c2ncn(-c3ccc(OC(F)(F)F)cc3)n2)cc1] P1567
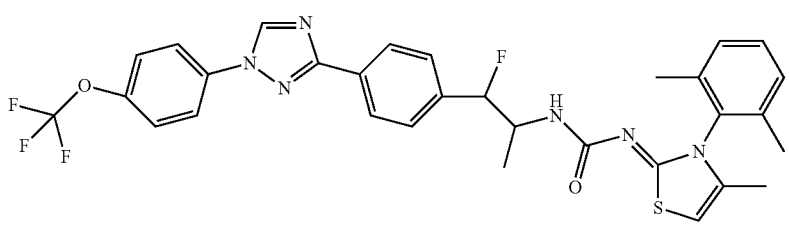 [SMILES: Cc1cccc(C)c1-n1c(C)cs/c1=N\C(=O)NC(C)C(F)c1ccc(-c2ncn(-c3ccc(OC(F)(F)F)cc3)n2)cc1] P1568
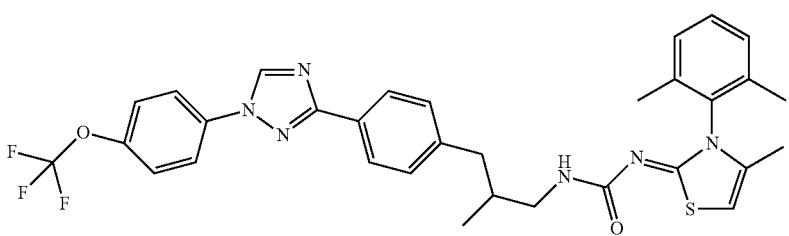 [SMILES: Cc1cccc(C)c1-n1c(C)cs/c1=N\C(=O)NCC(C)Cc1ccc(-c2ncn(-c3ccc(OC(F)(F)F)cc3)n2)cc1] P1569

TABLE P-Two-continued
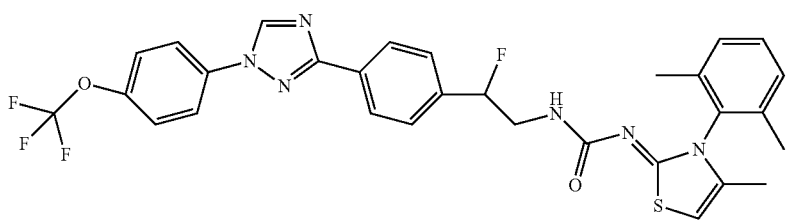 [SMILES: Cc1cccc(C)c1-n1c(C)cs/c1=N\C(=O)NCC(F)c1ccc(-c2ncn(-c3ccc(OC(F)(F)F)cc3)n2)cc1]
P1570
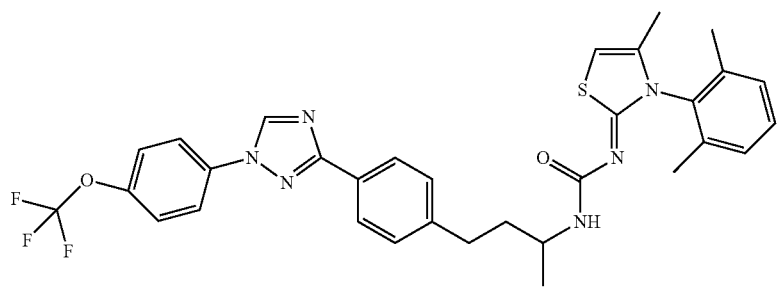 [SMILES: Cc1cccc(C)c1-n1c(C)cs/c1=N\C(=O)NC(C)CCc1ccc(-c2ncn(-c3ccc(OC(F)(F)F)cc3)n2)cc1]
P1571
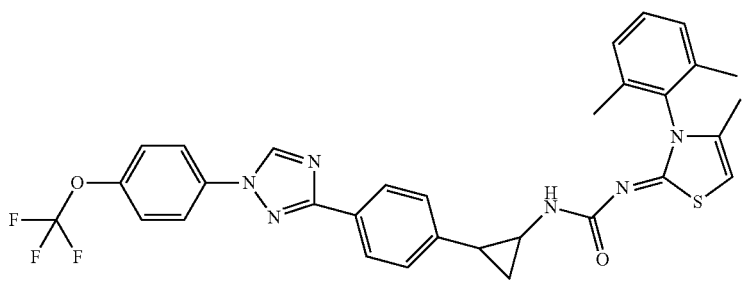 [SMILES: Cc1cccc(C)c1-n1c(C)cs/c1=N\C(=O)NC1CC1c1ccc(-c2ncn(-c3ccc(OC(F)(F)F)cc3)n2)cc1]
P1572
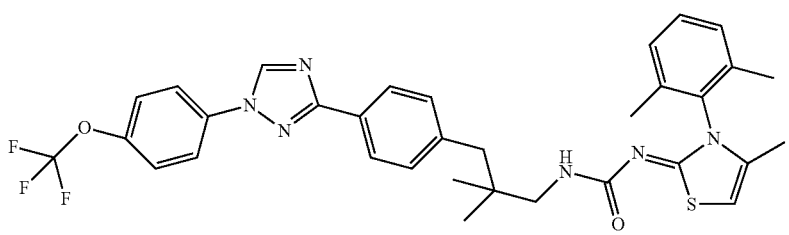 [SMILES: Cc1cccc(C)c1-n1c(C)cs/c1=N\C(=O)NCC(C)(C)Cc1ccc(-c2ncn(-c3ccc(OC(F)(F)F)cc3)n2)cc1]
P1573
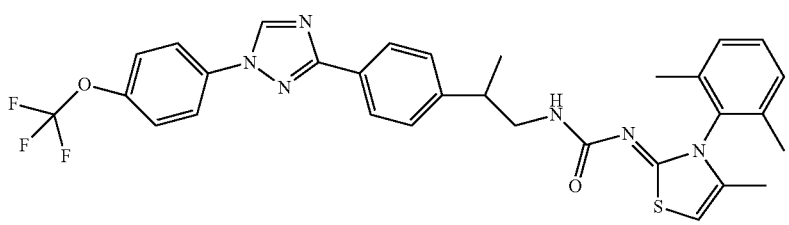 [SMILES: Cc1cccc(C)c1-n1c(C)cs/c1=N\C(=O)NCC(C)c1ccc(-c2ncn(-c3ccc(OC(F)(F)F)cc3)n2)cc1]
P1574
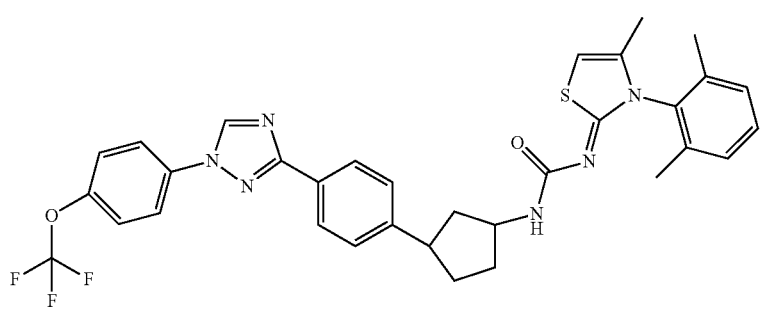 [SMILES: Cc1cccc(C)c1-n1c(C)cs/c1=N\C(=O)NC1CCC(c2ccc(-c3ncn(-c4ccc(OC(F)(F)F)cc4)n3)cc2)C1]
P1575

TABLE P-Two-continued
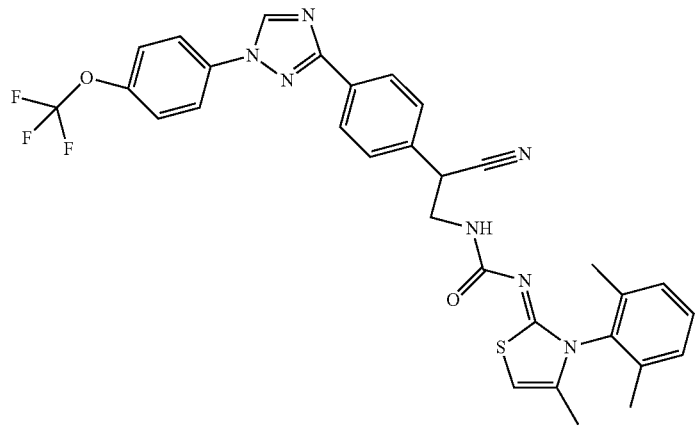 [SMILES: Cc1cccc(C)c1-n1c(C)cs/c1=N\C(=O)NCC(C#N)c1ccc(-c2ncn(-c3ccc(OC(F)(F)F)cc3)n2)cc1]
P1576
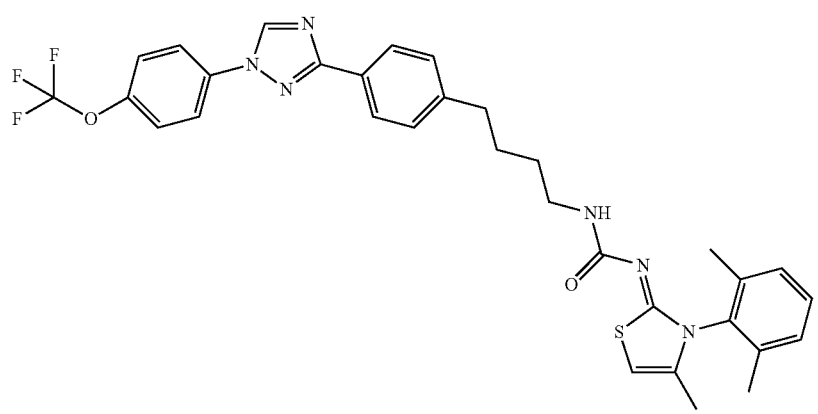 [SMILES: Cc1cccc(C)c1-n1c(C)cs/c1=N\C(=O)NCCCCc1ccc(-c2ncn(-c3ccc(OC(F)(F)F)cc3)n2)cc1]
P1577
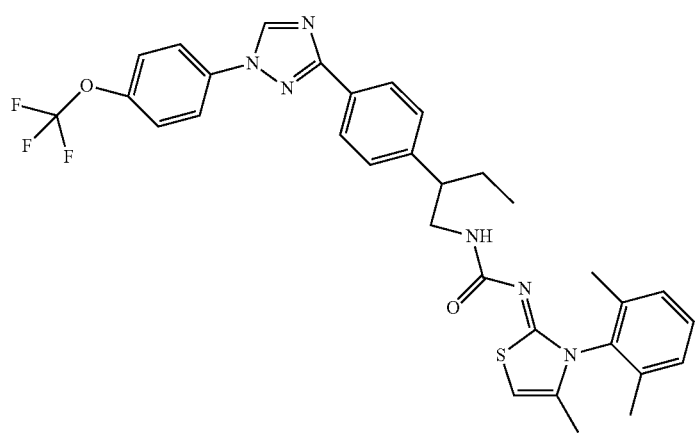 [SMILES: CCC(CNC(=O)/N=c1\scc(C)n1-c1c(C)cccc1C)c1ccc(-c2ncn(-c3ccc(OC(F)(F)F)cc3)n2)cc1]
P1578

TABLE P-Two-continued
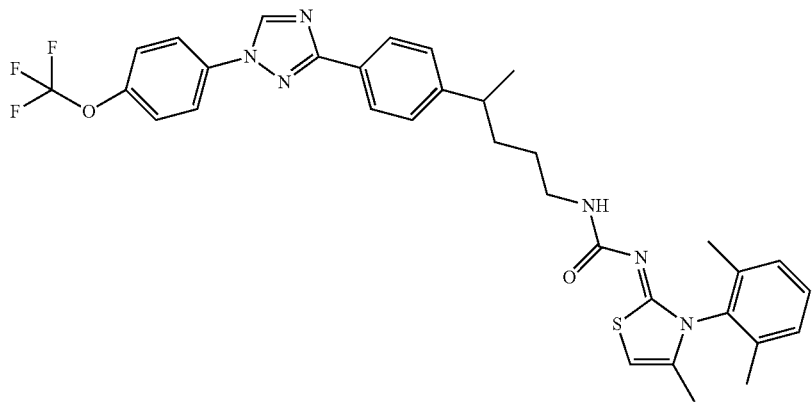 [SMILES: Cc1cccc(C)c1-n1c(C)cs/c1=N\C(=O)NCCCC(C)c1ccc(-c2ncn(-c3ccc(OC(F)(F)F)cc3)n2)cc1]
P1579
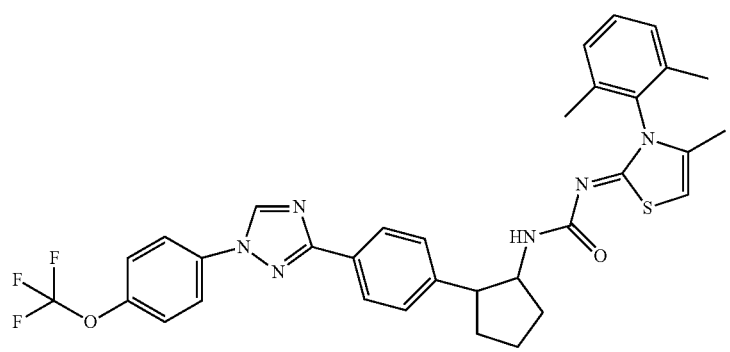 [SMILES: Cc1cccc(C)c1-n1c(C)cs/c1=N\C(=O)NC1CCCC1c1ccc(-c2ncn(-c3ccc(OC(F)(F)F)cc3)n2)cc1]
P1580
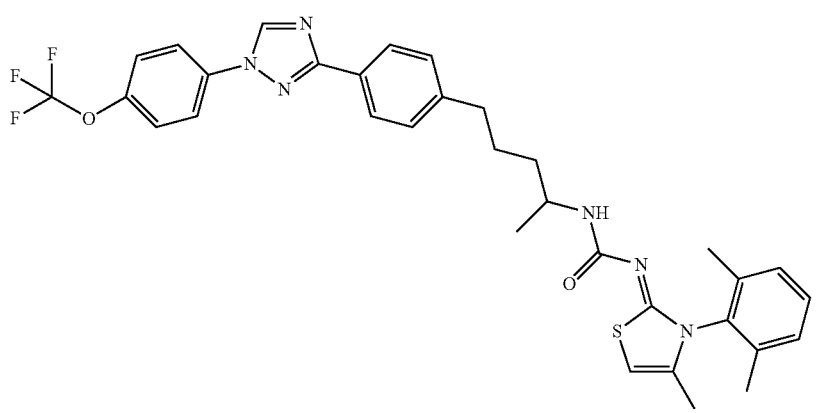 [SMILES: Cc1cccc(C)c1-n1c(C)cs/c1=N\C(=O)NC(C)CCCc1ccc(-c2ncn(-c3ccc(OC(F)(F)F)cc3)n2)cc1]
P1581
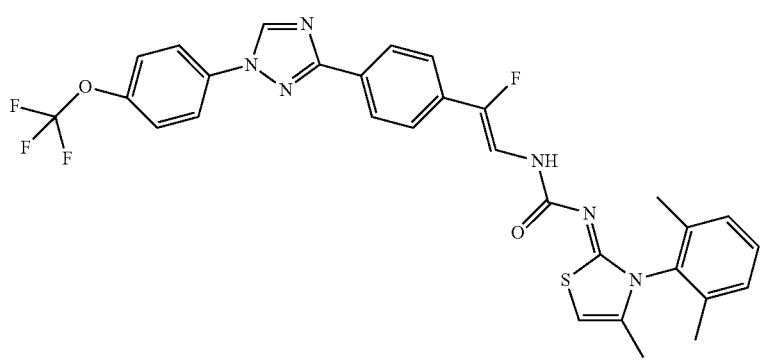
P1582

TABLE P-Two-continued
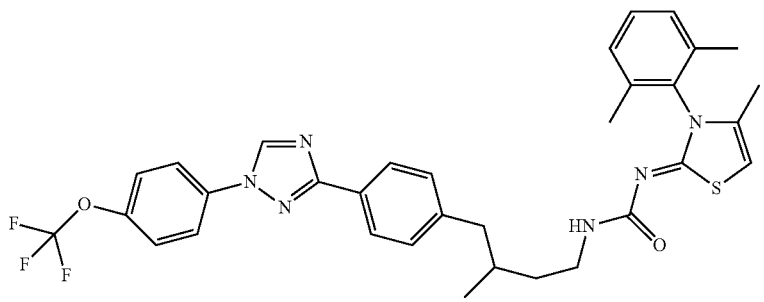 [SMILES: Cc1cccc(C)c1-n1c(C)cs/c1=N\C(=O)NCCC(C)Cc1ccc(-c2ncn(-c3ccc(OC(F)(F)F)cc3)n2)cc1]
P1583
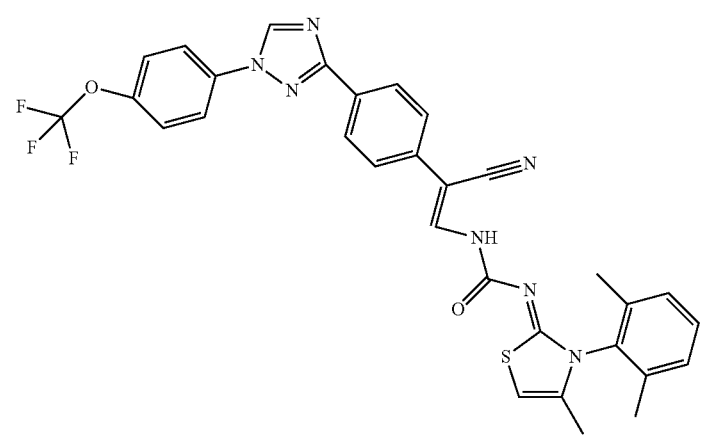 [SMILES: Cc1cccc(C)c1-n1c(C)cs/c1=N\C(=O)N/C=C(\C#N)c1ccc(-c2ncn(-c3ccc(OC(F)(F)F)cc3)n2)cc1]
P1584
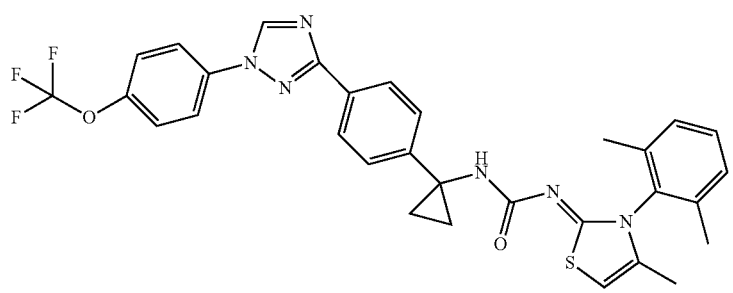 [SMILES: Cc1cccc(C)c1-n1c(C)cs/c1=N\C(=O)NC1(c2ccc(-c3ncn(-c4ccc(OC(F)(F)F)cc4)n3)cc2)CC1]
P1585
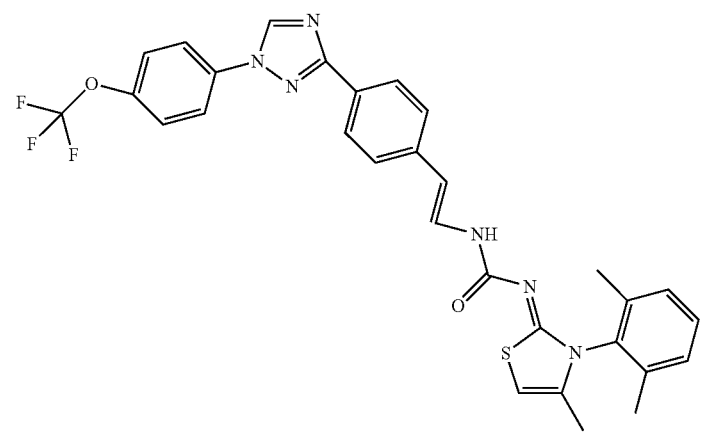 [SMILES: Cc1cccc(C)c1-n1c(C)cs/c1=N\C(=O)N/C=C/c1ccc(-c2ncn(-c3ccc(OC(F)(F)F)cc3)n2)cc1]
P1586

TABLE P-Two-continued
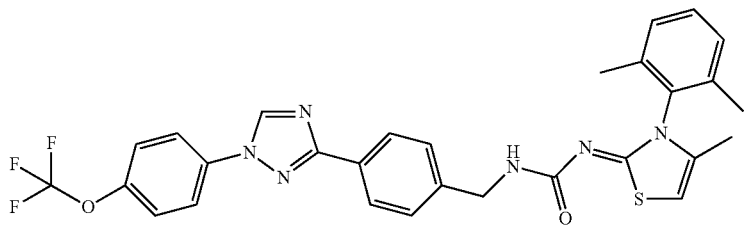 [SMILES: Cc1cccc(C)c1-n1c(C)cs/c1=N\C(=O)NCc1ccc(-c2ncn(-c3ccc(OC(F)(F)F)cc3)n2)cc1]
P1587
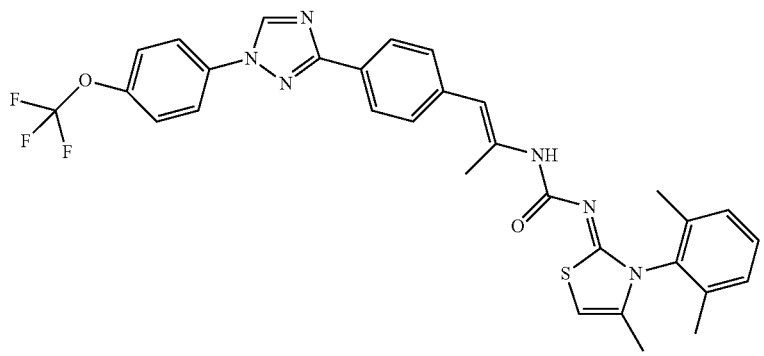 [SMILES: C/C(=C\c1ccc(-c2ncn(-c3ccc(OC(F)(F)F)cc3)n2)cc1)NC(=O)/N=c1\scc(C)n1-c1c(C)cccc1C]
P1588
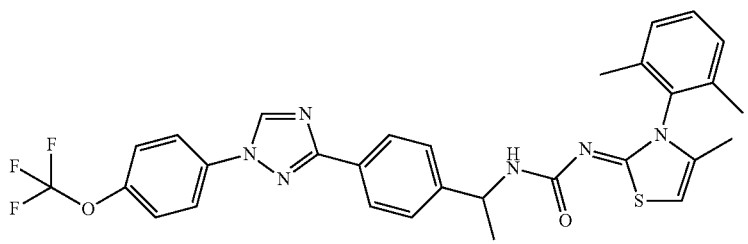 [SMILES: Cc1cccc(C)c1-n1c(C)cs/c1=N\C(=O)NC(C)c1ccc(-c2ncn(-c3ccc(OC(F)(F)F)cc3)n2)cc1]
P1589
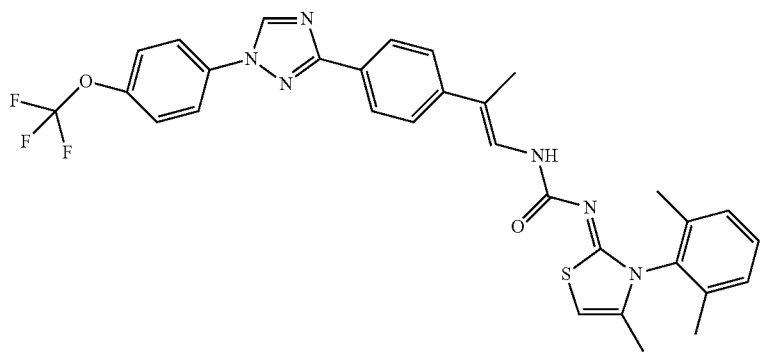 [SMILES: C/C(=C\NC(=O)/N=c1\scc(C)n1-c1c(C)cccc1C)c1ccc(-c2ncn(-c3ccc(OC(F)(F)F)cc3)n2)cc1]
P1590
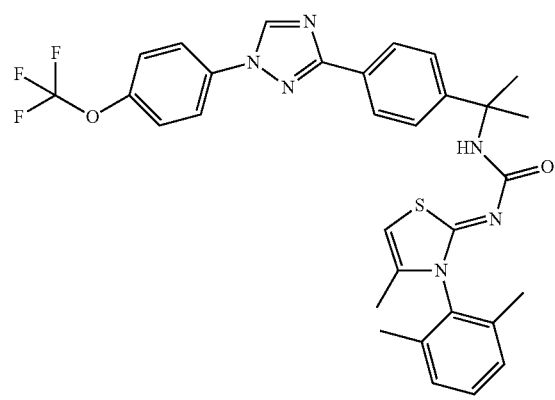 [SMILES: Cc1cccc(C)c1-n1c(C)cs/c1=N\C(=O)NC(C)(C)c1ccc(-c2ncn(-c3ccc(OC(F)(F)F)cc3)n2)cc1]
P1591

TABLE P-Two-continued
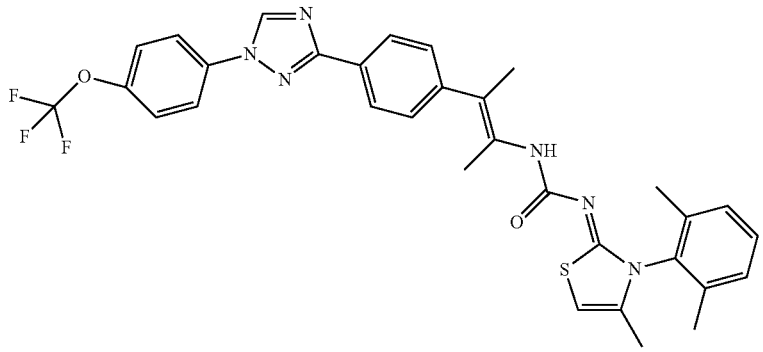 [SMILES: C/C(NC(=O)/N=c1\scc(C)n1-c1c(C)cccc1C)=C(/C)c1ccc(-c2ncn(-c3ccc(OC(F)(F)F)cc3)n2)cc1]
P1592
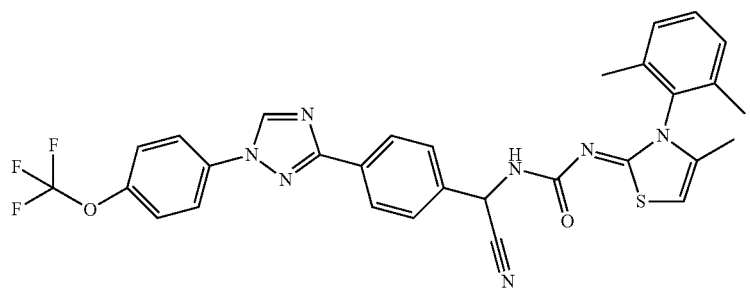 [SMILES: Cc1cccc(C)c1-n1c(C)cs/c1=N\C(=O)NC(C#N)c1ccc(-c2ncn(-c3ccc(OC(F)(F)F)cc3)n2)cc1]
P1593
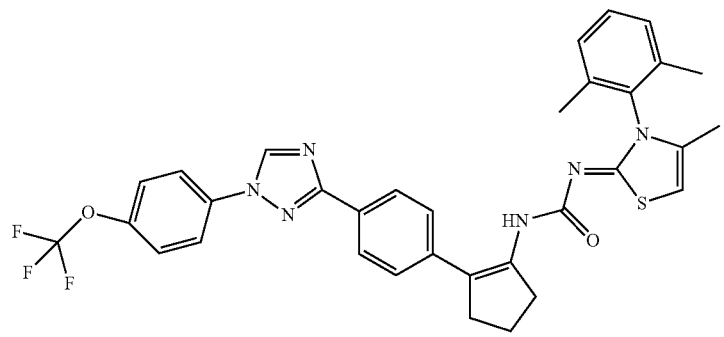 [SMILES: Cc1cccc(C)c1-n1c(C)cs/c1=N\C(=O)NC1=C(c2ccc(-c3ncn(-c4ccc(OC(F)(F)F)cc4)n3)cc2)CCC1]
P1594
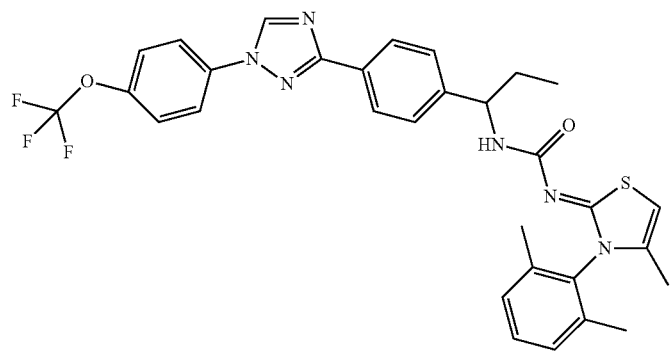 [SMILES: CCC(NC(=O)/N=c1\scc(C)n1-c1c(C)cccc1C)c1ccc(-c2ncn(-c3ccc(OC(F)(F)F)cc3)n2)cc1]
P1595

TABLE P-Two-continued
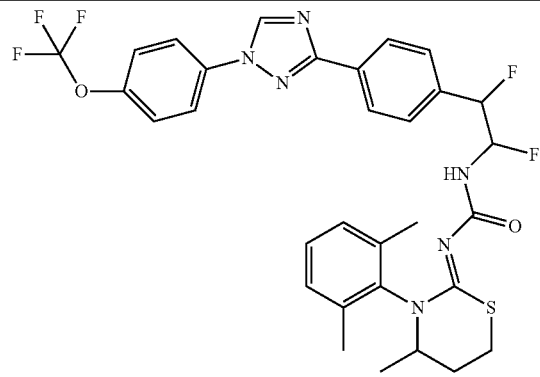
P1596
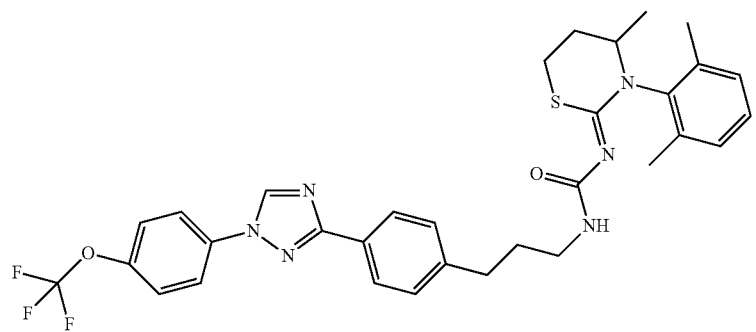 [SMILES: Cc1cccc(C)c1N1/C(=N/C(=O)NCCCc2ccc(-c3ncn(-c4ccc(OC(F)(F)F)cc4)n3)cc2)SCCC1C]
P1597
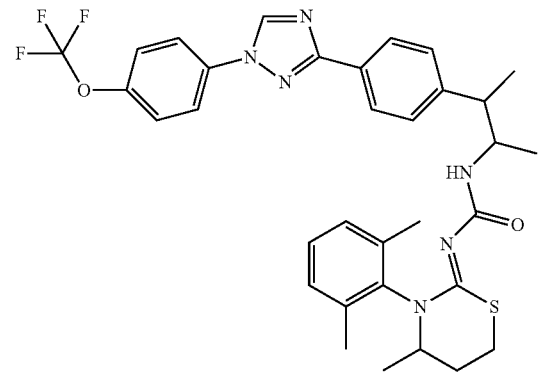 [SMILES: Cc1cccc(C)c1N1/C(=N/C(=O)NC(C)C(C)c2ccc(-c3ncn(-c4ccc(OC(F)(F)F)cc4)n3)cc2)SCCC1C]
P1598
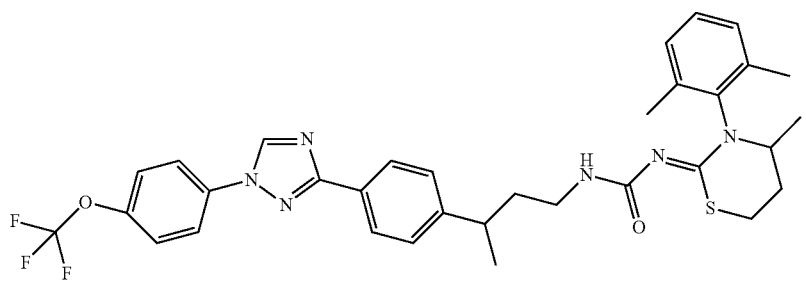 [SMILES: Cc1cccc(C)c1N1/C(=N/C(=O)NCCC(C)c2ccc(-c3ncn(-c4ccc(OC(F)(F)F)cc4)n3)cc2)SCCC1C]
P1599

TABLE P-Two-continued
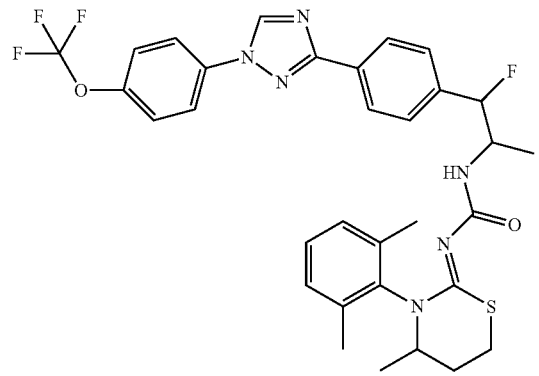 [SMILES: Cc1cccc(C)c1N1/C(=N/C(=O)NC(C)C(F)c2ccc(-c3ncn(-c4ccc(OC(F)(F)F)cc4)n3)cc2)SCCC1C]
P1600
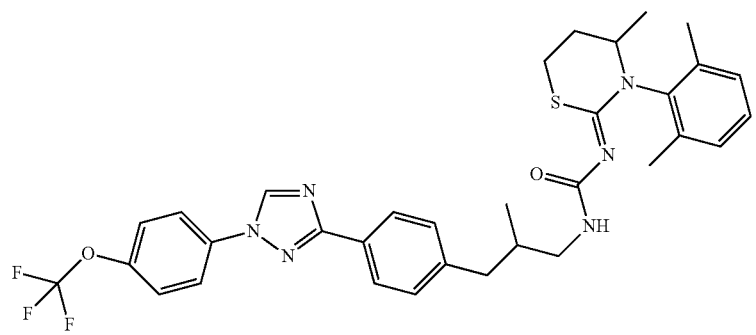 [SMILES: Cc1cccc(C)c1N1/C(=N/C(=O)NCC(C)Cc2ccc(-c3ncn(-c4ccc(OC(F)(F)F)cc4)n3)cc2)SCCC1C]
P1601
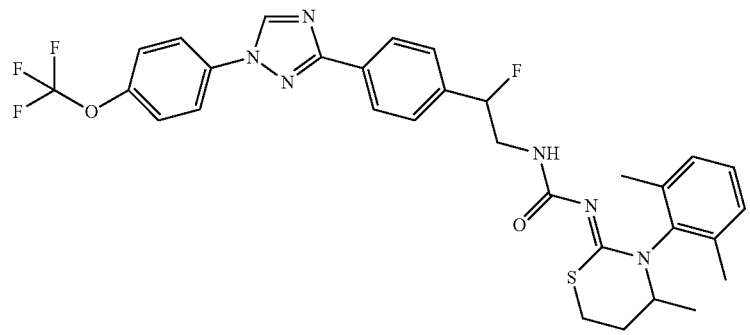 [SMILES: Cc1cccc(C)c1N1/C(=N/C(=O)NCC(F)c2ccc(-c3ncn(-c4ccc(OC(F)(F)F)cc4)n3)cc2)SCCC1C]
P1602
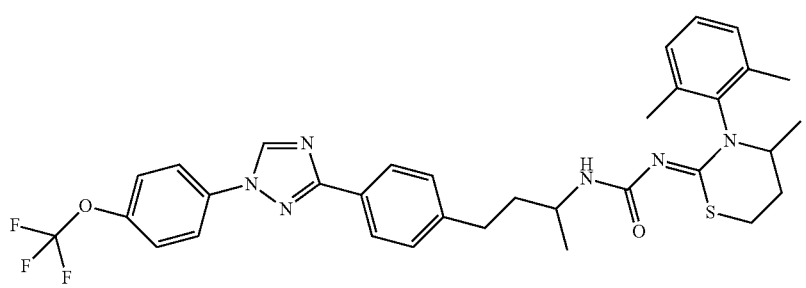 [SMILES: Cc1cccc(C)c1N1/C(=N/C(=O)NC(C)CCc2ccc(-c3ncn(-c4ccc(OC(F)(F)F)cc4)n3)cc2)SCCC1C]
P1603

TABLE P-Two-continued
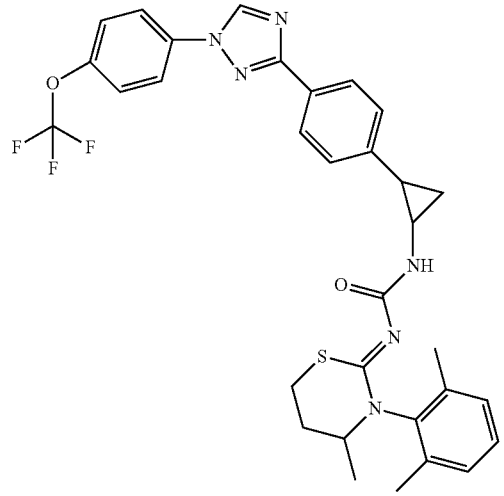 [SMILES: Cc1cccc(C)c1N1/C(=N/C(=O)NC2CC2c2ccc(-c3ncn(-c4ccc(OC(F)(F)F)cc4)n3)cc2)SCCC1C]
P1604
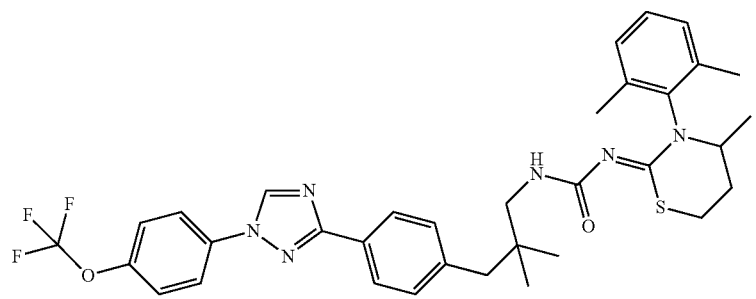 [SMILES: Cc1cccc(C)c1N1/C(=N/C(=O)NCC(C)(C)Cc2ccc(-c3ncn(-c4ccc(OC(F)(F)F)cc4)n3)cc2)SCCC1C]
P1605
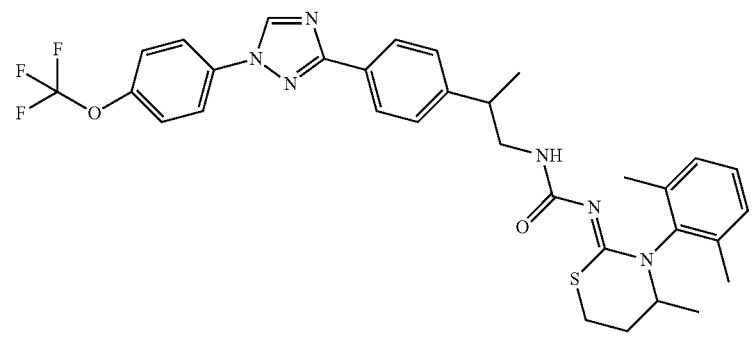 [SMILES: Cc1cccc(C)c1N1/C(=N/C(=O)NCC(C)c2ccc(-c3ncn(-c4ccc(OC(F)(F)F)cc4)n3)cc2)SCCC1C]
P1606
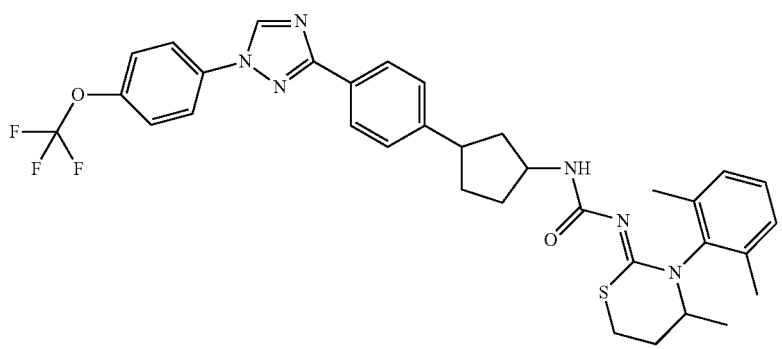 [SMILES: Cc1cccc(C)c1N1/C(=N/C(=O)NC2CCC(c3ccc(-c4ncn(-c5ccc(OC(F)(F)F)cc5)n4)cc3)C2)SCCC1C]
P1607

TABLE P-Two-continued
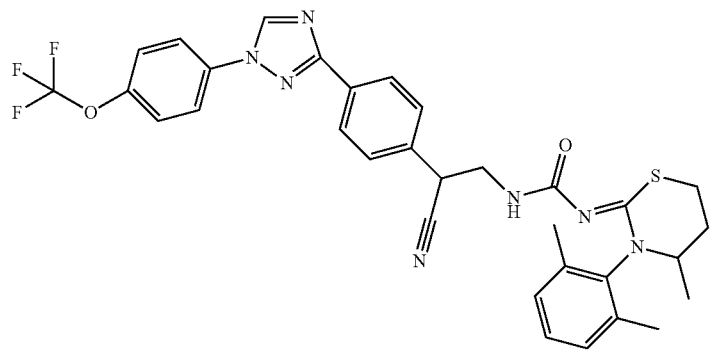 [SMILES: Cc1cccc(C)c1N1/C(=N/C(=O)NCC(C#N)c2ccc(-c3ncn(-c4ccc(OC(F)(F)F)cc4)n3)cc2)SCCC1C]
P1608
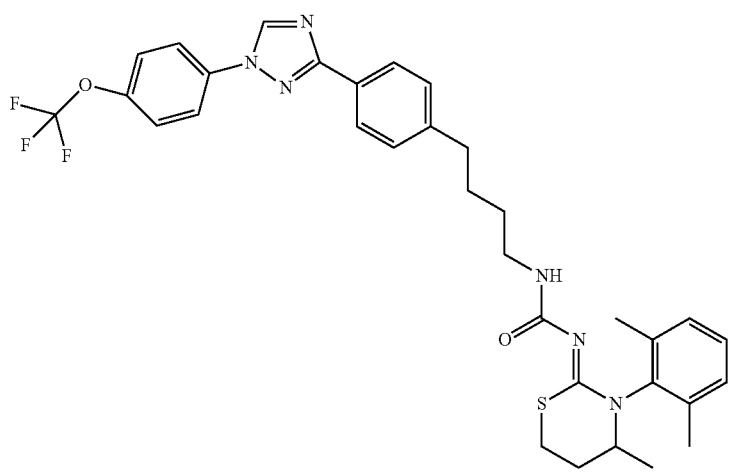 [SMILES: Cc1cccc(C)c1N1/C(=N/C(=O)NCCCCc2ccc(-c3ncn(-c4ccc(OC(F)(F)F)cc4)n3)cc2)SCCC1C]
P1609
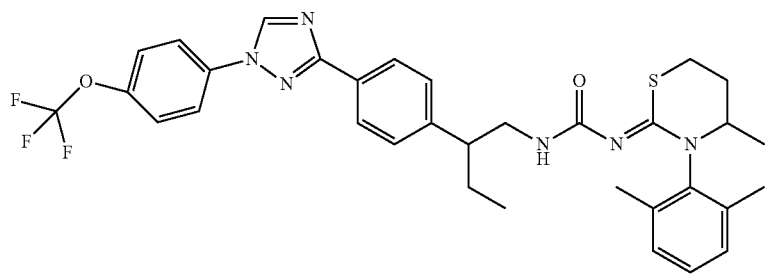 [SMILES: CCC(CNC(=O)/N=C1\SCCC(C)N1c1c(C)cccc1C)c1ccc(-c2ncn(-c3ccc(OC(F)(F)F)cc3)n2)cc1]
P1610
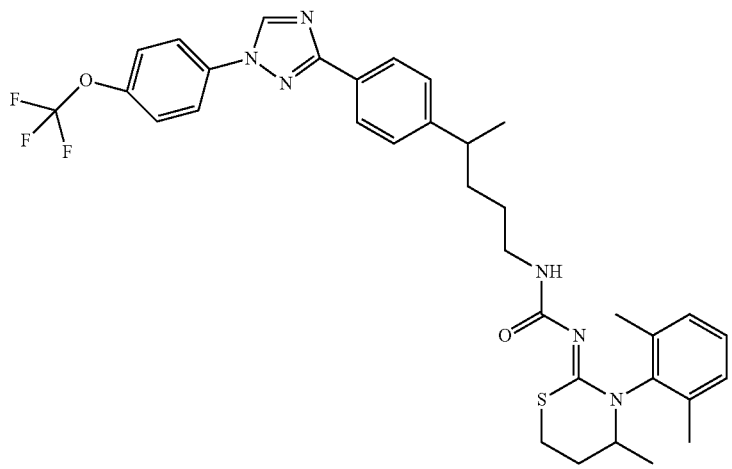 [SMILES: Cc1cccc(C)c1N1/C(=N/C(=O)NCCCC(C)c2ccc(-c3ncn(-c4ccc(OC(F)(F)F)cc4)n3)cc2)SCCC1C]
P1611

TABLE P-Two-continued
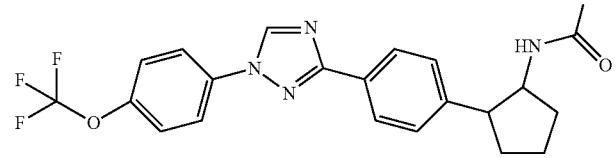
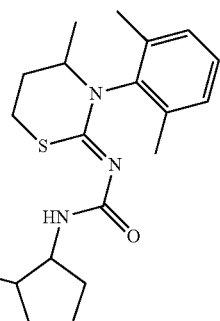
P1612
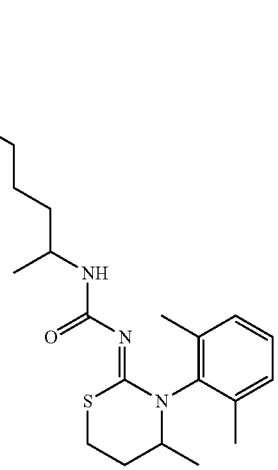
P1613
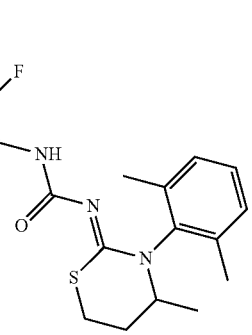
P1614
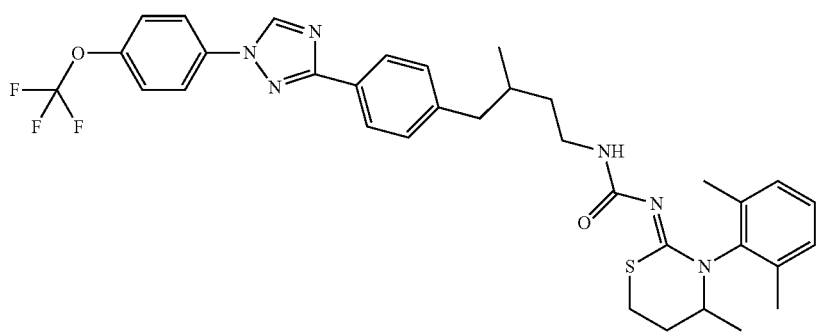 [SMILES: Cc1cccc(C)c1N1/C(=N/C(=O)NCCC(C)Cc2ccc(-c3ncn(-c4ccc(OC(F)(F)F)cc4)n3)cc2)SCCC1C]
P1615

TABLE P-Two-continued
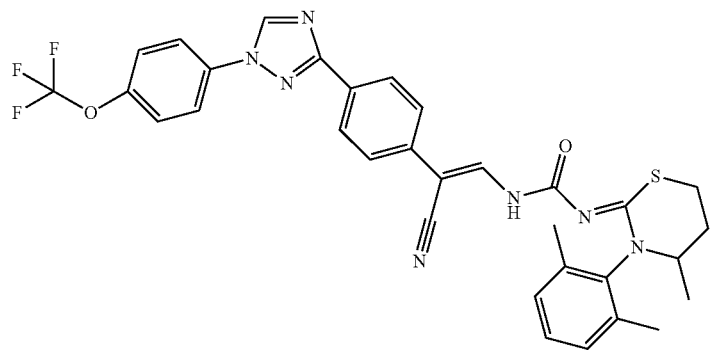 [SMILES: Cc1cccc(C)c1N1/C(=N/C(=O)N/C=C(\C#N)c2ccc(-c3ncn(-c4ccc(OC(F)(F)F)cc4)n3)cc2)SCCC1C]
P1616
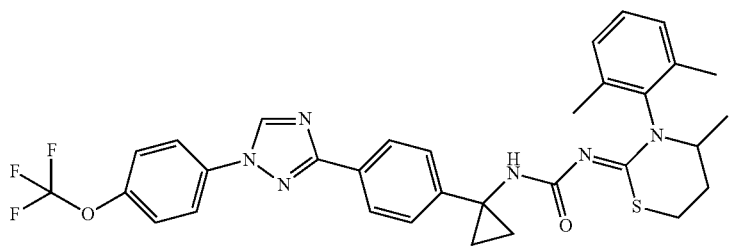 [SMILES: Cc1cccc(C)c1N1/C(=N/C(=O)NC2(c3ccc(-c4ncn(-c5ccc(OC(F)(F)F)cc5)n4)cc3)CC2)SCCC1C]
P1617
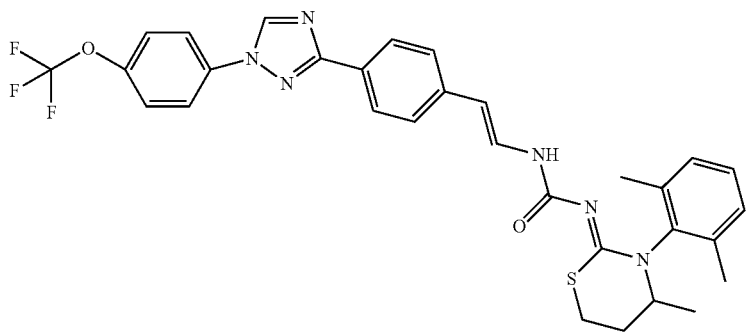 [SMILES: Cc1cccc(C)c1N1/C(=N/C(=O)N/C=C/c2ccc(-c3ncn(-c4ccc(OC(F)(F)F)cc4)n3)cc2)SCCC1C]
P1618
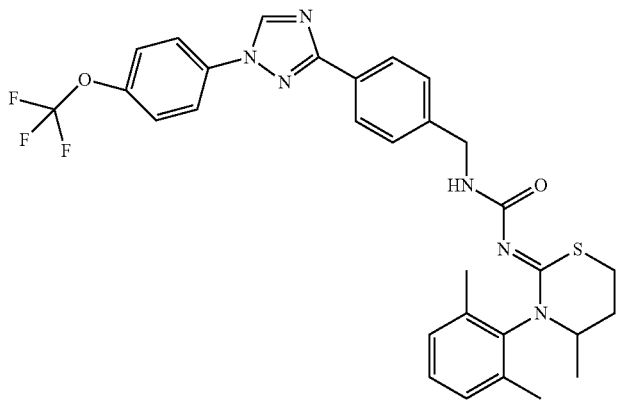 [SMILES: Cc1cccc(C)c1N1/C(=N/C(=O)NCc2ccc(-c3ncn(-c4ccc(OC(F)(F)F)cc4)n3)cc2)SCCC1C]
P1619
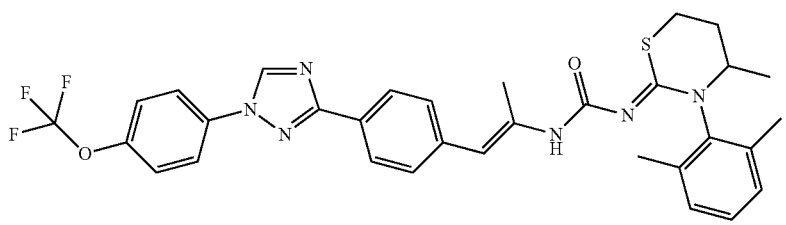 [SMILES: C/C(=C\c1ccc(-c2ncn(-c3ccc(OC(F)(F)F)cc3)n2)cc1)NC(=O)/N=C1\SCCC(C)N1c1c(C)cccc1C]
P1620

TABLE P-Two-continued
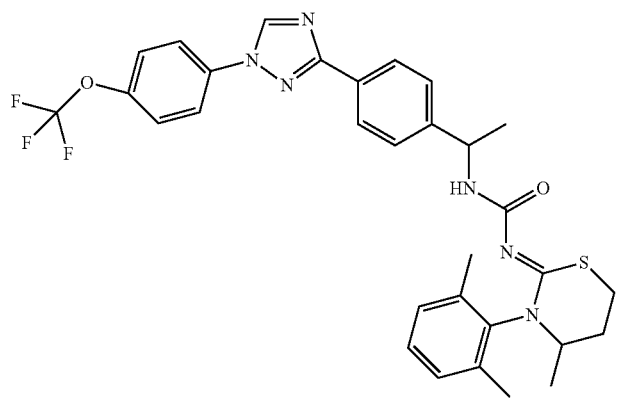 [SMILES: Cc1cccc(C)c1N1/C(=N/C(=O)NC(C)c2ccc(-c3ncn(-c4ccc(OC(F)(F)F)cc4)n3)cc2)SCCC1C]
P1621
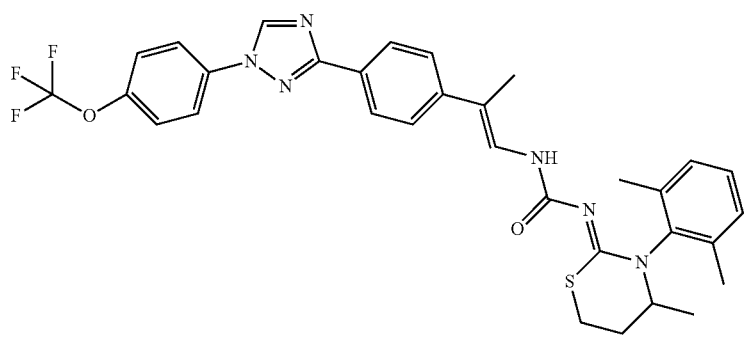 [SMILES: C/C(=C\NC(=O)/N=C1\SCCC(C)N1c1c(C)cccc1C)c1ccc(-c2ncn(-c3ccc(OC(F)(F)F)cc3)n2)cc1]
P1622
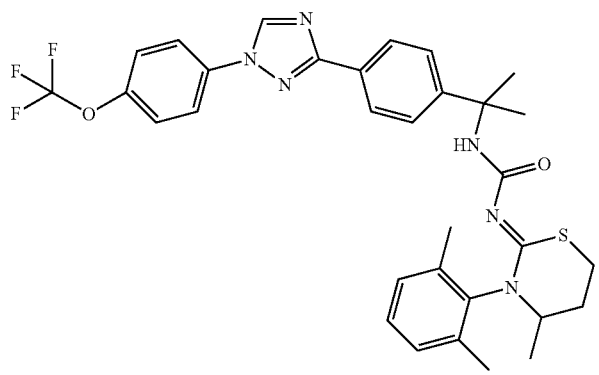 [SMILES: Cc1cccc(C)c1N1/C(=N/C(=O)NC(C)(C)c2ccc(-c3ncn(-c4ccc(OC(F)(F)F)cc4)n3)cc2)SCCC1C]
P1623
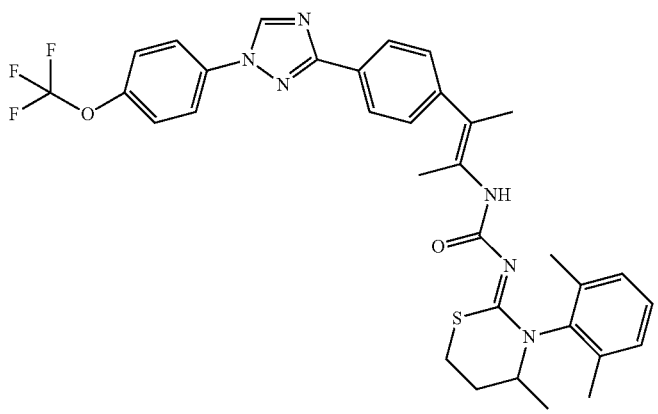 [SMILES: C/C(NC(=O)/N=C1\SCCC(C)N1c1c(C)cccc1C)=C(/C)c1ccc(-c2ncn(-c3ccc(OC(F)(F)F)cc3)n2)cc1]
P1624

TABLE P-Two-continued
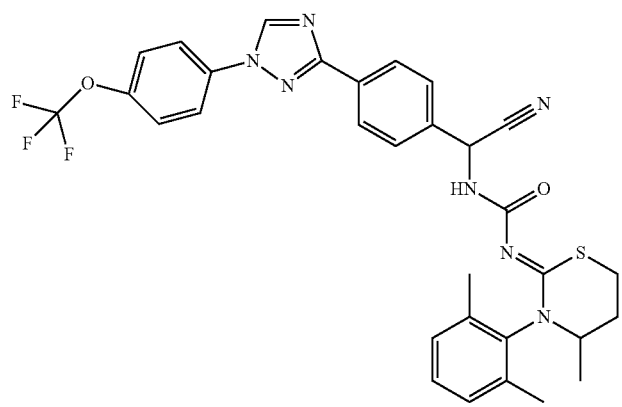 [SMILES: Cc1cccc(C)c1N1/C(=N/C(=O)NC(C#N)c2ccc(-c3ncn(-c4ccc(OC(F)(F)F)cc4)n3)cc2)SCCC1C] P1625
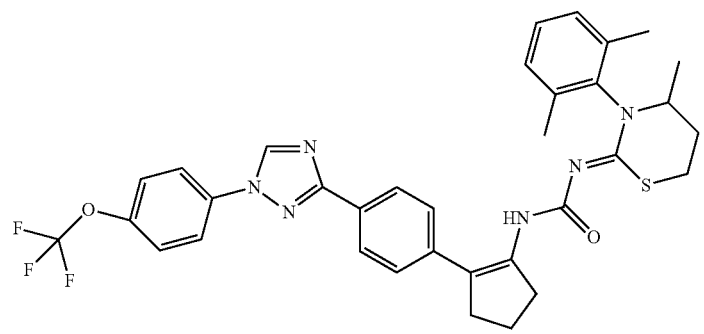 [SMILES: Cc1cccc(C)c1N1/C(=N/C(=O)NC2=C(c3ccc(-c4ncn(-c5ccc(OC(F)(F)F)cc5)n4)cc3)CCC2)SCCC1C] P1626
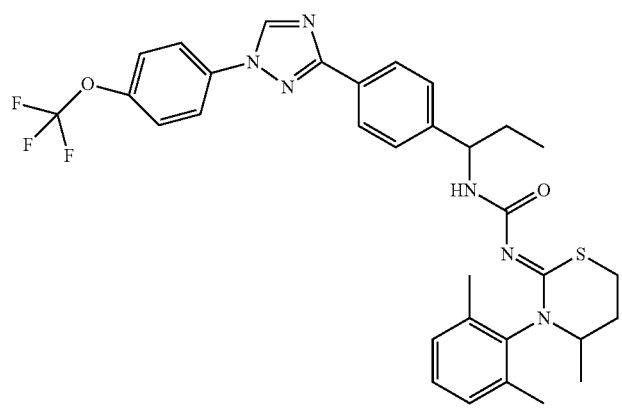 [SMILES: CCC(NC(=O)/N=C1\SCCC(C)N1c1c(C)cccc1C)c1ccc(-c2ncn(-c3ccc(OC(F)(F)F)cc3)n2)cc1] P1627
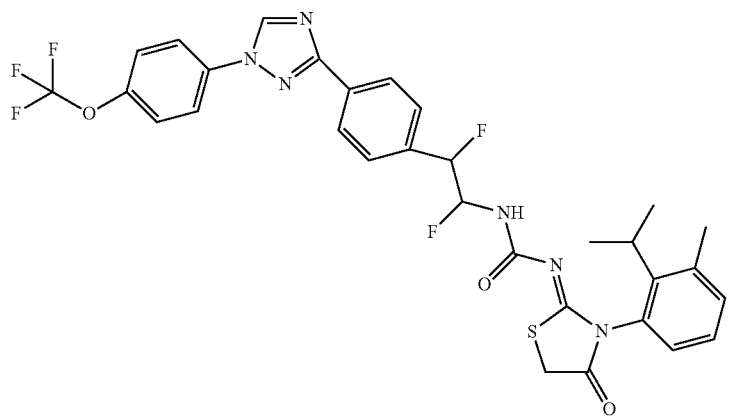 P1628

TABLE P-Two-continued
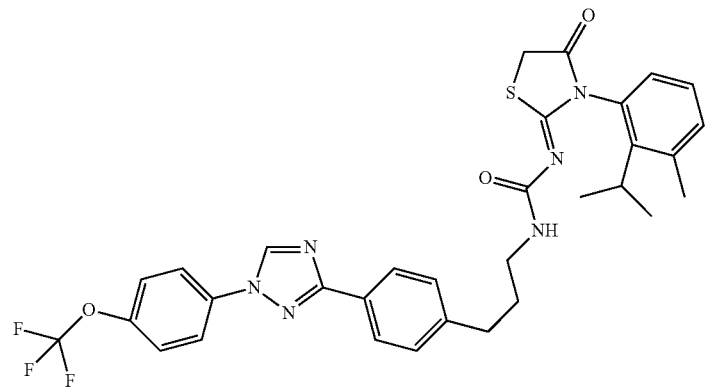 [SMILES: Cc1cccc(N2C(=O)CS/C2=N\C(=O)NCCCc2ccc(-c3ncn(-c4ccc(OC(F)(F)F)cc4)n3)cc2)c1C(C)C]
P1629
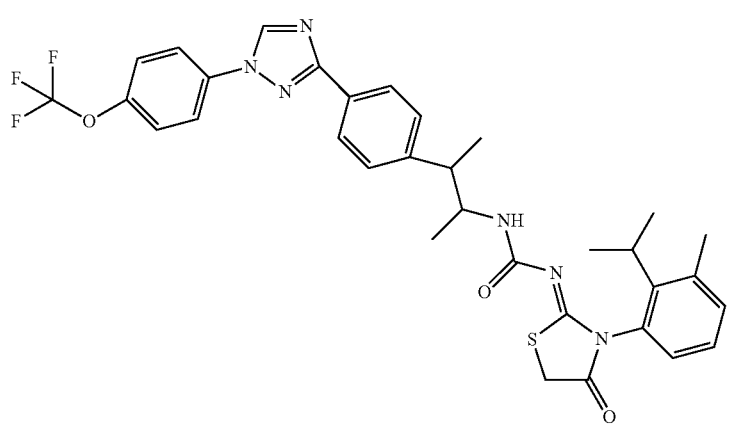 [SMILES: Cc1cccc(N2C(=O)CS/C2=N\C(=O)NC(C)C(C)c2ccc(-c3ncn(-c4ccc(OC(F)(F)F)cc4)n3)cc2)c1C(C)C]
P1630
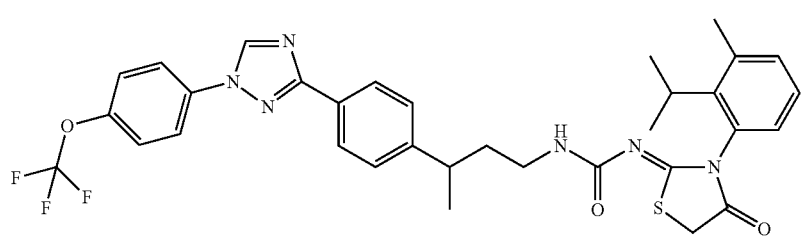 [SMILES: Cc1cccc(N2C(=O)CS/C2=N\C(=O)NCCC(C)c2ccc(-c3ncn(-c4ccc(OC(F)(F)F)cc4)n3)cc2)c1C(C)C]
P1631
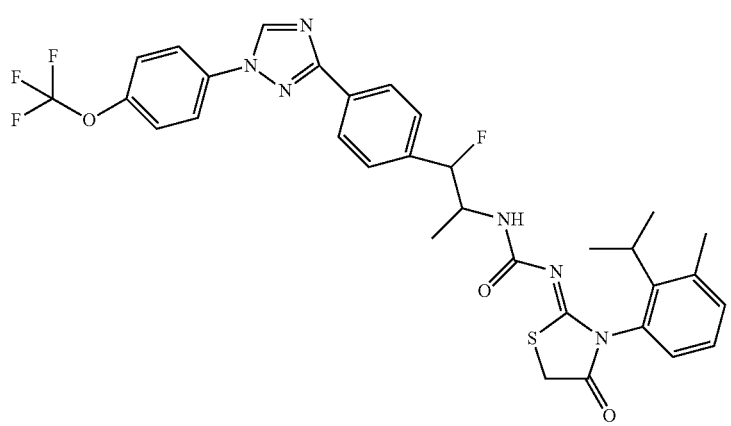
P1632

TABLE P-Two-continued
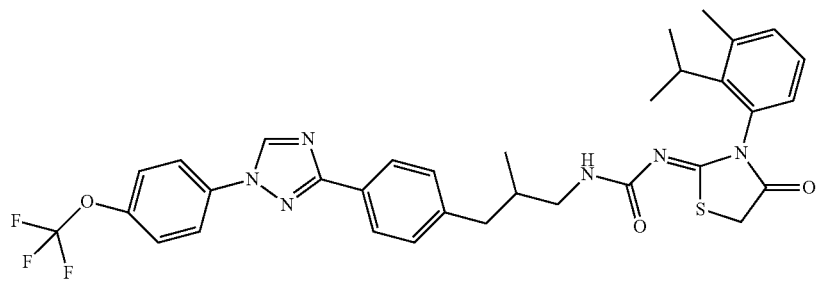 [SMILES: Cc1cccc(N2C(=O)CS/C2=N\C(=O)NCC(C)Cc2ccc(-c3ncn(-c4ccc(OC(F)(F)F)cc4)n3)cc2)c1C(C)C]
P1633
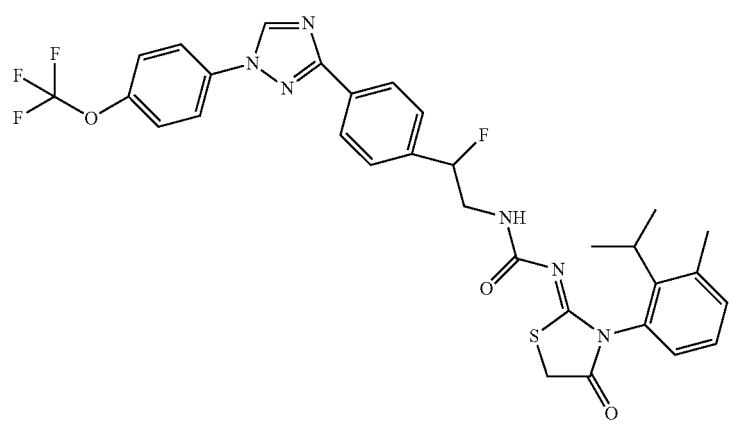 [SMILES: Cc1cccc(N2C(=O)CS/C2=N\C(=O)NCC(F)c2ccc(-c3ncn(-c4ccc(OC(F)(F)F)cc4)n3)cc2)c1C(C)C]
P1634
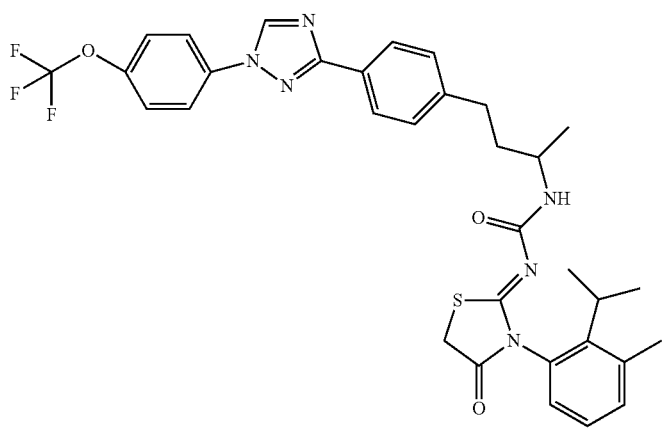 [SMILES: Cc1cccc(N2C(=O)CS/C2=N\C(=O)NC(C)CCc2ccc(-c3ncn(-c4ccc(OC(F)(F)F)cc4)n3)cc2)c1C(C)C]
P1635
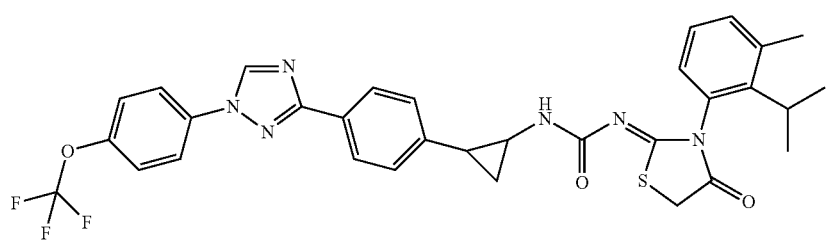 [SMILES: Cc1cccc(N2C(=O)CS/C2=N\C(=O)NC2CC2c2ccc(-c3ncn(-c4ccc(OC(F)(F)F)cc4)n3)cc2)c1C(C)C]
P1636

TABLE P-Two-continued
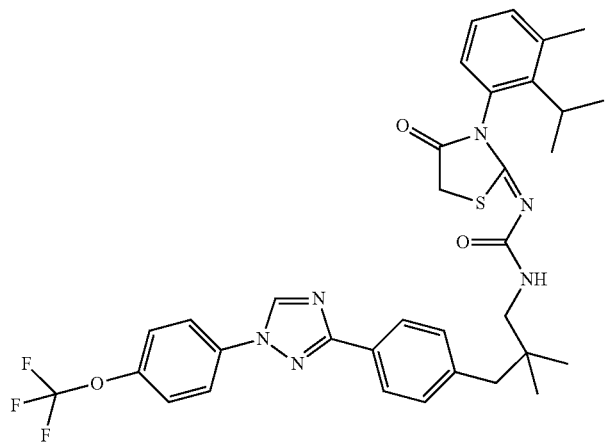 [SMILES: Cc1cccc(N2C(=O)CS/C2=N\C(=O)NCC(C)(C)Cc2ccc(-c3ncn(-c4ccc(OC(F)(F)F)cc4)n3)cc2)c1C(C)C]
P1637
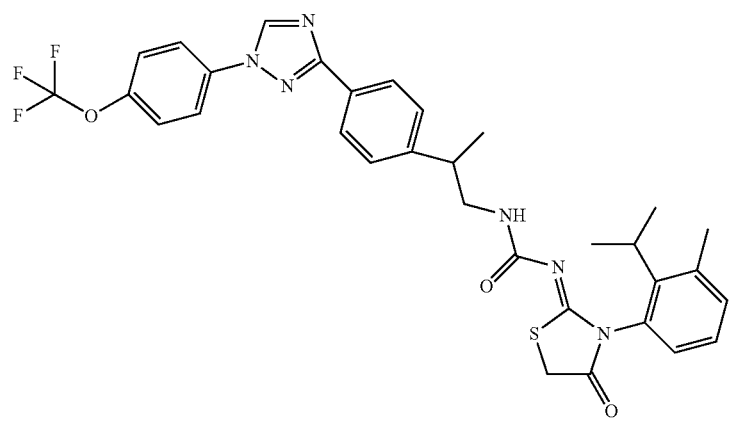 [SMILES: Cc1cccc(N2C(=O)CS/C2=N\C(=O)NCC(C)c2ccc(-c3ncn(-c4ccc(OC(F)(F)F)cc4)n3)cc2)c1C(C)C]
P1638
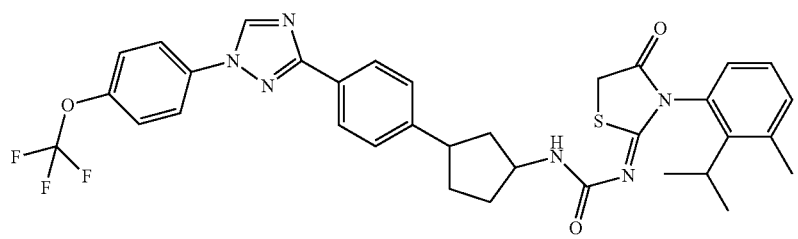 [SMILES: Cc1cccc(N2C(=O)CS/C2=N\C(=O)NC2CCC(c3ccc(-c4ncn(-c5ccc(OC(F)(F)F)cc5)n4)cc3)C2)c1C(C)C]
P1639
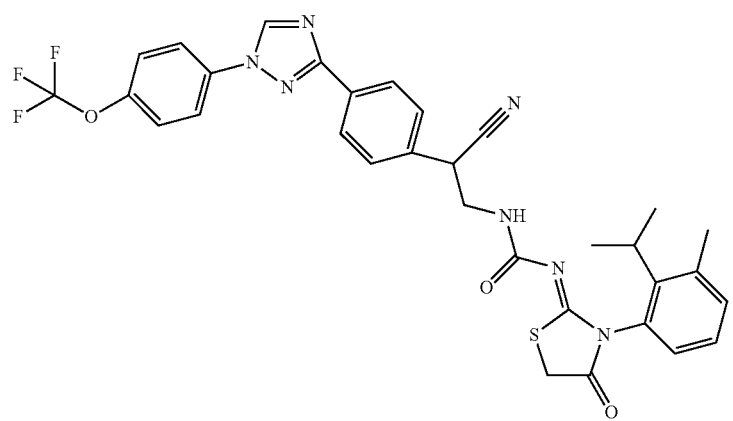 [SMILES: Cc1cccc(N2C(=O)CS/C2=N\C(=O)NCC(C#N)c2ccc(-c3ncn(-c4ccc(OC(F)(F)F)cc4)n3)cc2)c1C(C)C]
P1640

TABLE P-Two-continued
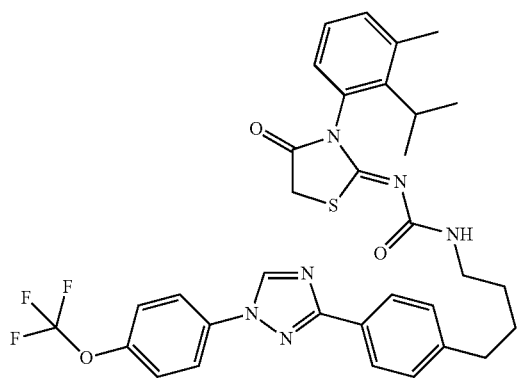 [SMILES: Cc1cccc(N2C(=O)CS/C2=N\C(=O)NCCCCc2ccc(-c3ncn(-c4ccc(OC(F)(F)F)cc4)n3)cc2)c1C(C)C]
P1641
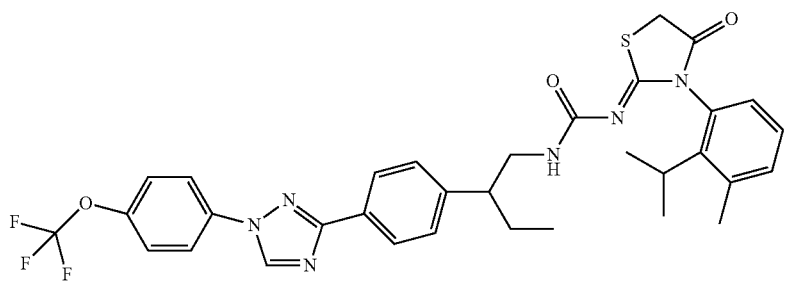 [SMILES: CCC(CNC(=O)/N=C1\SCC(=O)N1c1cccc(C)c1C(C)C)c1ccc(-c2ncn(-c3ccc(OC(F)(F)F)cc3)n2)cc1]
P1642
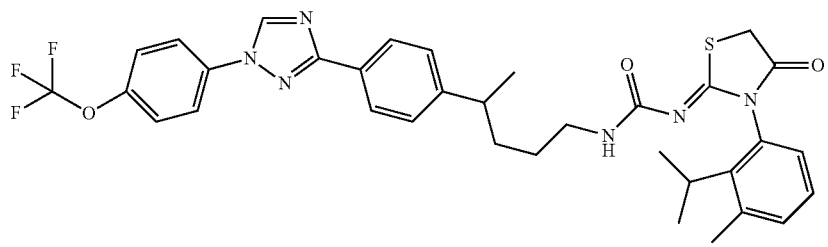 [SMILES: Cc1cccc(N2C(=O)CS/C2=N\C(=O)NCCCC(C)c2ccc(-c3ncn(-c4ccc(OC(F)(F)F)cc4)n3)cc2)c1C(C)C]
P1643
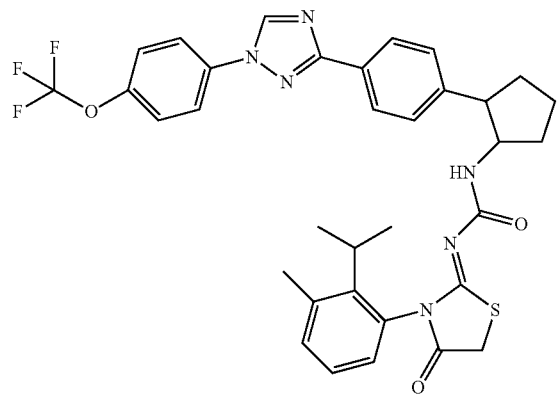 [SMILES: Cc1cccc(N2C(=O)CS/C2=N\C(=O)NC2CCCC2c2ccc(-c3ncn(-c4ccc(OC(F)(F)F)cc4)n3)cc2)c1C(C)C]
P1644
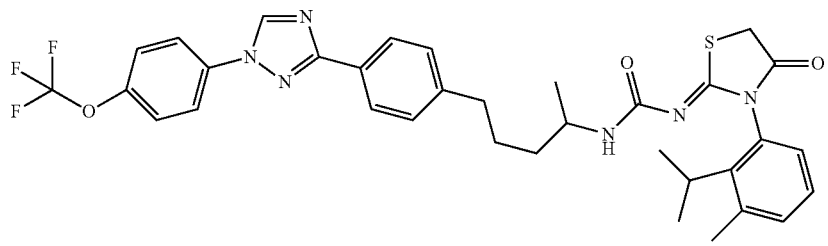 [SMILES: Cc1cccc(N2C(=O)CS/C2=N\C(=O)NC(C)CCCc2ccc(-c3ncn(-c4ccc(OC(F)(F)F)cc4)n3)cc2)c1C(C)C]
P1645

TABLE P-Two-continued
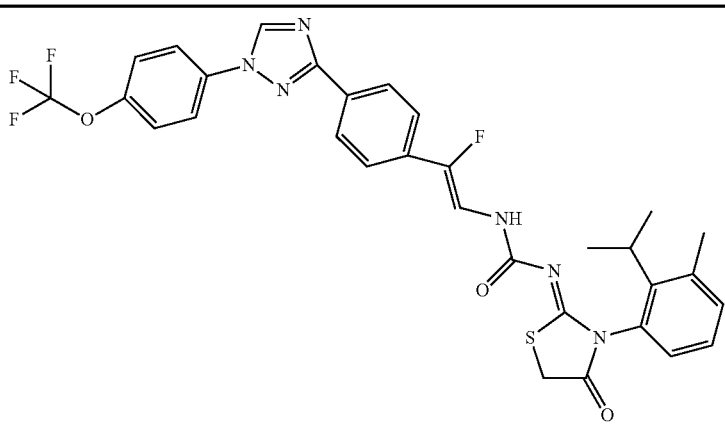
P1646
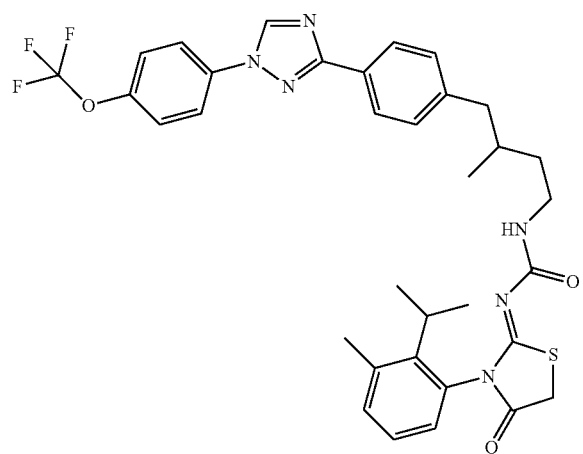 [SMILES: Cc1cccc(N2C(=O)CS/C2=N\C(=O)NCCC(C)Cc2ccc(-c3ncn(-c4ccc(OC(F)(F)F)cc4)n3)cc2)c1C(C)C]
P1647
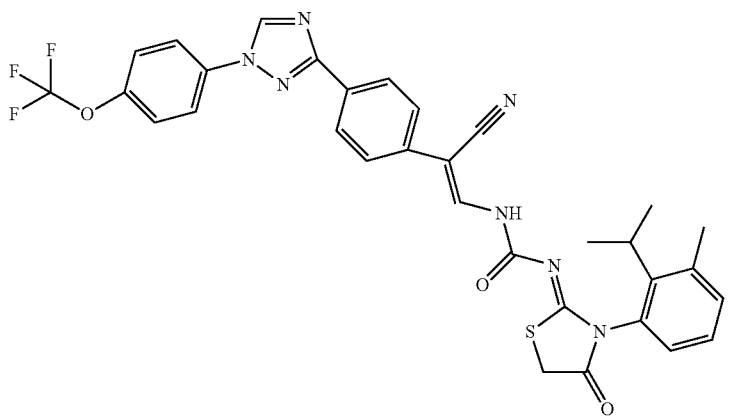 [SMILES: Cc1cccc(N2C(=O)CS/C2=N\C(=O)N/C=C(\C#N)c2ccc(-c3ncn(-c4ccc(OC(F)(F)F)cc4)n3)cc2)c1C(C)C]
P1648
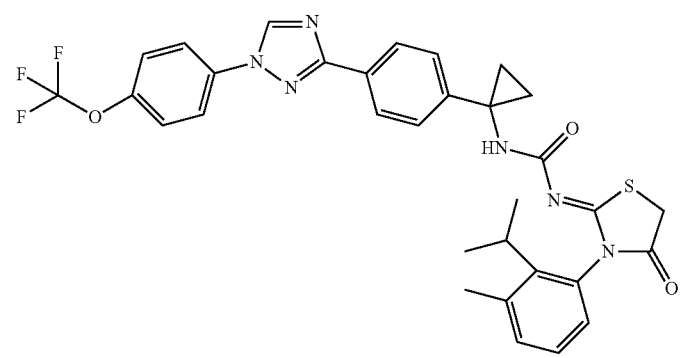 [SMILES: Cc1cccc(N2C(=O)CS/C2=N\C(=O)NC2(c3ccc(-c4ncn(-c5ccc(OC(F)(F)F)cc5)n4)cc3)CC2)c1C(C)C]
P1649

TABLE P-Two-continued
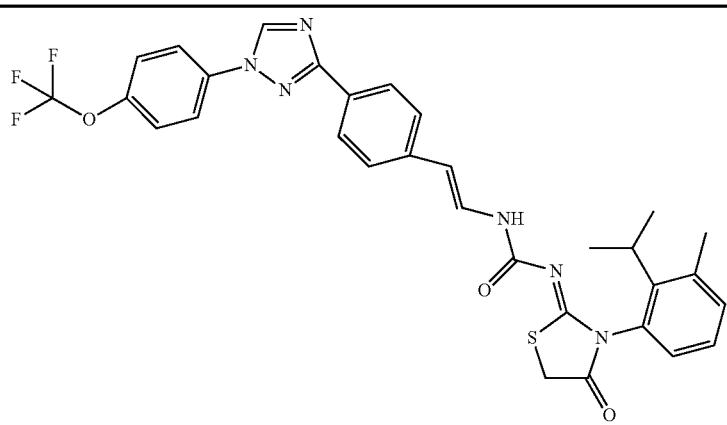
P1650
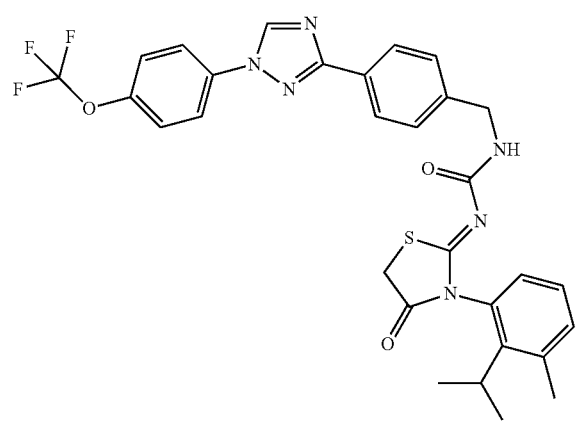 [SMILES: Cc1cccc(N2C(=O)CS/C2=N\C(=O)NCc2ccc(-c3ncn(-c4ccc(OC(F)(F)F)cc4)n3)cc2)c1C(C)C]
P1651
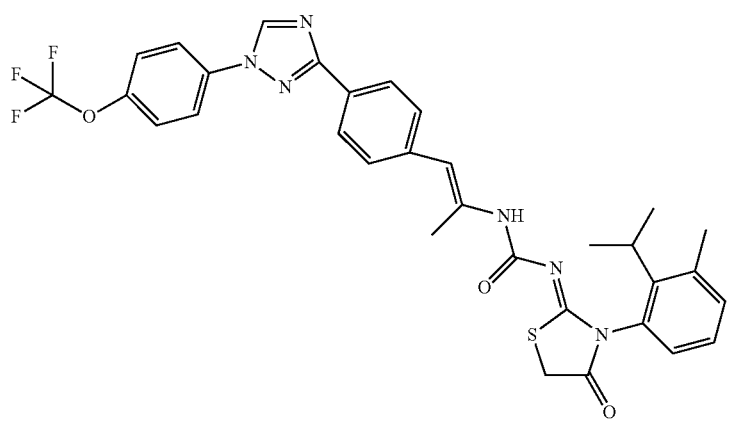 [SMILES: C/C(=C\c1ccc(-c2ncn(-c3ccc(OC(F)(F)F)cc3)n2)cc1)NC(=O)/N=C1\SCC(=O)N1c1cccc(C)c1C(C)C]
P1652
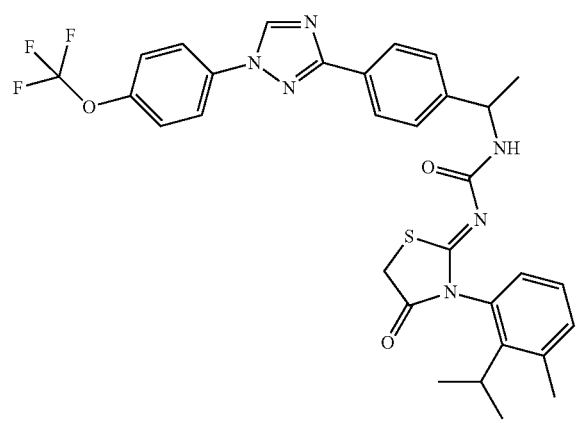 [SMILES: Cc1cccc(N2C(=O)CS/C2=N\C(=O)NC(C)c2ccc(-c3ncn(-c4ccc(OC(F)(F)F)cc4)n3)cc2)c1C(C)C]
P1653

TABLE P-Two-continued
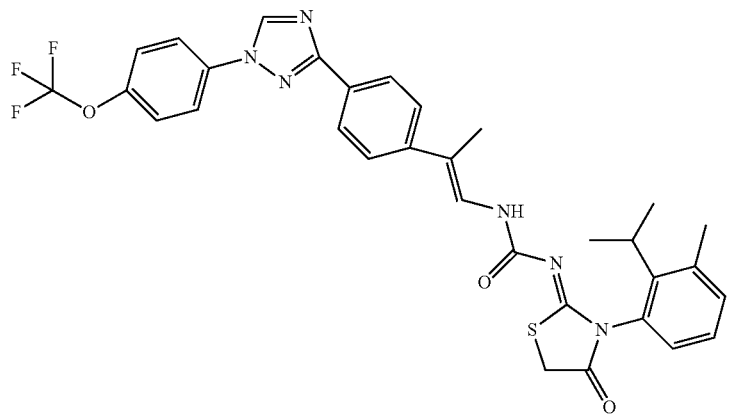 [SMILES: C/C(=C\NC(=O)/N=C1\SCC(=O)N1c1cccc(C)c1C(C)C)c1ccc(-c2ncn(-c3ccc(OC(F)(F)F)cc3)n2)cc1]
P1654
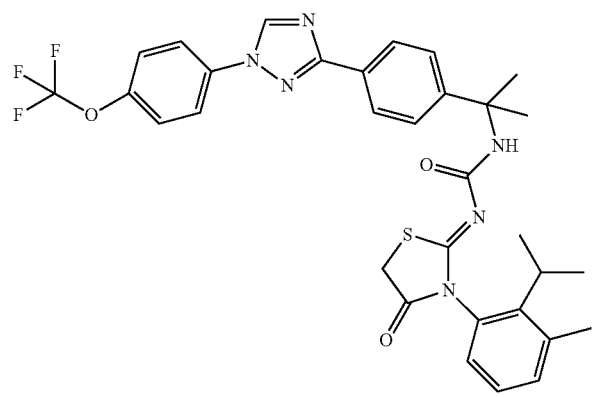 [SMILES: Cc1cccc(N2C(=O)CS/C2=N\C(=O)NC(C)(C)c2ccc(-c3ncn(-c4ccc(OC(F)(F)F)cc4)n3)cc2)c1C(C)C]
P1655
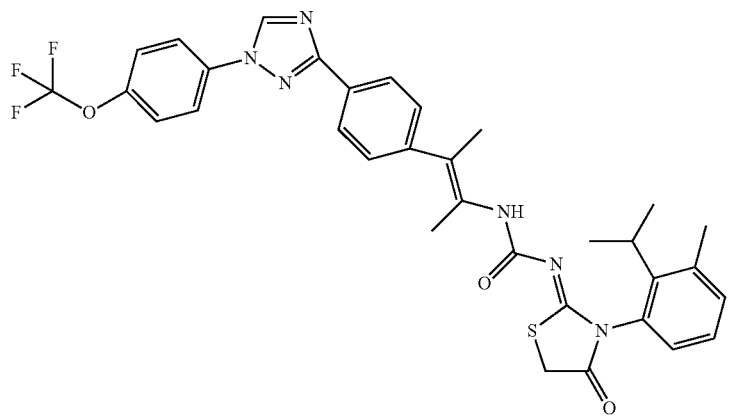 [SMILES: C/C(NC(=O)/N=C1\SCC(=O)N1c1cccc(C)c1C(C)C)=C(/C)c1ccc(-c2ncn(-c3ccc(OC(F)(F)F)cc3)n2)cc1]
P1656
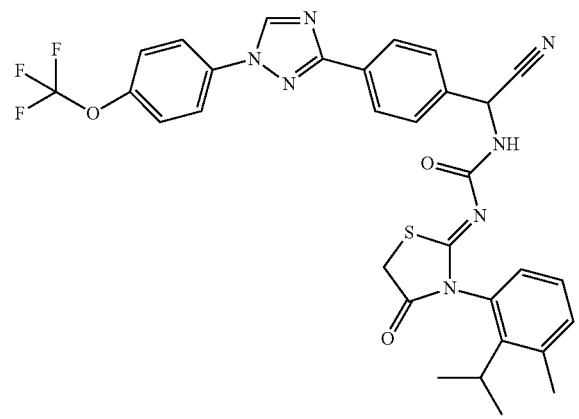 [SMILES: Cc1cccc(N2C(=O)CS/C2=N\C(=O)NC(C#N)c2ccc(-c3ncn(-c4ccc(OC(F)(F)F)cc4)n3)cc2)c1C(C)C]
P1657

TABLE P-Two-continued
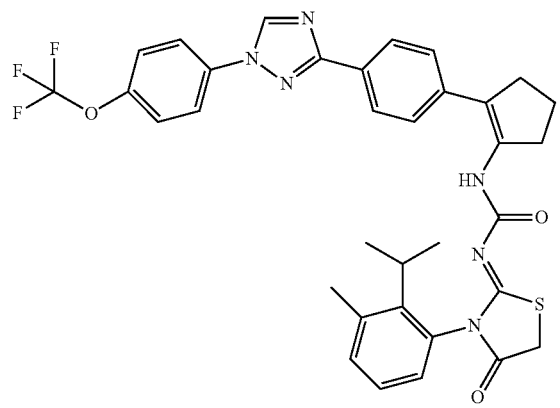 [SMILES: Cc1cccc(N2C(=O)CS/C2=N\C(=O)NC2=C(c3ccc(-c4ncn(-c5ccc(OC(F)(F)F)cc5)n4)cc3)CCC2)c1C(C)C]
P1658
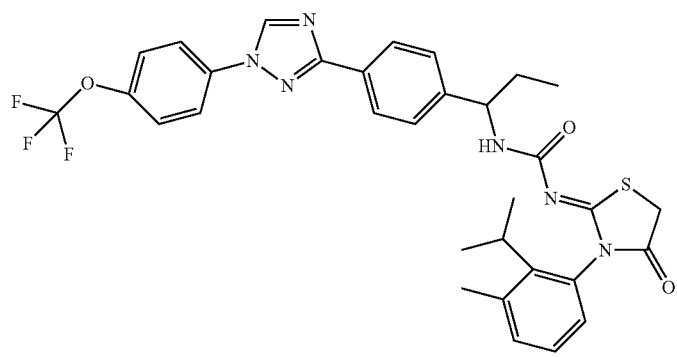 [SMILES: CCC(NC(=O)/N=C1\SCC(=O)N1c1cccc(C)c1C(C)C)c1ccc(-c2ncn(-c3ccc(OC(F)(F)F)cc3)n2)cc1]
P1659
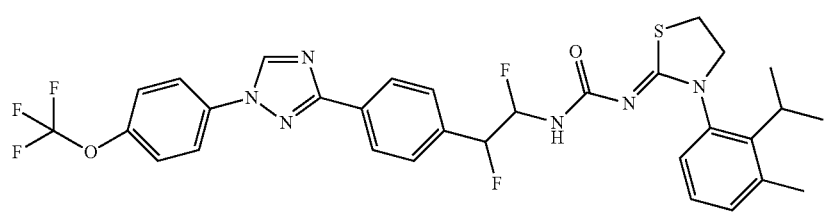 [SMILES: Cc1cccc(N2CCS/C2=N\C(=O)NC(F)C(F)c2ccc(-c3ncn(-c4ccc(OC(F)(F)F)cc4)n3)cc2)c1C(C)C]
P1660
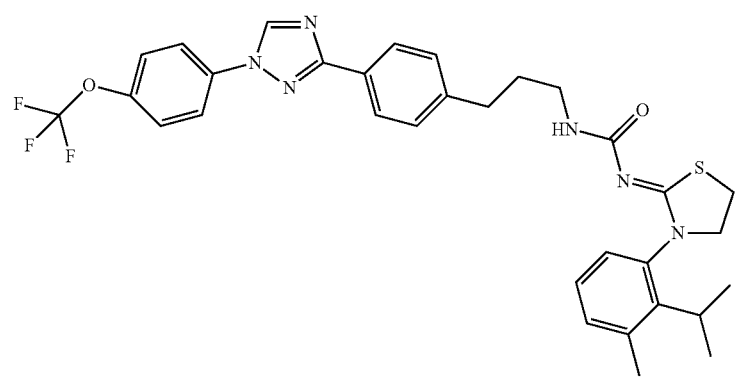 [SMILES: Cc1cccc(N2CCS/C2=N\C(=O)NCCCc2ccc(-c3ncn(-c4ccc(OC(F)(F)F)cc4)n3)cc2)c1C(C)C]
P1661
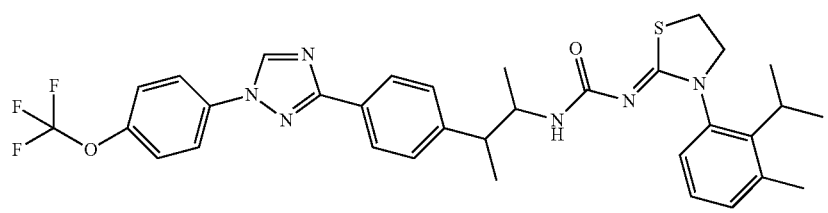 [SMILES: Cc1cccc(N2CCS/C2=N\C(=O)NC(C)C(C)c2ccc(-c3ncn(-c4ccc(OC(F)(F)F)cc4)n3)cc2)c1C(C)C]
P1662

TABLE P-Two-continued
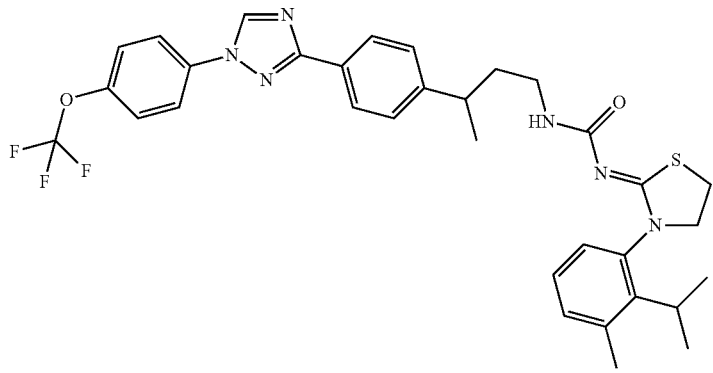 [SMILES: Cc1cccc(N2CCS/C2=N\C(=O)NCCC(C)c2ccc(-c3ncn(-c4ccc(OC(F)(F)F)cc4)n3)cc2)c1C(C)C]
P1663
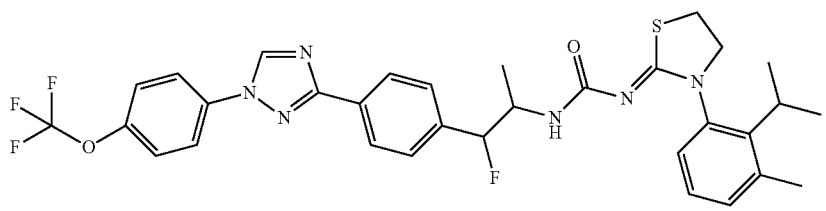 [SMILES: Cc1cccc(N2CCS/C2=N\C(=O)NC(C)C(F)c2ccc(-c3ncn(-c4ccc(OC(F)(F)F)cc4)n3)cc2)c1C(C)C]
P1664
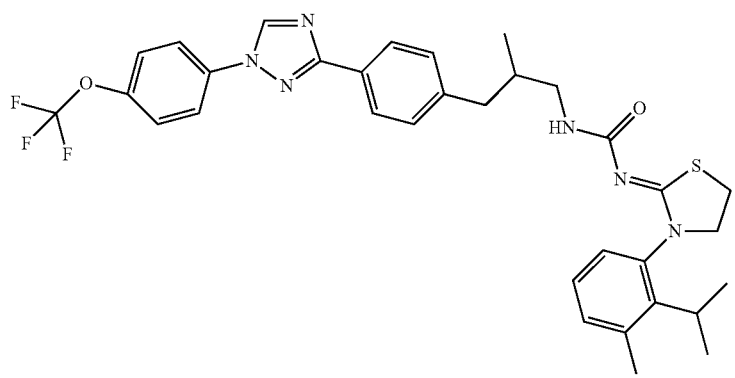 [SMILES: Cc1cccc(N2CCS/C2=N\C(=O)NCC(C)Cc2ccc(-c3ncn(-c4ccc(OC(F)(F)F)cc4)n3)cc2)c1C(C)C]
P1665
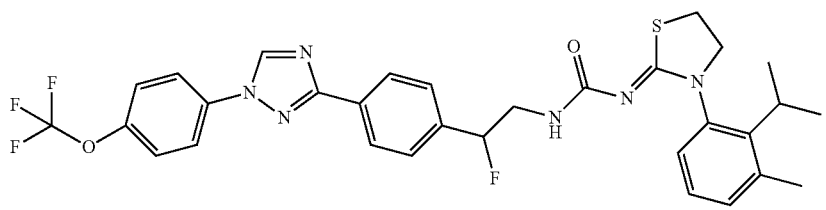
P1666
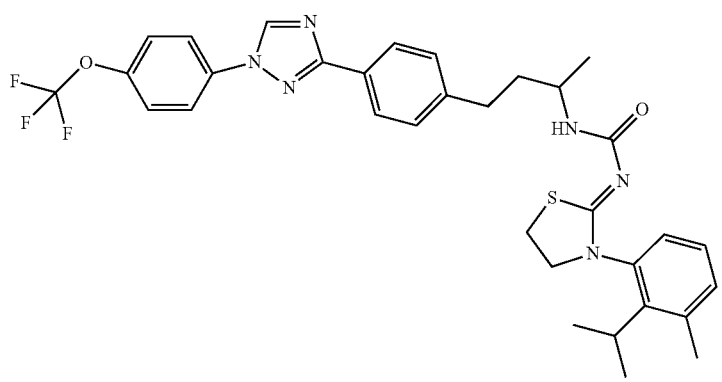 [SMILES: Cc1cccc(N2CCS/C2=N\C(=O)NC(C)CCc2ccc(-c3ncn(-c4ccc(OC(F)(F)F)cc4)n3)cc2)c1C(C)C]
P1667

TABLE P-Two-continued
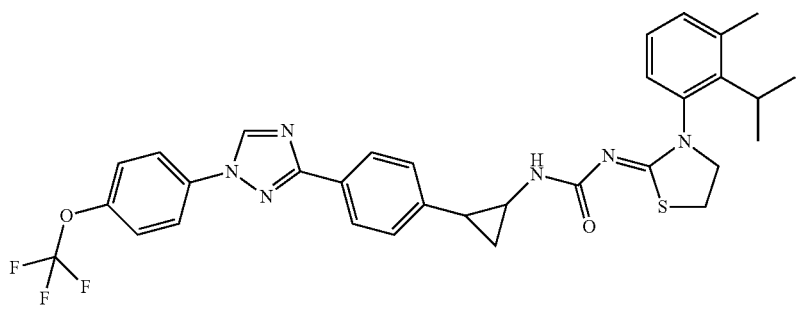 [SMILES: Cc1cccc(N2CCS/C2=N\C(=O)NC2CC2c2ccc(-c3ncn(-c4ccc(OC(F)(F)F)cc4)n3)cc2)c1C(C)C]
P1668
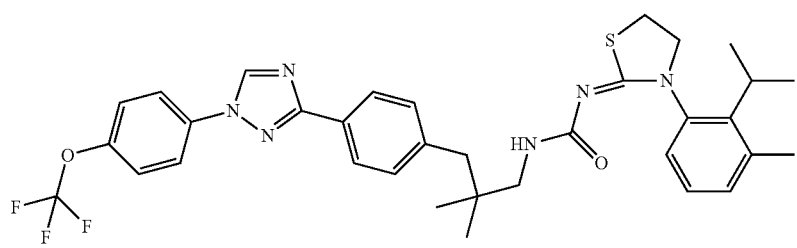 [SMILES: Cc1cccc(N2CCS/C2=N/C(=O)NCC(C)(C)Cc2ccc(-c3ncn(-c4ccc(OC(F)(F)F)cc4)n3)cc2)c1C(C)C]
P1669
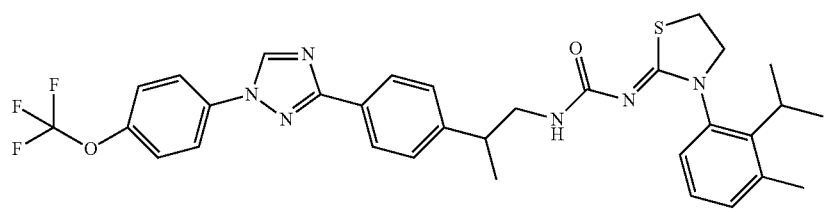 [SMILES: Cc1cccc(N2CCS/C2=N\C(=O)NCC(C)c2ccc(-c3ncn(-c4ccc(OC(F)(F)F)cc4)n3)cc2)c1C(C)C]
P1670
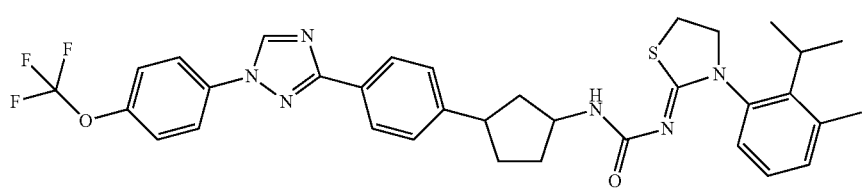 [SMILES: Cc1cccc(N2CCS/C2=N\C(=O)NC2CCC(c3ccc(-c4ncn(-c5ccc(OC(F)(F)F)cc5)n4)cc3)C2)c1C(C)C]
P1671
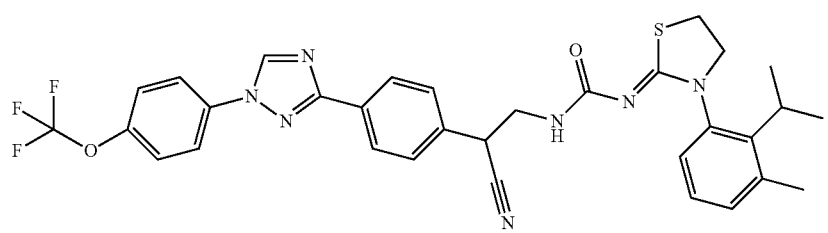 [SMILES: Cc1cccc(N2CCS/C2=N\C(=O)NCC(C#N)c2ccc(-c3ncn(-c4ccc(OC(F)(F)F)cc4)n3)cc2)c1C(C)C]
P1672

TABLE P-Two-continued
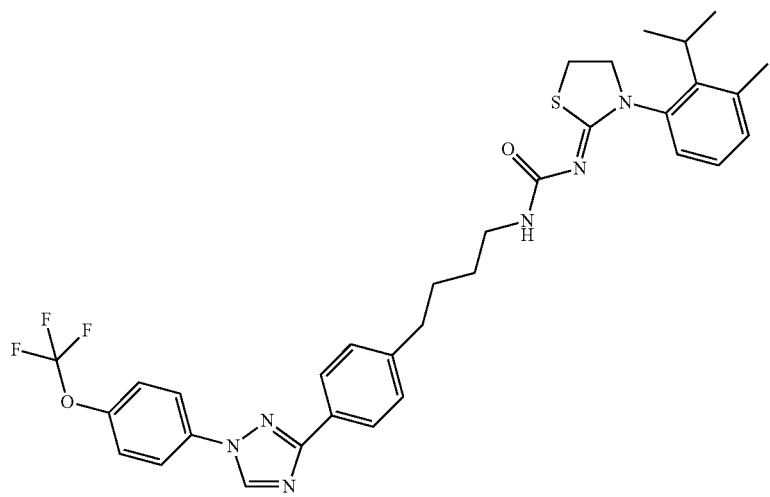 [SMILES: Cc1cccc(N2CCS/C2=N\C(=O)NCCCCc2ccc(-c3ncn(-c4ccc(OC(F)(F)F)cc4)n3)cc2)c1C(C)C]
P1673
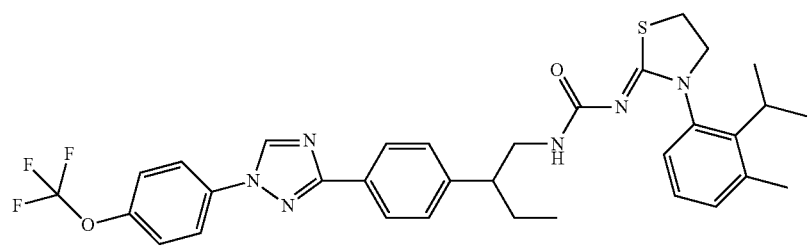 [SMILES: CCC(CNC(=O)/N=C1\SCCN1c1cccc(C)c1C(C)C)c1ccc(-c2ncn(-c3ccc(OC(F)(F)F)cc3)n2)cc1]
P1674
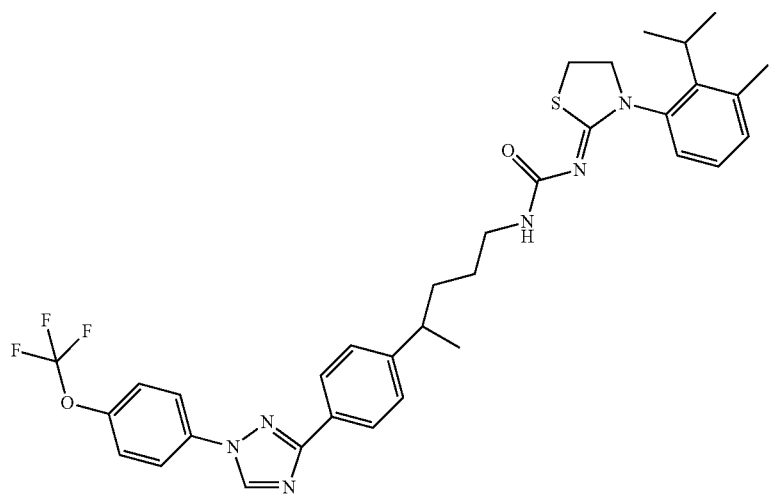 [SMILES: Cc1cccc(N2CCS/C2=N\C(=O)NCCCC(C)c2ccc(-c3ncn(-c4ccc(OC(F)(F)F)cc4)n3)cc2)c1C(C)C]
P1675
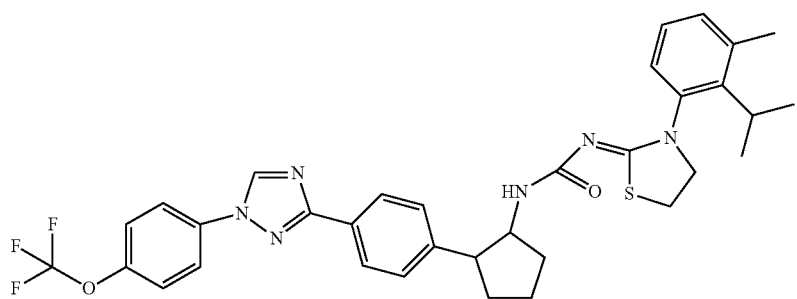 [SMILES: Cc1cccc(N2CCS/C2=N\C(=O)NC2CCCC2c2ccc(-c3ncn(-c4ccc(OC(F)(F)F)cc4)n3)cc2)c1C(C)C]
P1676

TABLE P-Two-continued
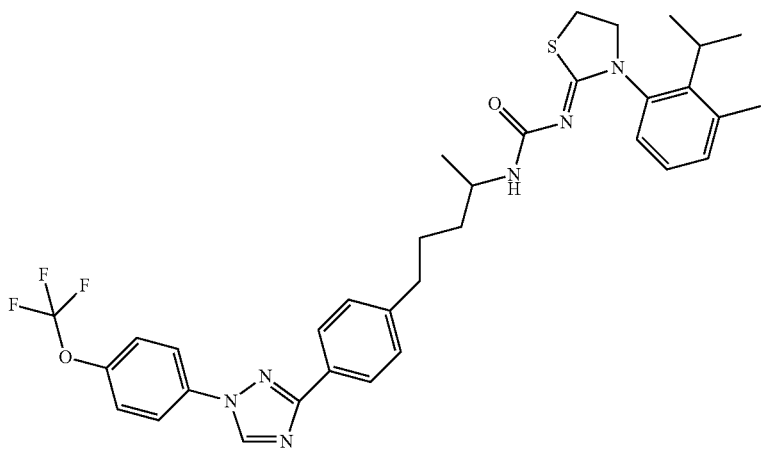 [SMILES: Cc1cccc(N2CCS/C2=N\C(=O)NC(C)CCCc2ccc(-c3ncn(-c4ccc(OC(F)(F)F)cc4)n3)cc2)c1C(C)C]
P1677
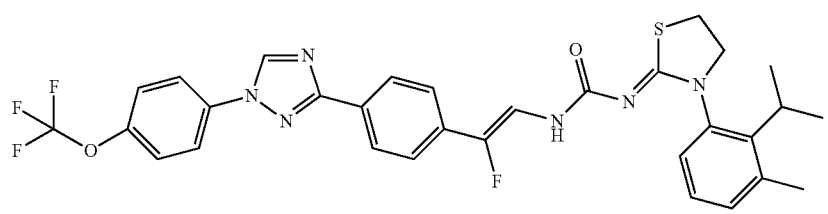 [SMILES: Cc1cccc(N2CCS/C2=N\C(=O)N/C=C(\F)c2ccc(-c3ncn(-c4ccc(OC(F)(F)F)cc4)n3)cc2)c1C(C)C]
P1678
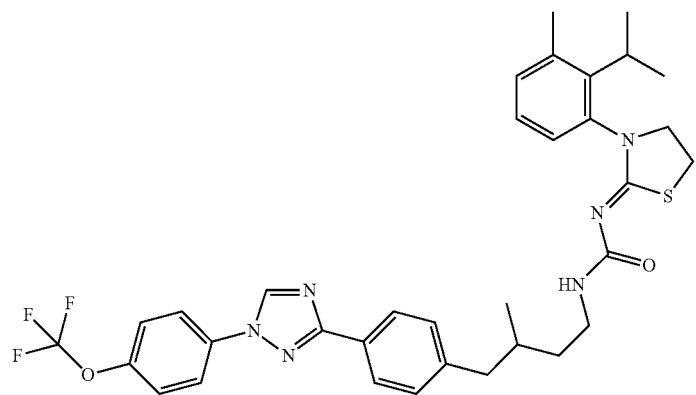 [SMILES: Cc1cccc(N2CCS/C2=N\C(=O)NCCC(C)Cc2ccc(-c3ncn(-c4ccc(OC(F)(F)F)cc4)n3)cc2)c1C(C)C]
P1679
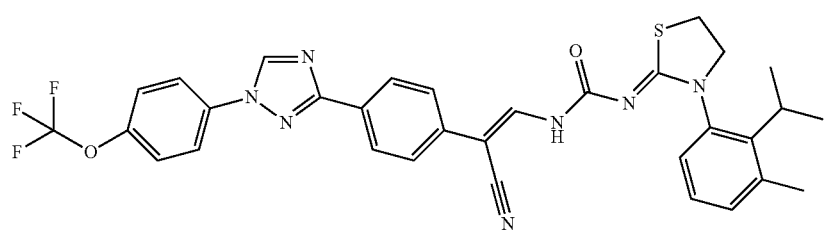 [SMILES: Cc1cccc(N2CCS/C2=N\C(=O)N/C=C(\C#N)c2ccc(-c3ncn(-c4ccc(OC(F)(F)F)cc4)n3)cc2)c1C(C)C]
P1680

TABLE P-Two-continued
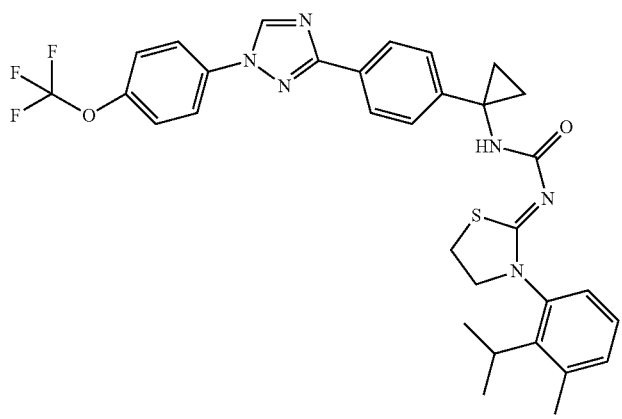 [SMILES: Cc1cccc(N2CCS/C2=N\C(=O)NC2(c3ccc(-c4ncn(-c5ccc(OC(F)(F)F)cc5)n4)cc3)CC2)c1C(C)C]
P1681
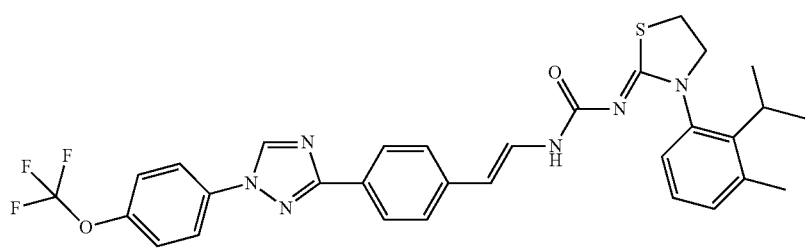 [SMILES: Cc1cccc(N2CCS/C2=N\C(=O)N/C=C/c2ccc(-c3ncn(-c4ccc(OC(F)(F)F)cc4)n3)cc2)c1C(C)C]
P1682
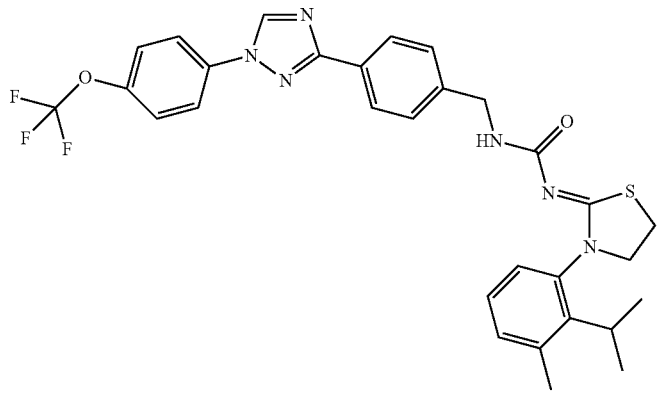 [SMILES: Cc1cccc(N2CCS/C2=N\C(=O)NCc2ccc(-c3ncn(-c4ccc(OC(F)(F)F)cc4)n3)cc2)c1C(C)C]
P1683
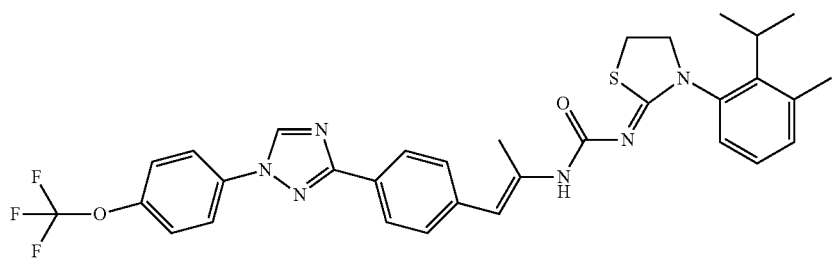 [SMILES: C/C(=C\c1ccc(-c2ncn(-c3ccc(OC(F)(F)F)cc3)n2)cc1)NC(=O)/N=C1\SCCN1c1cccc(C)c1C(C)C]
P1684

TABLE P-Two-continued
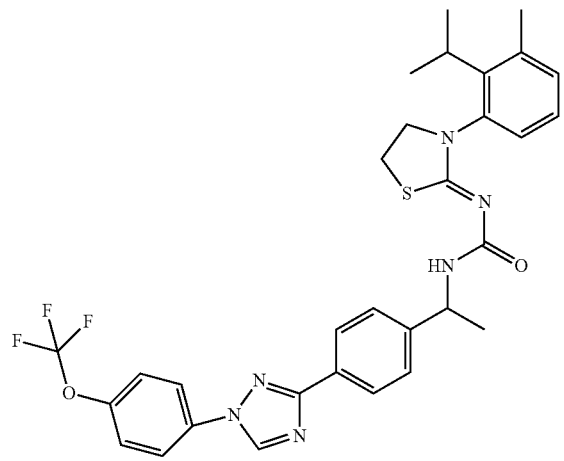 [SMILES: Cc1cccc(N2CCS/C2=N\C(=O)NC(C)c2ccc(-c3ncn(-c4ccc(OC(F)(F)F)cc4)n3)cc2)c1C(C)C]
P1685
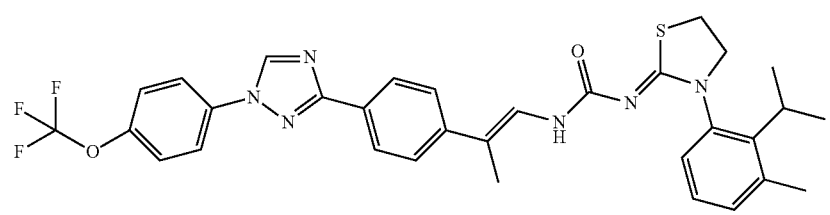 [SMILES: C/C(=C\NC(=O)/N=C1\SCCN1c1cccc(C)c1C(C)C)c1ccc(-c2ncn(-c3ccc(OC(F)(F)F)cc3)n2)cc1]
P1686
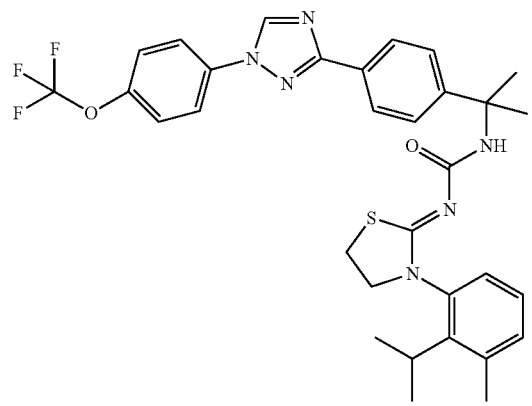 [SMILES: Cc1cccc(N2CCS/C2=N\C(=O)NC(C)(C)c2ccc(-c3ncn(-c4ccc(OC(F)(F)F)cc4)n3)cc2)c1C(C)C]
P1687
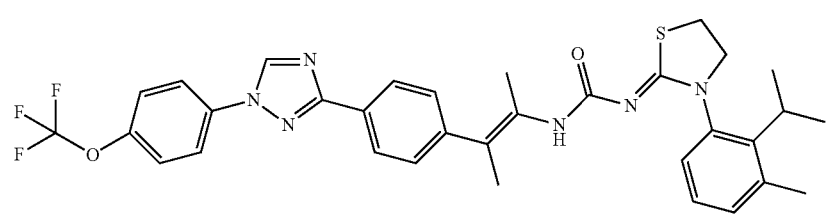 [SMILES: C/C(NC(=O)/N=C1\SCCN1c1cccc(C)c1C(C)C)=C(/C)c1ccc(-c2ncn(-c3ccc(OC(F)(F)F)cc3)n2)cc1]
P1688

TABLE P-Two-continued
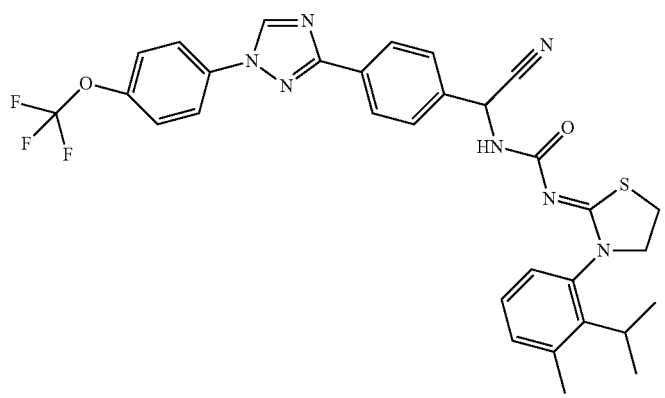 [SMILES: Cc1cccc(N2CCS/C2=N\C(=O)NC(C#N)c2ccc(-c3ncn(-c4ccc(OC(F)(F)F)cc4)n3)cc2)c1C(C)C]
P1689
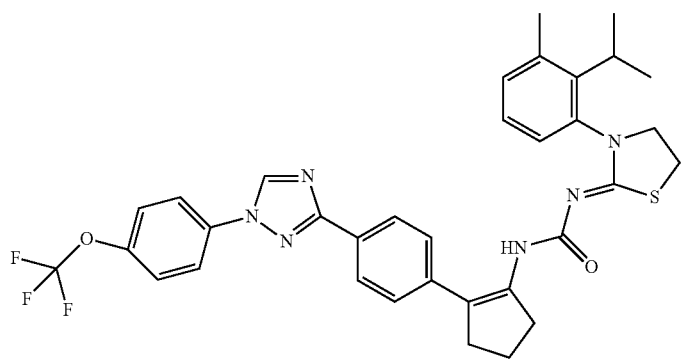 [SMILES: Cc1cccc(N2CCS/C2=N\C(=O)NC2=C(c3ccc(-c4ncn(-c5ccc(OC(F)(F)F)cc5)n4)cc3)CCC2)c1C(C)C]
P1690
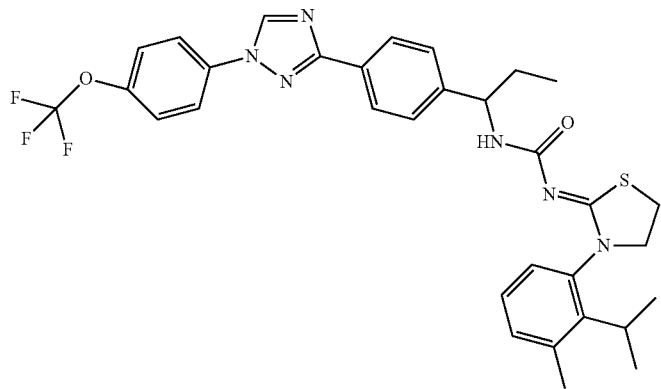 [SMILES: CCC(NC(=O)/N=C1\SCCN1c1cccc(C)c1C(C)C)c1ccc(-c2ncn(-c3ccc(OC(F)(F)F)cc3)n2)cc1]
P1691
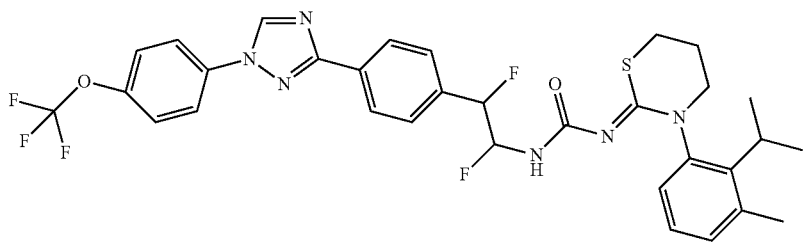
P1692

TABLE P-Two-continued
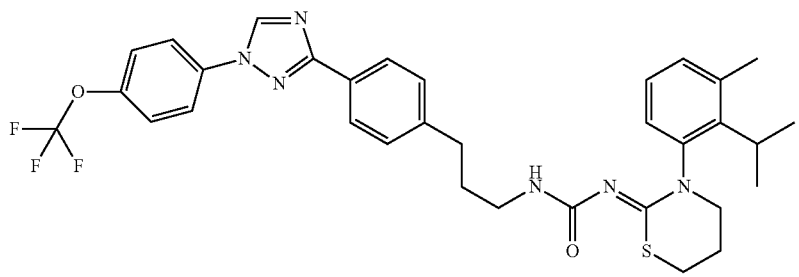 [SMILES: Cc1cccc(N2CCCS/C2=N\C(=O)NCCCc2ccc(-c3ncn(-c4ccc(OC(F)(F)F)cc4)n3)cc2)c1C(C)C]
P1693
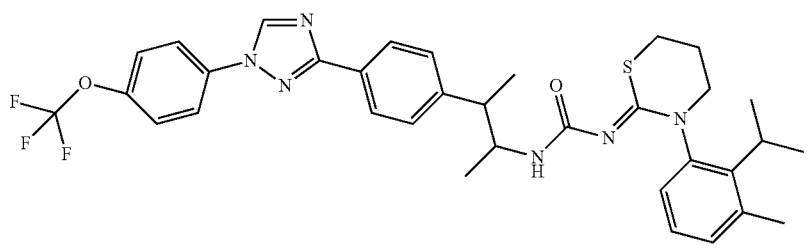 [SMILES: Cc1cccc(N2CCCS/C2=N\C(=O)NC(C)C(C)c2ccc(-c3ncn(-c4ccc(OC(F)(F)F)cc4)n3)cc2)c1C(C)C]
P1694
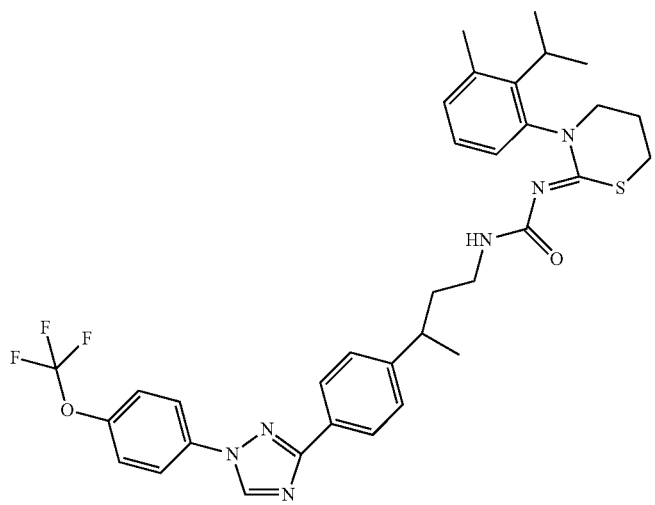 [SMILES: Cc1cccc(N2CCCS/C2=N\C(=O)NCCC(C)c2ccc(-c3ncn(-c4ccc(OC(F)(F)F)cc4)n3)cc2)c1C(C)C]
P1695
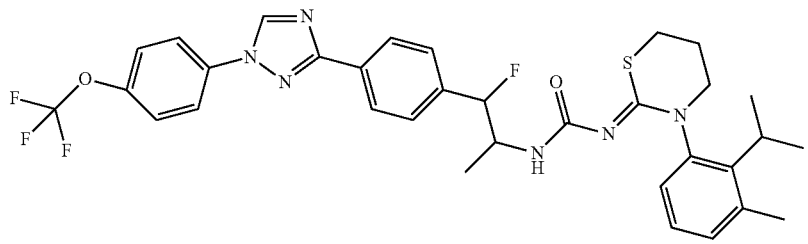 [SMILES: Cc1cccc(N2CCCS/C2=N\C(=O)NC(C)C(F)c2ccc(-c3ncn(-c4ccc(OC(F)(F)F)cc4)n3)cc2)c1C(C)C]
P1696
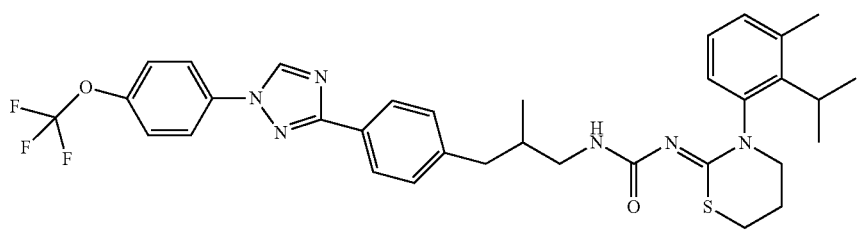 [SMILES: Cc1cccc(N2CCCS/C2=N\C(=O)NCC(C)Cc2ccc(-c3ncn(-c4ccc(OC(F)(F)F)cc4)n3)cc2)c1C(C)C]
P1697

TABLE P-Two-continued
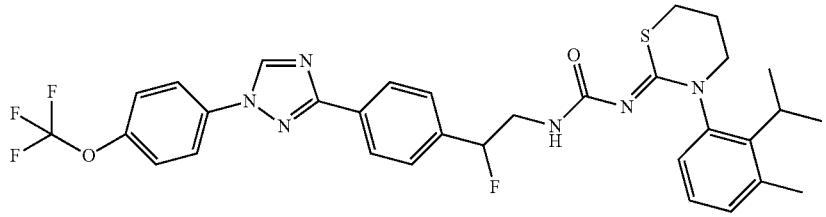 [SMILES: Cc1cccc(N2CCCS/C2=N\C(=O)NCC(F)c2ccc(-c3ncn(-c4ccc(OC(F)(F)F)cc4)n3)cc2)c1C(C)C]
P1698
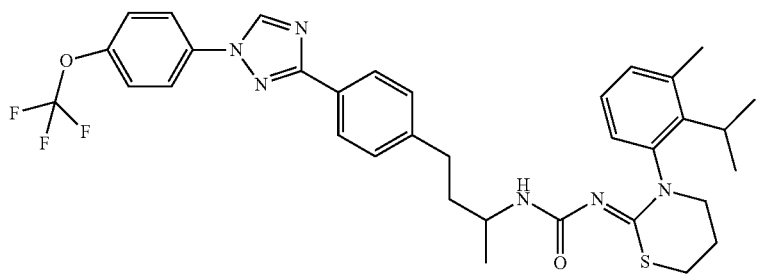 [SMILES: Cc1cccc(N2CCCS/C2=N\C(=O)NC(C)CCc2ccc(-c3ncn(-c4ccc(OC(F)(F)F)cc4)n3)cc2)c1C(C)C]
P1699
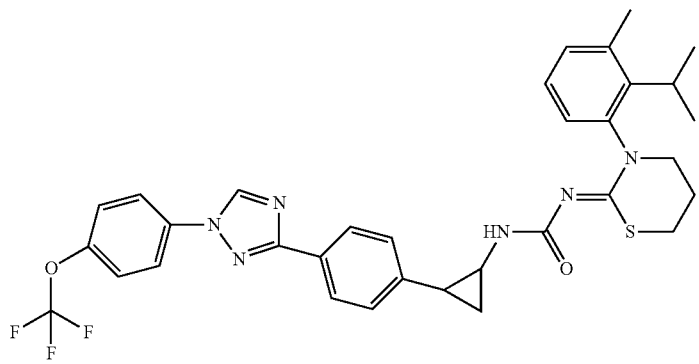 [SMILES: Cc1cccc(N2CCCS/C2=N\C(=O)NC2CC2c2ccc(-c3ncn(-c4ccc(OC(F)(F)F)cc4)n3)cc2)c1C(C)C]
P1700
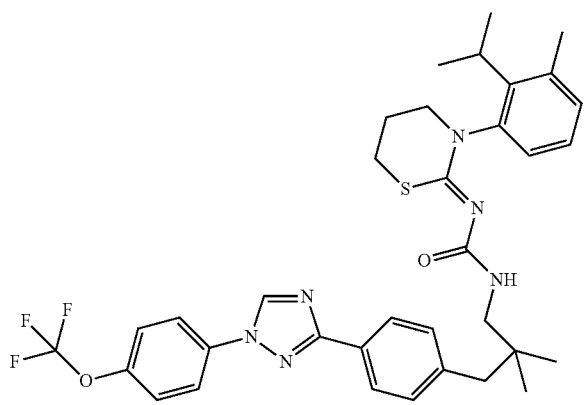 [SMILES: Cc1cccc(N2CCCS/C2=N\C(=O)NCC(C)(C)Cc2ccc(-c3ncn(-c4ccc(OC(F)(F)F)cc4)n3)cc2)c1C(C)C]
P1701
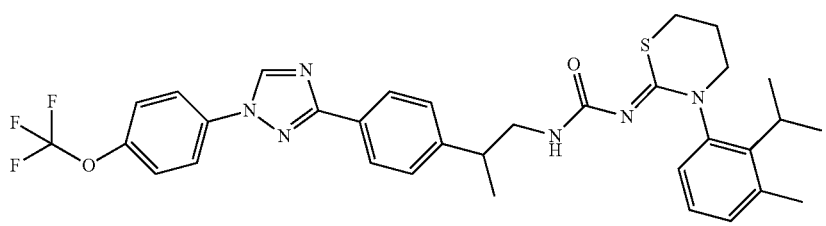 [SMILES: Cc1cccc(N2CCCS/C2=N\C(=O)NCC(C)c2ccc(-c3ncn(-c4ccc(OC(F)(F)F)cc4)n3)cc2)c1C(C)C]
P1702

TABLE P-Two-continued
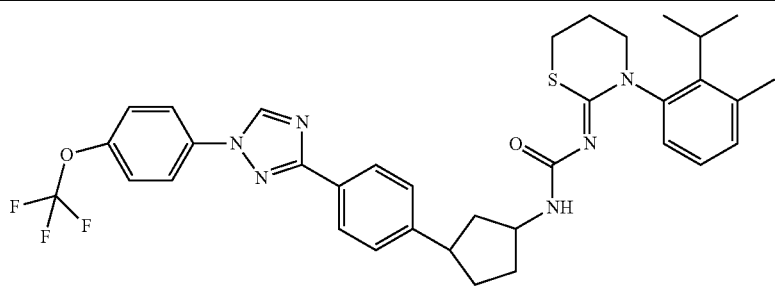
P1703
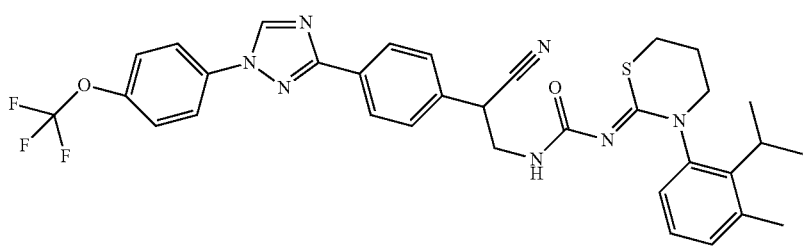 [SMILES: Cc1cccc(N2CCCS/C2=N\C(=O)NCC(C#N)c2ccc(-c3ncn(-c4ccc(OC(F)(F)F)cc4)n3)cc2)c1C(C)C]
P1704
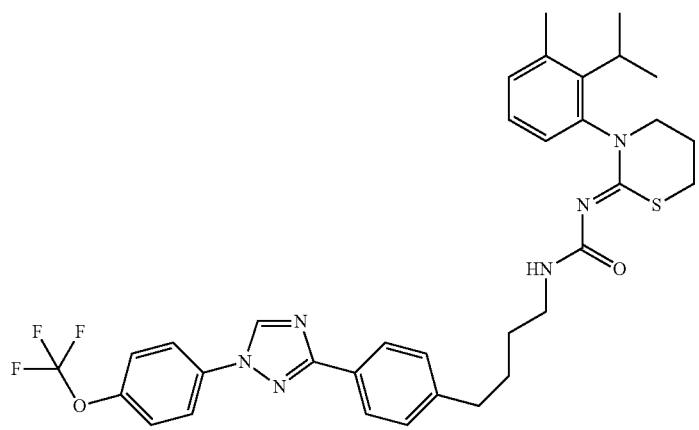 [SMILES: Cc1cccc(N2CCCS/C2=N\C(=O)NCCCCc2ccc(-c3ncn(-c4ccc(OC(F)(F)F)cc4)n3)cc2)c1C(C)C]
P1705
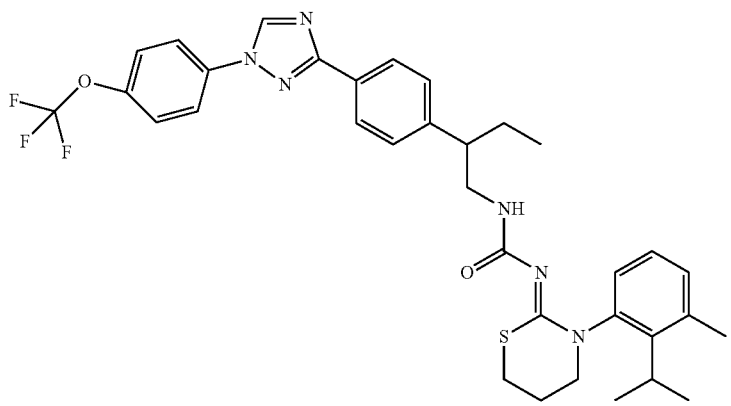 [SMILES: CCC(CNC(=O)/N=C1\SCCCN1c1cccc(C)c1C(C)C)c1ccc(-c2ncn(-c3ccc(OC(F)(F)F)cc3)n2)cc1]
P1706
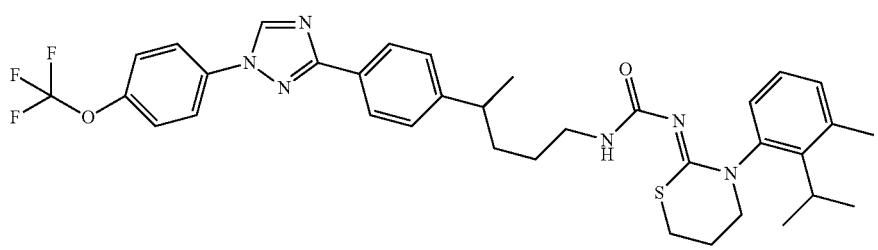 [SMILES: Cc1cccc(N2CCCS/C2=N\C(=O)NCCCC(C)c2ccc(-c3ncn(-c4ccc(OC(F)(F)F)cc4)n3)cc2)c1C(C)C]
P1707

TABLE P-Two-continued
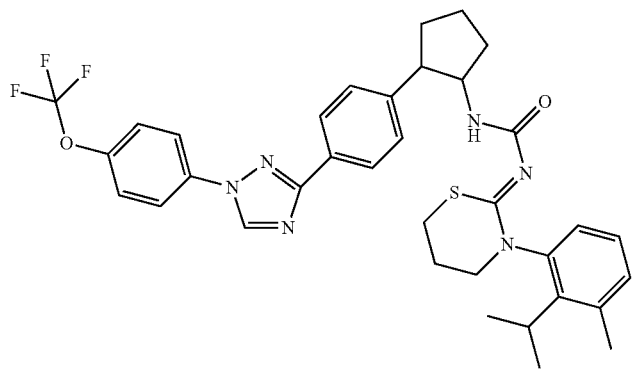 [SMILES: Cc1cccc(N2CCCS/C2=N\C(=O)NC2CCCC2c2ccc(-c3ncn(-c4ccc(OC(F)(F)F)cc4)n3)cc2)c1C(C)C]
P1708
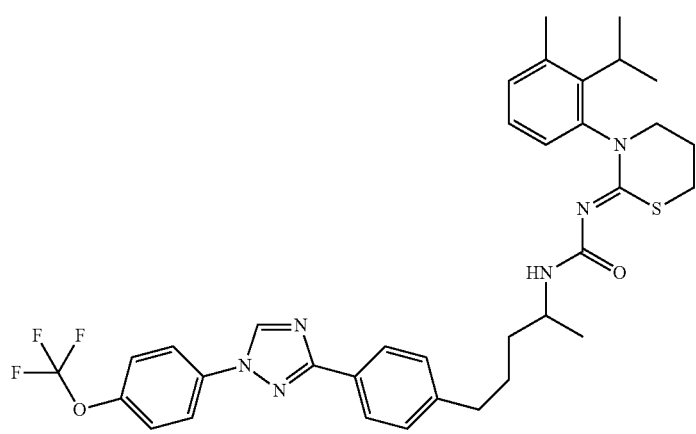 [SMILES: Cc1cccc(N2CCCS/C2=N\C(=O)NC(C)CCCc2ccc(-c3ncn(-c4ccc(OC(F)(F)F)cc4)n3)cc2)c1C(C)C]
P1709
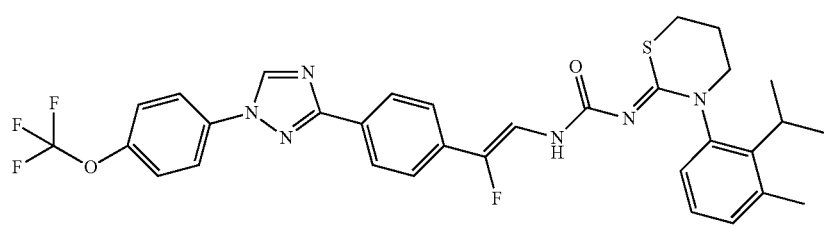 [SMILES: Cc1cccc(N2CCCS/C2=N\C(=O)N/C=C(\F)c2ccc(-c3ncn(-c4ccc(OC(F)(F)F)cc4)n3)cc2)c1C(C)C]
P1710
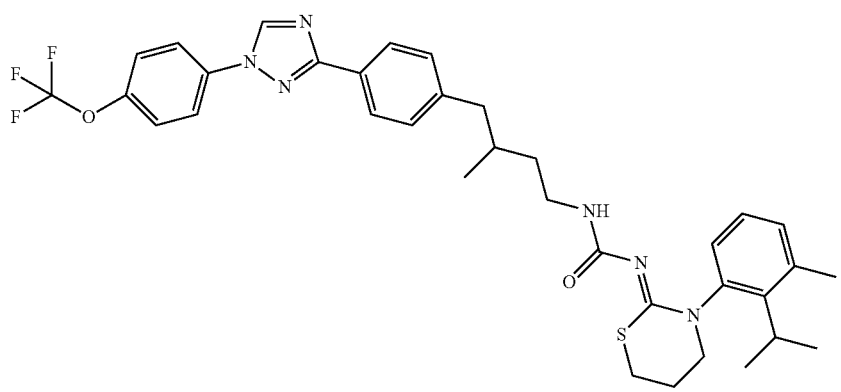 [SMILES: Cc1cccc(N2CCCS/C2=N\C(=O)NCCC(C)Cc2ccc(-c3ncn(-c4ccc(OC(F)(F)F)cc4)n3)cc2)c1C(C)C]
P1711
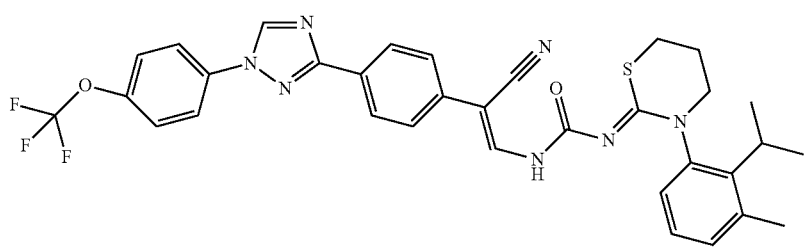 [SMILES: Cc1cccc(N2CCCS/C2=N\C(=O)N/C=C(\C#N)c2ccc(-c3ncn(-c4ccc(OC(F)(F)F)cc4)n3)cc2)c1C(C)C]
P1712

TABLE P-Two-continued
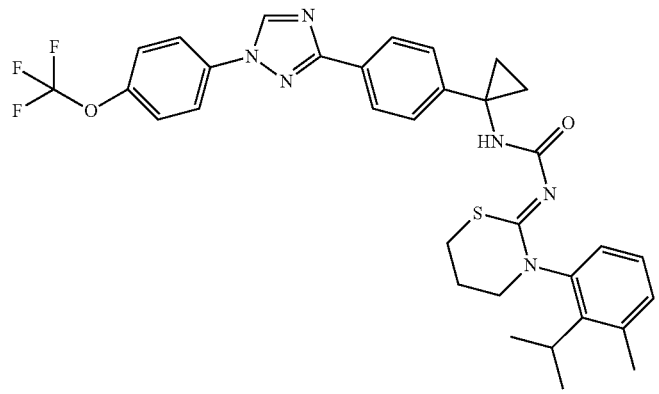 [SMILES: Cc1cccc(N2CCCS/C2=N\C(=O)NC2(c3ccc(-c4ncn(-c5ccc(OC(F)(F)F)cc5)n4)cc3)CC2)c1C(C)C] P1713
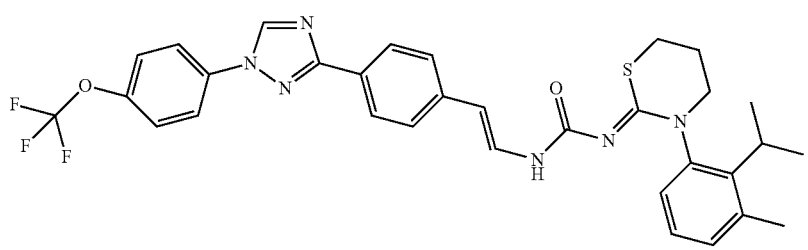 [SMILES: Cc1cccc(N2CCCS/C2=N\C(=O)N/C=C/c2ccc(-c3ncn(-c4ccc(OC(F)(F)F)cc4)n3)cc2)c1C(C)C] P1714
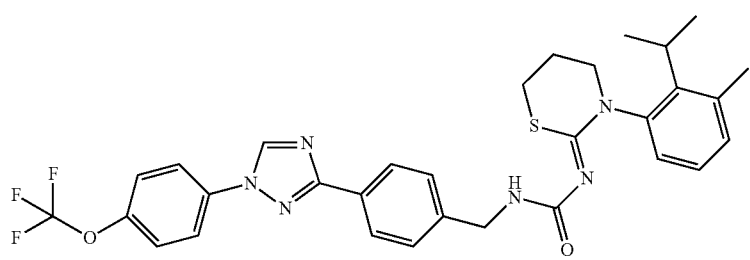 [SMILES: Cc1cccc(N2CCCS/C2=N\C(=O)NCc2ccc(-c3ncn(-c4ccc(OC(F)(F)F)cc4)n3)cc2)c1C(C)C] P1715
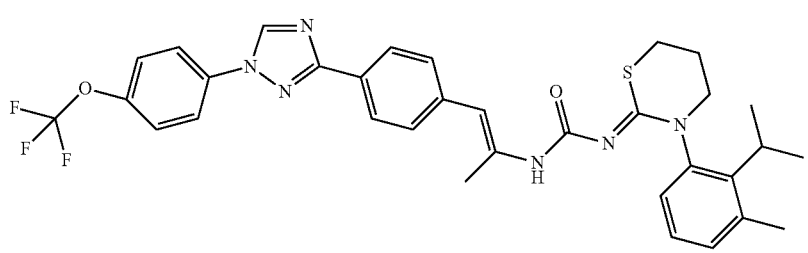 [SMILES: C/C(=C\c1ccc(-c2ncn(-c3ccc(OC(F)(F)F)cc3)n2)cc1)NC(=O)/N=C1\SCCCN1c1cccc(C)c1C(C)C] P1716
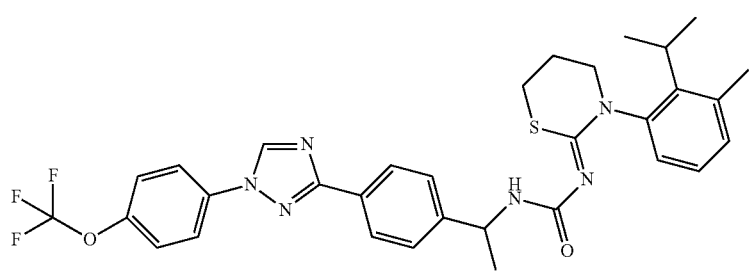 [SMILES: Cc1cccc(N2CCCS/C2=N\C(=O)NC(C)c2ccc(-c3ncn(-c4ccc(OC(F)(F)F)cc4)n3)cc2)c1C(C)C] P1717

TABLE P-Two-continued
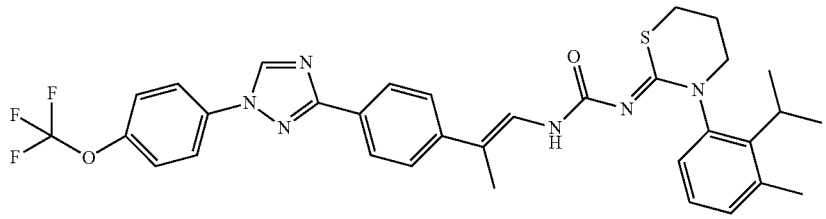 [SMILES: C/C(=C\NC(=O)/N=C1\SCCCN1c1cccc(C)c1C(C)C)c1ccc(-c2ncn(-c3ccc(OC(F)(F)F)cc3)n2)cc1]
P1718
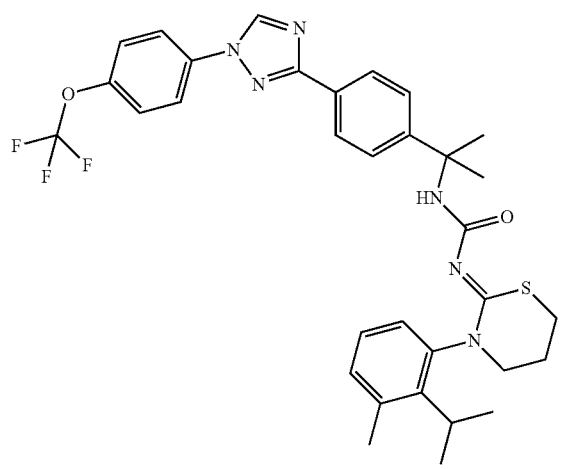 [SMILES: Cc1cccc(N2CCCS/C2=N\C(=O)NC(C)(C)c2ccc(-c3ncn(-c4ccc(OC(F)(F)F)cc4)n3)cc2)c1C(C)C]
P1719
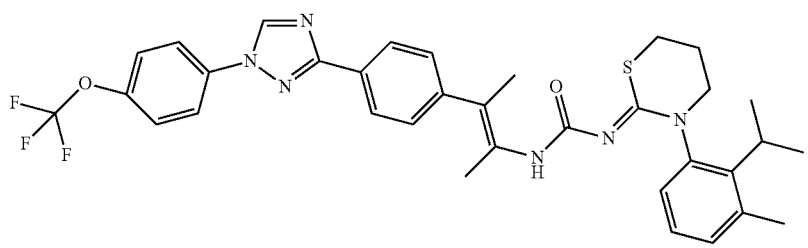 [SMILES: C/C(NC(=O)/N=C1\SCCCN1c1cccc(C)c1C(C)C)=C(/C)c1ccc(-c2ncn(-c3ccc(OC(F)(F)F)cc3)n2)cc1]
P1720
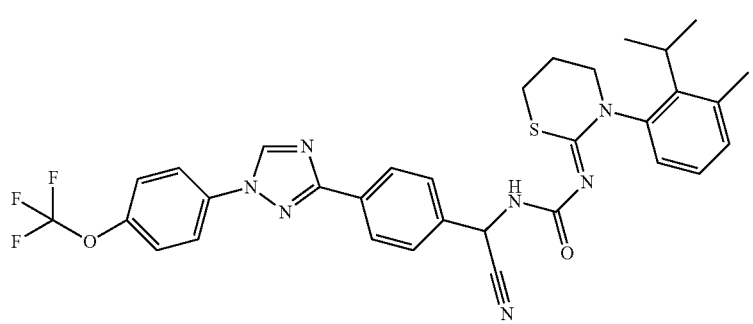 [SMILES: Cc1cccc(N2CCCS/C2=N\C(=O)NC(C#N)c2ccc(-c3ncn(-c4ccc(OC(F)(F)F)cc4)n3)cc2)c1C(C)C]
P1721
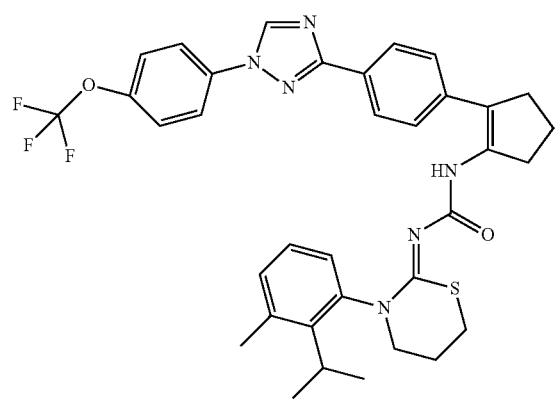 [SMILES: Cc1cccc(N2CCCS/C2=N\C(=O)NC2=C(c3ccc(-c4ncn(-c5ccc(OC(F)(F)F)cc5)n4)cc3)CCC2)c1C(C)C]
P1722

TABLE P-Two-continued
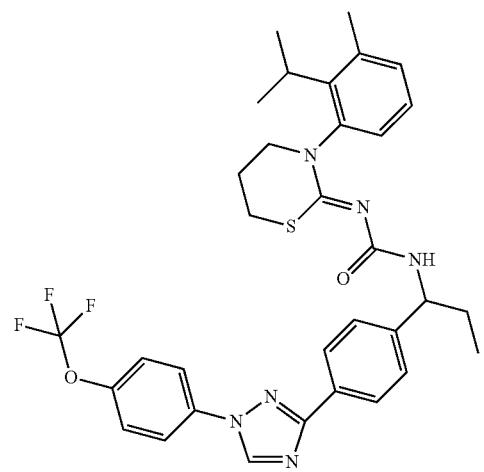 [SMILES: CCC(NC(=O)/N=C1\SCCCN1c1cccc(C)c1C(C)C)c1ccc(-c2ncn(-c3ccc(OC(F)(F)F)cc3)n2)cc1]
P1723
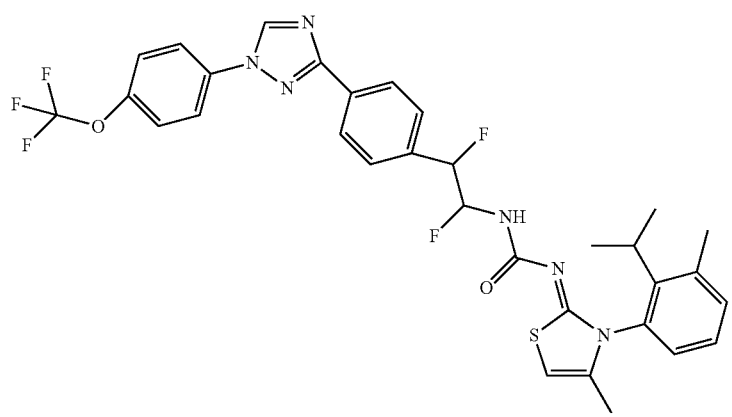 [SMILES: Cc1cccc(-n2c(C)cs/c2=N\C(=O)NC(F)C(F)c2ccc(-c3ncn(-c4ccc(OC(F)(F)F)cc4)n3)cc2)c1C(C)C]
P1724
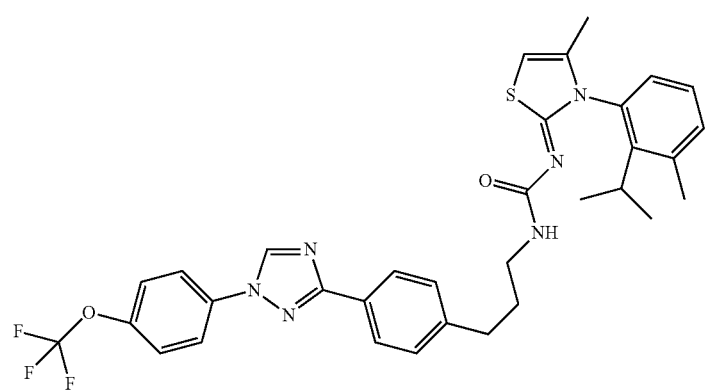 [SMILES: Cc1cccc(-n2c(C)cs/c2=N\C(=O)NCCCc2ccc(-c3ncn(-c4ccc(OC(F)(F)F)cc4)n3)cc2)c1C(C)C]
P1725

TABLE P-Two-continued
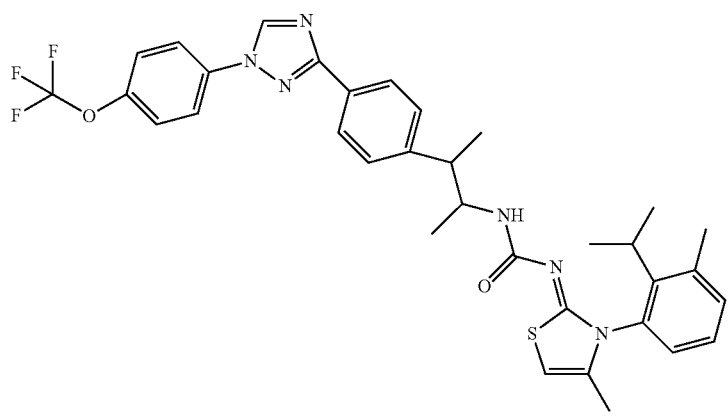 [SMILES: Cc1cccc(-n2c(C)cs/c2=N\C(=O)NC(C)C(C)c2ccc(-c3ncn(-c4ccc(OC(F)(F)F)cc4)n3)cc2)c1C(C)C]
P1726
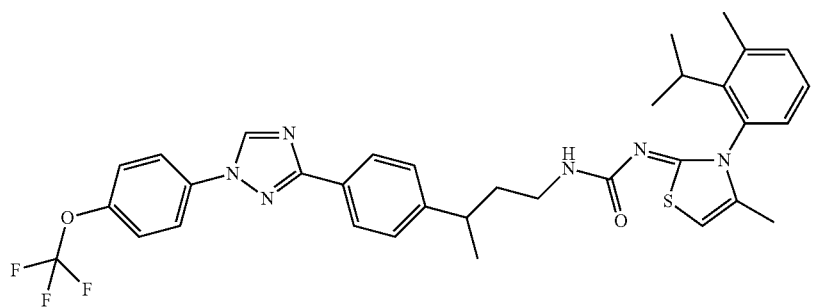 [SMILES: Cc1cccc(-n2c(C)cs/c2=N\C(=O)NCCC(C)c2ccc(-c3ncn(-c4ccc(OC(F)(F)F)cc4)n3)cc2)c1C(C)C]
P1727
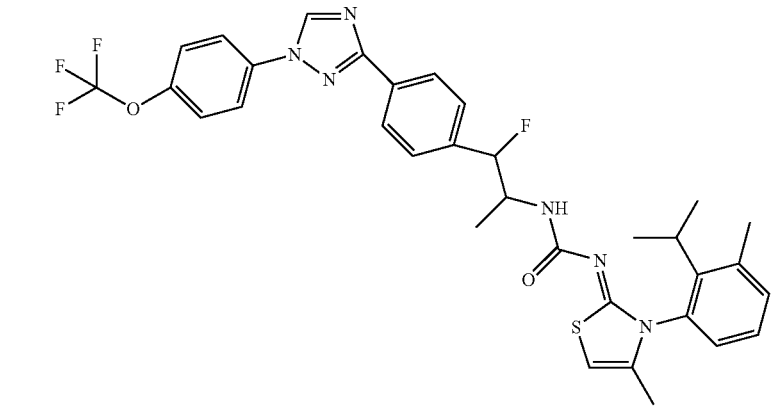 [SMILES: Cc1cccc(-n2c(C)cs/c2=N\C(=O)NC(C)C(F)c2ccc(-c3ncn(-c4ccc(OC(F)(F)F)cc4)n3)cc2)c1C(C)C]
P1728
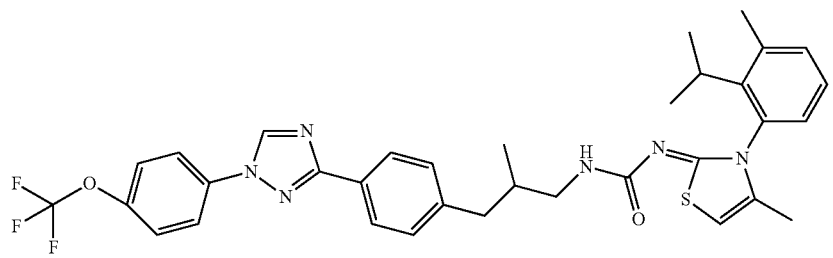 [SMILES: Cc1cccc(-n2c(C)cs/c2=N\C(=O)NCC(C)Cc2ccc(-c3ncn(-c4ccc(OC(F)(F)F)cc4)n3)cc2)c1C(C)C]
P1729

TABLE P-Two-continued
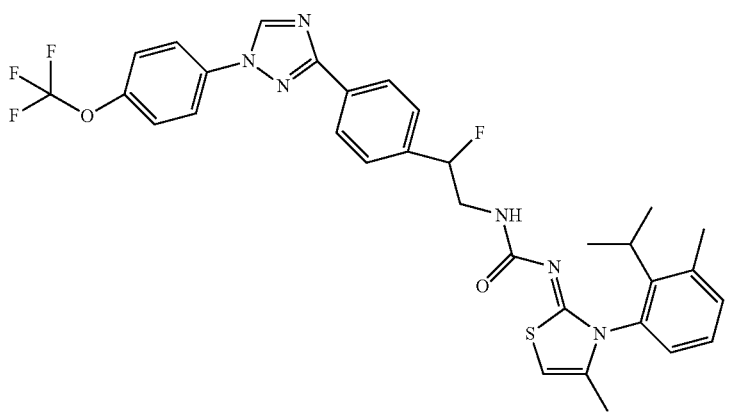 [SMILES: Cc1cccc(-n2c(C)cs/c2=N\C(=O)NCC(F)c2ccc(-c3ncn(-c4ccc(OC(F)(F)F)cc4)n3)cc2)c1C(C)C]
P1730
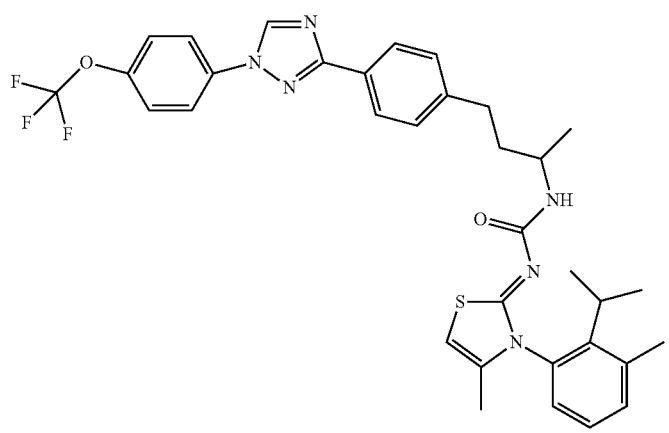 [SMILES: Cc1cccc(-n2c(C)cs/c2=N\C(=O)NC(C)CCc2ccc(-c3ncn(-c4ccc(OC(F)(F)F)cc4)n3)cc2)c1C(C)C]
P1731
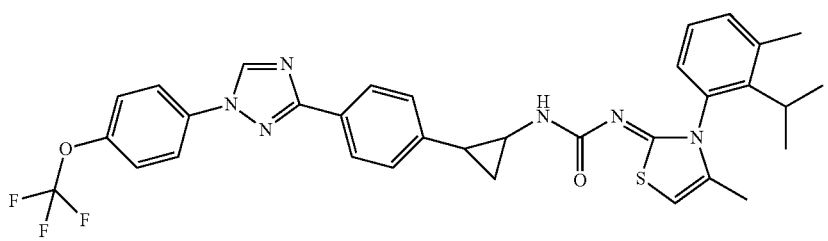 [SMILES: Cc1cccc(-n2c(C)cs/c2=N\C(=O)NC2CC2c2ccc(-c3ncn(-c4ccc(OC(F)(F)F)cc4)n3)cc2)c1C(C)C]
P1732
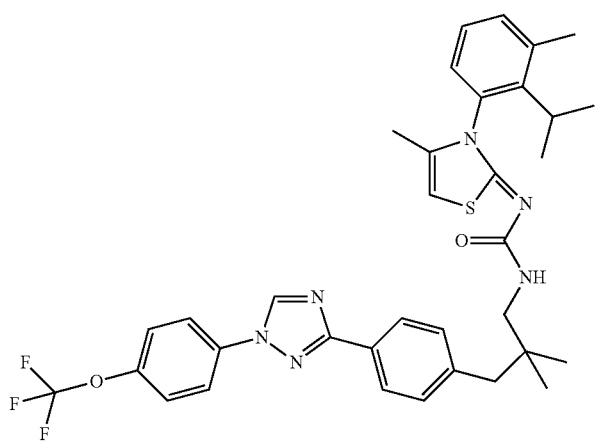 [SMILES: Cc1cccc(-n2c(C)cs/c2=N\C(=O)NCC(C)(C)Cc2ccc(-c3ncn(-c4ccc(OC(F)(F)F)cc4)n3)cc2)c1C(C)C]
P1733

TABLE P-Two-continued
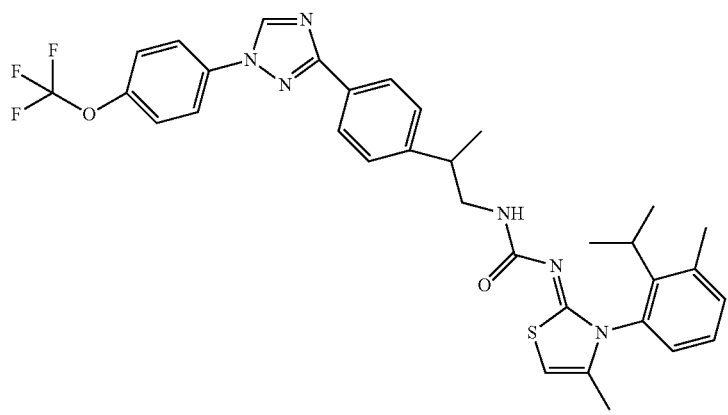 [SMILES: Cc1cccc(-n2c(C)cs/c2=N\C(=O)NCC(C)c2ccc(-c3ncn(-c4ccc(OC(F)(F)F)cc4)n3)cc2)c1C(C)C]
P1734
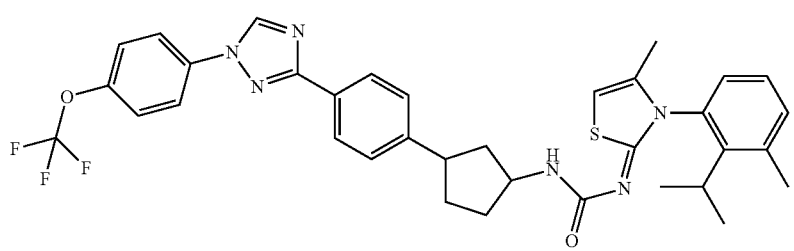 [SMILES: Cc1cccc(-n2c(C)cs/c2=N\C(=O)NC2CCC(c3ccc(-c4ncn(-c5ccc(OC(F)(F)F)cc5)n4)cc3)C2)c1C(C)C]
P1735
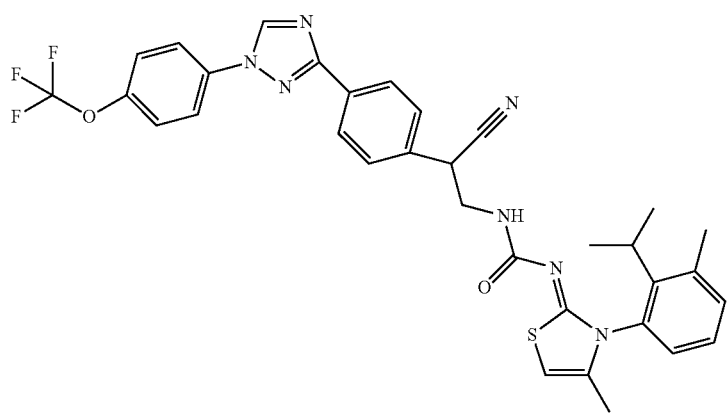 [SMILES: Cc1cccc(-n2c(C)cs/c2=N\C(=O)NCC(C#N)c2ccc(-c3ncn(-c4ccc(OC(F)(F)F)cc4)n3)cc2)c1C(C)C]
P1736
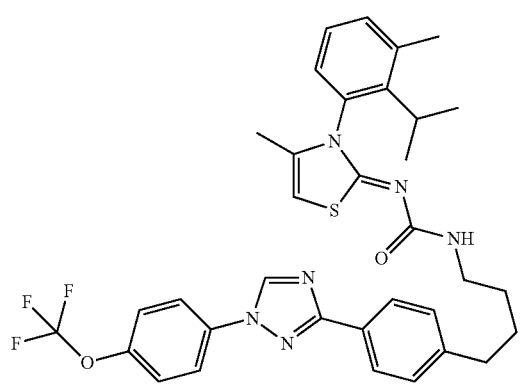 [SMILES: Cc1cccc(-n2c(C)cs/c2=N\C(=O)NCCCCc2ccc(-c3ncn(-c4ccc(OC(F)(F)F)cc4)n3)cc2)c1C(C)C]
P1737

TABLE P-Two-continued
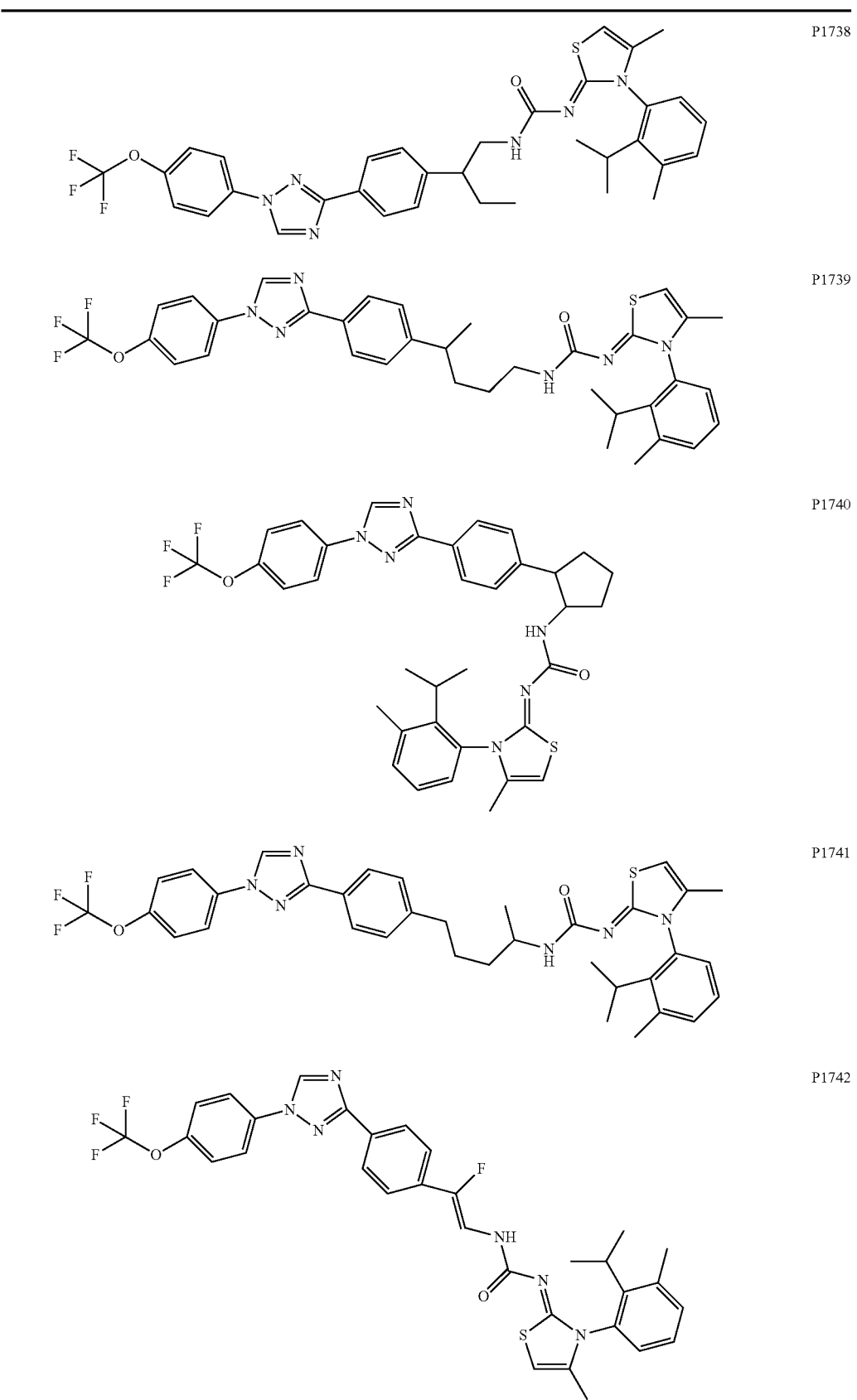

TABLE P-Two-continued
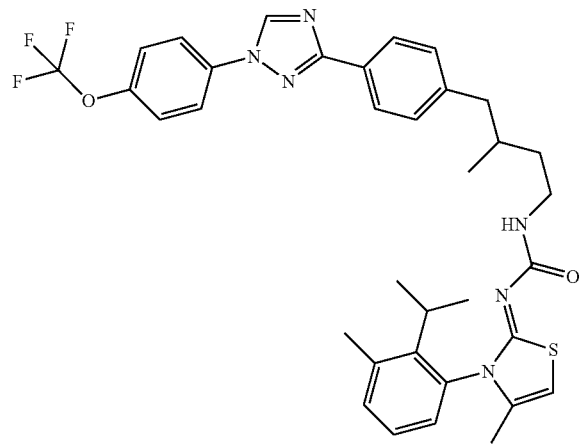 [SMILES: Cc1cccc(-n2c(C)cs/c2=N\C(=O)NCCC(C)Cc2ccc(-c3ncn(-c4ccc(OC(F)(F)F)cc4)n3)cc2)c1C(C)C]
P1743
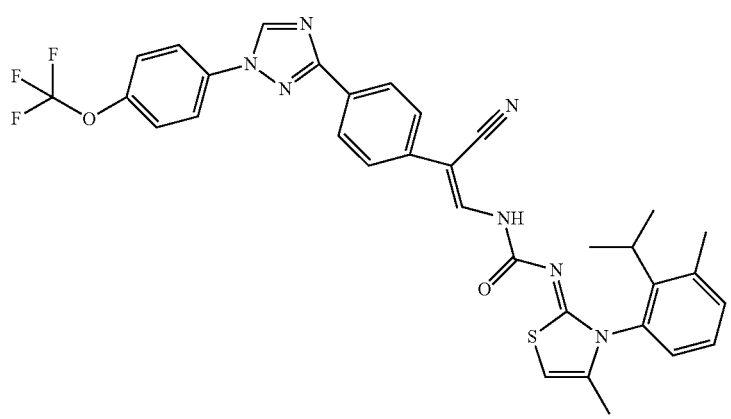 [SMILES: Cc1cccc(-n2c(C)cs/c2=N\C(=O)N/C=C(\C#N)c2ccc(-c3ncn(-c4ccc(OC(F)(F)F)cc4)n3)cc2)c1C(C)C]
P1744
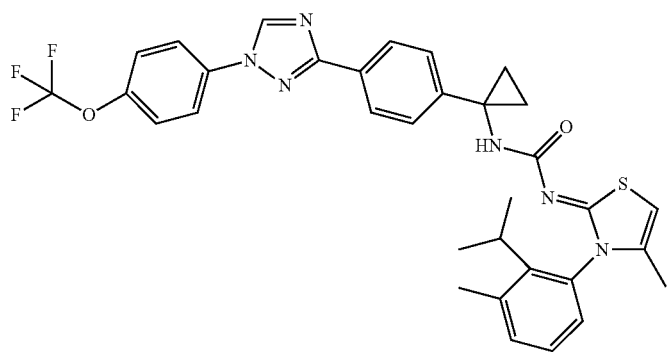
P1745
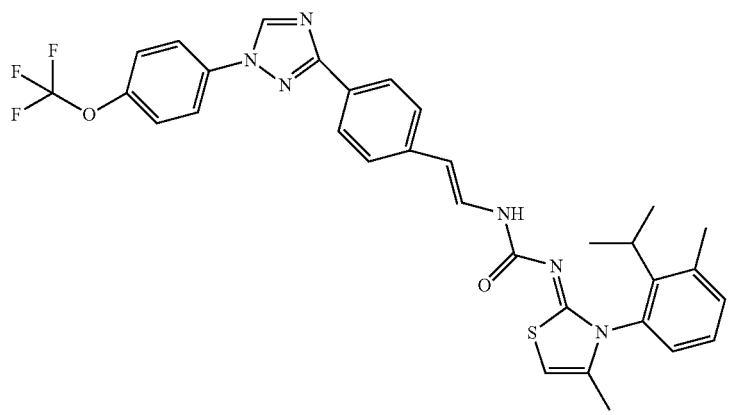 [SMILES: Cc1cccc(-n2c(C)cs/c2=N\C(=O)N/C=C/c2ccc(-c3ncn(-c4ccc(OC(F)(F)F)cc4)n3)cc2)c1C(C)C]
P1746

TABLE P-Two-continued
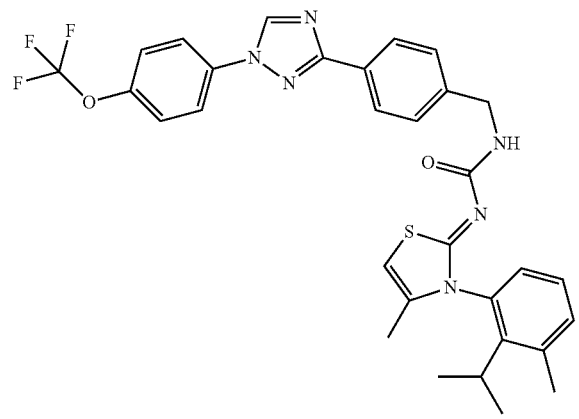 [SMILES: Cc1cccc(-n2c(C)cs/c2=N\C(=O)NCc2ccc(-c3ncn(-c4ccc(OC(F)(F)F)cc4)n3)cc2)c1C(C)C]
P1747
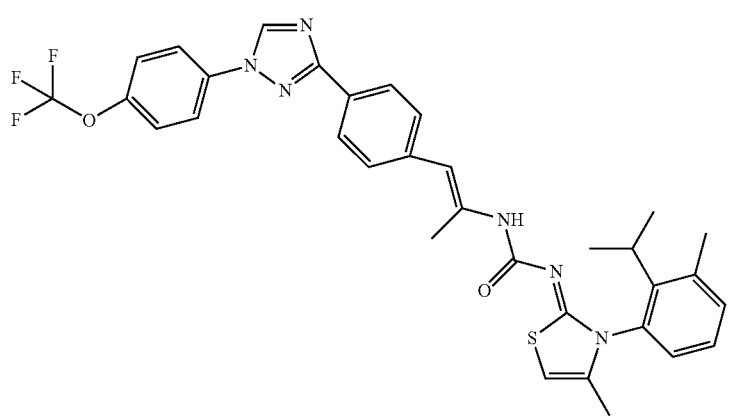 [SMILES: C/C(=C\c1ccc(-c2ncn(-c3ccc(OC(F)(F)F)cc3)n2)cc1)NC(=O)/N=c1\scc(C)n1-c1cccc(C)c1C(C)C]
P1748
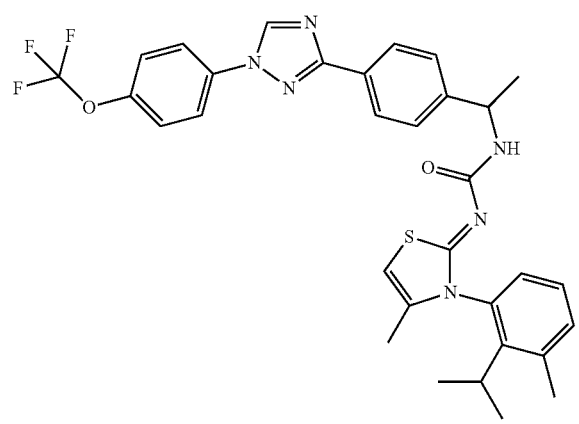 [SMILES: Cc1cccc(-n2c(C)cs/c2=N\C(=O)NC(C)c2ccc(-c3ncn(-c4ccc(OC(F)(F)F)cc4)n3)cc2)c1C(C)C]
P1749
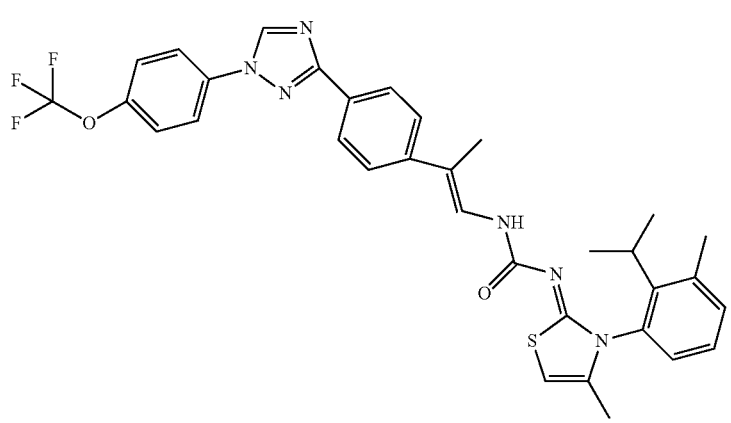 [SMILES: C/C(=C\NC(=O)/N=c1\scc(C)n1-c1cccc(C)c1C(C)C)c1ccc(-c2ncn(-c3ccc(OC(F)(F)F)cc3)n2)cc1]
P1750

TABLE P-Two-continued
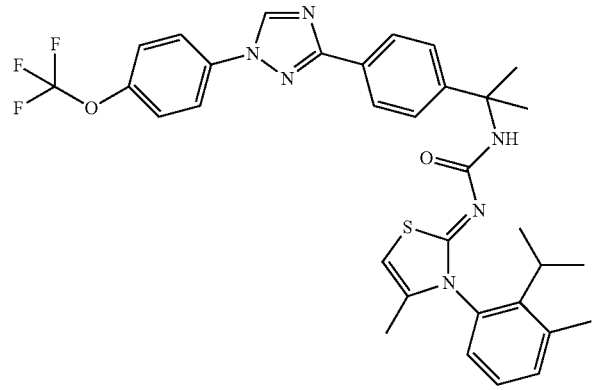 [SMILES: Cc1cccc(-n2c(C)cs/c2=N\C(=O)NC(C)(C)c2ccc(-c3ncn(-c4ccc(OC(F)(F)F)cc4)n3)cc2)c1C(C)C]
P1751
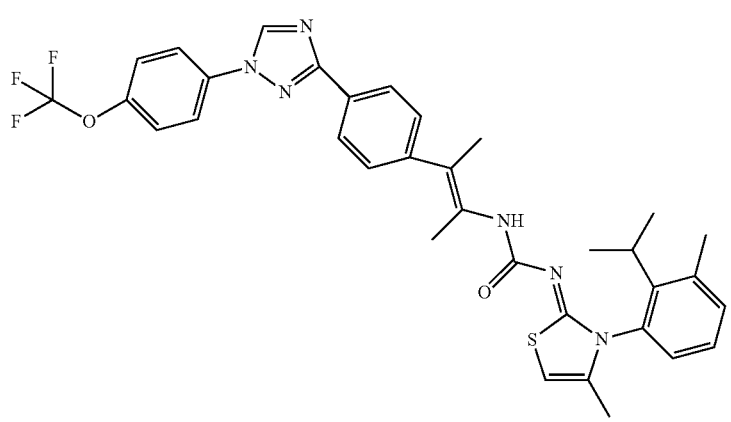 [SMILES: C/C(NC(=O)/N=c1\scc(C)n1-c1cccc(C)c1C(C)C)=C(/C)c1ccc(-c2ncn(-c3ccc(OC(F)(F)F)cc3)n2)cc1]
P1752
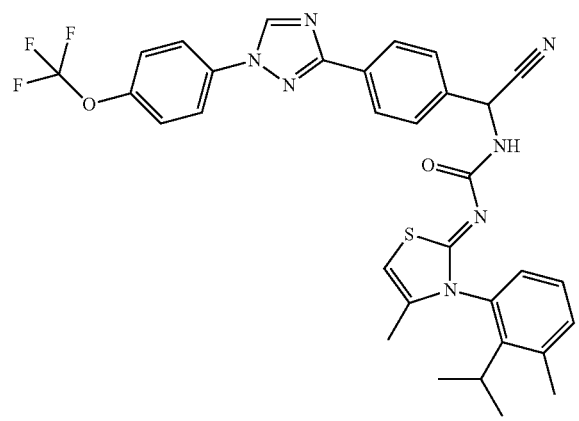 [SMILES: Cc1cccc(-n2c(C)cs/c2=N\C(=O)NC(C#N)c2ccc(-c3ncn(-c4ccc(OC(F)(F)F)cc4)n3)cc2)c1C(C)C]
P1753
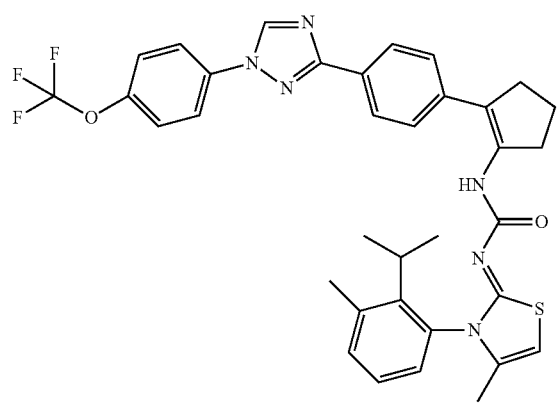 [SMILES: Cc1cccc(-n2c(C)cs/c2=N\C(=O)NC2=C(c3ccc(-c4ncn(-c5ccc(OC(F)(F)F)cc5)n4)cc3)CCC2)c1C(C)C]
P1754

TABLE P-Two-continued
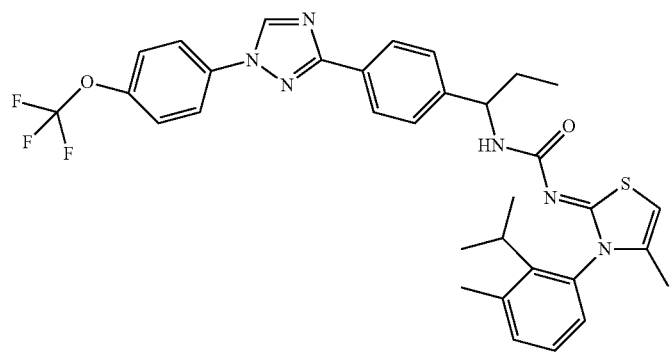 [SMILES: CCC(NC(=O)/N=c1\scc(C)n1-c1cccc(C)c1C(C)C)c1ccc(-c2ncn(-c3ccc(OC(F)(F)F)cc3)n2)cc1]
P1755
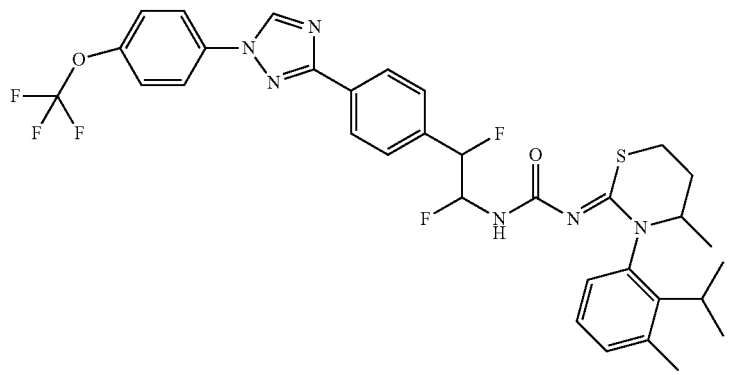 [SMILES: Cc1cccc(N2/C(=N/C(=O)NC(F)C(F)c3ccc(-c4ncn(-c5ccc(OC(F)(F)F)cc5)n4)cc3)SCCC2C)c1C(C)C]
P1756
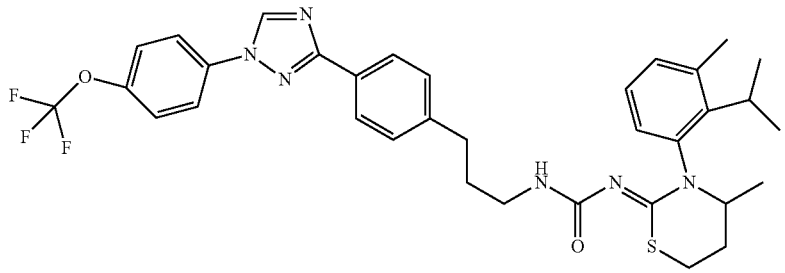 [SMILES: Cc1cccc(N2/C(=N/C(=O)NCCCc3ccc(-c4ncn(-c5ccc(OC(F)(F)F)cc5)n4)cc3)SCCC2C)c1C(C)C]
P1757
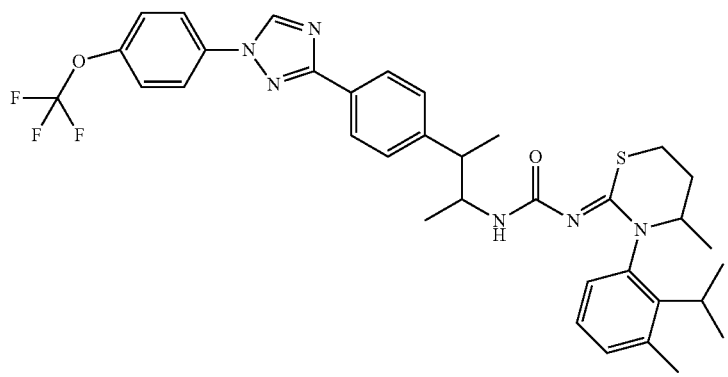 [SMILES: Cc1cccc(N2/C(=N/C(=O)NC(C)C(C)c3ccc(-c4ncn(-c5ccc(OC(F)(F)F)cc5)n4)cc3)SCCC2C)c1C(C)C]
P1758

TABLE P-Two-continued
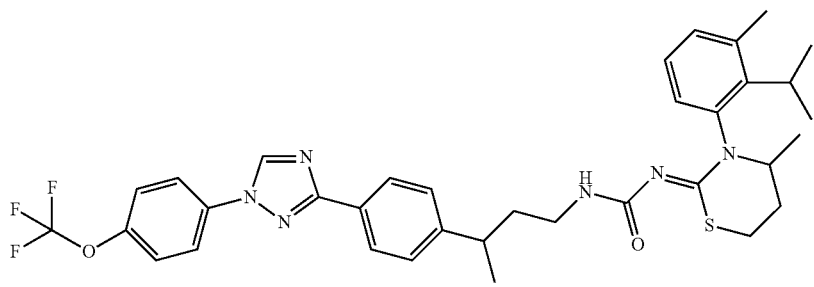 [SMILES: Cc1cccc(N2/C(=N/C(=O)NCCC(C)c3ccc(-c4ncn(-c5ccc(OC(F)(F)F)cc5)n4)cc3)SCCC2C)c1C(C)C]
P1759
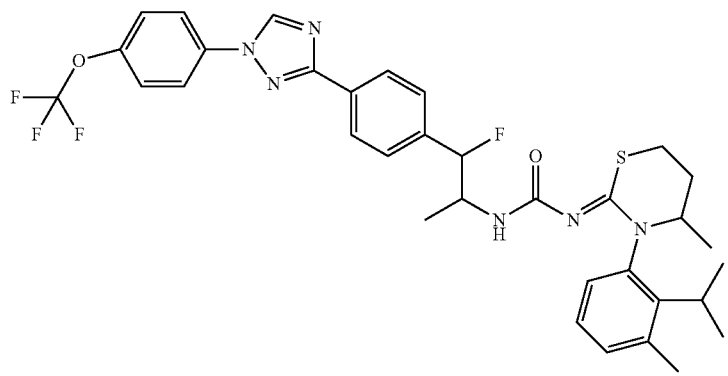 [SMILES: Cc1cccc(N2/C(=N/C(=O)NC(C)C(F)c3ccc(-c4ncn(-c5ccc(OC(F)(F)F)cc5)n4)cc3)SCCC2C)c1C(C)C]
P1760
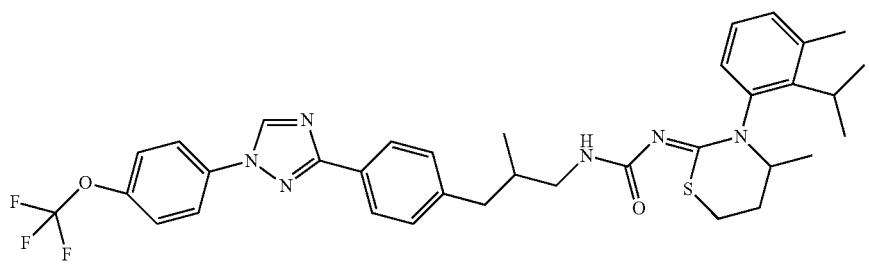 [SMILES: Cc1cccc(N2/C(=N/C(=O)NCC(C)Cc3ccc(-c4ncn(-c5ccc(OC(F)(F)F)cc5)n4)cc3)SCCC2C)c1C(C)C]
P1761
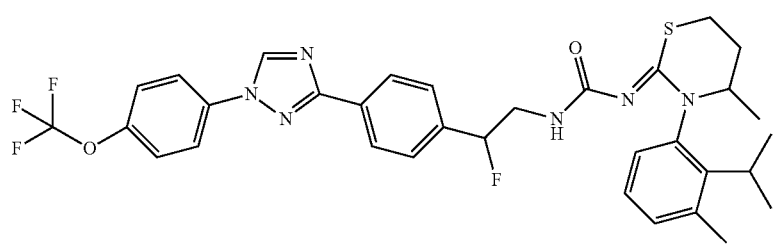 [SMILES: Cc1cccc(N2/C(=N/C(=O)NCC(F)c3ccc(-c4ncn(-c5ccc(OC(F)(F)F)cc5)n4)cc3)SCCC2C)c1C(C)C]
P1762
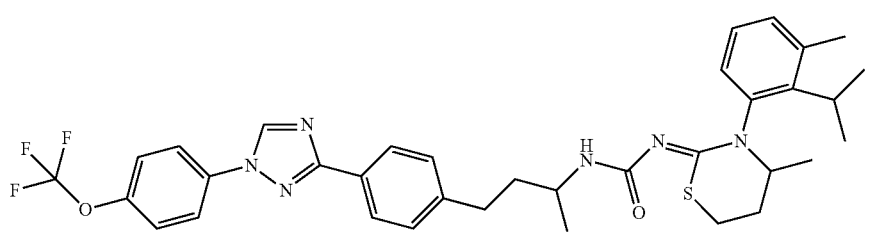 [SMILES: Cc1cccc(N2/C(=N/C(=O)NC(C)CCc3ccc(-c4ncn(-c5ccc(OC(F)(F)F)cc5)n4)cc3)SCCC2C)c1C(C)C]
P1763

TABLE P-Two-continued
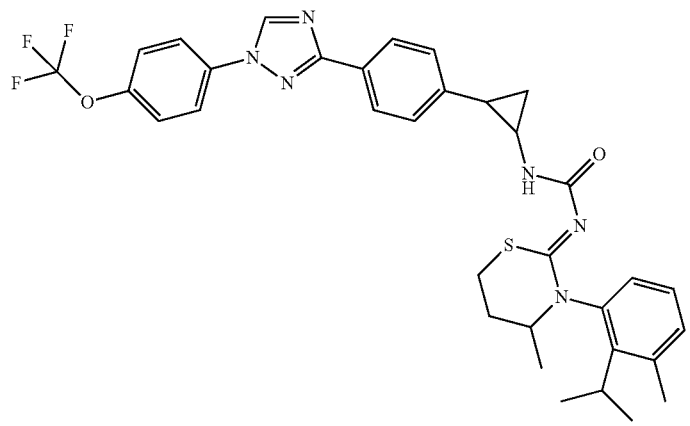 [SMILES: Cc1cccc(N2/C(=N/C(=O)NC3CC3c3ccc(-c4ncn(-c5ccc(OC(F)(F)F)cc5)n4)cc3)SCCC2C)c1C(C)C]
P1764
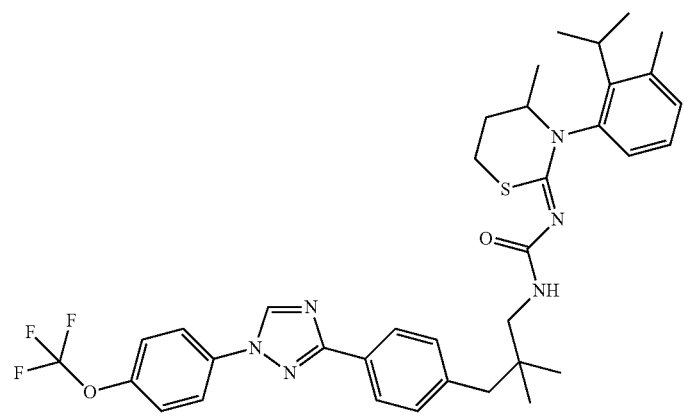 [SMILES: Cc1cccc(N2/C(=N/C(=O)NCC(C)(C)Cc3ccc(-c4ncn(-c5ccc(OC(F)(F)F)cc5)n4)cc3)SCCC2C)c1C(C)C]
P1765
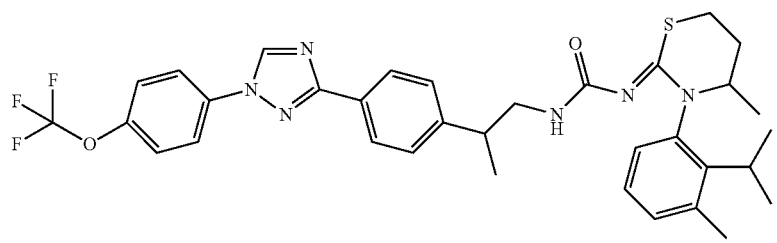 [SMILES: Cc1cccc(N2/C(=N/C(=O)NCC(C)c3ccc(-c4ncn(-c5ccc(OC(F)(F)F)cc5)n4)cc3)SCCC2C)c1C(C)C]
P1766
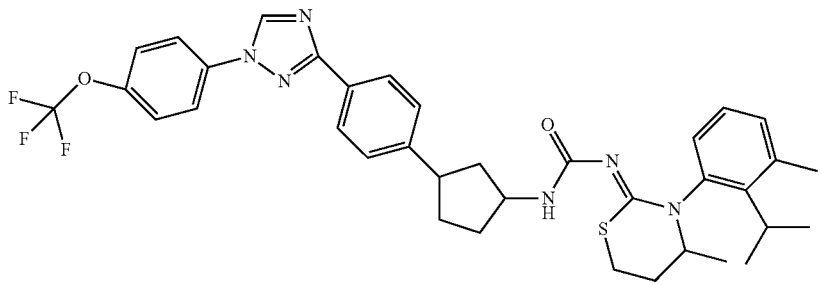 [SMILES: Cc1cccc(N2/C(=N/C(=O)NC3CCC(c4ccc(-c5ncn(-c6ccc(OC(F)(F)F)cc6)n5)cc4)C3)SCCC2C)c1C(C)C]
P1767
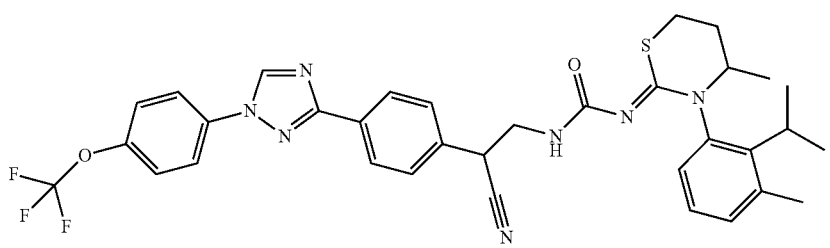 [SMILES: Cc1cccc(N2/C(=N/C(=O)NCC(C#N)c3ccc(-c4ncn(-c5ccc(OC(F)(F)F)cc5)n4)cc3)SCCC2C)c1C(C)C]
P1768

TABLE P-Two-continued
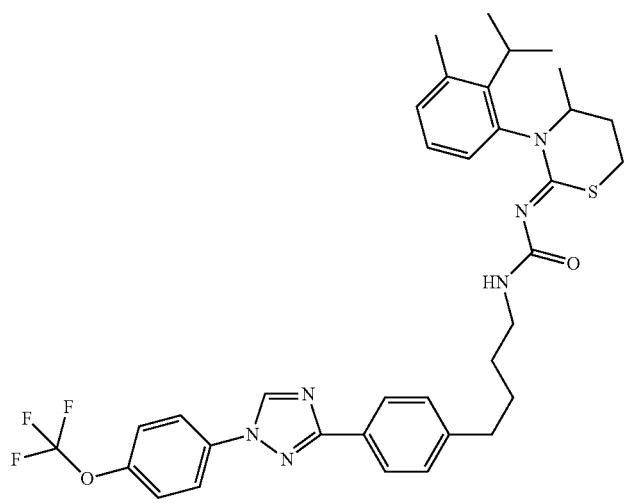 [SMILES: Cc1cccc(N2/C(=N/C(=O)NCCCCc3ccc(-c4ncn(-c5ccc(OC(F)(F)F)cc5)n4)cc3)SCCC2C)c1C(C)C]
P1769
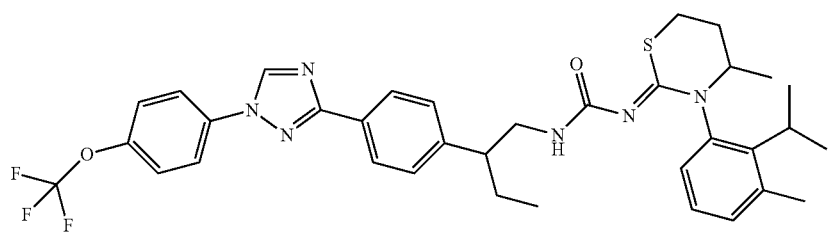 [SMILES: CCC(CNC(=O)/N=C1\SCCC(C)N1c1cccc(C)c1C(C)C)c1ccc(-c2ncn(-c3ccc(OC(F)(F)F)cc3)n2)cc1]
P1770
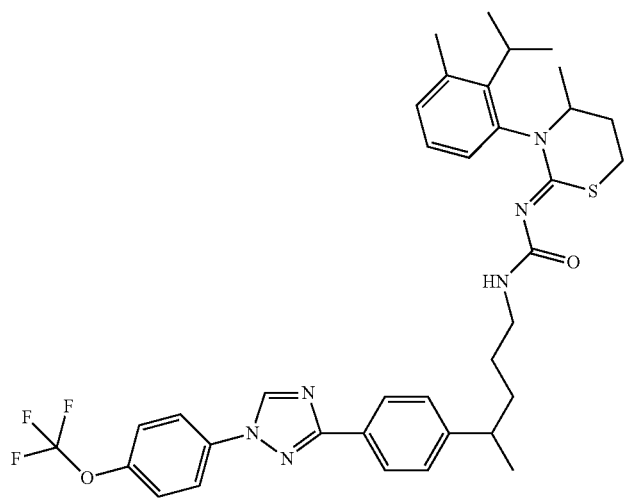 [SMILES: Cc1cccc(N2/C(=N/C(=O)NCCCC(C)c3ccc(-c4ncn(-c5ccc(OC(F)(F)F)cc5)n4)cc3)SCCC2C)c1C(C)C]
P1771
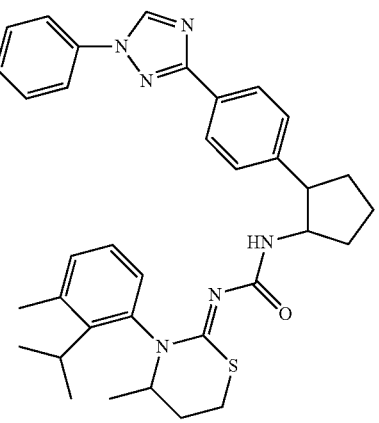
P1772

TABLE P-Two-continued
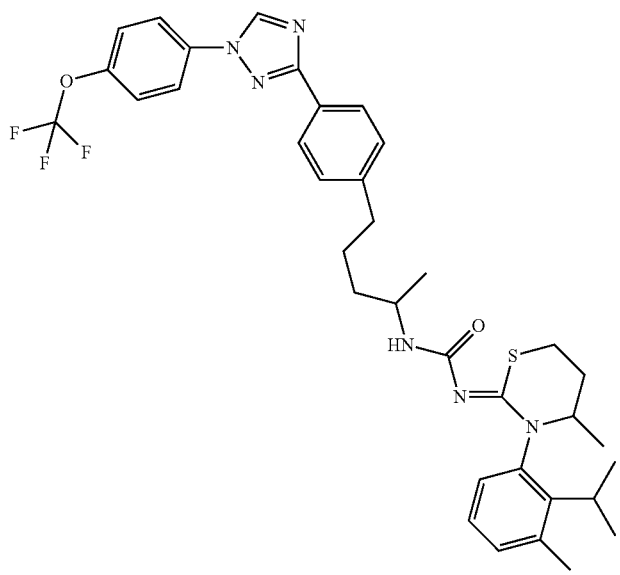 [SMILES: Cc1cccc(N2/C(=N/C(=O)NC(C)CCCc3ccc(-c4ncn(-c5ccc(OC(F)(F)F)cc5)n4)cc3)SCCC2C)c1C(C)C]
P1773
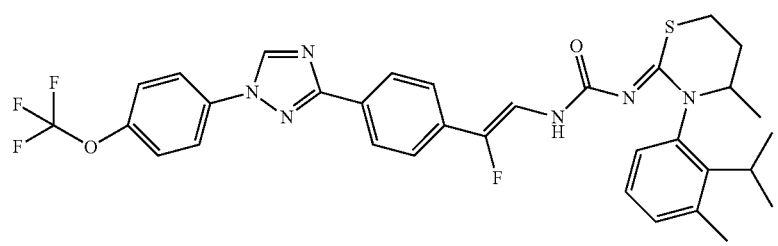 [SMILES: Cc1cccc(N2/C(=N/C(=O)N/C=C(\F)c3ccc(-c4ncn(-c5ccc(OC(F)(F)F)cc5)n4)cc3)SCCC2C)c1C(C)C]
P1774
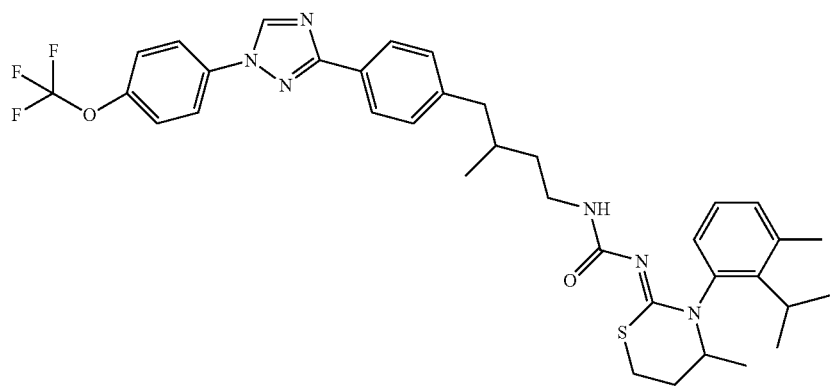 [SMILES: Cc1cccc(N2/C(=N/C(=O)NCCC(C)Cc3ccc(-c4ncn(-c5ccc(OC(F)(F)F)cc5)n4)cc3)SCCC2C)c1C(C)C]
P1775
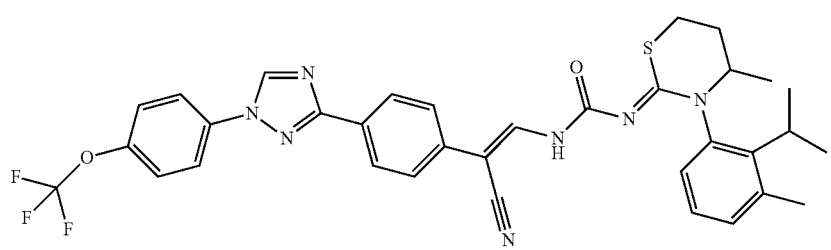 [SMILES: Cc1cccc(N2/C(=N/C(=O)N/C=C(\C#N)c3ccc(-c4ncn(-c5ccc(OC(F)(F)F)cc5)n4)cc3)SCCC2C)c1C(C)C]
P1776

TABLE P-Two-continued
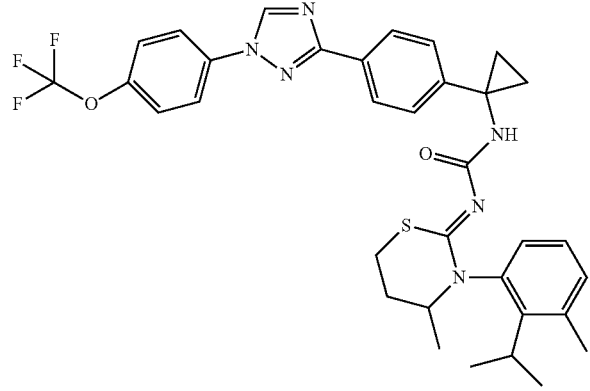 [SMILES: Cc1cccc(N2/C(=N/C(=O)NC3(c4ccc(-c5ncn(-c6ccc(OC(F)(F)F)cc6)n5)cc4)CC3)SCCC2C)c1C(C)C]
P1777
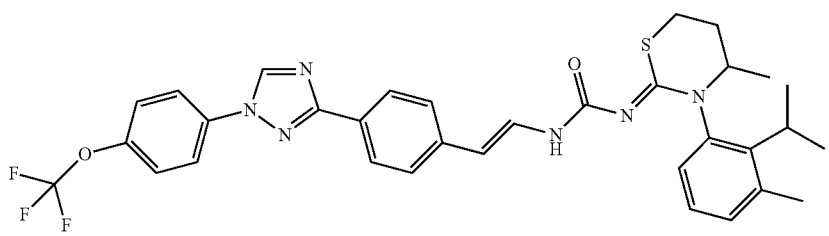 [SMILES: Cc1cccc(N2/C(=N/C(=O)N/C=C/c3ccc(-c4ncn(-c5ccc(OC(F)(F)F)cc5)n4)cc3)SCCC2C)c1C(C)C]
P1778
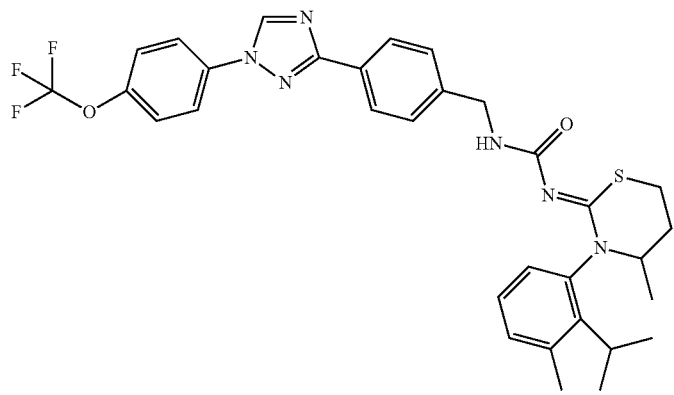 [SMILES: Cc1cccc(N2/C(=N/C(=O)NCc3ccc(-c4ncn(-c5ccc(OC(F)(F)F)cc5)n4)cc3)SCCC2C)c1C(C)C]
P1779
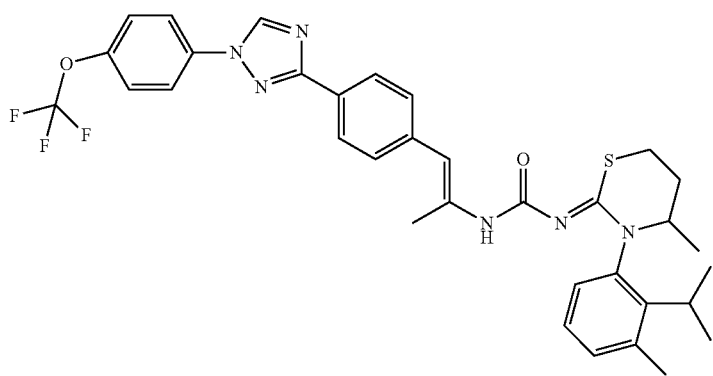 [SMILES: C/C(=C\c1ccc(-c2ncn(-c3ccc(OC(F)(F)F)cc3)n2)cc1)NC(=O)/N=C1\SCCC(C)N1c1cccc(C)c1C(C)C]
P1780

TABLE P-Two-continued
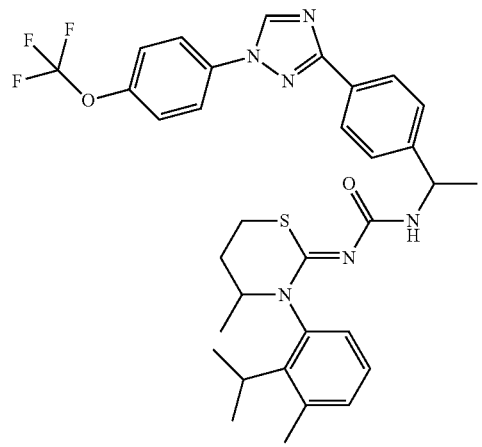 [SMILES: Cc1cccc(N2/C(=N/C(=O)NC(C)c3ccc(-c4ncn(-c5ccc(OC(F)(F)F)cc5)n4)cc3)SCCC2C)c1C(C)C]
P1781
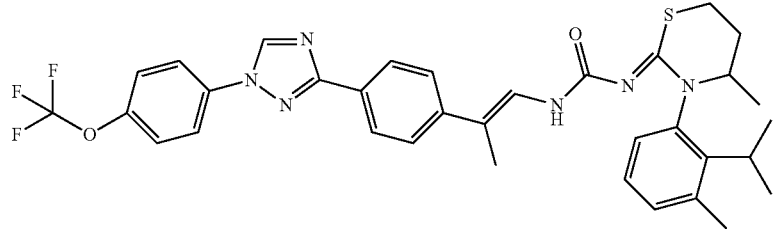 [SMILES: C/C(=C\NC(=O)/N=C1\SCCC(C)N1c1cccc(C)c1C(C)C)c1ccc(-c2ncn(-c3ccc(OC(F)(F)F)cc3)n2)cc1]
P1782
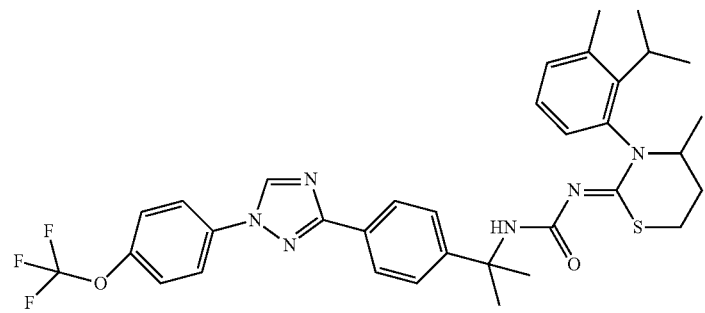 [SMILES: Cc1cccc(N2/C(=N/C(=O)NC(C)(C)c3ccc(-c4ncn(-c5ccc(OC(F)(F)F)cc5)n4)cc3)SCCC2C)c1C(C)C]
P1783
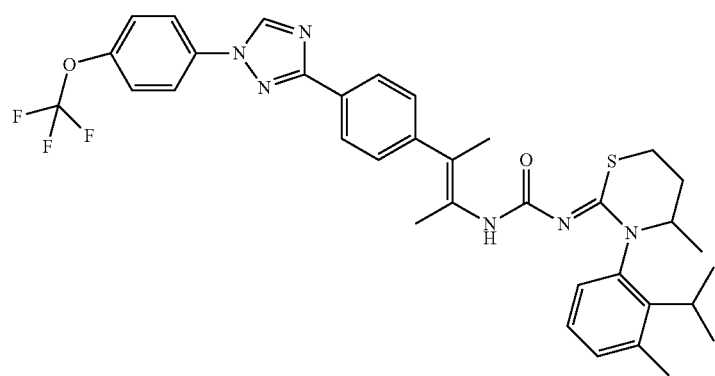 [SMILES: C/C(NC(=O)/N=C1\SCCC(C)N1c1cccc(C)c1C(C)C)=C(/C)c1ccc(-c2ncn(-c3ccc(OC(F)(F)F)cc3)n2)cc1]
P1784

TABLE P-Two-continued

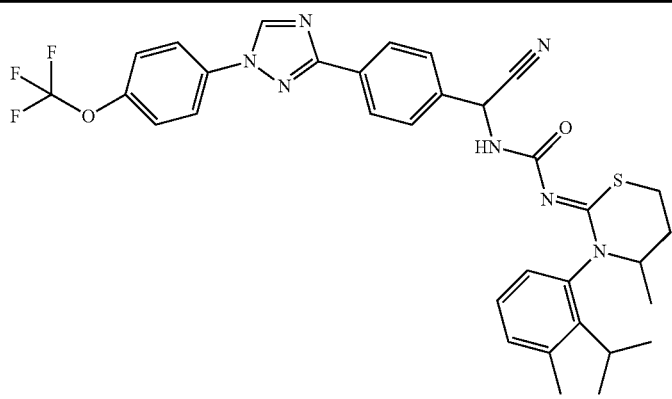

P1785

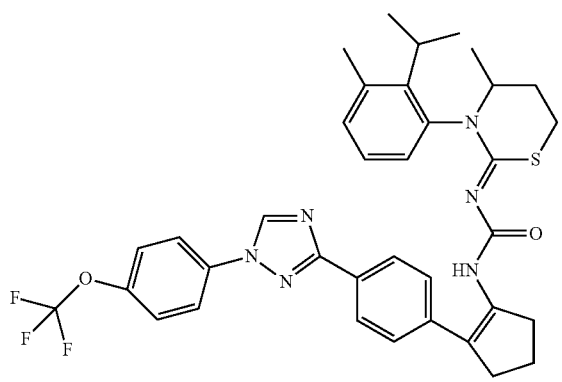 [SMILES: Cc1cccc(N2/C(=N/C(=O)NC3=C(c4ccc(-c5ncn(-c6ccc(OC(F)(F)F)cc6)n5)cc4)CCC3)SCCC2C)c1C(C)C]

P1786

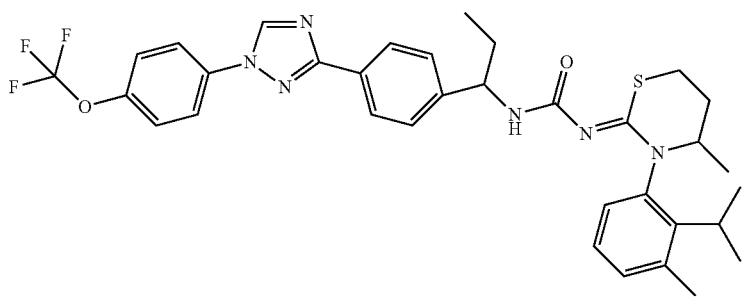 [SMILES: CCC(NC(=O)/N=C1\SCCC(C)N1c1cccc(C)c1C(C)C)c1ccc(-c2ncn(-c3ccc(OC(F)(F)F)cc3)n2)cc1]

P1787

Example A

Bioassays on Beet Armyworm (*Spodoptera exigua*) ("BAW") and Cabbage Looper (*Trichoplusia ni*) ("CL")

BAW has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. The Cabbage Looper is a member of the moth family Noctuidae. It is found throughout the world. It is attacks cabbage, cauliflower, broccoli, Brussel sprouts, tomatoes, cucumbers, potatoes, kale, turnips, mustard, peppers, eggplant, watermelons, melons, squash, cantaloupe, peas, beans, collards, lettuce, spinach, celery, parsley, beets, peas, alfalfa, soybeans, and cotton. This species is very destructive to plants due to its voracious consumption of leaves. In the case of cabbage, however, they feed not only on the wrapper leaves, but also may bore into the developing head. The larvae consume three times their weight in plant material daily. The feeding sites are marked by large accumulations of sticky, wet fecal material.

Consequently, because of the above factors control of these pests is important. Furthermore, molecules that control these pests (BAW and CL), which are known as chewing pests, are useful in controlling other pests that chew on plants.

Certain molecules disclosed in this document were tested against BAW and CEW using procedures described in the following examples. In the reporting of the results, the "BAW & CL Rating Table" was used (See Table Section).

Bioassays on BAW

Bioassays on BAW were conducted using a 128-well diet tray assay. one to five second instar BAW larvae were placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on Cabbage Looper in CL

Bioassays on CL were conducted using a 128-well diet tray assay. one to five second instar CL larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B

Bioassays on Green Peach Aphid ("GPA") (*Myzus persicae*)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides. Consequently, because of the above factors control of this pest is important. Furthermore, molecules that control this pest (GPA), which is known as a sucking pest, are useful in controlling other pests that suck on plants.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

Corrected % Control=100*(*X*−*Y*)/*X* where
X=No. of live aphids on solvent check plants and
Y=No. of live aphids on treated plants The results are indicated in the table entitled "Table ABC: Biological Results" (See Table Section).

Example C

Bioassays on Yellow Fever Mosquito "YFM" (*Aedes aegypti*)

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "break-heart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "YFM Rating Table" was used (See Table Section).

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water:acetone mixture is added to each well. A robot (Biomek® NXP Laboratory Automation Workstation) is programmed to dispense 15 µL aspirations from the master plate into an empty 96-well shallow plate ("daughter" plate). There are 6 reps ("daughter" plates) created per master. The created daughter plates are then immediately infested with YFM larvae.

The day before plates are to be treated, mosquito eggs are placed in Millipore water containing liver powder to begin hatching (4 g. into 400 mL). After the daughter plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality.

The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the molecules disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2$H (also known as deuterium) in place of $^1$H.

Molecules of Formula One may be made with different radionuclides. Of particular importance are molecules having $^{14}$C.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

In another embodiment, molecules of Formula One may be used in combination (such as, in a compositional mixture, or a simultaneous or sequential application) with one or more compounds each having a mode of action that is the same as, similar to, or different from, the mode of action ("MoA") of the molecules of Formula One. Modes of action include, for example the following: Acetylcholinesterase (AChE) inhibitors; GABA-gated chloride channel antagonists; Sodium channel modulators; Nicotinic acetylcholine (nAChR) agonists; Nicotinic acetylcholine receptor (nAChR) allosteric activators; Chloride channel activators; Juvenile hormone mimics; Miscellaneous non-specific (multi-site) inhibitors; Selective homopteran feeding blockers; Mite growth inhibitors; Microbial disruptors of insect midgut membranes; Inhibitors of mitochondrial ATP synthase; Uncouplers of oxidative phosphorylation via disruption of the proton gradient; Nicotinic acetylcholine receptor (nAChR) channel blockers; Inhibitors of chitin biosynthesis, type 0; Inhibitors of chitin biosynthesis, type 1; Moulting disruptor, Dipteran; Ecdysone receptor agonists; Octopamine receptor agonists; Mitochondrial complex III electron transport inhibitors; Mitochondrial complex I electron transport inhibitors; Voltage-dependent sodium channel blockers; Inhibitors of acetyl CoA carboxylase; Mitochondrial complex IV electron transport inhibitors; Mitochondrial complex II electron transport inhibitors; and Ryanodine receptor modulators.

In another embodiment, molecules of Formula One may be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

In another embodiment, the molecules of Formula One may be used in combination (such as, in a compositional mixture, or a simultaneous or sequential application) with one or more of the following compounds—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-diolamine, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, aciflurofen-sodium, aclonifen, acrep, acrinathrin, acrolein, acrylonitrile, acypetacs, acypetacs-copper, acypetacs-zinc, afidopyropen, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, anabasine sulfate, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzovindiflupyr, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clacyfos, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclopyrimorate, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-P-potassium, dichlorprop-P-sodium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlore, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, enoxastrobin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenoxystrobin, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halauxifen, halauxifen-methyl, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptafluthrin, heptenophos, heptopargil, herbimycin, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isofetamid, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquinbutyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxathiapiprolin, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentachlorophenyl laurate, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl) ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pyflubumide, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyriminostrobin, pyrimisulfan, pyrimitate, pyrinuron, pyriofenone, pyriprole, pyripropanol, pyriproxyfen, pyrisoxazole, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, rescalure, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolprocarb, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyricarb, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood.net/pesticides/index.html. Also consult "THE PESTICIDE MANUAL" 15th Edition, edited by C D S Tomlin, copyright 2009 by British Crop Production Council, or its prior, or more recent editions.

In another embodiment, molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on: entomopathogenic fungi (e.g. *Metarhizium anisopliae*); entomopathogenic nematodes (e.g. *Steinernema feltiae*); and entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

In another embodiment, the above possible combinations may be used in a wide variety of weight ratios. For example, a two component mixture, the weight ratio of a molecule of Formula One to another compound, can be from about 100:1 to about 1:100; in another example the weight ratio can be about 50:1 to about 1:50; in another example the weight ratio can be about 20:1 to about 1 to 20; in another example the weight ratio can be about 10:1 to about 1:10; in another example the weight ratio can be about 5:1 to 1:5; in another example the weight ratio can be about 3:1 to about 1:3; and in a final example the weight ratio can be about 1:1. However, preferably, weight ratios less than about 10:1 to about 1:10 are preferred. It is also preferred sometimes to use a three or four component mixture comprising one or more molecules of Formula One and one or more other compounds from the above possible combinations.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and 010 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. ants, aphids, beetles, bristletails, cockroaches, crickets, earwigs, fleas, flies, grasshoppers, leafhoppers, lice, locusts, mites, moths, nematodes, scales, symphylans, termites, thrips, ticks, wasps, and whiteflies.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus,* and *Pthirus pubis.*

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile,* and *Zabrus tenebrioides.*

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis,* and *Supella longipalpa.*

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anas-* trepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana, and Stomoxys calcitrans.

In another embodiment, the molecules of Formula One may be used to control pests of the Order Hemiptera. A non-exhaustive list of particular genera includes, but is not limited to, Adelges spp., Aulacaspis spp., Aphrophora spp., Aphis spp., Bemisia spp., Ceroplastes spp., Chionaspis spp., Chrysomphalus spp., Coccus spp., Empoasca spp., Lepidosaphes spp., Lagynotomus spp., Lygus spp., Macrosiphum spp., Nephotettix spp., Nezara spp., Philaenus spp., Phytocoris spp., Piezodorus spp., Planococcus spp., Pseudococcus spp., Rhopalosiphum spp., Saissetia spp., Therioaphis spp., Toumeyella spp., Toxoptera spp., Trialeurodes spp., Triatoma spp. and Unaspis spp. A non-exhaustive list of particular species includes, but is not limited to, Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis, and Zulia entrerriana.

In another embodiment, the molecules of Formula One may be used to control pests of the Order Hymenoptera. A non-exhaustive list of particular genera includes, but is not limited to, Acromyrmex spp., Atta spp., Camponotus spp., Diprion spp., Formica spp., Monomorium spp., Neodiprion spp., Pogonomyrmex spp., Polistes spp., Solenopsis spp., Vespula spp., and Xylocopa spp. A non-exhaustive list of particular species includes, but is not limited to, Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni, and Tapinoma sessile.

In another embodiment, the molecules of Formula One may be used to control pests of the Order Isoptera. A non-exhaustive list of particular genera includes, but is not limited to, Coptotermes spp., Cornitermes spp., Cryptotermes spp., Heterotermes spp., Kalotermes spp., Incisitermes spp., Macrotermes spp., Marginitermes spp., Microcerotermes spp., Procornitermes spp., Reticulitermes spp., Schedorhinotermes spp., and Zootermopsis spp. A non-exhaustive list of particular species includes, but is not limited to, Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis, and Reticulitermes virginicus.

In another embodiment, the molecules of Formula One may be used to control pests of the Order Lepidoptera. A non-exhaustive list of particular genera includes, but is not limited to, Adoxophyes spp., Agrotis spp., Argyrotaenia spp., Cacoecia spp., Caloptilia spp., Chilo spp., Chrysodeixis spp., Collas spp., Crambus spp., Diaphania spp., Diatraea spp., Earias spp., Ephestia spp., Epimecis spp., Feltia spp., Gortyna spp., Helicoverpa spp., Heliothis spp., Indarbela spp., Lithocolletis spp., Loxagrotis spp., Malacosoma spp., Peridroma spp., Phyllonorycter spp., Pseudaletia spp., Sesamia spp., Spodoptera spp., Synanthedon spp., and Yponomeuta spp. A non-exhaustive list of particular species includes, but is not limited to, Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia trans versa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda,

*Spodoptera eridania, Thecla basilides, Tineola bisselliella, Trichoplusia ni, Tuta absoluta, Zeuzera coffeae*, and *Zeuzera pyrina*.

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gaffinae*, and *Trichodectes canis*.

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothnps haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In another embodiment, the molecules of Formula One may be used to control pest of the Order Symphyla. A non-exhaustive list of particular sp. includes, but is not limited to, *Scutigerella immaculata*.

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Controlling pests of Phyla Nematoda, Arthropoda, and/or Mollusca generally means that pest populations, pest activity, or both, are reduced in an locus. This can come about when:

(a) pest populations are repulsed from a locus;

(b) pests are incapacitated in, or around, a locus; or (c) pests are exterminated in, or around, a locus.

Of course, a combination of these results can occur. Generally, pest populations, activity, or both are desirably reduced more than fifty percent, preferably more than 90 percent, and most preferably more than 98 percent. Generally, the locus is not in, or on, a human; consequently, the locus is generally a non-human locus.

In another embodiment, the locus to which a molecule of Formula One is applied can be any locus that is inhabited, or that may become inhabited, or that may be traversed, by a pest of Phyla Nematoda, Arthropoda, and/or Mollusca. For example, the locus can be:

(a) where crops, trees, fruits, cereals, fodder species, vines, turf, and/or ornamental plants, are growing;

(b) where domesticated animals are residing;

(c) the interior or exterior surfaces of buildings (such as places where grains are stored);

(d) the materials of construction used in buildings (such as impregnated wood); and (e) the soil around buildings.

Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

In another embodiment, molecules of Formula One are generally used in amounts from about 0.0001 grams per hectare to about 5000 grams per hectare to provide control. In another embodiment, it is preferred that molecules of Formula One are used in amounts from about 0.001 grams per hectare to about 500 grams per hectare. In another embodiment, it is more preferred that molecules of Formula One are used in amounts from about 0.01 gram per hectare to about 50 grams per hectare.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Table Section
TABLE 1
Structures for Intermediates
| No. | Preparation | Structure |
|---|---|---|
| C13 | Ex 9 | 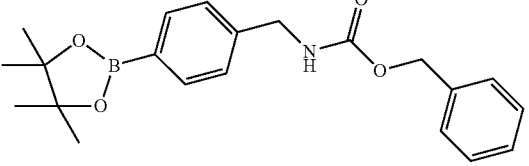 |
| C1b | Ex 1 | 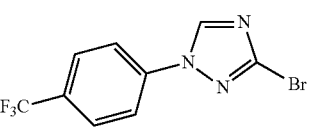 |
| C14 | Ex 10 | 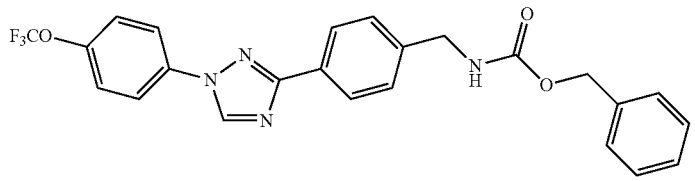 [SMILES: O=C(NCc1ccc(-c2ncn(-c3ccc(OC(F)(F)F)cc3)n2)cc1)OCc1ccccc1] |
| C8 | Ex 4 | 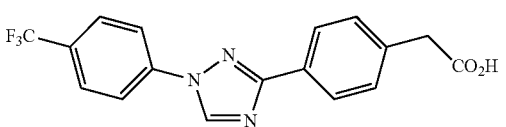 [SMILES: O=C(O)Cc1ccc(-c2ncn(-c3ccc(C(F)(F)F)cc3)n2)cc1] |
| C6 | Ex 4 | 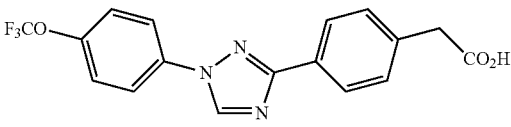 |
| C7 | Ex 4 | 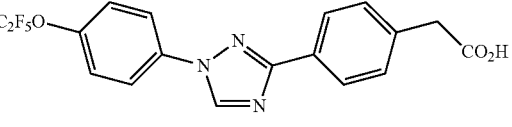 [SMILES: O=C(O)Cc1ccc(-c2ncn(-c3ccc(OC(F)(F)F)cc3)n2)cc1] |
| C15a | Ex 10a | 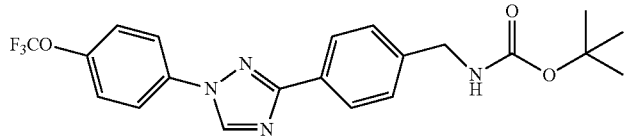 [SMILES: CC(C)(C)OC(=O)NCc1ccc(-c2ncn(-c3ccc(OC(F)(F)F)cc3)n2)cc1] |
| C16 | Ex 11 | 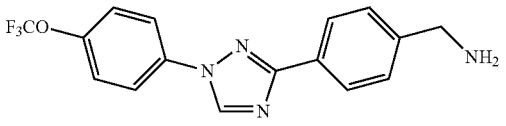 [SMILES: NCc1ccc(-c2ncn(-c3ccc(OC(F)(F)F)cc3)n2)cc1] |
| C15 | Ex 10 | 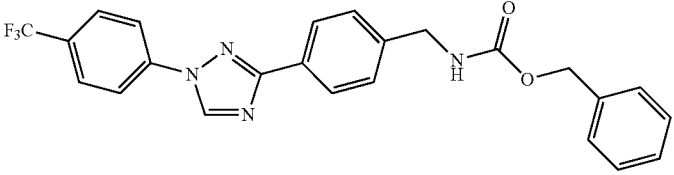 [SMILES: O=C(NCc1ccc(-c2ncn(-c3ccc(C(F)(F)F)cc3)n2)cc1)OCc1ccccc1] |
| C4 | Ex 3 | 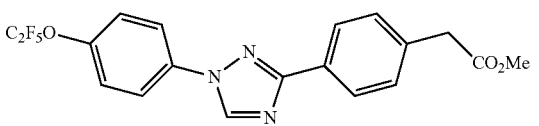 |

TABLE 1-continued

Structures for Intermediates

| No. | Preparation | Structure |
|---|---|---|
| C3 | Ex 3 | F₃CO-C₆H₄-[1,2,4-triazole]-C₆H₄-CH₂CO₂Me |
| C5 | Ex 3 | F₃C-C₆H₄-[1,2,4-triazole]-C₆H₄-CH₂CO₂Me |
| C53 | Ex 56 | F₃C-C₆H₄-[1,2,4-triazole]-C₆H₄-Br |
| C52 | Ex 56 | F₃CO-C₆H₄-[1,2,4-triazole]-C₆H₄-Br |
| C24 | Ex 24 | F₃CO-C₆H₄-[1,2,4-triazole]-C₆H₄-CH(OH)CH₃ |
| C19 | Ex 14 | F₃CO-C₆H₄-[1,2,4-triazole]-C₆H₄-(cyclopropyl)-CO₂Et |
| C20 | Ex 15 | F₃CO-C₆H₄-[1,2,4-triazole]-C₆H₄-(cyclopropyl)-CO₂H |
| C40 | Ex 43 | F₃CO-C₆H₄-[1,2,4-triazole]-C₆H₄-CH(CH₃)CH₂CO₂Et |
| C41 | Ex 44 | F₃CO-C₆H₄-[1,2,4-triazole]-C₆H₄-CH(CH₃)CH₂CO₂H |
| C37 | Ex 37 | F₃CO-C₆H₄-[1,2,4-triazole]-C₆H₄-CH₂CH(CH₃)CO₂Et |

TABLE 1-continued

Structures for Intermediates

| No. | Preparation | Structure |
|-----|-------------|-----------|
| C30 | Ex 30 | F₃CO-C₆H₄-[1,2,4-triazole]-C₆H₄-CH₂CH₂-CO₂Et |
| C32 | Ex 31 | F₃CO-C₆H₄-[1,2,4-triazole]-C₆H₄-CH₂CH₂-CO₂H |
| C31 | Ex 30 | C₂F₅O-C₆H₄-[1,2,4-triazole]-C₆H₄-CH₂CH₂-CO₂Et |
| C33 | Ex 31 | C₂F₅O-C₆H₄-[1,2,4-triazole]-C₆H₄-CH₂CH₂-CO₂H |
| C34a | Ex 32a | F₃CO-C₆H₄-[1,2,4-triazole]-C₆H₄-CH₂CH₂-NCO |
| C38 | Ex 38 | F₃CO-C₆H₄-[1,2,4-triazole]-C₆H₄-CH₂-CH(CH₃)-CO₂H |
| C39 | Ex 39 | F₃CO-C₆H₄-[1,2,4-triazole]-C₆H₄-CH₂-CH(CH₃)-NCO |
| C17 | Ex 13 | F₃CO-C₆H₄-[1,2,4-triazole]-C₆H₄-CH=CH-CO₂Et |
| C18 | Ex 13 | C₂F₅O-C₆H₄-[1,2,4-triazole]-C₆H₄-CH=CH-CO₂Et |
| C22 | Ex 20 | F₃CO-C₆H₄-[1,2,4-triazole]-C₆H₄-CH=CH-CO₂H |
| C36 | Ex 36 | F₃CO-C₆H₄-[1,2,4-triazole]-C₆H₄-CH=C(CH₃)-CO₂Et |

TABLE 1-continued

Structures for Intermediates

| No. | Preparation | Structure |
|---|---|---|
| C26 | Ex 26 | (F₃CO-phenyl)-triazole-phenyl-C(CH₃)=CH-CO₂Et |
| C27 | Ex 26 | (F₃CO-phenyl)-triazole-phenyl-C(CH₃)=CH-CO₂Et (isomer) |
| C28 | Ex 27 | (F₃CO-phenyl)-triazole-phenyl-C(CH₃)=CH-CO₂H |
| C50 | Ex 54 | (F₃CO-phenyl)-triazole-phenyl-CH₂CH₂-NH-C(=O)O-tBu |
| C55 | Ex 58 | (F₃CO-phenyl)-triazole-phenyl-CH₂CH₂-NH₃⁺ ⁻O₂CCF₃ |
| C43 | Ex 47 | (F₃CO-phenyl)-triazole-phenyl-CH=CH₂ |
| C44 | Ex 48 | (F₃CO-phenyl)-triazole-phenyl-CH₂CH₂-OH |
| C46 | Ex 50 | (F₃CO-phenyl)-triazole-phenyl-CH=C(CN)-CO₂Et |
| C47 | Ex 51 | (F₃CO-phenyl)-triazole-phenyl-CH=C(CN)-CO₂H |
| C45 | Ex 49 | (F₃CO-phenyl)-triazole-phenyl-CHF-CHF-CO₂Et |

TABLE 1-continued

Structures for Intermediates

| No. | Preparation | Structure |
|---|---|---|
| C58 | Ex 60 | 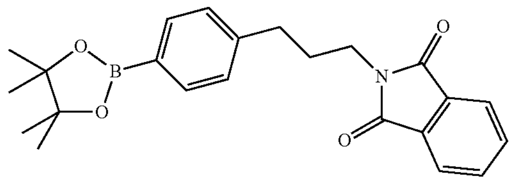 [SMILES: CC1(C)OB(c2ccc(CCCN3C(=O)c4ccccc4C3=O)cc2)OC1(C)C] |
| C59 | Ex 61 | 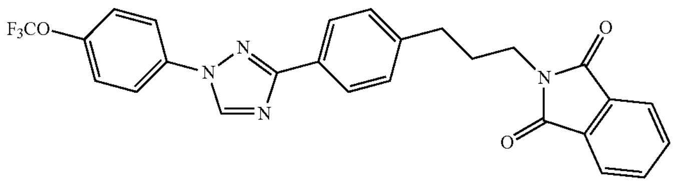 [SMILES: O=C1c2ccccc2C(=O)N1CCCc1ccc(-c2ncn(-c3ccc(OC(F)(F)F)cc3)n2)cc1] |
| C60 | Ex 62 | 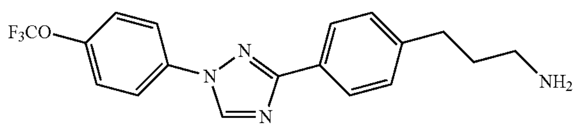 [SMILES: NCCCc1ccc(-c2ncn(-c3ccc(OC(F)(F)F)cc3)n2)cc1] |
| C61 | Ex 65 | 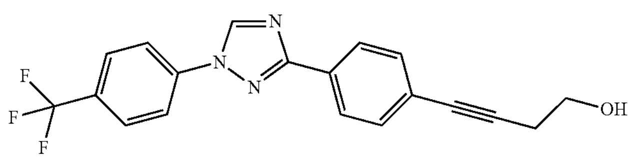 [SMILES: OCCC#Cc1ccc(-c2ncn(-c3ccc(C(F)(F)F)cc3)n2)cc1] |

TABLE 1A

Structures for Intermediates (CA)

| No. | Preparation | Structure |
|---|---|---|
| CA1 | Ex 10 | 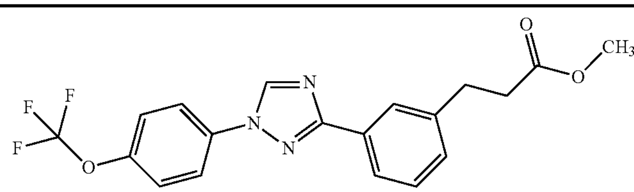 |
| CA2 | Ex 10 | 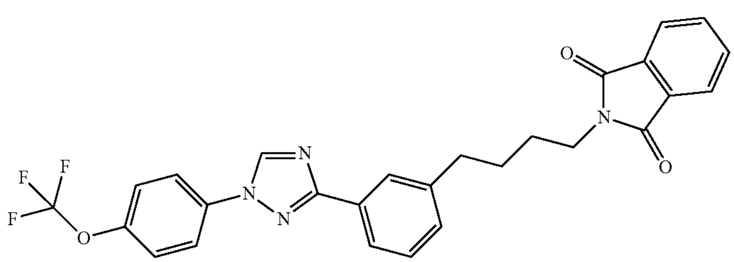 [SMILES: O=C1c2ccccc2C(=O)N1CCCCc1cccc(-c2ncn(-c3ccc(OC(F)(F)F)cc3)n2)c1] |
| CA3 | Ex 11 | 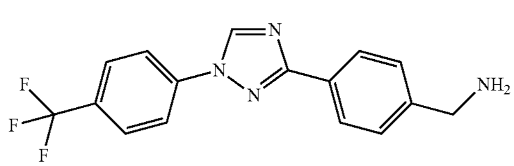 [SMILES: NCc1ccc(-c2ncn(-c3ccc(C(F)(F)F)cc3)n2)cc1] |

TABLE 1A-continued

Structures for Intermediates (CA)

| No. | Preparation | Structure |
|---|---|---|
| CA4 | Ex 13 | 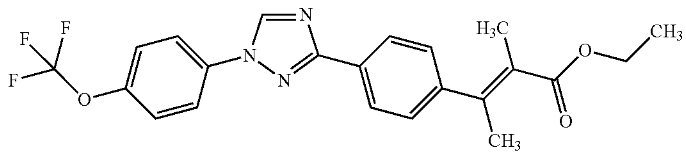 [SMILES: CCOC(=O)/C(C)=C(\C)c1ccc(-c2ncn(-c3ccc(OC(F)(F)F)cc3)n2)cc1] |
| CA5 | Ex 13 | 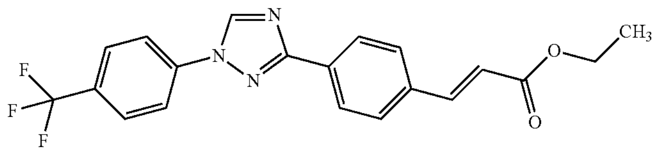 |
| CA6 | Ex 24 | 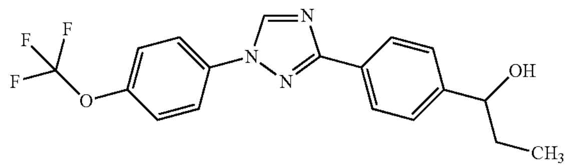 |
| CA7 | Ex 25 | 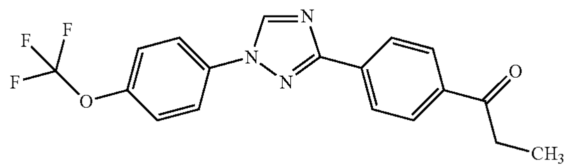 [SMILES: CCC(=O)c1ccc(-c2ncn(-c3ccc(OC(F)(F)F)cc3)n2)cc1] |
| CA8 | Ex 30 | 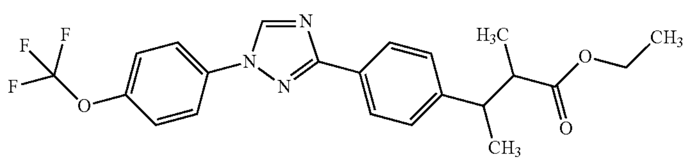 |
| CA9 | Ex 30 | 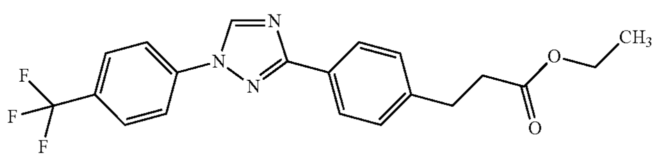 [SMILES: CCOC(=O)CCc1ccc(-c2ncn(-c3ccc(C(F)(F)F)cc3)n2)cc1] |
| CA10 | Ex 31 | 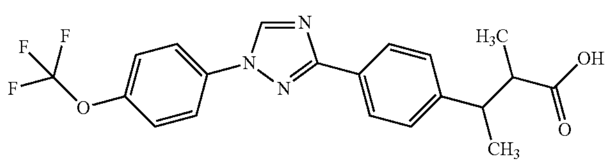 [SMILES: CC(C(=O)O)C(C)c1ccc(-c2ncn(-c3ccc(OC(F)(F)F)cc3)n2)cc1] |
| CA11 | Ex 31 | 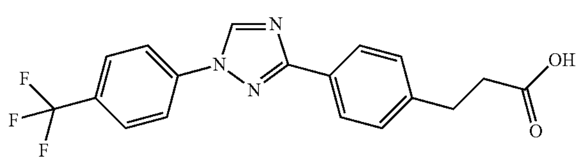 [SMILES: O=C(O)CCc1ccc(-c2ncn(-c3ccc(C(F)(F)F)cc3)n2)cc1] |
| CA12 | Ex 44 | 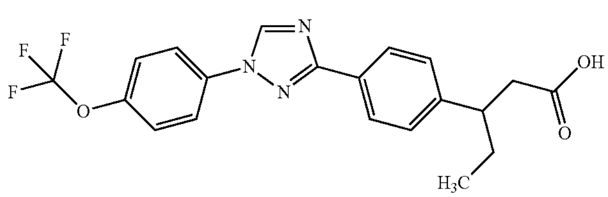 [SMILES: CCC(CC(=O)O)c1ccc(-c2ncn(-c3ccc(OC(F)(F)F)cc3)n2)cc1] |

TABLE 1A-continued
Structures for Intermediates (CA)
| No. | Preparation | Structure |
|---|---|---|
| CA13 | Ex 51 | 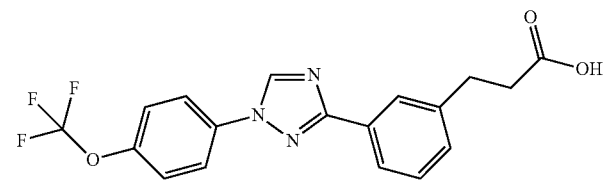 [SMILES: O=C(O)CCc1cccc(-c2ncn(-c3ccc(OC(F)(F)F)cc3)n2)c1] |
| CA14 | Ex 59 | 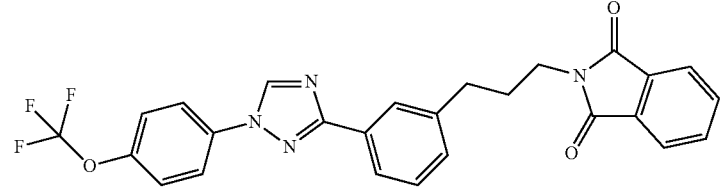 [SMILES: O=C1c2ccccc2C(=O)N1CCCc1cccc(-c2ncn(-c3ccc(OC(F)(F)F)cc3)n2)c1] |
| CA15 | Ex 59 | 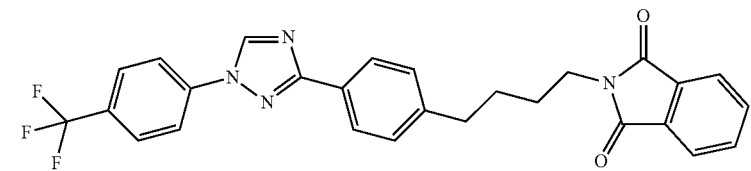 [SMILES: O=C1c2ccccc2C(=O)N1CCCCc1ccc(-c2ncn(-c3ccc(C(F)(F)F)cc3)n2)cc1] |
| CA16 | Ex 59 | 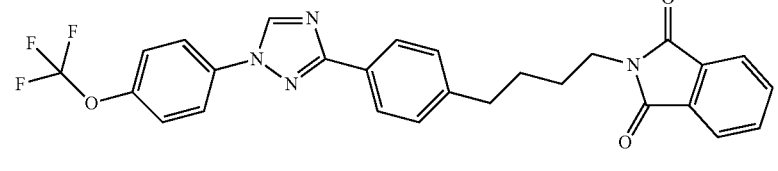 |
| CA17 | Ex 59 | 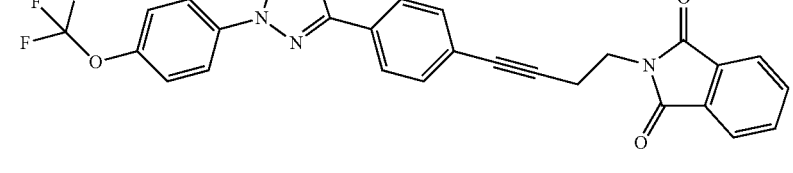 |
| CA18 | Ex 62 | 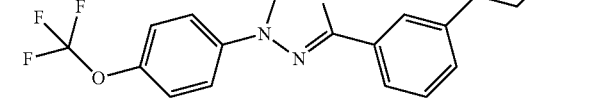 |
| CA19 | Ex 62 | 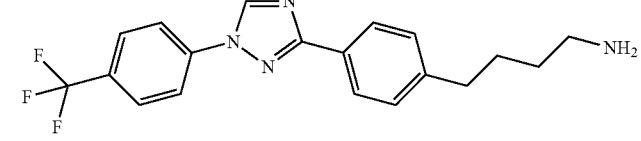 |
| CA20 | Ex 62 | 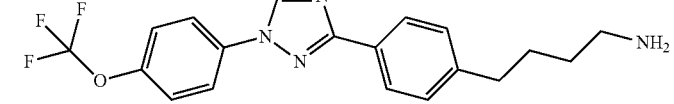 |
| CA21 | Ex 62 | 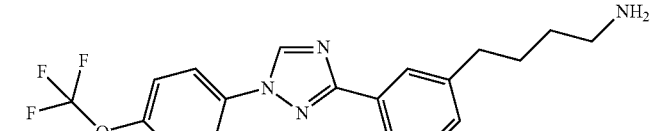 |

TABLE 1A-continued

Structures for Intermediates (CA)

| No. | Preparation | Structure |
|---|---|---|
| CA22 | Ex 62 | 1-(4-(trifluoromethoxy)phenyl)-3-(4-(4-aminobut-1-yn-1-yl)phenyl)-1H-1,2,4-triazole |
| CA23 | Ex 65 | 1-(4-(trifluoromethoxy)phenyl)-3-(4-(4-hydroxybut-1-yn-1-yl)phenyl)-1H-1,2,4-triazole |
| CA24 | Ex 66 | 1-(4-(trifluoromethyl)phenyl)-3-(4-(4-hydroxybutyl)phenyl)-1H-1,2,4-triazole |
| CA25 | Ex 66 | 1-(4-(trifluoromethoxy)phenyl)-3-(4-(4-hydroxybutyl)phenyl)-1H-1,2,4-triazole |
| CA26 | Ex 66 | 4-methyl-2-amino-1-propylbenzene |
| CA33 | Ex 68 | N-((5-methyl-2-propylphenyl)carbamothioyl)benzamide |
| CA35 | Ex 68 | N-((2-isopropyl-5-methoxyphenyl)carbamothioyl)benzamide |
| CA36 | Ex 68 | N-((2-ethyl-5-methylphenyl)carbamothioyl)benzamide |

TABLE 1A-continued

Structures for Intermediates (CA)

| No. | Preparation | Structure |
|---|---|---|
| CA37 | Ex 68 | 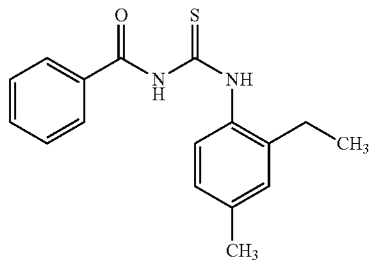 [SMILES: CCc1cc(C)ccc1NC(=S)NC(=O)c1ccccc1] |
| CA38 | Ex 69 | 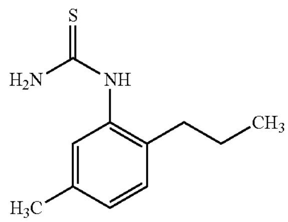 |
| CA40 | Ex 69 | 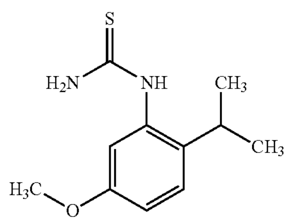 |
| CA41 | Ex 69 | 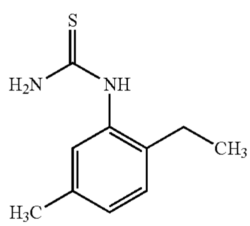 |
| CA42 | Ex 69 | 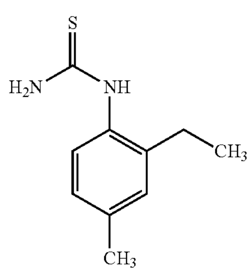 |
| CA44 | Ex 74 | 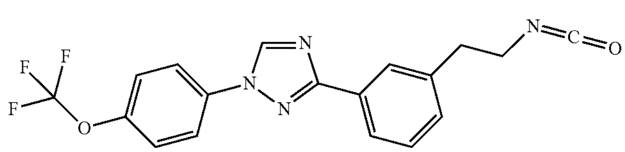 [SMILES: O=C=NCCc1cccc(-c2ncn(-c3ccc(OC(F)(F)F)cc3)n2)c1] |
| CA45 | Ex 76 | 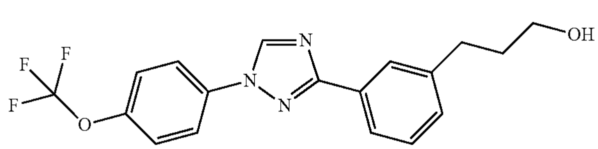 [SMILES: OCCCc1cccc(-c2ncn(-c3ccc(OC(F)(F)F)cc3)n2)c1] |

TABLE 1A-continued

Structures for Intermediates (CA)

| No. | Preparation | Structure |
|---|---|---|
| CA48 | Ex 81 | 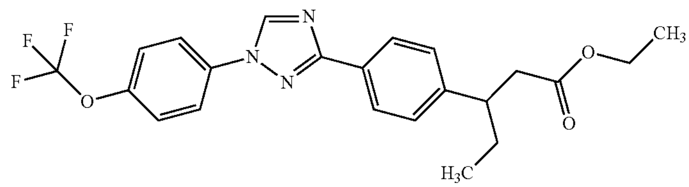 [SMILES: CCOC(=O)CC(CC)c1ccc(-c2ncn(-c3ccc(OC(F)(F)F)cc3)n2)cc1] |
| CA49 | Ex 83 | 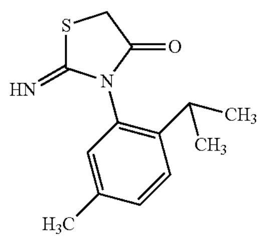 [SMILES: Cc1ccc(C(C)C)c(N2C(=N)SCC2=O)c1] |
| CA50 | Ex 84 | 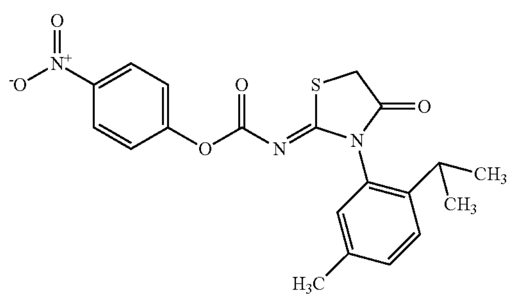 |
| CA51 | Ex 58a | 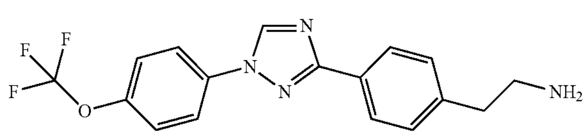 [SMILES: NCCc1ccc(-c2ncn(-c3ccc(OC(F)(F)F)cc3)n2)cc1] |

TABLE 1B

Structures for Intermediates (PC)

| No. | Preparation | Structure |
|---|---|---|
| PC1 | Ex 71 | 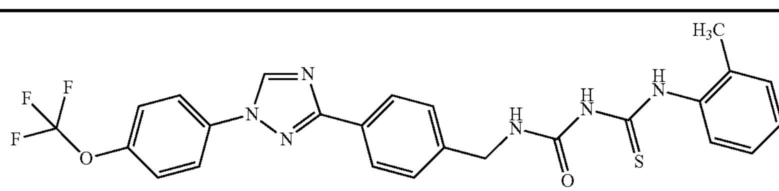 |
| PC2 | Ex 71 | 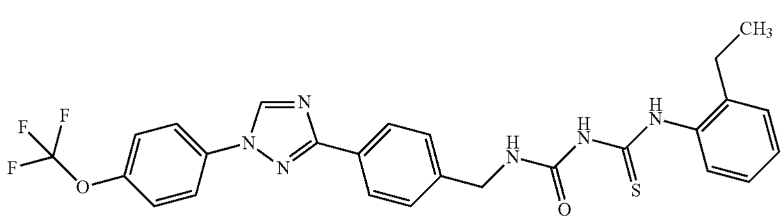 [SMILES: CCc1ccccc1NC(=S)NC(=O)NCc1ccc(-c2ncn(-c3ccc(OC(F)(F)F)cc3)n2)cc1] |

TABLE 1B-continued

Structures for Intermediates (PC)

| No. | Preparation | Structure |
|---|---|---|
| PC3 | Ex 71 | 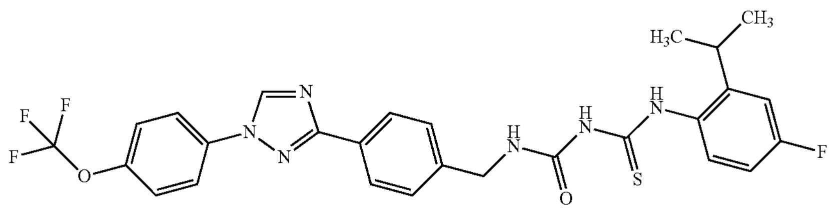 [SMILES: CC(C)c1cc(F)ccc1NC(=S)NC(=O)NCc1ccc(-c2ncn(-c3ccc(OC(F)(F)F)cc3)n2)cc1] |
| PC5 | Ex 71 | 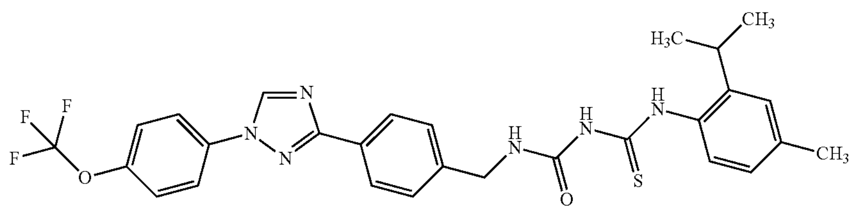 [SMILES: Cc1ccc(NC(=S)NC(=O)NCc2ccc(-c3ncn(-c4ccc(OC(F)(F)F)cc4)n3)cc2)c(C(C)C)c1] |
| PC6 | Ex 71 | 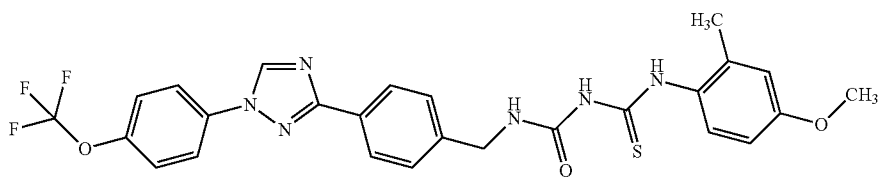 [SMILES: COc1ccc(NC(=S)NC(=O)NCc2ccc(-c3ncn(-c4ccc(OC(F)(F)F)cc4)n3)cc2)c(C)c1] |
| PC7 | Ex 71 | 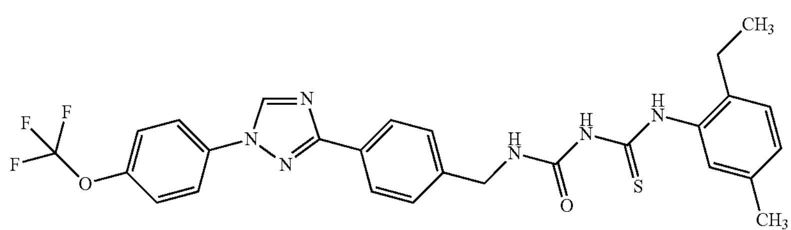 [SMILES: CCc1ccc(C)cc1NC(=S)NC(=O)NCc1ccc(-c2ncn(-c3ccc(OC(F)(F)F)cc3)n2)cc1] |
| PC8 | Ex 71 | 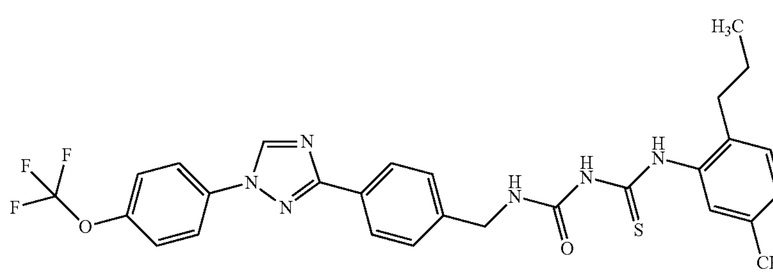 |
| PC14 | Ex 71 | 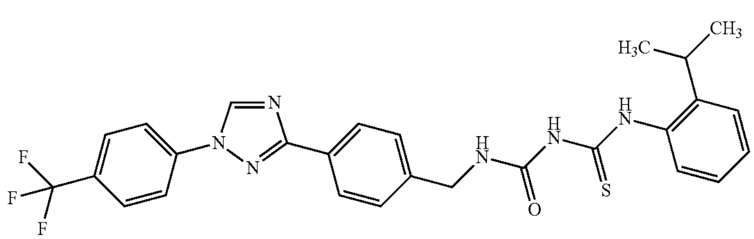 [SMILES: CC(C)c1ccccc1NC(=S)NC(=O)NCc1ccc(-c2ncn(-c3ccc(C(F)(F)F)cc3)n2)cc1] |

TABLE 1B-continued

Structures for Intermediates (PC)

| No. | Preparation | Structure |
|---|---|---|
| PC15 | Ex 71 | 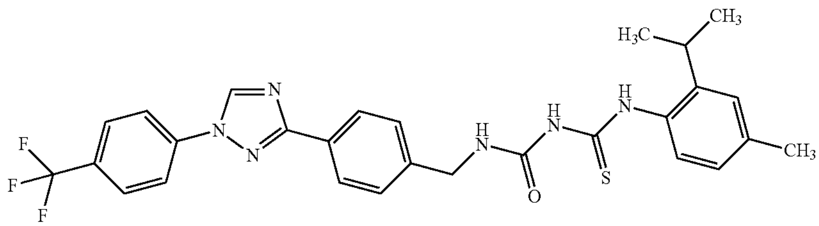 [SMILES: Cc1ccc(NC(=S)NC(=O)NCc2ccc(-c3ncn(-c4ccc(C(F)(F)F)cc4)n3)cc2)c(C(C)C)c1] |
| PC16 | Ex 71 | 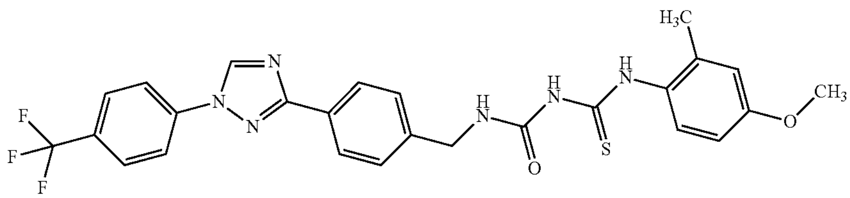 [SMILES: COc1ccc(NC(=S)NC(=O)NCc2ccc(-c3ncn(-c4ccc(C(F)(F)F)cc4)n3)cc2)c(C)c1] |
| PC74 | Ex 75 | 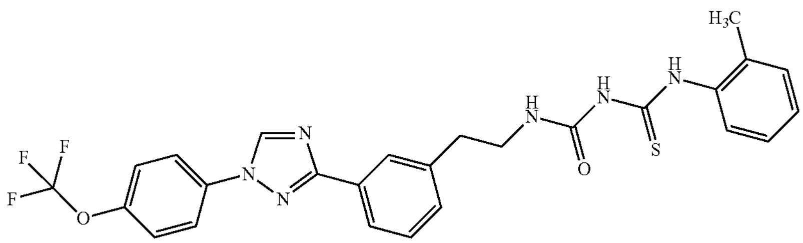 [SMILES: Cc1ccccc1NC(=S)NC(=O)NCCc1cccc(-c2ncn(-c3ccc(OC(F)(F)F)cc3)n2)c1] |
| PC75 | Ex 75 | 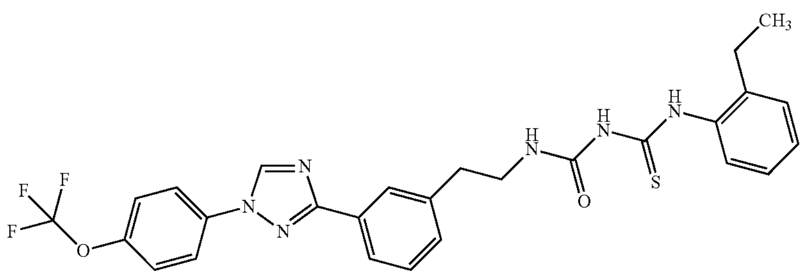 [SMILES: CCc1ccccc1NC(=S)NC(=O)NCCc1cccc(-c2ncn(-c3ccc(OC(F)(F)F)cc3)n2)c1] |
| PC76 | Ex 75 | 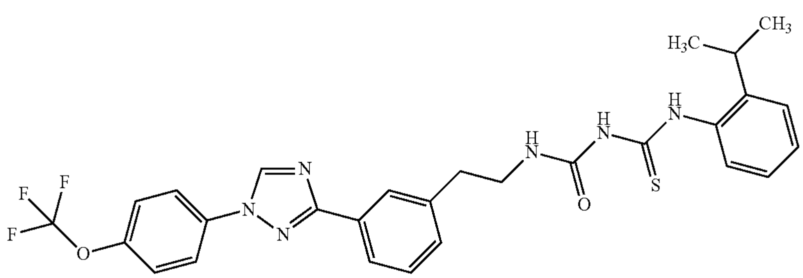 [SMILES: CC(C)c1ccccc1NC(=S)NC(=O)NCCc1cccc(-c2ncn(-c3ccc(OC(F)(F)F)cc3)n2)c1] |
| PC80 | Ex 75 | 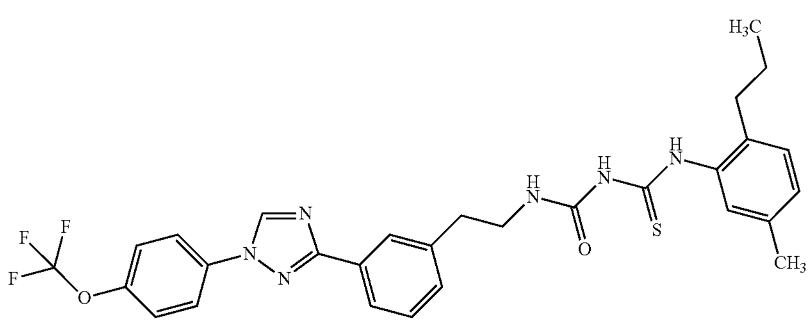 [SMILES: CCCc1ccc(C)cc1NC(=S)NC(=O)NCCc1cccc(-c2ncn(-c3ccc(OC(F)(F)F)cc3)n2)c1] |

TABLE 1B-continued
Structures for Intermediates (PC)
| No. | Preparation | Structure |
|-----|-------------|-----------|
| PC81 | Ex 75 | 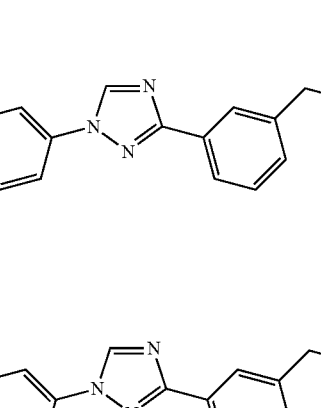 |
| PC83 | Ex 75 | 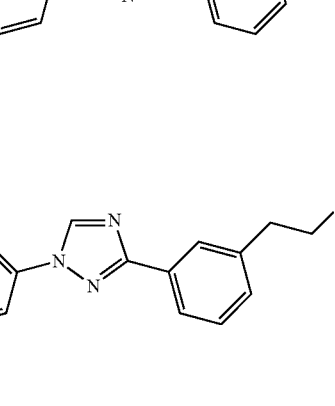 |
| PC84 | Ex 75 | 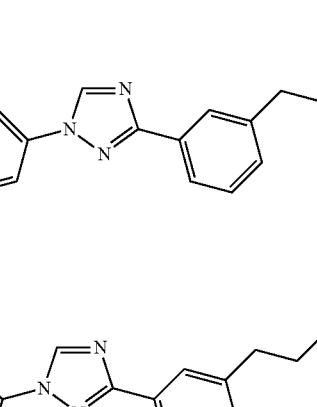 |
| PC85 | Ex 75 | 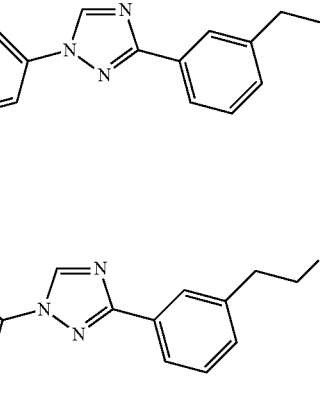 |
| PC87 | Ex 75 | 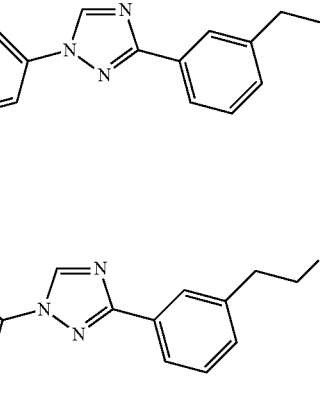 |
| PC92 | Ex 63 | 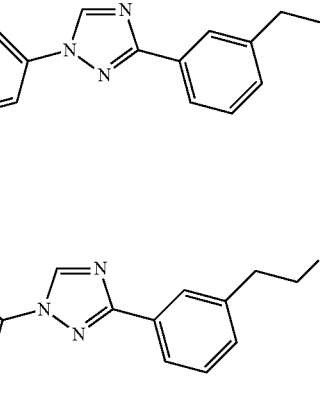 |

TABLE 1B-continued

Structures for Intermediates (PC)

| No. | Preparation | Structure |
|---|---|---|
| PC93 | Ex 63 | 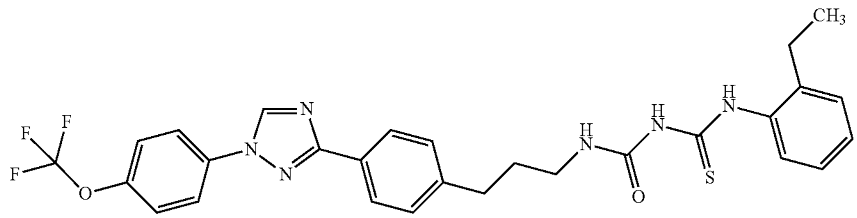 [SMILES: CCc1ccccc1NC(=S)NC(=O)NCCCc1ccc(-c2ncn(-c3ccc(OC(F)(F)F)cc3)n2)cc1] |
| PC94 | Ex 63 | 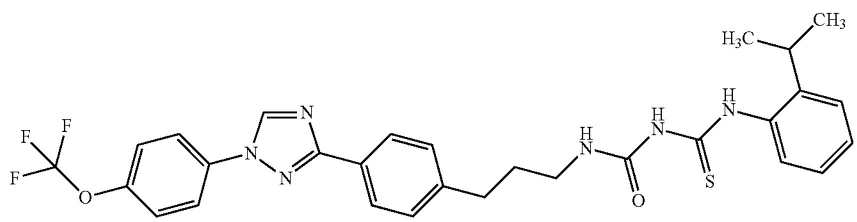 [SMILES: CC(C)c1ccccc1NC(=S)NC(=O)NCCCc1ccc(-c2ncn(-c3ccc(OC(F)(F)F)cc3)n2)cc1] |
| PC99 | Ex 63 | 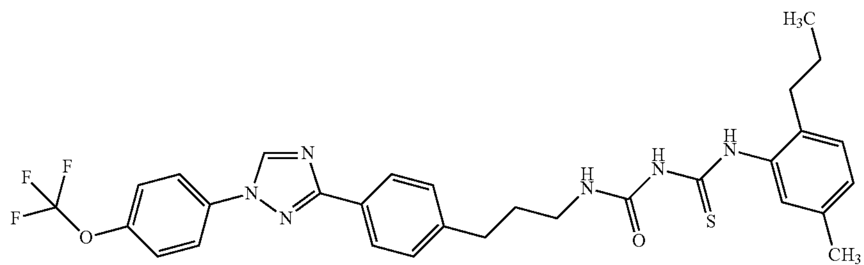 [SMILES: CCCc1ccc(C)cc1NC(=S)NC(=O)NCCCc1ccc(-c2ncn(-c3ccc(OC(F)(F)F)cc3)n2)cc1] |
| PC101 | Ex 63 | 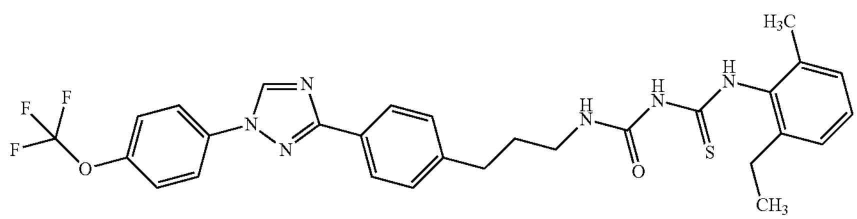 [SMILES: CCc1cccc(C)c1NC(=S)NC(=O)NCCCc1ccc(-c2ncn(-c3ccc(OC(F)(F)F)cc3)n2)cc1] |
| PC102 | Ex 63 | 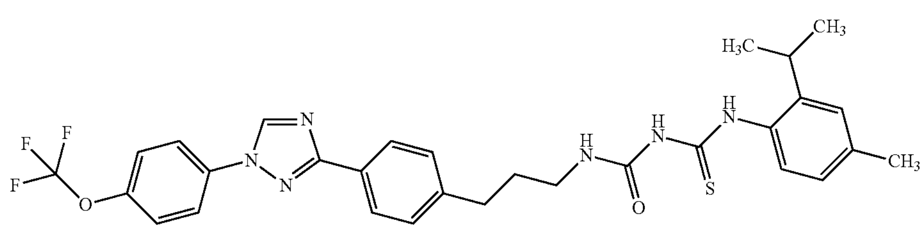 [SMILES: Cc1ccc(NC(=S)NC(=O)NCCCc2ccc(-c3ncn(-c4ccc(OC(F)(F)F)cc4)n3)cc2)c(C(C)C)c1] |
| PC103 | Ex 63 | 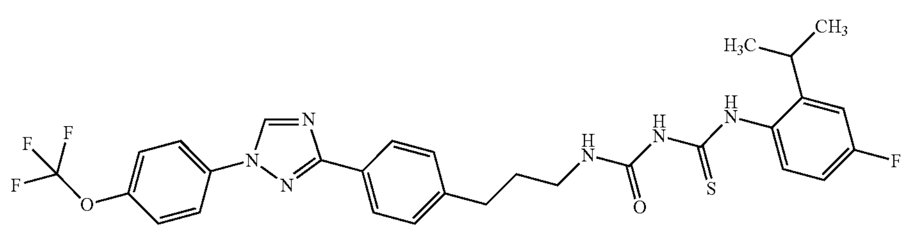 [SMILES: CC(C)c1cc(F)ccc1NC(=S)NC(=O)NCCCc1ccc(-c2ncn(-c3ccc(OC(F)(F)F)cc3)n2)cc1] |

TABLE 1B-continued
Structures for Intermediates (PC)
| No. | Preparation | Structure |
|---|---|---|
| PC105 | Ex 63 | 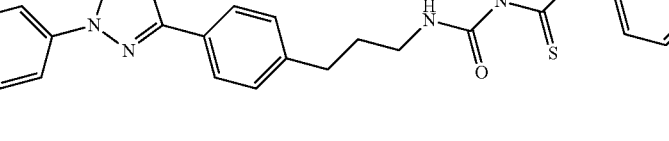 |
| PC118 | Ex 63 | 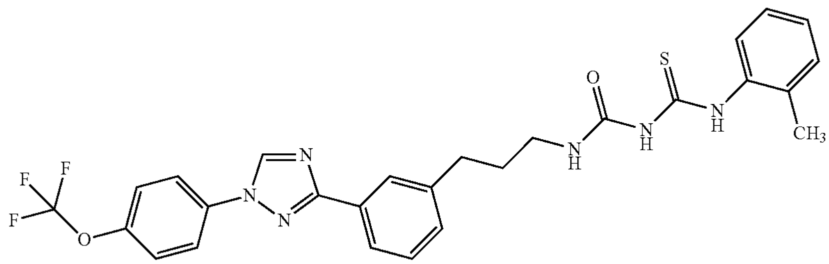 [SMILES: Cc1ccccc1NC(=S)NC(=O)NCCCc1cccc(-c2ncn(-c3ccc(OC(F)(F)F)cc3)n2)c1] |
| PC119 | Ex 63 | 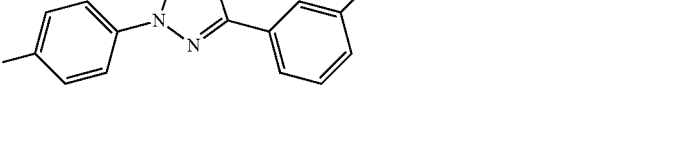 |
| PC120 | Ex 63 | 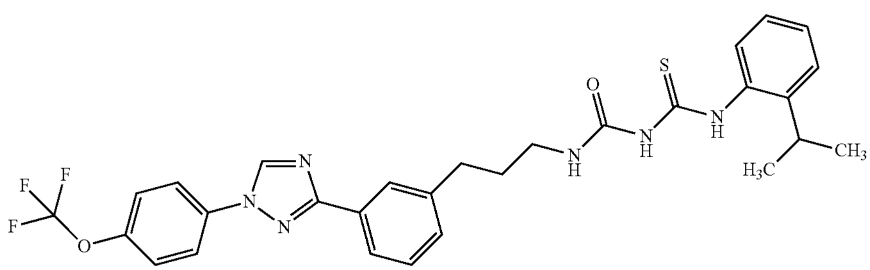 [SMILES: CC(C)c1ccccc1NC(=S)NC(=O)NCCCc1cccc(-c2ncn(-c3ccc(OC(F)(F)F)cc3)n2)c1] |
| PC124 | Ex 63 | 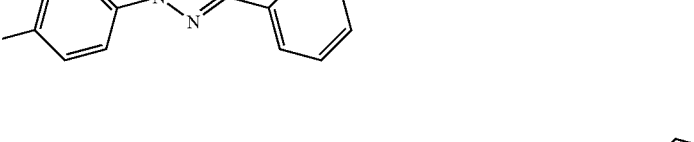 |

TABLE 1B-continued
Structures for Intermediates (PC)
| No. | Preparation | Structure |
|---|---|---|
| PC125 | Ex 63 | 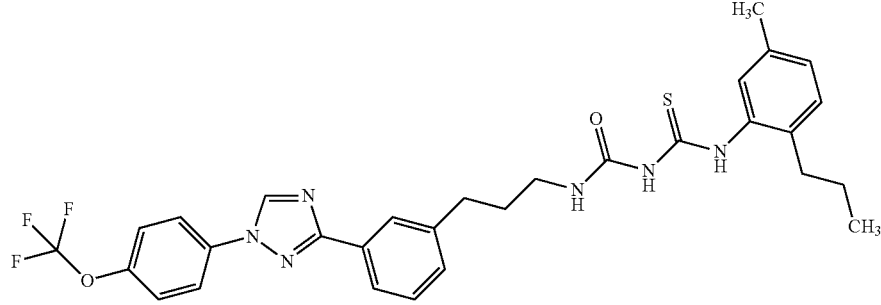 [SMILES: CCCc1ccc(C)cc1NC(=S)NC(=O)NCCCc1cccc(-c2ncn(-c3ccc(OC(F)(F)F)cc3)n2)c1] |
| PC127 | Ex 63 | 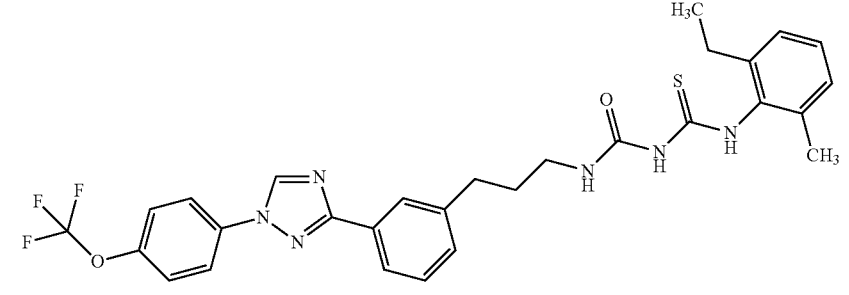 [SMILES: CCc1cccc(C)c1NC(=S)NC(=O)NCCCc1cccc(-c2ncn(-c3ccc(OC(F)(F)F)cc3)n2)c1] |
| PC128 | Ex 63 | 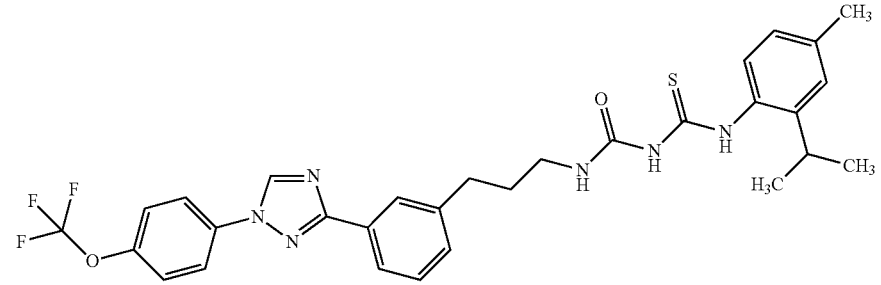 [SMILES: Cc1ccc(NC(=S)NC(=O)NCCCc2cccc(-c3ncn(-c4ccc(OC(F)(F)F)cc4)n3)c2)c(C(C)C)c1] |
| PC129 | Ex 63 | 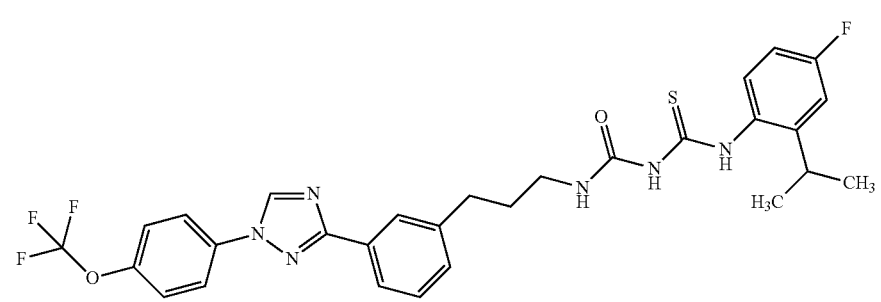 [SMILES: CC(C)c1cc(F)ccc1NC(=S)NC(=O)NCCCc1cccc(-c2ncn(-c3ccc(OC(F)(F)F)cc3)n2)c1] |
| PC131 | Ex 63 | 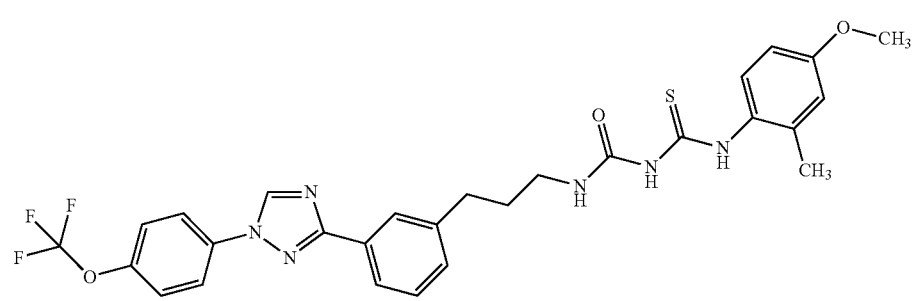 [SMILES: COc1ccc(NC(=S)NC(=O)NCCCc2cccc(-c3ncn(-c4ccc(OC(F)(F)F)cc4)n3)c2)c(C)c1] |

TABLE 1B-continued

Structures for Intermediates (PC)

| No. | Preparation | Structure |
| --- | --- | --- |
| PC144 | Ex 63 | 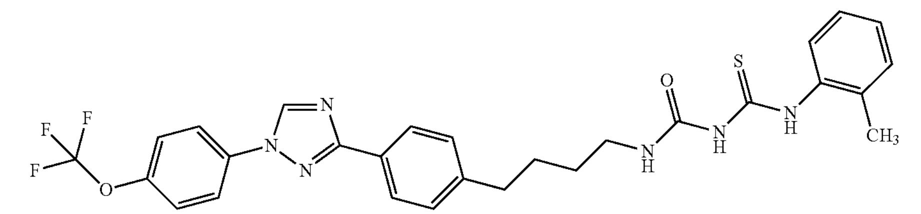 [SMILES: Cc1ccccc1NC(=S)NC(=O)NCCCCc1ccc(-c2ncn(-c3ccc(OC(F)(F)F)cc3)n2)cc1] |
| PC145 | Ex 63 | 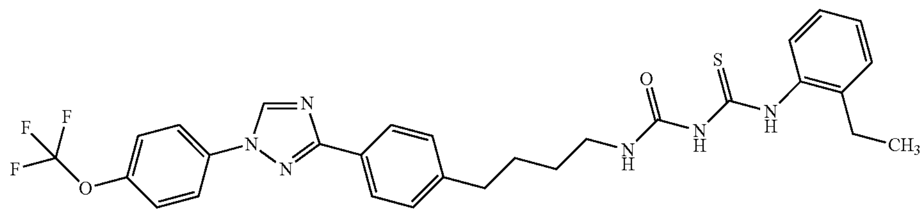 [SMILES: CCc1ccccc1NC(=S)NC(=O)NCCCCc1ccc(-c2ncn(-c3ccc(OC(F)(F)F)cc3)n2)cc1] |
| PC146 | Ex 63 | 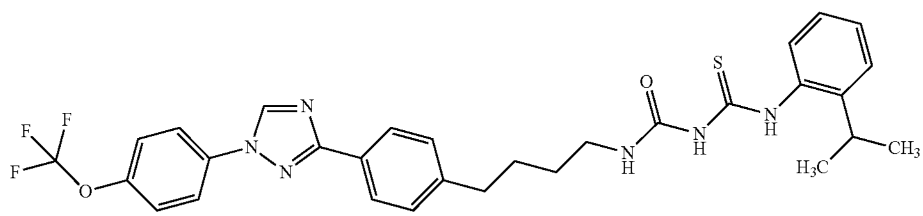 [SMILES: CC(C)c1ccccc1NC(=S)NC(=O)NCCCCc1ccc(-c2ncn(-c3ccc(OC(F)(F)F)cc3)n2)cc1] |
| PC150 | Ex 63 | 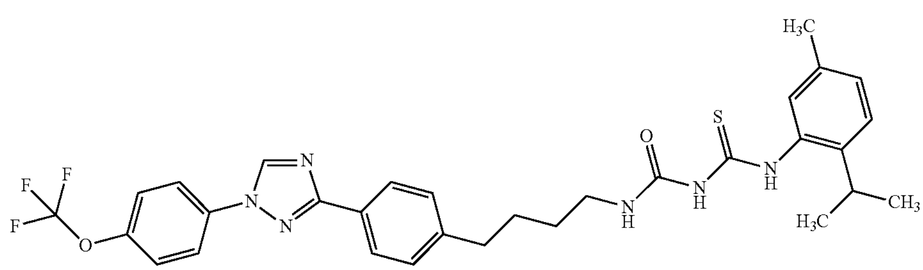 [SMILES: Cc1ccc(C(C)C)c(NC(=S)NC(=O)NCCCCc2ccc(-c3ncn(-c4ccc(OC(F)(F)F)cc4)n3)cc2)c1] |
| PC151 | Ex 63 | 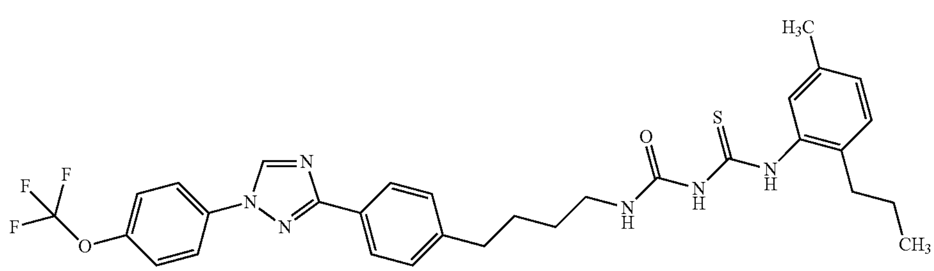 [SMILES: CCCc1ccc(C)cc1NC(=S)NC(=O)NCCCCc1ccc(-c2ncn(-c3ccc(OC(F)(F)F)cc3)n2)cc1] |
| PC152 | Ex 63 | 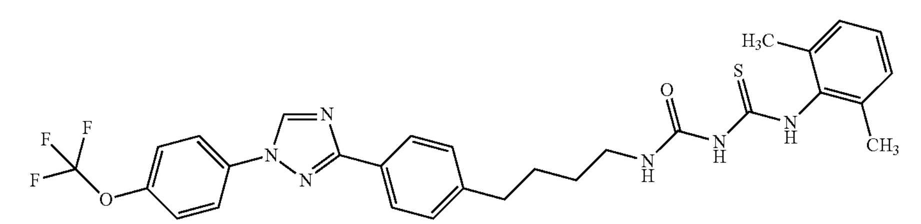 [SMILES: Cc1cccc(C)c1NC(=S)NC(=O)NCCCCc1ccc(-c2ncn(-c3ccc(OC(F)(F)F)cc3)n2)cc1] |

TABLE 1B-continued

Structures for Intermediates (PC)

| No. | Preparation | Structure |
|---|---|---|
| PC153 | Ex 63 | 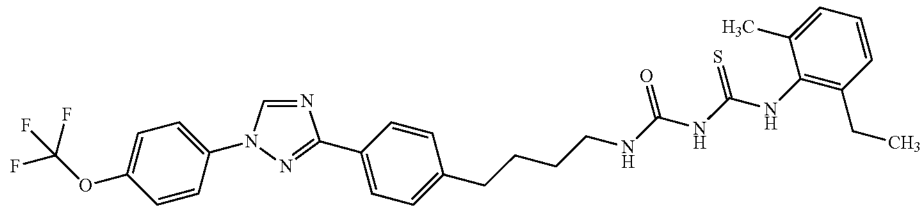 [SMILES: CCc1cccc(C)c1NC(=S)NC(=O)NCCCCc1ccc(-c2ncn(-c3ccc(OC(F)(F)F)cc3)n2)cc1] |
| PC154 | Ex 63 | 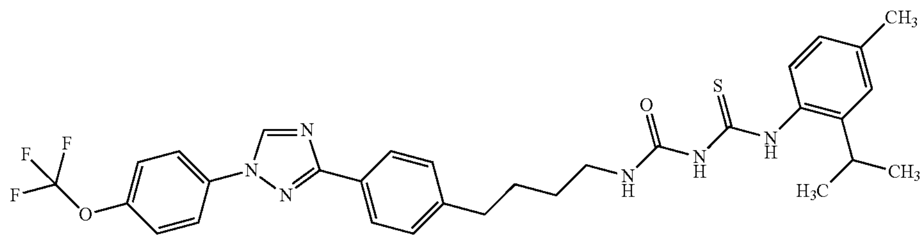 [SMILES: Cc1ccc(NC(=S)NC(=O)NCCCCc2ccc(-c3ncn(-c4ccc(OC(F)(F)F)cc4)n3)cc2)c(C(C)C)c1] |
| PC155 | Ex 63 | 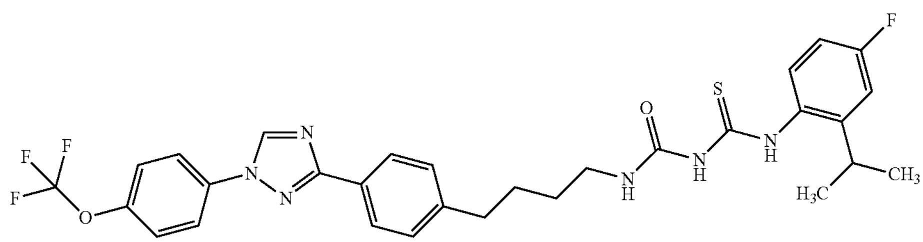 |
| PC156 | Ex 63 | 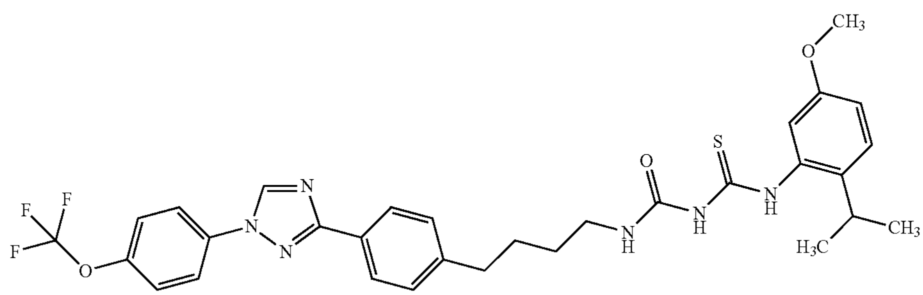 [SMILES: COc1ccc(C(C)C)c(NC(=S)NC(=O)NCCCCc2ccc(-c3ncn(-c4ccc(OC(F)(F)F)cc4)n3)cc2)c1] |
| PC159 | Ex 63 | 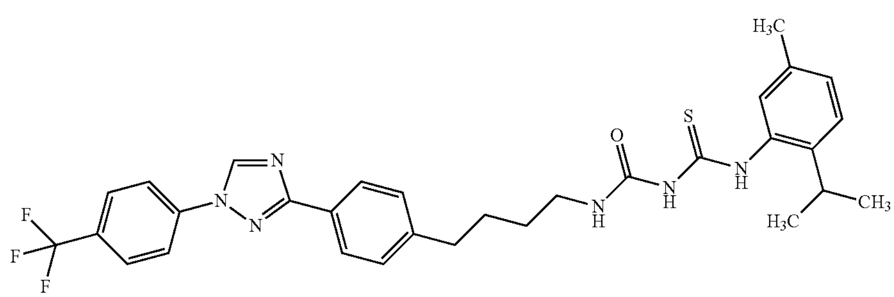 [SMILES: Cc1ccc(C(C)C)c(NC(=S)NC(=O)NCCCCc2ccc(-c3ncn(-c4ccc(C(F)(F)F)cc4)n3)cc2)c1] |
| PC160 | Ex 63 | 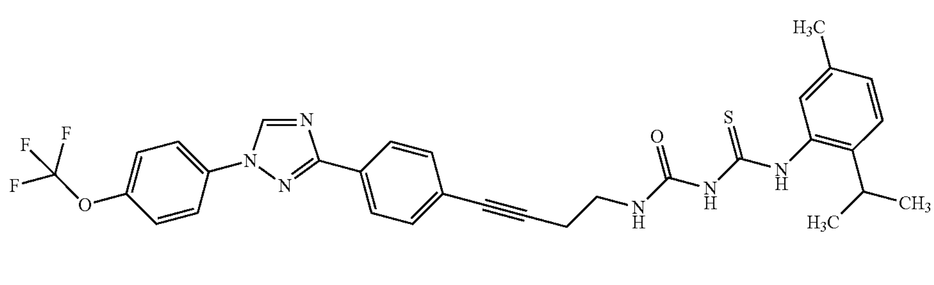 [SMILES: Cc1ccc(C(C)C)c(NC(=S)NC(=O)NCCC#Cc2ccc(-c3ncn(-c4ccc(OC(F)(F)F)cc4)n3)cc2)c1] |

TABLE 1B-continued
Structures for Intermediates (PC)
| No. | Preparation | Structure |
|---|---|---|
| PC170 | Ex 63 | 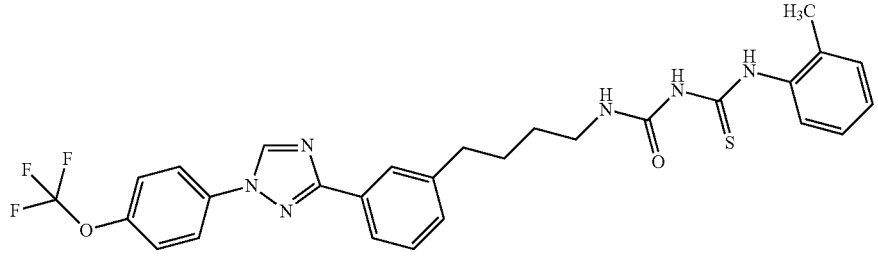 [SMILES: Cc1ccccc1NC(=S)NC(=O)NCCCCc1cccc(-c2ncn(-c3ccc(OC(F)(F)F)cc3)n2)c1] |
| PC171 | Ex 63 | 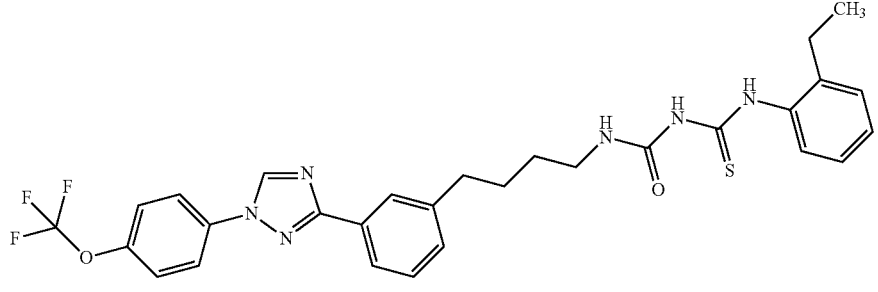 [SMILES: CCc1ccccc1NC(=S)NC(=O)NCCCCc1cccc(-c2ncn(-c3ccc(OC(F)(F)F)cc3)n2)c1] |
| PC172 | Ex 63 | 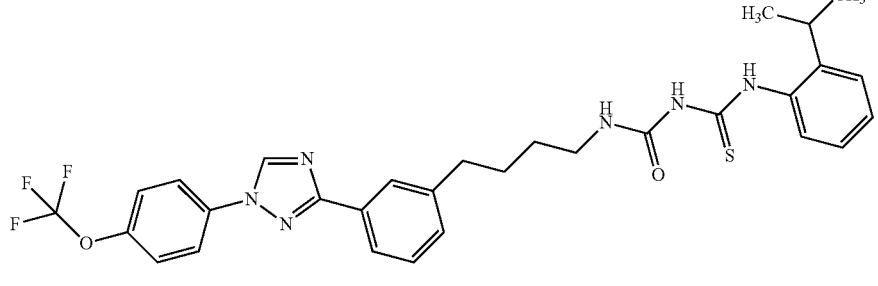 |
| PC176 | Ex 63 | 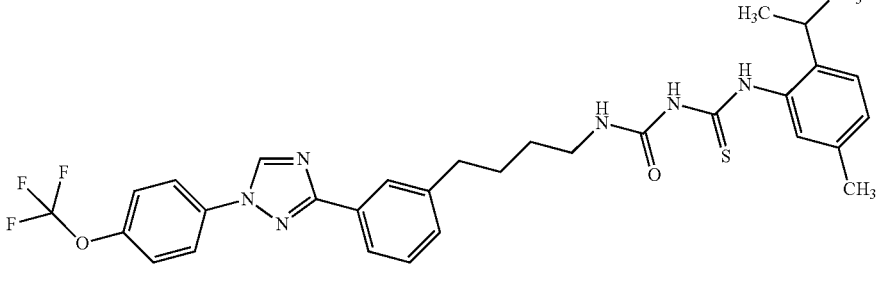 |
| PC179 | Ex 63 | 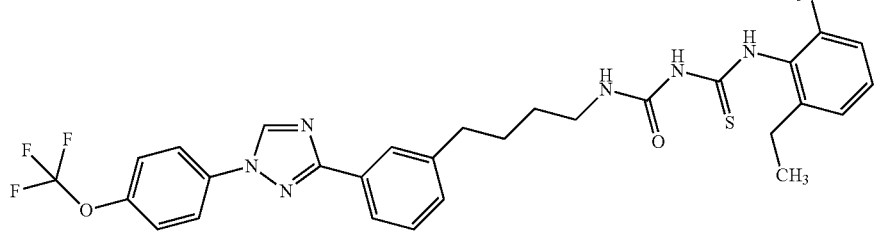 |

TABLE 1B-continued
Structures for Intermediates (PC)
| No. | Preparation | Structure |
|---|---|---|
| PC180 | Ex 63 | 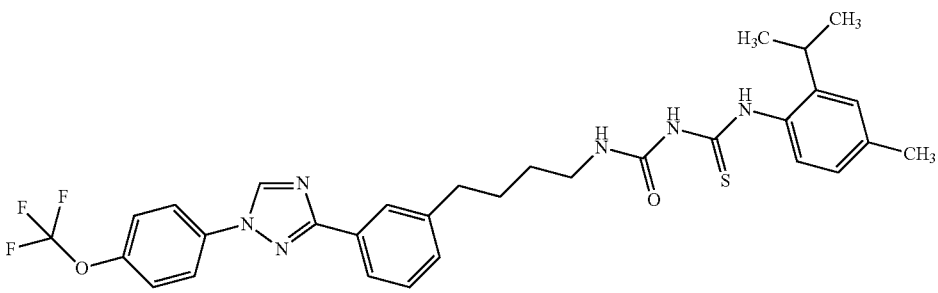 [SMILES: Cc1ccc(NC(=S)NC(=O)NCCCCc2cccc(-c3ncn(-c4ccc(OC(F)(F)F)cc4)n3)c2)c(C(C)C)c1] |
| PC181 | Ex 63 | 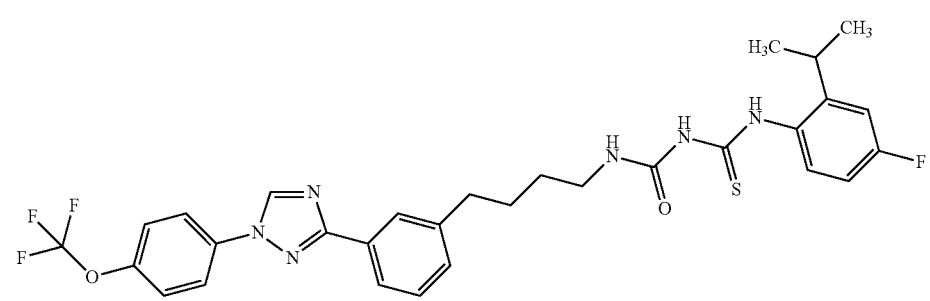 [SMILES: CC(C)c1cc(F)ccc1NC(=S)NC(=O)NCCCCc1cccc(-c2ncn(-c3ccc(OC(F)(F)F)cc3)n2)c1] |
| PC182 | Ex 63 | 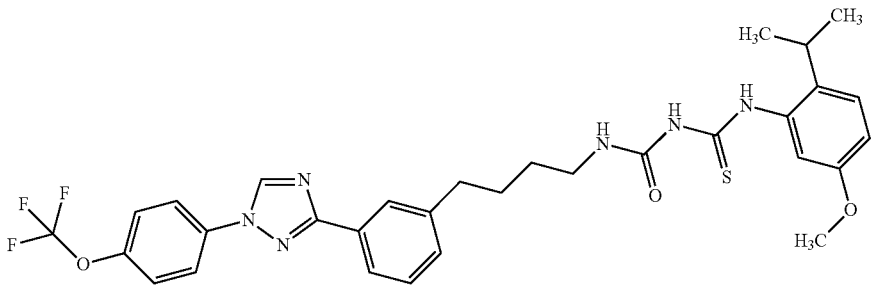 [SMILES: COc1ccc(C(C)C)c(NC(=S)NC(=O)NCCCCc2cccc(-c3ncn(-c4ccc(OC(F)(F)F)cc4)n3)c2)c1] |
TABLE 1C
Structures for Intermediates (CB)
| No. | Preparation | Structure |
|---|---|---|
| CB2 | Ex 8 | 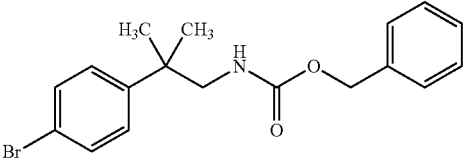 [SMILES: CC(C)(CNC(=O)OCc1ccccc1)c1ccc(Br)cc1] |
| CB3 | Ex 8 | 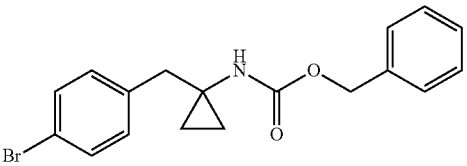 [SMILES: O=C(NC1(Cc2ccc(Br)cc2)CC1)OCc1ccccc1] |

TABLE 1C-continued

Structures for Intermediates (CB)

| No. | Preparation | Structure |
|---|---|---|
| CB7 | Ex 9 | 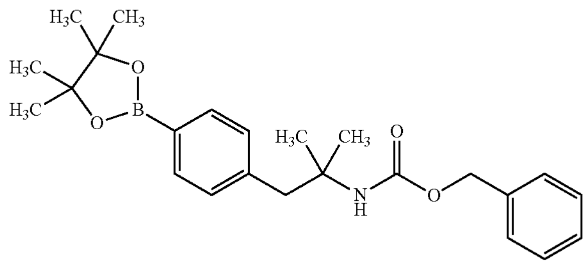 [SMILES: CC(C)(Cc1ccc(B2OC(C)(C)C(C)(C)O2)cc1)NC(=O)OCc1ccccc1] |
| CB8 | Ex 9 | 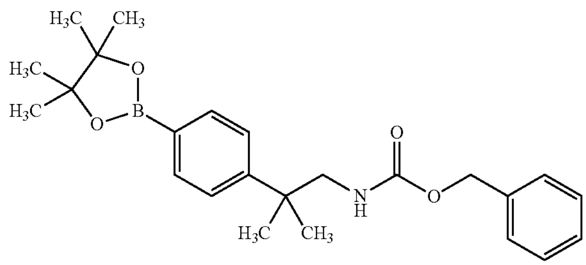 [SMILES: CC(C)(CNC(=O)OCc1ccccc1)c1ccc(B2OC(C)(C)C(C)(C)O2)cc1] |
| CB9 | Ex 9 | 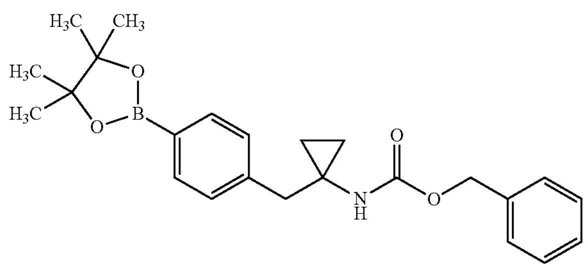 [SMILES: CC1(C)OB(c2ccc(CC3(NC(=O)OCc4ccccc4)CC3)cc2)OC1(C)C] |
| CB10 | Ex 10 | 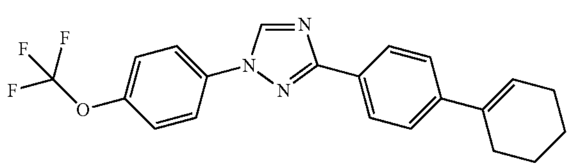 [SMILES: FC(F)(F)Oc1ccc(-n2cnc(-c3ccc(C4=CCCCC4)cc3)n2)cc1] |
| CB11 | Ex 10 | 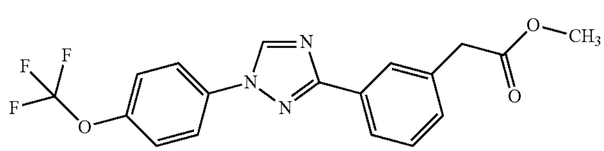 [SMILES: COC(=O)Cc1cccc(-c2ncn(-c3ccc(OC(F)(F)F)cc3)n2)c1] |
| CB12 | Ex 13 | 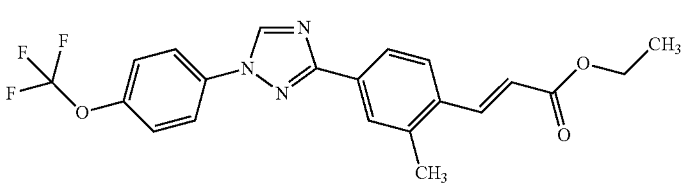 [SMILES: CCOC(=O)/C=C/c1ccc(-c2ncn(-c3ccc(OC(F)(F)F)cc3)n2)cc1C] |
| CB13 | Ex 13 | 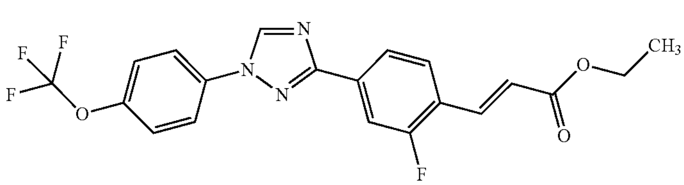 [SMILES: CCOC(=O)/C=C/c1ccc(-c2ncn(-c3ccc(OC(F)(F)F)cc3)n2)cc1F] |

TABLE 1C-continued

Structures for Intermediates (CB)

| No. | Preparation | Structure |
|-----|-------------|-----------|
| CB14 | Ex 13 | 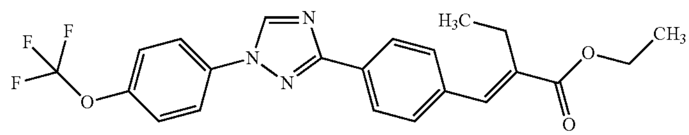 [SMILES: CCOC(=O)/C(=C/c1ccc(-c2ncn(-c3ccc(OC(F)(F)F)cc3)n2)cc1)CC] |
| CB15 | Ex 30 | 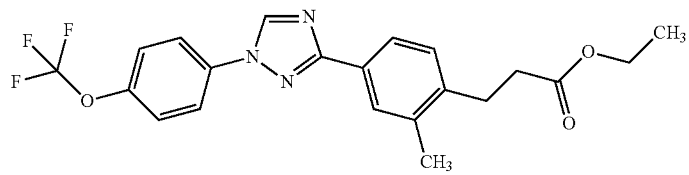 [SMILES: CCOC(=O)CCc1ccc(-c2ncn(-c3ccc(OC(F)(F)F)cc3)n2)cc1C] |
| CB16 | Ex 30 | 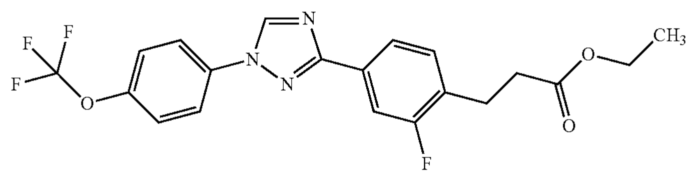 [SMILES: CCOC(=O)CCc1ccc(-c2ncn(-c3ccc(OC(F)(F)F)cc3)n2)cc1F] |
| CB17 | Ex 30 | 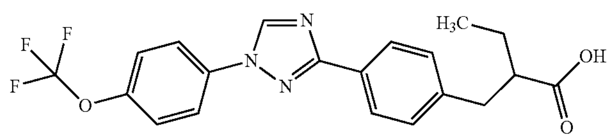 [SMILES: CCC(Cc1ccc(-c2ncn(-c3ccc(OC(F)(F)F)cc3)n2)cc1)C(=O)O] |
| CB18 | Ex 31 | 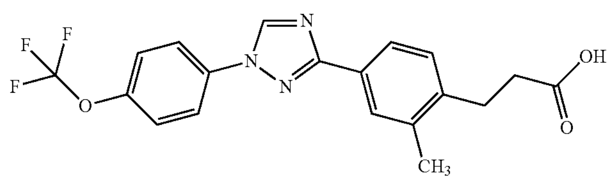 [SMILES: Cc1cc(-c2ncn(-c3ccc(OC(F)(F)F)cc3)n2)ccc1CCC(=O)O] |
| CB19 | Ex 31 | 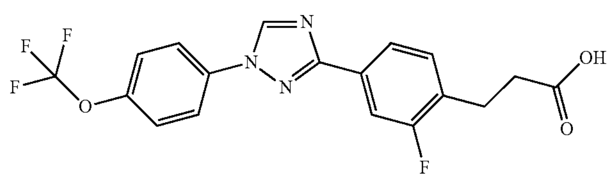 [SMILES: O=C(O)CCc1ccc(-c2ncn(-c3ccc(OC(F)(F)F)cc3)n2)cc1F] |
| CB23 | Ex 51 | 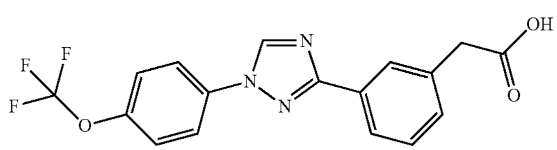 [SMILES: O=C(O)Cc1cccc(-c2ncn(-c3ccc(OC(F)(F)F)cc3)n2)c1] |
| CB24 | Ex 58 | 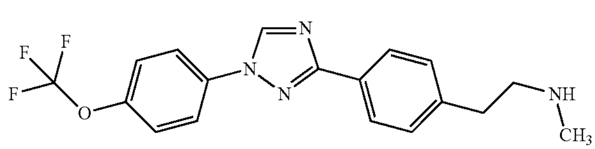 [SMILES: CNCCc1ccc(-c2ncn(-c3ccc(OC(F)(F)F)cc3)n2)cc1] |
| CB25 | Ex 58 | 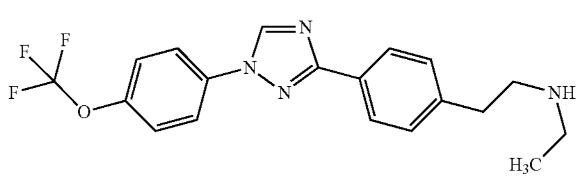 [SMILES: CCNCCc1ccc(-c2ncn(-c3ccc(OC(F)(F)F)cc3)n2)cc1] |

TABLE 1C-continued

Structures for Intermediates (CB)

| No. | Preparation | Structure |
|---|---|---|
| CB26 | Ex 58 | 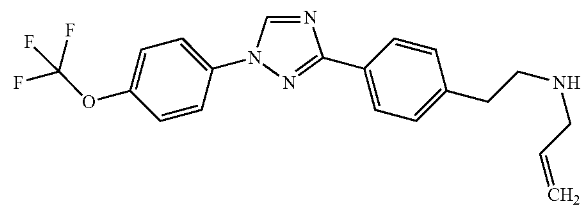 [SMILES: C=CCNCCc1ccc(-c2ncn(-c3ccc(OC(F)(F)F)cc3)n2)cc1] |
| CB27 | Ex 58 | 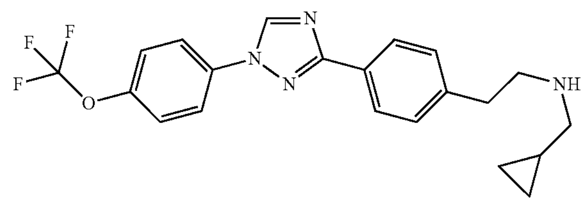 [SMILES: FC(F)(F)Oc1ccc(-n2cnc(-c3ccc(CCNCC4CC4)cc3)n2)cc1] |
| CB28 | Ex 66 | 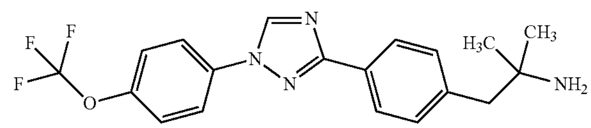 [SMILES: CC(C)(N)Cc1ccc(-c2ncn(-c3ccc(OC(F)(F)F)cc3)n2)cc1] |
| CB29 | Ex 66 | 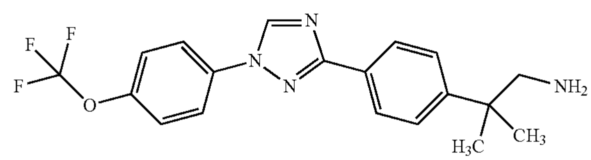 [SMILES: CC(C)(CN)c1ccc(-c2ncn(-c3ccc(OC(F)(F)F)cc3)n2)cc1] |
| CB30 | Ex 66 | 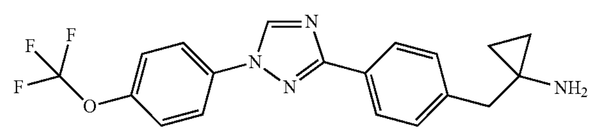 [SMILES: NC1(Cc2ccc(-c3ncn(-c4ccc(OC(F)(F)F)cc4)n3)cc2)CC1] |
| CB31 | Ex 68 | 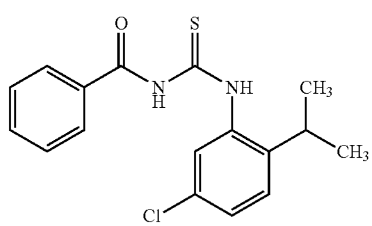 [SMILES: CC(C)c1ccc(Cl)cc1NC(=S)NC(=O)c1ccccc1] |
| CB32 | Ex 69 | 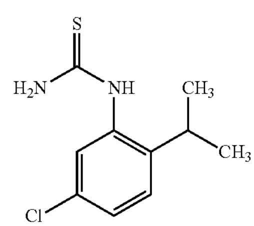 |
| CB33 | Ex 70 | 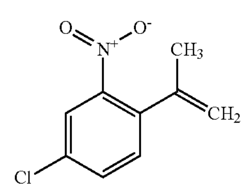 |

TABLE 1C-continued

Structures for Intermediates (CB)

| No. | Preparation | Structure |
|---|---|---|
| CB34 | Ex 74 | 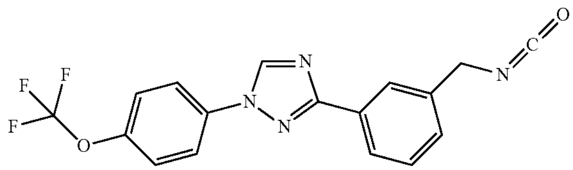 [SMILES: O=C=NCc1cccc(-c2ncn(-c3ccc(OC(F)(F)F)cc3)n2)c1] |
| CB35 | Ex 86 | 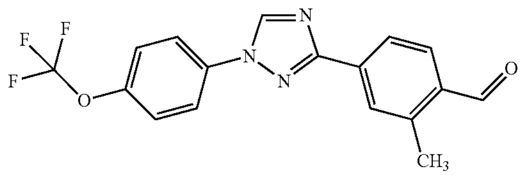 [SMILES: Cc1cc(-c2ncn(-c3ccc(OC(F)(F)F)cc3)n2)ccc1C=O] |
| CB36 | Ex 86 | 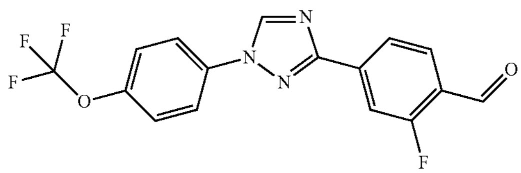 [SMILES: O=Cc1ccc(-c2ncn(-c3ccc(OC(F)(F)F)cc3)n2)cc1F] |
| CB37 | Ex 87 | 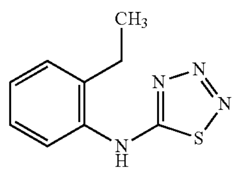 |
| CB38 | Ex 87 | 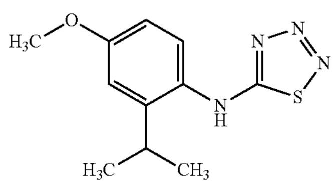 |
| CB39 | Ex 87 | 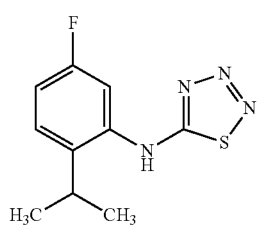 [SMILES: CC(C)c1ccc(F)cc1Nc1nnns1] |
| CB40 | Ex 87 | 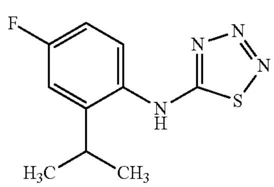 [SMILES: CC(C)c1cc(F)ccc1Nc1nnns1] |
| CB41 | Ex 87 | 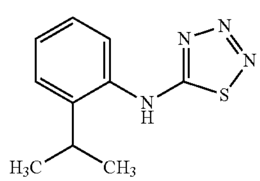 |

TABLE 1C-continued

Structures for Intermediates (CB)

| No. | Preparation | Structure |
|---|---|---|
| CB42 | Ex 88 | 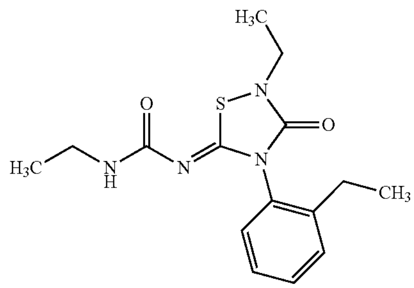 [SMILES: CCNC(=O)/N=c1\sn(CC)c(=O)n1-c1ccccc1CC] |
| CB43 | Ex 88 | 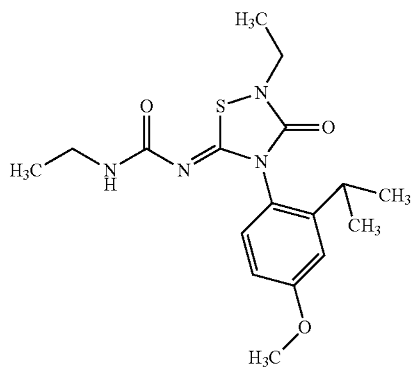 [SMILES: CCNC(=O)/N=c1\sn(CC)c(=O)n1-c1ccc(OC)cc1C(C)C] |
| CB44 | Ex 88 | 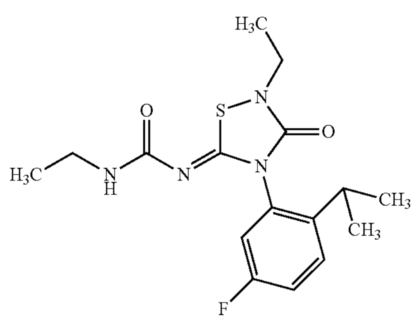 [SMILES: CCNC(=O)/N=c1\sn(CC)c(=O)n1-c1cc(F)ccc1C(C)C] |
| CB45 | Ex 88 | 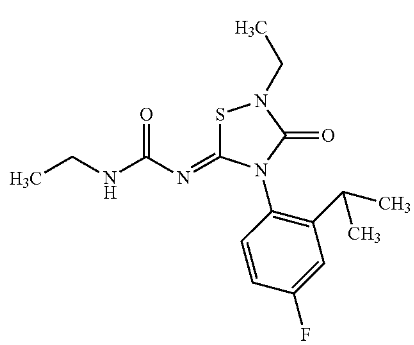 [SMILES: CCNC(=O)/N=c1\sn(CC)c(=O)n1-c1ccc(F)cc1C(C)C] |

TABLE 1C-continued

Structures for Intermediates (CB)

| No. | Preparation | Structure |
|---|---|---|
| CB46 | Ex 88 | 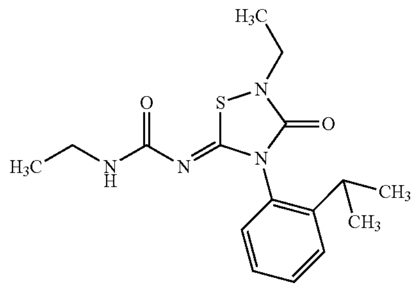 [SMILES: CCNC(=O)/N=c1\sn(CC)c(=O)n1-c1ccccc1C(C)C] |
| CB47 | Ex 89 | 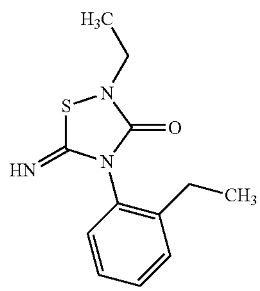 [SMILES: CCc1ccccc1-n1c(=N)sn(CC)c1=O] |
| CB48 | Ex 89 | 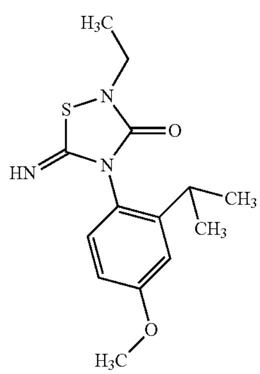 [SMILES: CCn1sc(=N)n(-c2ccc(OC)cc2C(C)C)c1=O] |
| CB49 | Ex 89 | 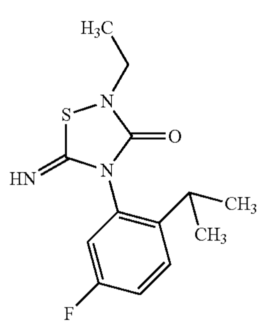 [SMILES: CCn1sc(=N)n(-c2cc(F)ccc2C(C)C)c1=O] |

1213

TABLE 1C-continued

Structures for Intermediates (CB)

| No. | Preparation | Structure |
|---|---|---|
| CB50 | Ex 89 | (structure) |
| CB51 | Ex 89 | (structure) |
| CB53 | Ex 91 | (structure) |
| CB54 | Ex 92 | (structure) |
| CB55 | Ex 93 | (structure) |
| CB56 | Ex 94 | (structure) |
| CB57 | Ex 97 | (structure) |

TABLE 1C-continued

Structures for Intermediates (CB)

| No. | Preparation | Structure |
|---|---|---|
| CB58 | Ex 98 | 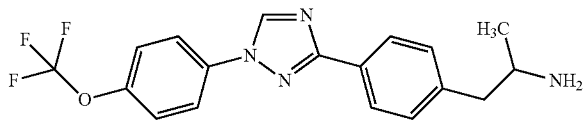 |
| CB59 | Ex 99 | 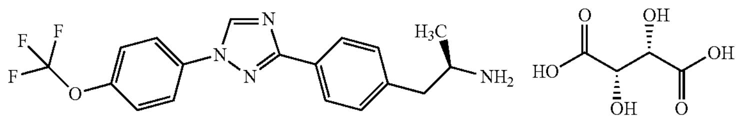 [SMILES: C[C@@H](N)Cc1ccc(-c2ncn(-c3ccc(OC(F)(F)F)cc3)n2)cc1 ; O=C(O)[C@@H](O)[C@H](O)C(=O)O] |
| CB60 | Ex 99 | 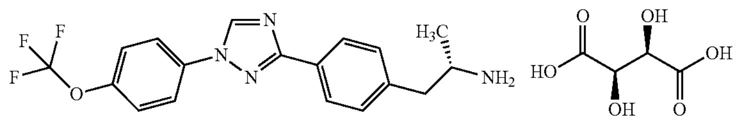 [SMILES: C[C@H](N)Cc1ccc(-c2ncn(-c3ccc(OC(F)(F)F)cc3)n2)cc1 ; O=C(O)[C@H](O)[C@@H](O)C(=O)O] |
| CB61 | Ex 100 | 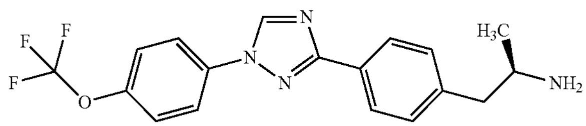 [SMILES: C[C@@H](N)Cc1ccc(-c2ncn(-c3ccc(OC(F)(F)F)cc3)n2)cc1] |
| CB62 | Ex 100 | 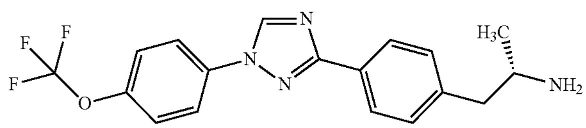 |
| CB63 | Ex 102 | 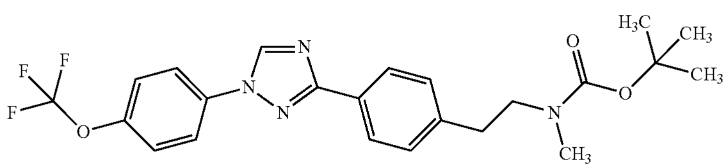 [SMILES: CN(CCc1ccc(-c2ncn(-c3ccc(OC(F)(F)F)cc3)n2)cc1)C(=O)OC(C)(C)C] |
| CB64 | Ex 102 | 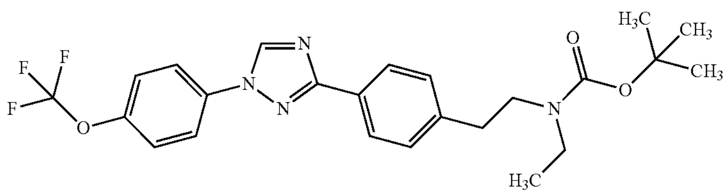 [SMILES: CCN(CCc1ccc(-c2ncn(-c3ccc(OC(F)(F)F)cc3)n2)cc1)C(=O)OC(C)(C)C] |
| CB65 | Ex 102 | 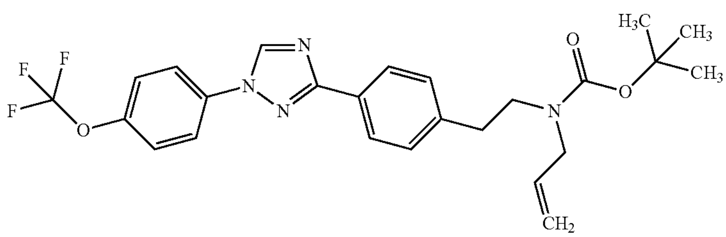 [SMILES: C=CCN(CCc1ccc(-c2ncn(-c3ccc(OC(F)(F)F)cc3)n2)cc1)C(=O)OC(C)(C)C] |
| CB66 | Ex 102 | 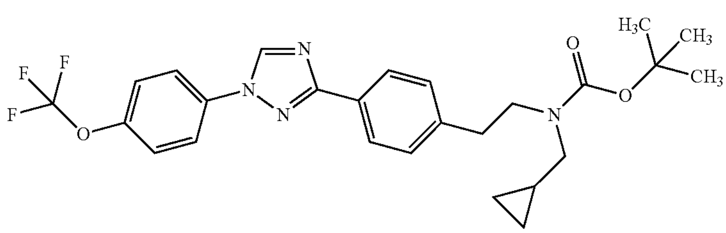 [SMILES: CC(C)(C)OC(=O)N(CCc1ccc(-c2ncn(-c3ccc(OC(F)(F)F)cc3)n2)cc1)CC1CC1] |

TABLE 1C-continued
Structures for Intermediates (CB)
| No. | Preparation | Structure |
|---|---|---|
| CB67 | Ex 103 | 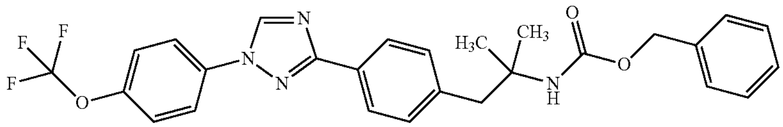 [SMILES: CC(C)(Cc1ccc(-c2ncn(-c3ccc(OC(F)(F)F)cc3)n2)cc1)NC(=O)OCc1ccccc1] |
| CB68 | Ex 103 | 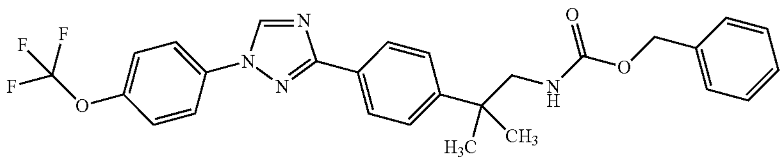 [SMILES: CC(C)(CNC(=O)OCc1ccccc1)c1ccc(-c2ncn(-c3ccc(OC(F)(F)F)cc3)n2)cc1] |
| CB69 | Ex 103 | 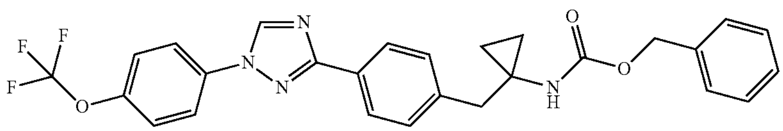 [SMILES: O=C(NC1(Cc2ccc(-c3ncn(-c4ccc(OC(F)(F)F)cc4)n3)cc2)CC1)OCc1ccccc1] |
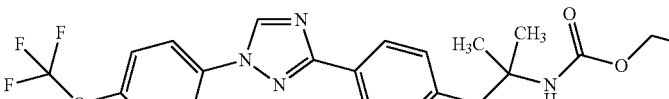
TABLE 2A
Structures for Molecules of Formula One
| No. | Structure |
|---|---|
| F1 | 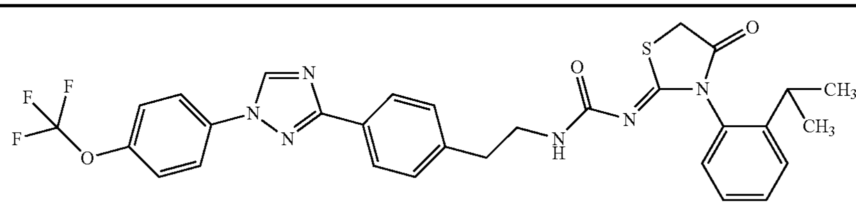 |
| F2 | 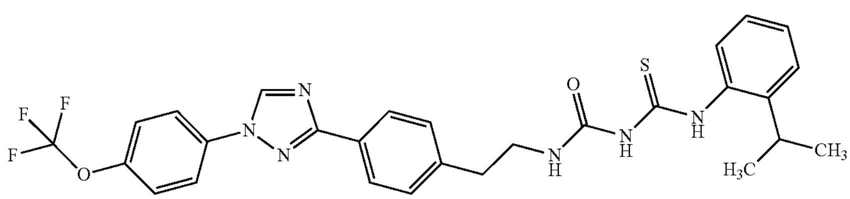 [SMILES: CC(C)c1ccccc1NC(=S)NC(=O)NCCc1ccc(-c2ncn(-c3ccc(OC(F)(F)F)cc3)n2)cc1] |
| F3 | 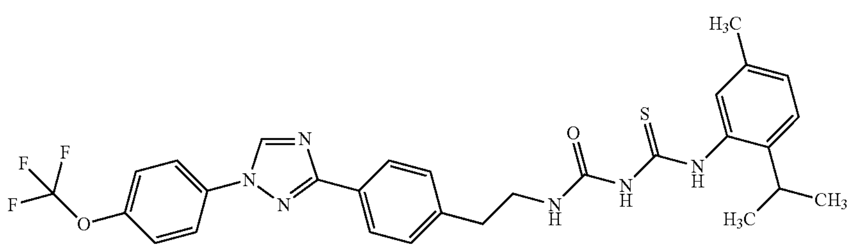 [SMILES: Cc1ccc(C(C)C)c(NC(=S)NC(=O)NCCc2ccc(-c3ncn(-c4ccc(OC(F)(F)F)cc4)n3)cc2)c1] |
| F4 | 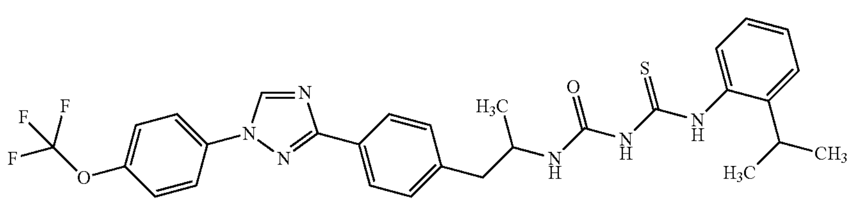 [SMILES: CC(Cc1ccc(-c2ncn(-c3ccc(OC(F)(F)F)cc3)n2)cc1)NC(=O)NC(=S)Nc1ccccc1C(C)C] |
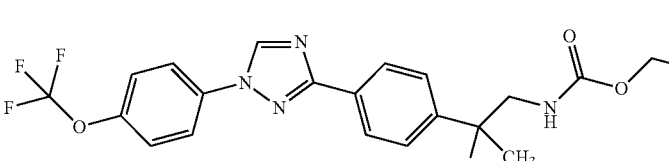
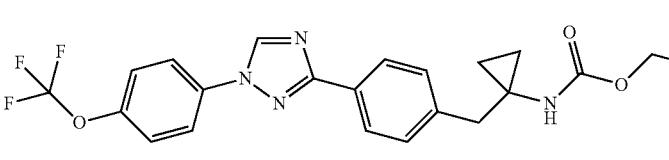

TABLE 2A-continued

Structures for Molecules of Formula One

| No. | Structure |
|---|---|
| F5 | 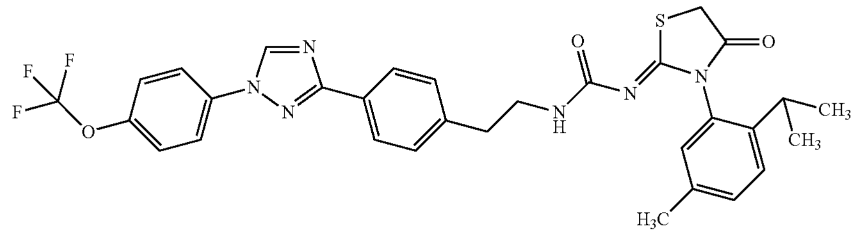 [SMILES: Cc1ccc(C(C)C)c(N2C(=O)CS/C2=N\C(=O)NCCc2ccc(-c3ncn(-c4ccc(OC(F)(F)F)cc4)n3)cc2)c1] |
| F5A | 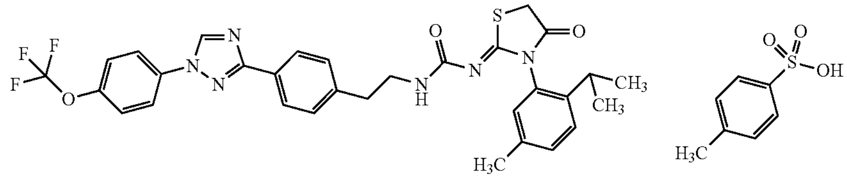 [SMILES: Cc1ccc(C(C)C)c(N2C(=O)CS/C2=N\C(=O)NCCc2ccc(-c3ncn(-c4ccc(OC(F)(F)F)cc4)n3)cc2)c1 ; Cc1ccc(S(=O)(=O)O)cc1] |
| F6 | 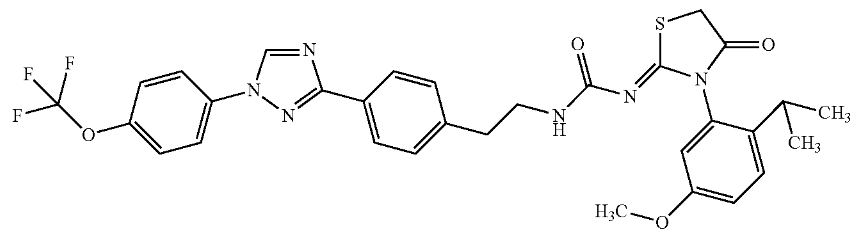 [SMILES: COc1ccc(C(C)C)c(N2C(=O)CS/C2=N\C(=O)NCCc2ccc(-c3ncn(-c4ccc(OC(F)(F)F)cc4)n3)cc2)c1] |
| F7 | 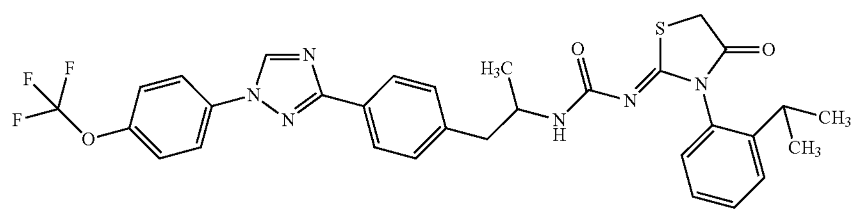 [SMILES: CC(Cc1ccc(-c2ncn(-c3ccc(OC(F)(F)F)cc3)n2)cc1)NC(=O)/N=C1\SCC(=O)N1c1ccccc1C(C)C] |
| F8 | 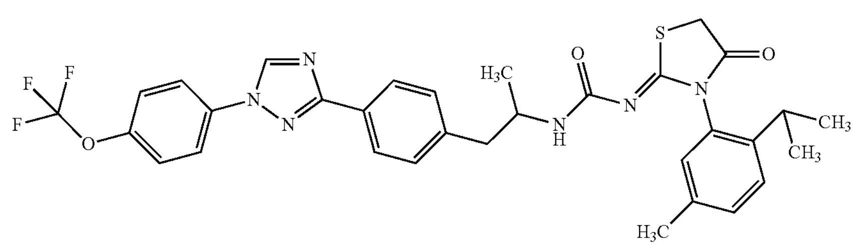 [SMILES: Cc1ccc(C(C)C)c(N2C(=O)CS/C2=N\C(=O)NC(C)Cc2ccc(-c3ncn(-c4ccc(OC(F)(F)F)cc4)n3)cc2)c1] |
| F9 | 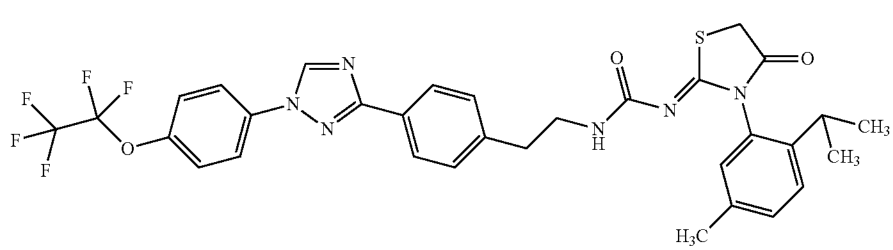 [SMILES: Cc1ccc(C(C)C)c(N2C(=O)CS/C2=N\C(=O)NCCc2ccc(-c3ncn(-c4ccc(OC(F)(F)C(F)(F)F)cc4)n3)cc2)c1] |

US 9,278,964 B2

TABLE 2A-continued

Structures for Molecules of Formula One

| No. | Structure |
|---|---|
| F10 | 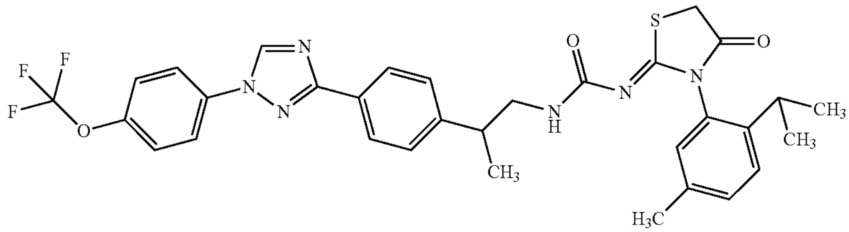 [SMILES: Cc1ccc(C(C)C)c(N2C(=O)CS/C2=N\C(=O)NCC(C)c2ccc(-c3ncn(-c4ccc(OC(F)(F)F)cc4)n3)cc2)c1] |
| F11 | 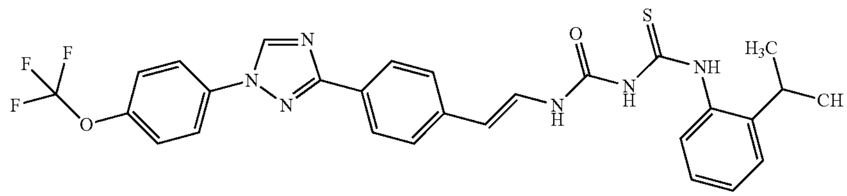 [SMILES: CC(C)c1ccccc1NC(=S)NC(=O)N/C=C/c1ccc(-c2ncn(-c3ccc(OC(F)(F)F)cc3)n2)cc1] |
| F12 | 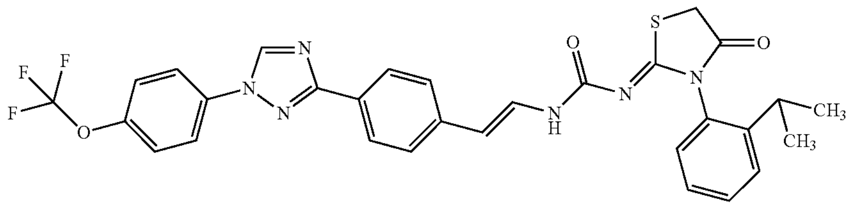 [SMILES: CC(C)c1ccccc1N1C(=O)CS/C1=N\C(=O)N/C=C/c1ccc(-c2ncn(-c3ccc(OC(F)(F)F)cc3)n2)cc1] |
| F13 | 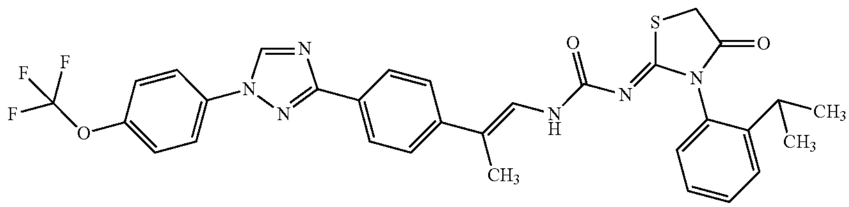 [SMILES: C/C(=C\NC(=O)/N=C1\SCC(=O)N1c1ccccc1C(C)C)c1ccc(-c2ncn(-c3ccc(OC(F)(F)F)cc3)n2)cc1] |
| F14 | 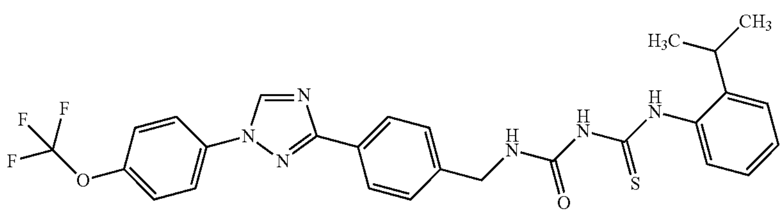 [SMILES: CC(C)c1ccccc1NC(=S)NC(=O)NCc1ccc(-c2ncn(-c3ccc(OC(F)(F)F)cc3)n2)cc1] |
| F15 | 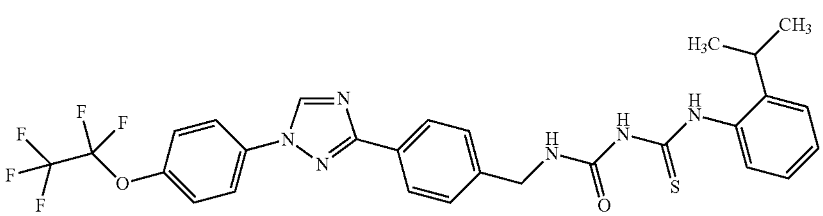 [SMILES: CC(C)c1ccccc1NC(=S)NC(=O)NCc1ccc(-c2ncn(-c3ccc(OC(F)(F)C(F)(F)F)cc3)n2)cc1] |
| F16 | 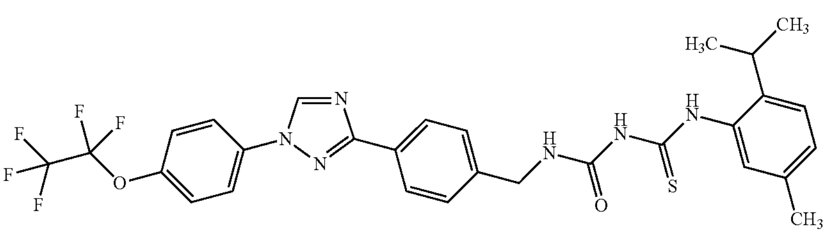 [SMILES: Cc1ccc(C(C)C)c(NC(=S)NC(=O)NCc2ccc(-c3ncn(-c4ccc(OC(F)(F)C(F)(F)F)cc4)n3)cc2)c1] |

TABLE 2A-continued

Structures for Molecules of Formula One

| No. | Structure |
| --- | --- |
| F17 | 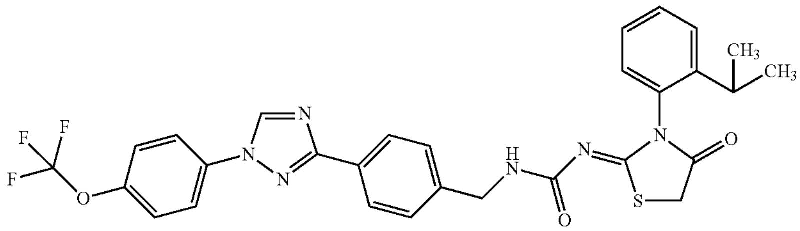 [SMILES: CC(C)c1ccccc1N1C(=O)CS/C1=N\C(=O)NCc1ccc(-c2ncn(-c3ccc(OC(F)(F)F)cc3)n2)cc1] |
| F18 | 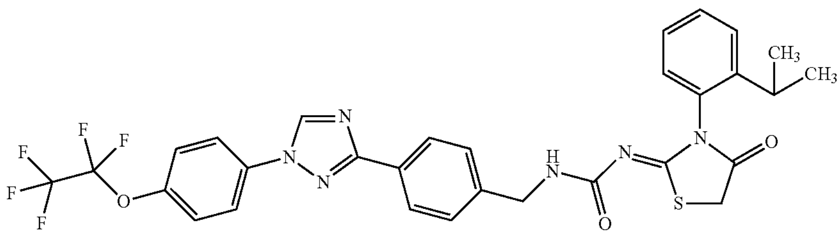 [SMILES: CC(C)c1ccccc1N1C(=O)CS/C1=N\C(=O)NCc1ccc(-c2ncn(-c3ccc(OC(F)(F)C(F)(F)F)cc3)n2)cc1] |
| F19 | 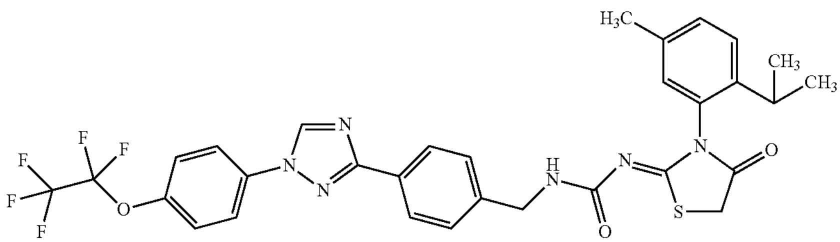 [SMILES: Cc1ccc(C(C)C)c(N2C(=O)CS/C2=N\C(=O)NCc2ccc(-c3ncn(-c4ccc(OC(F)(F)C(F)(F)F)cc4)n3)cc2)c1] |
| F20 | 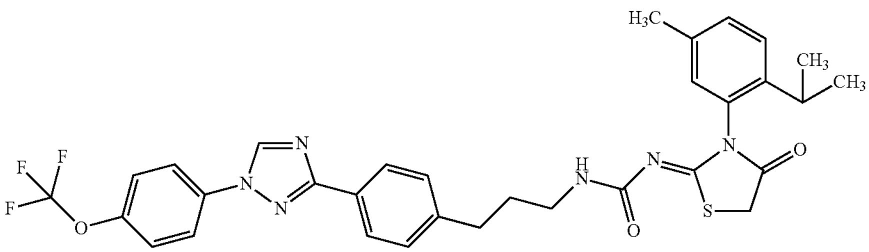 [SMILES: Cc1ccc(C(C)C)c(N2C(=O)CS/C2=N\C(=O)NCCCc2ccc(-c3ncn(-c4ccc(OC(F)(F)F)cc4)n3)cc2)c1] |
| F21 | 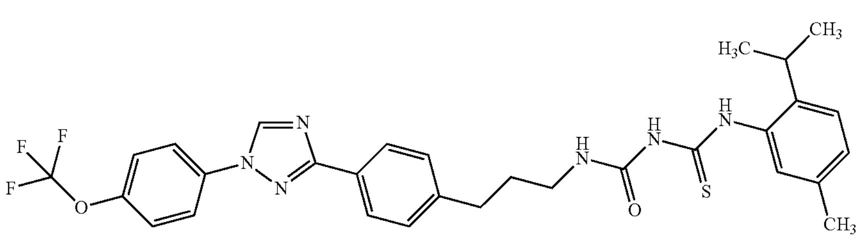 [SMILES: Cc1ccc(C(C)C)c(NC(=S)NC(=O)NCCCc2ccc(-c3ncn(-c4ccc(OC(F)(F)F)cc4)n3)cc2)c1] |
| F22 | 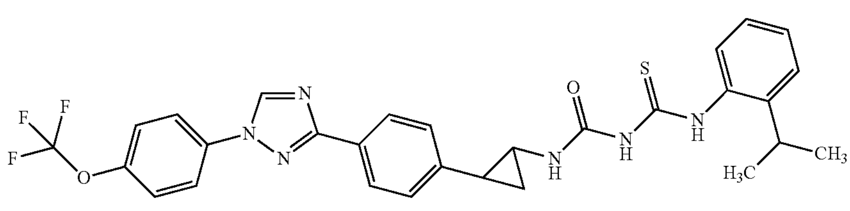 [SMILES: CC(C)c1ccccc1NC(=S)NC(=O)NC1CC1c1ccc(-c2ncn(-c3ccc(OC(F)(F)F)cc3)n2)cc1] |

TABLE 2A-continued

Structures for Molecules of Formula One

| No. | Structure |
|---|---|
| F23 | 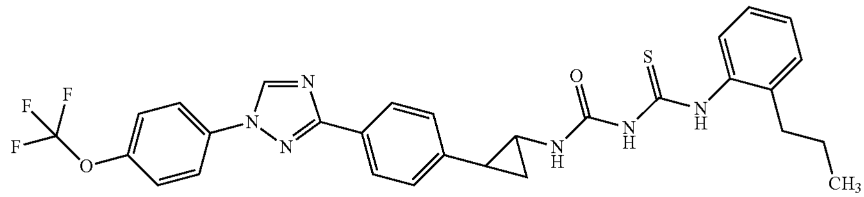 [SMILES: CCCc1ccccc1NC(=S)NC(=O)NC1CC1c1ccc(-c2ncn(-c3ccc(OC(F)(F)F)cc3)n2)cc1] |
| F24 | 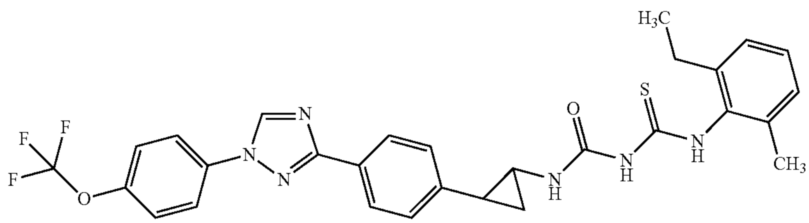 [SMILES: CCc1cccc(C)c1NC(=S)NC(=O)NC1CC1c1ccc(-c2ncn(-c3ccc(OC(F)(F)F)cc3)n2)cc1] |
| F25 | 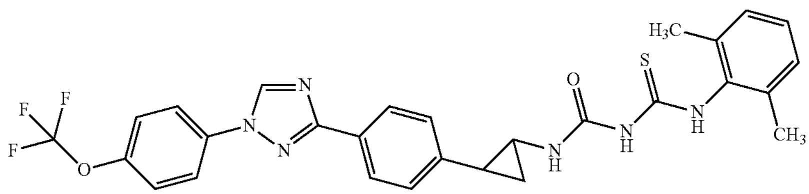 [SMILES: Cc1cccc(C)c1NC(=S)NC(=O)NC1CC1c1ccc(-c2ncn(-c3ccc(OC(F)(F)F)cc3)n2)cc1] |
| F26 | 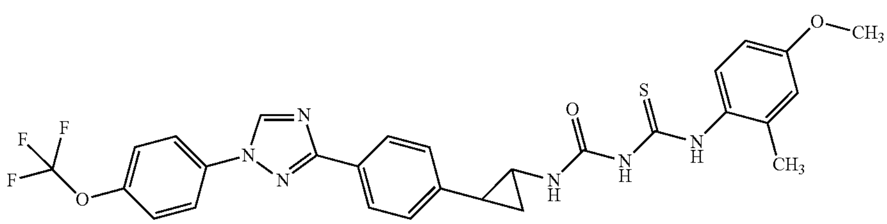 [SMILES: COc1ccc(NC(=S)NC(=O)NC2CC2c2ccc(-c3ncn(-c4ccc(OC(F)(F)F)cc4)n3)cc2)c(C)c1] |
| F27 | 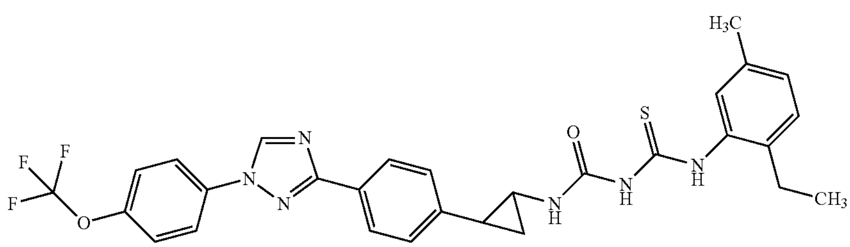 [SMILES: CCc1ccc(C)cc1NC(=S)NC(=O)NC1CC1c1ccc(-c2ncn(-c3ccc(OC(F)(F)F)cc3)n2)cc1] |
| F28 | 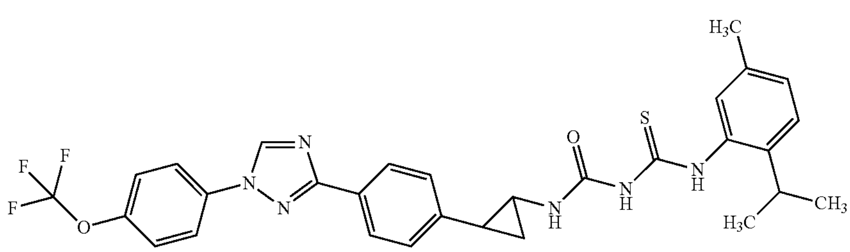 [SMILES: Cc1ccc(C(C)C)c(NC(=S)NC(=O)NC2CC2c2ccc(-c3ncn(-c4ccc(OC(F)(F)F)cc4)n3)cc2)c1] |
| F29 | 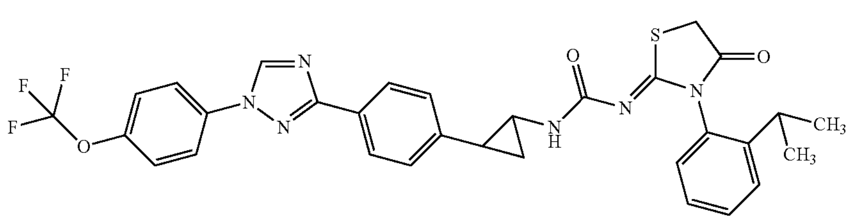 [SMILES: CC(C)c1ccccc1N1C(=O)CS/C1=N\C(=O)NC1CC1c1ccc(-c2ncn(-c3ccc(OC(F)(F)F)cc3)n2)cc1] |

TABLE 2A-continued
Structures for Molecules of Formula One
| No. | Structure |
|---|---|
| F30 | 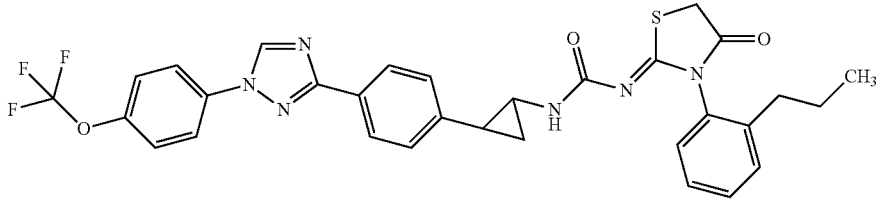 [SMILES: CCCc1ccccc1N1C(=O)CS/C1=N\C(=O)NC1CC1c1ccc(-c2ncn(-c3ccc(OC(F)(F)F)cc3)n2)cc1] |
| F31 | 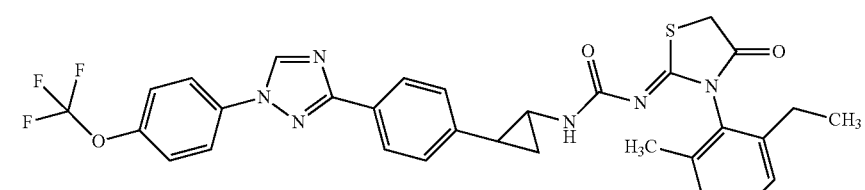 |
| F32 | 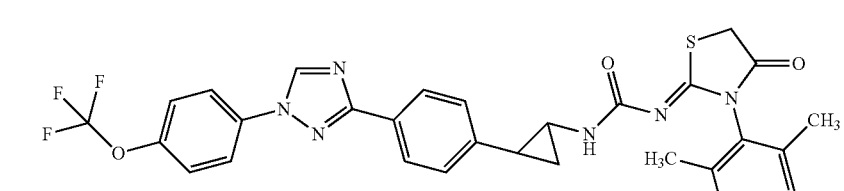 |
| F33 | 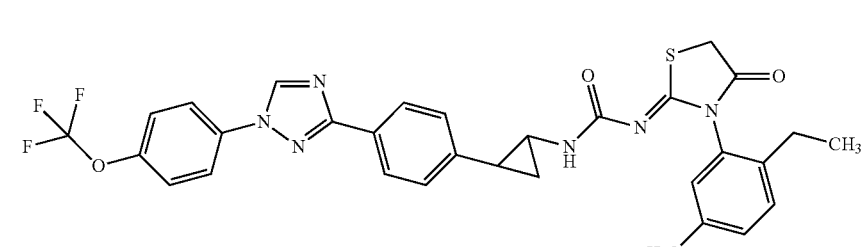 |
| F34 | 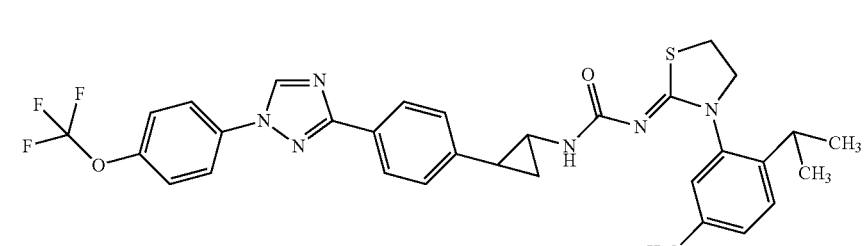 |
| F35 | 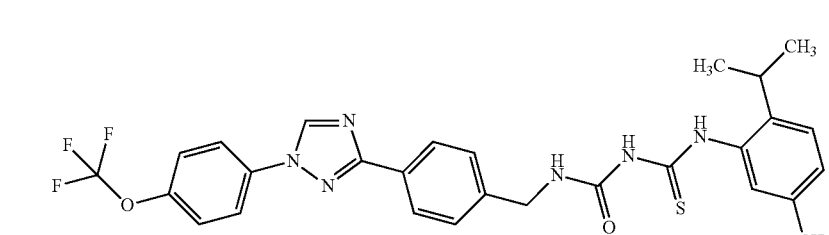 |

TABLE 2B
Exemplified Prophetic Structures (P) from Table P-One and P-Two for Molecules of Formula One
| No. | Structure |
|---|---|
| P1 | 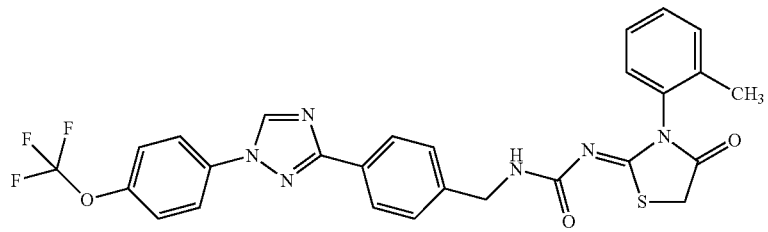 [SMILES: Cc1ccccc1N1C(=O)CS/C1=N\C(=O)NCc1ccc(-c2ncn(-c3ccc(OC(F)(F)F)cc3)n2)cc1] |
| P2, P532 | 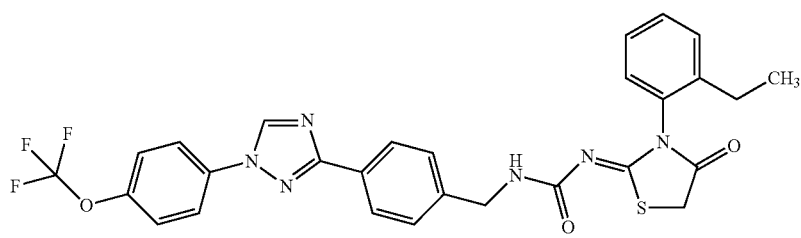 [SMILES: CCc1ccccc1N1C(=O)CS/C1=N\C(=O)NCc1ccc(-c2ncn(-c3ccc(OC(F)(F)F)cc3)n2)cc1] |
| P3, P1172 | 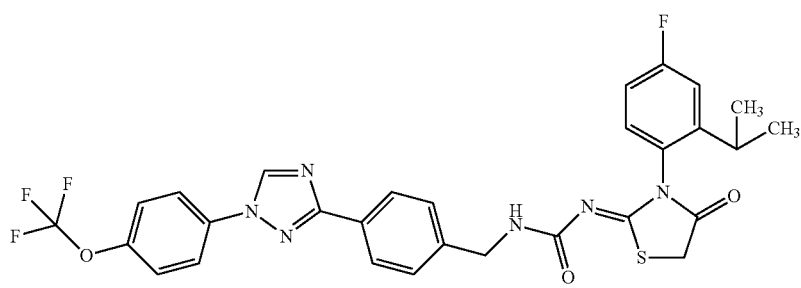 [SMILES: CC(C)c1cc(F)ccc1N1C(=O)CS/C1=N\C(=O)NCc1ccc(-c2ncn(-c3ccc(OC(F)(F)F)cc3)n2)cc1] |
| P5 | 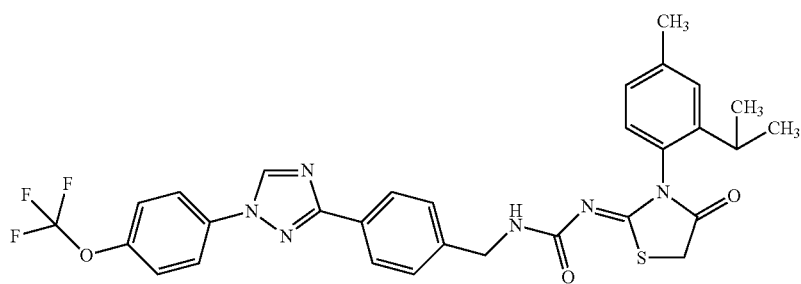 [SMILES: Cc1ccc(N2C(=O)CS/C2=N\C(=O)NCc2ccc(-c3ncn(-c4ccc(OC(F)(F)F)cc4)n3)cc2)c(C(C)C)c1] |
| P6 | 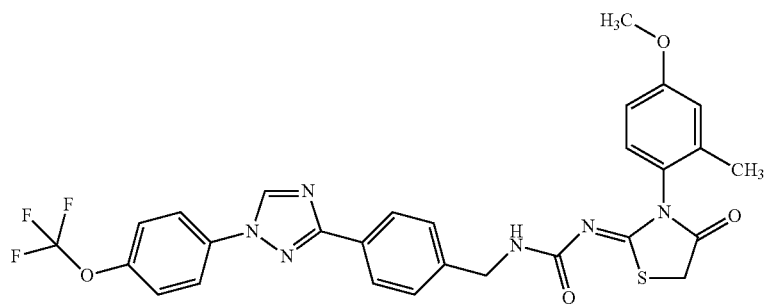 [SMILES: COc1ccc(N2C(=O)CS/C2=N\C(=O)NCc2ccc(-c3ncn(-c4ccc(OC(F)(F)F)cc4)n3)cc2)c(C)c1] |

TABLE 2B-continued

Exemplified Prophetic Structures (P) from Table P-One and P-Two for Molecules of Formula One

| No. | Structure |
|---|---|
| P7 | 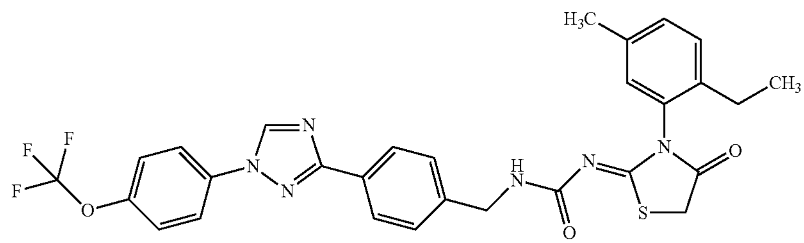 [SMILES: CCc1ccc(C)cc1N1C(=O)CS/C1=N\C(=O)NCc1ccc(-c2ncn(-c3ccc(OC(F)(F)F)cc3)n2)cc1] |
| P8, P852 | 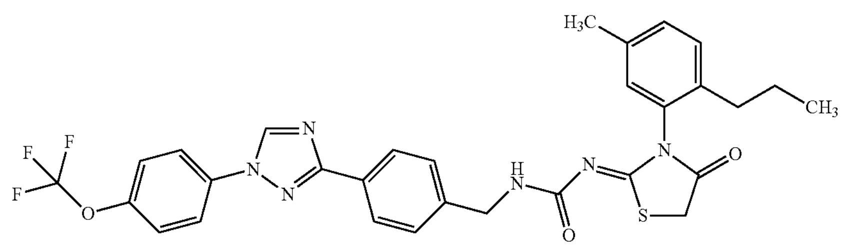 [SMILES: CCCc1ccc(C)cc1N1C(=O)CS/C1=N\C(=O)NCc1ccc(-c2ncn(-c3ccc(OC(F)(F)F)cc3)n2)cc1] |
| P14 | 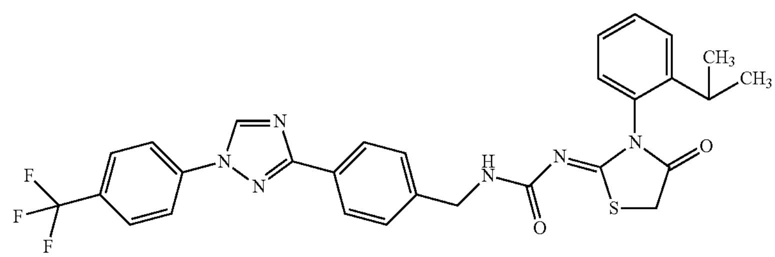 [SMILES: CC(C)c1ccccc1N1C(=O)CS/C1=N\C(=O)NCc1ccc(-c2ncn(-c3ccc(C(F)(F)F)cc3)n2)cc1] |
| P15 | 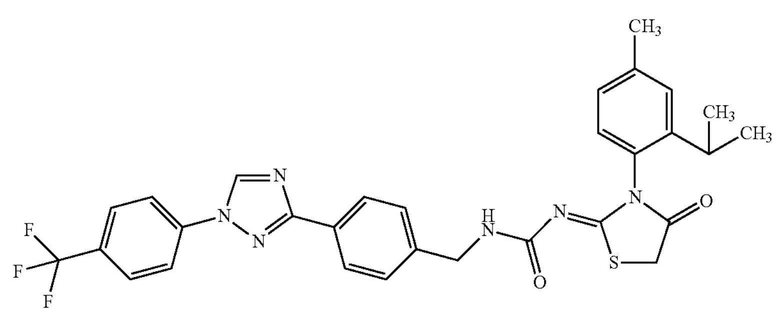 [SMILES: Cc1ccc(N2C(=O)CS/C2=N\C(=O)NCc2ccc(-c3ncn(-c4ccc(C(F)(F)F)cc4)n3)cc2)c(C(C)C)c1] |
| P20 | 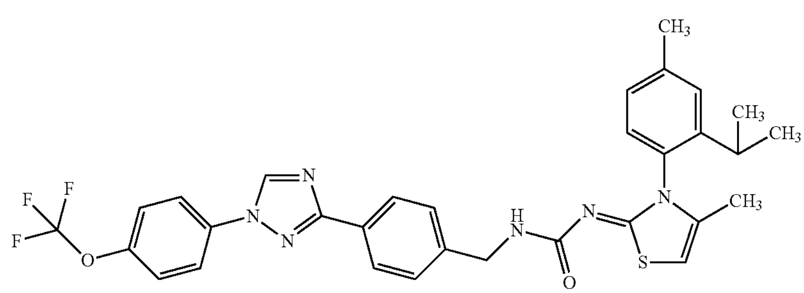 [SMILES: Cc1ccc(-n2c(C)cs/c2=N\C(=O)NCc2ccc(-c3ncn(-c4ccc(OC(F)(F)F)cc4)n3)cc2)c(C(C)C)c1] |

TABLE 2B-continued
Exemplified Prophetic Structures (P) from Table P-One and P-Two for Molecules of Formula One
| No. | Structure |
|---|---|
| P26 | 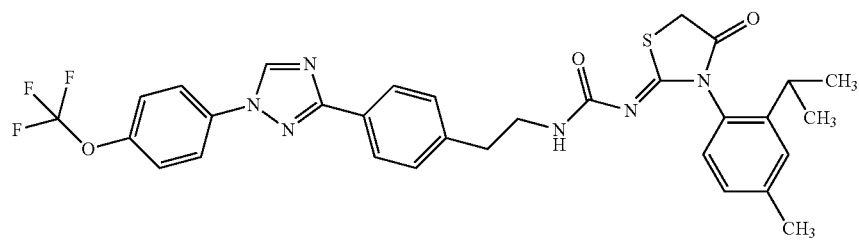 [SMILES: Cc1ccc(N2C(=O)CS/C2=N\C(=O)NCCc2ccc(-c3ncn(-c4ccc(OC(F)(F)F)cc4)n3)cc2)c(C(C)C)c1] |
| P27 | 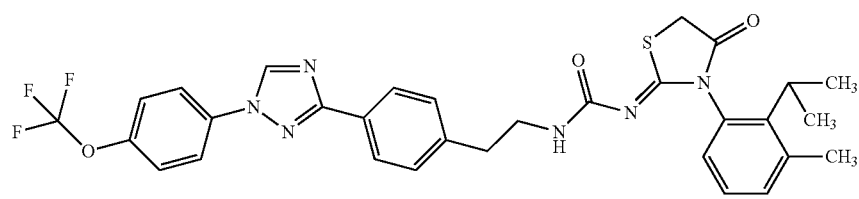 [SMILES: Cc1cccc(N2C(=O)CS/C2=N\C(=O)NCCc2ccc(-c3ncn(-c4ccc(OC(F)(F)F)cc4)n3)cc2)c1C(C)C] |
| P28 | 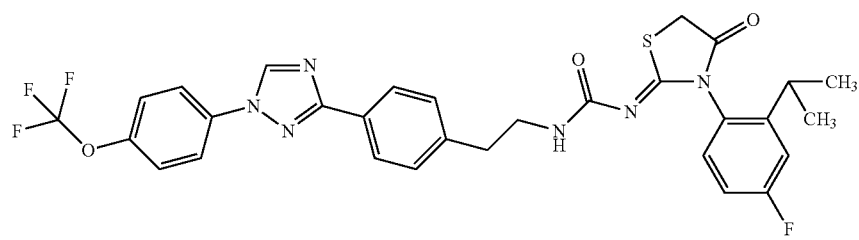 [SMILES: CC(C)c1cc(F)ccc1N1C(=O)CS/C1=N\C(=O)NCCc1ccc(-c2ncn(-c3ccc(OC(F)(F)F)cc3)n2)cc1] |
| P29 | 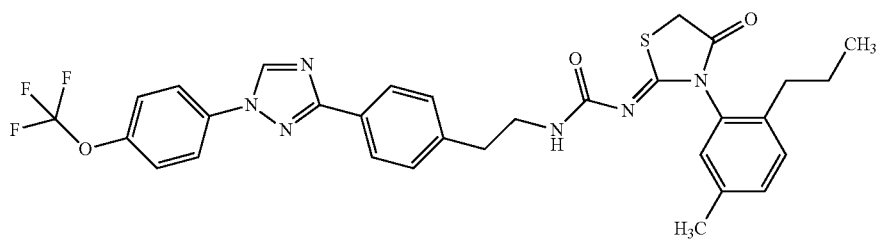 [SMILES: CCCc1ccc(C)cc1N1C(=O)CS/C1=N\C(=O)NCCc1ccc(-c2ncn(-c3ccc(OC(F)(F)F)cc3)n2)cc1] |
| P30 | 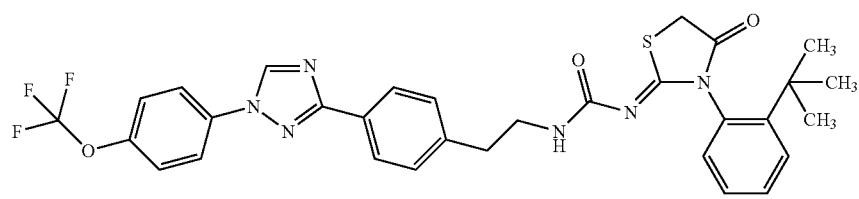 [SMILES: CC(C)(C)c1ccccc1N1C(=O)CS/C1=N\C(=O)NCCc1ccc(-c2ncn(-c3ccc(OC(F)(F)F)cc3)n2)cc1] |
| P31 | 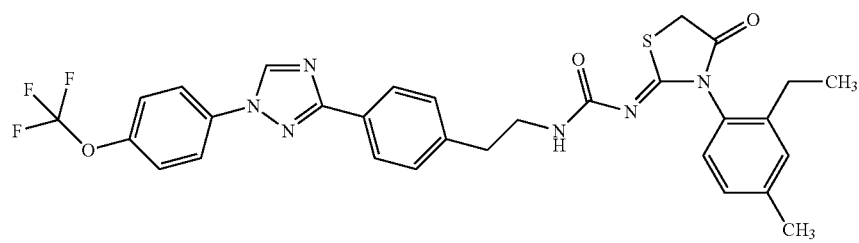 [SMILES: CCc1cc(C)ccc1N1C(=O)CS/C1=N\C(=O)NCCc1ccc(-c2ncn(-c3ccc(OC(F)(F)F)cc3)n2)cc1] |

TABLE 2B-continued

Exemplified Prophetic Structures (P) from Table P-One and P-Two for Molecules of Formula One

| No. | Structure |
|---|---|
| P33 | 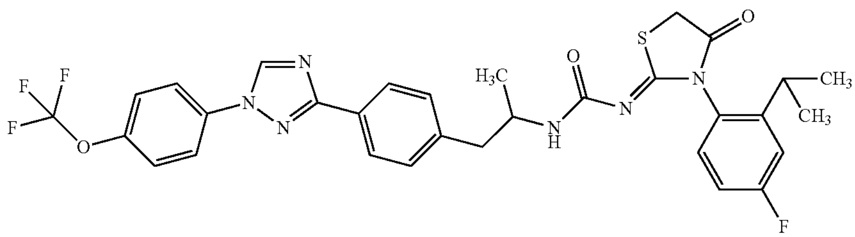 [SMILES: CC(Cc1ccc(-c2ncn(-c3ccc(OC(F)(F)F)cc3)n2)cc1)NC(=O)/N=C1\SCC(=O)N1c1ccc(F)cc1C(C)C] |
| P42 | 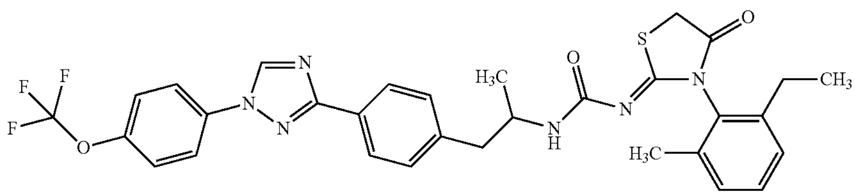 [SMILES: CCc1cccc(C)c1N1C(=O)CS/C1=N\C(=O)NC(C)Cc1ccc(-c2ncn(-c3ccc(OC(F)(F)F)cc3)n2)cc1] |
| P44 | 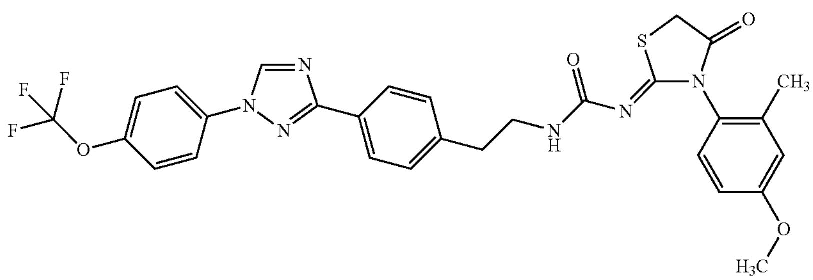 [SMILES: COc1ccc(N2C(=O)CS/C2=N\C(=O)NCCc2ccc(-c3ncn(-c4ccc(OC(F)(F)F)cc4)n3)cc2)c(C)c1] |
| P45 | 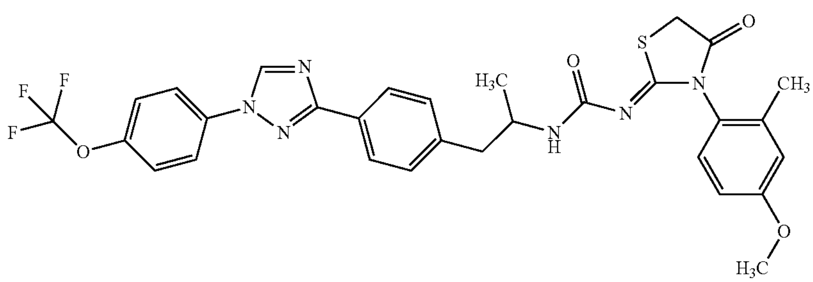 [SMILES: COc1ccc(N2C(=O)CS/C2=N\C(=O)NC(C)Cc2ccc(-c3ncn(-c4ccc(OC(F)(F)F)cc4)n3)cc2)c(C)c1] |
| P47 | 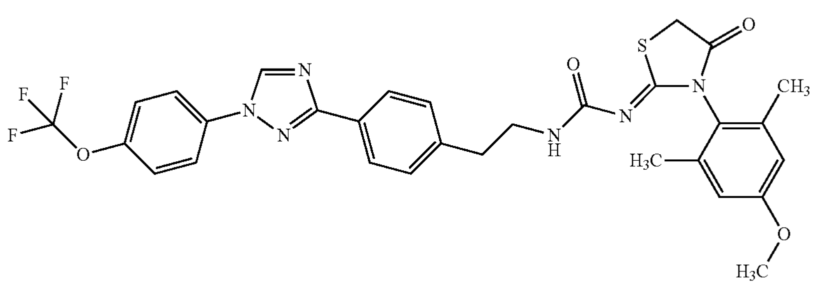 [SMILES: COc1cc(C)c(N2C(=O)CS/C2=N\C(=O)NCCc2ccc(-c3ncn(-c4ccc(OC(F)(F)F)cc4)n3)cc2)c(C)c1] |
| P49 | 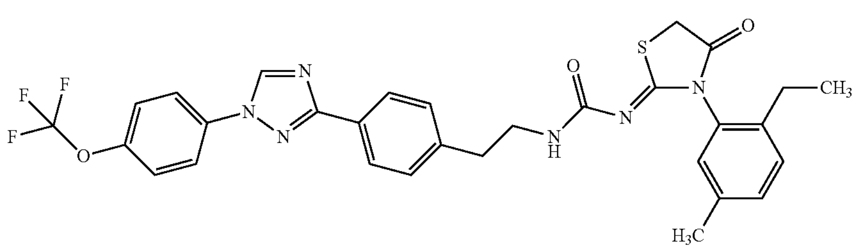 [SMILES: CCc1ccc(C)cc1N1C(=O)CS/C1=N\C(=O)NCCc1ccc(-c2ncn(-c3ccc(OC(F)(F)F)cc3)n2)cc1] |

TABLE 2B-continued
Exemplified Prophetic Structures (P) from Table P-One and P-Two for Molecules of Formula One
| No. | Structure |
|---|---|
| P50 | 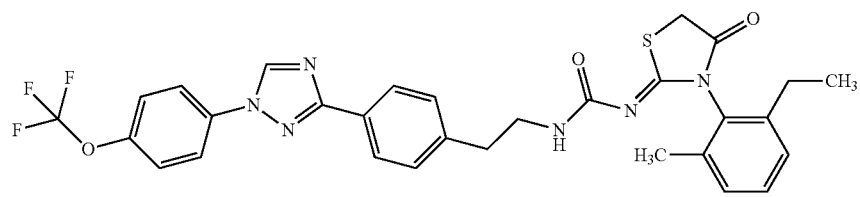 [SMILES: CCc1cccc(C)c1N1C(=O)CS/C1=N\C(=O)NCCc1ccc(-c2ncn(-c3ccc(OC(F)(F)F)cc3)n2)cc1] |
| P51 | 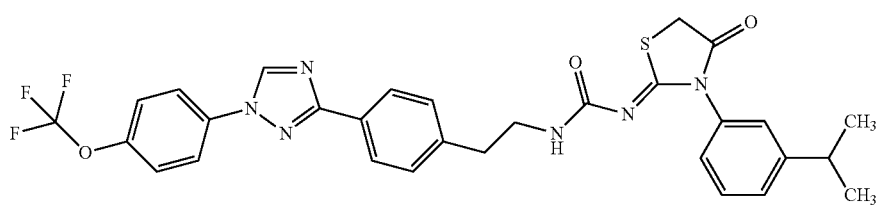 [SMILES: CC(C)c1cccc(N2C(=O)CS/C2=N\C(=O)NCCc2ccc(-c3ncn(-c4ccc(OC(F)(F)F)cc4)n3)cc2)c1] |
| P52 | 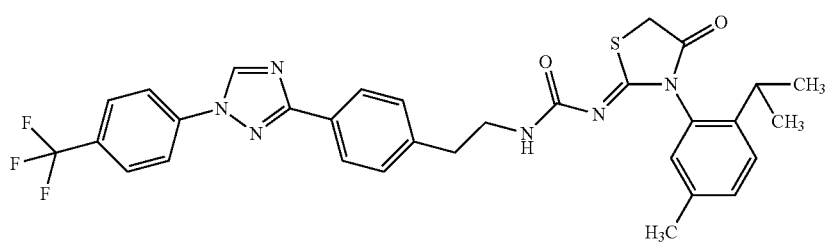 [SMILES: Cc1ccc(C(C)C)c(N2C(=O)CS/C2=N\C(=O)NCCc2ccc(-c3ncn(-c4ccc(C(F)(F)F)cc4)n3)cc2)c1] |
| P53 | 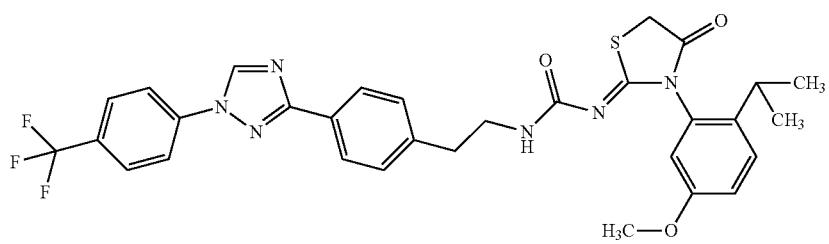 [SMILES: COc1ccc(C(C)C)c(N2C(=O)CS/C2=N\C(=O)NCCc2ccc(-c3ncn(-c4ccc(C(F)(F)F)cc4)n3)cc2)c1] |
| P57 | 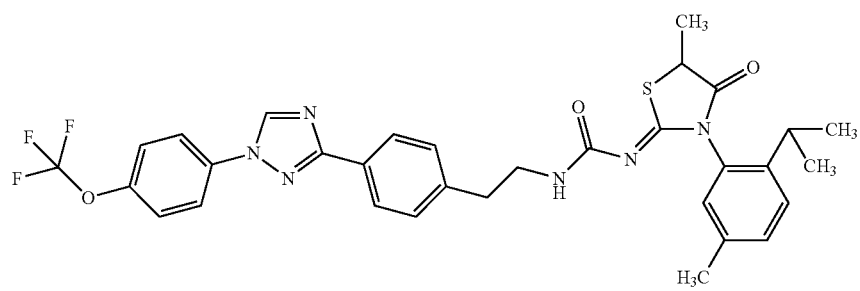 [SMILES: Cc1ccc(C(C)C)c(N2C(=O)C(C)S/C2=N\C(=O)NCCc2ccc(-c3ncn(-c4ccc(OC(F)(F)F)cc4)n3)cc2)c1] |
| P58 | 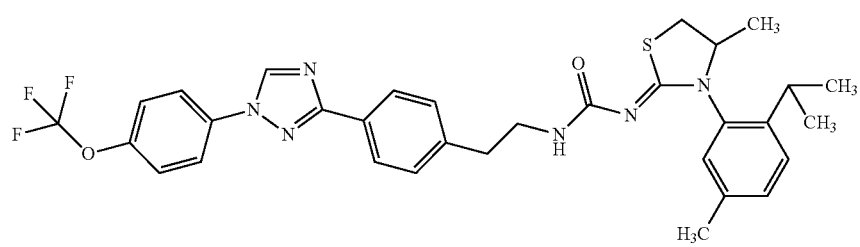 [SMILES: Cc1ccc(C(C)C)c(N2/C(=N/C(=O)NCCc3ccc(-c4ncn(-c5ccc(OC(F)(F)F)cc5)n4)cc3)SCC2C)c1] |

TABLE 2B-continued
Exemplified Prophetic Structures (P) from Table P-One and P-Two for Molecules of Formula One
| No. | Structure |
|---|---|
| P59 | 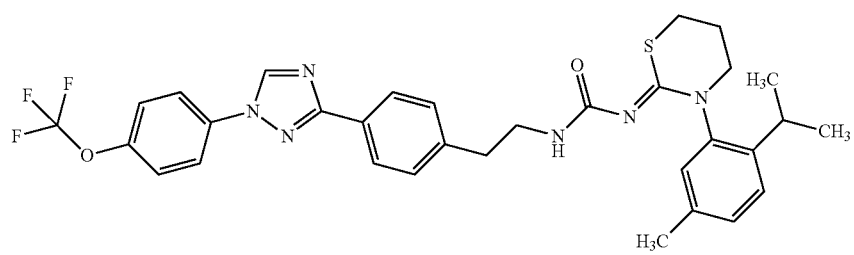 [SMILES: Cc1ccc(C(C)C)c(N2CCCS/C2=N\C(=O)NCCc2ccc(-c3ncn(-c4ccc(OC(F)(F)F)cc4)n3)cc2)c1] |
| P64 | 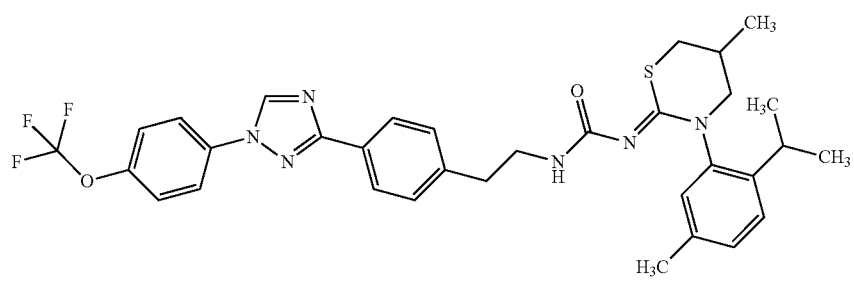 [SMILES: Cc1ccc(C(C)C)c(N2CC(C)CS/C2=N\C(=O)NCCc2ccc(-c3ncn(-c4ccc(OC(F)(F)F)cc4)n3)cc2)c1] |
| P65 | 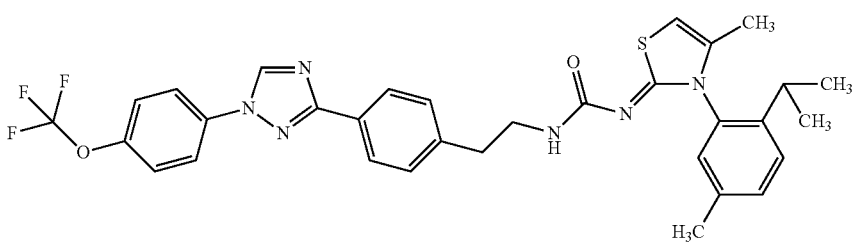 [SMILES: Cc1ccc(C(C)C)c(-n2c(C)cs/c2=N\C(=O)NCCc2ccc(-c3ncn(-c4ccc(OC(F)(F)F)cc4)n3)cc2)c1] |
| P66, P353 | 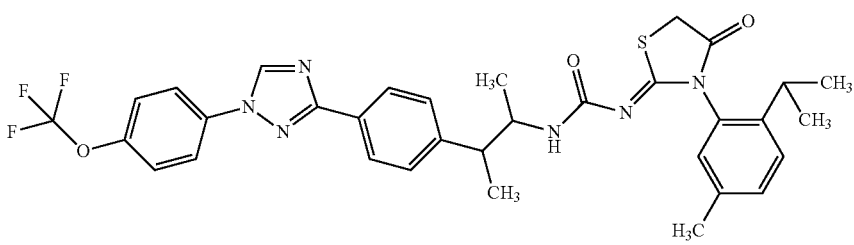 [SMILES: Cc1ccc(C(C)C)c(N2C(=O)CS/C2=N\C(=O)NC(C)C(C)c2ccc(-c3ncn(-c4ccc(OC(F)(F)F)cc4)n3)cc2)c1] |
| P74 | 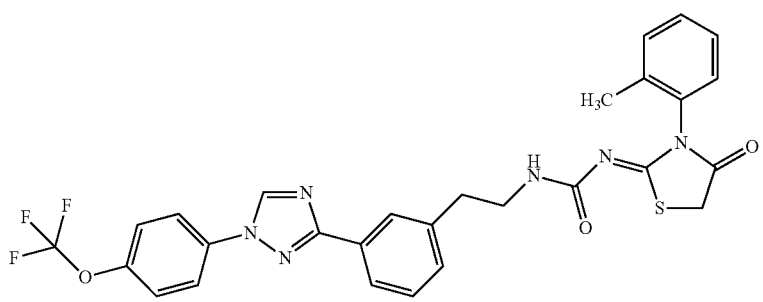 [SMILES: Cc1ccccc1N1C(=O)CS/C1=N\C(=O)NCCc1cccc(-c2ncn(-c3ccc(OC(F)(F)F)cc3)n2)c1] |

TABLE 2B-continued
Exemplified Prophetic Structures (P) from Table P-One and P-Two for Molecules of Formula One
| No. | Structure |
|---|---|
| P75 | 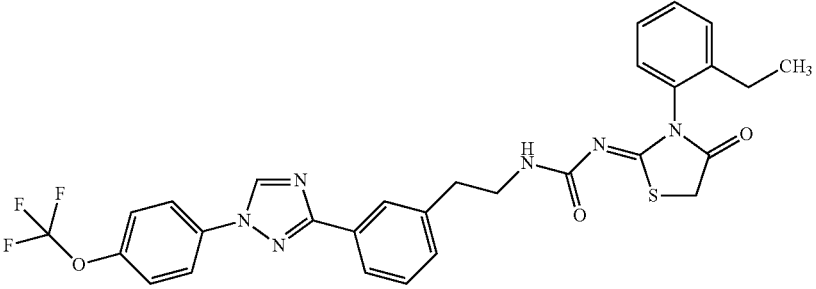 [SMILES: CCc1ccccc1N1C(=O)CS/C1=N\C(=O)NCCc1cccc(-c2ncn(-c3ccc(OC(F)(F)F)cc3)n2)c1] |
| P76 | 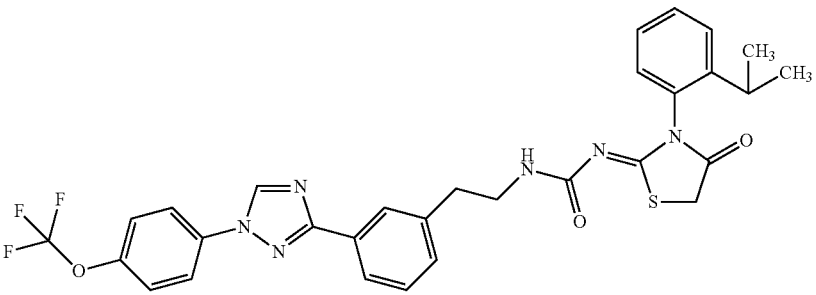 [SMILES: CC(C)c1ccccc1N1C(=O)CS/C1=N\C(=O)NCCc1cccc(-c2ncn(-c3ccc(OC(F)(F)F)cc3)n2)c1] |
| P80 | 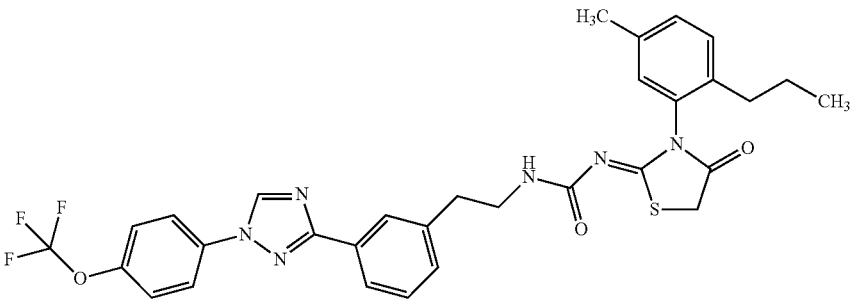 [SMILES: CCCc1ccc(C)cc1N1C(=O)CS/C1=N\C(=O)NCCc1cccc(-c2ncn(-c3ccc(OC(F)(F)F)cc3)n2)c1] |
| P81 | 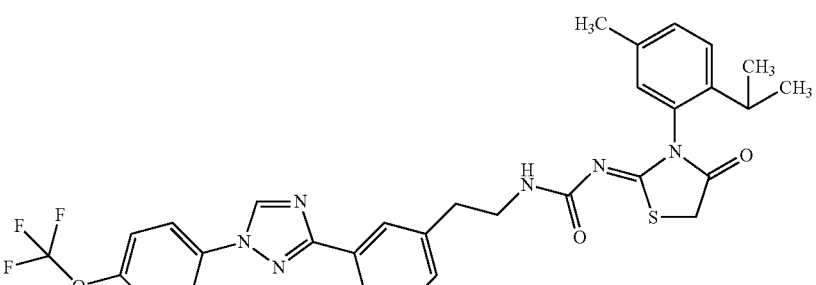 |
| P83 | 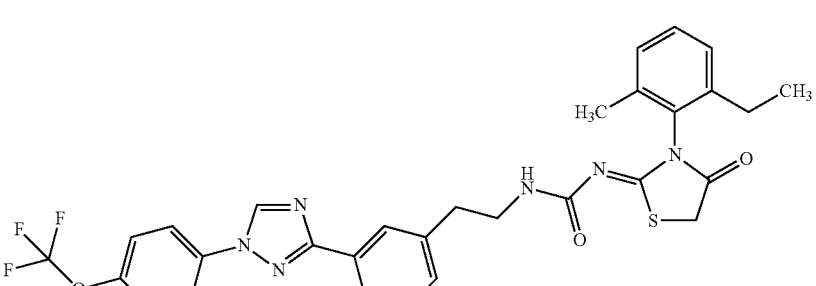 |

TABLE 2B-continued
Exemplified Prophetic Structures (P) from Table P-One and P-Two for Molecules of Formula One
| No. | Structure |
|---|---|
| P84 | 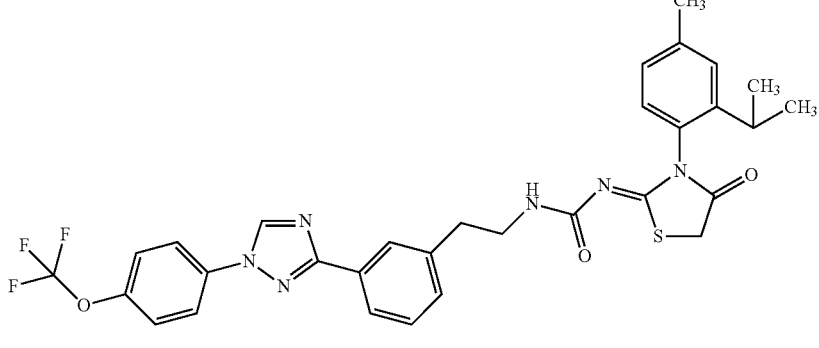 |
| P85 | 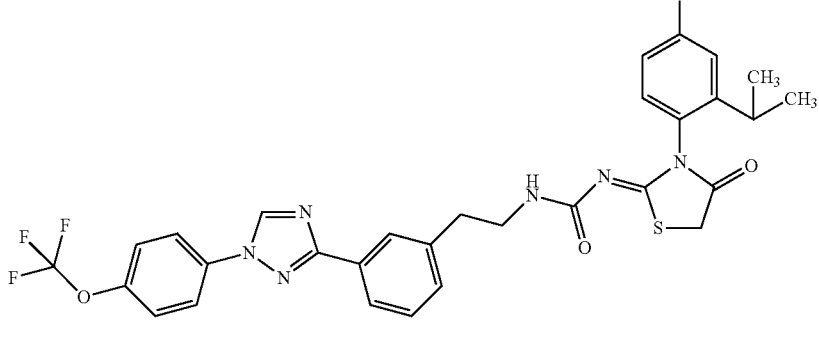 |
| P87 | 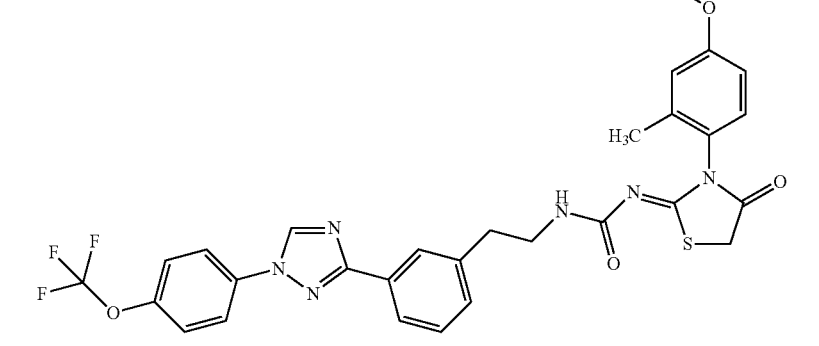 |
| P92 | 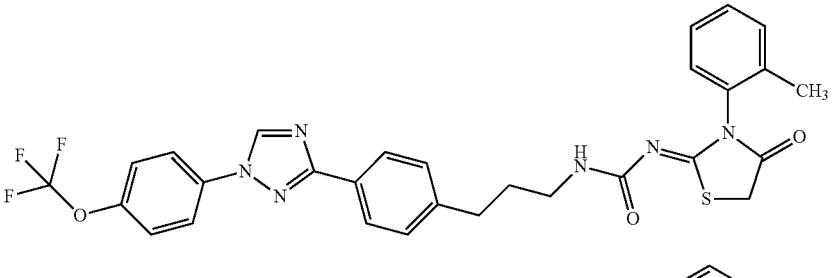 |
| P93, P510 | 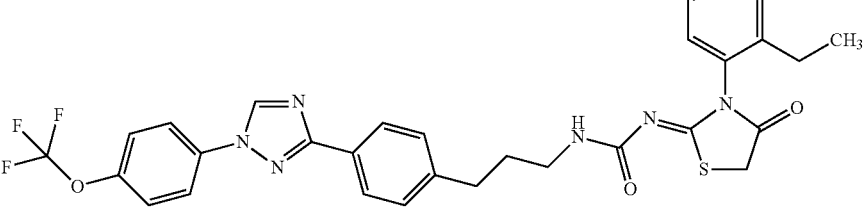 |

TABLE 2B-continued
Exemplified Prophetic Structures (P) from Table P-One and P-Two for Molecules of Formula One
| No. | Structure |
|---|---|
| P94, P197 | 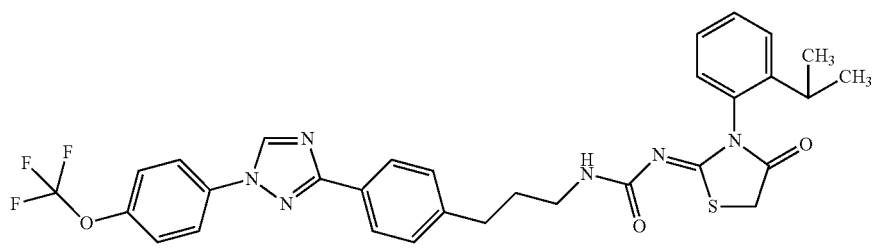 [SMILES: CC(C)c1ccccc1N1C(=O)CS/C1=N\C(=O)NCCCc1ccc(-c2ncn(-c3ccc(OC(F)(F)F)cc3)n2)cc1] |
| P99, P830 | 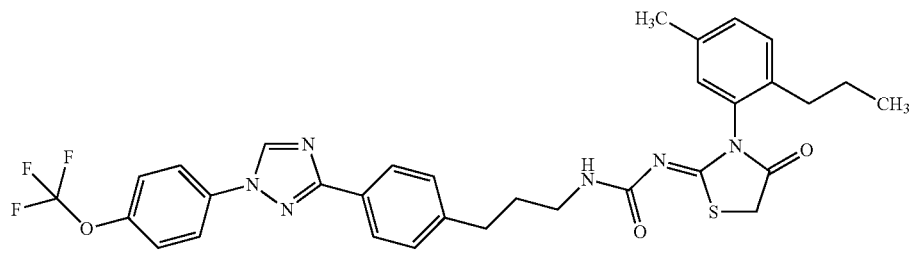 [SMILES: CCCc1ccc(C)cc1N1C(=O)CS/C1=N\C(=O)NCCCc1ccc(-c2ncn(-c3ccc(OC(F)(F)F)cc3)n2)cc1] |
| P101 | 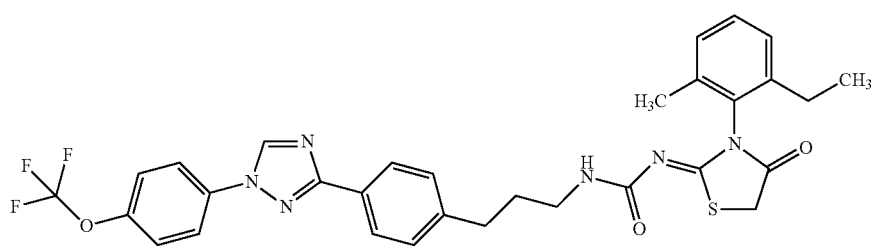 [SMILES: CCc1cccc(C)c1N1C(=O)CS/C1=N\C(=O)NCCCc1ccc(-c2ncn(-c3ccc(OC(F)(F)F)cc3)n2)cc1] |
| P102 | 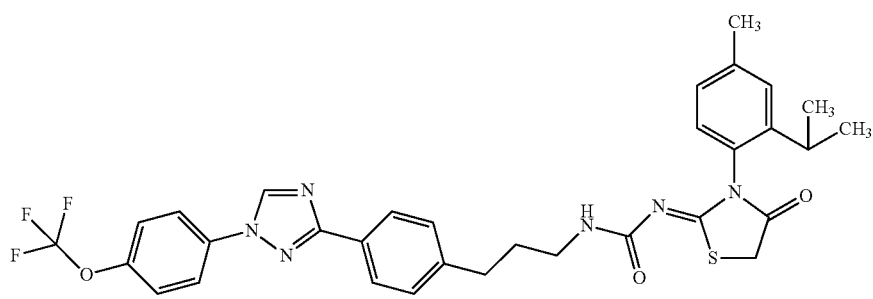 [SMILES: Cc1ccc(N2C(=O)CS/C2=N\C(=O)NCCCc2ccc(-c3ncn(-c4ccc(OC(F)(F)F)cc4)n3)cc2)c(C(C)C)c1] |
| P103, P1150 | 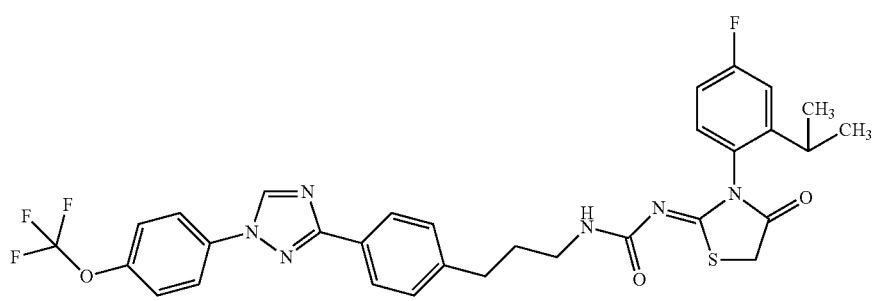 [SMILES: CC(C)c1cc(F)ccc1N1C(=O)CS/C1=N\C(=O)NCCCc1ccc(-c2ncn(-c3ccc(OC(F)(F)F)cc3)n2)cc1] |

TABLE 2B-continued

Exemplified Prophetic Structures (P) from Table P-One and P-Two for Molecules of Formula One

| No. | Structure |
|---|---|
| P105 | 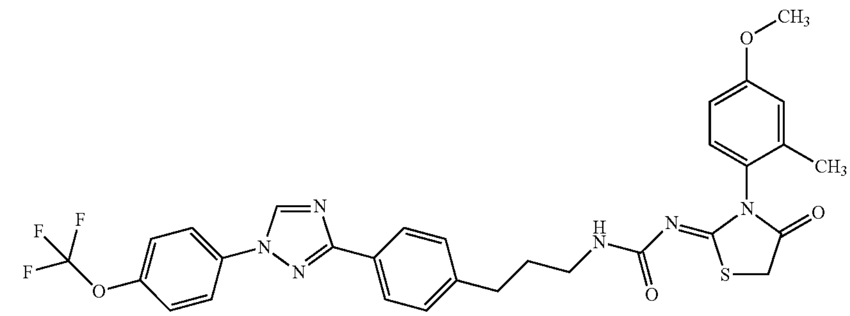 [SMILES: COc1ccc(N2C(=O)CS/C2=N\C(=O)NCCCc2ccc(-c3ncn(-c4ccc(OC(F)(F)F)cc4)n3)cc2)c(C)c1] |
| P118 | 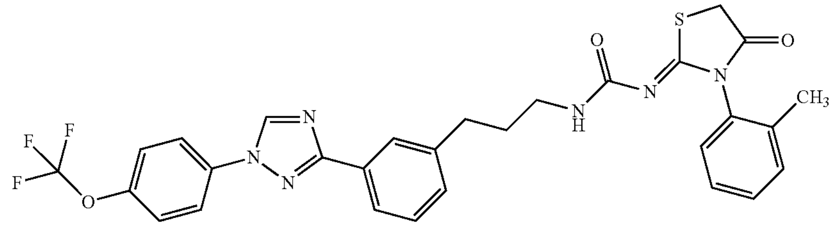 [SMILES: Cc1ccccc1N1C(=O)CS/C1=N\C(=O)NCCCc1cccc(-c2ncn(-c3ccc(OC(F)(F)F)cc3)n2)c1] |
| P119 | 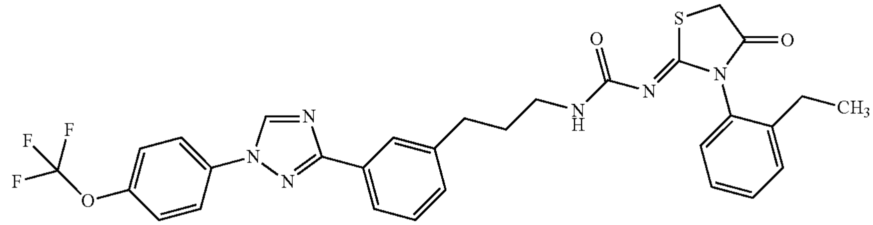 [SMILES: CCc1ccccc1N1C(=O)CS/C1=N\C(=O)NCCCc1cccc(-c2ncn(-c3ccc(OC(F)(F)F)cc3)n2)c1] |
| P120 | 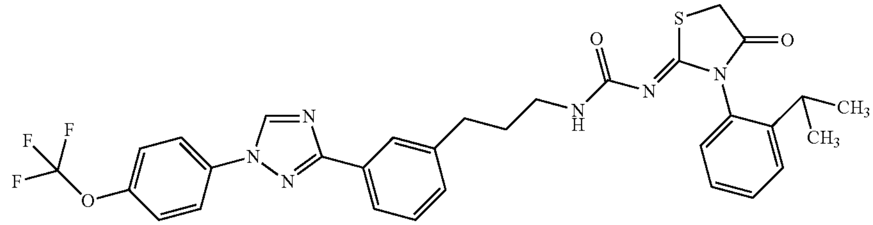 [SMILES: CC(C)c1ccccc1N1C(=O)CS/C1=N\C(=O)NCCCc1cccc(-c2ncn(-c3ccc(OC(F)(F)F)cc3)n2)c1] |
| P124 | 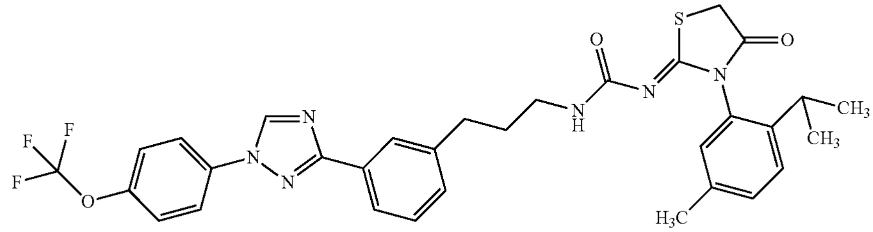 [SMILES: Cc1ccc(C(C)C)c(N2C(=O)CS/C2=N\C(=O)NCCCc2cccc(-c3ncn(-c4ccc(OC(F)(F)F)cc4)n3)c2)c1] |
| P125 | 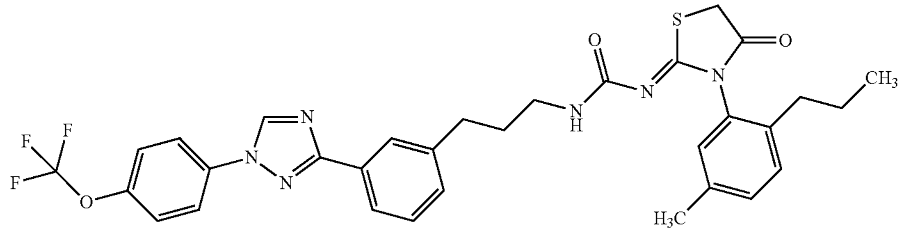 [SMILES: CCCc1ccc(C)cc1N1C(=O)CS/C1=N\C(=O)NCCCc1cccc(-c2ncn(-c3ccc(OC(F)(F)F)cc3)n2)c1] |

TABLE 2B-continued
Exemplified Prophetic Structures (P) from Table P-One and P-Two for Molecules of Formula One
| No. | Structure |
|---|---|
| P127 | 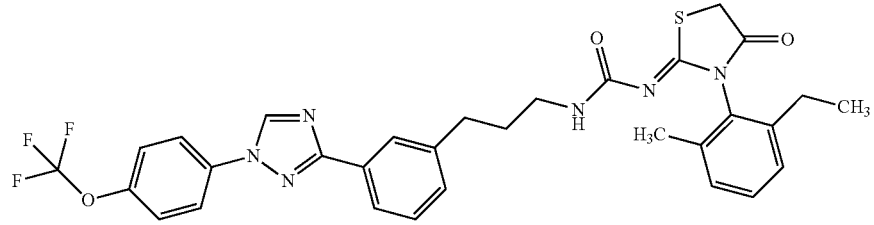 [SMILES: CCc1cccc(C)c1N1C(=O)CS/C1=N\C(=O)NCCCc1cccc(-c2ncn(-c3ccc(OC(F)(F)F)cc3)n2)c1] |
| P128 | 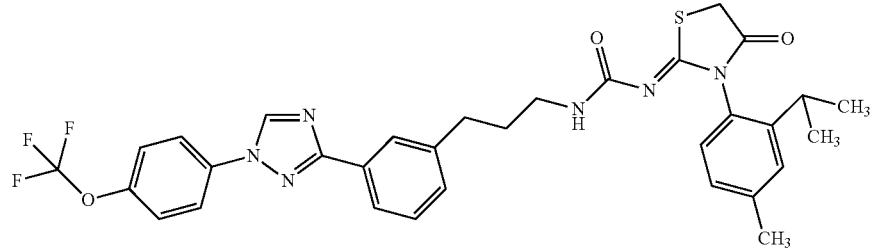 [SMILES: Cc1ccc(N2C(=O)CS/C2=N\C(=O)NCCCc2cccc(-c3ncn(-c4ccc(OC(F)(F)F)cc4)n3)c2)c(C(C)C)c1] |
| P129 | 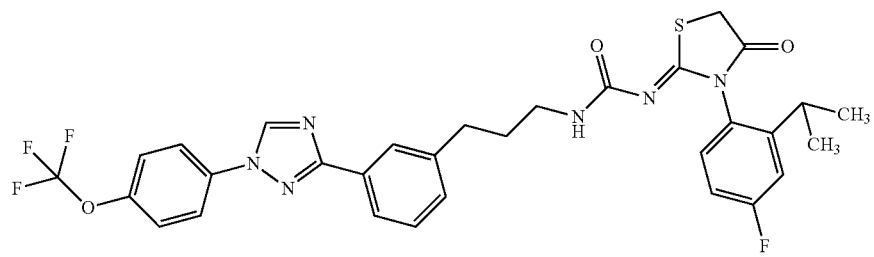 [SMILES: CC(C)c1cc(F)ccc1N1C(=O)CS/C1=N\C(=O)NCCCc1cccc(-c2ncn(-c3ccc(OC(F)(F)F)cc3)n2)c1] |
| P131 | 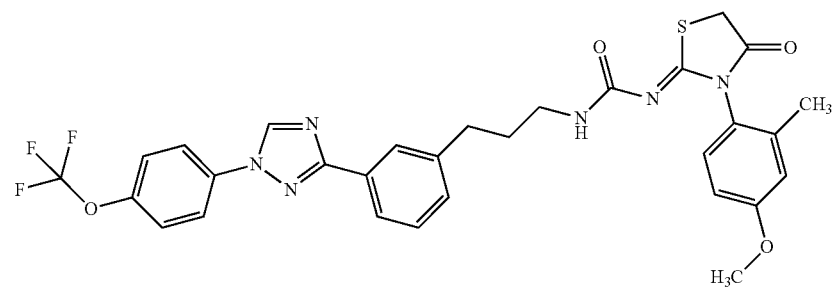 [SMILES: COc1ccc(N2C(=O)CS/C2=N\C(=O)NCCCc2cccc(-c3ncn(-c4ccc(OC(F)(F)F)cc4)n3)c2)c(C)c1] |
| P144 | 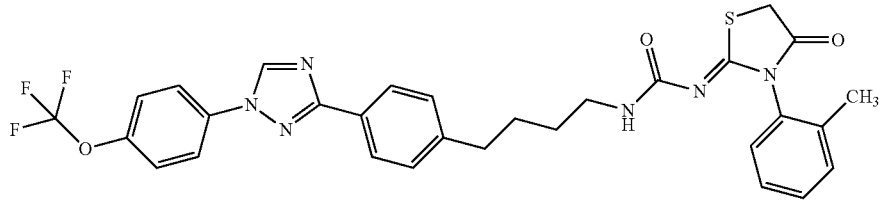 [SMILES: Cc1ccccc1N1C(=O)CS/C1=N\C(=O)NCCCCc1ccc(-c2ncn(-c3ccc(OC(F)(F)F)cc3)n2)cc1] |
| P145, P522 | 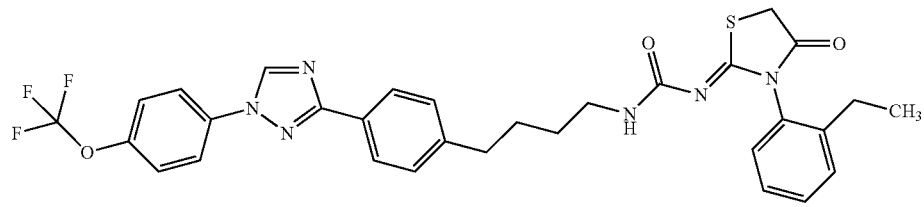 [SMILES: CCc1ccccc1N1C(=O)CS/C1=N\C(=O)NCCCCc1ccc(-c2ncn(-c3ccc(OC(F)(F)F)cc3)n2)cc1] |

TABLE 2B-continued

Exemplified Prophetic Structures (P) from Table P-One and P-Two for Molecules of Formula One

| No. | Structure |
|---|---|
| P146, P208 | 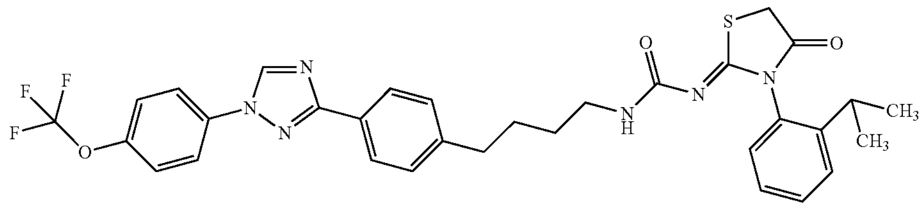 [SMILES: CC(C)c1ccccc1N1C(=O)CS/C1=N\C(=O)NCCCCc1ccc(-c2ncn(-c3ccc(OC(F)(F)F)cc3)n2)cc1] |
| P150, P363 | 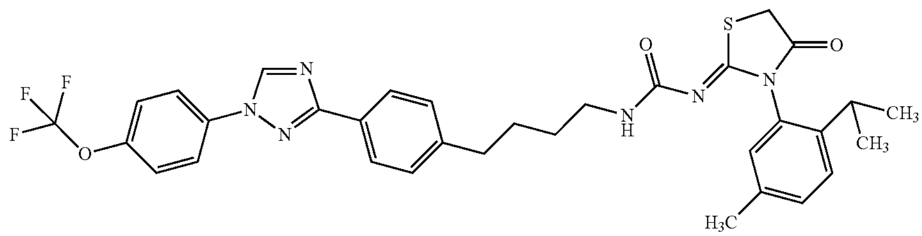 [SMILES: Cc1ccc(C(C)C)c(N2C(=O)CS/C2=N\C(=O)NCCCCc2ccc(-c3ncn(-c4ccc(OC(F)(F)F)cc4)n3)cc2)c1] |
| P151, P842 | 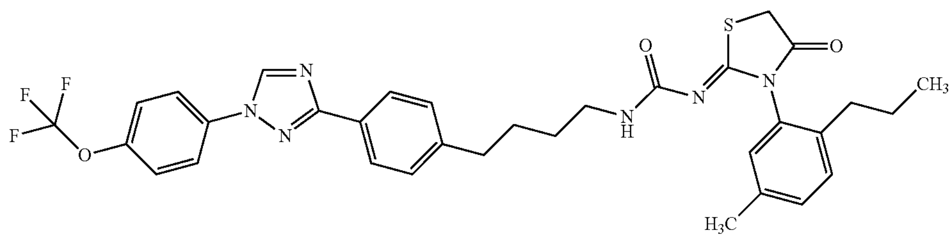 [SMILES: CCCc1ccc(C)cc1N1C(=O)CS/C1=N\C(=O)NCCCCc1ccc(-c2ncn(-c3ccc(OC(F)(F)F)cc3)n2)cc1] |
| P152, P1481 | 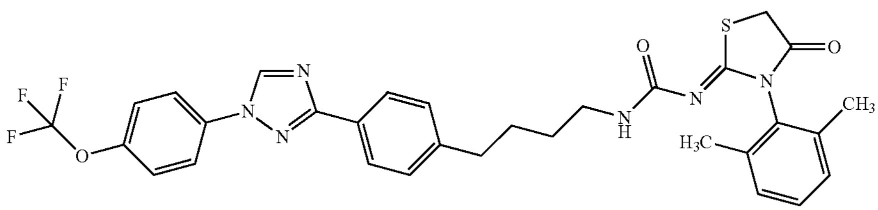 [SMILES: Cc1cccc(C)c1N1C(=O)CS/C1=N\C(=O)NCCCCc1ccc(-c2ncn(-c3ccc(OC(F)(F)F)cc3)n2)cc1] |
| P153 | 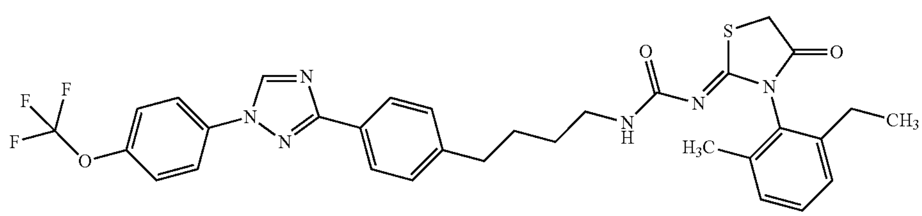 [SMILES: CCc1cccc(C)c1N1C(=O)CS/C1=N\C(=O)NCCCCc1ccc(-c2ncn(-c3ccc(OC(F)(F)F)cc3)n2)cc1] |
| P154 | 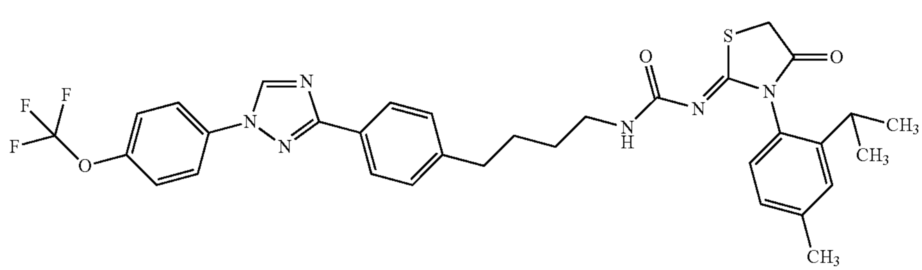 [SMILES: Cc1ccc(N2C(=O)CS/C2=N\C(=O)NCCCCc2ccc(-c3ncn(-c4ccc(OC(F)(F)F)cc4)n3)cc2)c(C(C)C)c1] |

TABLE 2B-continued

Exemplified Prophetic Structures (P) from Table P-One and P-Two for Molecules of Formula One

| No. | Structure |
|---|---|
| P155, P1162 | 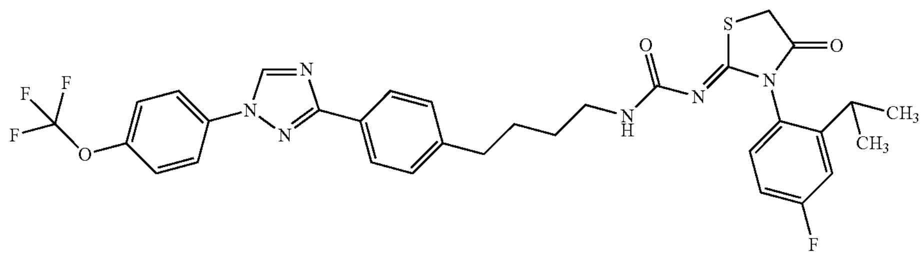 [SMILES: CC(C)c1cc(F)ccc1N1C(=O)CS/C1=N\C(=O)NCCCCc1ccc(-c2ncn(-c3ccc(OC(F)(F)F)cc3)n2)cc1] |
| P156, P682 | 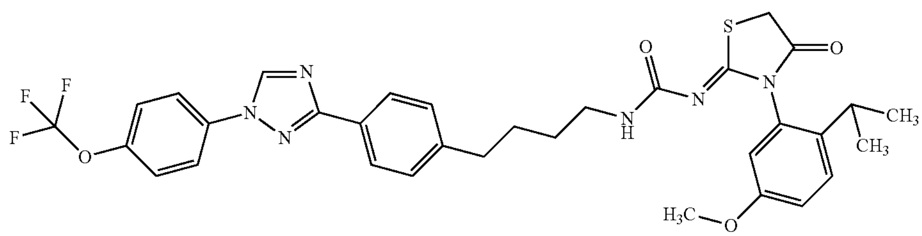 [SMILES: COc1ccc(C(C)C)c(N2C(=O)CS/C2=N\C(=O)NCCCCc2ccc(-c3ncn(-c4ccc(OC(F)(F)F)cc4)n3)cc2)c1] |
| P159 | 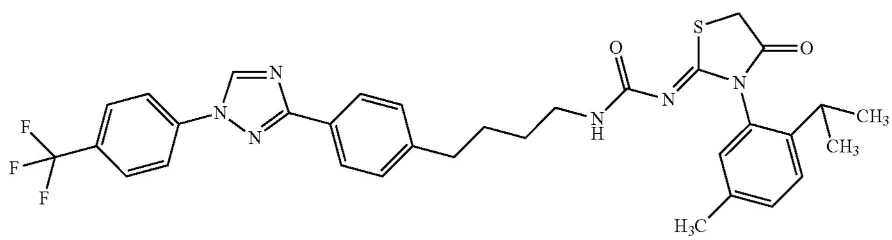 [SMILES: Cc1ccc(C(C)C)c(N2C(=O)CS/C2=N\C(=O)NCCCCc2ccc(-c3ncn(-c4ccc(C(F)(F)F)cc4)n3)cc2)c1] |
| P160 | 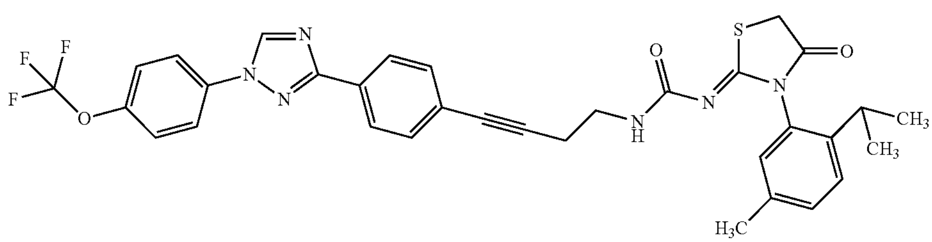 [SMILES: Cc1ccc(C(C)C)c(N2C(=O)CS/C2=N\C(=O)NCCC#Cc2ccc(-c3ncn(-c4ccc(OC(F)(F)F)cc4)n3)cc2)c1] |
| P170 | 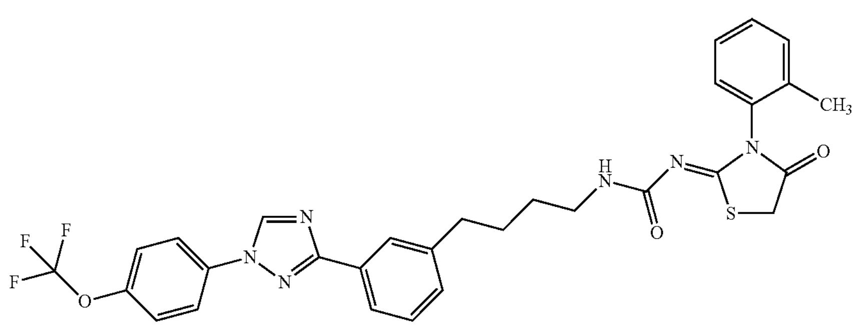 [SMILES: Cc1ccccc1N1C(=O)CS/C1=N\C(=O)NCCCCc1cccc(-c2ncn(-c3ccc(OC(F)(F)F)cc3)n2)c1] |

TABLE 2B-continued
Exemplified Prophetic Structures (P) from Table P-One and P-Two for Molecules of Formula One
| No. | Structure |
|---|---|
| P171 | 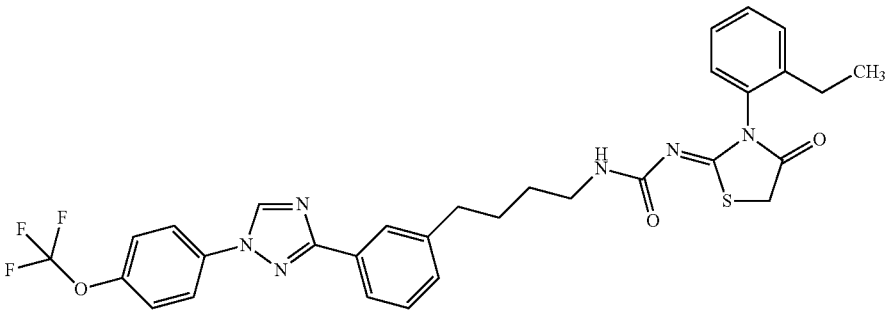 [SMILES: CCc1ccccc1N1C(=O)CS/C1=N\C(=O)NCCCCc1cccc(-c2ncn(-c3ccc(OC(F)(F)F)cc3)n2)c1] |
| P172 | 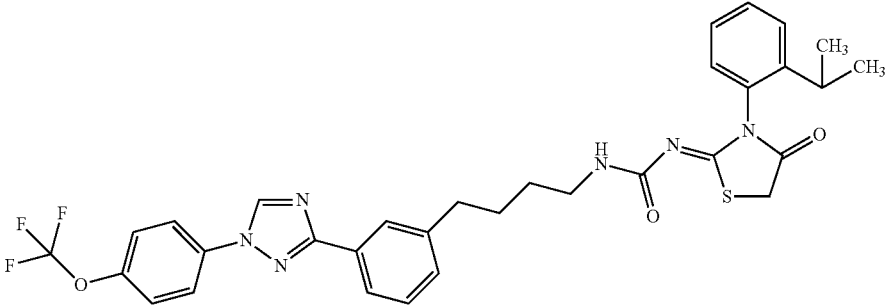 [SMILES: CC(C)c1ccccc1N1C(=O)CS/C1=N\C(=O)NCCCCc1cccc(-c2ncn(-c3ccc(OC(F)(F)F)cc3)n2)c1] |
| P176 | 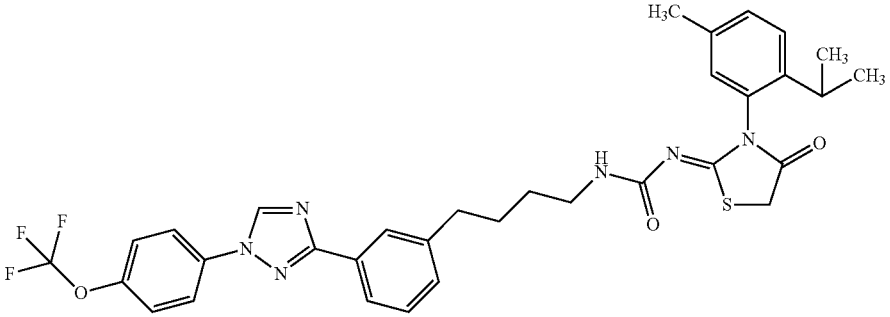 [SMILES: Cc1ccc(C(C)C)c(N2C(=O)CS/C2=N\C(=O)NCCCCc2cccc(-c3ncn(-c4ccc(OC(F)(F)F)cc4)n3)c2)c1] |
| P179 | 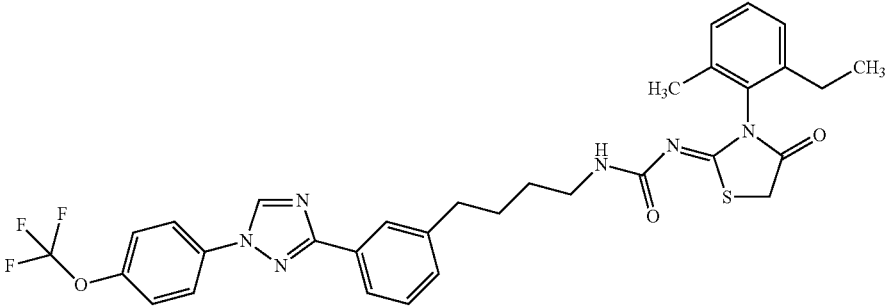 [SMILES: CCc1cccc(C)c1N1C(=O)CS/C1=N\C(=O)NCCCCc1cccc(-c2ncn(-c3ccc(OC(F)(F)F)cc3)n2)c1] |

TABLE 2B-continued
Exemplified Prophetic Structures (P) from Table P-One and P-Two for Molecules of Formula One
| No. | Structure |
|---|---|
| P180 | 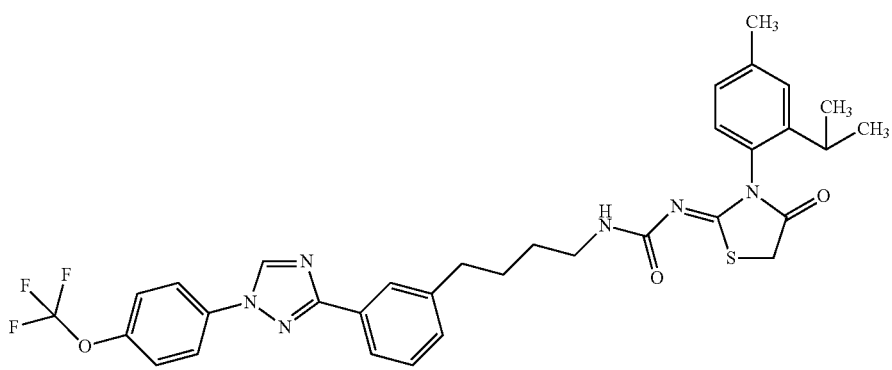 [SMILES: Cc1ccc(N2C(=O)CS/C2=N\C(=O)NCCCCc2cccc(-c3ncn(-c4ccc(OC(F)(F)F)cc4)n3)c2)c(C(C)C)c1] |
| P181 | 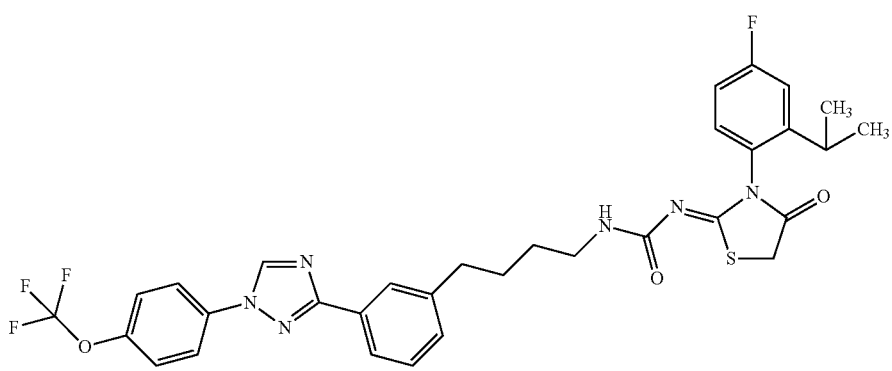 [SMILES: CC(C)c1cc(F)ccc1N1C(=O)CS/C1=N\C(=O)NCCCCc1cccc(-c2ncn(-c3ccc(OC(F)(F)F)cc3)n2)c1] |
| P182 | 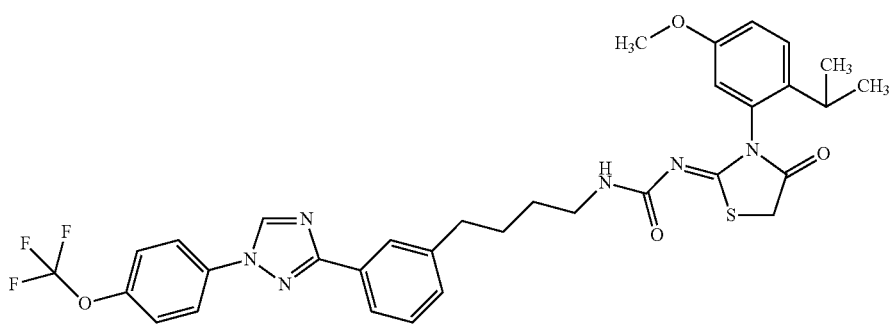 [SMILES: COc1ccc(C(C)C)c(N2C(=O)CS/C2=N\C(=O)NCCCCc2cccc(-c3ncn(-c4ccc(OC(F)(F)F)cc4)n3)c2)c1] |
| P205 | 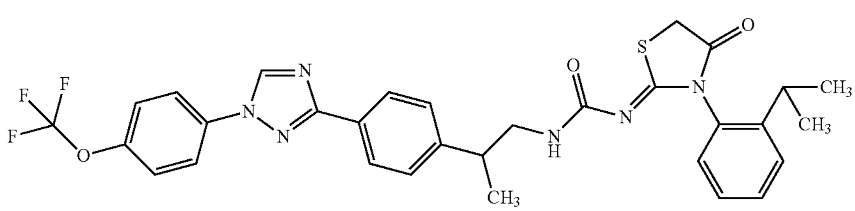 [SMILES: CC(C)c1ccccc1N1C(=O)CS/C1=N\C(=O)NCC(C)c1ccc(-c2ncn(-c3ccc(OC(F)(F)F)cc3)n2)cc1] |
| P209 | 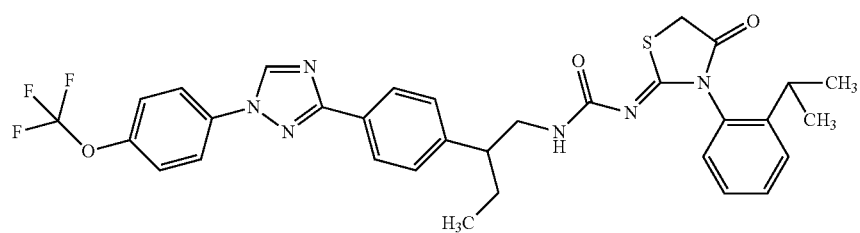 [SMILES: CCC(CNC(=O)/N=C1\SCC(=O)N1c1ccccc1C(C)C)c1ccc(-c2ncn(-c3ccc(OC(F)(F)F)cc3)n2)cc1] |

TABLE 2B-continued

Exemplified Prophetic Structures (P) from Table P-One and P-Two for Molecules of Formula One

| No. | Structure |
|---|---|
| P364 | 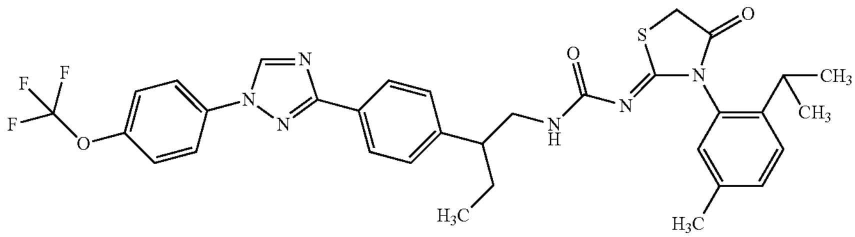 [SMILES: CCC(CNC(=O)/N=C1\SCC(=O)N1c1cc(C)ccc1C(C)C)c1ccc(-c2ncn(-c3ccc(OC(F)(F)F)cc3)n2)cc1] |
| P679 | 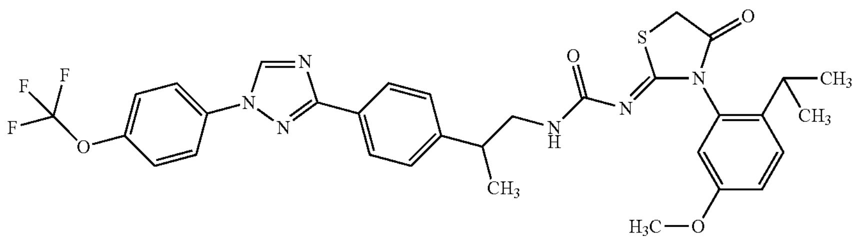 [SMILES: COc1ccc(C(C)C)c(N2C(=O)CS/C2=N\C(=O)NCC(C)c2ccc(-c3ncn(-c4ccc(OC(F)(F)F)cc4)n3)cc2)c1] |
| P683 | 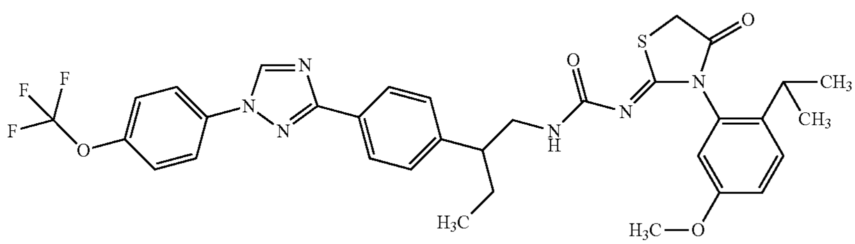 [SMILES: CCC(CNC(=O)/N=C1\SCC(=O)N1c1cc(OC)ccc1C(C)C)c1ccc(-c2ncn(-c3ccc(OC(F)(F)F)cc3)n2)cc1] |
| P1163 | 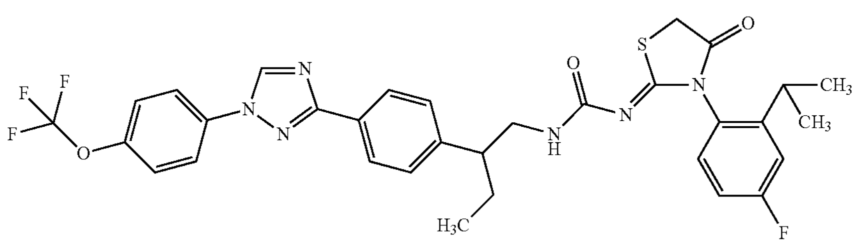 [SMILES: CCC(CNC(=O)/N=C1\SCC(=O)N1c1ccc(F)cc1C(C)C)c1ccc(-c2ncn(-c3ccc(OC(F)(F)F)cc3)n2)cc1] |

TABLE 2C

Additionally Exemplified Molecules (FB) of Formula One

| No. | Structure |
|---|---|
| FB1 | 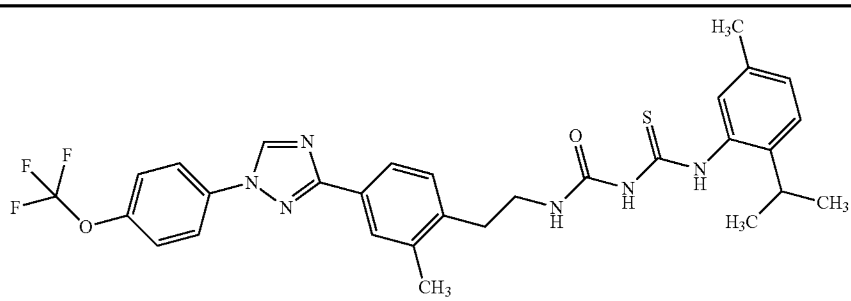 |

TABLE 2C-continued
Additionally Exemplified Molecules (FB) of Formula One
| No. | Structure |
|---|---|
| FB2 | 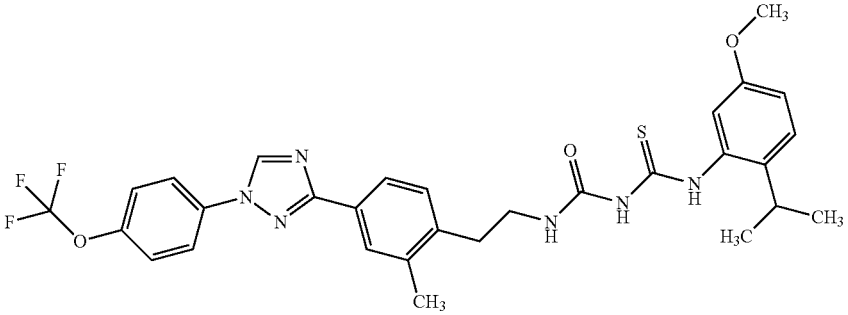 [SMILES: COc1ccc(C(C)C)c(NC(=S)NC(=O)NCCc2ccc(-c3ncn(-c4ccc(OC(F)(F)F)cc4)n3)cc2C)c1] |
| FB3 | 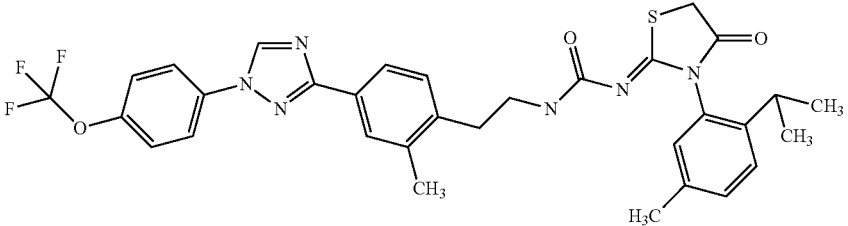 |
| FB4 | 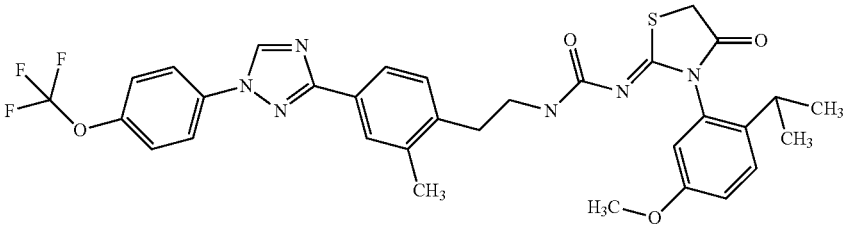 [SMILES: COc1ccc(C(C)C)c(N2C(=O)CS/C2=N\C(=O)NCCc2ccc(-c3ncn(-c4ccc(OC(F)(F)F)cc4)n3)cc2C)c1] |
| FB5 | 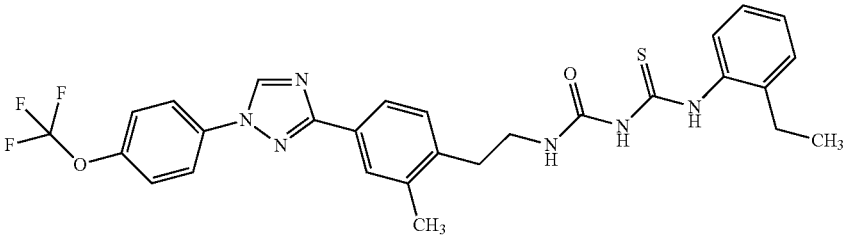 [SMILES: CCc1ccccc1NC(=S)NC(=O)NCCc1ccc(-c2ncn(-c3ccc(OC(F)(F)F)cc3)n2)cc1C] |
| FB6 | 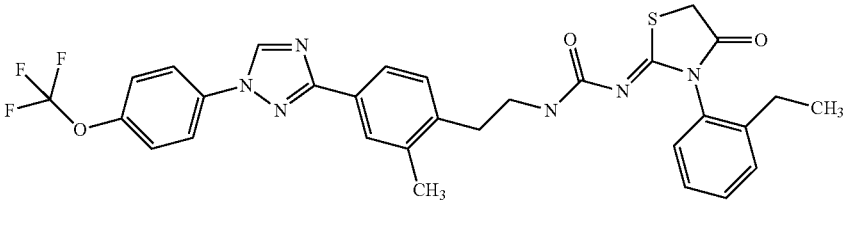 [SMILES: CCc1ccccc1N1C(=O)CS/C1=N\C(=O)NCCc1ccc(-c2ncn(-c3ccc(OC(F)(F)F)cc3)n2)cc1C] |
| FB7 | 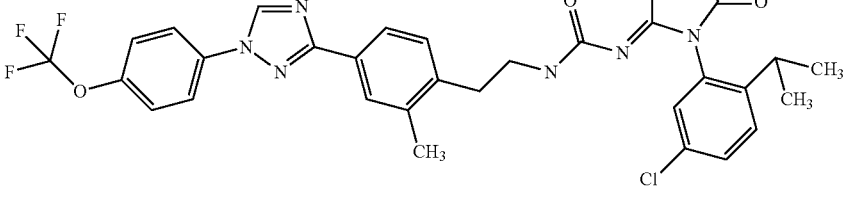 |

TABLE 2C-continued

Additionally Exemplified Molecules (FB) of Formula One

| No. | Structure |
|---|---|
| FB8 | 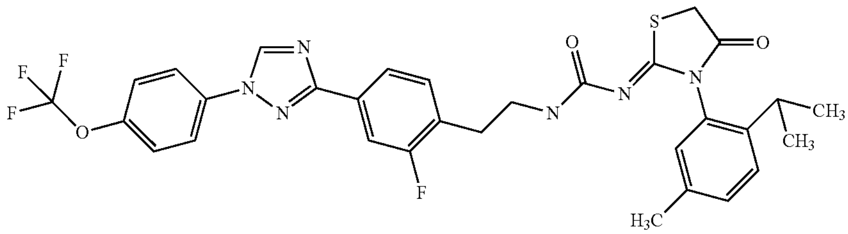 |
| FB9 | 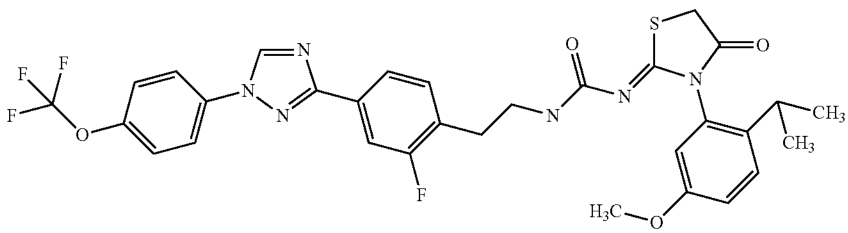 [SMILES: COc1ccc(C(C)C)c(N2C(=O)CS/C2=N\C(=O)NCCc2ccc(-c3ncn(-c4ccc(OC(F)(F)F)cc4)n3)cc2F)c1] |
| FB10 | 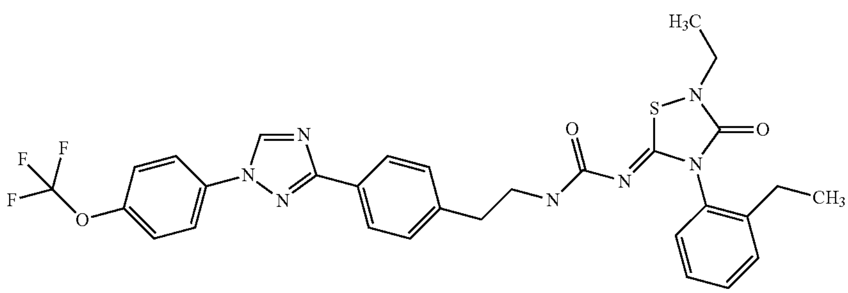 [SMILES: CCc1ccccc1-n1c(=O)n(CC)s/c1=N\C(=O)NCCc1ccc(-c2ncn(-c3ccc(OC(F)(F)F)cc3)n2)cc1] |
| FB11 | 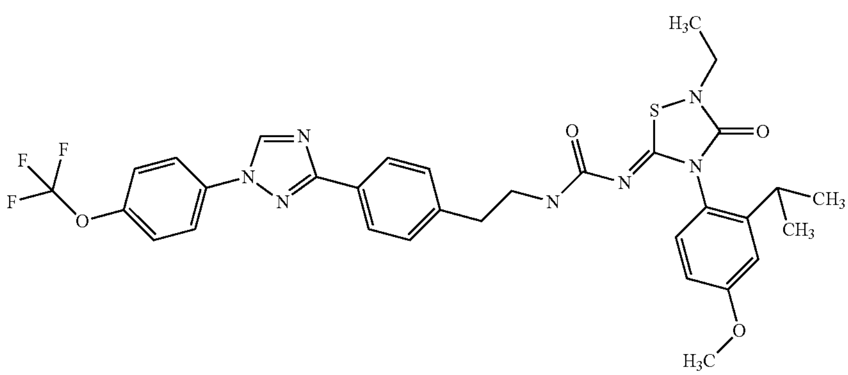 [SMILES: CCn1s/c(=N\C(=O)NCCc2ccc(-c3ncn(-c4ccc(OC(F)(F)F)cc4)n3)cc2)n(-c2ccc(OC)cc2C(C)C)c1=O] |
| FB12 | 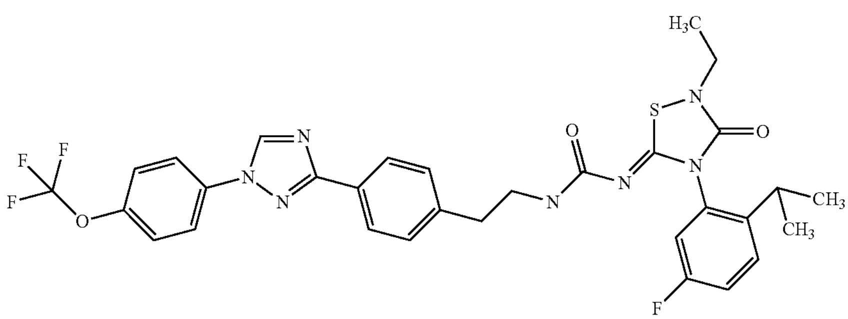 [SMILES: CCn1s/c(=N\C(=O)NCCc2ccc(-c3ncn(-c4ccc(OC(F)(F)F)cc4)n3)cc2)n(-c2cc(F)ccc2C(C)C)c1=O] |

TABLE 2C-continued
Additionally Exemplified Molecules (FB) of Formula One
| No. | Structure |
| --- | --- |
| FB13 | 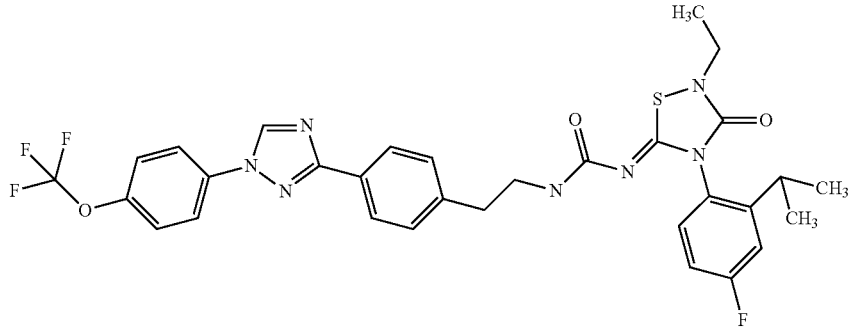 [SMILES: CCn1s/c(=N\C(=O)NCCc2ccc(-c3ncn(-c4ccc(OC(F)(F)F)cc4)n3)cc2)n(-c2ccc(F)cc2C(C)C)c1=O] |
| FB14 | 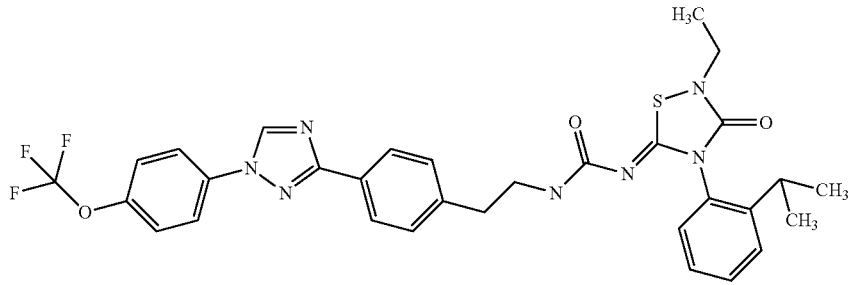 [SMILES: CCn1s/c(=N\C(=O)NCCc2ccc(-c3ncn(-c4ccc(OC(F)(F)F)cc4)n3)cc2)n(-c2ccccc2C(C)C)c1=O] |
| FB15 | 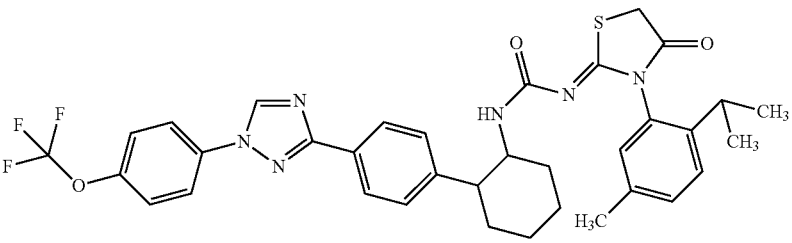 [SMILES: Cc1ccc(C(C)C)c(N2C(=O)CS/C2=N\C(=O)NC2CCCCC2c2ccc(-c3ncn(-c4ccc(OC(F)(F)F)cc4)n3)cc2)c1] |
| FB16 | 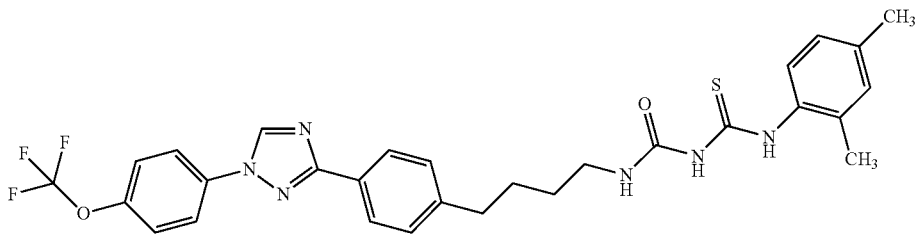 [SMILES: Cc1ccc(NC(=S)NC(=O)NCCCCc2ccc(-c3ncn(-c4ccc(OC(F)(F)F)cc4)n3)cc2)c(C)c1] |
| FB17 | 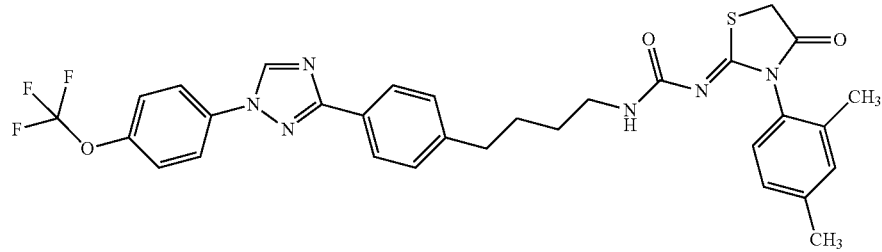 [SMILES: Cc1ccc(N2C(=O)CS/C2=N\C(=O)NCCCCc2ccc(-c3ncn(-c4ccc(OC(F)(F)F)cc4)n3)cc2)c(C)c1] |

TABLE 2C-continued

Additionally Exemplified Molecules (FB) of Formula One

| No. | Structure |
|---|---|
| FB18 | 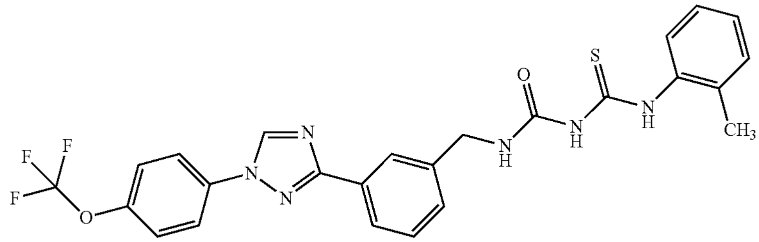 [SMILES: Cc1ccccc1NC(=S)NC(=O)NCc1cccc(-c2ncn(-c3ccc(OC(F)(F)F)cc3)n2)c1] |
| FB19 | 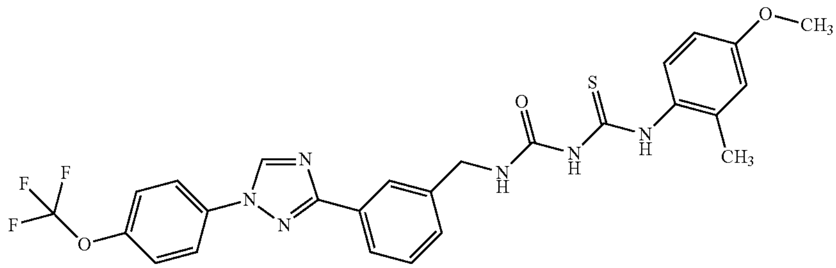 [SMILES: COc1ccc(NC(=S)NC(=O)NCc2cccc(-c3ncn(-c4ccc(OC(F)(F)F)cc4)n3)c2)c(C)c1] |
| FB20 | 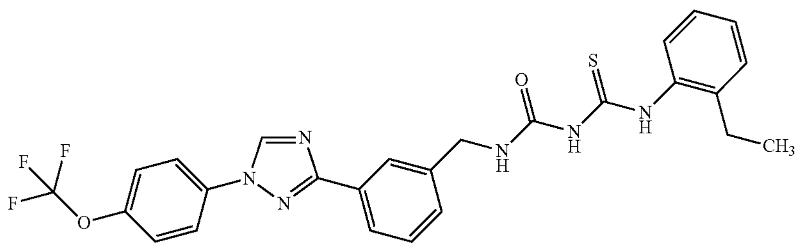 [SMILES: CCc1ccccc1NC(=S)NC(=O)NCc1cccc(-c2ncn(-c3ccc(OC(F)(F)F)cc3)n2)c1] |
| FB21 | 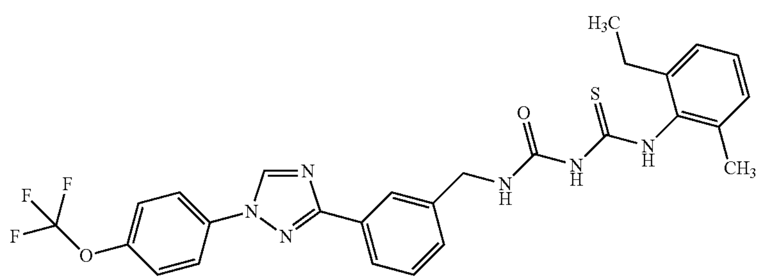 [SMILES: CCc1cccc(C)c1NC(=S)NC(=O)NCc1cccc(-c2ncn(-c3ccc(OC(F)(F)F)cc3)n2)c1] |
| FB22 | 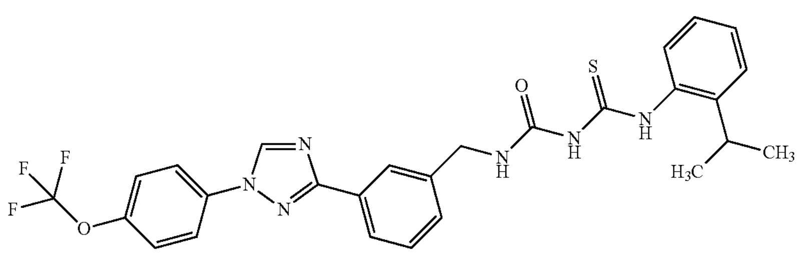 [SMILES: CC(C)c1ccccc1NC(=S)NC(=O)NCc1cccc(-c2ncn(-c3ccc(OC(F)(F)F)cc3)n2)c1] |
| FB23 | 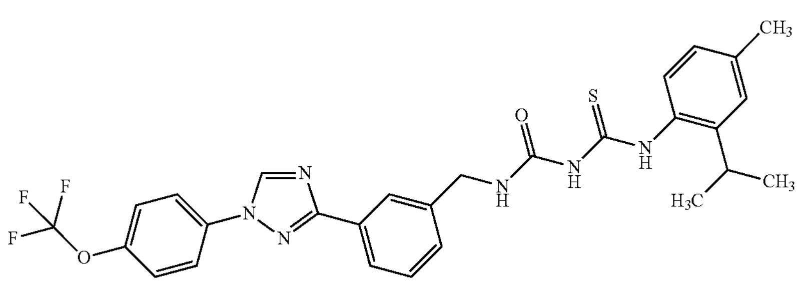 [SMILES: Cc1ccc(NC(=S)NC(=O)NCc2cccc(-c3ncn(-c4ccc(OC(F)(F)F)cc4)n3)c2)c(C(C)C)c1] |

TABLE 2C-continued
Additionally Exemplified Molecules (FB) of Formula One
| No. | Structure |
|---|---|
| FB24 | 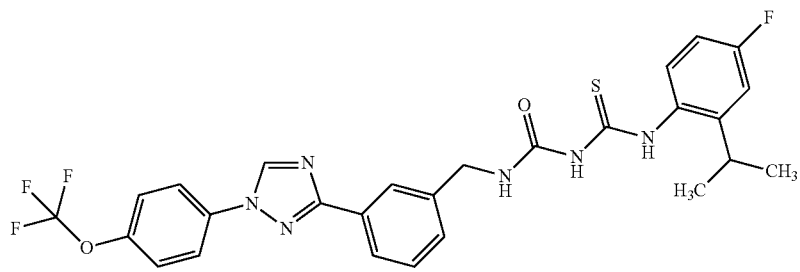 [SMILES: CC(C)c1cc(F)ccc1NC(=S)NC(=O)NCc1cccc(-c2ncn(-c3ccc(OC(F)(F)F)cc3)n2)c1] |
| FB25 | 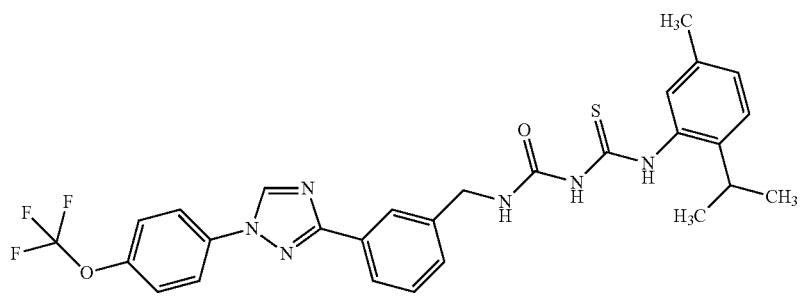 [SMILES: Cc1ccc(C(C)C)c(NC(=S)NC(=O)NCc2cccc(-c3ncn(-c4ccc(OC(F)(F)F)cc4)n3)c2)c1] |
| FB26 | 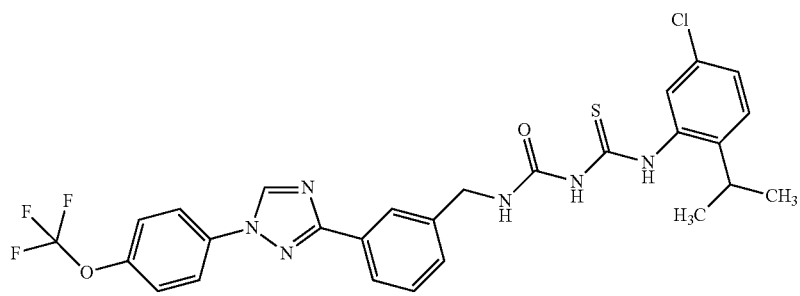 [SMILES: CC(C)c1ccc(Cl)cc1NC(=S)NC(=O)NCc1cccc(-c2ncn(-c3ccc(OC(F)(F)F)cc3)n2)c1] |
| FB27 | 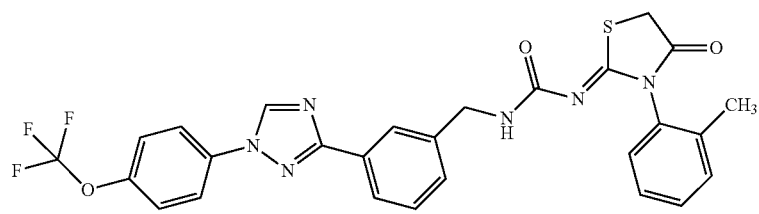 [SMILES: Cc1ccccc1N1C(=O)CS/C1=N\C(=O)NCc1cccc(-c2ncn(-c3ccc(OC(F)(F)F)cc3)n2)c1] |
| FB28 | 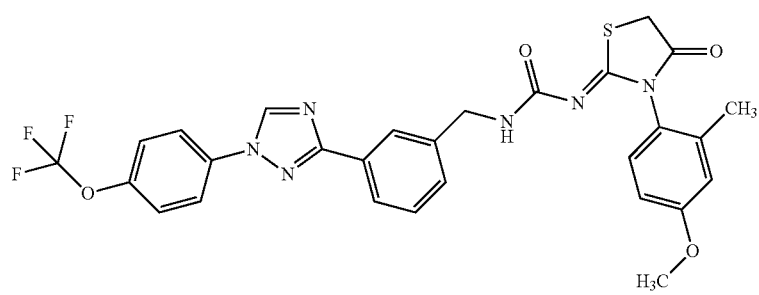 [SMILES: COc1ccc(N2C(=O)CS/C2=N\C(=O)NCc2cccc(-c3ncn(-c4ccc(OC(F)(F)F)cc4)n3)c2)c(C)c1] |

TABLE 2C-continued
Additionally Exemplified Molecules (FB) of Formula One
| No. | Structure |
|---|---|
| FB29 | 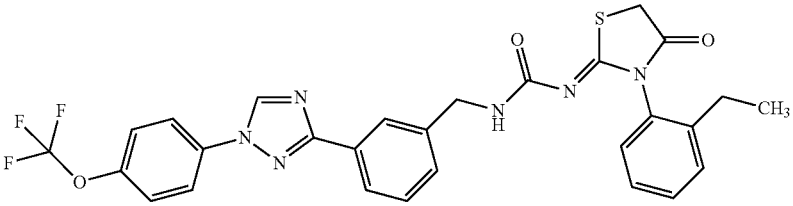 [SMILES: CCc1ccccc1N1C(=O)CS/C1=N\C(=O)NCc1cccc(-c2ncn(-c3ccc(OC(F)(F)F)cc3)n2)c1] |
| FB30 | 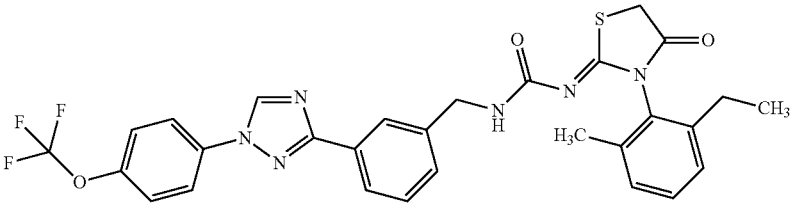 [SMILES: CCc1cccc(C)c1N1C(=O)CS/C1=N\C(=O)NCc1cccc(-c2ncn(-c3ccc(OC(F)(F)F)cc3)n2)c1] |
| FB31 | 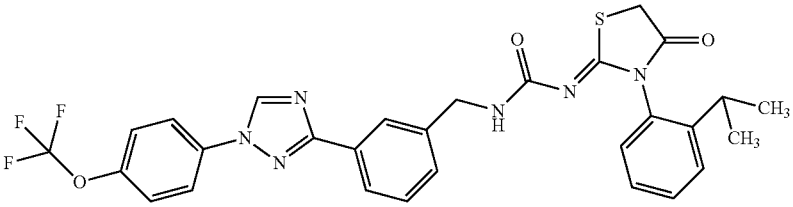 [SMILES: CC(C)c1ccccc1N1C(=O)CS/C1=N\C(=O)NCc1cccc(-c2ncn(-c3ccc(OC(F)(F)F)cc3)n2)c1] |
| FB32 | 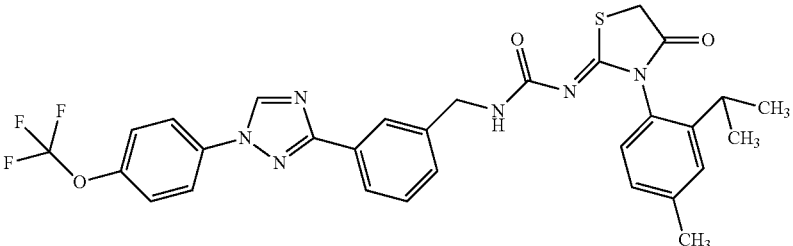 [SMILES: CC(C)c1cc(F)ccc1N1C(=O)CS/C1=N\C(=O)NCc1cccc(-c2ncn(-c3ccc(OC(F)(F)F)cc3)n2)c1] |
| FB33 | 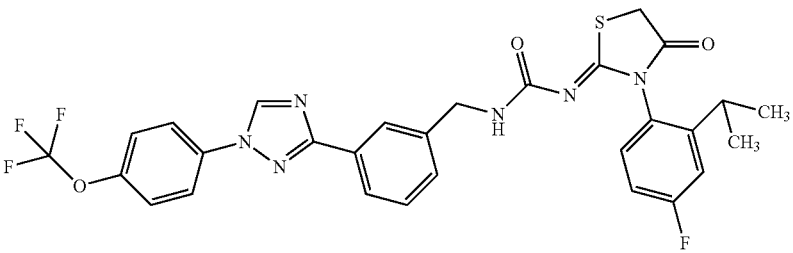 |
| FB34 | 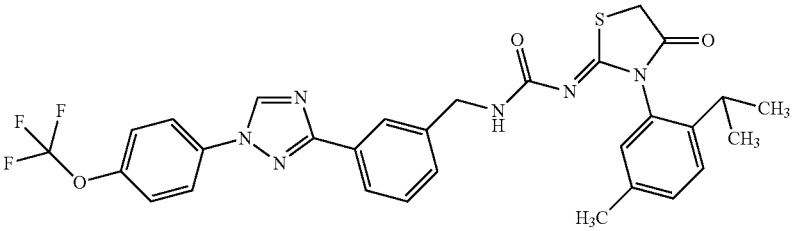 [SMILES: Cc1ccc(C(C)C)c(N2C(=O)CS/C2=N\C(=O)NCc2cccc(-c3ncn(-c4ccc(OC(F)(F)F)cc4)n3)c2)c1] |

TABLE 2C-continued

Additionally Exemplified Molecules (FB) of Formula One

| No. | Structure |
|---|---|
| FB35 | 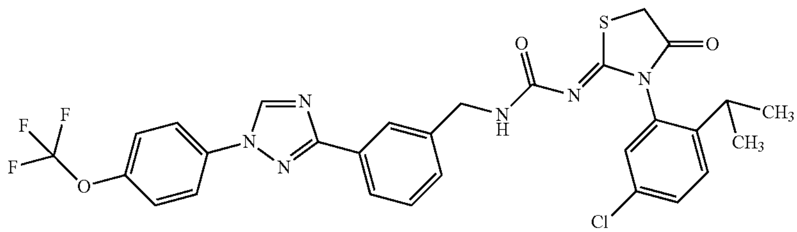 [SMILES: CC(C)c1ccc(Cl)cc1N1C(=O)CS/C1=N\C(=O)NCc1cccc(-c2ncn(-c3ccc(OC(F)(F)F)cc3)n2)c1] |
| FB36 | 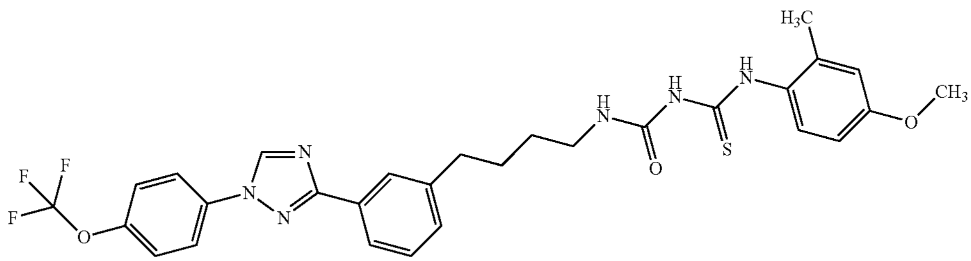 [SMILES: COc1ccc(NC(=S)NC(=O)NCCCCc2cccc(-c3ncn(-c4ccc(OC(F)(F)F)cc4)n3)c2)c(C)c1] |
| FB37 | 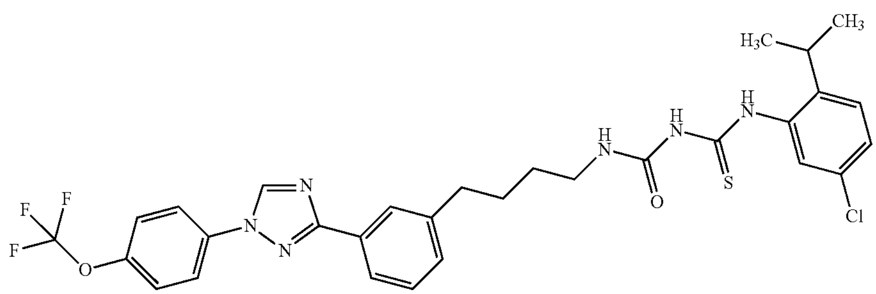 [SMILES: CC(C)c1ccc(Cl)cc1NC(=S)NC(=O)NCCCCc1cccc(-c2ncn(-c3ccc(OC(F)(F)F)cc3)n2)c1] |
| FB38 | 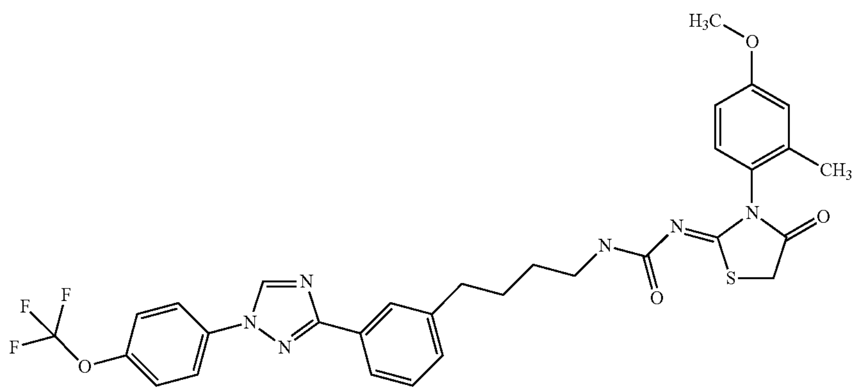 [SMILES: COc1ccc(N2C(=O)CS/C2=N\C(=O)NCCCCc2cccc(-c3ncn(-c4ccc(OC(F)(F)F)cc4)n3)c2)c(C)c1] |
| FB39 | 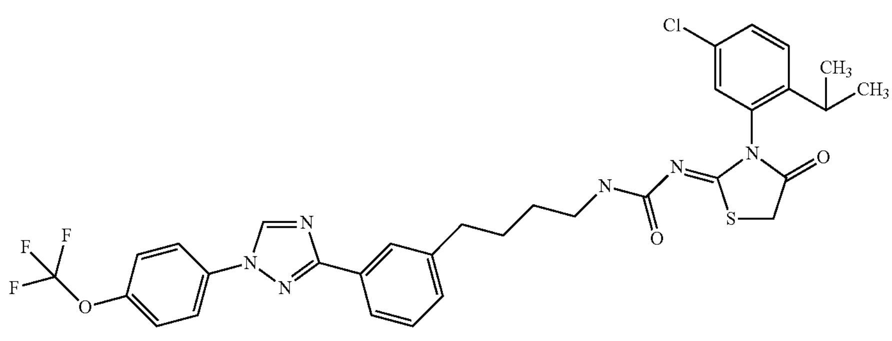 [SMILES: CC(C)c1ccc(Cl)cc1N1C(=O)CS/C1=N\C(=O)NCCCCc1cccc(-c2ncn(-c3ccc(OC(F)(F)F)cc3)n2)c1] |

TABLE 2C-continued

Additionally Exemplified Molecules (FB) of Formula One

| No. | Structure |
|---|---|
| FB40 | 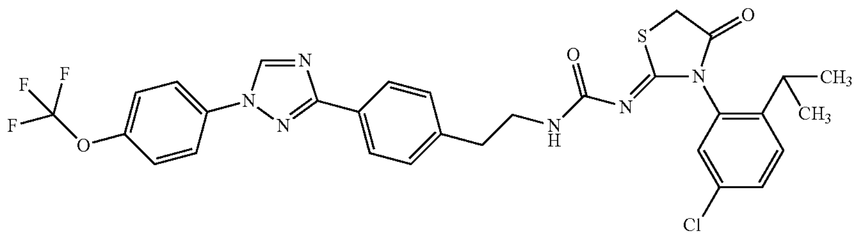 [SMILES: CC(C)c1ccc(Cl)cc1N1C(=O)CS/C1=N\C(=O)NCCc1ccc(-c2ncn(-c3ccc(OC(F)(F)F)cc3)n2)cc1] |
| FB41 | 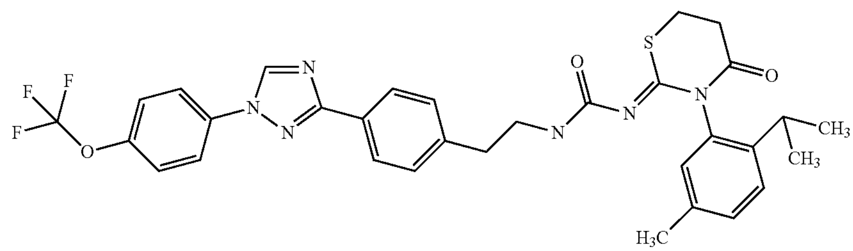 [SMILES: Cc1ccc(C(C)C)c(N2C(=O)CCS/C2=N\C(=O)NCCc2ccc(-c3ncn(-c4ccc(OC(F)(F)F)cc4)n3)cc2)c1] |
| FB42 | 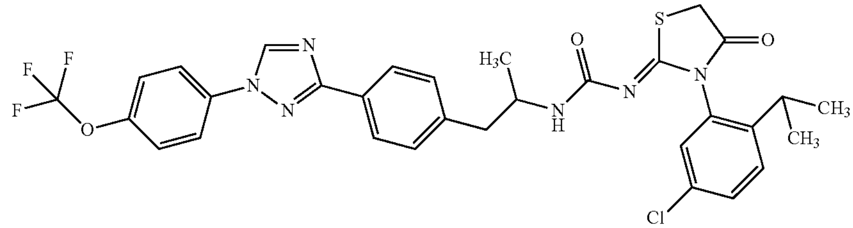 [SMILES: CC(Cc1ccc(-c2ncn(-c3ccc(OC(F)(F)F)cc3)n2)cc1)NC(=O)/N=C1\SCC(=O)N1c1cc(Cl)ccc1C(C)C] |
| FB43 | 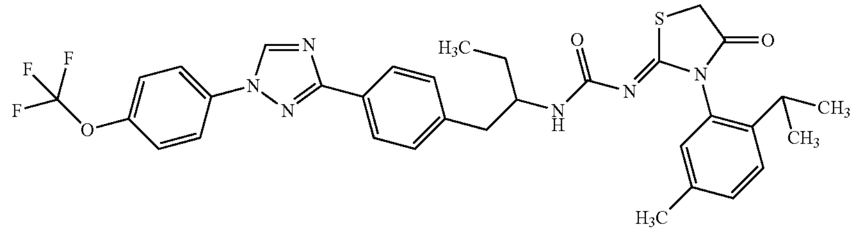 |
| FB44 | 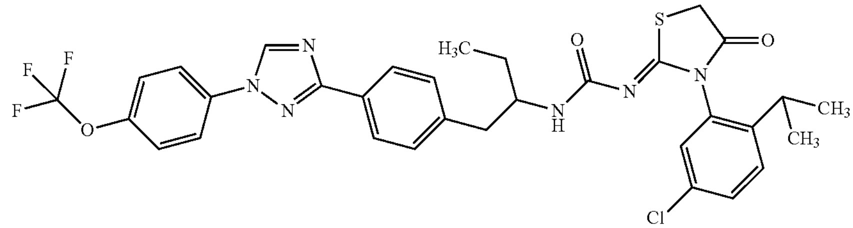 [SMILES: CCC(Cc1ccc(-c2ncn(-c3ccc(OC(F)(F)F)cc3)n2)cc1)NC(=O)/N=C1\SCC(=O)N1c1cc(Cl)ccc1C(C)C] |
| FB45 | 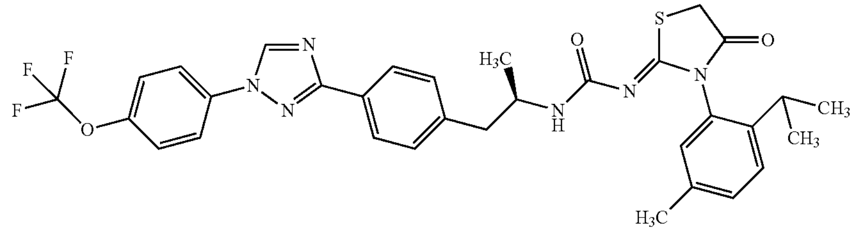 |

TABLE 2C-continued
Additionally Exemplified Molecules (FB) of Formula One
| No. | Structure |
|---|---|
| FB46 | 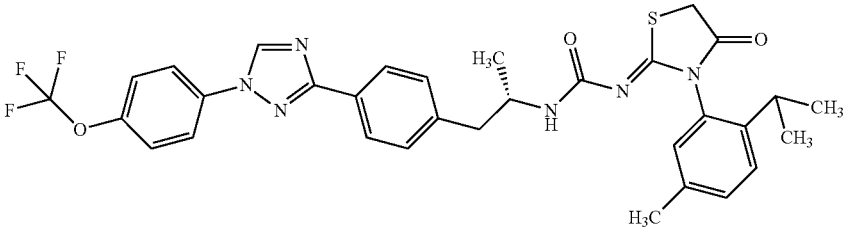 [SMILES: Cc1ccc(C(C)C)c(N2C(=O)CS/C2=N\C(=O)N[C@@H](C)Cc2ccc(-c3ncn(-c4ccc(OC(F)(F)F)cc4)n3)cc2)c1] |
| FB47 | 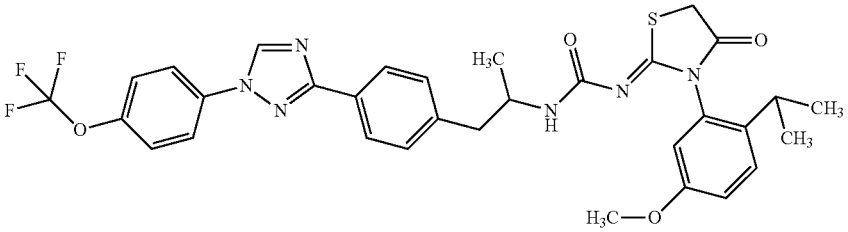 [SMILES: COc1ccc(C(C)C)c(N2C(=O)CS/C2=N\C(=O)NC(C)Cc2ccc(-c3ncn(-c4ccc(OC(F)(F)F)cc4)n3)cc2)c1] |
| FB48 | 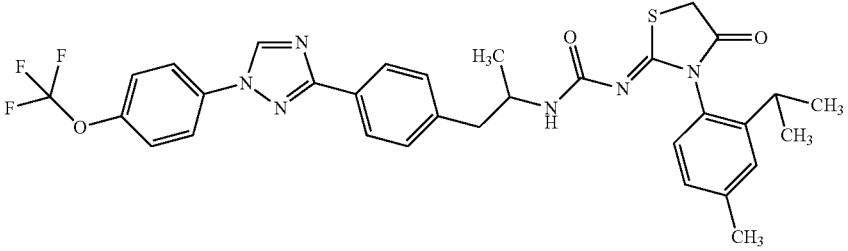 [SMILES: Cc1ccc(N2C(=O)CS/C2=N\C(=O)NC(C)Cc2ccc(-c3ncn(-c4ccc(OC(F)(F)F)cc4)n3)cc2)c(C(C)C)c1] |
| FB49 | 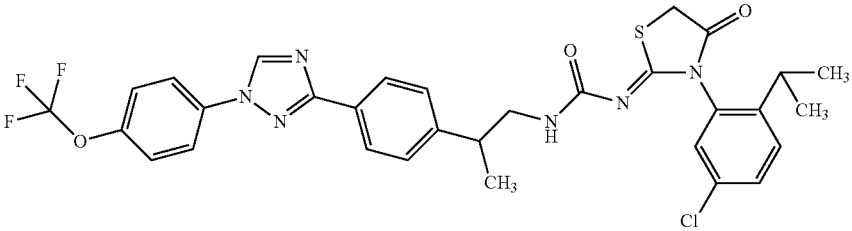 [SMILES: CC(C)c1ccc(Cl)cc1N1C(=O)CS/C1=N\C(=O)NCC(C)c1ccc(-c2ncn(-c3ccc(OC(F)(F)F)cc3)n2)cc1] |
| FB50 | 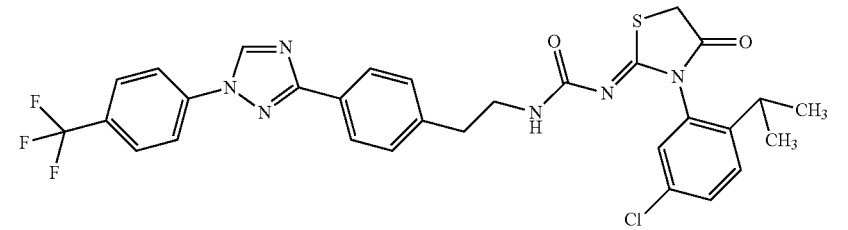 [SMILES: CC(C)c1ccc(Cl)cc1N1C(=O)CS/C1=N\C(=O)NCCc1ccc(-c2ncn(-c3ccc(C(F)(F)F)cc3)n2)cc1] |
| FB51 | 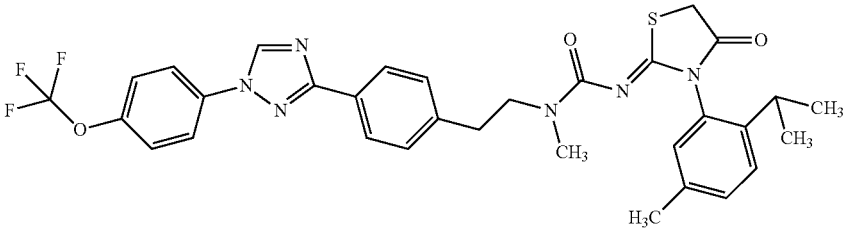 [SMILES: Cc1ccc(C(C)C)c(N2C(=O)CS/C2=N\C(=O)N(C)CCc2ccc(-c3ncn(-c4ccc(OC(F)(F)F)cc4)n3)cc2)c1] |

TABLE 2C-continued
Additionally Exemplified Molecules (FB) of Formula One
| No. | Structure |
|---|---|
| FB52 | 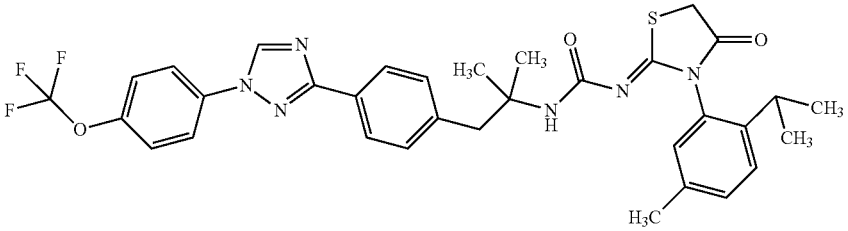 [SMILES: Cc1ccc(C(C)C)c(N2C(=O)CS/C2=N\C(=O)NC(C)(C)Cc2ccc(-c3ncn(-c4ccc(OC(F)(F)F)cc4)n3)cc2)c1] |
| FB53 | 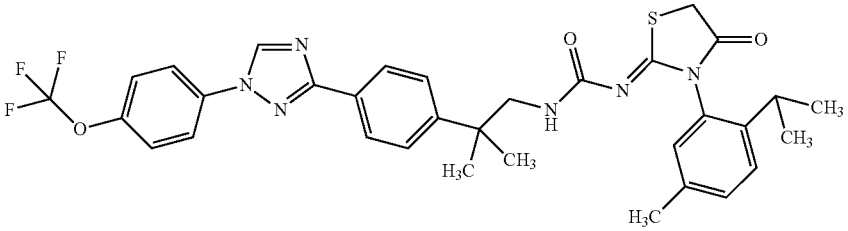 [SMILES: Cc1ccc(C(C)C)c(N2C(=O)CS/C2=N\C(=O)NCC(C)(C)c2ccc(-c3ncn(-c4ccc(OC(F)(F)F)cc4)n3)cc2)c1] |
| FB54 | 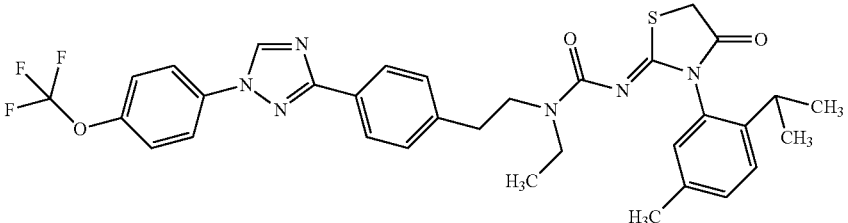 |
| FB55 | 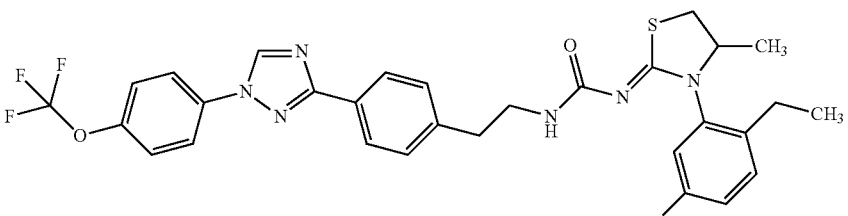 |
| FB56 | 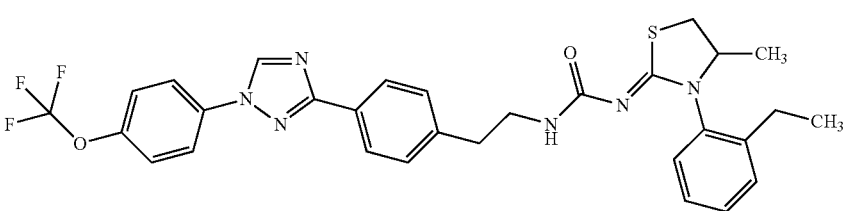 |
| FB57 | 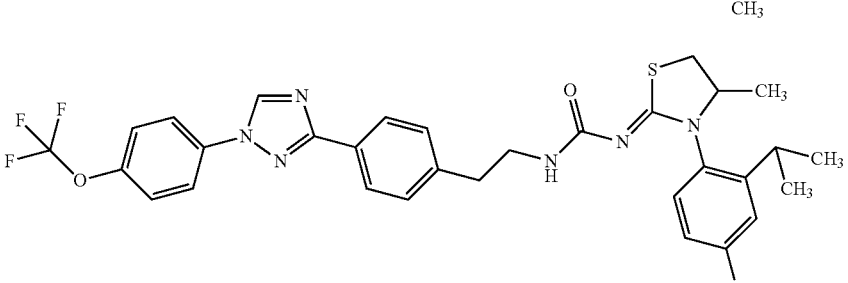 |

TABLE 2C-continued
Additionally Exemplified Molecules (FB) of Formula One
| No. | Structure |
|---|---|
| FB58 | 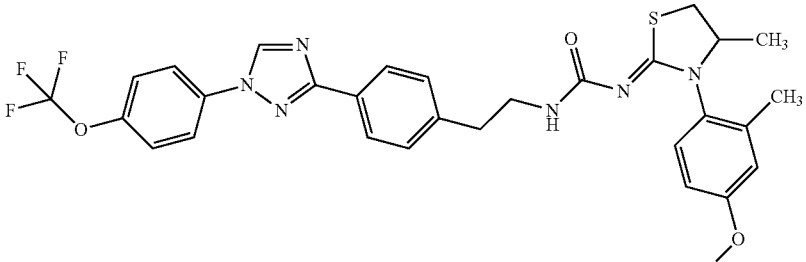 |
| FB59 | 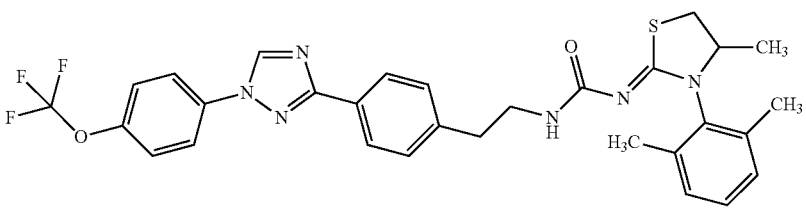 [SMILES: Cc1cccc(C)c1N1/C(=N/C(=O)NCCc2ccc(-c3ncn(-c4ccc(OC(F)(F)F)cc4)n3)cc2)SCC1C] |
| FB60 | 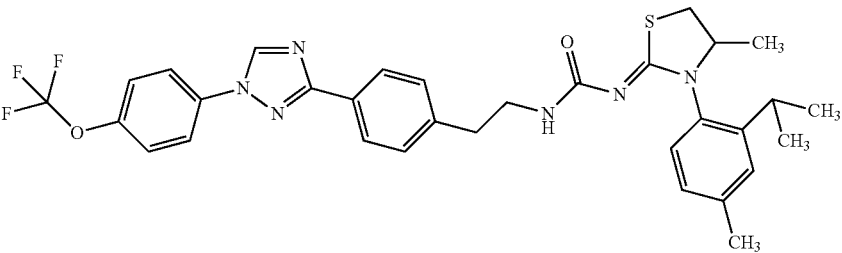 [SMILES: Cc1ccc(N2/C(=N/C(=O)NCCc3ccc(-c4ncn(-c5ccc(OC(F)(F)F)cc5)n4)cc3)SCC2C)c(C(C)C)c1] |
| FB61 | 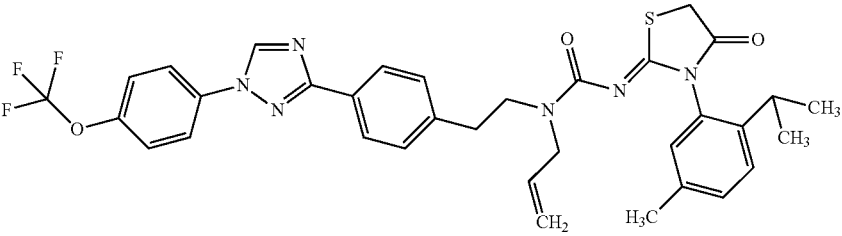 [SMILES: C=CCN(CCc1ccc(-c2ncn(-c3ccc(OC(F)(F)F)cc3)n2)cc1)C(=O)/N=C1\SCC(=O)N1c1cc(C)ccc1C(C)C] |
| FB62 | 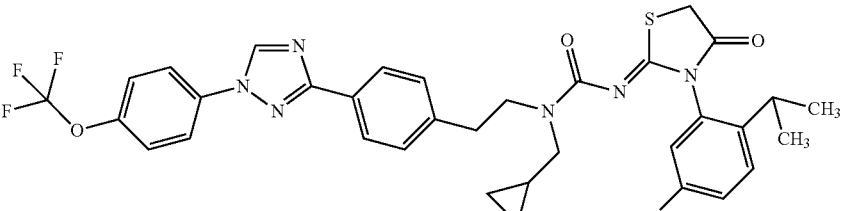 |
| FB63 | 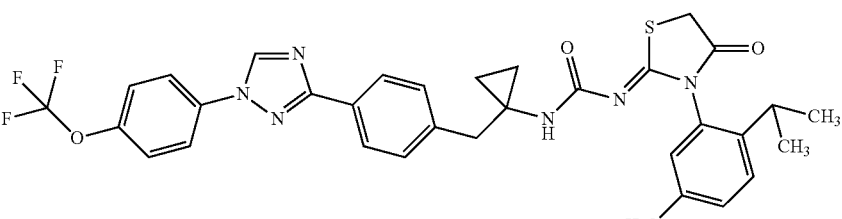 |

TABLE 2C-continued

Additionally Exemplified Molecules (FB) of Formula One

| No. | Structure |
|---|---|
| FB64 | 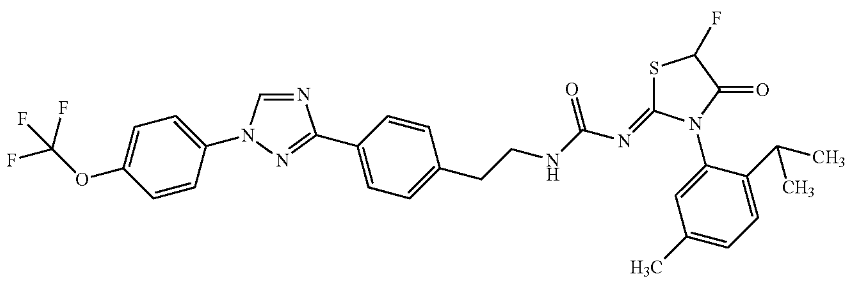 |
| FB65 | 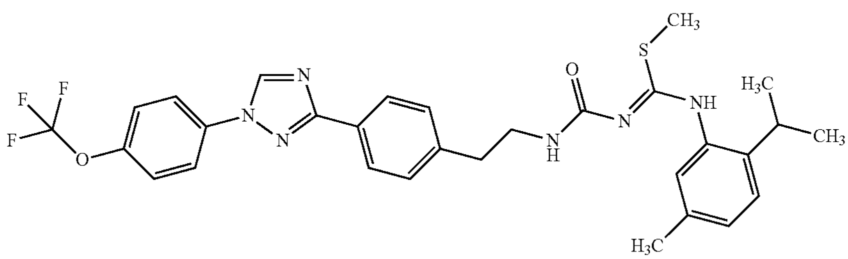 [SMILES: CS/C(=N\C(=O)NCCc1ccc(-c2ncn(-c3ccc(OC(F)(F)F)cc3)n2)cc1)Nc1cc(C)ccc1C(C)C] |
| FB66 | 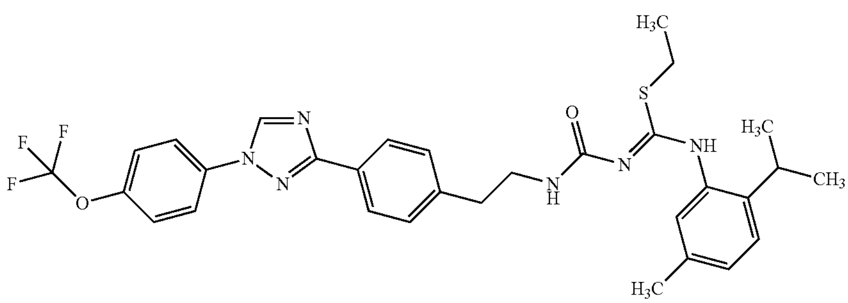 [SMILES: CCS/C(=N\C(=O)NCCc1ccc(-c2ncn(-c3ccc(OC(F)(F)F)cc3)n2)cc1)Nc1cc(C)ccc1C(C)C] |
| FB67 | 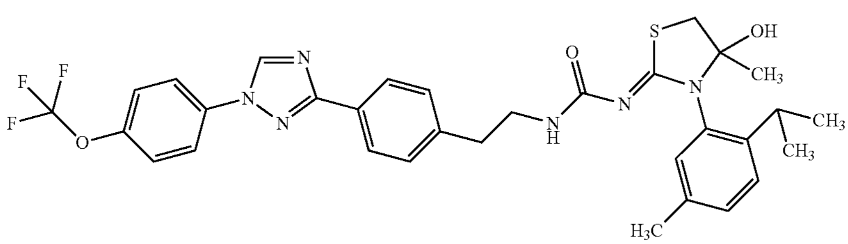 [SMILES: Cc1ccc(C(C)C)c(N2/C(=N/C(=O)NCCc3ccc(-c4ncn(-c5ccc(OC(F)(F)F)cc5)n4)cc3)SCC2(C)O)c1] |
| FB68 | 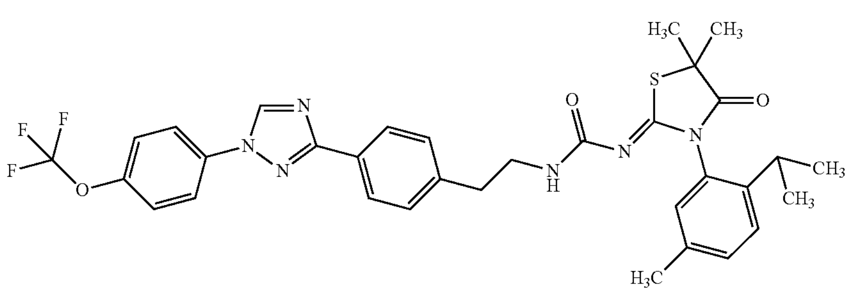 [SMILES: Cc1ccc(C(C)C)c(N2C(=O)C(C)(C)S/C2=N\C(=O)NCCc2ccc(-c3ncn(-c4ccc(OC(F)(F)F)cc4)n3)cc2)c1] |

TABLE 2C-continued
Additionally Exemplified Molecules (FB) of Formula One
| No. | Structure |
|---|---|
| FB69 | 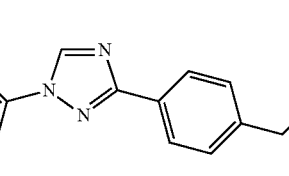 |
| FB70 | 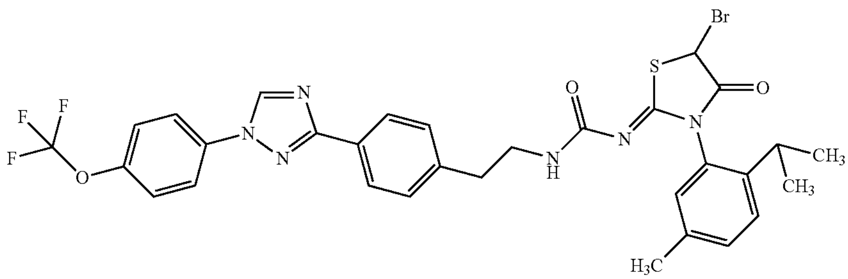 |
| FB71 | 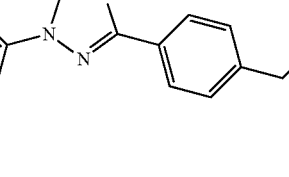 |
| FB72 | 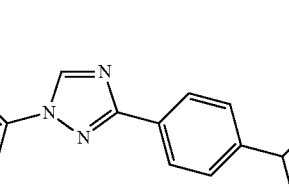 |
TABLE 3a
Analytical Data for Compounds in Table 2a.
| No. | Appearance | Mp (° C.) | ESIMS m/z | $^1$H NMR (δ)[a] | $^{13}$C NMR or $^{19}$F NMR (δ) |
|---|---|---|---|---|---|
| F1 | Clear oil | | 609 ([M + H]$^+$) | $^1$H NMR (400 MHz, CDCl$_3$) δ 8.55 (s, 1H), 8.08 (d, J = 8.2 Hz, 2H), 7.79 (d, J = 9.0 Hz, 2H), 7.43 (dd, J = 3.4, 2.1 Hz, 2H), 7.39 (d, J = 8.3 Hz, 2H), 7.31-7.24 (m, 3H), 7.03 (d, J = 7.6 Hz, 1H), 5.51 (t, J = 6.1 Hz, | $^{19}$F NMR (376 MHz, CDCl$_3$) δ −58.02 |

TABLE 3a-continued

Analytical Data for Compounds in Table 2a.

| No. | Appearance | Mp (° C.) | ESIMS m/z | ¹H NMR (δ)ᵃ | ¹³C NMR or ¹⁹F NMR (δ) |
|---|---|---|---|---|---|
| | | | | 1H), 3.93 (d, J = 1.4 Hz, 2H), 3.63-3.39 (m, 2H), 2.86 (t, J = 7.0 Hz, 2H), 2.68 (dt, J = 13.7, 6.9 Hz, 1H), 1.17 (dd, J = 6.8, 4.7 Hz, 6H) | |
| F2 | White powder | 150-153 | 569 ([M + H]⁺) | ¹H NMR (400 MHz, CDCl₃) δ 10.12 (s, 1H), 9.40 (s, 1H), 8.08 (dt, J = 4.3, 2.7 Hz, 3H), 7.63 (d, J = 8.3 Hz, 2H), 7.46-7.14 (m, 6H), 7.00 (s, 1H), 3.52-3.39 (m, 2H), 2.98 (dd, J = 13.7, 6.8 Hz, 1H), 2.86 (t, J = 6.9 Hz, 2H), 1.15 (d, J = 6.8 Hz, 6H) | ¹⁹F NMR (376 MHz, CDCl₃) δ −52.21 |
| F3 | White solid | 133-136, 148-149 | 582 ([M + H]⁺) | ¹H NMR (400 MHz, CDCl₃) δ 11.82 (s, 1H), 9.75 (s, 1H), 8.56 (s, 1H), 8.17-8.08 (m, 2H), 7.84-7.74 (m, 2H), 7.38 (dq, J = 8.0, 0.9 Hz, 2H), 7.30 (d, J = 7.9 Hz, 2H), 7.26-7.07 (m, 3H), 5.75 (s, 1H), 3.52 (d, J = 7.2 Hz, 2H), 3.12-2.97 (m, 1H), 2.90 (d, J = 7.5 Hz, 2H), 2.33 (s, 3H), 1.22 (d, J = 6.8 Hz, 6H) | ¹⁹F NMR (376 MHz, CDCl₃) δ −58.02 |
| F4 | White solid | 88° C. (dec) | 583 ([M + H]⁺) | ¹H NMR (400 MHz, CDCl₃) δ 11.90 (s, 1H), 9.96 (s, 1H), 8.55 (s, 1H), 8.12 (d, J = 8.2 Hz, 2H), 7.79 (d, J = 9.0 Hz, 2H), 7.42-7.33 (m, 5H), 7.30 (d, J = 8.2 Hz, 2H), 7.23 (dd, J = 12.0, 5.8 Hz, 1H), 5.81 (s, 1H), 4.19-4.13 (m, 1H), 3.13 (ddd, J = 27.5, 13.7, 6.9 Hz, 1H), 2.94 (dd, J = 13.4, 6.0 Hz, 1H), 2.74 (dd, J = 13.3, 7.6 Hz, 1H), 1.32-1.16 (m, 9H) | ¹⁹F NMR (376 MHz, CDCl₃) δ −58.03 |
| F5 | Pale pink solid | 102° C. (dec) | 623 ([M + H]⁺) | ¹H NMR (400 MHz, CDCl₃) δ 8.55 (s, 1H), 8.11-8.05 (m, 2H), 7.84-7.76 (m, 2H), 7.44-7.36 (m, 2H), 7.31 (d, J = 8.0 Hz, 1H), 7.27-7.25 (m, 3H), 6.85 (d, J = 0.8 Hz, 1H), 5.51 (t, J = 6.1 Hz, 1H), 3.92 (d, J = 1.7 Hz, 2H), 3.68-3.38 (m, 2H), 2.87 (t, J = 7.1 Hz, 2H), 2.73-2.52 (m, 1H), 2.33 (s, 3H), 1.15 (dd, J = 6.9, 2.4 Hz, 6H) | ¹⁹F NMR (376 MHz, CDCl₃) δ −58.02 |

TABLE 3a-continued

Analytical Data for Compounds in Table 2a.

| No. | Appearance | Mp (° C.) | ESIMS m/z | $^1$H NMR (δ)$^a$ | $^{13}$C NMR or $^{19}$F NMR (δ) |
|---|---|---|---|---|---|
| F5A | | 60-70 | | $^1$H NMR (400 MHz, DMSO-d$_6$) δ 9.39 (s, 1H), 8.13-8.03 (m, 2H), 8.03-7.96 (m, 2H), 7.69-7.57 (m, 3H), 7.50 (d, J = 7.8 Hz, 2H), 7.39-7.27 (m, 3H), 7.22 (dd, J = 8.0, 1.9 Hz, 1H), 7.13 (d, J = 7.8 Hz, 2H), 6.98 (dd, J = 1.7, 0.9 Hz, 1H), 4.11 (d, J = 17.9 Hz, 1H), 4.00 (d, J = 17.9 Hz, 1H), 3.27 (q, J = 6.8 Hz, 2H), 2.77 (t, J = 7.3 Hz, 2H), 2.61 (p, J = 6.8 Hz, 1H), 2.30 (s, 3H), 2.28 (s, 3H), 1.11 (d, J = 6.8 Hz, 3H), 1.09-1.04 (m, 3H) (SO$_3$H not observed) | |
| F6 | Orange solid | 110-118° C. | 639 ([M + H]$^+$) | $^1$H NMR (400 MHz, CDCl$_3$) δ 8.56 (d, J = 3.6 Hz, 1H), 8.12-8.05 (m, 2H), 7.84-7.76 (m, 2H), 7.39 (d, J = 8.3 Hz, 2H), 7.32 (d, J = 8.8 Hz, 1H), 7.29-7.25 (m, 2H), 6.99 (dd, J = 8.7, 2.7 Hz, 1H), 6.56 (d, J = 2.7 Hz, 1H), 5.52 (t, J = 5.9 Hz, 1H), 3.93 (d, J = 1.6 Hz, 2H), 3.77 (s, 3H), 3.67-3.38 (m, 2H), 2.87 (t, J = 7.1 Hz, 2H), 2.60 (dt, J = 13.7, 6.9 Hz, 1H), 1.20 (dt, J = 13.0, 6.8 Hz, 6H) | $^{19}$F NMR (376 MHz, CDCl$_3$) δ −58.02 |
| F7 | White solid | 114° C. (dec) | 623 ([M + H]$^+$) | $^1$H NMR (400 MHz, CDCl$_3$) δ 8.55 (d, J = 1.0 Hz, 1H), 8.12-8.03 (m, 2H), 7.85-7.75 (m, 2H), 7.50-7.43 (m, 2H), 7.43-7.37 (m, 2H), 7.35-7.30 (m, 1H), 7.29-7.22 (m, 2H), 7.09-7.01 (m, 1H), 5.35 (dd, J = 15.3, 8.4 Hz, 1H), 4.14 (dd, J = 14.6, 7.5 Hz, 1H), 3.92 (t, J = 1.8 Hz, 2H), 2.93 (ddd, J = 46.3, 13.4, 5.6 Hz, 1H), 2.83-2.59 (m, 2H), 1.17 (ddd, J = 6.6, 3.7, 2.7 Hz, 6H), 1.14-1.03 (m, 3H) | $^{19}$F NMR (376 MHz, CDCl$_3$) δ −58.02 |
| F8 | Off-white solid | 114° C. (dec) | 637 ([M + H]$^+$) | $^1$H NMR (400 MHz, CDCl$_3$) δ 8.56 (s, 1H), 8.12-8.02 (m, 2H), 7.84-7.74 (m, 2H), 7.39 (d, J = 8.6 Hz, 2H), 7.36-7.31 (m, 1H), 7.28 (d, J = 7.4 Hz, 2H), 7.24 (d, J = 8.1 Hz, | $^{19}$F NMR (376 MHz, CDCl$_3$) δ −58.03 |

TABLE 3a-continued

Analytical Data for Compounds in Table 2a.

| No. | Appearance | Mp (° C.) | ESIMS m/z | ¹H NMR (δ)[a] | ¹³C NMR or ¹⁹F NMR (δ) |
|---|---|---|---|---|---|
| | | | | 1H), 6.87 (d, J = 12.4 Hz, 1H), 5.36 (dd, J = 14.8, 8.4 Hz, 1H), 3.95-3.87 (m, 2H), 3.00 (dd, J = 13.6, 5.5 Hz, 1H), 2.87 (dd, J = 13.4, 5.6 Hz, 1H), 2.76 (dd, J = 13.4, 7.1 Hz, 1H), 2.71-2.57 (m, 1H), 2.35 (d, J = 7.9 Hz, 3H), 1.19-1.05 (m, 9H) | |
| F9 | Brown gum | | 673 ([M + H]⁺) | ¹H NMR (400 MHz, CDCl₃) δ 8.56 (s, 1H), 8.08 (d, J = 8.1 Hz, 2H), 7.85-7.77 (m, 2H), 7.43-7.37 (m, 2H), 7.31 (d, J = 8.0 Hz, 1H), 7.28-7.22 (m, 3H), 6.86-6.83 (m, 1H), 5.52 (t, J = 6.2 Hz, 1H), 3.92 (d, J = 1.7 Hz, 2H), 3.52 (ddt, J = 35.7, 13.7, 6.7 Hz, 2H), 2.87 (t, J = 7.1 Hz, 2H), 2.63 (p, J = 7.0 Hz, 1H), 2.33 (s, 3H), 1.15 (dd, J = 6.9, 2.2 Hz, 6H) | ¹⁹F NMR (376 MHz, CDCl₃) δ −85.89, −87.85 |
| F10 | Orange solid | 113° C. (dec) | 637 ([M + H]⁺) | ¹H NMR (400 MHz, CDCl₃) δ 8.55 (s, 1H), 8.08 (dd, J = 8.1, 5.9 Hz, 2H), 7.84-7.76 (m, 2H), 7.39 (dddd, J = 7.9, 3.0, 2.1, 1.2 Hz, 2H), 7.31-7.20 (m, 4H), 6.83 (ddd, J = 6.6, 1.8, 0.9 Hz, 1H), 5.42 (t, J = 4.0 Hz, 1H), 3.90 (s, 2H), 3.66-3.18 (m, 2H), 3.02 (p, J = 7.2 Hz, 1H), 2.60 (dq, J = 14.1, 7.0 Hz, 1H), 2.34-2.26 (m, 3H), 1.27 (d, J = 7.2 Hz, 3H), 1.17-1.07 (m, 6H) | ¹⁹F NMR (376 MHz, CDCl₃) δ −58.03 |
| F11 | Yellow solid | 178-182° C. | 567 ([M + H]⁺) | ¹H NMR (400 MHz, DMSO-d₆) δ 11.74 (s, 1H), 10.27 (s, 1H), 9.40 (s, 2H), 8.18-7.91 (m, 4H), 7.59 (dd, J = 24.9, 8.4 Hz, 4H), 7.41 (ddd, J = 9.4, 7.9, 4.1 Hz, 3H), 7.27 (dtd, J = 25.3, 7.4, 1.5 Hz, 2H), 6.25 (d, J = 14.6 Hz, 1H), 3.04 (dt, J = 13.7, 6.8 Hz, 1H), 1.19 (d, J = 6.9 Hz, 6H) | ¹⁹F NMR (376 MHz, DMSO-d₆) δ −56.96 |
| F12 | Orange solid | 128° C. (dec) | 607 ([M + H]⁺) | ¹H NMR (400 MHz, CDCl₃) δ 8.54 (s, 1H), 8.09 (d, J = 8.4 Hz, 2H), 7.81-7.76 (m, 2H), 7.52-7.47 (m, 2H), 7.48-7.41 (m, 1H), | ¹⁹F NMR (376 MHz, CDCl₃) δ −58.02 |

TABLE 3a-continued

Analytical Data for Compounds in Table 2a.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 7.41-7.35 (m, 5H), 7.34 (s, 1H), 7.10-7.05 (m, 1H), 6.03 (d, J = 14.6 Hz, 1H), 3.98 (d, J = 2.4 Hz, 2H), 2.69 (dt, J = 13.7, 6.8 Hz, 1H), 1.22-1.18 (m, 6H) | |
| F13 | Orange gum | | 621 ([M + H]$^+$) | $^1$H NMR (400 MHz, CDCl$_3$) δ 8.56 (d, J = 1.4 Hz, 1H), 8.16-8.06 (m, 2H), 7.87-7.74 (m, 2H), 7.53-7.45 (m, 3H), 7.42-7.30 (m, 3H), 7.26-7.21 (m, 2H), 7.14-7.01 (m, 2H), 3.98 (d, J = 2.2 Hz, 2H), 2.77-2.60 (m, 1H), 1.98 (d, J = 1.3 Hz, 3H), 1.21 (dd, J = 6.9, 5.1 Hz, 6H) | $^{19}$F NMR (376 MHz, CDCl$_3$) δ −58.02 |
| F14 | Yellow Solid | | ESIMS m/z 555 ([M + H]$^+$), 553 ([M − H]$^−$) | $^1$H NMR (400 MHz, DMSO-d$_6$) δ 11.95 (s, 1H), 10.26 (s, 1H), 9.43 (s, 1H), 8.21-8.06 (m, 4H), 7.65 (ddd, J = 7.9, 2.0, 1.0 Hz, 2H), 7.55 (t, J = 5.9 Hz, 1H), 7.53-7.47 (m, 2H), 7.44 (dd, J = 7.7, 1.5 Hz, 1H), 7.38 (dd, J = 7.7, 1.6 Hz, 1H), 7.30 (td, J = 7.5, 1.6 Hz, 1H), 7.23 (td, J = 7.5, 1.7 Hz, 1H), 4.46 (d, J = 5.8 Hz, 2H), 3.04 (hept, J = 6.8 Hz, 1H), 1.20 (d, J = 6.8 Hz, 6H). | $^{19}$F NMR (376 MHz, DMSO-d$_6$) δ −56.96. |
| F15 | Yellow Solid | | ESIMS m/z 605 ([M + H]$^+$), 603 ([M − H]$^−$) | $^1$H NMR (400 MHz, DMSO-d$_6$) δ 11.93 (s, 1H), 10.25 (s, 1H), 9.42 (s, 1H), 8.33-8.02 (m, 4H), 7.68-7.56 (m, 2H), 7.60-7.05 (m, 7H), 4.45 (d, J = 5.8 Hz, 2H), 3.02 (hept, J = 7.1 Hz, 1H), 1.18 (d, J = 6.8 Hz, 6H). | $^{19}$F NMR (376 MHz, DMSO-d$_6$) δ −85.19, −86.91. |
| F16 | Yellow Solid | | ESIMS m/z 619 ([M + H]$^+$), 617 [M − H)$^−$] | $^1$H NMR (400 MHz, DMSO-d$_6$) δ 11.89 (s, 1H), 10.25 (s, 1H), 9.44 (s, 1H), 8.17-8.08 (m, 4H), 7.73-7.61 (m, 2H), 7.60-7.40 (m, 3H), 7.33-7.18 (m, 2H), 7.17-7.05 (m, 1H), 4.46 (d, J = 5.8 Hz, 2H), 2.99 (hept, J = 6.6 Hz, 1H), 2.29 (s, 3H), 1.17 (d, J = 6.8 Hz, 6H). | $^{19}$F NMR (376 MHz, DMSO-d$_6$) δ −85.19, −86.91. |
| F17 | White Solid | | ESIMS m/z 595 ([M + H]$^+$), 593 ([M − H]$^−$) | $^1$H NMR (400 MHz, DMSO-d$_6$) δ 9.41 (d, J = 3.4 Hz, 1H), 8.18 (t, J = 6.3 Hz, 1H), 8.11-8.02 (m, 4H), 7.68-7.61 (m, 2H), 7.53-7.42 (m, 2H), 7.40-7.27 (m, | $^{19}$F NMR (376 MHz, DMSO-d$_6$) δ −56.96. |

TABLE 3a-continued

Analytical Data for Compounds in Table 2a.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 3H), 7.23 (dd, J = 7.9, 1.4 Hz, 1H), 4.37-4.00 (m, 4H), 2.71 (p, J = 6.8 Hz, 1H), 1.16 (dd, J = 27.4, 6.8 Hz, 6H). | |
| F18 | Off White Solid | | ESIMS m/z 645 ([M + H]$^+$), 643 ([M − H]$^−$) | $^1$H NMR (400 MHz, DMSO-d$_6$) δ 9.40 (d, J = 3.0 Hz, 1H), 8.16 (t, J = 6.3 Hz, 1H), 8.13-7.99 (m, 4H), 7.69-7.58 (m, 2H), 7.58-7.39 (m, 2H), 7.40-7.06 (m, 4H), 4.40-3.94 (m, 4H), 2.70 (p, J = 6.8 Hz, 1H), 1.22-1.08 (m, 6H). | $^{19}$F NMR (376 MHz, DMSO-d$_6$) δ −85.19, −86.92. |
| F19 | White Solid | | ESIMS m/z 659 ([M + H]$^+$), 657 ([M − H]$^−$) | $^1$H NMR (400 MHz, DMSO-d$_6$) δ 9.40 (s, 1H), 8.18 (t, J = 6.3 Hz, 1H), 8.15-7.98 (m, 4H), 7.68-7.57 (m, 2H), 7.51-7.19 (m, 4H), 7.05-6.96 (m, 1H), 4.42-3.92 (m, 4H), 2.64 (p, J = 6.9 Hz, 1H), 2.29 (s, 3H), 1.28-0.96 (m, 6H). | $^{19}$F NMR (376 MHz, DMSO-d$_6$) δ −85.21 (d, J = 9.4 Hz), −86.93 (d, J = 7.3 Hz). |
| F20 | White Solid | 124-128 | ESIMS m/z 637 ([M + H]$^+$) | $^1$H NMR (400 MHz, CDCl$_3$) δ 8.55 (s, 1H), 8.11-8.05 (m, 2H), 7.83-7.76 (m, 2H), 7.42-7.35 (m, 2H), 7.33 (d, J = 8.0 Hz, 1H), 7.26 (s, 3H), 6.87-6.83 (m, 1H), 5.48 (t, J = 6.1 Hz, 1H), 3.98-3.84 (m, 2H), 3.37-3.18 (m, 2H), 2.74-2.57 (m, 3H), 2.35 (s, 3H), 1.86 (dt, J = 14.8, 7.3 Hz, 2H), 1.16 (dd, J = 6.9, 2.7 Hz, 6H). | $^{19}$F NMR (376 MHz, CDCl$_3$) δ −58.03. |
| F21 | White Solid | 97 (dec.) | ESIMS m/z 597 ([M + H]$^+$) | $^1$H NMR (400 MHz, DMSO-d$_6$) δ 11.91 (s, 1H), 10.05 (s, 1H), 9.39 (s, 1H), 8.11-8.01 (m, 4H), 7.67-7.56 (m, 2H), 7.39 (d, J = 8.3 Hz, 2H), 7.22 (d, J = 7.9 Hz, 2H), 7.08 (d, J = 8.0 Hz, 2H), 3.16 (q, J = 6.5 Hz, 2H), 2.95 (p, J = 6.9 Hz, 1H), 2.74-2.66 (m, 2H), 2.26 (s, 3H), 1.88-1.76 (m, 2H), 1.14 (d, J = 6.8 Hz, 6H). | $^{19}$F NMR (376 MHz, DMSO-d$_6$) δ −56.96. |
| F22 | White solid | 197-198° C. | 581 ([M + H]$^+$) | $^1$H NMR (400 MHz, DMSO-d$_6$) δ 11.87 (s, 1H), 10.02 (s, 1H), 9.38 (s, 1H), 8.09-8.04 (m, 2H), 8.01 (d, J = 8.4 Hz, 2H), 7.62 (d, J = 8.3 Hz, 2H), 7.41-7.18 (m, 7H), 2.99 (dd, J = 13.7, 6.8 Hz, 1H), 2.90 (s, | $^{19}$F NMR (376 MHz, DMSO-d$_6$) δ −57.00 |

TABLE 3a-continued

Analytical Data for Compounds in Table 2a.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 1H), 2.16 (s, 1H), 1.36-1.22 (m, 3H), 1.17 (d, J = 7.3 Hz, 6H) | |
| F23 | Off-white solid | 185-190° C. | 581 ([M + H]$^+$) | $^1$H NMR (400 MHz, DMSO-d$_6$) δ 11.98 (s, 1H), 10.01 (s, 1H), 9.38 (s, 1H), 8.11-8.03 (m, 2H), 8.01 (d, J = 8.4 Hz, 2H), 7.67-7.52 (m, 3H), 7.39 (s, 1H), 7.35-7.15 (m, 5H), 2.88 (s, 1H), 2.53-2.50 (m, 2H), 2.15 (d, J = 6.4 Hz, 1H), 1.59-1.45 (m, 2H), 1.39-1.21 (m, 2H), 0.88 (t, J = 7.3 Hz, 3H) | $^{19}$F NMR (376 MHz, DMSO-d$_6$) δ −56.97 |
| F24 | White solid | 127° C. (dec) | 581 ([M + H]$^+$) | $^1$H NMR (400 MHz, DMSO-d$_6$) δ 11.51 (s, 1H), 10.01 (s, 1H), 9.38 (s, 1H), 8.10-8.03 (m, 2H), 8.01 (d, J = 8.1 Hz, 2H), 7.61 (d, J = 8.5 Hz, 2H), 7.36 (s, 1H), 7.29 (dd, J = 8.3, 1.3 Hz, 2H), 7.22-7.02 (m, 3H), 2.90 (d, J = 3.3 Hz, 1H), 2.53-2.45 (m, 2H), 2.17 (d, J = 6.1 Hz, 4H), 1.35-1.18 (m, 2H), 1.12 (q, J = 7.5 Hz, 3H) | $^{19}$F NMR (376 MHz, DMSO-d$_6$) δ −56.97 |
| F25 | White solid | 127° C. (dec) | 567 ([M + H]$^+$) | $^1$H NMR (400 MHz, DMSO-d$_6$) δ 11.46 (s, 1H), 10.00 (s, 1H), 9.38 (s, 1H), 8.11-8.04 (m, 2H), 8.01 (d, J = 8.4 Hz, 2H), 7.61 (d, J = 8.3 Hz, 2H), 7.35 (s, 1H), 7.30 (d, J = 8.4 Hz, 2H), 7.16-7.03 (m, 3H), 2.89 (d, J = 3.1 Hz, 1H), 2.51 (s, 1H), 2.16 (d, J = 7.2 Hz, 6H), 1.34-1.23 (m, 2H) | $^{19}$F NMR (376 MHz, DMSO-d$_6$) δ −56.97 |
| F26 | White oily solid | | 583 ([M + H]$^+$) | $^1$H NMR (400 MHz, DMSO-d$_6$) δ 11.70 (s, 1H), 9.95 (s, 1H), 9.38 (s, 1H), 8.11-8.05 (m, 2H), 8.01 (d, J = 8.4 Hz, 2H), 7.62 (d, J = 8.3 Hz, 2H), 7.32 (dd, J = 23.5, 8.5 Hz, 4H), 6.91-6.69 (m, 2H), 3.74 (s, 3H), 2.87 (s, 1H), 2.16 (s, 4H), 1.34-1.18 (m, 2H) | $^{19}$F NMR (376 MHz, DMSO-d$_6$) δ −56.98 |
| F27 | Off-white solid | 111-121° C. | 581 ([M + H]$^+$) | $^1$H NMR (400 MHz, CDCl$_3$) δ 11.92 (s, 1H), 10.23 (s, 1H), 8.60 (s, 1H), 8.13-8.01 (m, 2H), 7.78 (d, J = 9.0 Hz, 2H), 7.37 (d, J = 8.7 Hz, 3H), 7.26 (s, 1H), 7.19 (d, J = 7.9 Hz, | $^{19}$F NMR (376 MHz, CDCl$_3$) δ −58.02 |

TABLE 3a-continued

Analytical Data for Compounds in Table 2a.

| No. | Appearance | Mp (° C.) | ESIMS m/z | ¹H NMR (δ)ᵃ | ¹³C NMR or ¹⁹F NMR (δ) |
|---|---|---|---|---|---|
| | | | | 3H), 7.11 (d, J = 7.6 Hz, 1H), 2.86 (s, 1H), 2.69-2.53 (m, 2H), 2.34 (s, 4H), 1.21 (t, J = 7.6 Hz, 5H) | |
| F28 | White solid | 181-184° C. | 595 ([M + H]⁺) | ¹H NMR (400 MHz, CDCl₃) δ 11.70 (d, J = 130.0 Hz, 1H), 10.03 (d, J = 115.9 Hz, 1H), 8.58 (s, 1H), 8.09 (d, J = 8.1 Hz, 2H), 7.79 (d, J = 9.0 Hz, 2H), 7.38 (d, J = 8.4 Hz, 3H), 7.27-7.25 (m, 1H), 7.18 (dd, J = 21.1, 8.0 Hz, 4H), 3.07 (dt, J = 13.9, 6.8 Hz, 1H), 2.87 (s, 1H), 2.34 (s, 3H), 2.18 (s, 1H), 1.28-1.19 (m, 8H) | ¹⁹F NMR (376 MHz, CDCl₃) δ −58.03 |
| F29 | Off-white solid | 116° C. (dec) | 621 ([M + H]⁺) | ¹H NMR (400 MHz, CDCl₃) δ 8.54 (s, 1H), 8.07 (d, J = 8.3 Hz, 2H), 7.79 (d, J = 9.0 Hz, 2H), 7.48-7.43 (m, 2H), 7.38 (d, J = 8.4 Hz, 2H), 7.35-7.28 (m, 1H), 7.23-7.17 (m, 2H), 7.05 (dd, J = 7.5, 2.7 Hz, 1H), 5.69 (dd, J = 7.1, 2.9 Hz, 1H), 3.94 (d, J = 2.3 Hz, 2H), 2.98-2.90 (m, 1H), 2.74-2.63 (m, 1H), 2.13-2.03 (m, 1H), 1.33-1.22 (m, 2H), 1.22-1.16 (m, 6H) | ¹⁹F NMR (376 MHz, CDCl₃) δ −58.04 |
| F30 | Off-white oily solid | | 621 ([M + H]⁺) | ¹H NMR (400 MHz, CDCl₃) δ 8.54 (s, 1H), 8.08 (d, J = 8.3 Hz, 2H), 7.79 (d, J = 9.0 Hz, 2H), 7.46-7.30 (m, 5H), 7.21 (dd, J = 8.3, 2.7 Hz, 2H), 7.07 (d, J = 7.8 Hz, 1H), 5.69 (s, 1H), 3.93 (d, J = 2.6 Hz, 2H), 2.93 (s, 1H), 2.40 (dd, J = 8.7, 6.9 Hz, 2H), 2.09 (d, J = 9.7 Hz, 1H), 1.64-1.56 (m, 2H), 1.36-1.13 (m, 2H), 0.93 (td, J = 7.3, 1.8 Hz, 3H) | ¹⁹F NMR (376 MHz, CDCl₃) δ −58.04 |
| F31 | Clear oil | | 621 ([M + H]⁺) | ¹H NMR (400 MHz, CDCl₃) δ 8.54 (s, 1H), 8.07 (d, J = 8.3 Hz, 2H), 7.79 (d, J = 9.0 Hz, 2H), 7.41-7.29 (m, 3H), 7.20 (dd, J = 13.3, 7.9 Hz, 4H), 5.72 (s, 1H), 3.95 (s, 2H), 2.94 (dd, J = 7.4, 4.1 Hz, 1H), 2.43 (q, J = 7.7 Hz, 2H), 2.16-2.06 (m, 4H), 1.31-1.22 (m, | ¹⁹F NMR (376 MHz, CDCl₃) δ −58.03 |

TABLE 3a-continued

Analytical Data for Compounds in Table 2a.

| No. | Appearance | Mp (° C.) | ESIMS m/z | $^1$H NMR (δ)[a] | $^{13}$C NMR or $^{19}$F NMR (δ) |
|---|---|---|---|---|---|
| F32 | Clear oil | | 607 ([M + H]$^+$) | 2H), 1.17 (td, J = 7.6, 2.4 Hz, 3H) $^1$H NMR (400 MHz, CDCl$_3$) δ 8.54 (s, 1H), 8.08 (d, J = 8.3 Hz, 2H), 7.82-7.76 (m, 2H), 7.38 (d, J = 8.4 Hz, 2H), 7.28 (d, J = 7.8 Hz, 1H), 7.19 (dd, J = 17.5, 7.9 Hz, 4H), 5.71 (s, 1H), 3.95 (s, 2H), 2.94 (td, J = 7.6, 3.3 Hz, 1H), 2.13 (d, J = 1.3 Hz, 6H), 2.12-2.06 (m, 1H), 1.32-1.17 (m, 2H) | $^{19}$F NMR (376 MHz, CDCl$_3$) δ −58.04 |
| F33 | Yellow solid | 124° C. (dec) | 621 ([M + H]$^+$) | $^1$H NMR (400 MHz, CDCl$_3$) δ 8.54 (s, 1H), 8.08 (d, J = 8.3 Hz, 2H), 7.79 (d, J = 9.0 Hz, 2H), 7.38 (d, J = 8.3 Hz, 2H), 7.28 (d, J = 7.9 Hz, 1H), 7.25-7.16 (m, 2H), 6.89 (s, 1H), 5.71 (s, 1H), 3.92 (d, J = 2.0 Hz, 2H), 2.94 (dd, J = 7.2, 3.6 Hz, 1H), 2.47-2.38 (m, 2H), 2.36 (d, J = 2.3 Hz, 3H), 2.10 (ddd, J = 9.6, 6.4, 3.4 Hz, 1H), 1.33-1.19 (m, 2H), 1.16 (td, J = 7.6, 2.7 Hz, 3H) | $^{19}$F NMR (376 MHz, CDCl$_3$) δ −58.03 |
| F34 | Yellow oil | | 621 ([M + H]$^+$) | $^1$H NMR (400 MHz, CDCl$_3$) δ 8.53 (s, 1H), 8.04 (d, J = 8.1 Hz, 2H), 7.78 (d, J = 8.9 Hz, 3H), 7.37 (d, J = 8.5 Hz, 4H), 7.19 (dd, J = 12.6, 7.2 Hz, 2H), 6.91 (s, 1H), 5.42 (d, J = 11.2 Hz, 1H), 3.95-3.82 (m, 1H), 3.76 (ddd, J = 10.3, 7.5, 5.5 Hz, 1H), 3.26 (dd, J = 15.0, 7.2 Hz, 2H), 2.96-2.81 (m, 2H), 2.37-2.30 (m, 3H), 2.05-1.96 (m, 1H), 1.29-1.05 (m, 8H) | $^{19}$F NMR (376 MHz, CDCl$_3$) δ −58.02 |
| F35 | Yellow solid | | ESIMS m/z 569 ([M + H]$^+$), 567 ([M − H]$^-$) | $^1$H NMR (400 MHz, DMSO-d$_6$) δ 11.89 (s, 1H), 10.25 (s, 1H), 9.43 (s, 1H), 8.19-8.05 (m, 4H), 7.72-7.60 (m, 2H), 7.59-7.46 (m, 3H), 7.29-7.21 (m, 2H), 7.11 (dd, J = 8.2, 1.7 Hz, 1H), 4.46 (d, J = 5.8 Hz, 2H), 2.99 (p, J = 6.9 Hz, 1H), 2.29 (s, 3H), 1.17 (d, J = 6.9 Hz, 6H) | $^{19}$F NMR (376 MHz, DMSO-d$_6$) δ −56.96 |

[a]All $^1$H NMR data measured in CDCl$_3$ at 400 MHz unless otherwise noted

TABLE 3b

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P1 | White solid | | ESIMS m/z 567 ([M + H]$^+$), 565 ([M − H]$^−$) | $^1$H NMR (400 MHz, DMSO-d$_6$) δ 9.39 (s, 1H), 8.17 (t, J = 6.3 Hz, 1H), 8.11-8.00 (m, 4H), 7.67-7.58 (m, 2H), 7.40-7.28 (m, 5H), 7.28-7.23 (m, 1H), 4.25 (qd, J = 15.4, 6.3 Hz, 2H), 4.17-3.98 (m, 2H), 2.10 (s, 3H) | $^{19}$F NMR (376 MHz, DMSO-d$_6$) δ −56.97 |
| P2, P532 | White solid | | ESIMS m/z 581 ([M + H]$^+$), 579 ([M − H]$^−$) | $^1$H NMR (400 MHz, DMSO-d$_6$) δ 9.38 (s, 1H), 8.15 (t, J = 6.3 Hz, 1H), 8.07-8.05 (m, 2H), 8.03 (d, J = 8.2 Hz, 2H), 7.64-7.60 (m, 3H), 7.41-7.39 (m, 2H), 7.36-7.33 (m, 2H), 7.23 (dt, J = 7.9, 0.9 Hz, 1H), 4.30-4.18 (m, 2H), 4.17-3.99 (m, 2H), 2.41 (q, J = 7.6 Hz, 2H), 1.11 (t, J = 7.6 Hz, 3H) | $^{19}$F NMR (376 MHz, DMSO-d$_6$) δ −56.97 |
| P3, P1172 | Off-white solid | | ESIMS m/z 613 ([M + H]$^+$), 611 ([M − H]$^−$) | $^1$H NMR (400 MHz, DMSO-d$_6$) δ 9.39 (s, 1H), 8.17 (t, J = 6.3 Hz, 1H), 8.13-7.99 (m, 5H), 7.62 (d, J = 8.6 Hz, 2H), 7.40-7.27 (m, 3H), 7.16 (td, J = 8.4, 2.9 Hz, 1H), 4.25 (dd, J = 10.6, 6.3 Hz, 2H), 4.19-3.95 (m, 2H), 2.75-2.61 (m, 1H), 1.20-1.08 (m, 6H) | $^{19}$F NMR (376 MHz, DMSO-d$_6$) δ −56.97 (d, J = 3.4 Hz), −112.07 (d, J = 3.6 Hz) |
| P5 | Off-white solid | | ESIMS m/z 609 ([M + H]$^+$), 607 ([M − H]$^−$) | 8.55 (s, 1H), 8.11 (d, J = 8.3 Hz, 2H), 7.79 (d, J = 9.0 Hz, 2H), 7.40-7.32 (m, 4H), 7.22 (d, J = 2.0 Hz, 1H), 7.12-7.08 (m, 1H), 6.94 (d, J = 8.0 Hz, 1H), 5.83 (t, J = 6.1 Hz, 1H), 4.47 (t, J = 6.5 Hz, 2H), 3.93 (d, J = 1.8 Hz, 2H), 2.65 (p, J = 6.9 Hz, 1H), 2.38 (s, 3H), 1.17 (d, J = 6.8 Hz, 6H) | $^{19}$F NMR (376 MHz, CDCl$_3$) δ −58.02 |
| P6 | Off-white solid | | ESIMS m/z 597 ([M + H]$^+$), 595 ([M − H]$^−$) | $^1$H NMR (400 MHz, DMSO-d$_6$) δ 9.39 (s, 1H), 8.17 (t, J = 6.3 Hz, 1H), 8.13-7.99 (m, 4H), 7.70-7.56 (m, 2H), 7.41-7.31 (m, 2H), 7.15 (d, J = 8.7 Hz, 1H), 6.93 (d, J = 2.8 Hz, 1H), 6.86 (dd, J = 8.7, 2.9 Hz, 1H), | $^{19}$F NMR (376 MHz, CDCl$_3$) δ −56.96 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 4.25 (qd, J = 15.4, 6.3 Hz, 2H), 4.16-3.94 (m, 2H), 3.78 (s, 3H), 2.05 (s, 3H). | |
| P7 | Off White Solid | | ESIMS m/z 595 ([M + H]$^+$), 593 ([M − H]$^-$) | $^1$H NMR (400 MHz, DMSO-d$_6$) δ 9.39 (s, 1H), 8.19 (t, J = 6.3 Hz, 1H), 8.13-7.95 (m, 4H), 7.63 (d, J = 8.5 Hz, 2H), 7.38-7.17 (m, 4H), 7.04 (d, J = 1.9 Hz, 1H), 4.24 (dd, J = 13.7, 6.3 Hz, 2H), 4.13 (d, J = 18.1 Hz, 1H), 4.07 (d, J = 17.9 Hz, 1H), 3.39 (q, J = 7.0 Hz, 2H), 2.32 (s, 3H), 1.10-1.08 (m, 3H). | $^{19}$F NMR (376 MHz, CDCl$_3$) δ −52.22 |
| P8, P852 | Off White Solid | | ESIMS m/z 609 ([M + H]$^+$) | $^1$H NMR (400 MHz, DMSO-d$_6$) δ 9.45 (s, 1H), 8.23 (t, J = 6.3 Hz, 1H), 8.18-8.05 (m, 4H), 7.68 (d, J = 8.7 Hz, 2H), 7.44-7.38 (m, 2H), 7.37-7.23 (m, 2H), 7.10 (d, J = 1.8 Hz, 1H), 4.30 (t, J = 6.7 Hz, 2H), 4.23-4.02 (m, 2H), 3.50-3.42 (m, 2H), 2.37 (s, 3H), 1.63-1.47 (m, 2H), 1.15 (t, J = 7.0 Hz, 3H) | $^{19}$F NMR (376 MHz, CDCl$_3$) δ −52.21 |
| P14 | White Solid | | ESIMS m/z 579 ([M + H]$^+$), 577 ([M − H]$^-$) | $^1$H NMR (400 MHz, DMSO-d$_6$) δ 9.52 (s, 1H), 8.18 (dd, J = 7.2, 4.5 Hz, 3H), 8.08-8.02 (m, 2H), 8.02-7.94 (m, 2H), 7.58-7.40 (m, 2H), 7.39-7.27 (m, 3H), 7.21 (dd, J = 7.9, 1.4 Hz, 1H), 4.32-4.18 (m, 2H), 4.18-3.98 (m, 2H), 2.70 (p, J = 6.8 Hz, 1H), 1.20-1.08 (m, 6H) | $^{19}$F NMR (376 MHz, CDCl$_3$) δ −60.80 |
| P15 | Light Yellow Solid | | ESMIS m/z 593 ([M + H]$^+$), 591 ([M − H]$^-$) | $^1$H NMR (400 MHz, DMSO-d$_6$) δ 9.52 (s, 1H), 8.20 (d, J = 8.4 Hz, 2H), 8.15 (t, J = 6.3 Hz, 1H), 8.11-8.04 (m, 2H), 8.00 (d, J = 8.5 Hz, 2H), 7.40-7.33 (m, 2H), 7.33-7.27 (m, 1H), 7.15-7.03 (m, 2H), 4.34-4.20 (m, 2H), 4.18-3.97 (m, 2H), 2.66 (p, J = 6.8 Hz, 1H), 2.37 (s, 3H), 1.11 (dt, J = 7.0, 3.6 Hz, 6H) | $^{19}$F NMR (376 MHz, CDCl$_3$) δ −60.80 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P20 | Off White Solid | | ESIMS m/z 607 ([M + H]$^+$) | $^1$H NMR (400 MHz, DMSO-d$_6$) δ 9.38 (s, 1H), 8.14-8.01 (m, 4H), 7.70 (s, 1H), 7.62 (dq, J = 7.7, 1.0 Hz, 2H), 7.45-7.35 (m, 2H), 7.34-7.27 (m, 1H), 7.15 (t, J = 1.3 Hz, 2H), 6.66 (q, J = 0.9 Hz, 1H), 4.47-4.28 (m, 2H), 2.73-2.62 (m, 1H), 2.39 (s, 3H), 2.10 (d, J = 1.1 Hz, 3H), 1.10 (d, J = 6.8 Hz, 3H), 1.00 (d, J = 6.8 Hz, 3H) | $^{19}$F NMR (376 MHz, CDCl$_3$) δ −56.96 |
| P26 | Brown Oil | | ESIMS m/z 623 ([M + H]$^+$) | 8.55 (s, 1H), 8.08 (d, J = 8.2 Hz, 2H), 7.83-7.75 (m, 2H), 7.44-7.35 (m, 2H), 7.28-7.25 (m, 2H), 7.23-7.18 (m, 1H), 7.09 (ddd, J = 8.0, 2.0, 0.8 Hz, 1H), 6.91 (d, J = 8.0 Hz, 1H), 5.51 (t, J = 6.2 Hz, 1H), 3.91 (d, J = 1.5 Hz, 2H), 3.52 (ddt, J = 30.1, 13.6, 6.7 Hz, 2H), 2.86 (t, J = 7.1 Hz, 2H), 2.63 (p, J = 6.8 Hz, 1H), 2.38 (s, 3H), 1.16 (dd, J = 6.9, 4.5 Hz, 6H) | $^{19}$F NMR (376 MHz, CDCl$_3$) δ −58.03 |
| P27 | Yellow Oil | | ESIMS m/z 623 ([M + H]$^+$) | 8.55 (s, 1H), 8.11-8.05 (m, 2H), 7.84-7.72 (m, 2H), 7.43-7.35 (m, 2H), 7.27-7.25 (m, 1H), 7.25 (s, 1H), 7.24-7.14 (m, 2H), 6.84 (dd, J = 7.3, 2.0 Hz, 1H), 5.51 (t, J = 6.1 Hz, 1H), 3.91 (d, J = 1.5 Hz, 2H), 3.52 (dp, J = 25.1, 6.7 Hz, 2H), 2.95 (dq, J = 15.6, 7.6 Hz, 1H), 2.87 (td, J = 7.0, 2.1 Hz, 2H), 2.47 (s, 3H), 1.25 (d, J = 7.2 Hz, 6H) | $^{19}$F NMR (376 MHz, CDCl$_3$) δ −58.03 |
| P28 | Brown Foamy Solid | | ESIMS m/z 627 ([M + H]$^+$) | 8.55 (s, 1H), 8.11-8.05 (m, 2H), 7.83-7.74 (m, 2H), 7.39 (dd, J = 9.1, 1.0 Hz, 2H), 7.29-7.24 (m, 2H), 7.09 (dd, J = 9.9, 2.6 Hz, 1H), 7.06-6.93 (m, 2H), 5.48 (t, J = 6.2 Hz, 1H), 3.92 (d, J = 1.7 Hz, 2H), 3.53 (dp, J = 25.1, 6.7 Hz, 2H), 2.87 (t, J = 7.0 Hz, 2H), | $^{19}$F NMR (376 MHz, CDCl$_3$) δ −58.02, −110.68 |

TABLE 3b-continued

Analytical Data for Compounds in Table 2b.

| No. | Appearance | Mp (° C.) | ESIMS m/z | ¹H NMR (δ)ᵃ | ¹³C NMR or ¹⁹F NMR (δ) |
|---|---|---|---|---|---|
| P29 | Pale Pink Solid | | ESIMS m/z 623 ([M + H]⁺) | 2.64 (pd, J = 6.9, 1.9 Hz, 1H), 1.15 (t, J = 6.9 Hz, 6H) 8.55 (s, 1H), 8.12-8.04 (m, 2H), 7.83-7.75 (m, 2H), 7.43-7.35 (m, 2H), 7.30-7.26 (m, 2H), 7.25-7.17 (m, 2H), 6.90-6.83 (m, 1H), 5.52 (t, J = 6.2 Hz, 1H), 3.91 (d, J = 2.4 Hz, 2H), 3.62-3.43 (m, 2H), 2.88 (t, J = 7.1 Hz, 2H), 2.43-2.23 (m, 5H), 1.60-1.48 (m, 2H), 0.90 (t, J = 7.3 Hz, 3H) | ¹⁹F NMR (376 MHz, CDCl₃) δ −58.03 |
| P30 | Pink Solid | | ESIMS m/z 623 ([M + H]⁺) | 8.55 (s, 1H), 8.11-8.04 (m, 2H), 7.83-7.77 (m, 2H), 7.59 (dd, J = 8.2, 1.5 Hz, 1H), 7.44-7.36 (m, 3H), 7.30 (dd, J = 7.7, 1.5 Hz, 1H), 7.27-7.25 (m, 3H), 6.89 (dd, J = 7.8, 1.5 Hz, 1H), 3.87 (s, 2H), 3.51 (dh, J = 27.3, 6.9 Hz, 2H), 2.87 (td, J = 7.0, 2.8 Hz, 2H), 1.31 (s, 9H) | ¹⁹F NMR (376 MHz, CDCl₃) δ −58.03 |
| P31 | Off-White Solid | | ESIMS m/z 609 ([M + H]⁺) | 8.55 (s, 1H), 8.09 (d, J = 8.2 Hz, 2H), 7.80 (d, J = 9.0 Hz, 2H), 7.43-7.35 (m, 2H), 7.28 (s, 2H), 7.17 (d, J = 2.0 Hz, 1H), 7.11 (dd, J = 8.0, 2.0 Hz, 1H), 6.94 (d, J = 7.9 Hz, 1H), 5.51 (t, J = 6.2 Hz, 1H), 3.91 (d, J = 1.5 Hz, 2H), 3.52 (qd, J = 7.0, 2.6 Hz, 2H), 2.87 (t, J = 7.1 Hz, 2H), 2.50-2.32 (m, 5H), 1.15 (t, J = 7.6 Hz, 3H) | ¹⁹F NMR (376 MHz, CDCl₃) δ −58.03 |
| P33 | Brown Solid | 105 (dec.) | ESIMS m/z 641 ([M + H]⁺) | 8.56 (d, J = 0.6 Hz, 1H), 8.08 (dd, J = 10.1, 8.2 Hz, 2H), 7.84-7.76 (m, 2H), 7.43-7.37 (m, 2H), 7.30-7.27 (m, 1H), 7.25-7.22 (m, 1H), 7.11 (dd, J = 9.8, 2.6 Hz, 1H), 7.02 (dddd, J = 11.3, 7.3, 6.0, 2.9 Hz, 2H), 5.31 (dd, J = 11.9, 8.5 Hz, 1H), 4.23-4.10 (m, 1H), 3.91 (t, J = 1.8 Hz, 2H), 3.06-2.59 (m, 3H), 1.22-1.05 (m, 9H) | ¹⁹F NMR (376 MHz, CDCl₃) δ −58.03, −110.63, −110.66, −110.66 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P42 | Off-White Solid | | ESIMS m/z 623 ([M + H]$^+$) | 8.56 (s, 1H), 8.13-8.03 (m, 2H), 7.83-7.75 (m, 2H), 7.42-7.27 (m, 6H), 7.25-7.13 (m, 1H), 5.42-5.29 (m, 1H), 3.93 (d, J = 0.9 Hz, 2H), 3.04-2.83 (m, 1H), 2.70 (td, J = 13.5, 7.8 Hz, 2H), 2.42 (q, J = 7.9 Hz, 2H), 2.12 (d, J = 5.3 Hz, 3H), 1.16 (td, J = 7.6, 2.1 Hz, 3H), 1.10 (dd, J = 6.7, 2.6 Hz, 3H) | $^{19}$F NMR (376 MHz, CDCl$_3$) δ −58.03 |
| P44 | Yellow Solid | | ESIMS m/z 611 ([M + H]$^+$) | 8.55 (s, 1H), 8.15-8.04 (m, 2H), 7.86-7.74 (m, 2H), 7.39 (d, J = 8.4 Hz, 2H), 7.28 (d, J = 8.2 Hz, 2H), 7.00 (d, J = 8.2 Hz, 1H), 6.82 (d, J = 8.6 Hz, 2H), 5.52 (t, J = 6.2 Hz, 1H), 3.91 (s, 2H), 3.80 (s, 3H), 3.53 (q, J = 6.9 Hz, 2H), 2.88 (t, J = 7.2 Hz, 2H), 2.11 (s, 3H) | $^{19}$F NMR (376 MHz, CDCl$_3$) δ −58.03 |
| P45 | Brown Solid | | ESIMS m/z 625 ([M + H]$^+$) | 8.56 (d, J = 0.6 Hz, 1H), 8.12-8.05 (m, 2H), 7.80 (d, J = 9.0 Hz, 2H), 7.44-7.35 (m, 2H), 7.30-7.27 (m, 2H), 7.02 (dd, J = 9.1, 7.1 Hz, 1H), 6.84 (qd, J = 5.5, 4.6, 1.8 Hz, 2H), 5.38 (dd, J = 8.4, 5.7 Hz, 1H), 3.96-3.84 (m, 3H), 3.82 (d, J = 0.7 Hz, 3H), 2.98 (ddd, J = 13.3, 9.9, 5.4 Hz, 1H), 2.69 (td, J = 13.9, 7.9 Hz, 1H), 2.12 (d, J = 3.0 Hz, 3H), 1.10 (dd, J = 6.7, 1.1 Hz, 3H) | $^{19}$F NMR (376 MHz, CDCl$_3$) δ −58.03 |
| P47 | Yellow Oil | | ESIMS m/z 625 ([M + H]$^+$) | 8.55 (s, 1H), 8.09 (d, J = 8.2 Hz, 2H), 7.79 (d, J = 9.0 Hz, 2H), 7.39 (ddt, J = 7.7, 1.9, 1.0 Hz, 2H), 7.30-7.26 (m, 2H), 6.67 (s, 2H), 5.56 (t, J = 6.2 Hz, 1H), 3.92 (s, 2H), 3.78 (s, 3H), 3.59-3.40 (m, 2H), 2.88 (t, J = 7.2 Hz, 2H), 2.08 (s, 6H) | $^{19}$F NMR (376 MHz, CDCl$_3$) δ −58.02 |
| P49 | Pink Solid | | ESIMS m/z 609 ([M + H]$^+$) | 8.55 (s, 1H), 8.14-8.04 (m, 2H), 7.83-7.74 (m, 2H), 7.39 (dd, J = 8.9, 1.0 Hz, 2H), | $^{19}$F NMR (376 MHz, CDCl$_3$) δ −58.03 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 7.28-7.24 (m, 3H), 7.23-7.18 (m, 1H), 6.88 (s, 1H), 5.52 (t, J = 6.1 Hz, 1H), 3.91 (d, J = 1.6 Hz, 2H), 3.52 (p, J = 6.8 Hz, 2H), 2.88 (t, J = 7.1 Hz, 2H), 2.48-2.35 (m, 2H), 2.34 (s, 3H), 1.14 (t, J = 7.6 Hz, 3H) | |
| P50 | Off-White Solid | | ESIMS m/z 609 ([M + H]$^+$) | 8.55 (s, 1H), 8.09 (d, J = 8.2 Hz, 2H), 7.80 (d, J = 9.0 Hz, 2H), 7.46-7.34 (m, 2H), 7.33-7.26 (m, 3H), 7.17 (dd, J = 15.0, 7.5 Hz, 2H), 5.51 (t, J = 6.0 Hz, 1H), 3.94 (s, 2H), 3.52 (dp, J = 13.4, 6.6 Hz, 2H), 2.87 (t, J = 7.2 Hz, 2H), 2.41 (qd, J = 7.6, 2.6 Hz, 2H), 2.11 (s, 3H), 1.15 (t, J = 7.6 Hz, 3H) | $^{19}$F NMR (376 MHz, CDCl$_3$) δ −58.03 |
| P51 | Dark Brown Oil | | ESIMS m/z 609 ([M + H]$^+$) | 8.55 (s, 1H), 8.17-8.05 (m, 2H), 7.85-7.71 (m, 2H), 7.44-7.34 (m, 3H), 7.32-7.27 (m, 3H), 7.10-6.96 (m, 2H), 5.52 (t, J = 6.2 Hz, 1H), 3.90 (s, 2H), 3.60-3.44 (m, 2H), 2.91 (dt, J = 23.2, 7.0 Hz, 3H), 1.25 (d, J = 6.9 Hz, 6H) | $^{19}$F NMR (376 MHz, CDCl$_3$) δ −58.02 |
| P52 | Tan Glassy Foam | | ESIMS m/z 607 ([M + H]$^+$) | 8.64 (s, 1H), 8.09 (d, J = 8.2 Hz, 2H), 7.95-7.86 (m, 2H), 7.84-7.75 (m, 2H), 7.32-7.22 (m, 4H), 6.85 (dd, J = 1.8, 0.9 Hz, 1H), 5.51 (t, J = 6.2 Hz, 1H), 3.92 (d, J = 1.8 Hz, 2H), 3.52 (ddt, J = 35.1, 13.6, 6.7 Hz, 2H), 2.87 (t, J = 7.1 Hz, 2H), 2.62 (dq, J = 14.3, 7.2 Hz, 1H), 2.33 (d, J = 0.7 Hz, 3H), 1.15 (dd, J = 6.9, 2.3 Hz, 6H) | $^{19}$F NMR (376 MHz, CDCl$_3$) δ −62.49 |
| P53 | Brown Foam | | ESIMS m/z 623 ([M + H]$^+$) | 8.65 (s, 1H), 8.14-8.05 (m, 2H), 7.95-7.86 (m, 2H), 7.84-7.75 (m, 2H), 7.34-7.27 (m, 3H), 6.99 (dd, J = 8.7, 2.7 Hz, 1H), 6.56 (d, J = 2.7 Hz, 1H), 5.53 (t, J = 6.2 Hz, 1H), 3.93 (d, J = 1.7 Hz, 2H), 3.77 (s, 3H), 3.53 (ddt, J = 29.0, 13.7, 6.7 Hz, 2H), | $^{19}$F NMR (376 MHz, CDCl$_3$) δ −62.49 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P57 | Clear Sticky Oil | | ESIMS m/z 637 ([M + H]$^+$) | 2.88 (t, J = 7.1 Hz, 2H), 2.60 (p, J = 6.9 Hz, 1H), 1.20-1.06 (m, 6H) 8.55 (s, 1H), 8.11-8.05 (m, 2H), 7.83-7.76 (m, 2H), 7.41-7.34 (m, 2H), 7.33-7.21 (m, 4H), 6.90-6.77 (m, 1H), 5.51 (t, J = 6.2 Hz, 1H), 4.10-4.03 (m, 1H), 3.64-3.39 (m, 2H), 2.87 (t, J = 7.1 Hz, 2H), 2.73-2.51 (m, 1H), 2.33 (q, J = 0.7 Hz, 3H), 1.73 (dd, J = 7.3, 4.5 Hz, 3H), 1.14 (ddd, J = 7.1, 4.5, 2.9 Hz, 6H) | $^{19}$F NMR (376 MHz, CDCl$_3$) δ −58.02 |
| P58 | Yellow Oil | | ESIMS m/z 623 ([M + H]$^+$) | 8.54 (d, J = 1.2 Hz, 1H), 8.06 (d, J = 8.2 Hz, 2H), 7.83-7.73 (m, 2H), 7.42-7.34 (m, 2H), 7.25 (dt, J = 8.0, 2.1 Hz, 3H), 7.19-7.09 (m, 1H), 6.87-6.77 (m, 1H), 5.18 (dt, J = 25.9, 6.2 Hz, 1H), 4.24-3.93 (m, 1H), 3.64-3.26 (m, 3H), 3.05-2.63 (m, 4H), 2.31 (d, J = 8.5 Hz, 3H), 1.26-1.11 (m, 9H) | |
| P59 | White Solid | | ESIMS m/z 623 ([M + H]$^+$) | 8.53 (d, J = 13.4 Hz, 1H), 8.13-8.02 (m, 2H), 7.83-7.73 (m, 2H), 7.42-7.27 (m, 2H), 7.26-7.17 (m, 4H), 7.01 (dd, J = 59.3, 7.4 Hz, 1H), 6.86 (d, J = 1.3 Hz, 1H), 4.92 (t, J = 6.1 Hz, 1H), 3.78-3.63 (m, 1H), 3.49 (td, J = 14.1, 13.0, 6.9 Hz, 2H), 3.32 (dq, J = 13.4, 7.0 Hz, 1H), 3.07 (q, J = 6.0 Hz, 2H), 2.99-2.73 (m, 3H), 2.50-2.26 (m, 4H), 1.16 (dd, J = 8.2, 6.9 Hz, 6H) | $^{19}$F NMR (376 MHz, CDCl$_3$) δ −58.03 |
| P64 | White Solid | | ESIMS m/z 637 ([M + H]$^+$) | 8.55 (d, J = 1.8 Hz, 1H), 8.14 (dd, J = 8.2, 5.4 Hz, 1H), 8.06 (d, J = 8.1 Hz, 1H), 7.85-7.75 (m, 2H), 7.39 (d, J = 8.5 Hz, 2H), 7.34-7.25 (m, 3H), 7.20 (dd, J = 8.0, 3.5 Hz, 1H), 7.12-6.81 (m, | $^{19}$F NMR (376 MHz, CDCl$_3$) δ −58.03 |

TABLE 3b-continued

Analytical Data for Compounds in Table 2b.

| No. | Appearance | Mp (° C.) | ESIMS m/z | ¹H NMR (δ)ᵃ | ¹³C NMR or ¹⁹F NMR (δ) |
|---|---|---|---|---|---|
| | | | | 2H), 4.92 (d, J = 6.4 Hz, 1H), 3.71-3.16 (m, 5H), 3.08-2.76 (m, 5H), 2.67-2.37 (m, 2H), 2.30 (s, 3H), 1.22-1.08 (m, 6H) | |
| P65 | Orange Solid | | ESIMS m/z 621 ([M + H]⁺) | 8.57 (s, 1H), 8.15-8.08 (m, 2H), 7.81 (d, J = 9.0 Hz, 2H), 7.43-7.29 (m, 5H), 7.23 (d, J = 1.8 Hz, 2H), 7.02-6.94 (m, 1H), 6.27 (d, J = 1.2 Hz, 1H), 3.76-3.62 (m, 2H), 2.98 (q, J = 6.5 Hz, 2H), 2.80 (p, J = 6.9 Hz, 1H), 2.31 (s, 3H), 2.21 (d, J = 1.1 Hz, 3H), 1.11 (dd, J = 19.2, 6.9 Hz, 6H) | ¹⁹F NMR (376 MHz, CDCl₃) δ −58.03 |
| P66, P353 | Off-White Powder | 122 (dec.) | ESIMS m/z 651 ([M + H]⁺) | 8.57-8.52 (m, 1H), 8.13-8.02 (m, 2H), 7.84-7.76 (m, 2H), 7.43-7.36 (m, 2H), 7.35-7.29 (m, 2H), 7.26 (s, 2H), 6.85 (dd, J = 15.7, 1.8 Hz, 1H), 5.25 (dd, J = 23.9, 9.0 Hz, 1H), 4.21-4.03 (m, 1H), 3.98-3.85 (m, 2H), 3.08-2.75 (m, 1H), 2.63 (ddq, J = 28.1, 14.0, 7.0 Hz, 1H), 2.39-2.29 (m, 3H), 1.36-0.89 (m, 12H) | ¹⁹F NMR (376 MHz, CDCl₃) δ −58.03 |
| P74 | White Solid | | ESIMS m/z 581 ([M + H]⁺), 579 ([M − H]⁻) | ¹H NMR (400 MHz, DMSO-d₆) δ 9.41 (s, 1H), 8.13-8.06 (m, 2H), 7.98-7.89 (m, 2H), 7.72-7.59 (m, 3H), 7.43 (t, J = 7.6 Hz, 1H), 7.37-7.25 (m, 4H), 7.21 (dt, J = 7.5, 1.1 Hz, 1H), 4.15-3.96 (m, 2H), 3.28 (dt, J = 8.3, 6.6 Hz, 2H), 2.86-2.74 (m, 2H), 2.04 (s, 3H) | ¹⁹F NMR (376 MHz, CDCl₃) δ −56.96 |
| P75 | White Solid | | ESIMS m/z 595 ([M + H]⁺), 593 ([M − H]⁻) | ¹H NMR (400 MHz, DMSO-d₆) δ 9.41 (s, 1H), 8.16-8.04 (m, 2H), 7.99-7.87 (m, 2H), 7.74-7.59 (m, 3H), 7.48-7.33 (m, 3H), 7.34-7.24 (m, 2H), 7.22-7.16 (m, 1H), 4.18-3.94 (m, 2H), 3.27 (td, J = 7.8, 7.2, 3.9 Hz, 2H), 2.84-2.76 (m, 2H), 2.35 (q, J = 7.6 Hz, 2H), 1.04 (t, J = 7.6 Hz, 3H) | ¹⁹F NMR (376 MHz, CDCl₃) δ −56.96 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P76 | White Solid | | ESIMS m/z 609 ([M + H]$^+$), 607 ([M − H]$^−$) | $^1$H NMR (400 MHz, DMSO-d$_6$) δ 9.41 (s, 1H), 8.14-8.04 (m, 2H), 7.96-7.88 (m, 2H), 7.68-7.58 (m, 3H), 7.47-7.37 (m, 3H), 7.32-7.23 (m, 2H), 7.16 (dd, J = 7.9, 1.3 Hz, 1H), 4.16-3.94 (m, 2H), 3.27 (q, J = 6.9 Hz, 2H), 2.84-2.75 (m, 2H), 2.63 (p, J = 6.8 Hz, 1H), 1.10-1.03 (m, 6H) | $^{19}$F NMR (376 MHz, CDCl$_3$) δ −56.96 |
| P80 | White Solid | | ESIMS m/z 623 ([M + H]$^+$), 621 ([M − H]$^−$) | $^1$H NMR (400 MHz, DMSO-d$_6$) δ 9.41 (s, 1H), 8.13-8.05 (m, 2H), 7.98-7.89 (m, 2H), 7.69-7.58 (m, 3H), 7.42 (t, J = 7.6 Hz, 1H), 7.28 (dt, J = 7.7, 1.4 Hz, 1H), 7.22 (d, J = 7.9 Hz, 1H), 7.19-7.13 (m, 1H), 7.02-6.95 (m, 1H), 4.15-3.93 (m, 2H), 3.28 (dt, J = 10.3, 7.3 Hz, 2H), 2.80 (t, J = 7.4 Hz, 2H), 2.30-2.20 (m, 5H), 1.51-1.33 (m, 2H), 0.79 (t, J = 7.3 Hz, 3H) | $^{19}$F NMR (376 MHz, CDCl$_3$) δ −56.97 |
| P81 | Yellow Solid | | ESIMS m/z 623 ([M + H]$^+$), 621 ([M − H]$^−$) | $^1$H NMR (400 MHz, DMSO-d$_6$) δ 9.41 (s, 1H), 8.12-8.05 (m, 2H), 7.96-7.89 (m, 2H), 7.69-7.59 (m, 3H), 7.41 (t, J = 7.7 Hz, 1H), 7.33-7.25 (m, 2H), 7.23-7.18 (m, 1H), 6.96 (dd, J = 1.8, 0.9 Hz, 1H), 4.15-3.94 (m, 2H), 3.27 (q, J = 6.9 Hz, 2H), 2.86-2.73 (m, 2H), 2.63-2.53 (m, 1H), 2.25 (s, 3H), 1.04 (dd, J = 6.9, 4.8 Hz, 6H) | $^{19}$F NMR (376 MHz, CDCl$_3$) δ −56.96 |
| P83 | White Solid | | ESIMS m/z 609 ([M + H]$^+$), 607 ([M − H]$^−$) | $^1$H NMR (400 MHz, DMSO-d$_6$) δ 9.41 (s, 1H), 8.13-8.06 (m, 2H), 7.97-7.88 (m, 2H), 7.72-7.59 (m, 3H), 7.41 (t, J = 7.6 Hz, 1H), 7.31-7.24 (m, 2H), 7.20-7.11 (m, 2H), 4.15 (d, J = 1.7 Hz, 2H), 3.27 (dt, J = 8.1, 6.2 Hz, 2H), 2.84-2.75 (m, 2H), 2.32 (q, J = 7.6 Hz, 2H), 1.99 (d, J = 0.8 Hz, 3H), 1.03 (t, J = 7.6 Hz, 3H) | $^{19}$F NMR (376 MHz, CDCl$_3$) δ −56.97 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P84 | White Solid | | ESIMS m/z 623 ([M + H]$^+$), 621 ([M − H]$^−$) | $^1$H NMR (400 MHz, DMSO-d$_6$) δ 9.41 (s, 1H), 8.14-8.04 (m, 2H), 7.97-7.88 (m, 2H), 7.68-7.59 (m, 3H), 7.41 (t, J = 7.6 Hz, 1H), 7.27 (dt, J = 7.7, 1.5 Hz, 1H), 7.22 (d, J = 1.8 Hz, 1H), 7.09-6.99 (m, 2H), 4.13-3.94 (m, 2H), 3.32-3.23 (m, 2H), 2.85-2.75 (m, 2H), 2.58 (p, J = 6.8 Hz, 1H), 2.32 (s, 3H), 1.05 (dd, J = 6.9, 3.6 Hz, 6H) | $^{19}$F NMR (376 MHz, CDCl$_3$) δ −56.97 |
| P85 | White Solid | | ESIMS m/z 627 ([M + H]$^+$), 625 ([M − H]$^−$) | $^1$H NMR (400 MHz, DMSO-d$_6$) δ 9.41 (s, 1H), 8.15-8.03 (m, 2H), 7.97-7.87 (m, 2H), 7.69-7.58 (m, 3H), 7.41 (t, J = 7.6 Hz, 1H), 7.32-7.22 (m, 3H), 7.12 (td, J = 8.4, 2.9 Hz, 1H), 4.15-3.93 (m, 2H), 3.32-3.23 (m, 2H), 2.85-2.76 (m, 2H), 2.61 (tt, J = 7.6, 3.8 Hz, 1H), 1.09-1.02 (m, 6H) | $^{19}$F NMR (376 MHz, CDCl$_3$) δ −56.97, −112.11 |
| P87 | White Solid | | ESIMS m/z 611 ([M + H]$^+$), 609 ([M − H]$^−$) | $^1$H NMR (400 MHz, DMSO-d$_6$) δ 9.41 (s, 1H), 8.17-8.02 (m, 2H), 7.99-7.88 (m, 2H), 7.71-7.57 (m, 3H), 7.47-7.39 (m, 1H), 7.29 (dt, J = 7.7, 1.4 Hz, 1H), 7.10 (d, J = 8.6 Hz, 1H), 6.90-6.86 (m, 1H), 6.83 (ddd, J = 8.7, 2.8, 0.7 Hz, 1H), 4.13-3.92 (m, 2H), 3.76 (s, 3H), 3.28 (td, J = 8.1, 7.1, 4.4 Hz, 2H), 2.86-2.76 (m, 2H), 1.99 (s, 3H) | $^{19}$F NMR (376 MHz, CDCl$_3$) δ −56.97 |
| P92 | Light Yellow Solid | | ESIMS m/z 595 ([M + H]$^+$), 593 ([M − H]$^−$) | $^1$H NMR (400 MHz, DMSO-d$_6$) δ 9.38 (s, 1H), 8.13-8.04 (m, 2H), 8.04-7.97 (m, 2H), 7.68-7.57 (m, 3H), 7.41-7.27 (m, 5H), 7.27-7.16 (m, 1H), 4.16-3.95 (m, 2H), 3.10-2.95 (m, 2H), 2.60 (t, J = 7.7 Hz, 2H), 2.08 (s, 3H), 1.72 (p, J = 7.1 Hz, 2H) | $^{19}$F NMR (376 MHz, CDCl$_3$) δ −56.96 |
| P93 | Light Yellow Solid | | ESIMS m/z 609 ([M + H]$^+$), 607 ([M − H]$^−$) | $^1$H NMR (400 MHz, DMSO-d$_6$) δ 9.38 (s, 1H), 8.11-8.04 (m, 2H), | $^{19}$F NMR (376 MHz, CDCl$_3$) δ −56.97 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 8.04-7.97 (m, 2H), 7.66-7.58 (m, 3H), 7.45-7.37 (m, 2H), 7.37-7.27 (m, 3H), 7.22 (dt, J = 7.9, 1.0 Hz, 1H), 4.17-3.95 (m, 2H), 3.04 (dp, J = 16.0, 6.4 Hz, 2H), 2.59 (t, J = 7.7 Hz, 2H), 2.39 (q, J = 7.6 Hz, 2H), 1.82-1.64 (m, 2H), 1.10 (td, J = 7.3, 1.9 Hz, 3H) | |
| P94 | Yellow Solid | | ESIMS m/z 623 ([M + H]$^+$), 621 ([M − H]$^−$) | $^1$H NMR (400 MHz, DMSO-d$_6$) δ 9.38 (s, 1H), 8.12-8.04 (m, 2H), 8.04-7.97 (m, 2H), 7.67-7.57 (m, 3H), 7.51-7.39 (m, 2H), 7.35-7.26 (m, 3H), 7.19 (dd, J = 7.8, 1.4 Hz, 1H), 4.22-3.93 (m, 2H), 3.04 (p, J = 6.7 Hz, 2H), 2.68 (p, J = 6.8 Hz, 1H), 2.59 (dd, J = 8.6, 6.8 Hz, 2H), 1.81-1.62 (m, 2H), 1.18-1.06 (m, 6H) | $^{19}$F NMR (376 MHz, CDCl$_3$) δ −56.97 |
| P99 | Light Yellow Solid | | ESIMS m/z 637 ([M + H]$^+$), 635 ([M − H]$^−$) | $^1$H NMR (400 MHz, DMSO-d$_6$) δ 9.38 (s, 1H), 8.13-8.04 (m, 2H), 8.04-7.97 (m, 2H), 7.68-7.57 (m, 3H), 7.39-7.29 (m, 2H), 7.25 (d, J = 7.9 Hz, 1H), 7.22-7.15 (m, 1H), 7.06-6.98 (m, 1H), 4.20-3.93 (m, 2H), 3.04 (p, J = 6.8 Hz, 2H), 2.59 (dd, J = 8.6, 6.7 Hz, 2H), 2.28 (d, J = 10.1 Hz, 5H), 1.72 (p, J = 7.2 Hz, 2H), 1.48 (qd, J = 7.4, 1.9 Hz, 2H), 0.84 (t, J = 7.3 Hz, 3H) | $^{19}$F NMR (376 MHz, CDCl$_3$) δ −56.97 |
| P101 | Light Yellow Solid | | ESIMS m/z 623 ([M + H]$^+$), 621 ([M − H]$^−$) | $^1$H NMR (400 MHz, DMSO-d$_6$) δ 9.38 (s, 1H), 8.14-8.04 (m, 2H), 8.04-7.98 (m, 2H), 7.71-7.59 (m, 3H), 7.38-7.27 (m, 3H), 7.25-7.17 (m, 2H), 4.16 (d, J = 1.0 Hz, 2H), 3.04 (q, J = 6.6 Hz, 2H), 2.60 (t, J = 7.7 Hz, 2H), 2.36 (q, J = 7.6 Hz, 2H), 2.05 (s, 3H), 1.73 (t, J = 7.4 Hz, 2H), 1.09 (t, J = 7.6 Hz, 3H) | $^{19}$F NMR (376 MHz, CDCl$_3$) δ −56.96 |
| P102 | Yellow Solid | | ESIMS m/z 637 ([M + H]$^+$), 635 ([M − H]$^−$) | $^1$H NMR (400 MHz, DMSO-d$_6$) δ 9.38 (s, 1H), | $^{19}$F NMR (376 MHz, CDCl$_3$) δ −56.97 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 8.13-8.04 (m, 2H), 8.04-7.96 (m, 2H), 7.67-7.57 (m, 3H), 7.37-7.29 (m, 2H), 7.27 (d, J = 1.9 Hz, 1H), 7.13-7.01 (m, 2H), 4.17-3.91 (m, 2H), 3.04 (p, J = 6.7 Hz, 2H), 2.60 (dt, J = 15.4, 7.4 Hz, 3H), 2.34 (s, 3H), 1.72 (p, J = 7.1 Hz, 2H), 1.16-1.06 (m, 6H) | |
| P103 | Light Yellow Solid | | ESIMS m/z 641 ([M + H]$^+$), 639 ([M − H]$^−$) | $^1$H NMR (400 MHz, DMSO-d$_6$) δ 9.38 (s, 1H), 8.15-8.04 (m, 2H), 8.04-7.98 (m, 2H), 7.71-7.59 (m, 3H), 7.37-7.25 (m, 4H), 7.15 (td, J = 8.4, 2.9 Hz, 1H), 4.18-3.92 (m, 2H), 3.04 (dq, J = 13.2, 6.6 Hz, 2H), 2.75-2.54 (m, 3H), 1.72 (p, J = 7.1 Hz, 2H), 1.13-1.05 (m, 6H) | $^{19}$F NMR (376 MHz, CDCl$_3$) δ −56.97, −112.12 |
| P105 | Light Yellow Solid | | ESIMS m/z 625 ([M + H]$^+$), 623 ([M − H]$^−$) | $^1$H NMR (400 MHz, DMSO-d$_6$) δ 9.38 (s, 1H), 8.14-8.04 (m, 2H), 8.04-7.96 (m, 2H), 7.71-7.55 (m, 3H), 7.38-7.29 (m, 2H), 7.13 (d, J = 8.6 Hz, 1H), 6.92 (d, J = 2.9 Hz, 1H), 6.85 (dd, J = 8.6, 2.9 Hz, 1H), 4.12-3.93 (m, 2H), 3.78 (s, 3H), 3.16-2.93 (m, 2H), 2.60 (t, J = 7.6 Hz, 2H), 2.04 (s, 3H), 1.80-1.63 (m, 2H) | $^{19}$F NMR (376 MHz, CDCl$_3$) δ −56.97 |
| P118 | Off White Solid | | ESIMS m/z 595 ([M + H]$^+$), 593 ([M − H]$^−$) | $^1$H NMR (400 MHz, DMSO-d$_6$) δ 9.40 (s, 1H), 8.13-8.04 (m, 2H), 7.92 (dd, J = 7.1, 1.4 Hz, 2H), 7.68-7.58 (m, 3H), 7.46-7.39 (m, 1H), 7.39-7.27 (m, 4H), 7.27-7.20 (m, 1H), 4.17-3.94 (m, 2H), 3.16-2.96 (m, 2H), 2.63 (t, J = 7.7 Hz, 2H), 2.09 (s, 3H), 1.74 (p, J = 7.3 Hz, 2H) | $^{19}$F NMR (376 MHz, CDCl$_3$) δ −56.96 |
| P119 | Off White Solid | | ESIMS m/z 609 ([M + H]$^+$), 607 ([M − H]$^−$) | $^1$H NMR (400 MHz, DMSO-d$_6$) δ 9.40 (s, 1H), 8.14-8.04 (m, 2H), 7.92 (dd, J = 6.3, 1.4 Hz, 2H), 7.68-7.56 (m, 3H), 7.47-7.37 (m, 3H), 7.37-7.26 (m, 2H), | $^{19}$F NMR (376 MHz, CDCl$_3$) δ −56.97 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 7.22 (d, J = 7.8 Hz, 1H), 4.21-3.92 (m, 2H), 3.16-2.96 (m, 2H), 2.62 (t, J = 7.7 Hz, 2H), 2.40 (q, J = 7.6 Hz, 2H), 1.74 (p, J = 7.1 Hz, 2H), 1.10 (t, J = 7.3, 2.7 Hz, 3H) | |
| P120 | Off White Solid | | ESIMS m/z 623 ([M + H]$^+$), 621 ([M − H]$^−$) | $^1$H NMR (400 MHz, DMSO-d$_6$) δ 9.40 (s, 1H), 8.16-8.04 (m, 2H), 7.92 (tt, J = 3.1, 1.4 Hz, 2H), 7.69-7.58 (m, 3H), 7.48 (dd, J = 7.9, 1.6 Hz, 1H), 7.46-7.38 (m, 2H), 7.30 (td, J = 7.5, 1.6 Hz, 2H), 7.20 (dd, J = 7.8, 1.4 Hz, 1H), 4.21-3.93 (m, 2H), 3.06 (qd, J = 6.8, 3.5 Hz, 2H), 2.65 (dt, J = 26.1, 7.3 Hz, 3H), 1.73 (p, J = 7.3 Hz, 2H), 1.09 (dt, J = 7.0, 3.6 Hz, 6H) | $^{19}$F NMR (376 MHz, CDCl$_3$) δ −56.97 |
| P124 | Off White Solid | | ESIMS m/z 637 ([M + H]$^+$), 635 ([M − H]$^−$) | $^1$H NMR (400 MHz, DMSO-d$_6$) δ 9.40 (s, 1H), 8.14-8.02 (m, 2H), 7.92 (tt, J = 3.1, 1.4 Hz, 2H), 7.70-7.56 (m, 3H), 7.42 (t, J = 7.8 Hz, 1H), 7.35 (d, J = 8.0 Hz, 1H), 7.29 (dt, J = 7.8, 1.5 Hz, 1H), 7.23 (dd, J = 8.1, 1.9 Hz, 1H), 6.99 (dd, J = 1.9, 0.9 Hz, 1H), 4.20-3.92 (m, 2H), 3.06 (qd, J = 6.9, 3.3 Hz, 2H), 2.71-2.54 (m, 3H), 2.29 (s, 3H), 1.85-1.62 (m, 2H), 1.16-1.03 (m, 6H) | $^{19}$F NMR (376 MHz, CDCl$_3$) δ −56.97 |
| P125 | Off White Solid | | ESIMS m/z 637 ([M + H]$^+$), 635 ([M − H]$^−$) | $^1$H NMR (400 MHz, DMSO-d$_6$) δ 9.40 (s, 1H), 8.15-8.03 (m, 2H), 7.92 (dt, J = 5.8, 1.6 Hz, 2H), 7.69-7.57 (m, 3H), 7.42 (dd, J = 8.3, 7.6 Hz, 1H), 7.30 (dt, J = 7.6, 1.5 Hz, 1H), 7.25 (d, J = 7.9 Hz, 1H), 7.19 (ddd, J = 7.8, 1.9, 0.8 Hz, 1H), 7.02 (dd, J = 1.8, 0.9 Hz, 1H), 4.20-3.89 (m, 2H), 3.06 (ddd, J = 12.1, 6.9, 4.9 Hz, 2H), 2.62 (t, J = 7.7 Hz, 2H), 2.29 (d, J = 2.9 Hz, 5H), 1.74 (p, J = 7.3 Hz, 2H), | $^{19}$F NMR (376 MHz, CDCl$_3$) δ −56.97 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P127 | Off White Solid | | ESIMS m/z 623 ([M + H]$^+$), 621 ([M − H]$^−$) | $^1$H NMR (400 MHz, DMSO-d$_6$) δ 9.40 (s, 1H), 8.12-8.05 (m, 2H), 7.96-7.89 (m, 2H), 7.71-7.58 (m, 3H), 7.41 (dd, J = 8.6, 7.3 Hz, 1H), 7.30 (t, J = 7.5 Hz, 2H), 7.25-7.17 (m, 2H), 4.15 (d, J = 1.0 Hz, 2H), 3.06 (q, J = 6.7 Hz, 2H), 2.63 (t, J = 7.7 Hz, 2H), 2.36 (q, J = 7.5 Hz, 2H), 2.05 (s, 3H), 1.82-1.65 (m, 2H), 1.57-1.39 (m, 2H), 1.09 (t, J = 7.3, 3.2 Hz, 3H), 0.84 (t, J = 7.3 Hz, 3H) | $^{19}$F NMR (376 MHz, CDCl$_3$) δ −56.97 |
| P128 | Off White Solid | | ESIMS m/z 637 ([M + H]$^+$), 635 ([M − H]$^−$) | $^1$H NMR (400 MHz, DMSO-d$_6$) δ 9.40 (s, 1H), 8.14-8.04 (m, 2H), 7.92 (dp, J = 5.2, 1.6 Hz, 2H), 7.69-7.56 (m, 3H), 7.42 (t, J = 7.9 Hz, 1H), 7.33-7.23 (m, 2H), 7.14-7.01 (m, 2H), 4.17-3.92 (m, 2H), 3.05 (qd, J = 6.9, 3.5 Hz, 2H), 2.68-2.56 (m, 3H), 2.34 (s, 3H), 1.80-1.65 (m, 2H), 1.16-1.08 (m, 6H) | $^{19}$F NMR (376 MHz, CDCl$_3$) δ −56.97 |
| P129 | Off White Solid | | ESIMS m/z 641 ([M + H]$^+$), 639 ([M − H]$^−$) | $^1$H NMR (400 MHz, DMSO-d$_6$) δ 9.40 (s, 1H), 8.15-8.04 (m, 2H), 7.92 (tt, J = 3.1, 1.4 Hz, 2H), 7.69-7.58 (m, 3H), 7.42 (t, J = 7.8 Hz, 1H), 7.37-7.25 (m, 3H), 7.15 (ddd, J = 8.7, 8.1, 2.9 Hz, 1H), 4.18-3.91 (m, 2H), 3.06 (qd, J = 6.9, 3.4 Hz, 2H), 2.73-2.56 (m, 3H), 1.83-1.64 (m, 2H), 1.17-1.05 (m, 6H) | $^{19}$F NMR (376 MHz, CDCl$_3$) δ −56.97, −112.13 |
| P131 | Off White Solid | | ESIMS m/z 625 ([M + H]$^+$), 623 ([M − H]$^−$) | $^1$H NMR (400 MHz, DMSO-d$_6$) δ 9.40 (s, 1H), 8.13-8.05 (m, 2H), 7.93 (dd, J = 7.3, 1.4 Hz, 2H), 7.69-7.58 (m, 3H), 7.42 (td, J = 7.4, 1.0 Hz, 1H), 7.30 (dt, J = 7.6, 1.5 Hz, 1H), 7.13 (d, J = 8.6 Hz, 1H), 6.92 (dd, J = 2.8, 0.8 Hz, 1H), 6.86 (ddd, J = 8.7, 3.0, 0.7 Hz, 1H), 4.16-3.91 (m, 2H), 3.39 (q, J = 7.0 Hz, 1H), 3.34 (s, 2H), | $^{19}$F NMR (376 MHz, CDCl$_3$) δ −56.97 |

TABLE 3b-continued

Analytical Data for Compounds in Table 2b.

| No. | Appearance | Mp (° C.) | ESIMS m/z | ¹H NMR (δ)ᵃ | ¹³C NMR or ¹⁹F NMR (δ) |
|---|---|---|---|---|---|
| | | | | 3.16-2.96 (m, 2H), 2.64 (dd, J = 8.7, 6.7 Hz, 2H), 2.04 (s, 3H), 1.74 (p, J = 7.3 Hz, 2H) | |
| P144 | White Foam | | ESIMS m/z 609 ([M + H]⁺) | 8.54 (s, 1H), 8.08 (d, J = 8.1 Hz, 2H), 7.85-7.75 (m, 2H), 7.42-7.36 (m, 3H), 7.36-7.28 (m, 3H), 7.26 (s, 1H), 7.13-7.07 (m, 1H), 5.39 (s, 1H), 4.00-3.82 (m, 2H), 3.25 (qd, J = 6.9, 4.2 Hz, 2H), 2.67 (t, J = 7.5 Hz, 2H), 2.15 (s, 3H), 1.77-1.61 (m, 2H), 1.52 (d, J = 0.5 Hz, 2H) | ¹⁹F NMR (376 MHz, CDCl₃) δ −58.02 |
| P145 | White Solid | 82-88 | ESIMS m/z 623 ([M + H]⁺) | 8.54 (s, 1H), 8.08 (d, J = 8.2 Hz, 2H), 7.83-7.76 (m, 2H), 7.47-7.35 (m, 5H), 7.32 (td, J = 7.4, 2.0 Hz, 1H), 7.24 (s, 1H), 7.07 (dd, J = 7.8, 1.3 Hz, 1H), 5.39 (t, J = 6.1 Hz, 1H), 3.98-3.81 (m, 2H), 3.36-3.09 (m, J = 6.8 Hz, 2H), 2.66 (t, J = 7.5 Hz, 2H), 2.45 (qd, J = 7.6, 1.8 Hz, 2H), 1.75-1.61 (m, 2H), 1.52 (s, 2H), 1.17 (t, J = 7.6 Hz, 3H) | |
| P146 | White Solid | 89-92 | ESIMS m/z 637 ([M + H]⁺) | 8.54 (s, 1H), 8.11-8.05 (m, 2H), 7.84-7.76 (m, 2H), 7.47-7.42 (m, 2H), 7.38 (dt, J = 8.0, 1.0 Hz, 2H), 7.30 (ddd, J = 7.9, 5.6, 3.2 Hz, 1H), 7.25-7.22 (m, 2H), 7.07-7.01 (m, 1H), 5.38 (t, J = 6.0 Hz, 1H), 4.04-3.81 (m, 2H), 3.33-3.16 (m, 2H), 2.67 (dt, J = 10.3, 7.2 Hz, 3H), 1.73-1.60 (m, 2H), 1.60-1.46 (m, 2H), 1.17 (dd, J = 6.9, 3.2 Hz, 6H) | |
| P150 | White Solid | 100-105 | ESIMS m/z 651 ([M + H]⁺) | 8.55 (s, 1H), 8.11-8.05 (m, 2H), 7.83-7.76 (m, 2H), 7.39 (dd, J = 9.0, 0.9 Hz, 2H), 7.33 (d, J = 8.0 Hz, 1H), 7.26 (s, 3H), 6.86 (dd, J = 1.9, 0.9 Hz, 1H), 5.43 (t, J = 6.1 Hz, 1H), 4.02-3.82 (m, 2H), 3.34-3.16 (m, J = 6.6 Hz, 2H), 2.65 (dt, J = 10.6, | ¹⁹F NMR (376 MHz, CDCl₃) δ −58.03 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 7.1 Hz, 3H), 2.35 (s, 3H), 1.75-1.60 (m, 2H), 1.60-1.47 (m, 2H), 1.21-1.07 (m, 6H) | |
| P151 | White Solid | 78-82 | ESIMS m/z 651 ([M + H]$^+$) | 8.54 (s, 1H), 8.12-8.05 (m, 2H), 7.84-7.75 (m, 2H), 7.41-7.35 (m, 2H), 7.24 (d, J = 3.8 Hz, 3H), 7.22-7.17 (m, 1H), 6.90-6.85 (m, 1H), 5.41 (t, J = 6.1 Hz, 1H), 3.97-3.80 (m, 2H), 3.36-3.13 (m, 2H), 2.67 (t, J = 7.5 Hz, 2H), 2.42-2.23 (m, 5H), 1.75-1.61 (m, 2H), 1.61-1.48 (m, 4H), 0.89 (t, J = 7.3 Hz, 3H) | |
| P152 | White Solid | | ESIMS m/z 623 ([M + H]$^+$) | 8.54 (s, 1H), 8.08 (d, J = 8.1 Hz, 2H), 7.84-7.76 (m, 2H), 7.42-7.34 (m, 1H), 7.26 (s, 4H), 7.20-7.12 (m, 2H), 5.40 (s, 1H), 3.92 (s, 2H), 3.25 (q, J = 6.8 Hz, 2H), 2.67 (t, J = 7.5 Hz, 2H), 2.12 (d, J = 0.7 Hz, 6H), 1.66 (q, J = 7.7 Hz, 2H), 1.52 (s, 2H) | $^{19}$F NMR (376 MHz, CDCl$_3$) δ −58.02 |
| P153 | White Foam | | ESIMS m/z 637 ([M + H]$^+$) | 8.54 (s, 1H), 8.12-8.05 (m, 2H), 7.84-7.74 (m, 2H), 7.43-7.36 (m, 2H), 7.32 (t, J = 7.6 Hz, 1H), 7.24 (s, 1H), 7.18 (dd, J = 15.3, 7.6 Hz, 3H), 5.40 (s, 1H), 3.92 (s, 2H), 3.25 (q, J = 6.7 Hz, 2H), 2.67 (t, J = 7.5 Hz, 2H), 2.42 (dt, J = 8.9, 7.4 Hz, 2H), 2.11 (s, 3H), 1.66 (p, J = 7.4 Hz, 2H), 1.59-1.47 (m, 2H), 1.16 (t, J = 7.6 Hz, 3H) | $^{19}$F NMR (376 MHz, CDCl$_3$) δ −58.02 |
| P154 | White Solid | 101-108 | ESIMS m/z 651 ([M + H]$^+$) | 8.54 (s, 1H), 8.12-8.04 (m, 2H), 7.84-7.75 (m, 2H), 7.43-7.35 (m, 2H), 7.25-7.21 (m, 3H), 7.11 (ddd, J = 8.1, 2.0, 0.8 Hz, 1H), 6.92 (d, J = 8.0 Hz, 1H), 5.40 (t, J = 6.1 Hz, 1H), 3.97-3.79 (m, 2H), 3.37-3.16 (m, 2H), 2.65 (q, J = 7.1 Hz, 2H), 2.40 (s, 3H), 1.73-1.59 (m, 2H), 1.52 (s, 3H), 1.16 (dd, J = 6.9, 2.7 Hz, 6H) | |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P155 | White Solid | | ESIMS m/z 655 ([M + H]$^+$) | 8.55 (s, 1H), 8.12-8.05 (m, 2H), 7.84-7.75 (m, 2H), 7.44-7.35 (m, 2H), 7.30-7.21 (m, 2H), 7.11 (dd, J = 9.9, 2.6 Hz, 1H), 7.08-6.94 (m, 2H), 5.40 (t, J = 6.1 Hz, 1H), 4.00-3.81 (m, 2H), 3.37-3.16 (m, 2H), 2.67 (t, J = 7.3 Hz, 3H), 1.65 (q, J = 7.8 Hz, 2H), 1.55 (s, 2H), 1.16 (dd, J = 6.9, 5.1 Hz, 6H) | $^{19}$F NMR (376 MHz, CDCl$_3$) δ −58.03, −110.71 |
| P156 | White Solid | | ESIMS m/z 667 ([M + H]$^+$) | 8.55 (s, 1H), 8.12-8.04 (m, 2H), 7.85-7.71 (m, 2H), 7.42-7.36 (m, 1H), 7.34 (d, J = 8.7 Hz, 1H), 7.26 (s, 3H), 7.01 (dd, J = 8.7, 2.7 Hz, 1H), 6.57 (d, J = 2.7 Hz, 1H), 5.44 (t, J = 6.1 Hz, 1H), 3.98-3.85 (m, 2H), 3.79 (s, 3H), 3.26 (hept, J = 6.7 Hz, 2H), 2.66 (t, J = 7.5 Hz, 2H), 2.63-2.56 (m, 1H), 1.65 (q, J = 7.6 Hz, 2H), 1.56 (s, 2H), 1.14 (dd, J = 6.9, 4.4 Hz, 6H) | $^{19}$F NMR (376 MHz, CDCl$_3$) δ −58.03 |
| P159 | White Solid. | 110-117 | ESIMS m/z 635 ([M + H]$^+$) | 8.64 (s, 1H), 8.09 (d, J = 8.2 Hz, 2H), 7.94-7.88 (m, 2H), 7.83-7.76 (m, 2H), 7.33 (d, J = 8.0 Hz, 1H), 7.28-7.23 (m, 3H), 6.89-6.83 (m, 1H), 5.44 (t, J = 6.1 Hz, 1H), 4.00-3.80 (m, 2H), 3.41-3.15 (m, 2H), 2.77-2.53 (m, 3H), 2.44-2.28 (m, 3H), 1.71-1.61 (m, 2H), 1.59-1.50 (m, 2H), 1.15 (d, J = 6.9 Hz, 6H) | $^{19}$F NMR (376 MHz, CDCl$_3$) δ −62.48 |
| P160 | Yellow Solid | 107-113 | ESIMS m/z 647 ([M + H]$^+$) | 8.57 (s, 1H), 8.13-8.08 (m, 2H), 7.83-7.77 (m, 2H), 7.47-7.42 (m, 2H), 7.39 (dt, J = 8.0, 1.0 Hz, 2H), 7.33 (d, J = 8.0 Hz, 1H), 7.26 (s, 1H), 6.89-6.85 (m, 1H), 5.78 (t, J = 6.2 Hz, 1H), 4.01-3.82 (m, 2H), 3.47 (qd, J = 6.6, 3.2 Hz, 2H), 2.64 (dq, J = 10.9, 6.4 Hz, 3H), 2.34 (s, 3H), 1.21-1.09 (m, 6H) | $^{19}$F NMR (376 MHz, CDCl$_3$) δ −58.02 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P170 | White Solid | | ESIMS m/z 609 ([M + H]$^+$) | $^1$H NMR (400 MHz, DMSO-d$_6$) δ 9.40 (s, 1H), 8.13-8.05 (m, 2H), 7.92 (dt, J = 6.5, 1.5 Hz, 2H), 7.68-7.60 (m, 2H), 7.57 (t, J = 5.9 Hz, 1H), 7.46-7.37 (m, 1H), 7.37-7.25 (m, 4H), 7.25-7.17 (m, 1H), 4.13-3.92 (m, 2H), 3.04 (dp, J = 19.5, 6.5 Hz, 2H), 2.65 (t, J = 7.6 Hz, 2H), 2.06 (s, 3H), 1.64-1.50 (m, 2H), 1.50-1.37 (m, 2H) | $^{19}$F NMR (376 MHz, CDCl$_3$) δ −56.96 |
| P171 | White Solid | | ESIMS m/z 623 ([M + H]$^+$) | $^1$H NMR (400 MHz, DMSO-d$_6$) δ 9.40 (s, 1H), 8.13-8.05 (m, 2H), 7.92 (ddt, J = 5.2, 2.9, 1.7 Hz, 2H), 7.68-7.60 (m, 2H), 7.56 (t, J = 5.9 Hz, 1H), 7.46-7.35 (m, 3H), 7.34-7.25 (m, 2H), 7.20 (dt, J = 7.8, 0.9 Hz, 1H), 4.15-3.93 (m, 2H), 3.03 (dp, J = 16.6, 6.5 Hz, 2H), 2.64 (t, J = 7.6 Hz, 2H), 2.37 (q, J = 7.6 Hz, 2H), 1.54 (q, J = 7.7 Hz, 2H), 1.49-1.37 (m, 2H), 1.07 (t, J = 7.6 Hz, 3H) | $^{19}$F NMR (376 MHz, CDCl$_3$) δ −56.96 |
| P172 | White Solid | | ESIMS m/z 637 ([M + H]$^+$) | $^1$H NMR (400 MHz, DMSO-d$_6$) δ 9.40 (s, 1H), 8.13-8.04 (m, 2H), 7.91 (tt, J = 3.2, 1.5 Hz, 2H), 7.63 (ddt, J = 7.9, 1.9, 1.0 Hz, 2H), 7.55 (t, J = 5.8 Hz, 1H), 7.47-7.37 (m, 3H), 7.32-7.24 (m, 2H), 7.17 (dd, J = 7.9, 1.4 Hz, 1H), 4.14-3.93 (m, 2H), 3.03 (qd, J = 6.8, 2.3 Hz, 2H), 2.64 (td, J = 7.3, 4.2 Hz, 3H), 1.63-1.48 (m, 2H), 1.49-1.37 (m, 2H), 1.13-1.05 (m, 6H) | $^{19}$F NMR (376 MHz, CDCl$_3$) δ −56.96 |
| P176 | White Solid | | ESIMS m/z 651 ([M + H]$^+$) | $^1$H NMR (400 MHz, DMSO-d$_6$) δ 9.40 (s, 1H), 8.14-8.04 (m, 2H), 7.92 (dt, J = 3.9, 1.7 Hz, 2H), 7.67-7.60 (m, 2H), 7.57 (t, J = 5.9 Hz, 1H), 7.41 (t, J = 7.8 Hz, 1H), 7.36-7.26 (m, 2H), 7.21 (dd, J = 8.2, 1.8 Hz, 1H), | $^{19}$F NMR (376 MHz, CDCl$_3$) δ −56.97 |

TABLE 3b-continued

Analytical Data for Compounds in Table 2b.

| No. | Appearance | Mp (° C.) | ESIMS m/z | ¹H NMR (δ)[a] | ¹³C NMR or ¹⁹F NMR (δ) |
|---|---|---|---|---|---|
| | | | | 7.00-6.95 (m, 1H), 4.12-3.92 (m, 2H), 3.03 (q, J = 7.4, 7.0 Hz, 2H), 2.61 (dt, J = 17.5, 7.2 Hz, 3H), 2.26 (s, 3H), 1.66-1.49 (m, 2H), 1.49-1.37 (m, 2H), 1.10-1.01 (m, 6H) | |
| P179 | White Solid | | ESIMS m/z 637 ([M + H]⁺) | ¹H NMR (400 MHz, DMSO-d₆) δ 9.40 (s, 1H), 8.13-8.05 (m, 2H), 7.97-7.87 (m, 2H), 7.68-7.55 (m, 3H), 7.41 (dd, J = 8.2, 7.6 Hz, 1H), 7.28 (ddd, J = 7.4, 4.4, 2.8 Hz, 2H), 7.22-7.14 (m, 2H), 4.14 (d, J = 1.0 Hz, 2H), 3.03 (q, J = 6.6 Hz, 2H), 2.64 (t, J = 7.5 Hz, 2H), 2.34 (q, J = 7.5 Hz, 2H), 2.02 (s, 3H), 1.62-1.49 (m, 2H), 1.50-1.37 (m, 2H), 1.08-1.02 (m, 3H) | ¹⁹F NMR (376 MHz, CDCl₃) δ -56.96 |
| P180 | White Solid | | ESIMS m/z 651 ([M + H]⁺) | ¹H NMR (400 MHz, DMSO-d₆) δ 9.40 (s, 1H), 8.13-8.06 (m, 2H), 7.92 (dp, J = 5.1, 1.6 Hz, 2H), 7.68-7.60 (m, 2H), 7.55 (t, J = 5.9 Hz, 1H), 7.45-7.37 (m, 1H), 7.28 (dt, J = 7.7, 1.5 Hz, 1H), 7.26-7.20 (m, 1H), 7.09-7.00 (m, 2H), 4.13-3.91 (m, 2H), 3.10-2.96 (m, 2H), 2.61 (dt, J = 16.9, 7.1 Hz, 3H), 2.32 (s, 3H), 1.63-1.48 (m, 2H), 1.48-1.37 (m, 2H), 1.11-1.02 (m, 6H) | ¹⁹F NMR (376 MHz, CDCl₃) δ -56.97 |
| P181 | White Solid | | ESIMS m/z 655 ([M + H]⁺) | ¹H NMR (400 MHz, DMSO-d₆) δ 9.40 (s, 1H), 8.12-8.05 (m, 2H), 7.96-7.89 (m, 2H), 7.63 (dp, J = 7.7, 0.9 Hz, 2H), 7.56 (t, J = 5.9 Hz, 1H), 7.46-7.37 (m, 1H), 7.33-7.23 (m, 3H), 7.12 (td, J = 8.4, 2.9 Hz, 1H), 4.14-3.91 (m, 2H), 3.11-2.96 (m, 2H), 2.72-2.56 (m, 3H), 1.55 (dq, J = 12.1, 7.7, 6.9 Hz, 2H), 1.44 (q, J = 7.6, 7.2 Hz, 2H), 1.12-1.03 (m, 6H) | ¹⁹F NMR (376 MHz, CDCl₃) δ -56.96, -112.17 |

TABLE 3b-continued

Analytical Data for Compounds in Table 2b.

| No. | Appearance | Mp (° C.) | ESIMS m/z | $^1$H NMR (δ)$^a$ | $^{13}$C NMR or $^{19}$F NMR (δ) |
|---|---|---|---|---|---|
| P182 | White Solid | | ESIMS m/z 667 ([M + H]$^+$) | $^1$H NMR (400 MHz, DMSO-d$_6$) δ 9.40 (s, 1H), 8.13-8.05 (m, 2H), 7.92 (dt, J = 4.0, 1.8 Hz, 2H), 7.60 (dd, J = 21.0, 7.3 Hz, 3H), 7.41 (t, J = 7.9 Hz, 1H), 7.36-7.25 (m, 2H), 6.98 (dd, J = 8.7, 2.8 Hz, 1H), 6.80 (d, J = 2.7 Hz, 1H), 4.13-3.89 (m, 2H), 3.71 (s, 3H), 3.03 (q, J = 7.5, 6.8 Hz, 2H), 2.60 (dt, J = 28.9, 7.1 Hz, 3H), 1.65-1.49 (m, 2H), 1.43 (dq, J = 13.4, 7.0 Hz, 2H), 1.05 (dd, J = 16.4, 6.8 Hz, 6H) | $^{19}$F NMR (376 MHz, CDCl$_3$) δ −56.96 |
| P205 | Brown Solid | | ESIMS m/z 623 ([M + H]$^+$) | 8.55 (s, 1H), 8.13-8.03 (m, 2H), 7.85-7.75 (m, 2H), 7.47-7.35 (m, 4H), 7.30-7.23 (m, 3H), 7.01 (ddt, J = 7.6, 6.7, 0.7 Hz, 1H), 5.39 (s, 1H), 3.97-3.87 (m, 2H), 3.65-2.94 (m, 3H), 2.74-2.56 (m, 1H), 1.28 (dd, J = 6.9, 1.5 Hz, 3H), 1.21-1.07 (m, 6H) | $^{19}$F NMR (376 MHz, CDCl$_3$) δ −58.03 |
| P209 | Brown Foam | | ESIMS m/z 637 ([M + H]$^+$) | 8.55 (s, 1H), 8.11-8.04 (m, 2H), 7.83-7.74 (m, 2H), 7.43-7.35 (m, 4H), 7.29-7.18 (m, 3H), 7.00 (tt, J = 8.1, 1.1 Hz, 1H), 5.32 (d, J = 16.6 Hz, 1H), 3.94-3.85 (m, 2H), 3.79-3.54 (m, 1H), 3.27 (dddd, J = 53.3, 13.9, 9.0, 5.2 Hz, 1H), 2.82-2.56 (m, 2H), 1.82-1.56 (m, 2H), 1.19-1.02 (m, 6H), 0.86-0.74 (m, 3H) | $^{19}$F NMR (376 MHz, CDCl$_3$) δ −58.02 |
| P364 | Pink Solid | | ESIMS m/z 651 ([M + H]$^+$) | 8.56 (s, 1H), 8.08 (dd, J = 8.2, 6.4 Hz, 2H), 7.84-7.76 (m, 2H), 7.39 (dq, J = 7.7, 1.1 Hz, 2H), 7.26 (s, 4H), 6.81 (d, J = 7.6 Hz, 1H), 5.35 (d, J = 5.7 Hz, 1H), 3.94-3.84 (m, 2H), 3.67 (ddt, J = 49.5, 13.1, 6.5 Hz, 1H), 3.39-3.15 (m, 1H), 2.80-2.53 (m, 2H), 2.30 (dt, J = 4.4, 0.7 Hz, 3H), 1.80-1.56 (m, 2H), 1.10 (ddd, | $^{19}$F NMR (376 MHz, CDCl$_3$) δ −58.02 |

TABLE 3b-continued

Analytical Data for Compounds in Table 2b.

| No. | Appearance | Mp (° C.) | ESIMS m/z | $^1$H NMR (δ)[a] | $^{13}$C NMR or $^{19}$F NMR (δ) |
|---|---|---|---|---|---|
| | | | | J = 18.9, 10.4, 6.8 Hz, 6H), 0.81 (t, J = 7.3 Hz, 3H) | |
| P679 | Brown Solid | | ESIMS m/z 653 ([M + H]$^+$) | 8.55 (s, 1H), 8.13-8.03 (m, 2H), 7.86-7.72 (m, 2H), 7.39 (ddd, J = 8.0, 1.8, 0.9 Hz, 2H), 7.32-7.26 (m, 3H), 6.97 (ddd, J = 8.8, 4.4, 2.7 Hz, 1H), 6.53 (dd, J = 6.4, 2.7 Hz, 1H), 5.49-5.28 (m, 1H), 3.91 (t, J = 1.4 Hz, 2H), 3.75 (d, J = 3.1 Hz, 3H), 3.69-3.20 (m, 2H), 3.02 (dt, J = 13.9, 6.9 Hz, 1H), 2.57 (h, J = 7.0 Hz, 1H), 1.29 (dd, J = 7.1, 1.5 Hz, 3H), 1.16-1.04 (m, 6H) | $^{19}$F NMR (376 MHz, CDCl$_3$) δ −58.03 |
| P683 | Brown Foam | | ESIMS m/z 667 ([M + H]$^+$) | 8.55 (s, 1H), 8.13-8.02 (m, 2H), 7.83-7.76 (m, 2H), 7.42-7.34 (m, 2H), 7.31-7.19 (m, 3H), 6.95 (ddd, J = 8.5, 5.4, 2.7 Hz, 1H), 6.52 (dd, J = 7.9, 2.7 Hz, 1H), 5.38 (s, 1H), 3.90 (t, J = 1.6 Hz, 2H), 3.79-3.57 (m, 4H), 3.28 (dddd, J = 52.9, 13.9, 9.0, 5.2 Hz, 1H), 2.81-2.47 (m, 2H), 1.81-1.55 (m, 2H), 1.15-1.00 (m, 6H), 0.81 (t, J = 7.3 Hz, 3H) | $^{19}$F NMR (376 MHz, CDCl$_3$) δ −58.02 |
| P1163 | Brown Foam | | ESIMS m/z 655 ([M + H]$^+$) | 8.56 (s, 1H), 8.12-8.05 (m, 2H), 7.84-7.77 (m, 2H), 7.43-7.36 (m, 2H), 7.26-7.18 (m, 2H), 7.05 (ddd, J = 9.9, 4.8, 2.5 Hz, 1H), 7.01-6.89 (m, 2H), 5.29 (t, J = 6.2 Hz, 1H), 3.95-3.85 (m, 2H), 3.81-3.57 (m, 1H), 3.27 (dddd, J = 46.1, 13.9, 9.1, 5.1 Hz, 1H), 2.81-2.50 (m, 2H), 1.67 (ddd, J = 56.8, 15.2, 8.0 Hz, 2H), 1.18-0.97 (m, 6H), 0.82 (t, J = 7.3 Hz, 3H) | $^{19}$F NMR (376 MHz, CDCl$_3$) δ −58.02, −110.70, −110.72 |

[a] All $^1$H NMR data measured in CDCl$_3$ at 400 MHz unless otherwise noted

TABLE 3c

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| FB1 | White solid | | ESIMS m/z 596 [M]$^+$ | $^1$H NMR (400 MHz, CDCl$_3$) δ 11.84 (s, 1 H), 9.72 (s, 1 H), 8.54 (s, 1 H), 7.99 (s, 1 H), 7.95 (d, J = 8.8 Hz, 2 H), 7.82-7.74 (m, 4 H), 7.37 (ddd, J = 9.0, 2.1, 1.0 Hz, 4 H), 3.45-3.31 (m, 2 H), 3.09 (dt, J = 22.4, 6.8 Hz, 1 H), 2.91 (t, J = 7.3 Hz, 2 H), 2.42 (s, 3 H), 2.32 (d, J = 0.8 Hz, 3 H), 1.26-1.18 (m, 6 H) | $^{19}$F NMR (376 MHz, CDCl$_3$) δ −58.03 |
| FB2 | Yellow solid | | ESIMS m/z 612 [M]$^+$ | $^1$H NMR (400 MHz, CDCl$_3$) δ 11.97 (s, 1 H), 10.39-9.51 (m, 2 H), 8.54 (s, 1 H), 7.99-7.90 (m, 3 H), 7.81-7.75 (m, 3 H), 7.37 (ddd, J = 7.8, 2.1, 1.0 Hz, 3 H), 7.24 (s, 1 H), 3.77 (s, 3 H), 3.36 (q, J = 6.7 Hz, 2 H), 3.04 (p, J = 6.7 Hz, 1 H), 2.90 (t, J = 7.3 Hz, 2 H), 2.41 (s, 3 H), 1.23 (t, J = 6.6 Hz, 6 H) | $^{19}$F NMR (376 MHz, CDCl$_3$) δ −58.03 |
| FB3 | Yellow wax | | ESIMS m/z 636 [M]$^+$ | $^1$H NMR (400 MHz, CDCl$_3$) δ 8.55 (s, 1 H), 7.96 (d, J = 1.8 Hz, 1 H), 7.93-7.88 (m, 1 H), 7.80 (d, J = 9.0 Hz, 2 H), 7.41-7.36 (m, 3 H), 7.31 (d, J = 8.0 Hz, 1 H), 7.19 (d, J = 7.9 Hz, 1 H), 6.85 (d, J = 1.8 Hz, 1 H), 5.56 (t, J = 6.3 Hz, 1 H), 3.92 (d, J = 2.2 Hz, 2 H), 3.58-3.36 (m, 2 H), 2.87 (t, J = 7.2 Hz, 2 H), 2.64 (p, J = 6.8 Hz, 1 H), 2.38 (s, 3 H), 2.36-2.31 (m, 3 H), 1.16 (d, J = 6.9 Hz, 6 H) | $^{19}$F NMR (376 MHz, CDCl$_3$) δ −58.03 |
| FB4 | Light Yellow solid | | ESIMS m/z 652 [M]$^+$ | $^1$H NMR (400 MHz, CDCl$_3$) δ 8.54 (s, 1 H), 7.99-7.95 (m, 1 H), 7.90 (ddd, J = 7.7, 2.0, 0.7 Hz, 1 H), 7.79 (d, J = 9.0 Hz, 2 H), 7.38 (dt, J = 8.0, 1.0 Hz, 2 H), 7.32 (d, J = 8.8 Hz, 1 H), 7.19 (d, J = 7.9 Hz, 1 H), 6.99 (dd, J = 8.7, 2.7 Hz, 1 H), 6.56 (d, J = 2.7 Hz, 1 H), 5.57 (t, J = 6.3 Hz, 1 H), 3.93 (d, J = 2.0 Hz, 2 H), 3.77 (s, 3 H), 3.48 (dp, J = 25.0, 6.9 Hz, 2 H), 2.87 (t, J = 7.2 Hz, 2 H), 2.61 (p, J = 6.8 Hz, 1 H), 2.38 | $^{19}$F NMR (376 MHz, CDCl$_3$) δ −58.03 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | (s, 3 H), 1.14 (dd, J = 6.9, 3.5 Hz, 6 H) | |
| FB5 | Yellow solid | | ESIMS m/z 568 [M]$^+$ | $^1$H NMR (400 MHz, CDCl$_3$) δ 11.99 (s, 1 H), 10.16 (s, 1 H), 8.53 (d, J = 2.6 Hz, 1 H), 7.95 (ddd, J = 14.0, 7.1, 1.7 Hz, 2 H), 7.80-7.73 (m, 2 H), 7.40-7.32 (m, 5 H), 7.25-7.15 (m, 3 H), 3.50 (q, J = 6.8 Hz, 1 H), 3.37 (dd, J = 7.5, 5.7 Hz, 1 H), 2.95-2.86 (m, 1 H), 2.83 (t, J = 6.9 Hz, 1 H), 2.65 (q, J = 7.5 Hz, 2 H), 2.40 (s, 3 H), 1.27-1.16 (m, 3 H) | $^{19}$F NMR (376 MHz, CDCl$_3$) δ −58.03 |
| FB6 | Pink solid | | ESIMS m/z 608 [M]$^+$ | $^1$H NMR (400 MHz, CDCl$_3$) δ 8.55 (s, 1 H), 7.99-7.95 (m, 1 H), 7.94-7.88 (m, 1 H), 7.83-7.75 (m, 2 H), 7.43-7.35 (m, 4 H), 7.33-7.28 (m, 1 H), 7.20 (d, J = 7.9 Hz, 1 H), 7.07 (dd, J = 7.8, 1.3 Hz, 1 H), 5.55 (t, J = 6.2 Hz, 1 H), 3.93 (d, J = 1.6 Hz, 2 H), 3.47 (ddd, J = 11.0, 7.0, 3.4 Hz, 2 H), 2.92-2.83 (m, 2 H), 2.51-2.41 (m, 2 H), 2.38 (s, 3 H), 1.18 (t, J = 7.6 Hz, 3 H) | $^{19}$F NMR (376 MHz, CDCl$_3$) δ −58.03 |
| FB7 | Pink solid | | ESIMS m/z 658 [M]$^+$ | $^1$H NMR (400 MHz, CDCl$_3$) δ 8.54 (d, J = 3.2 Hz, 1 H), 8.00-7.89 (m, 2 H), 7.82-7.74 (m, 2 H), 7.41-7.34 (m, 4 H), 7.21 (dd, J = 14.3, 7.9 Hz, 1 H), 7.06 (d, J = 2.1 Hz, 1 H), 5.54 (t, J = 6.3 Hz, 1 H), 3.93 (d, J = 1.9 Hz, 2 H), 3.59-3.35 (m, 2 H), 2.94-2.83 (m, 3 H), 2.39 (d, J = 10.8 Hz, 3 H), 1.15 (t, J = 6.6 Hz, 6 H) | $^{19}$F NMR (376 MHz, CDCl$_3$) δ −58.03 |
| FB8 | Orange oil | | ESIMS m/z 640 [M]$^+$ | $^1$H NMR (400 MHz, CDCl$_3$) δ 8.55 (s, 1 H), 7.92-7.82 (m, 3 H), 7.79 (dd, J = 9.1, 1.3 Hz, 3 H), 7.42-7.37 (m, 2 H), 7.33-7.28 (m, 1 H), 6.89-6.78 (m, 1 H), 5.54 (t, J = 6.2 Hz, 1 H), 3.92 (d, J = 1.7 Hz, 2 H), 3.04 (t, J = 7.7 Hz, 2 H), 2.91 (t, J = 7.0 Hz, 2 H), 2.73-2.61 (m, 1 H), 2.33 (t, J = | $^{19}$F NMR (376 MHz, CDCl$_3$) δ −58.02, −117.98 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 0.7 Hz, 3 H), 1.15 (dt, J = 6.8, 0.9 Hz, 6 H) | |
| FB9 | Pink solid | | ESIMS m/z 656 [M]$^+$ | $^1$H NMR (400 MHz, CDCl$_3$) δ 8.55 (s, 1 H), 7.89-7.82 (m, 2 H), 7.79 (d, J = 9.1 Hz, 2 H), 7.43-7.37 (m, 4 H), 7.32 (d, J = 8.8 Hz, 1 H), 6.99 (dd, J = 8.7, 2.7 Hz, 1 H), 6.56 (d, J = 2.7 Hz, 1 H), 3.92 (d, J = 1.6 Hz, 2 H), 3.77 (s, 3 H), 3.52 (ddt, J = 30.6, 13.9, 6.7 Hz, 2 H), 2.91 (t, J = 7.0 Hz, 2 H), 2.60 (p, J = 6.7 Hz, 1 H), 1.14 (dd, J = 6.9, 4.7 Hz, 6 H) | $^{19}$F NMR (376 MHz, CDCl$_3$) δ −58.02, −117.96 |
| FB10 | White solid | | ESIMS m/z 624 ([M + H]$^+$) | $^1$H NMR (400 MHz, DMSO-d$_6$) δ 9.39 (s, 1 H), 8.10-7.99 (m, 5 H), 7.66-7.57 (m, 2 H), 7.43-7.39 (m, 2 H), 7.39-7.32 (m, 2 H), 7.32-7.22 (m, 2 H), 4.06-3.62 (m, 2 H), 3.09-2.90 (m, 4 H), 2.24 (qd, J = 7.5, 2.1 Hz, 2 H), 0.98 (dt, J = 14.4, 7.3 Hz, 6 H) | $^{13}$C NMR (101 MHz, DMSO-d$_6$) δ 165.51, 164.05, 162.06, 151.48, 147.08, 143.76, 141.37, 139.84, 135.72, 134.04, 129.59, 129.44, 129.22, 129.06, 129.01, 128.46, 126.92, 126.15, 122.60, 121.11, 44.12, 34.76, 33.99, 23.50, 14.51, 13.81 |
| FB11 | Yellow solid | | ESIMS m/z 668 ([M + H]$^+$) | $^1$H NMR (400 MHz, CDCl$_3$) δ 8.56 (s, 1 H), 8.13 (d, J = 8.2 Hz, 2 H), 7.80 (d, J = 9.0 Hz, 2 H), 7.42-7.32 (m, 4 H), 7.05 (d, J = 8.7 Hz, 1 H), 6.91 (d, J = 2.8 Hz, 1 H), 6.80 (dd, J = 8.6, 2.8 Hz, 1 H), 5.48 (t, J = 5.8 Hz, 1 H), 4.05-3.82 (m, 2 H), 3.82 (s, 3 H), 3.34-3.18 (m, 2 H), 3.09 (td, J = 7.2, 2.3 Hz, 2 H), 2.66-2.50 (m, 1 H), 1.16-1.02 (m, 9 H) | $^{13}$C NMR (101 MHz, CDCl$_3$) δ 167.30, 165.12, 163.79, 161.04, 152.95, 148.80, 148.55, 141.92, 139.76, 136.06, 129.92, 129.70, 129.36, 127.30, 126.04, 122.85, 121.61, 113.01, 112.25, 100.44, 55.80, |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | | 45.46, 36.03, 35.27, 29.26, 23.98, 23.89, 15.29 |
| FB12 | Yellow oil | | ESIMS m/z 655 [M]$^+$ | $^1$H NMR (400 MHz, CDCl$_3$) δ 8.56 (s, 1 H), 8.14 (d, J = 8.2 Hz, 2 H), 7.80 (d, J = 9.0 Hz, 2 H), 7.41-7.32 (m, 5 H), 7.14 (td, J = 8.3, 2.7 Hz, 1 H), 6.85 (dd, J = 8.7, 2.7 Hz, 1 H), 5.52 (t, J = 5.8 Hz, 1 H), 4.04-3.76 (m, 2 H), 3.38-3.18 (m, 2 H), 3.09 (td, J = 7.2, 2.9 Hz, 2 H), 2.58 (p, J = 6.8 Hz, 1 H), 1.16-1.06 (m, 9 H) | $^{19}$F NMR (376 MHz, CDCl$_3$) δ −58.02, −115.49 |
| FB13 | Yellow oil | | ESIMS m/z 656 ([M + H]$^+$) | $^1$H NMR (400 MHz, CDCl$_3$) δ 8.56 (s, 1 H), 8.13 (d, J = 8.2 Hz, 2 H), 7.84-7.72 (m, 2 H), 7.42-7.31 (m, 4 H), 7.16-7.03 (m, 2 H), 6.96 (ddd, J = 8.7, 7.6, 2.9 Hz, 1 H), 5.47 (t, J = 5.9 Hz, 1 H), 4.04-3.76 (m, 2 H), 3.35-3.17 (m, 2 H), 3.09 (td, J = 7.2, 2.5 Hz, 2 H), 2.66-2.49 (m, 1 H), 1.19-0.99 (m, 9 H) | (101 MHz, CDCl$_3$) δ 166.98, 164.98, 163.74, 162.68, 152.58, 149.93, 148.79, 141.93, 139.63, 136.04, 130.80, 130.71, 129.70, 129.40, 127.30, 122.85, 121.61, 114.63, 114.36, 114.13, 45.42, 36.06, 35.24, 29.37, 23.86, 23.74, 15.28 |
| FB14 | Yellow solid | | ESIMS m/z 638 ([M + H]$^+$) | $^1$H NMR (400 MHz, CDCl$_3$) δ 8.56 (s, 1 H), 8.17-8.10 (m, 2 H), 7.86-7.72 (m, 2 H), 7.46-7.33 (m, 7 H), 7.17-7.05 (m, 1 H), 5.47 (t, J = 5.8 Hz, 1 H), 4.06-3.75 (m, 2 H), 3.34-3.16 (m, 2 H), 3.10 (td, J = 7.2, 2.3 Hz, 2 H), 2.64 (p, J = 6.9 Hz, 1 H), 1.20-1.06 (m, 10 H) | $^{13}$C NMR (101 MHz, CDCl$_3$) δ 166.95, 165.08, 163.79, 152.72, 148.79, 147.10, 141.93, 139.74, 136.07, 133.27, 130.62, 129.71, 129.38, 128.93, 127.32, 127.26, 122.86, 121.62, 119.57, 77.80, 45.46, |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | | 36.03, 35.29, 29.03, 24.04, 23.95, 15.29 |
| FB15 | Red oil | | ESIMS m/z 677 ([M + H]$^+$) | 1:1 Mixture of diastereoisomers $^1$H NMR (600 MHz, CDCl$_3$) δ 8.60 (d, J = 11.3 Hz, 1 H), 8.15-8.04 (m, 2 H), 7.89-7.78 (m, 2 H), 7.44 (dd, J = 8.7, 5.9 Hz, 2 H), 7.35-7.31 (m, 2 H), 7.30-7.26 (m, 2 H), 6.87-6.73 (m, 1 H), 5.30 (dd, J = 37.0, 8.8 Hz, 1 H), 3.92-3.81 (m, 2 H), 3.54 (q, J = 7.0 Hz, 1 H), 2.62 (td, J = 14.0, 7.2 Hz, 1 H), 2.41-2.26 (m, 4 H), 2.02-1.80 (m, 3 H), 1.77-1.45 (m, 3 H), 1.34-1.10 (m, 6 H), 0.90 (dd, J = 155.3, 6.8 Hz, 2 H) | $^{13}$C NMR (151 MHz, CDCl$_3$) δ 173.06, 168.38, 163.84, 161.44, 148.68, 145.96, 143.44, 141.77, 136.97, 135.96, 132.82, 131.29, 129.14, 128.89, 128.64, 128.19, 127.07, 126.78, 122.74, 121.46, 53.43, 50.50, 36.05, 34.39, 33.22, 28.56, 26.41, 25.58, 24.18, 23.89, 21.04 |
| FB16 | White solid | | ESIMS m/z 583 ([M + H]$^+$) | $^1$H NMR (400 MHz, DMSO-d$_6$) δ 11.91 (s, 1 H), 9.95 (s, 1 H), 9.37 (s, 1 H), 8.11-7.94 (m, 4 H), 7.66-7.56 (m, 2 H), 7.44 (d, J = 8.0 Hz, 1 H), 7.36 (d, J = 8.1 Hz, 2 H), 7.06 (d, J = 1.9 Hz, 1 H), 7.00 (d, J = 8.0 Hz, 2 H), 3.17 (q, J = 6.5 Hz, 2 H), 2.68 (t, J = 7.5 Hz, 2 H), 2.26 (s, 3 H), 2.15 (s, 3 H), 1.64 (q, J = 7.6 Hz, 2 H), 1.51 (q, J = 7.2 Hz, 2 H) | $^{19}$F NMR (376 MHz, DMSO-d$_6$) δ −56.97 |
| FB17 | White foam | | ESIMS m/z 623 ([M + H]$^+$) | $^1$H NMR (400 MHz, CDCl$_3$) δ 8.54 (s, 1 H), 8.11-8.06 (m, 2 H), 7.83-7.76 (m, 2 H), 7.38 (dd, J = 9.1, 1.0 Hz, 1 H), 7.26 (s, 3 H), 7.14 (dd, J = 1.5, 0.8 Hz, 1 H), 7.13-7.08 (m, 1 H), 6.97 (d, J = 8.0 Hz, 1 H), 5.41 (t, J = 6.1 Hz, 1 H), 3.97-3.77 (m, 2 H), 3.25 (qd, J = 6.9, 4.1 Hz, 2 H), 2.67 (t, J = 7.5 Hz, 2 H), 2.36 (s, 3 H), 2.10 (s, 3 H), 1.73-1.61 | $^{19}$F NMR (376 MHz, CDCl$_3$) δ −58.02 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | (m, 2 H), 1.60-1.45 (m, 2 H) | |
| FB18 | Off-white solid | | ESIMS m/z 527 ([M + H]$^+$) | $^1$H NMR (400 MHz, DMSO-d$_6$) δ 11.98 (s, 1 H), 10.24 (s, 1 H), 9.43 (s, 1 H), 8.16-7.97 (m, 4 H), 7.69-7.59 (m, 3 H), 7.59-7.50 (m, 2 H), 7.44 (dt, J = 7.6, 1.5 Hz, 1 H), 7.31-7.25 (m, 1 H), 7.20 (pd, J = 7.5, 1.9 Hz, 2 H), 4.47 (d, J = 5.9 Hz, 2 H), 2.22 (s, 3 H) | $^{19}$F NMR (376 MHz, DMSO-d$_6$) δ −56.96 |
| FB19 | Off-white solid | | ESIMS m/z 557 ([M + H]$^+$) | $^1$H NMR (400 MHz, DMSO-d$_6$) δ 11.76 (s, 1 H), 10.19 (s, 1 H), 9.43 (s, 1 H), 8.13-8.06 (m, 3 H), 8.03 (dt, J = 7.7, 1.4 Hz, 1 H), 7.68-7.60 (m, 2 H), 7.58-7.49 (m, 2 H), 7.44 (dt, J = 7.7, 1.5 Hz, 1 H), 7.38 (d, J = 8.7 Hz, 1 H), 6.84 (d, J = 2.9 Hz, 1 H), 6.77 (dd, J = 8.7, 2.9 Hz, 1 H), 4.46 (d, J = 5.8 Hz, 2 H), 3.75 (s, 3 H), 2.17 (s, 3 H) | $^{19}$F NMR (376 MHz, DMSO-d$_6$) δ −56.95 |
| FB20 | Off-white solid | | ESIMS m/z 541 ([M + H]$^+$) | $^1$H NMR (400 MHz, DMSO-d$_6$) δ 12.01 (s, 1 H), 10.27 (s, 1 H), 9.45 (s, 1 H), 8.15-8.08 (m, 3 H), 8.06 (dt, J = 7.8, 1.4 Hz, 1 H), 7.65 (ddd, J = 7.9, 2.0, 1.0 Hz, 2 H), 7.62-7.52 (m, 3 H), 7.46 (dt, J = 7.8, 1.5 Hz, 1 H), 7.33-7.27 (m, 1 H), 7.27-7.20 (m, 2 H), 4.49 (d, J = 5.8 Hz, 2 H), 2.57 (q, J = 7.6 Hz, 2 H), 1.14 (t, J = 7.5 Hz, 3 H) | $^{19}$F NMR (376 MHz, DMSO-d$_6$) δ −56.96 |
| FB21 | Off-white solid | | ESIMS m/z 555 ([M + H]$^+$) | $^1$H NMR (400 MHz, DMSO-d$_6$) δ 11.59 (s, 1 H), 10.25 (s, 1 H), 9.45 (s, 1 H), 8.15-8.08 (m, 3 H), 8.06 (dt, J = 7.7, 1.4 Hz, 1 H), 7.69-7.62 (m, 2 H), 7.59-7.52 (m, 2 H), 7.46 (dt, J = 7.7, 1.4 Hz, 1 H), 7.19 (dd, J = 8.0, 6.9 Hz, 1 H), 7.15-7.09 (m, 2 H), 4.49 (d, J = 5.8 Hz, 2 H), 2.56-2.48 (m, 2 H), 2.20 (s, 3 H), 1.13 (t, J = 7.6 Hz, 3 H) | $^{19}$F NMR (376 MHz, DMSO-d$_6$) δ −56.97 |
| FB22 | Off-white solid | | ESIMS m/z 555 ([M + H]$^+$) | $^1$H NMR (400 MHz, DMSO-d$_6$) δ 11.95 (s, 1 H), 10.28 (s, 1 H), 9.45 (s, 1 H), 8.16-8.08 (m, 3 H), | $^{19}$F NMR (376 MHz, DMSO-d$_6$) δ −56.96 |

TABLE 3c-continued

Analytical Data for Compounds in Table 2c.

| No. | Appearance | Mp (° C.) | ESIMS m/z | ¹H NMR (δ)$^a$ | ¹³C NMR or ¹⁹F NMR (δ) |
|---|---|---|---|---|---|
| | | | | 7.68-7.62 (m, 2 H), 7.61-7.51 (m, 2 H), 7.50-7.40 (m, 3 H), 7.37 (dd, J = 7.8, 1.6 Hz, 1 H), 7.29 (td, J = 7.5, 1.5 Hz, 1 H), 7.23 (td, J = 7.5, 1.7 Hz, 1 H), 4.49 (d, J = 5.8 Hz, 2 H), 3.03 (hept, J = 6.5 Hz, 1 H), 1.18 (d, J = 6.8 Hz, 6 H) | |
| FB23 | Off-white solid | | ESIMS m/z 569 ([M + H]⁺) | ¹H NMR (400 MHz, DMSO-d₆) δ 11.85 (s, 1 H), 10.36-10.12 (m, 1 H), 9.45 (s, 1 H), 8.16-8.08 (m, 3 H), 8.06 (dt, J = 7.7, 1.4 Hz, 1 H), 7.69-7.62 (m, 2 H), 7.61-7.52 (m, 2 H), 7.46 (dt, J = 7.7, 1.5 Hz, 1 H), 7.28 (d, J = 8.0 Hz, 1 H), 7.19-7.14 (m, 1 H), 7.08-6.99 (m, 1 H), 4.48 (d, J = 5.8 Hz, 2 H), 2.98 (p, J = 6.9 Hz, 1 H), 2.33 (s, 3 H), 1.17 (d, J = 6.8 Hz, 6 H) | ¹⁹F NMR (376 MHz, DMSO-d₆) δ −56.96 |
| FB24 | Off-white solid | | ESIMS m/z 573 ([M + H]⁺) | ¹H NMR (400 MHz, DMSO-d₆) δ 11.83 (s, 1 H), 10.31 (s, 1 H), 9.45 (s, 1 H), 8.16-8.08 (m, 3 H), 8.06 (dt, J = 7.6, 1.5 Hz, 1 H), 7.69-7.63 (m, 2 H), 7.60-7.52 (m, 2 H), 7.46 (dt, J = 7.7, 1.5 Hz, 1 H), 7.41 (dd, J = 8.8, 5.6 Hz, 1 H), 7.18 (dd, J = 10.4, 3.0 Hz, 1 H), 7.06 (td, J = 8.5, 3.0 Hz, 1 H), 4.49 (d, J = 5.8 Hz, 2 H), 3.00 (pd, J = 6.8, 1.6 Hz, 1 H), 1.17 (d, J = 6.8 Hz, 6 H) | ¹⁹F NMR (376 MHz, DMSO-d₆) δ −56.97, −114.35 |
| FB25 | Off-white solid | | ESIMS m/z 569 ([M + H]⁺) | ¹H NMR (400 MHz, DMSO-d₆) δ 11.90 (s, 1 H), 10.25 (s, 1 H), 9.45 (s, 1 H), 8.15-8.08 (m, 3 H), 8.06 (dt, J = 7.8, 1.6 Hz, 1 H), 7.69-7.62 (m, 2 H), 7.56 (dt, J = 11.3, 6.7 Hz, 2 H), 7.46 (dt, J = 7.8, 1.5 Hz, 1 H), 7.24 (d, J = 8.1 Hz, 2 H), 7.14-7.07 (m, 1 H), 4.49 (d, J = 5.8 Hz, 2 H), 2.98 (p, J = 6.9 Hz, 1 H), 2.28 (s, 3 H), 1.15 (d, J = 6.8 Hz, 6 H) | ¹⁹F NMR (376 MHz, DMSO-d₆) δ −56.96 |
| FB26 | Off-white solid | | ESIMS m/z 589 ([M + H]⁺) | ¹H NMR (400 MHz, DMSO-d₆) δ 12.02 (s, 1 H), 10.37 (s, 1 H), 9.45 (s, 1 H), 8.15-8.08 (m, 3 H), 8.06 (dt, J = 7.7, | ¹⁹F NMR (376 MHz, DMSO-d₆) δ −56.96 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 1.5 Hz, 1 H), 7.70-7.62 (m, 2 H), 7.62-7.52 (m, 3 H), 7.46 (dt, J = 7.8, 1.4 Hz, 1 H), 7.42-7.31 (m, 2 H), 4.49 (d, J = 5.8 Hz, 2 H), 3.01 (p, J = 6.8 Hz, 1 H), 1.17 (d, J = 6.8 Hz, 6 H) | |
| FB27 | Off-white solid | | ESIMS m/z 567 ([M + H]$^+$) | $^1$H NMR (400 MHz, DMSO-d$_6$) δ 9.40 (s, 1 H), 8.22 (t, J = 6.3 Hz, 1 H), 8.13-8.03 (m, 2 H), 8.01-7.93 (m, 2 H), 7.63 (dq, J = 7.9, 1.0 Hz, 2 H), 7.45 (t, J = 7.6 Hz, 1 H), 7.40-7.28 (m, 4 H), 7.28-7.21 (m, 1 H), 4.35-4.19 (m, 2 H), 4.17-3.96 (m, 2 H), 2.10 (s, 3 H) | $^{19}$F NMR (376 MHz, DMSO-d$_6$) δ −56.96 |
| FB28 | Light orange solid | | ESIMS m/z 597 ([M + H]$^+$) | $^1$H NMR (400 MHz, DMSO-d$_6$) δ 9.40 (s, 1 H), 8.22 (t, J = 6.3 Hz, 1 H), 8.11-8.03 (m, 2 H), 8.02-7.93 (m, 2 H), 7.69-7.59 (m, 2 H), 7.45 (t, J = 7.6 Hz, 1 H), 7.33 (dt, J = 7.7, 1.5 Hz, 1 H), 7.15 (d, J = 8.7 Hz, 1 H), 6.92 (d, J = 2.8 Hz, 1 H), 6.86 (dd, J = 8.7, 2.9 Hz, 1 H), 4.35-4.19 (m, 2 H), 4.15-3.93 (m, 2 H), 3.78 (s, 3 H), 2.05 (s, 3 H) | $^{19}$F NMR (376 MHz, DMSO-d$_6$) δ −56.96 |
| FB29 | White solid | | ESIMS m/z 581 ([M + H]$^+$) | $^1$H NMR (400 MHz, DMSO-d$_6$) δ 9.40 (s, 1 H), 8.22 (t, J = 6.3 Hz, 1 H), 8.12-8.03 (m, 2 H), 8.01-7.93 (m, 2 H), 7.68-7.59 (m, 2 H), 7.48-7.38 (m, 3 H), 7.37-7.28 (m, 2 H), 7.24 (dt, J = 7.8, 1.0 Hz, 1 H), 4.36-4.18 (m, 2 H), 4.18-3.95 (m, 2 H), 2.40 (q, J = 7.6 Hz, 2 H), 1.10 (td, J = 7.3, 1.6 Hz, 3 H) | $^{19}$F NMR (376 MHz, DMSO-d$_6$) δ −56.96 |
| FB30 | White solid | | ESIMS m/z 595 ([M + H]$^+$) | $^1$H NMR (400 MHz, DMSO-d$_6$) δ 9.40 (s, 1 H), 8.25 (t, J = 6.3 Hz, 1 H), 8.15-8.02 (m, 2 H), 8.01-7.94 (m, 2 H), 7.63 (ddd, J = 7.9, 2.1, 1.0 Hz, 2 H), 7.49-7.42 (m, 1 H), 7.37-7.27 (m, 2 H), 7.26-7.15 (m, 2 H), 4.26 (d, J = 6.3 Hz, 2 H), 4.18 (d, J = 1.2 Hz, 2 H), 2.37 (q, J = 7.5 Hz, 2 H), 2.06 (s, 3 H), 1.12-1.07 (m, 3 H) | $^{19}$F NMR (376 MHz, DMSO-d$_6$) δ −56.96 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| FB31 | Light yellow solid | | ESIMS m/z 595 ([M + H]$^+$) | $^1$H NMR (400 MHz, DMSO-d$_6$) δ 9.40 (s, 1 H), 8.22 (t, J = 6.3 Hz, 1 H), 8.13-8.02 (m, 2 H), 8.00-7.92 (m, 2 H), 7.70-7.57 (m, 2 H), 7.53-7.39 (m, 3 H), 7.37-7.26 (m, 2 H), 7.21 (dd, J = 7.8, 1.4 Hz, 1 H), 4.35-4.19 (m, 2 H), 4.18-3.96 (m, 2 H), 2.68 (h, J = 7.0 Hz, 1 H), 1.13-1.04 (m, 6 H) | $^{19}$F NMR (376 MHz, DMSO-d$_6$) δ −56.97 |
| FB32 | Light orange solid | | ESIMS m/z 609 ([M + H]$^+$) | $^1$H NMR (400 MHz, DMSO-d$_6$) δ 9.40 (s, 1 H), 8.21 (t, J = 6.3 Hz, 1 H), 8.11-8.02 (m, 2 H), 8.01-7.91 (m, 2 H), 7.67-7.59 (m, 2 H), 7.44 (td, J = 7.5, 0.9 Hz, 1 H), 7.31 (dt, J = 7.7, 1.4 Hz, 1 H), 7.29-7.24 (m, 1 H), 7.16-7.02 (m, 2 H), 4.35-4.18 (m, 2 H), 4.18-3.93 (m, 2 H), 2.63 (p, J = 6.8 Hz, 1 H), 2.34 (s, 3 H), 1.12-1.02 (m, 6 H) | $^{19}$F NMR (376 MHz, DMSO-d$_6$) δ −56.97 |
| FB33 | Off-white solid | | ESIMS m/z 613 ([M + H]$^+$) | $^1$H NMR (400 MHz, DMSO-d$_6$) δ 9.40 (s, 1 H), 8.22 (t, J = 6.3 Hz, 1 H), 8.12-8.02 (m, 2 H), 7.96 (dd, J = 7.4, 1.4 Hz, 2 H), 7.69-7.59 (m, 2 H), 7.44 (td, J = 7.4, 1.0 Hz, 1 H), 7.37-7.28 (m, 3 H), 7.15 (td, J = 8.4, 2.9 Hz, 1 H), 4.37-4.19 (m, 2 H), 4.19-3.93 (m, 2 H), 2.67 (tt, J = 7.4, 5.7 Hz, 1 H), 1.16-1.03 (m, 6 H) | $^{19}$F NMR (376 MHz, DMSO-d$_6$) δ −56.96, −112.09 |
| FB34 | Off-white solid | | ESIMS m/z 609 ([M + H]$^+$) | $^1$H NMR (400 MHz, DMSO-d$_6$) δ 9.40 (s, 1 H), 8.24 (t, J = 6.3 Hz, 1 H), 8.13-8.03 (m, 2 H), 7.96 (dt, J = 9.2, 1.5 Hz, 2 H), 7.69-7.58 (m, 2 H), 7.44 (t, J = 7.6 Hz, 1 H), 7.40-7.27 (m, 2 H), 7.28-7.20 (m, 1 H), 7.01 (dd, J = 1.7, 0.9 Hz, 1 H), 4.35-4.19 (m, 2 H), 4.18-3.94 (m, 2 H), 2.63 (p, J = 6.8 Hz, 1 H), 2.28 (s, 3 H), 1.12-1.03 (m, 6 H) | $^{19}$F NMR (376 MHz, DMSO-d$_6$) δ −56.98 |
| FB35 | Light yellow solid | | ESIMS m/z 629 ([M + H]$^+$) | $^1$H NMR (400 MHz, DMSO-d$_6$) δ 9.40 (s, 1 H), 8.27 (t, J = 6.3 Hz, 1 H), 8.11-8.03 (m, 2 H), 8.01-7.92 (m, 2 H), 7.69-7.58 (m, 2 H), 7.57-7.47 (m, 2 H), 7.47-7.39 (m, 2 H), 7.32 | $^{19}$F NMR (376 MHz, DMSO-d$_6$) δ −56.97 |

TABLE 3c-continued

Analytical Data for Compounds in Table 2c.

| No. | Appearance | Mp (° C.) | ESIMS m/z | ¹H NMR (δ)$^a$ | ¹³C NMR or ¹⁹F NMR (δ) |
|---|---|---|---|---|---|
| | | | | (dt, J = 7.7, 1.5 Hz, 1 H), 4.41-4.20 (m, 2 H), 4.19-3.88 (m, 2 H), 2.69 (p, J = 6.8 Hz, 1 H), 1.17-1.05(m, 6 H) | |
| FB36 | White solid | | ESIMS m/z 599 ([M + H]⁺) | ¹H NMR (400 MHz, DMSO-d₆) δ 11.80 (s, 1 H), 9.96 (s, 1 H), 9.39 (s, 1 H), 8.13-8.04 (m, 2 H), 7.98 (t, J = 1.6 Hz, 1 H), 7.94 (dt, J = 7.7, 1.4 Hz, 1 H), 7.62 (dq, J = 9.1, 1.0 Hz, 2 H), 7.44 (t, J = 7.6 Hz, 1 H), 7.40-7.31 (m, 2 H), 7.01 (t, J = 5.6 Hz, 1 H), 6.82 (d, J = 2.9 Hz, 1 H), 6.75 (dd, J = 8.7, 2.9 Hz, 1 H), 3.74 (s, 3 H), 3.18 (q, J = 6.4 Hz, 2 H), 2.72 (t, J = 7.6 Hz, 2 H), 2.14 (s, 3 H), 1.65 (q, J = 7.6 Hz, 2 H), 1.52 (p, J = 6.9 Hz, 2 H) | ¹⁹F NMR (376 MHz, DMSO-d₆) δ −56.96 |
| FB37 | White solid | | ESIMS m/z 631 ([M + H]⁺) | ¹H NMR (400 MHz, DMSO-d₆) δ 12.08 (s, 1 H), 10.15 (s, 1 H), 9.41 (s, 1 H), 8.13-8.07 (m, 2 H), 8.00 (t, J = 1.7 Hz, 1 H), 7.96 (dt, J = 7.7, 1.4 Hz, 1 H), 7.64 (dq, J = 7.9, 1.0 Hz, 2 H), 7.59 (d, J = 2.2 Hz, 1 H), 7.46 (t, J = 7.6 Hz, 1 H), 7.41-7.30 (m, 3 H), 7.05 (t, J = 5.7 Hz, 1 H), 3.21 (q, J = 6.5 Hz, 2 H), 2.98 (p, J = 6.8 Hz, 1 H), 2.74 (t, J = 7.6 Hz, 2 H), 1.68 (q, J = 7.6 Hz, 2 H), 1.54 (p, J = 6.9 Hz, 2 H), 1.15 (d, J = 6.8 Hz, 6 H) | ¹⁹F NMR (376 MHz, DMSO-d₆) δ −56.96 |
| FB38 | White solid | | ESIMS m/z 639 ([M + H]⁺) | ¹H NMR (400 MHz, DMSO-d₆) δ 9.40 (s, 1 H), 8.13-8.04 (m, 2 H), 7.92 (dt, J = 6.6, 1.5 Hz, 2 H), 7.63 (dp, J = 7.9, 1.0 Hz, 2 H), 7.56 (t, J = 5.9 Hz, 1 H), 7.46-7.37 (m, 1 H), 7.30 (dt, J = 7.7, 1.5 Hz, 1 H), 7.11 (d, J = 8.6 Hz, 1 H), 6.89 (dd, J = 2.9, 0.8 Hz, 1 H), 6.83 (ddd, J = 8.7, 2.9, 0.7 Hz, 1 H), 4.11-3.90 (m, 2 H), 3.76 (s, 3 H), 3.03 (dh, J = 19.9, 6.5 Hz, 2 H), 2.65 (t, J = 7.6 Hz, 2 H), 2.02 (s, 3 H), 1.64-1.50 (m, 2 H), 1.50-1.37 (m, 2 H) | ¹⁹F NMR (376 MHz, DMSO-d₆) δ −56.96 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| FB39 | White solid | | ESIMS m/z 671 ([M + H]$^+$) | $^1$H NMR (400 MHz, DMSO-d$_6$) δ 9.40 (s, 1 H), 8.13-8.04 (m, 2 H), 7.92 (ddt, J = 3.8, 2.9, 1.4 Hz, 2 H), 7.67-7.57 (m, 3 H), 7.53-7.45 (m, 2 H), 7.45-7.37 (m, 2 H), 7.28 (dt, J = 7.7, 1.5 Hz, 1 H), 4.14-3.87 (m, 2 H), 3.04 (qd, J = 6.9, 2.9 Hz, 2 H), 2.73-2.56 (m, 3 H), 1.55 (dq, J = 8.9, 7.2 Hz, 2 H), 1.49-1.37 (m, 2 H), 1.11-1.02 (m, 6 H) | $^{19}$F NMR (376 MHz, DMSO-d$_6$) δ −56.97 |
| FB40 | Brown glassy foam | | ESIMS m/z 671 ([M + H]$^+$) | $^1$H NMR (400 MHz, CDCl$_3$) δ 8.54 (s, 1 H), 8.12-8.03 (m, 2 H), 7.84-7.74 (m, 2 H), 7.39 (ddt, J = 6.9, 2.8, 1.7 Hz, 3 H), 7.34 (d, J = 8.5 Hz, 1 H), 7.27 (s, 2 H), 7.05 (d, J = 2.1 Hz, 1 H), 5.47 (t, J = 6.1 Hz, 1 H), 3.92 (d, J = 1.5 Hz, 2 H), 3.53 (dp, J = 26.7, 6.7 Hz, 2 H), 2.88 (t, J = 6.6 Hz, 2 H), 2.64 (p, J = 6.9 Hz, 1 H), 1.14 (dd, J = 8.8, 6.9 Hz, 6 H) | $^{19}$F NMR (376 MHz, CDCl$_3$) δ −58.02 |
| FB41 | Yellow oil | | ESIMS m/z 637 ([M + H]$^+$) | $^1$H NMR (400 MHz, CDCl$_3$) δ 8.56 (s, 1 H), 8.08 (d, J = 8.2 Hz, 2 H), 7.82-7.79 (m, 3 H), 7.39 (dt, J = 8.1, 1.0 Hz, 3 H), 7.24 (d, J = 3.7 Hz, 2 H), 7.16 (dd, J = 8.0, 1.8 Hz, 1 H), 6.76 (dd, J = 1.8, 0.9 Hz, 1 H), 5.18 (t, J = 6.2 Hz, 1 H), 3.46 (ddt, J = 36.9, 13.6, 6.7 Hz, 2 H), 3.19-3.10 (m, 3 H), 3.04-2.89 (m, 1 H), 2.85 (t, J = 7.0 Hz, 2 H), 2.62 (p, J = 7.0 Hz, 1 H), 2.30 (t, J = 0.7 Hz, 3 H), 1.12 (dd, J = 6.9, 4.6 Hz, 6 H) | $^{19}$F NMR (376 MHz, CDCl$_3$) δ −58.03 |
| FB42 | Brown oil | | ESIMS m/z 658 ([M + H]$^+$) | $^1$H NMR (400 MHz, CDCl$_3$) δ 8.56 (s, 1 H), 8.08 (dd, J = 15.7, 8.2 Hz, 2 H), 7.80 (d, J = 9.0 Hz, 2 H), 7.44-7.34 (m, 4 H), 7.29 (d, J = 8.2 Hz, 1 H), 7.26-7.21 (m, 1 H), 7.08 (dd, J = 13.8, 2.1 Hz, 1 H), 5.34 (dd, J = 15.4, 8.5 Hz, 1 H), 3.96-3.84 (m, 2 H), 3.01 (dd, J = 13.4, 5.6 Hz, 1 H), 2.87 (dd, J = 13.5, 5.8 | $^{19}$F NMR (376 MHz, CDCl$_3$) δ −58.03 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | Hz, 1 H), 2.77 (dd, J = 13.5, 7.0 Hz, 1 H), 2.71-2.57 (m, 1 H), 1.20-1.06 (m, 9 H) | |
| FB43 | Peach glassy foam | | ESIMS m/z 431 ([M + H]$^+$) | $^1$H NMR (400 MHz, CDCl$_3$) δ 8.56 (s, 1 H), 8.20-8.10 (m, 2 H), 7.84-7.74 (m, 2 H), 7.39 (dt, J = 8.0, 1.0 Hz, 2 H), 7.36-7.29 (m, 2 H), 3.68 (tdd, J = 8.3, 5.3, 4.4 Hz, 1 H), 2.98-2.77 (m, 2 H), 1.76-1.64 (m, 1 H), 1.61-1.51 (m, 1 H), 1.05 (t, J = 7.4 Hz, 3 H) | $^{19}$F NMR (376 MHz, CDCl$_3$) δ −58.03 |
| FB44 | Tan glassy foam | 90 (dec.) | ESIMS m/z 672 ([M + H]$^+$) | $^1$H NMR (400 MHz, CDCl$_3$) δ 8.56 (s, 1 H), 8.07 (dd, J = 18.4, 8.2 Hz, 2 H), 7.84-7.75 (m, 2 H), 7.43-7.34 (m, 4 H), 7.31-7.27 (m, 1 H), 7.25-7.19 (m, 1 H), 7.08 (dd, J = 12.4, 2.1 Hz, 1 H), 5.26 (t, J = 9.2 Hz, 1 H), 4.02-3.93 (m, 1 H), 3.91 (dd, J = 3.7, 1.1 Hz, 2 H), 2.96-2.73 (m, 2 H), 2.63 (h, J = 6.8 Hz, 1 H), 1.42-1.28 (m, 2 H), 1.20-1.09 (m, 6 H), 0.90 (dt, J = 24.3, 7.4 Hz, 3 H) | $^{19}$F NMR (376 MHz, CDCl$_3$) δ −58.02 |
| FB45 | Yellow oil | | ESIMS m/z 637 ([M + H]$^+$) | $^1$H NMR (400 MHz, CDCl$_3$) δ 8.55 (d, J = 0.8 Hz, 1 H), 8.11-8.02 (m, 2 H), 7.84-7.75 (m, 2 H), 7.43-7.35 (m, 2 H), 7.33 (dd, J = 8.2, 1.1 Hz, 1 H), 7.30-7.21 (m, 3 H), 6.87 (ddd, J = 12.7, 1.8, 0.9 Hz, 1 H), 5.39 (dd, J = 16.1, 8.5 Hz, 1 H), 4.20-4.11 (m, 1 H), 3.91 (dd, J = 2.5, 1.8 Hz, 2 H), 3.02-2.85 (m, 1 H), 2.81-2.58 (m, 2 H), 2.35 (d, J = 7.6 Hz, 3 H), 1.15 (ddd, J = 6.9, 4.3, 1.5 Hz, 6 H), 1.09 (t, J = 6.6 Hz, 3 H) | $^{19}$F NMR (376 MHz, CDCl$_3$) δ −58.02 |
| FB46 | Off-white foam | | ESIMS m/z 637 ([M + H]$^+$) | $^1$H NMR (400 MHz, CDCl$_3$) δ 8.55 (d, J = 0.6 Hz, 1 H), 8.13-8.02 (m, 2 H), 7.84-7.75 (m, 2 H), 7.43-7.36 (m, 2 H), 7.36-7.31 (m, 1 H), 7.30-7.21 (m, 3 H), 6.90-6.84 (m, 1 H), 5.37 (dd, J = 15.4, 8.4 Hz, 1 H), 4.20-4.11 (m, 1 H), 3.98-3.84 (m, 2 H), 2.94 (ddd, J = 51.6, 13.4, 5.5 Hz, 1 H), 2.76 (dd, J = | $^{19}$F NMR (376 MHz, CDCl$_3$) δ −58.02 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 13.5, 7.1 Hz, 1 H), 2.70-2.58 (m, 1 H), 2.35 (d, J = 7.9 Hz, 3 H), 1.17-1.14 (m, 6 H), 1.09 (t, J = 6.8 Hz, 3 H) | |
| FB47 | Brown oil | | ESIMS m/z 637 ([M + H]$^+$) | $^1$H NMR (400 MHz, CDCl$_3$) δ 8.56 (d, J = 0.8 Hz, 1 H), 8.07 (dd, J = 11.2, 8.2 Hz, 2 H), 7.85-7.77 (m, 2 H), 7.43-7.36 (m, 2 H), 7.34 (d, J = 8.8 Hz, 1 H), 7.31-7.27 (m, 1 H), 7.26-7.21 (m, 1 H), 7.02 (dt, J = 8.8, 3.1 Hz, 1 H), 6.58 (dd, J = 11.5, 2.7 Hz, 1 H), 5.37 (dd, J = 14.6, 8.5 Hz, 1 H), 4.12 (m, 2 H), 3.96-3.88 (m, 2 H), 3.79 (d, J = 5.1 Hz, 2 H), 3.05-2.55 (m, 3 H), 1.18-1.10 (m, 9 H) | $^{19}$F NMR (376 MHz, CDCl$_3$) δ −58.03 |
| FB48 | Brown oil | | ESIMS m/z 637 ([M + H]$^+$) | $^1$H NMR (400 MHz, CDCl$_3$) δ 8.56 (d, J = 0.9 Hz, 1 H), 8.07 (dd, J = 10.2, 8.2 Hz, 2 H), 7.84-7.77 (m, 2 H), 7.43-7.36 (m, 2 H), 7.28 (dd, J = 7.4, 1.4 Hz, 1 H), 7.26-7.22 (m, 2 H), 7.17-7.07 (m, 1 H), 6.94 (dd, J = 11.5, 8.0 Hz, 1 H), 5.36 (dd, J = 14.4, 8.4 Hz, 1 H), 4.22-4.10 (m, 1 H), 3.91 (t, J = 1.8 Hz, 2 H), 3.05-2.60 (m, 3 H), 2.40 (d, J = 2.5 Hz, 3 H), 1.21-1.05 (m, 9 H) | $^{19}$F NMR (376 MHz, CDCl$_3$) δ −58.03 |
| FB49 | Brown oil | | ESIMS m/z 658 ([M + H]$^+$) | $^1$H NMR (400 MHz, CDCl$_3$) δ 8.56 (s, 1 H), 8.09 (ddd, J = 9.2, 5.5, 3.8 Hz, 2 H), 7.80 (d, J = 9.0 Hz, 2 H), 7.38 (ddt, J = 8.7, 6.8, 2.6 Hz, 3 H), 7.32 (dd, J = 8.5, 4.3 Hz, 1 H), 7.29 (d, J = 7.7 Hz, 2 H), 7.03 (dd, J = 6.6, 2.1 Hz, 1 H), 5.39 (s, 1 H), 3.91 (d, J = 2.1 Hz, 2 H), 3.65-3.22 (m, 2 H), 3.02 (d, J = 10.0 Hz, 1 H), 2.62 (tt, J = 14.6, 7.6 Hz, 1 H), 1.32-1.27 (m, 3 H), 1.20-1.04 (m, 6 H) | $^{19}$F NMR (376 MHz, CDCl$_3$) δ −58.03 |
| FB50 | Clear oil | | ESIMS m/z 628 ([M + H]$^+$) | $^1$H NMR (400 MHz, CDCl$_3$) δ 8.68-8.61 (m, 1 H), 8.15-8.04 (m, 2 H), 7.95-7.85 (m, 2 H), 7.85-7.77 (m, 2 H), 7.45-7.37 (m, 1 H), 7.35 (d, J = 8.5 Hz, 1 H), 7.31-7.27 (m, 2 H), | $^{19}$F NMR (376 MHz, CDCl$_3$) δ −62.49 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 7.06 (d, J = 2.1 Hz, 1 H), 5.52 (t, J = 6.2 Hz, 1 H), 3.93 (d, J = 1.6 Hz, 2 H), 3.53 (ddt, J = 25.1, 13.6, 6.7 Hz, 2 H), 2.88 (t, J = 6.9 Hz, 2 H), 2.71-2.57 (m, 1 H), 1.20-1.07 (m, 6 H) | |
| FB51 | Pale orange foam | 99 (dec.) | ESIMS m/z 637 ([M + H]$^+$) | $^1$H NMR (400 MHz, CDCl$_3$) δ 8.56 (d, J = 8.0 Hz, 1 H), 8.00 (d, J = 8.1 Hz, 2 H), 7.82 (d, J = 8.9 Hz, 2 H), 7.46-7.36 (m, 3 H), 7.31 (dd, J = 8.2, 6.4 Hz, 1 H), 6.93 (d, J = 1.1 Hz, 1 H), 6.75 (d, J = 8.2 Hz, 2 H), 3.93 (d, J = 5.1 Hz, 2 H), 3.63-3.34 (m, 1 H), 3.20 (ddd, J = 13.5, 9.2, 6.6 Hz, 1 H), 2.99 (s, 3 H), 2.77-2.68 (m, 1 H), 2.63-2.51 (m, 2 H), 2.35 (d, J = 0.7 Hz, 3 H), 1.21-1.12 (m, 6 H) | $^{19}$F NMR (376 MHz, CDCl$_3$) δ −58.02 |
| FB52 | Brown oil | | ESIMS m/z 651 ([M + H]$^+$) | $^1$H NMR (400 MHz, CDCl$_3$) δ 8.56 (d, J = 4.5 Hz, 1 H), 8.12-8.02 (m, 2 H), 7.83-7.75 (m, 2 H), 7.43-7.35 (m, 2 H), 7.30 (d, J = 8.1 Hz, 2 H), 7.20 (d, J = 8.1 Hz, 2 H), 6.87 (d, J = 1.3 Hz, 1 H), 5.21 (s, 1 H), 3.95 (d, J = 2.6 Hz, 2 H), 3.28-2.96 (m, 2 H), 2.66 (p, J = 6.8 Hz, 1 H), 2.32 (s, 3 H), 1.25 (d, J = 5.1 Hz, 6 H), 1.14 (ddd, J = 10.9, 6.9, 4.7 Hz, 6 H) | $^{19}$F NMR (376 MHz, CDCl$_3$) δ −58.03 |
| FB53 | Brown glassy foam | | ESIMS m/z 651 ([M + H]$^+$) | $^1$H NMR (400 MHz, CDCl$_3$) δ 8.56 (s, 1 H), 8.09 (d, J = 8.4 Hz, 2 H), 7.80 (d, J = 9.0 Hz, 2 H), 7.44-7.35 (m, 4 H), 7.28 (d, J = 8.1 Hz, 1 H), 7.24-7.19 (m, 1 H), 6.86-6.77 (m, 1 H), 5.27 (s, 1 H), 3.89 (d, J = 0.9 Hz, 2 H), 3.56 (dd, J = 13.7, 7.2 Hz, 1 H), 3.41 (dd, J = 13.7, 5.9 Hz, 1 H), 2.59 (p, J = 6.9 Hz, 1 H), 2.31 (d, J = 0.7 Hz, 3 H), 1.35 (d, J = 2.5 Hz, 6 H), 1.11 (dd, J = 11.5, 6.9 Hz, 6 H) | $^{19}$F NMR (376 MHz, CDCl$_3$) δ −58.03 |
| FB54 | Red solid | 95 (dec.) | ESIMS m/z 651 ([M + H]$^+$) | $^1$H NMR (400 MHz, CDCl$_3$) δ 8.56 (d, J = 8.6 Hz, 1 H), 8.04 (dd, J = 40.0, 8.1 Hz, 2 H), 7.85-7.76 (m, 2 H), 7.44-7.35 (m, 3 H), 7.35-7.28 | $^{19}$F NMR (376 MHz, CDCl$_3$) δ −58.02 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | (m, 1 H), 7.25-7.19 (m, 1 H), 6.98-6.84 (m, 1 H), 6.70 (d, J = 8.2 Hz, 1 H), 3.93 (dd, J = 5.9, 4.2 Hz, 2 H), 3.61-2.45 (m, 7 H), 2.40-2.25 (m, 3 H), 1.32-1.07 (m, 9 H) | |
| FB55 | Yellow oil | | ESIMS m/z 609 ([M + H]$^+$) | $^1$H NMR (400 MHz, CDCl$_3$) δ 8.55 (d, J = 0.7 Hz, 1 H), 8.15-8.04 (m, 2 H), 7.84-7.74 (m, 2 H), 7.38 (d, J = 8.6 Hz, 2 H), 7.28 (d, J = 2.3 Hz, 1 H), 7.25-7.01 (m, 3 H), 6.91-6.78 (m, 1 H), 5.28-5.13 (m, 1 H), 4.25-3.89 (m, 1 H), 3.62-3.28 (m, 2 H), 3.04-2.73 (m, 3 H), 2.70-2.37 (m, 3 H), 2.32 (d, J = 7.6 Hz, 3 H), 1.29-1.13 (m, 6 H) | $^{19}$F NMR (376 MHz, CDCl$_3$) δ −58.03 |
| FB56 | Yellow oil | | ESIMS m/z 609 ([M + H]$^+$) | $^1$H NMR (400 MHz, CDCl$_3$) δ 8.59-8.47 (m, 1 H), 8.13-8.01 (m, 2 H), 7.80 (dd, J = 9.8, 3.0 Hz, 2 H), 7.46-7.34 (m, 3 H), 7.28 (d, J = 1.7 Hz, 2 H), 7.13 (s, 1 H), 7.08-6.99 (m, 1 H), 6.92 (dd, J = 16.0, 8.0 Hz, 1 H), 5.18 (d, J = 6.4 Hz, 1 H), 4.26-3.92 (m, 1 H), 3.59-3.27 (m, 2 H), 3.02-2.76 (m, 3 H), 2.62-2.38 (m, 2 H), 2.37-2.26 (m, 3 H), 1.37-1.08 (m, 6 H) | $^{19}$F NMR (376 MHz, CDCl$_3$) δ −58.03 |
| FB57 | Yellow oil | | ESIMS m/z 627 ([M + H]$^+$) | $^1$H NMR (400 MHz, CDCl$_3$) δ 8.57-8.52 (m, 1 H), 8.14-8.02 (m, 2 H), 7.84-7.75 (m, 2 H), 7.44-7.34 (m, 2 H), 7.27-7.22 (m, 2 H), 7.15-6.78 (m, 4 H), 5.13 (d, J = 19.1 Hz, 1 H), 4.41-4.16 (m, 1 H), 3.62-3.28 (m, 2 H), 3.20-2.73 (m, 4 H), 1.32-1.10 (m, 9 H) | $^{19}$F NMR (376 MHz, CDCl$_3$) δ −58.03, −112.99 |
| FB58 | Yellow oil | | ESIMS m/z 611 ([M + H]$^+$) | $^1$H NMR (400 MHz, CDCl$_3$) δ 8.58-8.48 (m, 1 H), 8.16-8.00 (m, 2 H), 7.87-7.67 (m, 2 H), 7.43-7.17 (m, 6 H), 7.08-6.90 (m, 1 H), 6.83-6.69 (m, 1 H), 5.21 (s, 1 H), 4.25-3.92 (m, 1 H), 3.77 (d, J = 14.8 Hz, 3 H), 3.64-3.27 (m, 2 H), 3.06-2.75 (m, 3 H), 2.24-2.10 (m, 3 H), 1.28-1.11 (m, 3 H) | $^{19}$F NMR (376 MHz, CDCl$_3$) δ −58.03 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| FB59 | Clear oil | | ESIMS m/z 595 ([M + H]$^+$) | $^1$H NMR (400 MHz, CDCl$_3$) δ 8.55 (dd, J = 4.6, 1.1 Hz, 1 H), 8.12-8.04 (m, 2 H), 7.87-7.70 (m, 2 H), 7.46-7.34 (m, 3 H), 7.28 (d, J = 7.9 Hz, 2 H), 7.22-7.02 (m, 3 H), 5.20 (t, J = 6.1 Hz, 1 H), 4.22-4.11 (m, 1 H), 3.55-3.31 (m, 3 H), 2.95 (dd, J = 11.0, 8.4 Hz, 1 H), 2.87-2.80 (m, 1 H), 2.18 (d, J = 12.6 Hz, 6 H), 1.16 (d, J = 6.3 Hz, 3 H) | $^{19}$F NMR (376 MHz, CDCl$_3$) δ −58.03 |
| FB60 | Yellow foam | | ESIMS m/z 623 ([M + H]$^+$) | $^1$H NMR (400 MHz, CDCl$_3$) δ 8.58-8.53 (m, 1 H), 8.13-8.01 (m, 2 H), 7.84-7.75 (m, 2 H), 7.39 (dd, J = 9.1, 3.2 Hz, 2 H), 7.28-7.23 (m, 3 H), 7.18-7.12 (m, 1 H), 7.02 (dt, J = 8.1, 2.2 Hz, 1 H), 6.89 (dd, J = 14.0, 8.0 Hz, 1 H), 5.24-5.08 (m, 1 H), 4.24-3.91 (m, 1 H), 3.63-3.29 (m, 3 H), 3.04-2.74 (m, 3 H), 2.35 (d, J = 4.0 Hz, 3 H), 1.34-1.06 (m, 9 H) | $^{19}$F NMR (376 MHz, CDCl$_3$) δ −58.03 |
| FB61 | Brown oil | | ESIMS m/z 663 ([M + H]$^+$) | $^1$H NMR (400 MHz, CDCl$_3$) δ 8.56 (d, J = 7.7 Hz, 1 H), 8.11-7.95 (m, 2 H), 7.85-7.75 (m, 2 H), 7.40 (td, J = 4.3, 1.2 Hz, 3 H), 7.32-7.21 (m, 2 H), 6.98-6.82 (m, 1 H), 6.73-6.65 (m, 1 H), 5.87-5.38 (m, 1 H), 5.15 (ddd, J = 13.8, 3.7, 1.6 Hz, 1 H), 4.99-4.67 (m, 1 H), 4.03-3.96 (m, 1 H), 3.94 (d, J = 5.4 Hz, 2 H), 3.64-3.47 (m, 1 H), 3.36-3.12 (m, 2 H), 2.98-2.63 (m, 2 H), 2.59-2.51 (m, 1 H), 2.38-2.29 (m, 3 H), 1.22-1.09 (m, 6 H) | $^{19}$F NMR (376 MHz, CDCl$_3$) δ −58.02 |
| FB62 | Red-orange oil | | ESIMS m/z 677 ([M + H]$^+$) | $^1$H NMR (400 MHz, CDCl$_3$) δ 8.56 (d, J = 8.5 Hz, 1 H), 8.13-7.94 (m, 2 H), 7.85-7.75 (m, 2 H), 7.44-7.22 (m, 5 H), 6.97-6.80 (m, 1 H), 6.71-6.63 (m, 1 H), 3.94 (dd, J = 6.0, 4.4 Hz, 2 H), 3.78-3.47 (m, 1 H), 3.42-3.17 (m, 3 H), 3.03-2.87 (m, 1 H), 2.81-2.55 (m, 2 H), 2.33 (t, J = 1.1 Hz, 3 H), 1.22-1.08 (m, 6 H), 1.09-0.94 (m, 1 H), 0.62- | $^{19}$F NMR (376 MHz, CDCl$_3$) δ −58.02 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 0.44 (m, 2 H), 0.31-0.17 (m, 2 H) | |
| FB63 | Red oil | | ESIMS m/z 649 ([M + H]$^+$) | $^1$H NMR (400 MHz, CDCl$_3$) δ 8.56 (d, J = 2.1 Hz, 1 H), 8.19-8.00 (m, 2 H), 7.83-7.75 (m, 2 H), 7.44-7.34 (m, 3 H), 7.28 (s, 1 H), 7.26-7.16 (m, 2 H), 6.89 (s, 1 H), 5.63 (s, 1 H), 3.93 (d, J = 2.5 Hz, 2 H), 3.19 (d, J = 13.9 Hz, 1 H), 2.75 (d, J = 13.9 Hz, 1 H), 2.61 (dd, J = 13.8, 7.0 Hz, 1 H), 2.30 (s, 3 H), 1.13 (dd, J = 13.3, 6.8 Hz, 6 H), 0.97-0.64 (m, 4 H) | $^{19}$F NMR (376 MHz, CDCl$_3$) δ −58.03 |
| FB64 | Yellow oil | | ESIMS m/z 641 ([M + H]$^+$) | $^1$H NMR (400 MHz, CDCl$_3$) δ 8.56 (s, 1 H), 8.13-8.05 (m, 2 H), 7.85-7.74 (m, 2 H), 7.44-7.35 (m, 2 H), 7.32 (dd, J = 8.1, 4.9 Hz, 1 H), 7.29-7.25 (m, 3 H), 6.92-6.81 (m, 1 H), 6.31 (dd, J = 55.6, 11.8 Hz, 1 H), 5.62 (s, 1 H), 3.54 (ddt, J = 32.1, 13.7, 6.7 Hz, 2 H), 2.88 (t, J = 7.0 Hz, 2 H), 2.73-2.48 (m, 1 H), 2.37-2.30 (m, 3 H), 1.15 (ddd, J = 9.6, 6.8, 2.8 Hz, 6 H) | $^{19}$F NMR (376 MHz, CDCl$_3$) δ −58.03, −159.92, −160.90 |
| FB65 | Clear oil | | ESIMS m/z 597 ([M + H]$^+$) | $^1$H NMR (400 MHz, CDCl$_3$) δ 8.56 (d, J = 7.8 Hz, 1 H), 8.21-8.01 (m, 2 H), 7.80 (dd, J = 10.0, 3.1 Hz, 2 H), 7.46-7.35 (m, 3 H), 7.30 (d, J = 8.1 Hz, 1 H), 7.22 (d, J = 7.9 Hz, 1 H), 7.13 (d, J = 8.0 Hz, 1 H), 7.05 (s, 1 H), 5.40 (d, J = 6.2 Hz, 1 H), 3.59 (p, J = 7.1 Hz, 2 H), 3.14 (dt, J = 13.5, 6.7 Hz, 1 H), 2.95 (q, J = 6.3, 5.5 Hz, 2 H), 2.46-2.22 (m, 6 H), 1.16 (dd, J = 35.5, 6.9 Hz, 6 H) | |
| FB66 | Clear oil | | ESIMS m/z 611 ([M + H]$^+$) | $^1$H NMR (400 MHz, CDCl$_3$) δ 11.53 (s, 1 H), 8.64-8.52 (m, 1 H), 8.24-7.97 (m, 2 H), 7.86-7.73 (m, 4 H), 7.49-7.18 (m, 4 H), 7.17-6.97 (m, 1 H), 5.40 (t, J = 6.1 Hz, 1 H), 3.71-3.46 (m, 2 H), 3.28-2.78 (m, 5 H), 2.29 (d, J = 18.6 | $^{19}$F NMR (376 MHz, CDCl$_3$) δ −58.02 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | Hz, 3 H), 2.17 (d, J = 2.5 Hz, 3 H), 1.42-1.12 (m, 6 H) | |
| FB67 | Clear oil | | ESIMS m/z 639 ([M + H]$^+$) | $^1$H NMR (400 MHz, CDCl$_3$) δ 10.16 (t, J = 5.6 Hz, 1 H), 8.55 (d, J = 2.6 Hz, 1 H), 8.06 (dd, J = 8.3, 2.0 Hz, 2 H), 7.85-7.74 (m, 2 H), 7.39 (dq, J = 8.0, 1.1 Hz, 2 H), 7.30 (d, J = 8.2 Hz, 2 H), 7.13 (d, J = 7.8 Hz, 1 H), 6.65-6.55 (m, 1 H), 5.21 (t, J = 6.1 Hz, 1 H), 3.59 (tt, J = 12.6, 6.7 Hz, 2 H), 3.32-2.99 (m, 2 H), 2.99-2.76 (m, 3 H), 2.27 (d, J = 0.8 Hz, 2 H), 2.17 (s, 3 H), 1.88-1.84 (m, 2 H), 1.11 (dd, J = 6.9, 3.2 Hz, 6 H) | |
| FB68 | Pale yellow foam | | ESIMS m/z 651 ([M + H]$^+$) | $^1$H NMR (400 MHz, CDCl$_3$) δ 8.55 (s, 1 H), 8.08 (d, J = 8.2 Hz, 1 H), 7.83-7.76 (m, 3 H), 7.44-7.38 (m, 2 H), 7.33-7.20 (m, 3 H), 6.85 (dd, J = 1.9, 0.9 Hz, 1 H), 5.54 (t, J = 6.2 Hz, 1 H), 3.51 (ddt, J = 35.0, 13.7, 6.7 Hz, 2 H), 2.86 (t, J = 7.1 Hz, 2 H), 2.64 (hept, J = 6.9 Hz, 1 H), 2.33 (s, 3 H), 1.73 (d, J = 2.3 Hz, 6 H), 1.14 (dd, J = 11.2, 6.8 Hz, 6 H) | $^{19}$F NMR (376 MHz, CDCl$_3$) δ −58.03 |
| FB69 | White foam | | ESIMS m/z 649 ([M + H]$^+$) | $^1$H NMR (400 MHz, CDCl$_3$) δ 8.55 (s, 1 H), 8.13-8.02 (m, 2 H), 7.84-7.73 (m, 2 H), 7.42-7.35 (m, 2 H), 7.33-7.20 (m, 4 H), 6.89 (dd, J = 1.9, 0.9 Hz, 1 H), 5.57 (t, J = 6.2 Hz, 1 H), 3.68-3.34 (m, 2 H), 2.86 (t, J = 7.1 Hz, 2 H), 2.67 (hept, J = 6.9 Hz, 1 H), 2.32 (s, 3 H), 1.77 (q, J = 4.4 Hz, 2 H), 1.50-1.39 (m, 2 H), 1.15 (dd, J = 10.5, 6.8 Hz, 6 H) | $^{19}$F NMR (376 MHz, CDCl$_3$) δ −58.02 |
| FB70 | Clear colorless oil | | ESIMS m/z 701 ([M + H]$^+$) | $^1$H NMR (400 MHz, CDCl$_3$) δ 8.55 (s, 1 H), 8.13-8.01 (m, 2 H), 7.88-7.71 (m, 2 H), 7.45-7.35 (m, 2 H), 7.32 (d, J = 8.1 Hz, 1 H), 7.29-7.22 (m, 3 H), 6.87 (dd, J = 1.9, 0.9 Hz, 1 H), 5.65 (t, J = 6.2 Hz, 1 H), 3.69-3.37 | $^{19}$F NMR (376 MHz, CDCl$_3$) δ −58.03 |

TABLE 3c-continued

Analytical Data for Compounds in Table 2c.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | (m, 2 H), 2.92-2.75 (m, 3 H), 2.33 (s, 3 H), 1.18 (dd, J = 6.9, 5.0 Hz, 6 H) | |
| FB71 | Yellow oil | | ESIMS m/z 701 ([M + H]$^+$) | $^1$H NMR (400 MHz, CDCl$_3$) δ 8.56 (d, J = 1.1 Hz, 1 H), 8.21-8.10 (m, 2 H), 7.84-7.75 (m, 2 H), 7.48 (dd, J = 8.3, 6.1 Hz, 2 H), 7.44-7.36 (m, 2 H), 7.35-7.29 (m, 1 H), 7.29-7.22 (m, 1 H), 6.85 (t, J = 2.0 Hz, 1 H), 5.86 (dt, J = 25.1, 6.3 Hz, 1 H), 5.12 (ddd, J = 14.0, 8.2, 6.1 Hz, 1 H), 4.04-3.74 (m, 4 H), 2.61 (ddq, J = 13.6, 10.1, 6.4 Hz, 1 H), 2.33 (s, 3 H), 1.20-1.05 (m, 6 H). | $^{19}$F NMR (376 MHz, CDCl$_3$) δ −58.01 |
| FB72 | White solid | 180-185 | | $^1$H NMR (400 MHz, CDCl$_3$) δ 8.55 (s, 1 H), 8.08 (dd, J = 8.2, 1.0 Hz, 2 H), 7.85-7.74 (m, 2 H), 7.45-7.35 (m, 2 H), 7.33-7.20 (m, 4 H), 6.87-6.80 (m, 1 H), 5.54 (t, J = 5.9 Hz, 1 H), 4.13 (d, J = 6.5 Hz, 1 H), 3.70 (d, J = 1.1 Hz, 1 H), 3.65-3.53 (m, 1 H), 3.53-3.40 (m, 1 H), 2.87 (t, J = 7.0 Hz, 2 H), 2.68-2.54 (m, 1 H), 2.33 (s, 3 H), 1.49-1.38 (m, 6 H), 1.14 (td, J = 6.7, 4.2 Hz, 6 H) | |

$^a$All $^1$H NMR data measured in CDCl$_3$ at 400 MHz unless otherwise noted

| % Control (or Mortality) | Rating |
|---|---|
| BAW and CL Rating Table | |
| 50-100 | A |
| More than 0-Less than 50 | B |
| Not Tested | C |
| No activity noticed in this bioassay | D |
| GPA & YFM Rating Table | |
| 80-100 | A |
| More than 0-Less than 80 | B |
| Not Tested | C |
| No activity noticed in this bioassay | D |

TABLE ABC

Biological Results (F)

| | Insect species | | | |
|---|---|---|---|---|
| No. | BAW | CL | GPA | YFM |
| F1 | A | A | D | C |
| F2 | A | A | B | A |
| F3 | A | A | B | C |
| F4 | A | A | C | C |
| F5 | A | A | A | A |
| F5A | A | A | C | C |
| F6 | A | A | B | A |
| F7 | A | A | B | A |
| F8 | A | A | D | C |
| F9 | A | A | D | A |
| F10 | A | A | B | A |
| F11 | A | A | D | C |
| F12 | A | A | D | C |
| F13 | A | A | D | C |
| F14 | A | A | D | A |

TABLE ABC-continued

Biological Results (F)

| No. | BAW | CL | GPA | YFM |
|---|---|---|---|---|
| F15 | A | A | C | C |
| F16 | A | A | C | C |
| F17 | A | A | C | C |
| F18 | A | A | C | C |
| F19 | A | A | C | C |
| F20 | A | A | C | A |
| F21 | A | A | D | A |
| F22 | A | A | D | C |
| F23 | A | A | D | C |
| F24 | A | A | D | C |
| F25 | A | A | D | C |
| F26 | A | A | C | C |
| F27 | A | A | D | C |
| F28 | A | A | D | C |
| F29 | A | A | D | A |
| F30 | A | A | D | C |
| F31 | A | A | D | C |
| F32 | A | A | D | C |
| F33 | A | A | D | C |
| F34 | A | A | D | C |
| F35 | A | C | C | C |

TABLE ABC (P)

Biological Results

| No. | BAW | CL | GPA | YFM |
|---|---|---|---|---|
| P1 | A | A | C | C |
| P2, P532 | A | A | C | C |
| P3, P1172 | A | A | C | C |
| P5 | A | A | C | C |
| P6 | A | A | C | C |
| P7 | A | A | C | C |
| P8, P852 | A | A | C | C |
| P14 | A | A | C | C |
| P15 | A | A | C | C |
| P20 | C | A | C | C |
| P26 | A | A | C | A |
| P27 | A | A | C | A |
| P28 | A | A | D | A |
| P29 | A | A | C | A |
| P30 | A | A | C | A |
| P31 | A | A | C | A |
| P33 | A | A | C | A |
| P42 | A | A | C | A |
| P44 | A | A | D | A |
| P45 | A | A | C | A |
| P47 | A | A | C | A |
| P49 | A | A | C | A |
| P50 | A | A | C | A |
| P51 | A | A | B | A |
| P52 | A | A | D | A |
| P53 | A | A | C | A |
| P57 | A | A | C | A |
| P58 | A | A | C | C |
| P59 | A | A | C | C |
| P64 | A | A | C | C |
| P65 | A | A | C | A |
| P66, P353 | A | A | C | A |
| P74 | A | A | C | C |
| P75 | A | A | C | C |
| P76 | A | A | C | C |
| P80 | A | A | C | C |
| P81 | C | A | C | C |
| P83 | A | A | C | C |
| P84 | A | A | C | C |
| P85 | A | A | C | C |
| P87 | A | A | C | C |

TABLE ABC (P)-continued

Biological Results

| No. | BAW | CL | GPA | YFM |
|---|---|---|---|---|
| P92 | A | A | C | C |
| P93, P510 | A | A | C | C |
| P94, P197 | A | A | C | C |
| P99, P830 | A | A | C | C |
| P101 | B | A | C | D |
| P102 | A | A | C | C |
| P103, P1150 | A | A | C | C |
| P105 | A | A | C | C |
| P118 | A | A | C | C |
| P119 | A | A | C | C |
| P120 | A | A | C | C |
| P124 | A | A | C | C |
| P125 | A | A | C | C |
| P127 | A | A | C | C |
| P128 | A | A | C | C |
| P129 | A | A | C | C |
| P131 | A | A | C | C |
| P144 | A | A | C | A |
| P145, P522 | A | A | D | A |
| P146, P208 | A | A | C | A |
| P150, P363 | A | A | B | A |
| P151, P842 | A | A | C | A |
| P152, P1481 | D | A | C | A |
| P153 | D | A | C | D |
| P154 | A | A | C | B |
| P155, P1162 | A | A | C | A |
| P156, P682 | A | A | C | A |
| P159 | A | A | B | A |
| P160 | A | A | C | B |
| P170 | D | A | C | C |
| P171 | A | A | C | C |
| P172 | A | A | C | C |
| P176 | A | A | C | C |
| P179 | D | D | C | C |
| P180 | D | A | C | C |
| P181 | A | A | C | C |
| P182 | A | A | C | C |
| P205 | A | A | C | A |
| P209 | A | C | C | A |
| P364 | A | A | C | C |
| P679 | A | A | C | A |
| P683 | A | C | C | A |
| P1163 | A | C | C | D |

TABLE ABC (PC)

Biological Results

| No. | BAW | CL | GPA | YFM |
|---|---|---|---|---|
| PC1 | A | A | C | C |
| PC2 | C | C | C | C |
| PC3 | A | A | C | C |
| PC5 | A | A | C | C |
| PC6 | C | C | C | C |
| PC7 | A | A | C | C |
| PC8 | A | A | C | C |
| PC14 | C | C | C | C |
| PC15 | A | A | C | C |
| PC16 | C | C | C | C |
| PC74 | A | A | C | C |
| PC75 | D | C | C | C |
| PC76 | C | C | C | C |
| PC80 | C | C | C | C |
| PC81 | C | C | C | C |
| PC83 | A | A | C | C |
| PC84 | C | C | C | C |
| PC85 | C | C | C | C |
| PC87 | D | A | C | C |

TABLE ABC (PC)-continued

Biological Results

| No. | BAW | CL | GPA | YFM |
|---|---|---|---|---|
| PC92 | A | A | C | C |
| PC93 | A | A | C | C |
| PC94 | A | A | C | C |
| PC99 | A | D | C | C |
| PC101 | A | A | C | C |
| PC102 | A | D | C | C |
| PC103 | B | D | C | C |
| PC105 | D | D | C | C |
| PC118 | D | C | C | C |
| PC119 | A | A | C | C |
| PC120 | A | A | C | C |
| PC124 | A | A | C | C |
| PC125 | A | A | C | C |
| PC127 | A | A | C | C |
| PC128 | A | A | C | C |
| PC129 | A | A | C | C |
| PC131 | A | A | C | C |
| PC144 | A | A | C | C |
| PC145 | A | A | C | C |
| PC146 | A | A | C | C |
| PC150 | A | A | C | C |
| PC151 | A | A | C | C |
| PC152 | A | A | C | C |
| PC153 | D | A | D | B |
| PC154 | A | A | C | C |
| PC155 | A | A | C | C |
| PC156 | A | A | C | C |
| PC159 | A | A | C | C |
| PC160 | A | A | C | D |
| PC170 | B | A | C | C |
| PC171 | B | A | C | C |
| PC172 | A | A | C | C |
| PC176 | B | A | C | C |
| PC179 | B | A | C | C |
| PC180 | B | D | C | C |
| PC181 | B | D | C | C |
| PC182 | D | A | C | C |

TABLE ABC (FB)

Biological Results

| No. | BAW | CL | GPA | YFM |
|---|---|---|---|---|
| FB1 | A | A | C | C |
| FB2 | A | A | C | C |
| FB3 | A | A | C | C |
| FB4 | A | A | C | C |
| FB5 | A | A | C | C |
| FB6 | A | A | C | C |
| FB7 | A | A | C | C |
| FB8 | A | A | C | C |
| FB9 | A | A | C | C |
| FB10 | A | A | C | C |
| FB11 | B | A | C | C |
| FB12 | A | A | C | C |
| FB13 | B | A | C | C |
| FB14 | A | A | C | C |
| FB15 | A | A | C | C |
| FB16 | D | A | C | C |
| FB17 | A | A | C | A |
| FB18 | A | A | C | C |
| FB19 | A | A | C | C |
| FB20 | A | A | C | C |
| FB21 | A | A | C | C |
| FB22 | A | A | C | C |
| FB23 | A | A | C | C |
| FB24 | A | A | C | C |
| FB25 | A | A | C | C |
| FB26 | A | A | C | C |
| FB27 | A | A | C | C |
| FB28 | A | A | C | C |
| FB29 | A | A | C | C |
| FB30 | A | A | C | C |
| FB31 | A | A | C | C |
| FB32 | A | A | C | C |
| FB33 | A | A | C | C |
| FB34 | A | A | C | C |
| FB35 | A | A | C | C |
| FB36 | B | A | C | C |
| FB37 | B | B | C | C |
| FB38 | B | A | C | C |
| FB39 | A | A | C | C |
| FB40 | A | A | C | A |
| FB41 | A | A | C | A |
| FB42 | A | A | C | A |
| FB43 | A | A | B | A |
| FB44 | A | A | B | A |
| FB45 | A | A | C | C |
| FB46 | A | A | C | C |
| FB47 | A | A | C | A |
| FB48 | A | A | C | A |
| FB49 | A | A | C | A |
| FB50 | A | A | C | C |
| FB51 | A | A | C | A |
| FB52 | A | A | C | C |
| FB53 | A | A | C | B |
| FB54 | A | A | C | A |
| FB55 | A | A | C | C |
| FB56 | A | A | C | A |
| FB57 | A | A | C | A |
| FB58 | A | A | C | A |
| FB59 | A | A | C | A |
| FB60 | A | A | C | A |
| FB61 | A | A | C | A |
| FB62 | A | A | C | A |
| FB63 | A | A | C | A |
| FB64 | A | A | C | C |
| FB65 | A | A | C | A |
| FB66 | A | A | C | C |
| FB67 | A | A | C | A |
| FB68 | A | A | C | C |
| FB69 | A | A | C | C |
| FB70 | A | A | C | A |
| FB71 | A | A | C | A |
| FB72 | A | A | C | C |

We claim:

1. A molecule having the following formula ("Formula One")

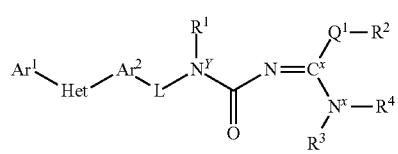

Formula One and tautomers thereof, wherein:
(A) $Ar^1$ is substituted phenyl wherein said substituted phenyl has one or more substituents independently selected from $C_1$-$C_6$ haloalkyl and $C_1$-$C_6$ haloalkoxy;
(B) Het is 1,2,4 triazolyl;
(C) $Ar^2$ is phenyl, or substituted phenyl wherein said substituted phenyl has one or more substituents independently selected from F, Cl, Br, I, and $C_1$-$C_6$ alkyl;
(D) $R^1$ is H, $C_1$-$C_6$ alkyl, or $C_2$-$C_6$ alkenyl, wherein said alkyl is optionally substituted with a $C_3$-$C_6$ cycloalkyl;

(E) $R^2$ is (J), H, or $C_1$-$C_6$ alkyl;
(F) $R^3$ is phenyl, wherein said phenyl is optionally substituted with one or more substituents independently selected from F, Cl, Br, I, $C_1$-$C_6$ alkyl, and $C_1$-$C_6$ alkoxy;
(G) $R^4$ is (J), H, or $C_1$-$C_6$ alkyl;
(H) $Q^1$ is S;
(J) $R^2$ and $R^4$ may be a 1- to 4-membered saturated or unsaturated, hydrocarbyl link, which may contain one or more heteroatoms selected from nitrogen, sulfur, and oxygen, and together with $C^x(Q^1)(N^x)$ forms a cyclic structure, wherein said hydrocarbyl link may optionally be substituted with one or more substituents independently selected from $R^5$, $R^6$, and $R^7$, wherein each $R^5$, $R^6$, and $R^7$ is selected from H, F, Cl, Br, I, CN, $C_1$-$C_6$ alkyl, and oxo; and
(L) L is linker selected from
  (1) a saturated or unsaturated, substituted or unsubstituted, linear ($C_1$-$C_4$)hydrocarbyl linker, and
  (2) a saturated or unsaturated, substituted or unsubstituted, cyclic ($C_3$-$C_8$)hydrocarbyl group linker,
wherein each of said linkers connects $Ar^2$ to $N^Y$ and wherein said substituted linear ($C_1$-$C_4$)hydrocarbyl linker and substituted cyclic ($C_3$-$C_8$)hydrocarbyl linker has one or more substituents independently selected from $R^8$, $R^9$, $R^{10}$, $R^{11}$, and $R^{12}$, wherein each $R^8$, $R^9$, $R^{10}$, $R^{11}$, and $R^{12}$, is selected from F, Cl, Br, I, CN, oxo, $C_1$-$C_6$ alkyl, $C_2$-$C_6$ alkenyl, $C_2$-$C_6$ haloalkenyl, $C_2$-$C_6$ alkynyl, $C_1$-$C_6$ haloalkyl, $C_3$-$C_6$ cycloalkyl, $C_3$-$C_6$ cycloalkenyl, $C_3$-$C_6$ halocycloalkyl, and phenyl.

2. A molecule according to claim 1 wherein said molecule is a tautomer having the following formula

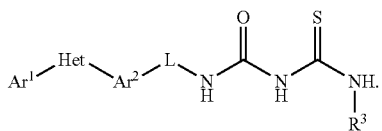

3. A process comprising: applying a molecule according to claim 1 to a locus to control a pest, in an amount sufficient to control such pest.

* * * * *